United States Patent
Clarke et al.

(10) Patent No.: US 9,850,483 B2
(45) Date of Patent: Dec. 26, 2017

(54) METHODS AND SYSTEMS FOR ANALYSIS OF SINGLE CELLS

(75) Inventors: Michael F. Clarke, Stanford, CA (US); Stephen R. Quake, Stanford, CA (US); Piero D. Dalerba, Palo Alto, CA (US); Huiping Liu, Chicago, IL (US); Anne A. Leyrat, San Carlos, CA (US); Tomer Kalisky, Givat Shmuel (IL); Maximilian Diehn, Stanford, CA (US); Michael Rothenberg, Menlo Park, CA (US); Jianbin Wang, Millbrae, CA (US); Neethan Lobo, San Francisco, CA (US)

(73) Assignee: The Board of Trustees of the Leland Stanford Junior University CA (US)

( * ) Notice: Subject to any disclaimer, the term of this patent is extended or adjusted under 35 U.S.C. 154(b) by 0 days.

(21) Appl. No.: 13/811,065

(22) PCT Filed: Jul. 19, 2011

(86) PCT No.: PCT/US2011/044574
§ 371 (c)(1),
(2), (4) Date: Apr. 29, 2013

(87) PCT Pub. No.: WO2012/012458
PCT Pub. Date: Jan. 26, 2012

(65) Prior Publication Data
US 2013/0225435 A1  Aug. 29, 2013

Related U.S. Application Data

(60) Provisional application No. 61/399,973, filed on Jul. 19, 2010.

(51) Int. Cl.
*G01N 33/50* (2006.01)
*C12N 15/10* (2006.01)
*C12Q 1/68* (2006.01)

(52) U.S. Cl.
CPC ....... *C12N 15/1072* (2013.01); *C12Q 1/6809* (2013.01); *C12Q 1/6886* (2013.01); *C12Q 2600/106* (2013.01); *C12Q 2600/158* (2013.01)

(58) Field of Classification Search
CPC  C12N 15/1072; C12Q 1/6809; C12Q 1/6886; C12Q 2600/106; C12Q 2600/158
See application file for complete search history.

(56) References Cited

U.S. PATENT DOCUMENTS 7,507,528 B2  3/2009  Albert et al.
2009/0093374 A1*  4/2009  Suh et al. .................. 506/10
(Continued)

FOREIGN PATENT DOCUMENTS

WO  WO-03/023057 A2  3/2003
WO  WO-2006048291 A2  5/2006
(Continued)

OTHER PUBLICATIONS

Chung et al., Recent advances in miniaturized microfluidic flow cytometry for clinical use, Electrophoresis 2007, 28, 4511-4520.*
(Continued)

*Primary Examiner* — Reza Ghafoorian
(74) *Attorney, Agent, or Firm* — Schwegman Lundberg & Woessner, P.A.

(57) ABSTRACT

Methods are provided for diagnosis and prognosis of disease by analyzing expression of a set of genes obtained from single cell analysis. Classification allows optimization of treatment, and determination of whether on whether to proceed with a specific therapy, and how to optimize dose, choice of treatment, and the like. Single cell analysis also provides for the identification and development of therapies which target mutations and/or pathways in disease-state cells.

11 Claims, 489 Drawing Sheets

(56) References Cited

U.S. PATENT DOCUMENTS

| | | | |
|---|---|---|---|
| 2009/0098594 A1* | 4/2009 | Fantl et al. | 435/29 |
| 2009/0170715 A1* | 7/2009 | Glinsky | 506/8 |
| 2010/0159445 A1* | 6/2010 | Lustig et al. | 435/6 |
| 2010/0255471 A1* | 10/2010 | Clarke et al. | 435/6 |

FOREIGN PATENT DOCUMENTS

| | | | |
|---|---|---|---|
| WO | WO 2007/114896 | * | 10/2007 |
| WO | WO-2007114896 A2 | | 10/2007 |
| WO | WO-2010085498 A1 | | 7/2010 |

OTHER PUBLICATIONS

Roach, A Microwell Array Cytometry System for High Throughput Single Cell Biology and Bioinformatics, Submitted to the Division of Health Sciences and Technology in partial fulfillment of the requirements for the degree of Doctor of Philosophy in Electrical and Biomedical Engineering at the Massachusetts Institute of Technology, Feb. 2009.*

Zhong et al., Microfluidic Devices for Investigating Stem Cell Gene Regulation via Single-Cell Analysis, Current Medicinal Chemistry, 2008, vol. 15, No. 28, pp. 2897-2900.*

Zhong et al., A microfluidic process for gene expression profiling of single human embryonic stem cells, Lab Chip, 2008, vol. 8, pp. 68-74.*

Chen et al., Microfluidic Devices for Hight-Throughput Gene Expression Profiling of Single hESC-Derived Neural Stem Cell, Methods in Molecular Biology, vol. 438; pp. 239-303.*

"International Application Serial No. PCT/US2011/44574, Search Report mailed Dec. 7, 2011", 2 pgs.

"International Application Serial No. PCT/US2011/44574, Written Opinion mailed Dec. 7, 2011", 4 pgs.

Canadian Application No. 2,806,632, Office Action mailed Oct. 29, 2015, 5 pgs.

"Australian Application Serial No. 2011282233, First Examiner Report dated Dec. 5, 2013", 3 pgs.

"Australian Serial No. 2011282233, Subsequent Examiners Report dated Apr. 4, 2014", 3 pgs.

"Canadian Application Serial No. [Pending], Voluntary Amendment dated Jan. 23, 2013", 5 pgs.

"European Application Serial No. 11810302.7, Extended European Search Report dated Mar. 17, 2014", 5 pgs.

"International Application Serial No. PCT/US2011/044574, International Preliminary Report on Patentability dated Jan. 31, 2013", 4 pgs.

"New Zealand Application Serial No. 607234, Subsequent Examiners Report dated Jan. 13, 2014", 2 pgs.

"New Zealand Application Serial No. 607234, Amendment dated Feb. 17, 2013", 9 pgs.

Bontoux, N, et al., "Integrating whole transcriptome assays on a lab-on-a-chip for single cell gene profiling", Lab on a Chip, vol. 8, No. 3, (Jan. 1, 2008), 443.

"Australian Application Serial No. 2011282233, Response dated Mar. 12, 2014 to First Examiner Report dated Dec. 5, 2013", 156 pgs.

"European Application Serial No. 11810302.7, Office Action dated Mar. 7, 2013", 2 pgs.

"European Application Serial No. 11810302.7, Office Action dated Apr. 3, 2014", 1 pg.

"European Application Serial No. 11810302.7, Response dated Sep. 16, 2013 to Office Action dated Mar. 7, 2013", 5 pgs.

"European Application Serial No. 11810302.7, Response dated Sep. 26, 2014 to Office Action dated Apr. 3, 2014", 9 pgs.

"New Zealand Application Serial No. 607234, Examiners Report dated Jul. 3, 2013". 2 pgs.

"New Zealand Application Serial No. 607234, Response dated May 30, 2014 to Subsequent Examiners Report dated Jan. 13, 2014", 2 pgs.

"New Zealand Application Serial No. 607234, Response dated Dec. 20, 2013 to Examiners Report dated Jul. 3, 2013", 6 pgs.

Fu, Anne Y., et al., "A microfabricated Fluorescence-activated cell sorter", *Nature Biotechnology*:17, (1999), 1109-1111.

Fu, Anne Y, et al., "An Integrated Microfabricated Cell Sorter", *Analytical Chemistry*:74(11), (2002), 2451-2457.

Tokimitsu, Yoshiharu, et al., "Single Lymphocyte Analysis with a Microwell Array Chip", *Cytometry Part A 71A*, (2007), 1003-1010.

Yamamura, Shohel, et al., "Single-Cell Microarray for Analyzing Cellular Response", *Analytical Chemistry* 77(24), (Dec. 15, 2005), 8050-8056.

Australian Serial No. 2011282233, Response dated Oct. 13, 2014 to Subsequent Examiners Report dated Apr. 4, 2014, 162 pgs.

* cited by examiner

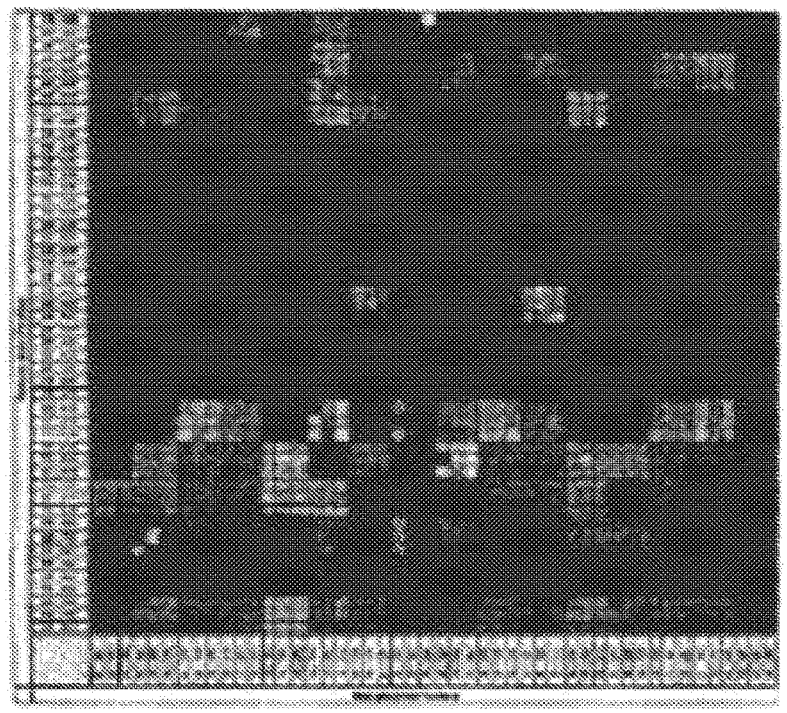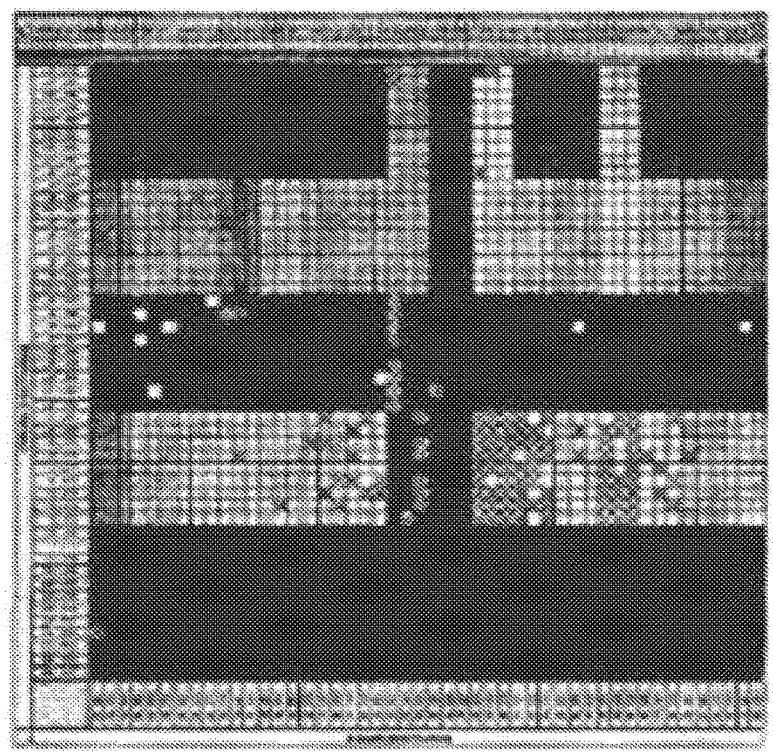
FIG. 1

FIG. 4

We first cleaned all cells with GAPDH=0, ACTB=0 or TACSTD1 (EpCAM)=0 chose 450 cells out of 462 cells (12 cells discarded, or 3% of total)

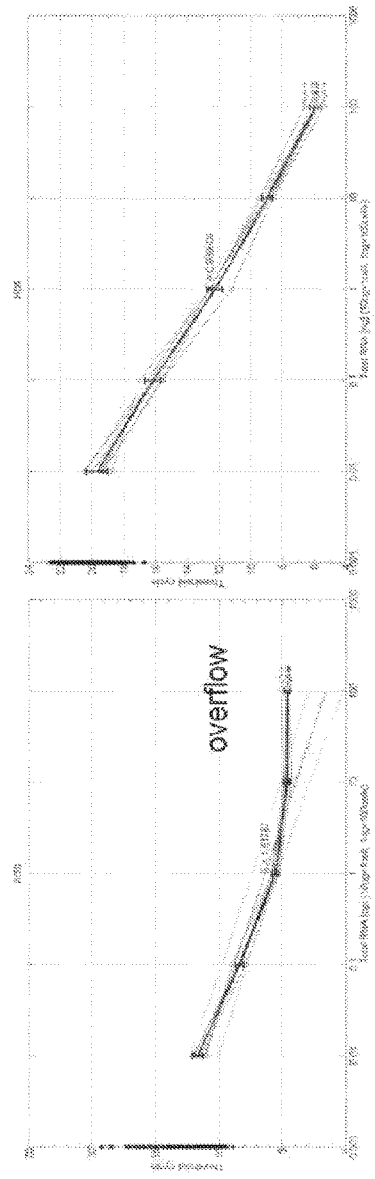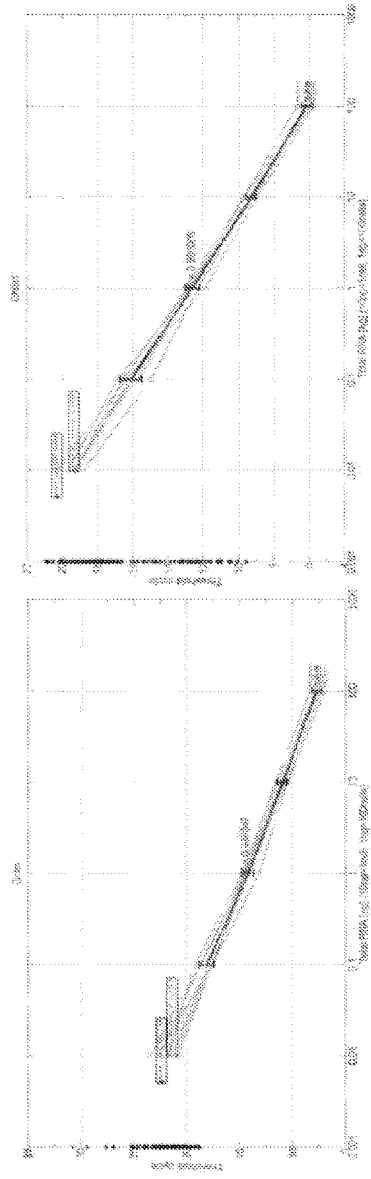
FIG. 68

"mean-centered-max-normalized"

For each gene we took:

$$\frac{C_T - \langle C_T \rangle_{C_T < 40}}{-\min(C_T)}$$

- Subtract the global mean
- Divide by minimal $C_T$
- All $C_T$'s higher than 1 are substituted by 1 (apart from SampleData which is substituted by 3 in order to give it more weight).

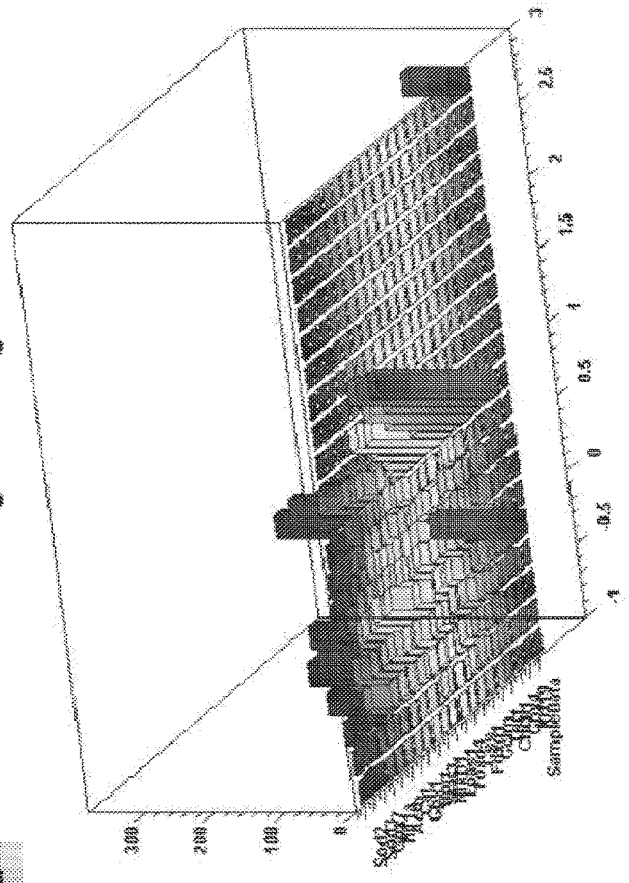

Histogram of genes

We assume that the global mean will represent an "absolute" expression level for which the TG cells will be higher and the NTG cells will be lower (or vice versa).

Dividing by the minimal $C_T$ provides additional normalization for comparing the highest levels of all genes.

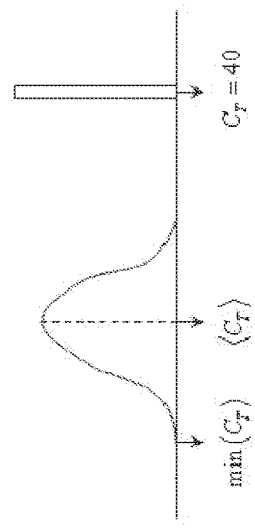

FIG. 85

We remove cells for which Hprt1 is not expressed, or for which none of the Keratins (Krt14-870, Krt17-207, Krt18—706, Krt19--980) are expressed.

→chose 448 cells out of 504 cells (56 cells discarded, or 12% of total)

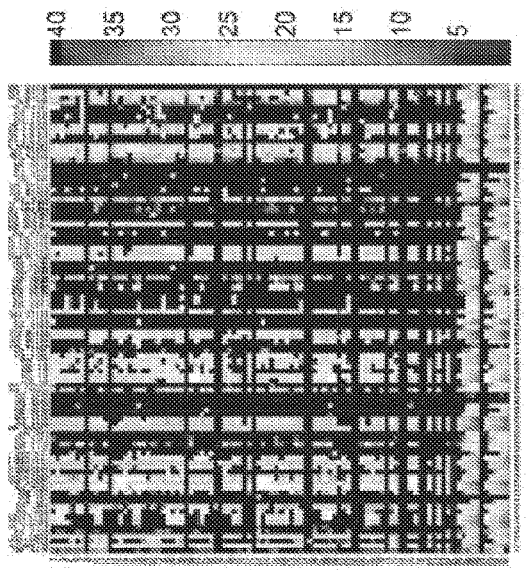
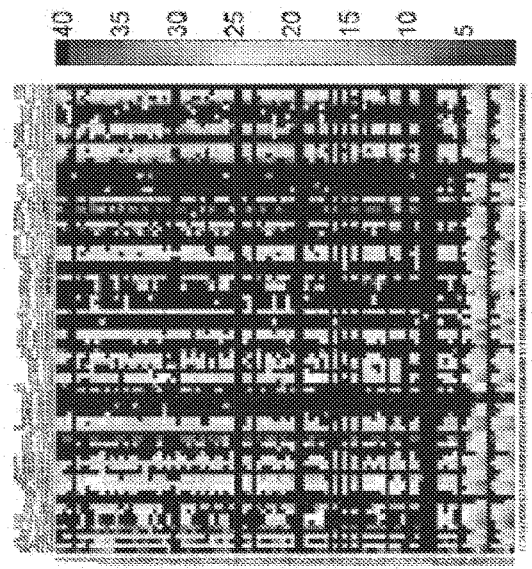
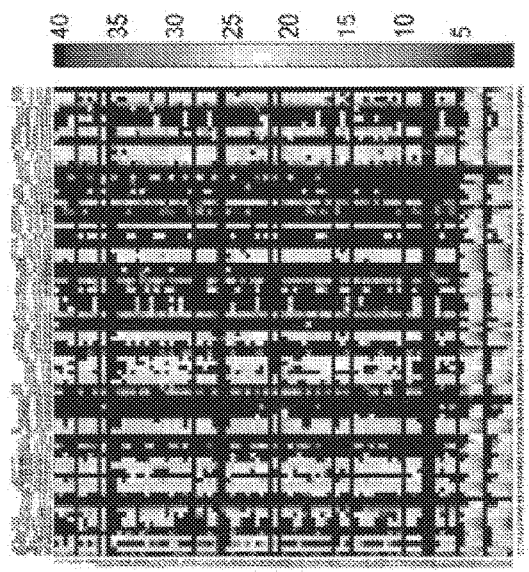
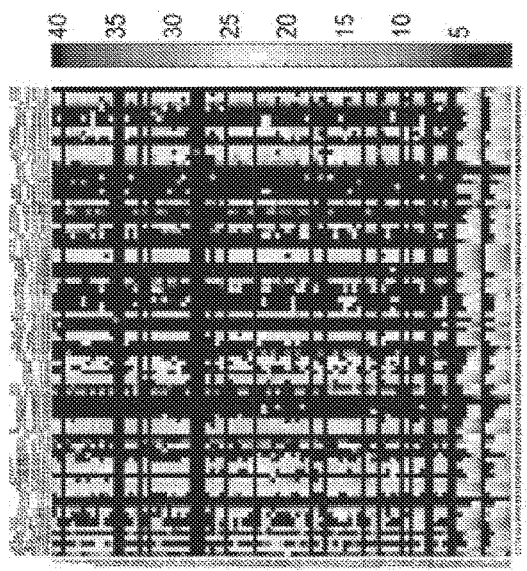
FIG. 104 chose 268 cells out of 336 cells (68 cells discarded, or 21% of total)

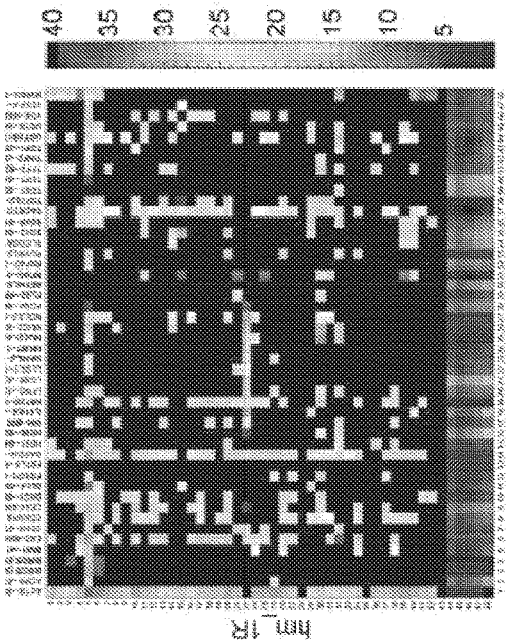
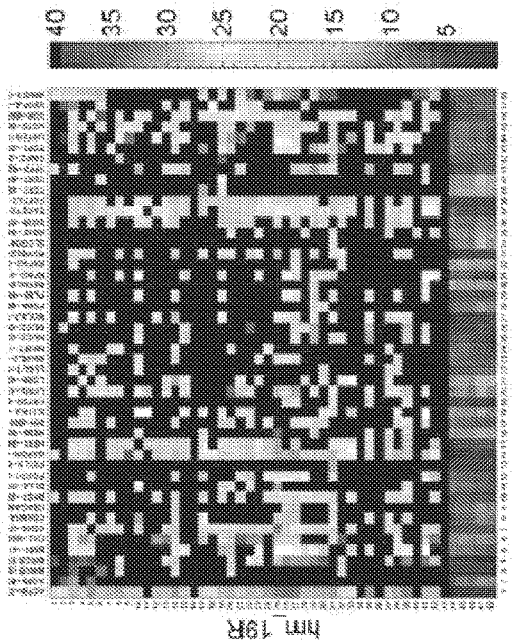
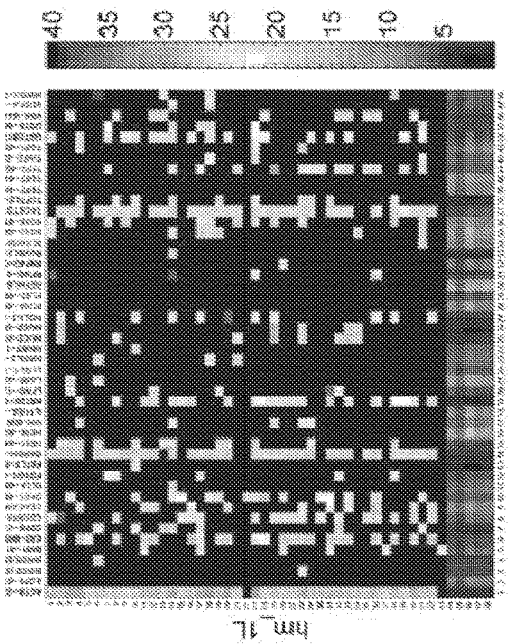
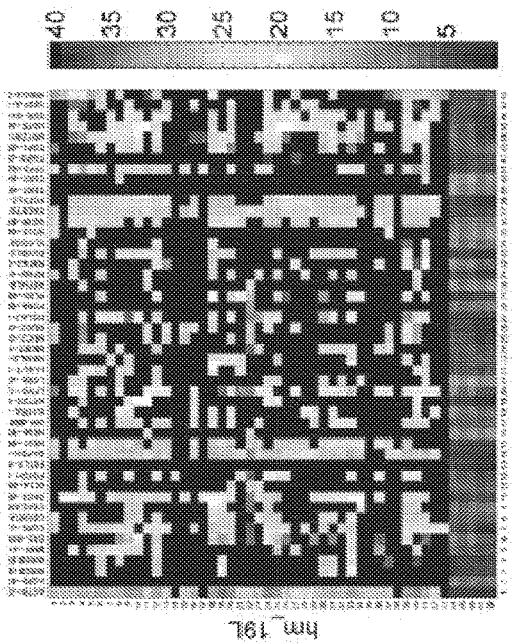
FIG. 116

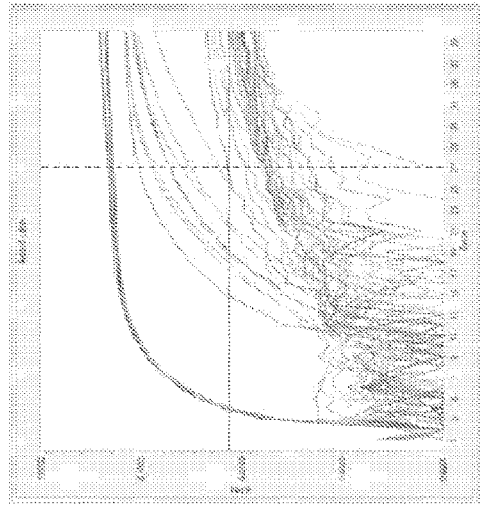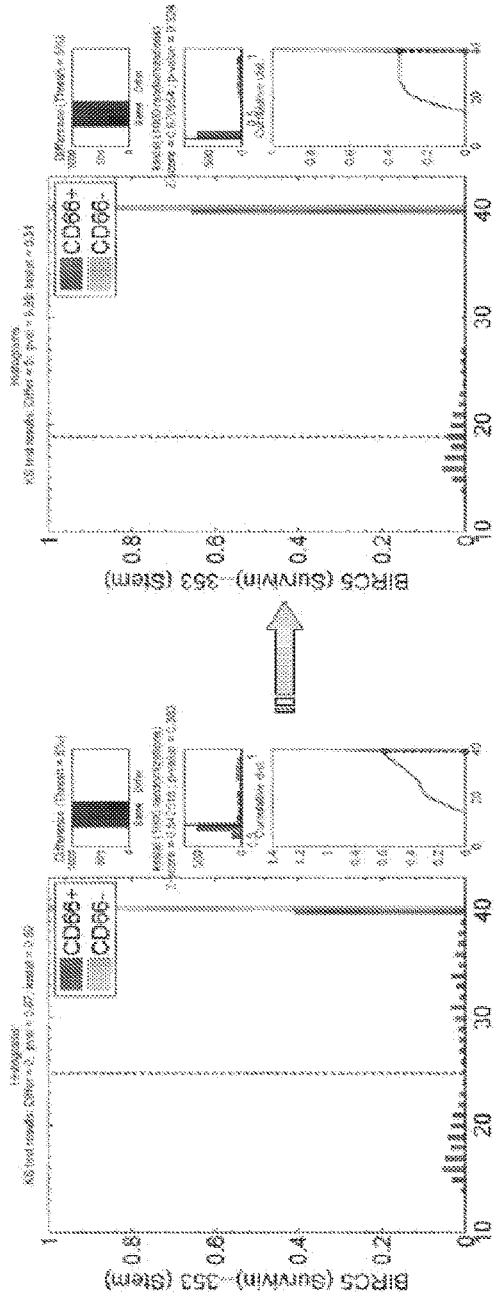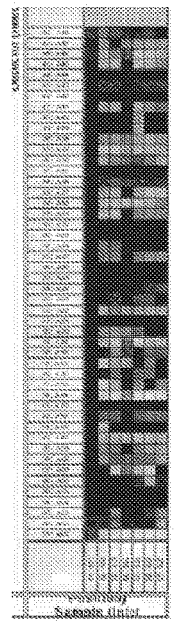
FIG. 150

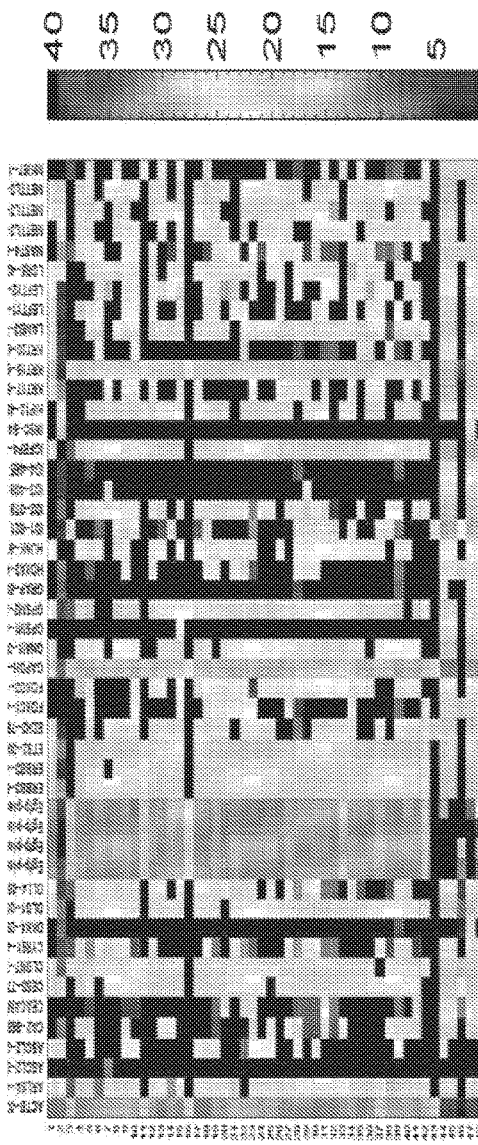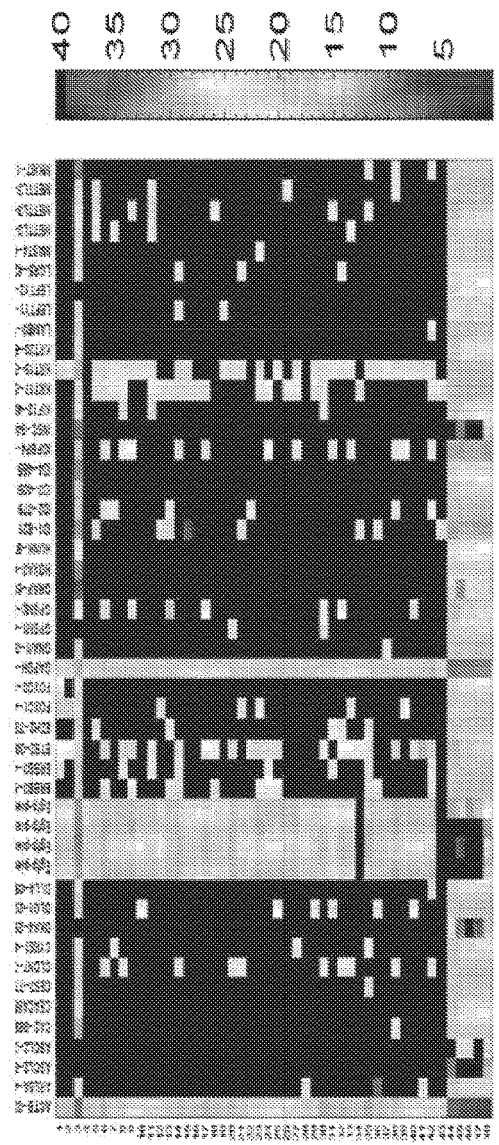
FIG. 243

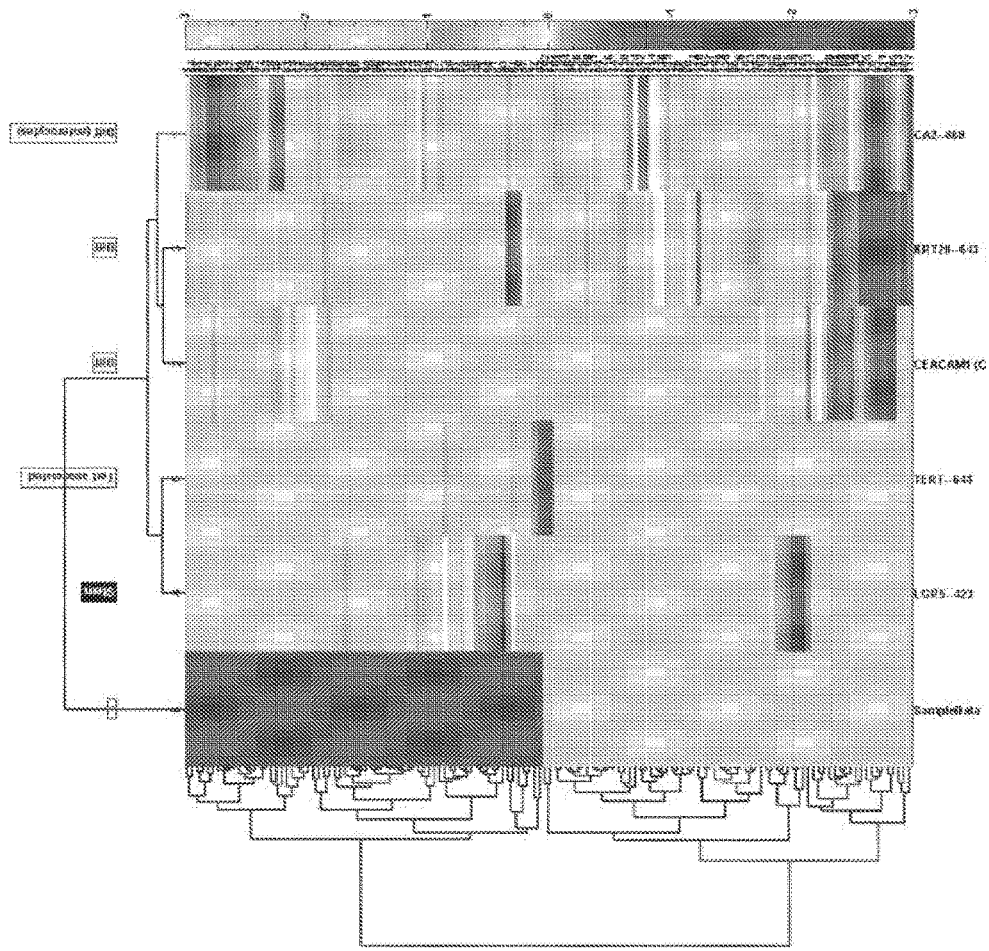
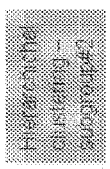
FIG. 257

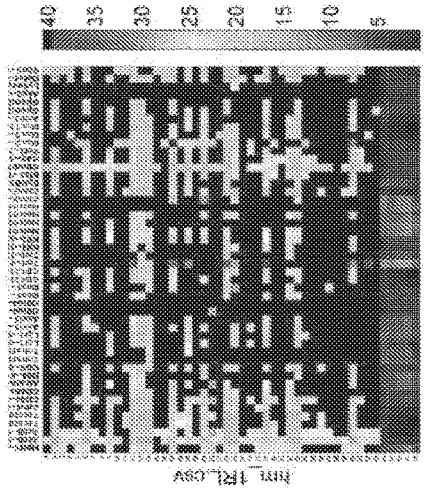
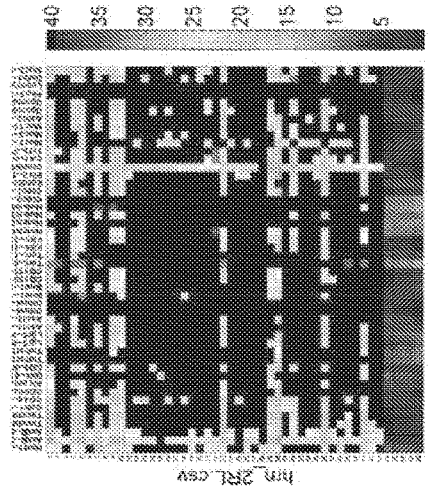
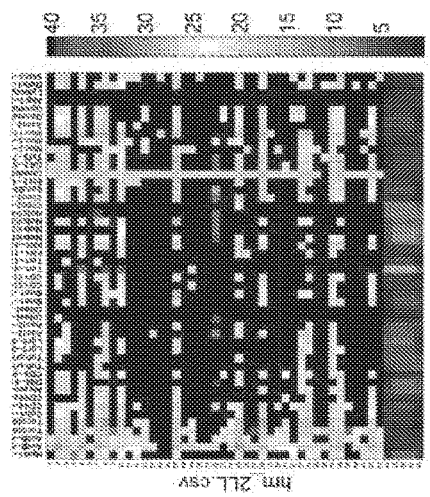
FIG. 394

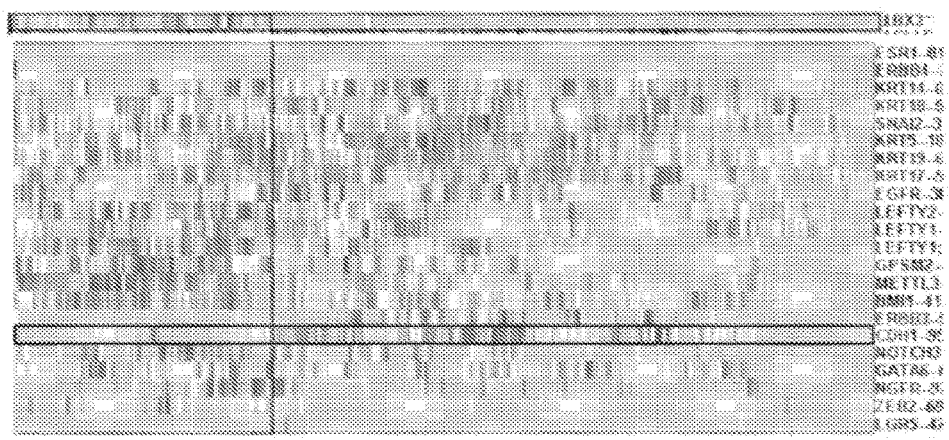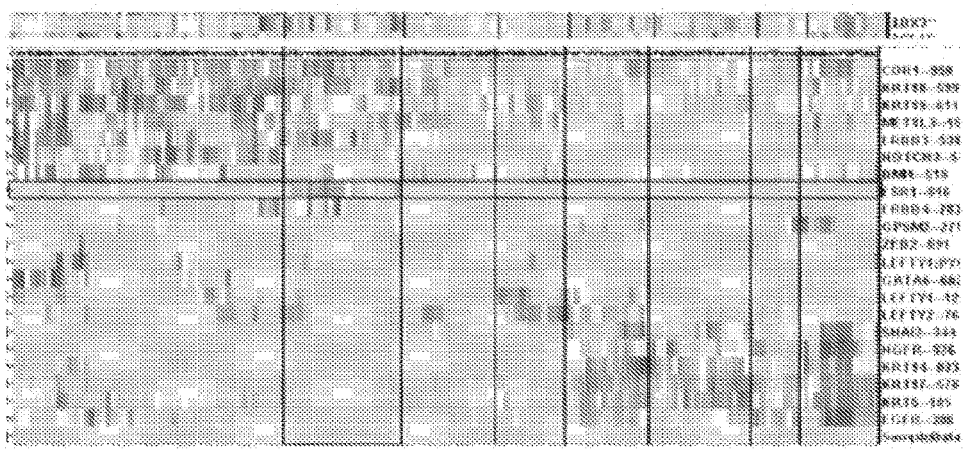
FIG. 464

On-chip washing. Fibroblast cells and epithelial cells were mixed and stained with anti-ESA-Alexa488. Light scattering (red) and Alexa488 (green) images were taken and overlaid after on-chip washing.

GFP cells demo sorting. GFP fluorescence (red) and bright field micrograph (grey scale) were overlaid and phenotypes could be distinguished (left). Genotypes of sorted cells were verified by Taqman gene expression assays (right).

METHODS AND SYSTEMS FOR ANALYSIS OF SINGLE CELLS

CLAIM OF PRIORITY

This application is a U.S. National Stage Filing under 35 U.S.C. 371 from International Application No. PCT/US2011/044574, filed on 19 Jul. 2011, and published as WO 2012/012458 on 26 Jan. 2012, which claims the benefit of priority to U.S. Provisional Patent Application Ser. No. 61/399,973, filed on Jul. 19, 2010, which applications and publication are incorporated herein by reference in their entirety.

GOVERNMENT RIGHTS

This invention was made with Government support under federal grants U54 CA 126524 awarded by the National Cancer Institute. The Government has certain rights in this invention.

BACKGROUND OF THE INVENTION

In recent years, analysis of gene expression patterns has provided a way to improve the diagnosis and risk stratification of many diseases. For example, unsupervised analysis of global gene expression patterns has identified molecularly distinct subtypes of cancer, distinguished by extensive differences in gene expression, in diseases that were considered homogeneous based on classical diagnostic methods. Such molecular subtypes are often associated with different clinical outcomes. Global gene expression pattern can also be examined for features that correlate with clinical behavior to create prognostic signatures.

Cancer, like many diseases, is frequently not the result of a single, well-defined cause, but rather can be viewed as several diseases, each caused by different aberrations in informational pathways, which ultimately result in apparently similar pathologic phenotypes. Identification of polynucleotides that are differentially expressed in cancerous, pre-cancerous, or low metastatic potential cells relative to normal cells of the same tissue type can provide the basis for diagnostic tools, facilitates drug discovery by providing for targets for candidate agents, and further serves to identify therapeutic targets for cancer therapies that are more tailored for the type of cancer to be treated.

Identification of differentially expressed gene products also furthers the understanding of the progression and nature of complex diseases, and is key to identifying the genetic factors that are responsible for the phenotypes associated with development of, for example, the metastatic or inflammatory phenotypes. Identification of gene products that are differentially expressed at various stages, and in various types of cells, can both provide for early diagnostic tests, and further serve as therapeutic targets. Additionally, the product of a differentially expressed gene can be the basis for screening assays to identify chemotherapeutic agents that modulate its activity (e.g. its expression, biological activity, and the like).

Early disease diagnosis is of central importance to halting disease progression, and reducing morbidity. Analysis of a patient samples to identify gene expression patterns provides the basis for more specific, rational disease therapy that may result in diminished adverse side effects relative to conventional therapies. Furthermore, confirmation that a lesion poses less risk to the patient (e.g., that a tumor is benign) can avoid unnecessary therapies. In short, identification of gene expression patterns in disease-associated cells can provide the basis of therapeutics, diagnostics, prognostics, therametrics, and the like.

As another example, infectious diseases cause damage to tissues and organs that lead to the morbidity and mortality of a particular organism. In the case of influenza A infections, the most frequent cause of hospitalization and death is infection of the lung tissue. However, the precise cells that are infected by influenza, and the cells that repair the damaged lungs are not understood at the single cell level. Such knowledge could help to identify therapeutic targets for intervention, such as novel drugs to prevent viral infection and new treatments to ameliorate morbidity.

Many tumors contain mixed populations of cancer cells that might differ with respect to their signaling pathways that they use for their growth and survival. Since these cancer cells differ with respect to their response to a particular therapy, resistance of a particular population of cancer stem cells contributes to relapse after cytoxic radiotherapy and chemotherapy. As such, treatment failures in the clinic may be due partly to the resistance of a particular population of cancer cells to therapy The often-observed initial shrinkage of a tumor soon after treatment may reflect nothing more than relative sensitivity of one sub population of cancer cells, which could comprise the bulk of a tumor, and may not be important to long term survival. Thus, the most important clinical variable for assessing treatment response and prognosis may not be the absolute tumor size but rather the absolute number of a particular population of cancer cells remaining after treatment. If one could identify differences in the signaling pathways used by these different populations of cancer cells within a tumor, then one could design therapies that target each population of cells. By targeting all populations, one could eliminate a tumor by treating with drugs that affect each different population.

As another example, inflammatory bowel disease results in disruption of the normal structure of the intestine resulting in problems such as diarrhea, bleeding and malabsorption. These problems are caused by destruction of the normal mucosal lining of the gut. The mucosal lining of the colon consists of crypts, where goblet cells, stem cells and progenitor cells are at the base of the crypt, while the mature cells including enterocytes and goblet cells reside at the top of the crypt. With inflammatory bowel disease, it is not clear which cell populations are damaged and the signaling pathways that are required to repair the damaged mucosa.

Methods of precisely determining the number and phenotype of cells in disease lesions using small numbers of cells is of great interest for prognosis, diagnosis identification of signaling pathways that can be targeted by specific therapeutics, of multiple diseases, including inflammatory bowel disease, infections, cancers, autoimmune diseases such as rheumatoid arthritis, and infections. The present invention addresses this issue.

SUMMARY OF THE INVENTION

Compositions and methods are provided for the use of single cell gene expression profiling and/or transcriptome analysis. One method provided herein is a method of identifying different cell populations in a heterogeneous solid tumor sample, comprising: randomly partitioning individual cells from the tumor into discrete locations; performing transcriptome analysis on a plurality of genes of the individually partitioned cells in the discrete locations; and performing clustering analysis to identify one or more different cell populations. In some instances, the individual cells are not enriched prior to partitioning. Transcriptome analysis can be performed on at least 1000 individual cells simultaneously. Transcriptome analysis can be performed using nucleic acid analysis. The discrete locations can be on a planar substrate. In some embodiments, the random partitioning is performed in a microfluidic system. Transcriptome analysis can comprise analyzing expressed RNA, non-expressed RNA, or both. Transcriptome analysis can be whole transcriptome analysis. Transcriptome analysis can comprise amplifying RNA using a single set of primer pairs, which in some embodiments are not nested primers. Transcriptome analysis can be performed simultaneously or substantially in real time on all or a subset of individual cells. The one or more cell populations can be normal stem cells, normal progenitor cells, normal mature cells, inflammatory cells, cancer cells, cancer stem cells or non-tumorigenic stem cells.

Also provided herein is a method for treating a condition in a subject comprising: administering one or more therapeutic agents that selectively binds, inhibits, or modulates one or more targets listed Table 1 and/or Table 2 or a pathway of a target listed in Table 1 and/or Table 2. Targets in some embodiments are not Notch4, or Tert, or both. Agents can be antagonists, or inhibitors of a Nodal pathway. Targets can include LEFTY1, LEFTY2 and CFTR, a cell surface marker and/or a messenger RNA. A condition to be treated can be breast cancer, colon cancer, ulcerative colitis, or inflammatory bowel disease. In some embodiments, the therapeutic agent is an antibody or antibody fragment, small molecule, nucleic acid, RNA, DNA, RNA-DNA chimera, protein, or peptide. A nucleic acid can be a siRNA.

Further provided herein is a method of analyzing a heterogeneous tumor biopsy from a subject, comprising: randomly partitioning cells from the biopsy into discrete locations; performing transcriptome analysis on at least 50 genes of the individually partitioned cells; and using transcriptome data to identify one or more characteristic of the tumor. The performing step can be performed without prior enrichment of a cell type. A characteristic identified can be the presence, absence, or number of cancer cells. A characteristic identified can also be the presence, absence or number of stem cells, early progenitor cells, initial differentiated progenitor cells, late differentiated progenitor cells, or mature cells. A characteristic identified can also be effectiveness of a therapeutic agent in eliminating one or more of the cells. A characteristic identified can also be activity of a signaling pathway, for example, a pathway specific to a cancer stem cell, a differentiated cancer cell, a mature cancer cell, or combination thereof. A method disclosed herein can further comprise the step of using the characteristic to diagnose a subject with cancer or a cancer stage.

Another method disclosed herein is a method of identifying a signaling pathway utilized by a disease-state cell, comprising: randomly partitioning cells from a heterogeneous sample; performing transcriptome analysis on the partitioned cells; using transcriptome analysis to identify at least one disease-state cell; comparing the transcriptome analysis of the at least one disease-state cell to transcriptome of: a) a non-disease state cell; b) a different disease-state cell; and c) a disease-state stem cell; and identifying a signaling pathway that is expressed in (i) the disease-state cell, (ii) the disease-state stem cell, and (iii) optionally in the different disease-state cell, but not in a non-disease-state cell, thereby identifying a signaling pathway utilized by a disease-state cell. The disease state can be cancer, ulcerative colitis or inflammatory bowel disease. In some embodiments, the signaling pathway is required for survival of said disease state cell.

The present disclosure also provides method for diagnosing a subject with a condition comprising: randomly partitioning cells from a heterogeneous sample; performing a first transcriptome analysis on partitioned cells; using transcriptome analysis to identify at least one disease-state cell by comparing the first transcriptome analysis from the at least one disease-state cell to a second transcriptome analysis from a non-disease state cell, thereby diagnosing the presence or absence of a condition associated with the disease state cell in said subject. The disease state can be breast cancer, colon cancer, ulcerative colitis or inflammatory bowel disease. Transcriptome analysis can comprise analyzing expressed RNA, non-expressed RNA, or both. Transcriptome analysis can be whole transcriptome analysis.

Yet another method provided herein is a method for screening for a therapeutic agent comprising: exposing a first subject with disease-state cells to one or more test agents; obtaining a heterogeneous tumor biopsy from the subject from a region of interest; performing transcriptome analysis on at least one individual cell from the heterogeneous tumor biopsy, wherein the biopsy comprises one or more disease state cells; and comparing the transcriptome analysis to a transcriptome derived from either: (i) a second subject without the disease-state cells; or (ii) the first subject prior to said exposing step; and identifying an agent that affect a transcriptome of cells from the test area to be more like those of the second subject or the first subject prior to exposure. The condition can be breast cancer, colon cancer, ulcerative colitis, or inflammatory bowel disease. A therapeutic agent can be an antibody or antibody fragment, small molecule, nucleic acid (for example an siRNA), RNA, DNA, RNA-DNA chimera, protein, or peptide.

The present disclosure also provides a method of determining the potential effectiveness of a therapeutic agent against a disease, comprising: separating a first population of disease-state cells into individual locations, wherein the individual locations comprise an individual cell; determining the expression level of at least one nucleic acid or protein from at least one of the individual cells, thereby producing a disease-state expression signature; exposing a second population of disease state cells to an agent; separating the second population of disease-state cells into individual locations, wherein the individual locations comprise an individual cell; determining the expression level of at least one nucleic acid or protein from at least one of the individual cells from the second population; and comparing the expression level from the individual cell from the second population to the disease-state expression signature, thereby determining the effectiveness of the agent against the disease. The exposing step can be performed in vivo. In some instances, the first population and the second population are isolated from a subject, for example, a human. The disease can be cancer, ulcerative colitis or inflammatory bowel disease. The nucleic acid or the protein can be a cancer cell marker, a cancer stem cell marker or both. An expression level can be an mRNA expression level. In some embodiments, determining the mRNA expression level comprises detection of expression or lack of expression of 10 or more nucleic acids. An expression level can also be a protein expression level. The separating steps can comprise exposing the population of cells to an antibody that specifically binds a protein present on the individual cells.

Further provided herein is a method of determining likelihood of a response by a subject to a therapeutic agent, comprising: separating a population of cells from a subject into individual locations, wherein the individual locations comprise an individual cell and wherein at least one of the individual cells is a disease-state cell; determining the expression level of at least one nucleic acid or protein from at least one of the disease-state individual cells, wherein the nucleic acid or protein is a target of a therapeutic agent; and determining likelihood of a response by a subject based on the expression level of the at least one nucleic acid or protein. An expression level can be an mRNA expression level. In some embodiments, determining the mRNA expression level comprises detection of expression or lack of expression of 10 or more nucleic acids. An expression level can also be a protein expression level. The separating steps can comprise exposing the population of cells to an antibody that specifically binds a protein present on the individual cells. The therapeutic agent can be an anti-cancer agent.

Another method detailed herein provides a prognostic or diagnostic method utilizing gene expression from individual cells, comprising the steps of: separating cells from a heterogeneous sample into separately addressable positions; lysing individual cells, and dividing the resulting lysates into at least two portions; amplifying mRNA or cDNA derived therefrom from the individual cells; determining gene expression profiles from one of the lysate portions, wherein the gene expression profile provides sub-population information; and performing transcriptome analysis on at least one cell in a target sub-population. In some methods, at least $10^2$ or at least $10^3$ individual cells are analyzed. Cells can be sorted for expression of at least one cell surface marker. Cells analyzed by the methods disclosed herein can be stem cells, for example hematopoietic stem cells. Initial samples can comprise less than $10^6$ cells or less than $10^5$ cells. Cells can be sorted for expression of at least one of CD34 and Thy1. In some embodiments, expression of at least one or at least five (5) hematopoietic stem cell associated gene is determined Transcriptome analysis is whole transcriptome analysis.

Further provided herein is a method of classifying a stem cell, comprising the steps of: (a) obtaining a stem cell transcriptome profile from a sample; and (b) comparing the obtained transcriptome profile to a reference stem cell transcriptome profile. A transcriptome profile can comprise a dataset obtained from at least about 5 stem cell-associated proteins. Stem cells analyzed can be cancer stem cells, hematopoietic stem cells, intestinal stem cells, leukemia stem cells, or lung stem cells. Samples analyzed can include cells from a cancer, for example a breast carcinoma, or colon carcinoma. Transcriptome profile analysis can also comprise the additional steps of: extracting mRNA from a sample of stem cells; quantitating the level of one or more mRNA species corresponding to stem cell specific sequences; and comparing the level of one or more mRNA species to the level of said mRNA species in a reference sample.

Also provided herein is a method of collecting data regarding a transcriptome, comprising the steps of: collecting data regarding a transcriptome using any of the methods described herein and sending said data to a computer. A computer can be connected to a sequencing apparatus. Data corresponding to a transcriptome can further be stored after sending, for example the data can be stored on a computer-readable medium which can be extracted from the computer. Data can be transmitted from the computer to a remote location, for example, via the internet.

Further provided herein is a method of analyzing a heterogeneous tumor biopsy from a human subject, comprising the steps of: randomly partitioning cells from the biopsy into discrete locations; collecting individually partitioned cells from the discrete locations using an automated device; performing transcriptome analysis on at least 50 genes of the individually partitioned cells; and using transcriptome data to identify one or more therapeutic targets for treatment of said heterogeneous tumor. The one or more therapeutic targets can be a DNA or RNA methyltransferase, methyltransferase-like enzyme or a derivative thereof. The one or more therapeutic targets can also be a histone lysine methyltransferase, histone arginine methyltransferase or a derivative thereof. The one or more therapeutic targets can also be a histone demethylase or a derivative thereof, or a protein kinase or a derivative thereof.

Further provided herein is a method of analyzing a heterogeneous tumor biopsy from a human subject, comprising the steps of: randomly partitioning cells from the biopsy into discrete locations; collecting individually partitioned cells from the discrete locations using an automated device; performing transcriptome analysis on at least 50 genes of the individually partitioned cells; and using transcriptome data to identify one or more diagnostic markers present in the tumor biopsy for the detection of cancer and assessment of the cancer stage. The one or more diagnostic markers can be a DNA or RNA methyltransferase, methyltransferase-like enzyme or a derivative thereof. The one or more diagnostic markers can also be a histone lysine methyltransferase, histone arginine methyltransferase or a derivative thereof. The one or more diagnostic markers can also be a histone demethylase or a derivative thereof. Finally, the one or more diagnostic markers can be a protein kinase or a derivative thereof.

Also provided herein is a method of analyzing a heterogeneous tumor biopsy from a human subject, comprising the steps of: randomly partitioning cells from the biopsy into discrete locations; collecting individually partitioned cells from the discrete locations using an automated device; performing transcriptome analysis on at least 50 genes of the individually partitioned cells; and using transcriptome data to identify one or more diagnostic markers for the assessment of the effectiveness of treatment of said heterogeneous tumor. The one or more therapeutic targets can be a DNA or RNA methyltransferase, methyltransferase-like enzyme or a derivative thereof. The one or more therapeutic targets can also be a histone lysine methyltransferase, histone arginine methyltransferase or a derivative thereof. The one or more therapeutic targets can also be a histone demethylase or a derivative thereof, or a protein kinase or a derivative thereof.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 1. Single-cell gene expression analysis by real-time PCR of human "colorectal cancer stem cells" (EpCAM$^{high}$) purified from human colorectal cancer tissues xenografted in NOD/SCID mice (tumor #4m6). In the first experiment (panel A), 16 single-cells have been analyzed for the expression of 5 genes, performing 27 replicates for each cell-gene combination; in this experiment, each mRNA preparation from an individual single-cell is used in 3 consecutive rows of the reaction matrix, and each gene-specific primer set is used in 9 consecutive columns, with the only exception of the first three where no primers were added; the levels of gene expression for each individual cell can be visualized as 3×9 blocks using a color scale. In the second experiment (panel B), a similar approach was followed, whereas 16 single-cells have been analyzed for the expression of 16 genes, performing 9 replicates for each cell-gene combination; in this second case, each mRNA preparation from an individual single-cell is used in 3 consecutive rows of the reaction matrix, and each gene-specific primer set is used in 3 consecutive columns, so that the levels of gene expression for each individual cell can be visualized as 3×3 blocks using a color scale. In both cases, the: assay displays a high level of reproducibility and consistency within each set of replicates.

FIG. 4. The CT values of real-time PCR analysis for microRNAs (miRs) levels comparing primary TICs and MTICs.

FIG. 40 6 samples, 5 in duplicate, of colon single-cell analysis is shown. Possible genes for targeting of tumors are analyzed for their expression.

FIG. 68 standard curves of ACTB, HPRT GCLM, and Chi311 generated from the qPCR reactions of NTG and TG cells.

FIG. 82 TG and NTG cells were compared in mean-clustering of glutathione-related genes including HIF1a.

FIG. 85 method of calculation of "mean-centered-max-normalized."

FIG. 104 heat maps from four different chip-runs of colon cancer samples.

Figure 123:

FIG. 123 histograms depicting gene expression levels in CD66+ or CD66– cells of TACSTD1, TCF7L2, TERT, TERT-669, TFF3, TINF2, TOP1, UGT8, and UGT2B17.

Figure 124:
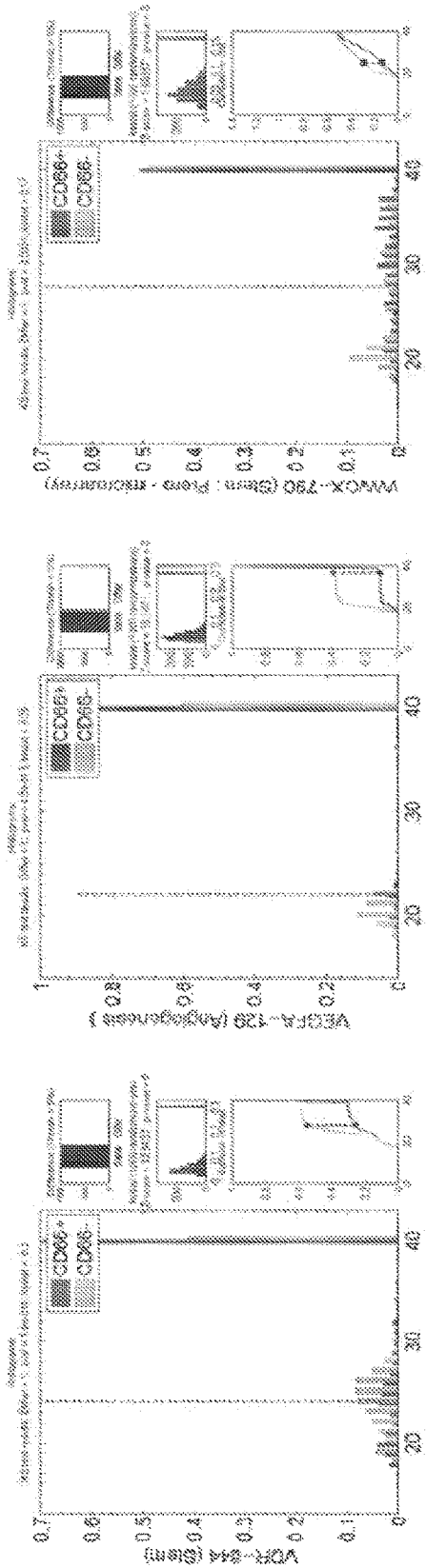

FIG. 124 histograms depicting gene expression levels in CD66+ or CD66– cells of VDR, VEGFA, and WWOX.

Figure 125:
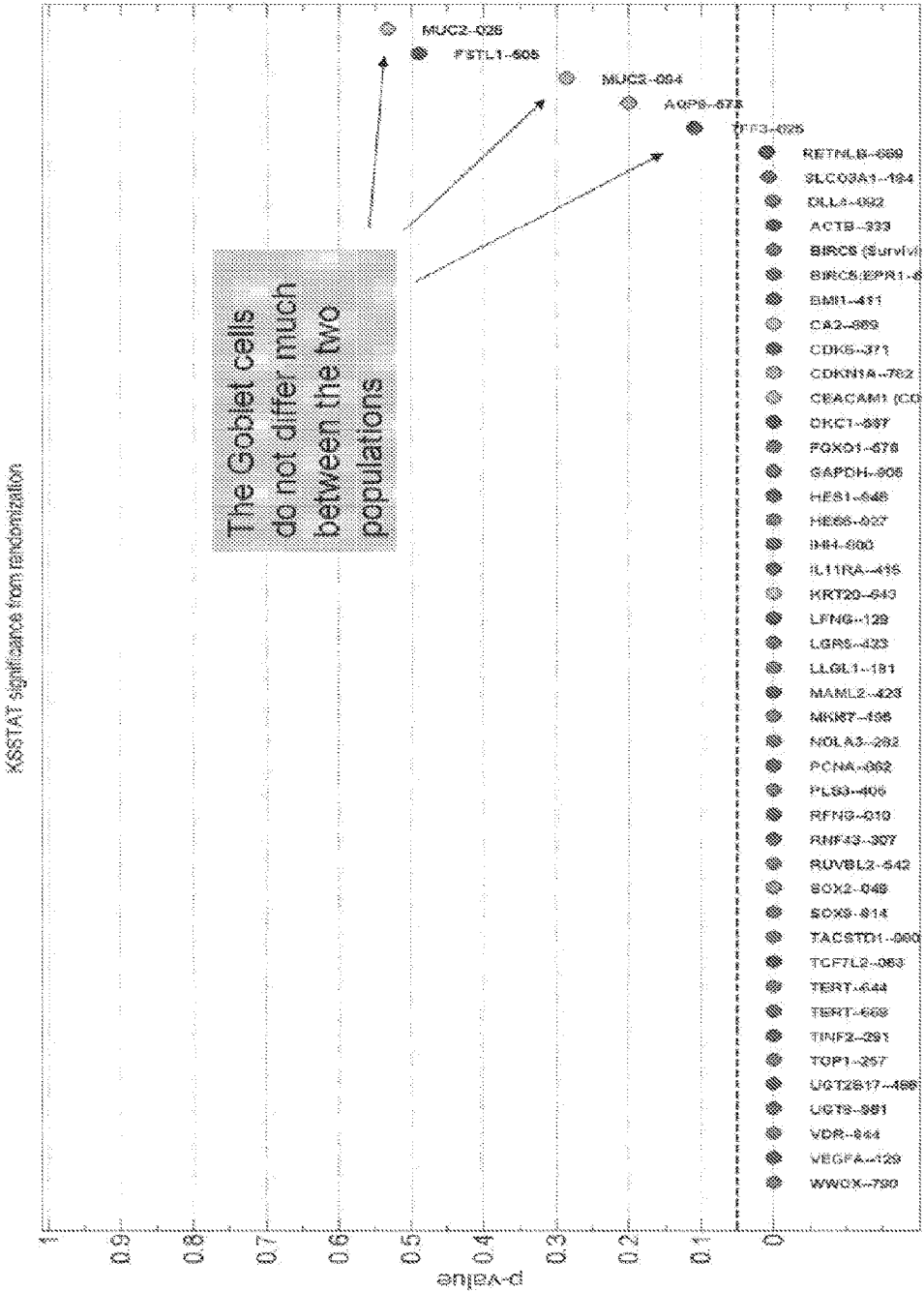

FIG. 125 Kolmogorov-Smirnov statistical significance test for genes expressed in NTCC and CoCSC cells, plotted against p-value.

Figure 126:
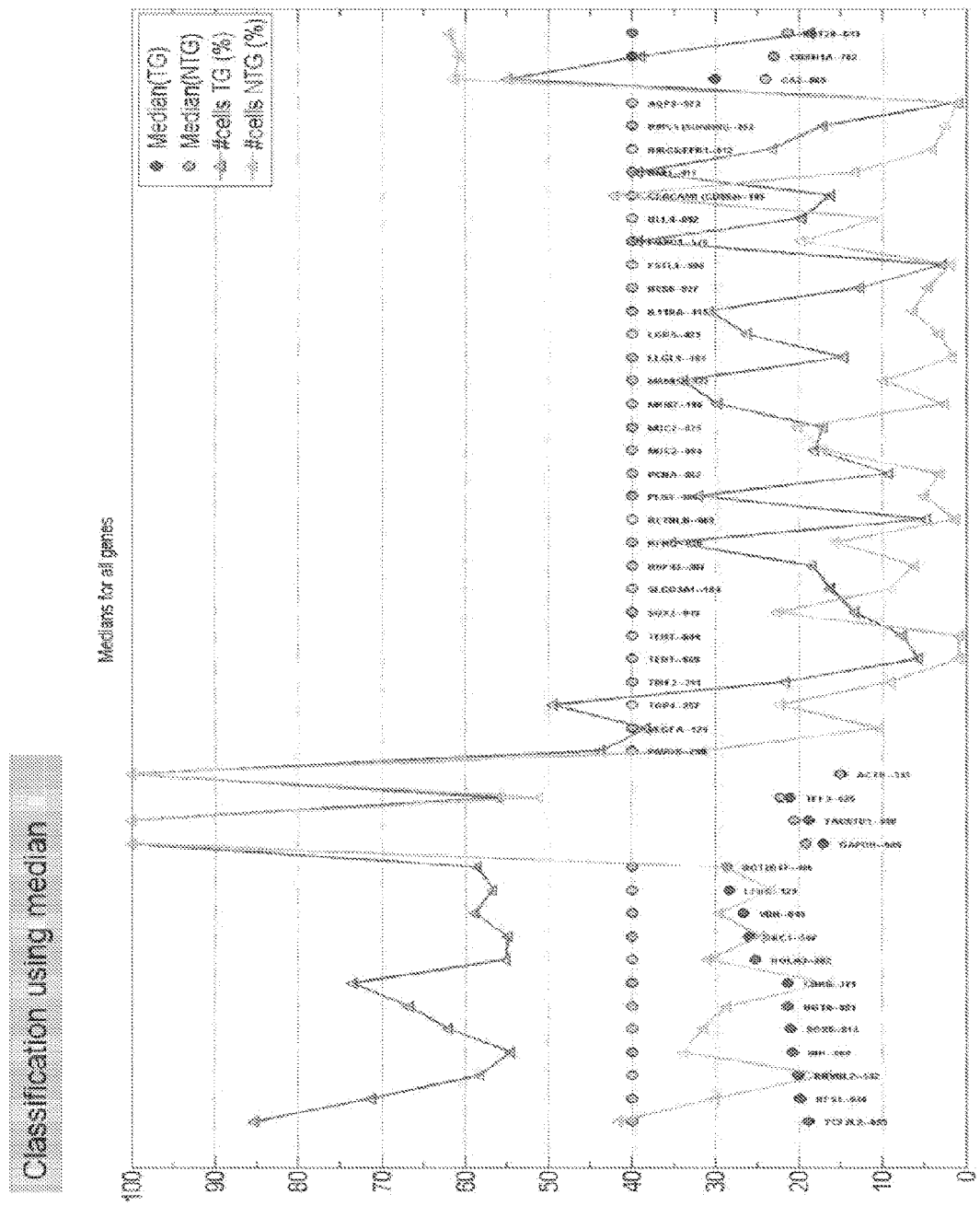

FIG. 126 medians for all genes in a graph format.

Figure 127:
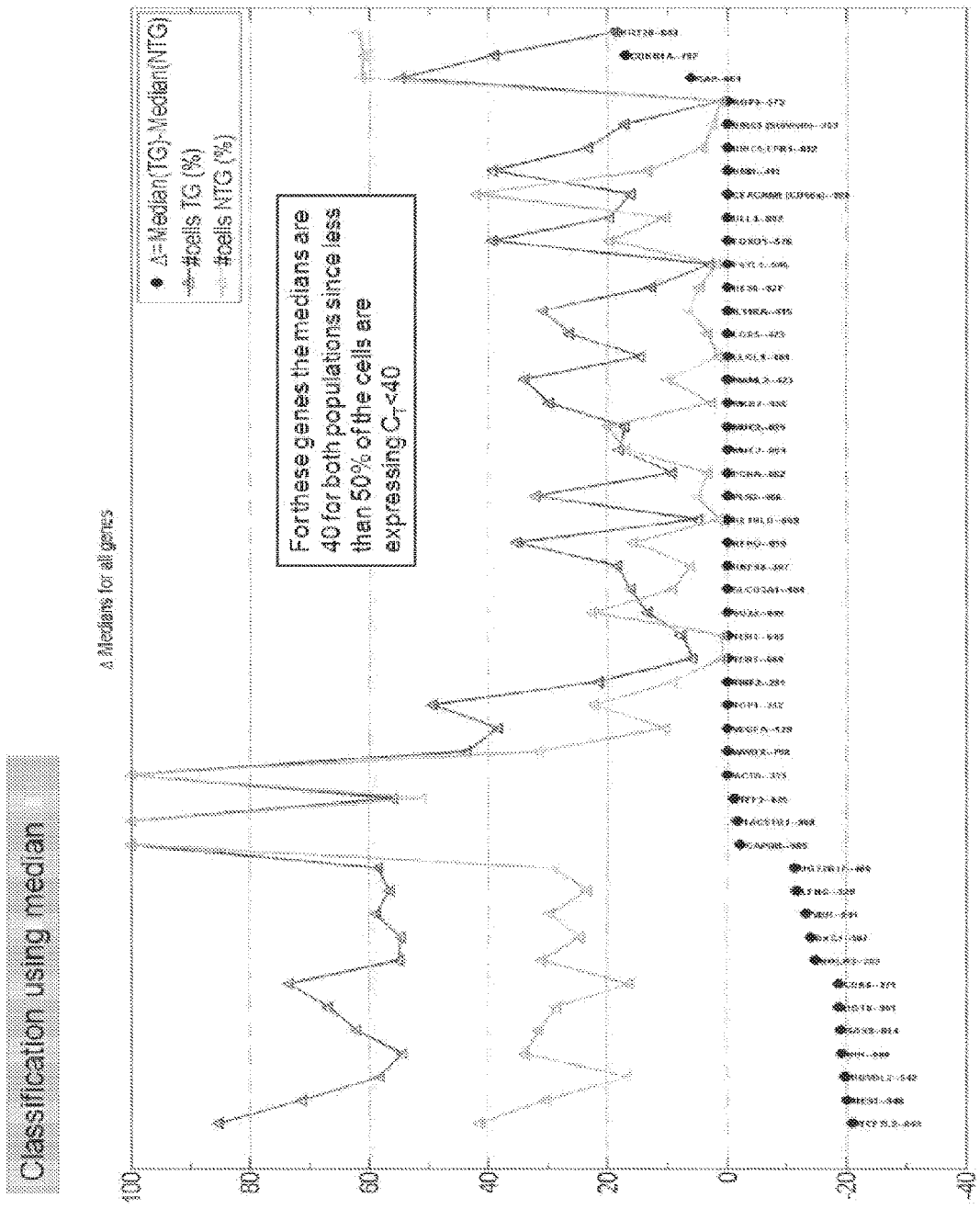

FIG. 127 delta medians for all genes in a graph format.

Figure 128:
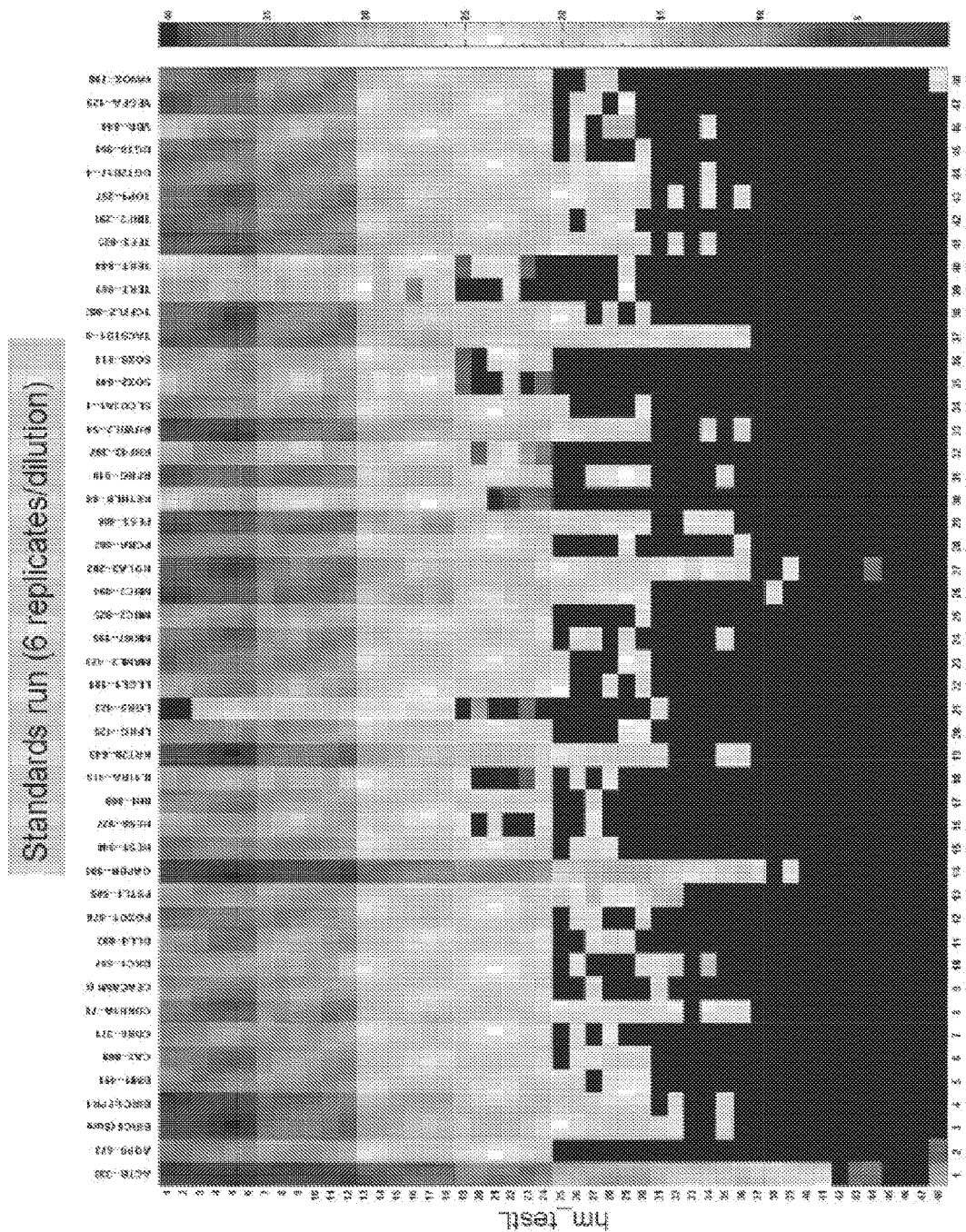

FIG. 128 a heat map for 6 replicates.

Figure 129:
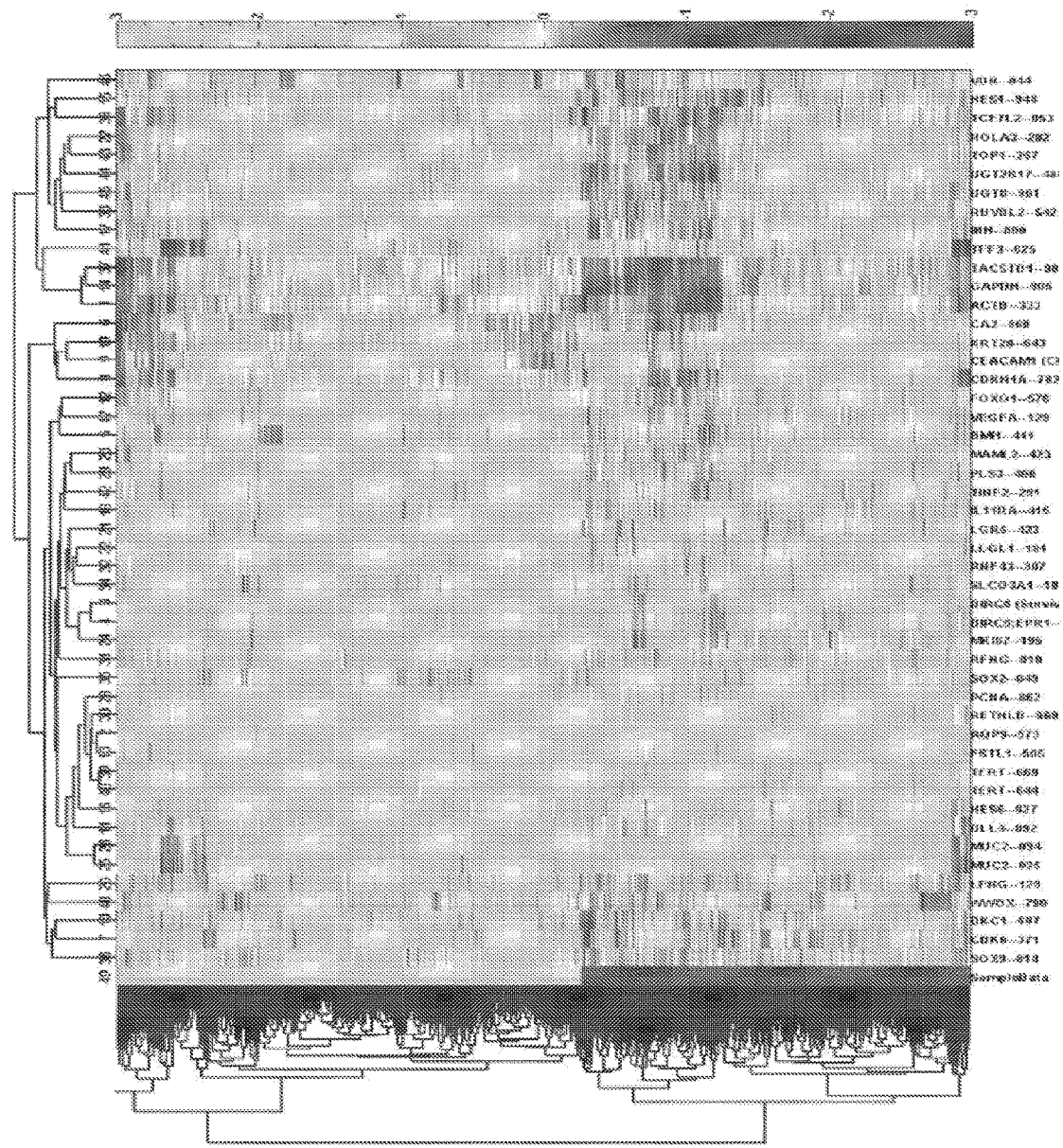

FIG. 129 results of hierarchical clustering showing MUC2, MKI67, TERT, LGR5, TFF3 and CA2 were differentially expressed in stem enriched cells or in mature enriched cells.

Figure 130:
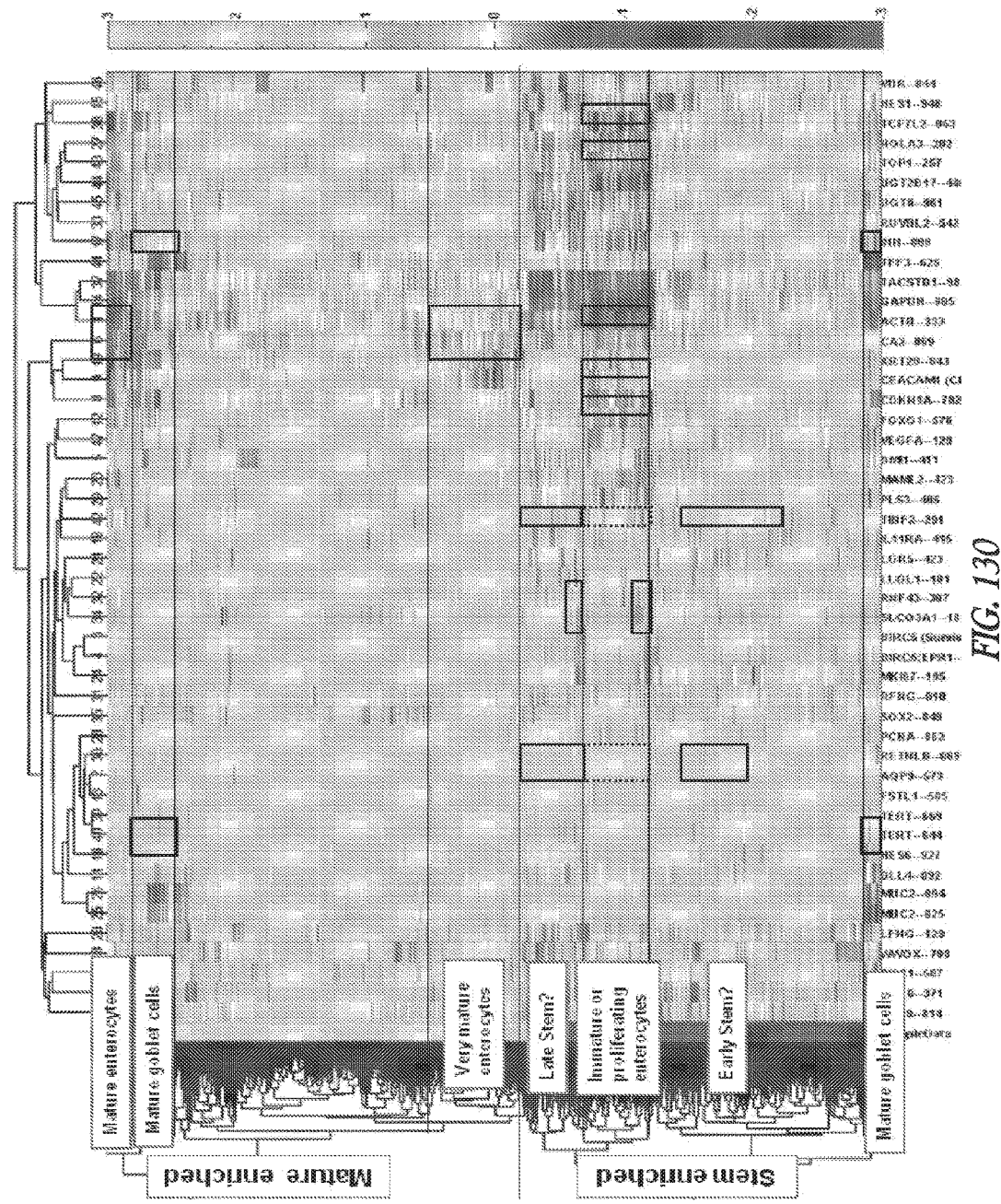

FIG. 130 different rendering of FIG. 129.

Figure 131:
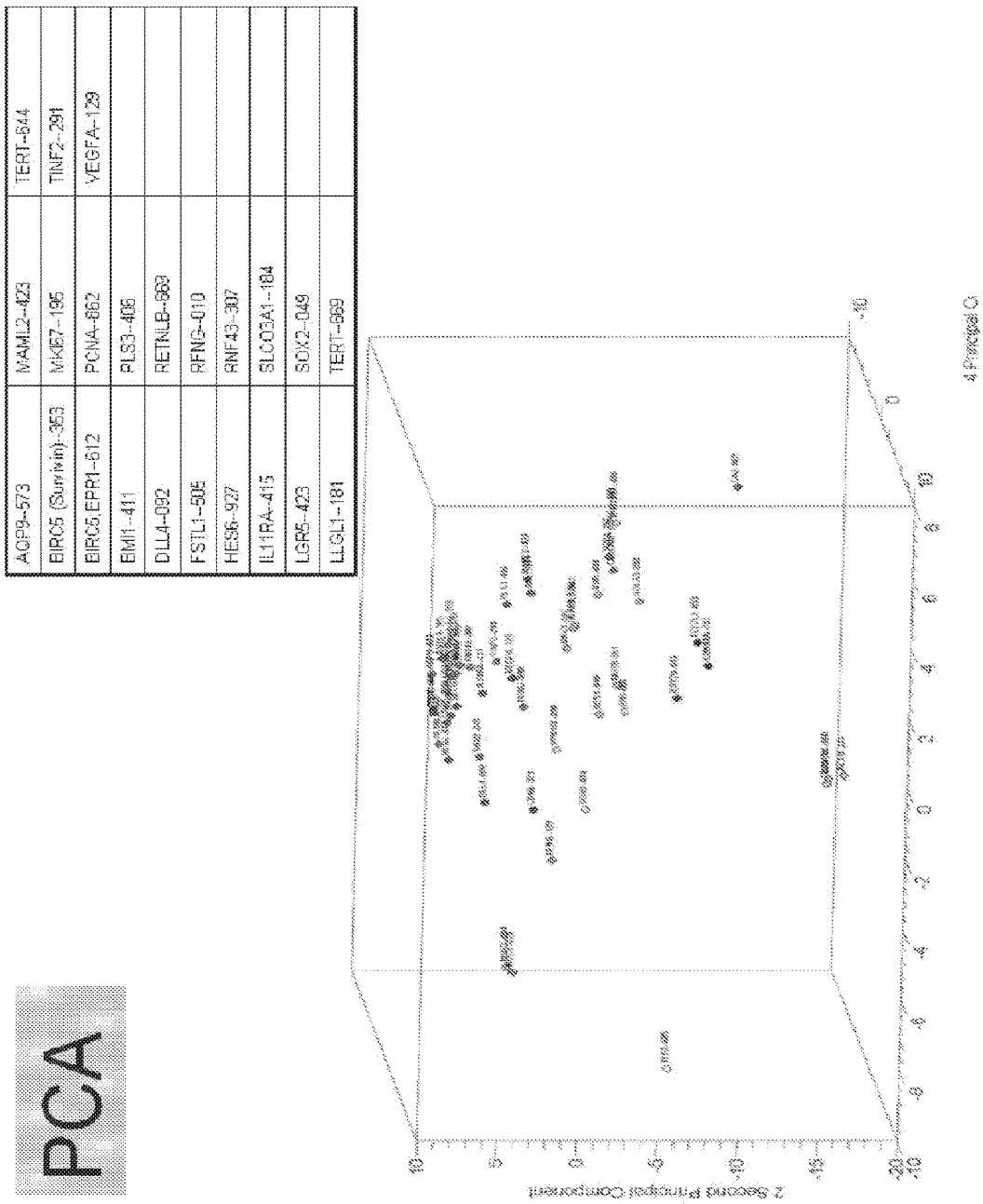

FIG. 131 genes correlated with TERT that were identified in a principal component analysis.

Figure 132:
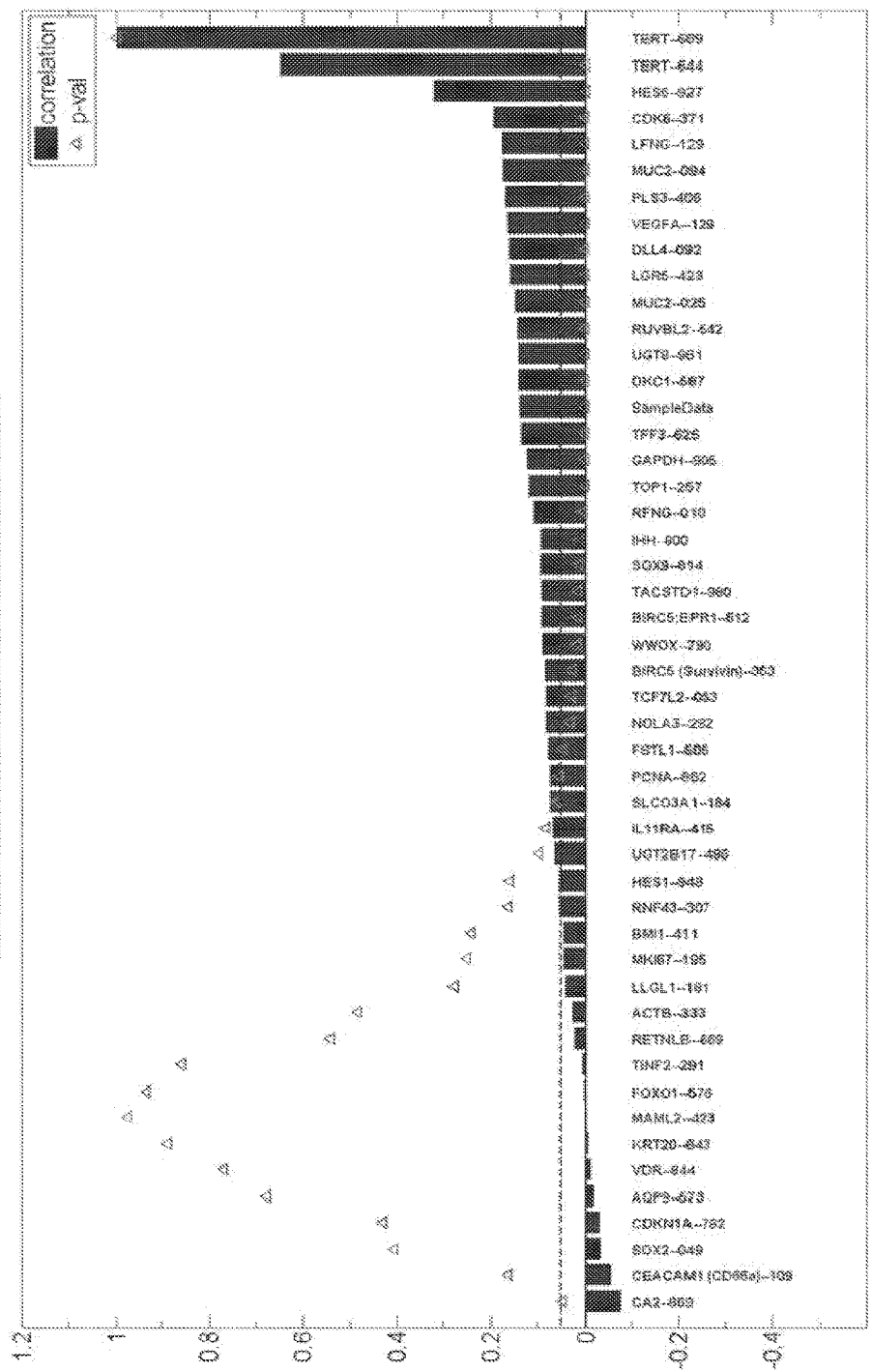

FIG. 132 gene expressions correlated to TERT expression.

Figure 133:
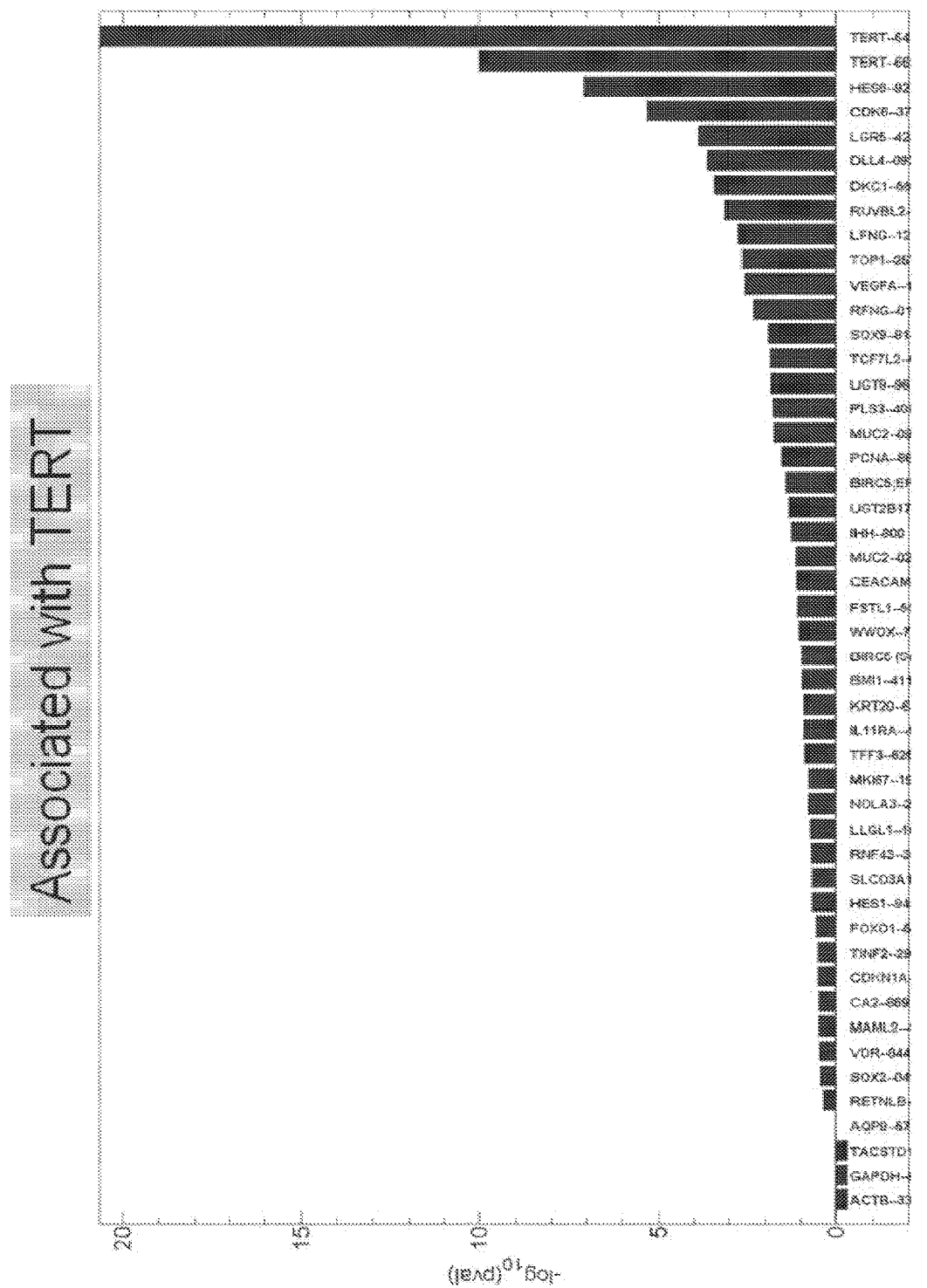

FIG. 133 genes associated with TERT expression.

Figure 134:
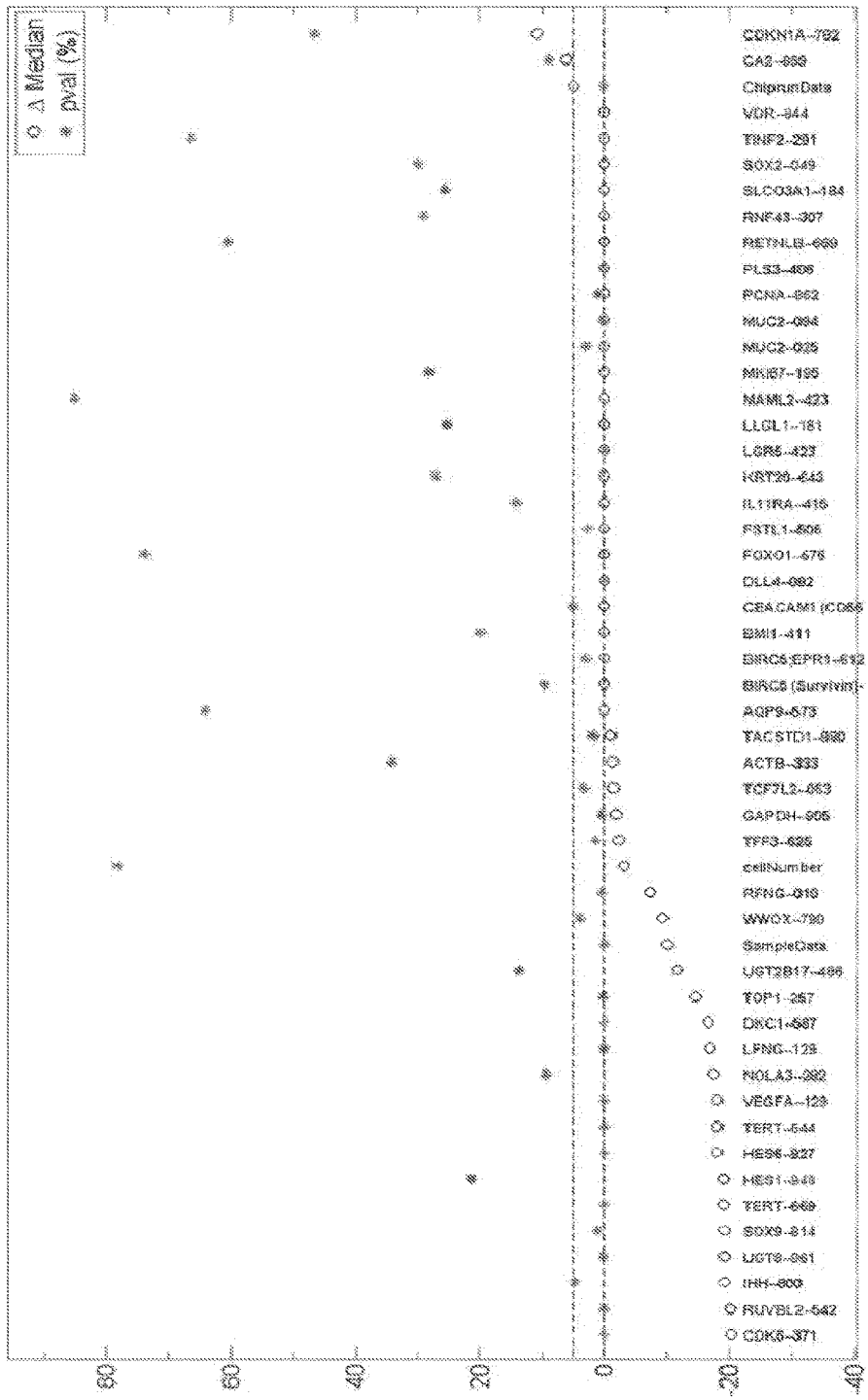

FIG. 134 gene expressions associated with TERT expression using median value.

Figure 135:
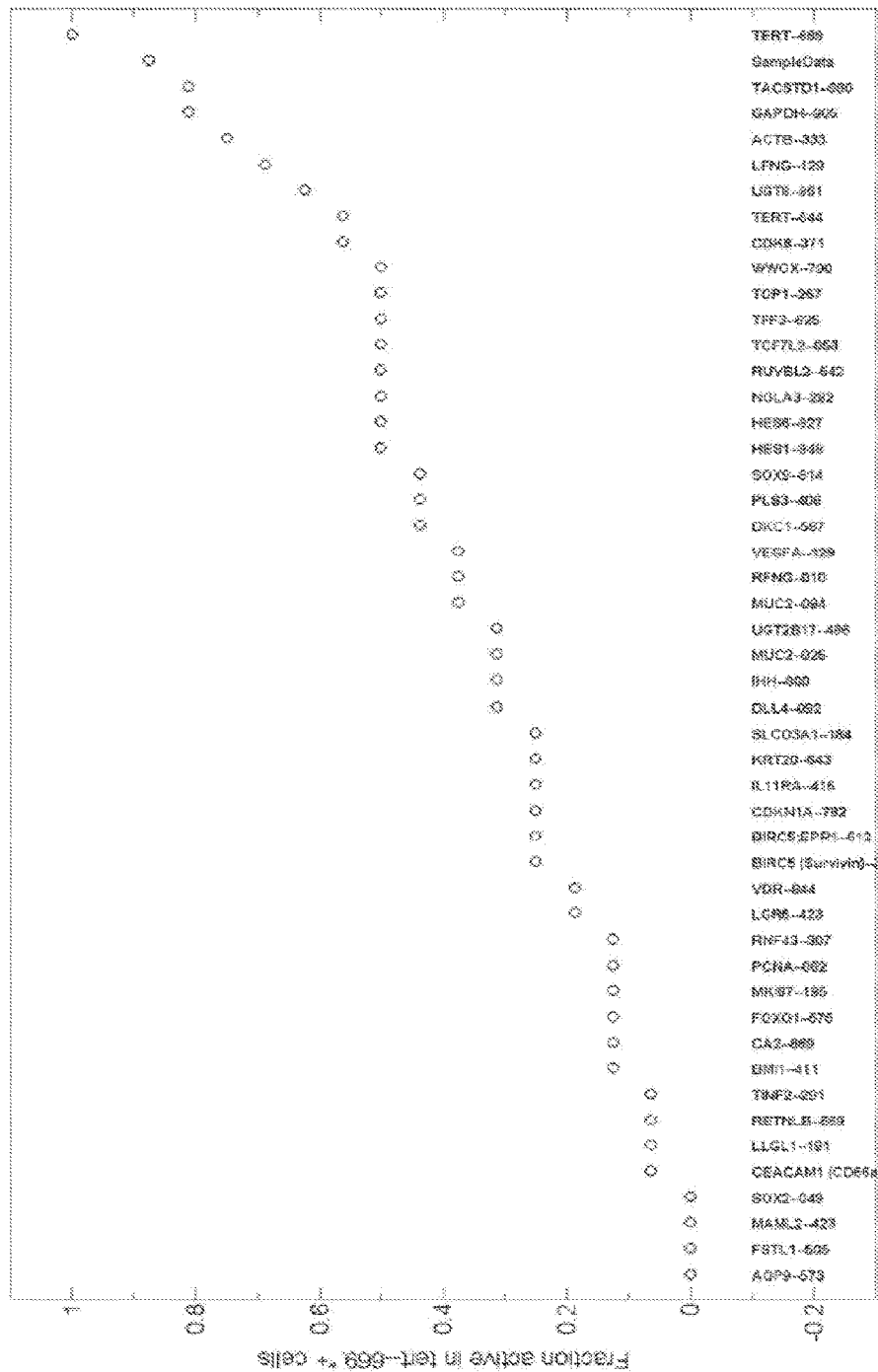

FIG. 135 genes co-activated with TERT.

Figure 136:
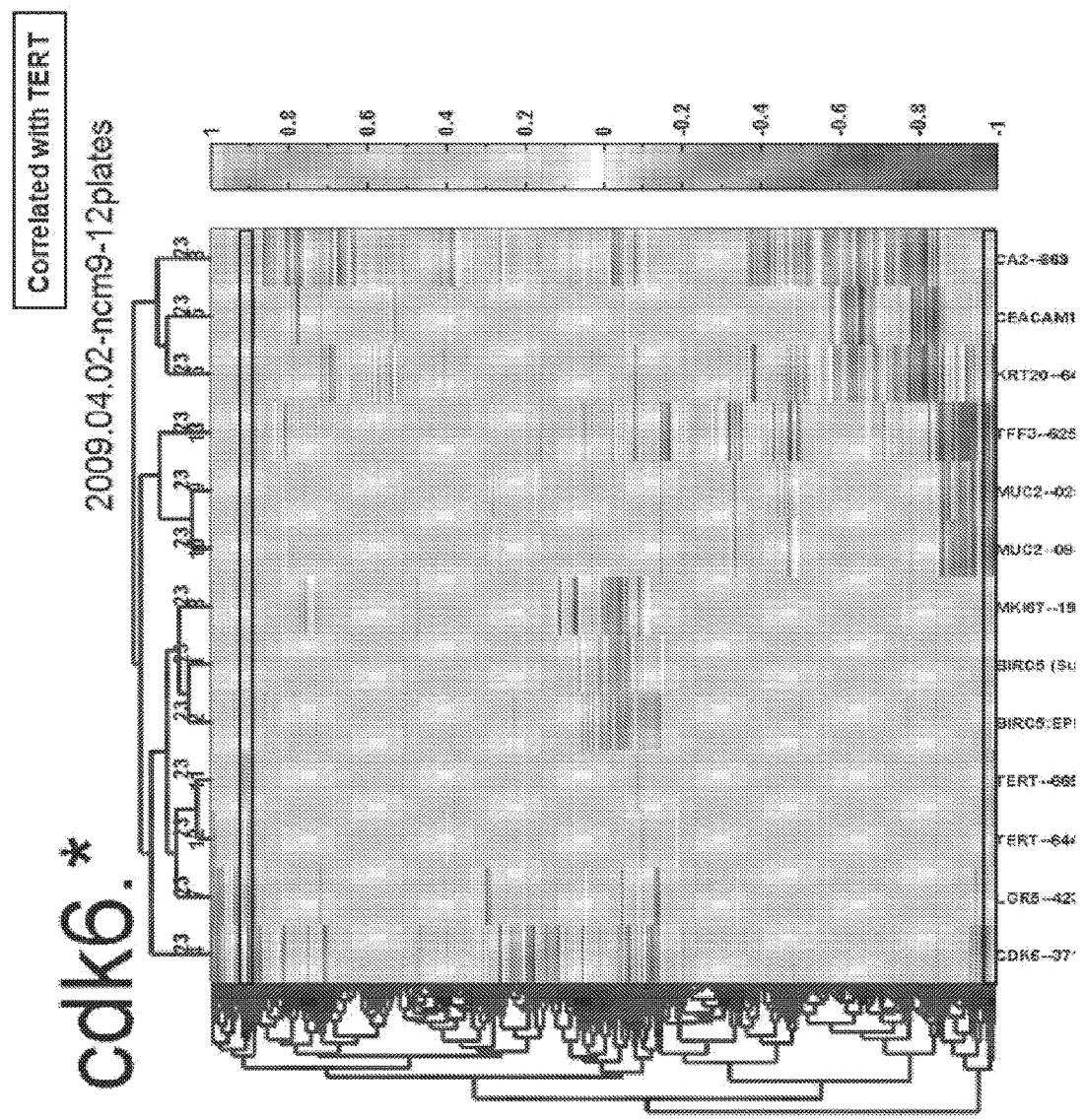

FIG. 136 CDK6 expression is correlated with TERT expression.

Figure 137:
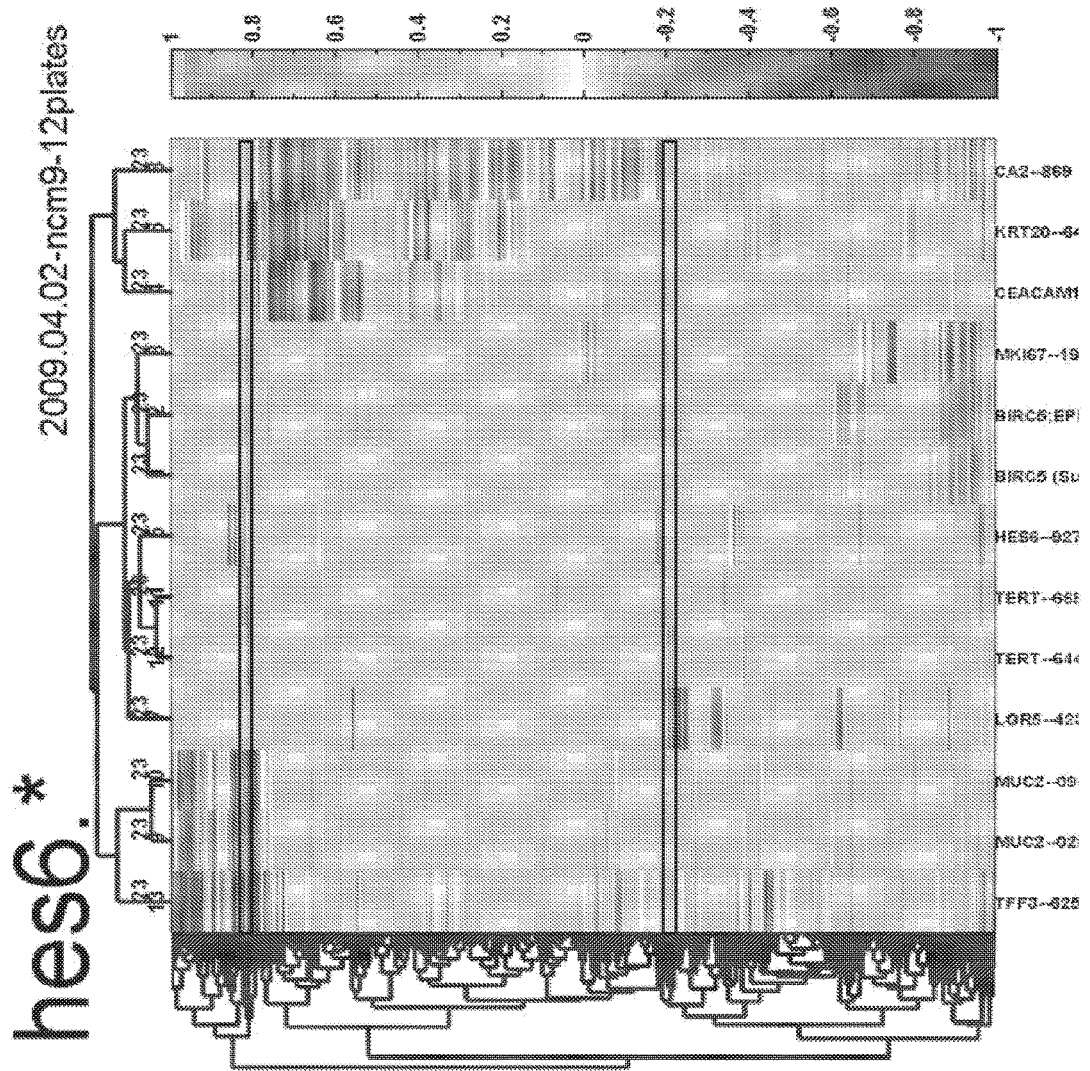

FIG. 137 HES6 expression in relation to TERT expression.

Figure 138:
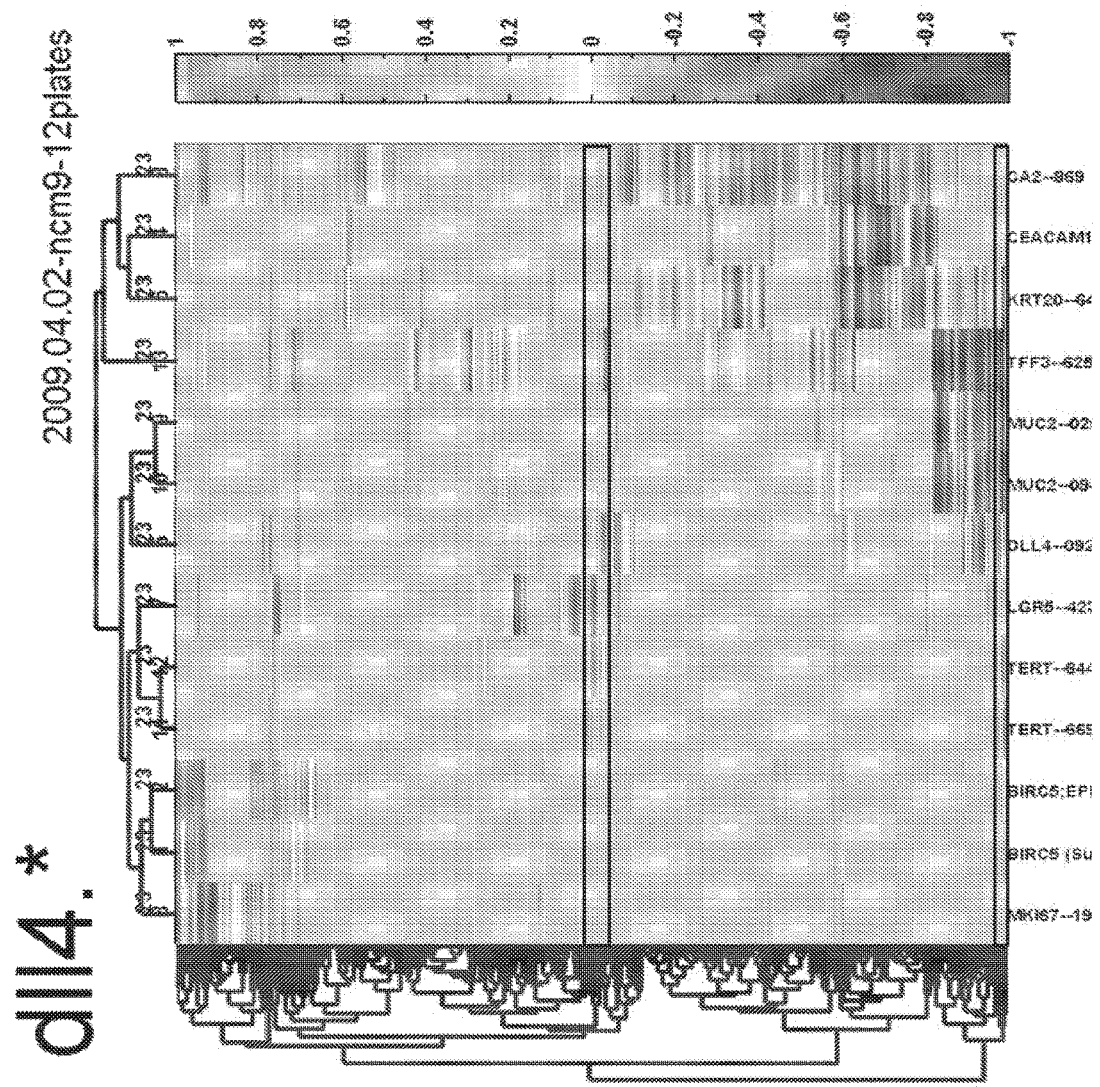

FIG. 138 DLL4 expression in relation to TERT expression.

Figure 139:
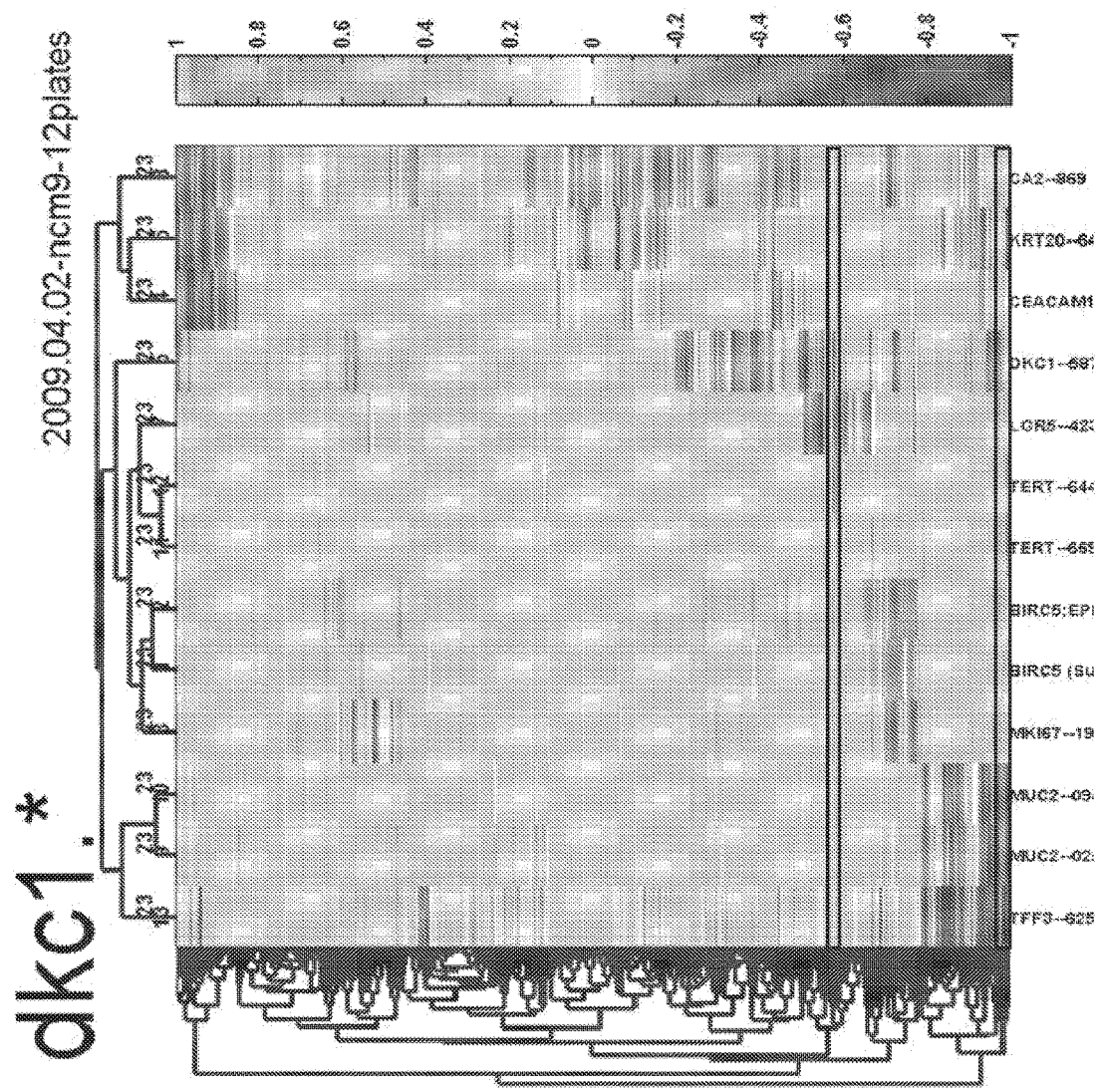

FIG. 139 DKC1 expression in relation to TERT expression

Figure 140:
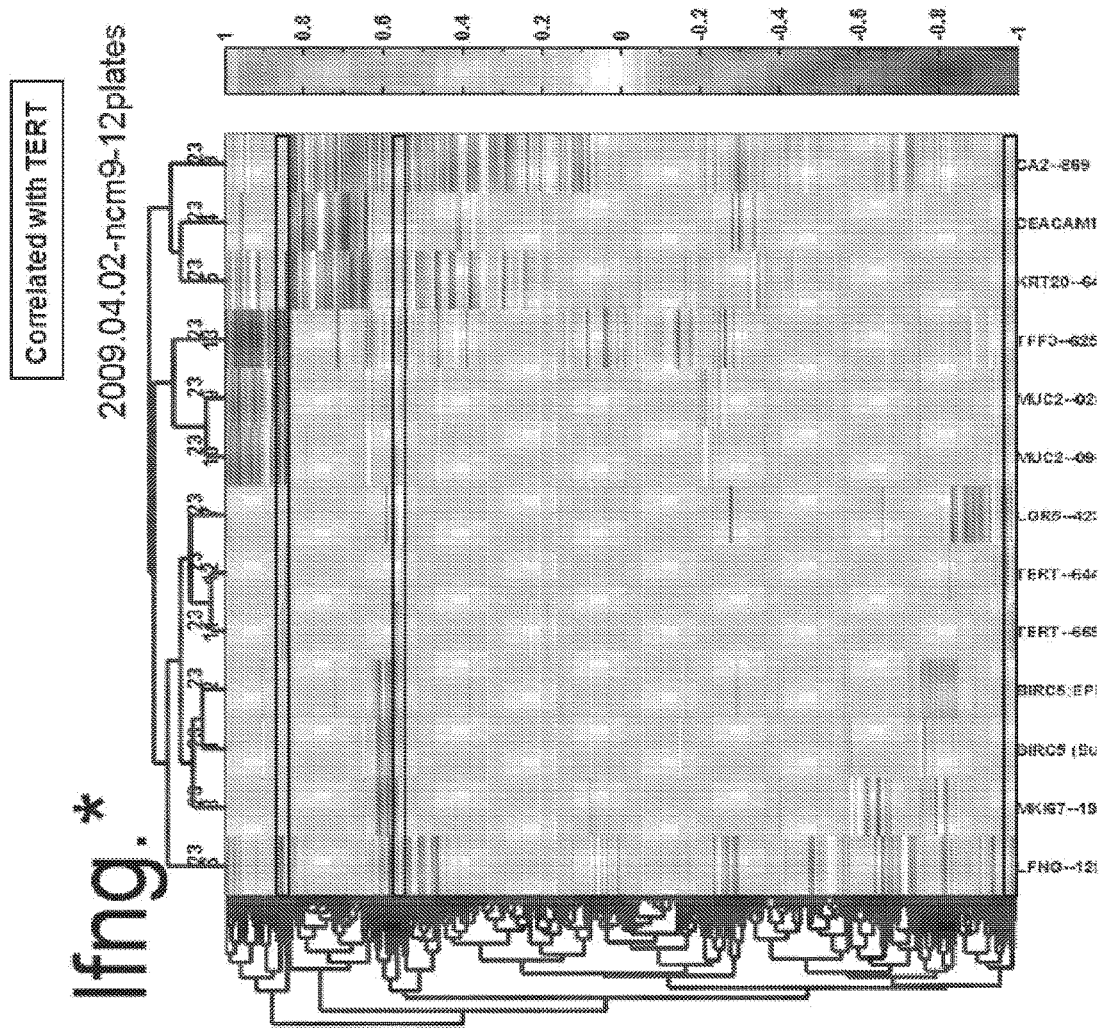

FIG. 140 IFNG expression is correlated with TERT expression.

Figure 141:
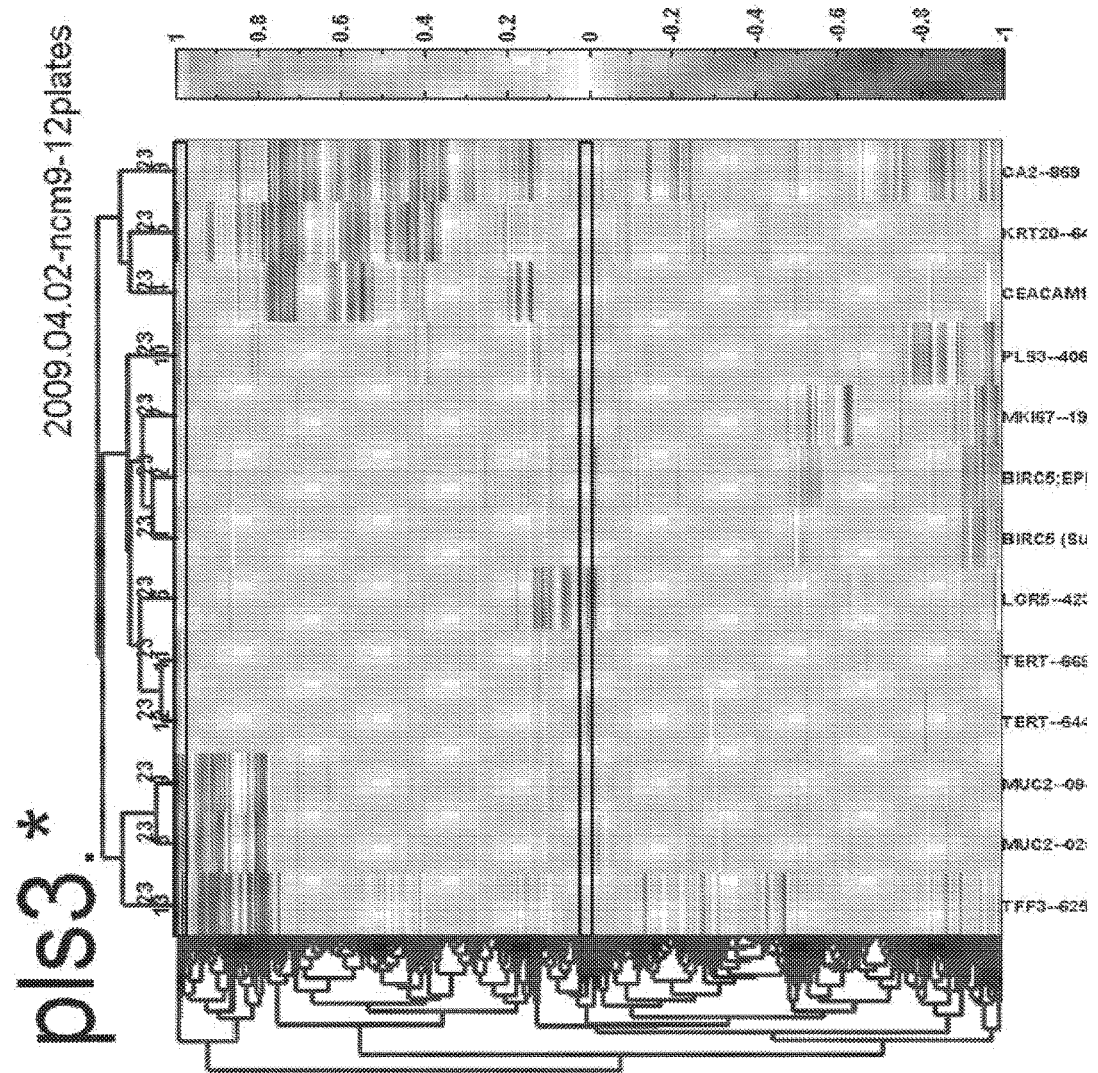

FIG. 141 PLS3 expression in relation to TERT expression.

Figure 142:
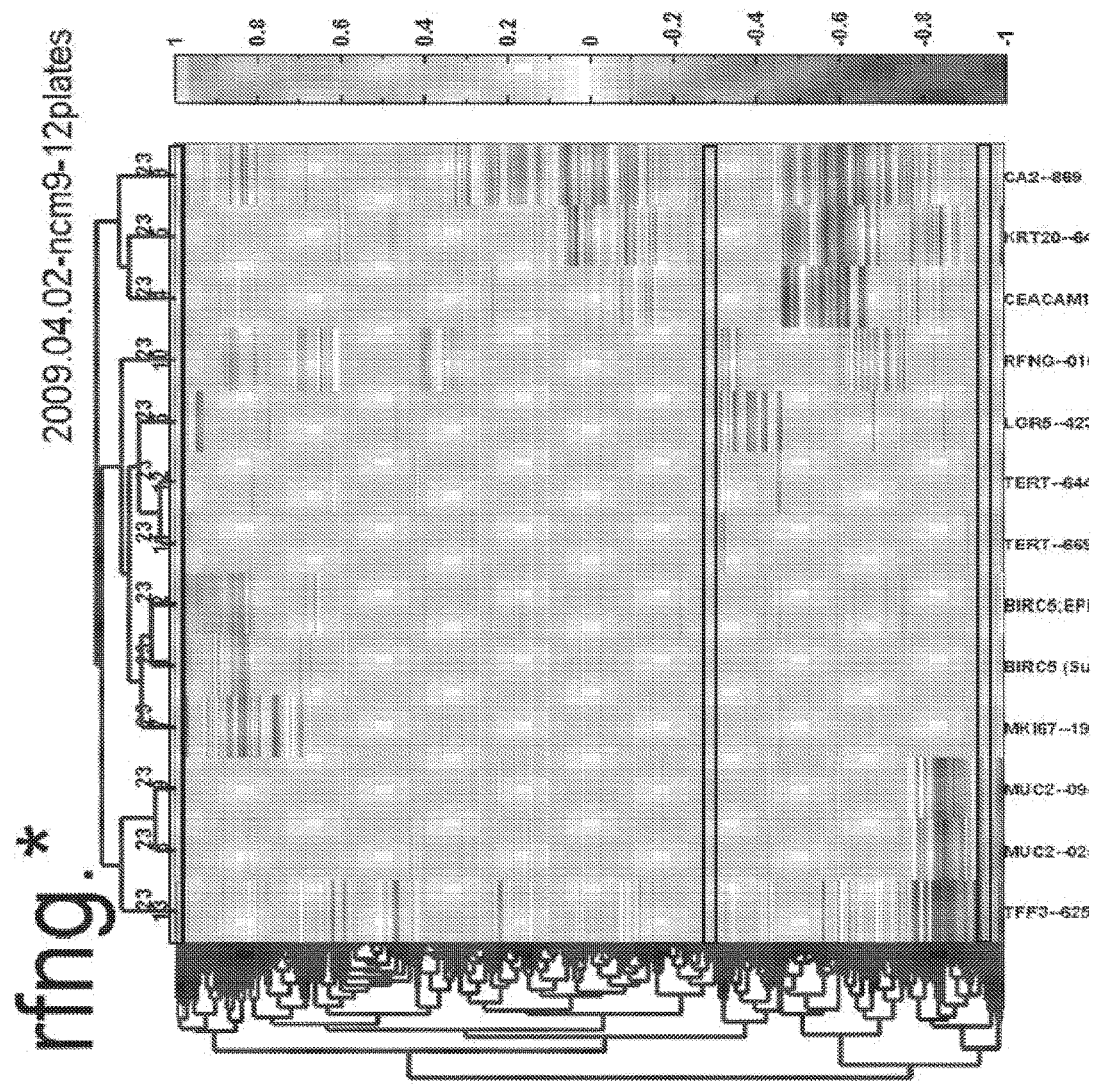

FIG. 142 RFNG expression in relation to TERT expression.

Figure 143:
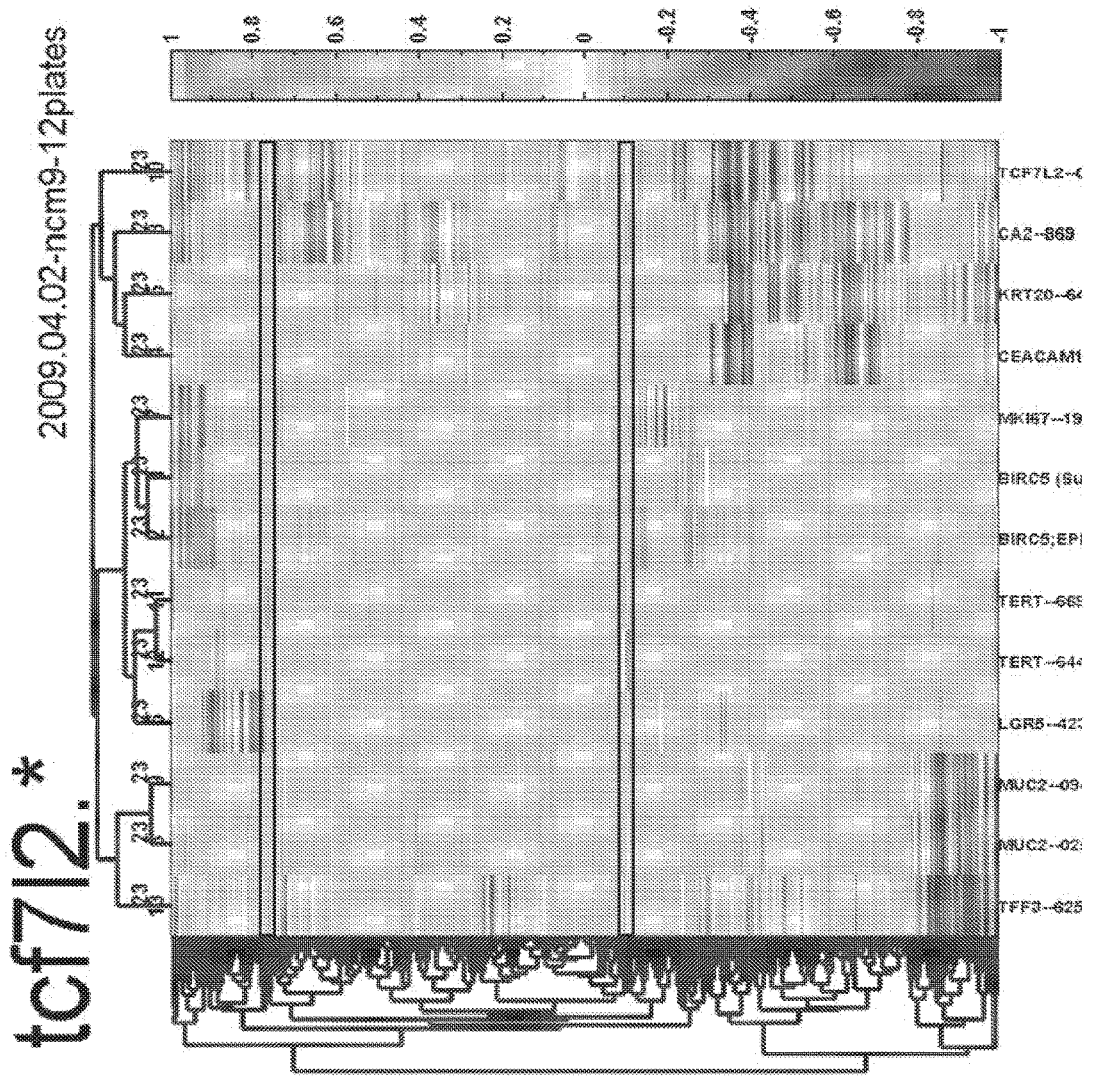

FIG. 143 TCF712 expression in relation to TERT expression.

Figure 144:
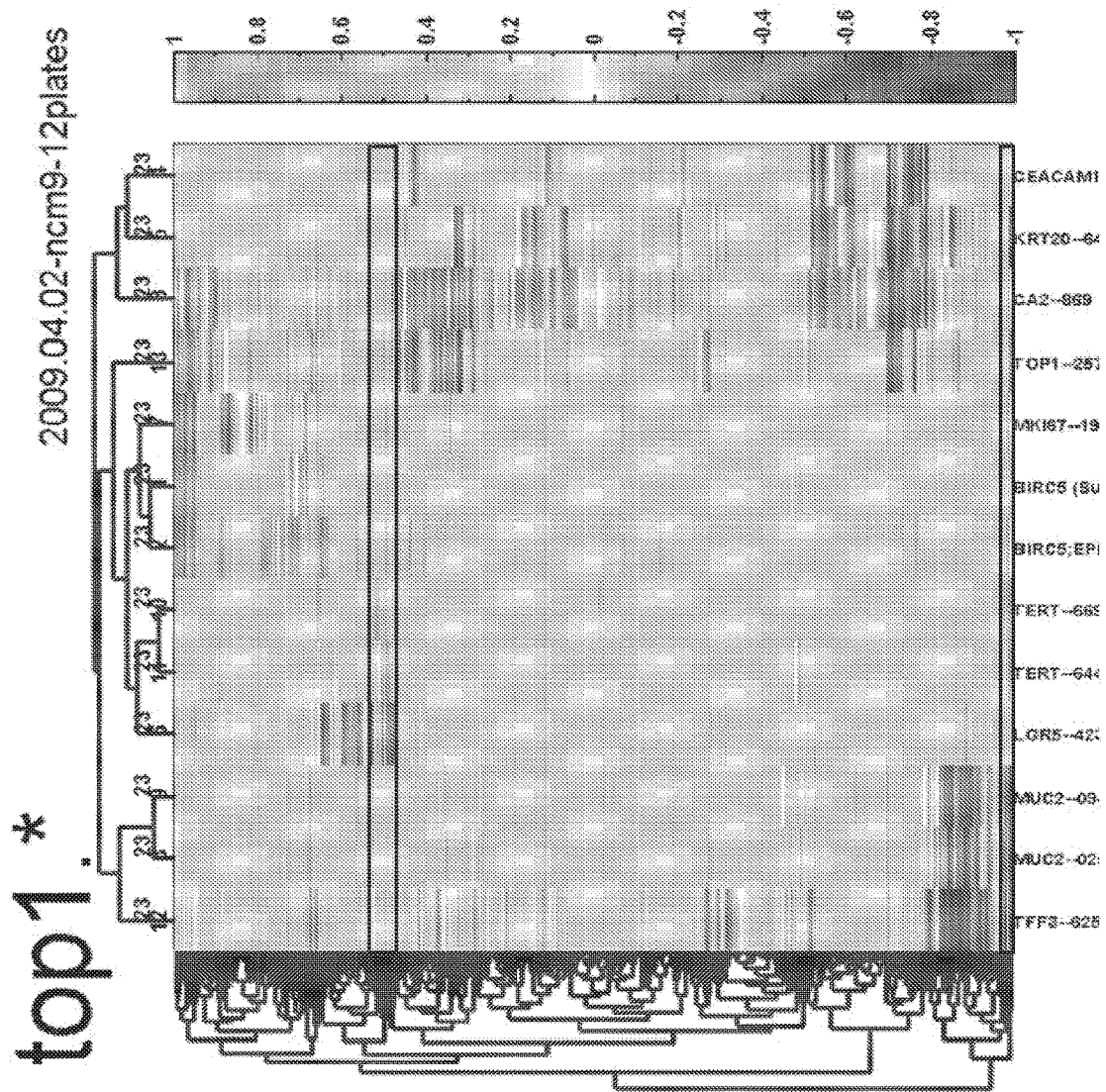

FIG. 144 TOP1 expression in relation to TERT expression.

Figure 145:
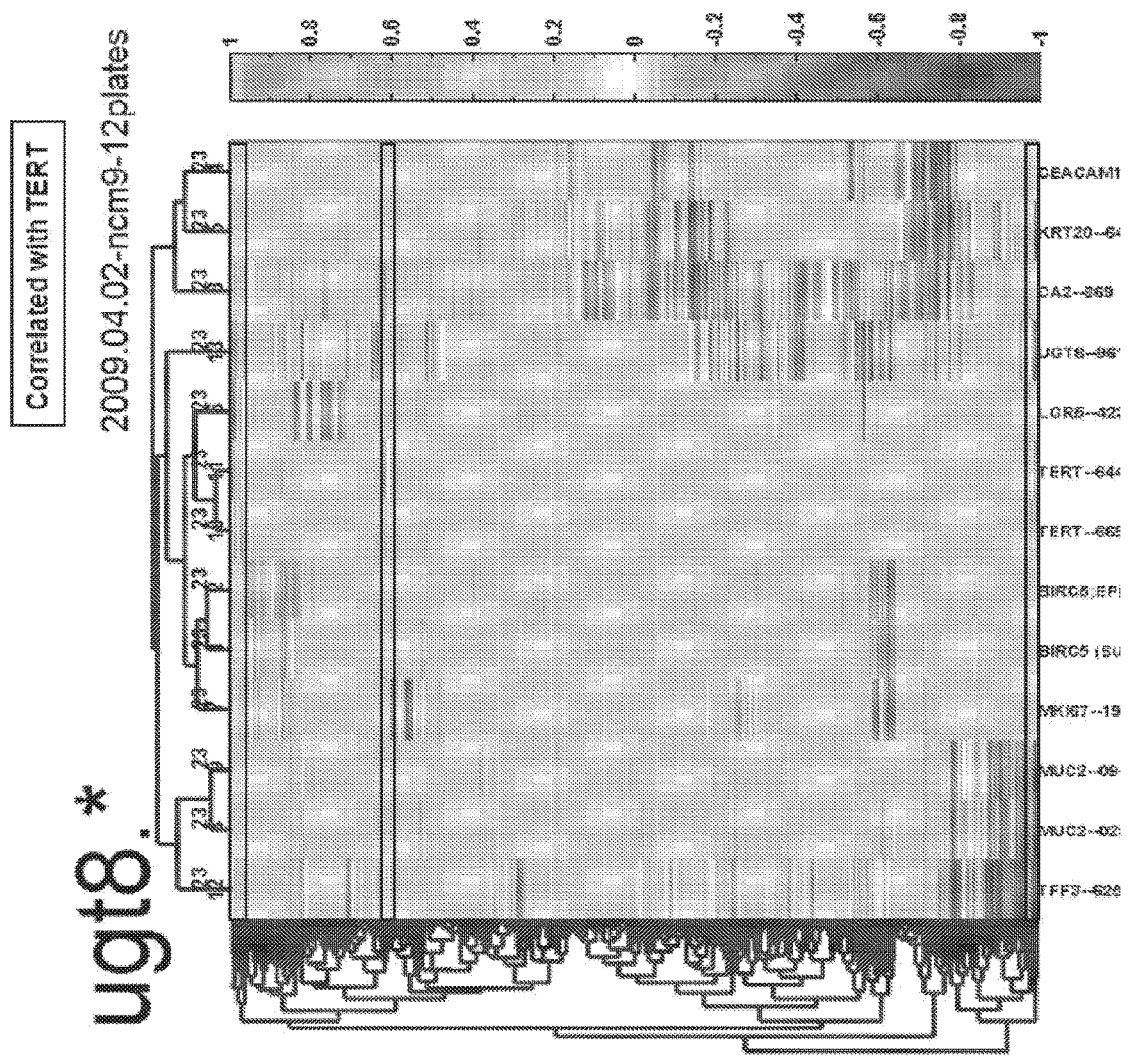

FIG. 145 UGT8 expression is correlated with TERT expression.

Figure 146:
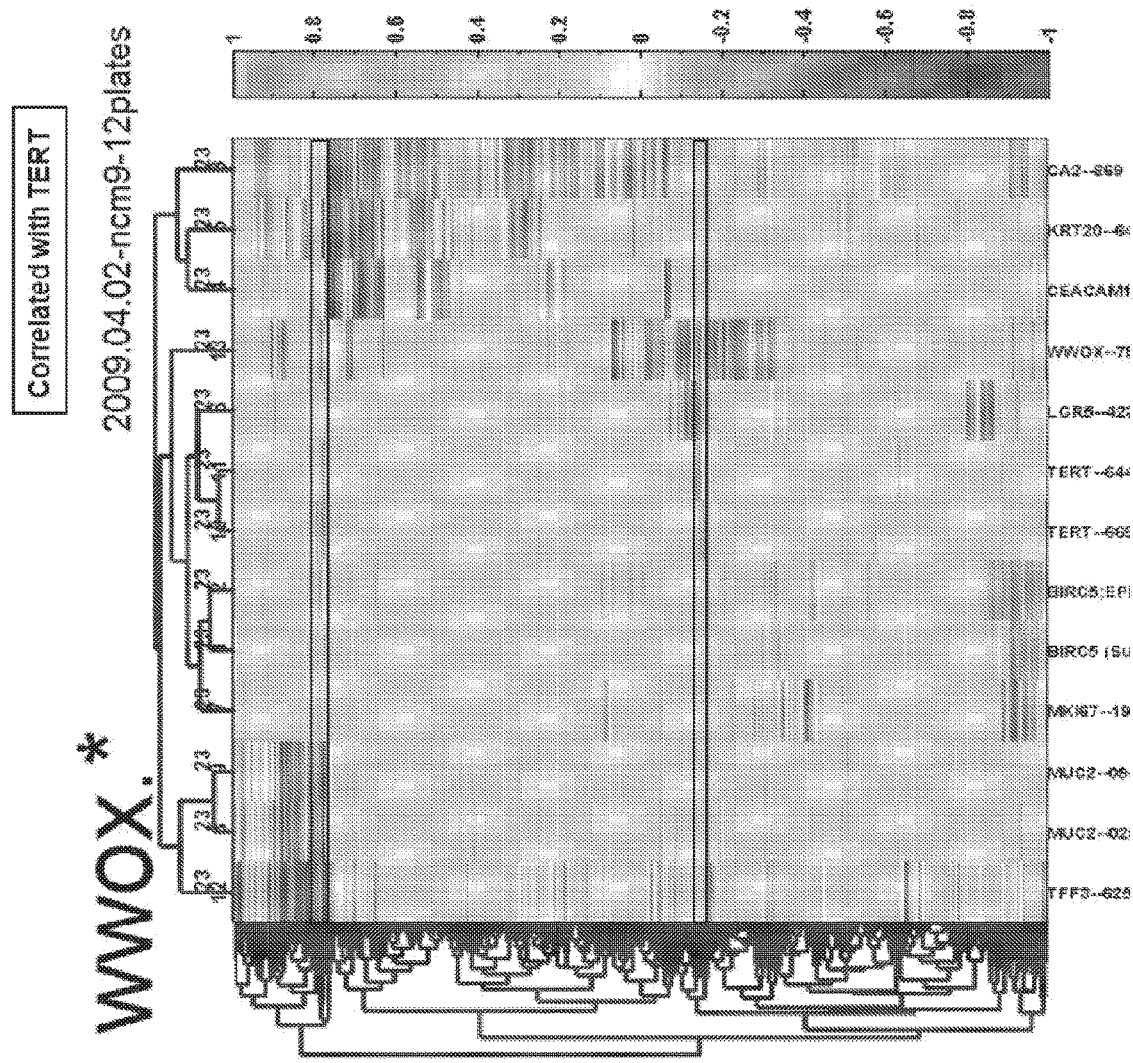

FIG. 146 WWOX expression is correlated with TERT expression.

Figure 147:
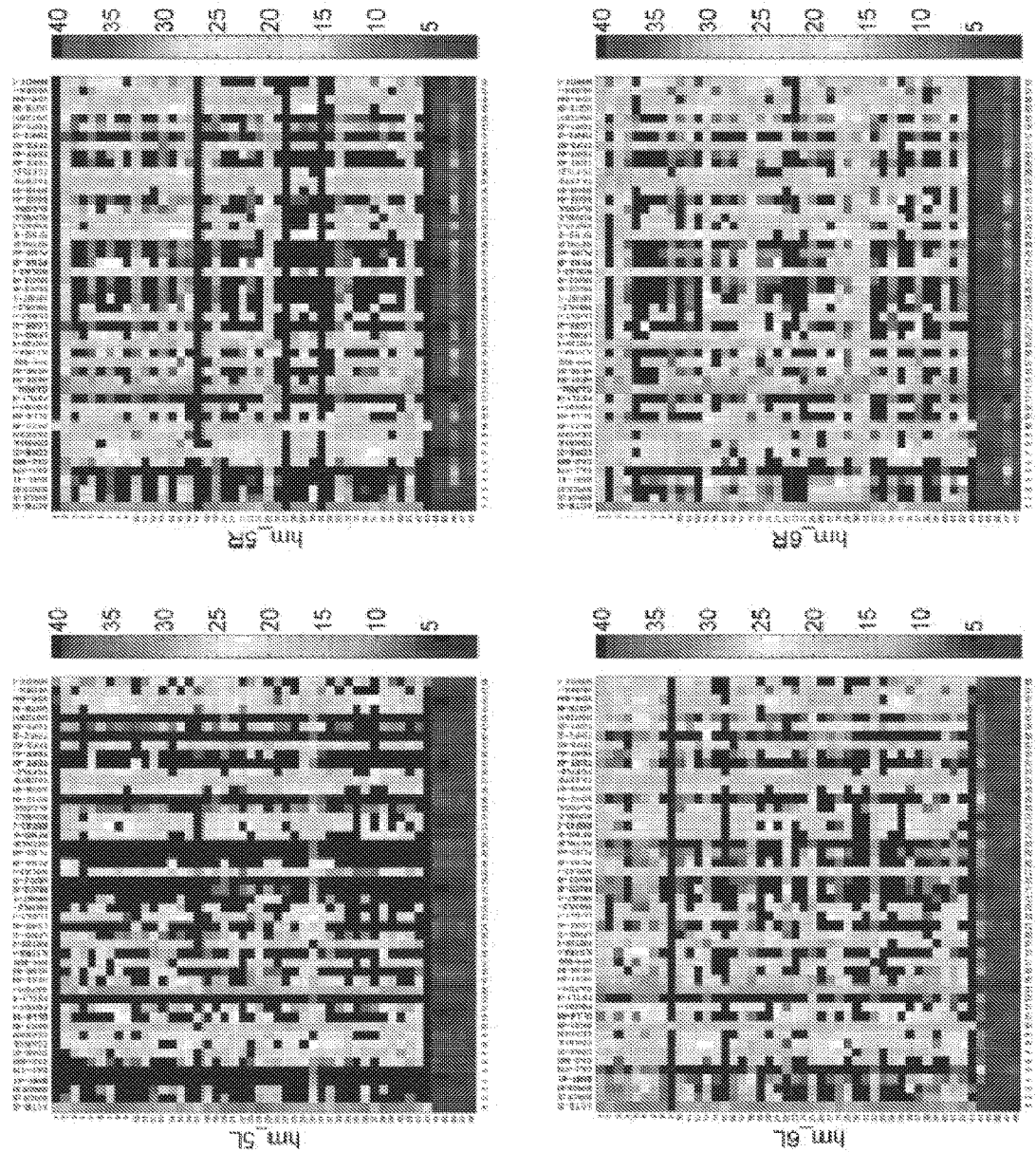

FIG. 147 heat maps from 4 different chip-runs. Cells were taken from xenograft of colon cells. The cells were FACS sorted with EpCAM and CD66a surface markers. Colon cancer stem cells (CoCSC) were defined as EpCAM$^{high}$/CD166+ cells.

Figure 148:
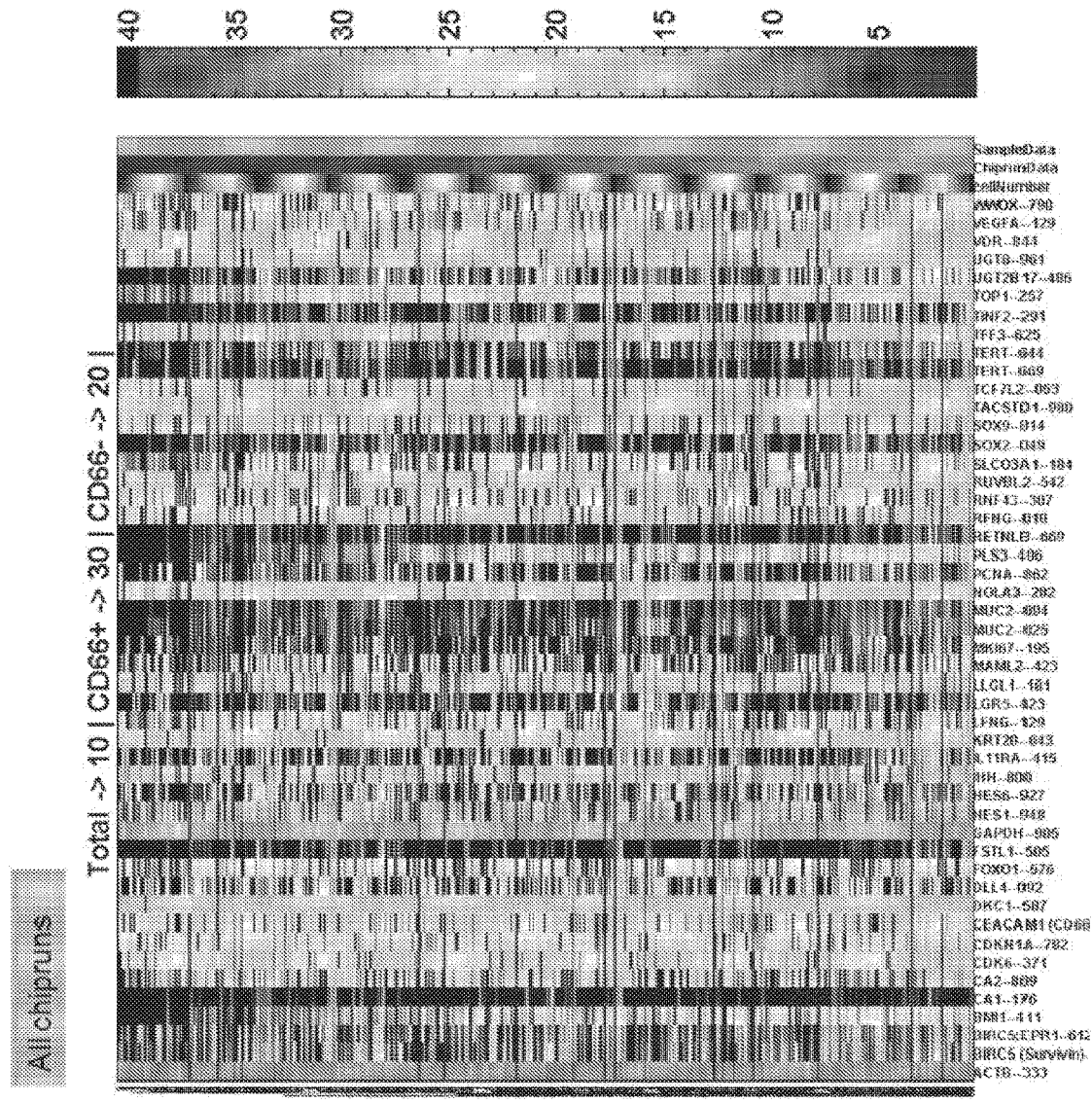

FIG. 148 a combined heat map comparing the four chip-runs.

Figure 149:
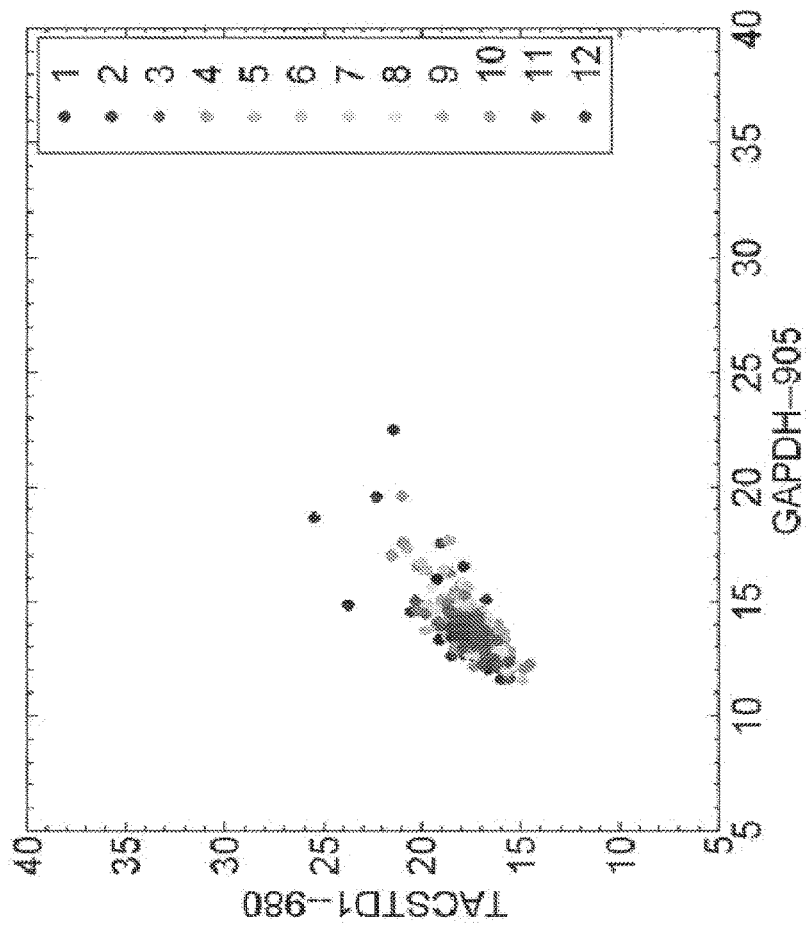

FIG. 149 selection of cells for single cell gene expression analysis. Out of 504 cells tested, 21 cells were discarded by examining GAPDH and TACSTD1 gene expression levels, and 483 cells were selected for further analysis.

FIG. 150 further removal of cells that for every gene, where $C_T$ values are higher than some gene-dependent threshold.

Figure 151:
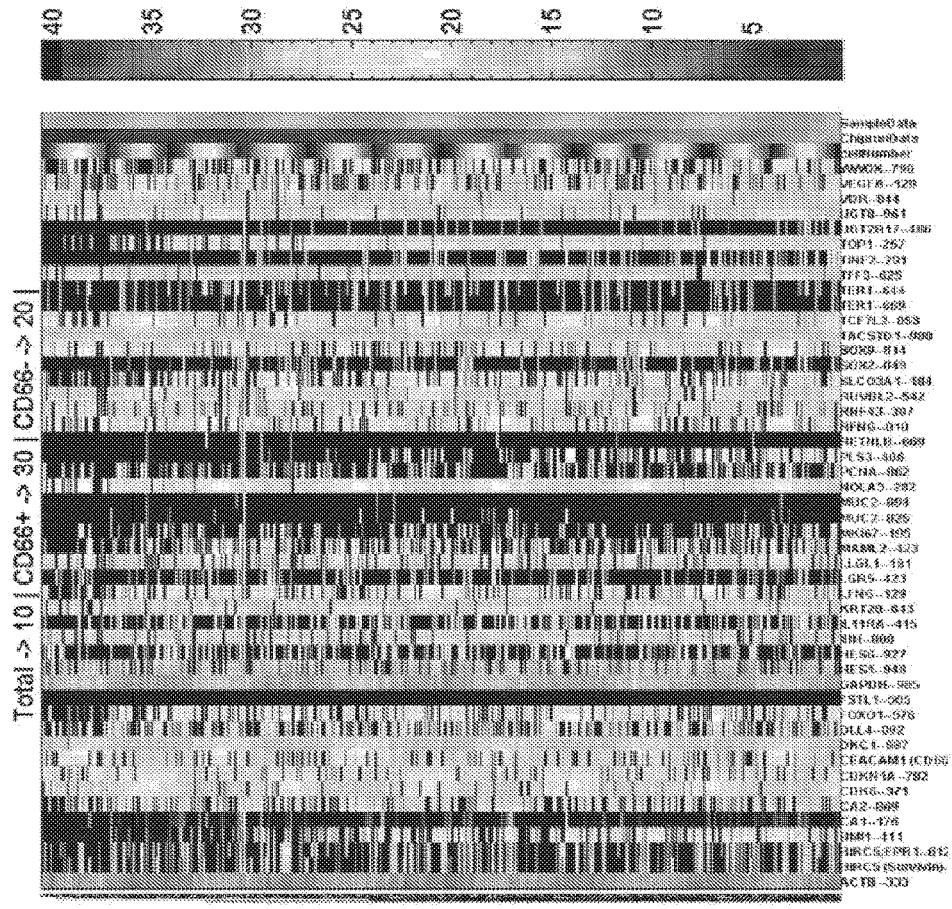

FIG. 151 a combined heat map after the clean up of unwanted cells.

Figure 152:
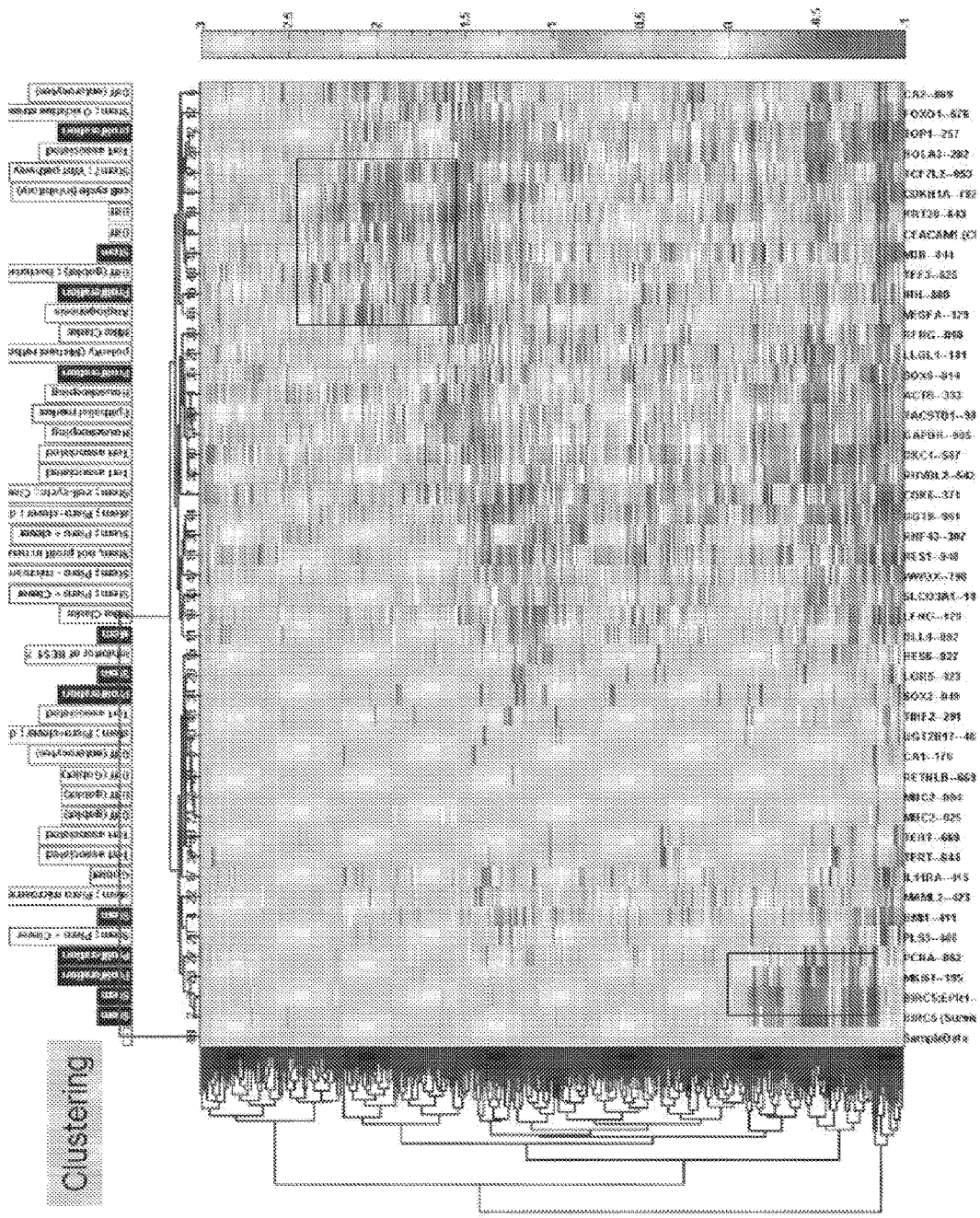

FIG. 152 hierarchical clustering. Genes expressed in certain cell types are marked by a black square.

Figure 153:
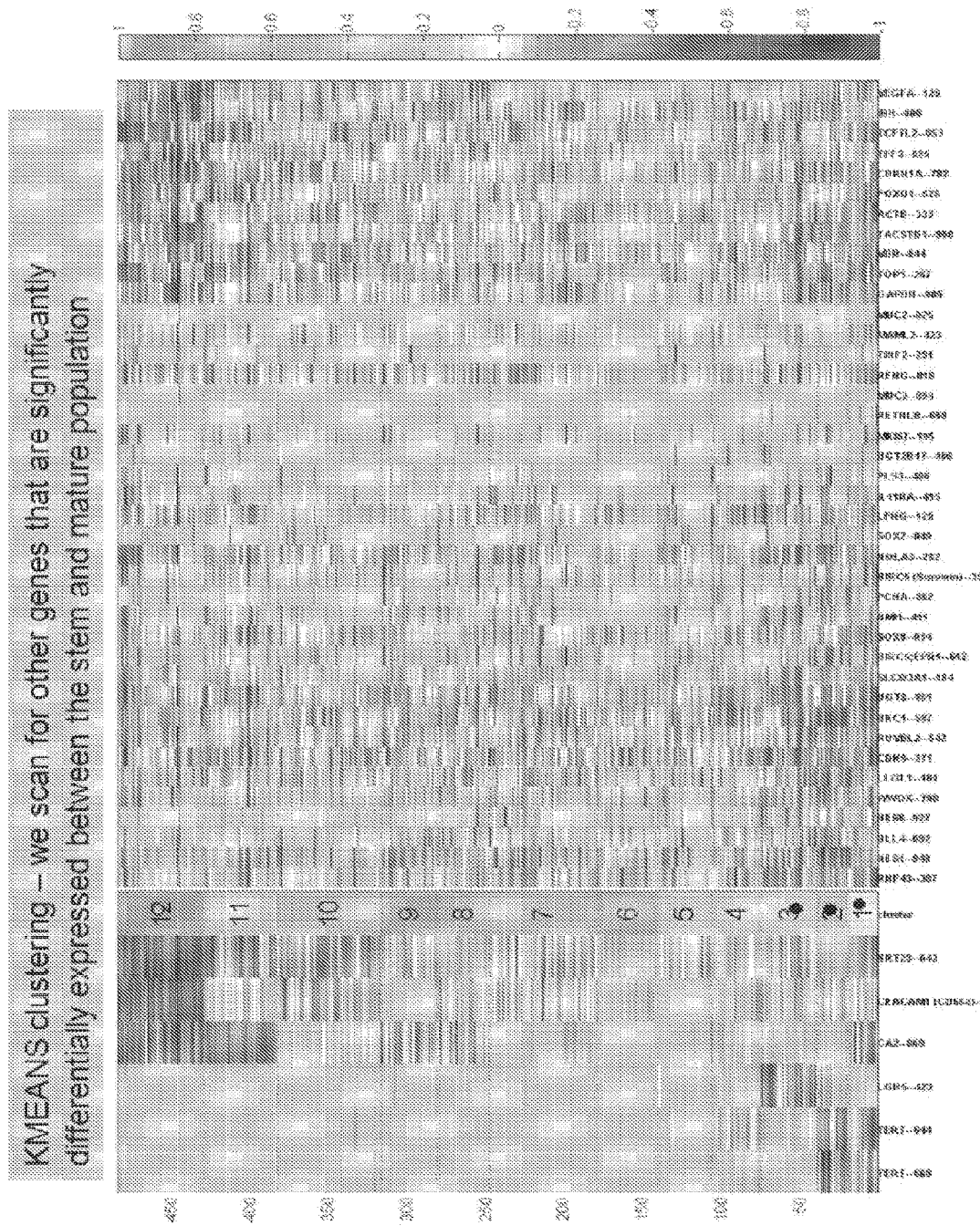
Figure 154:
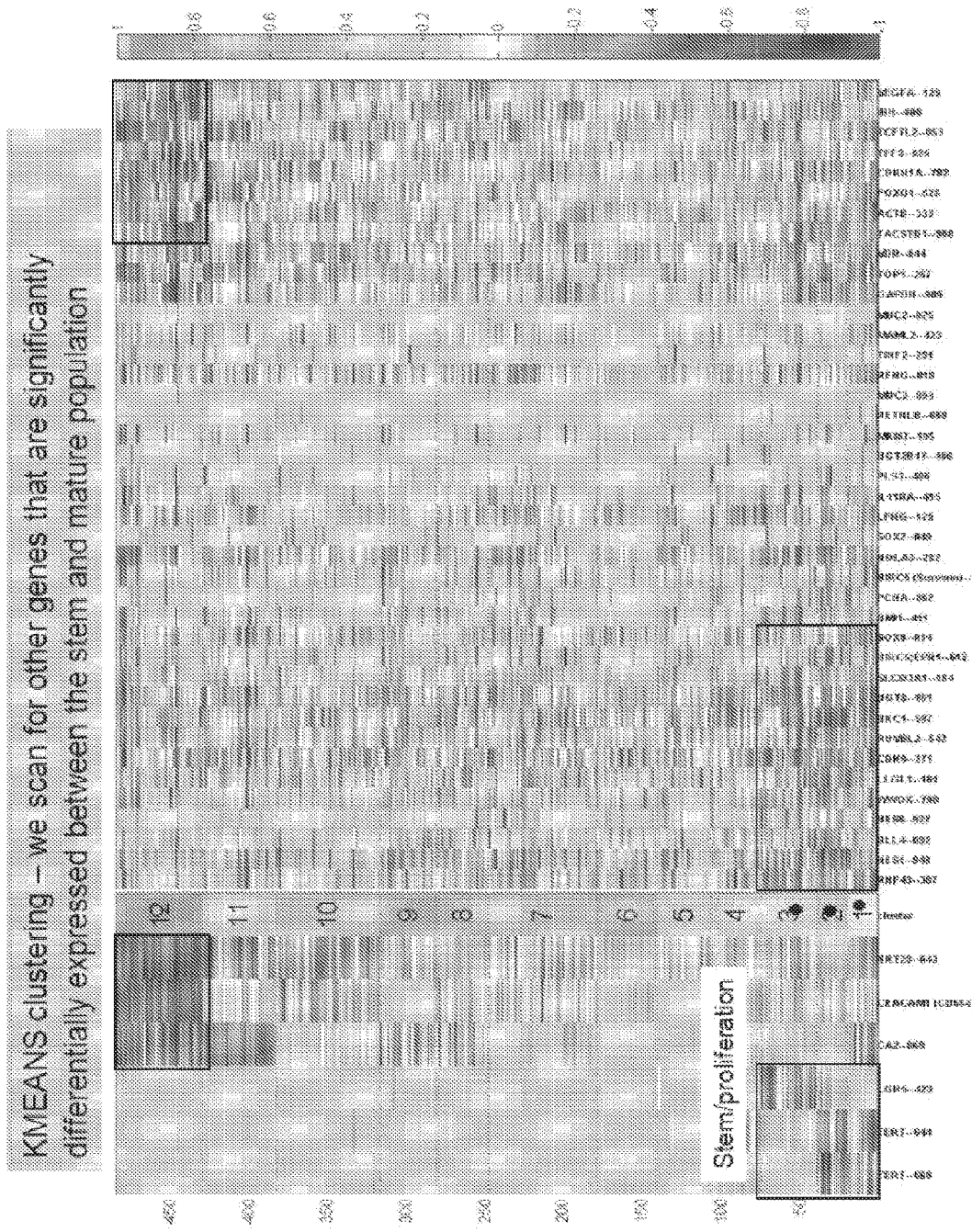

FIG. 153 k-means clustering map identifying differentially expressed genes between mature population and stem/proliferating population FIG. 154 k-means clustering identifying differentially expressed genes between mature population and stem/proliferating population. Genes significantly differentially expressed are marked by a square.

Figure 155:
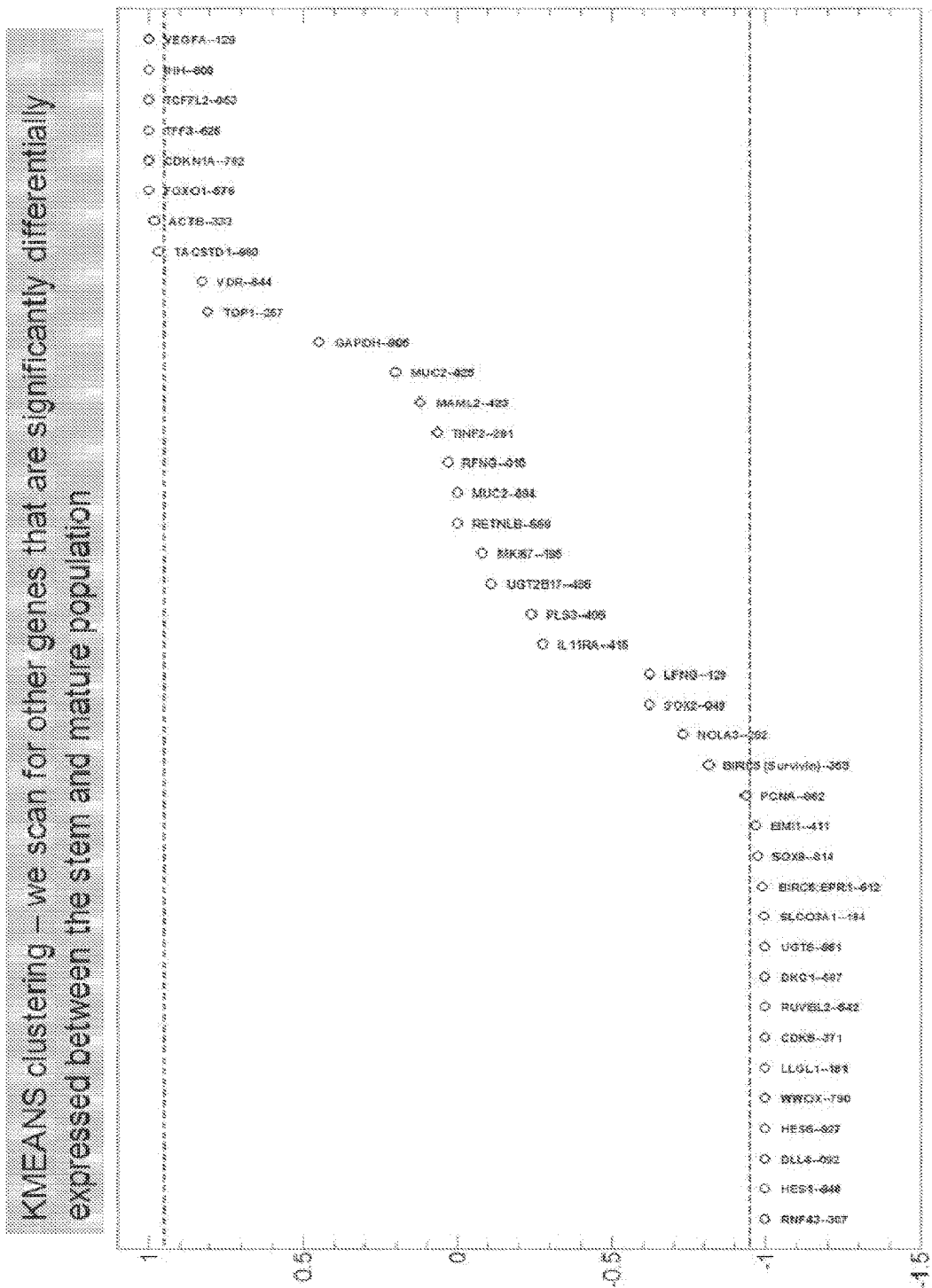

FIG. 155 k-means clustering identifying differentially expressed genes between mature population and stem/proliferating population.

Figure 156:
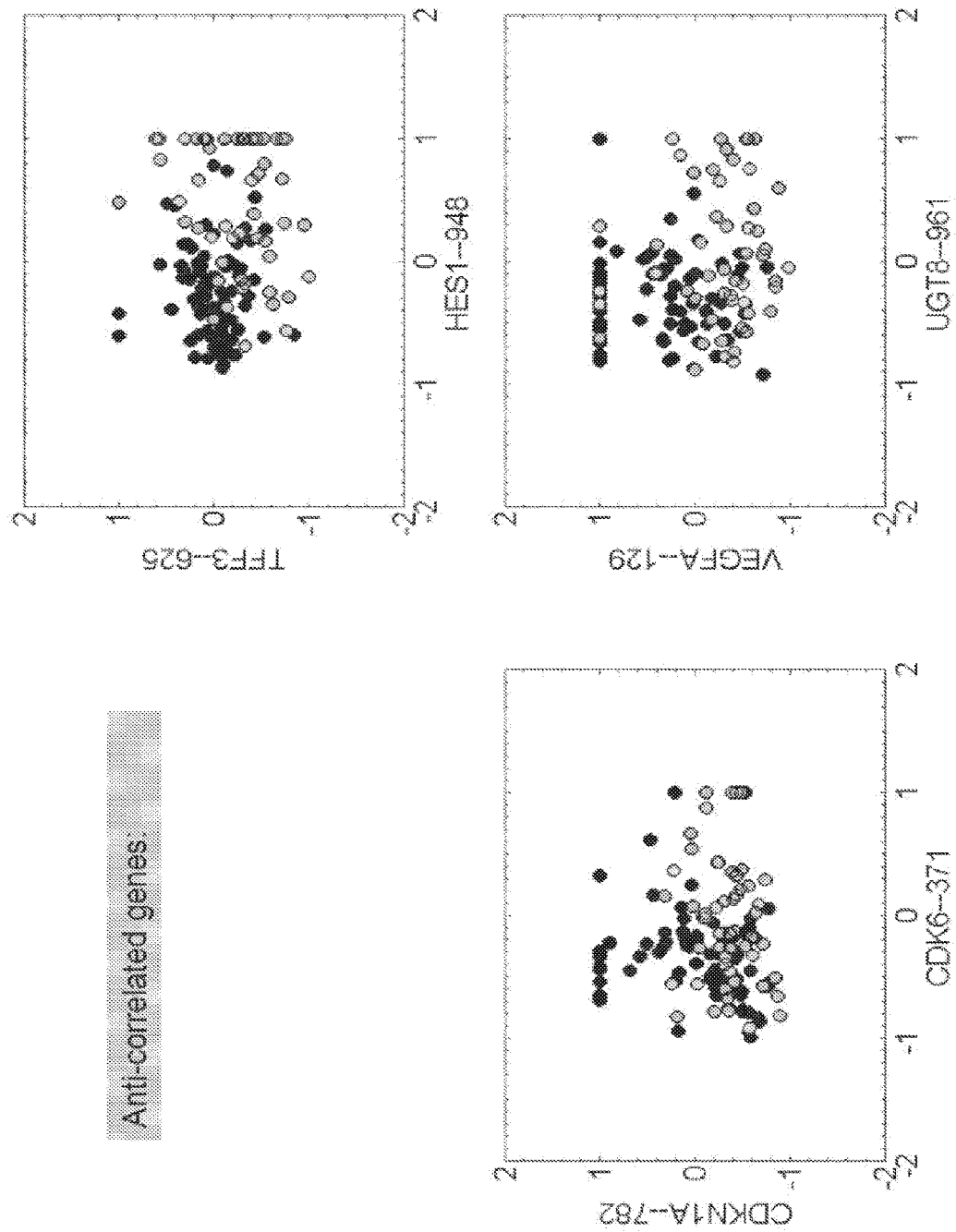

FIG. 156 patterns of anti-correlated gene expressions between the populations, e.g., HES1 and TFF3, CDK6 and CDKN1A, and UGT8 and VEGFA.

Figure 157:
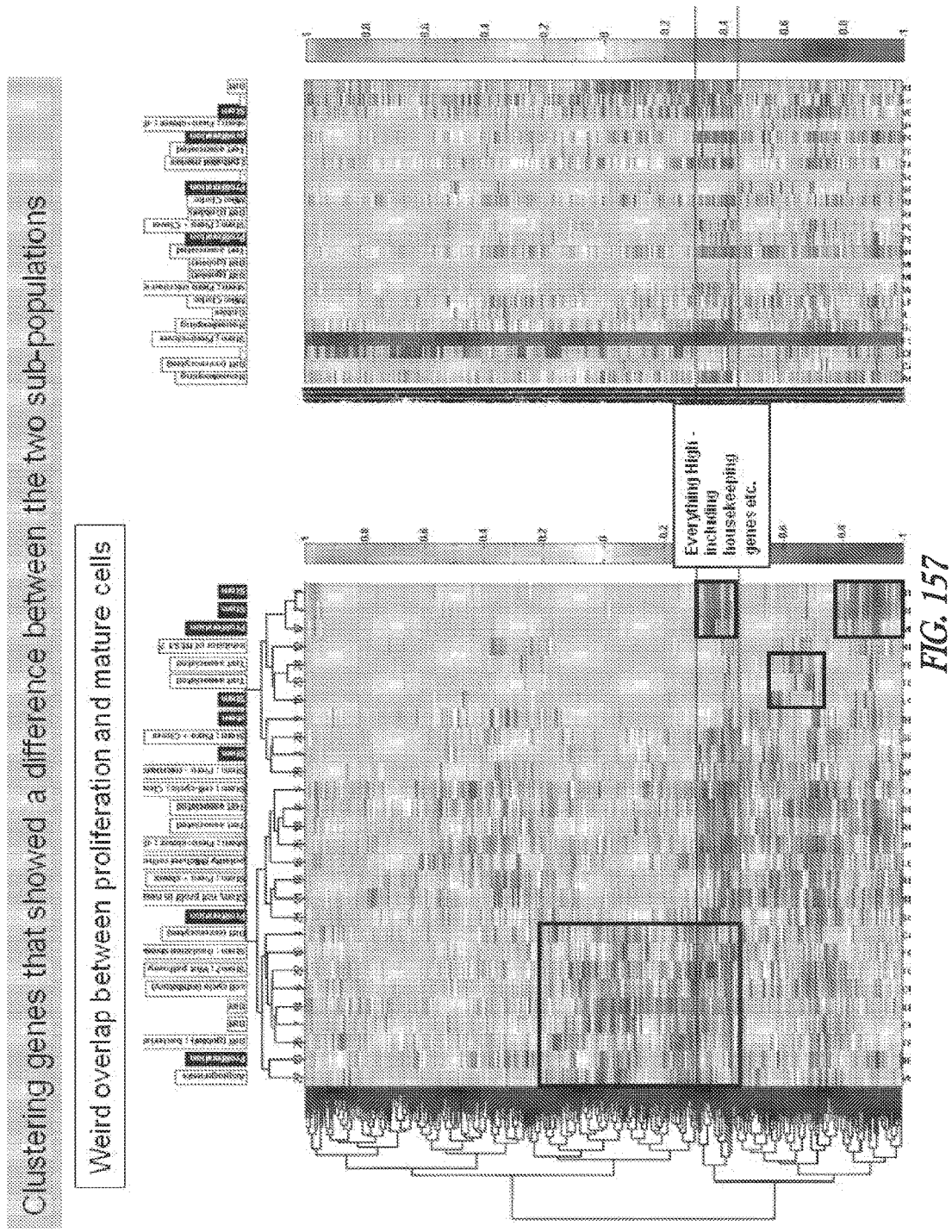

FIG. 157 clustering of genes showing a difference between mature and proliferating cells.

Figure 158:
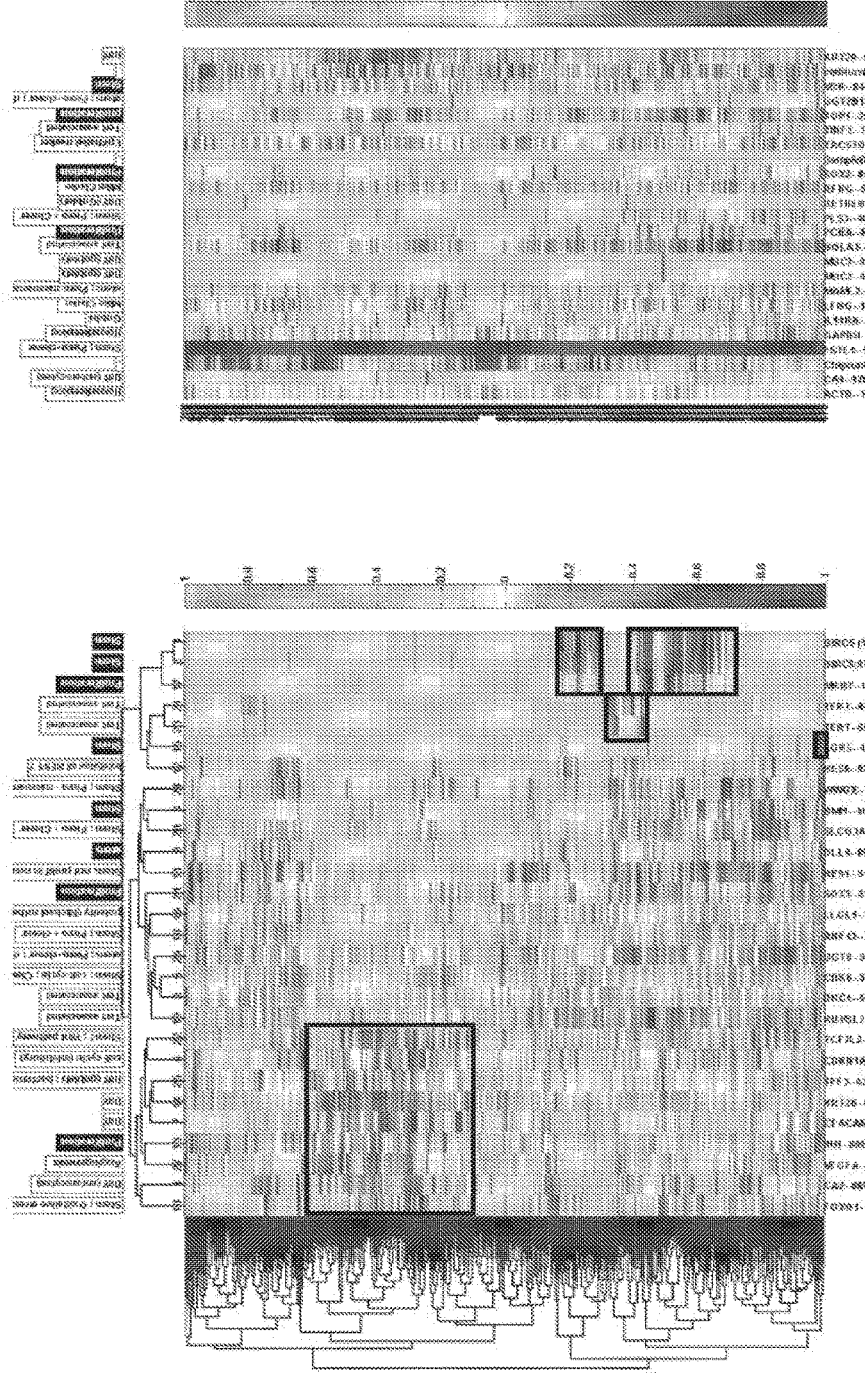
Figure 159:
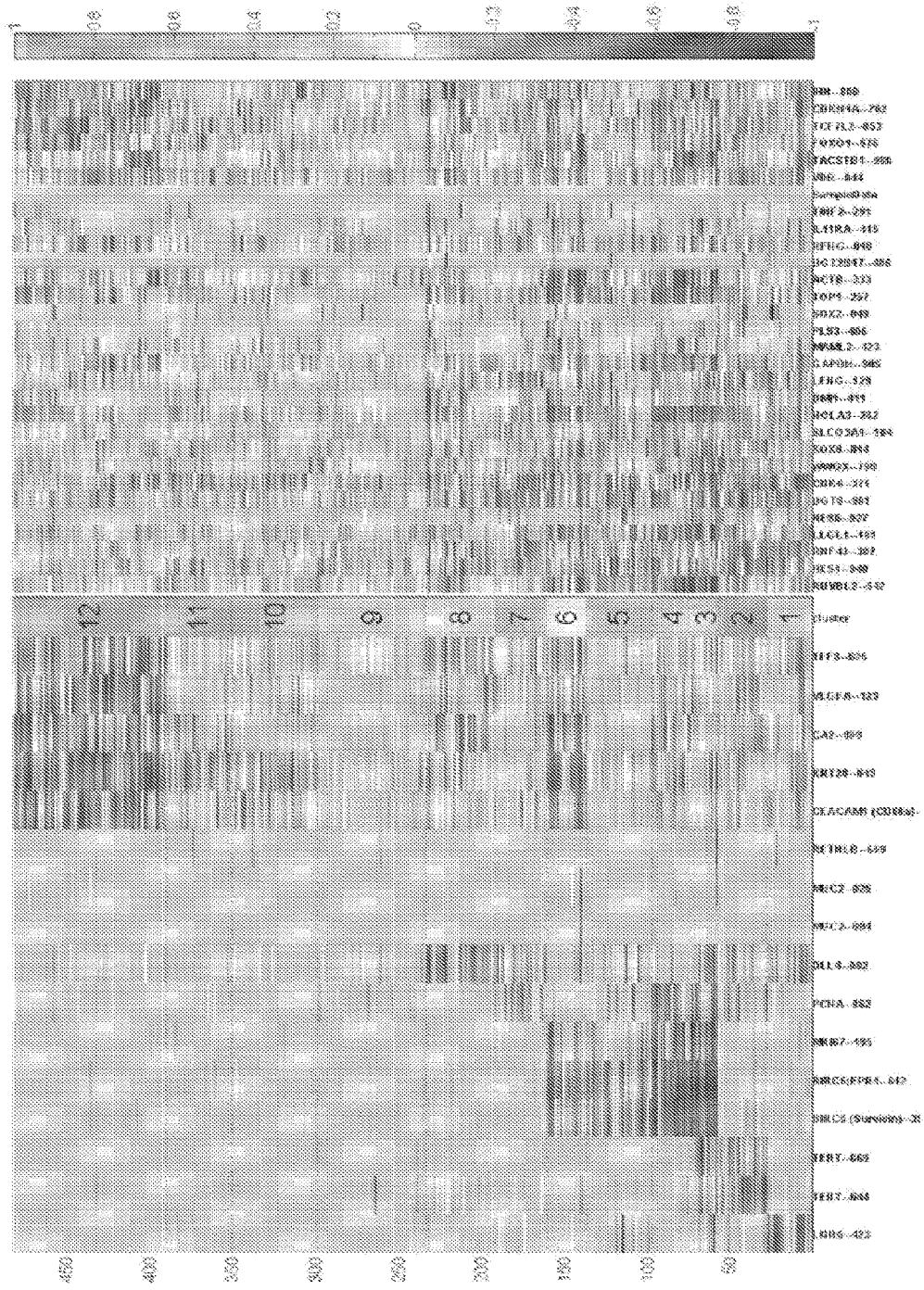

FIG. 158 clustering map after normalization with ACTB, GAPDH, and TACSTD1 showed a difference between the two sub-populations FIG. 159 k-mean clustering for stem, proliferation, and mature genes.

Figure 160:
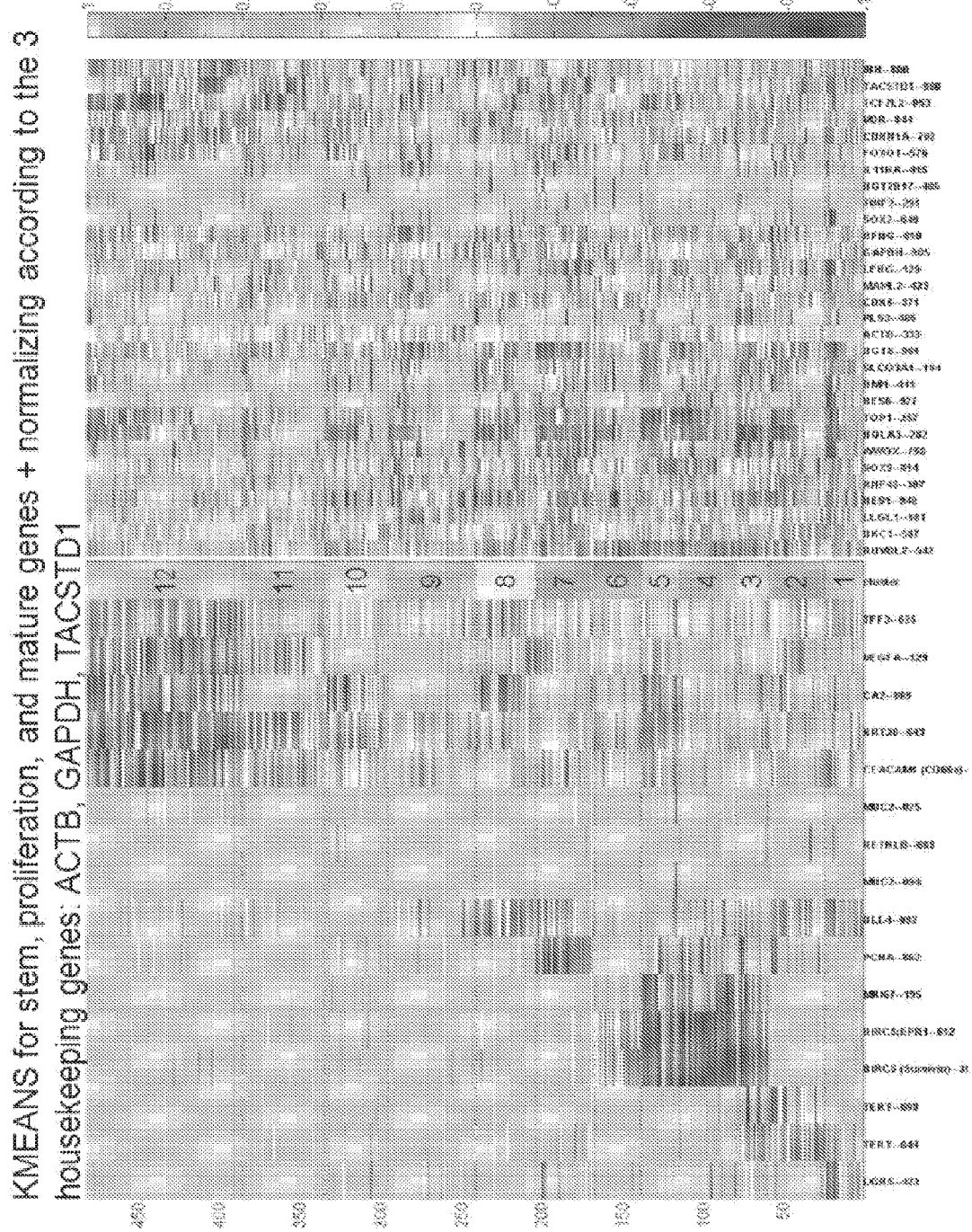

FIG. 160 k-mean clustering for stem, proliferation, and mature genes after normalization with ACTB, GAPDH, and TACSTD1.

Figure 161:
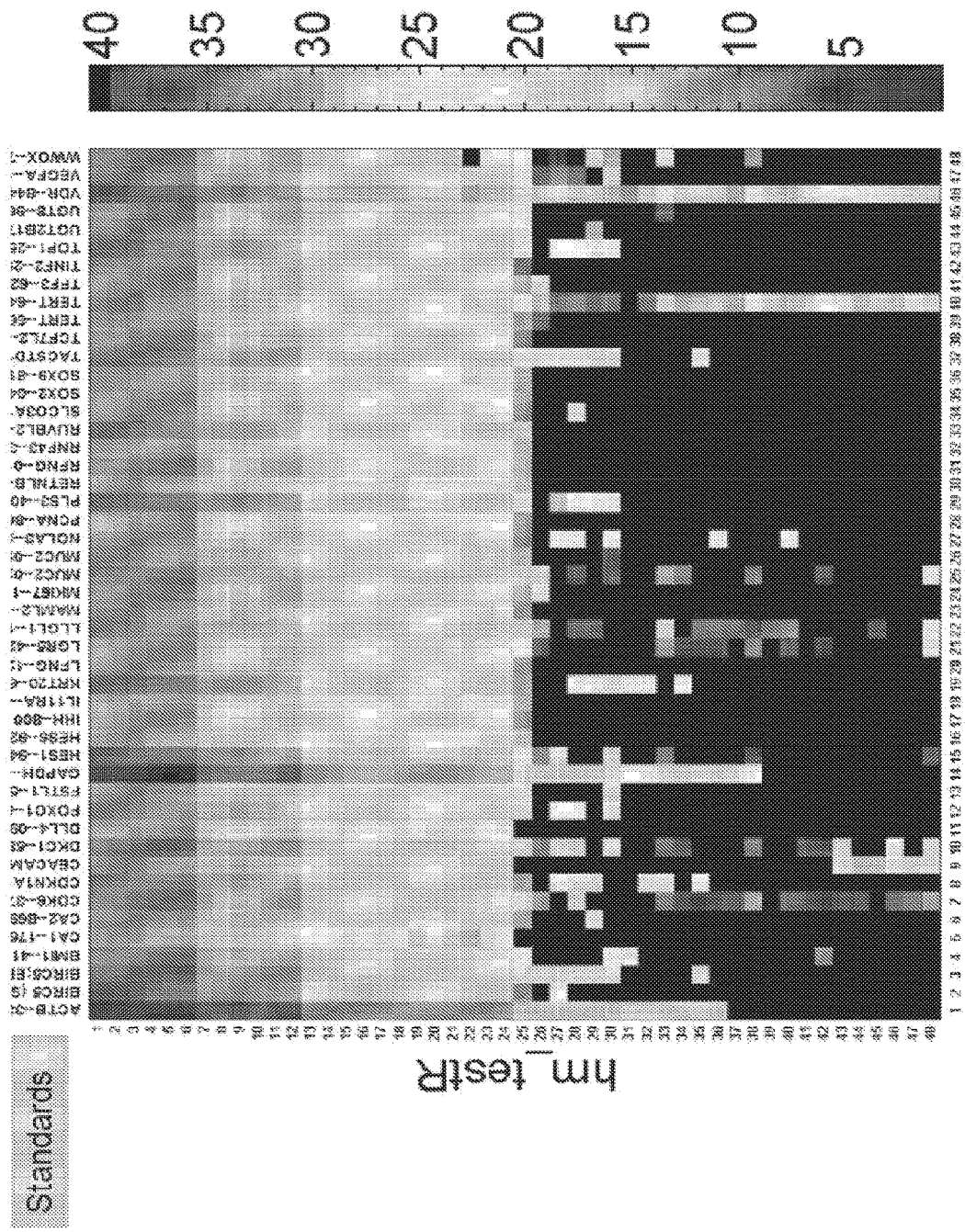

FIG. 161 a heat map of a standard run.

Figure 162:
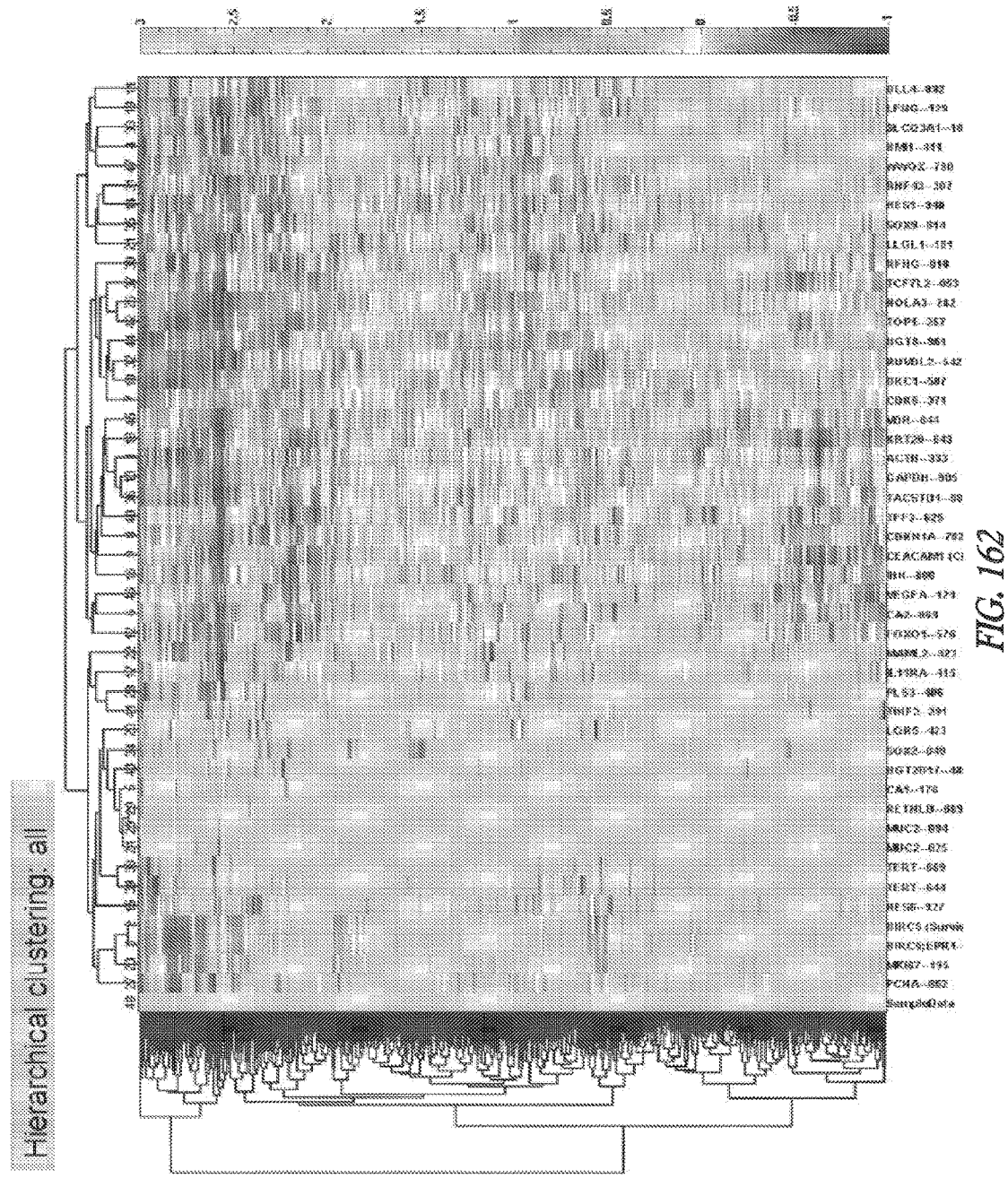

FIG. 162 result of hierarchical clustering demonstrating certain genes are differentially expressed, e.g., PCNA, MK167, TERT, CD66a, TFF3, KRT20, WWOX, and BMI1.

Figure 163:
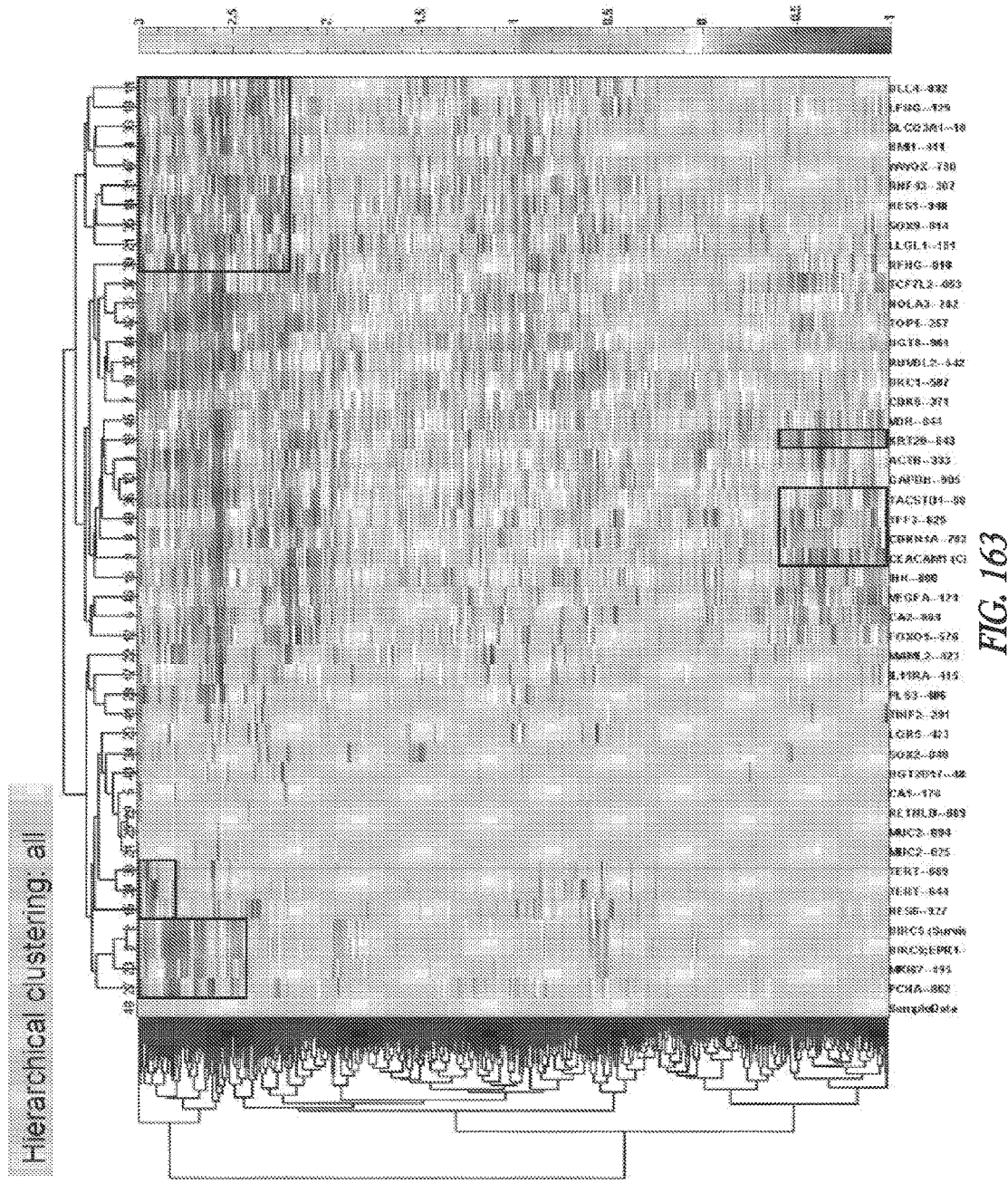

FIG. 163 a depiction of differentially expressed genes.

Figure 164:
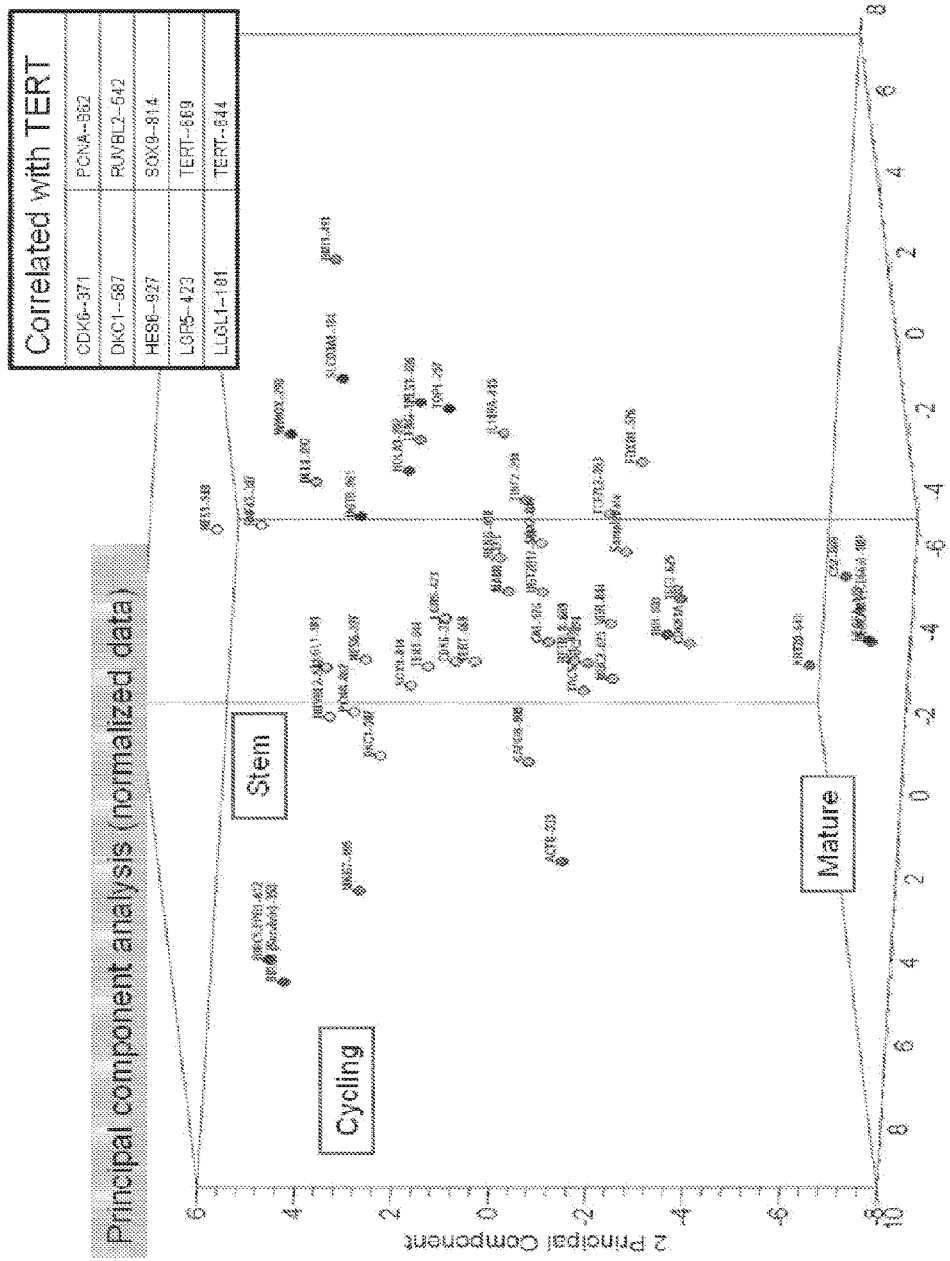

FIG. 164 genes correlated with TERT that were identified in a principal component analysis.

Figure 165:
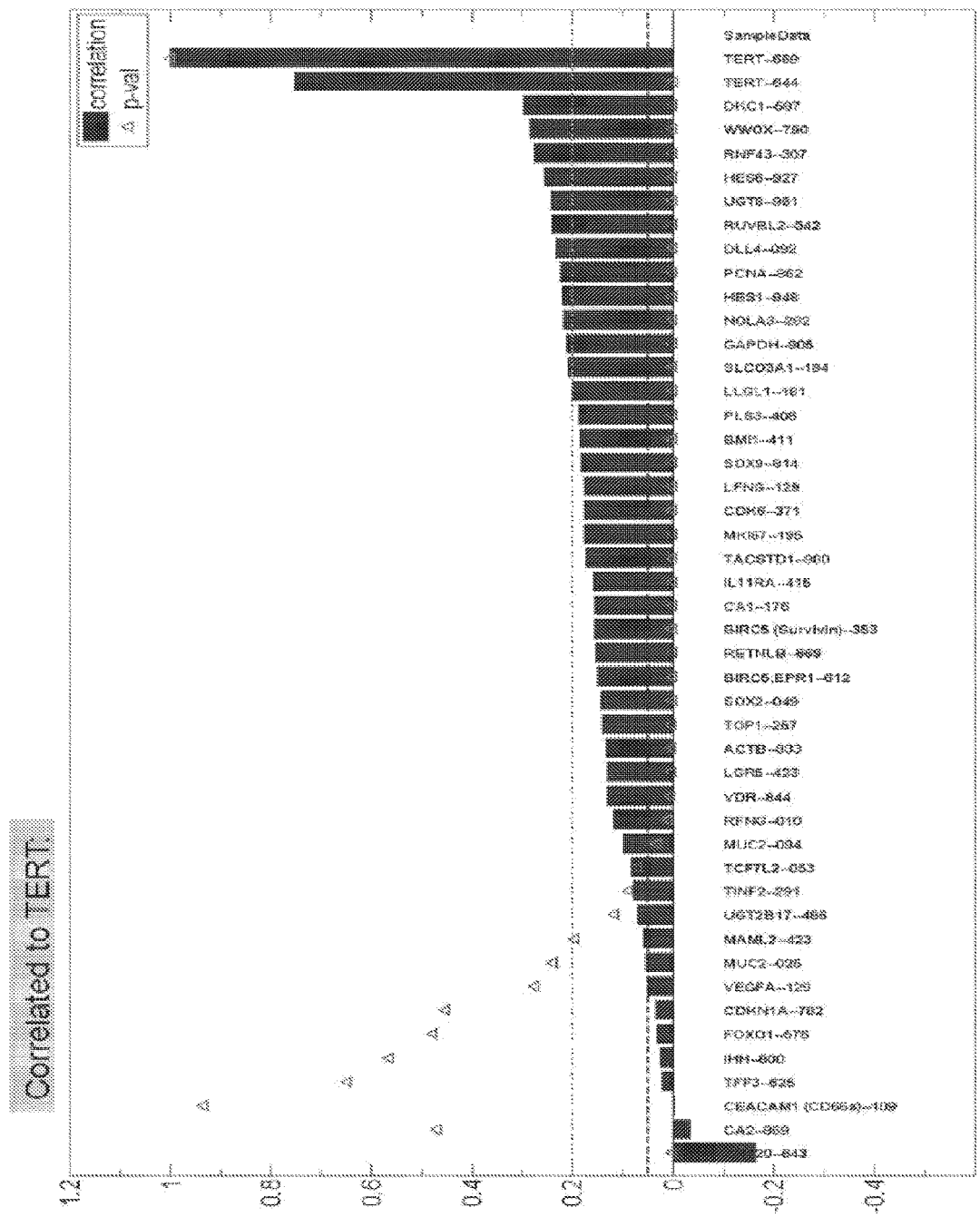

FIG. 165 gene expressions correlated to TERT expression.

Figure 166:
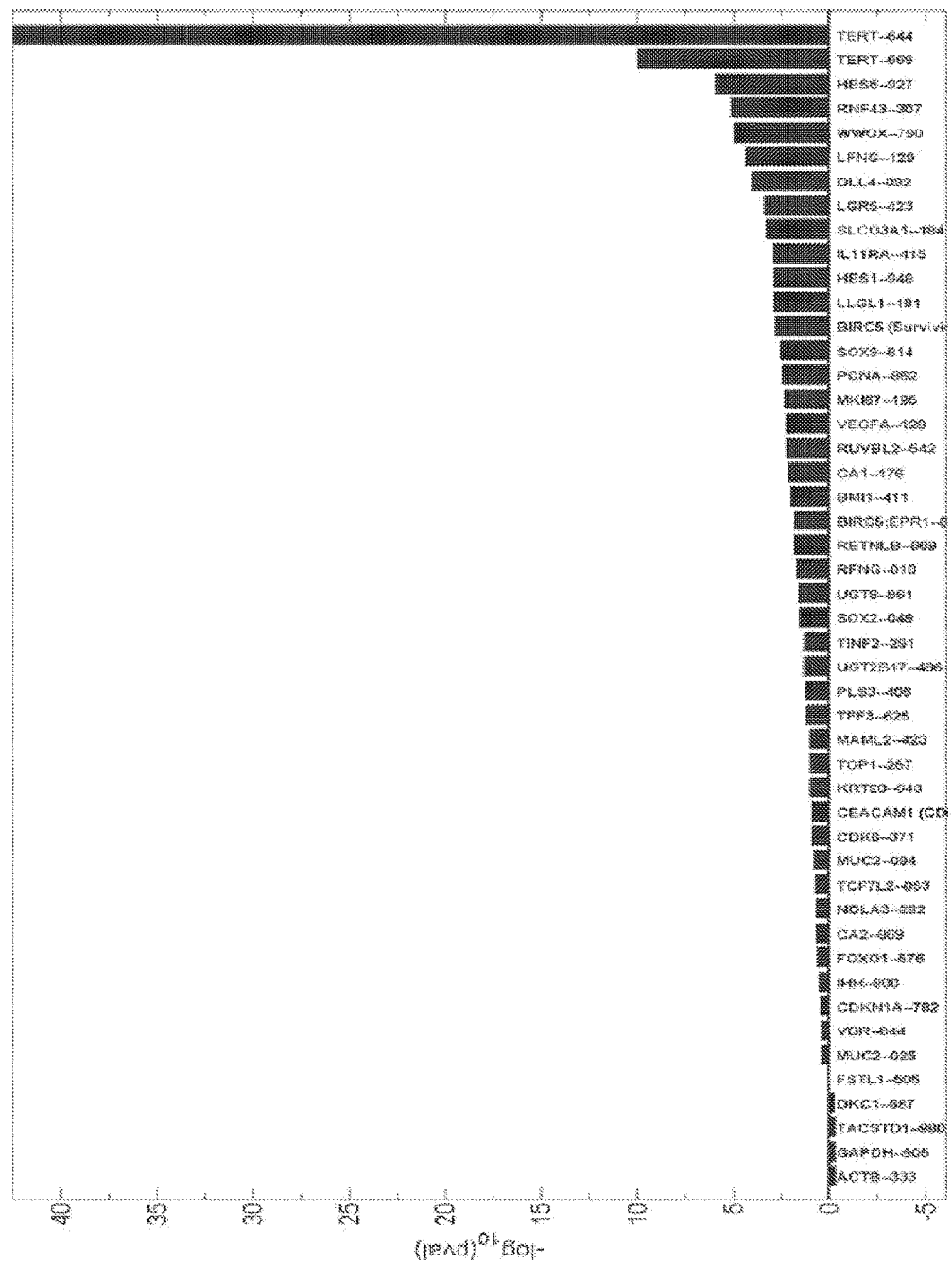

FIG. 166 gene expressions associated with TERT expression.

Figure 167:
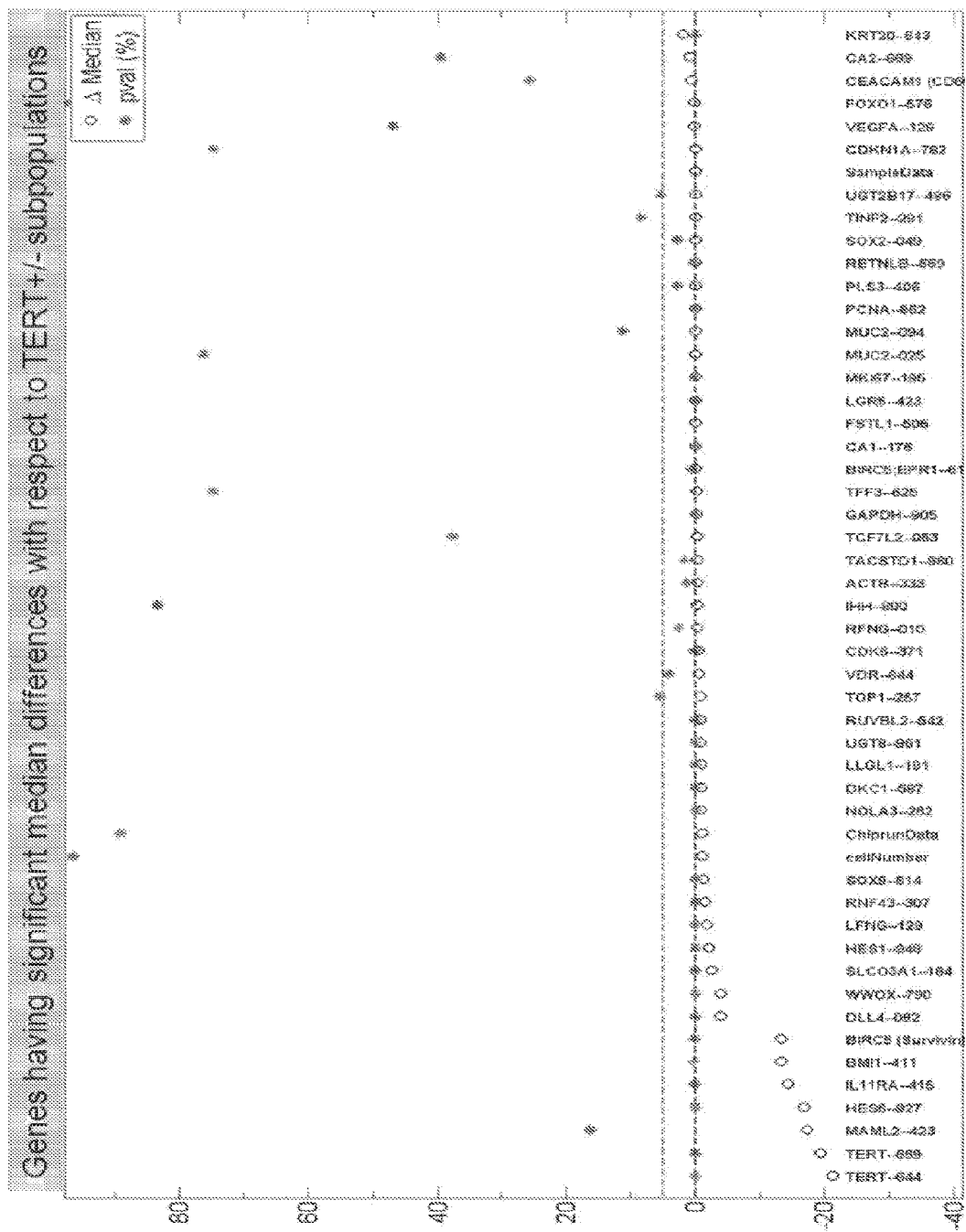

FIG. 167 genes having significant difference with TERT expression.

Figure 168:
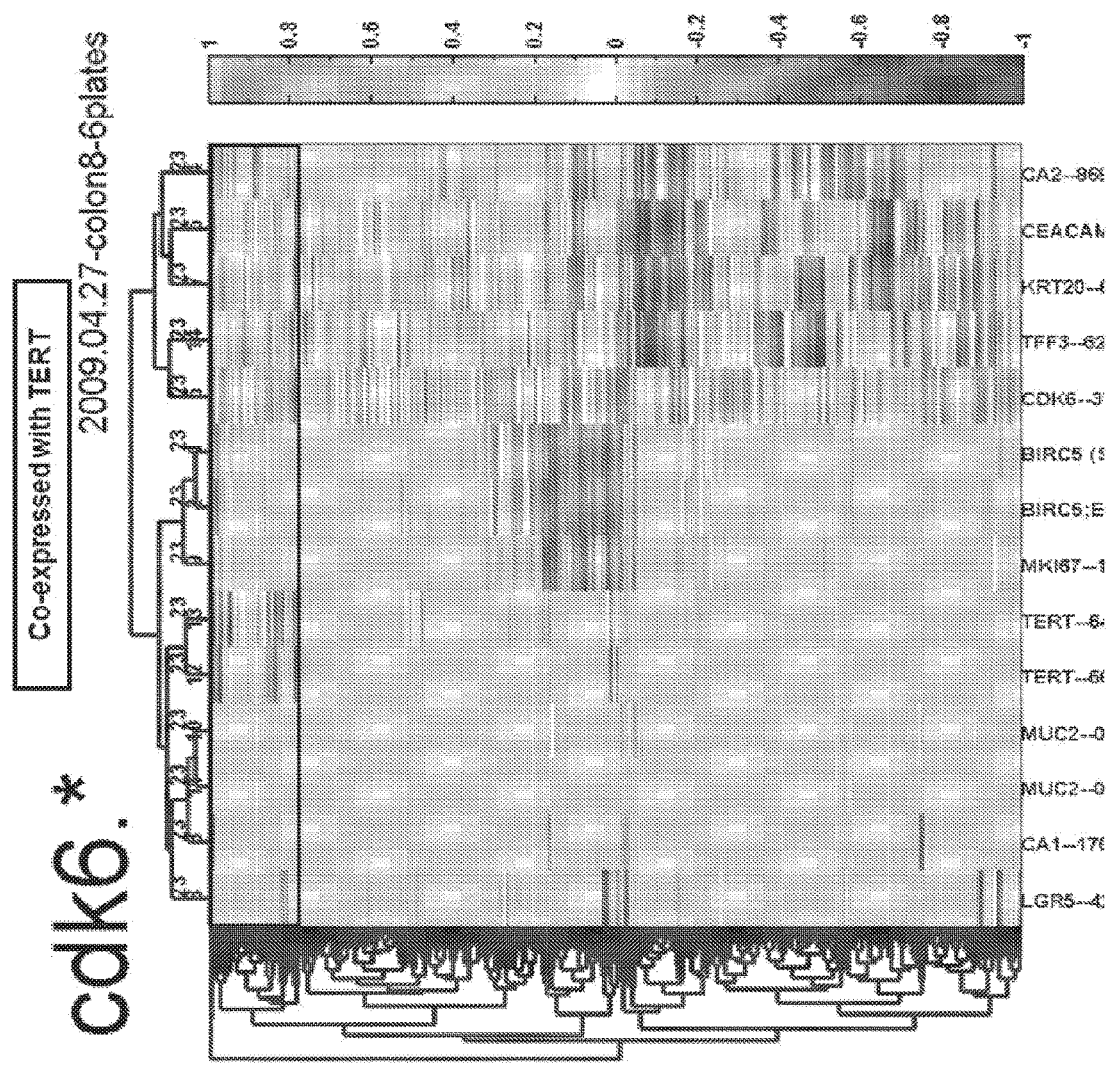

FIG. 168 CDK6 is co-expressed with TERT.

Figure 169:
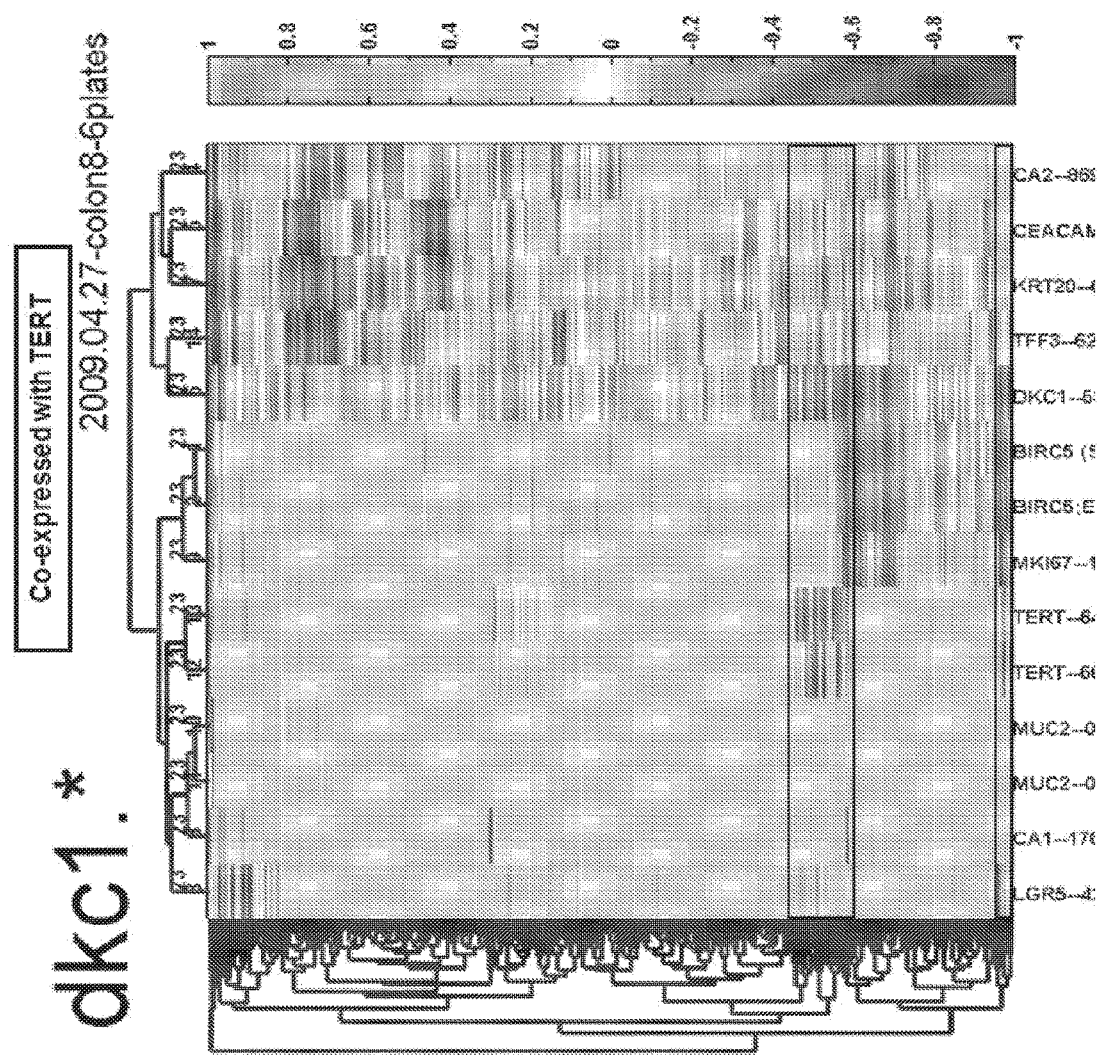

FIG. 169 DKC1 is co-expressed with TERT.

Figure 170:
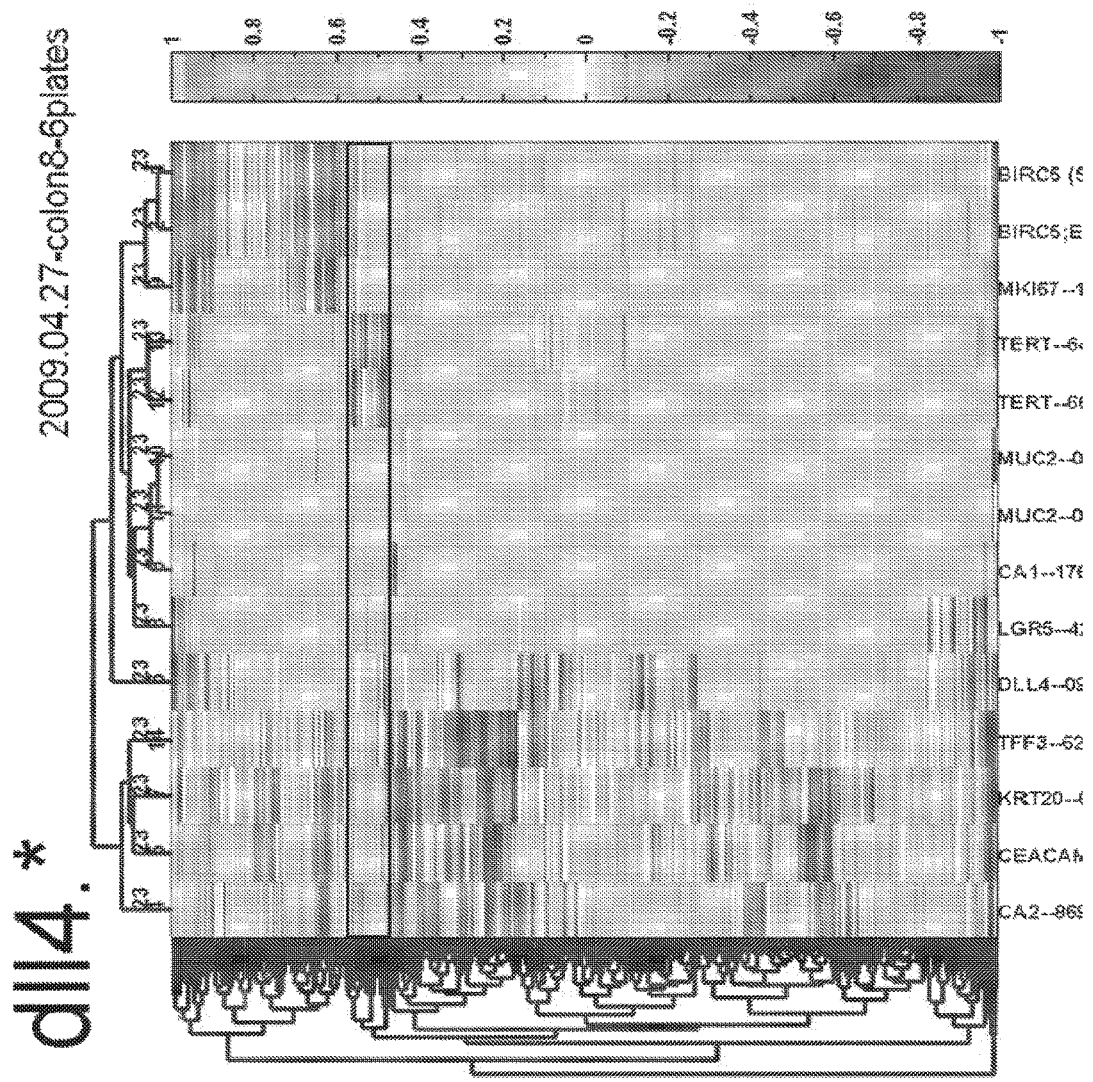

FIG. 170 DLL4 expression in relation to TERT expression.

Figure 171:
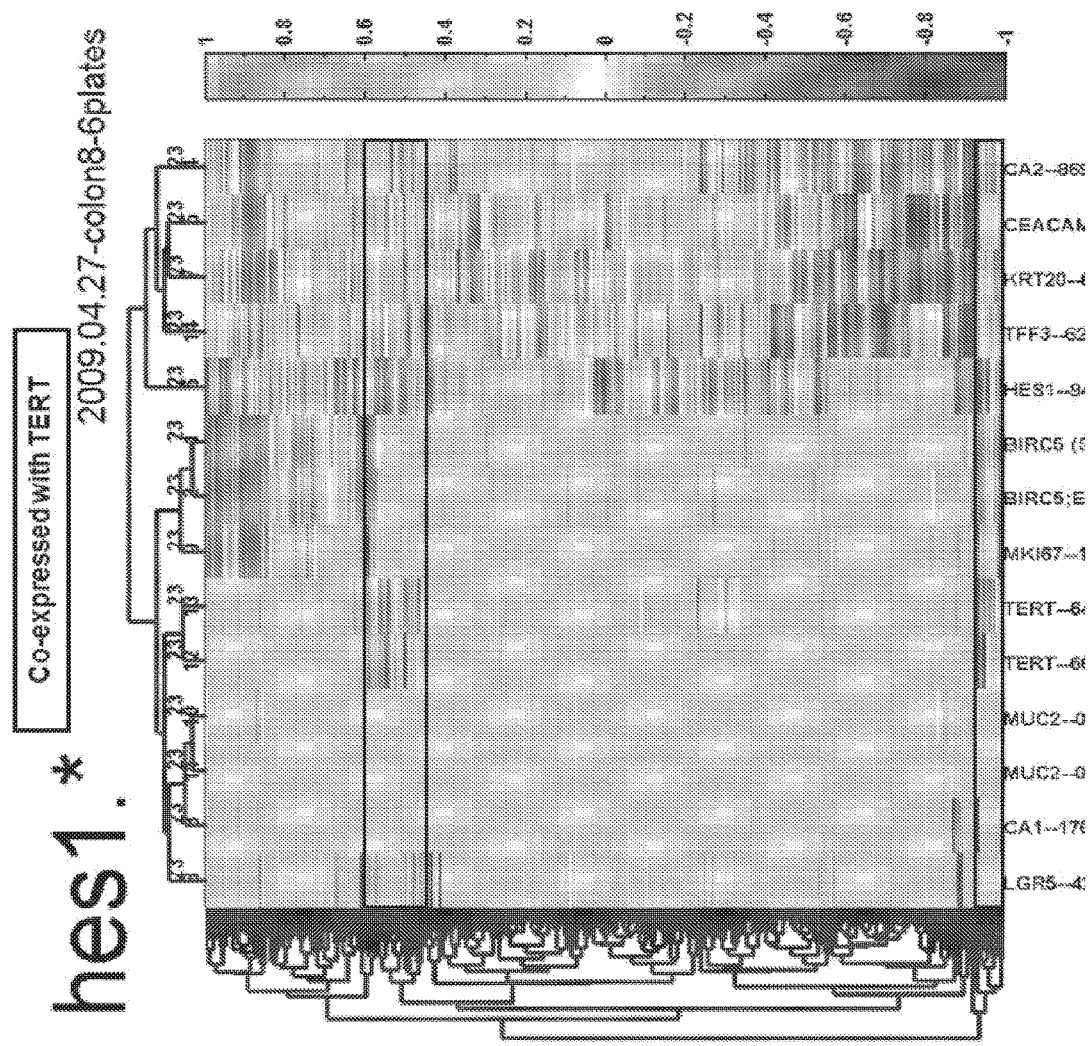

FIG. 171 HES1 is co-expressed with TERT.

Figure 172:
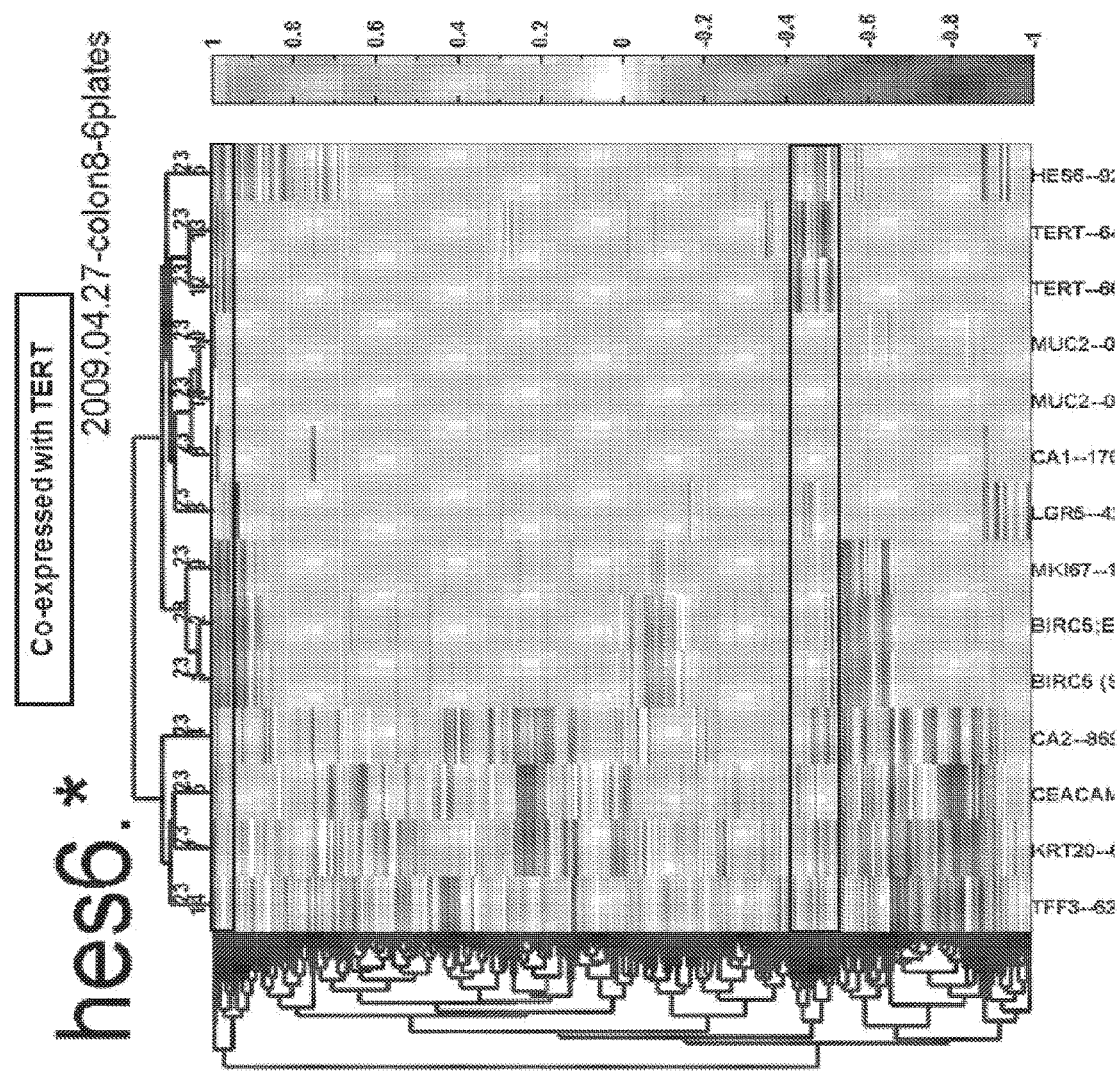

FIG. 172 HES6 is co-expressed with TERT.

Figure 173:
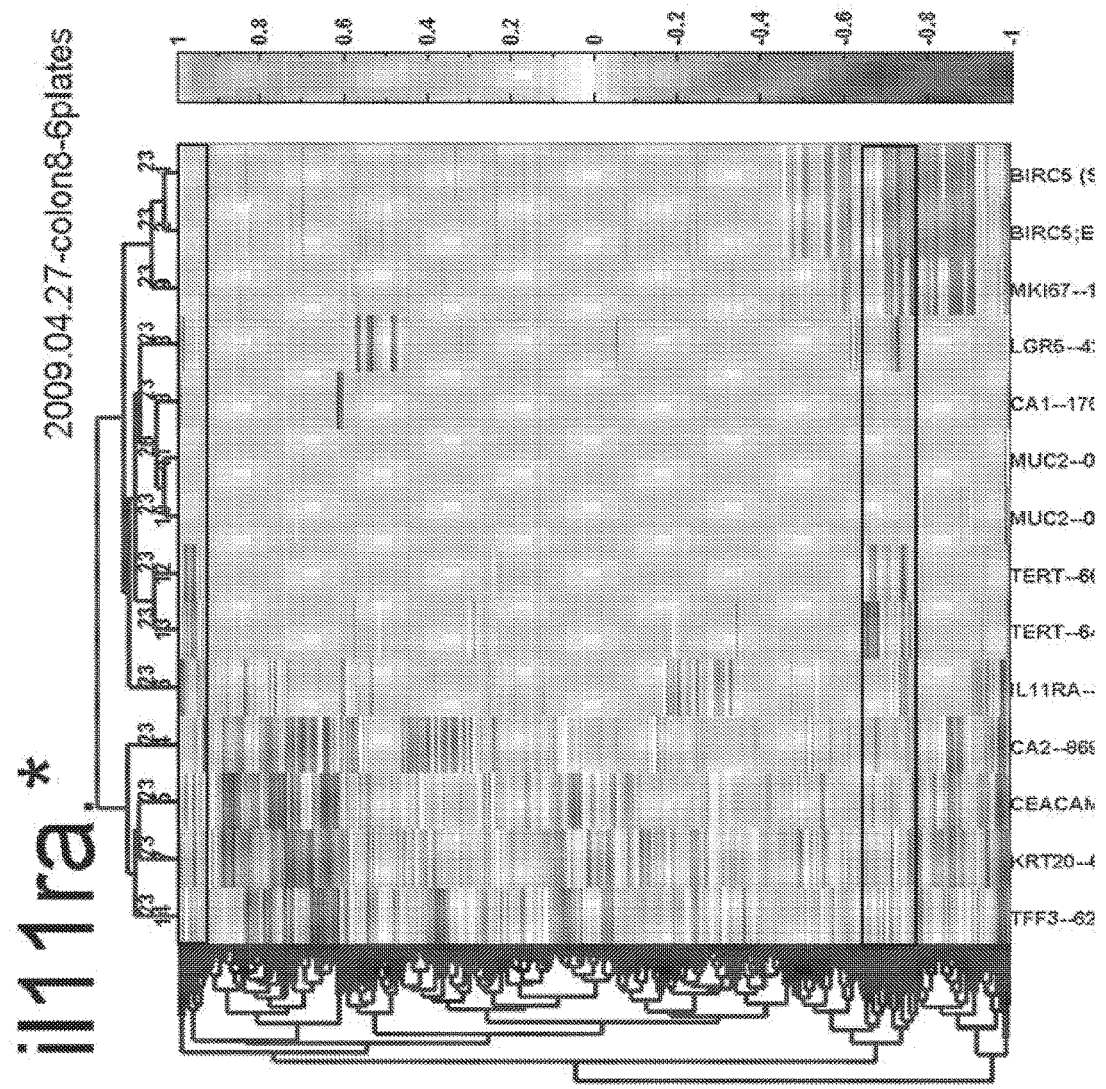

FIG. 173 IL11RA expression in relation to TERT expression.

Figure 174:
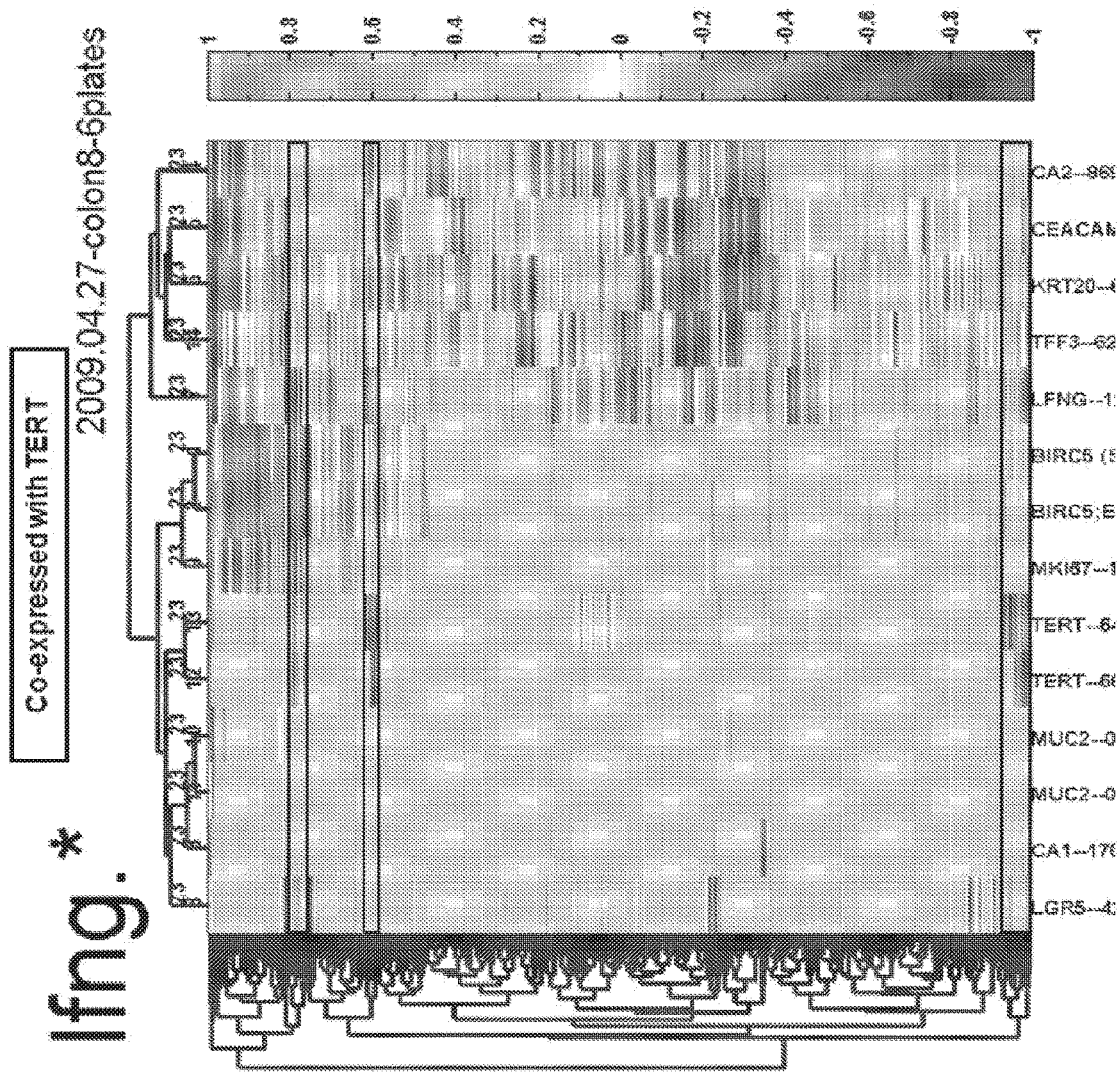

FIG. 174 LFNG is co-expressed with TERT.

Figure 175:
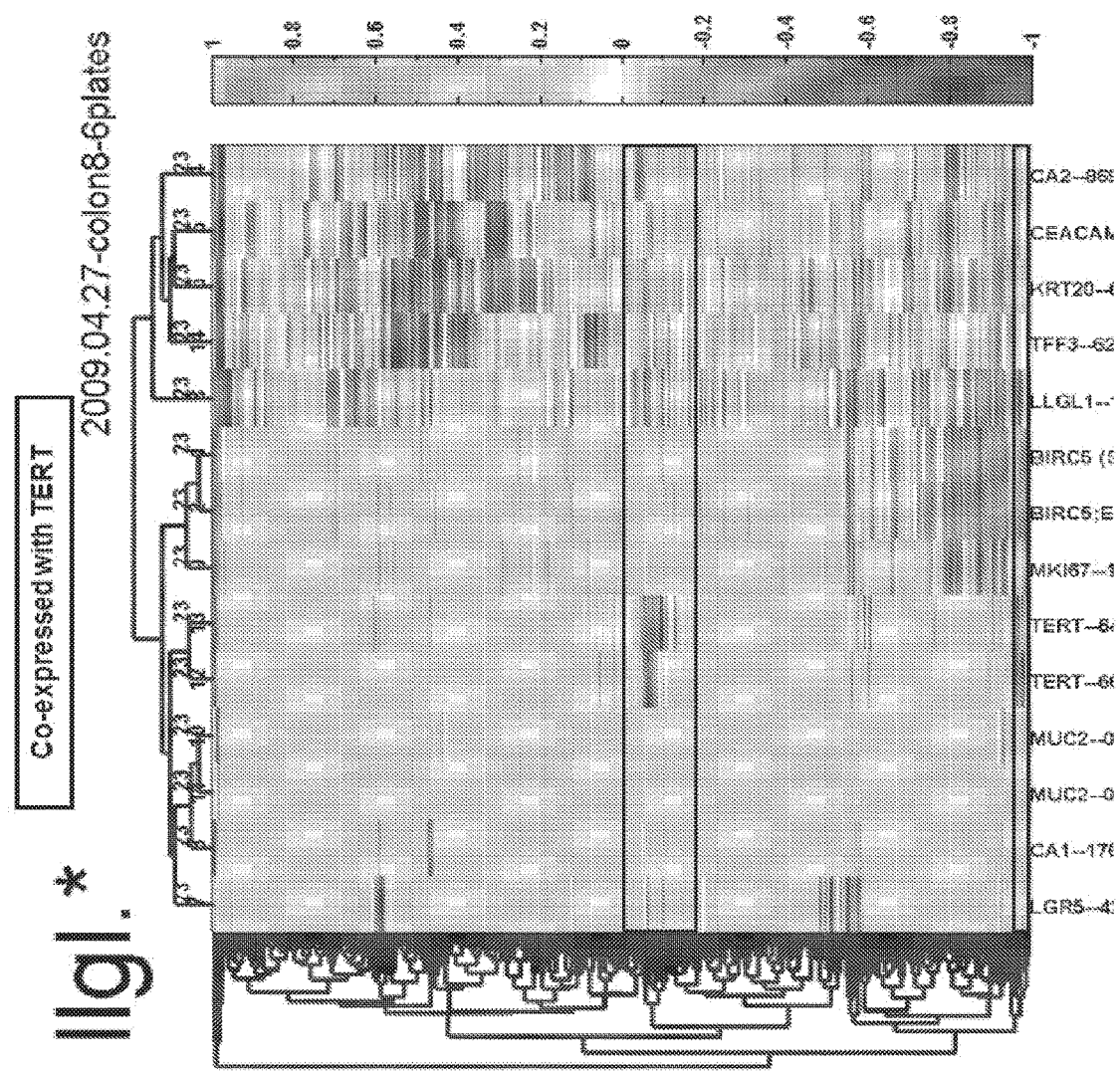

FIG. 175 LLGL is co-expressed with TERT.

Figure 176:
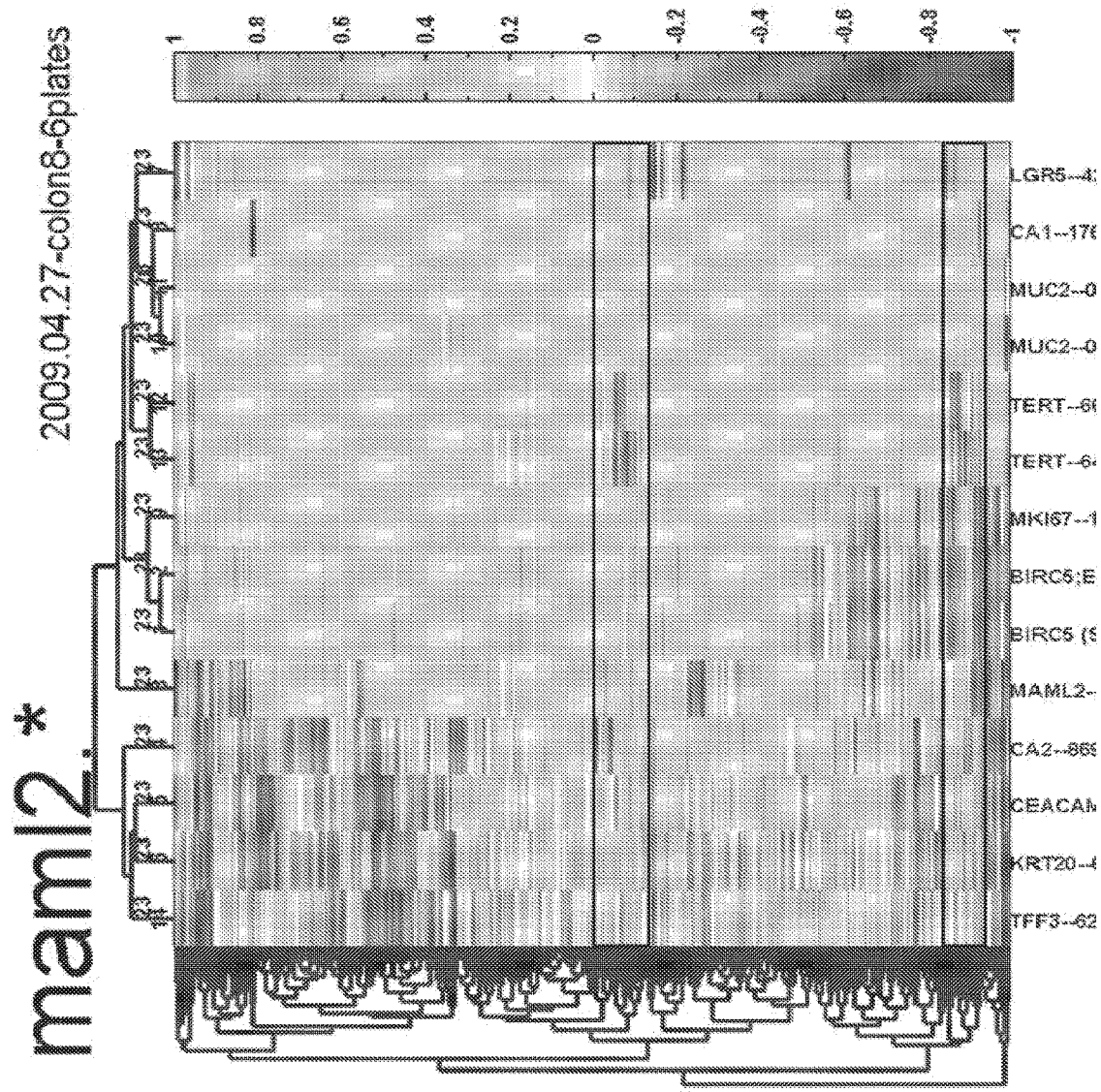

FIG. 176 MAML2 expression in relation to TERT expression.

Figure 177:
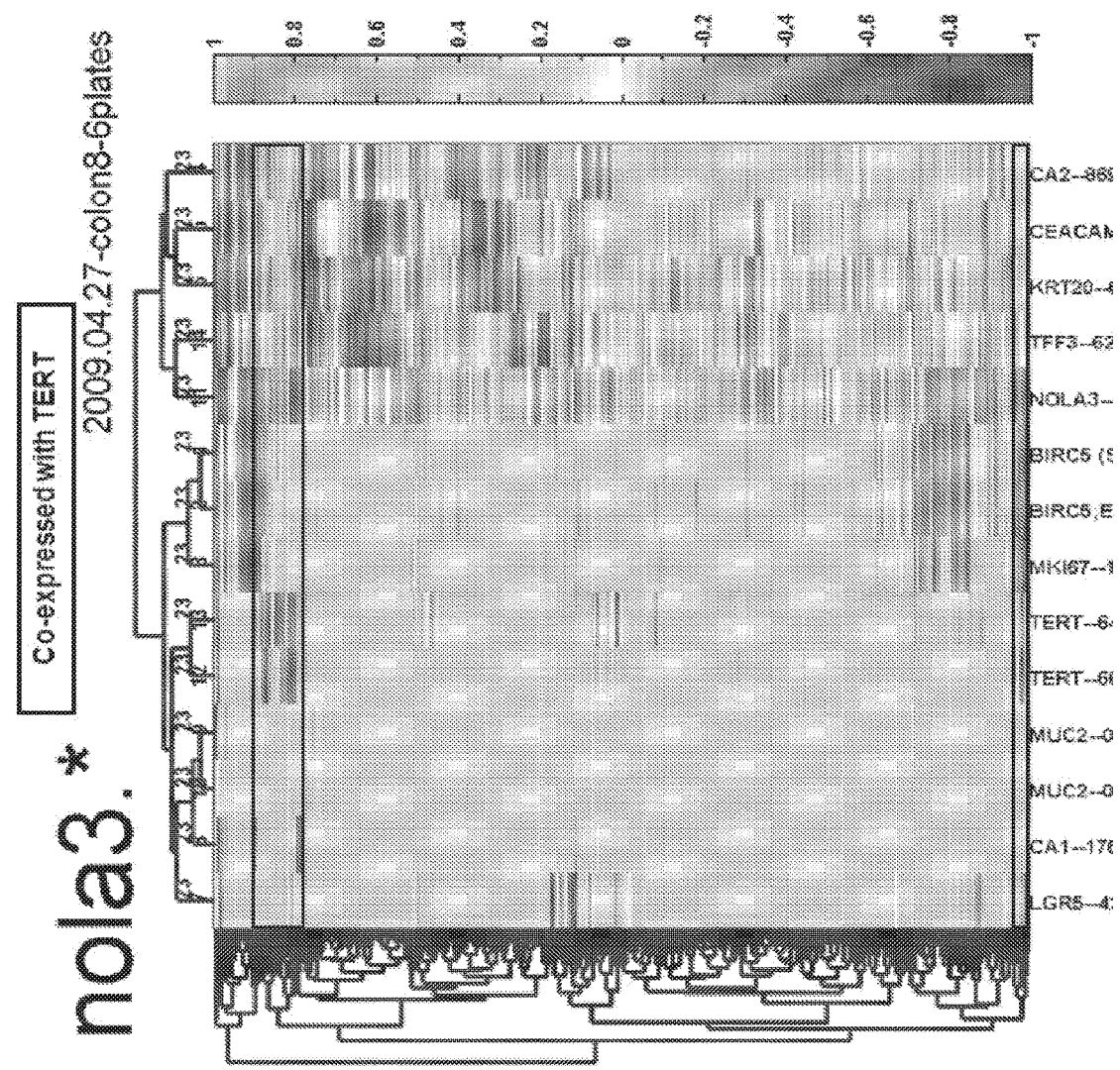

FIG. 177 NOLA3 is co-expressed with TERT.

Figure 178:
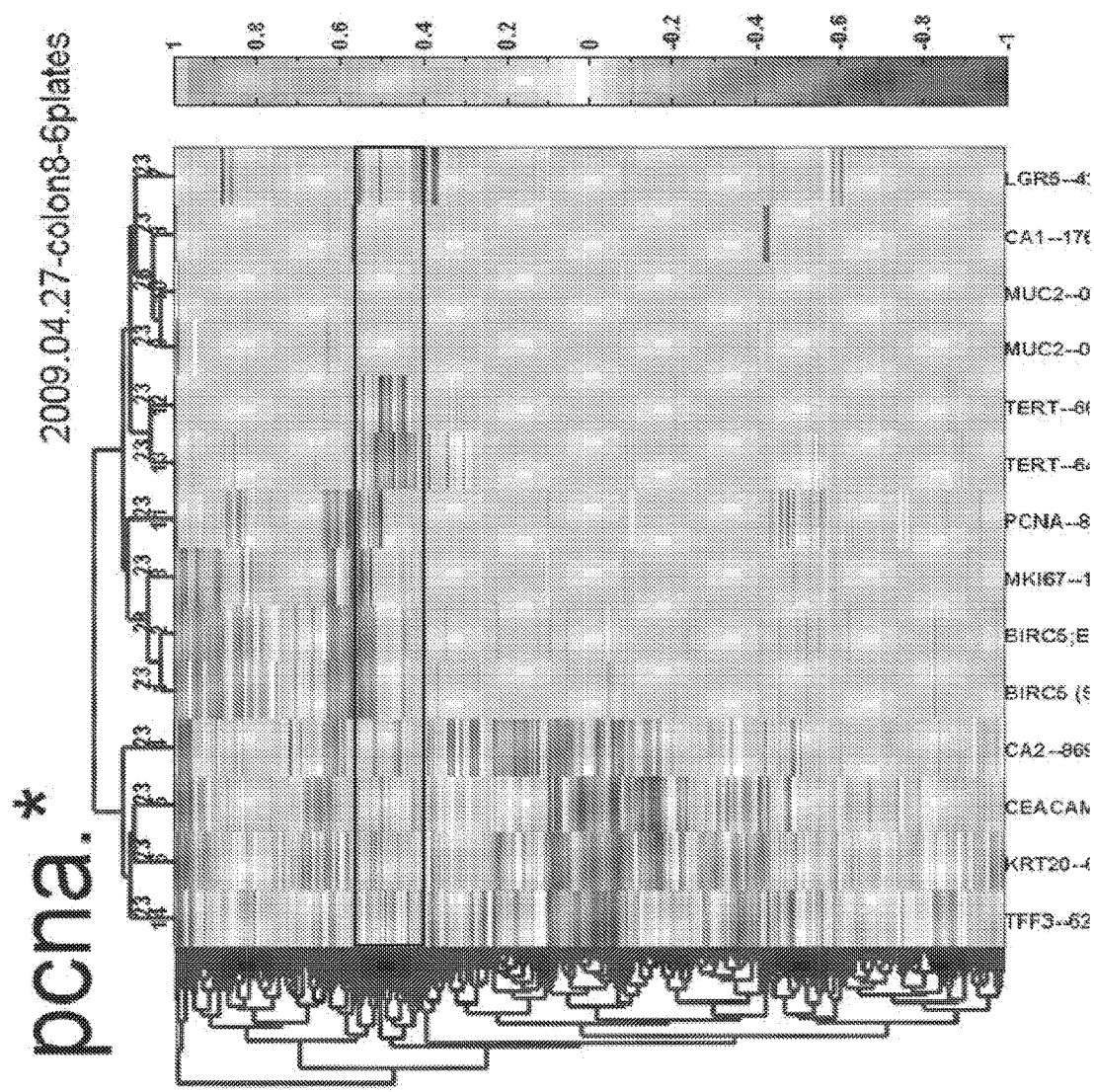

FIG. 178 PCNA expression in relation to TERT expression.

Figure 179:
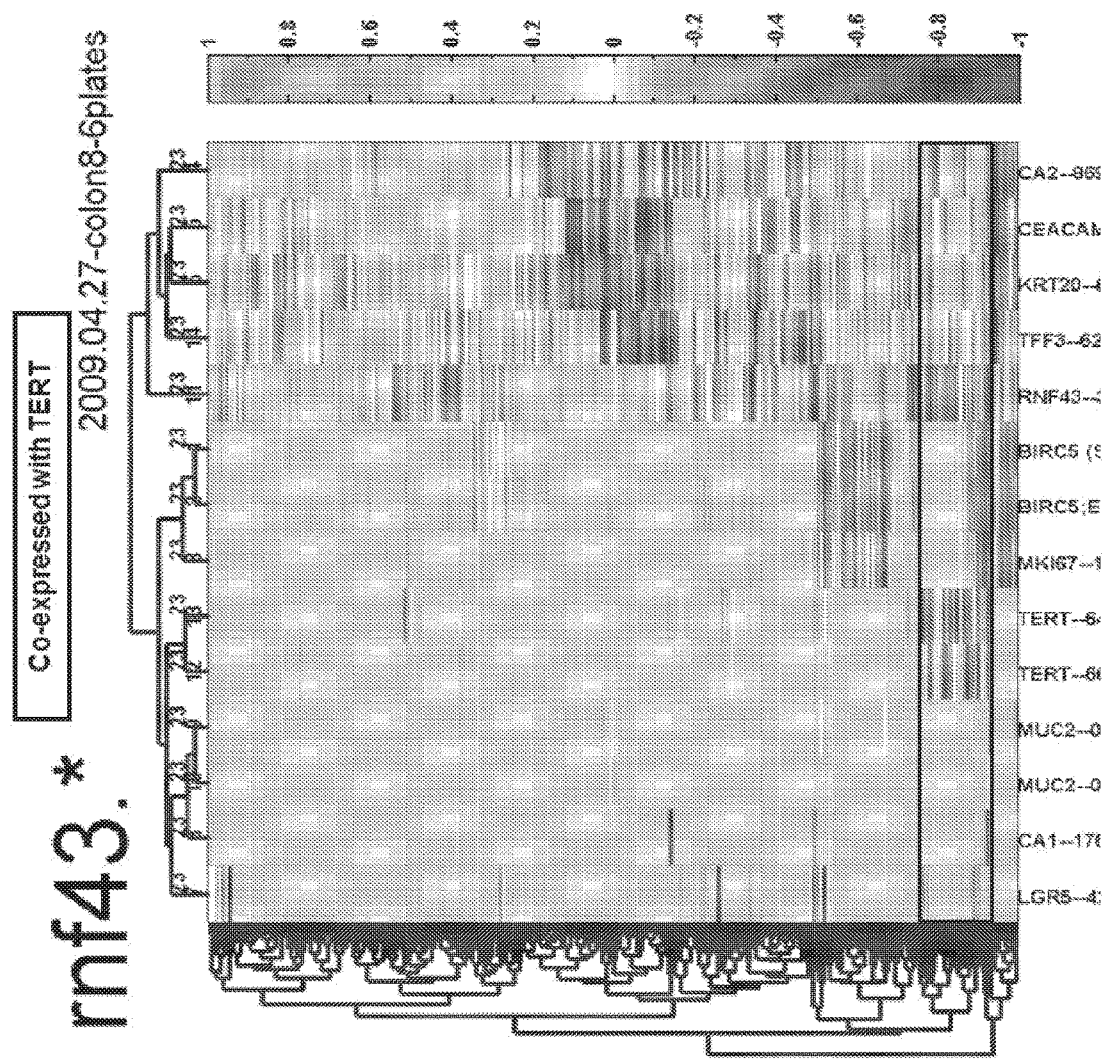

FIG. 179 RNF43 is co-expressed with TERT.

Figure 180:
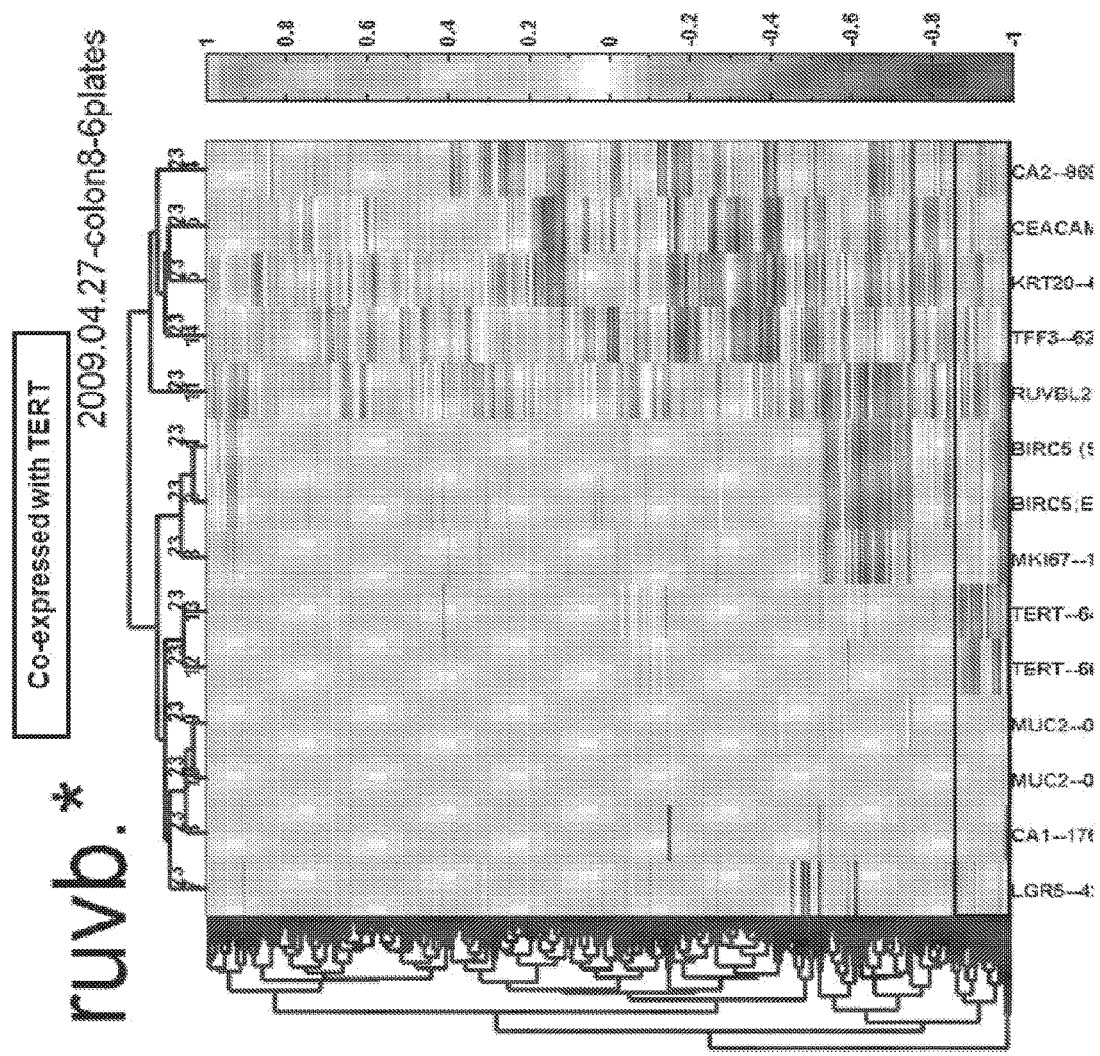

FIG. 180 RUVB is co-expressed with TERT.

Figure 181:
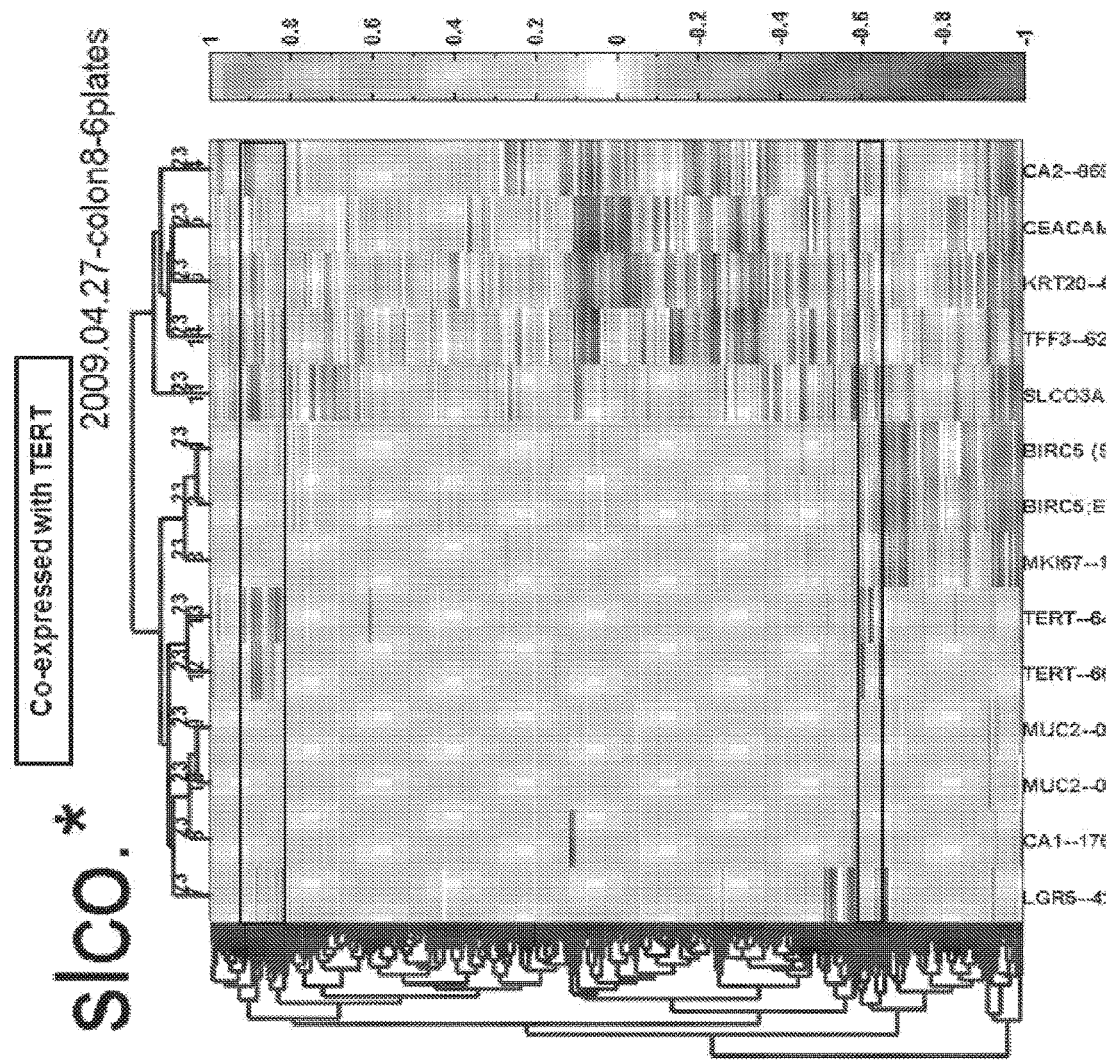

FIG. 181 SLCO is co-expressed with TERT.

Figure 182:
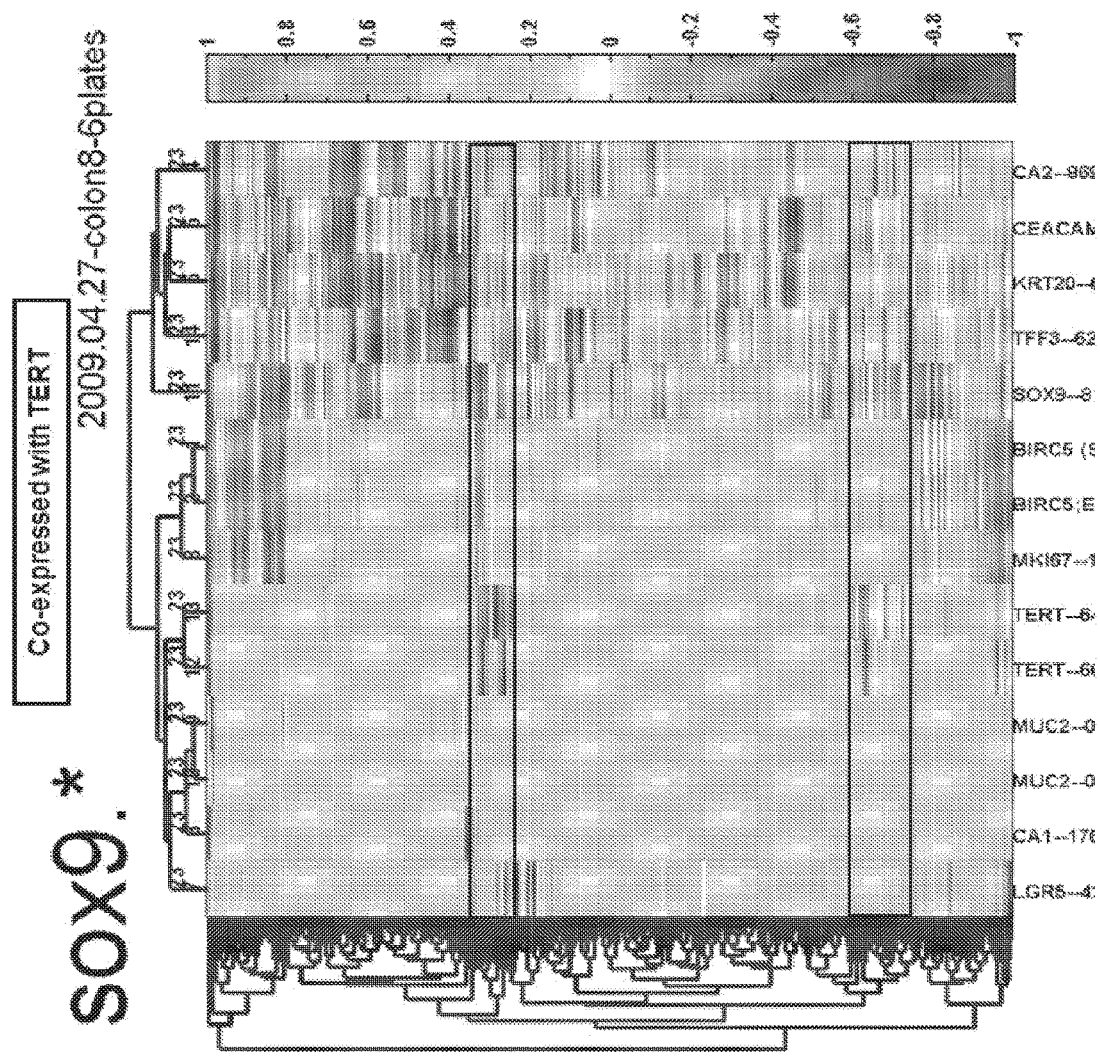

FIG. 182 SOX9 is co-expressed with TERT.

Figure 183:
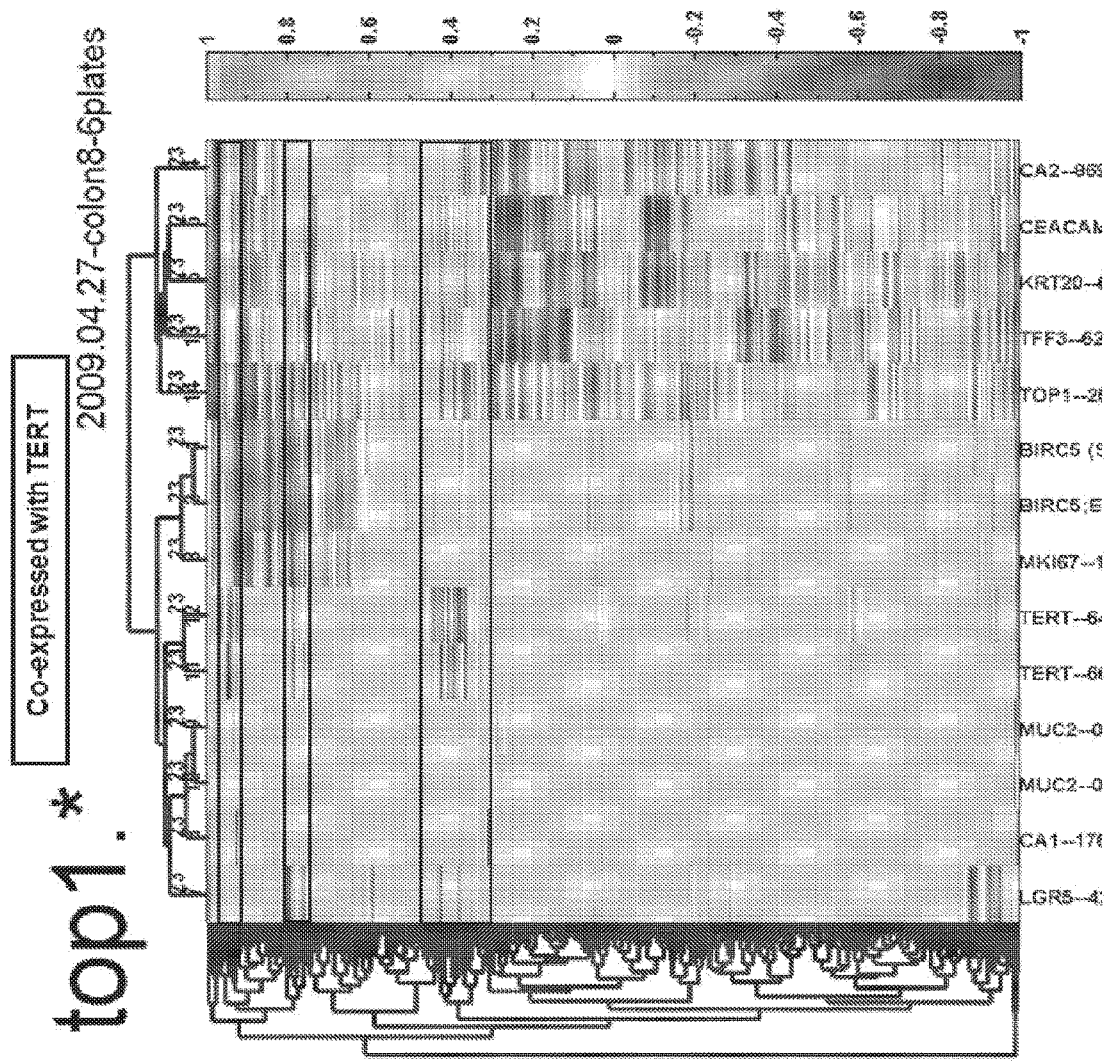

FIG. 183 TOP1 is co-expressed with TERT.

Figure 184:
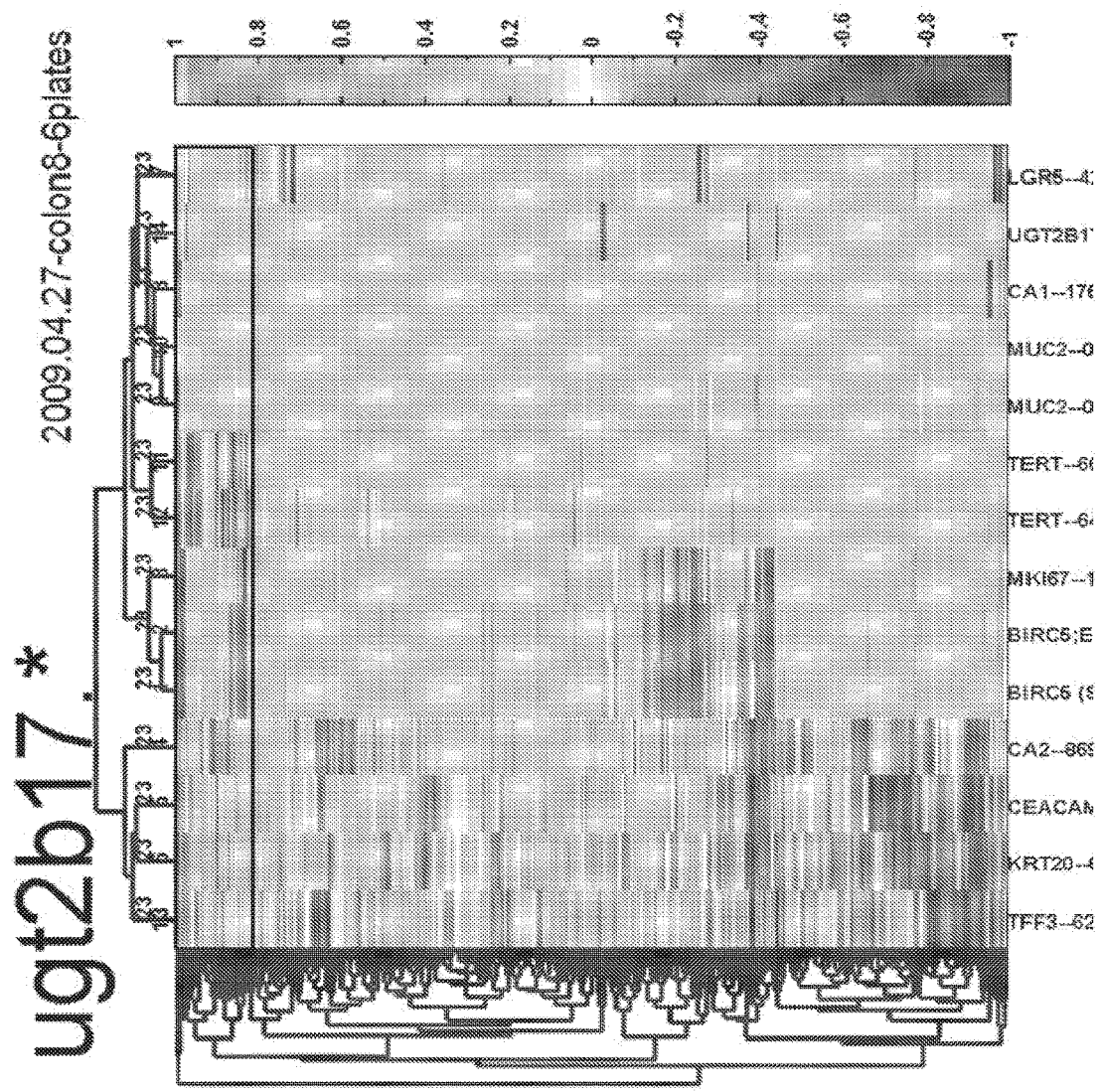

FIG. 184 UGT2B 17 expression in relation to TERT expression.

Figure 185:
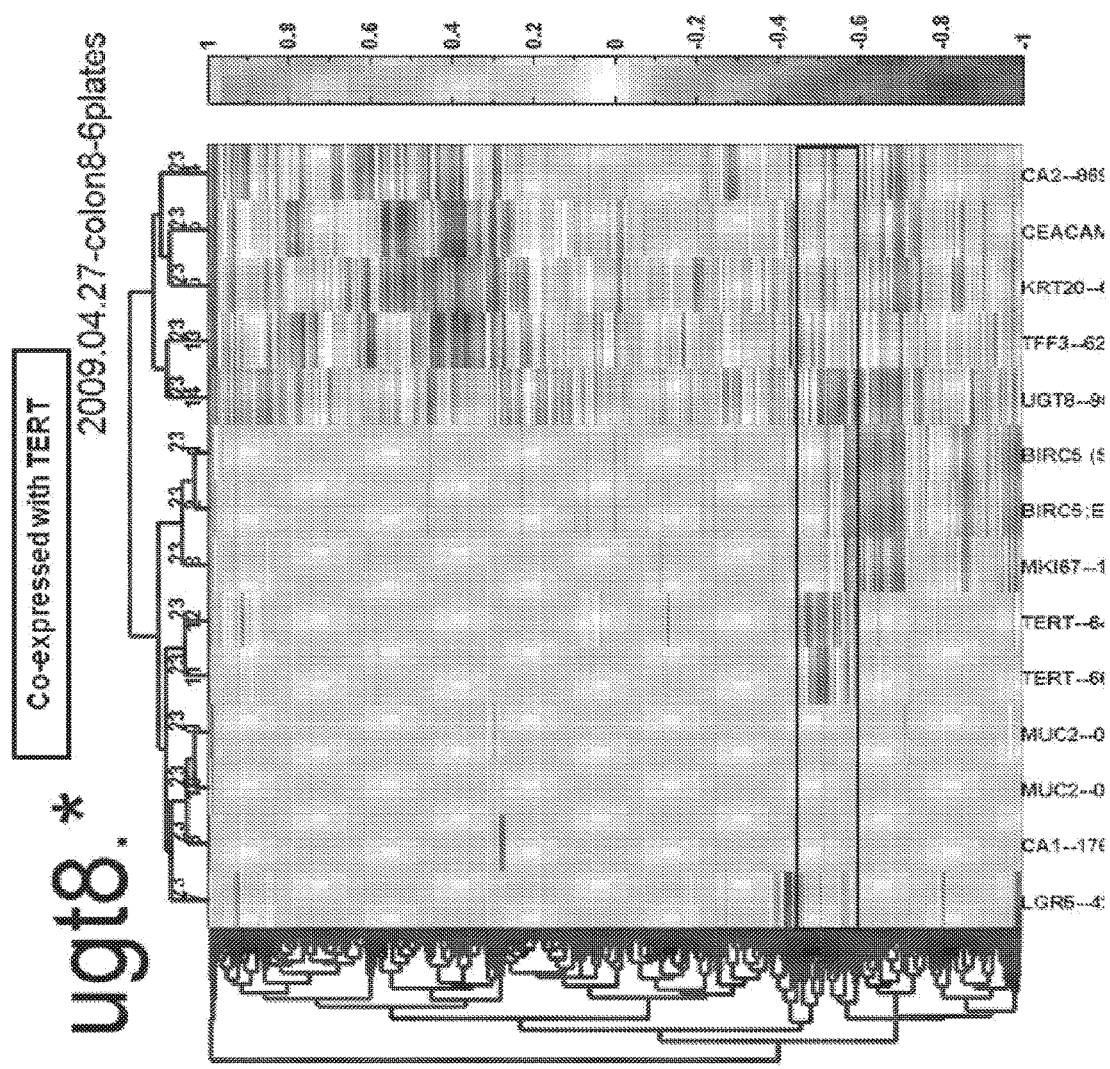

FIG. 185 UGT8 is co-expressed with TERT.

Figure 186:
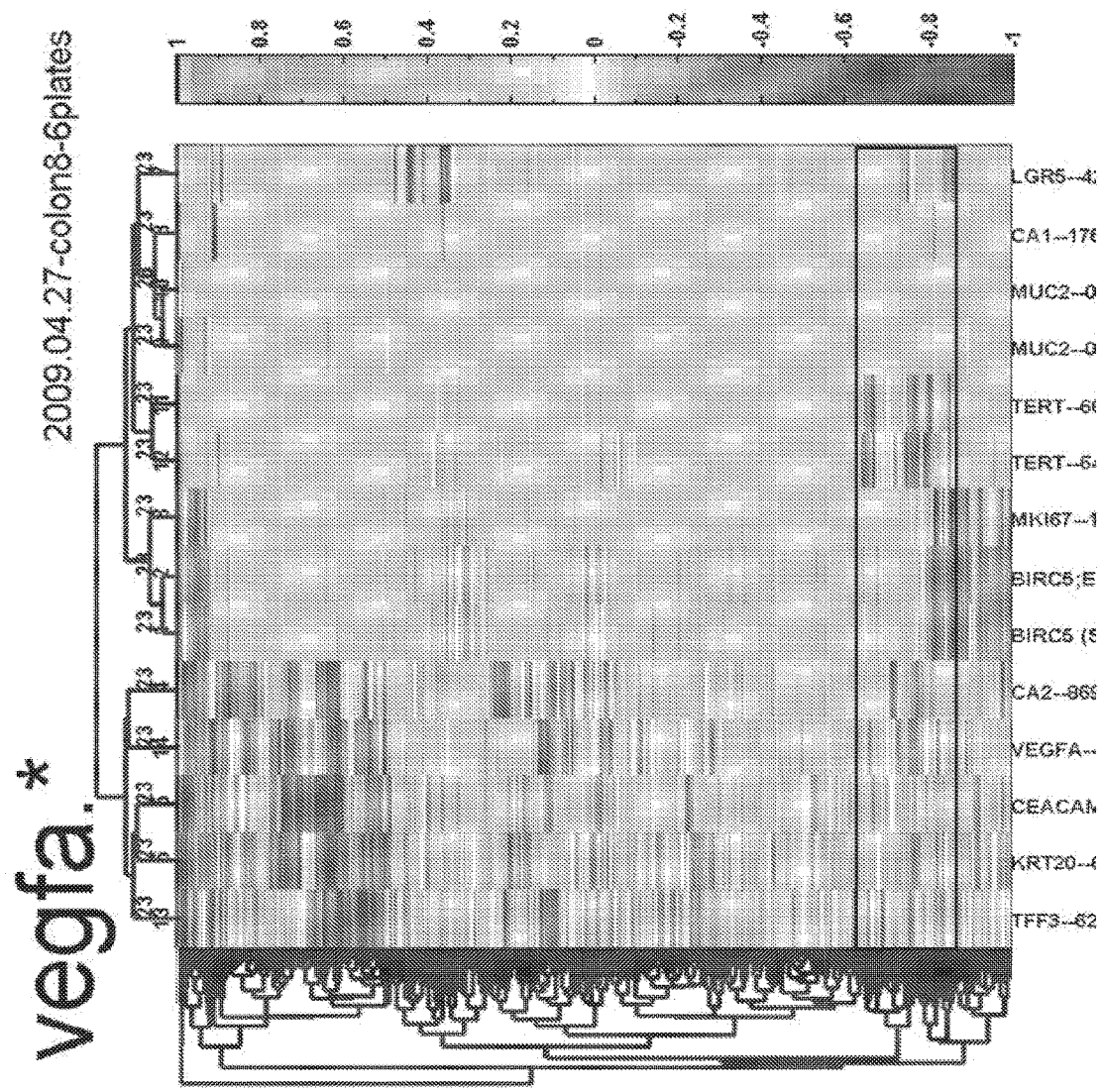

FIG. 186 VEGFA expression in relation to TERT expression.

Figure 187:
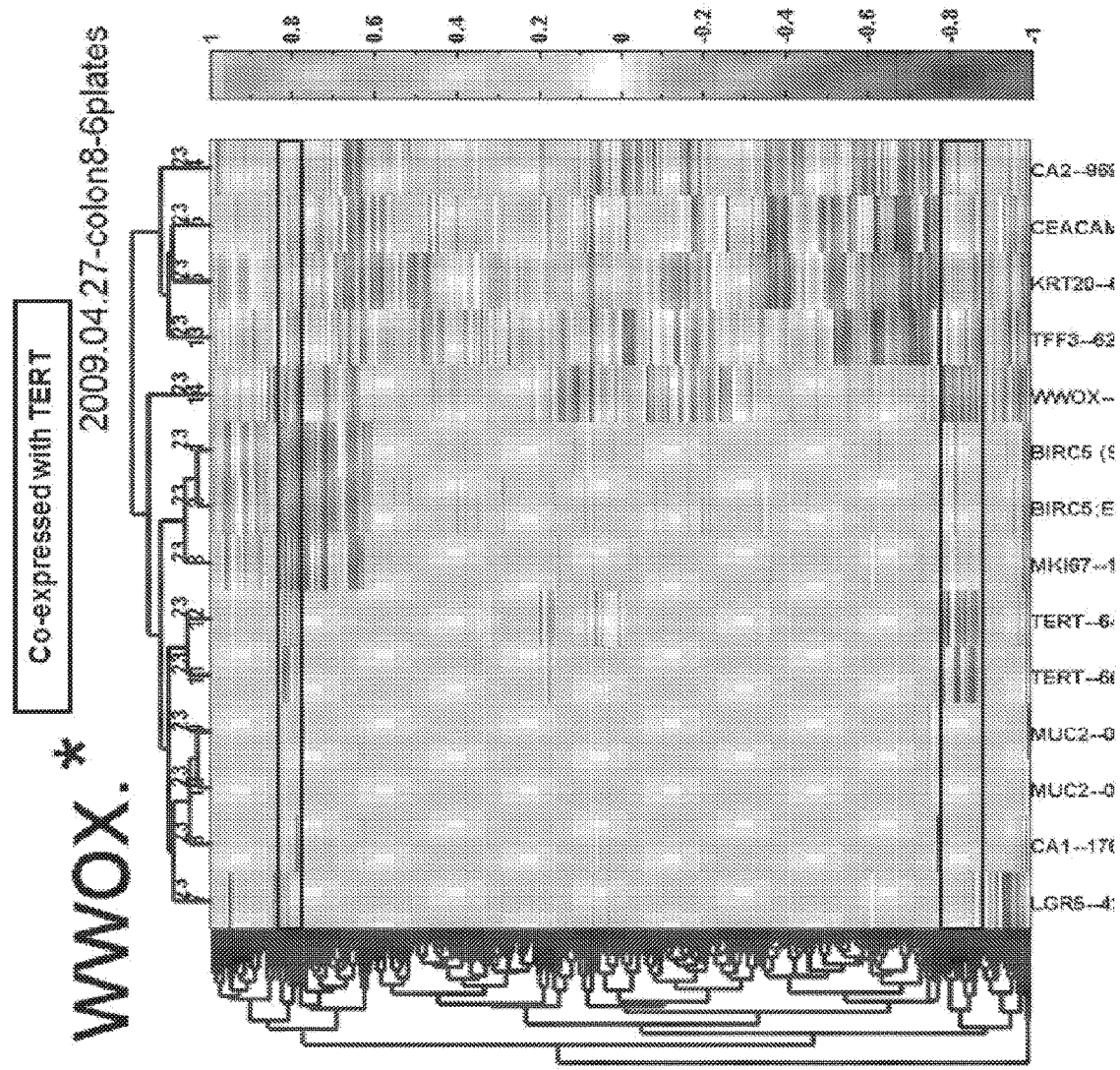

FIG. 187 WWOX is co-expressed with TERT.

Figure 188:
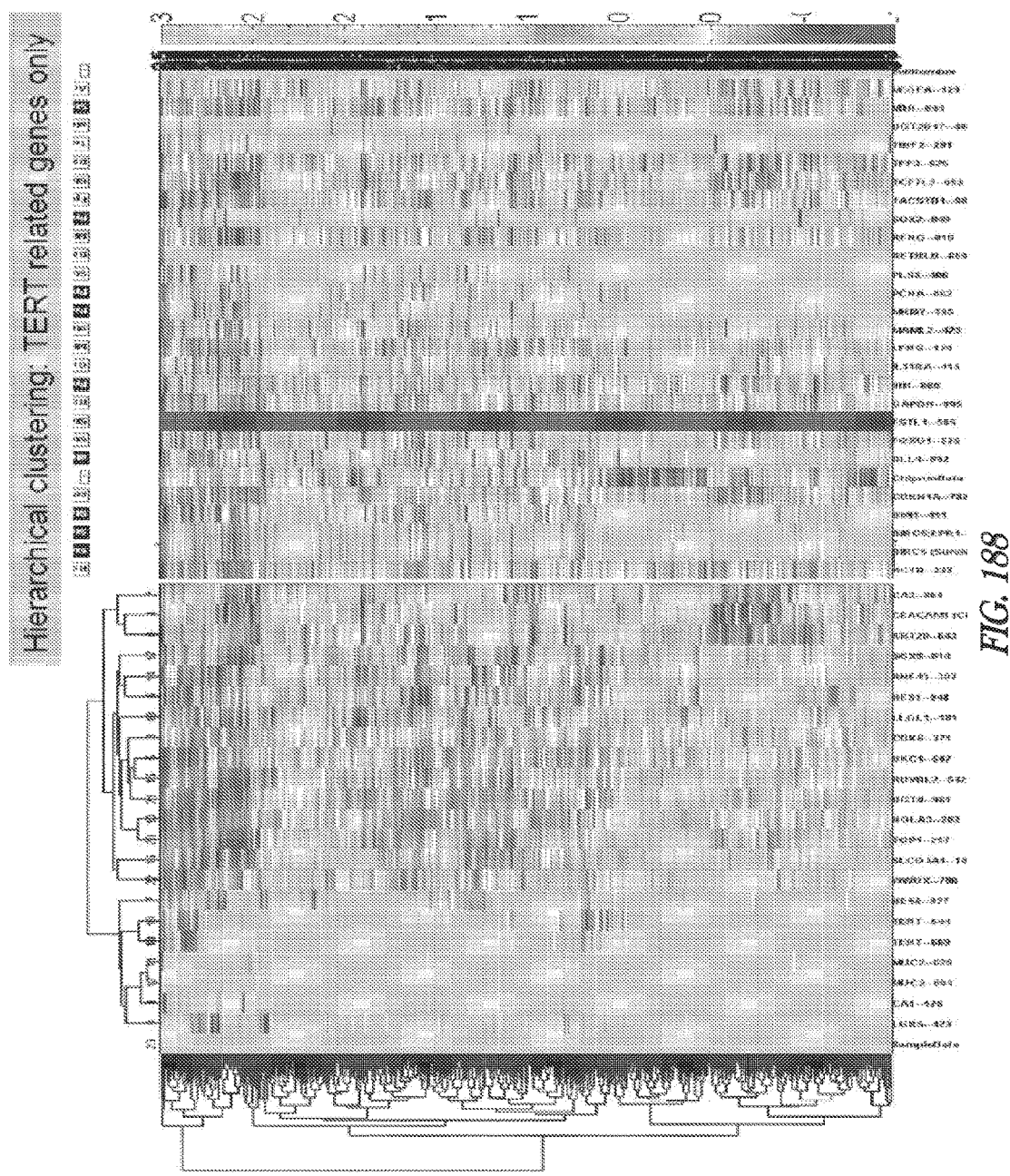

FIG. 188 hierarchical clustering showing only TERT-related gene.

Figure 189:
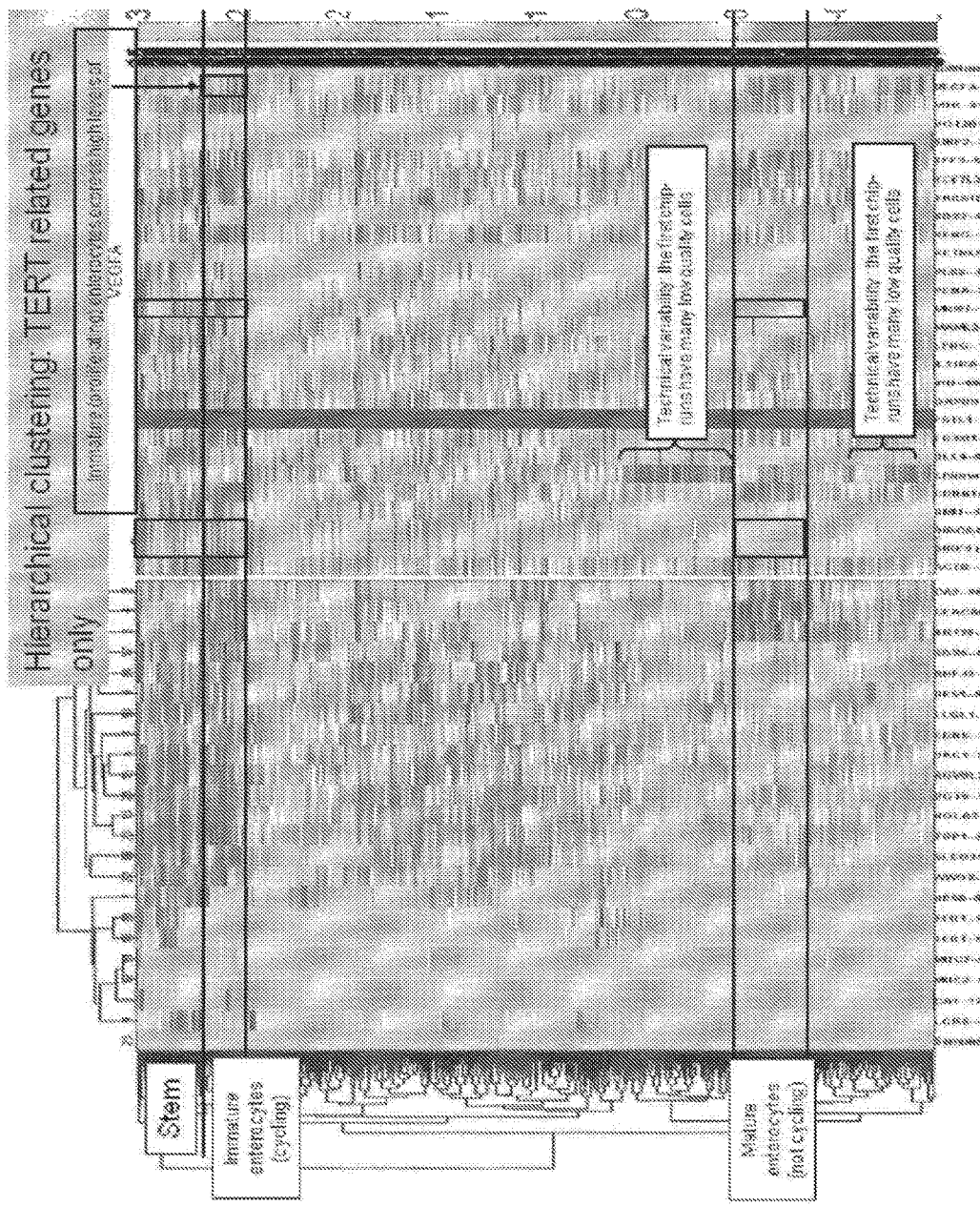

FIG. 189 hierarchical clustering showing only TERT-related gene. Cell types are shown.

Figure 190:
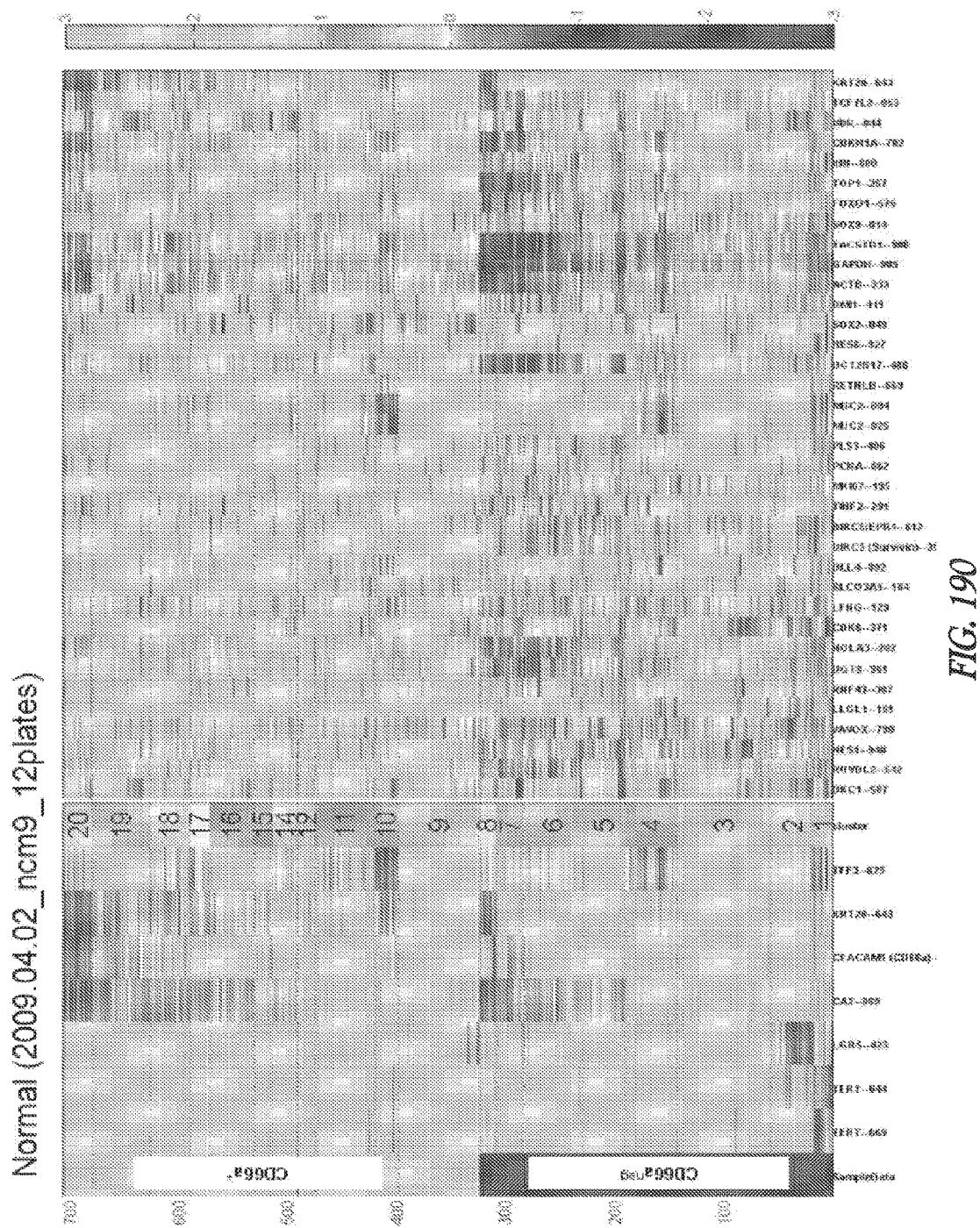

FIG. 190 hierarchical clustering comparing normal cells that are CD66a− population to CD66a+ population.

Figure 191:
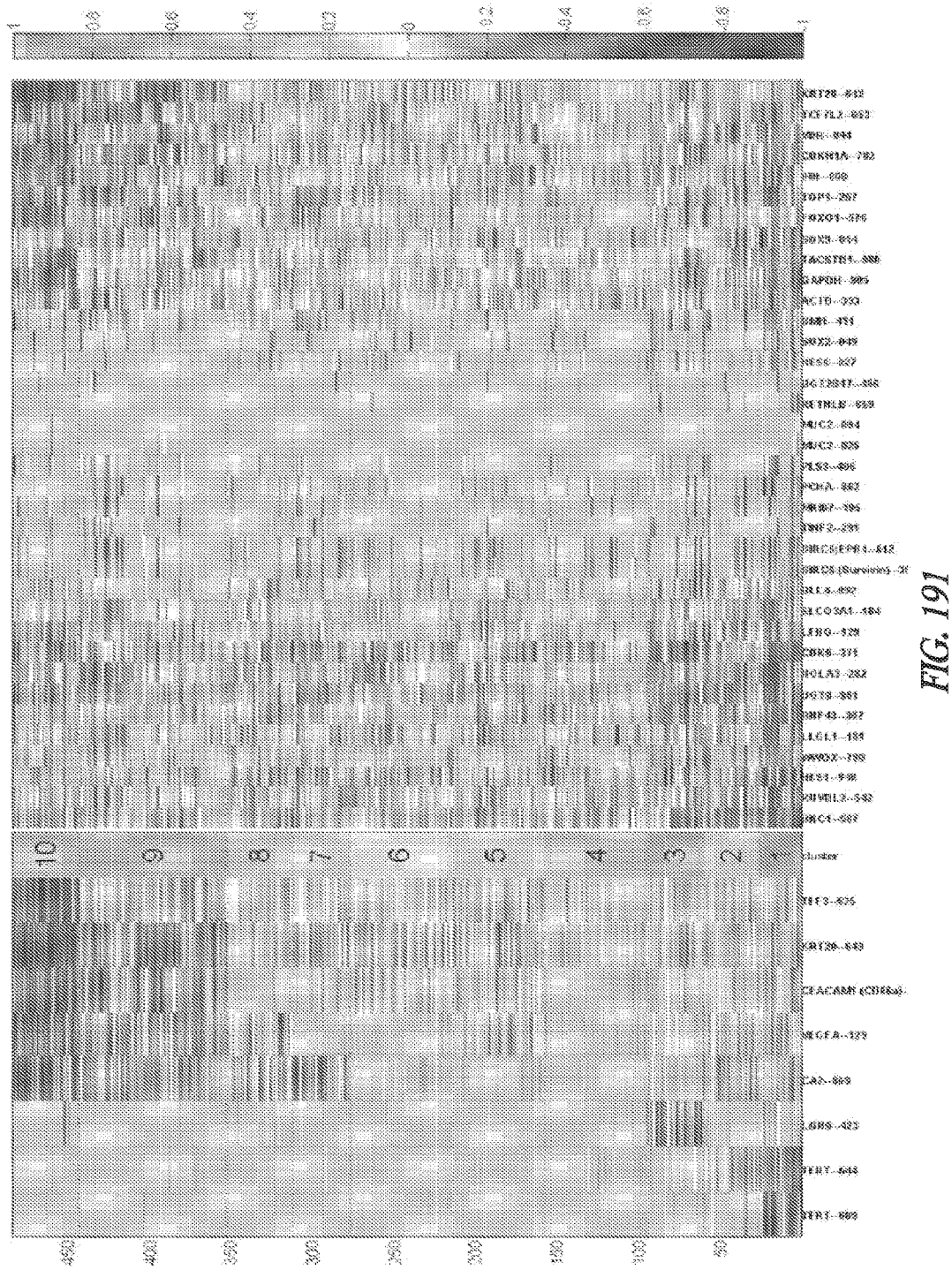

FIG. 191 hierarchical clustering comparing cancer cells that are CD66a− population to CD66a+ population.

Figure 192:
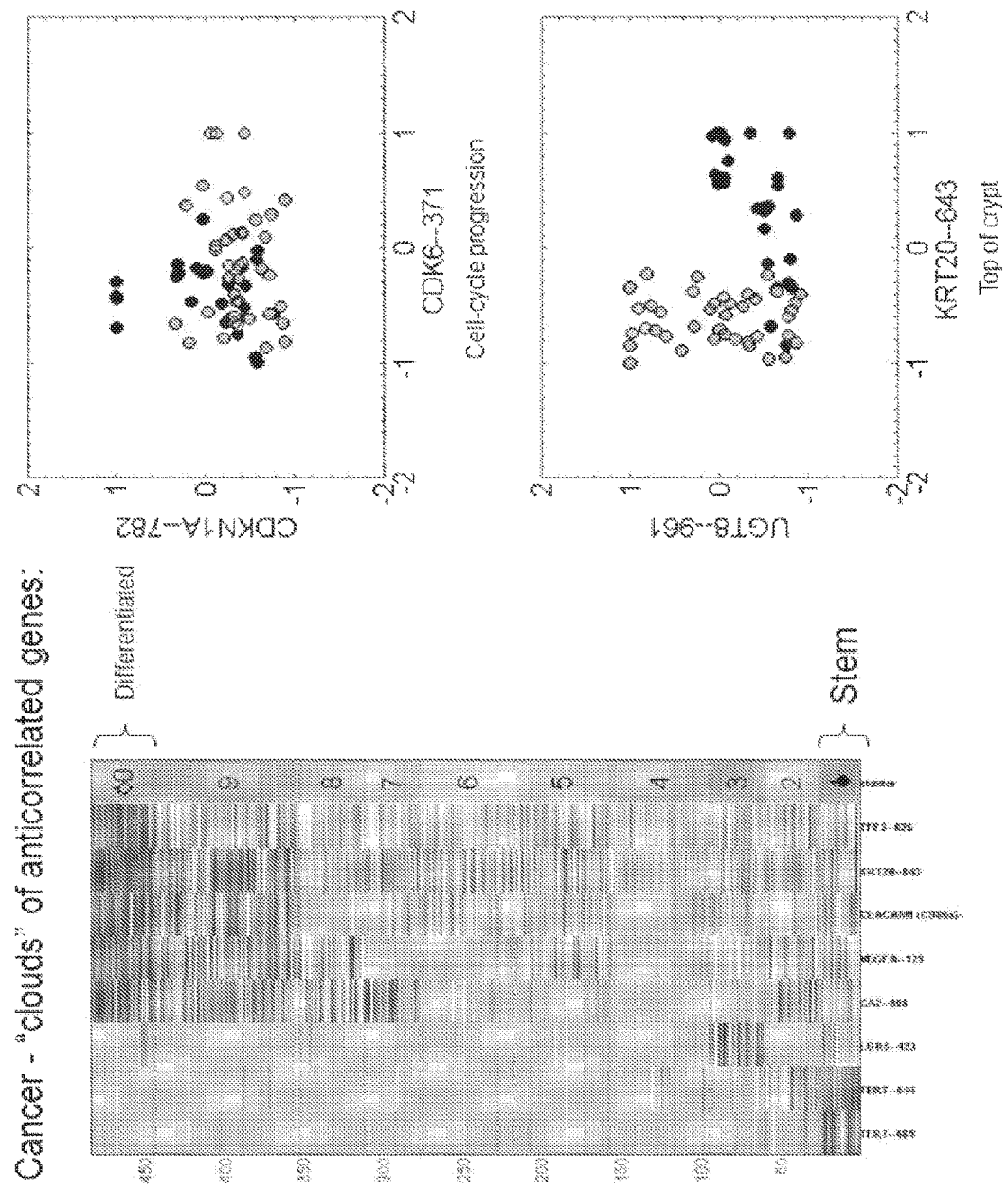

FIG. 192 hierarchical clustering, depicting anti-correlated gene pairs such as CDKN1A and CDK6, and KRT20 and UGT8.

Figure 193:
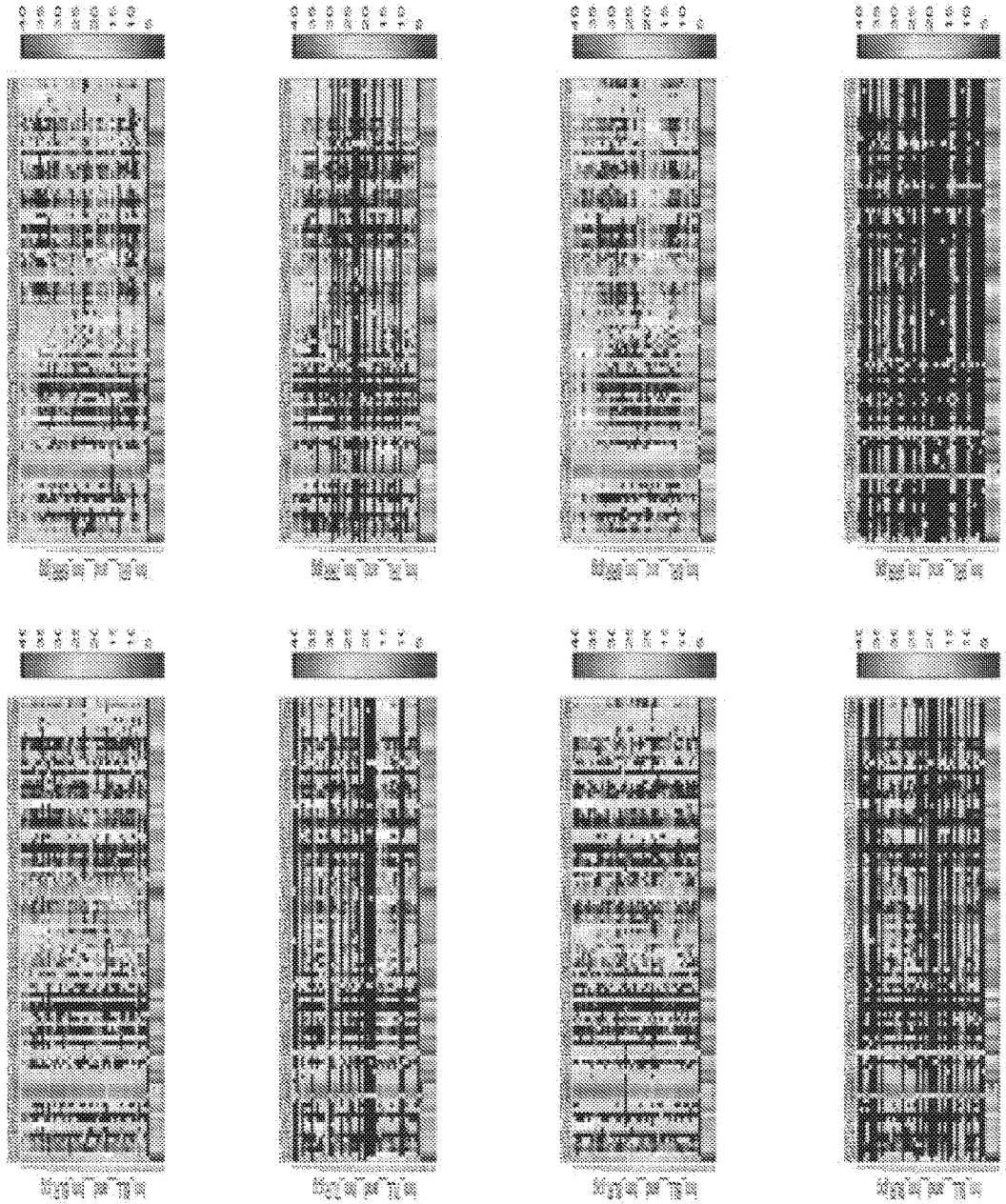

FIG. 193 heat maps from eight different chip-runs of samples. Cells were taken from xenograft (m10) of colon cells. The cells were FACS sorted with EGFP and CD66a. Mature non-tumorigenic cells were defined as EGFP+/CD66a+ cells. CoCSC cells were defined as EGFP+ cells.

Figure 194:
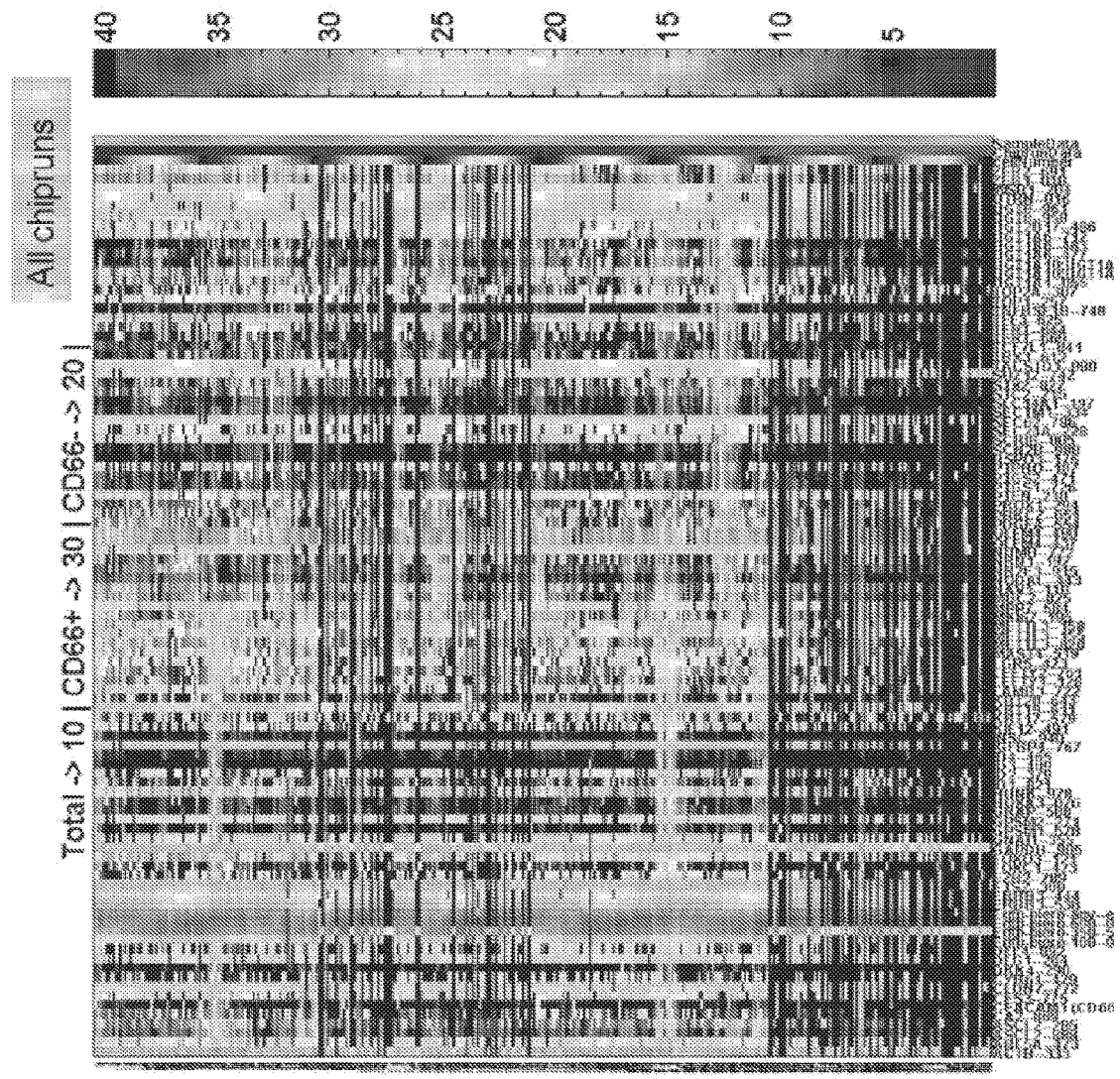

FIG. 194 a combined heat map comparing the eight chip-runs.

Figure 195:
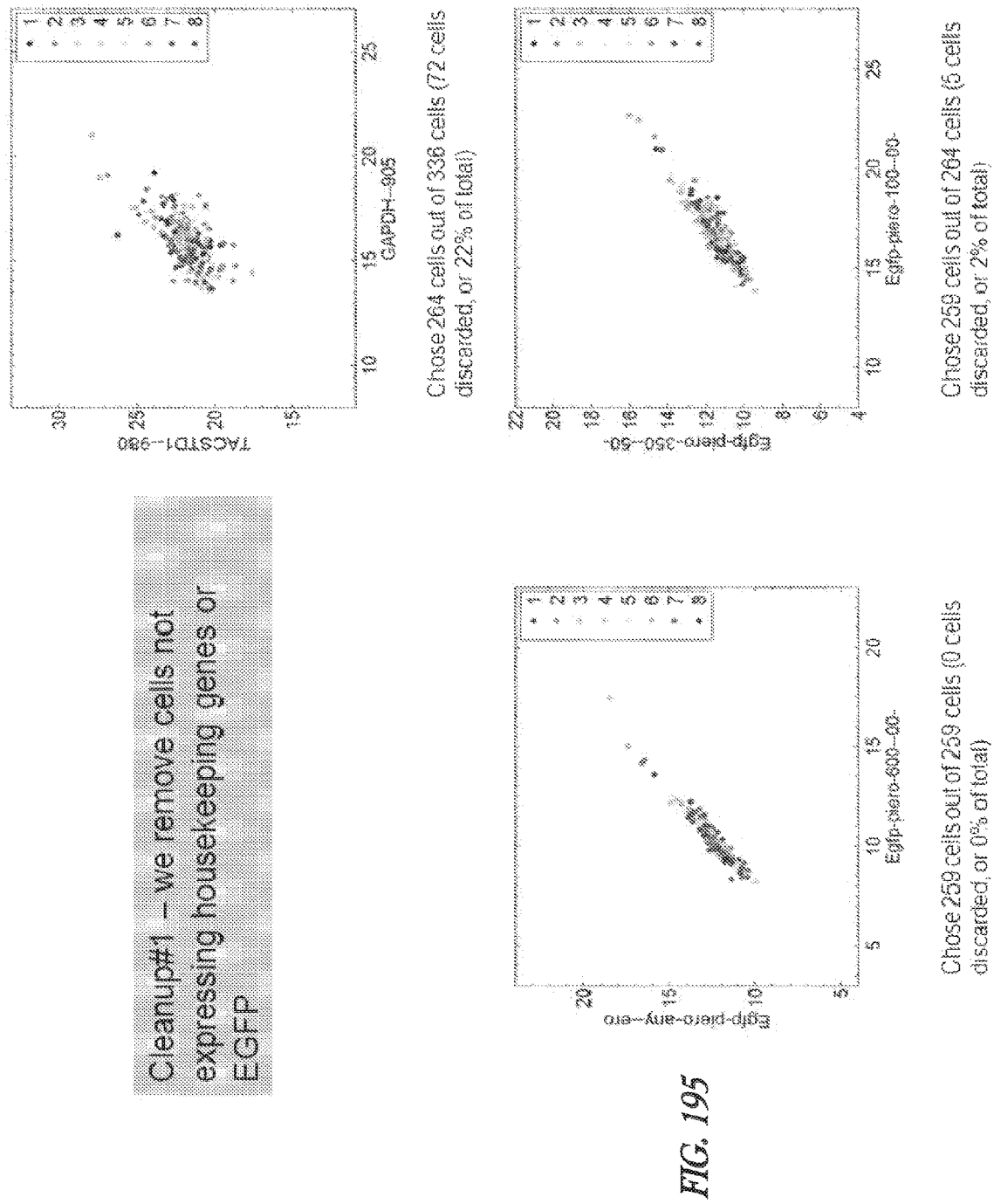

FIG. 195 selection of cells for single cell gene expression analysis. Out of 336 cells tested, 72 cells were discarded, by examining GAPDH and TACSTD1 gene expression levels, and 264 cells were selected. Of the 264 cells, 5 cells were further discarded by examining EGFP expression levels, and 259 cells were selected for further analysis.

Figure 196:
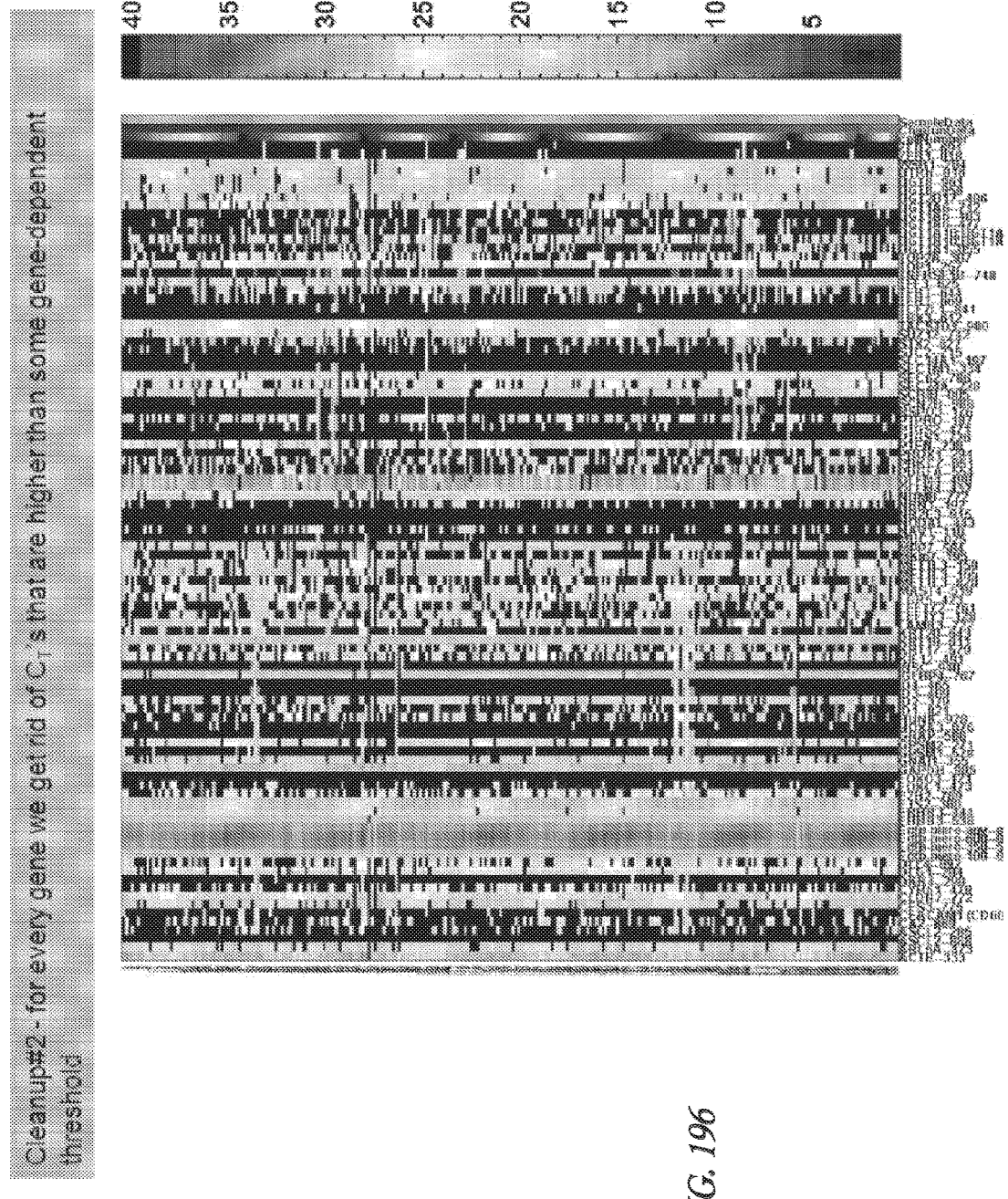

FIG. 196 further removal of cells that for every gene, where $C_T$ values are higher than some gene-dependent threshold, the cells were removed.

Figure 197:

FIG. 197 that all colon cells were confirmed to express EGFP.

Figure 198:
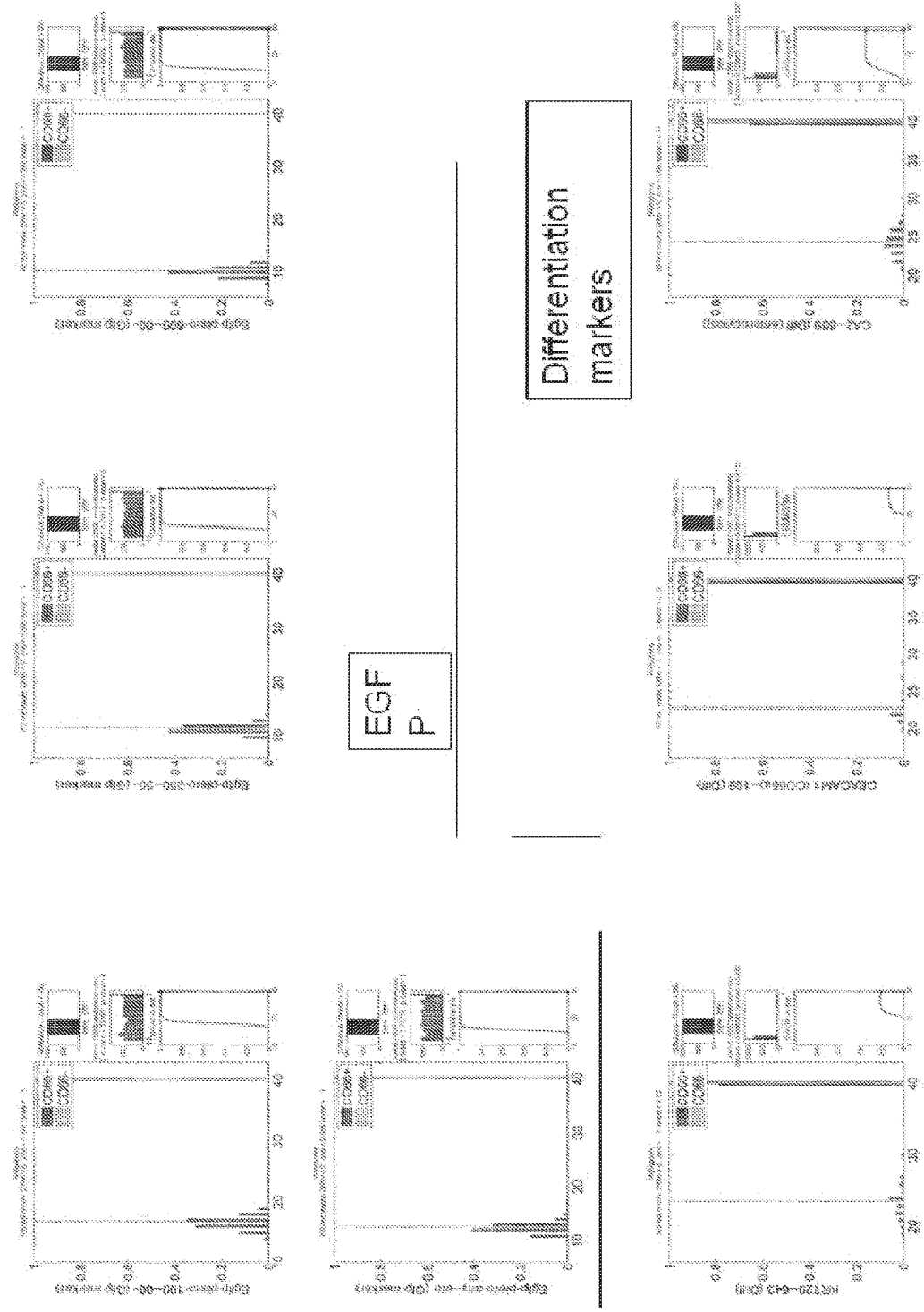

FIG. 198 histograms depicting gene expression levels of EGFP, KRT20, CD66A, and CA2

Figure 199:
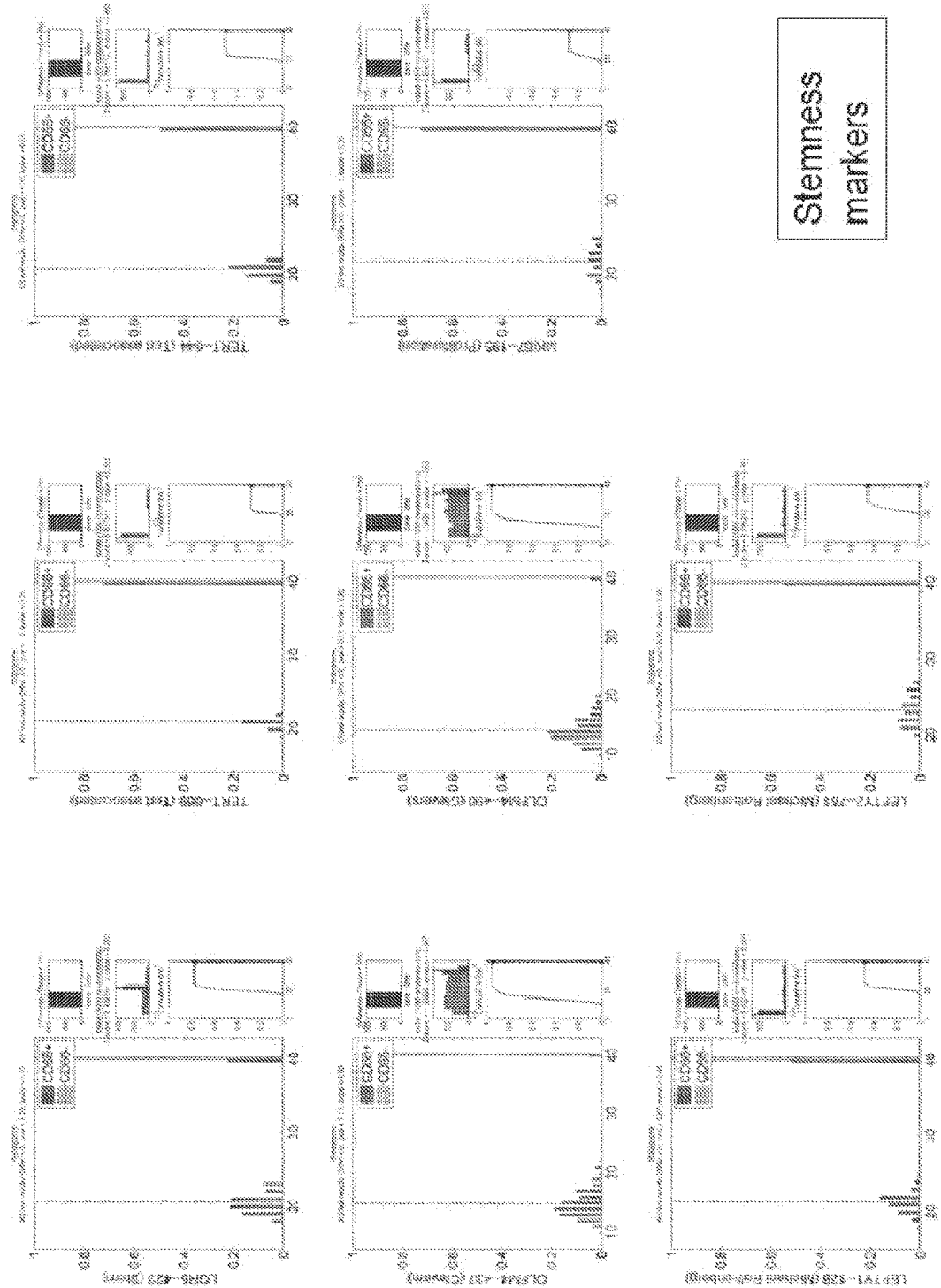

FIG. 199 histograms depicting gene expression levels of, LGR5, TERT, OLFM4, MK167, LEFGY1, and LEFTY2.

Figure 200:
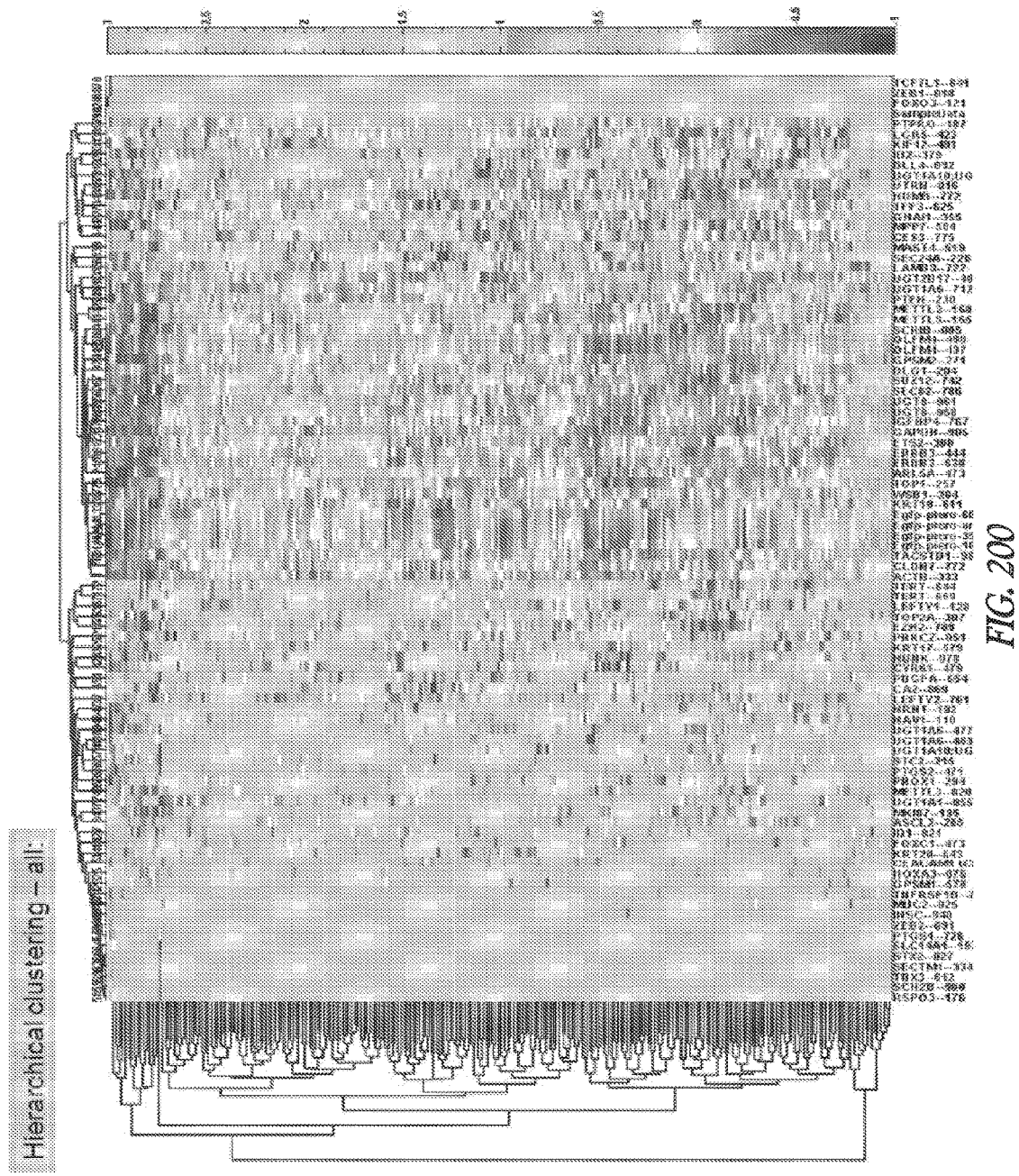

FIG. 200 hierarchical clustering of all genes.

Figure 201:
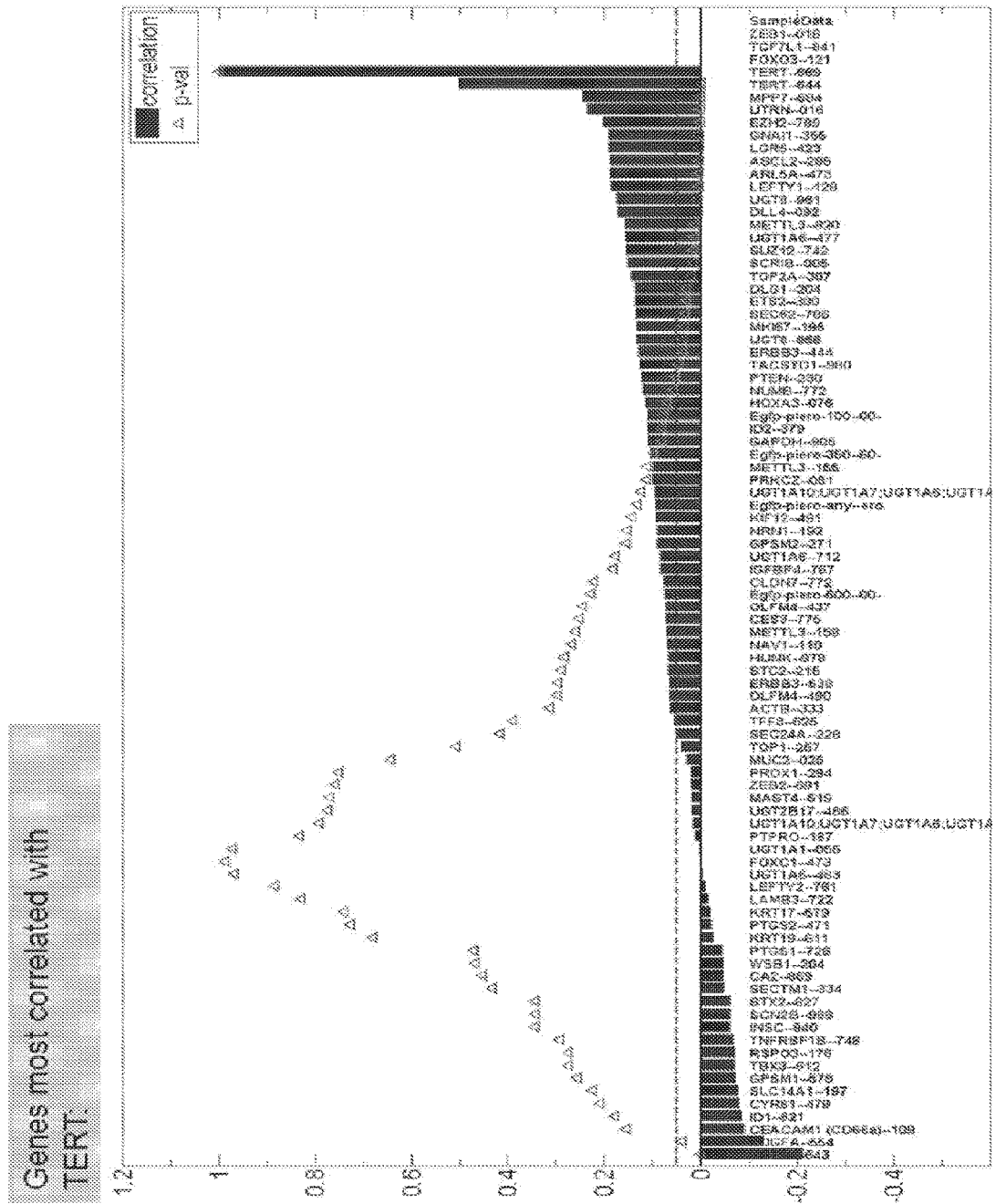

FIG. 201 gene expressions correlated to TERT expression.

Figure 202:
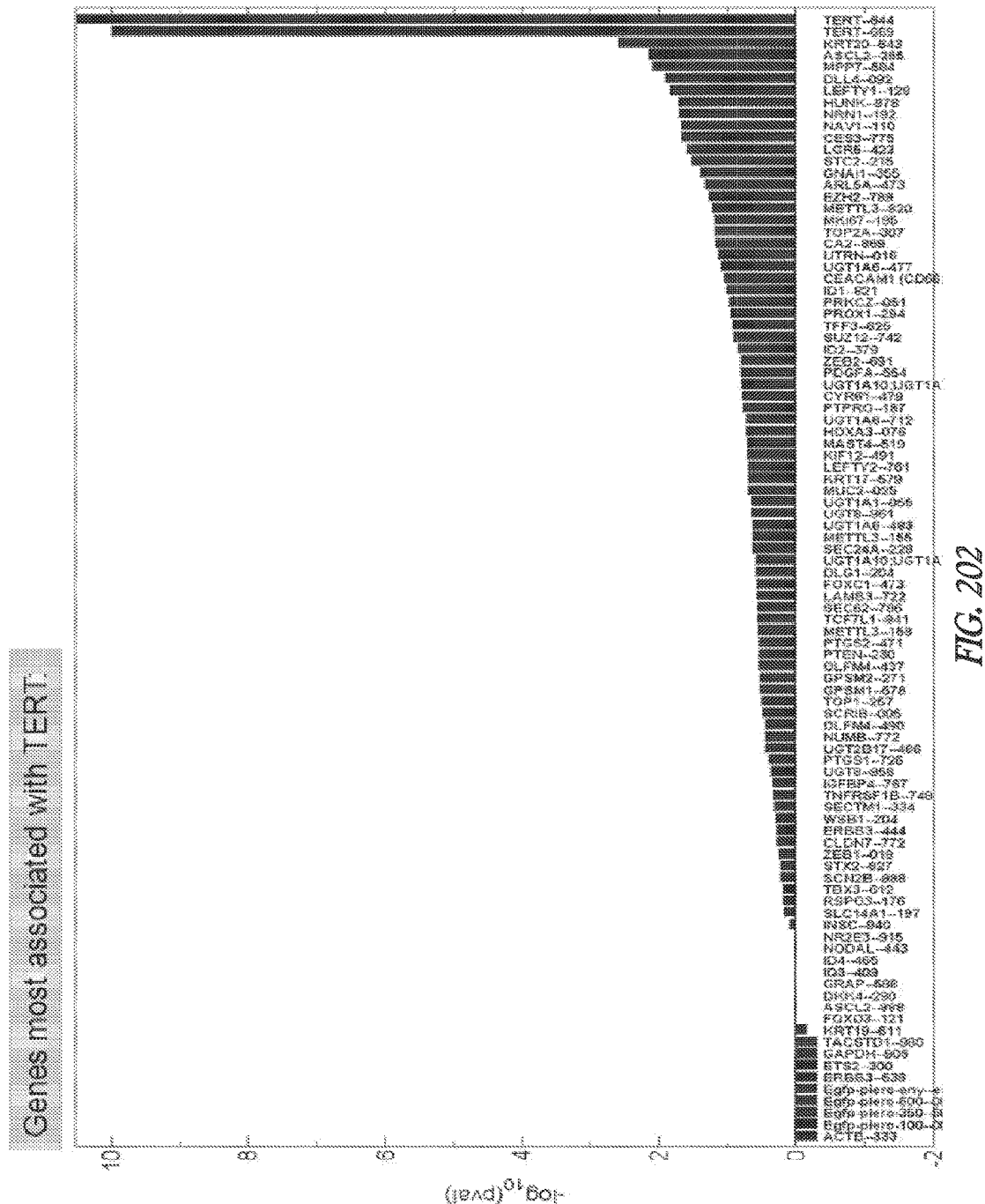

FIG. 202 gene expressions associated with TERT expression.

Figure 203:
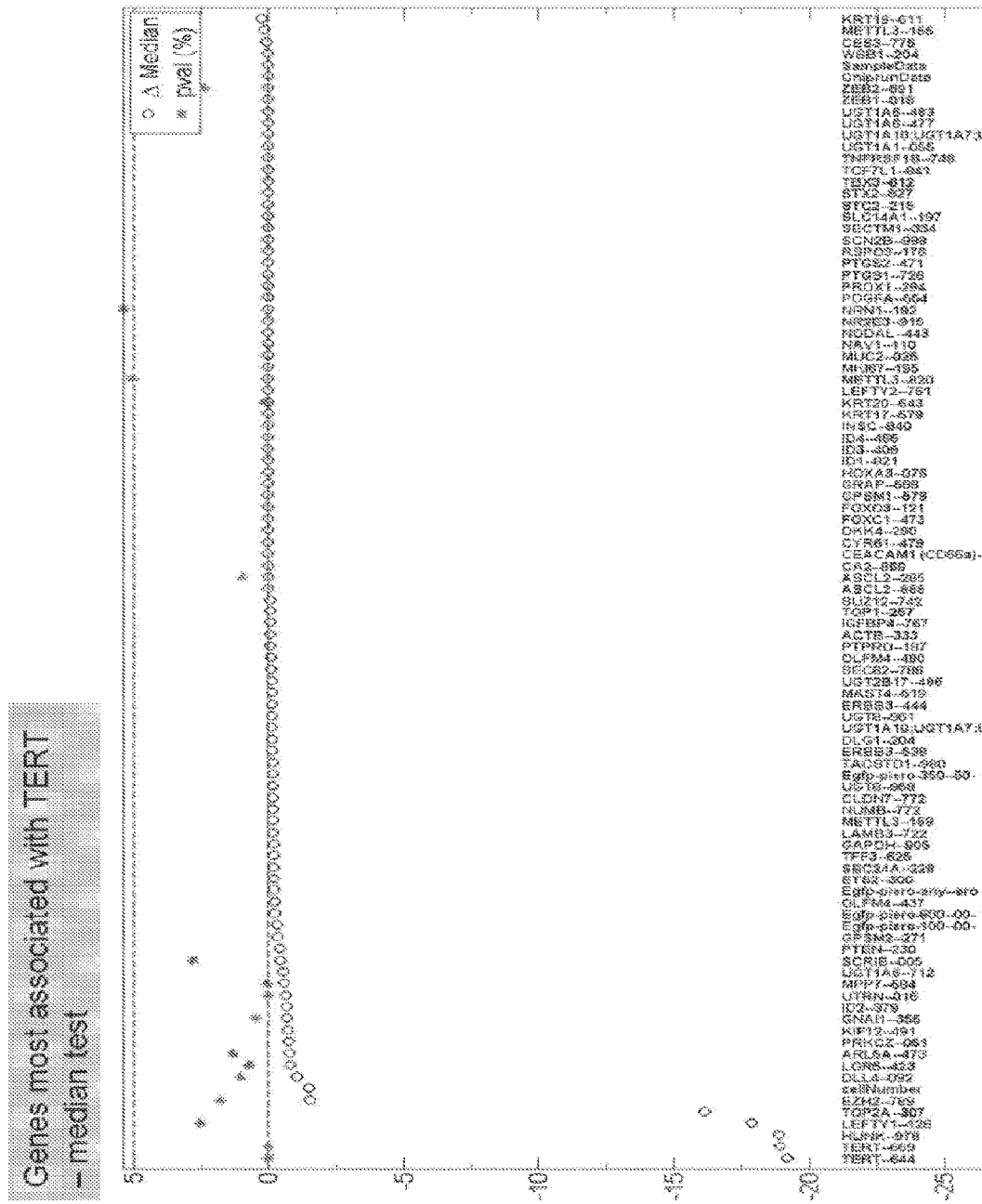

FIG. 203 gene expressions associated with TERT expression using median value.

Figure 204:
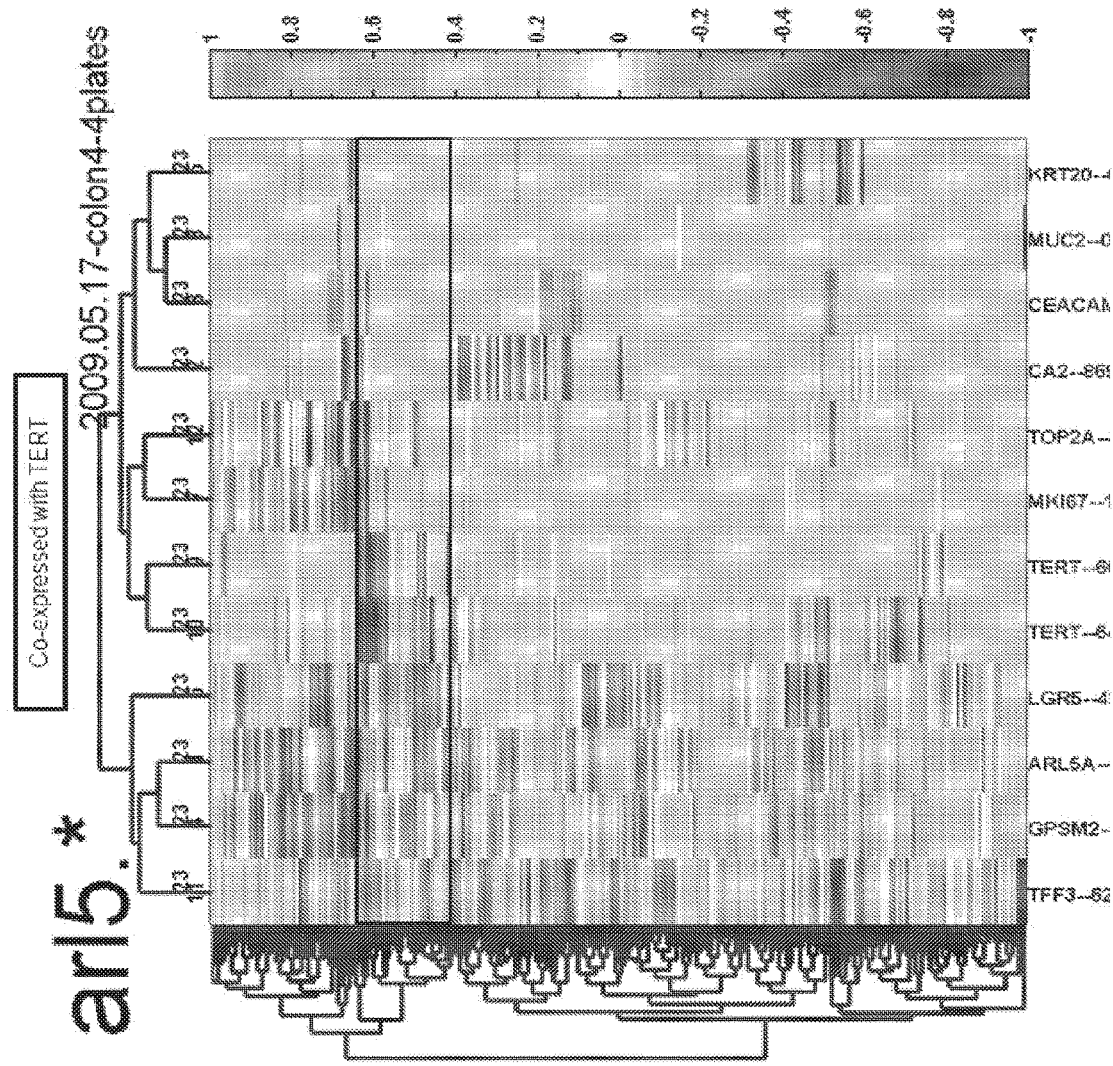

FIG. 204 ARL5 is co-expressed with TERT.

Figure 205:
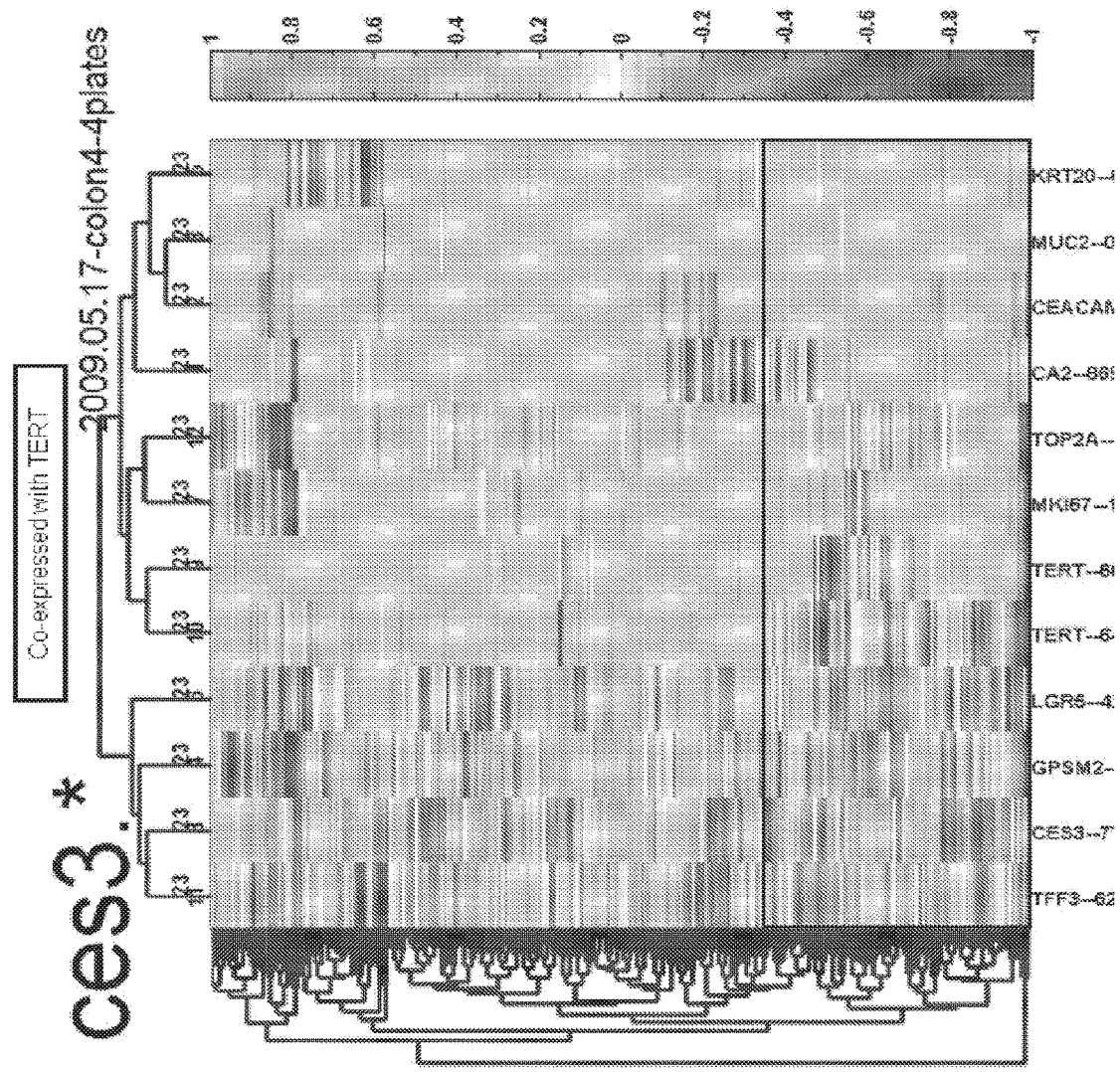

FIG. 205 CES3 is co-expressed with TERT.

Figure 206:
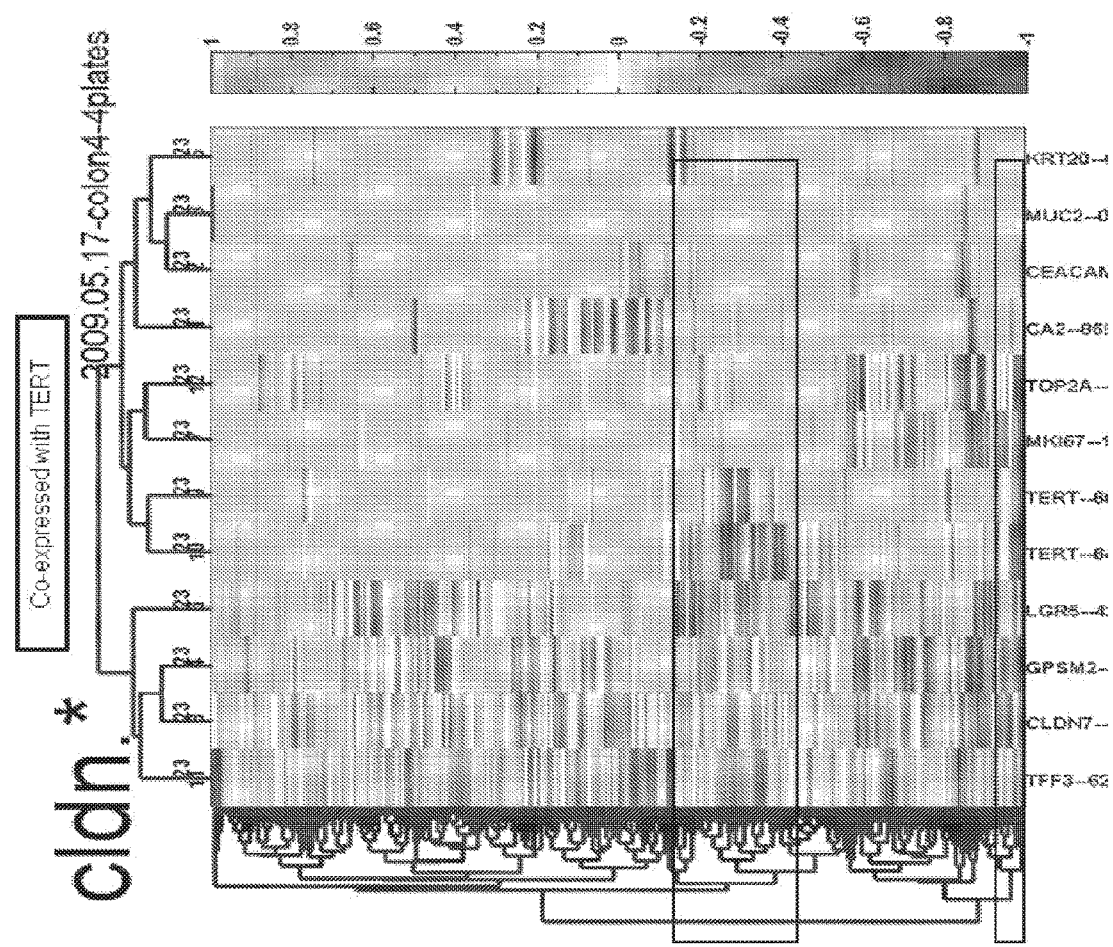

FIG. 206 CLDN is co-expressed with TERT.

Figure 207:
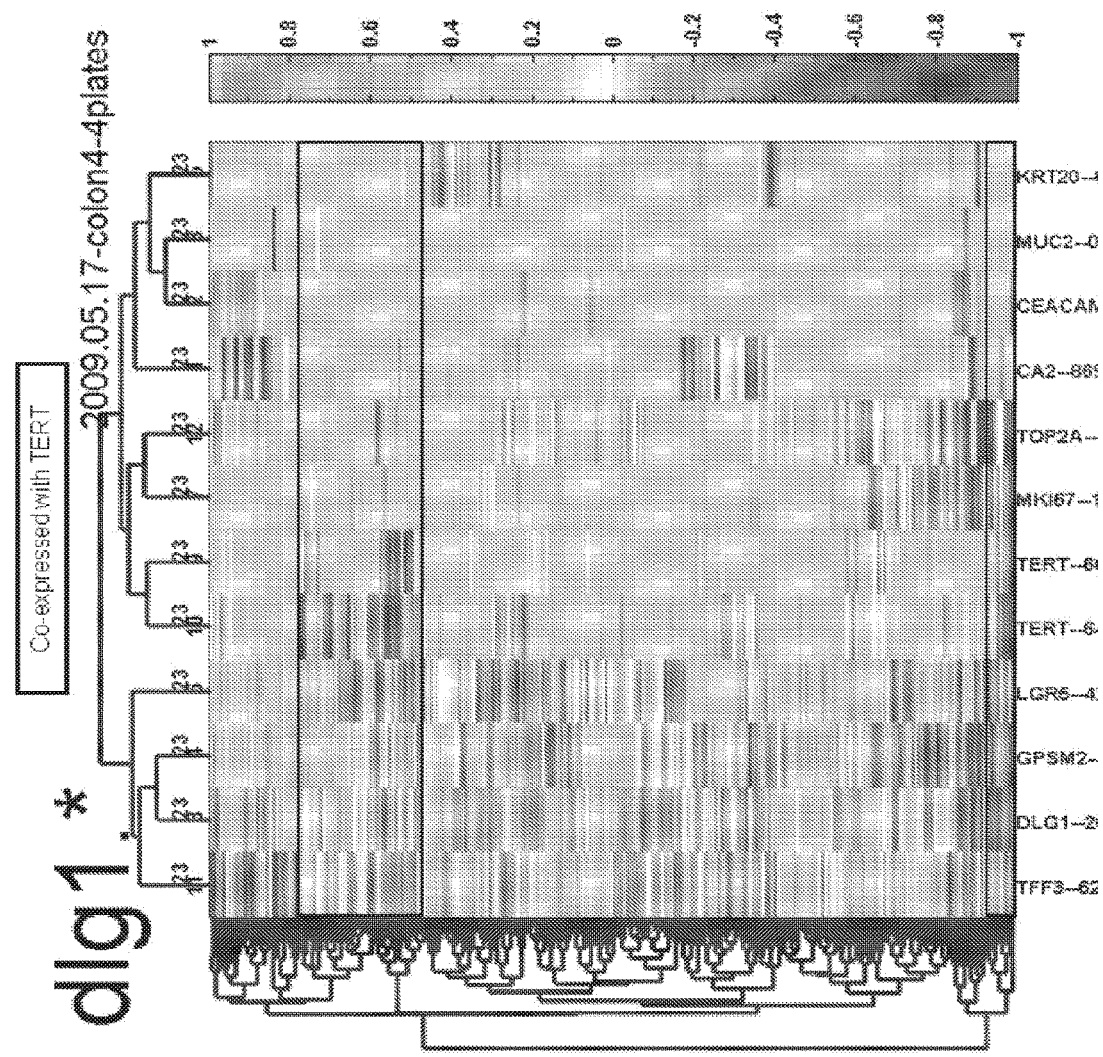

FIG. 207 DIG1 is co-expressed with TERT.

Figure 208:
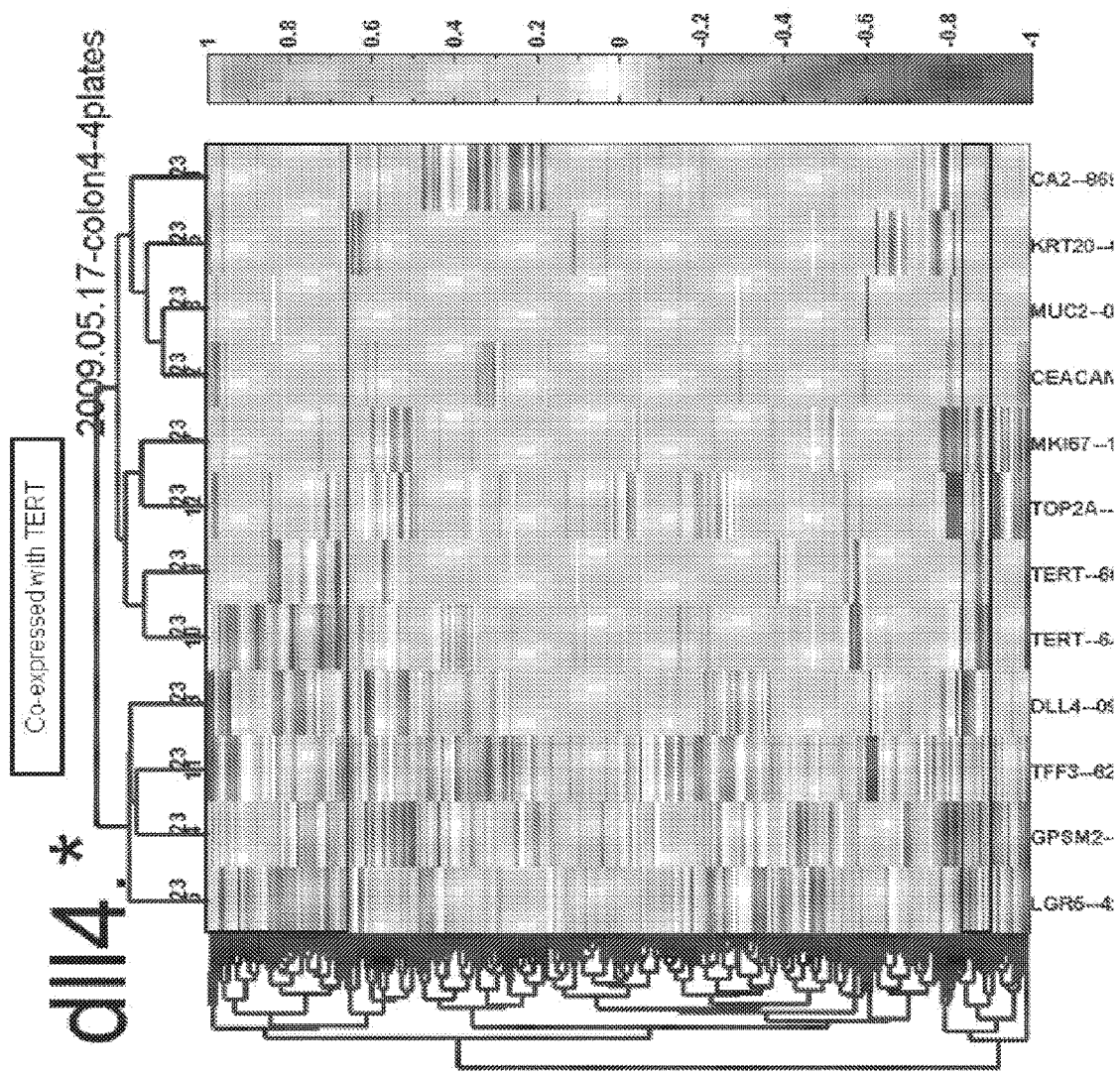

FIG. 208 DLL4 is co-expressed with TERT.

Figure 209:
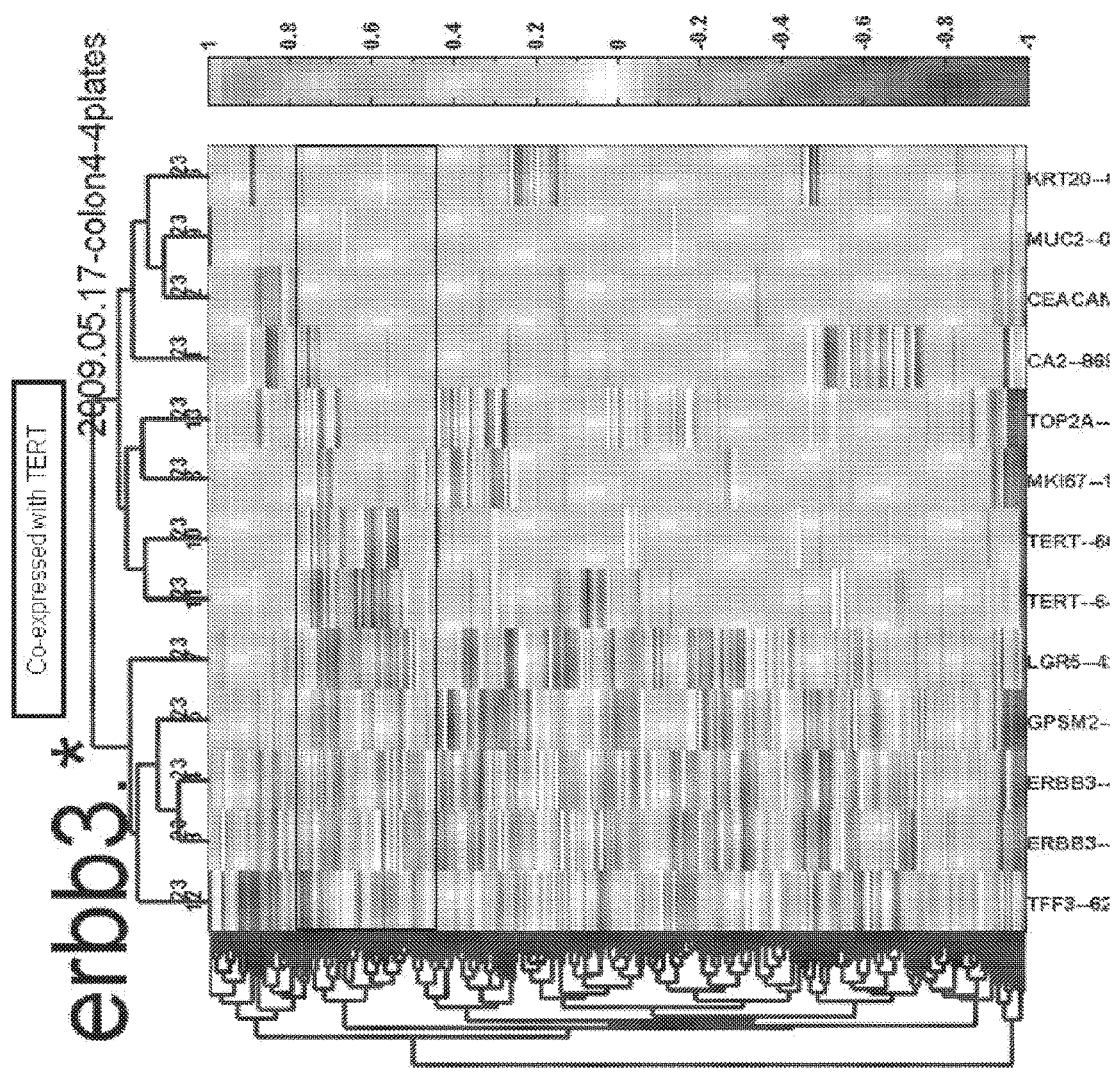

FIG. 209 ERBB3 is co-expressed with TERT.

Figure 210:
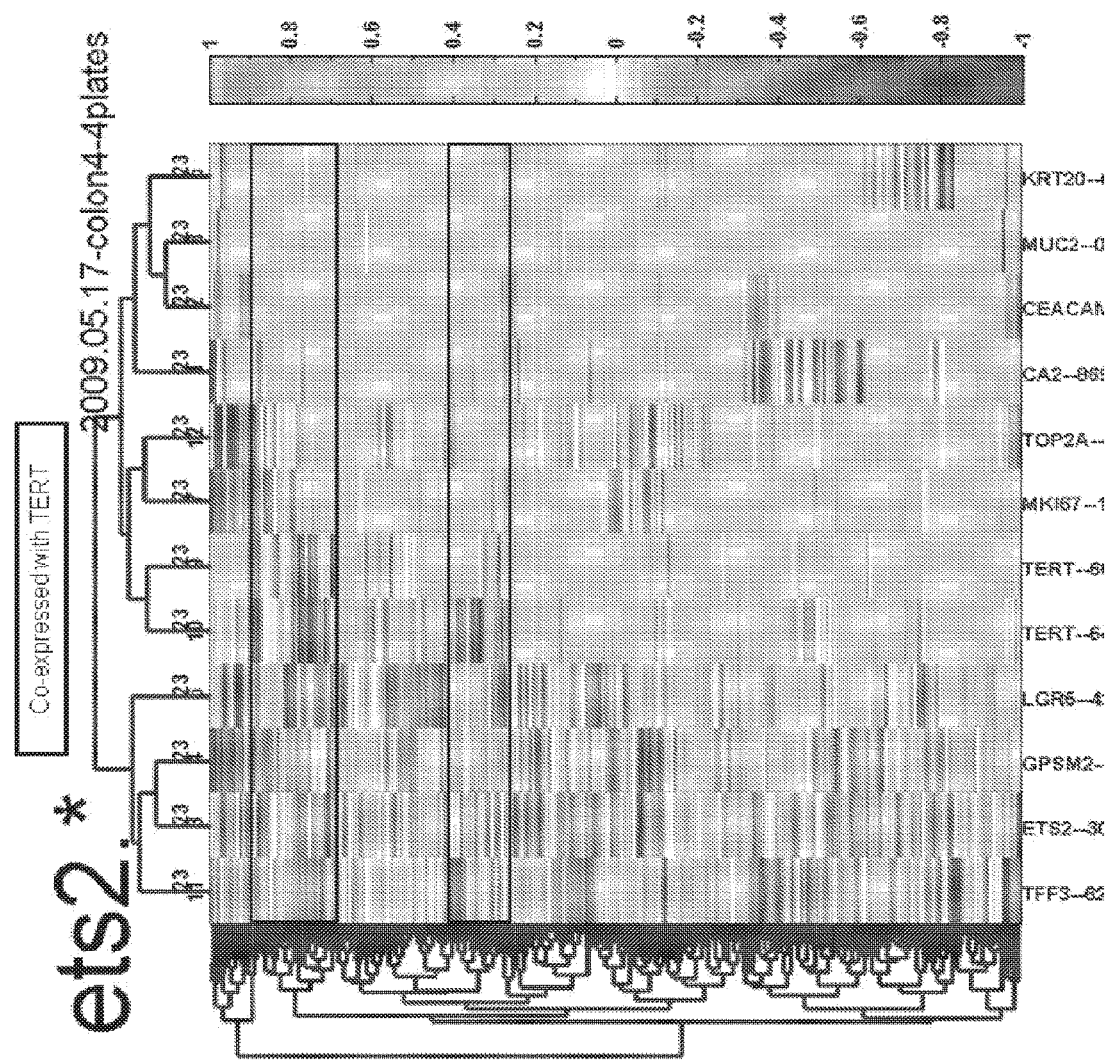

FIG. 210 ETS2 is co-expressed with TERT.

Figure 211:
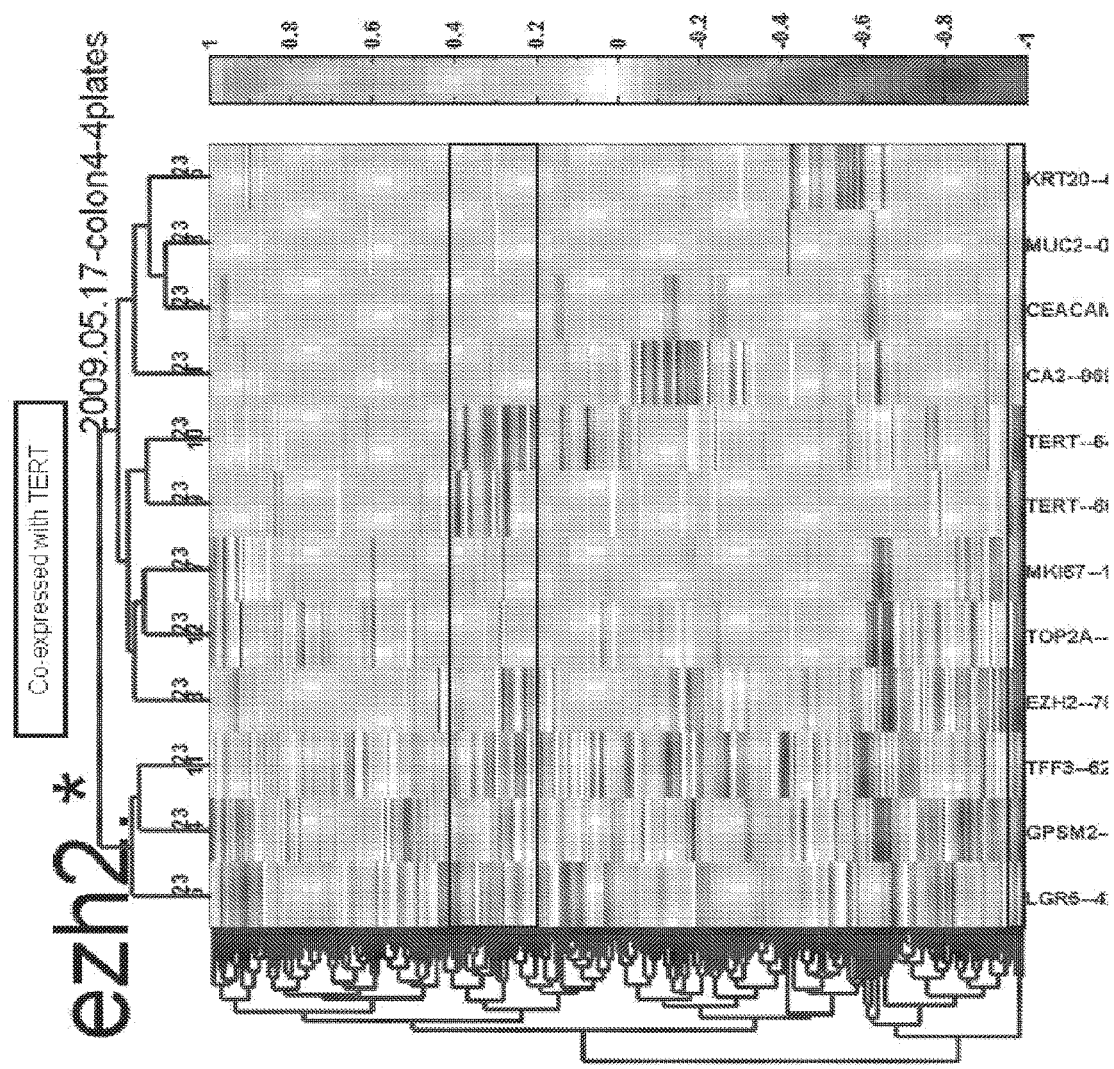

FIG. 211 EZH2 is co-expressed with TERT.

Figure 212:
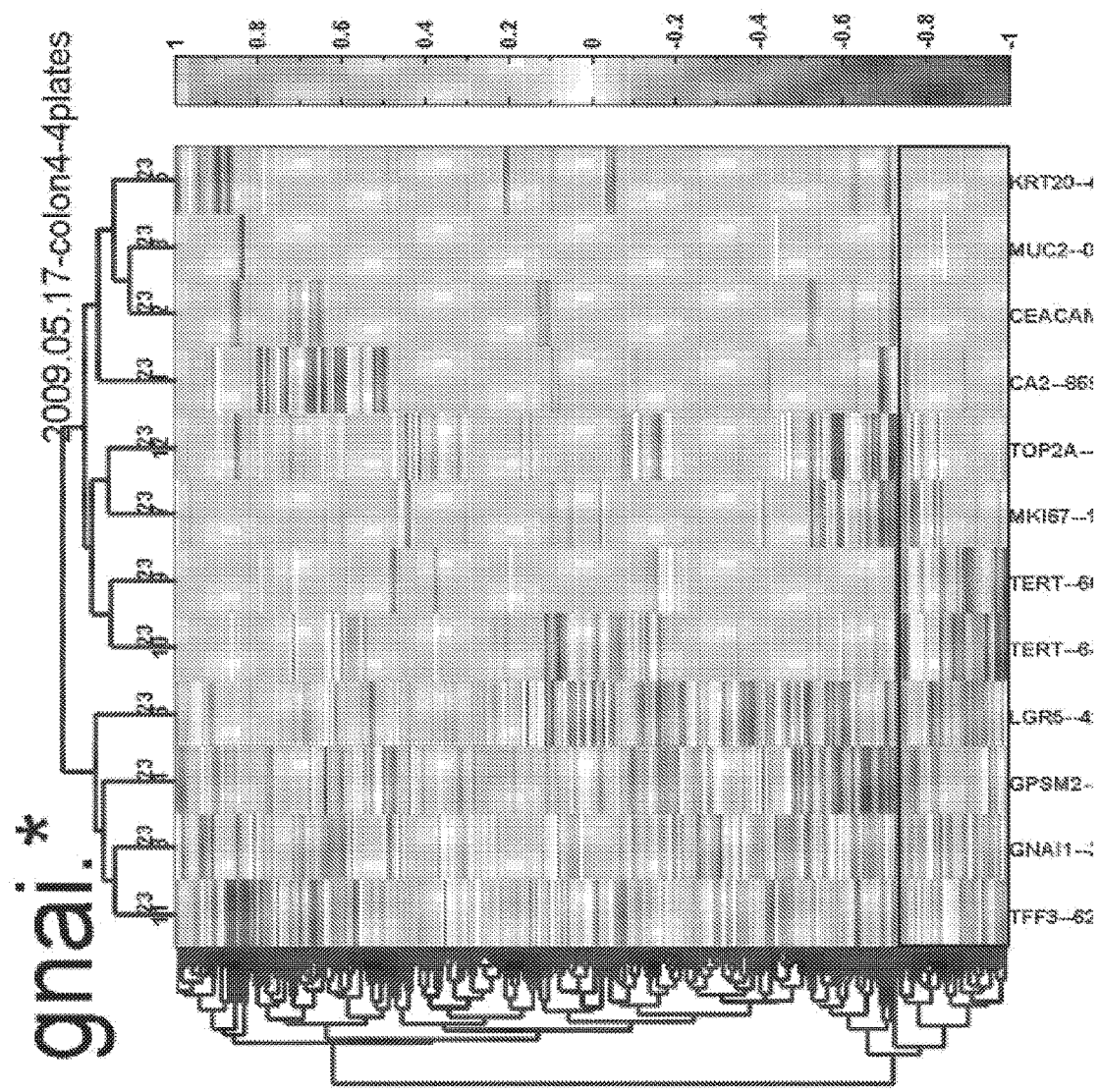

FIG. 212 GNAI expression in relation to TERT expression.

Figure 213:
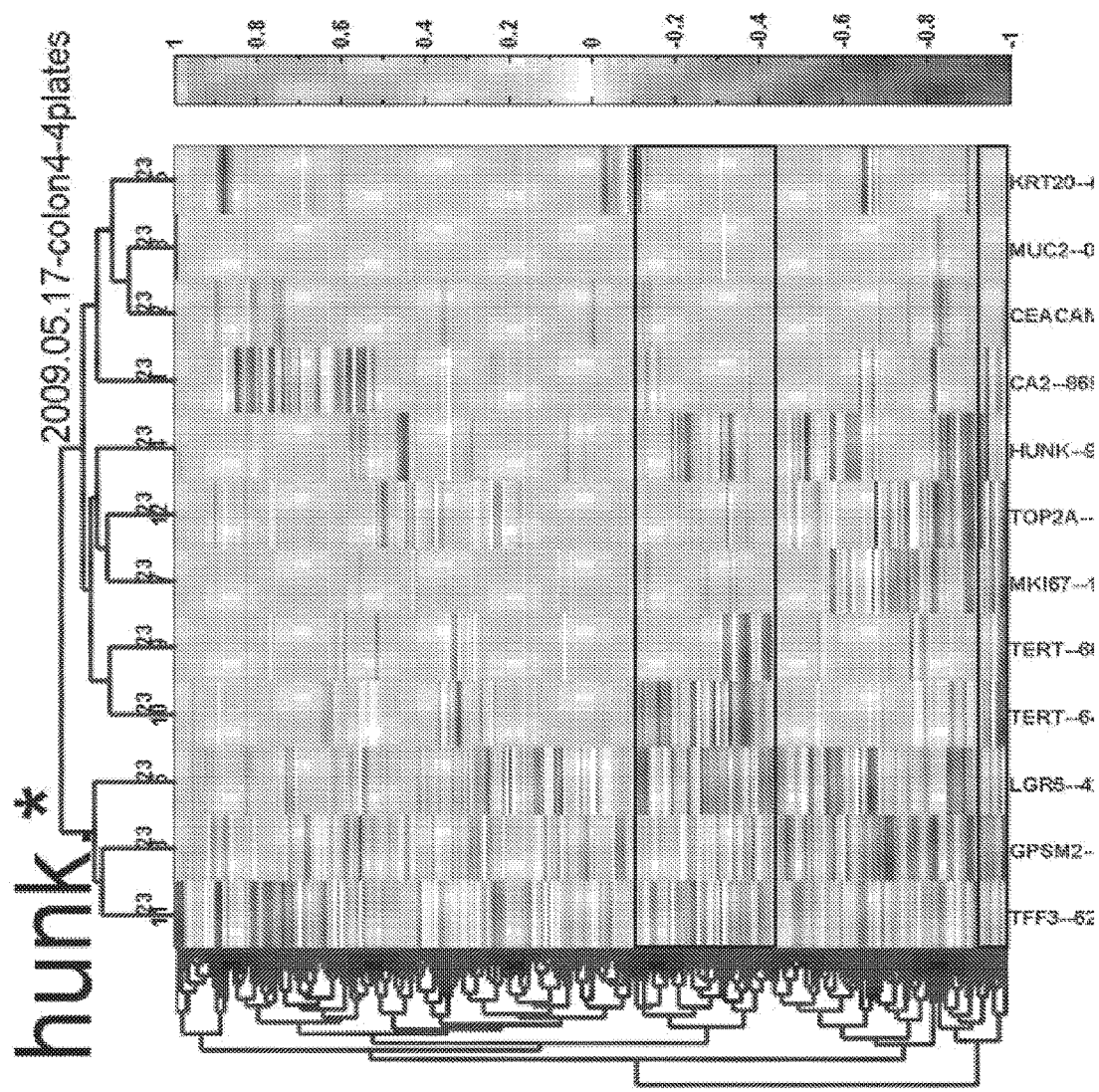

FIG. 213 HUNK expression in relation to TERT expression.

Figure 214:
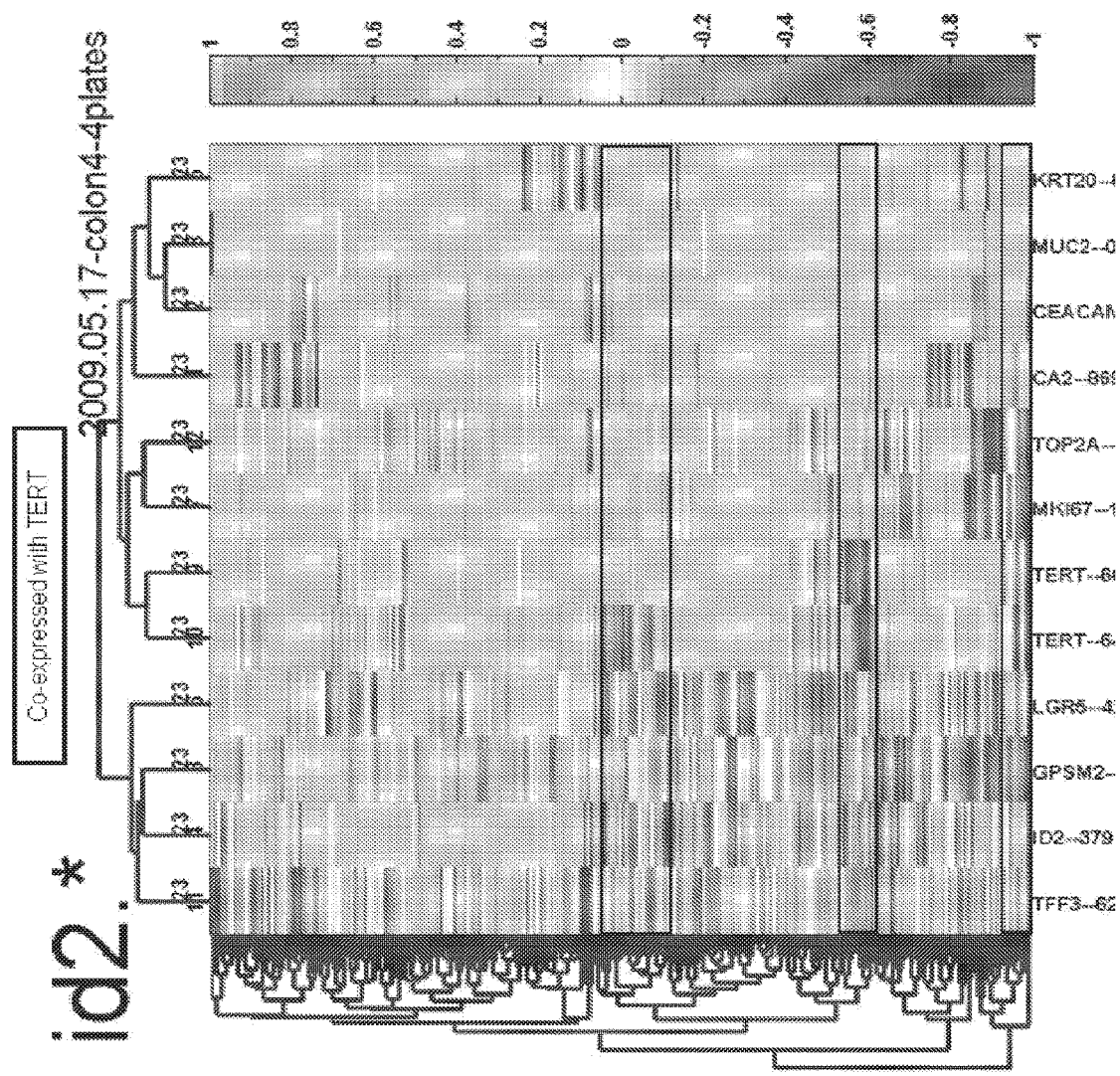

FIG. 214 ID2 is co-expressed with TERT.

Figure 215:
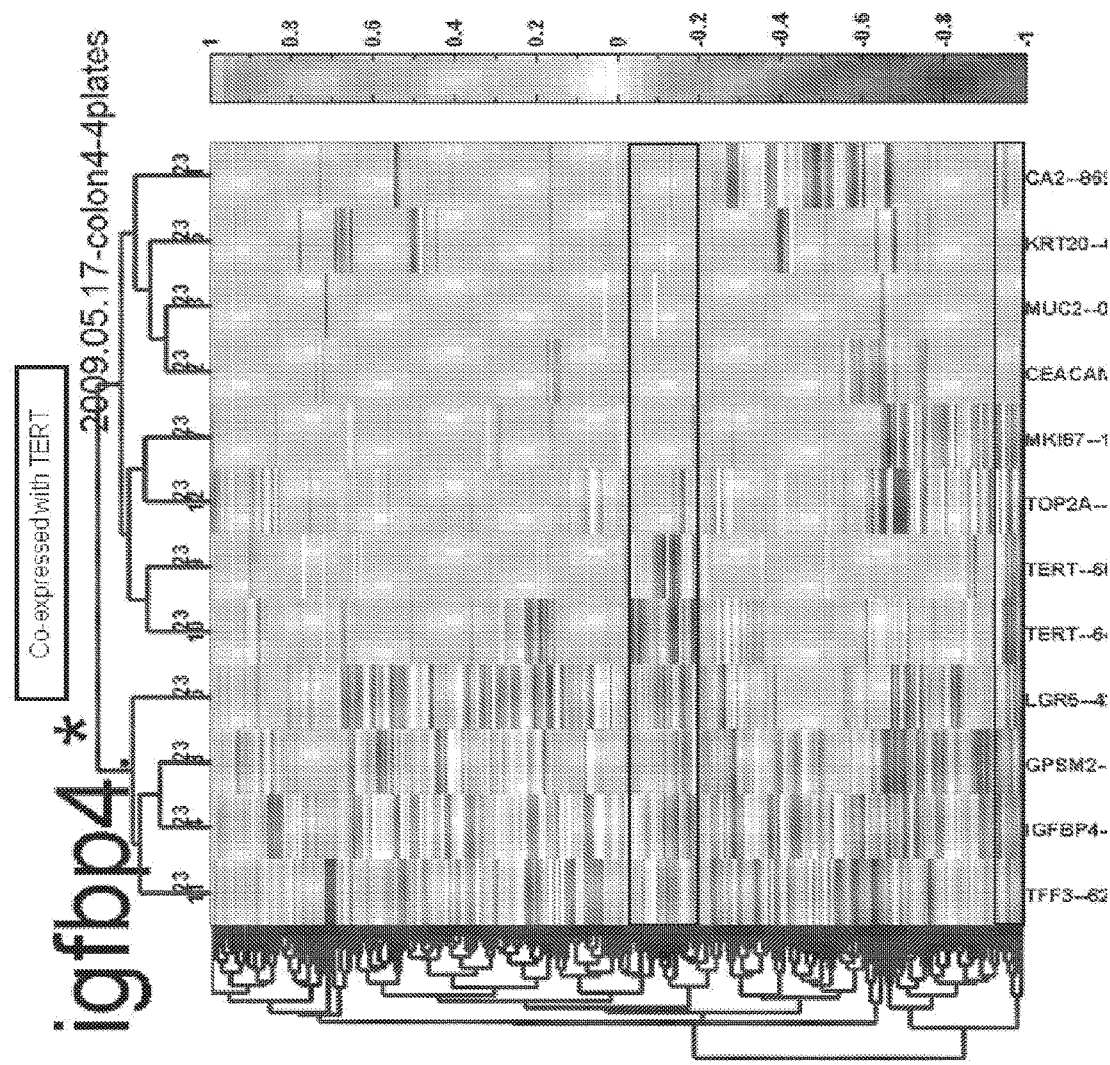

FIG. 215 IGFPB4 is co-expressed with TERT.

Figure 216:
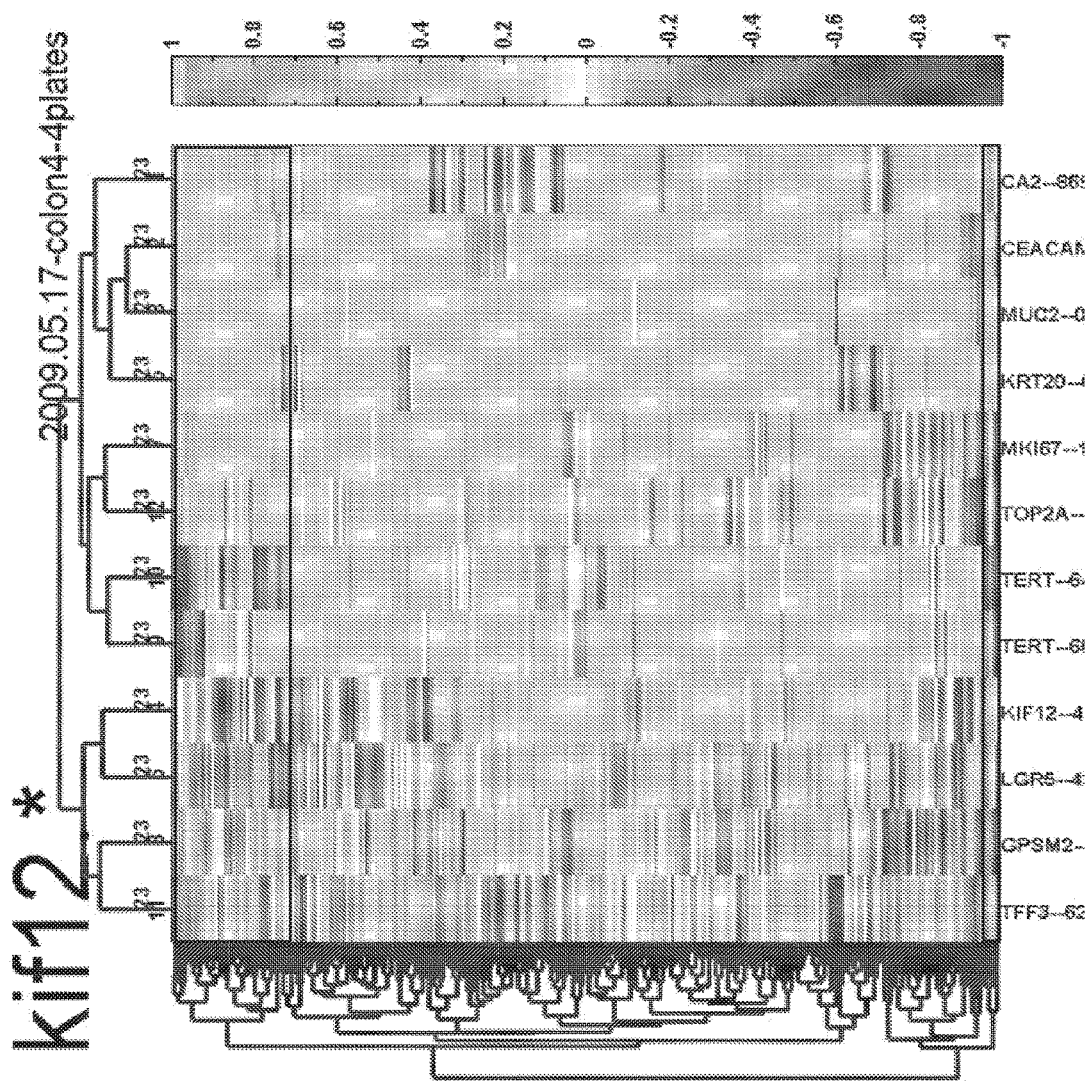

FIG. 216 KIF12 expression in relation to TERT expression.

Figure 217:
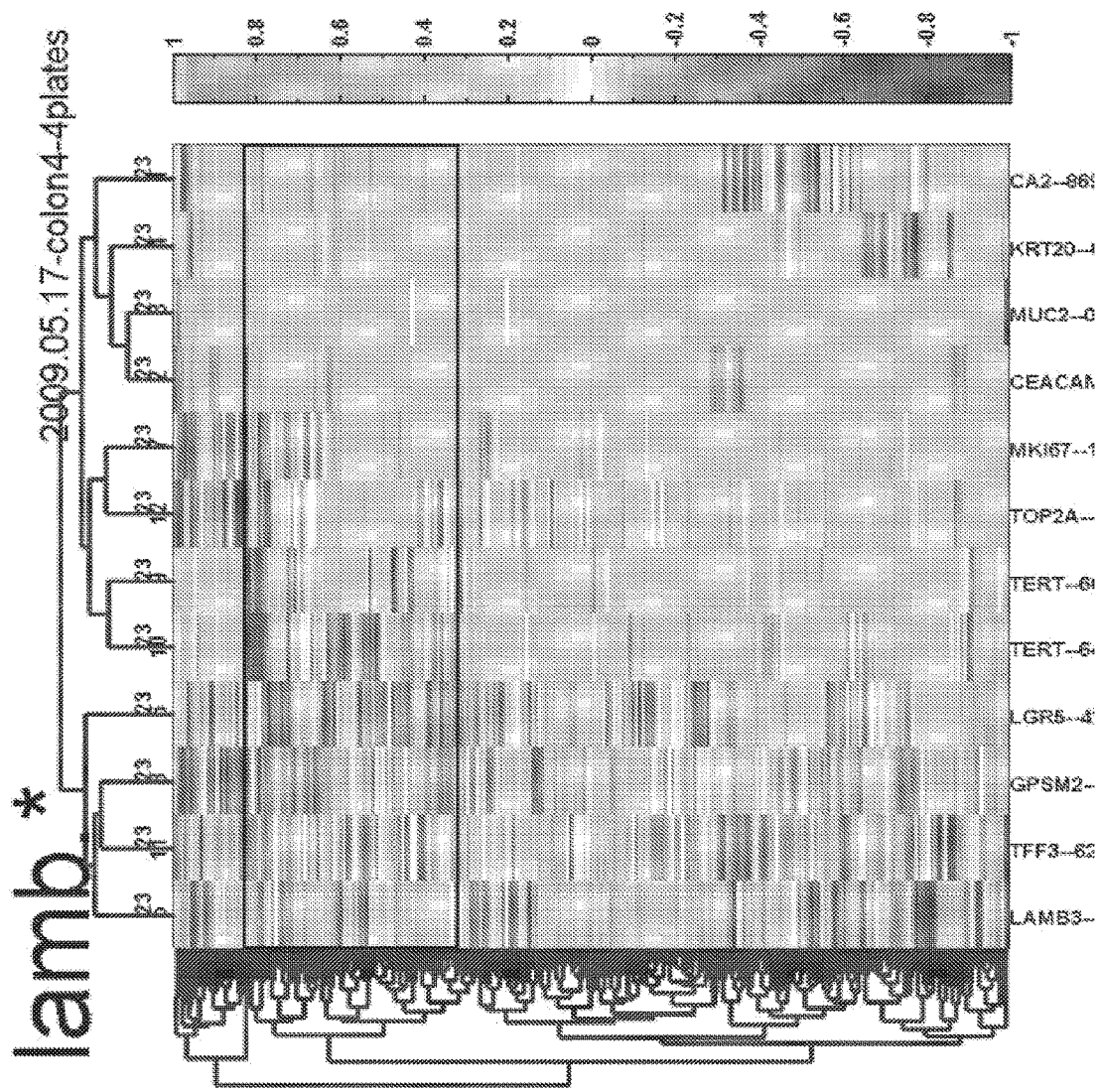

FIG. 217 LABM expression in relation to TERT expression.

Figure 218:
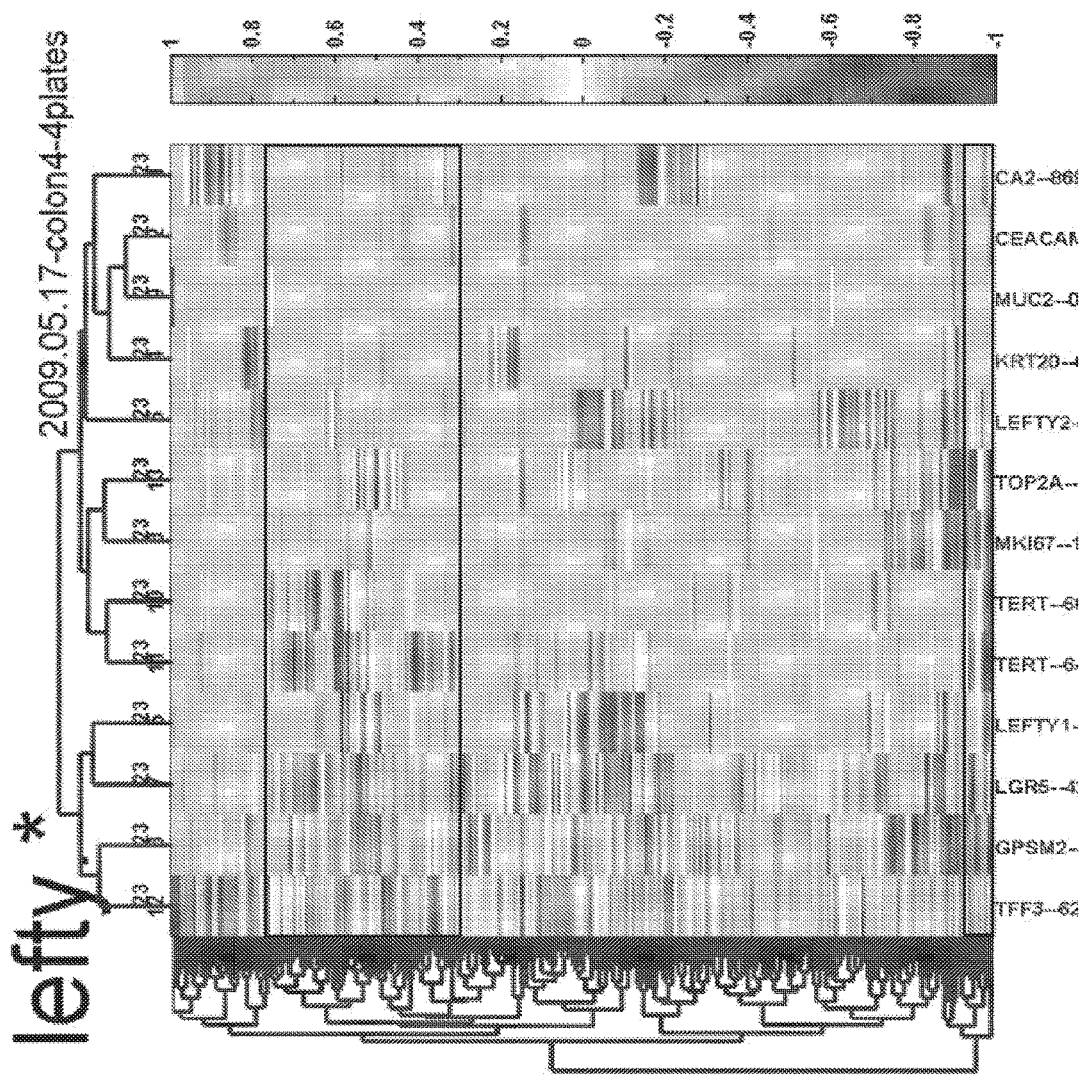

FIG. 218 LEFTY expression in relation to TERT expression.

Figure 219:
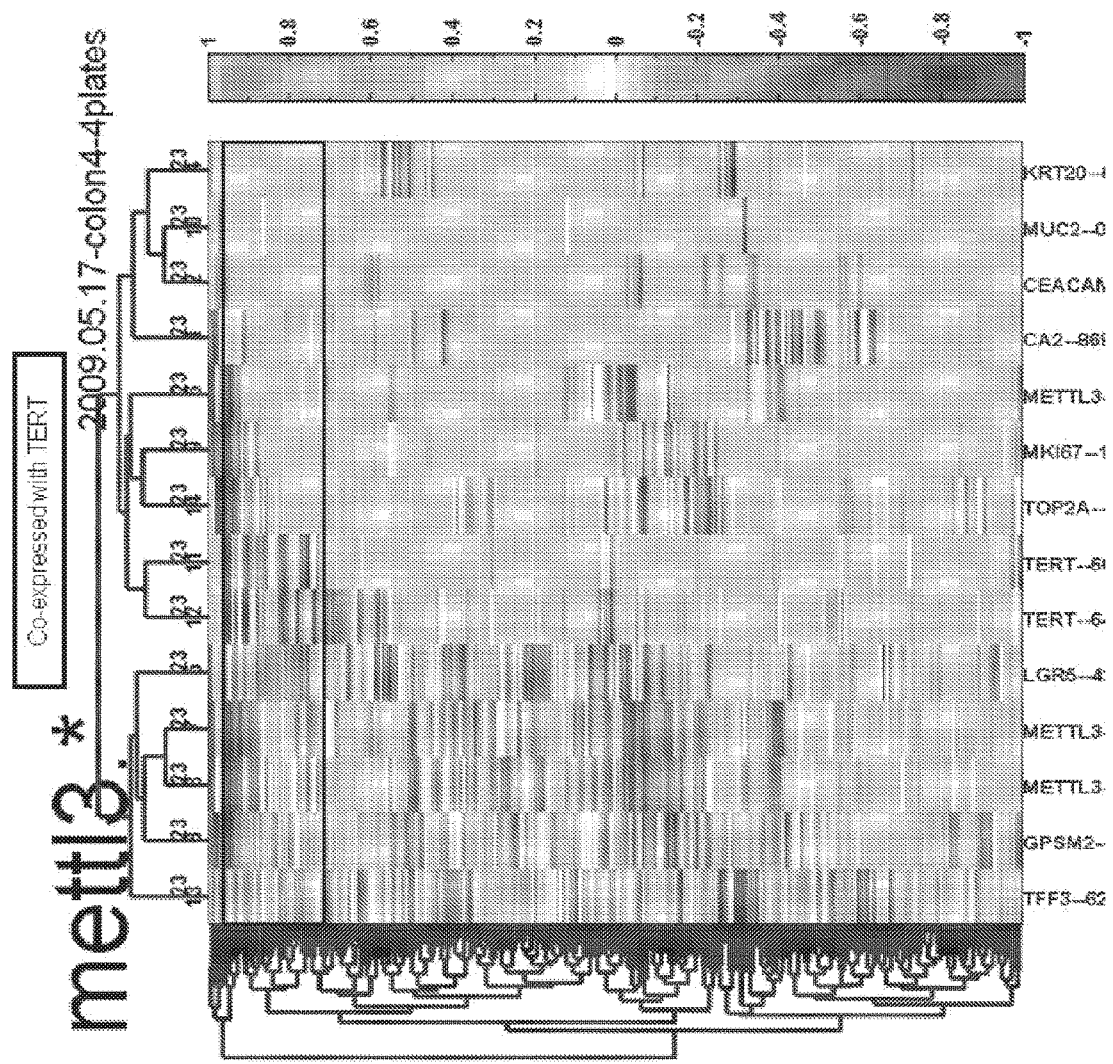

FIG. 219 METTL3 is co-expressed with TERT.

Figure 220:
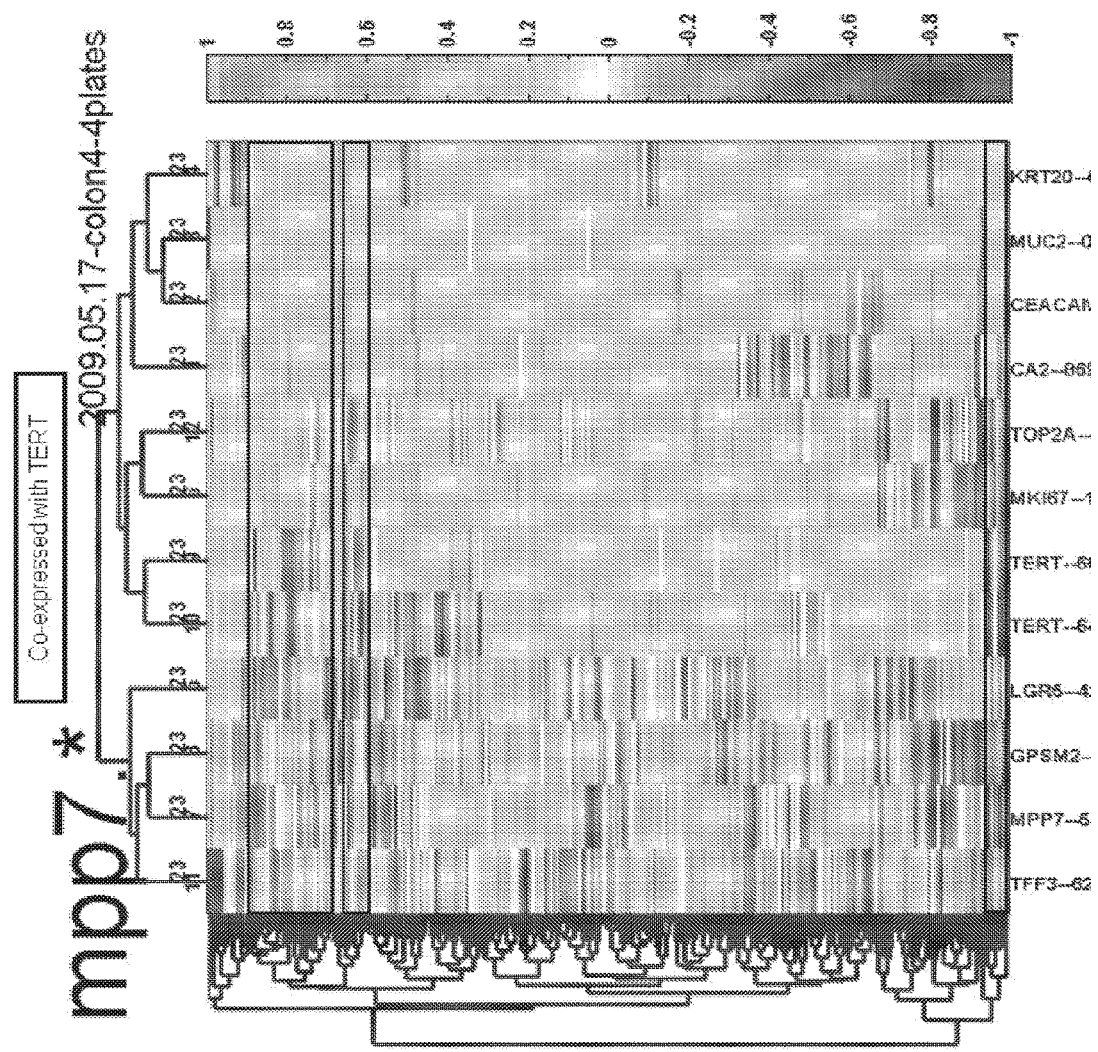

FIG. 220 MPP7 is co-expressed with TERT.

Figure 221:
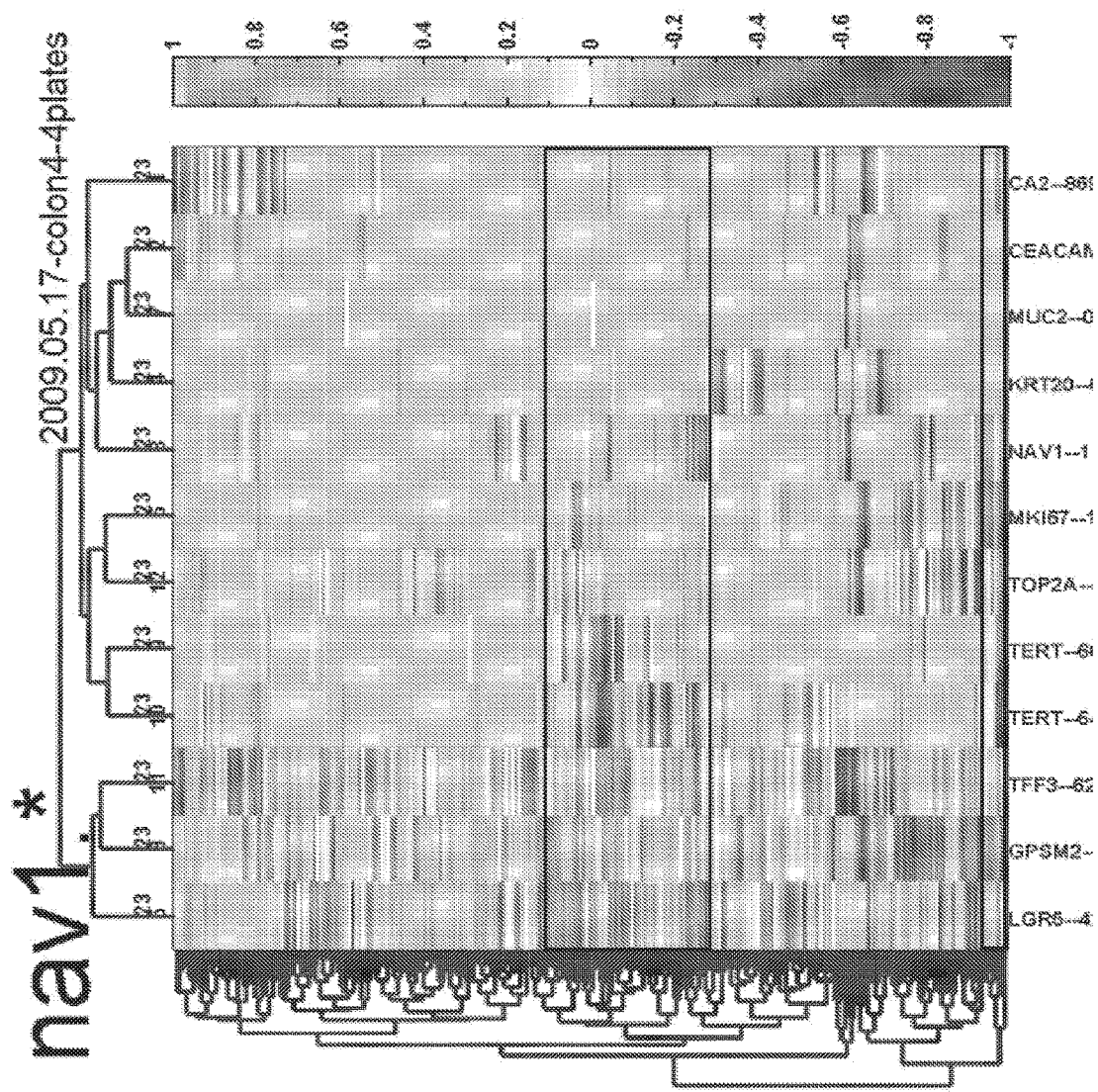

FIG. 221 NAV1 expression in relation to TERT expression.

Figure 222:
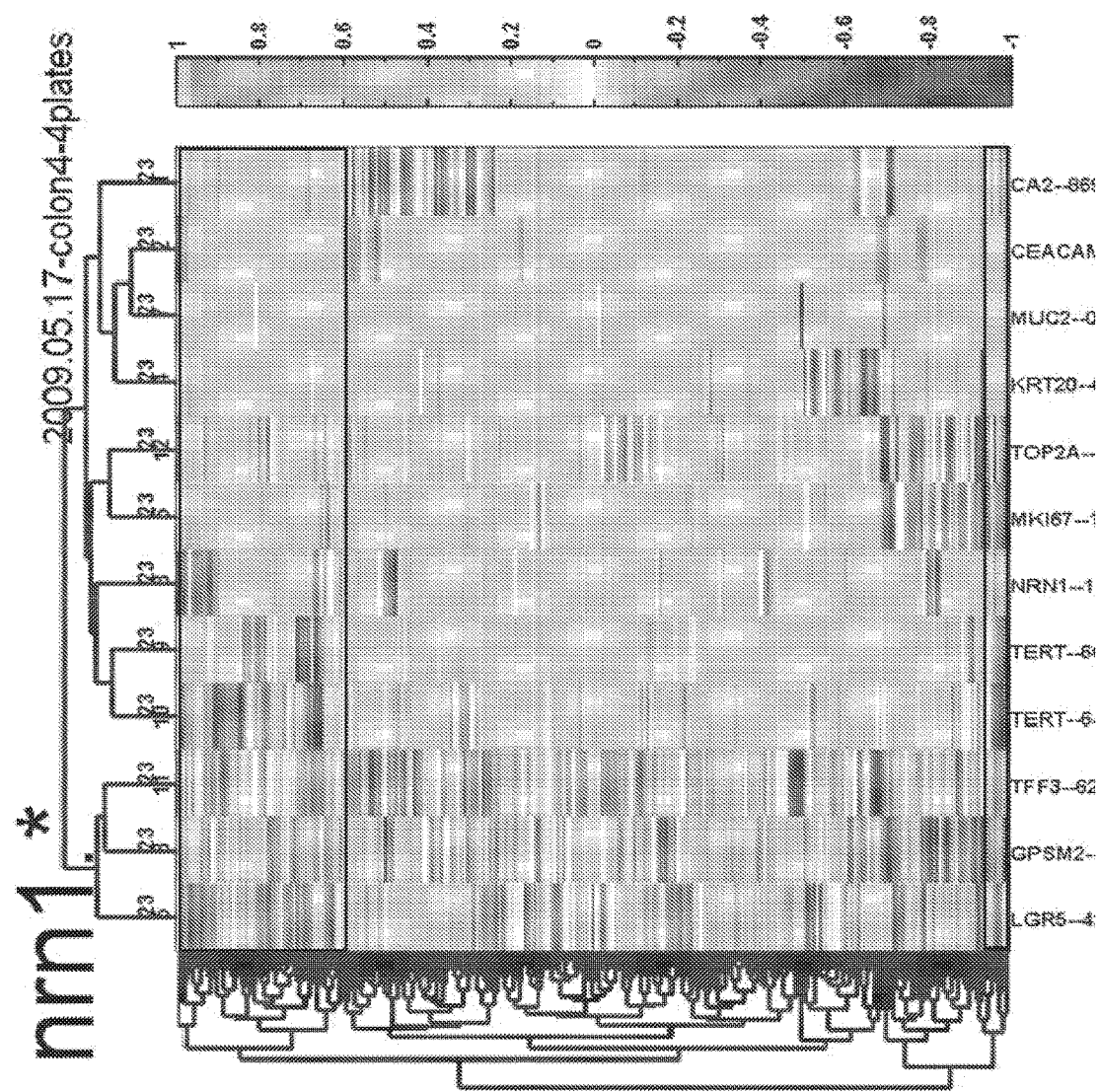

FIG. 222 NRN1 expression in relation to TERT expression.

Figure 223:

FIG. 223 NUMB is co-expressed with TERT.

Figure 224:
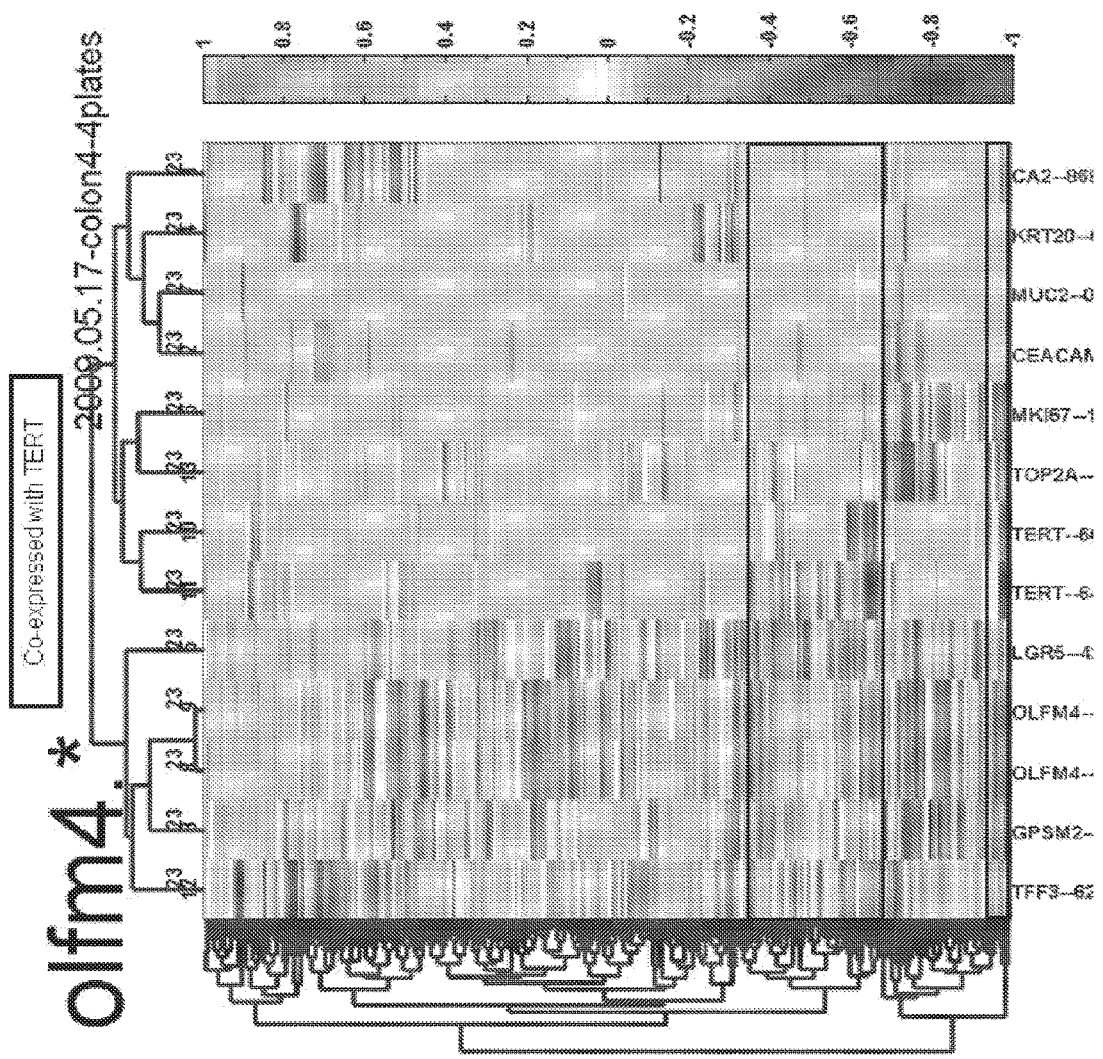

FIG. 224 OLFM4 is co-expressed with TERT.

Figure 225:
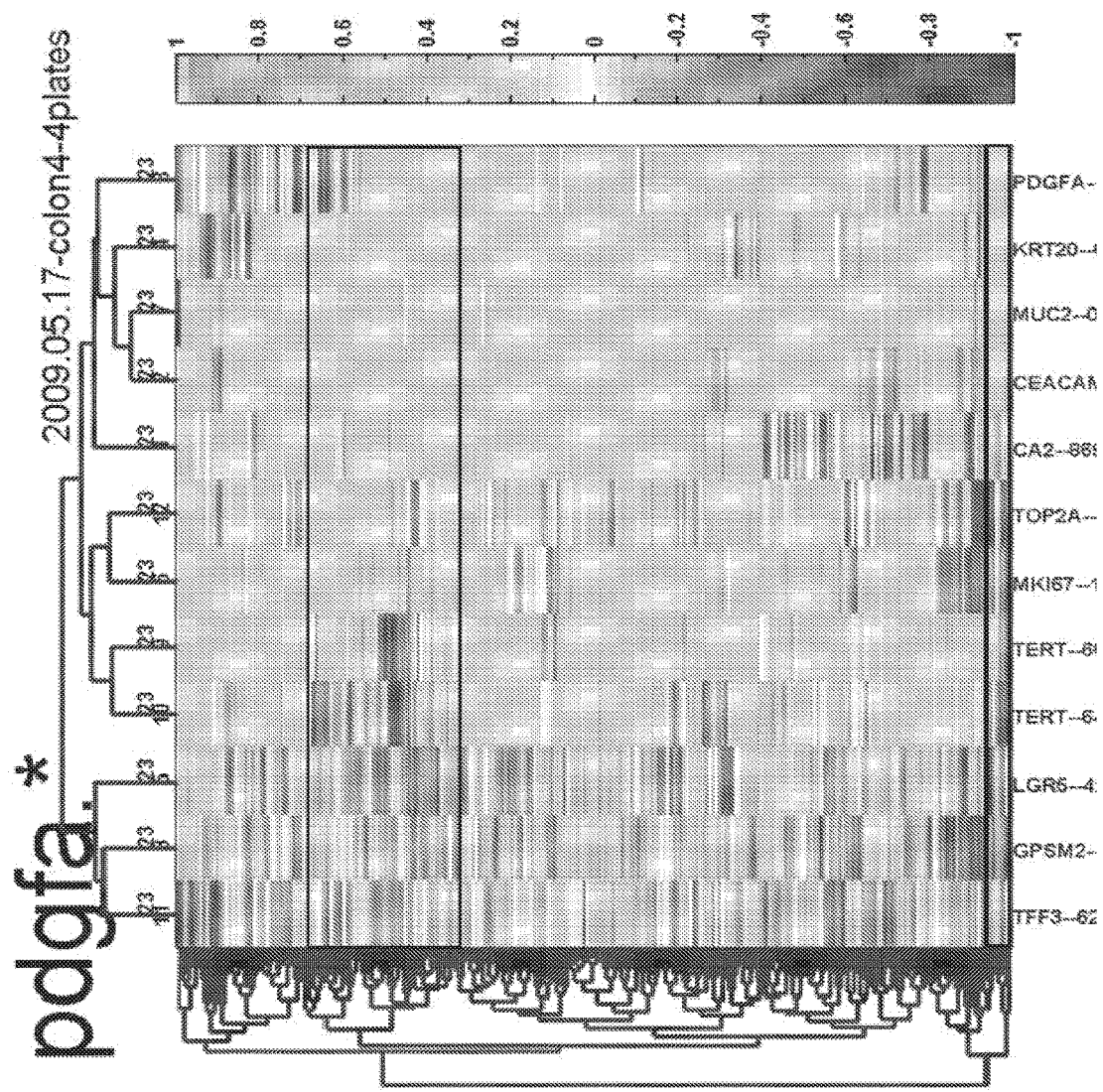

FIG. 225 PDGFA expression in relation to TERT expression.

Figure 226:
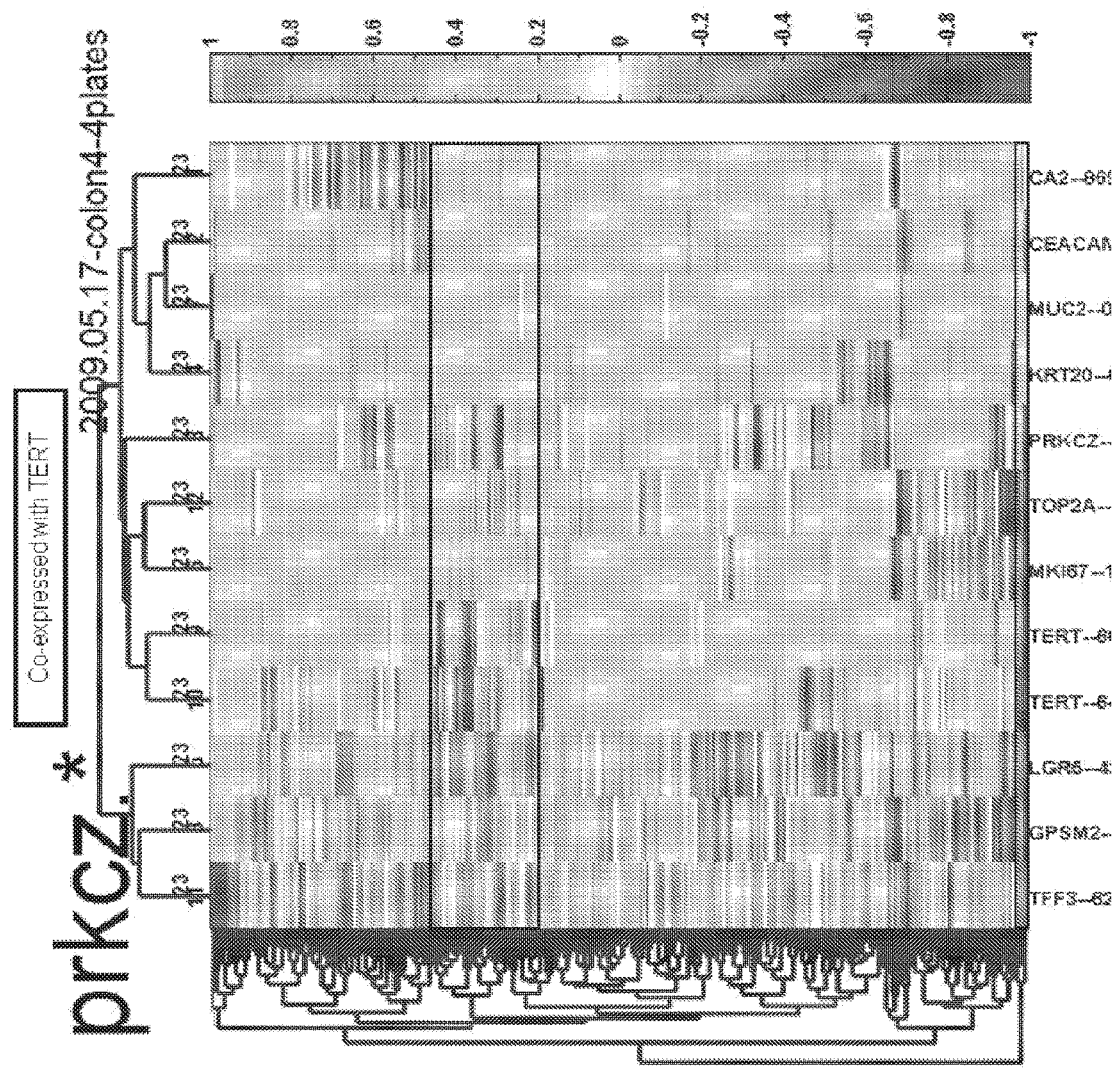

FIG. 226 PRKCZ is co-expressed with TERT.

Figure 227:
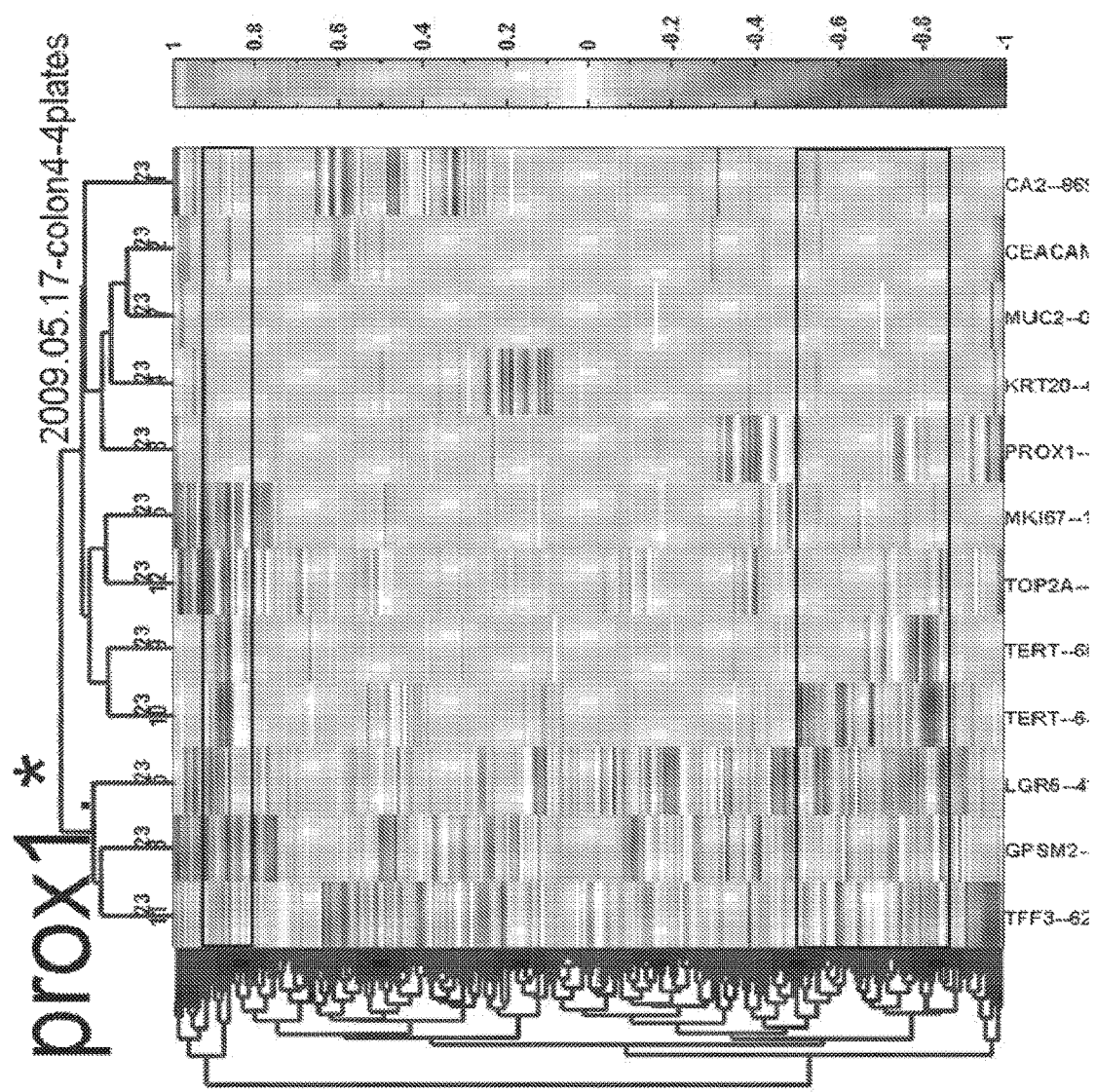
Figure 228:
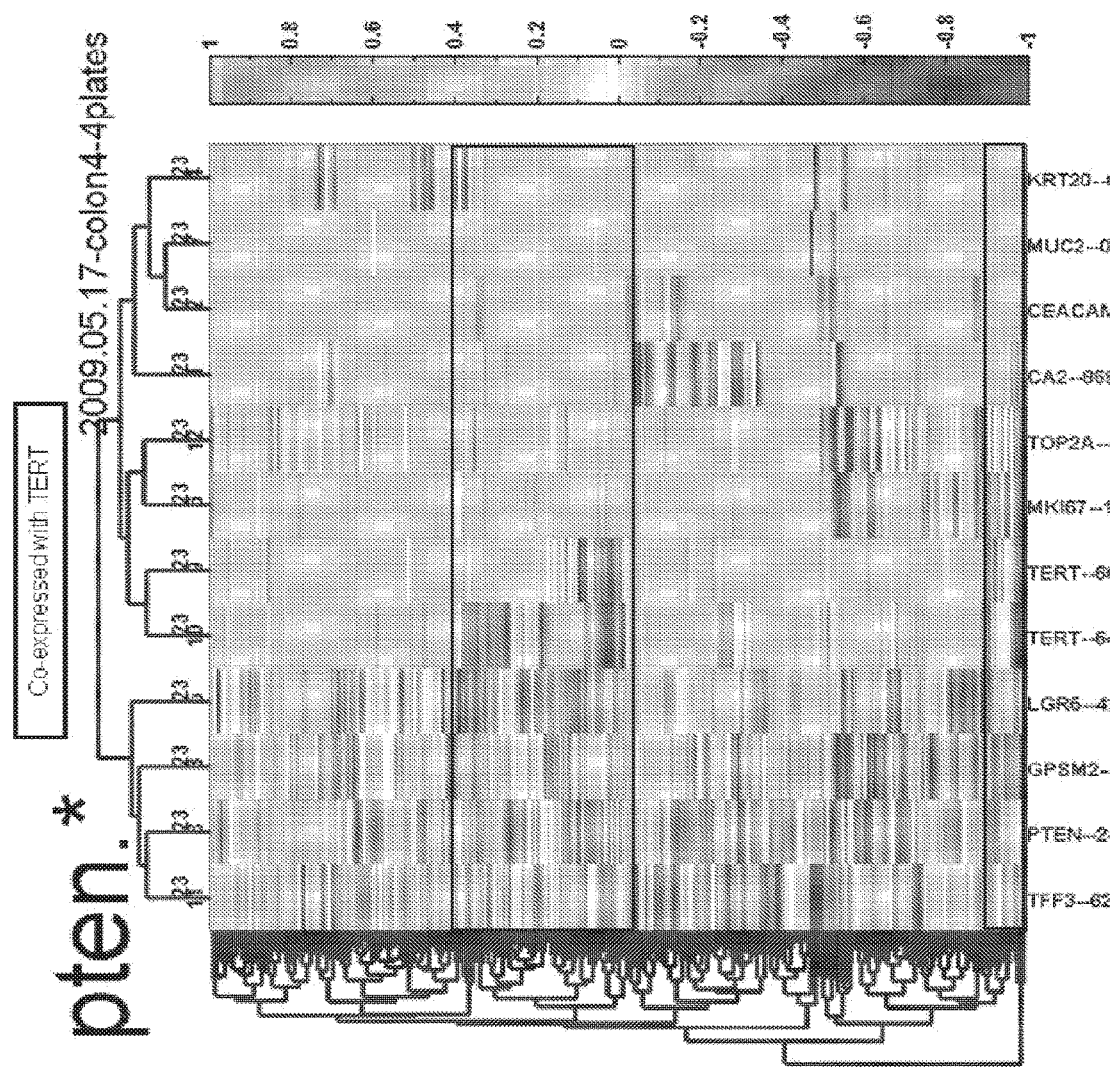
Figure 229:
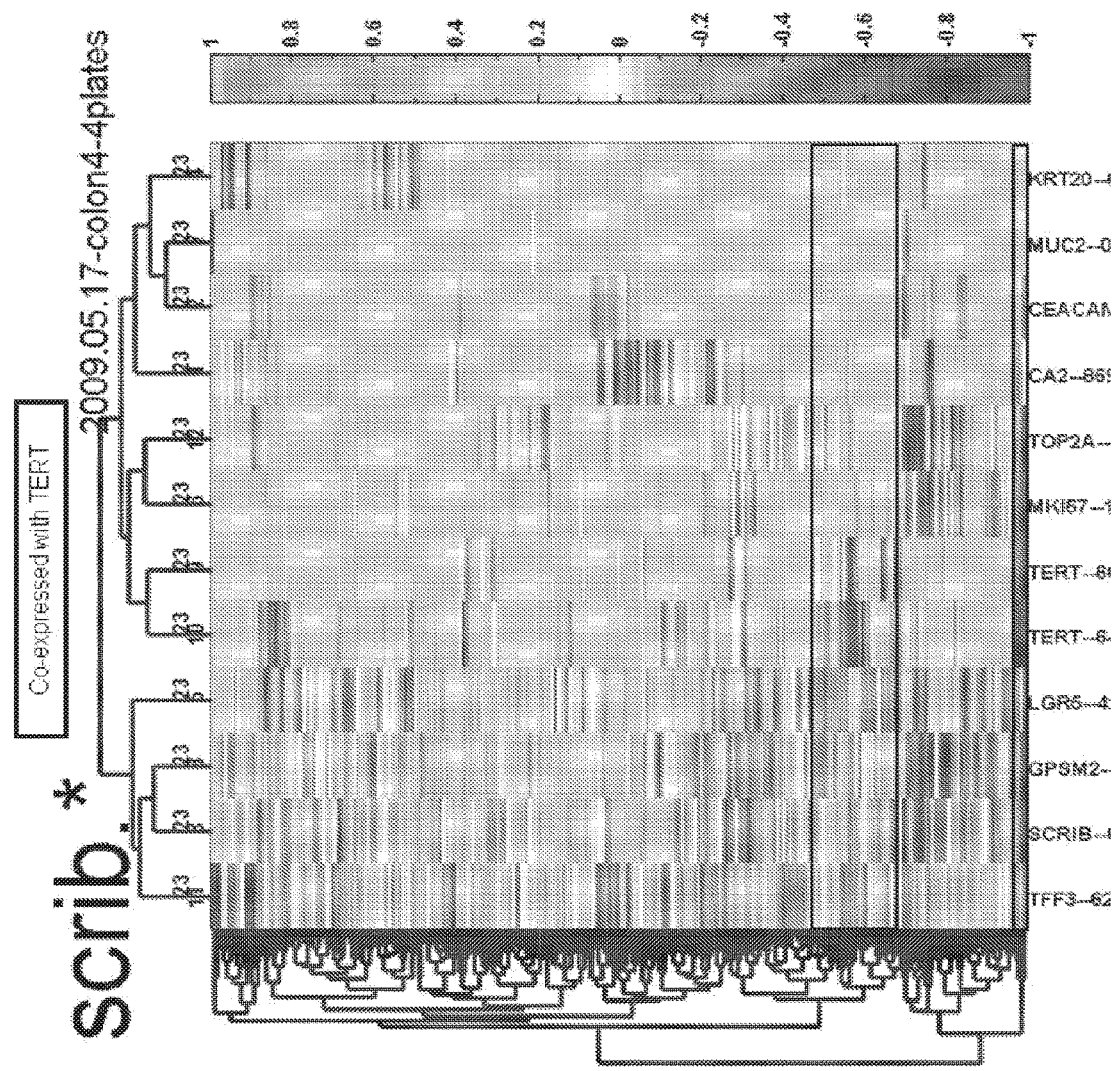
Figure 230:
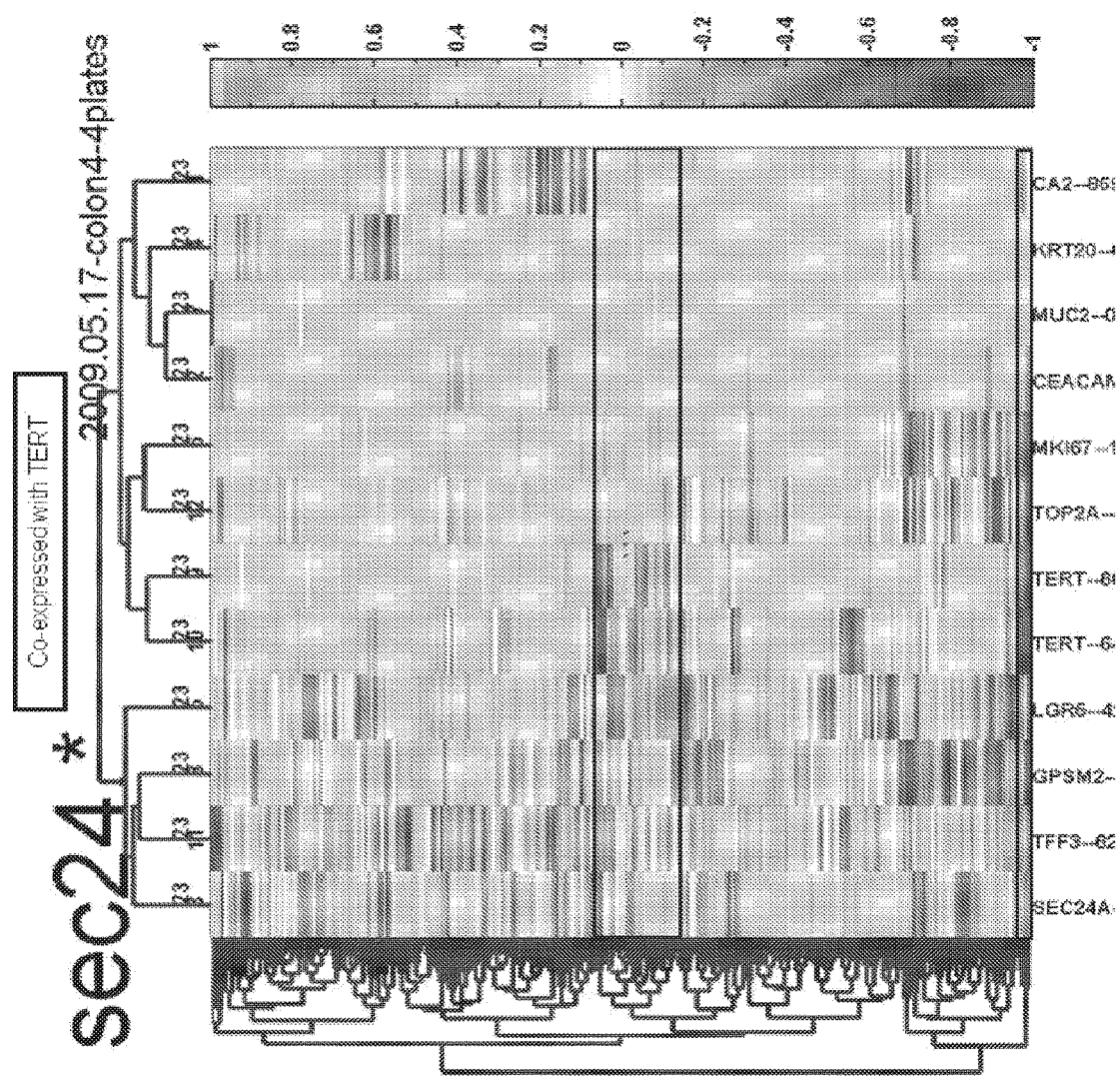
Figure 231:
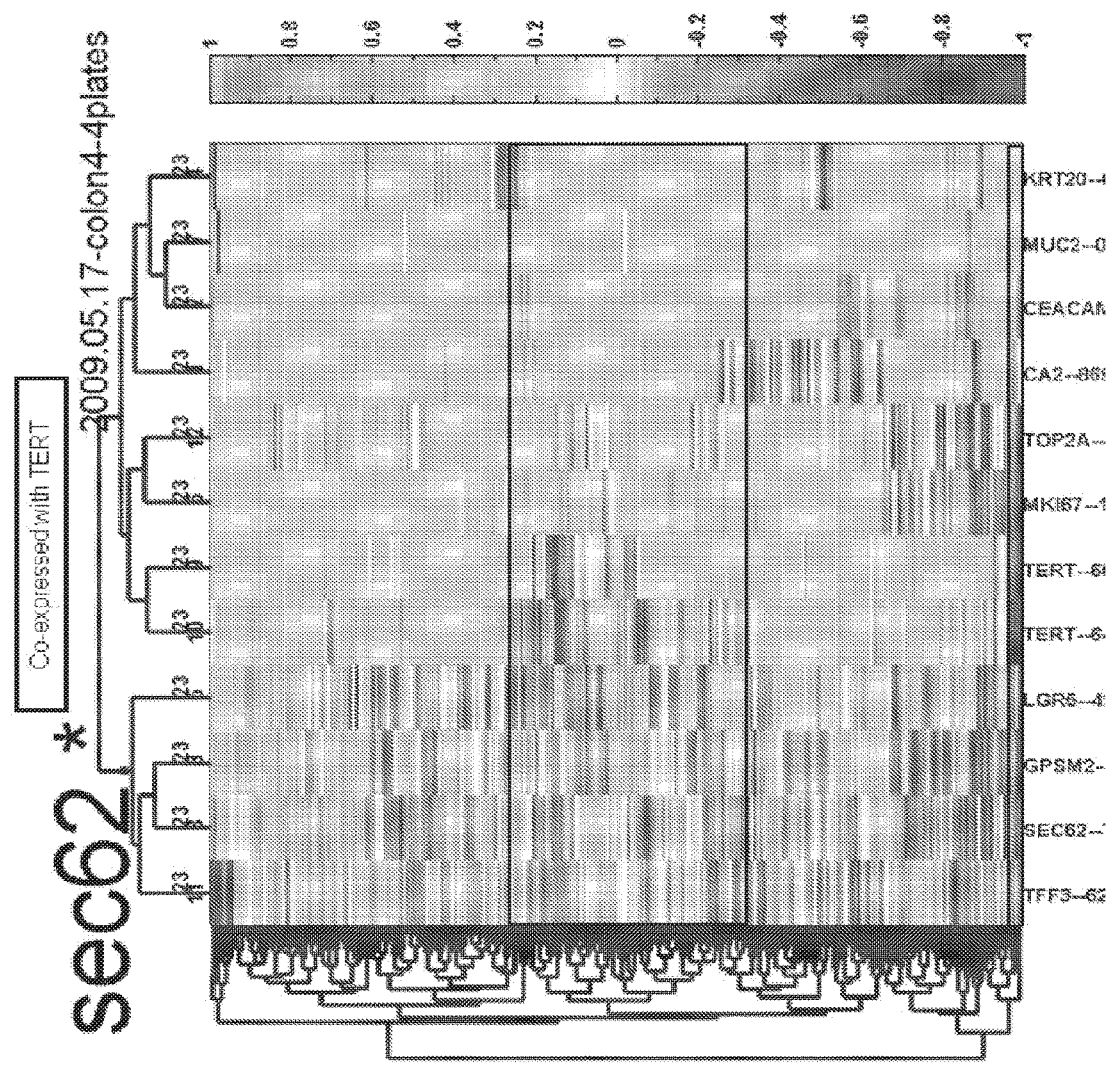
Figure 232:
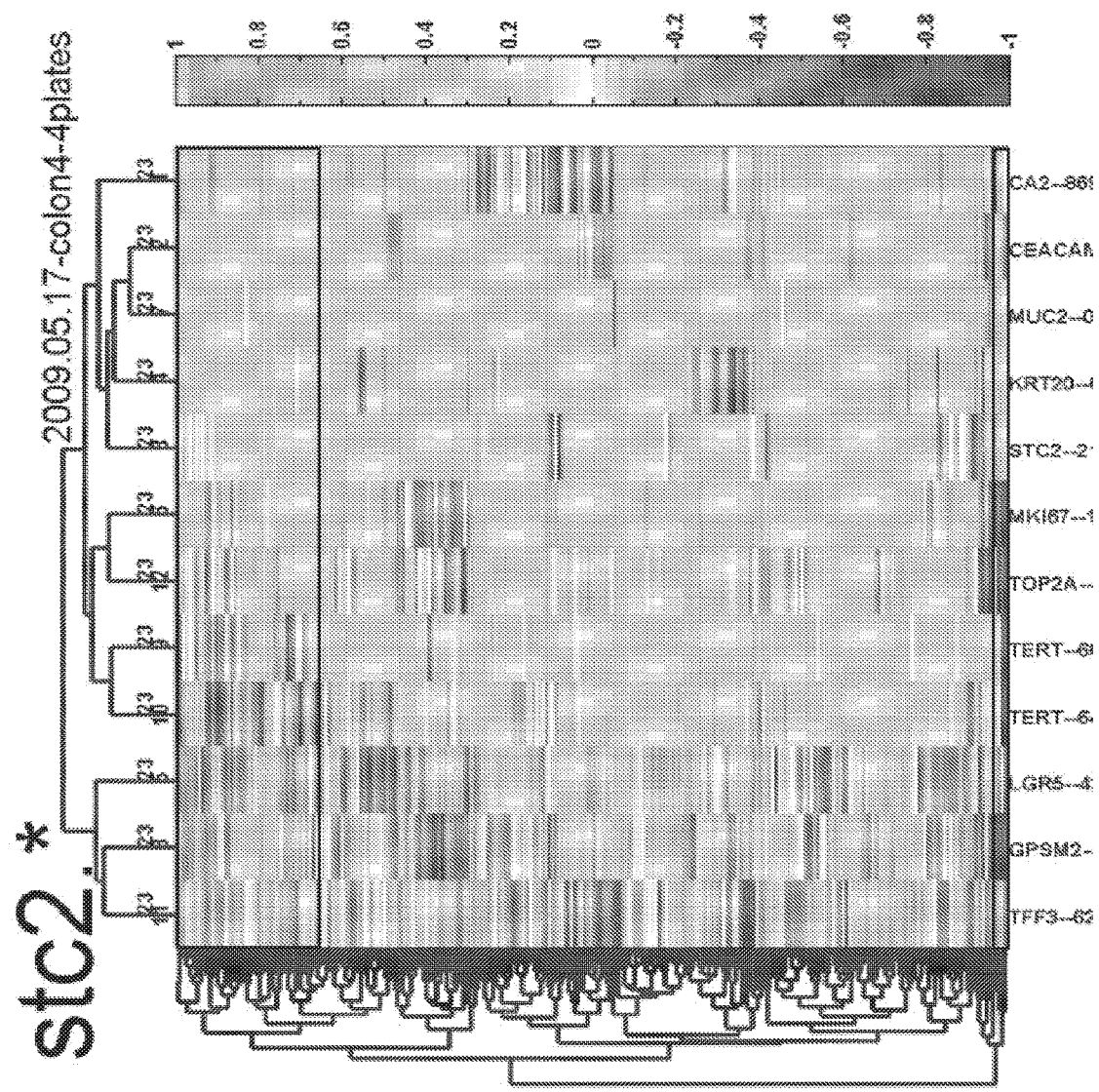
Figure 233:
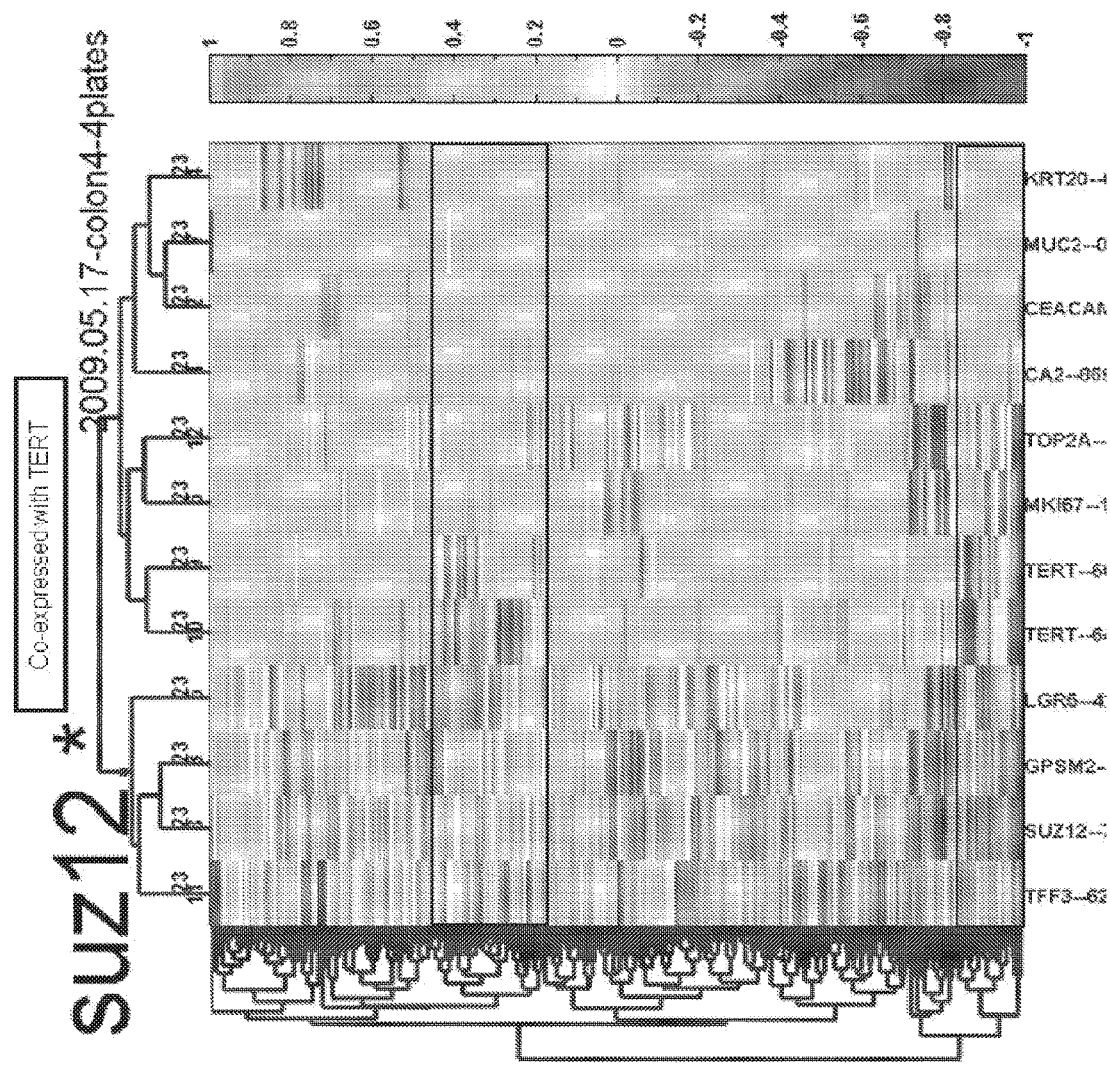
Figure 234:
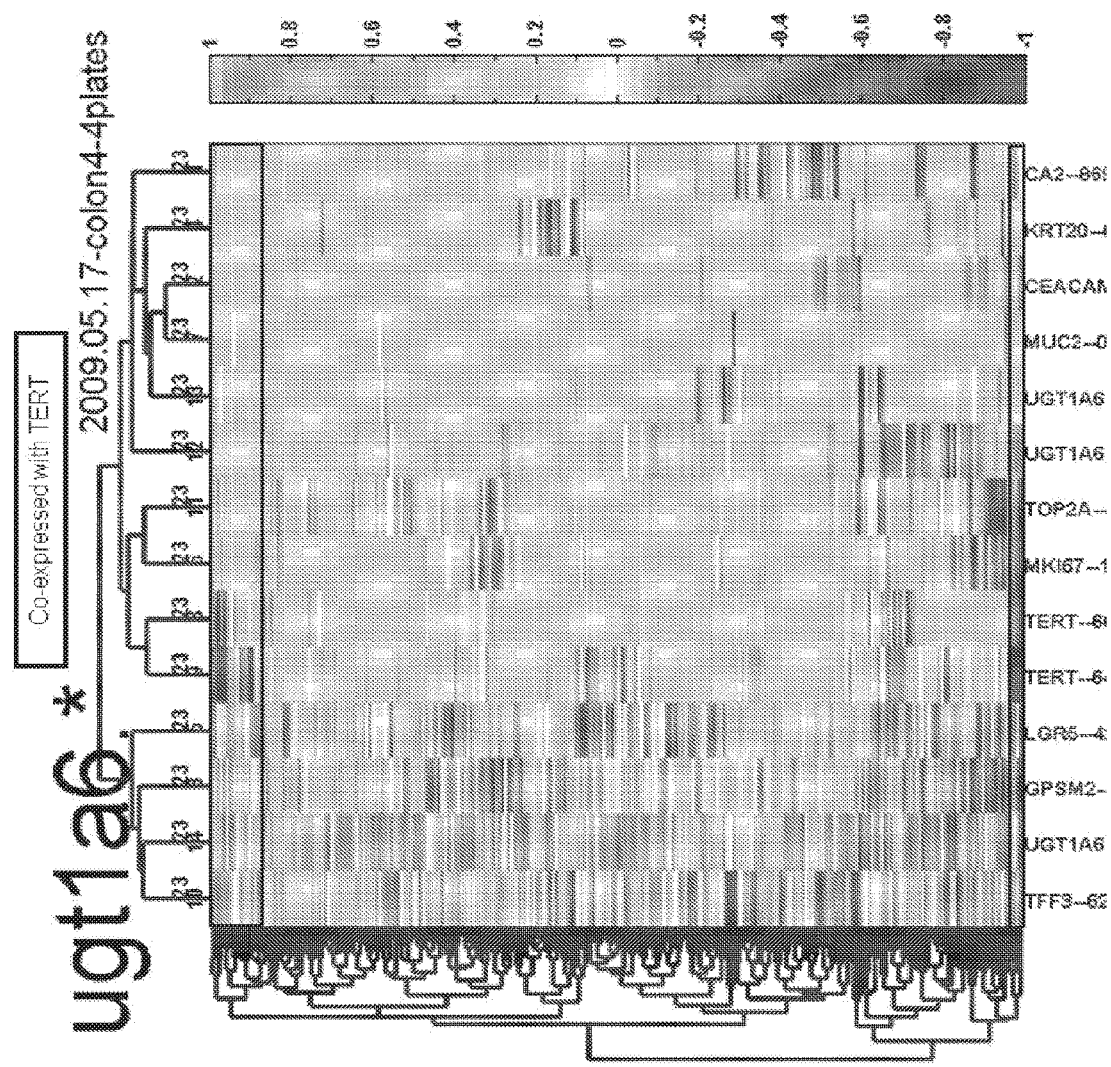
Figure 235:
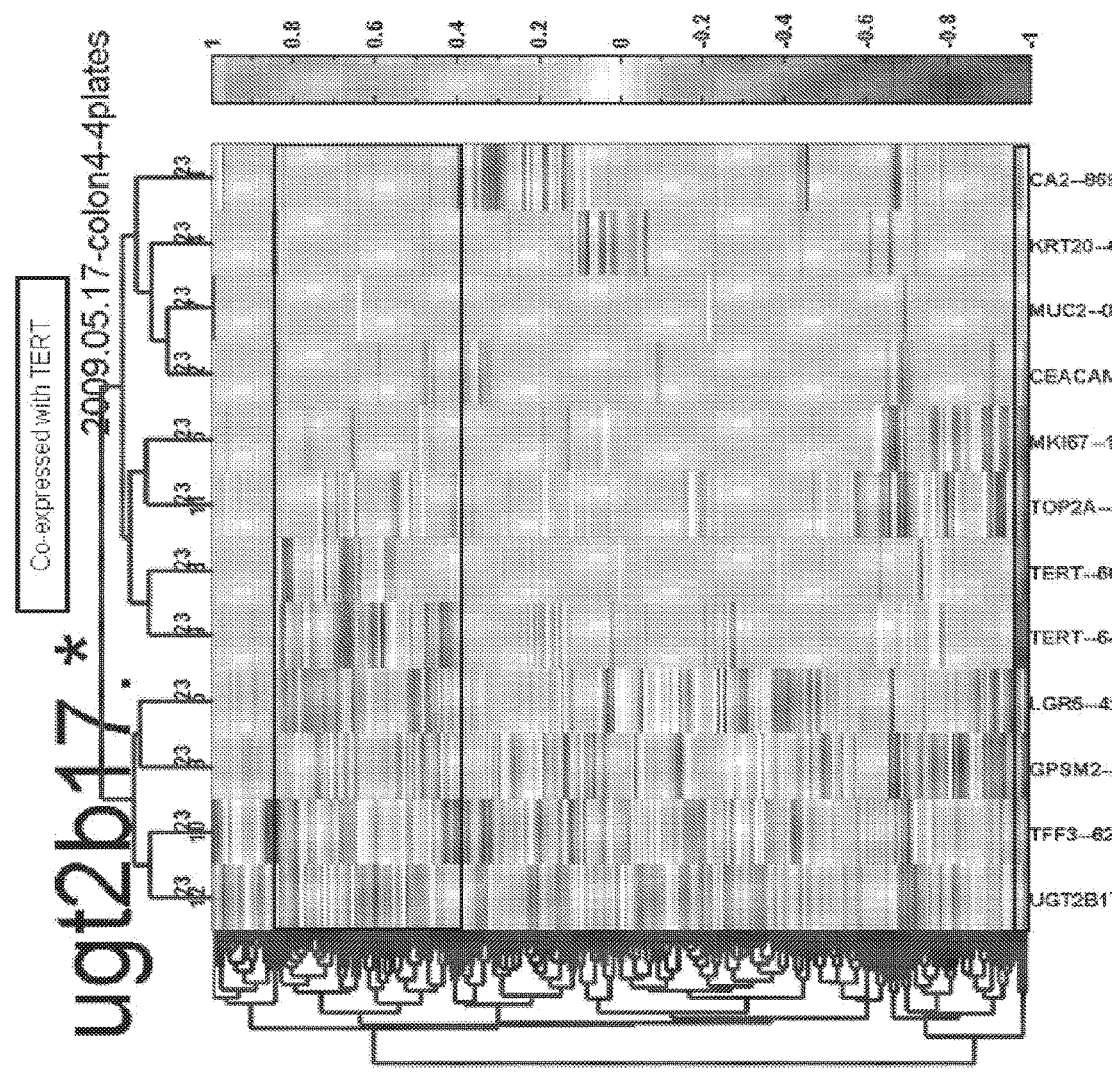
Figure 236:
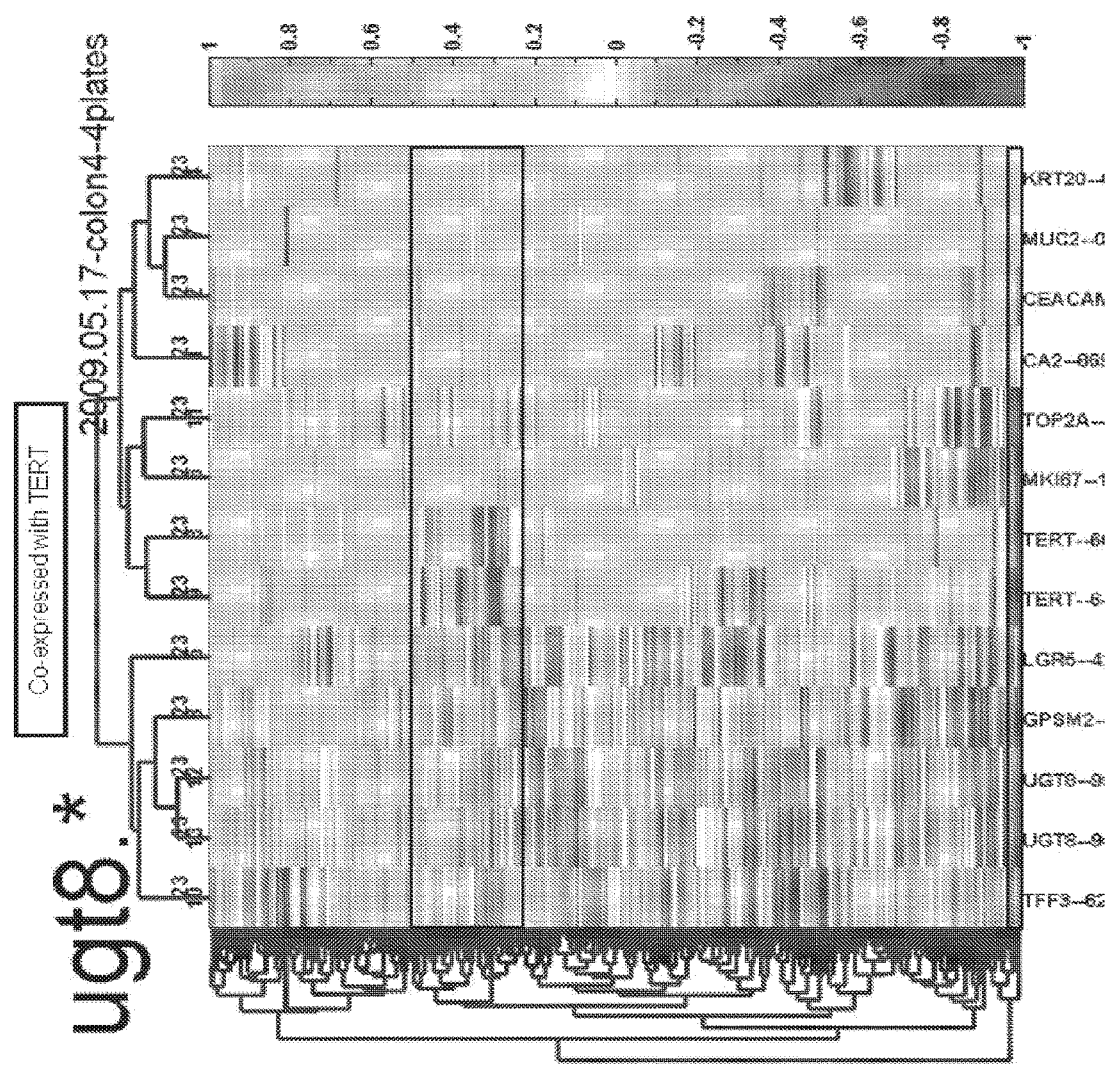
Figure 237:
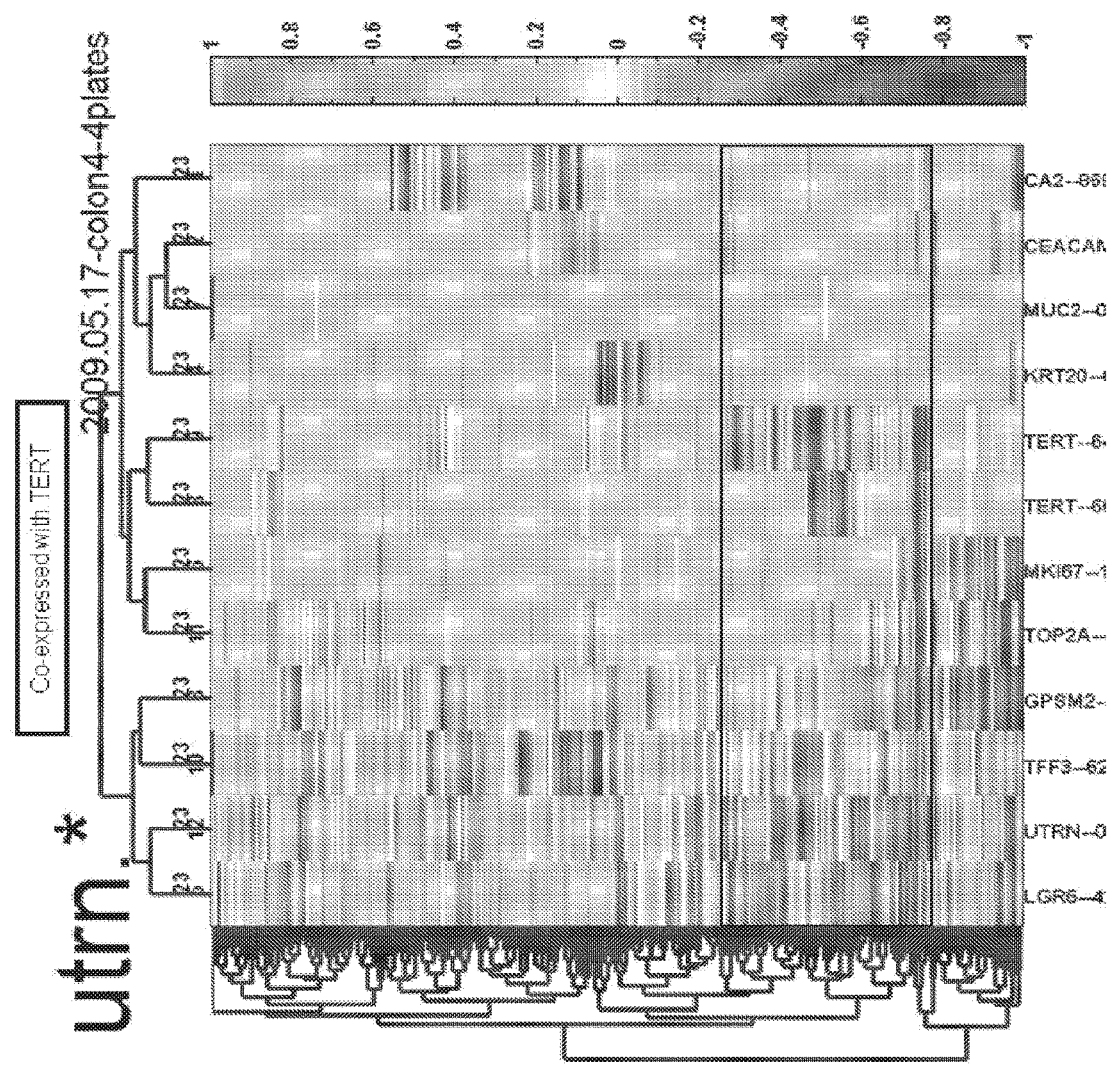
Figure 238:
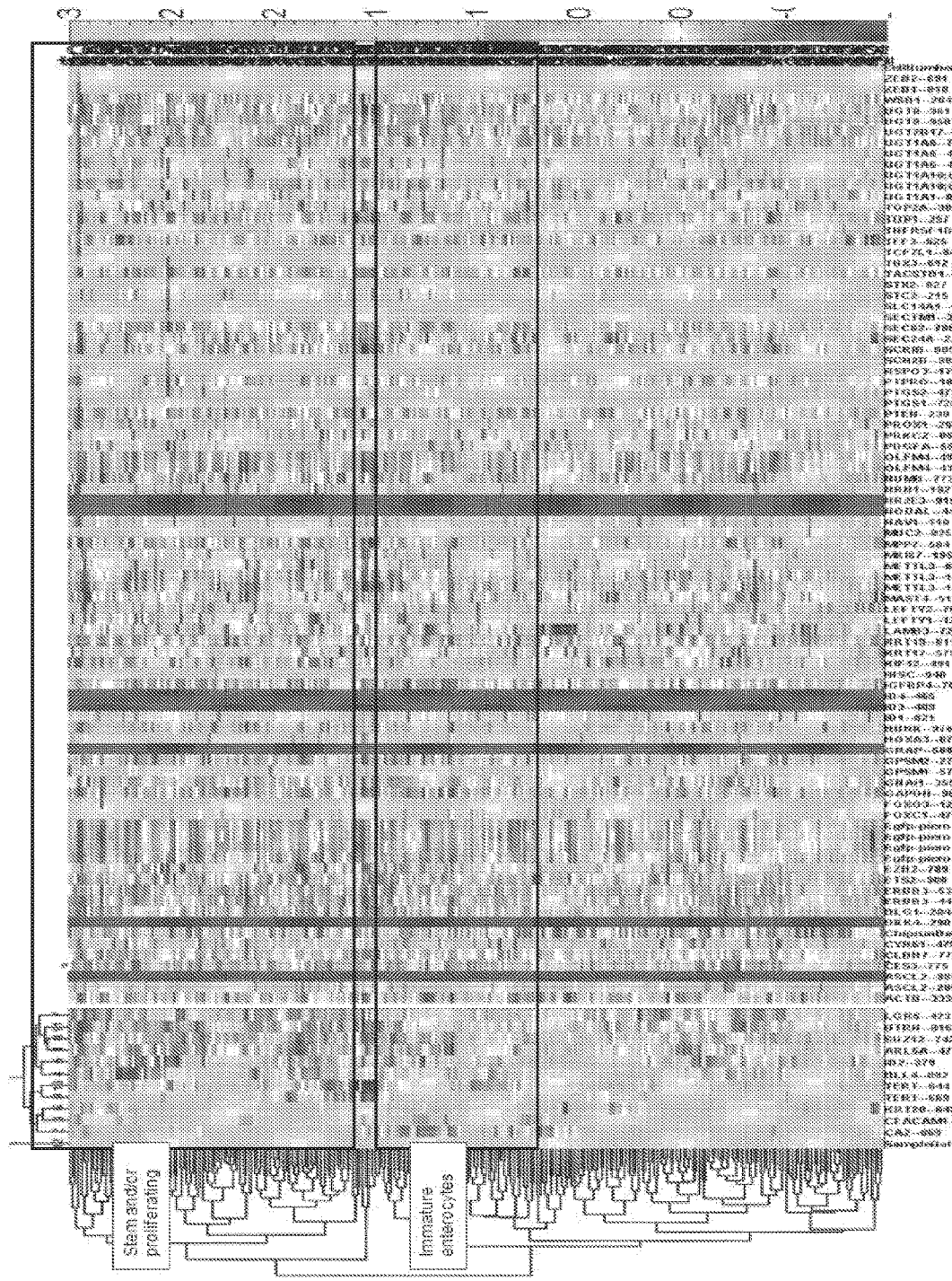
Figure 239:
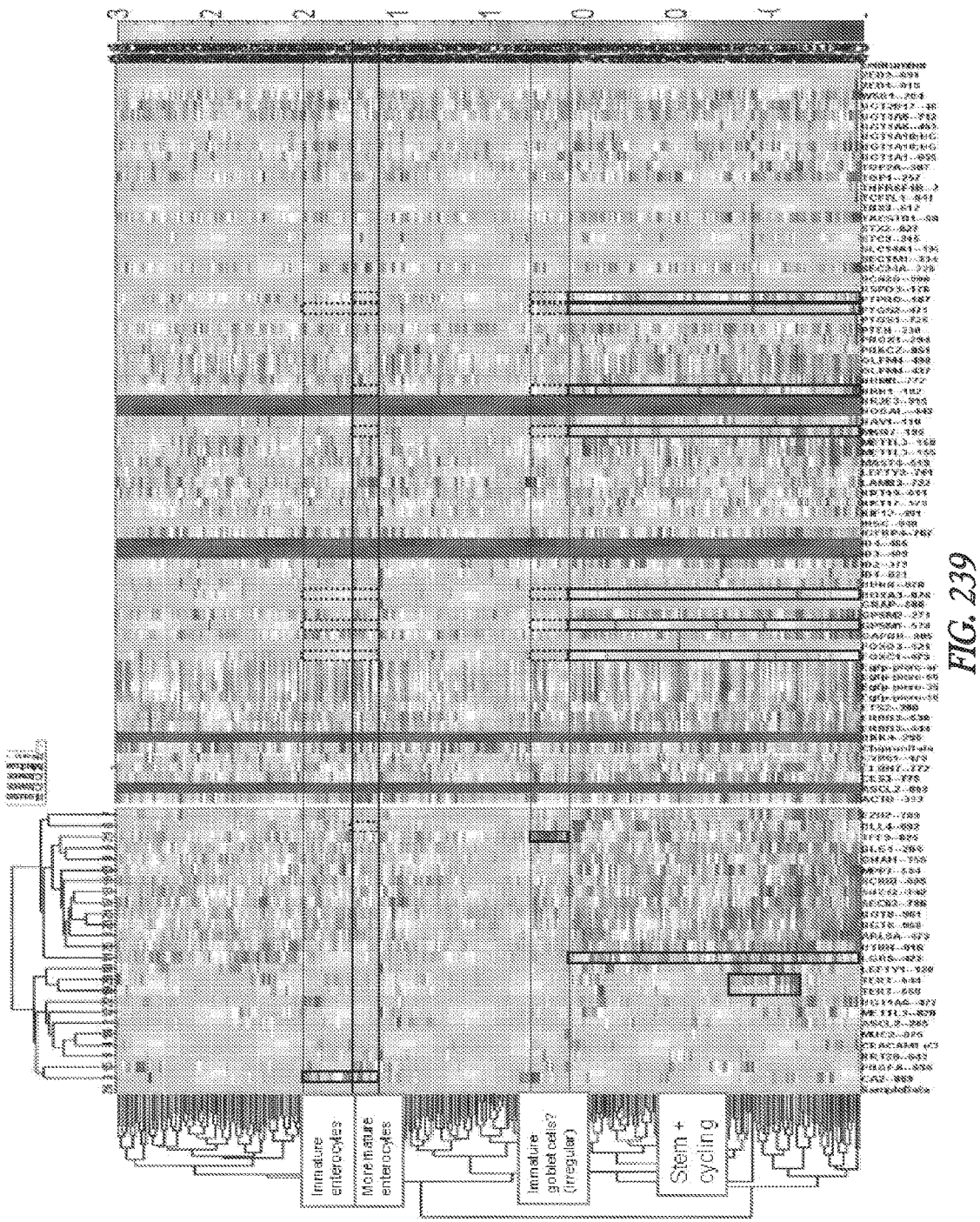
Figure 240:
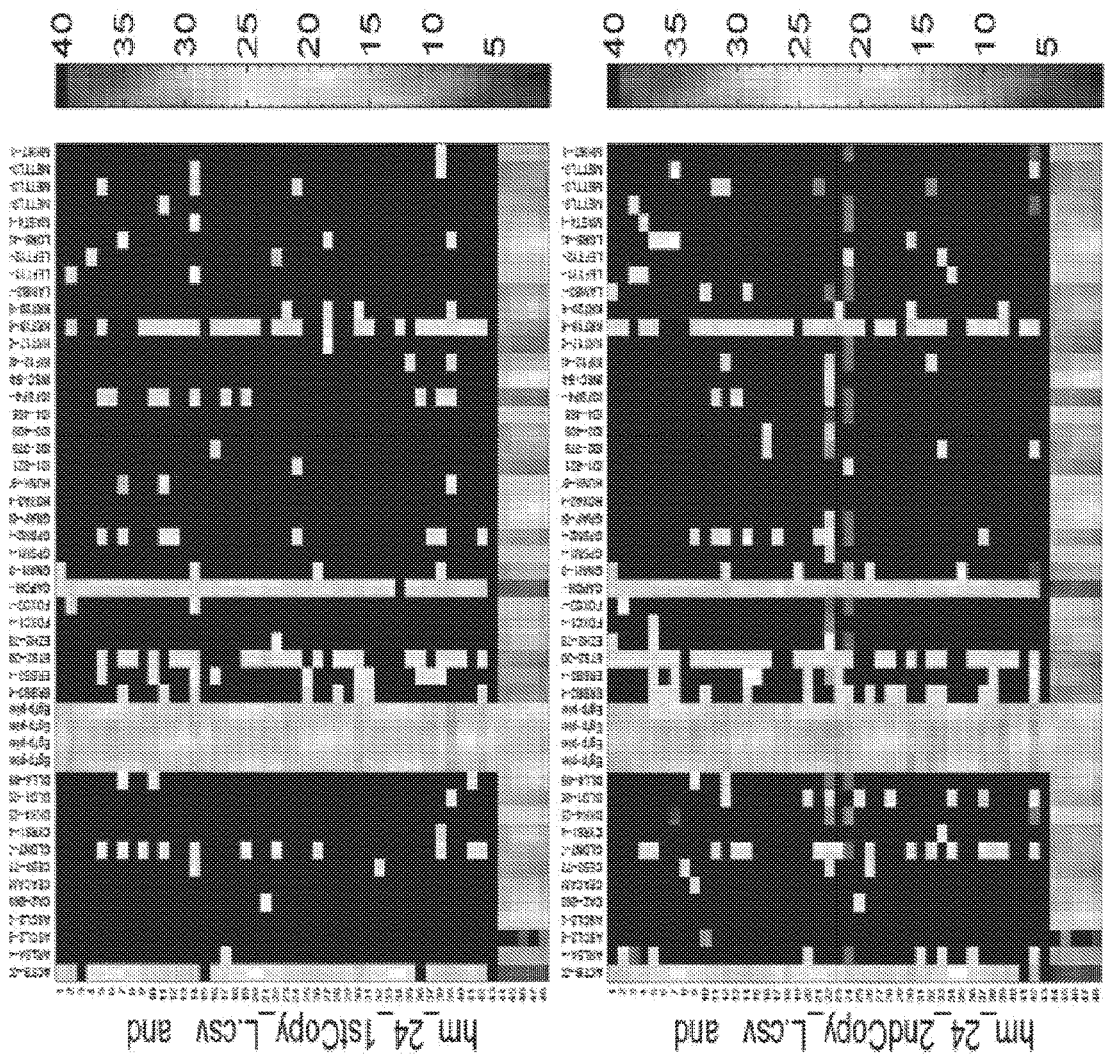
Figure 241:
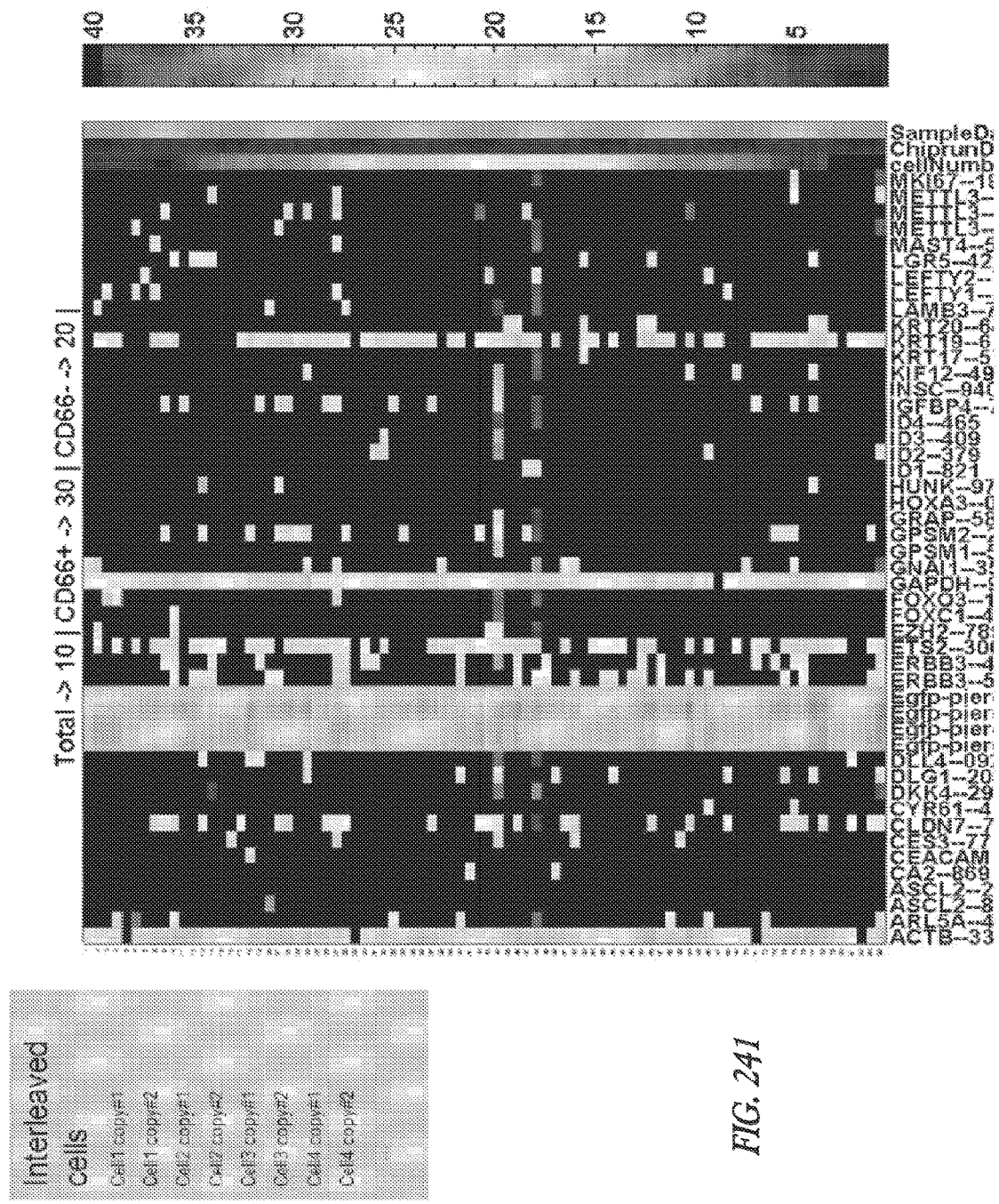
Figure 242:
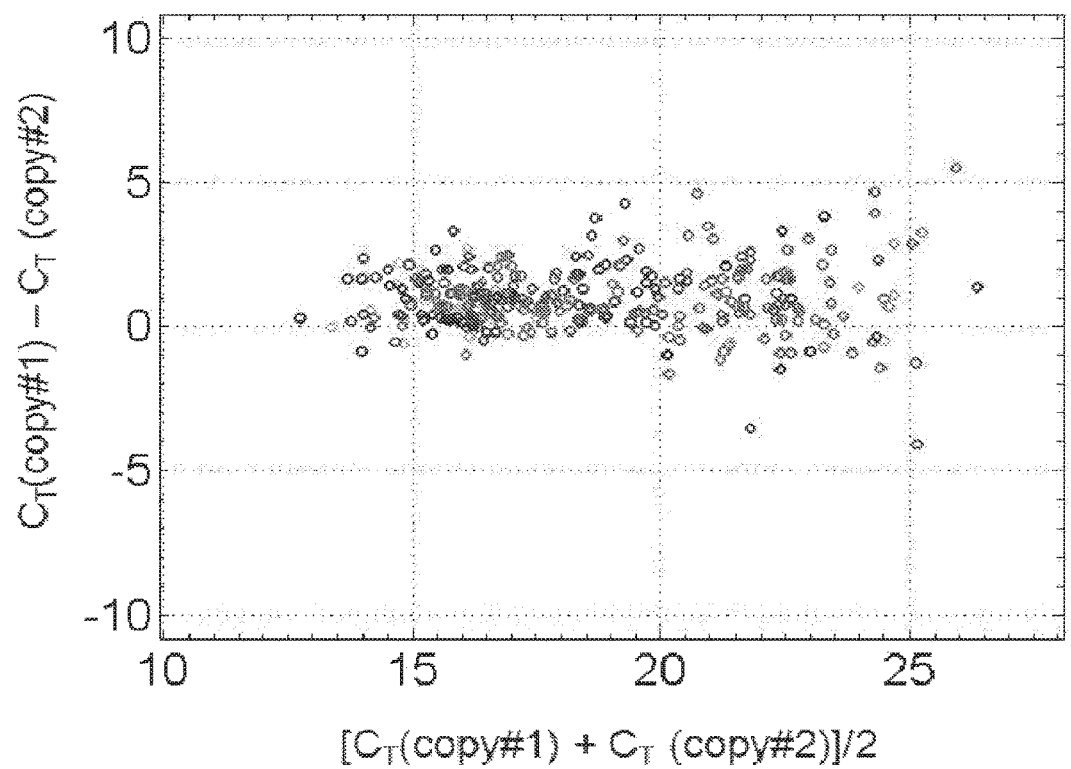
Figure 244:
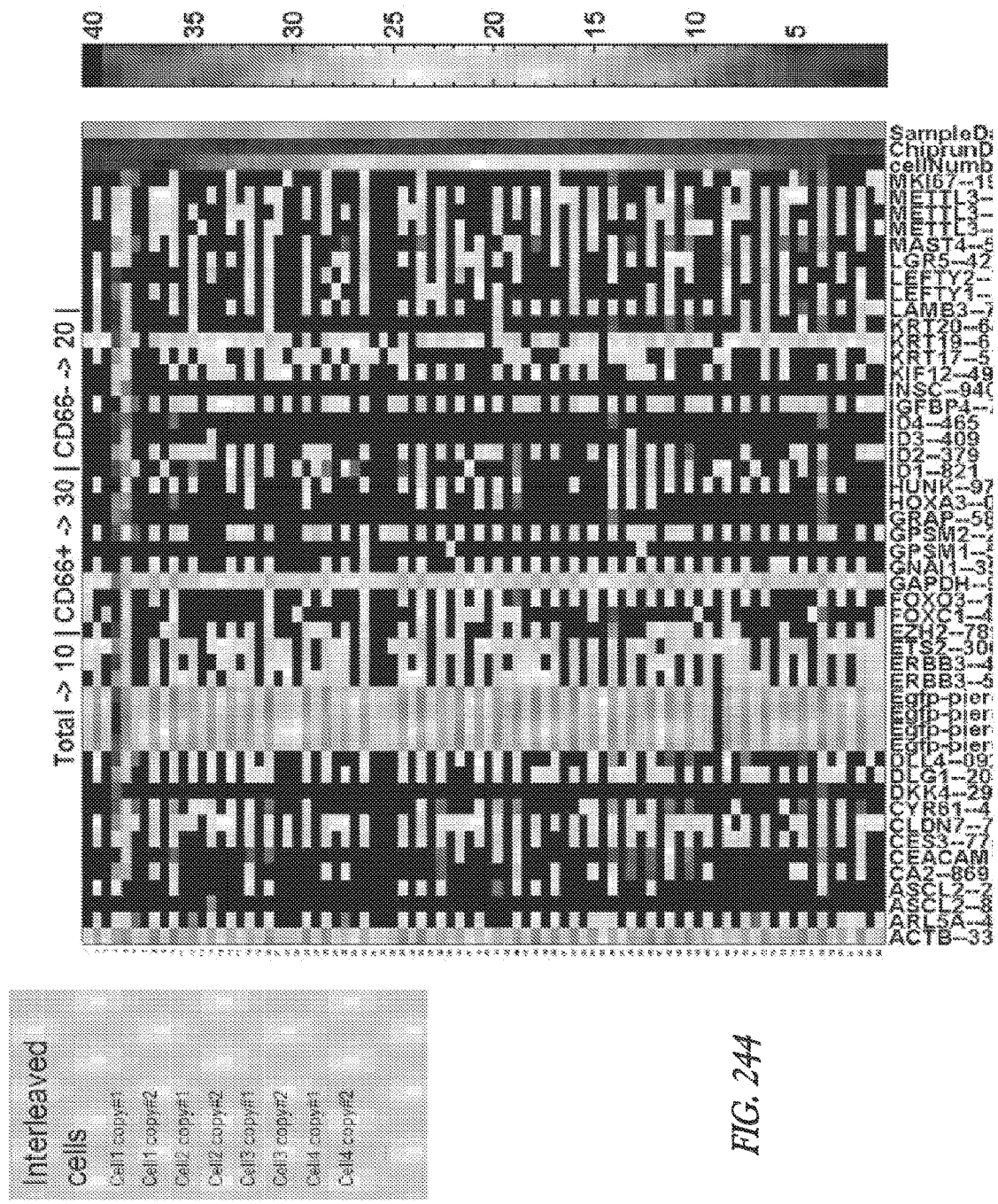
Figure 245:
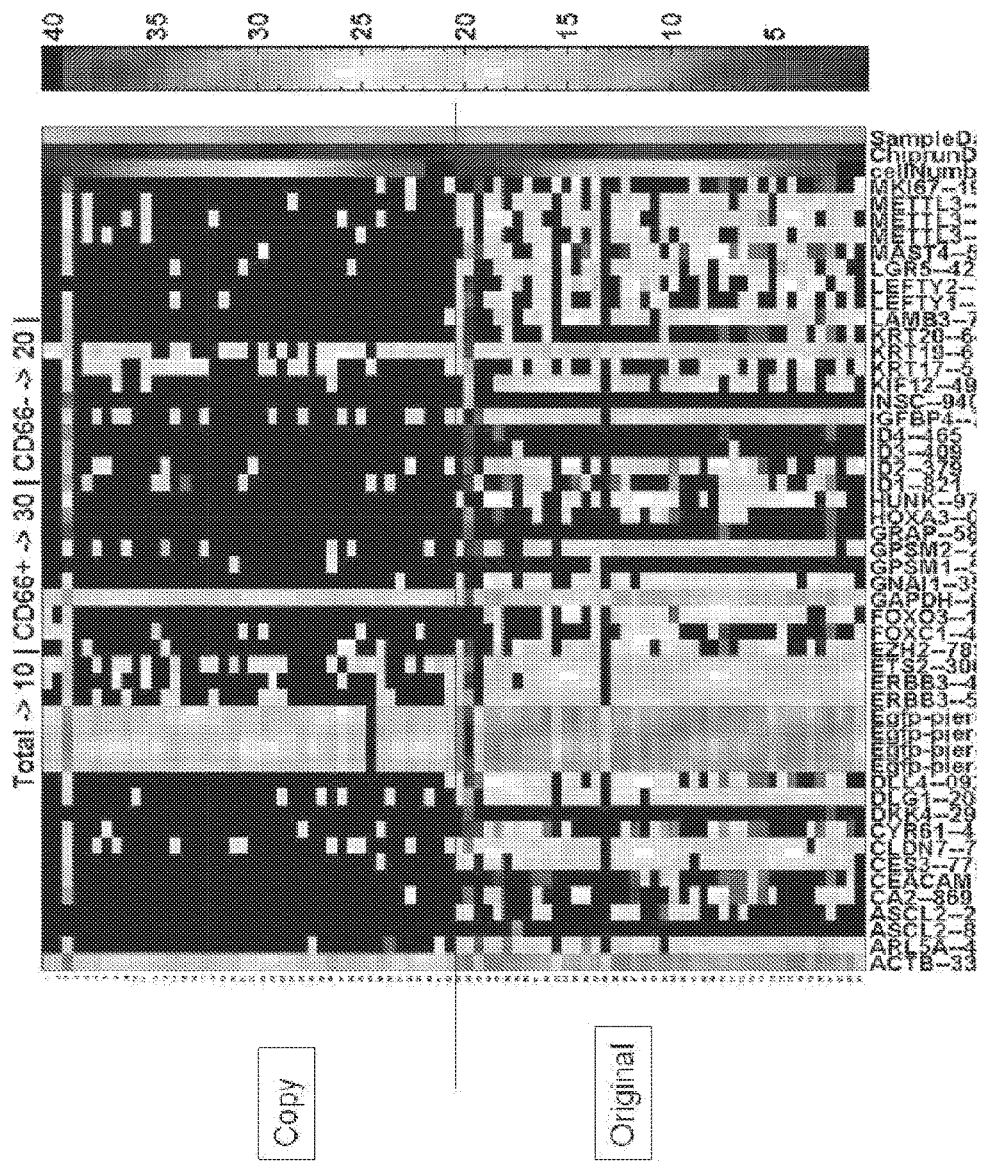
Figure 246:
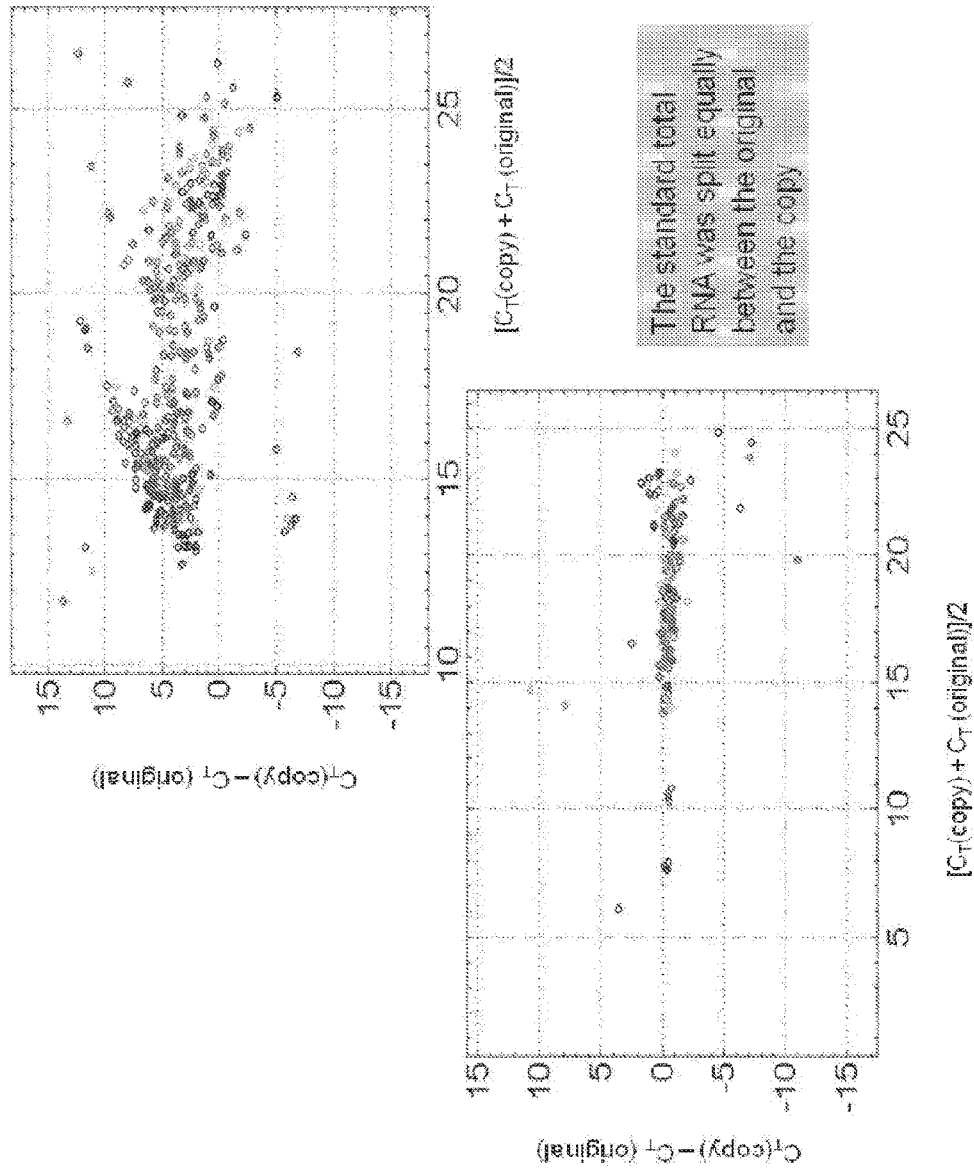
Figure 247:
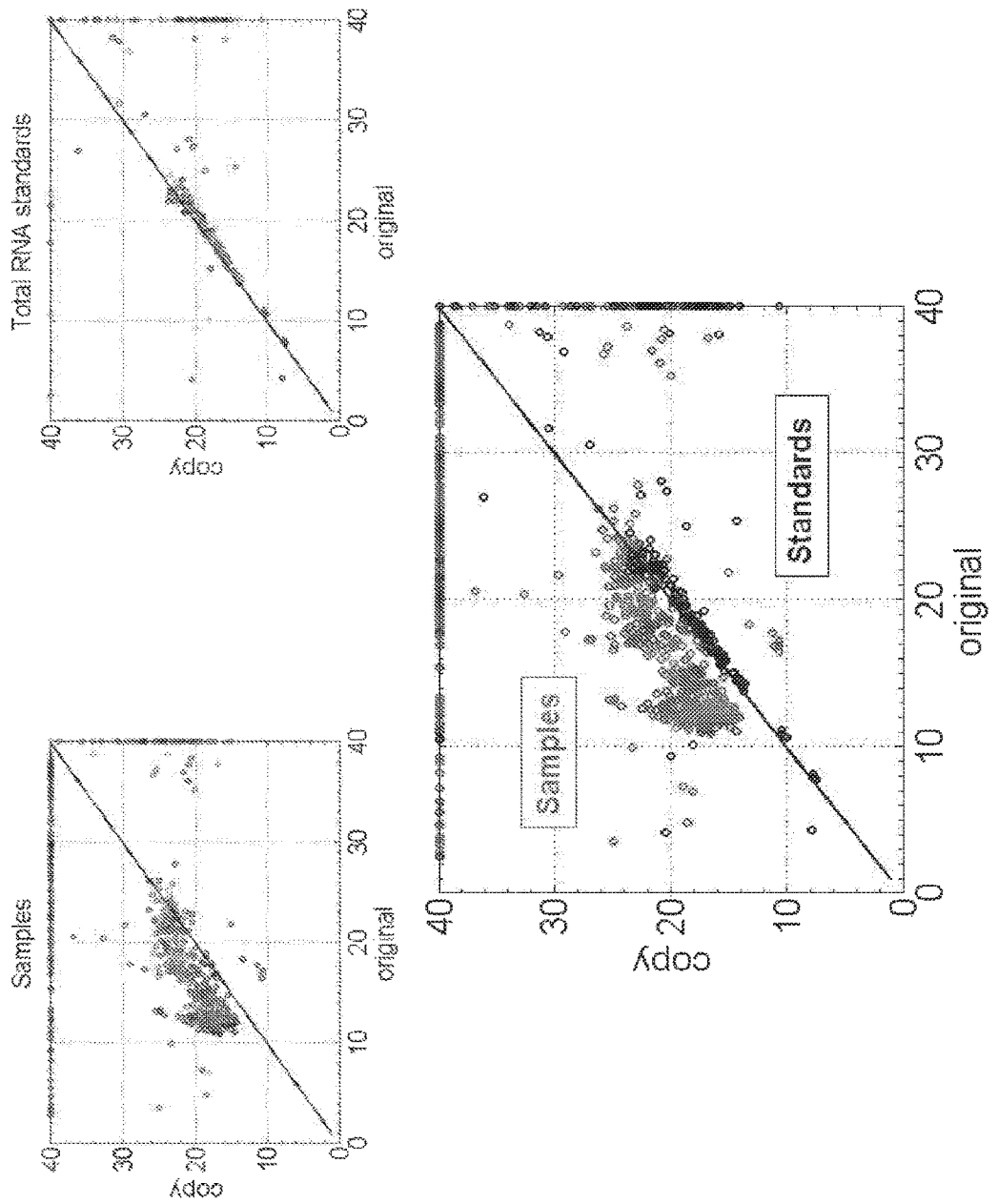
Figure 248:
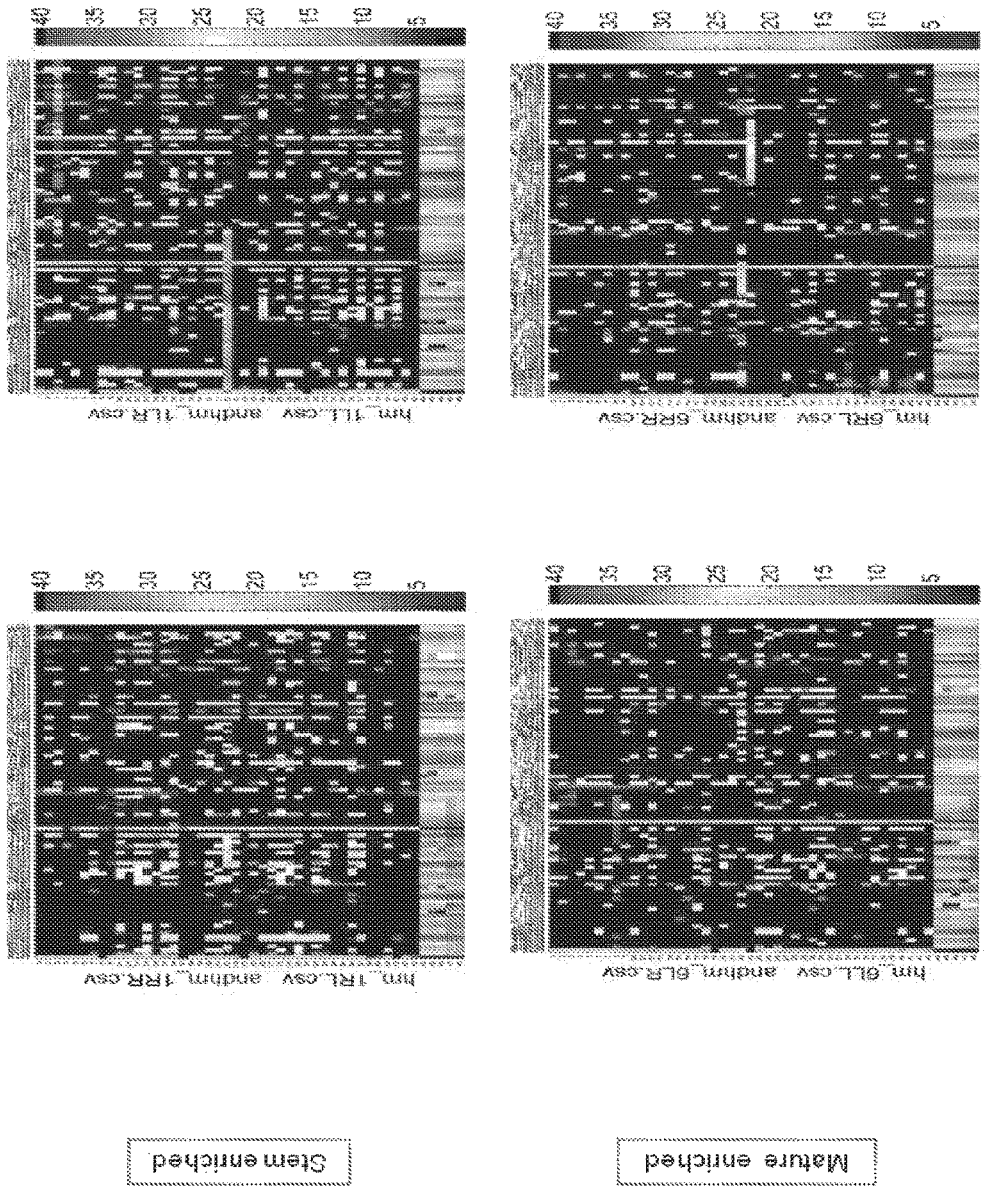
Figure 249:
Figure 250:
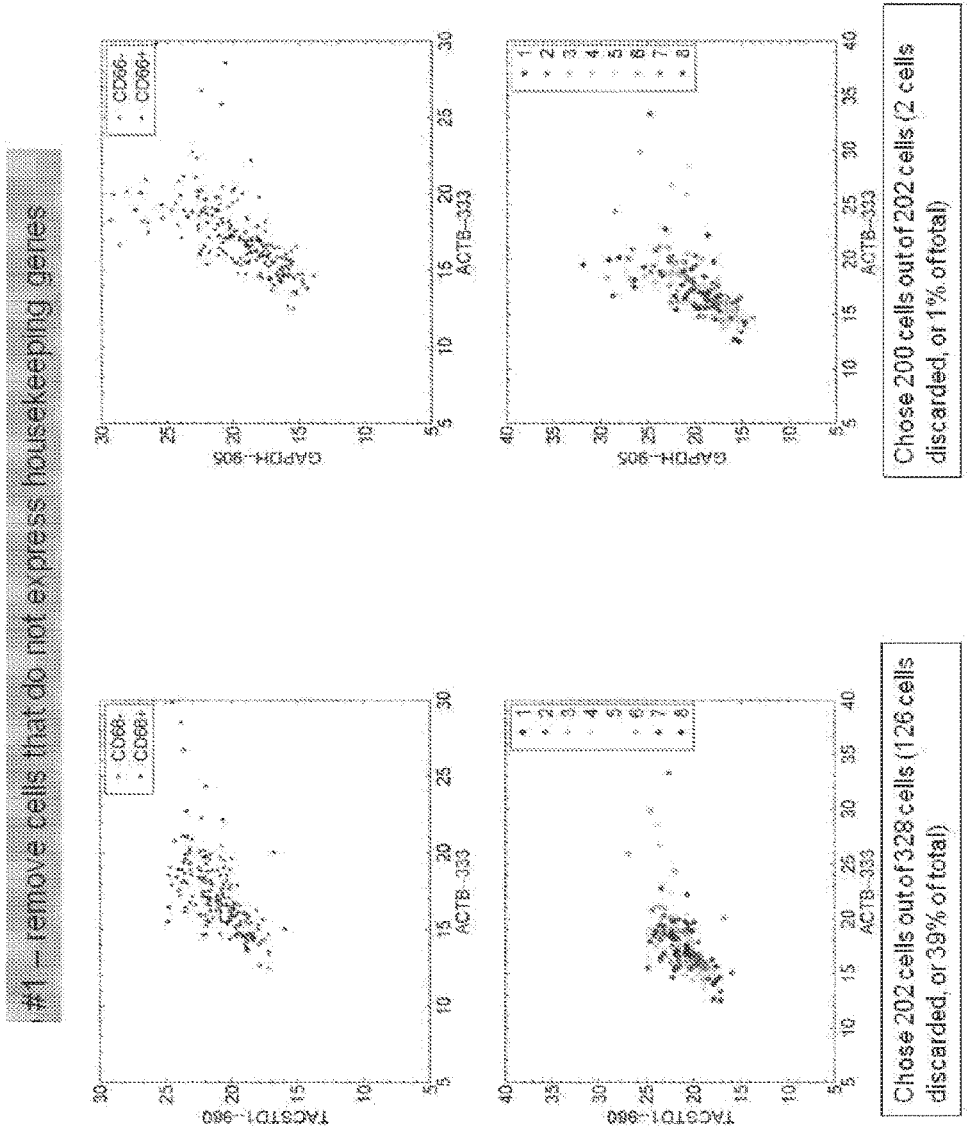
Figure 251:
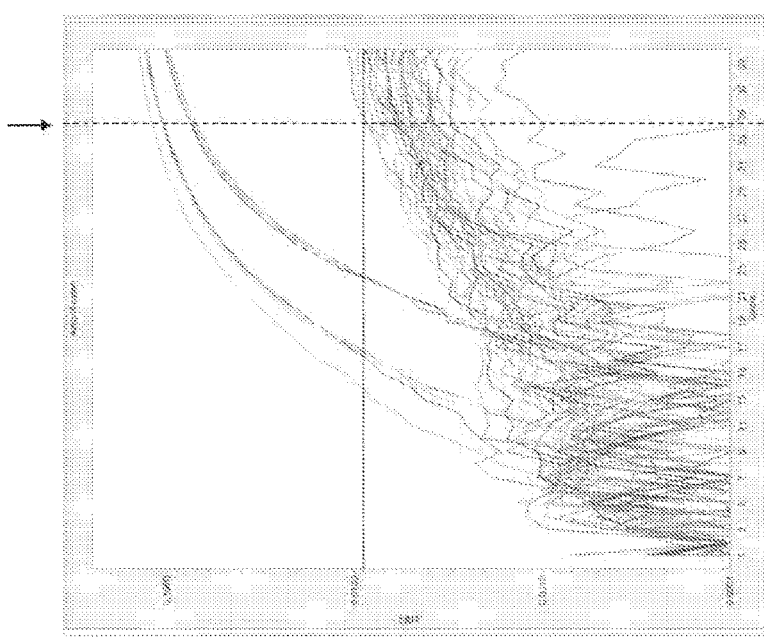
Figure 252:
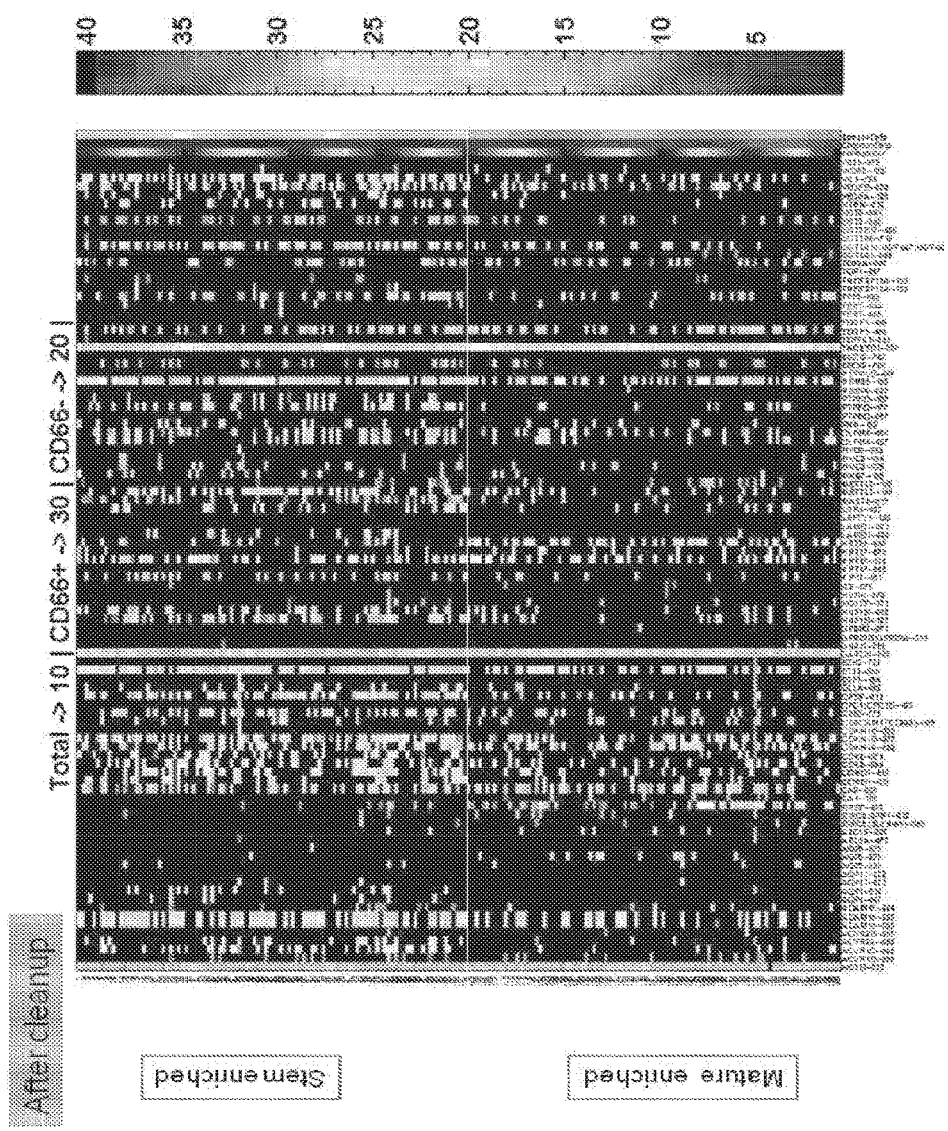
Figure 253:
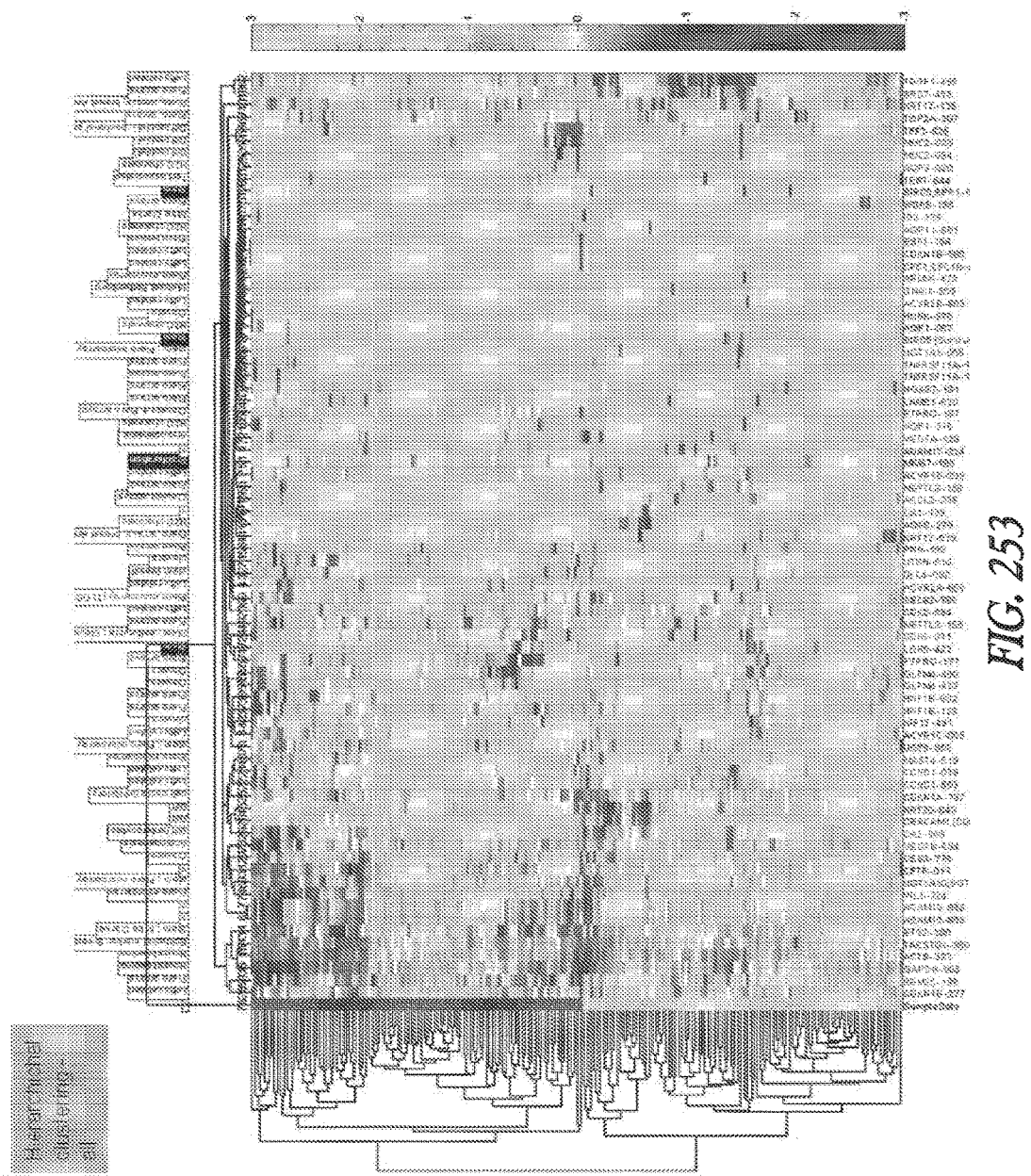
Figure 254:
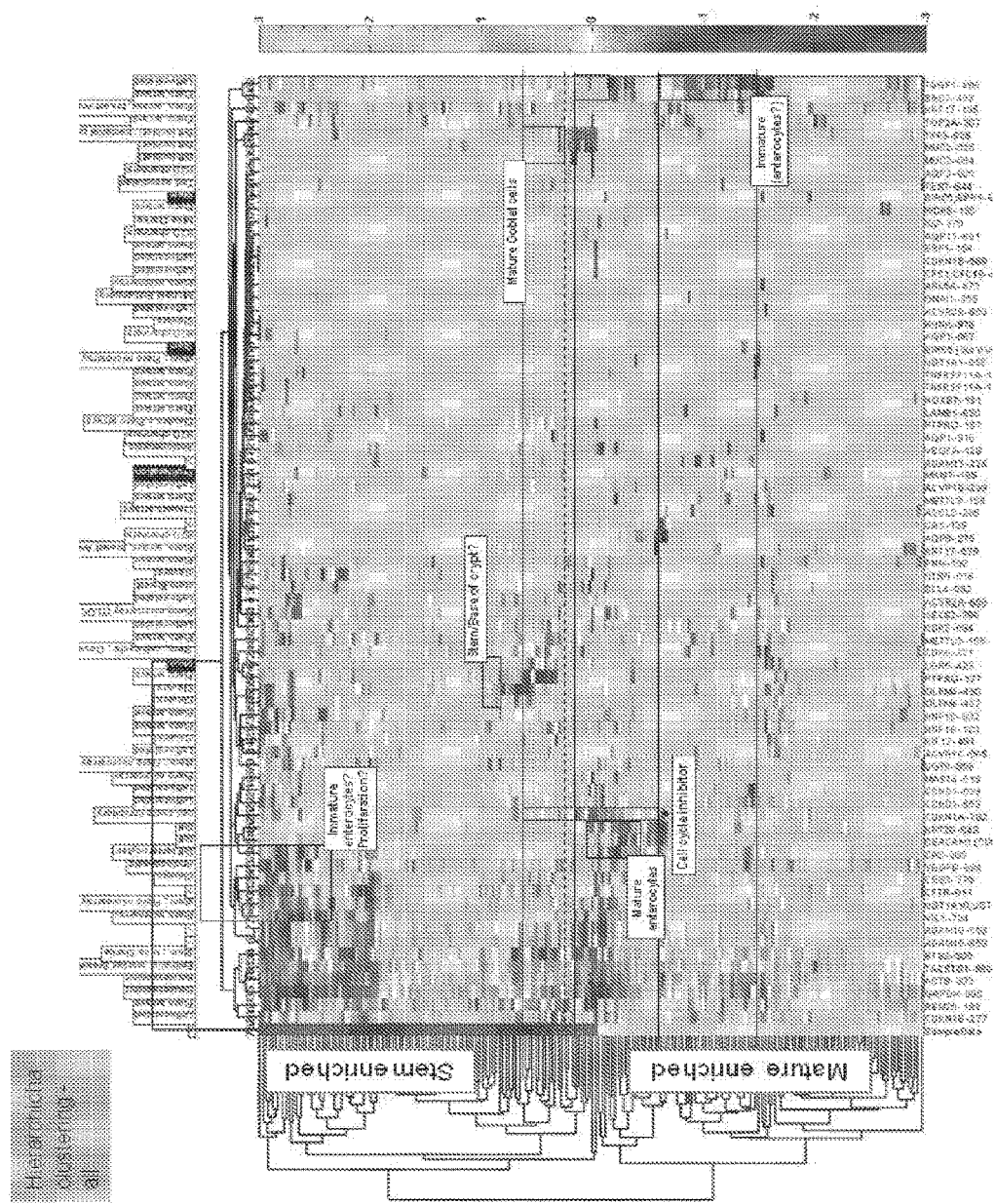
Figure 255:
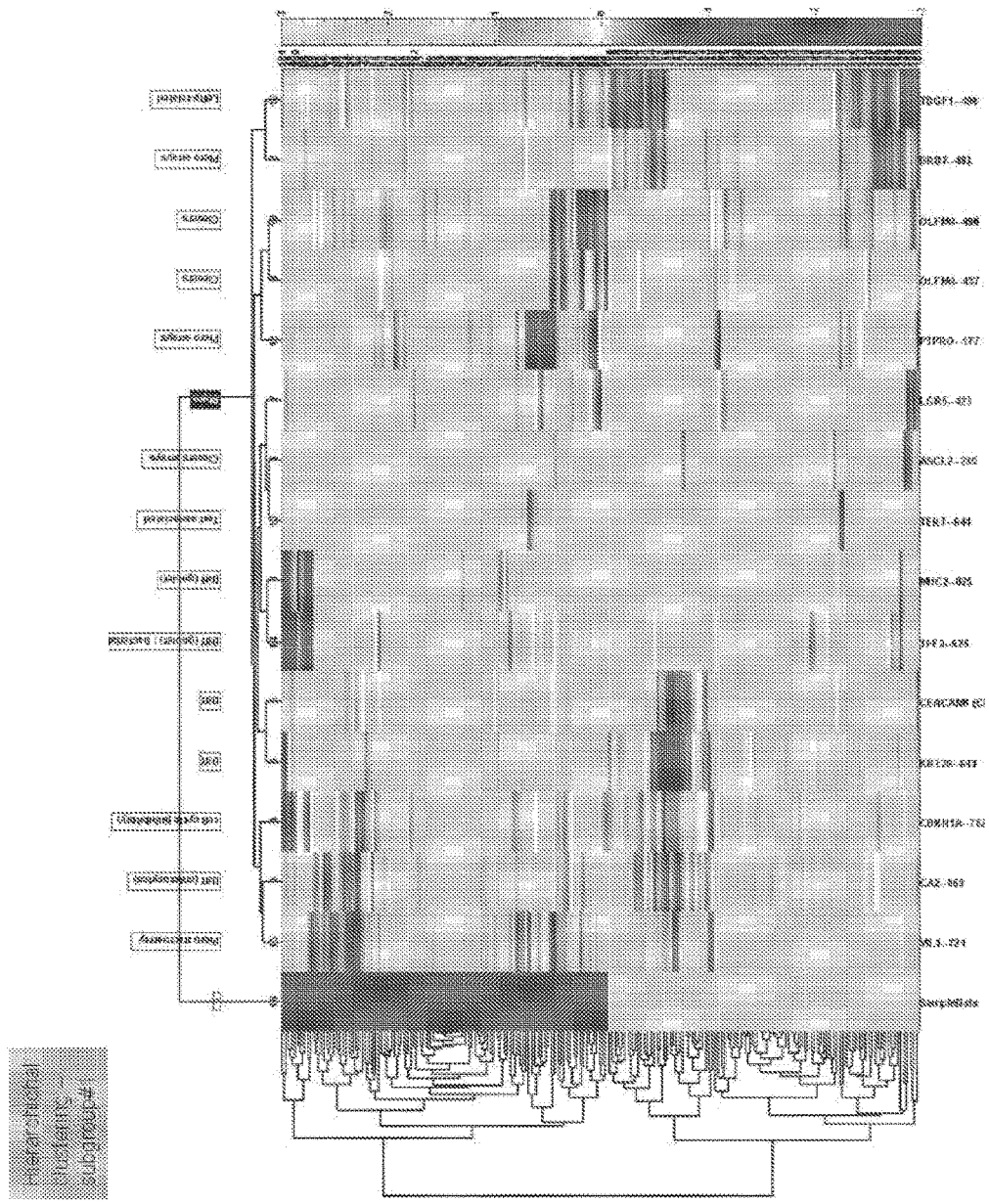
Figure 256:
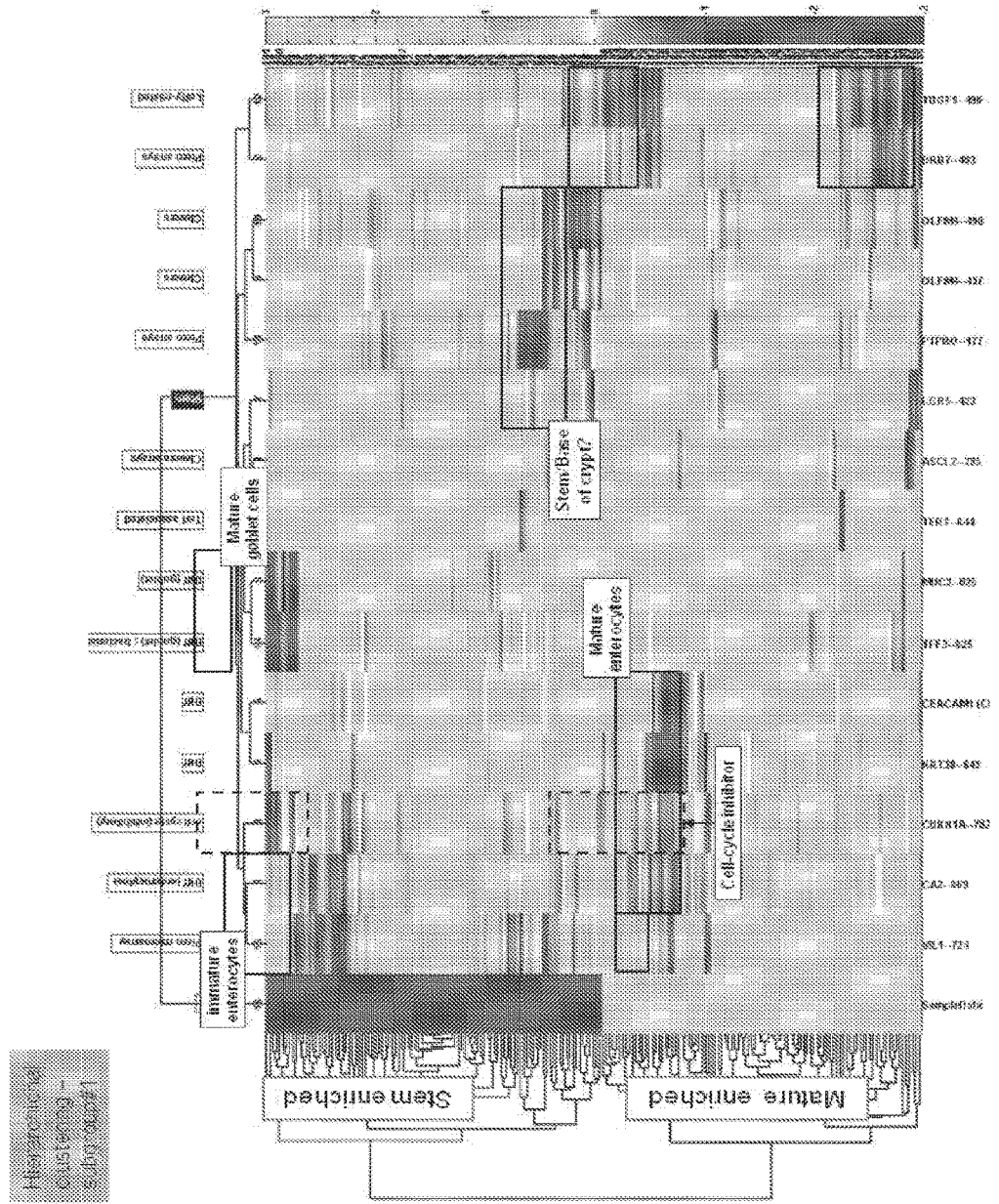
Figure 258:
Figure 259:
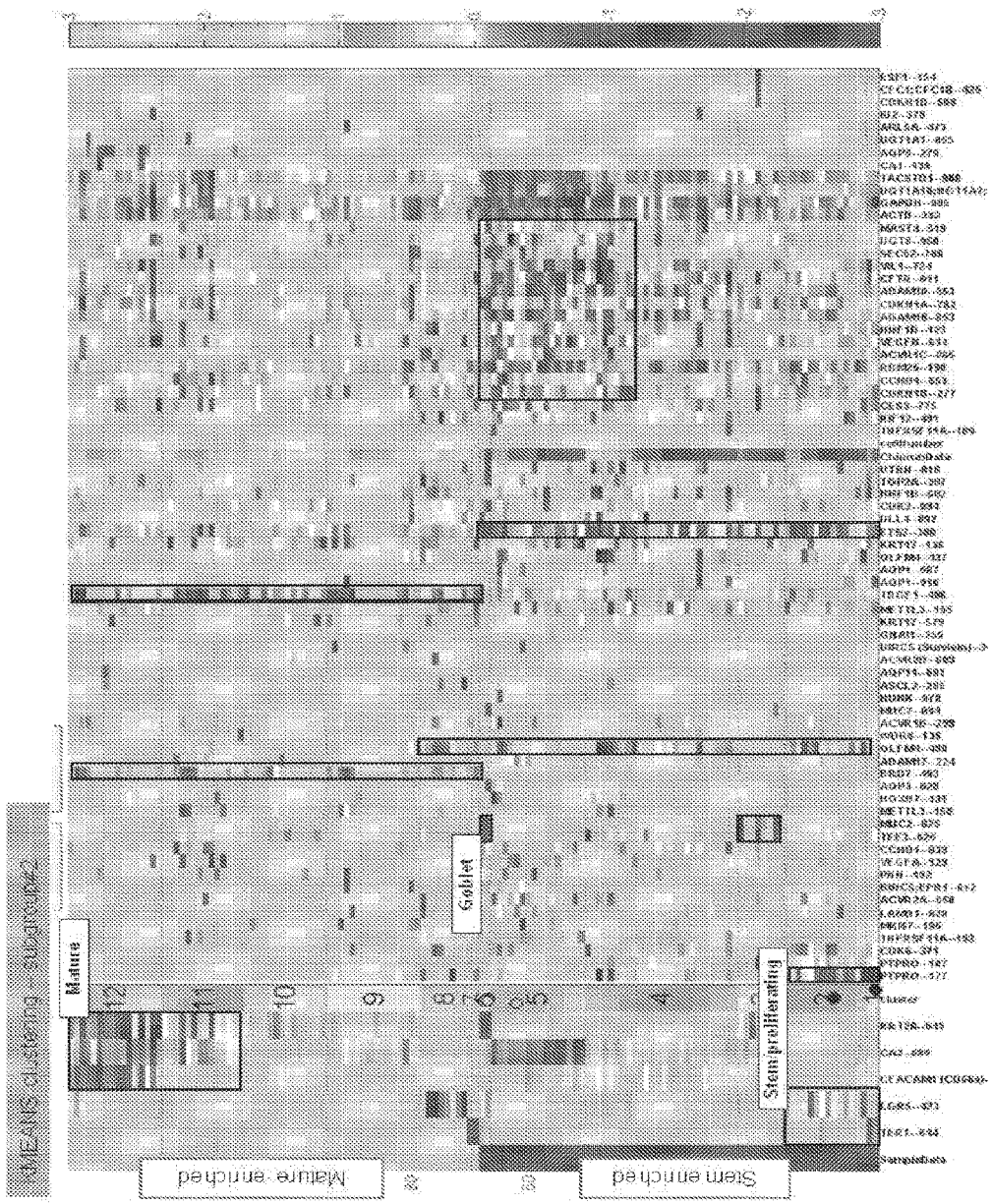
Figure 260:
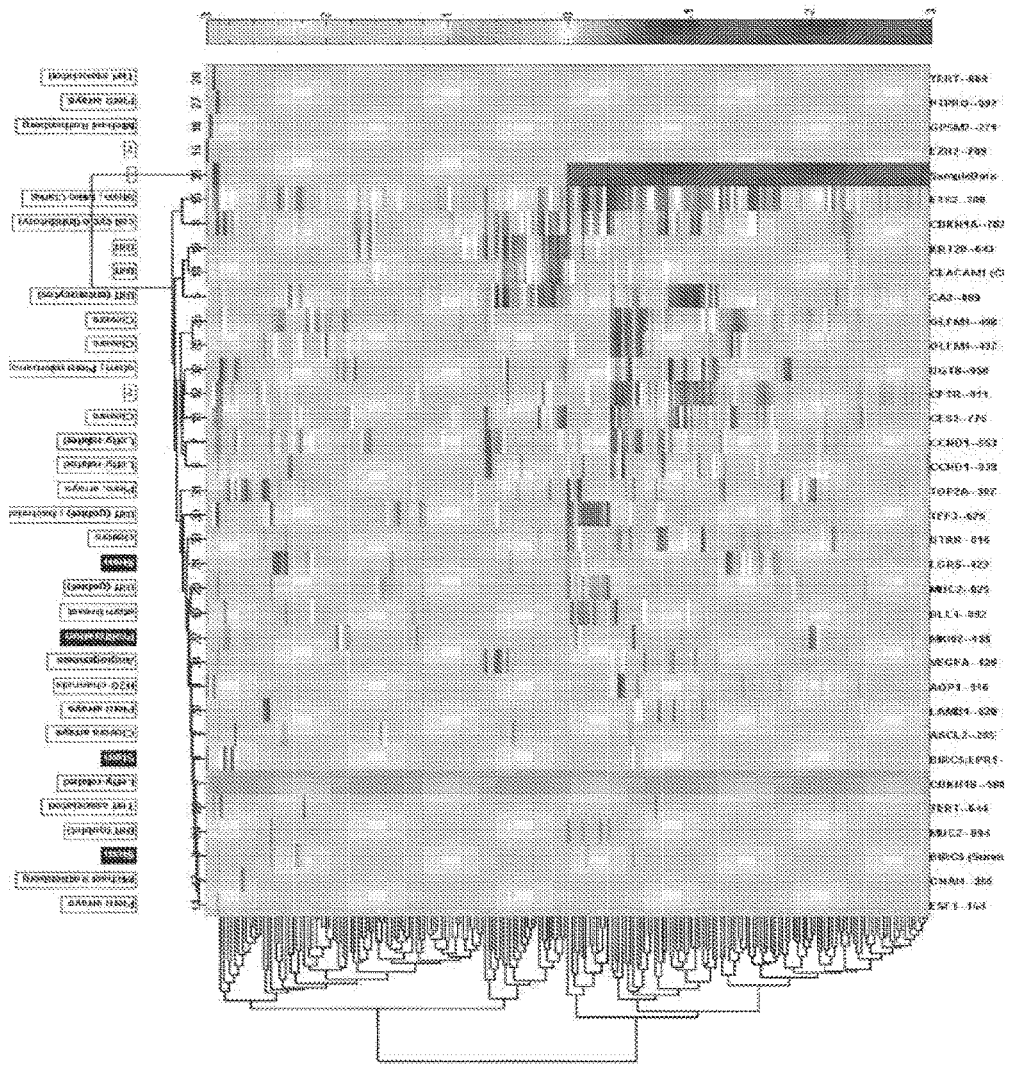
Figure 261:
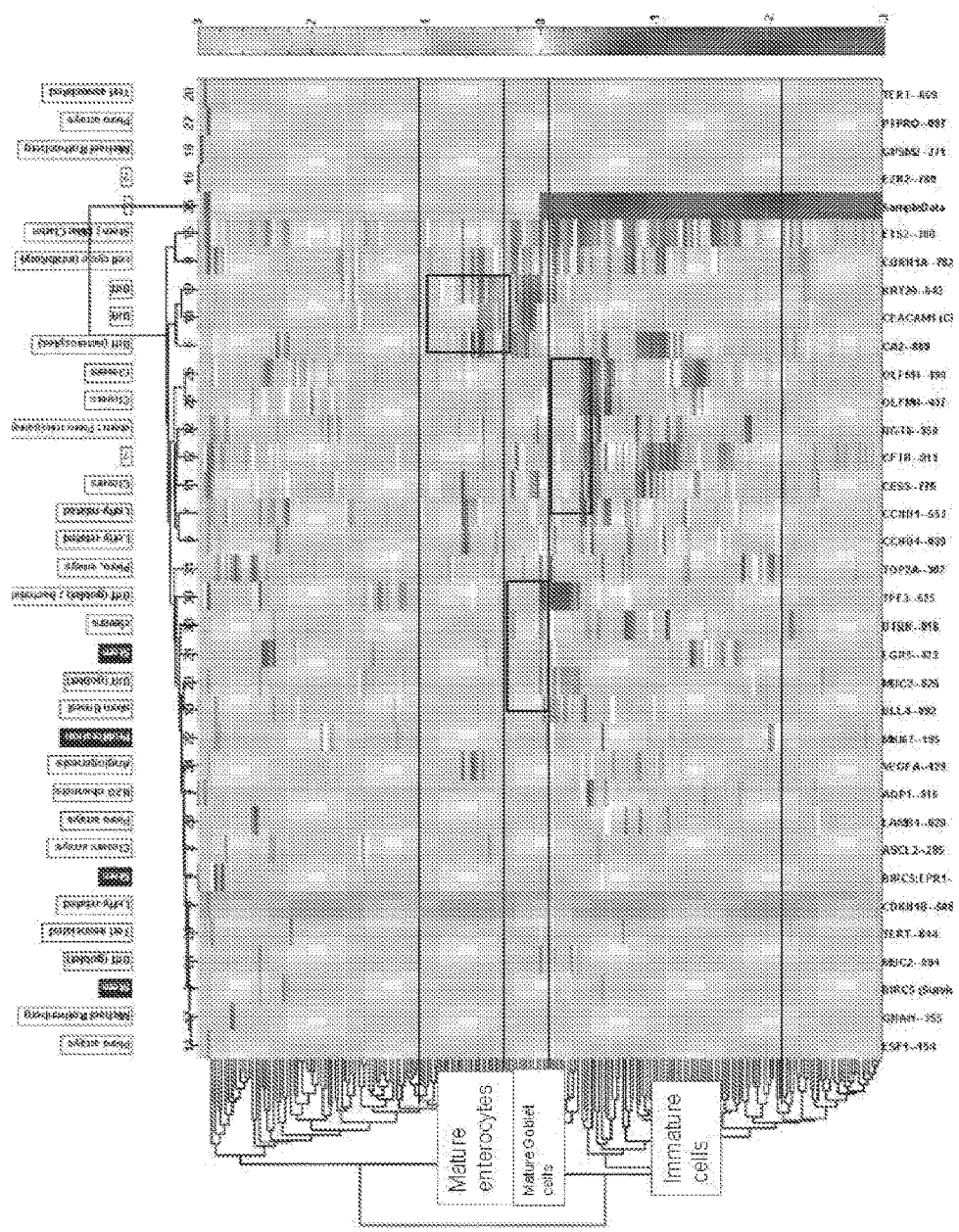
Figure 262:
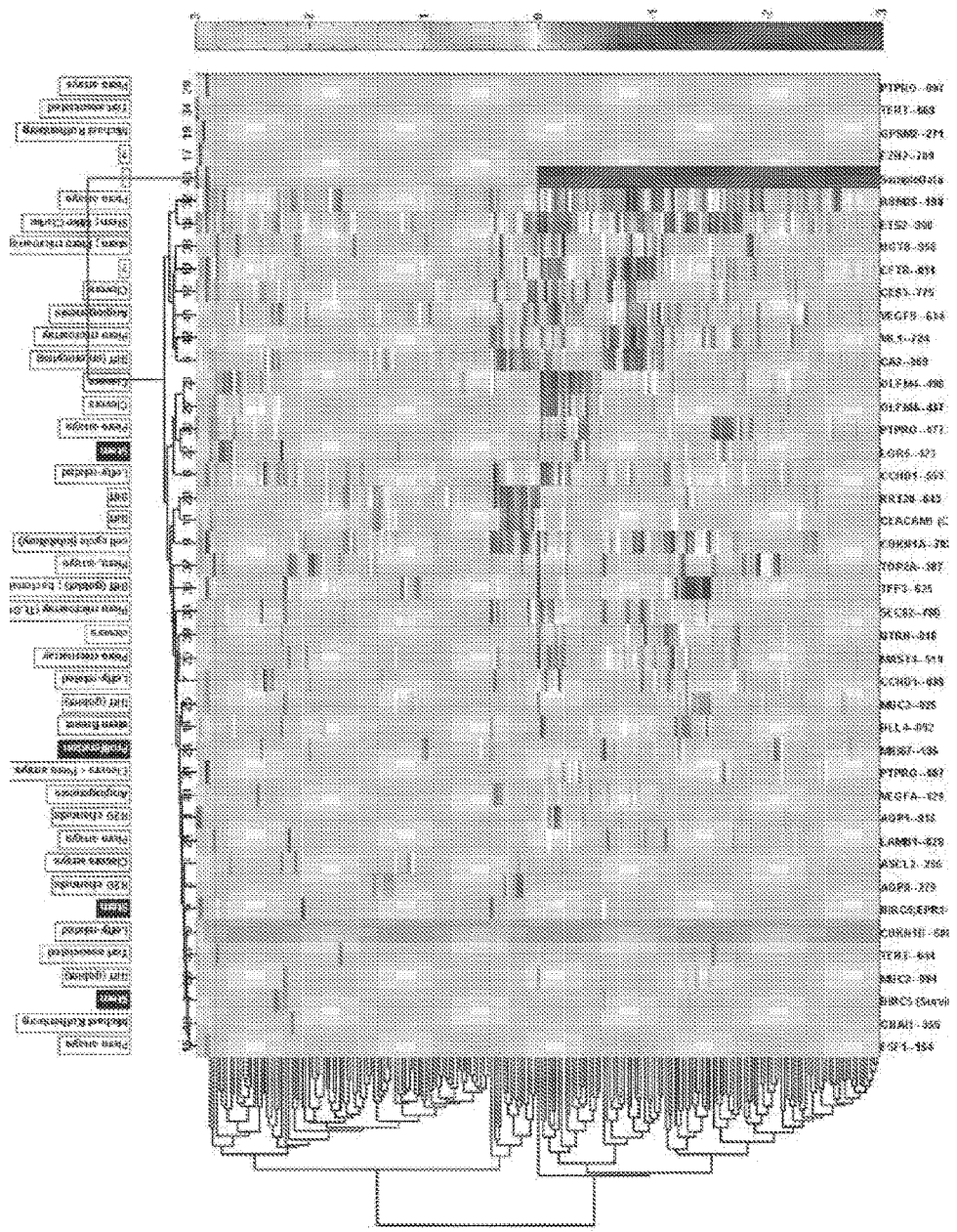
Figure 263:
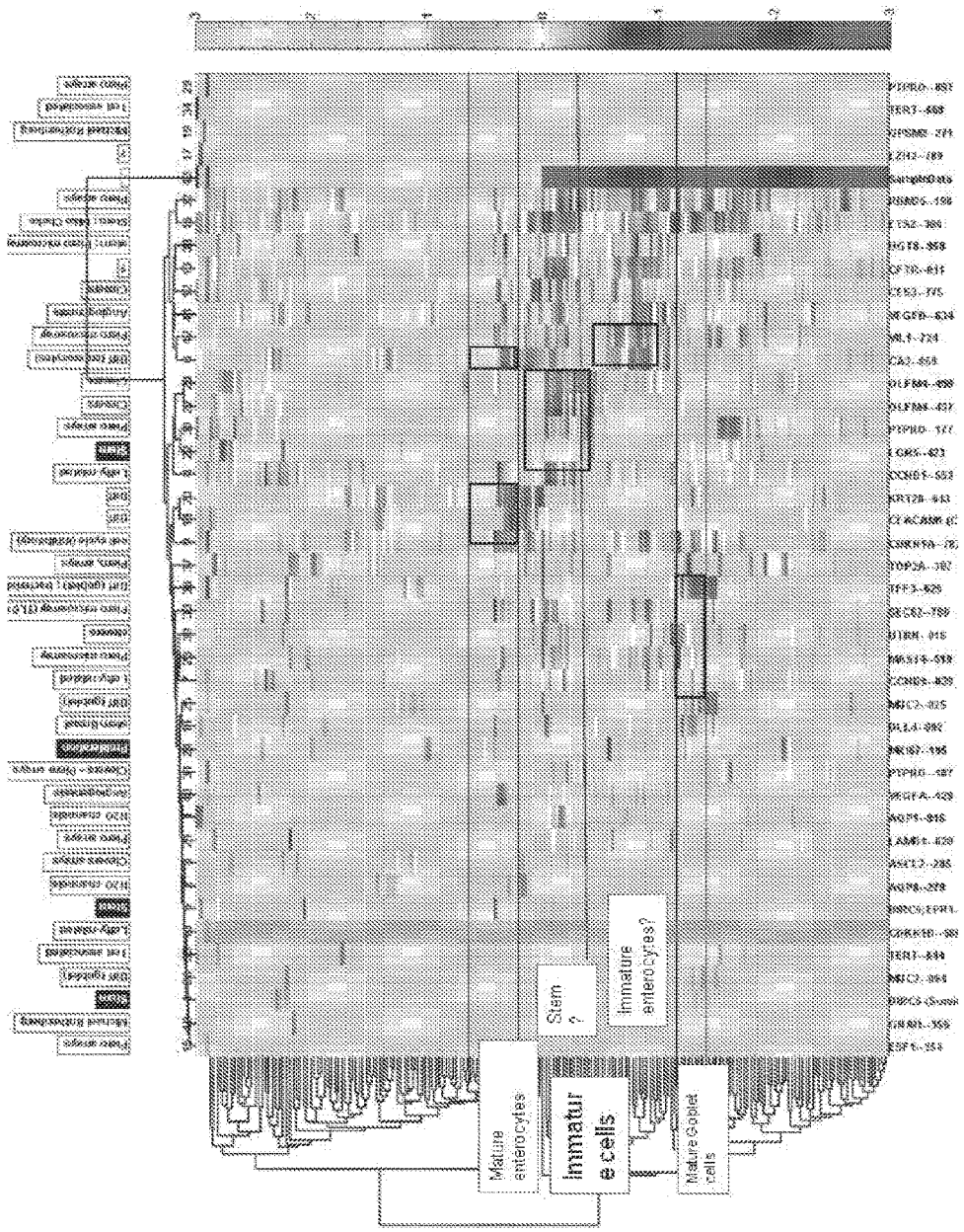
Figure 264:
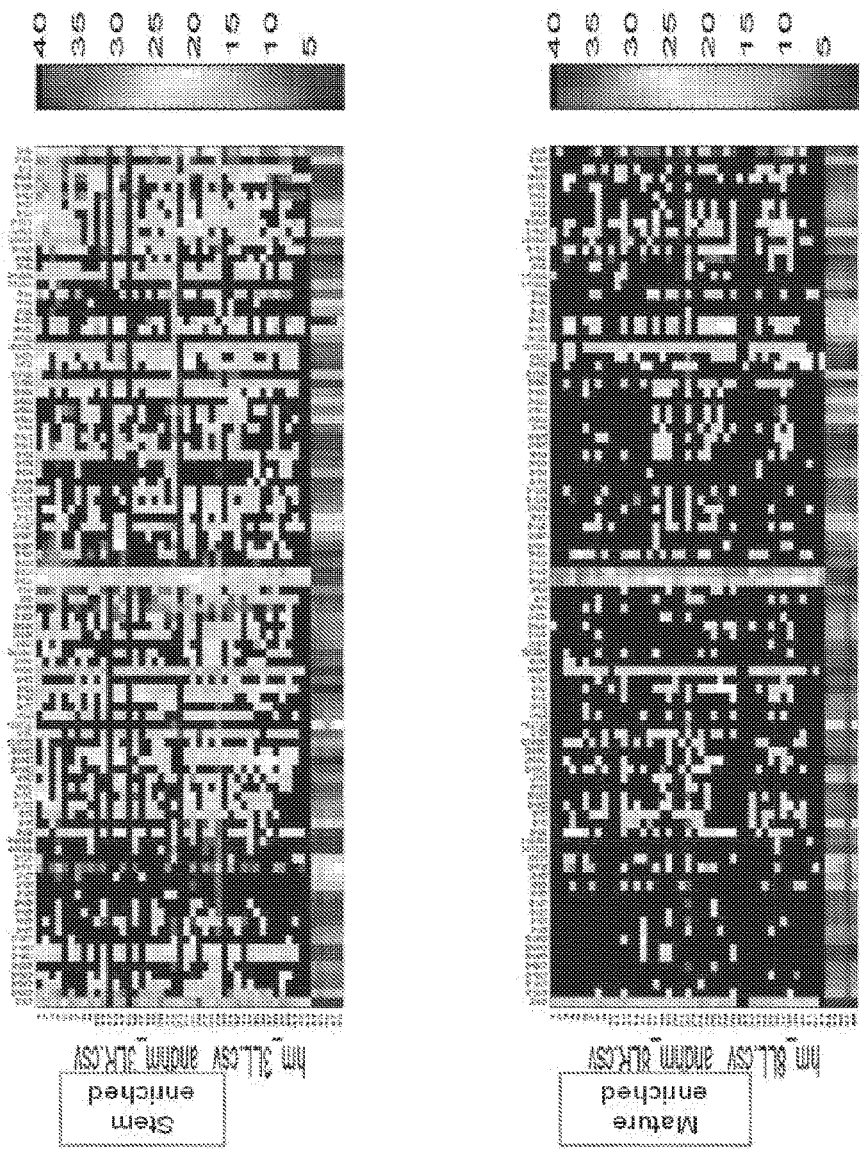
Figure 265:
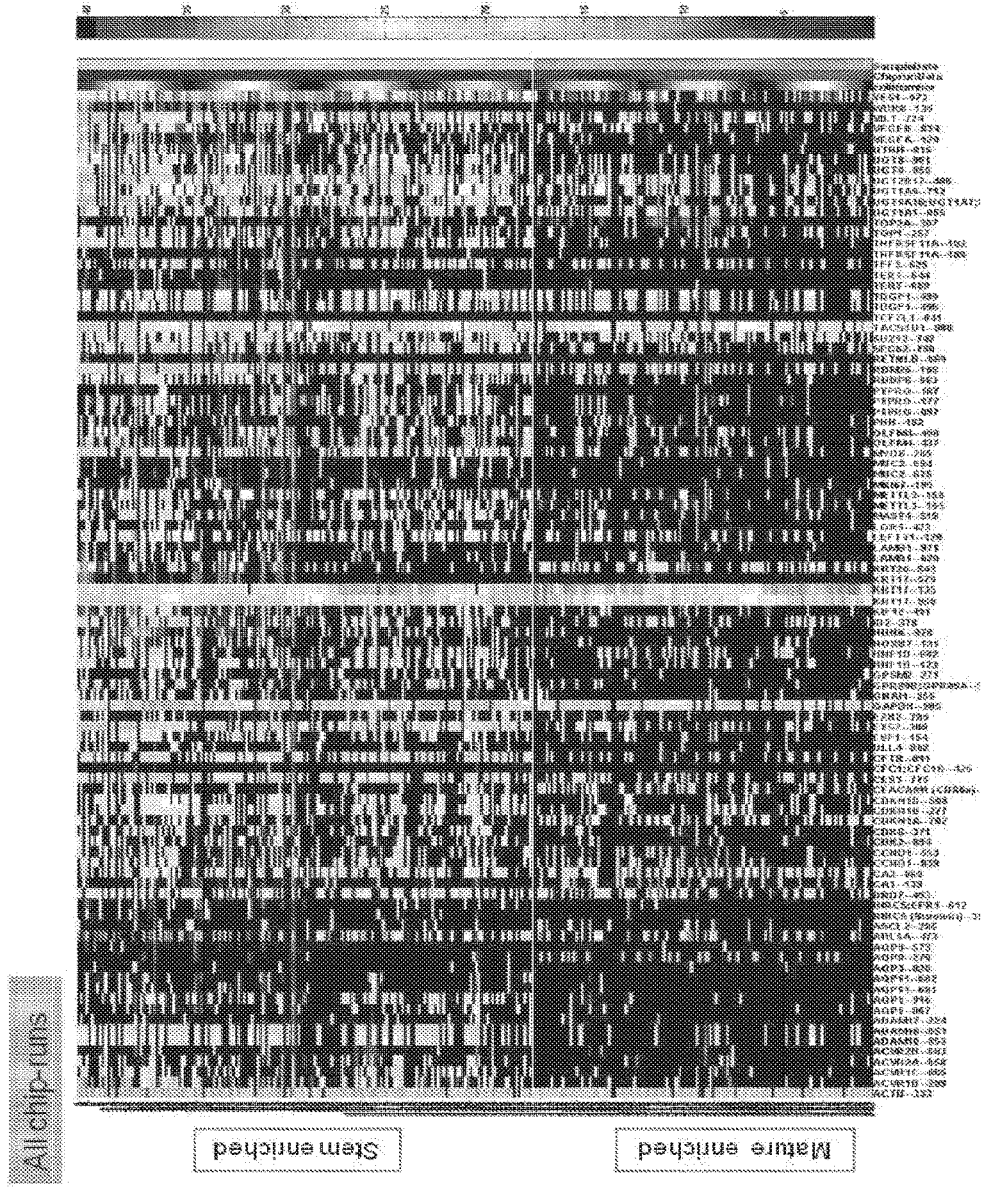
Figure 266:
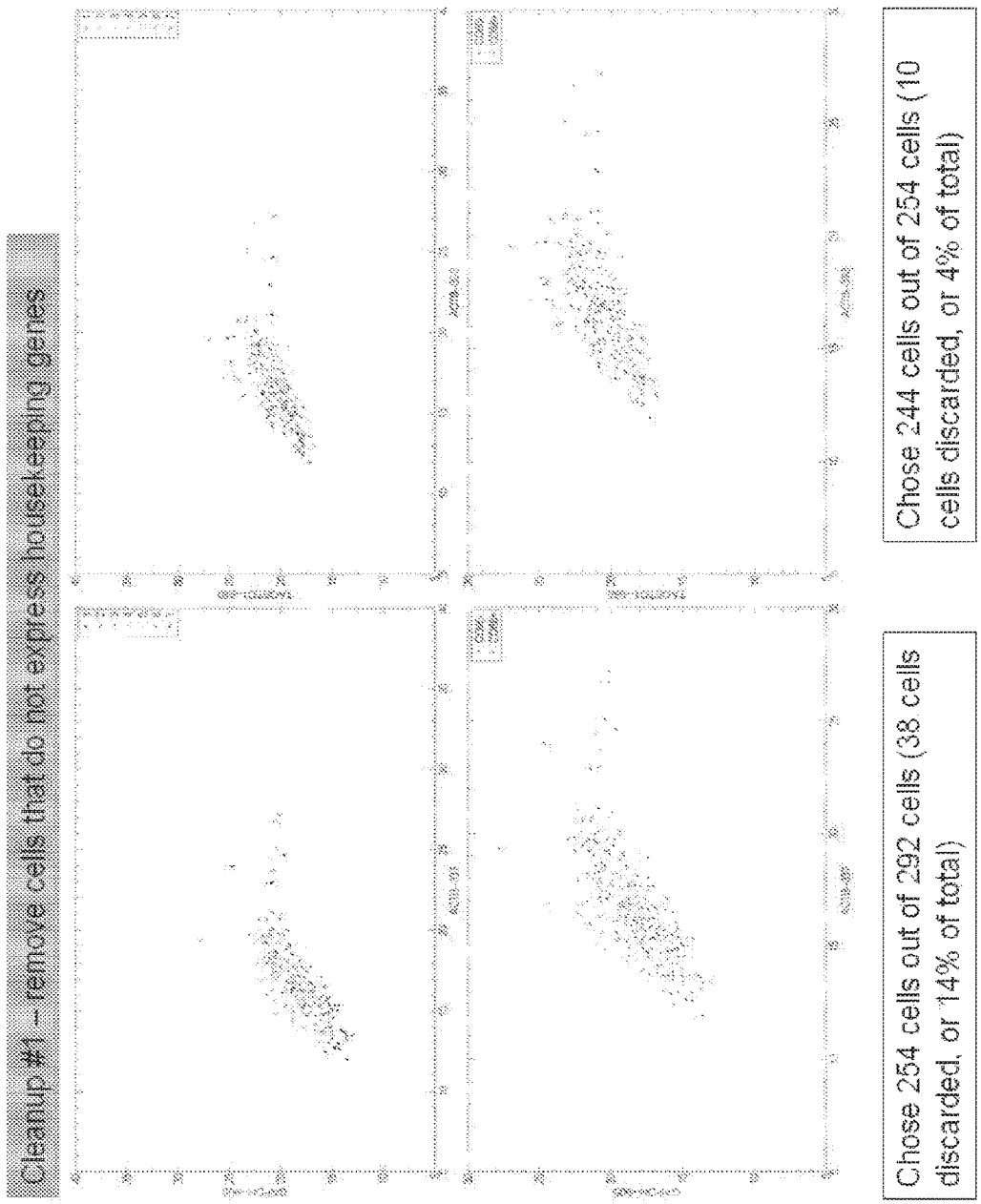
Figure 267:
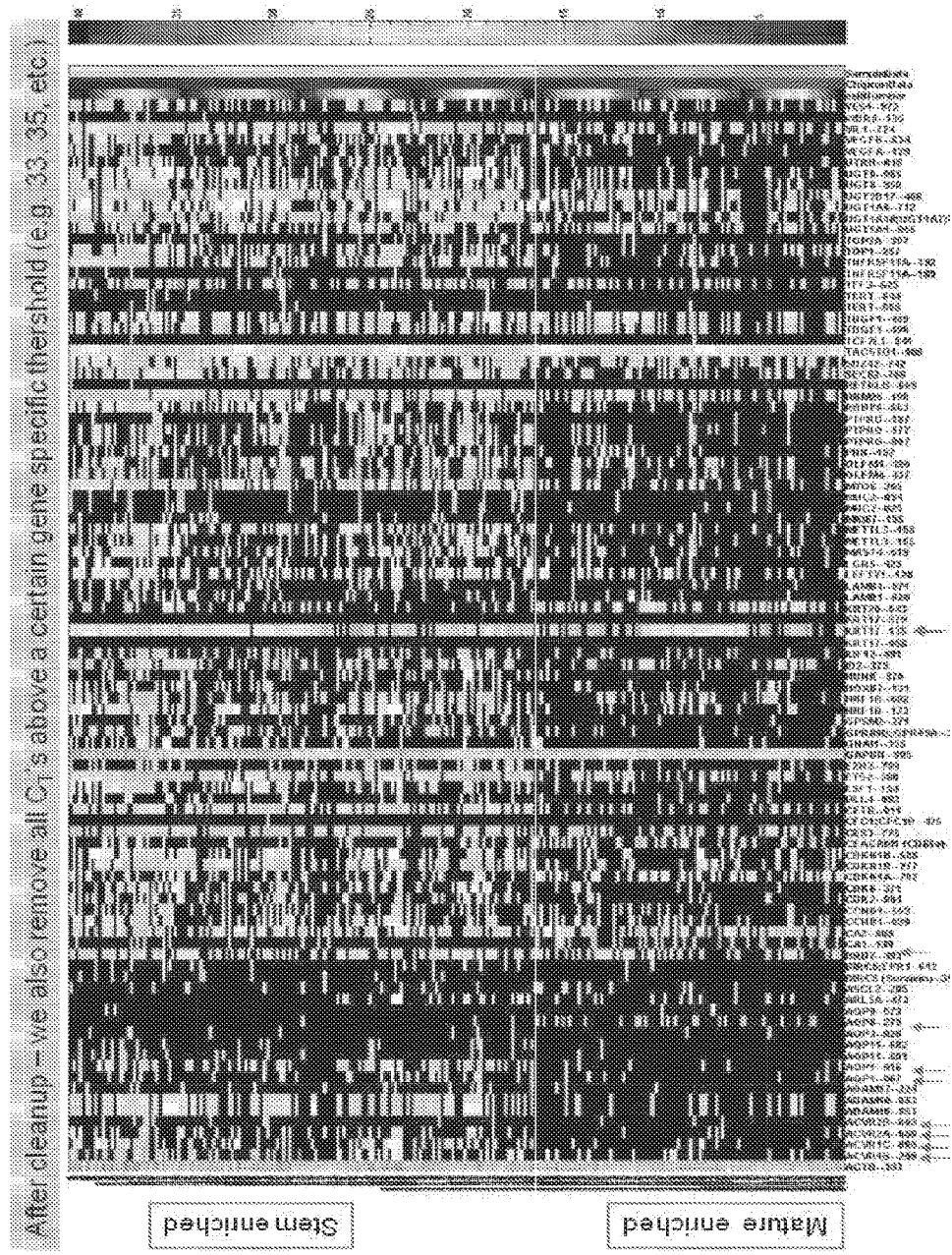
Figure 268:
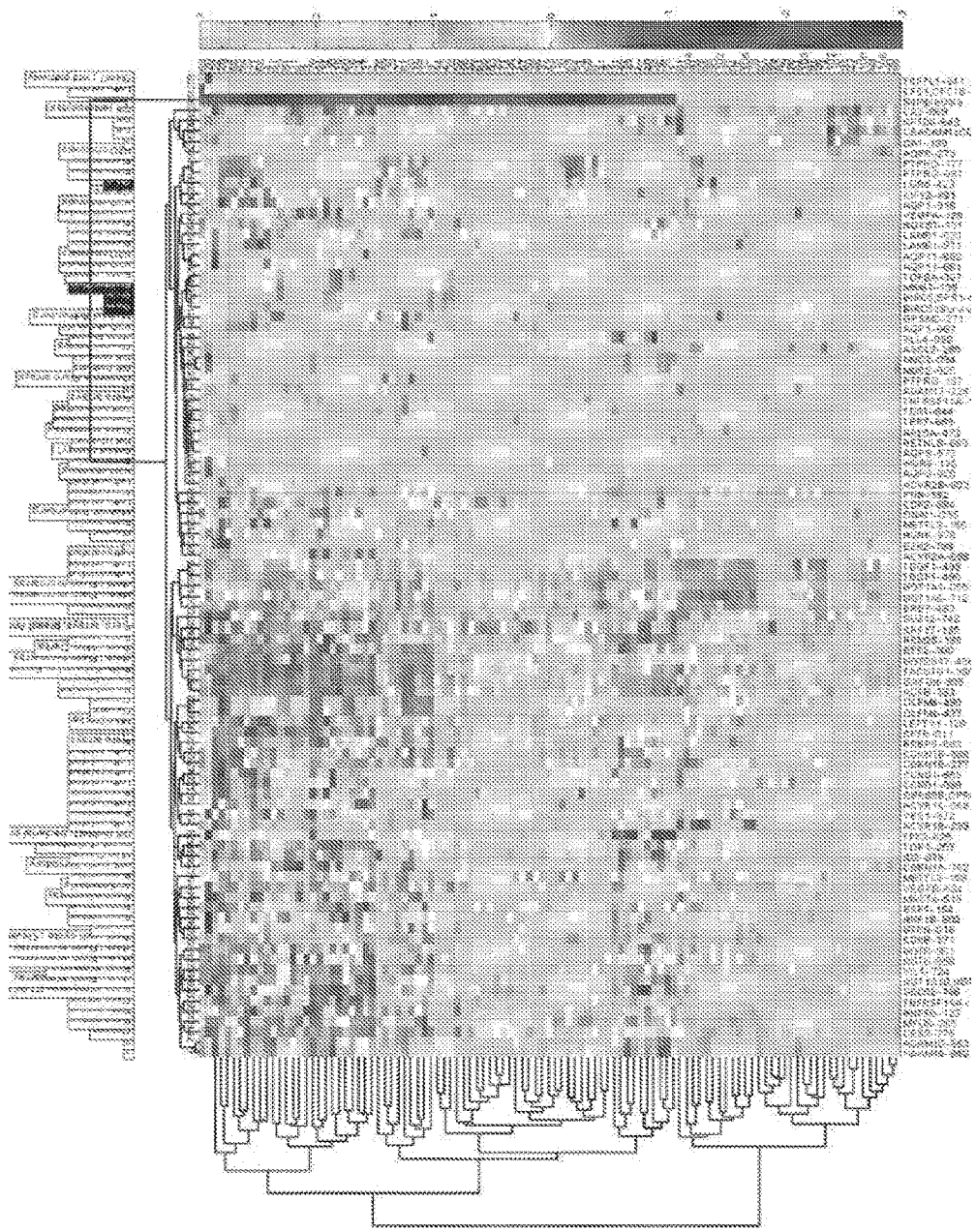
Figure 269:
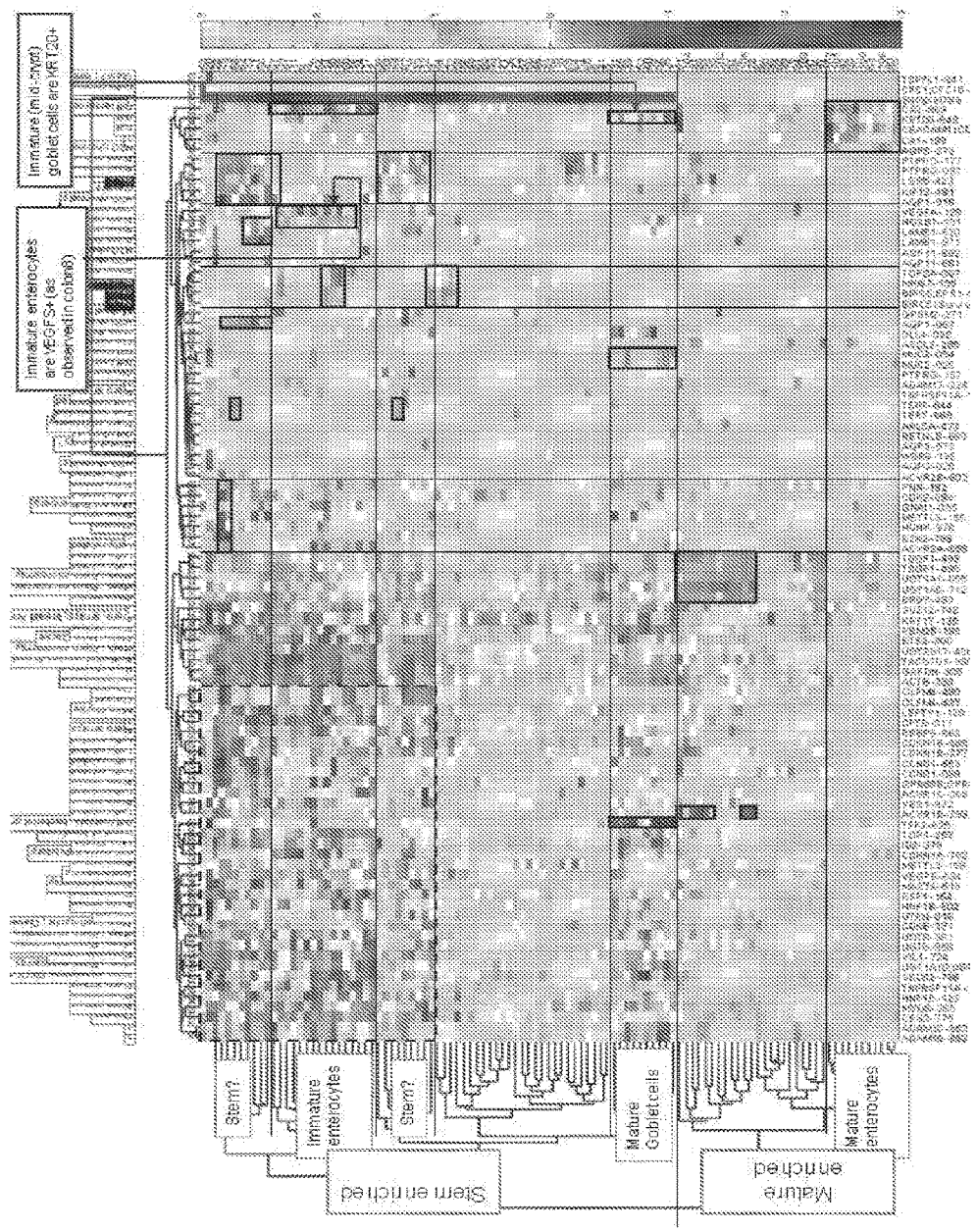
Figure 270:
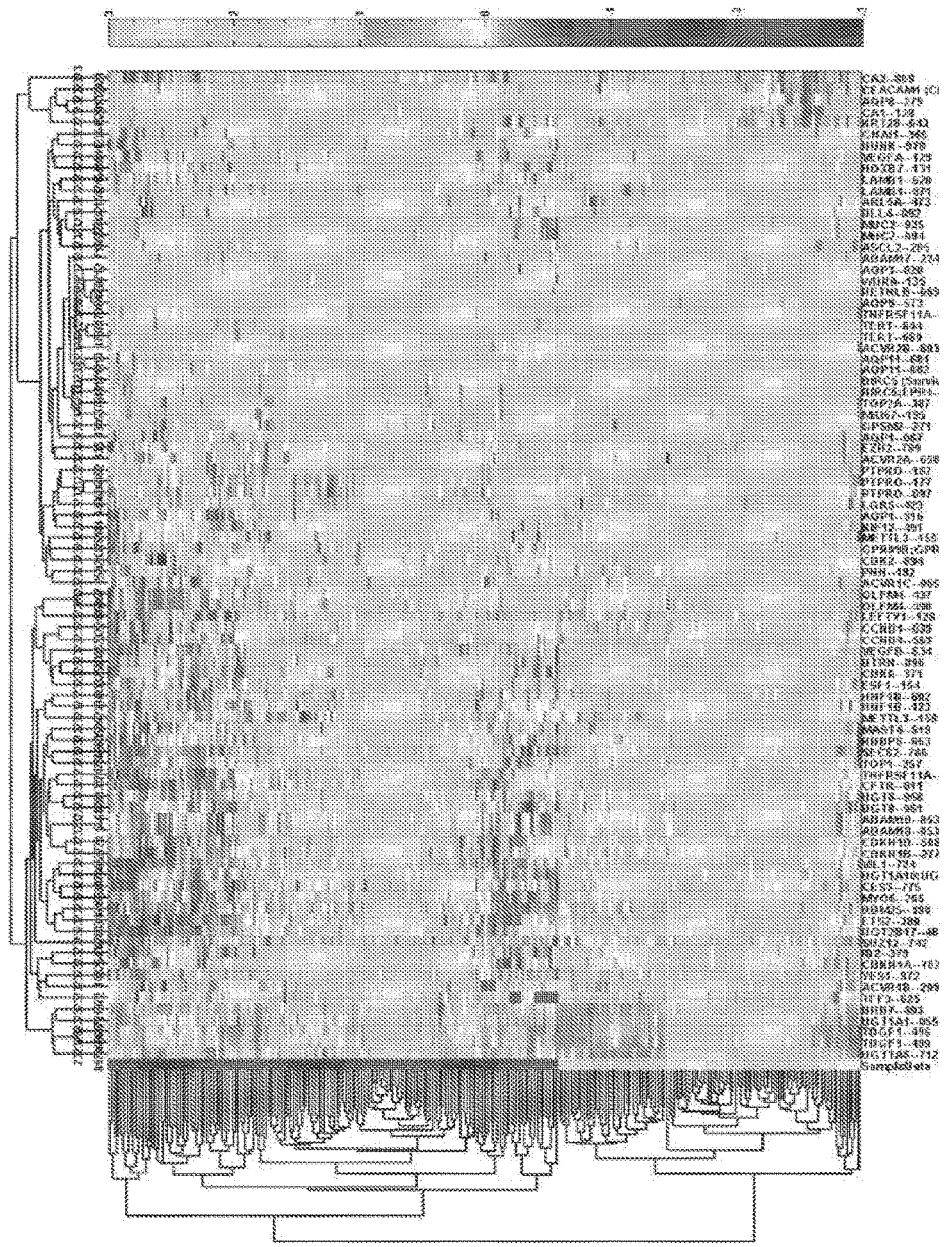
Figure 271:
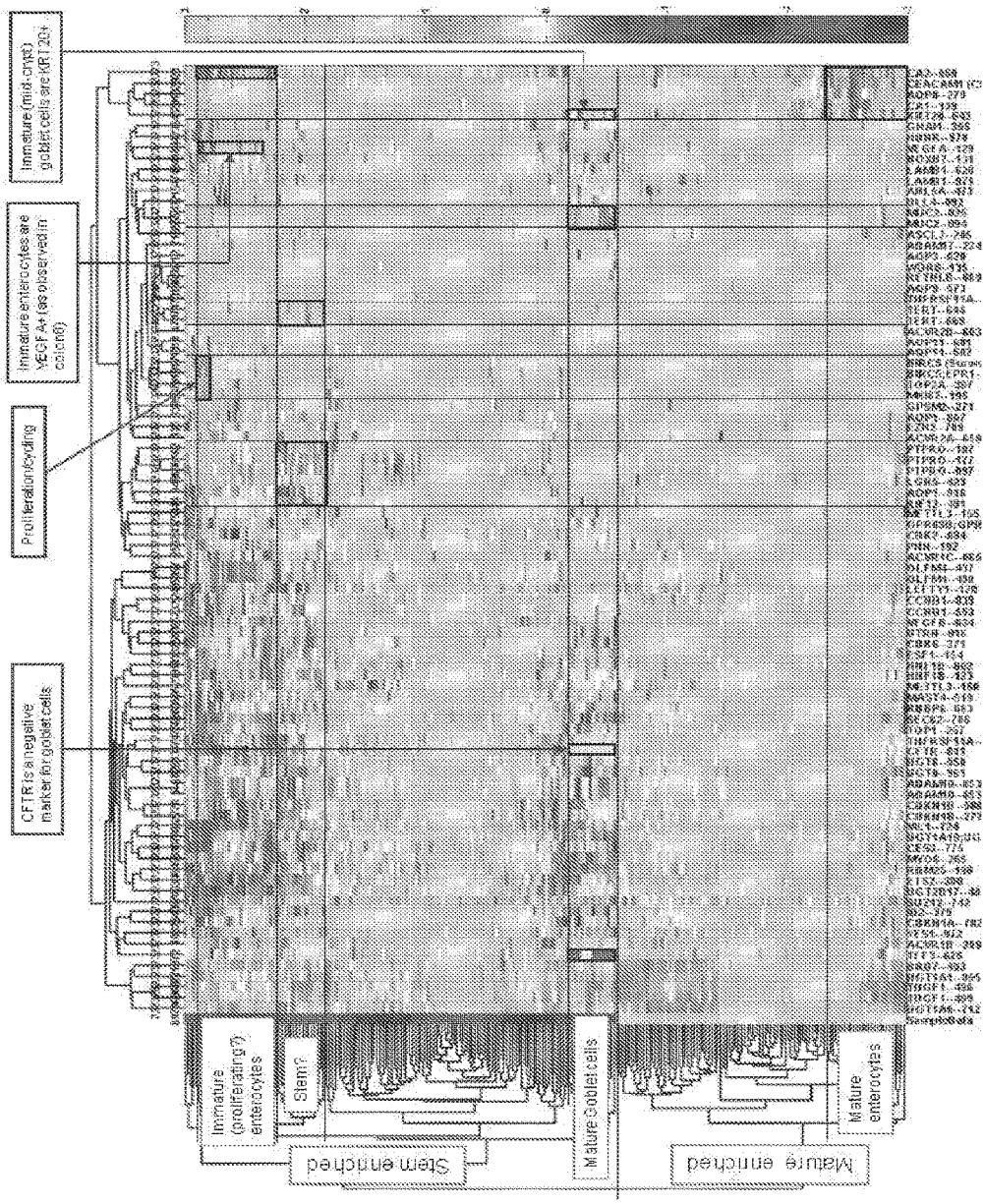
Figure 272:
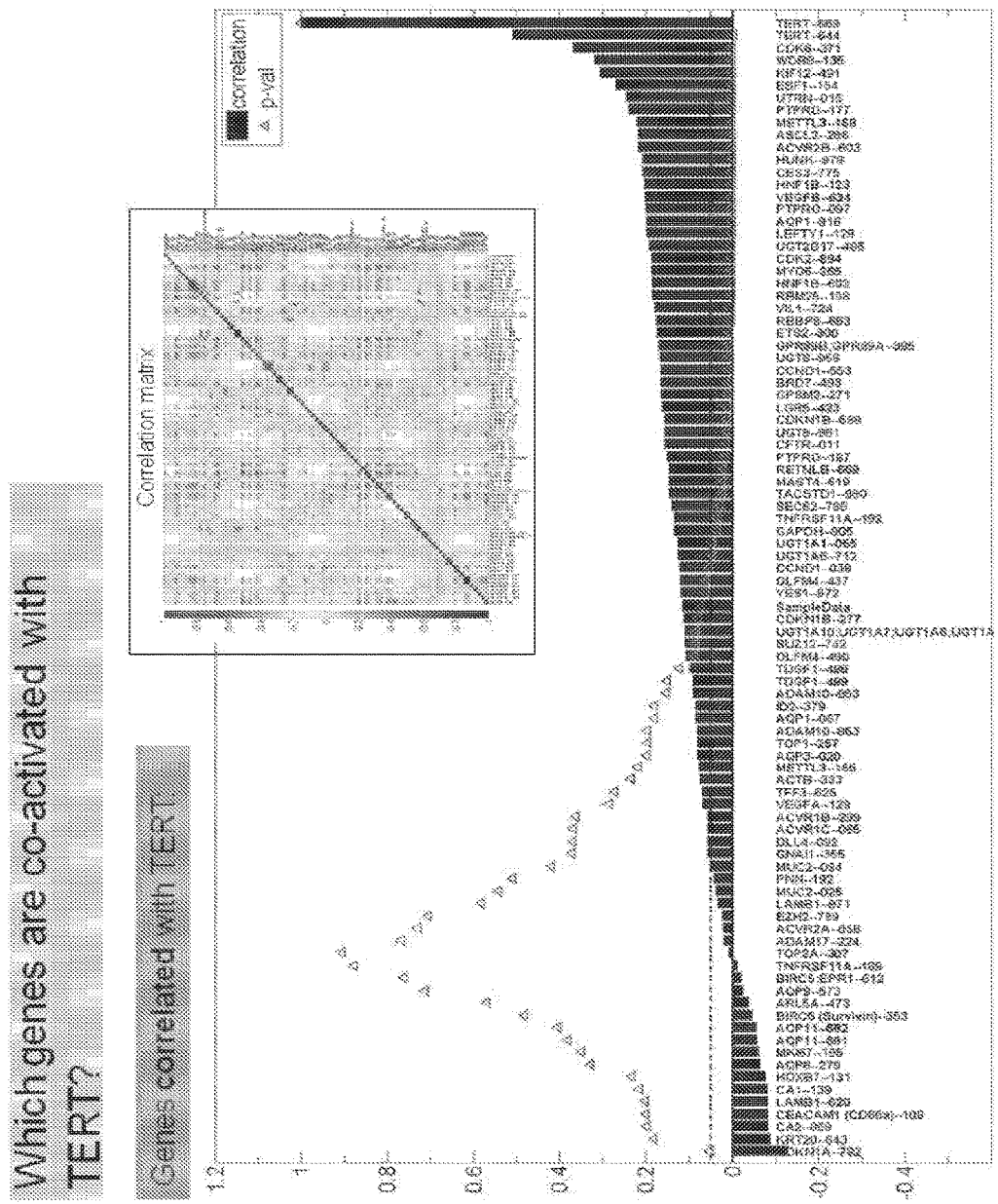
Figure 273:
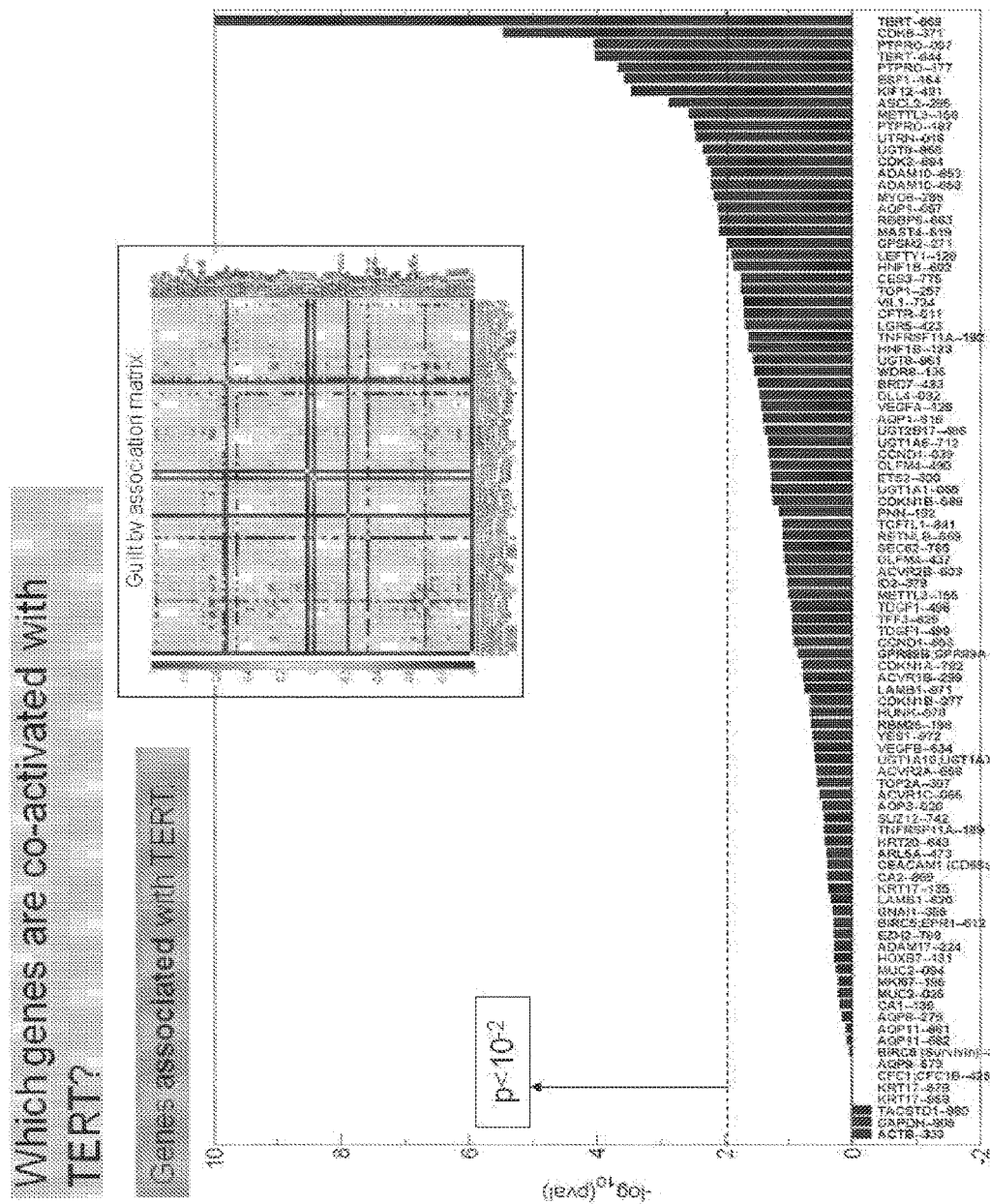
Figure 274:
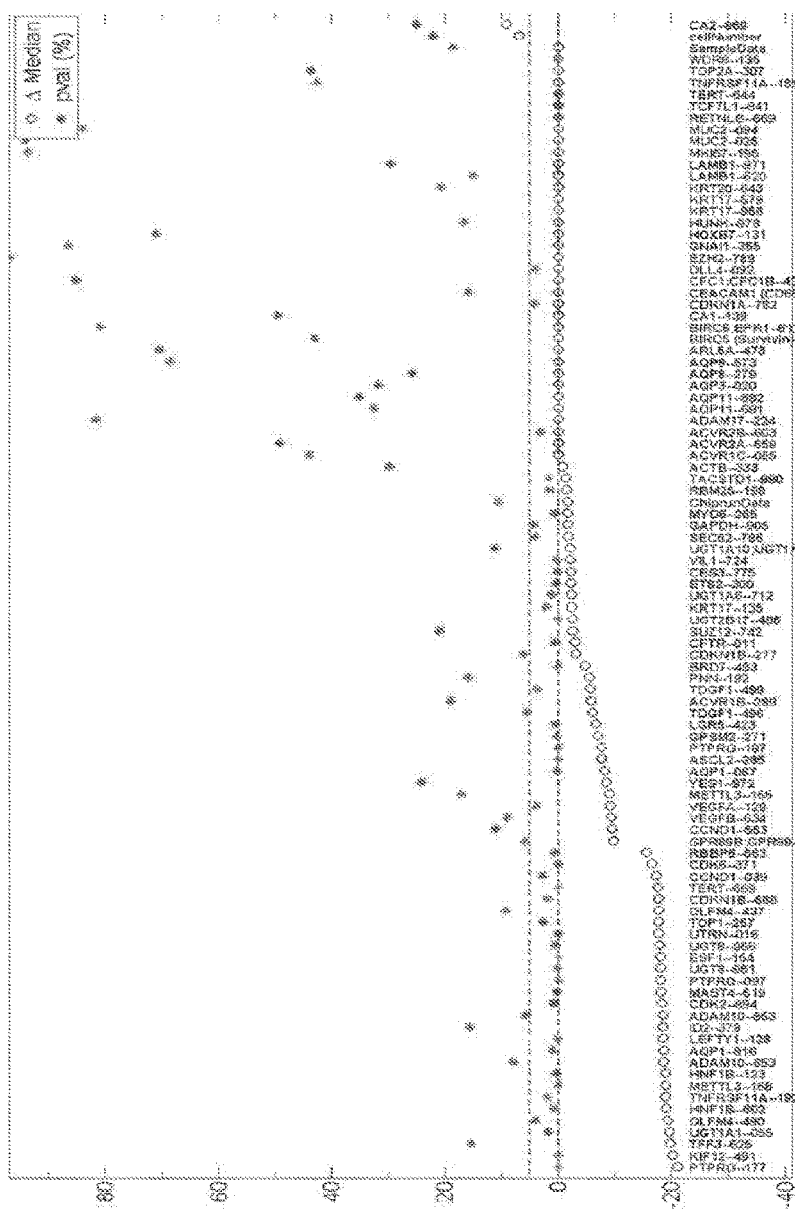
Figure 275:
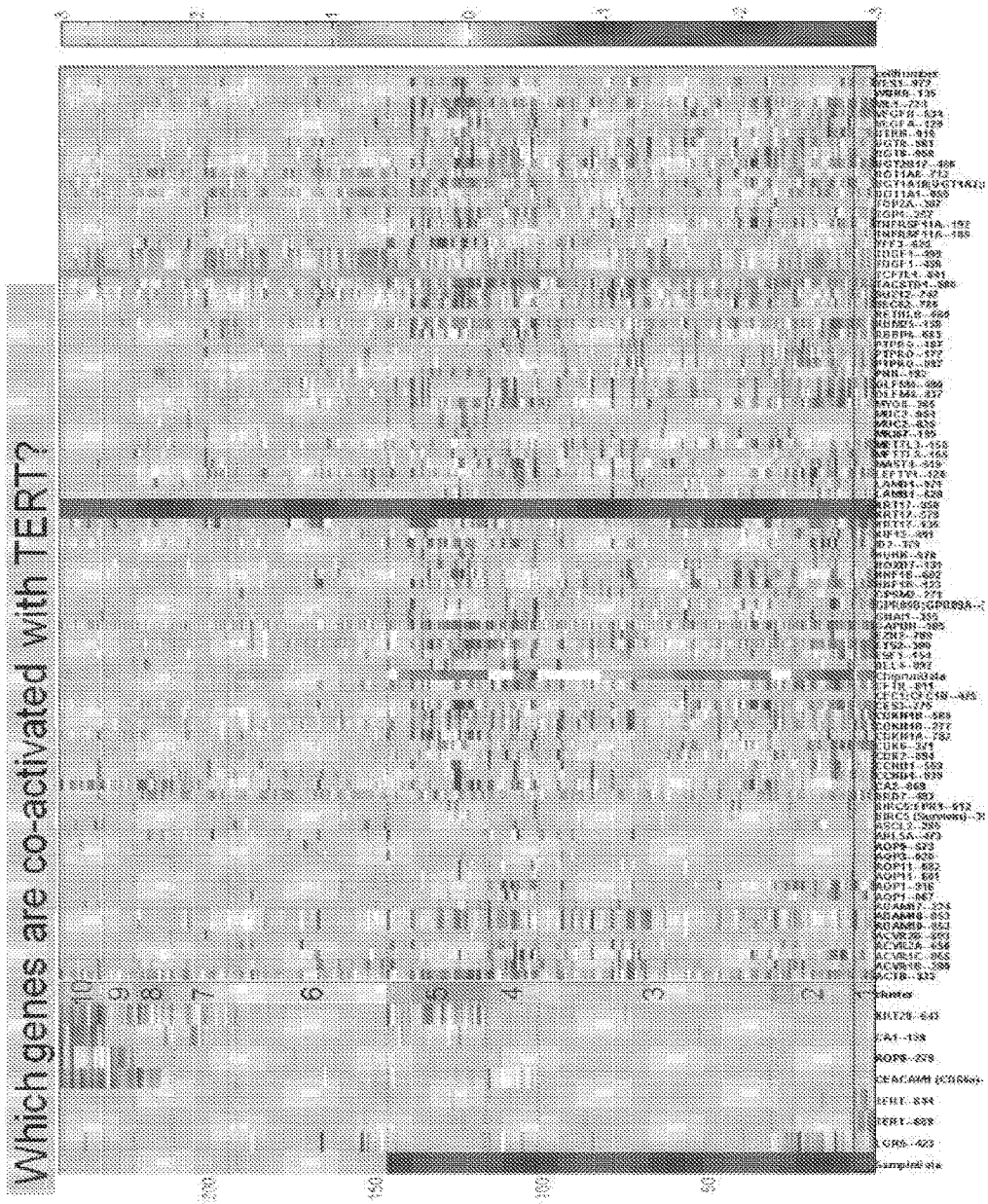
Figure 276:
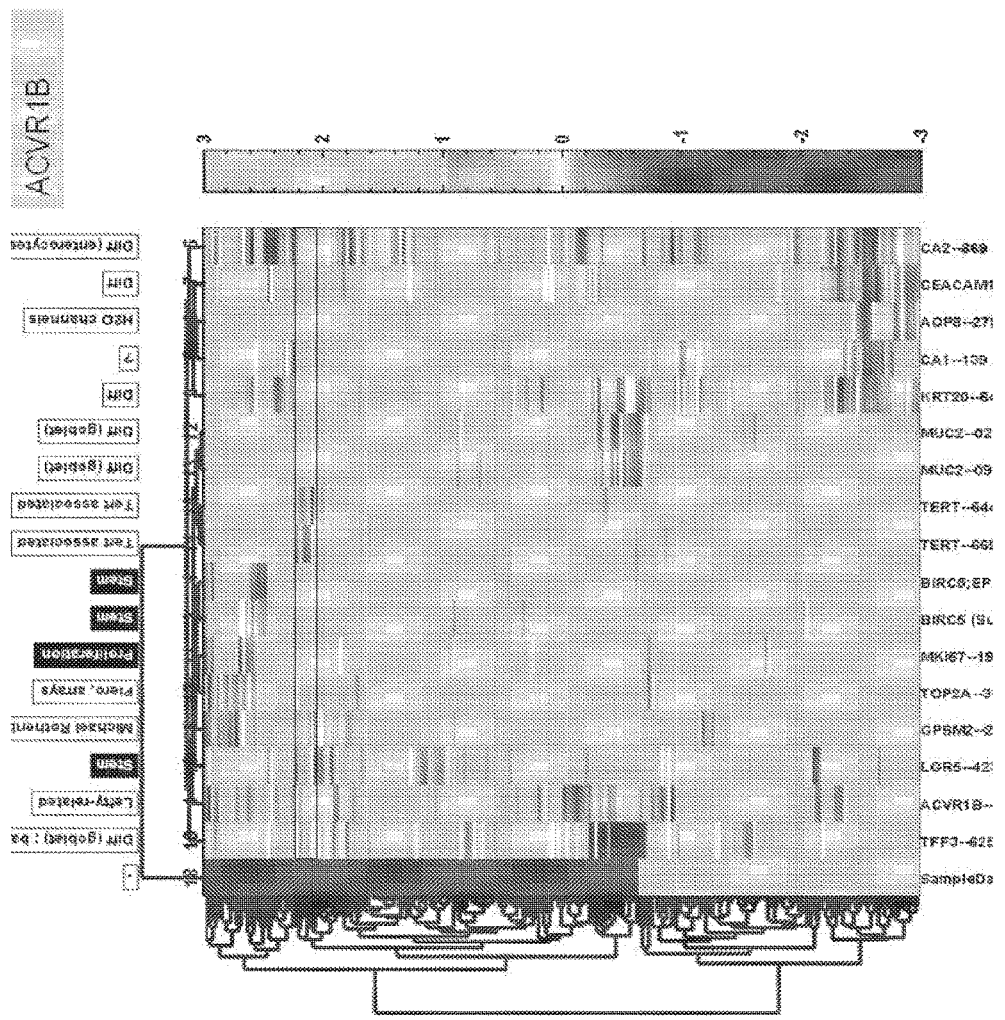
Figure 277:
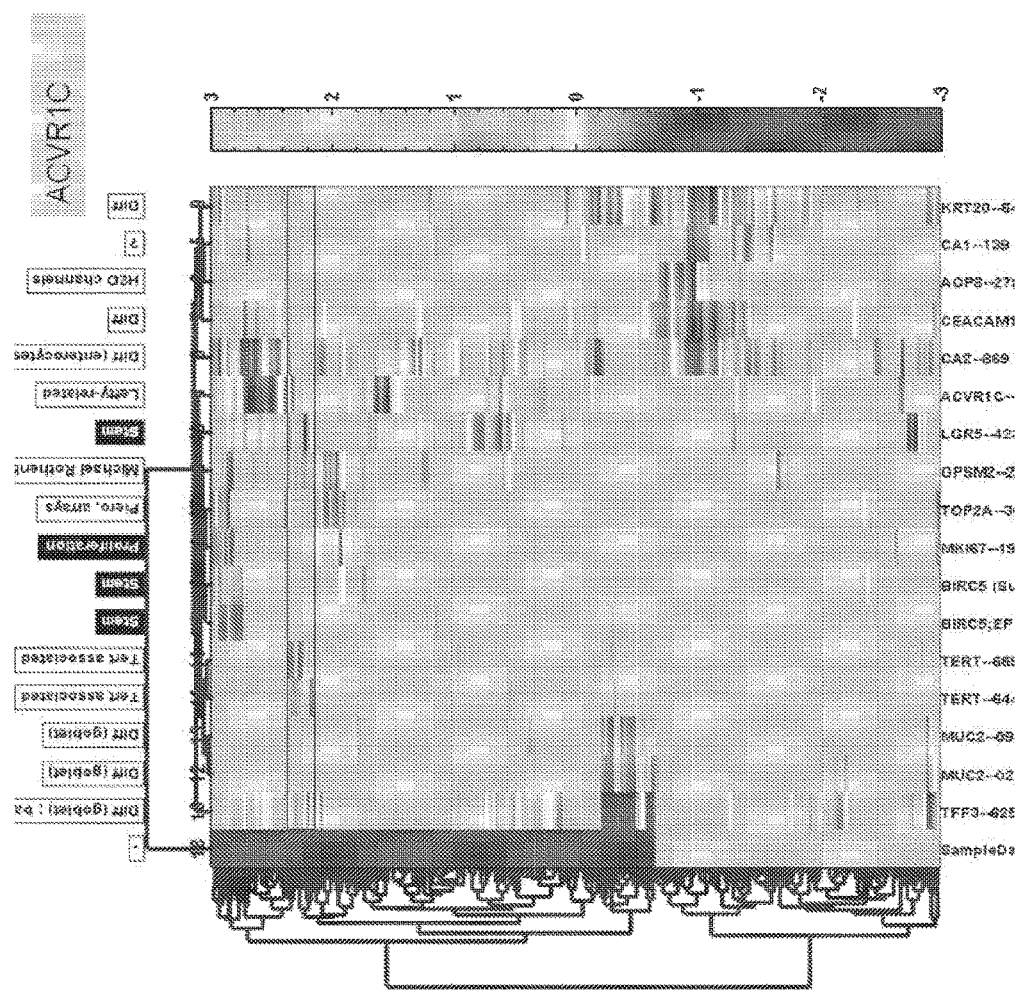
Figure 278:
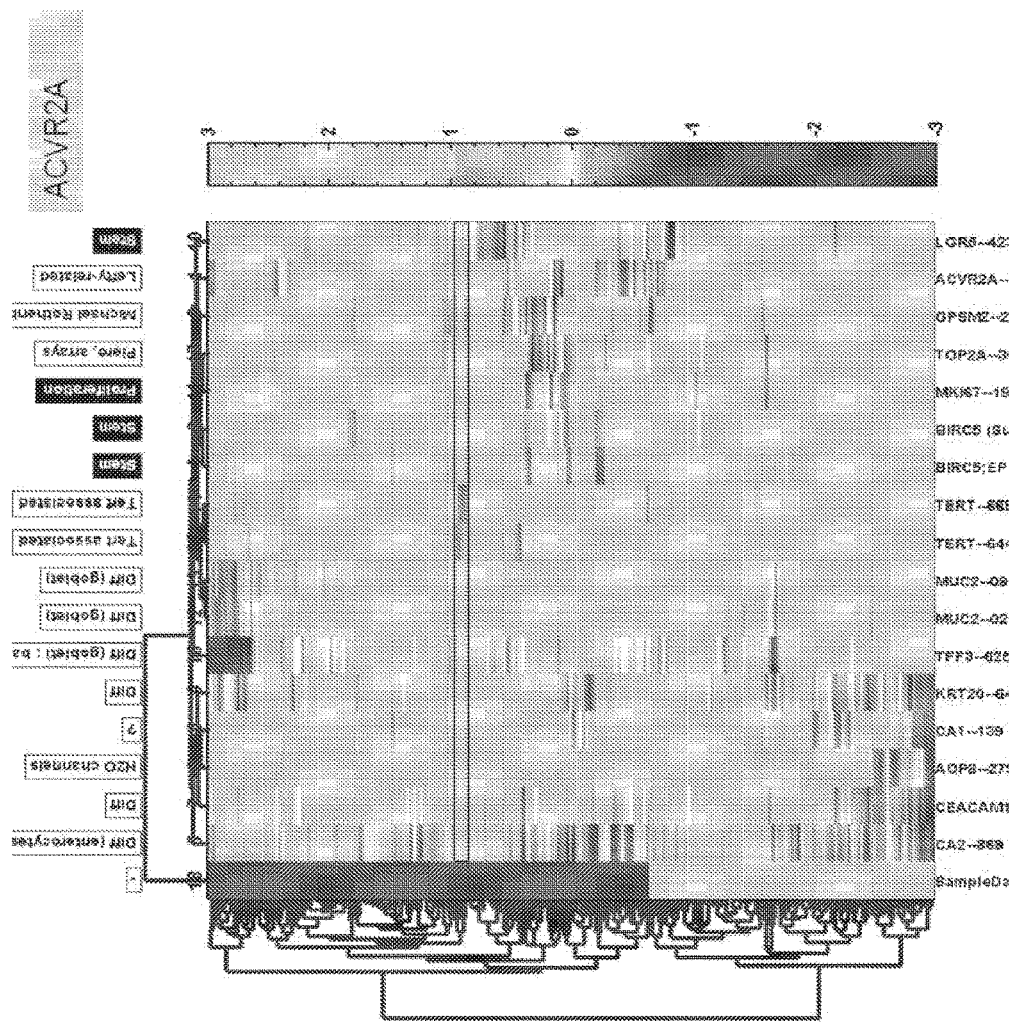
Figure 279:
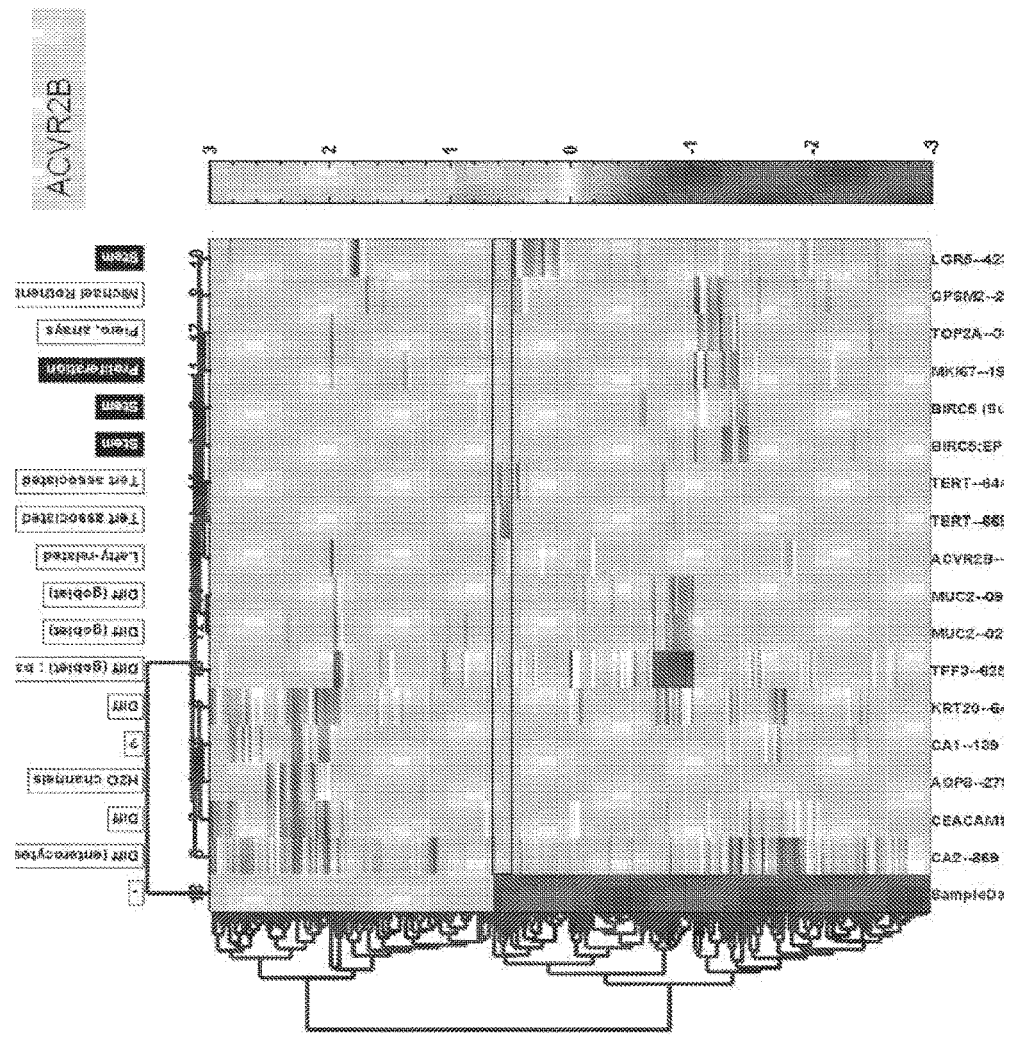
Figure 280:
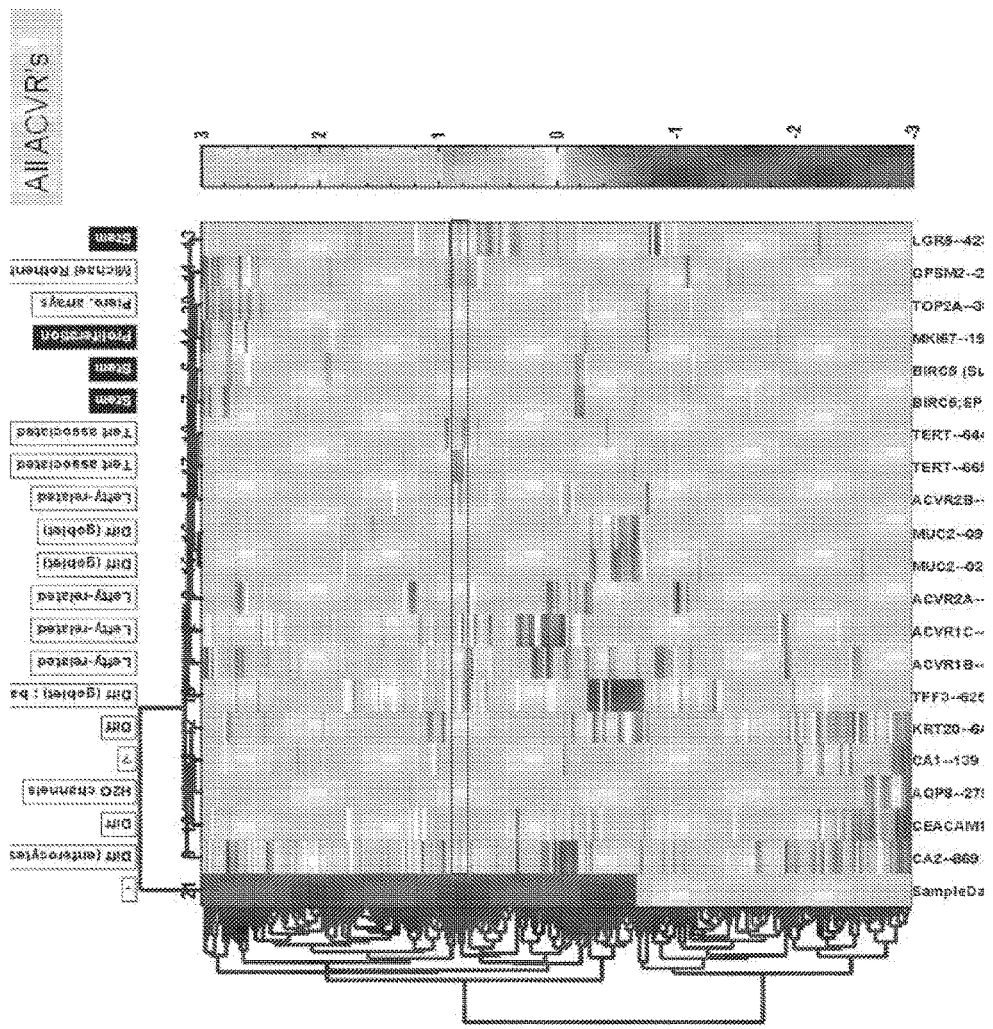
Figure 281:
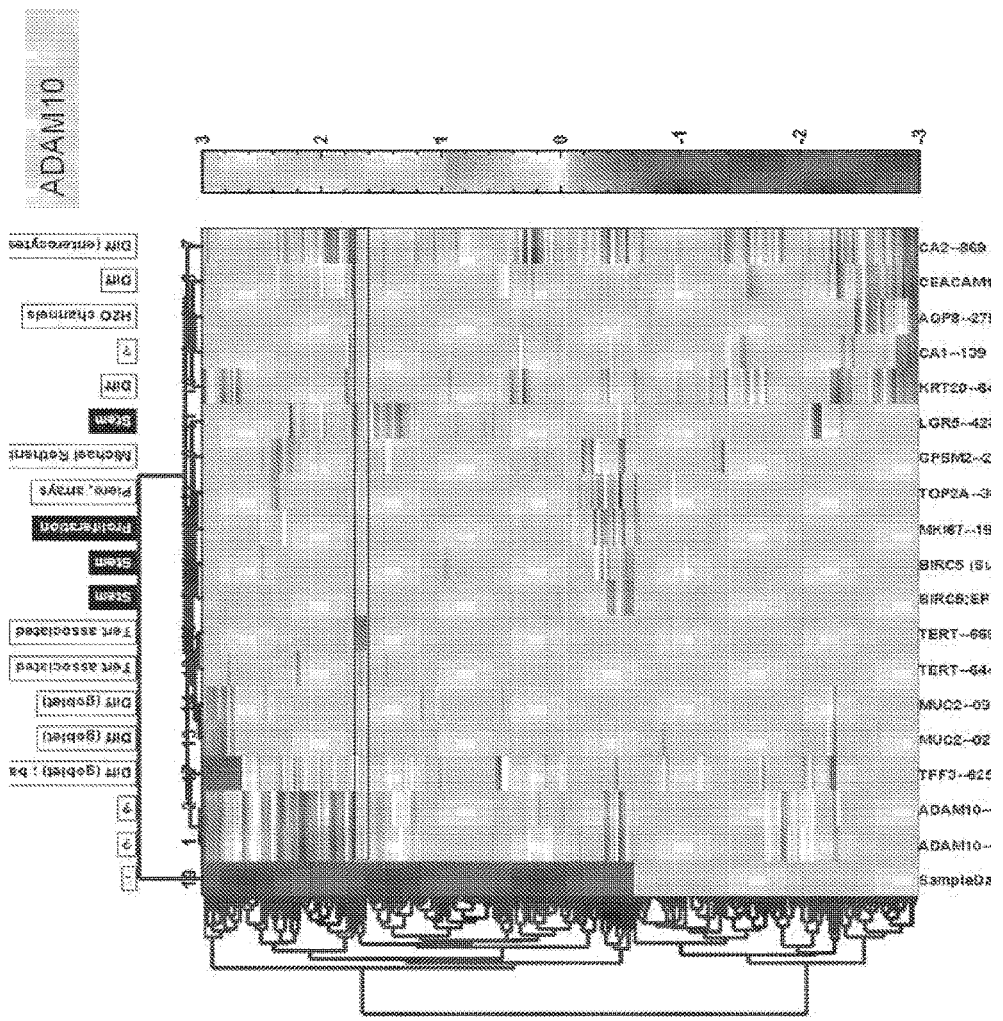
Figure 282:
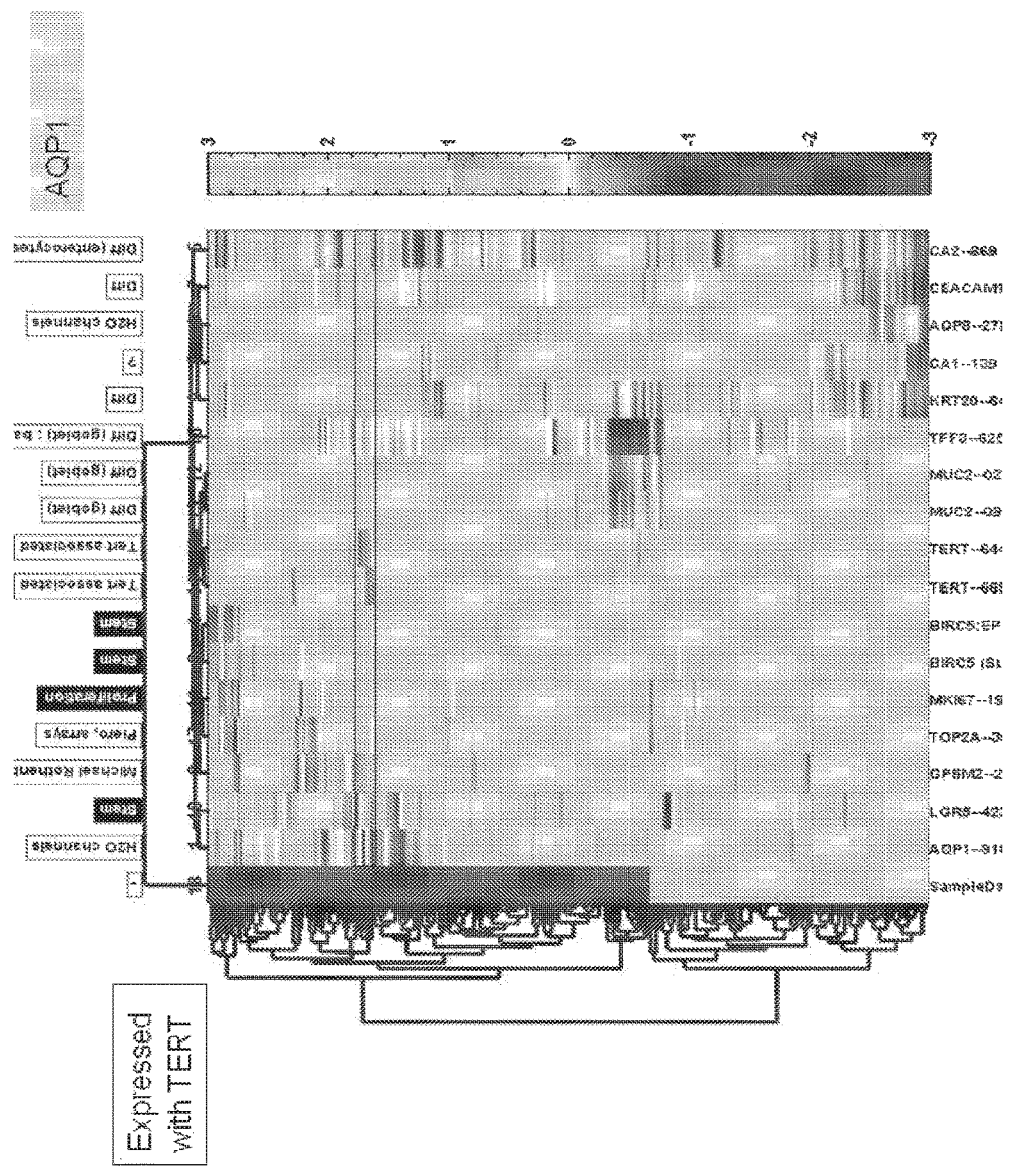
Figure 283:
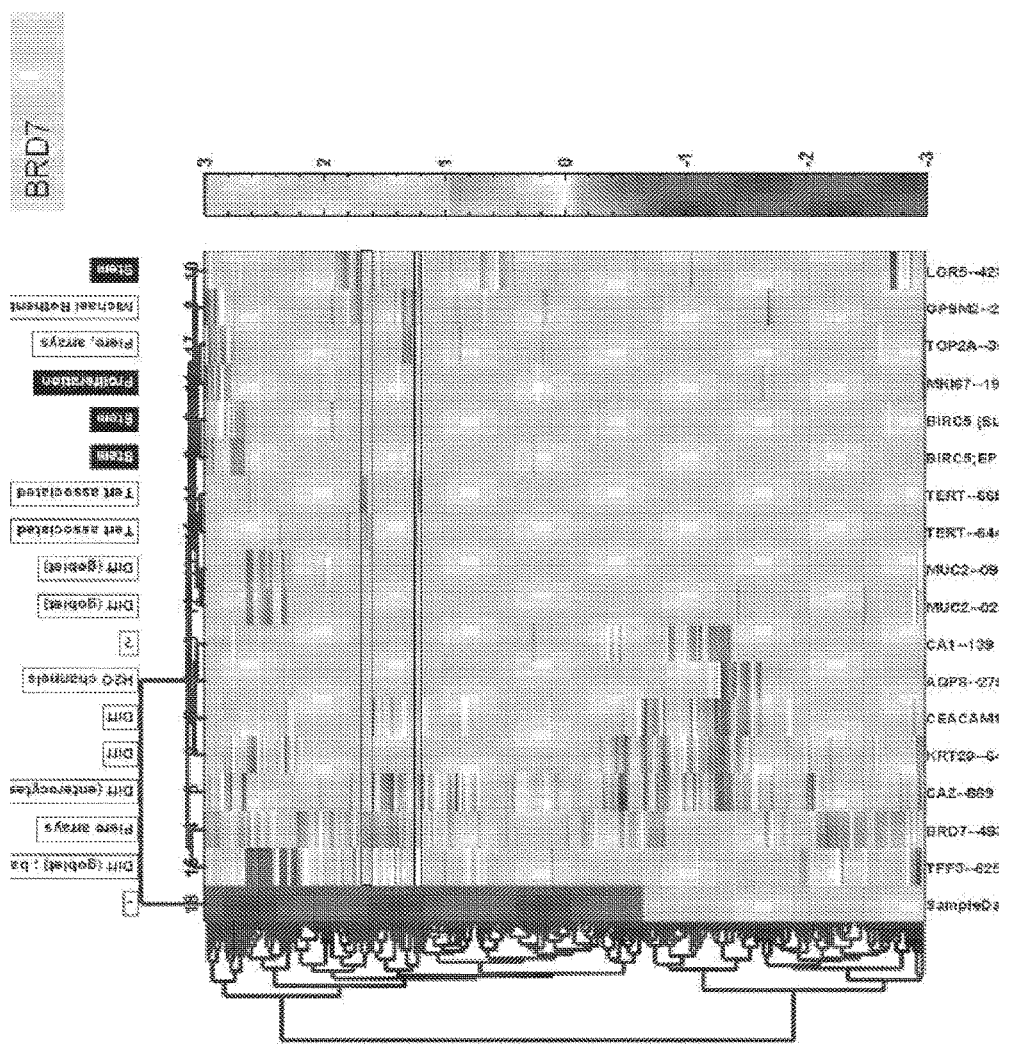
Figure 284:
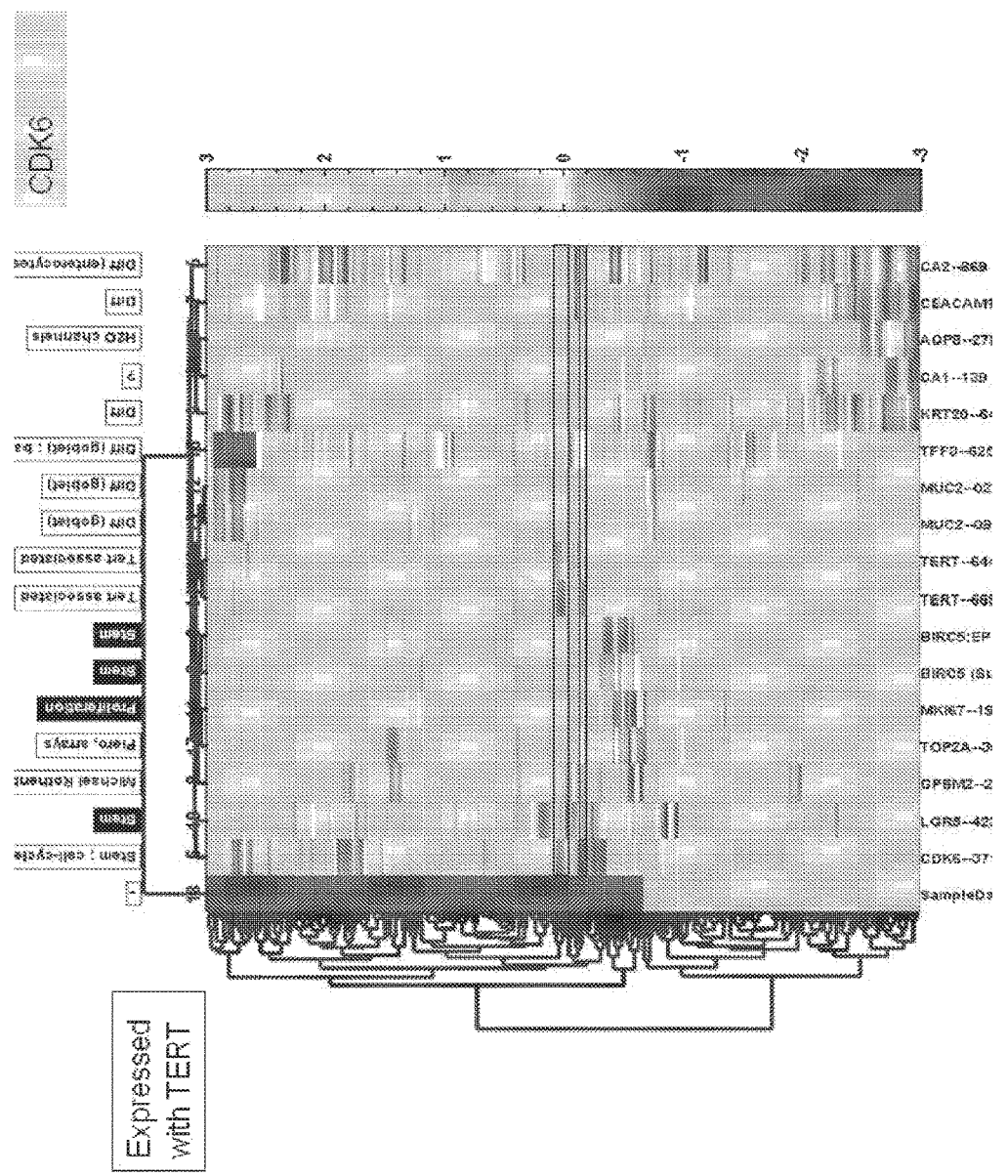
Figure 285:
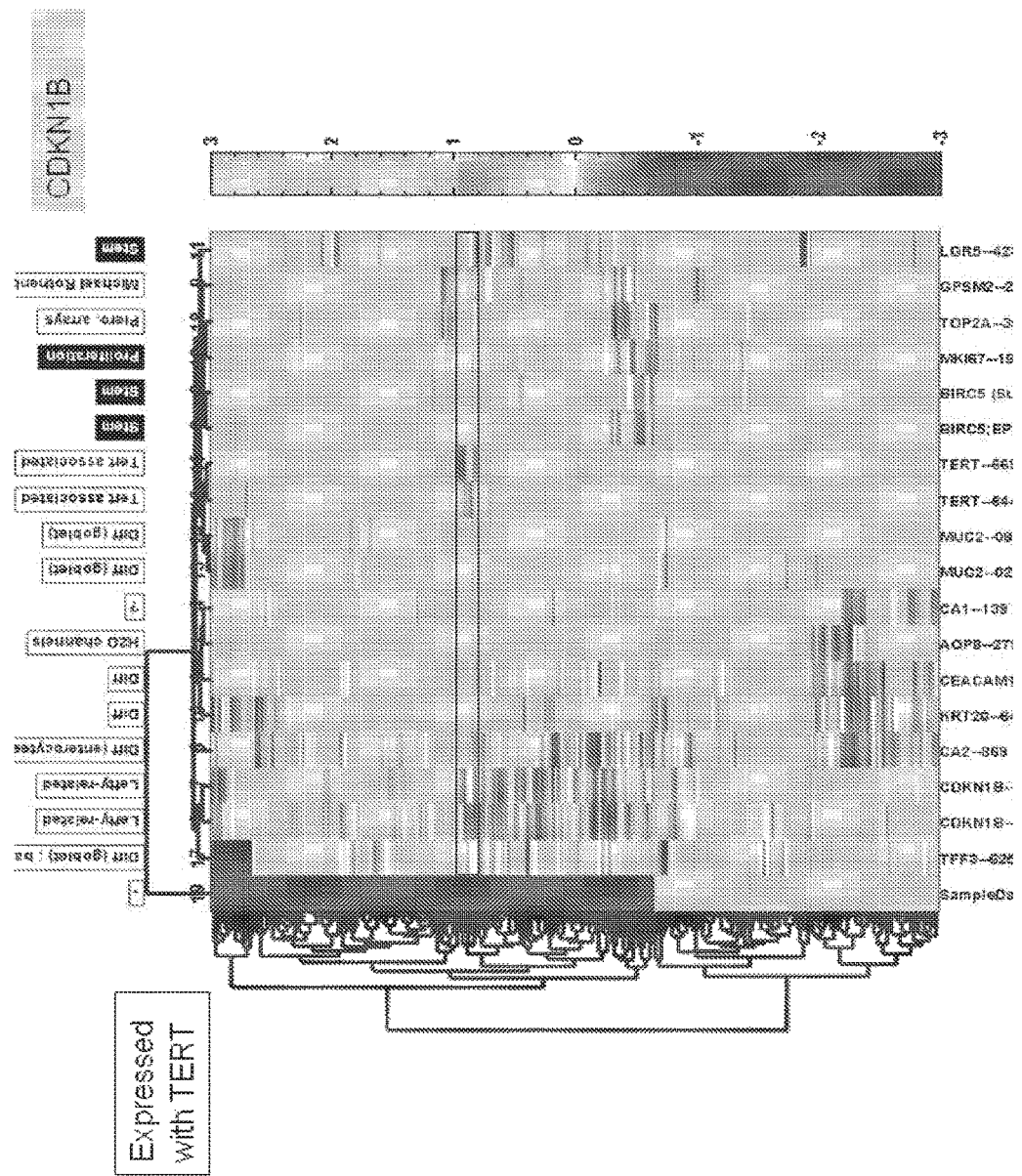
Figure 286:
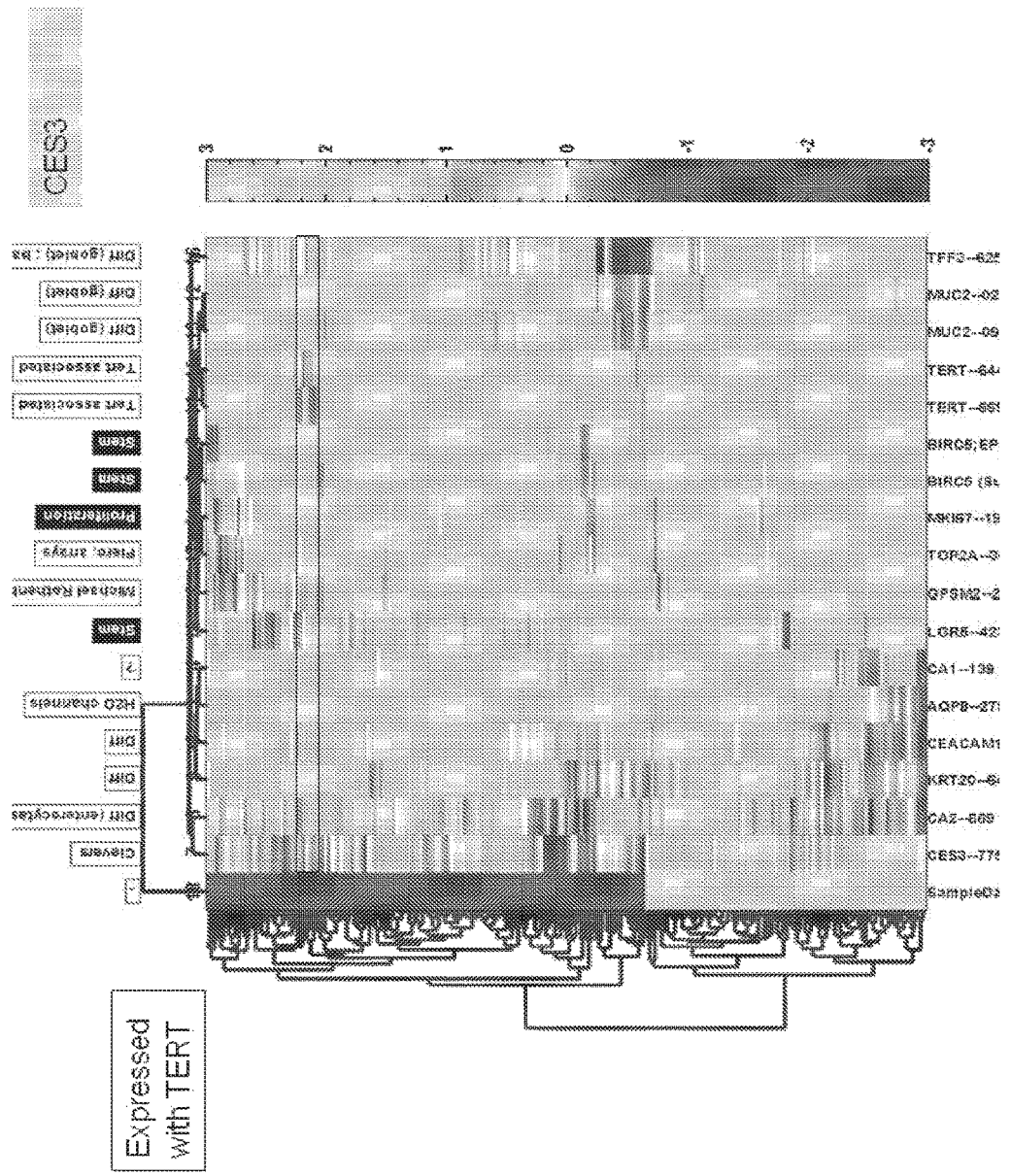
Figure 287:
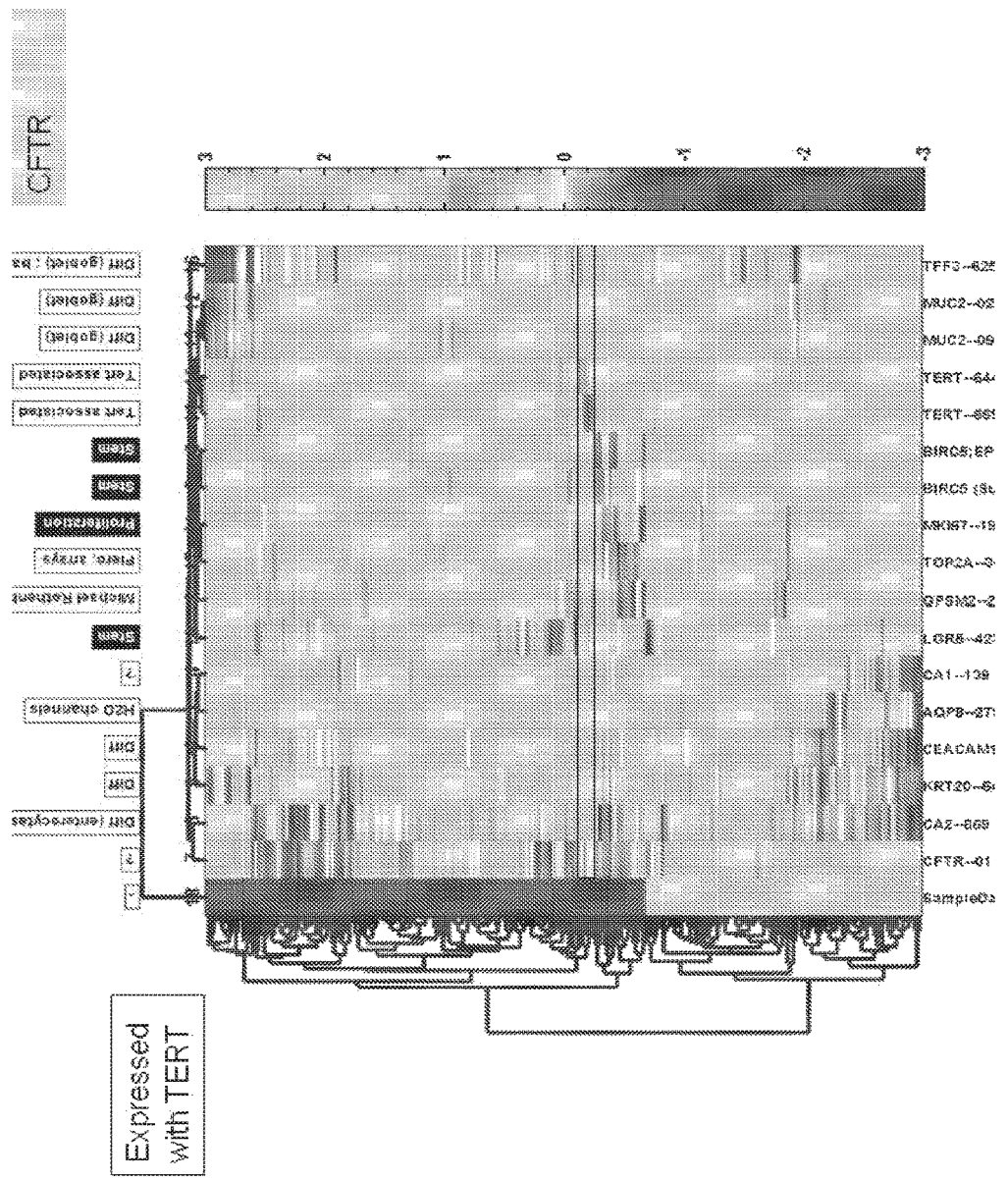
Figure 288:
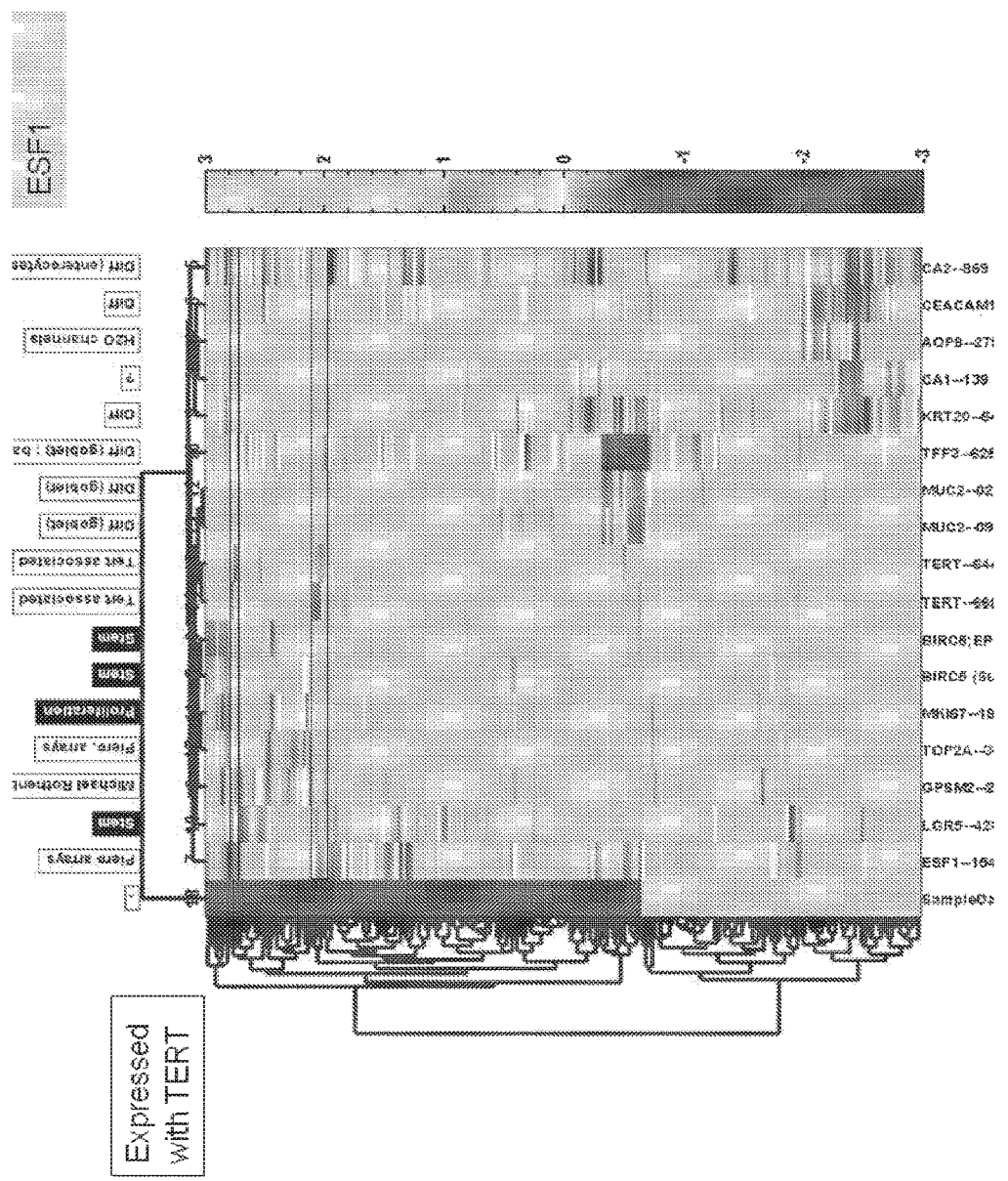
Figure 289:
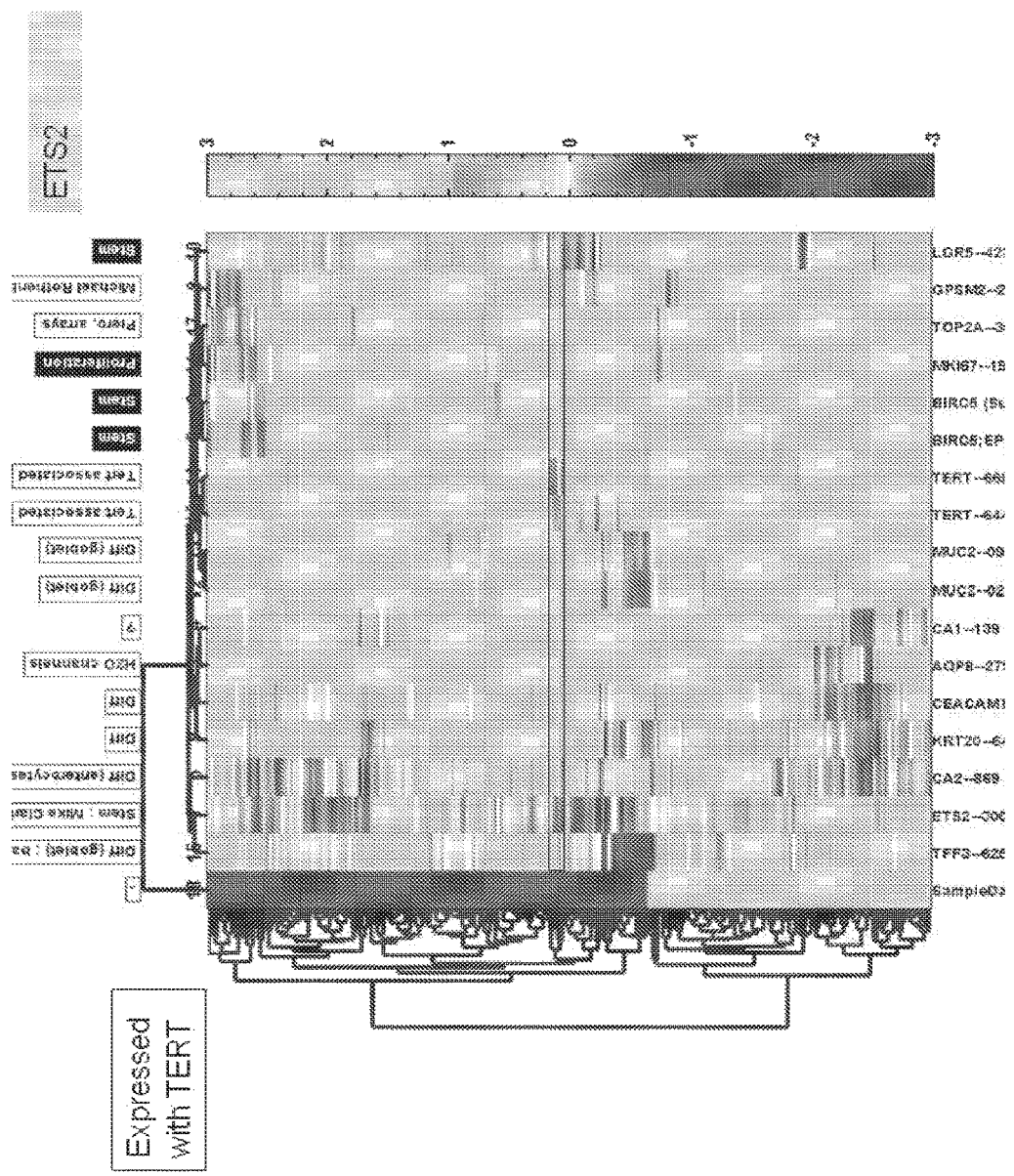

FIG. 227 PROX1 expression in relation to TERT expression.
FIG. 228 PTEN is co-expressed with TERT.
FIG. 229 SCRIB is co-expressed with TERT.
FIG. 230 SEC24 is co-expressed with TERT.
FIG. 231 SEC62 is co-expressed with TERT.
FIG. 232 STC2 expression in relation to TERT expression.
FIG. 233 SUZ12 is co-expressed with TERT.
FIG. 234 UGT1A6 is co-expressed with TERT.
FIG. 235 UGT2B17 is co-expressed with TERT.
FIG. 236 UGT8 is co-expressed with TERT.
FIG. 237 UTRN is co-expressed with TERT.
FIG. 238 hierarchical clustering of immature enterocyte signature and genes differentially expressed in various cell types.
FIG. 239 hierarchical clustering illustrating immature enterocyte, more mature enterocytes, immature goblet cells, and stem and cycling population.
FIG. 240 heat maps from two different chip-runs of samples. Cells were taken from xenograft (m10) of colon cells. The cells were FACS sorted with EGFP, and CD66a. Mature non-tumorigenic cells were defined as EGFP+/CD66a+ cells. CoCSC cells were defined as EGFP+ cells.
FIG. 241 a combined heat map comparing the two chip-runs.
FIG. 242 A difference between copy numbers was observed
FIG. 243 a combined heat map comparing another two chip-runs.
FIG. 244 a combined heat map.
FIG. 245 a heat map comparing the copy to the original.
FIG. 246 that the total RNA was split equally between the original and the copy.
FIG. 247 a comparison between samples and standards.
FIG. 248 heat maps from four different chip-runs of samples. Cells were taken from normal colonic mucosa. The cells were FACS sorted with EpCAM and CD66a. Normal NTCC was defined as EpCAM+/CD66a+ cells. Normal CoCSC cells were defined as EpCAM+/CD66a$^{low}$ cells.
FIG. 249 a combined heat map comparing the four chip-runs.
FIG. 250 selection of cells for single cell gene expression analysis. Out of 328 cells tested, 126 cells were discarded by examining GAPDH and ACTB gene expression levels, and 202 cells were selected. Of the 202 cells, 2 cells were further discarded by examining GAPDH and TACSTD1 gene expression levels, and 200 cells were selected for further analysis.
FIG. 251 further removal of cells that for every gene, where $C_T$ values are higher than some gene-dependent threshold, cells were removed.
FIG. 252 a combined heat map after the clean up of unwanted cells.
FIG. 253 a hierarchical clustering of all genes.
FIG. 254 a hierarchical clustering of all genes. Cell types are marked.
FIG. 255 a hierarchical clustering of subgroup 1 genes.
FIG. 256 a hierarchical clustering of subgroup 1 genes. Cell types are marked.
FIG. 257 a hierarchical clustering of subgroup 2 genes.
FIG. 258 k-means hierarchical clustering of subgroup 2 genes.
FIG. 259 k-means hierarchical clustering of subgroup 2 genes. Cell types are marked.
FIG. 260 hierarchical clustering of genes differentially expressed.
FIG. 261 hierarchical clustering of genes differentially expressed. Markers for immature population were identified as LGR5, ASCL2, LEFTY1, TERT, PTPRO, OLFM, METTL3, LIF12, EZH2, UTRN, UGT8, AQP1, ETS2, LAMB1, CDKN1B, SUZ12, ESF1, CFTR, RBM25, CES3, VIL1, VEGFB, SEC62, MAST4, and DLL4. Gene expressions for mature enterocytes were identified as KRT20, CEACAM1, CDKN1A, CA2 and VEGFA.
FIG. 262 hierarchical clustering of genes differentially expressed.
FIG. 263 hierarchical clustering of genes differentially expressed. Gene expressions for immature cycling population were identified as BIRC, TOP2A, MKI67, and GPSM2. Gene expressions for mature goblet cells were identified as TFF3 and MUC2.
FIG. 264 heat maps from two different chip-runs of samples. Cells were taken from normal colonic mucosa. The cells were FACS sorted with EpCAM and CD66a. Normal NTCC was defined as EpCAM+/CD66a+ cells. Normal CoCSC cells were defined as EpCAM+/CD66a$^+$ cells.
FIG. 265 a combined heat map comparing the two chip-runs.
FIG. 266 selection of cells for single cell gene expression analysis. Out of 292 cells tested, 38 cells were discarded by examining GAPDH and ACTB gene expression levels, and 254 cells were selected. Of the 254 cells, 10 cells were further discarded by examining GAPDH and TACSTD1 gene expression levels, and 244 cells were selected for further analysis.
FIG. 267 a combined heat map after the clean up of unwanted cells.
FIG. 268 gene expressions associated with TERT expression.
FIG. 269 hierarchical clustering identifying differentially expressed genes between the groups. Cell types are marked.
FIG. 270 hierarchical clustering identifying differentially expressed genes between the groups.
FIG. 271 hierarchical clustering identifying differentially expressed genes between the groups. Cell types, and genes of interest are marked.
FIG. 272 expression is correlated with TERT expression.
FIG. 273 gene expressions associated with TERT expression.
FIG. 274 genes having significant difference in median between TERT+ and TERT− cells.
FIG. 275 genes co-activated with TERT.
FIG. 276 ACVR1B expression in relation to TERT expression.
FIG. 277 ACVR$^1$C expression in relation to TERT expression.
FIG. 278 ACVR2A expression in relation to TERT expression.
FIG. 279 ACVR2B expression in relation to TERT expression.
FIG. 280 all ACVRs expression in relation to TERT expression.
FIG. 281 ADAM10 expression in relation to TERT expression.
FIG. 282 AQP1 is expressed with TERT.
FIG. 283 BRD7 expression in relation to TERT expression.
FIG. 284 CDK6 is expressed with TERT.
FIG. 285 CDKNB1 is expressed with TERT.
FIG. 286 CES3 is expressed with TERT.
FIG. 287 CFTR is expressed with TERT.
FIG. 288 ESF1 is expressed with TERT.
FIG. 289 ETS2 is expressed with TERT.

Figure 290:
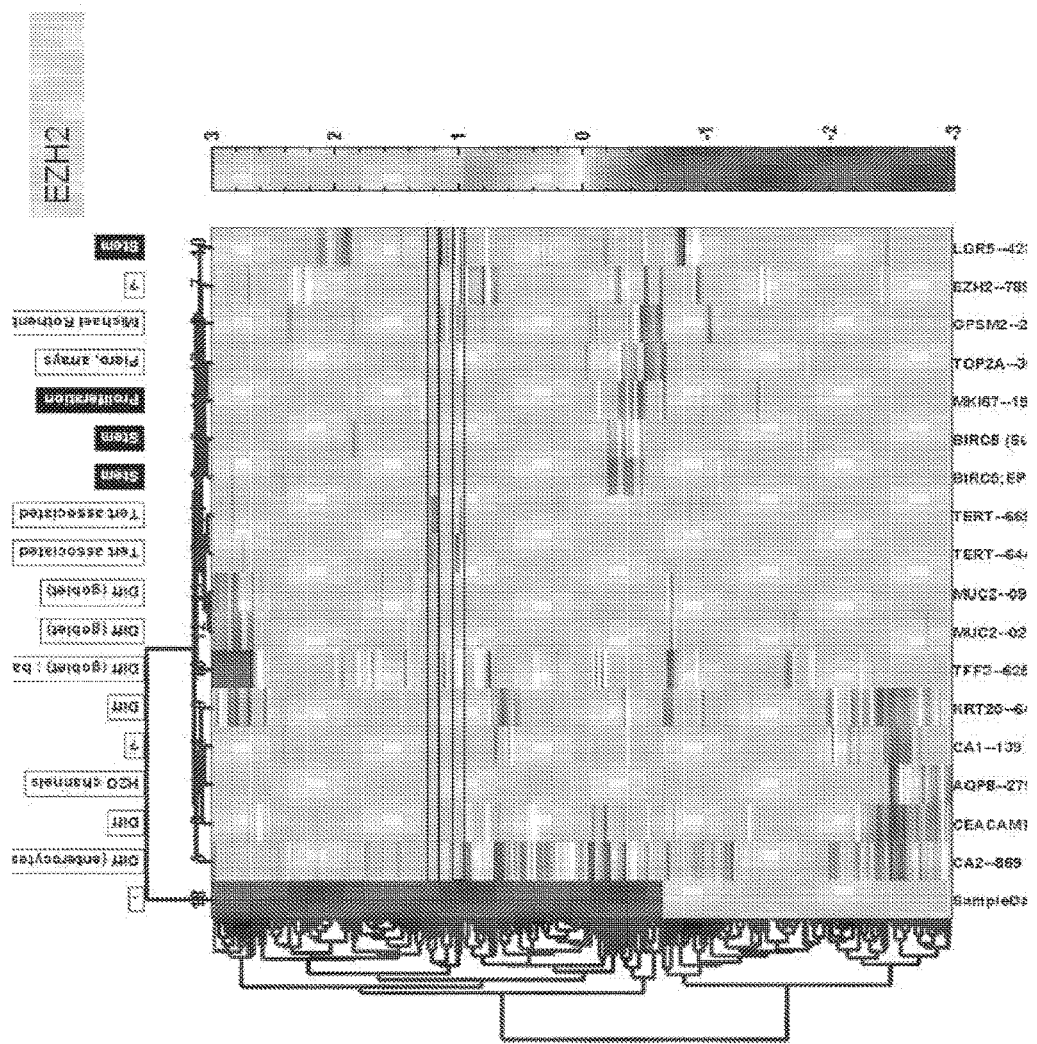
Figure 291:
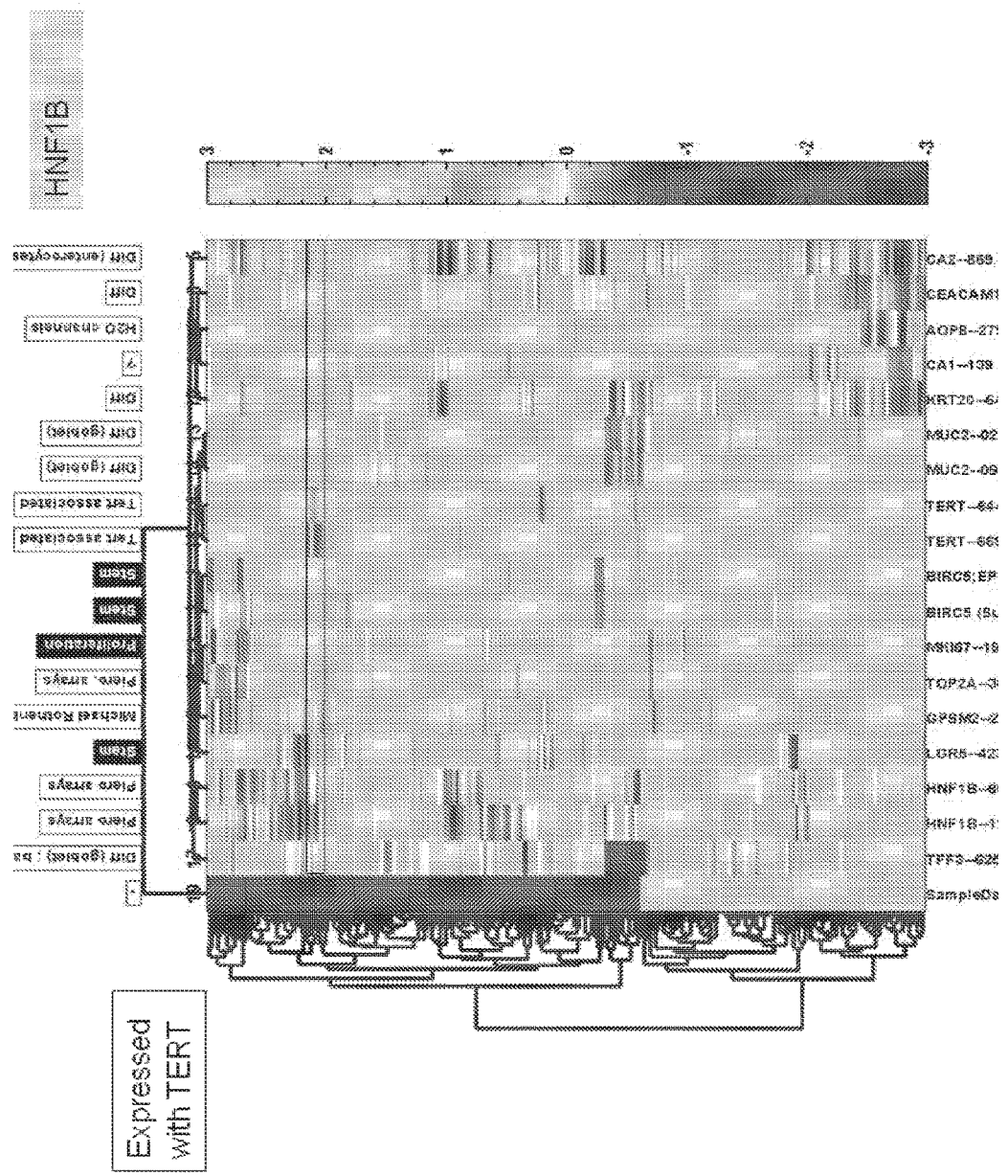
Figure 292:
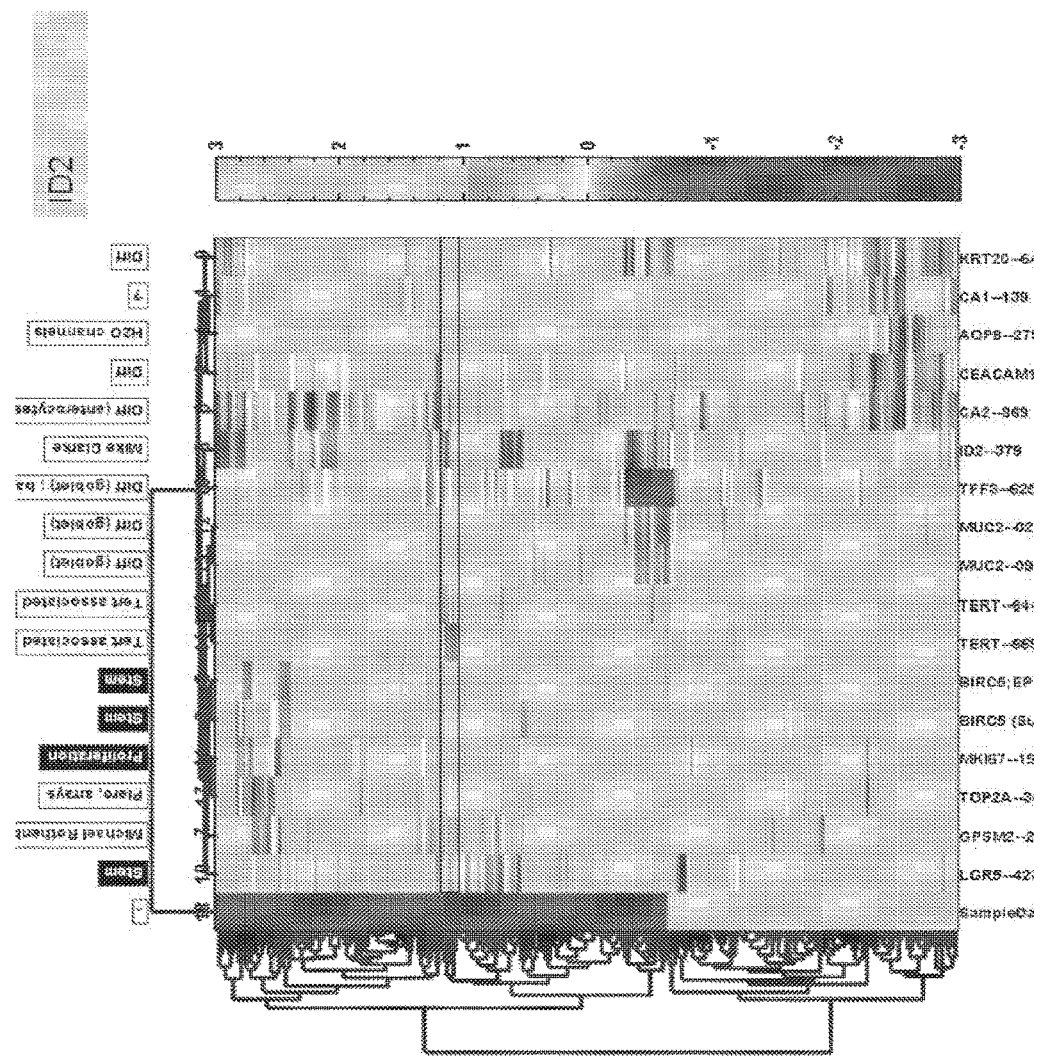
Figure 293:
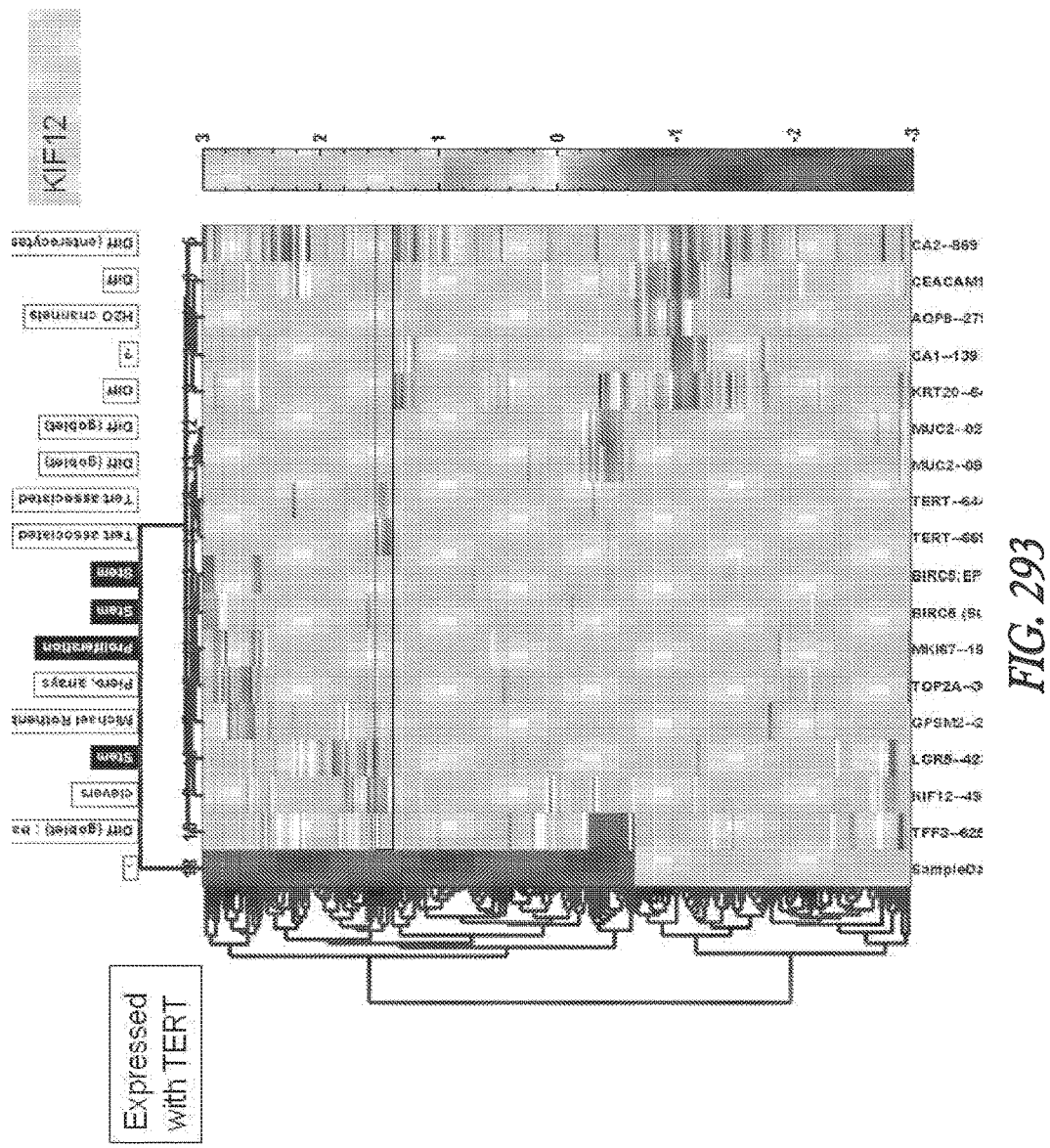
Figure 294:
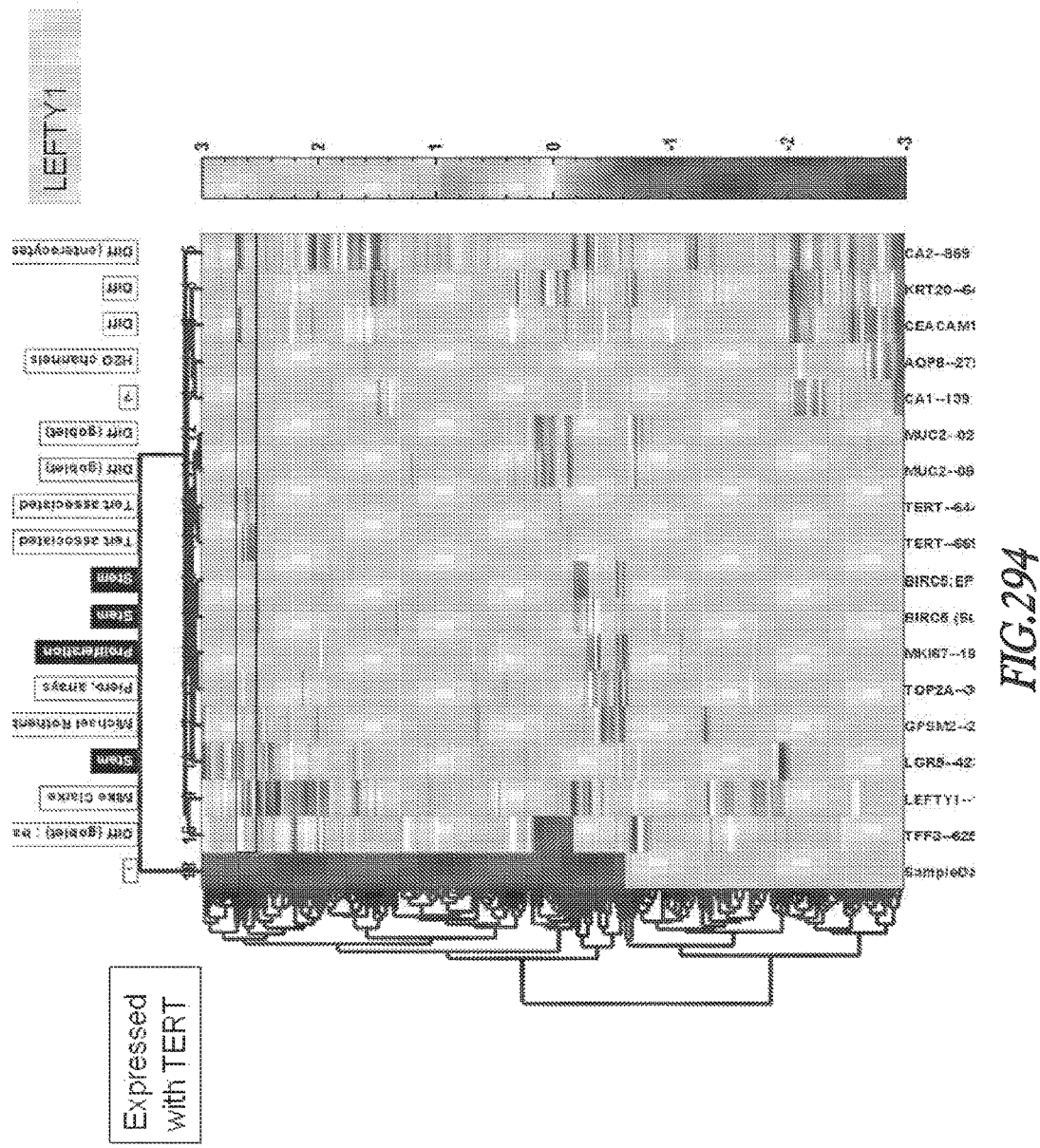
Figure 295:
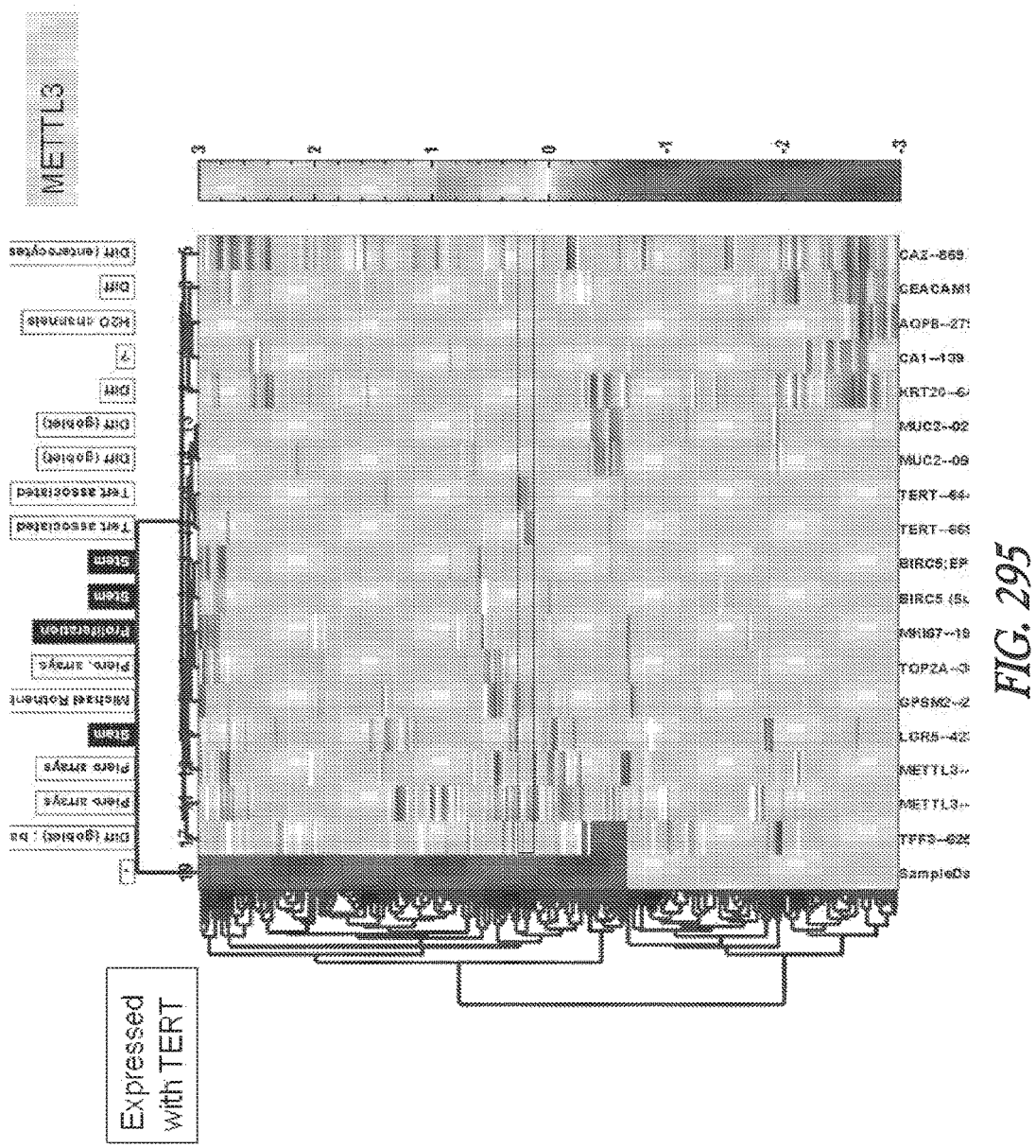
Figure 296:
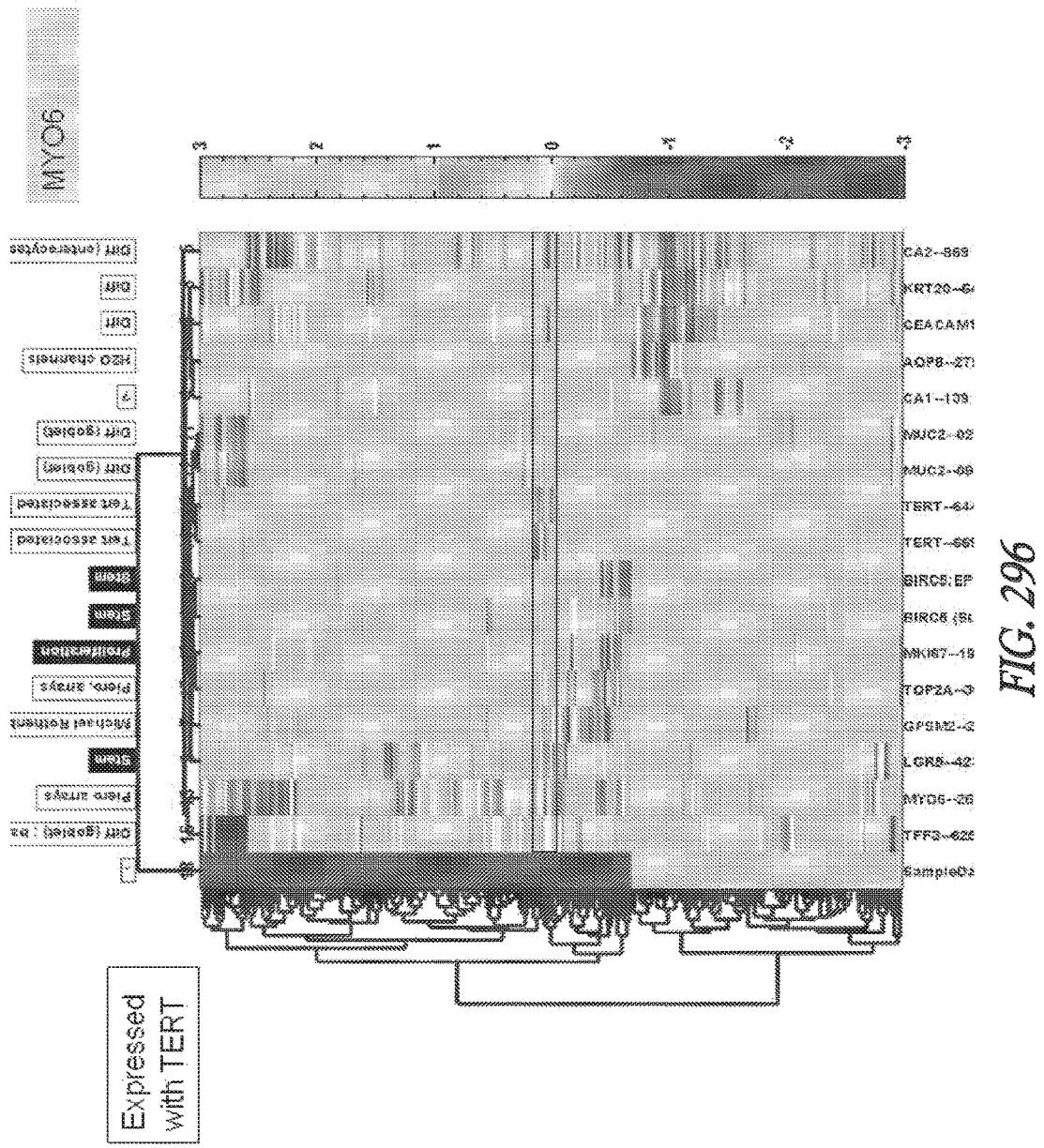
Figure 297:
Figure 298:
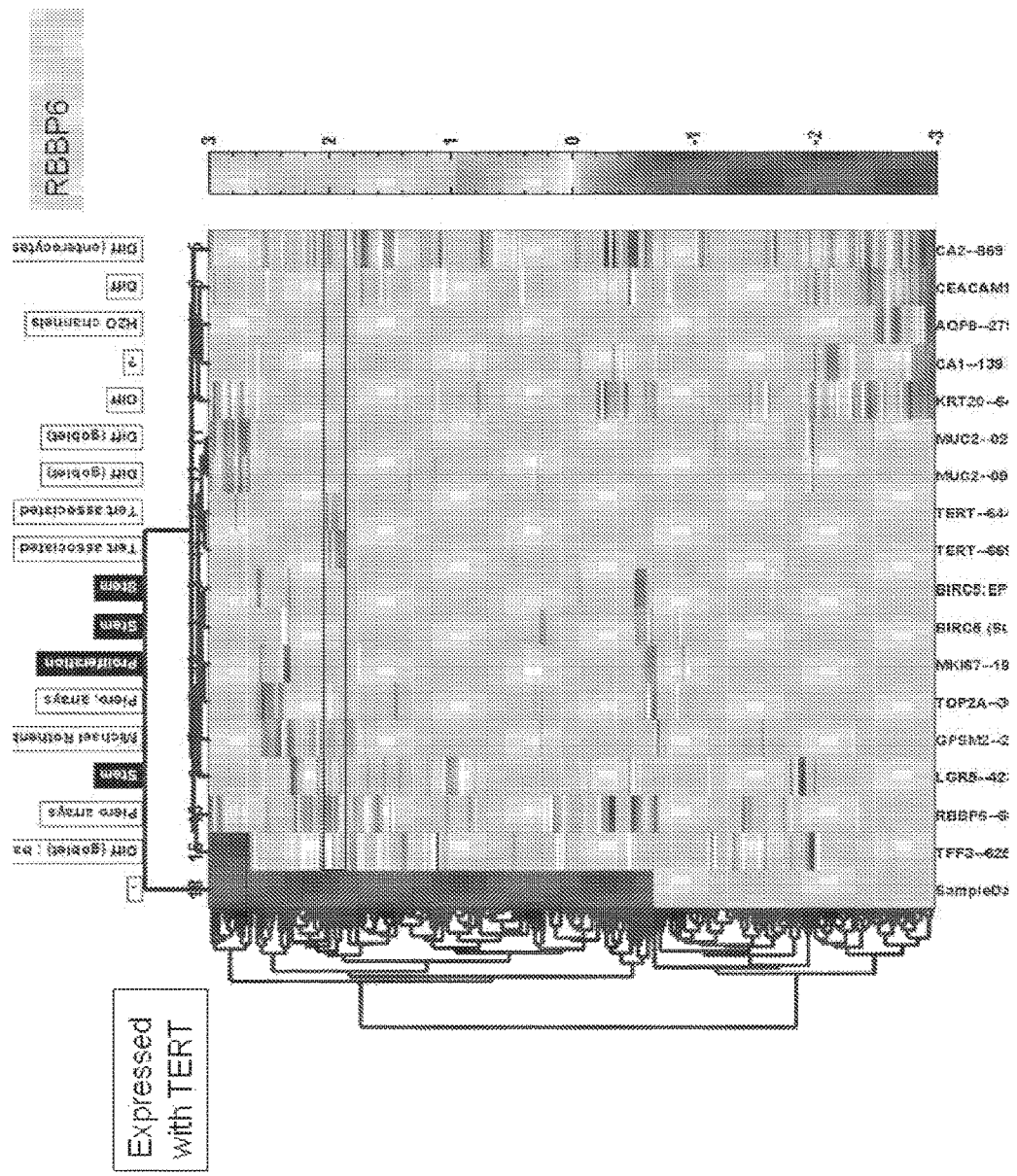
Figure 299:
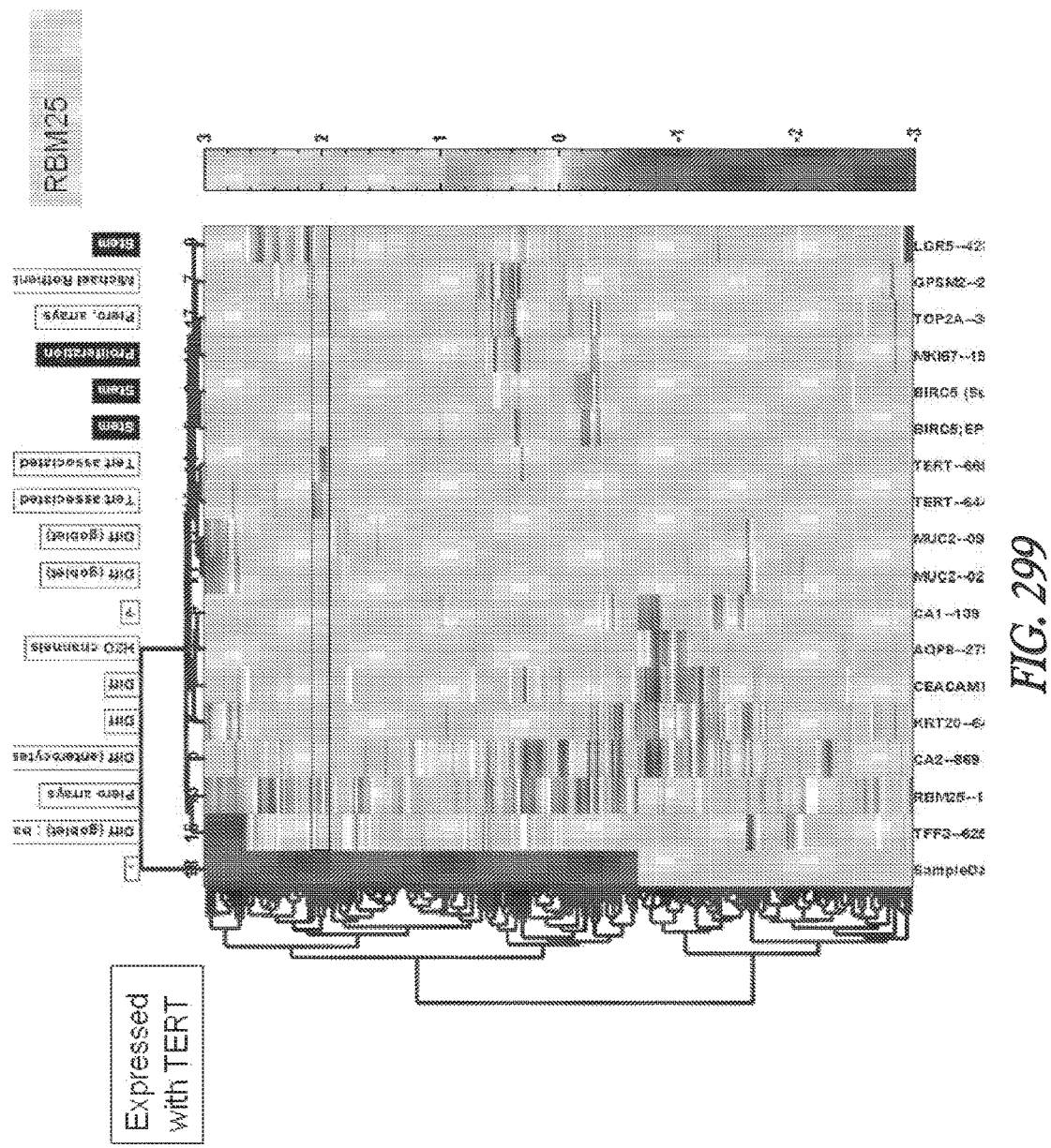
Figure 300:
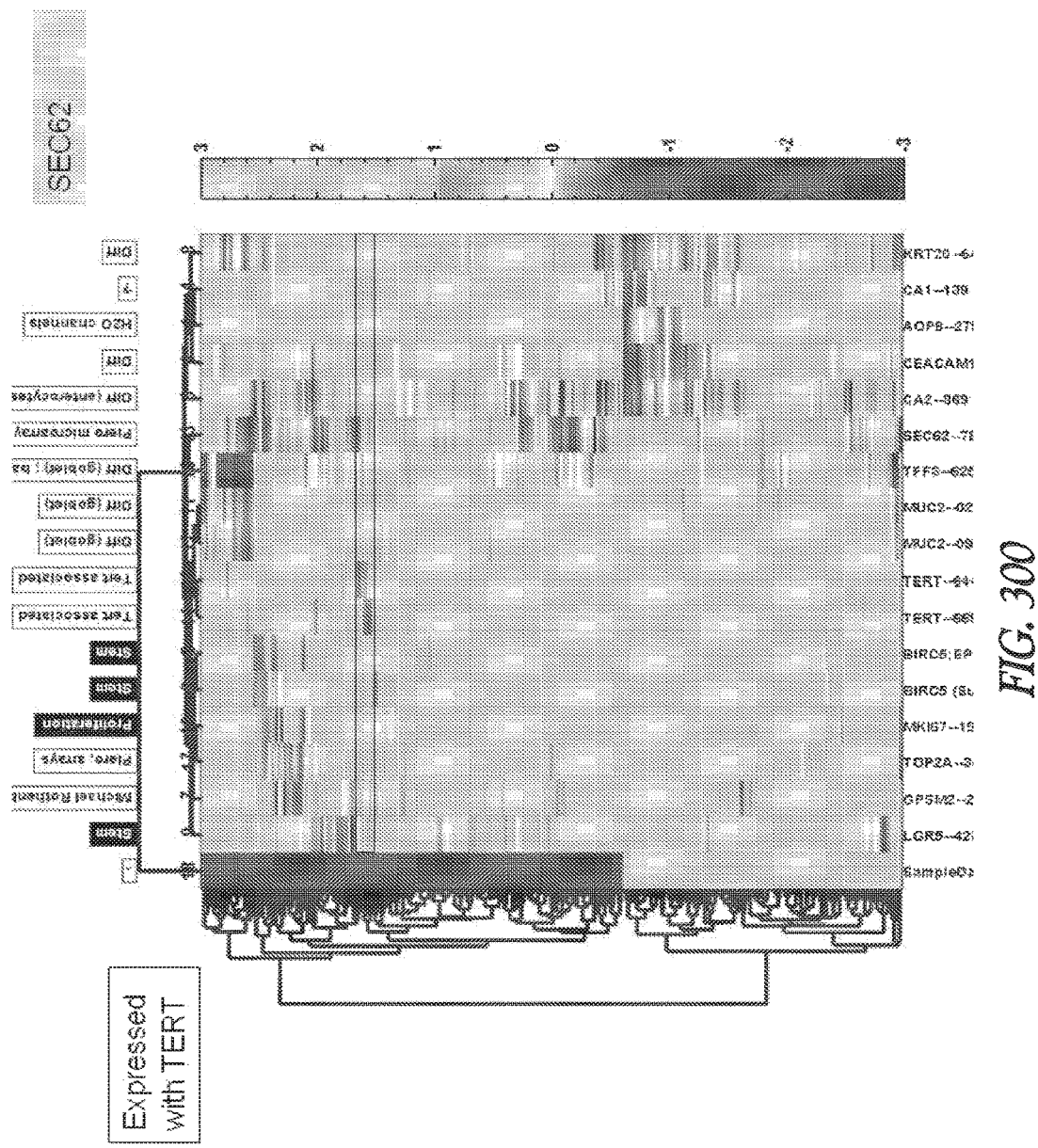
Figure 301:
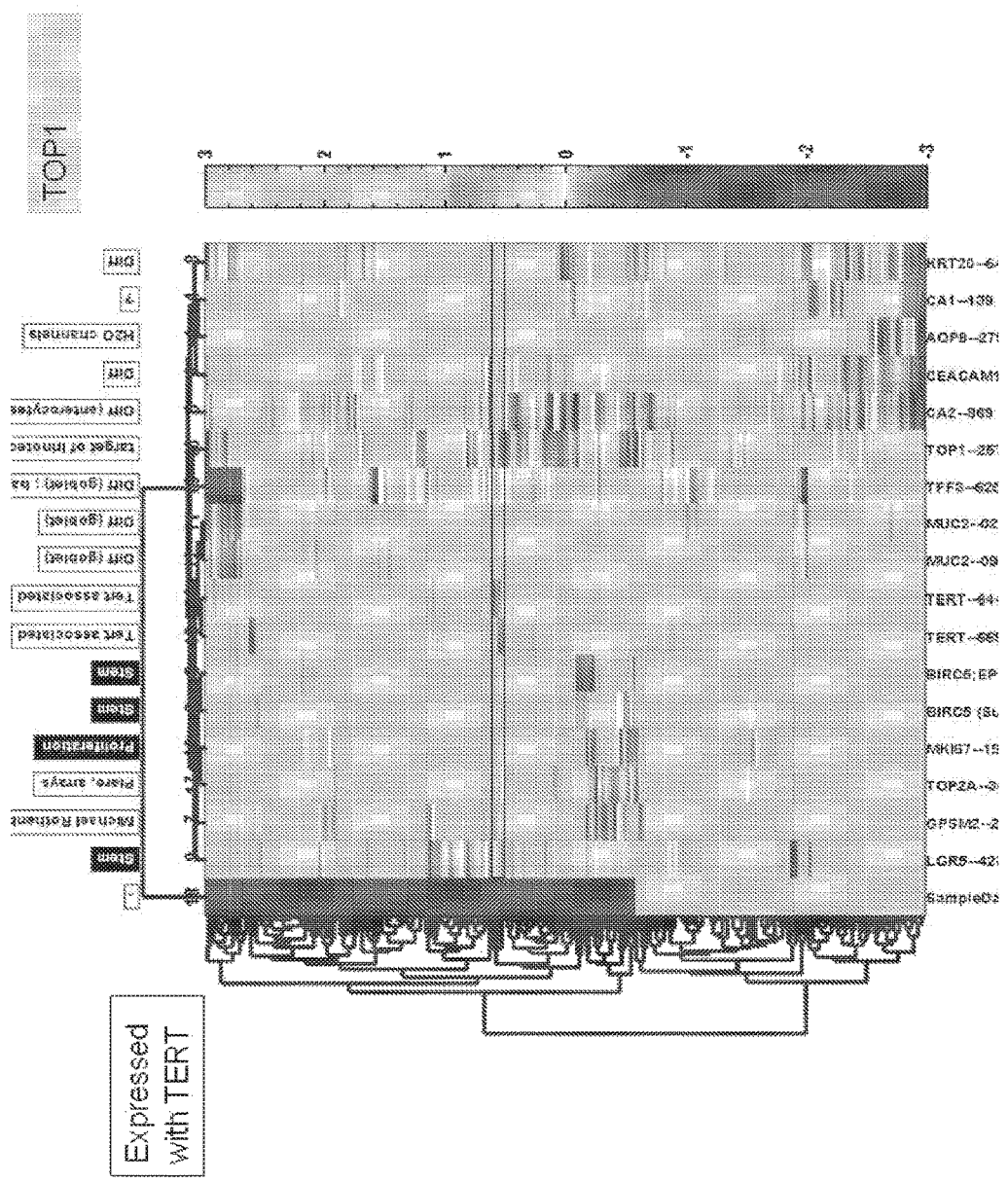
Figure 302:
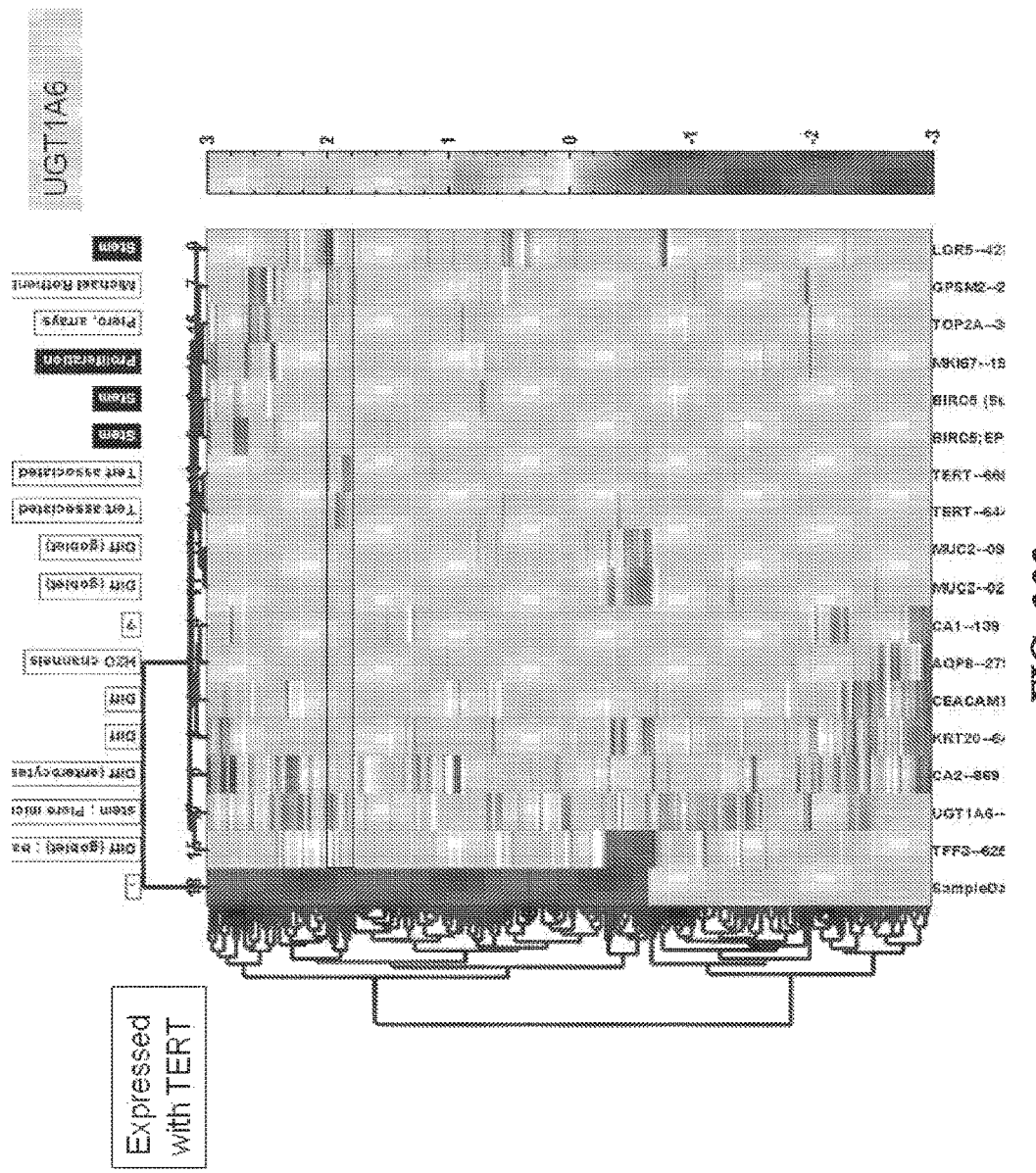
Figure 303:
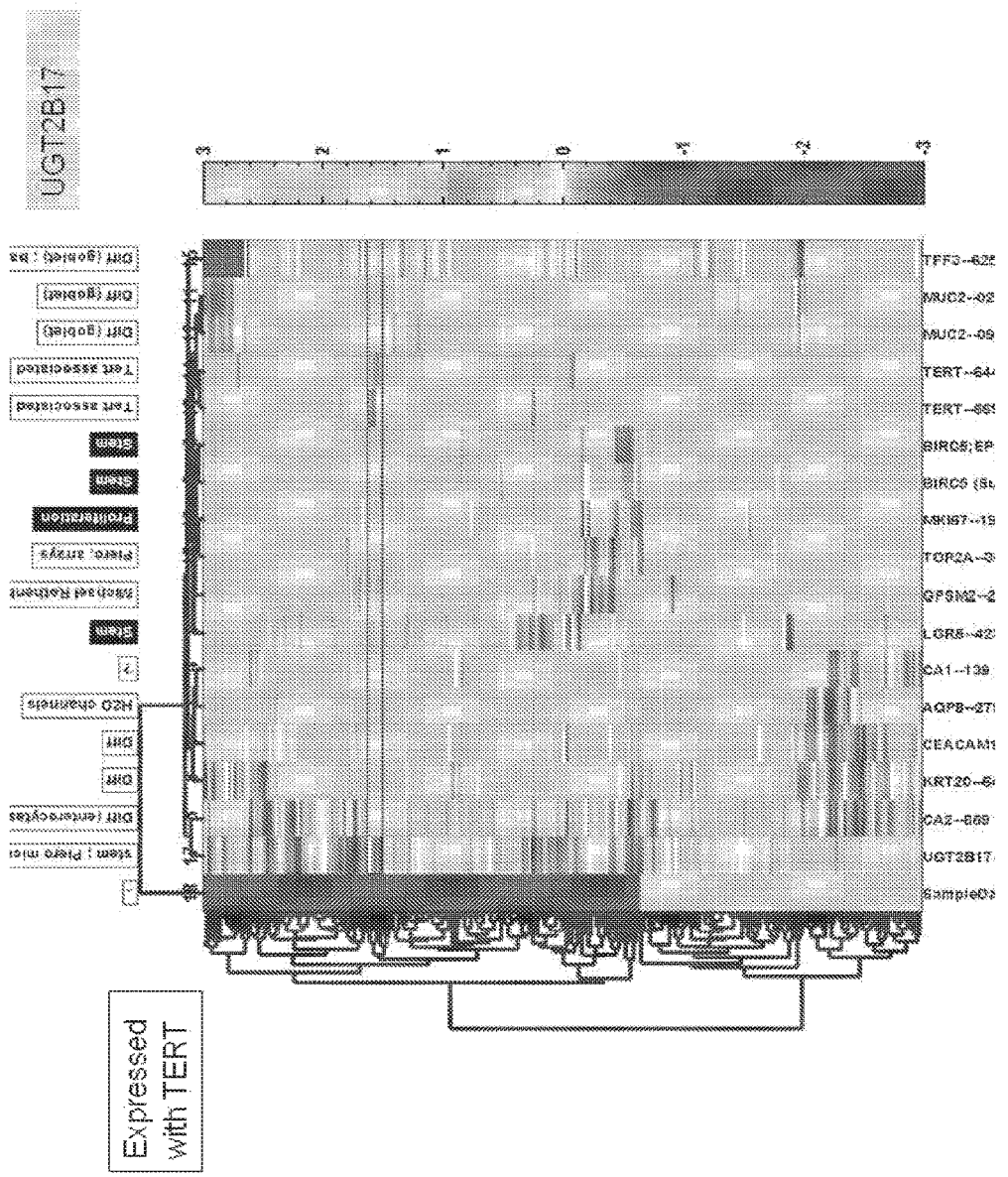
Figure 304:
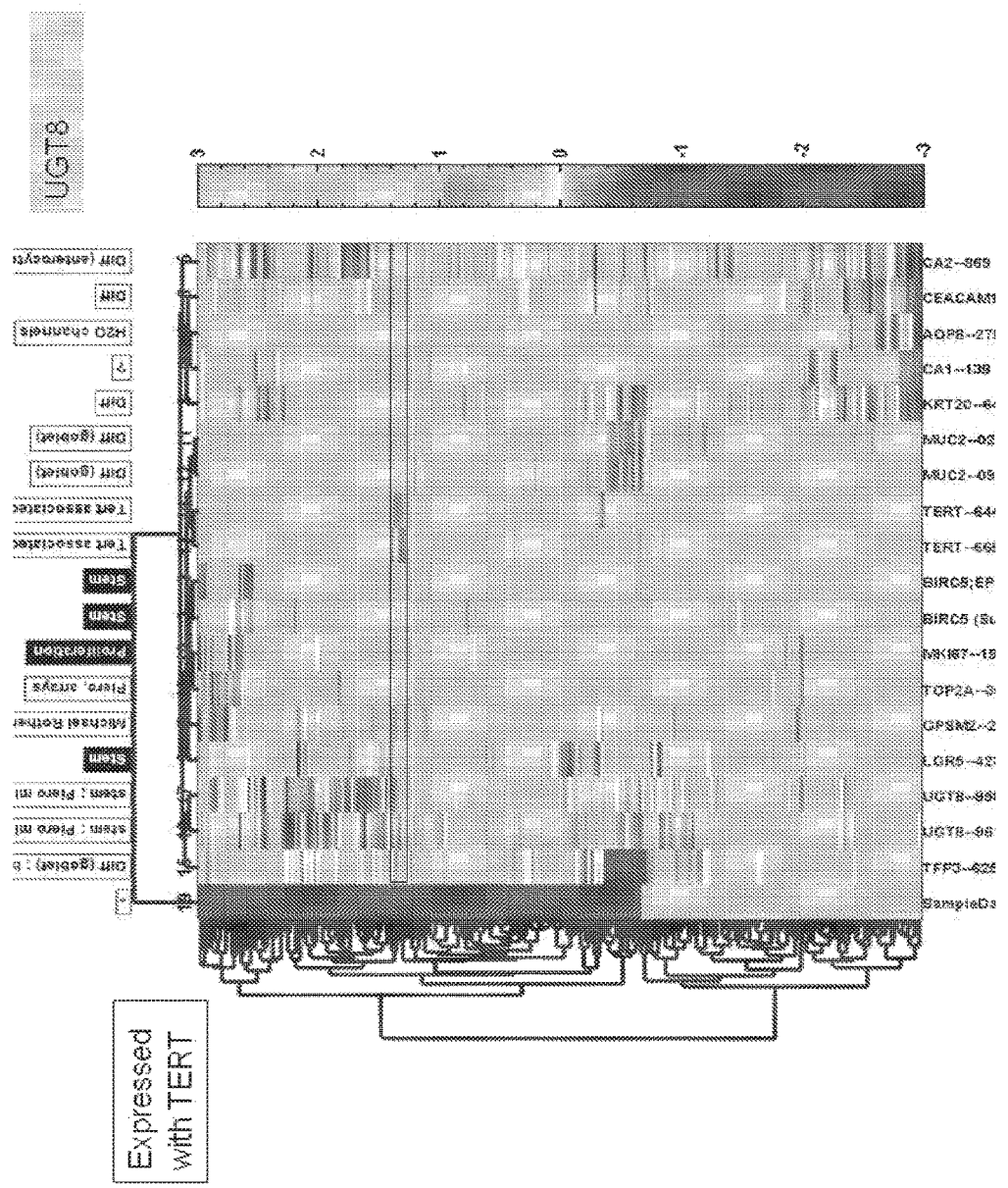
Figure 305:
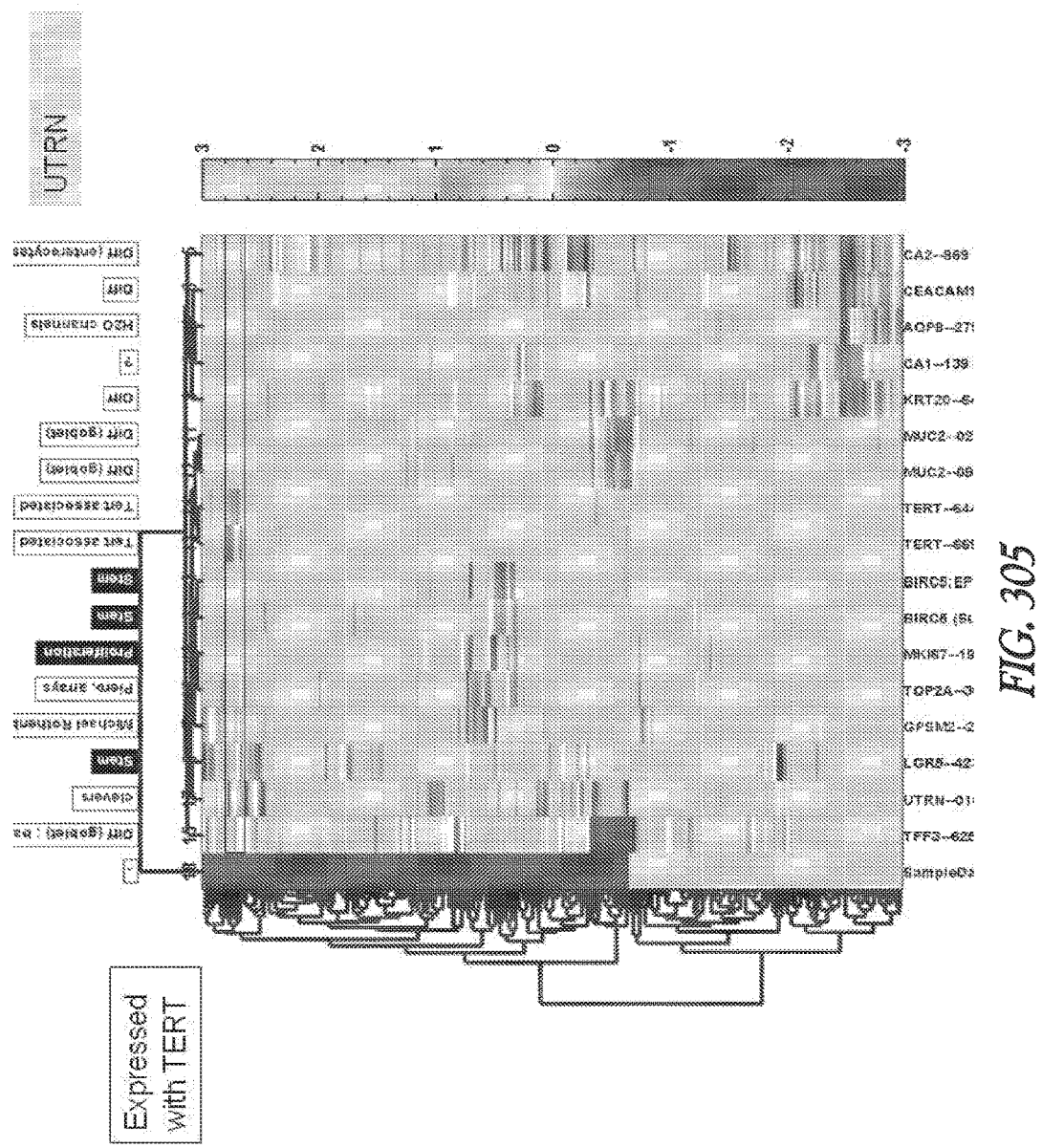
Figure 306:
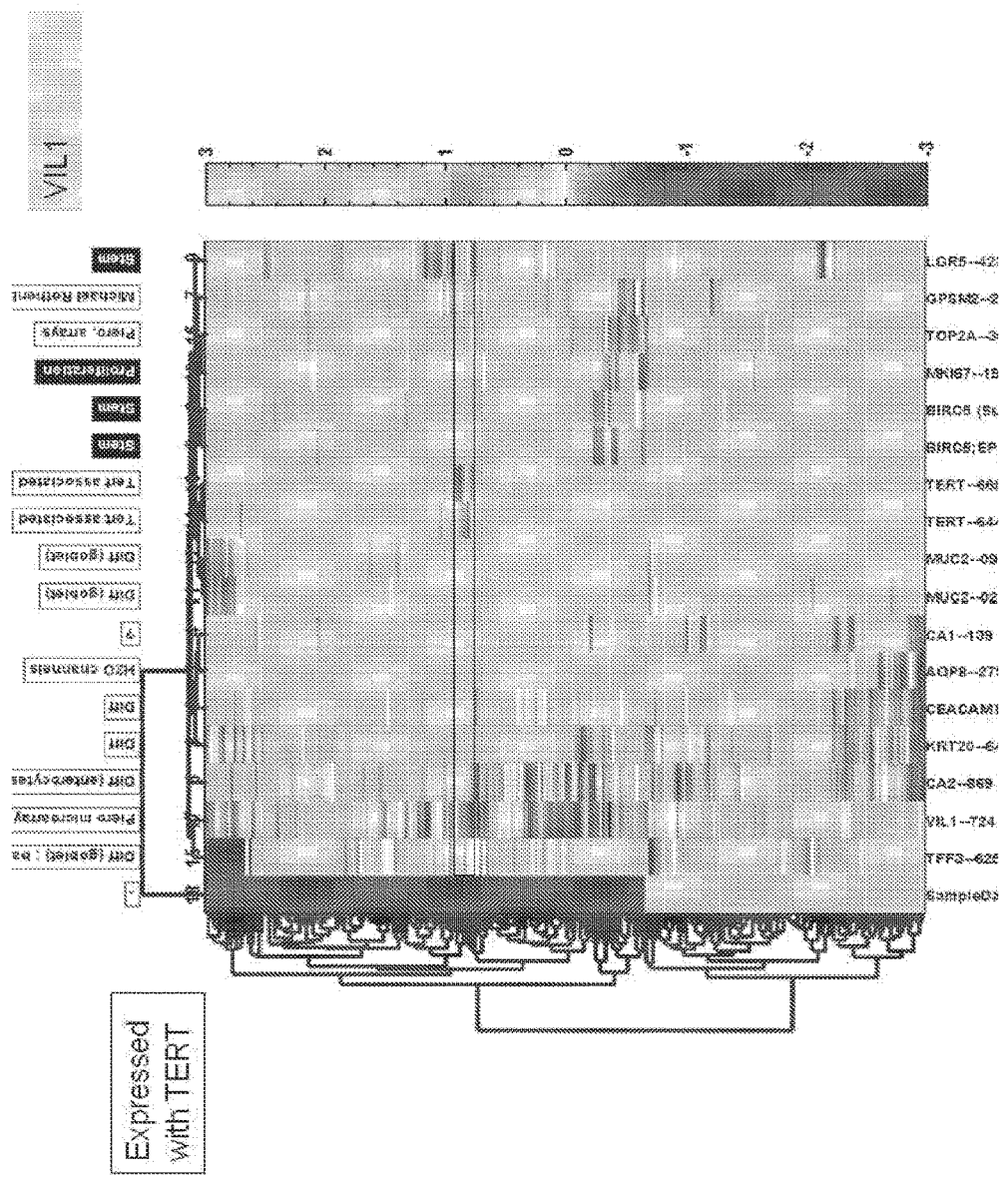
Figure 307:
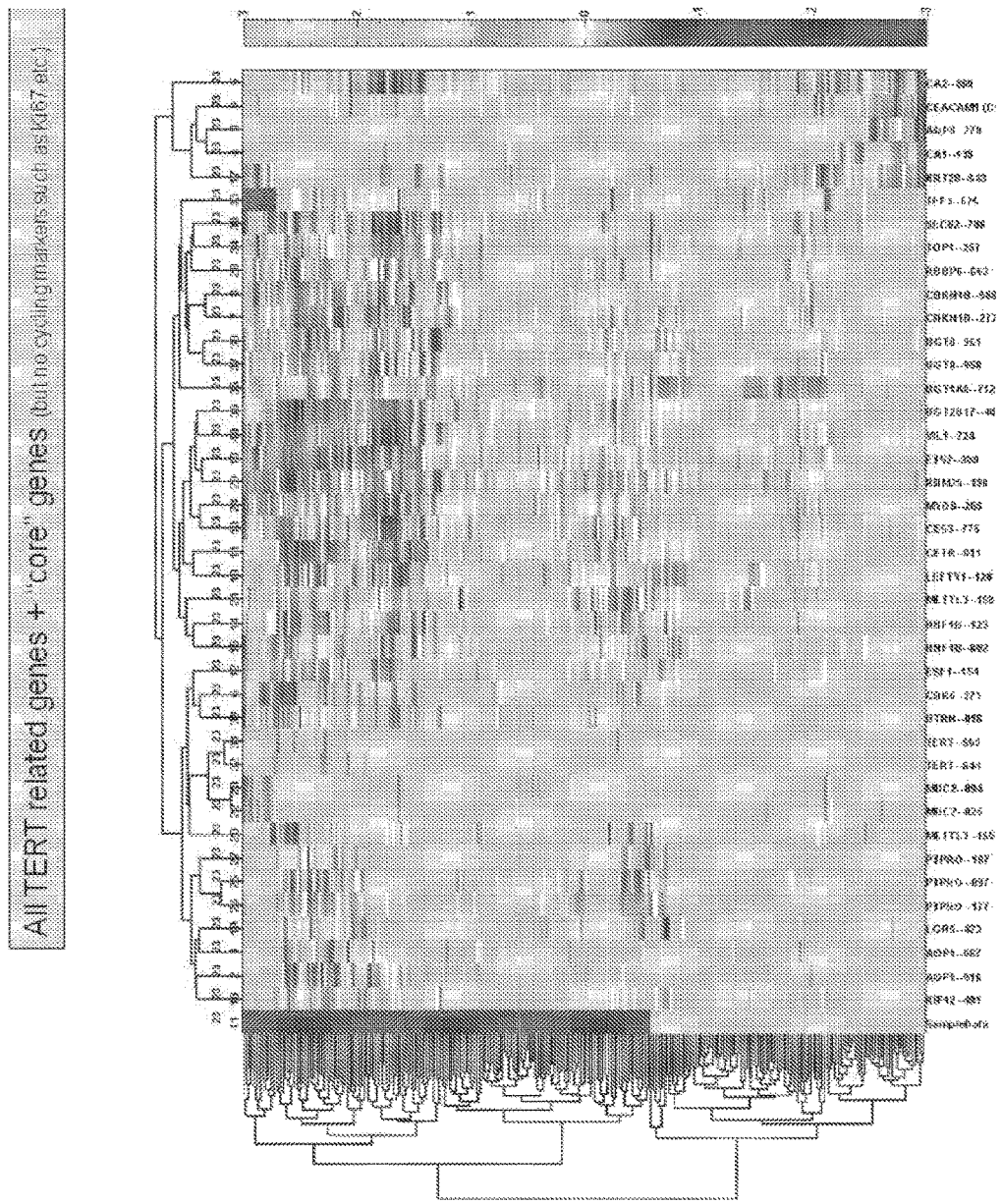
Figure 308:
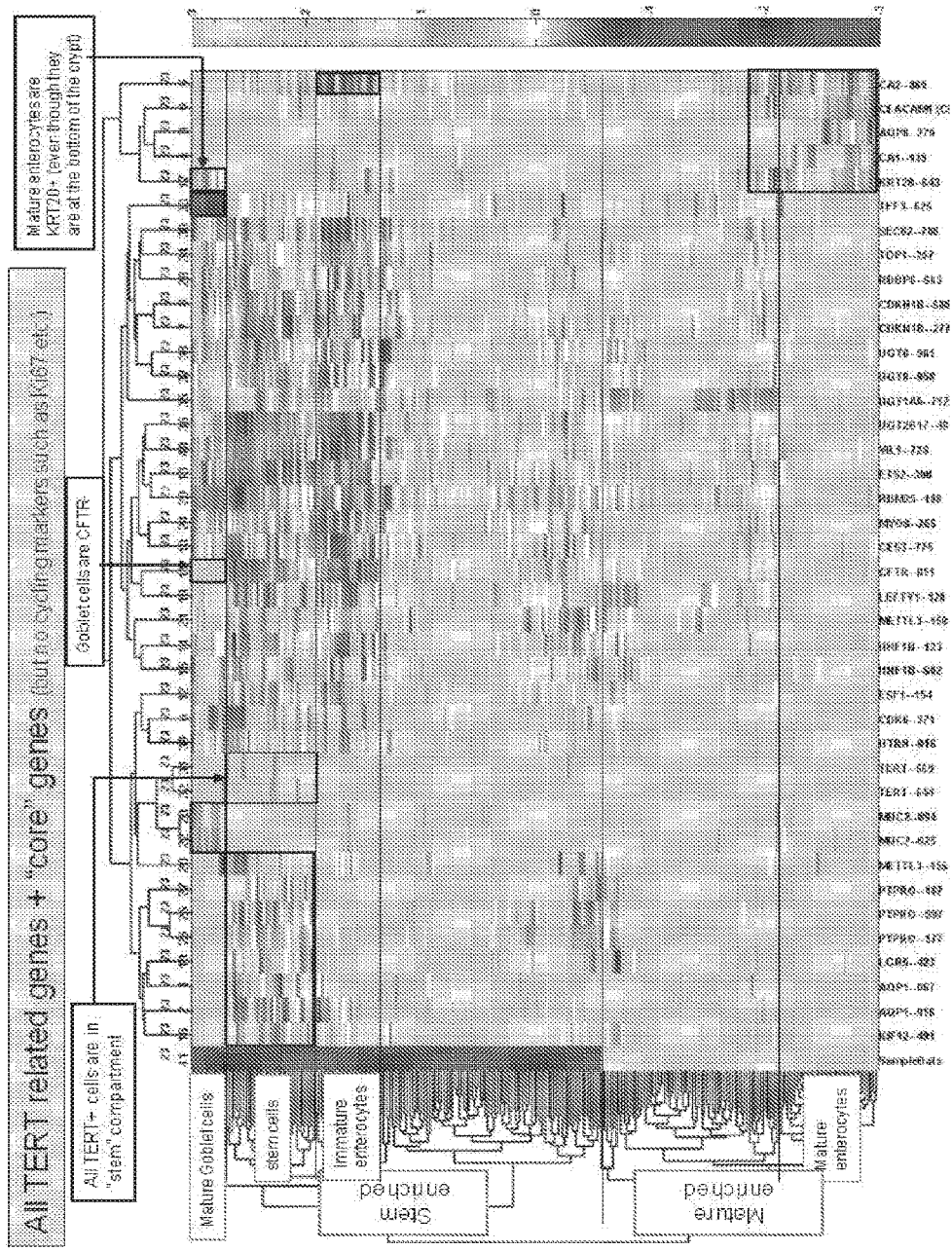
Figure 309:
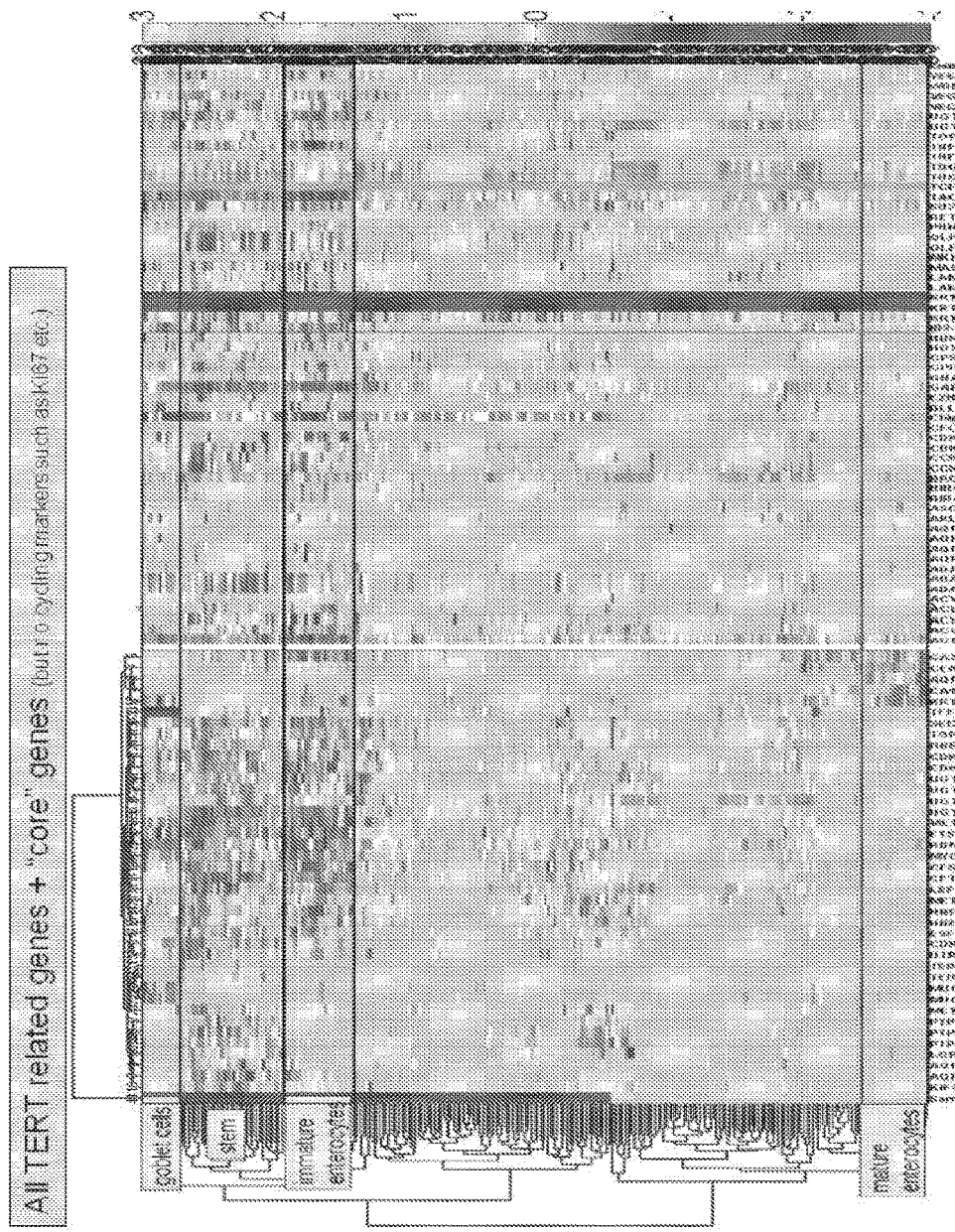
Figure 310:
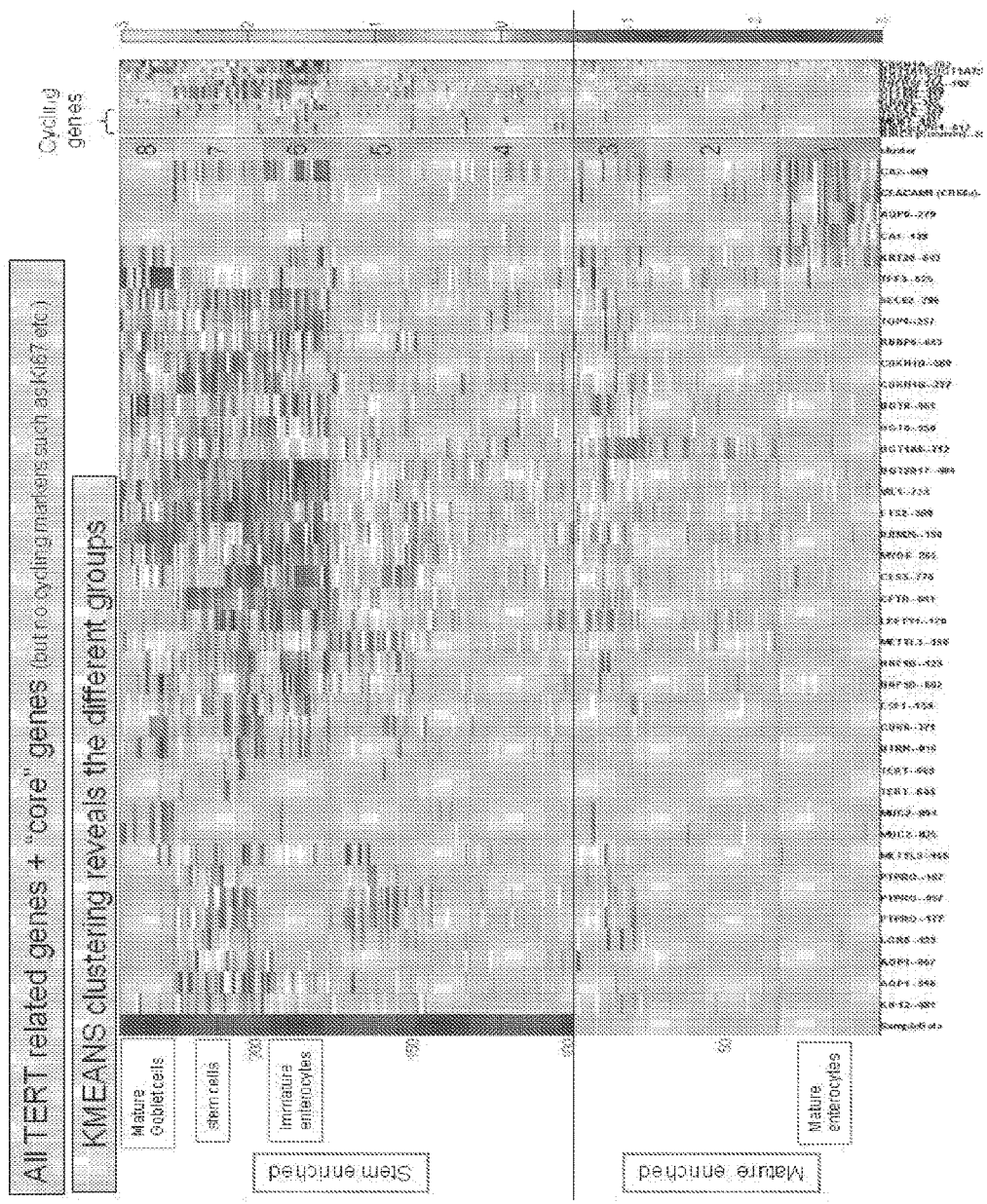
Figure 311:
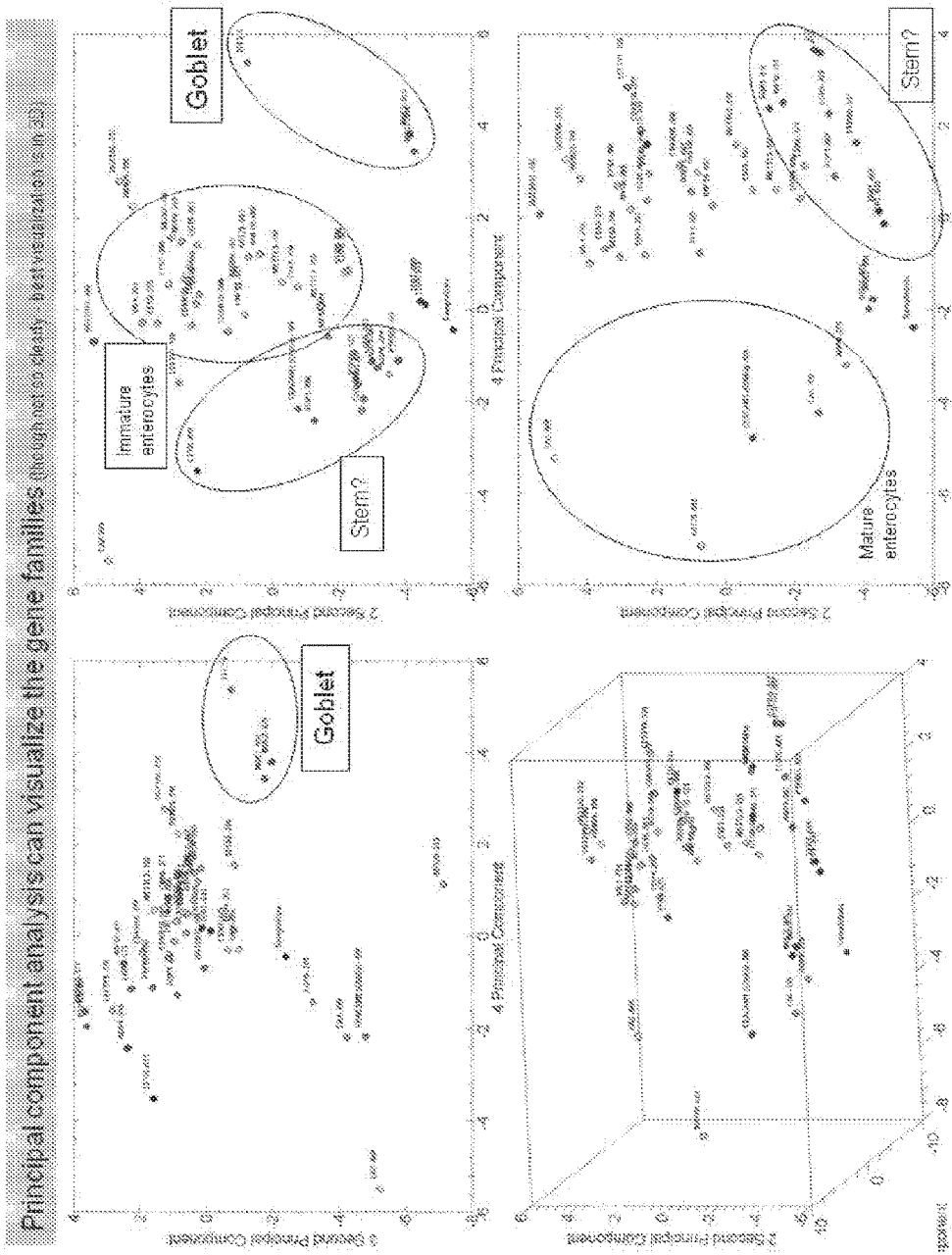
Figure 312:
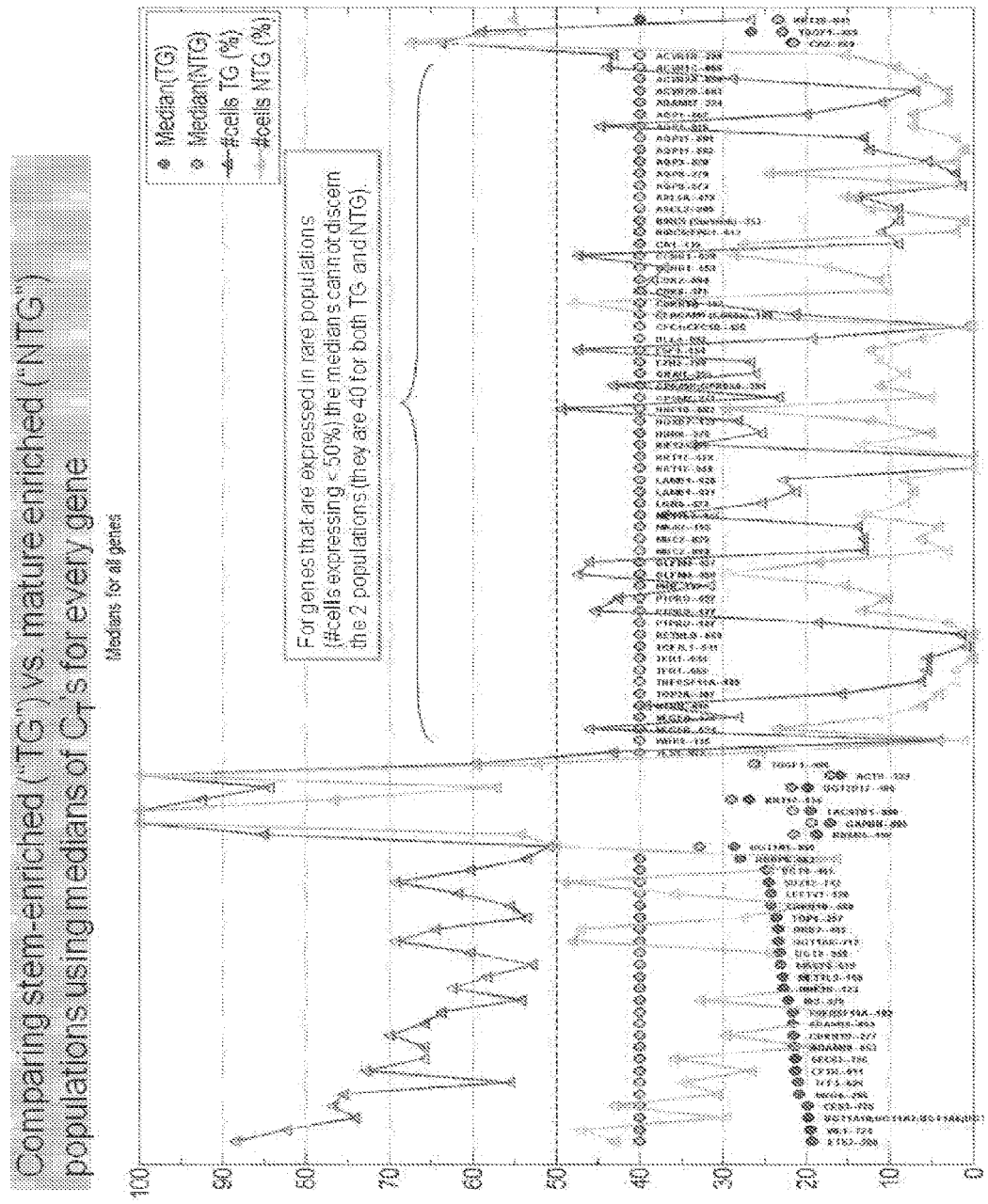
Figure 313:
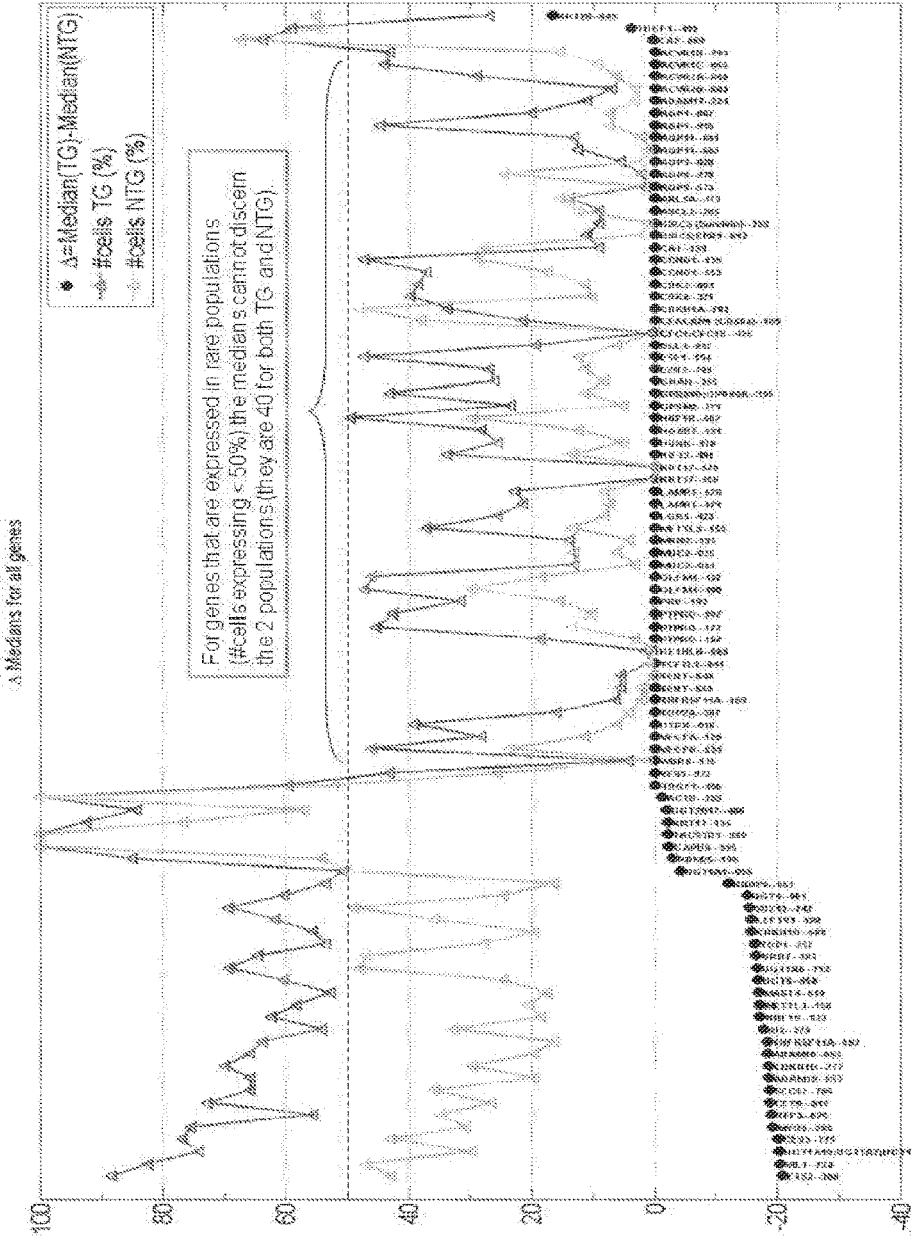
Figure 314:
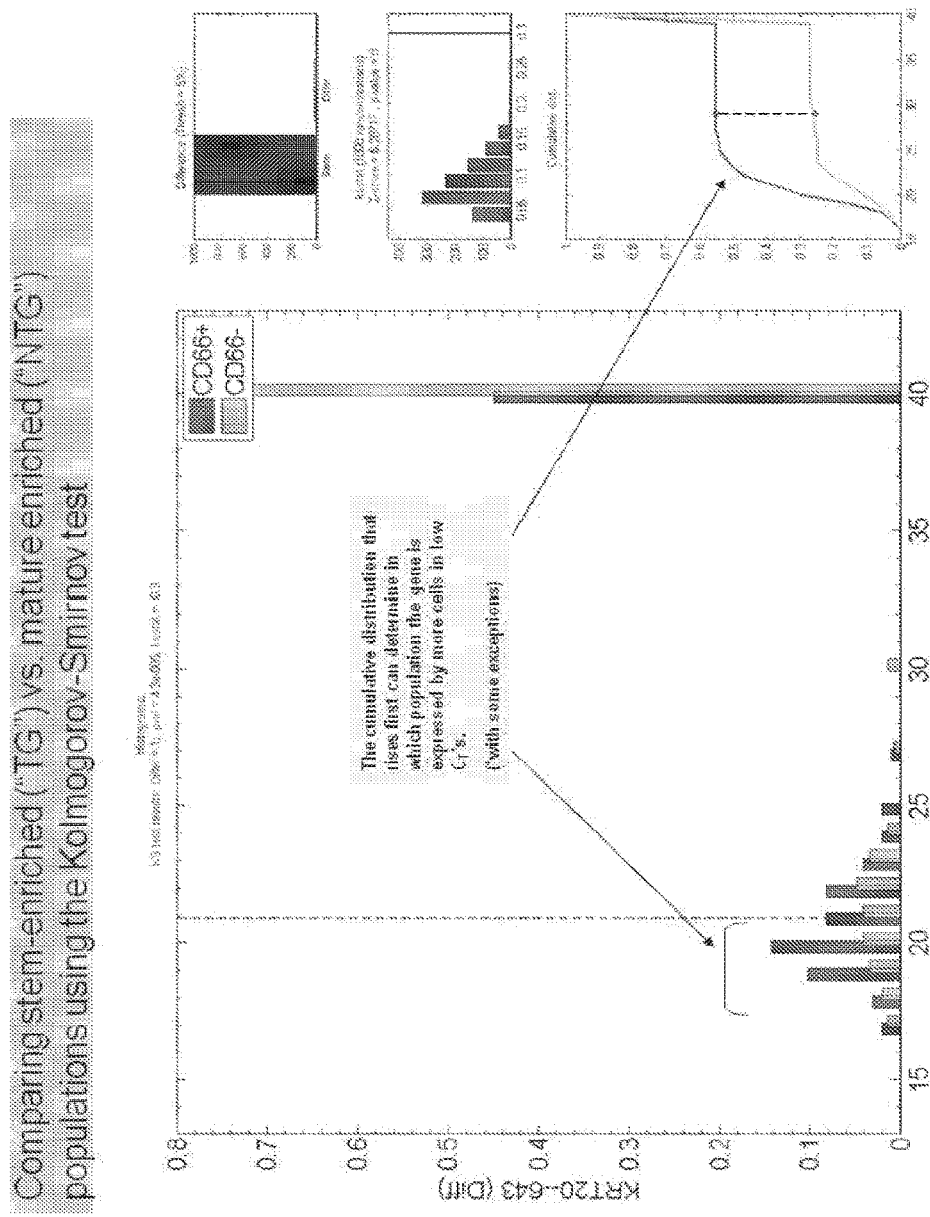
Figure 315:
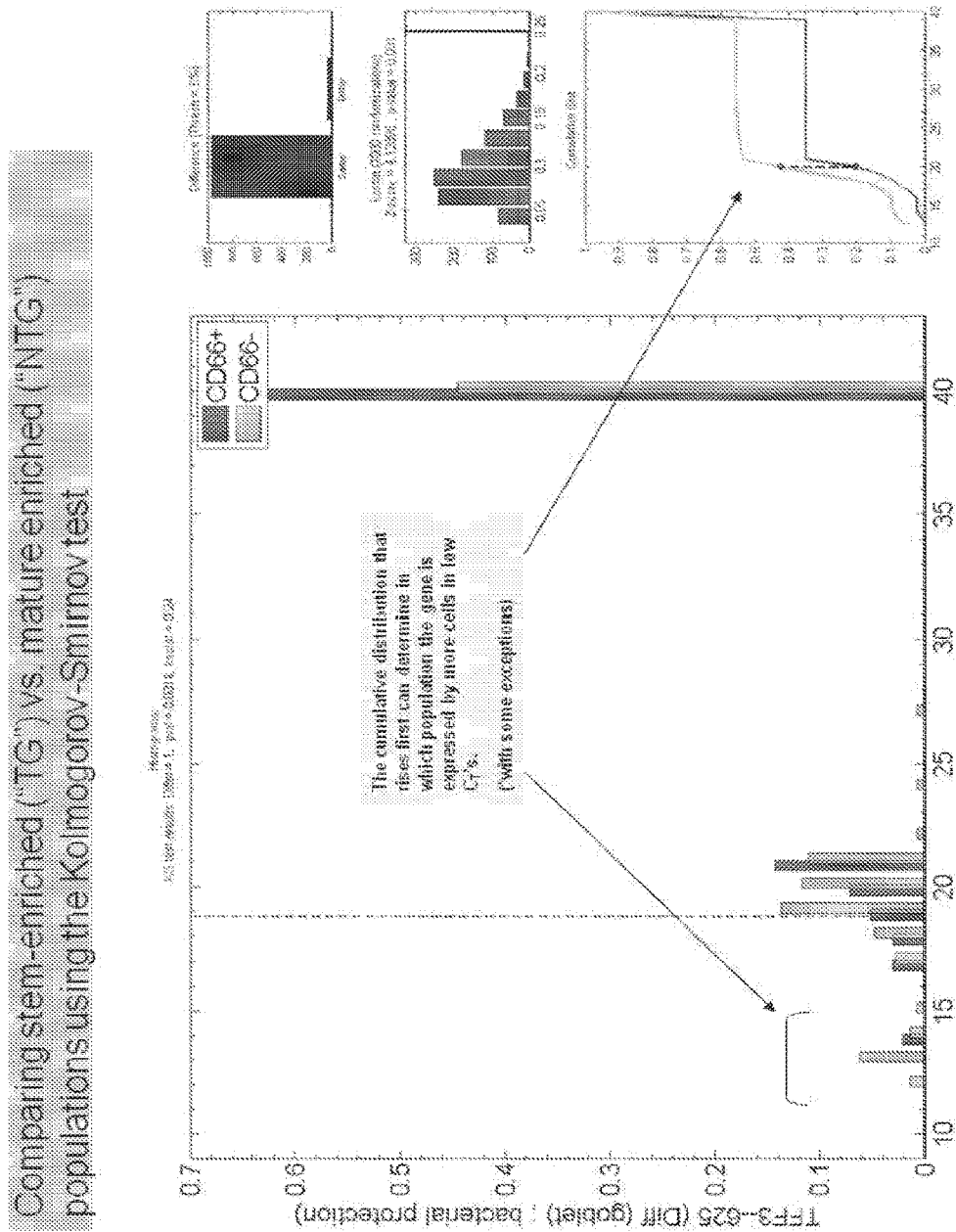
Figure 316:
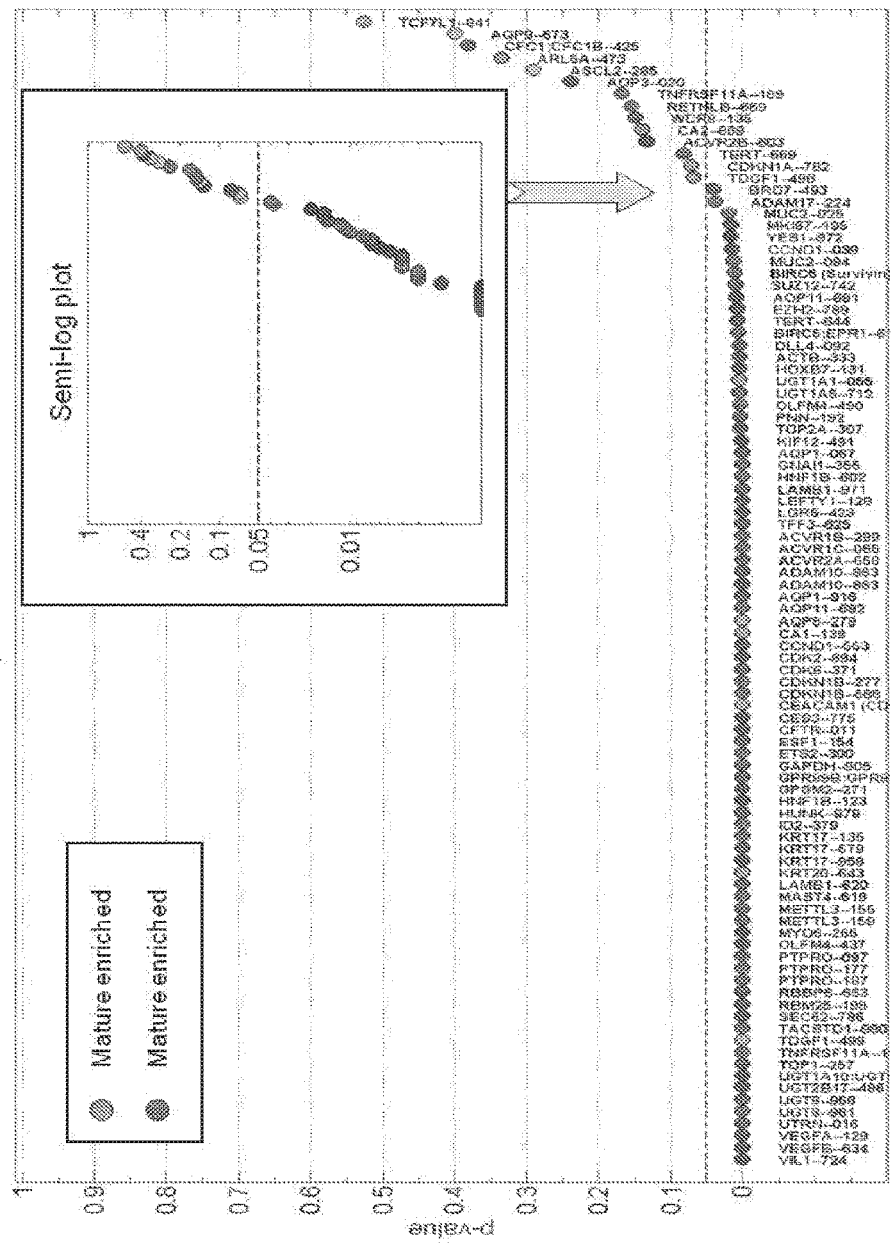
Figure 317:
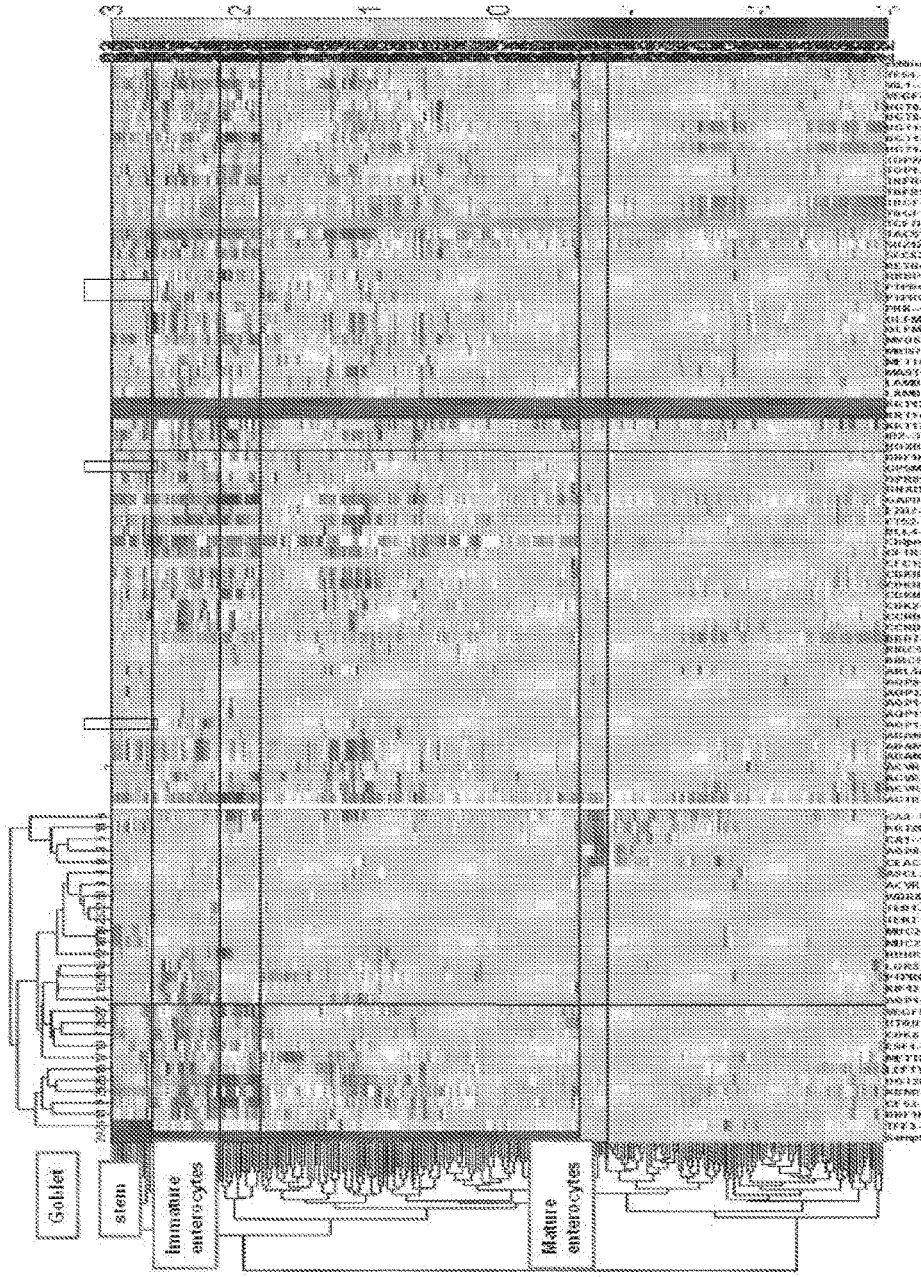
Figure 318:
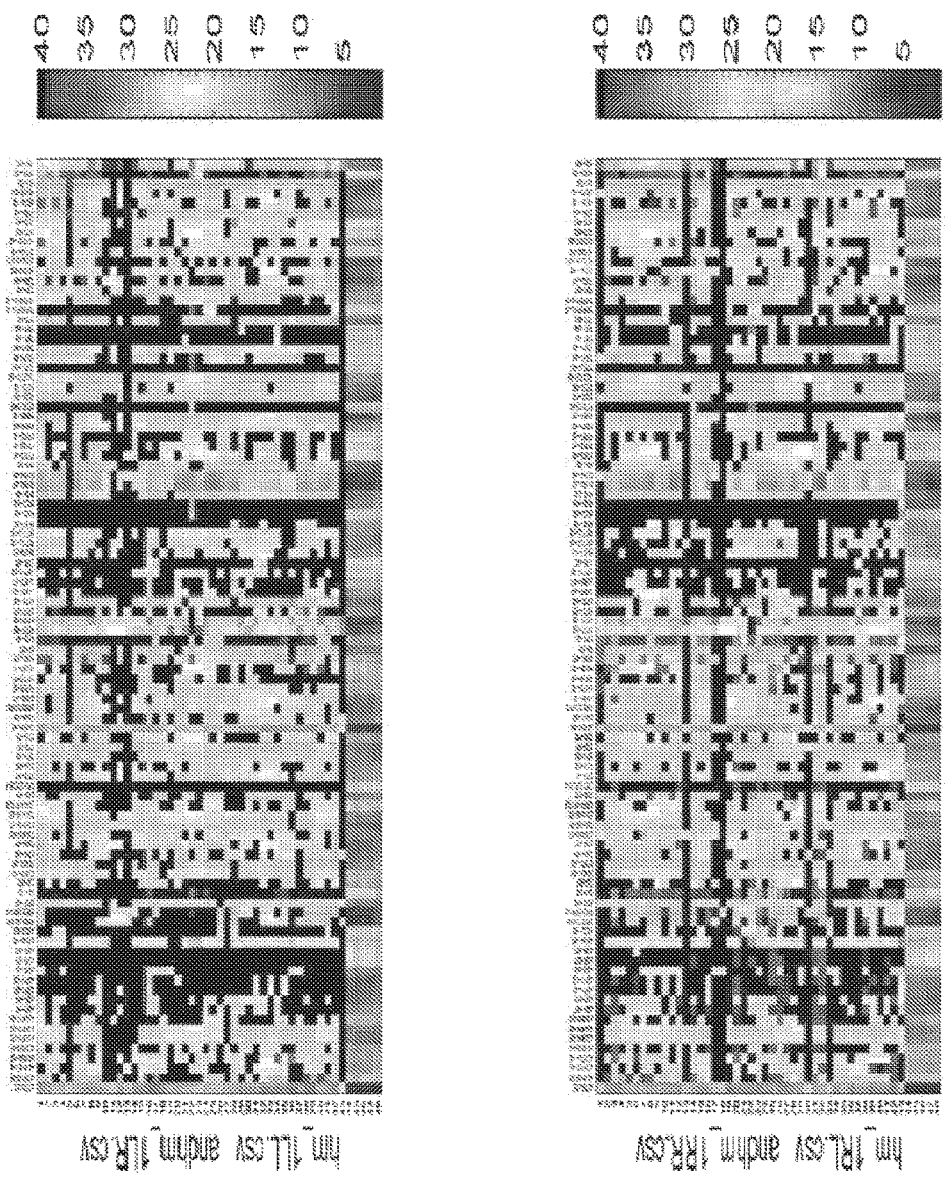
Figure 319:
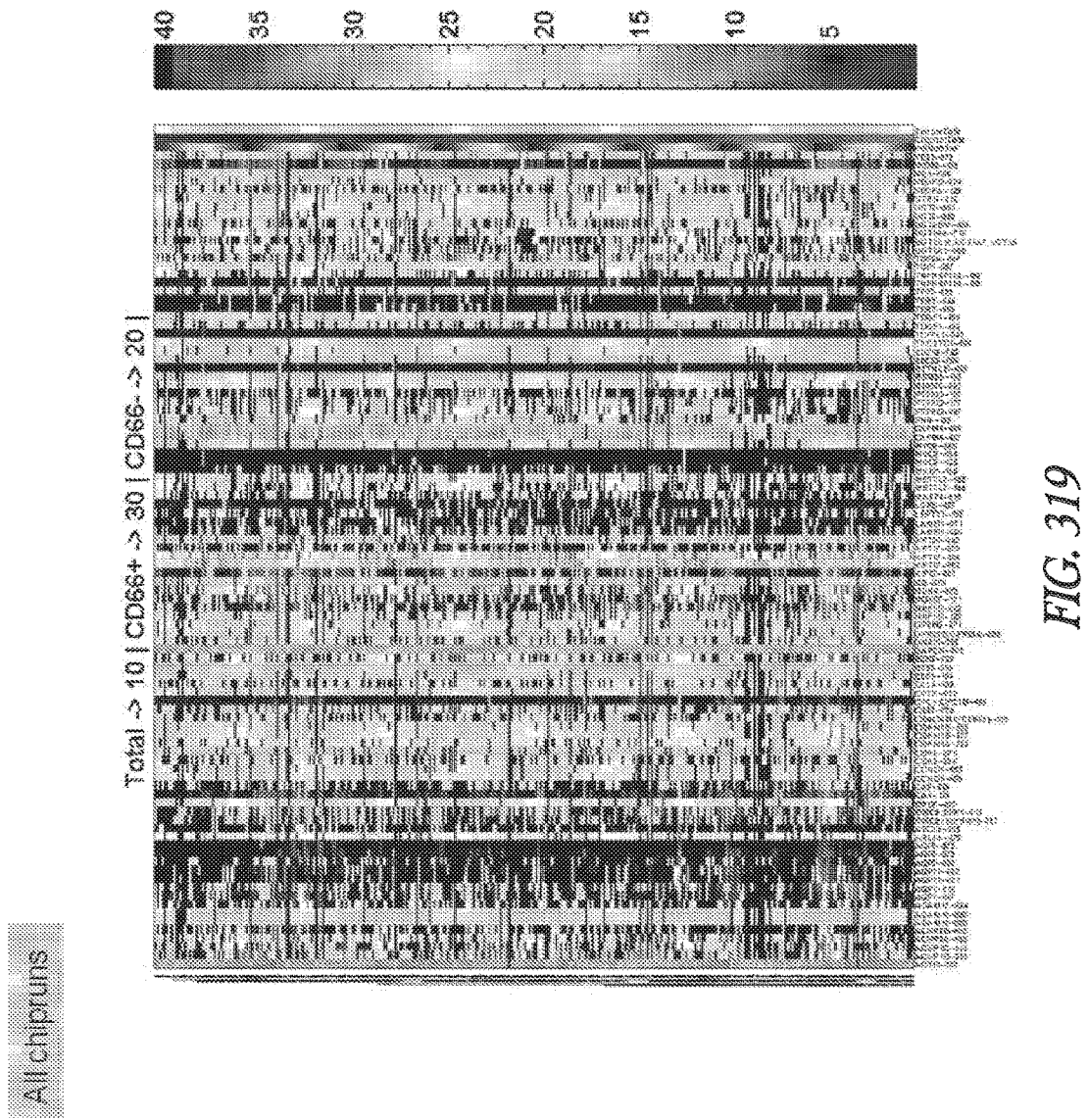
Figure 320:
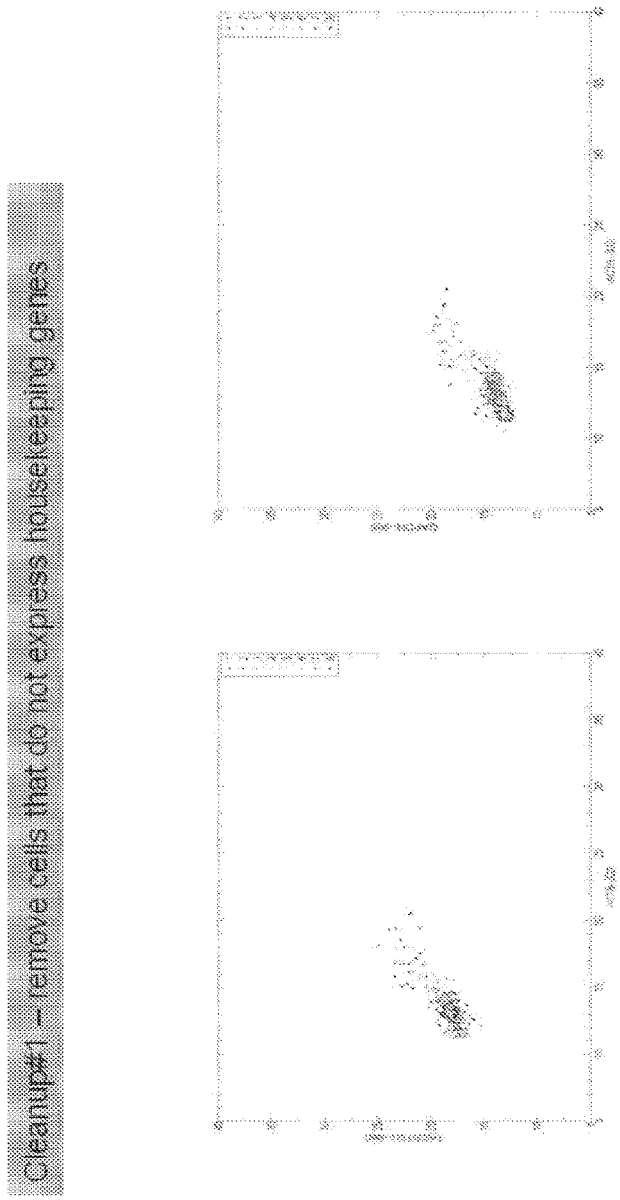
Figure 321:
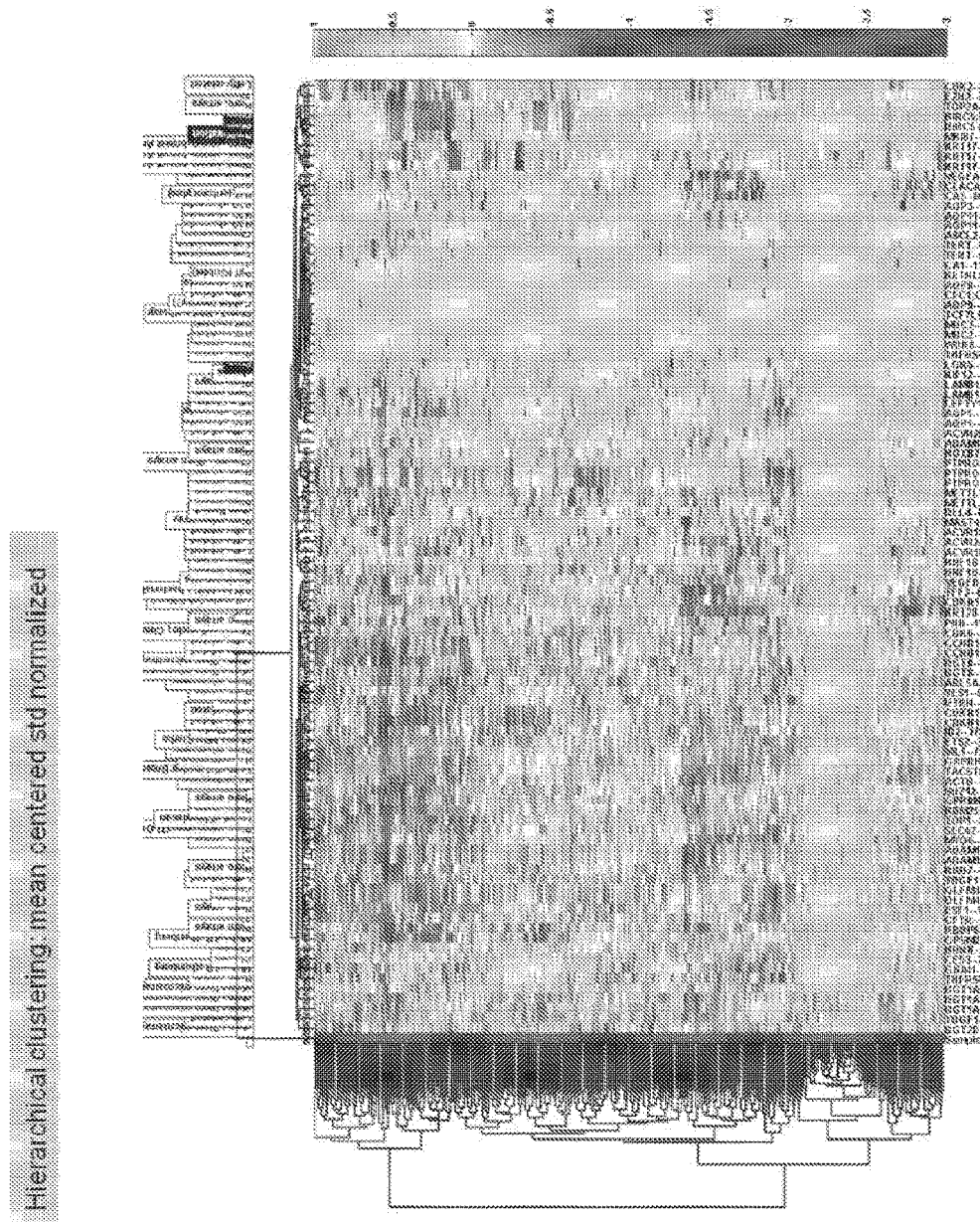
Figure 322:
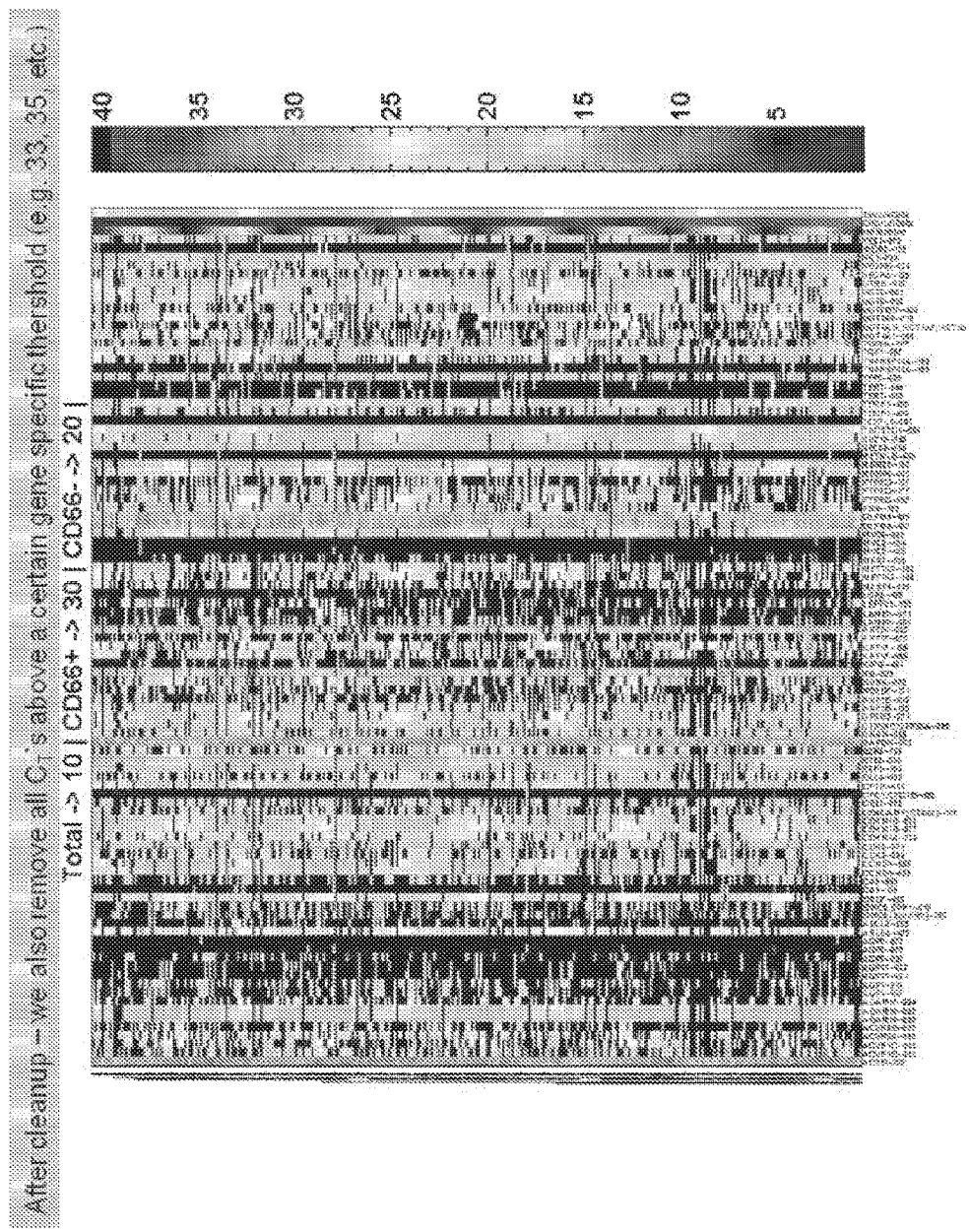
Figure 323:
Figure 324:
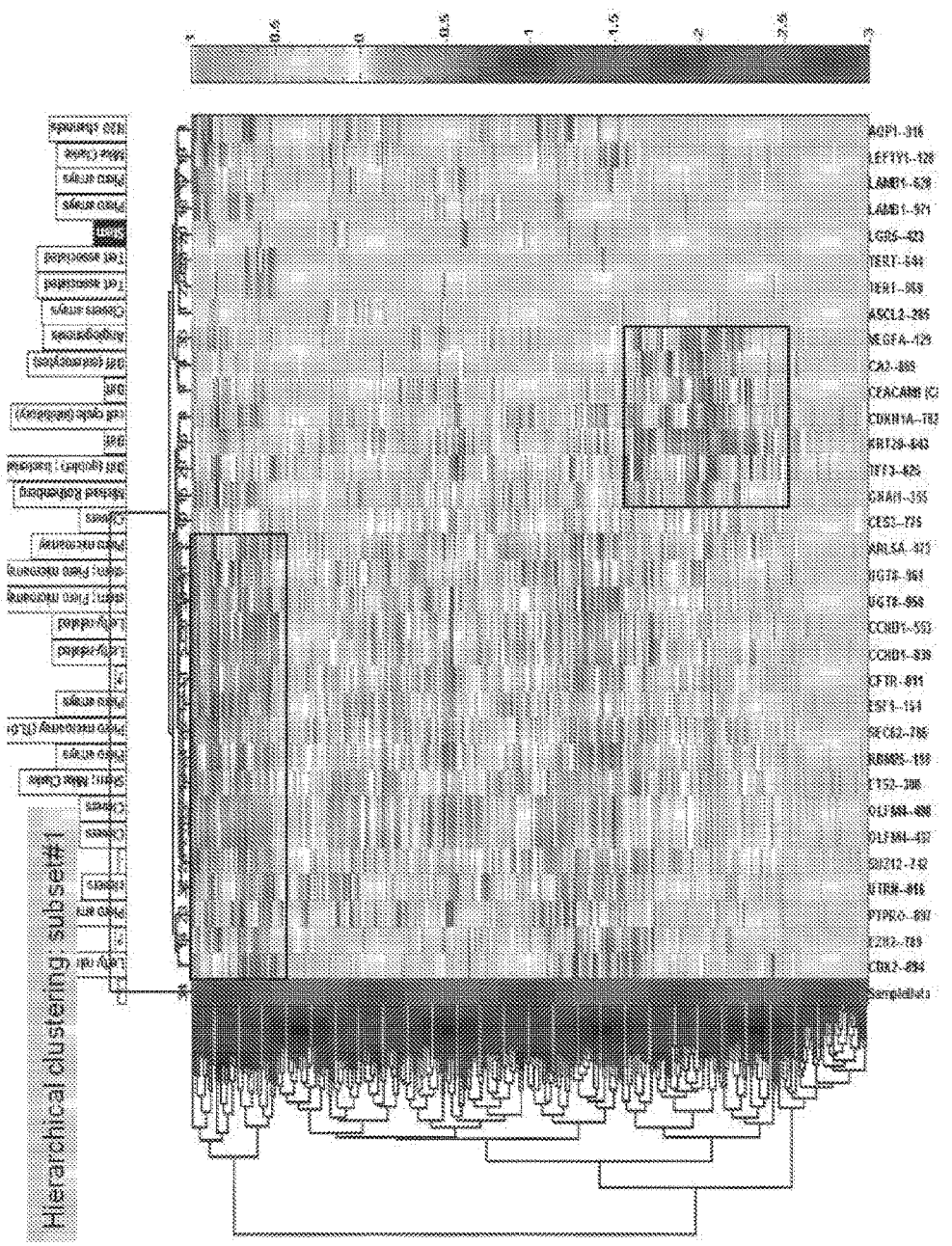
Figure 325:
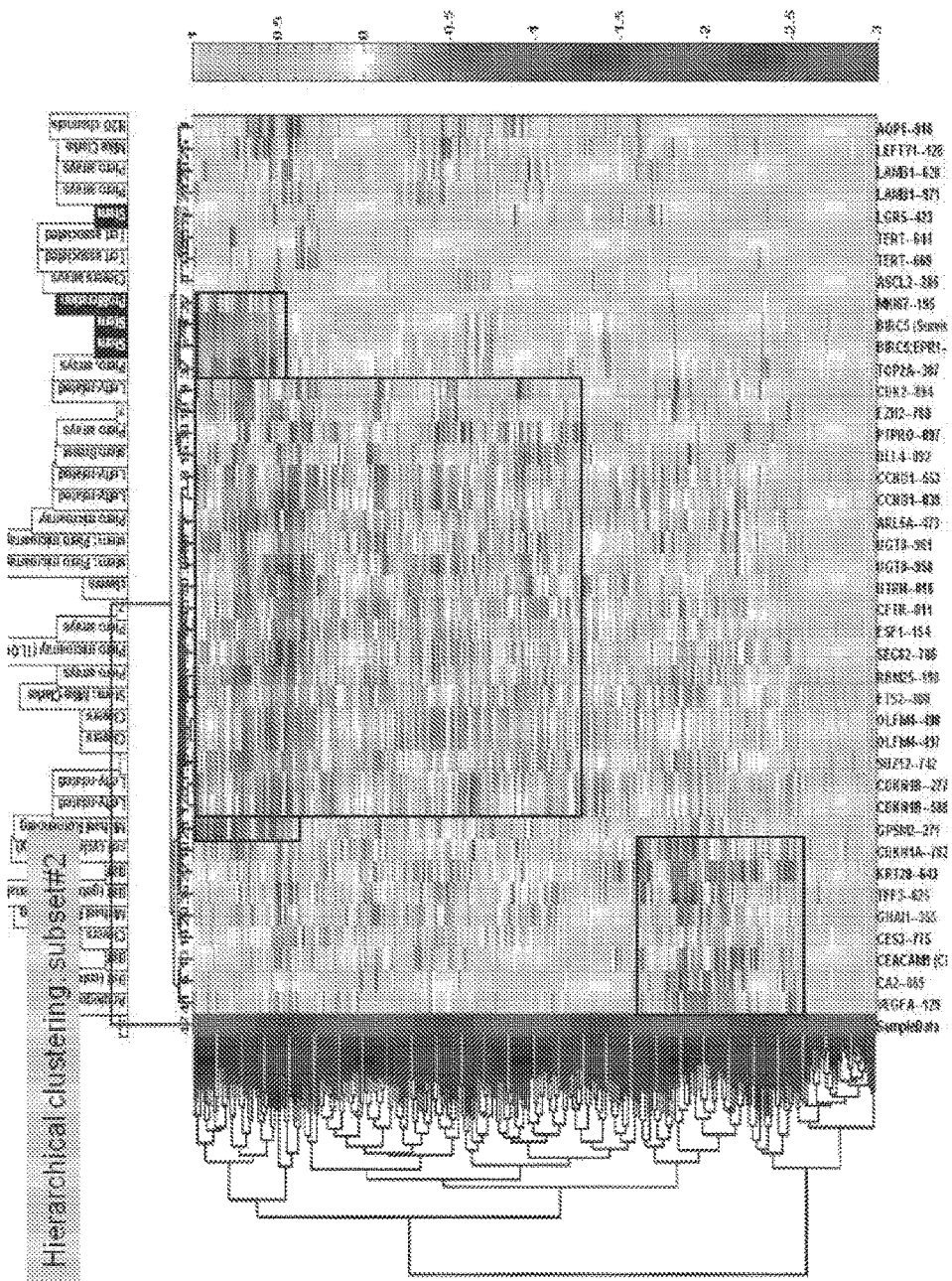
Figure 326:
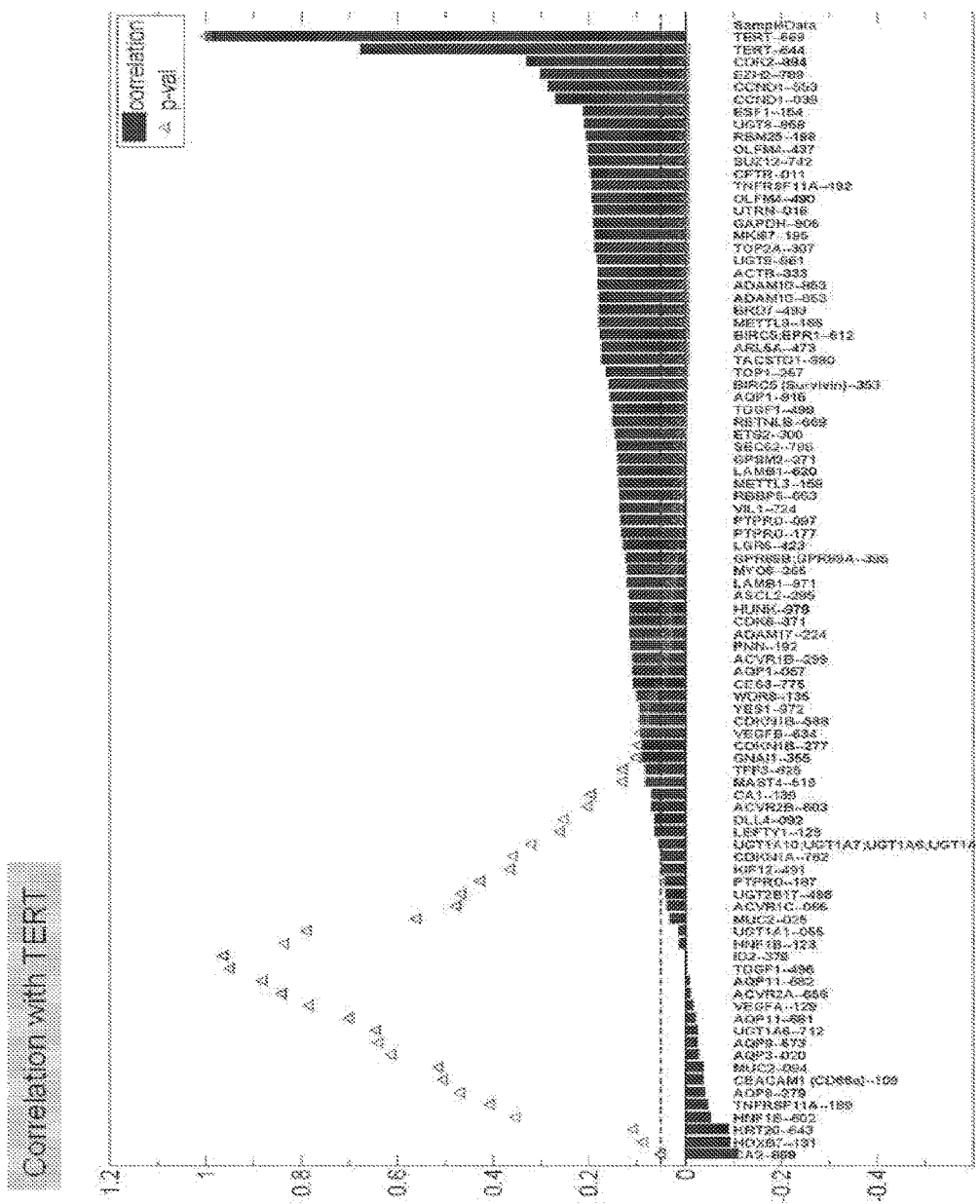
Figure 327:
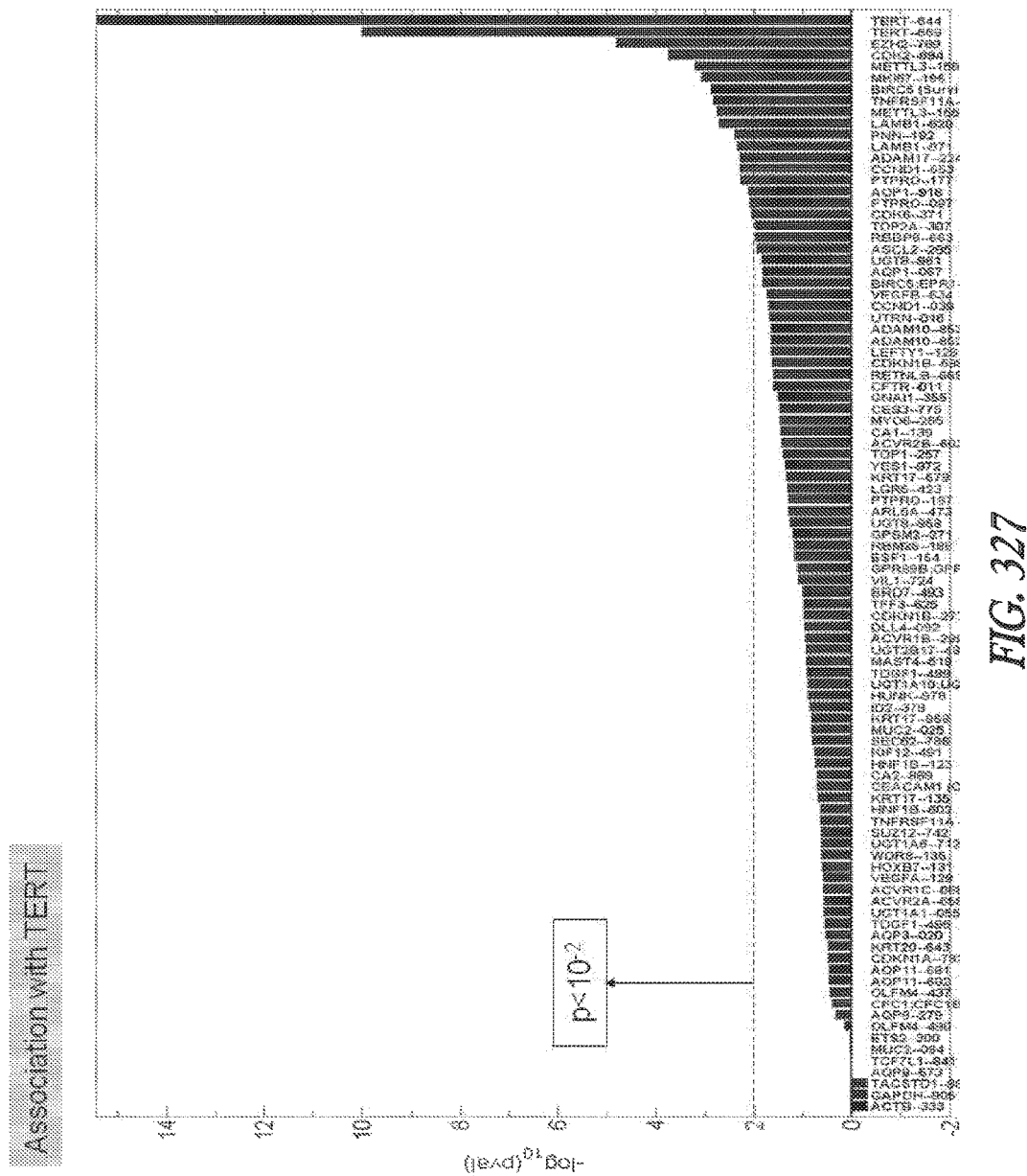
Figure 328:
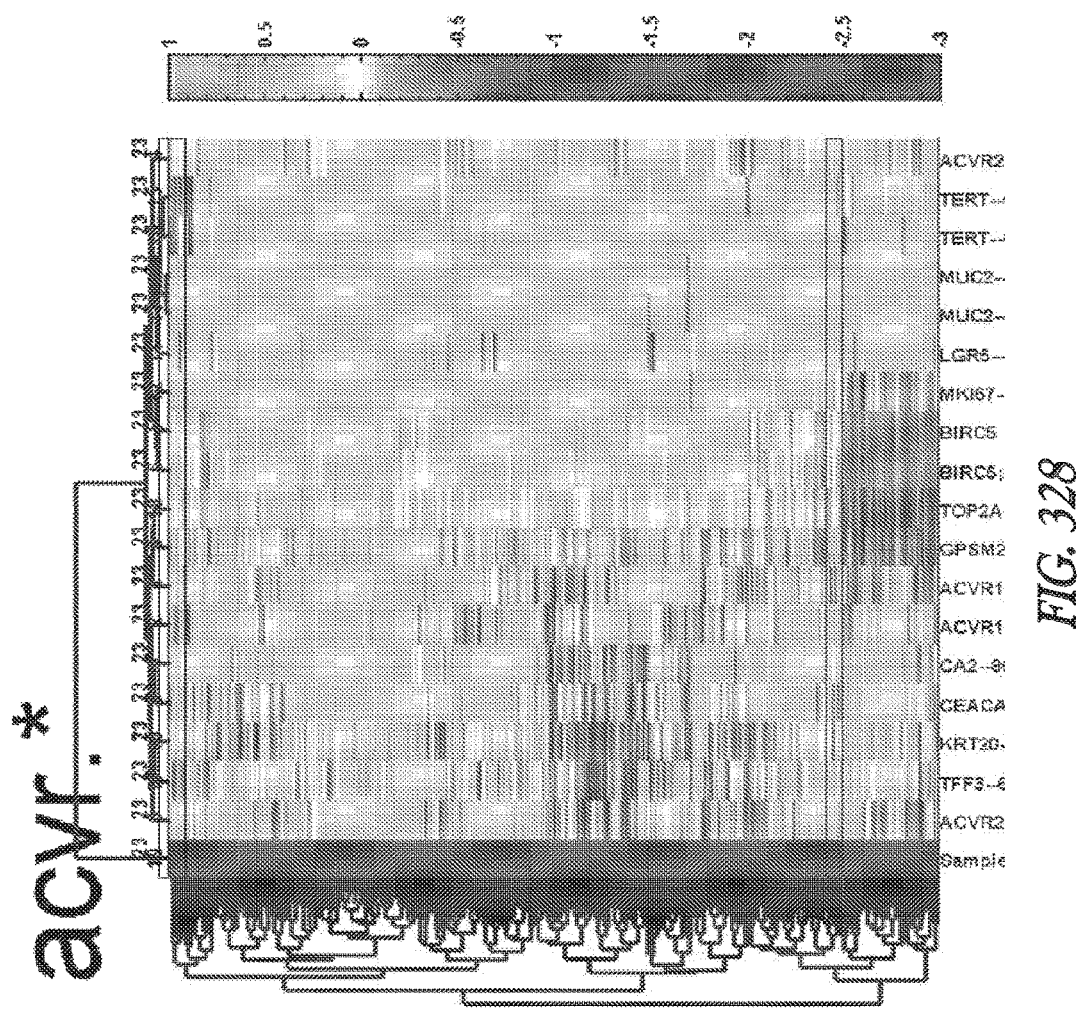
Figure 329:
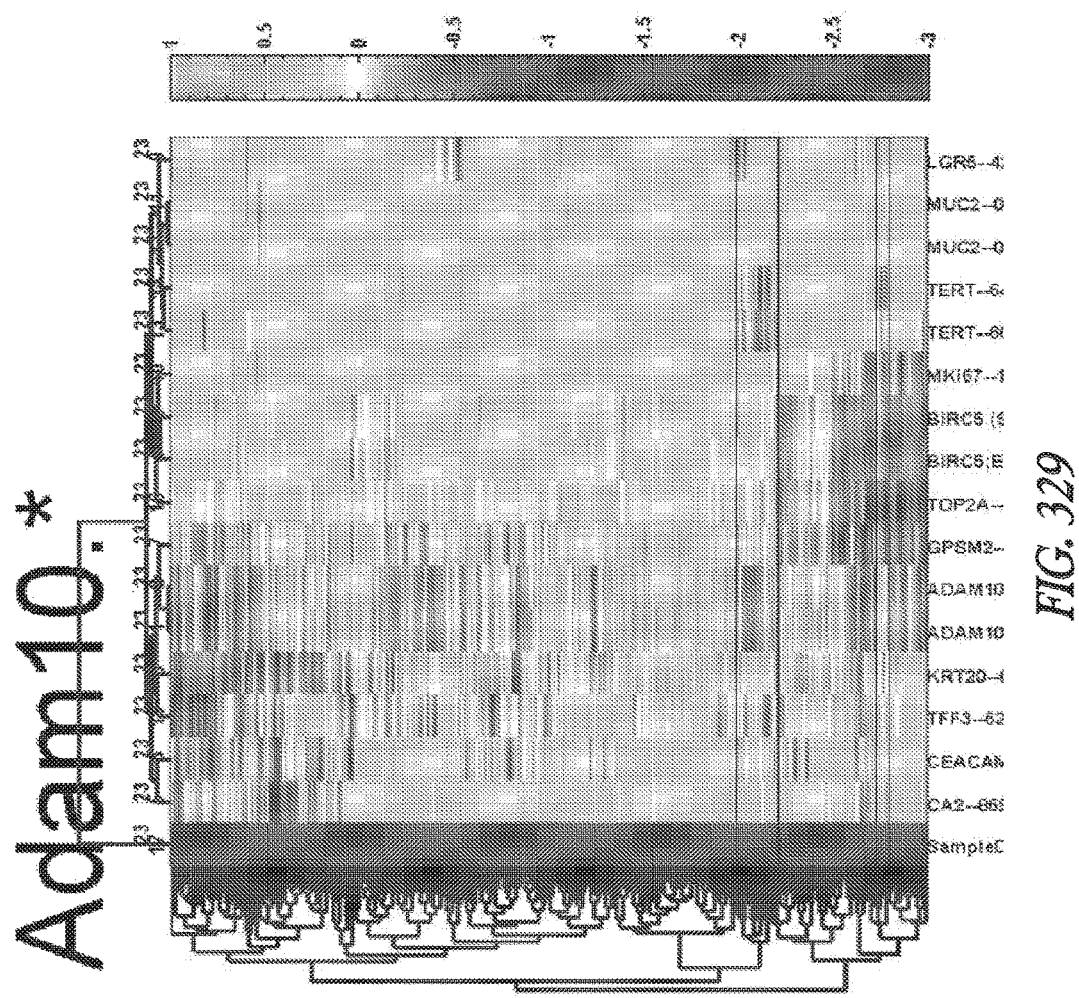
Figure 330:
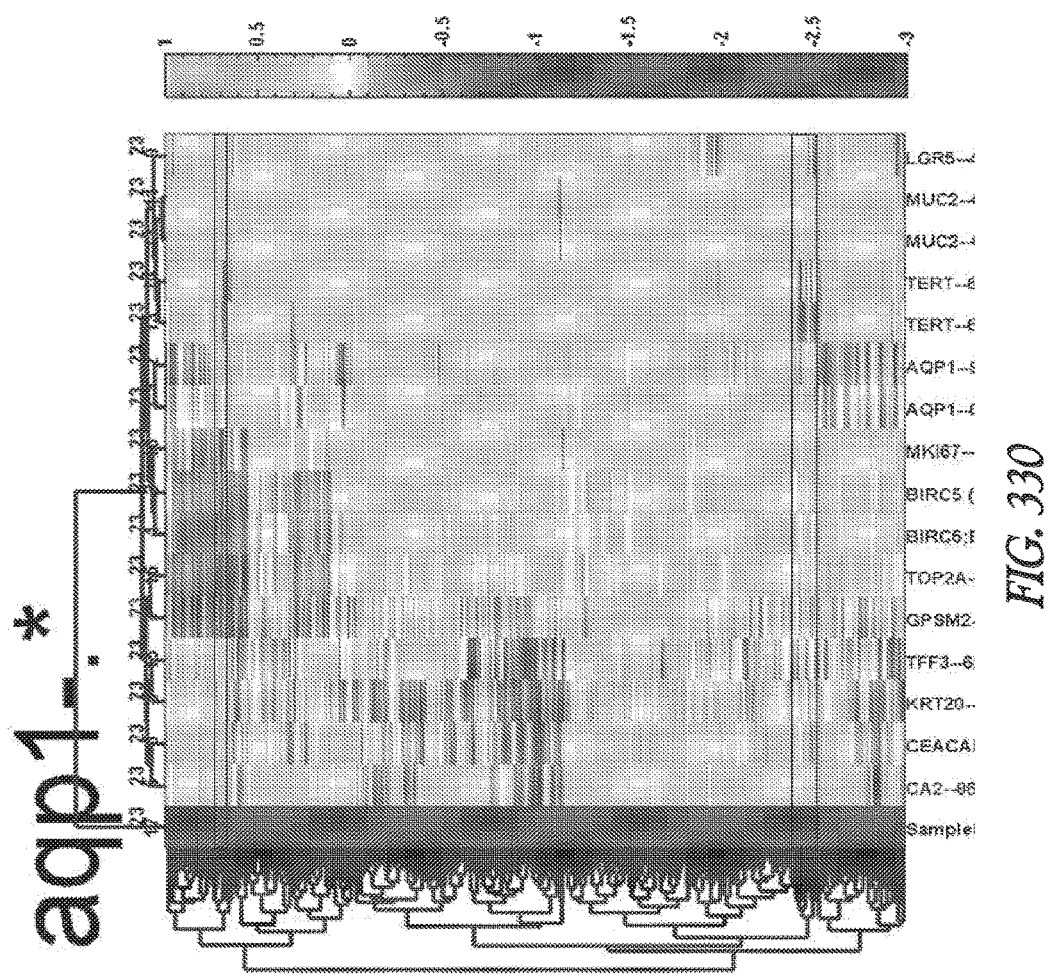
Figure 331:
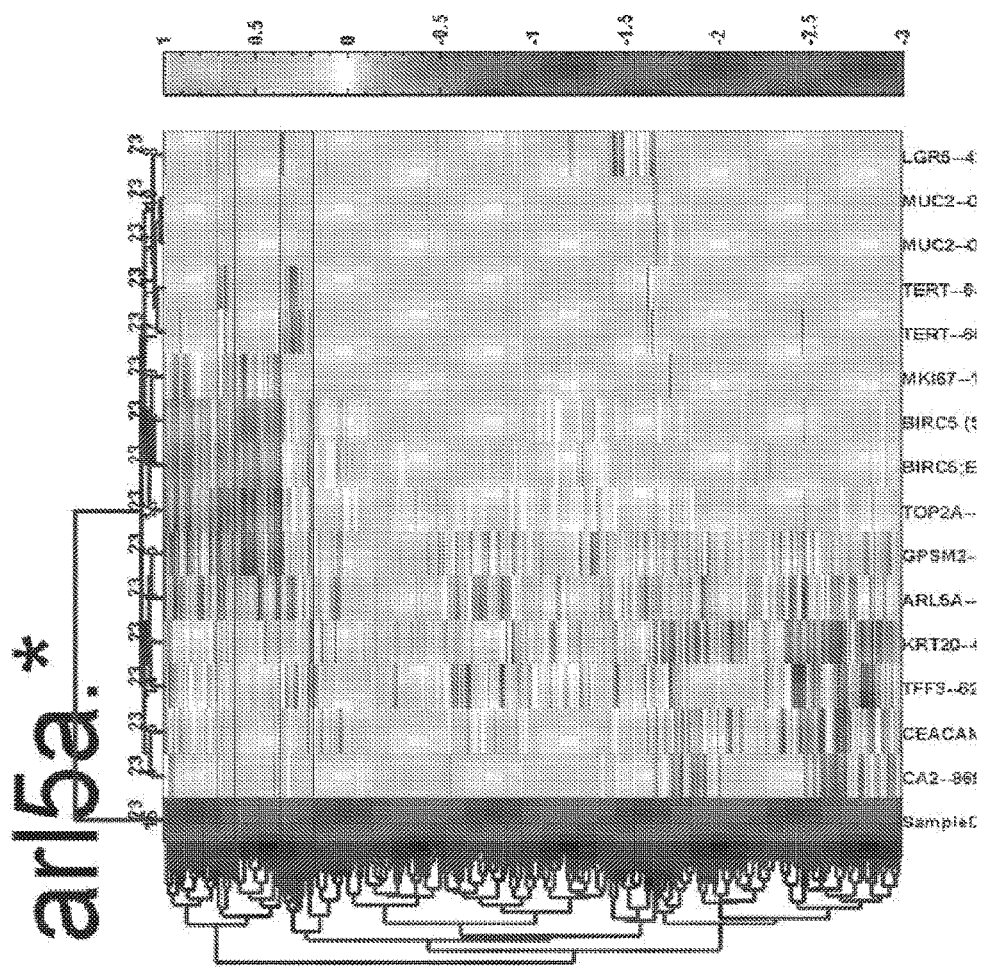
Figure 332:
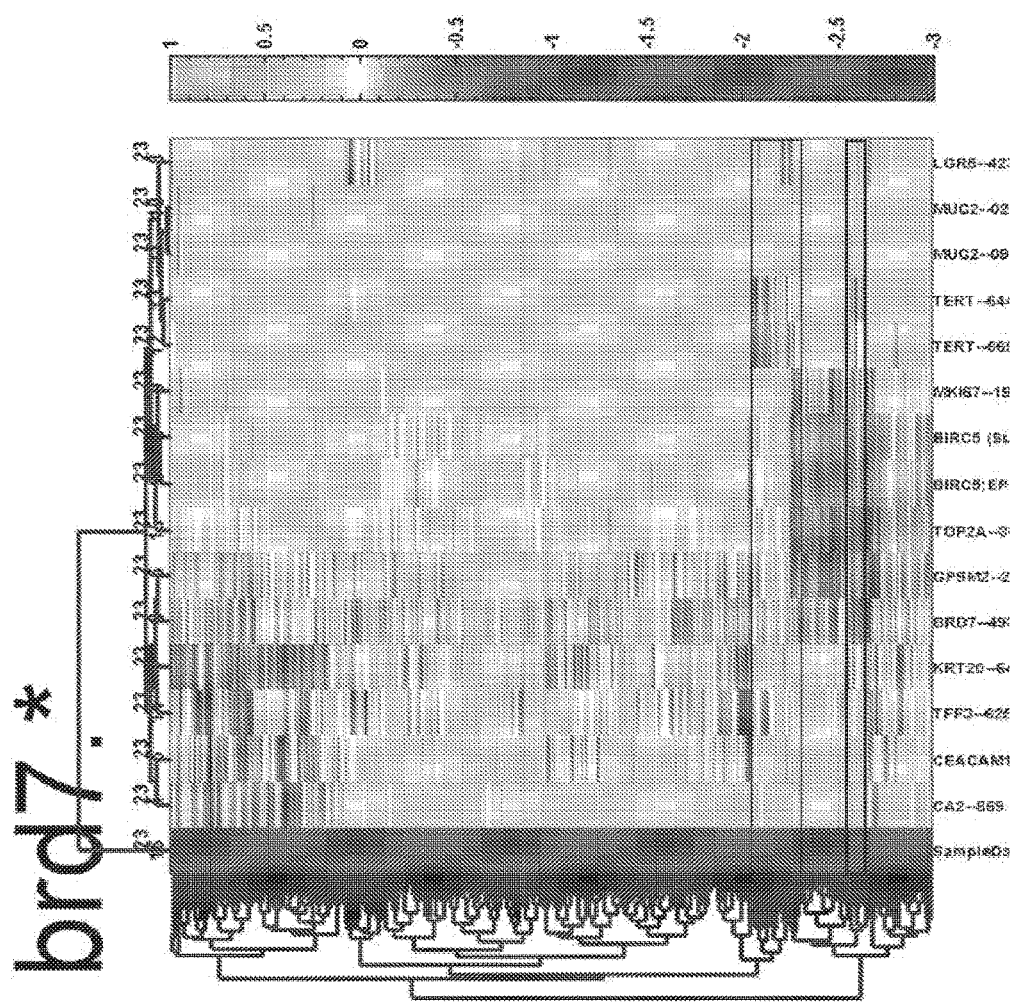
Figure 333:
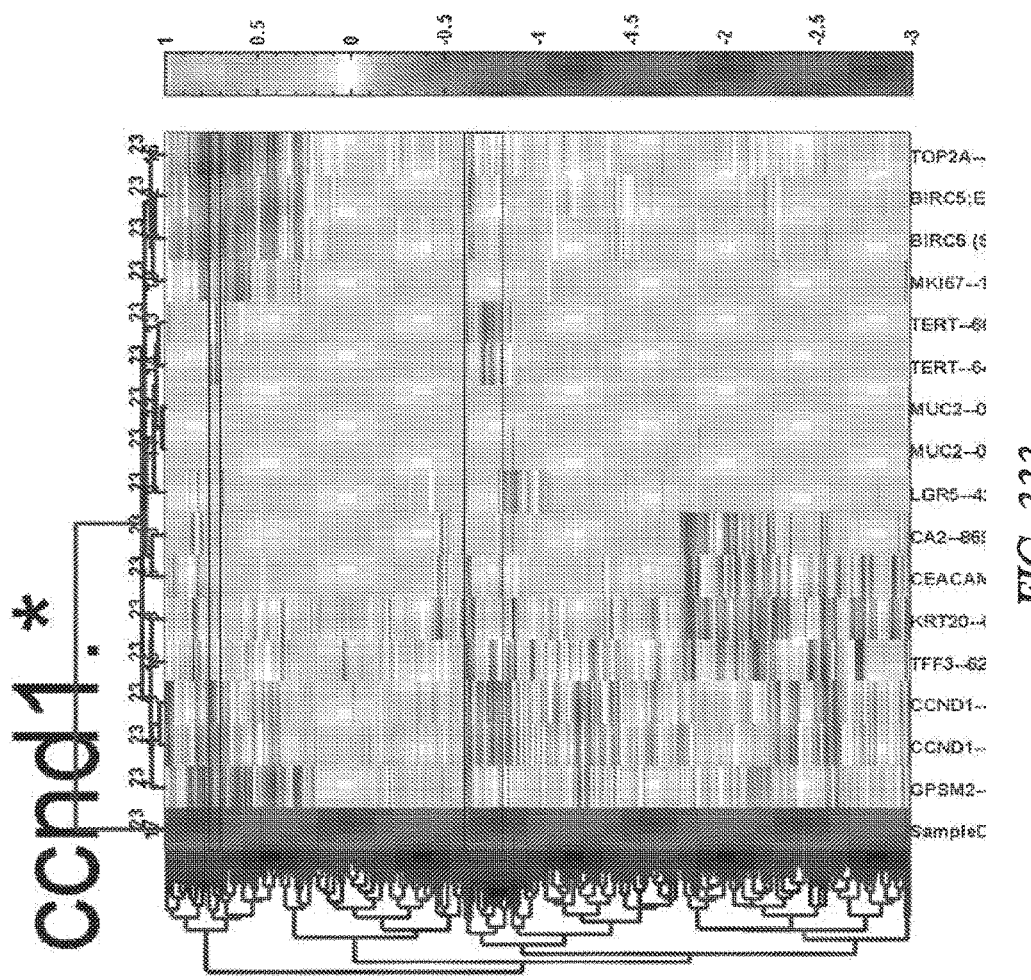
Figure 334:
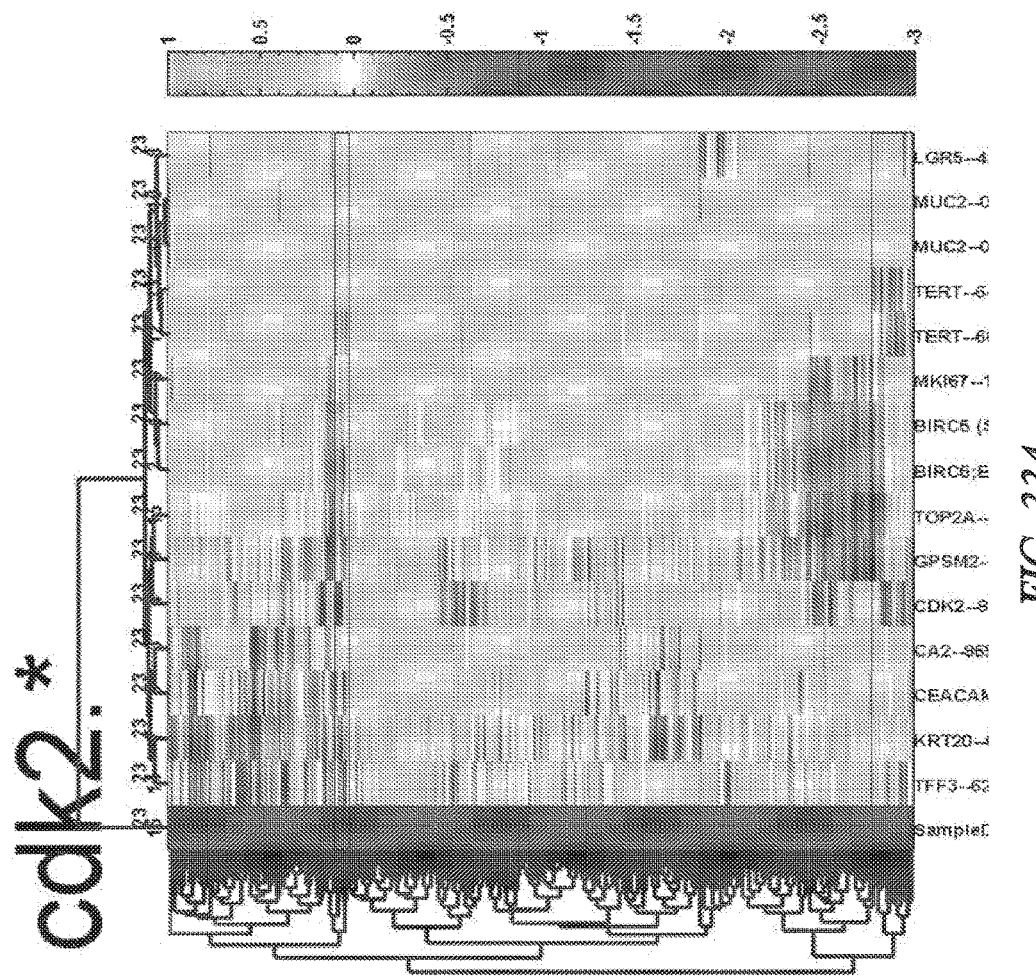
Figure 335:
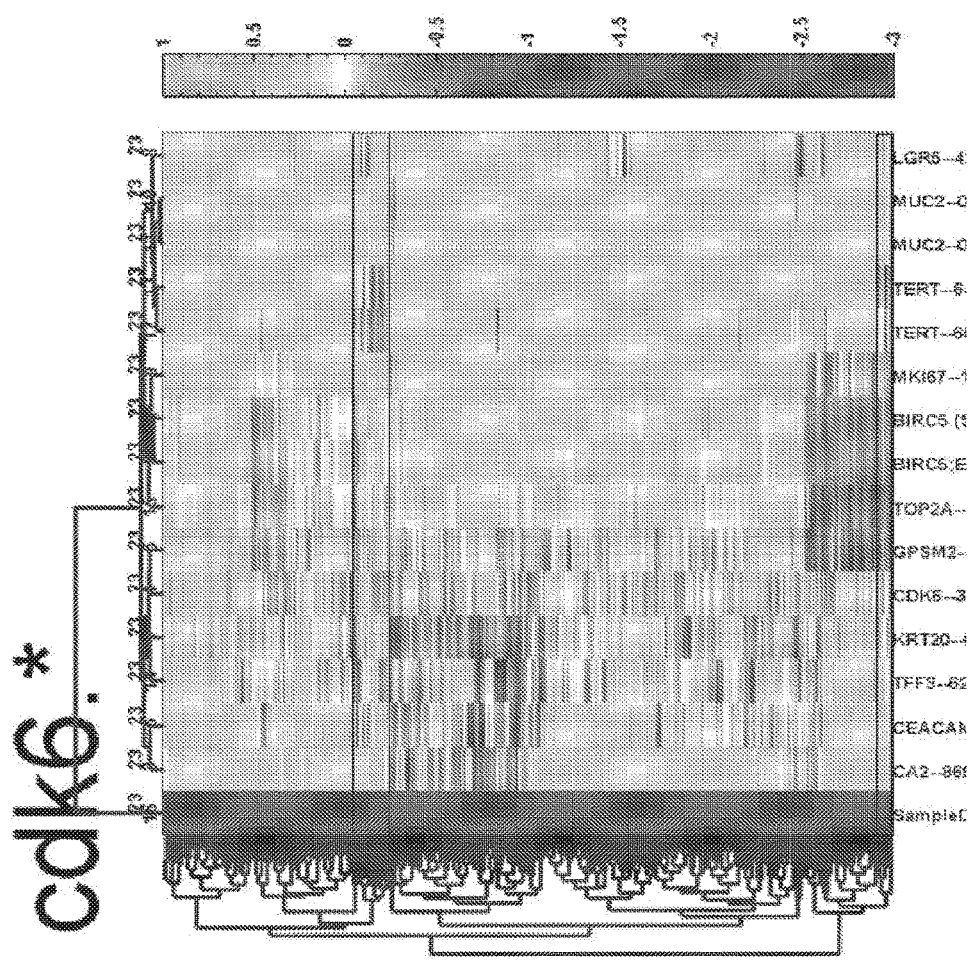
Figure 336:
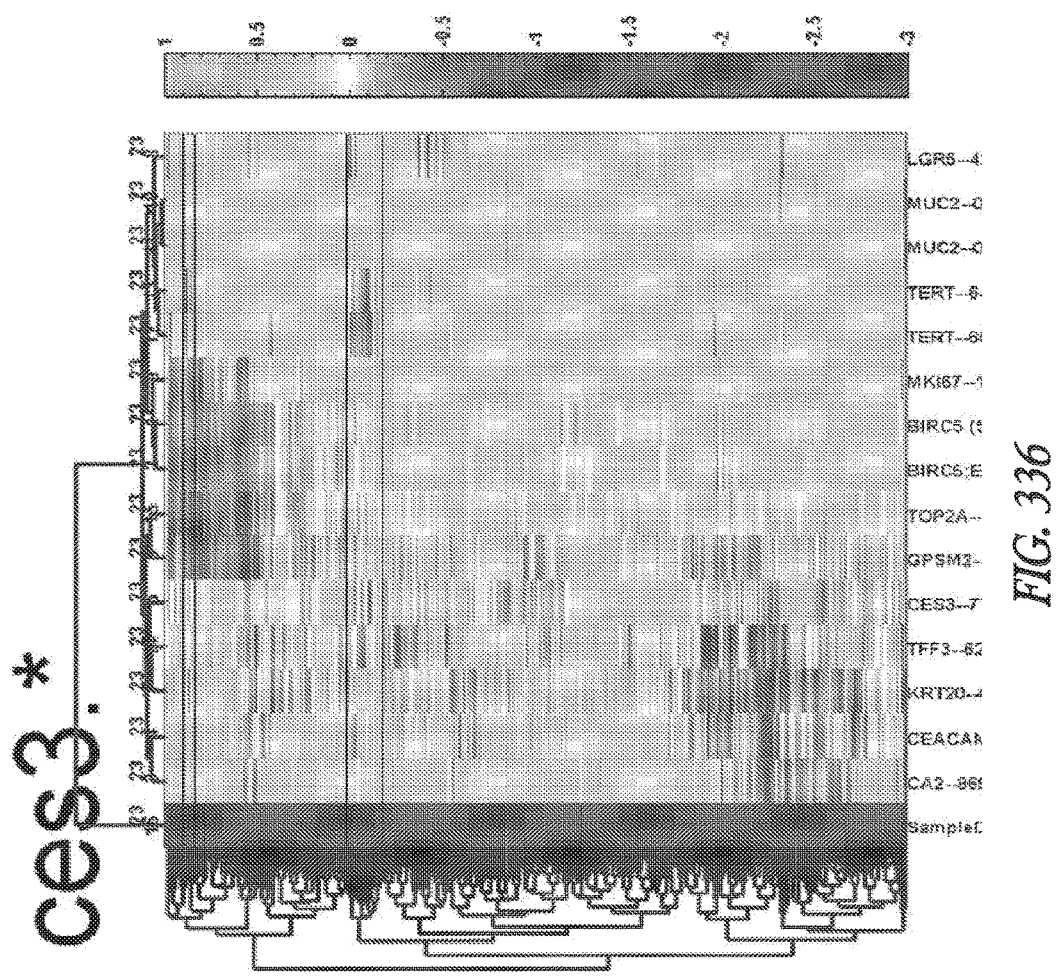
Figure 337:
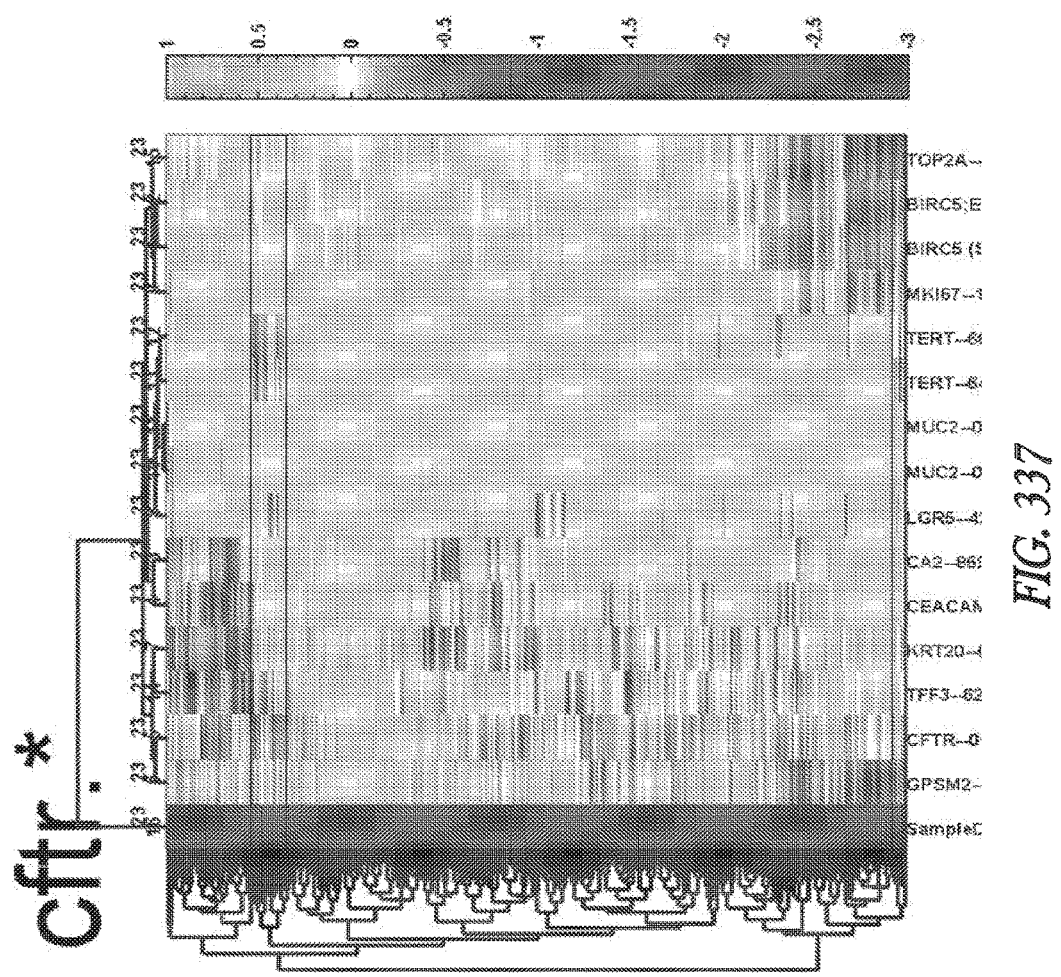
Figure 338:
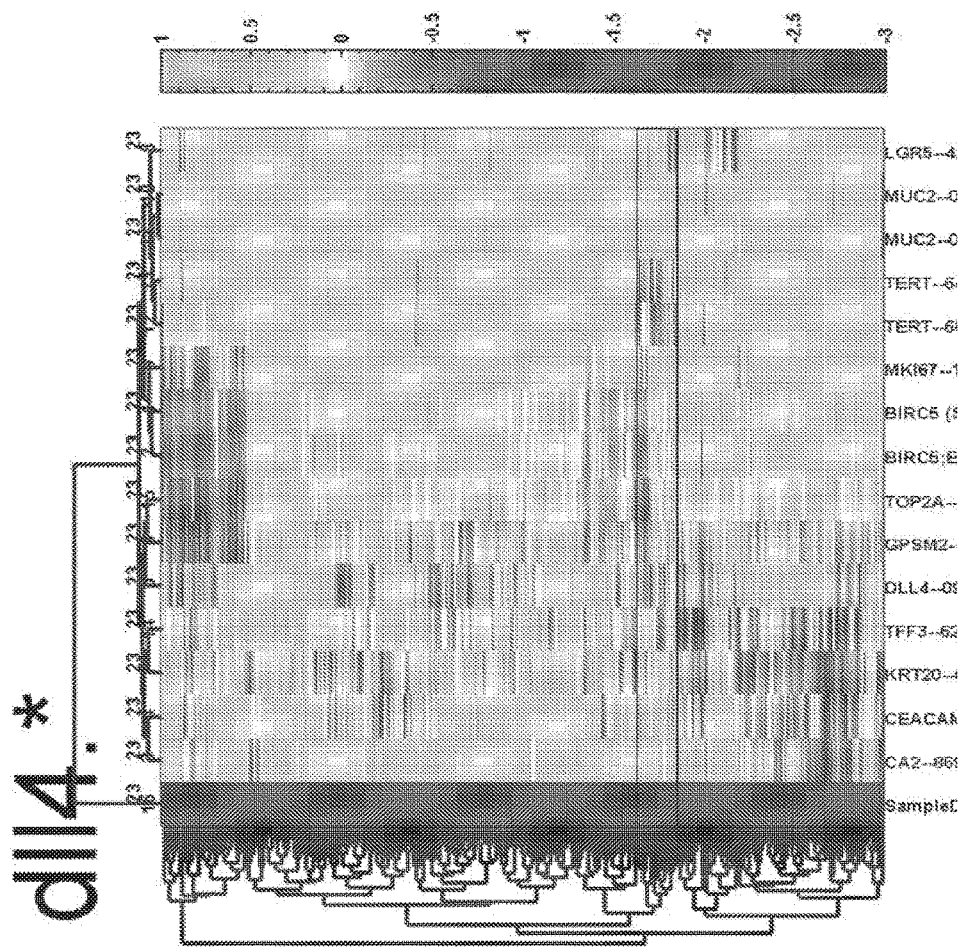
Figure 339:
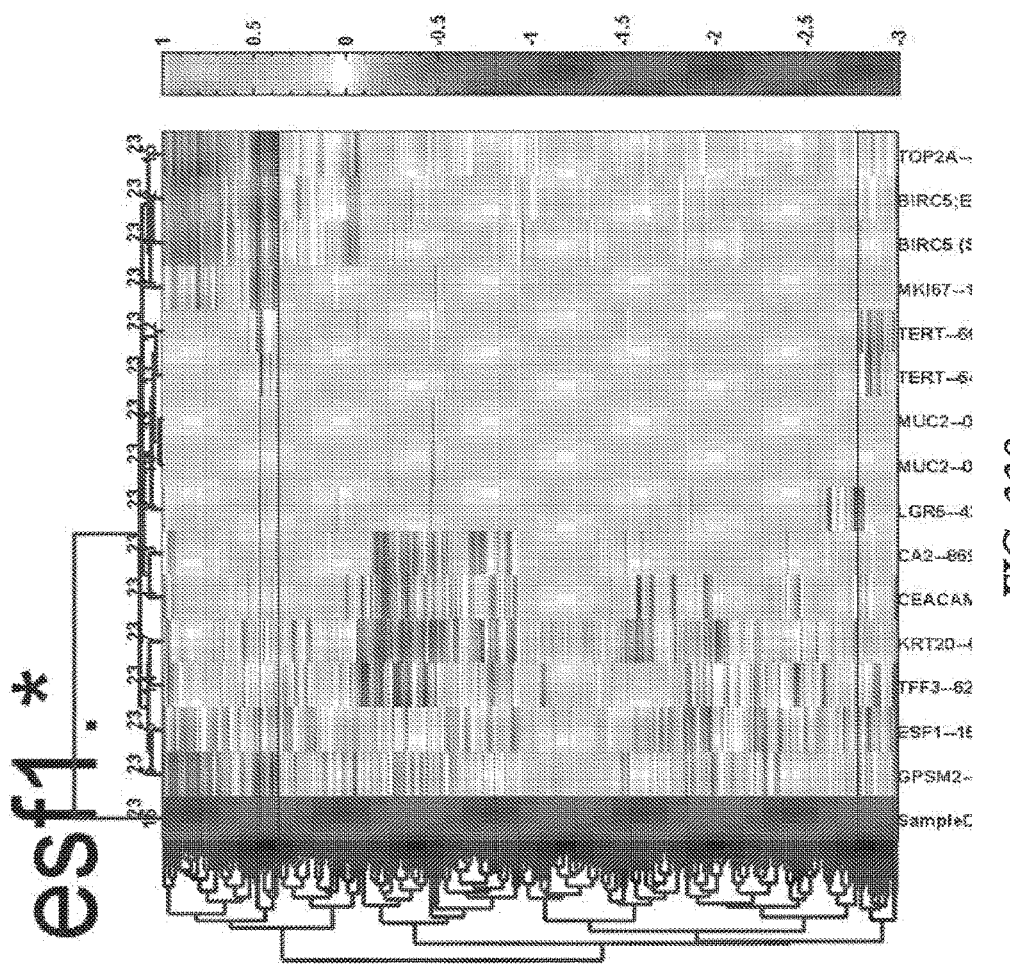
Figure 340:
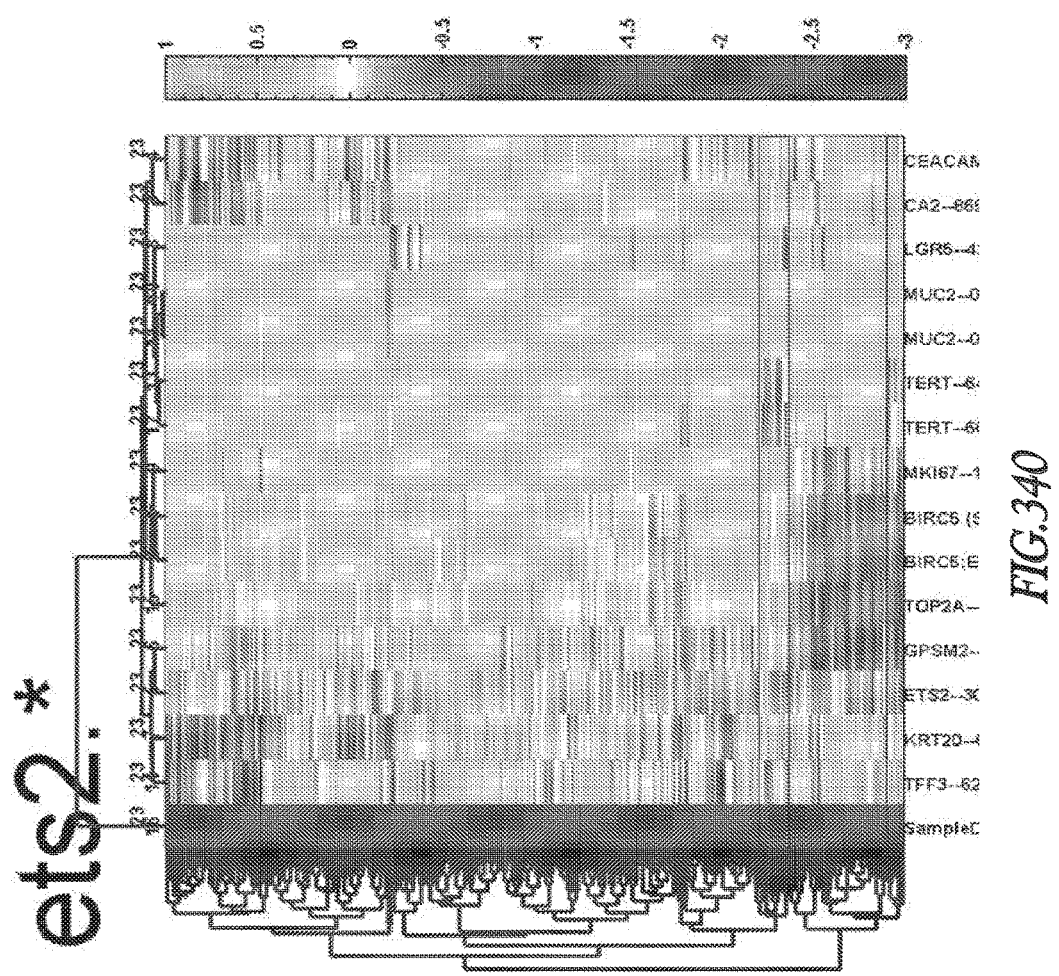
Figure 341:
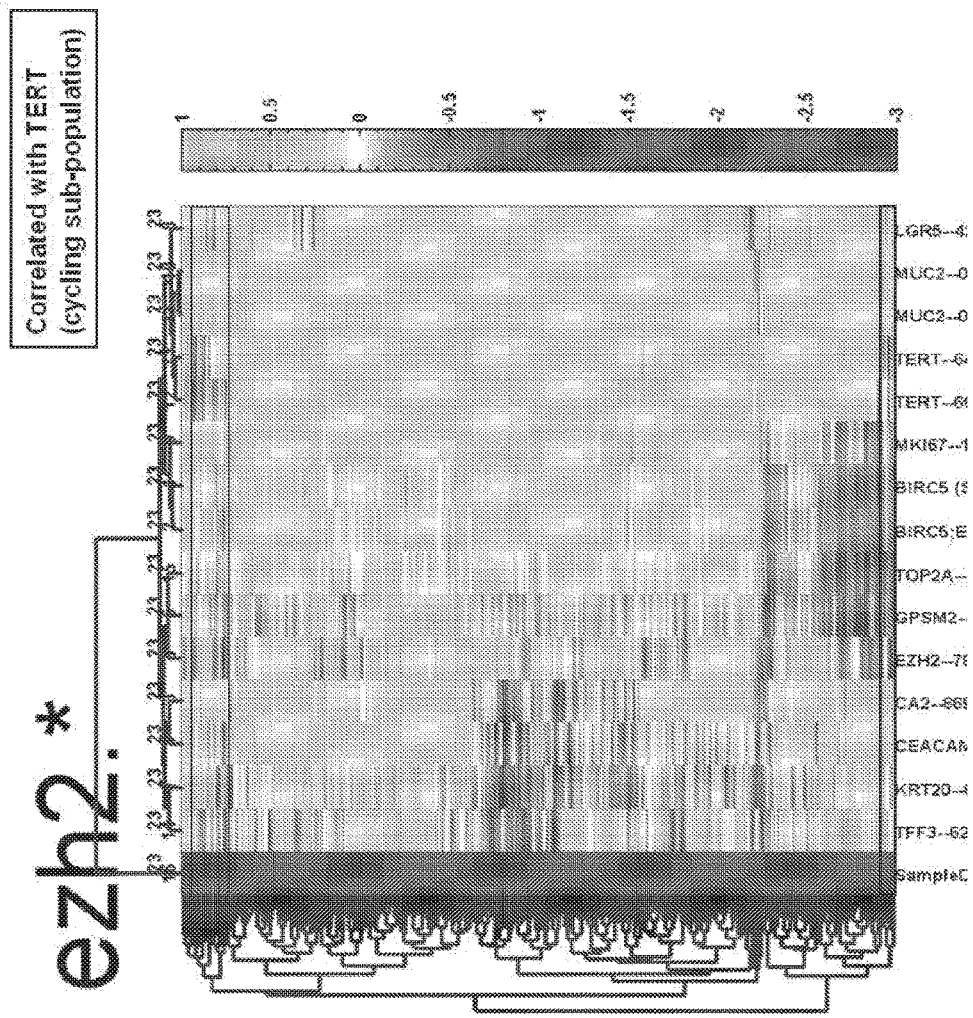
Figure 342:
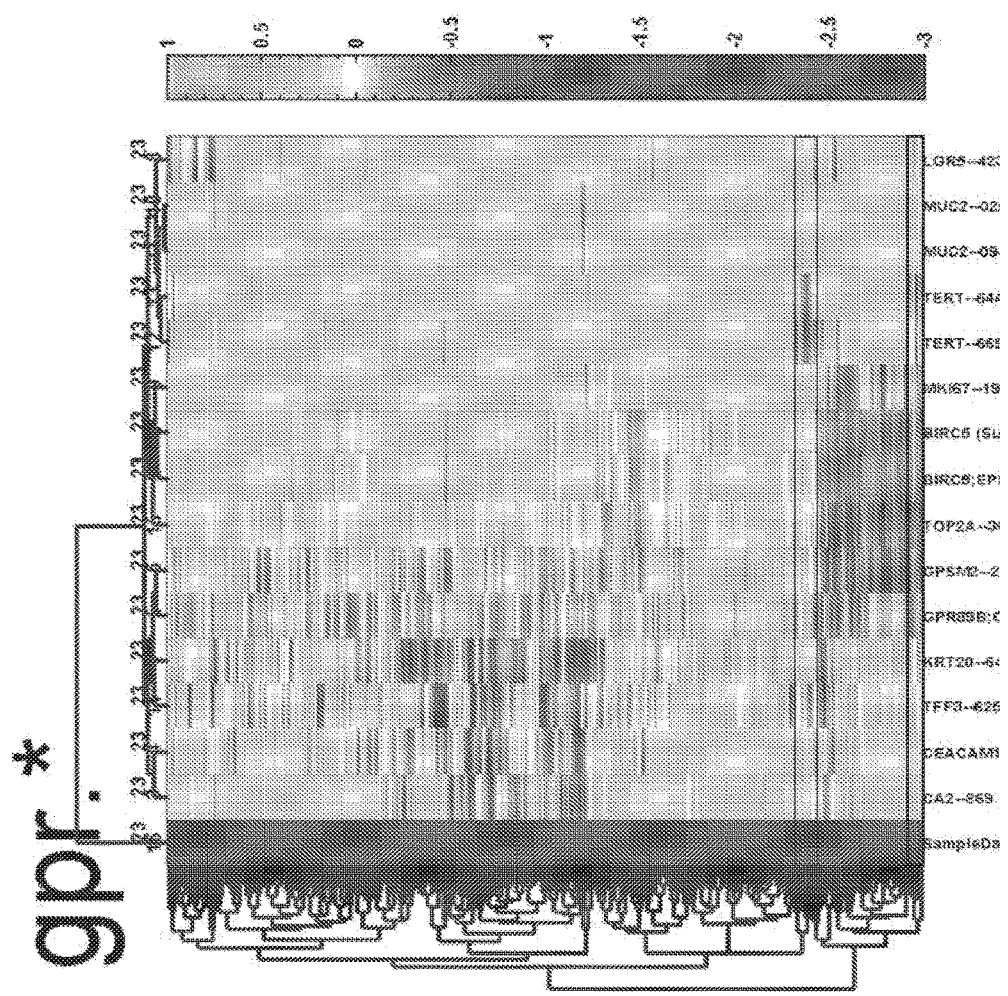
Figure 343:
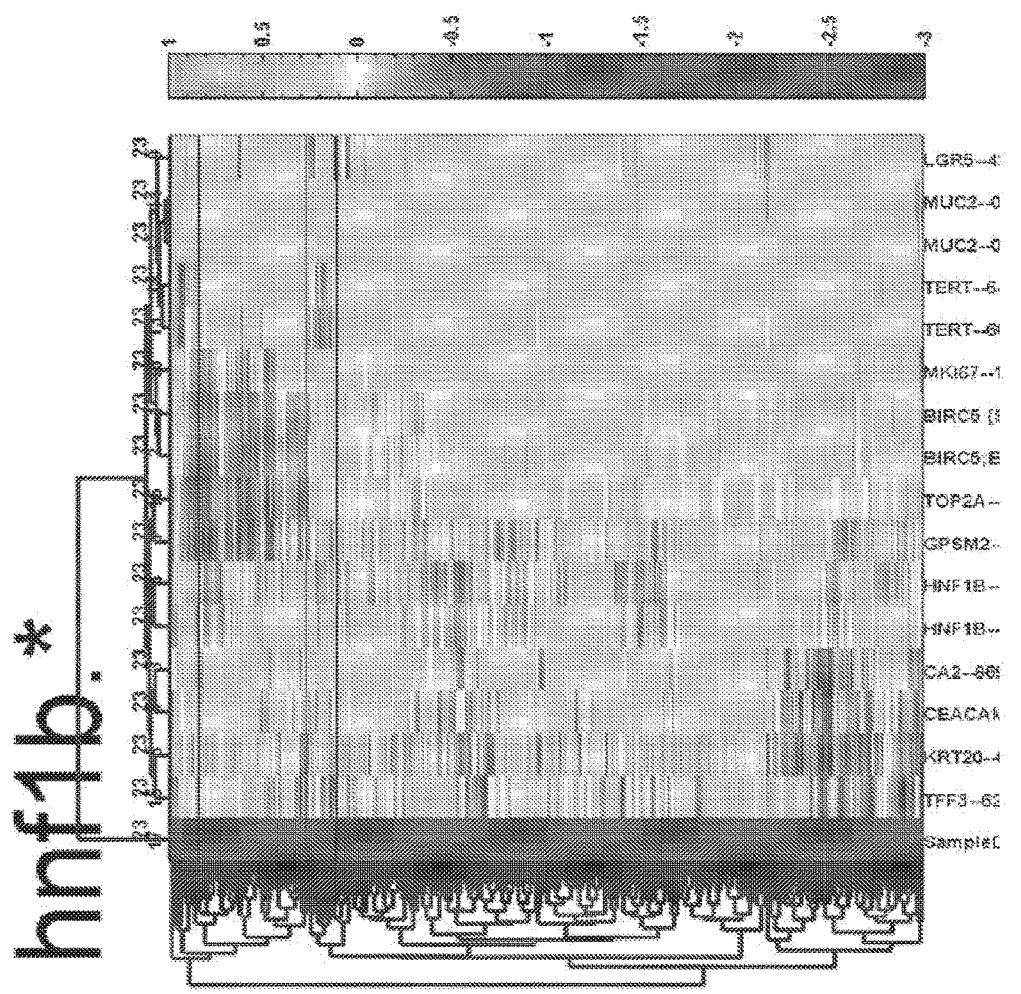
Figure 344:
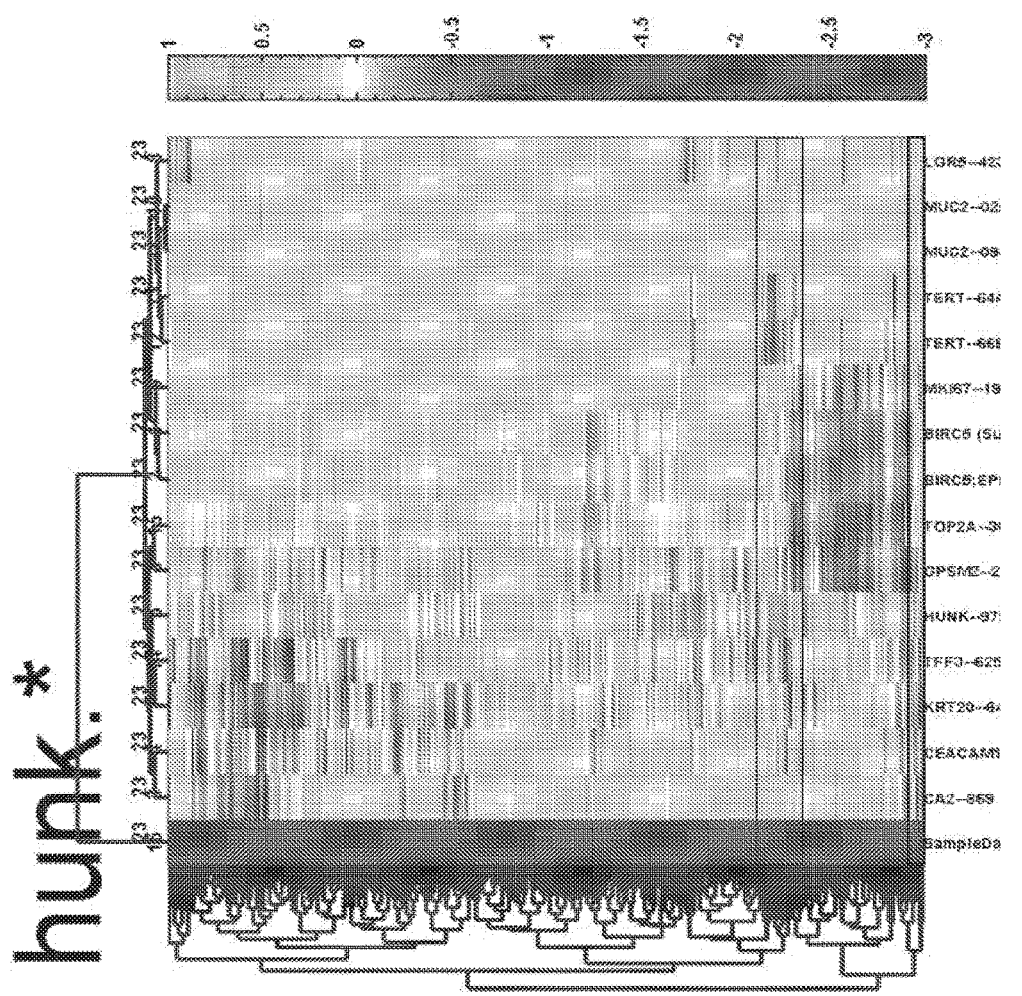
Figure 345:
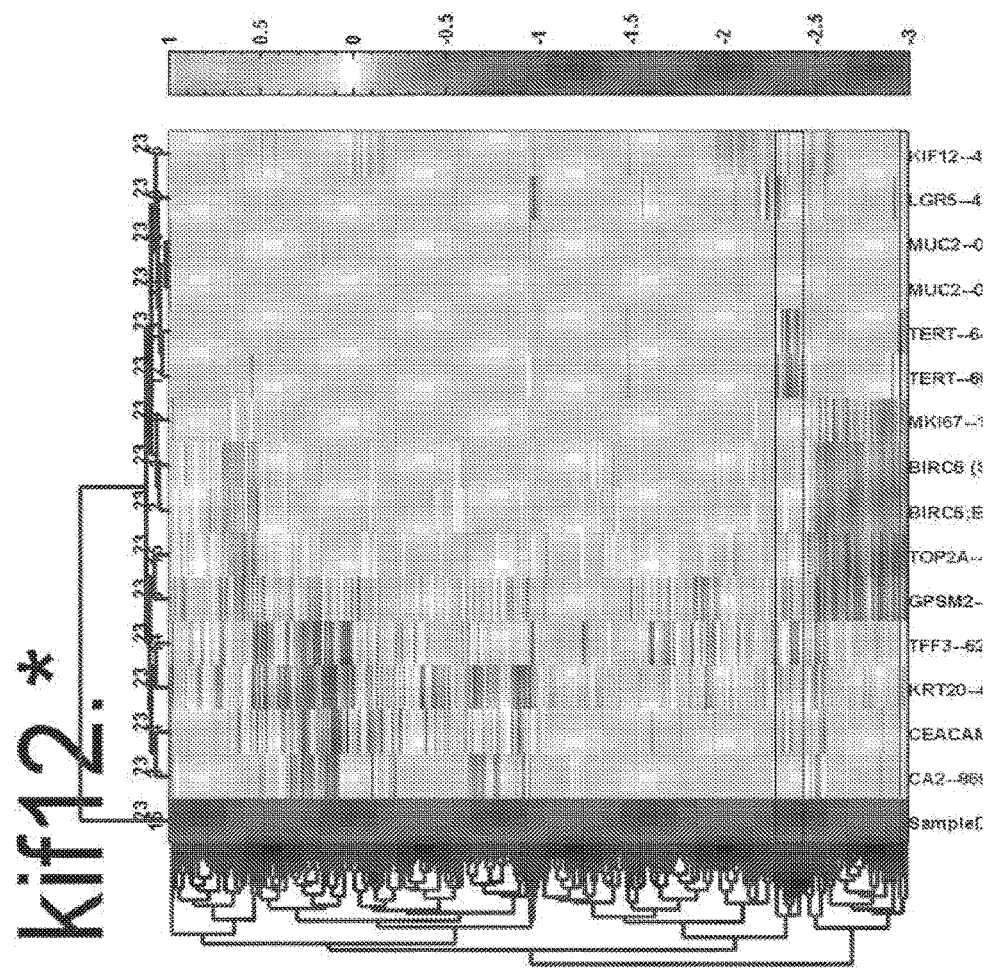
Figure 346:
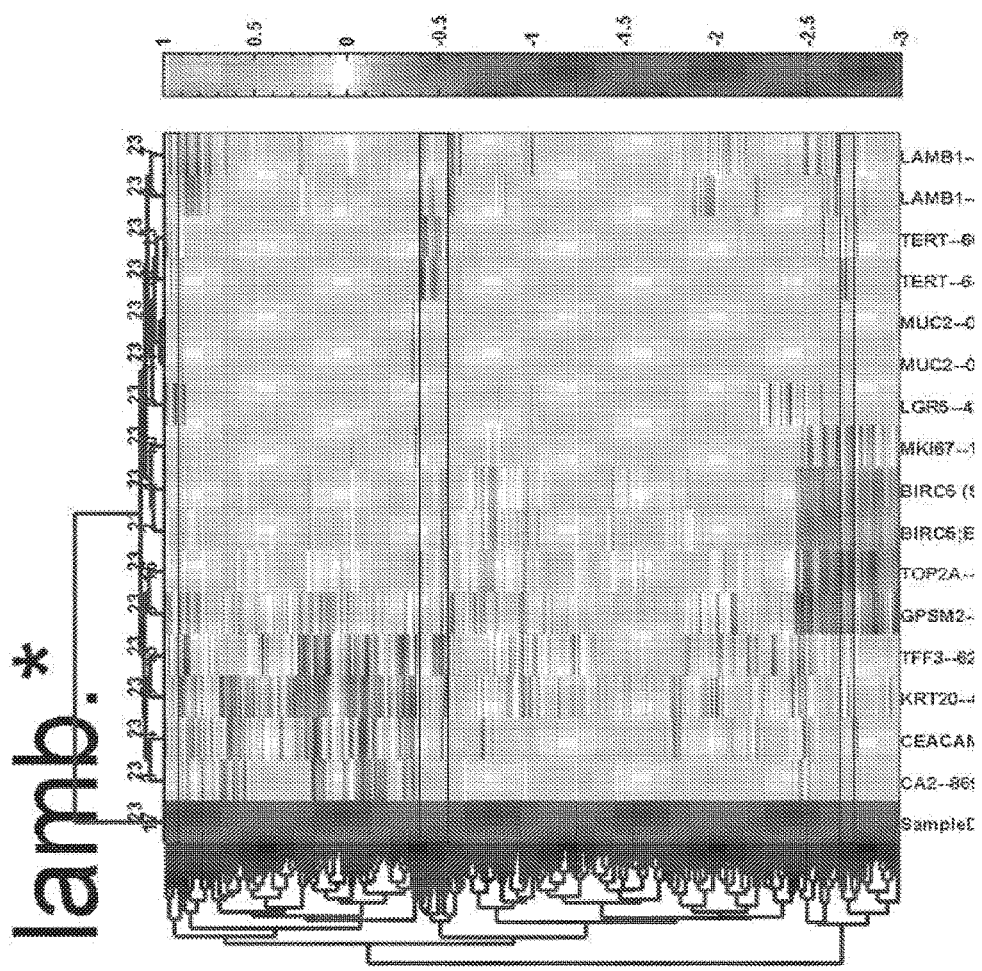
Figure 347:
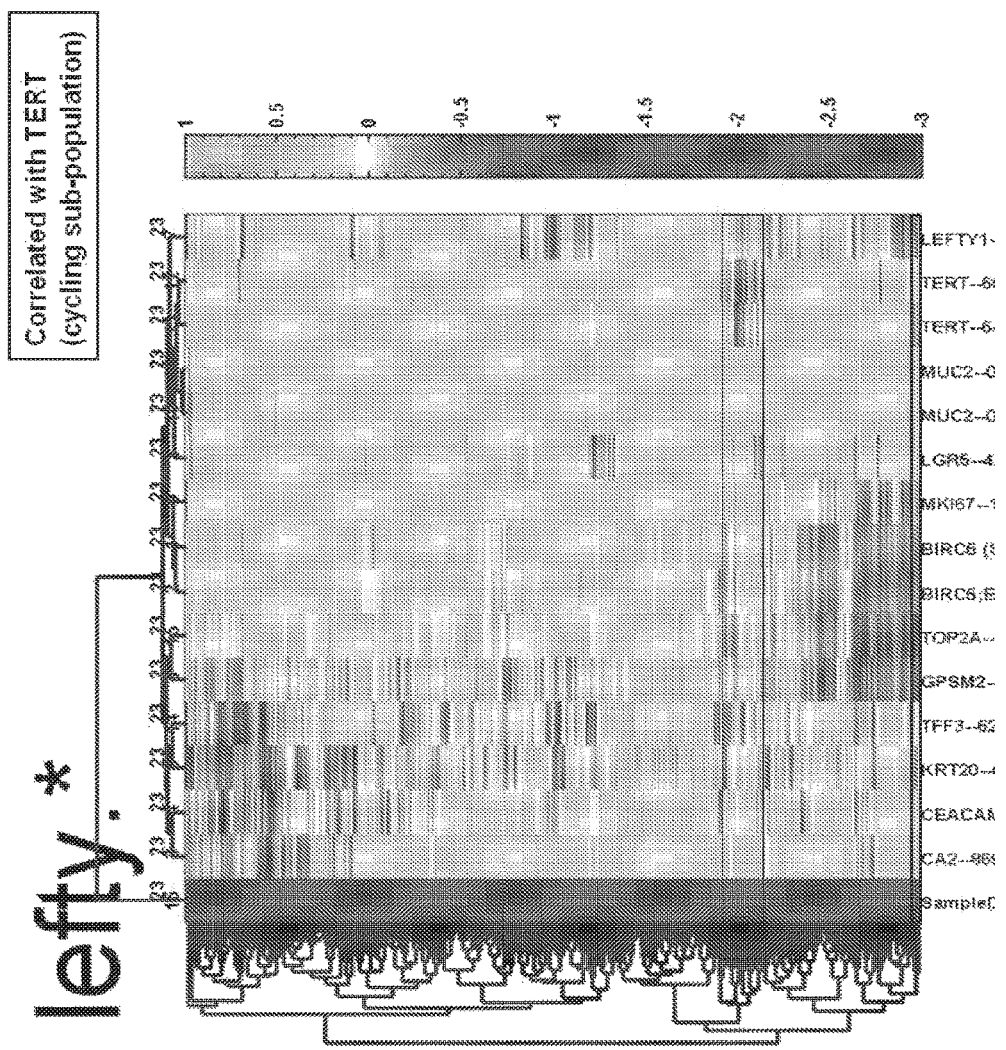
Figure 348:
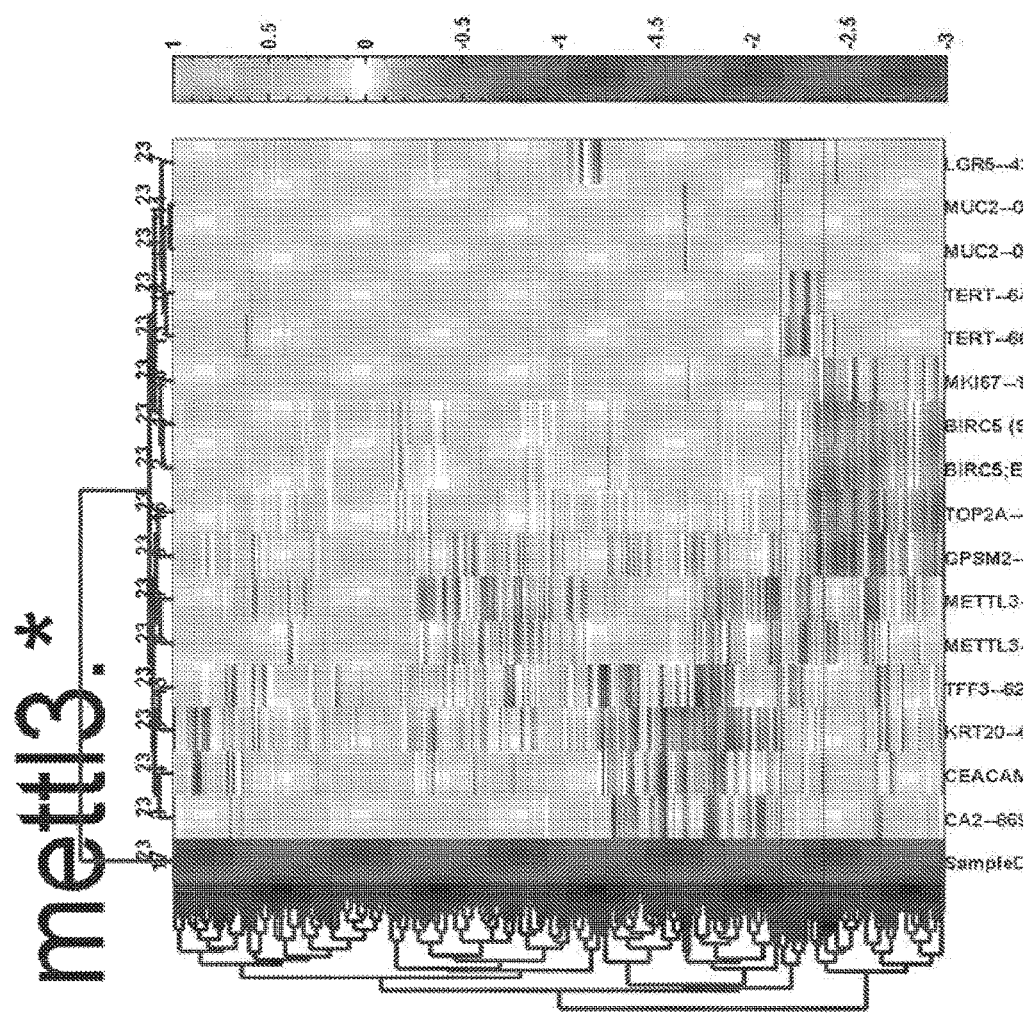
Figure 349:
Figure 350:
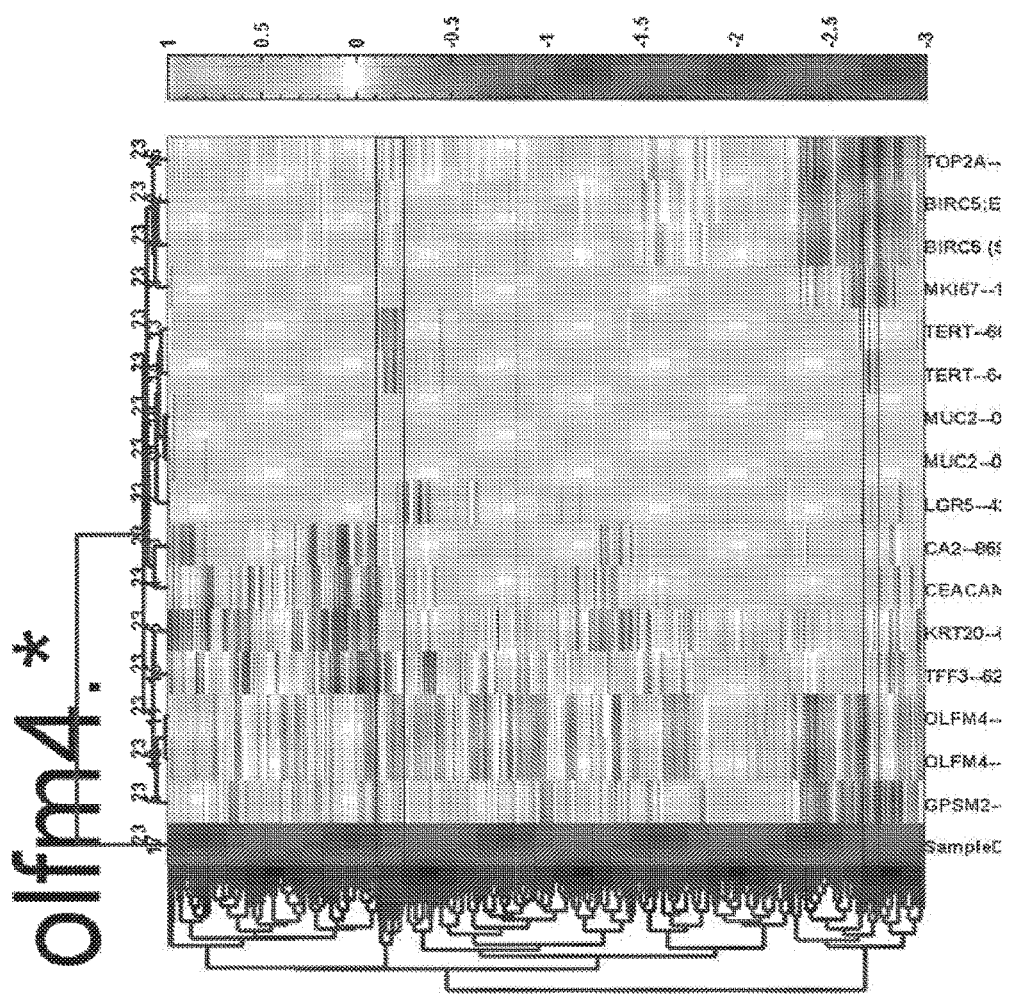
Figure 351:
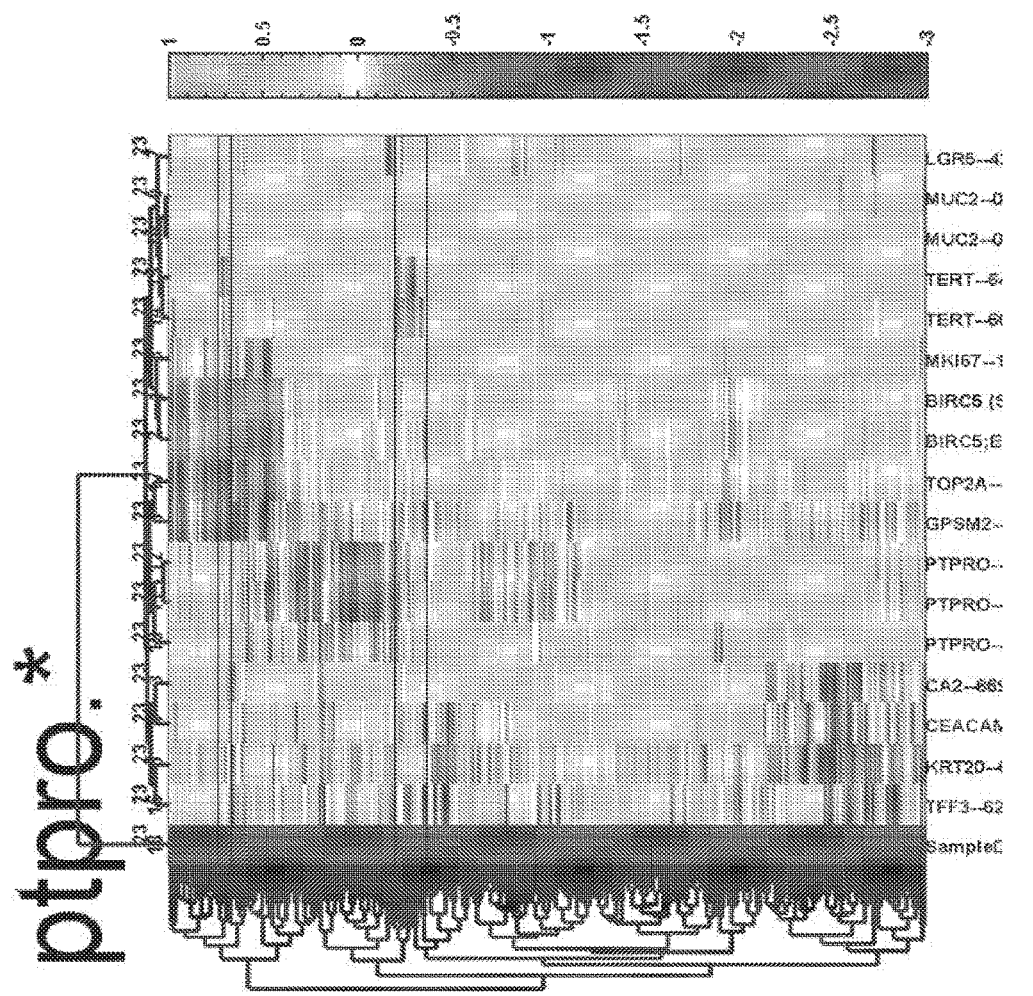
Figure 352:
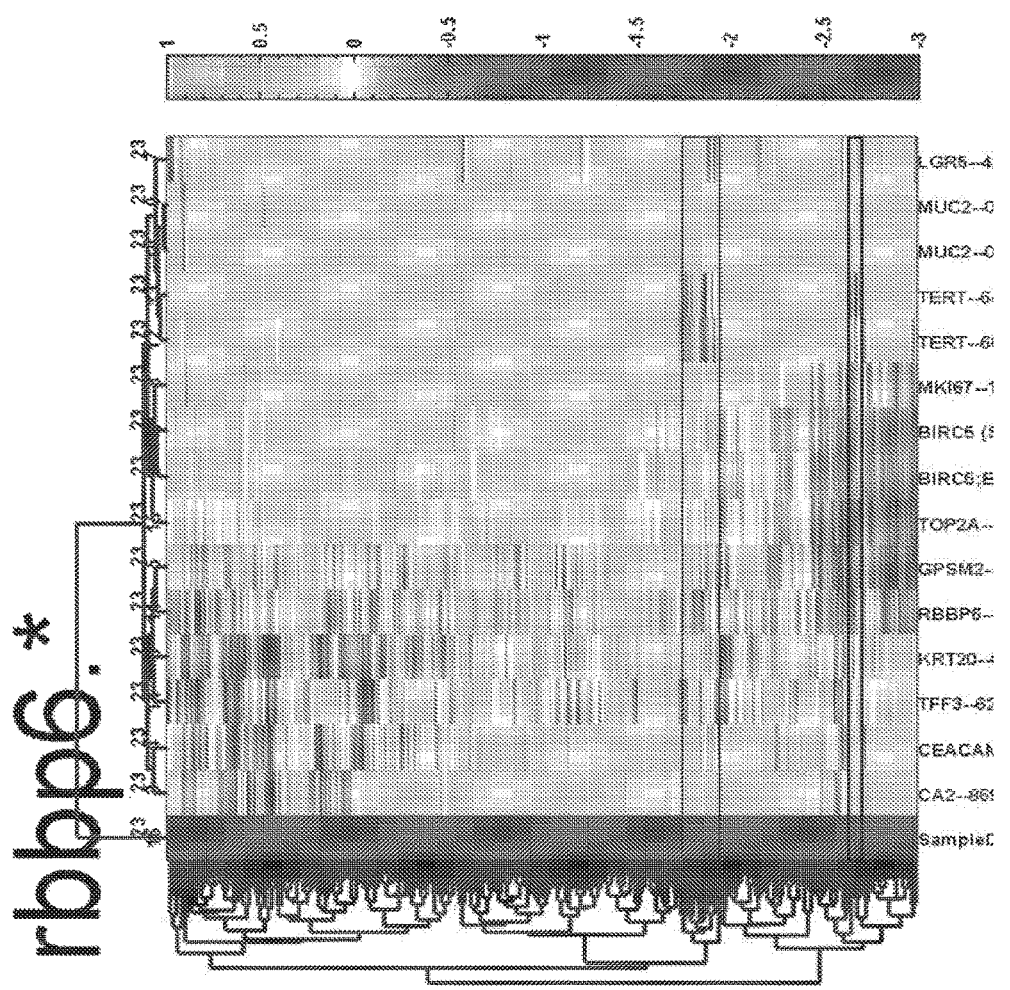
Figure 353:
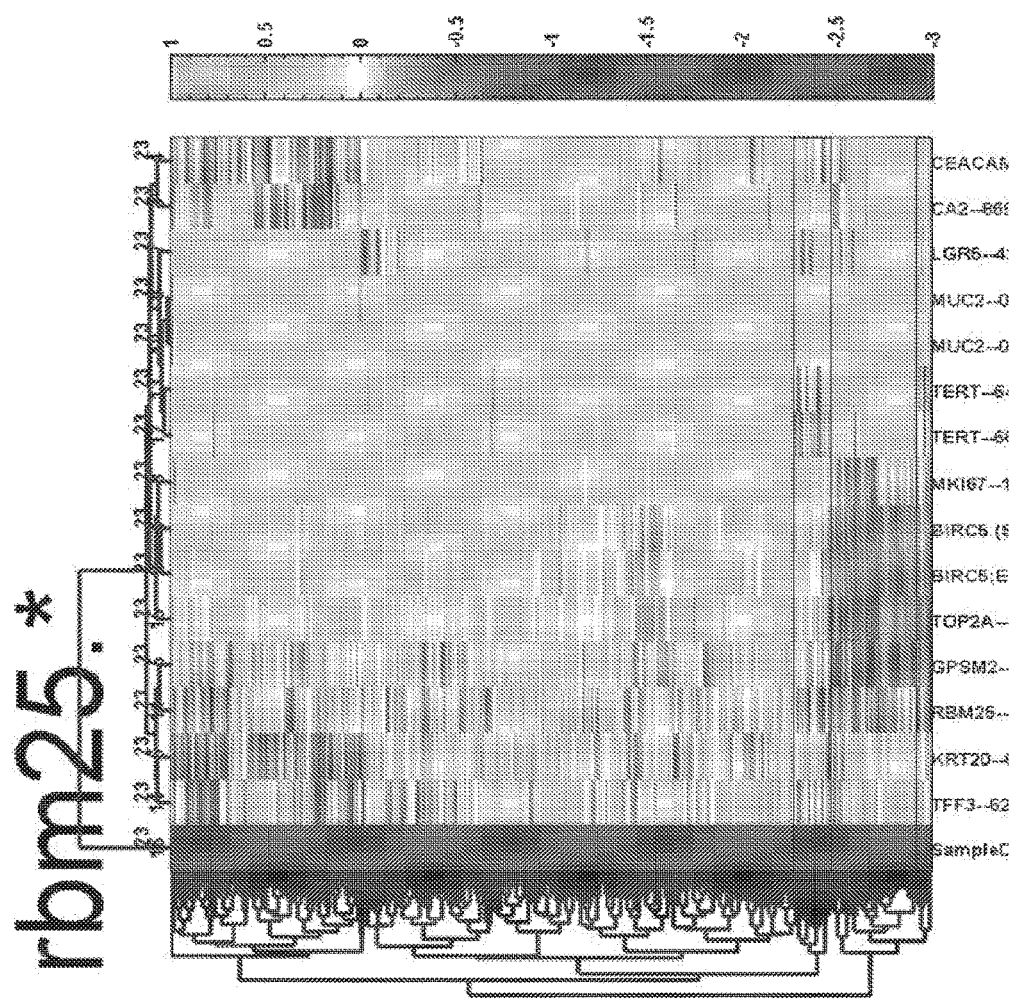
Figure 354:
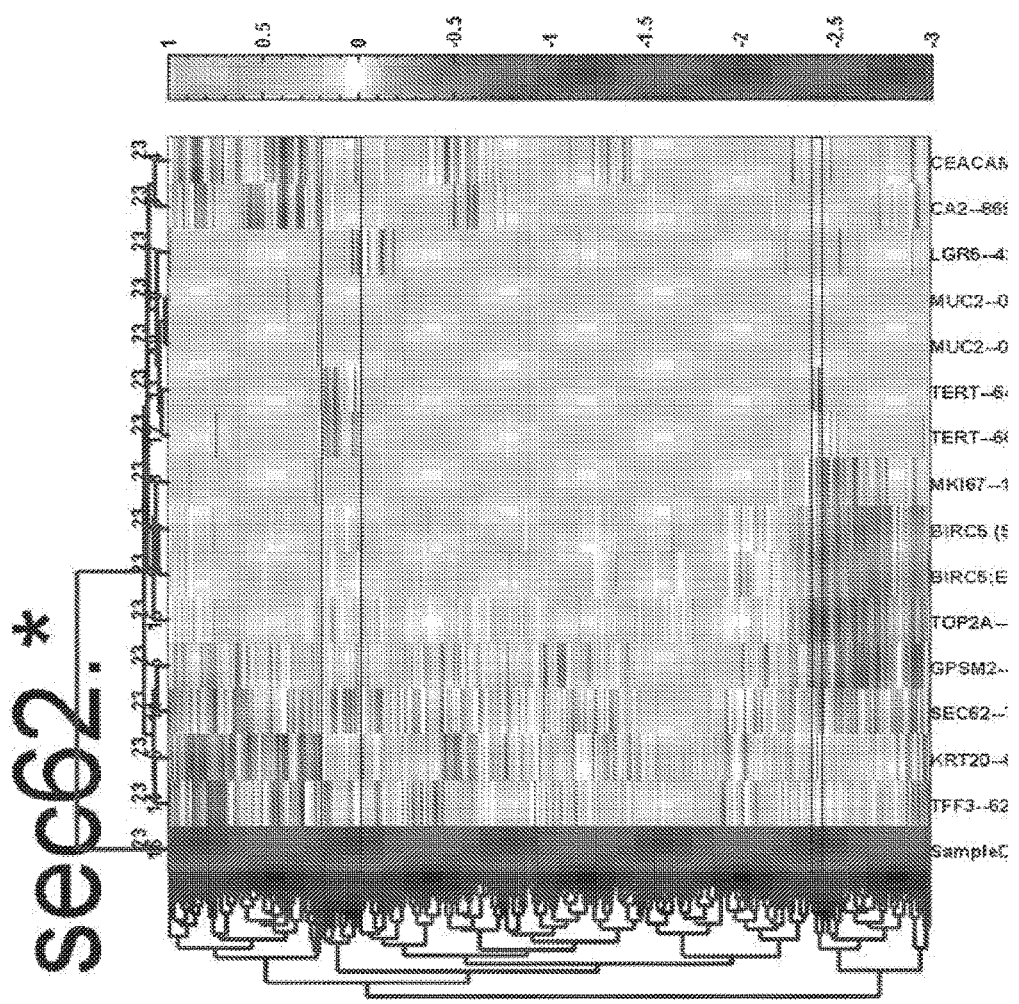
Figure 355:
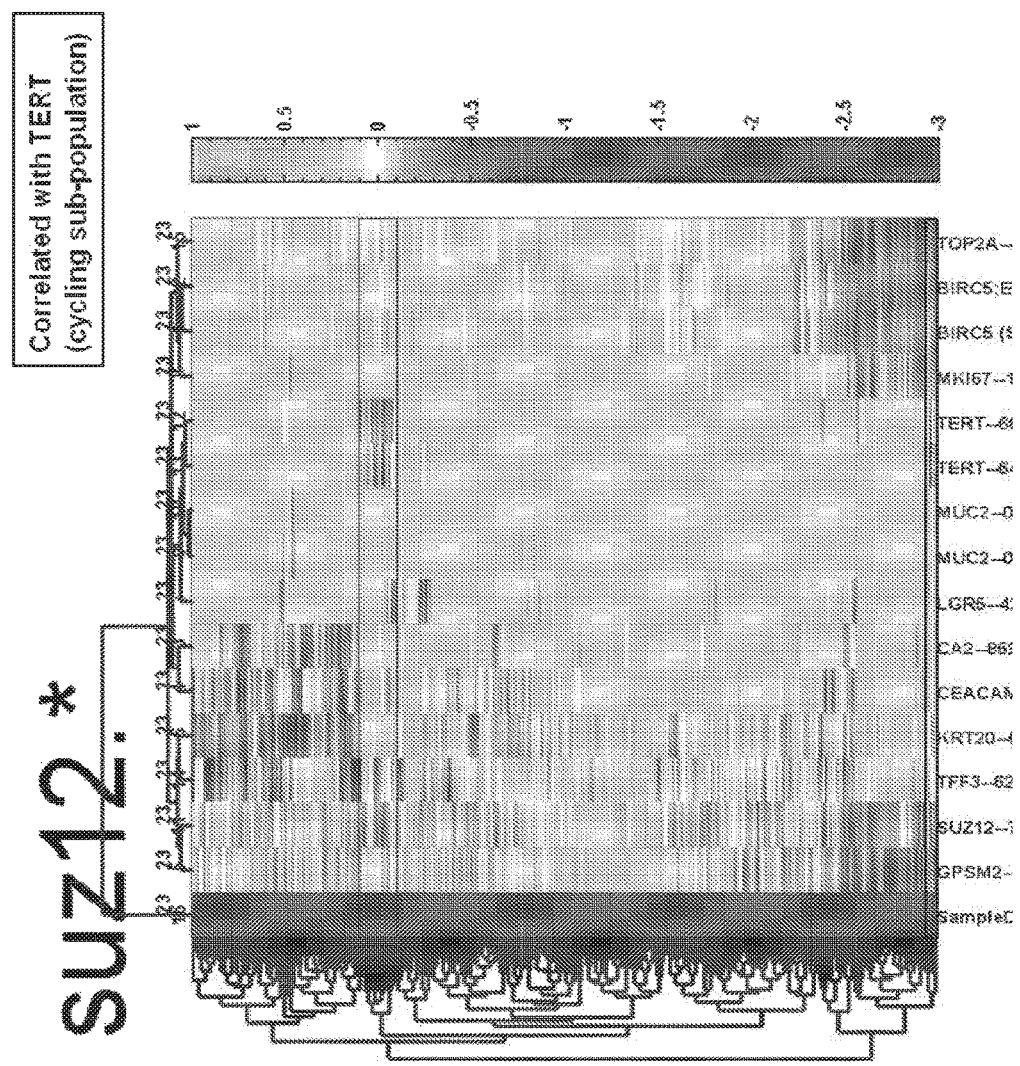
Figure 356:
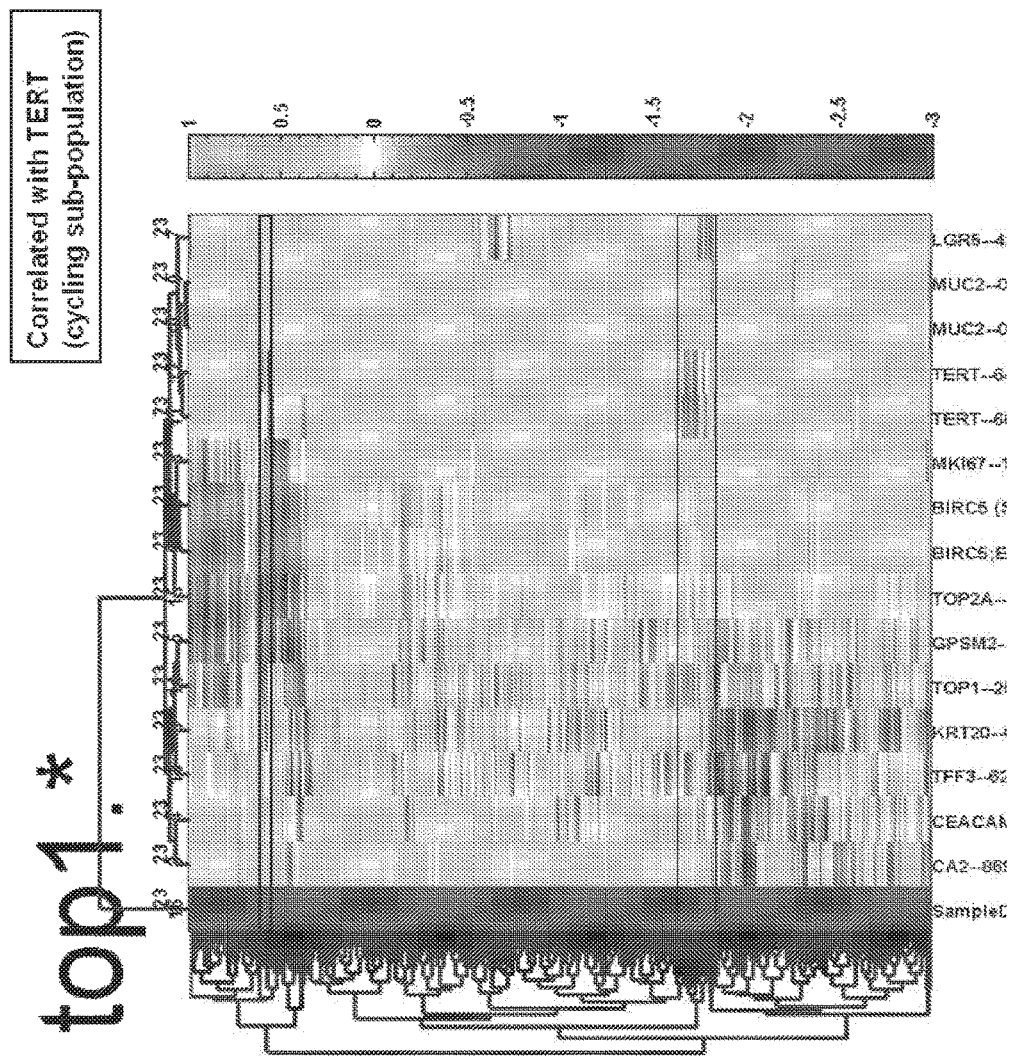
Figure 357:
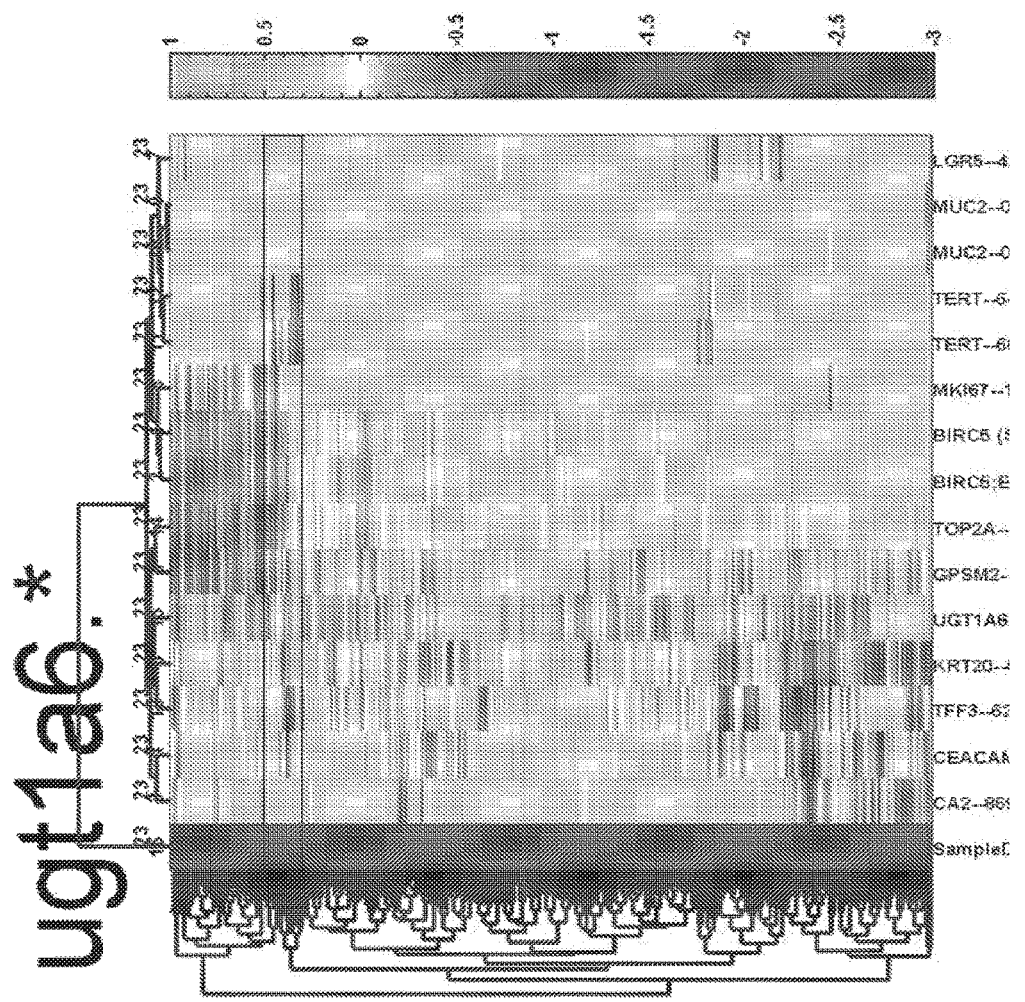
Figure 358:
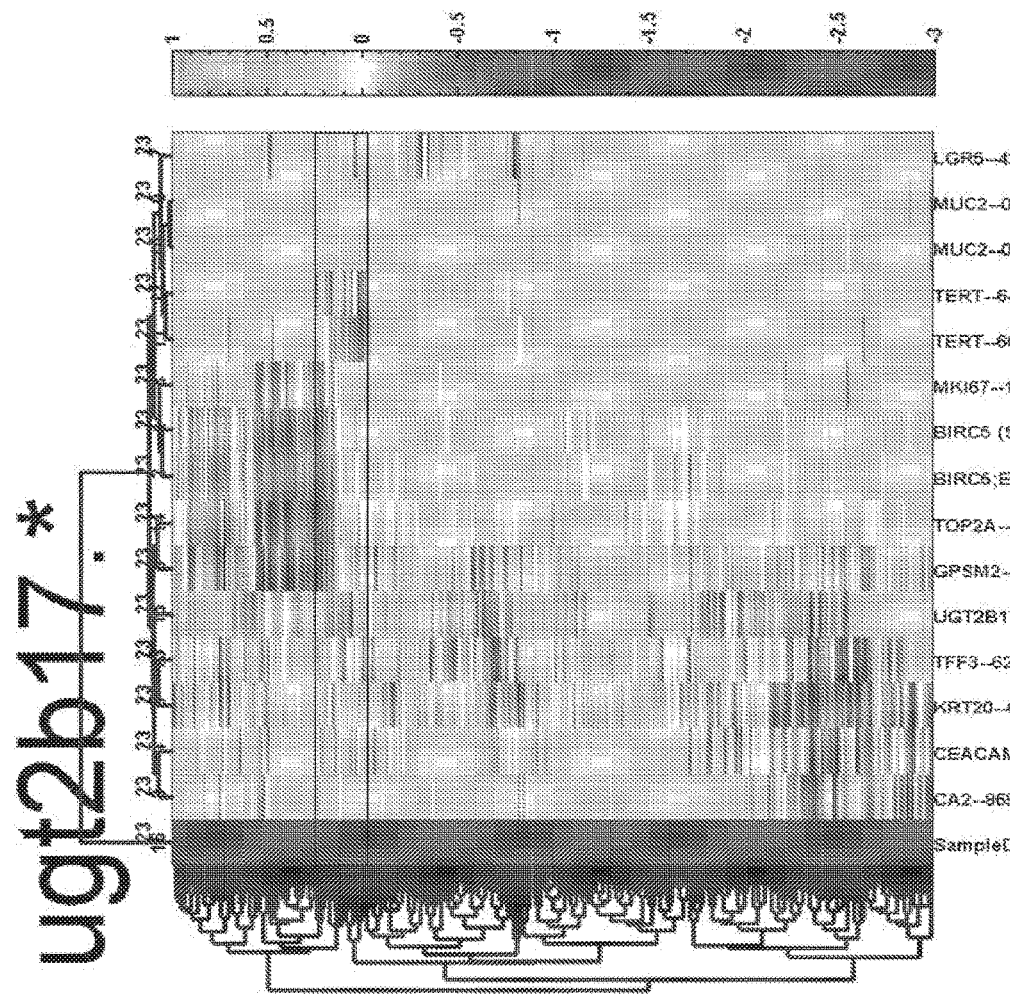
Figure 359:
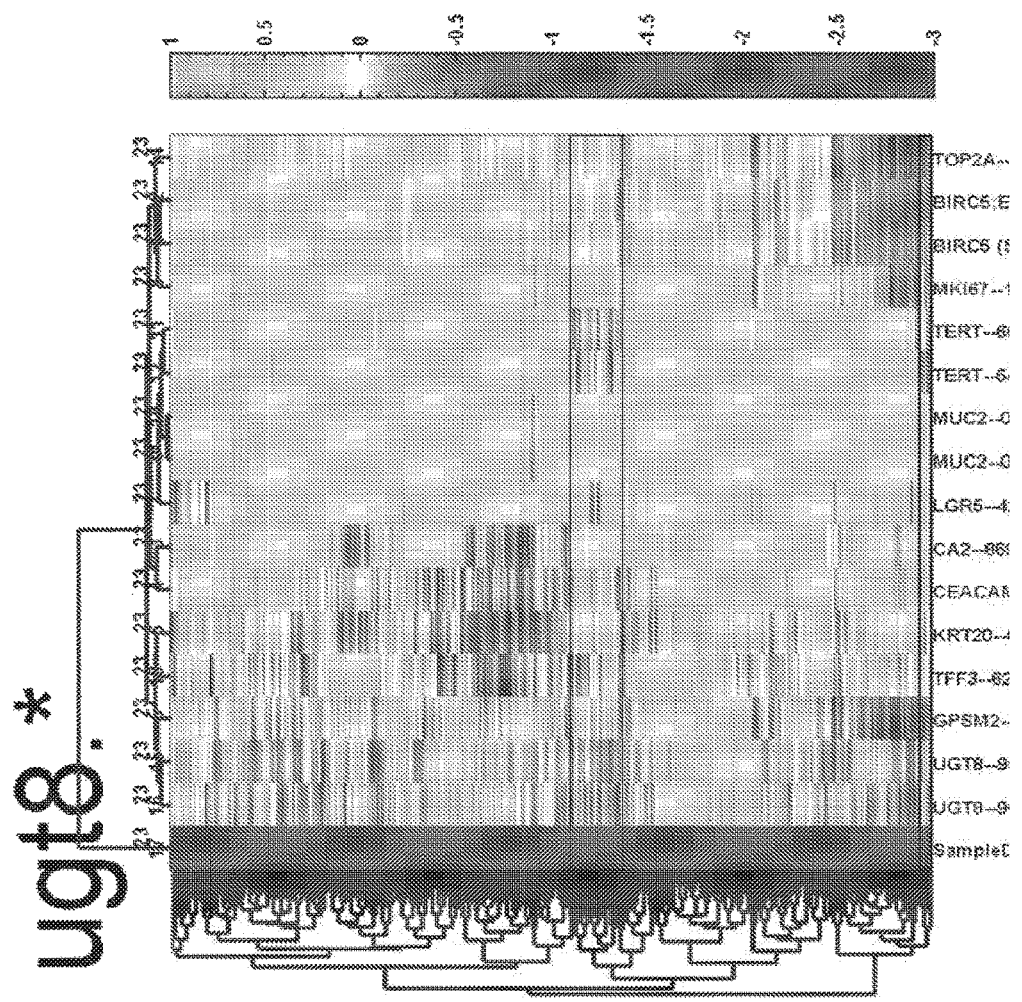
Figure 360:
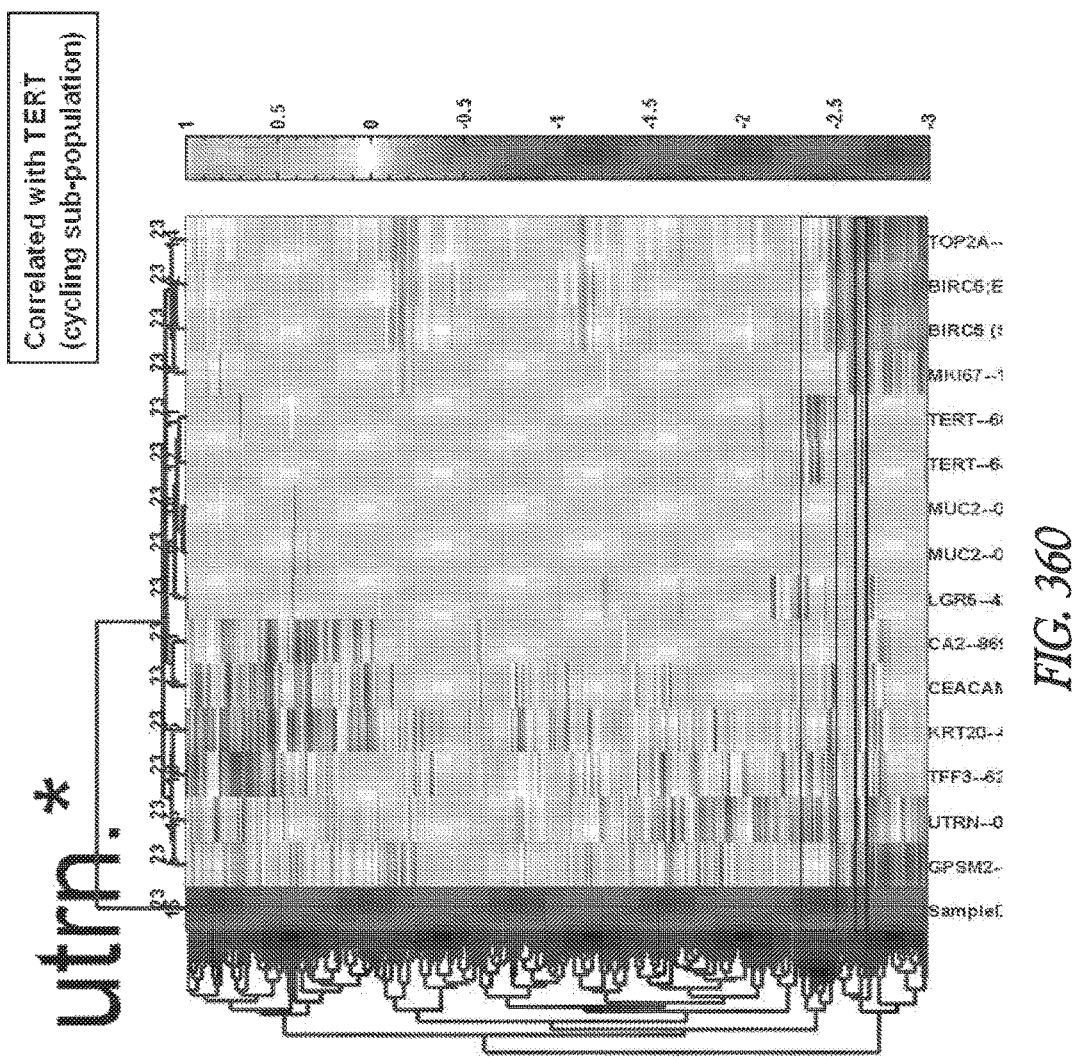
Figure 361:
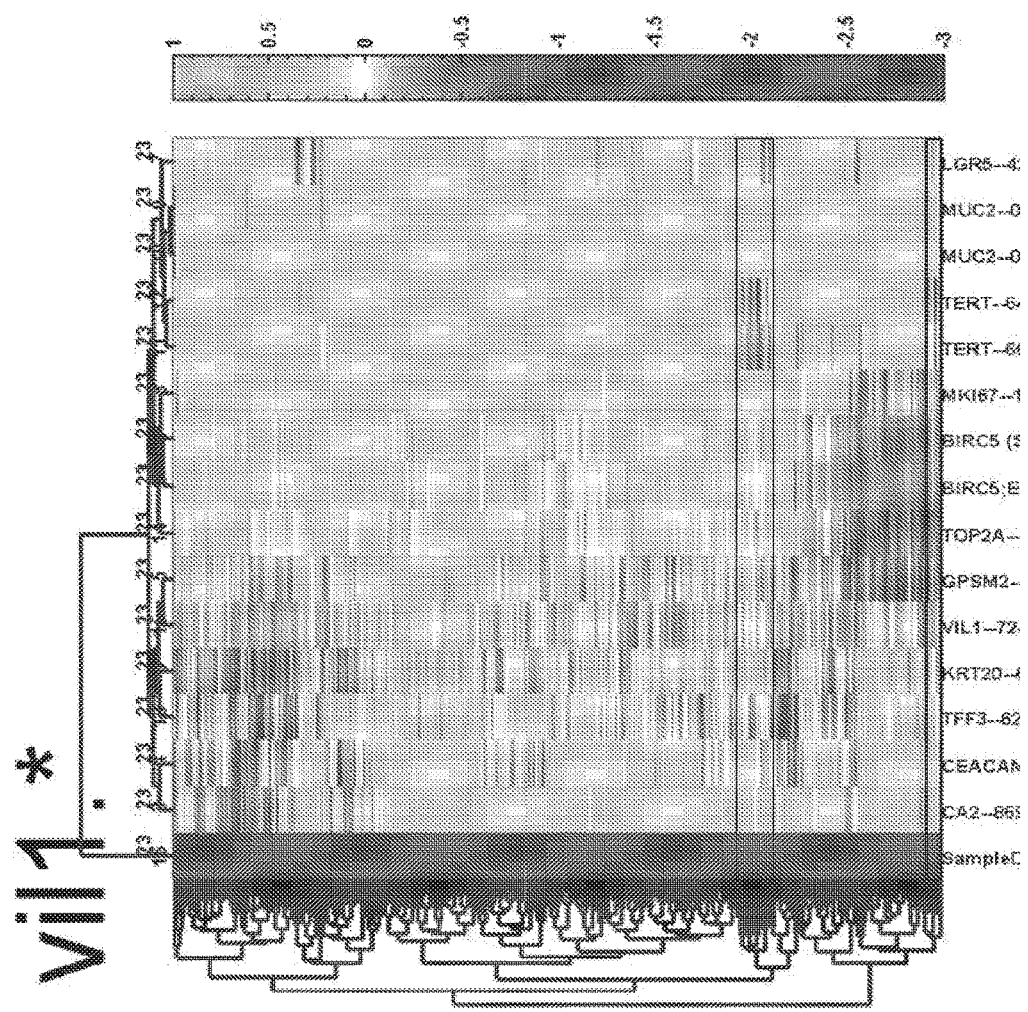

FIG. 290 EZH2 expression in relation to TERT expression.
FIG. 291 HNFB1 is expressed with TERT.
FIG. 292 ID2 expression in relation to TERT expression.
FIG. 293 KIF12 is expressed with TERT.
FIG. 294 LEFTY1 is expressed with TERT.
FIG. 295 METTL3 is expressed with TERT.
FIG. 296 MYO6 is expressed with TERT.
FIG. 297 PTPRO is expressed with TERT.
FIG. 298 RBBP6 is expressed with TERT.
FIG. 299 RBM25 is expressed with TERT.
FIG. 300 SEC62 is expressed with TERT.
FIG. 301 TOP1 is expressed with TERT.
FIG. 302 UGT1A6 is expressed with TERT.
FIG. 303 UGT2B 17 is expressed with TERT.
FIG. 304 UGT8 is expressed with TERT.
FIG. 305 UTRN is expressed with TERT.
FIG. 306 VIL1 is expressed with TERT.
FIG. 307 a hierarchical clustering of all TERT-related genes and core genes.
FIG. 308 a hierarchical clustering of all TERT-related genes and core genes but no cycling markers such as K167.
FIG. 309 a hierarchical clustering of all TERT-related genes and core genes. Cell types are marked.
FIG. 310 k-means clustering of all TERT-related genes and core genes.
FIG. 311 genes correlated with TERT that were identified in a principal component analysis.
FIG. 312 comparison of TG and NTG populations using median of $C_T$ value for every gene.
FIG. 313 delta medians for all genes in a graph format.
FIG. 314 Kolmogorov-Smirnov statistical significance test for genes expressed in TG or NTG cells, against KRT20.
FIG. 315 Kolmogorov-Smirnov statistical significance test for genes expressed in TG or NTG cells, against TFF3.
FIG. 316 Kolmogorov-Smirnov statistical significance test for genes expressed in TG or NTG cells, against p-value.
FIG. 317 a representation of hierarchical clustering by cell types.
FIG. 318 heat maps from 4 different chip-runs of samples. Cells were taken from xenograft (m6).
FIG. 319 a combined heat map comparing the four chip-runs.
FIG. 320 selection of cells for single cell gene expression analysis. Out of 335 cells tested, 5 cells were discarded by examining TACSTD1 and ACTB gene expression levels, and 330 cells were selected. Of the 330 cells, no cells were further discarded by examining GAPDH and ACTB gene expression levels, and 330 cells were selected for further analysis.
FIG. 321 a combined heat map after the clean up of unwanted cells.
FIG. 322 A representative clustering by mean-centered standard normalized, and a clustering of a subset are illustrated
FIG. 323 A representative clustering by mean-centered standard normalized, and a clustering of a subset are illustrated
FIG. 324 A representative clustering by mean-centered standard normalized, and a clustering of a subset are illustrated
FIG. 325 A representative clustering by mean-centered standard normalized, and a clustering of a subset are illustrated FIG. 326 gene expressions correlated with TERT expression.
FIG. 327 gene expressions associated with TERT expression.
FIG. 328 ACVR expression in relation to TERT expression.
FIG. 329 ADAM10 expression in relation to TERT expression.
FIG. 330 AQP1 expression in relation to TERT expression.
FIG. 331 ARL5A expression in relation to TERT expression.
FIG. 332 BRD7 expression in relation to TERT expression.
FIG. 333 CCND1 expression in relation to TERT expression.
FIG. 334 CDK2 expression in relation to TERT expression.
FIG. 335 CDK6 expression in relation to TERT expression
FIG. 336 CES6 expression in relation to TERT expression.
FIG. 337 CFTR expression in relation to TERT expression.
FIG. 338 DLL4 expression in relation to TERT expression.
FIG. 339 ESF1 expression in relation to TERT expression.
FIG. 340 ETS2 expression in relation to TERT expression.
FIG. 341 EZH2 expression is correlated with TERT expression.
FIG. 342 GPR expression in relation to TERT expression.
FIG. 343 HNF1B expression in relation to TERT expression.
FIG. 344 HUNK expression in relation to TERT expression.
FIG. 345 KIF12 expression in relation to TERT expression.
FIG. 346 LAMB expression in relation to TERT expression.
FIG. 347 LEFTY expression is correlated with TERT expression.
FIG. 348 METTL3 expression in relation to TERT expression.
FIG. 349 MYO6 expression in relation to TERT expression.
FIG. 350 OLFM4 expression in relation to TERT expression.
FIG. 351 PTPRO expression in relation to TERT expression.
FIG. 352 RBBP6 expression in relation to TERT expression.
FIG. 353 RBM25 expression in relation to TERT expression.
FIG. 354 SEC62 expression in relation to TERT expression.
FIG. 355 SUZ12 expression is correlated with TERT expression.
FIG. 356 TOP1 expression is correlated with TERT expression.
FIG. 357 UGT1A6 expression in relation to TERT expression.
FIG. 358 UGT2B 17 expression in relation to TERT expression.
FIG. 359 UGT8 expression in relation to TERT expression.
FIG. 360 UTRN expression is correlated with TERT expression.
FIG. 361 VIL1 expression in relation to TERT expression.

Figure 362:
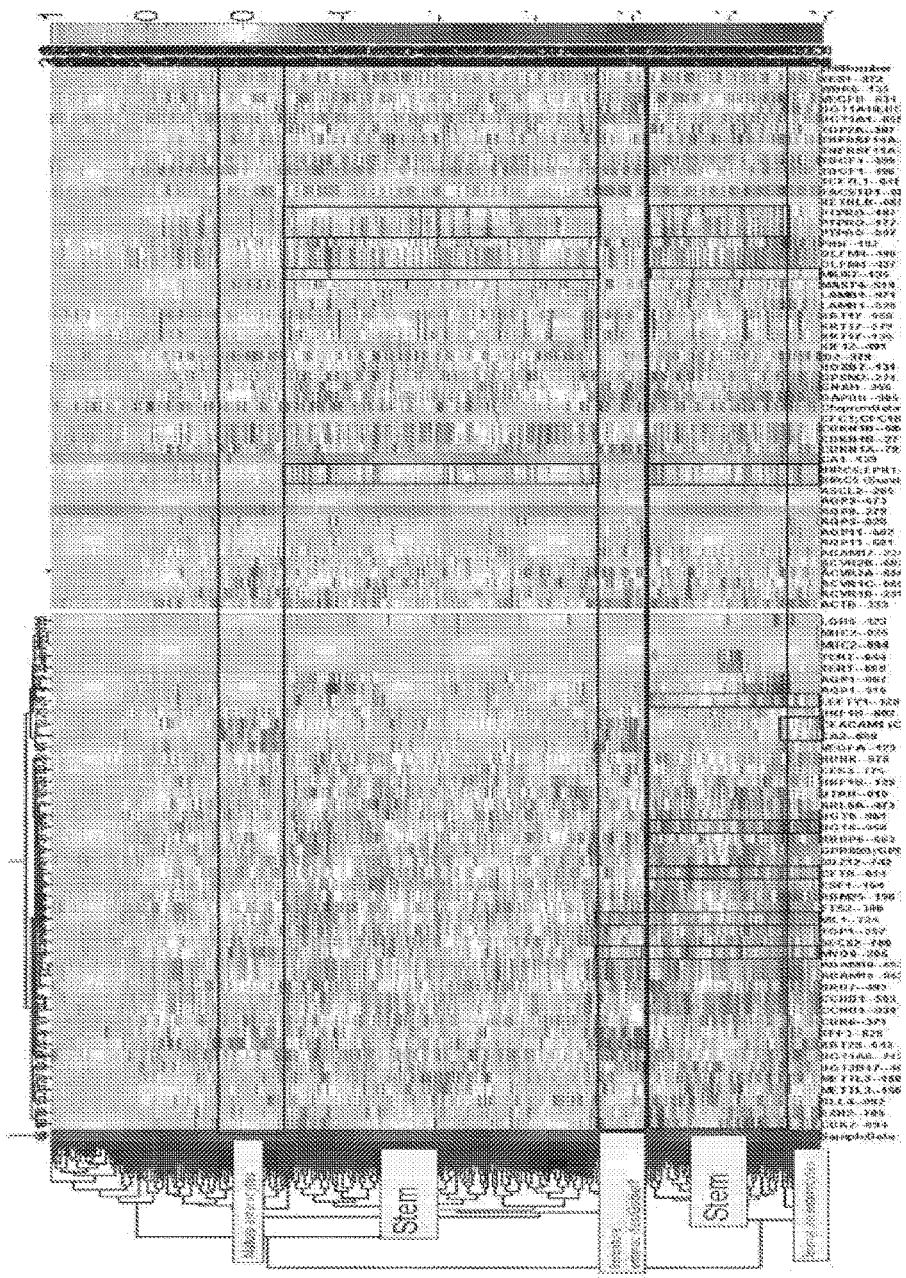

FIG. 362 a representation of hierarchical clustering by cell type, showing stem, mature enterocytes, immature enterocytes and goblet cells.

Figure 363:
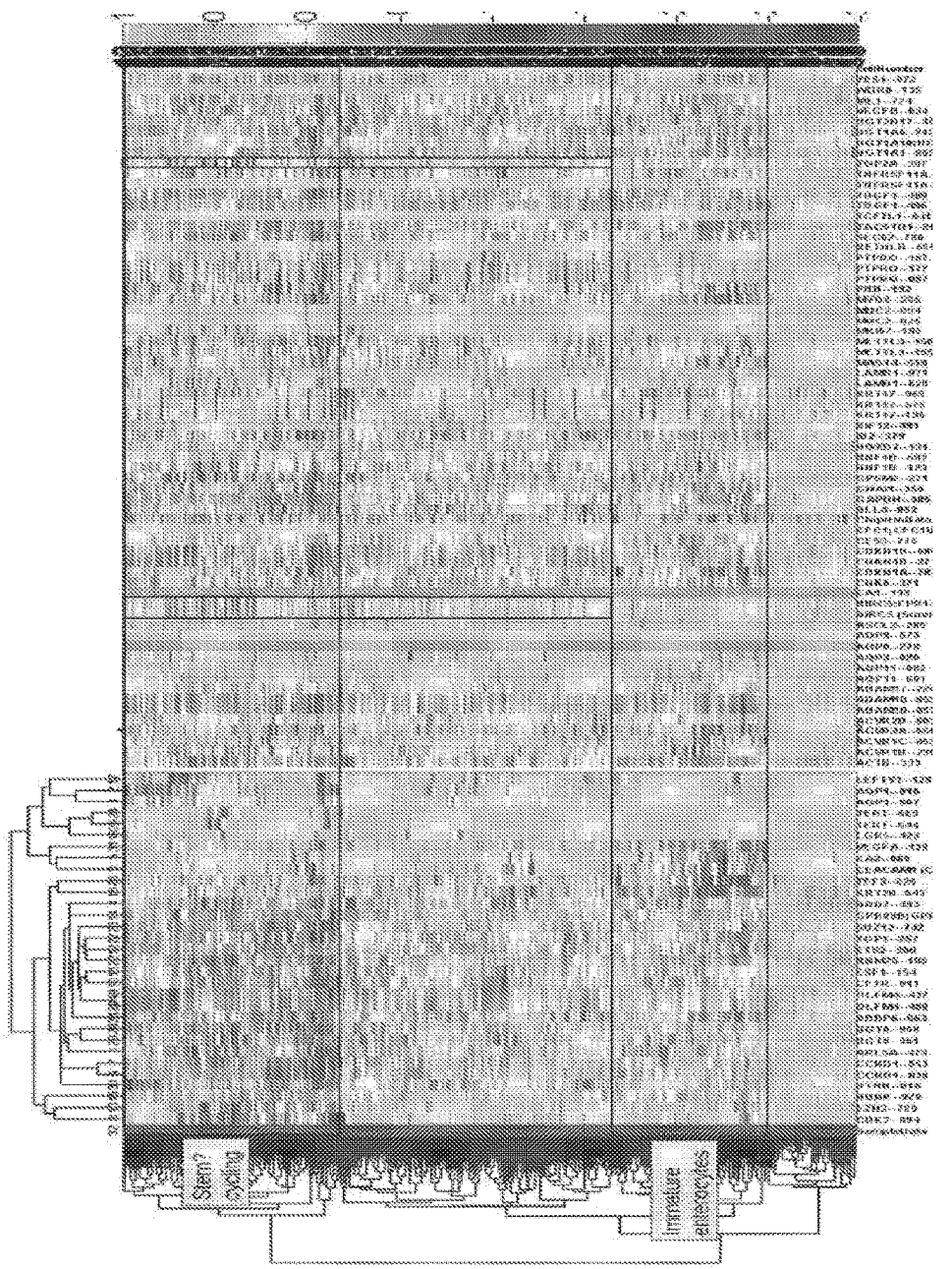

FIG. 363 a representation of hierarchical clustering by cell types, showing cycling stem cells and immature enterocytes.

Figure 364:
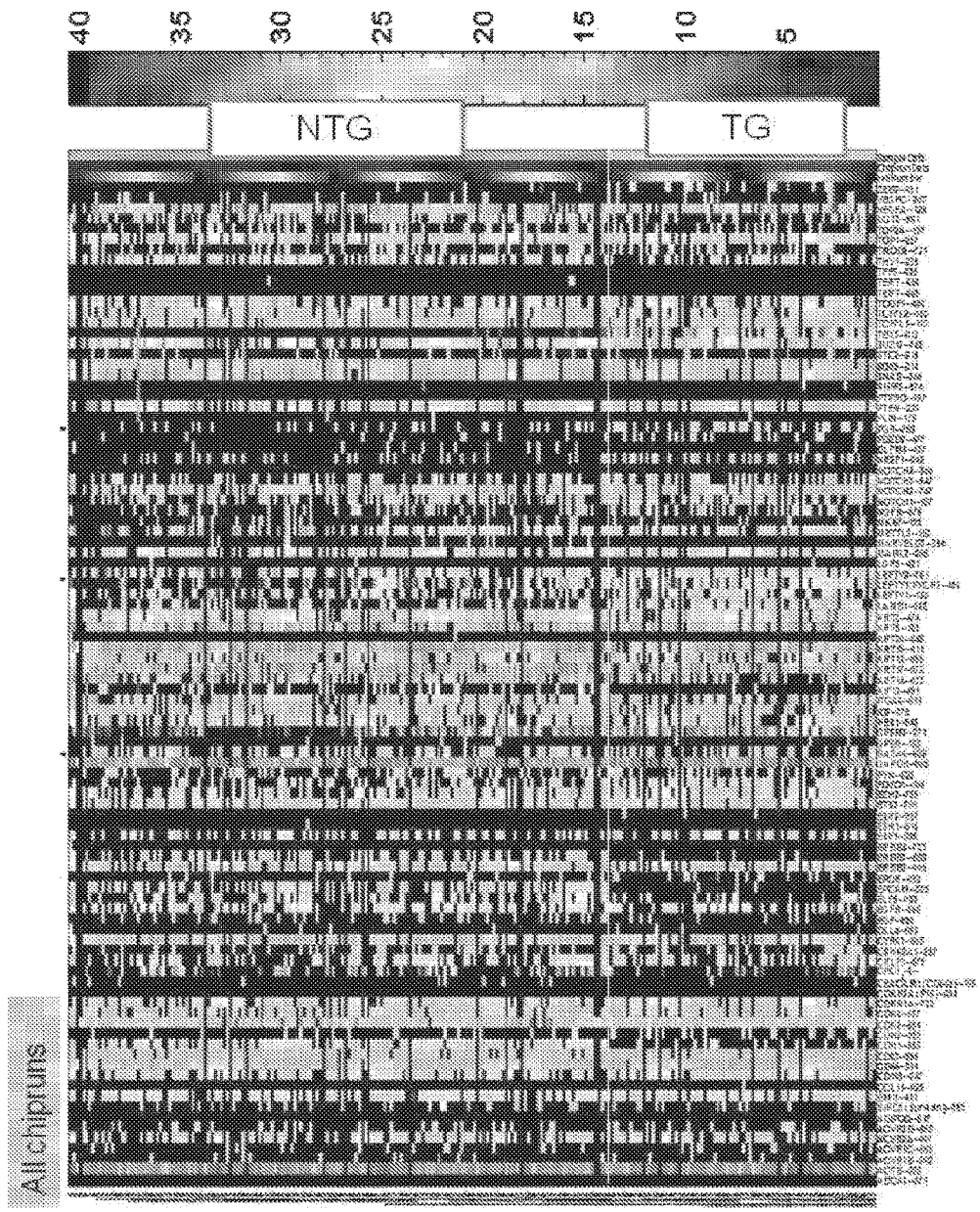

FIG. 364 a combined heat map comparing all chip-runs. Cells were taken from xerograft (m4) breast cancer sample. The cells were FACS sorted with CD24. Br-CSC cells were defined as CD24– cells.

Figure 365:
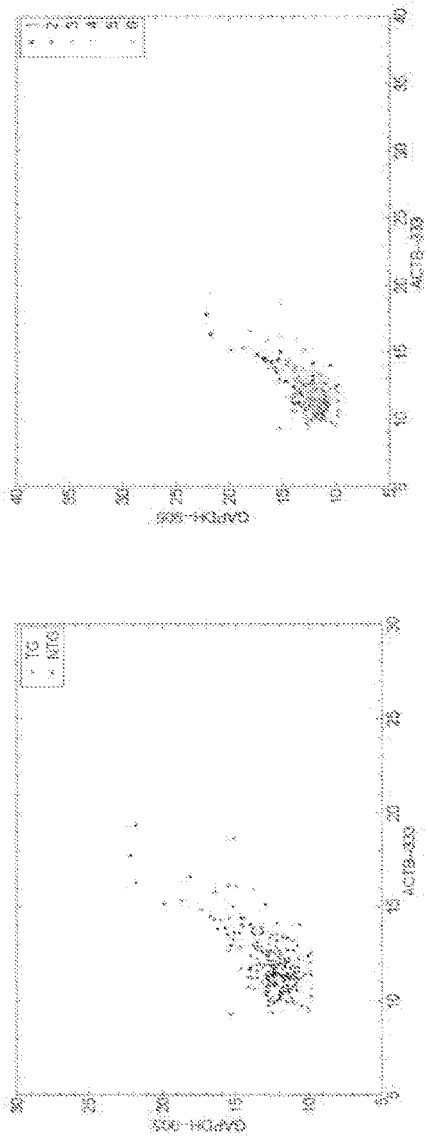

FIG. 365 selection of cells for single cell gene expression analysis.

Figure 366:
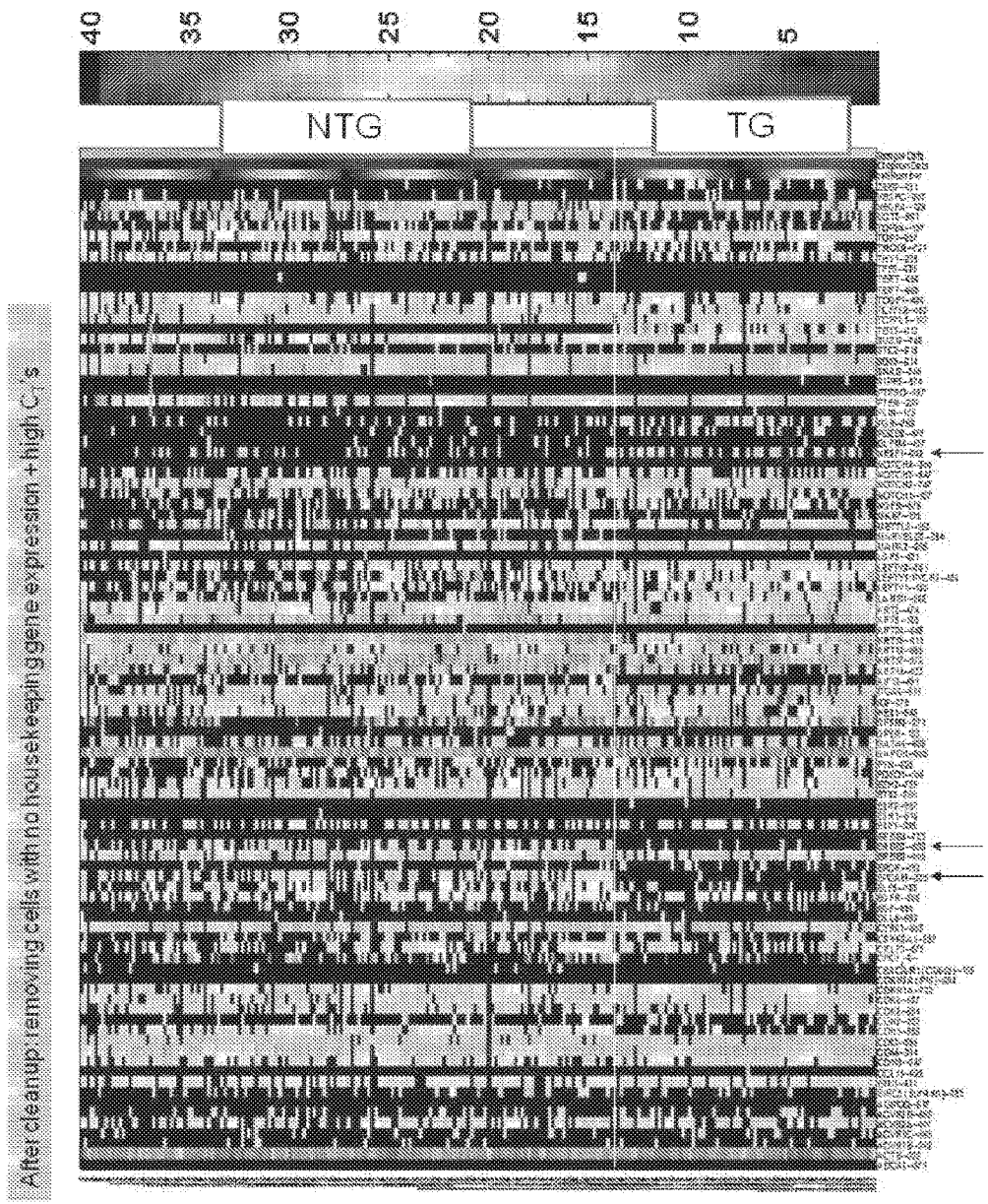

FIG. 366 a combined heat map after the clean up of unwanted cells.

Figure 367:
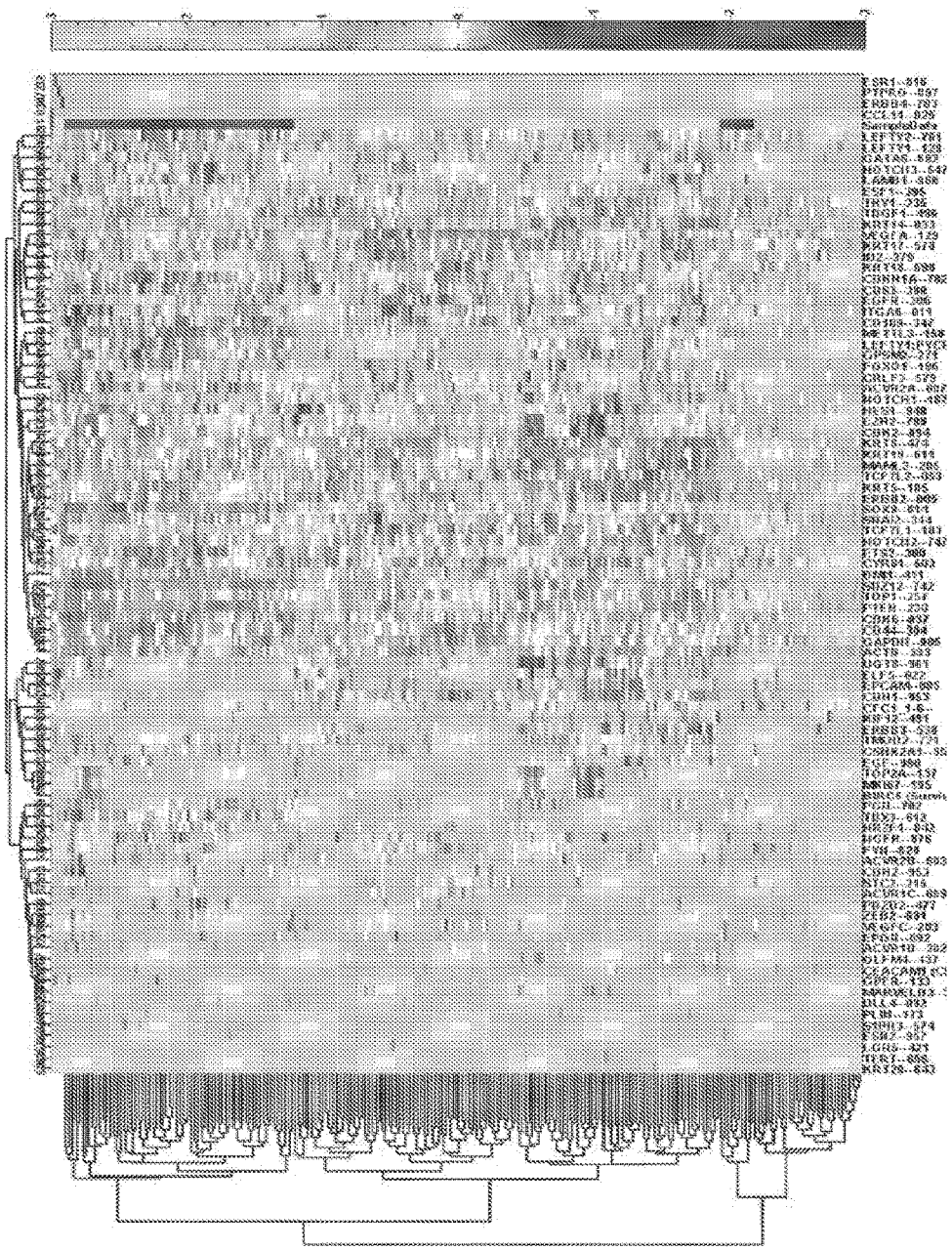

FIG. 367 a representative hierarchical clustering.

Figure 368:
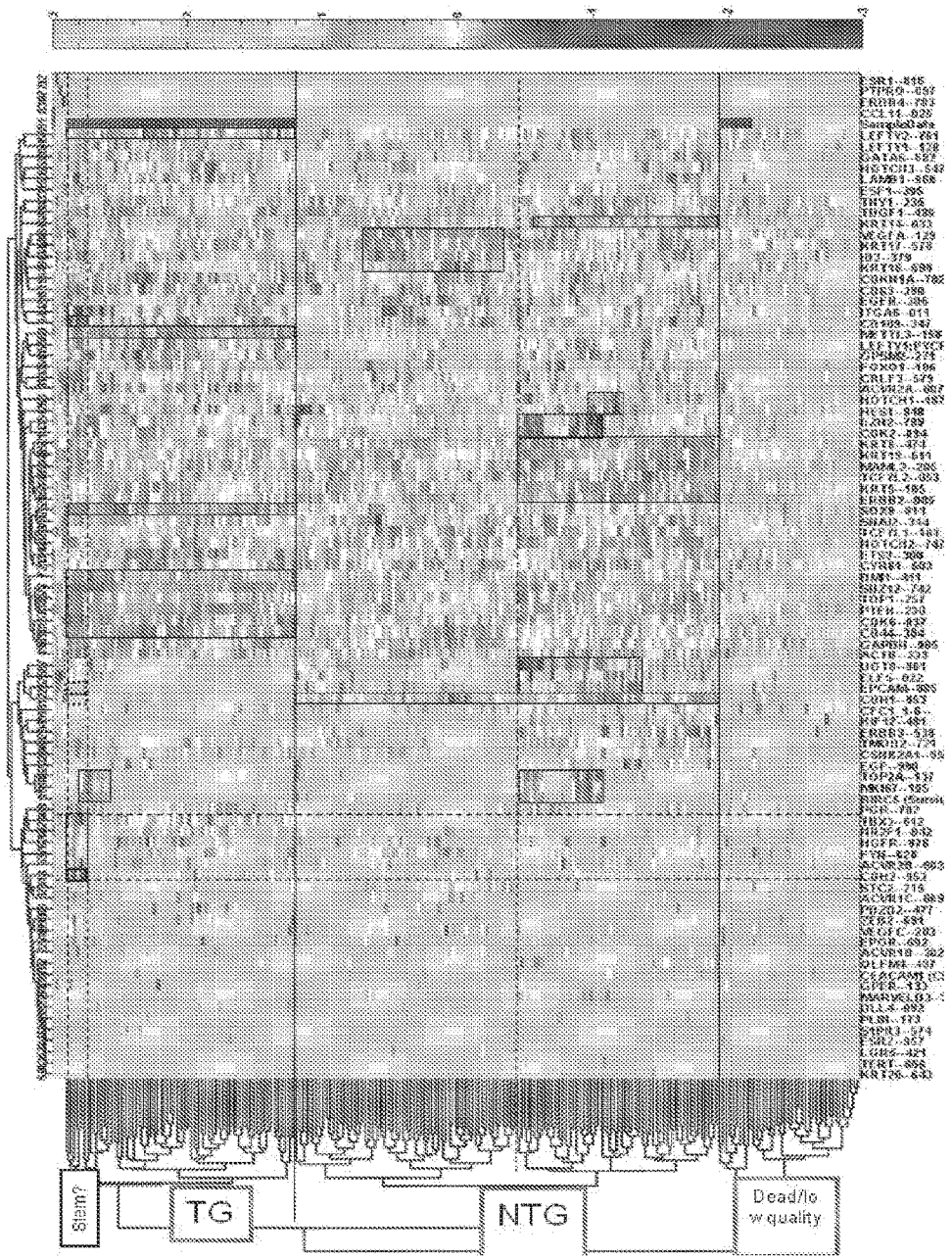

FIG. 368 a representative hierarchical clustering. Cell types are marked.

Figure 369:
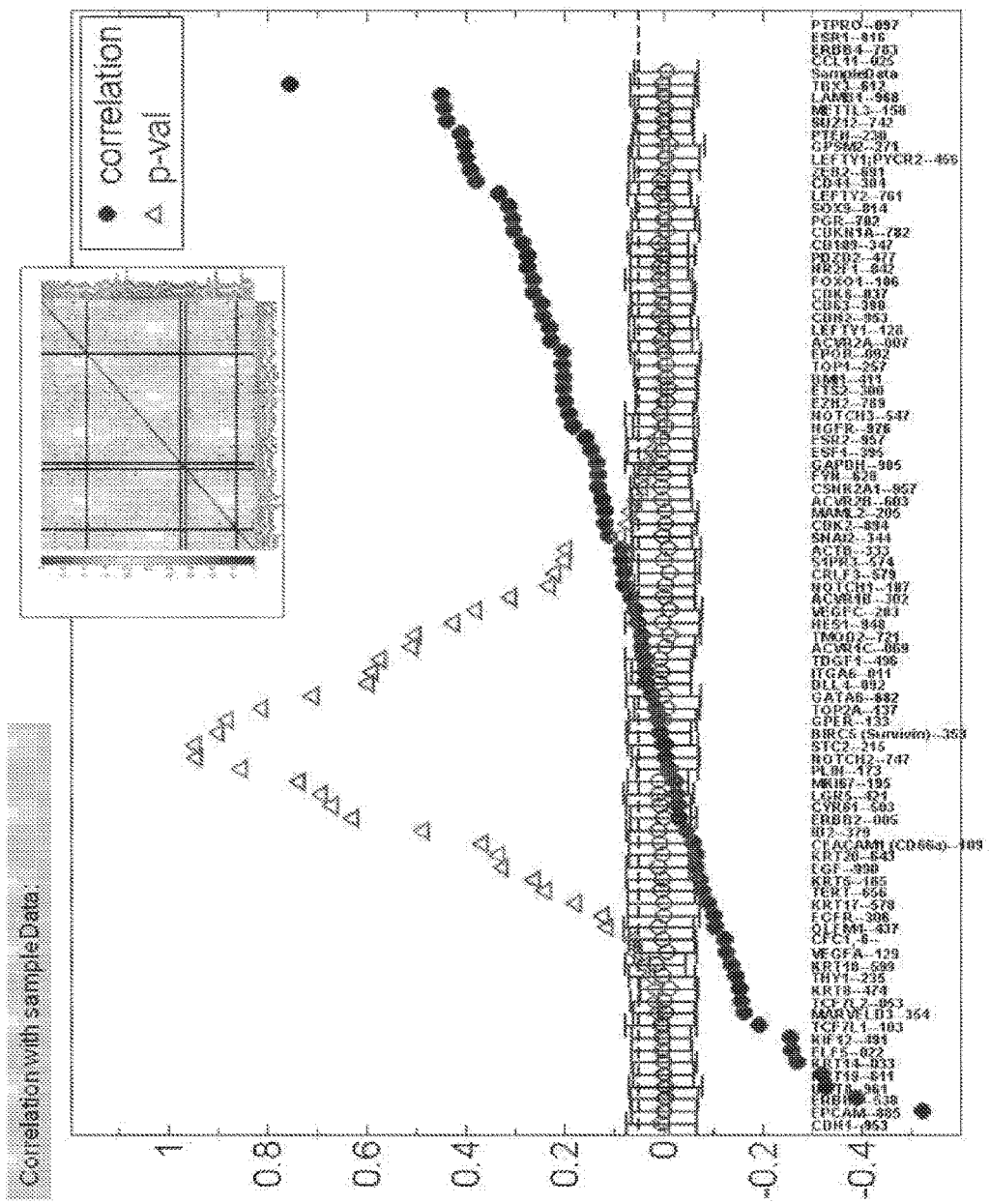

FIG. 369 a correlation graph showing the genes that are most differentially expressed.

Figure 370:
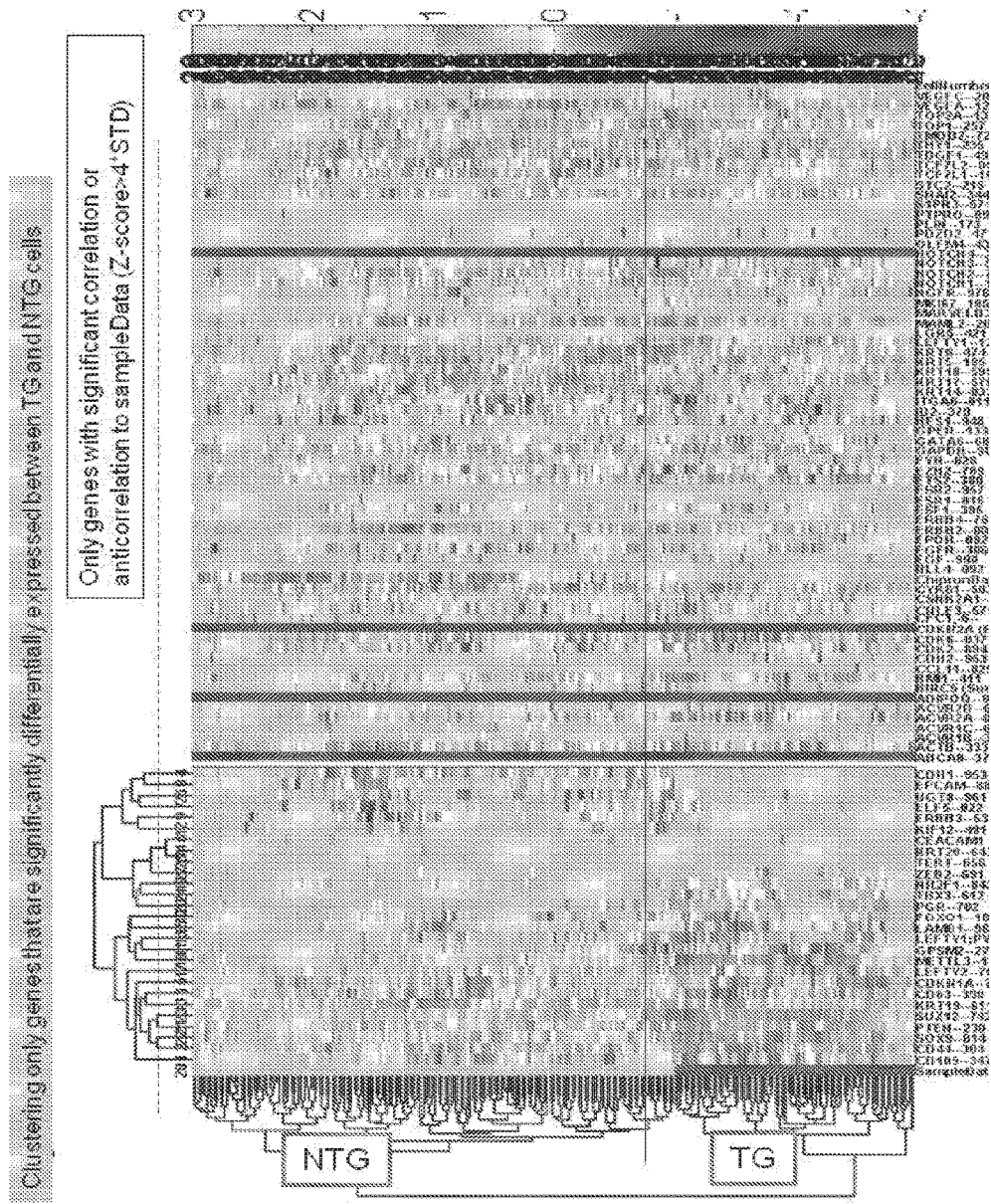

FIG. 370 a representation of clustering with only genes that are significantly differentially expressed between TG and NTG cells.

Figure 371:
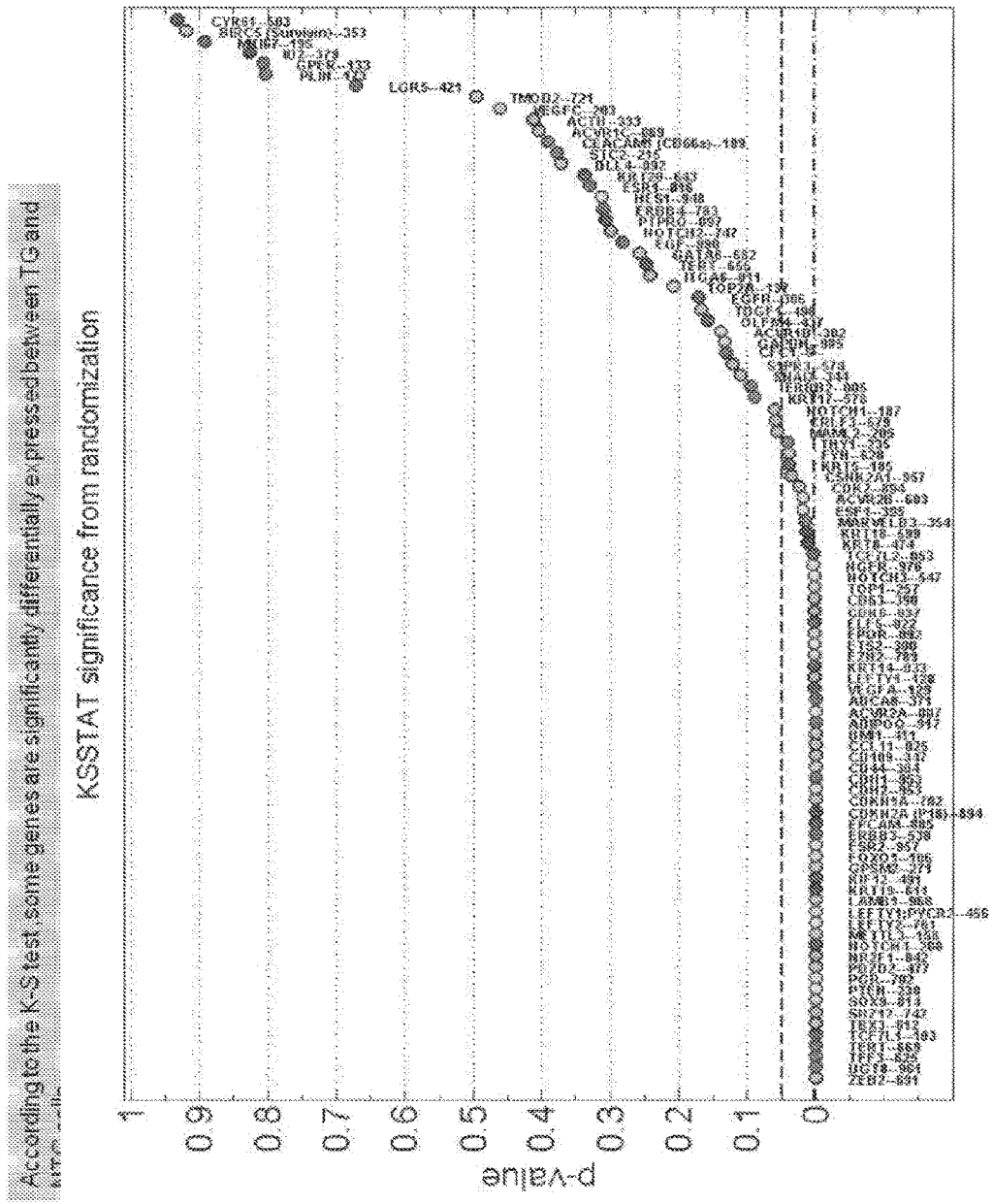

FIG. 371 result of K-S stat test showing that some genes are significantly differentially expressed between TG and NTG cells. Data is plotted against p-value.

Figure 372:
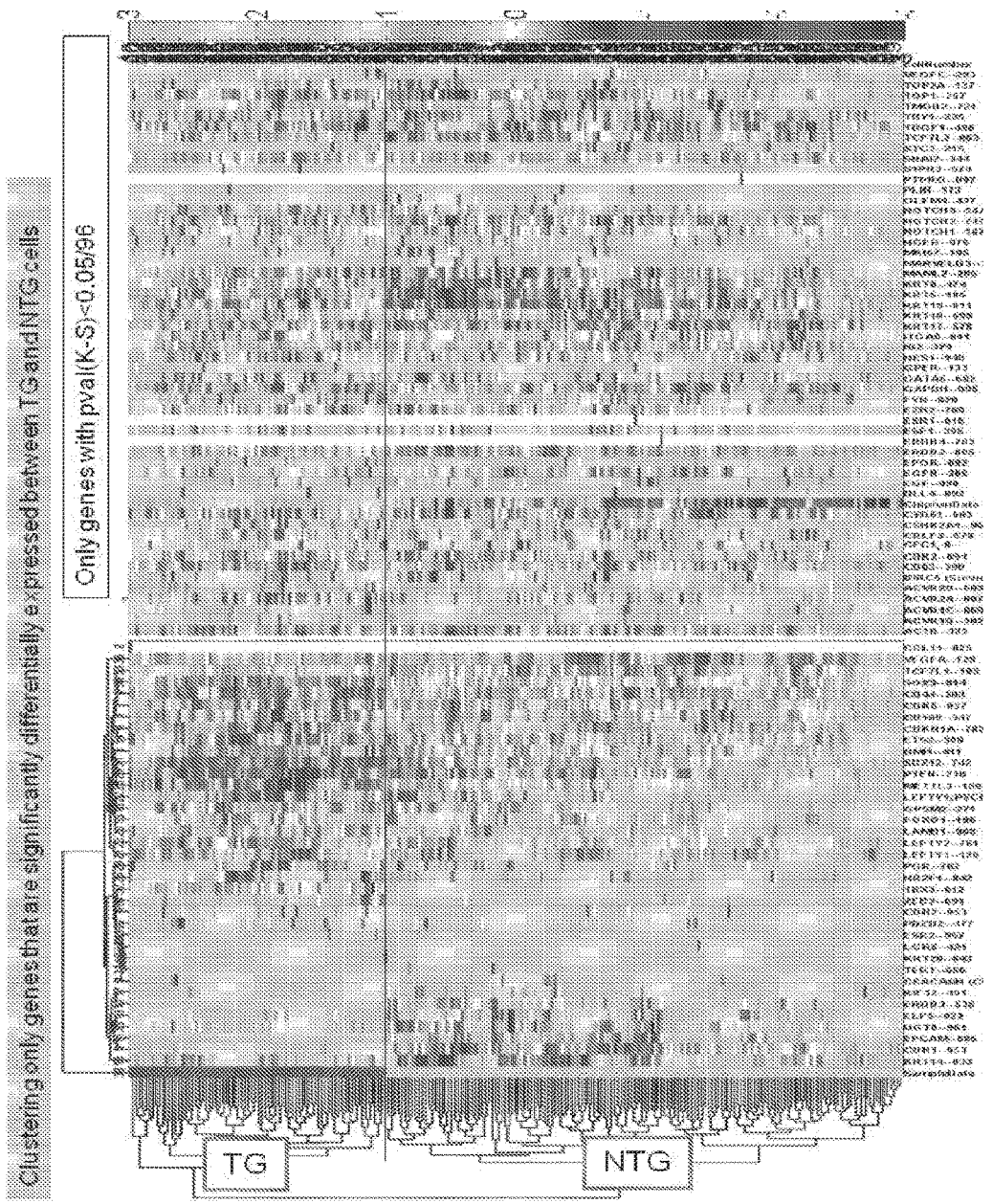

FIG. 372 a representation of clustering with only genes that are significantly differentially expressed between TG and NTG cells with pval (K-S) less then 0.05/96 well.

Figure 373:
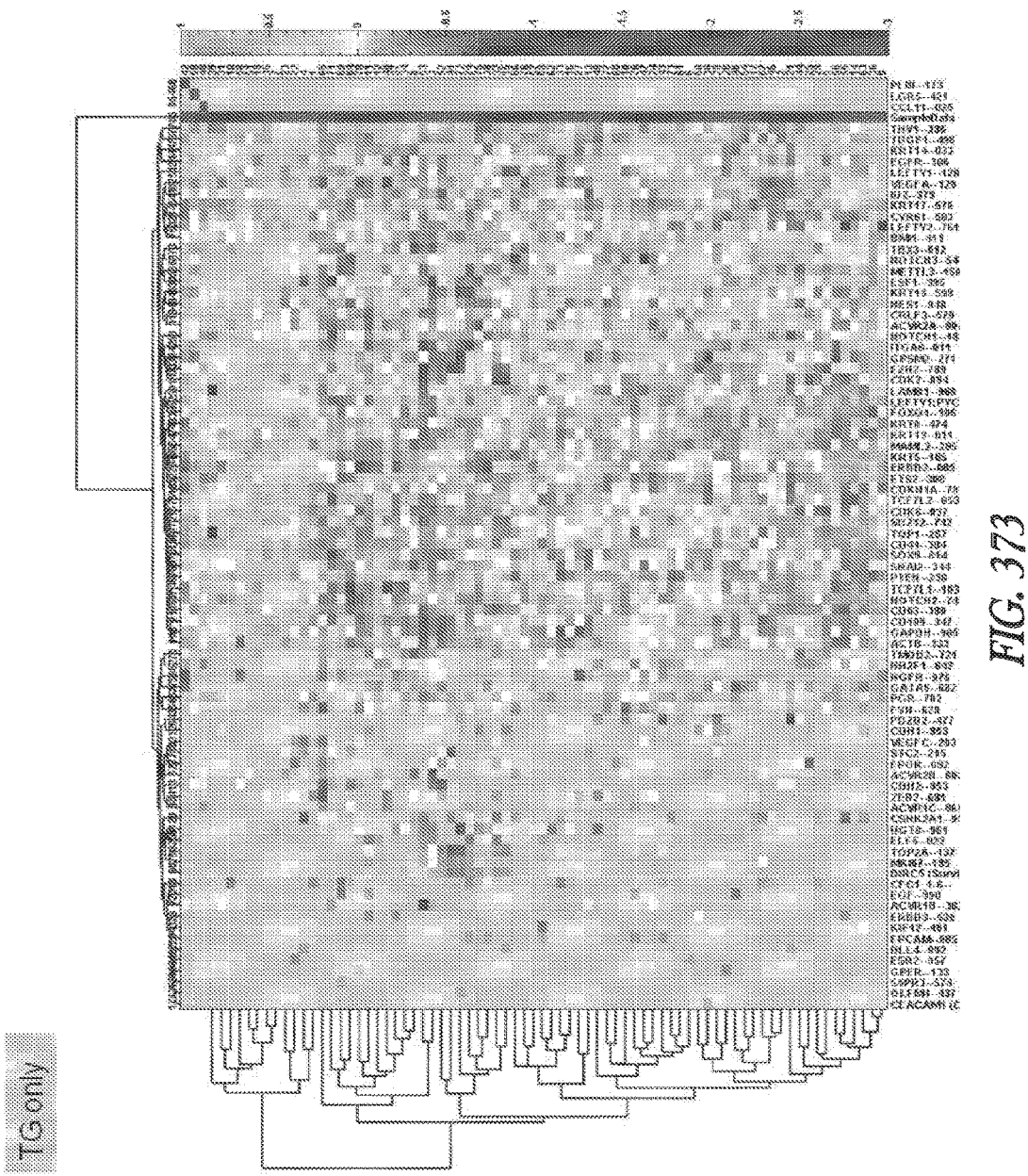

FIG. 373 genes differentially expressed in TG population.

Figure 374:
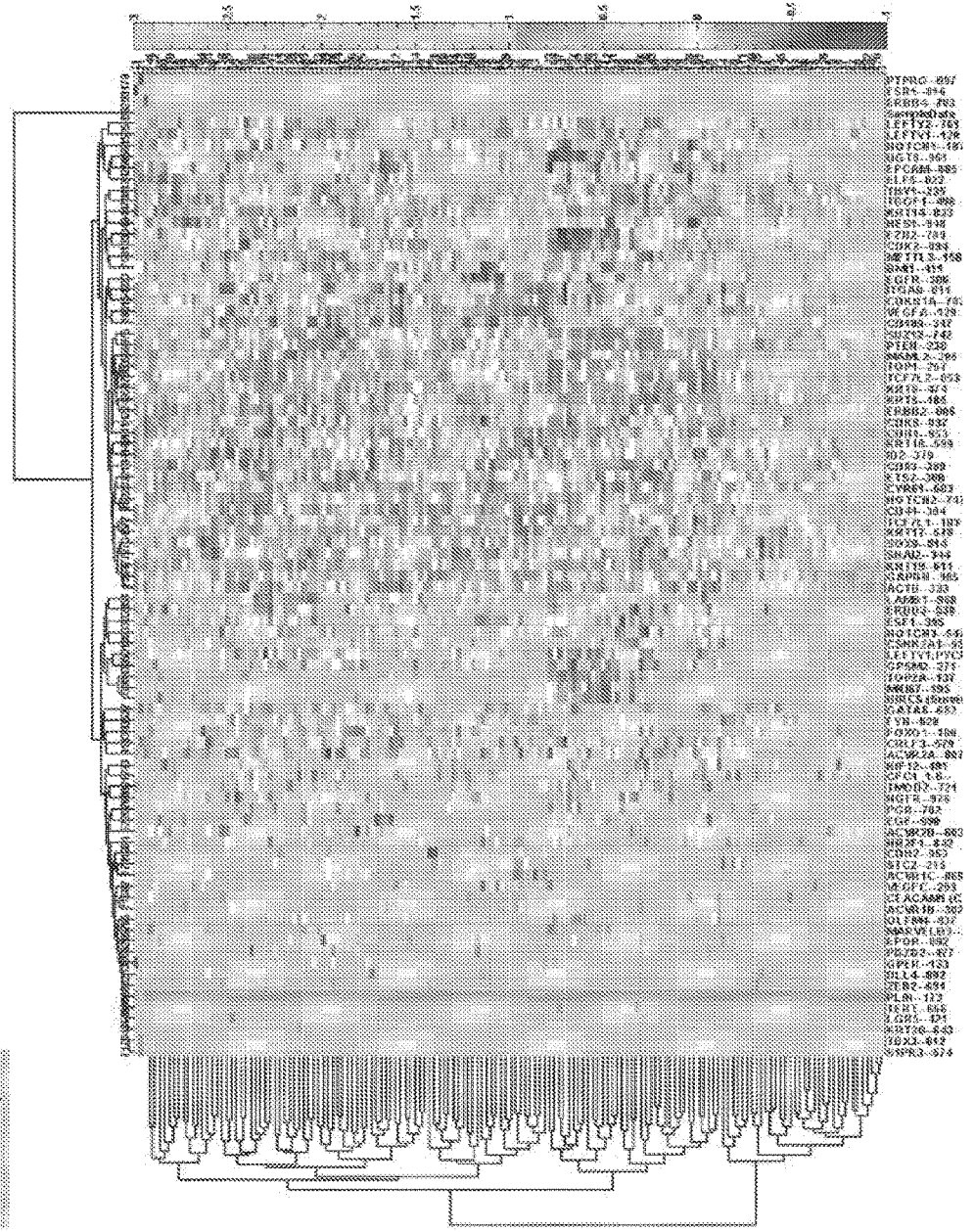

FIG. 374 genes differentially expressed in NTG population.

Figure 375:
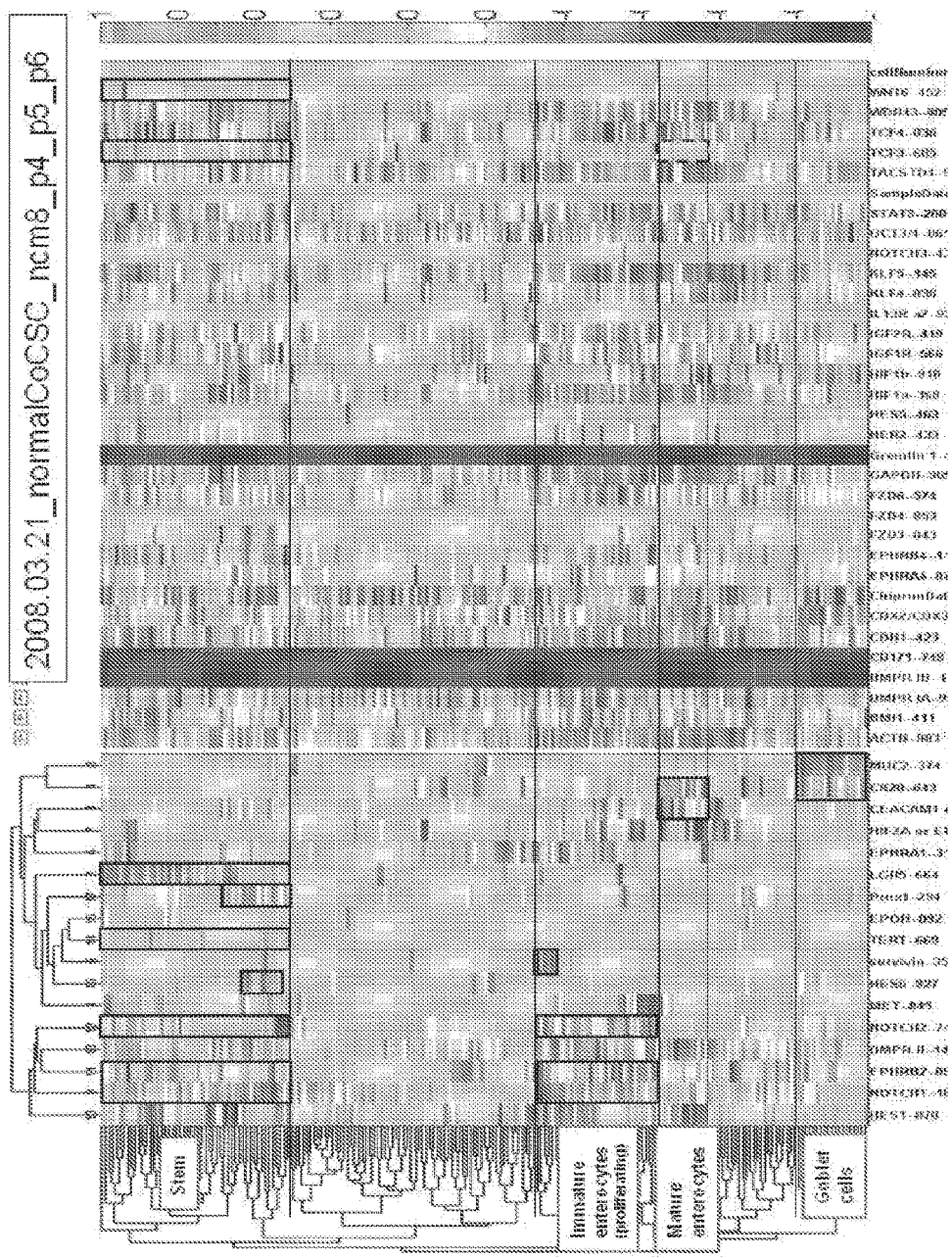

FIG. 375 a representative hierarchical clustering experiment.

Figure 376:
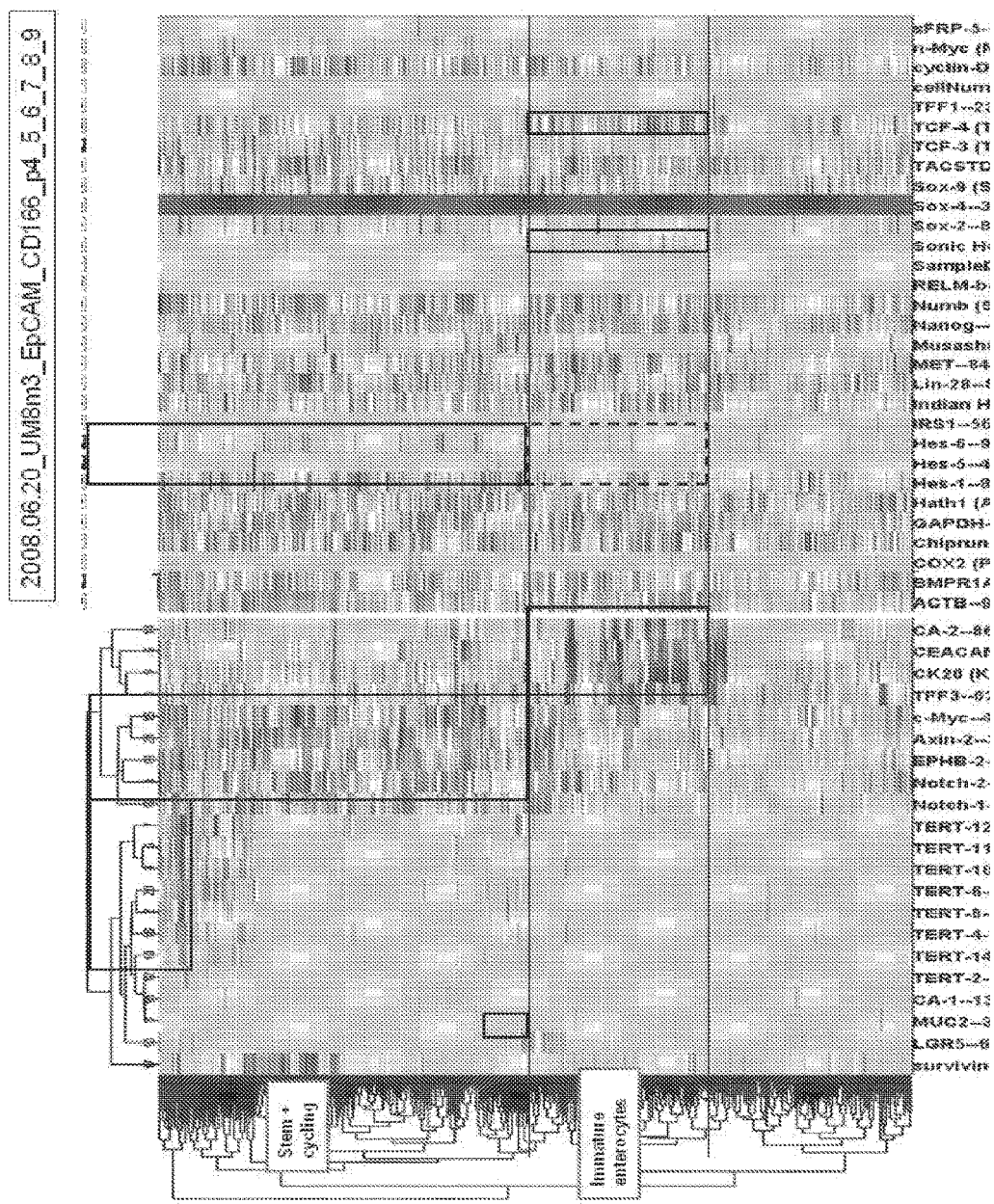

FIG. 376 a representative hierarchical clustering experiment.

Figure 377:
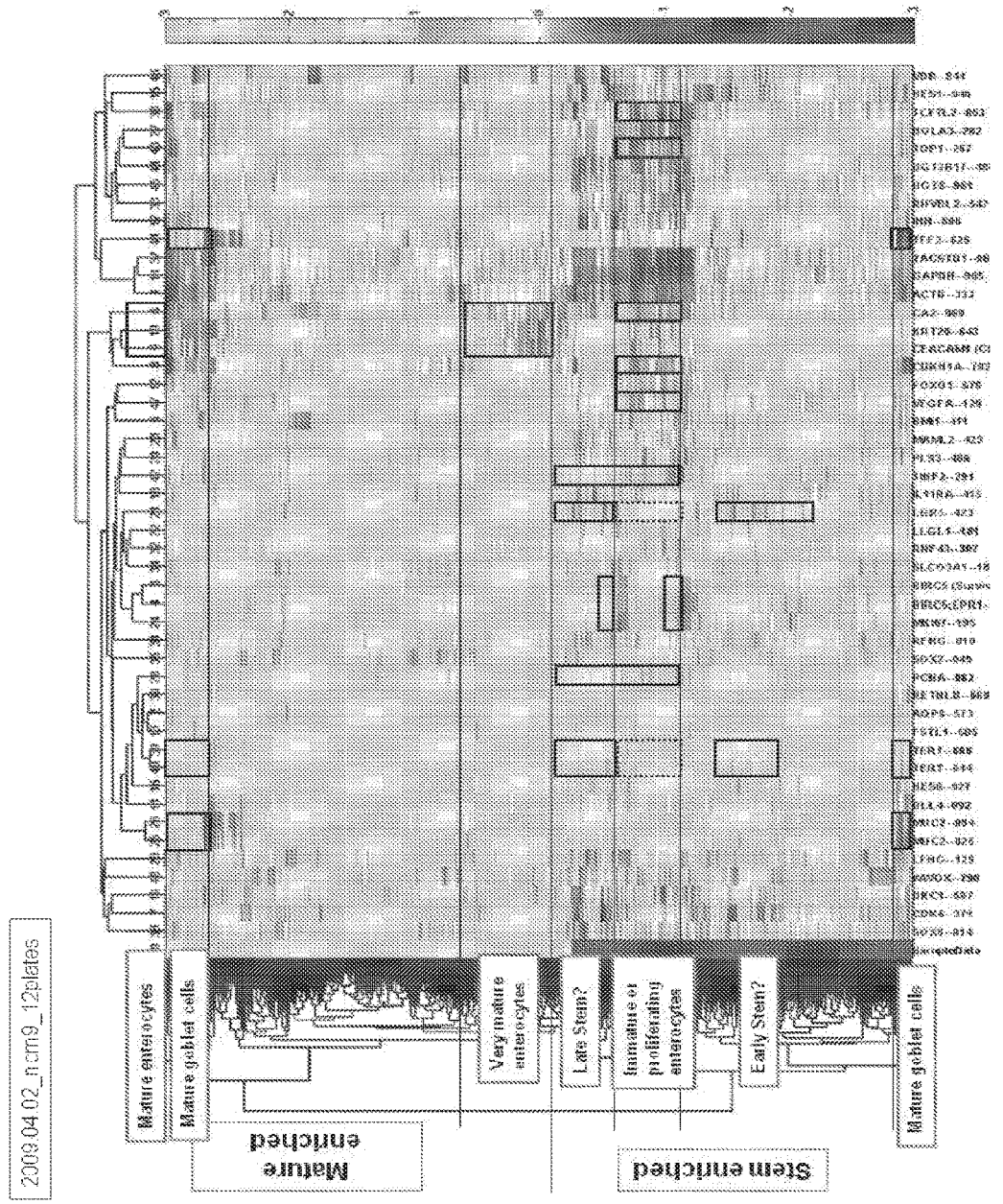

FIG. 377 a representative hierarchical clustering experiment.

Figure 378:
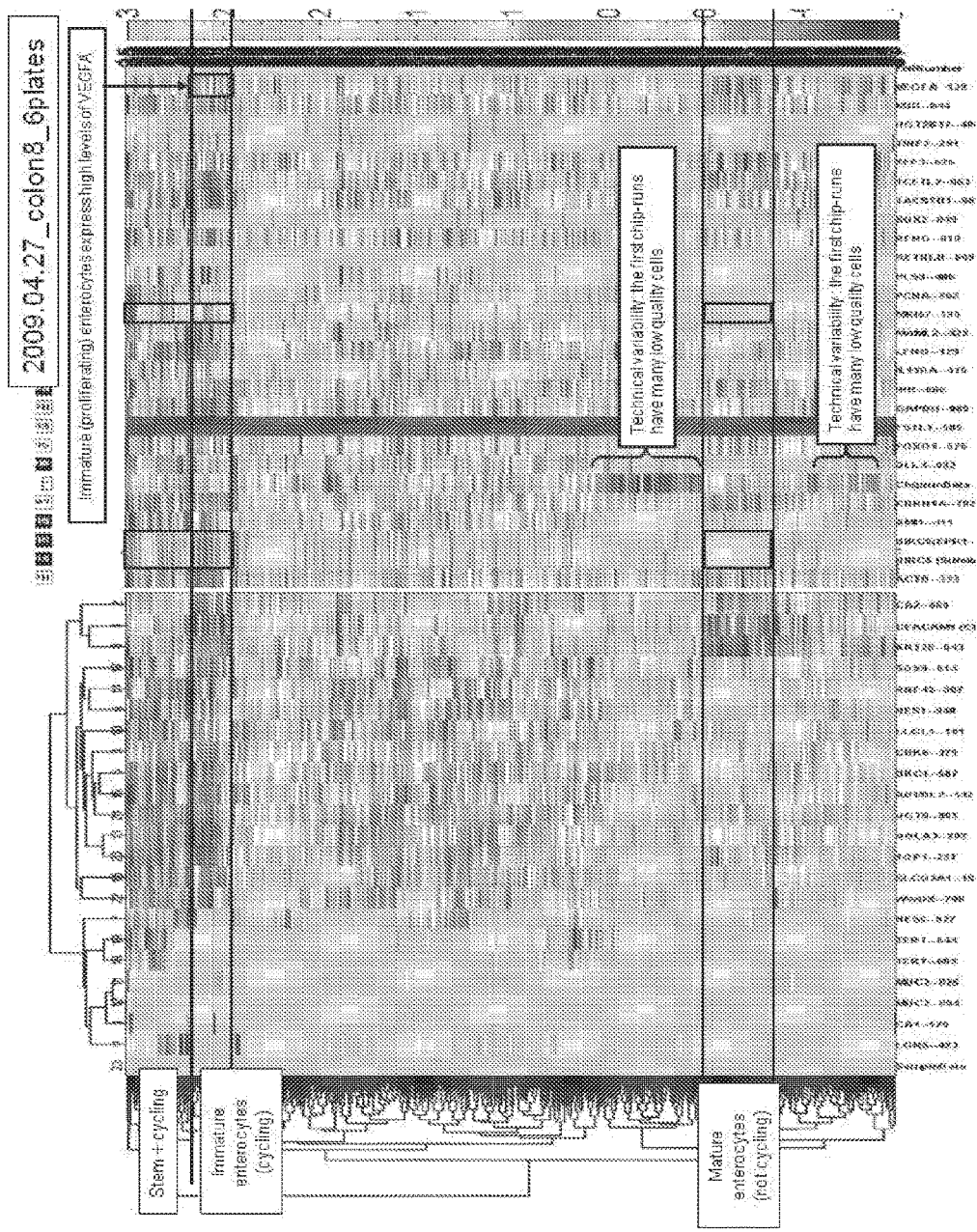

FIG. 378 a representative hierarchical clustering experiment.

Figure 379:
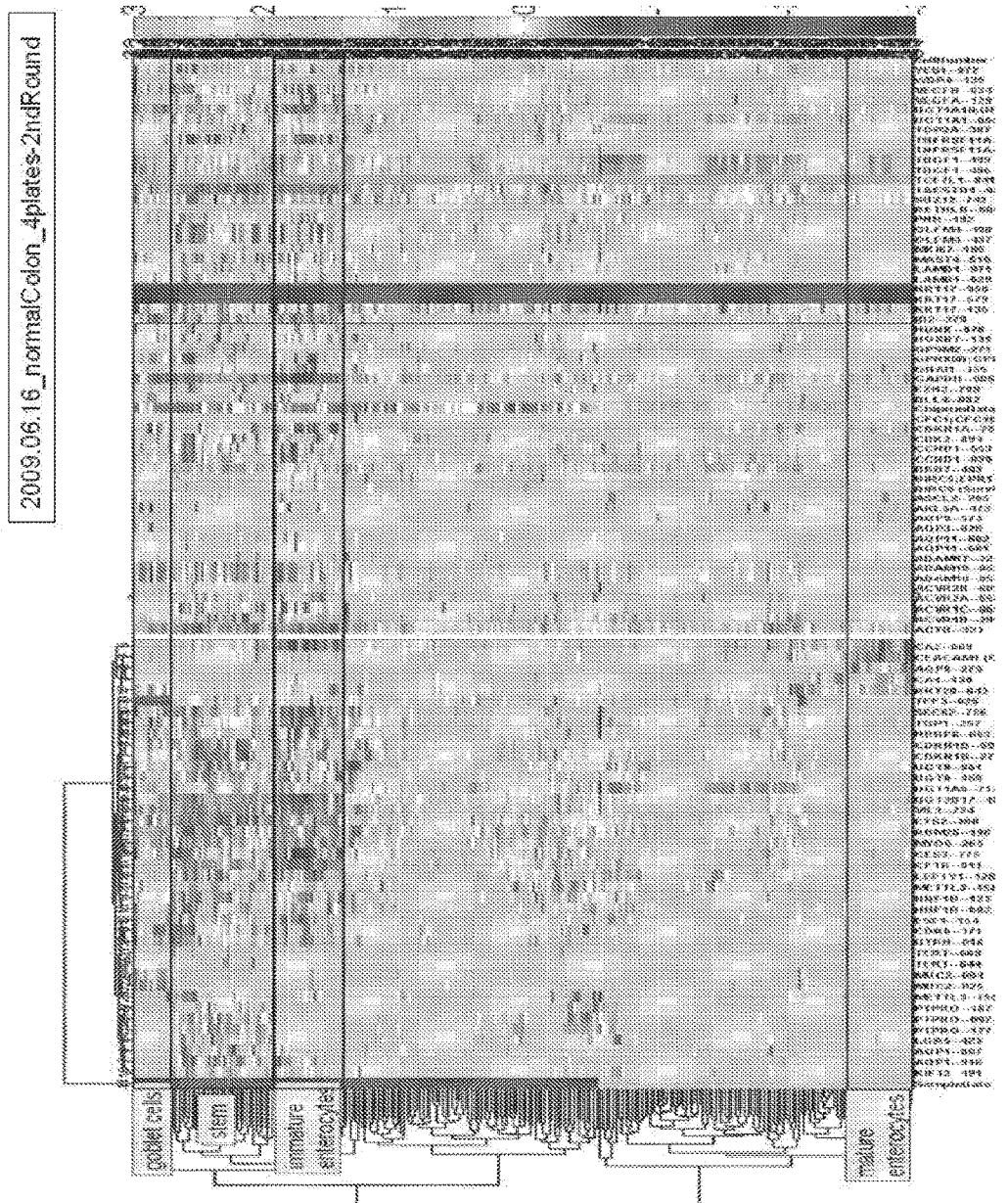

FIG. 379 a representative hierarchical clustering experiment.

Figure 380:
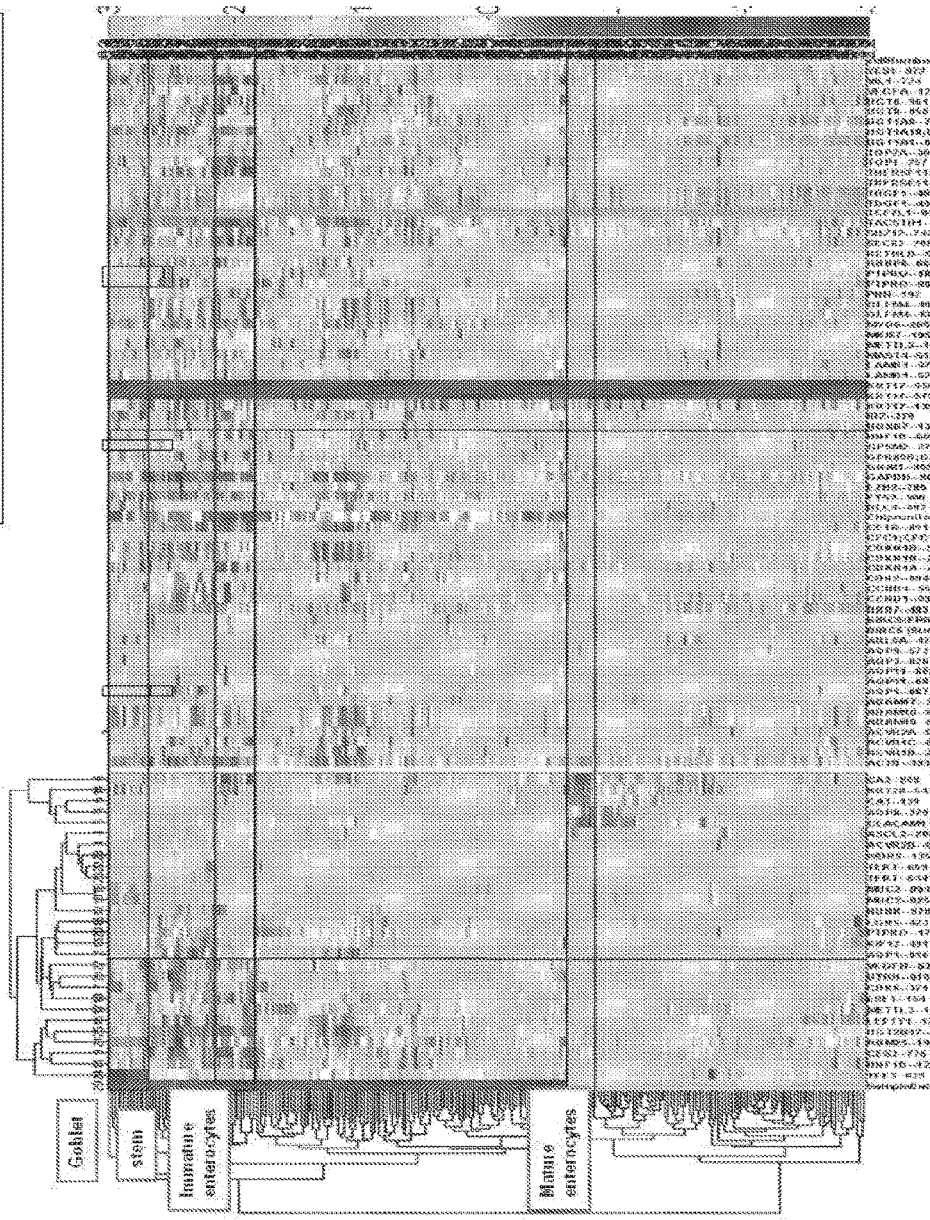

FIG. 380 a representative hierarchical clustering experiment, showing goblet, stem, immature enterocytes and mature enterocytes.

Figure 381:
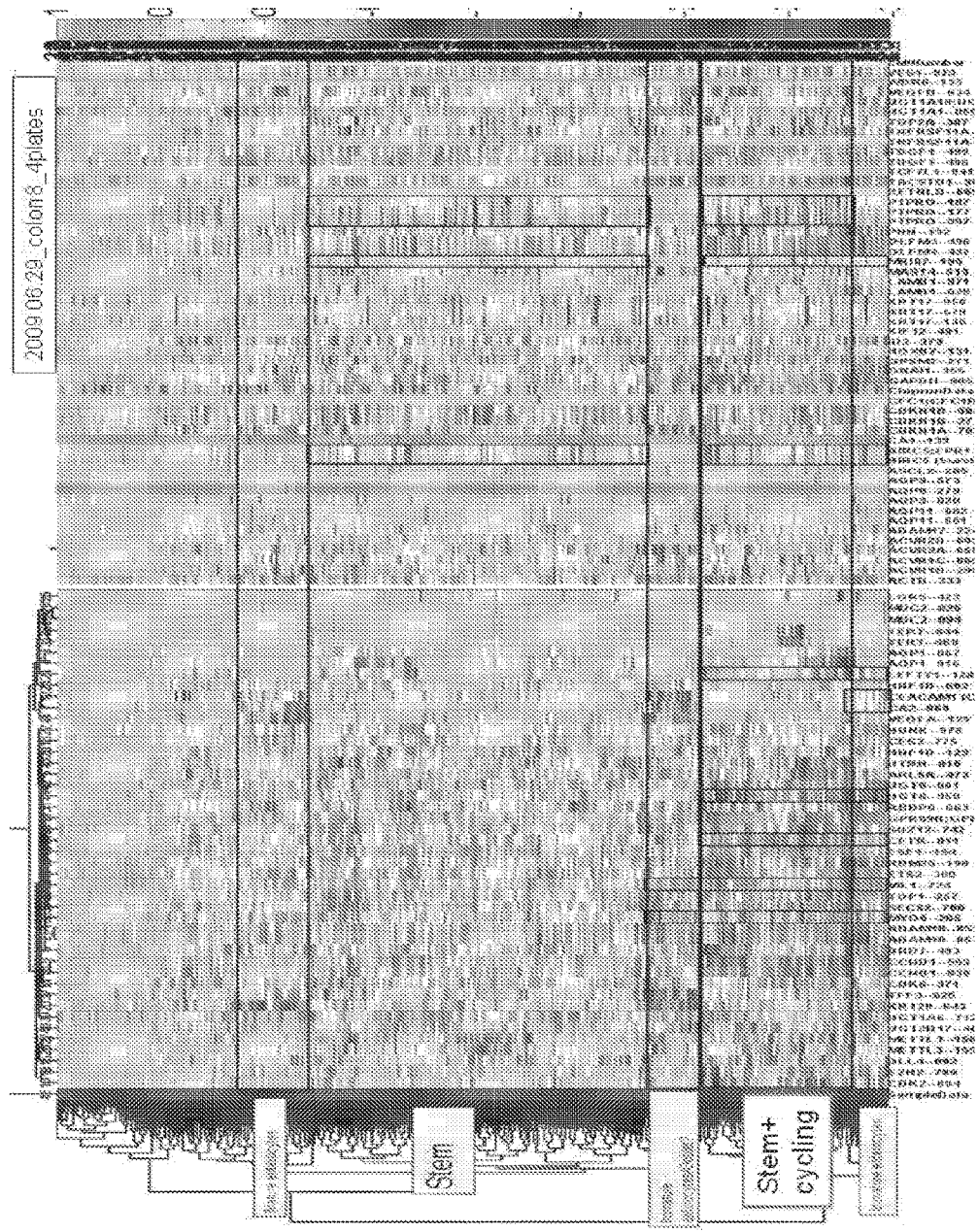

FIG. 381 a representative hierarchical clustering experiment.

Figure 382:
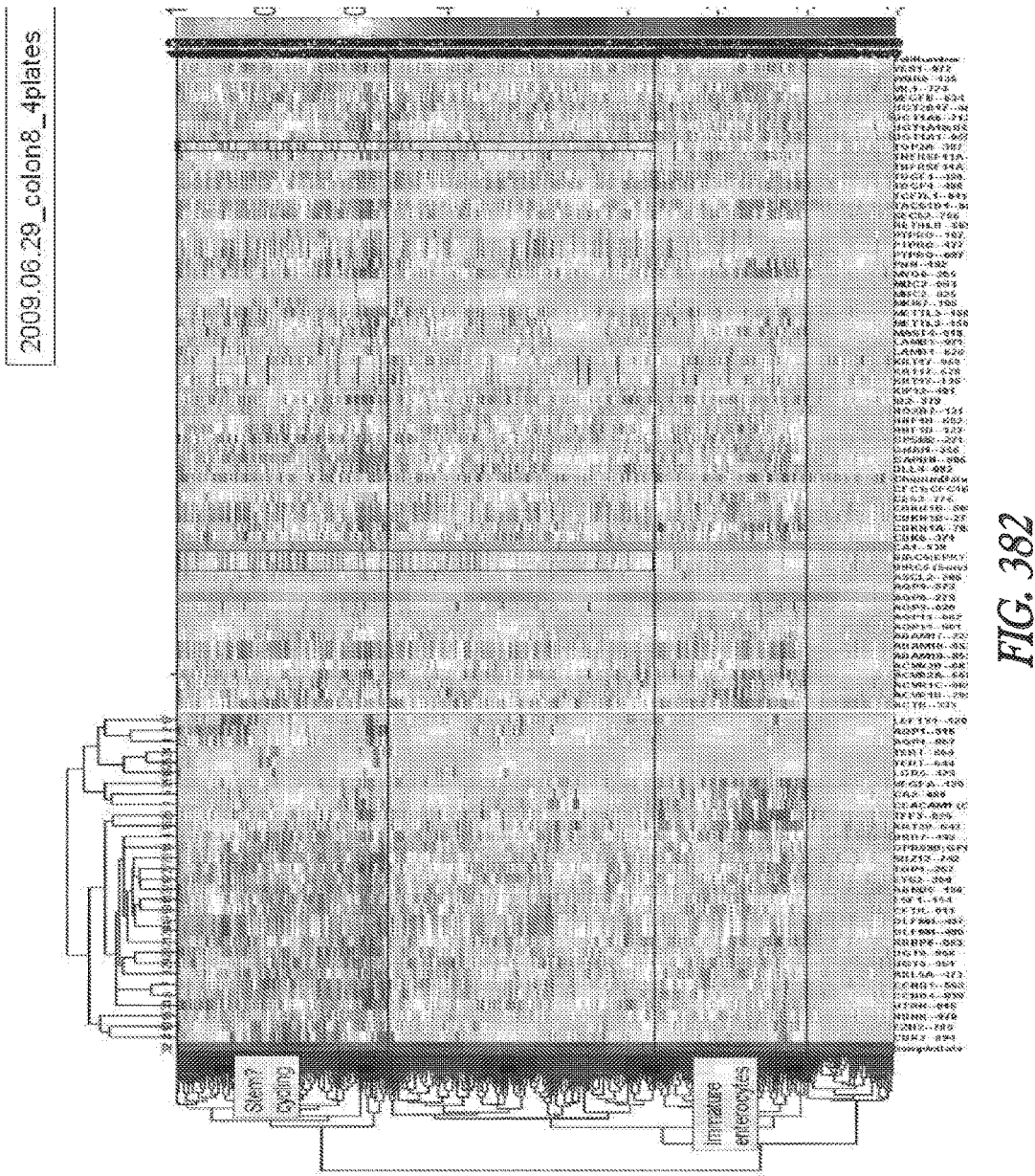

FIG. 382 a representative hierarchical clustering experiment, showing cycling stem cells and immature enterocytes.

Figure 383:
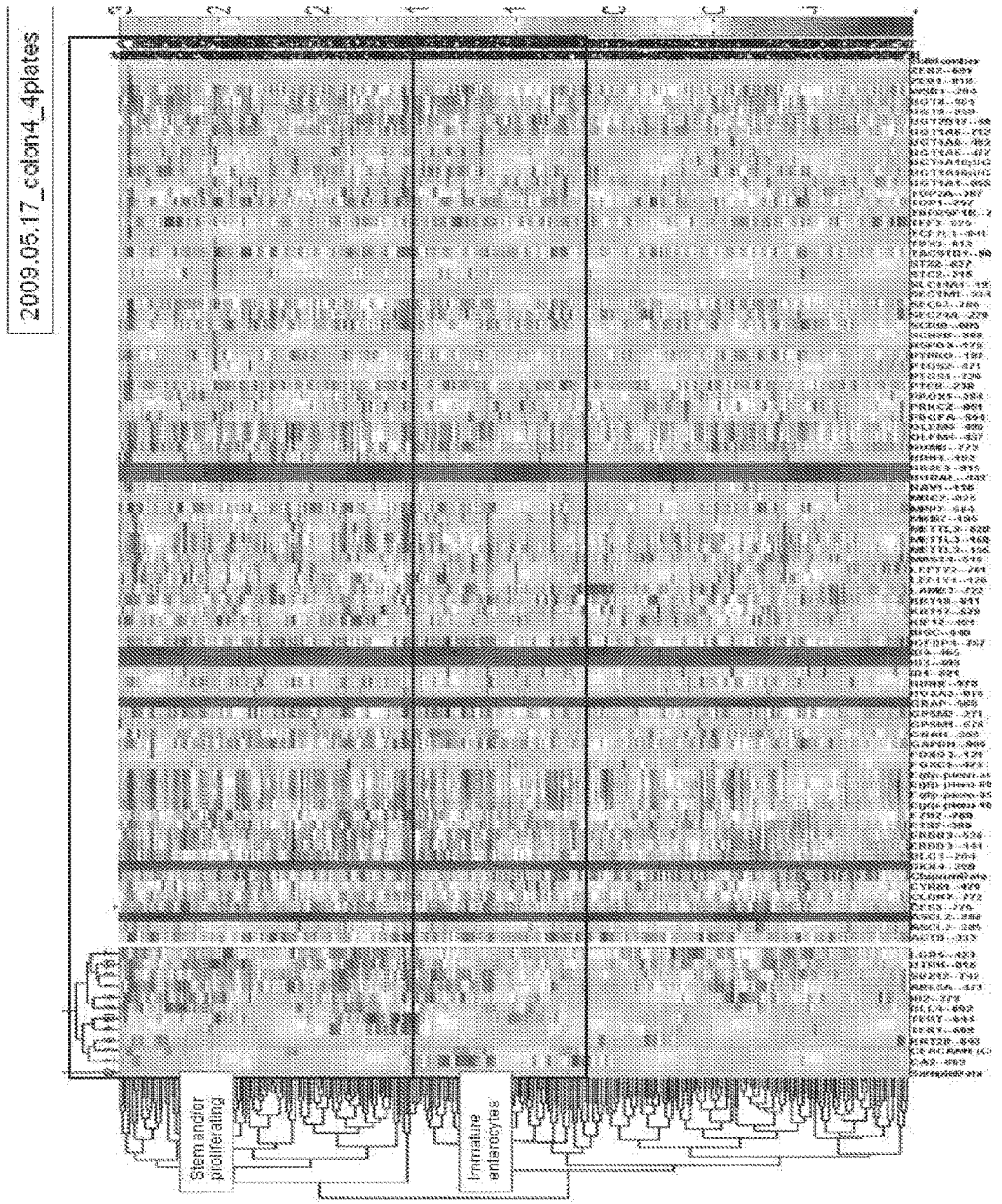

FIG. 383 a representative hierarchical clustering experiment.

Figure 384:
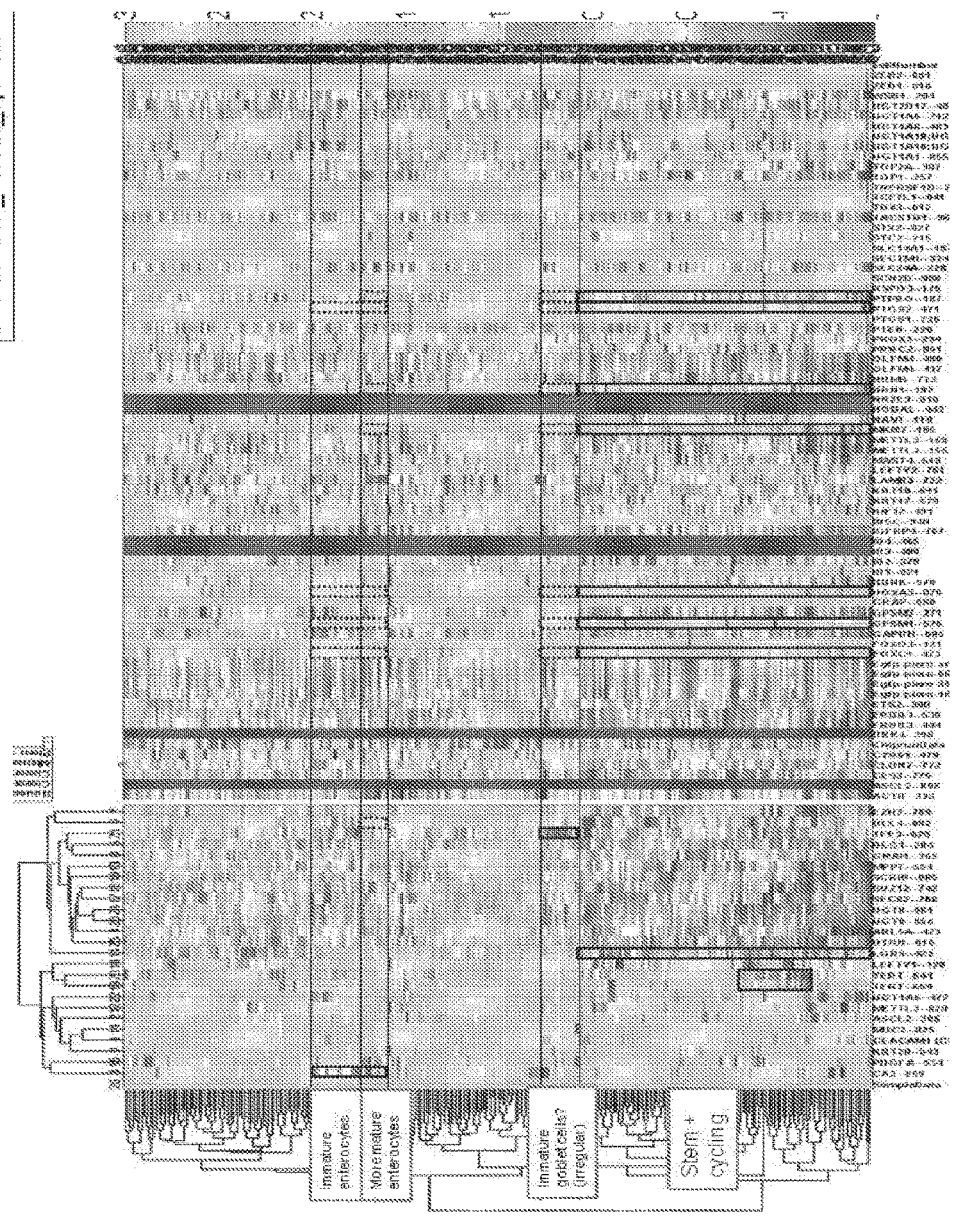

FIG. 384 a representative hierarchical clustering experiment, showing goblet, stem, immature enterocytes and mature enterocytes.

Figure 385:
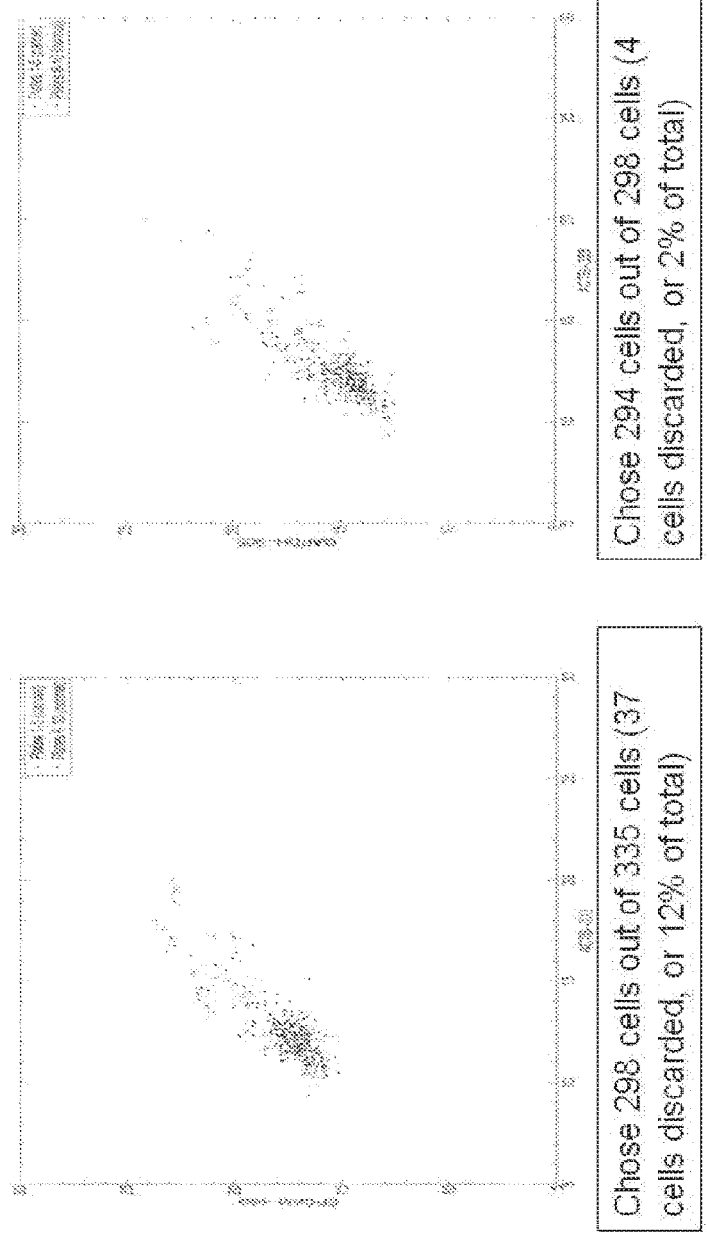

FIG. 385 selection of cells for single cell gene expression analysis. Cells were taken from normal mucosal biopsy or primary tumor. Cells from both samples were FACS sorted for EpCAM+/CD166+ cells. Out of 335 cells tested, 37 cells were discarded by examining EPCAM and ACTB gene expression levels, and 298 cells were selected. Of the 298 cells, 4 cells were further discarded by examining GAPDH and ACTB gene expression levels, and 294 cells were selected for further analysis.

Figure 386:
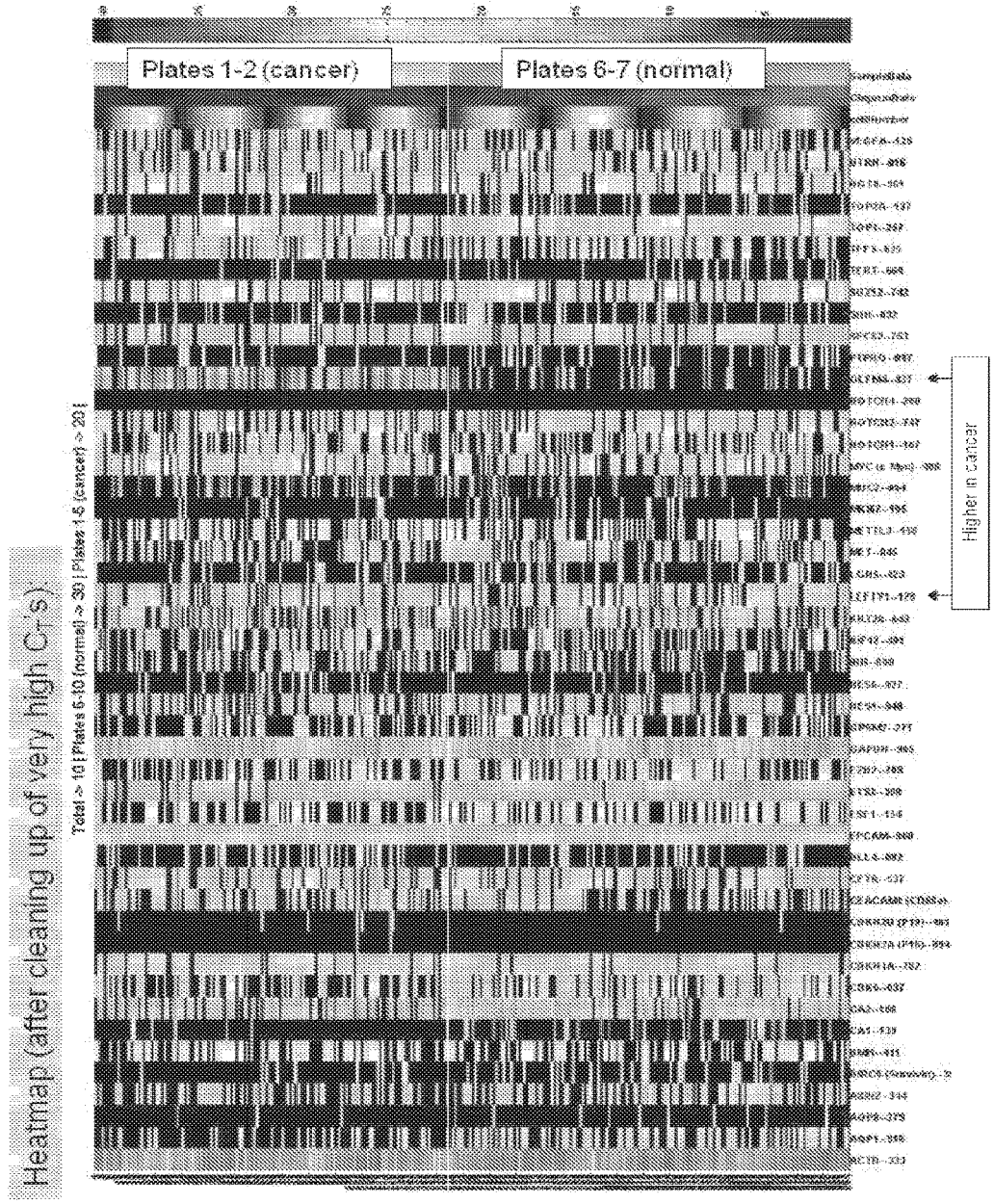

FIG. 386 a combined heat map after the clean up of unwanted cells.

Figure 387:
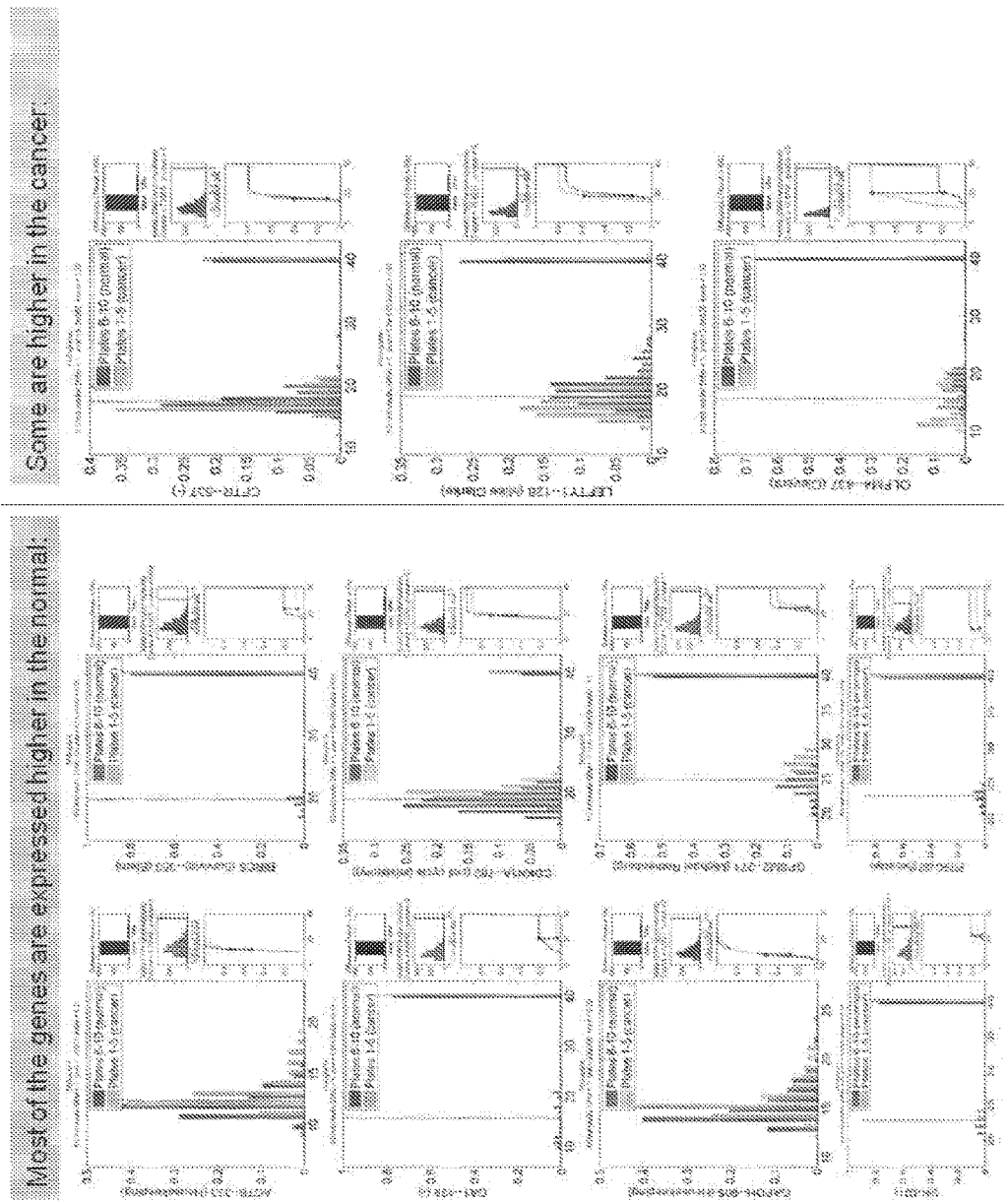

FIG. 387 histograms depicting gene expression levels in normal mucosa or in primary tumor cells are illustrated for the following genes: ACTB, CA1, GAPDH, SHH, BIRC5, CDKN1A, GPSM2, PRPRO, CFTR, LEFTY1, and OLFM.

Figure 388:
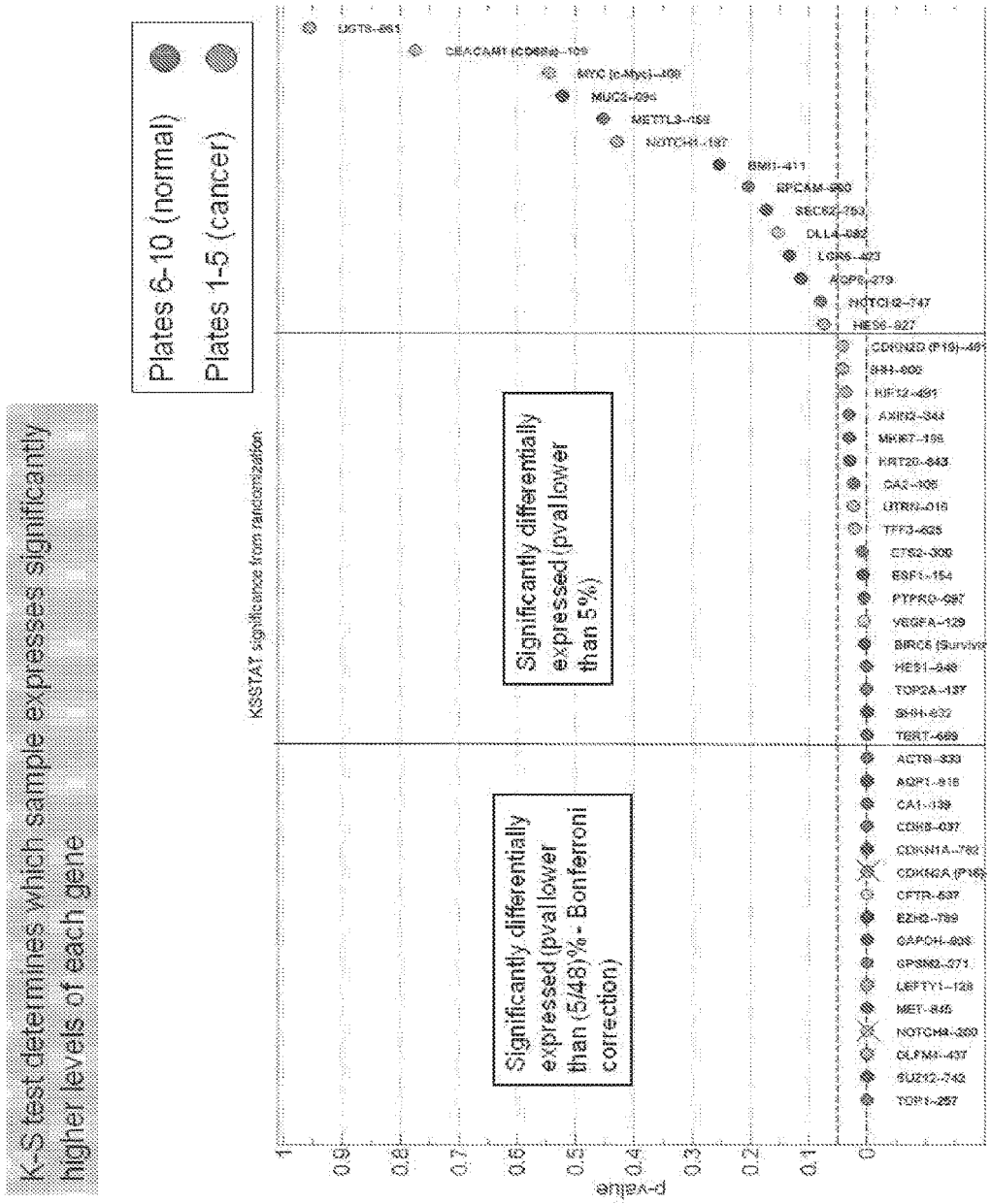

FIG. 388 Kolmogorov-Smirnov statistical significance test for genes expressed in normal or primary tumor cells identified samples expressing significantly higher levels of each gene.

Figure 389:
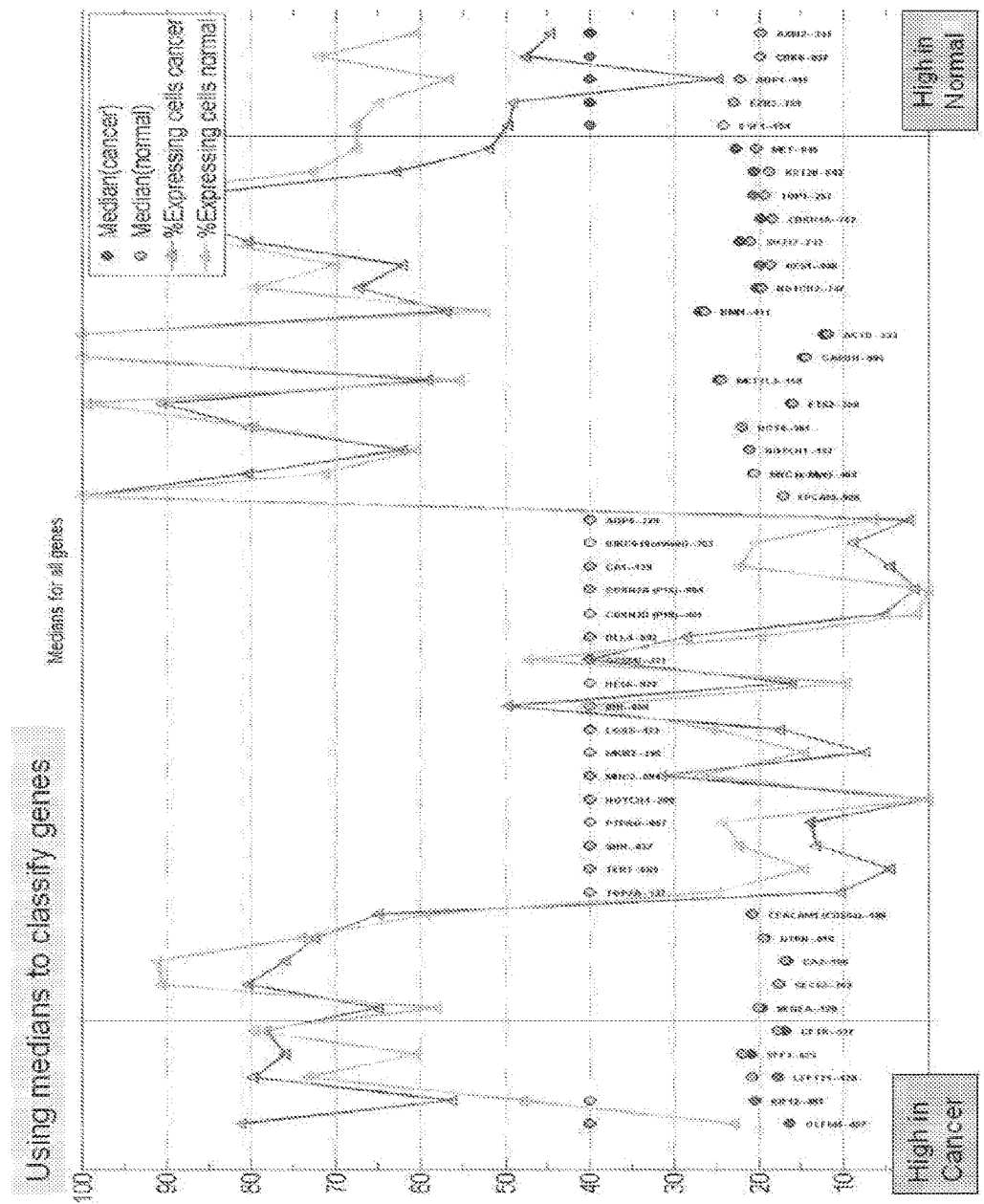

FIG. 389 genes classified using medians value.

Figure 390:
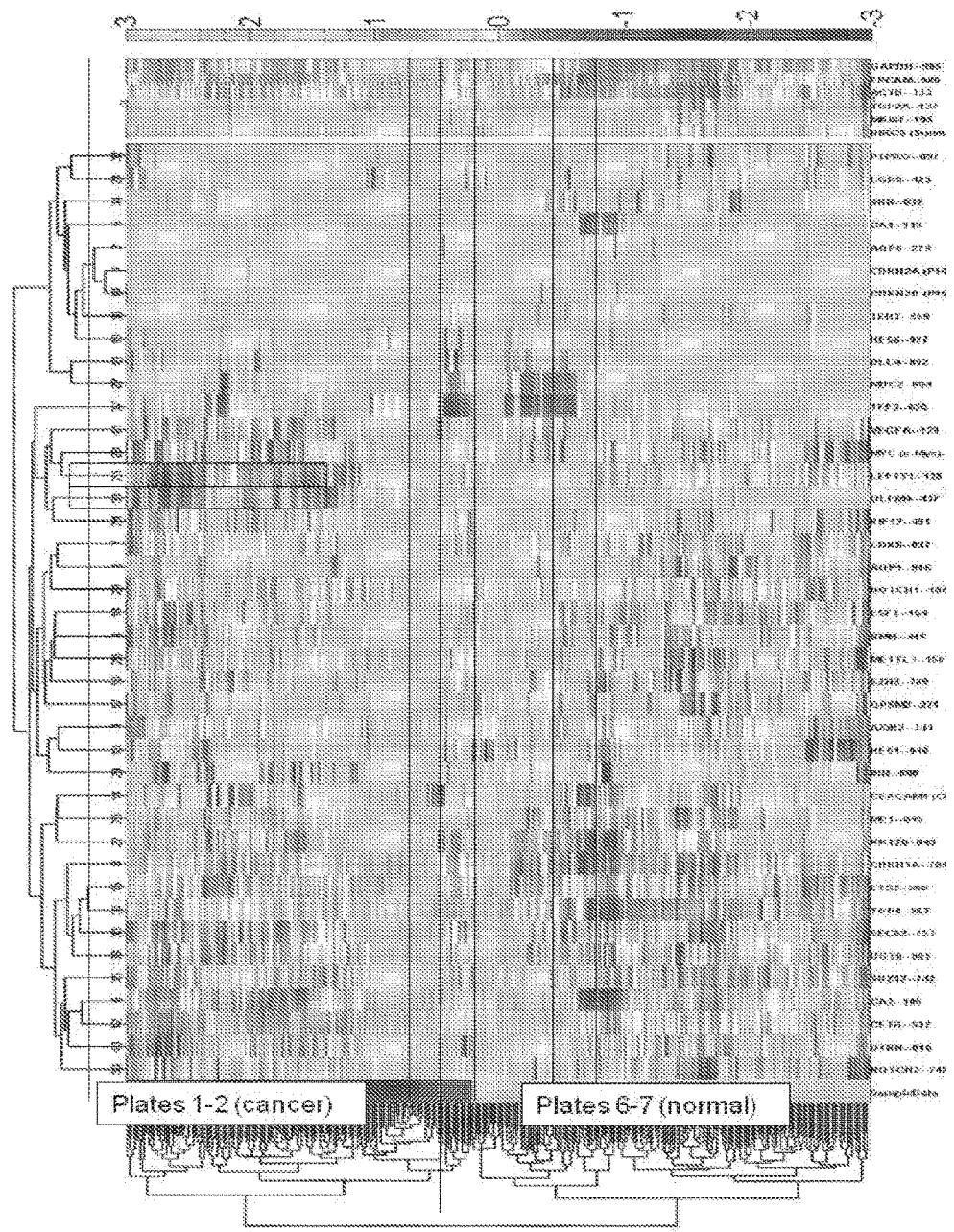

FIG. 390 a representative hierarchical clustering for cancer samples and normal samples.

Figure 391:
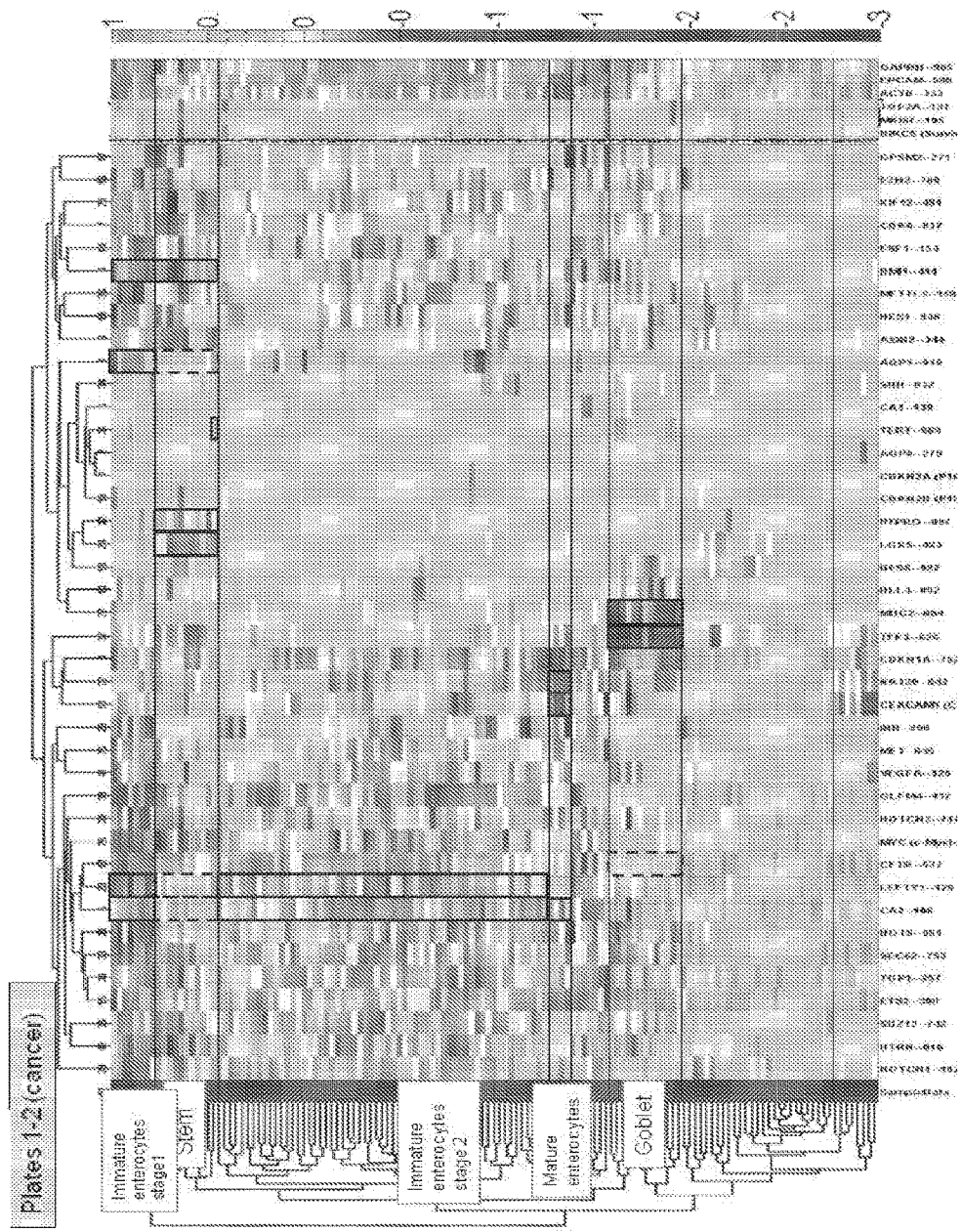

FIG. 391 a representative hierarchical clustering for cancer cells.

Figure 392:
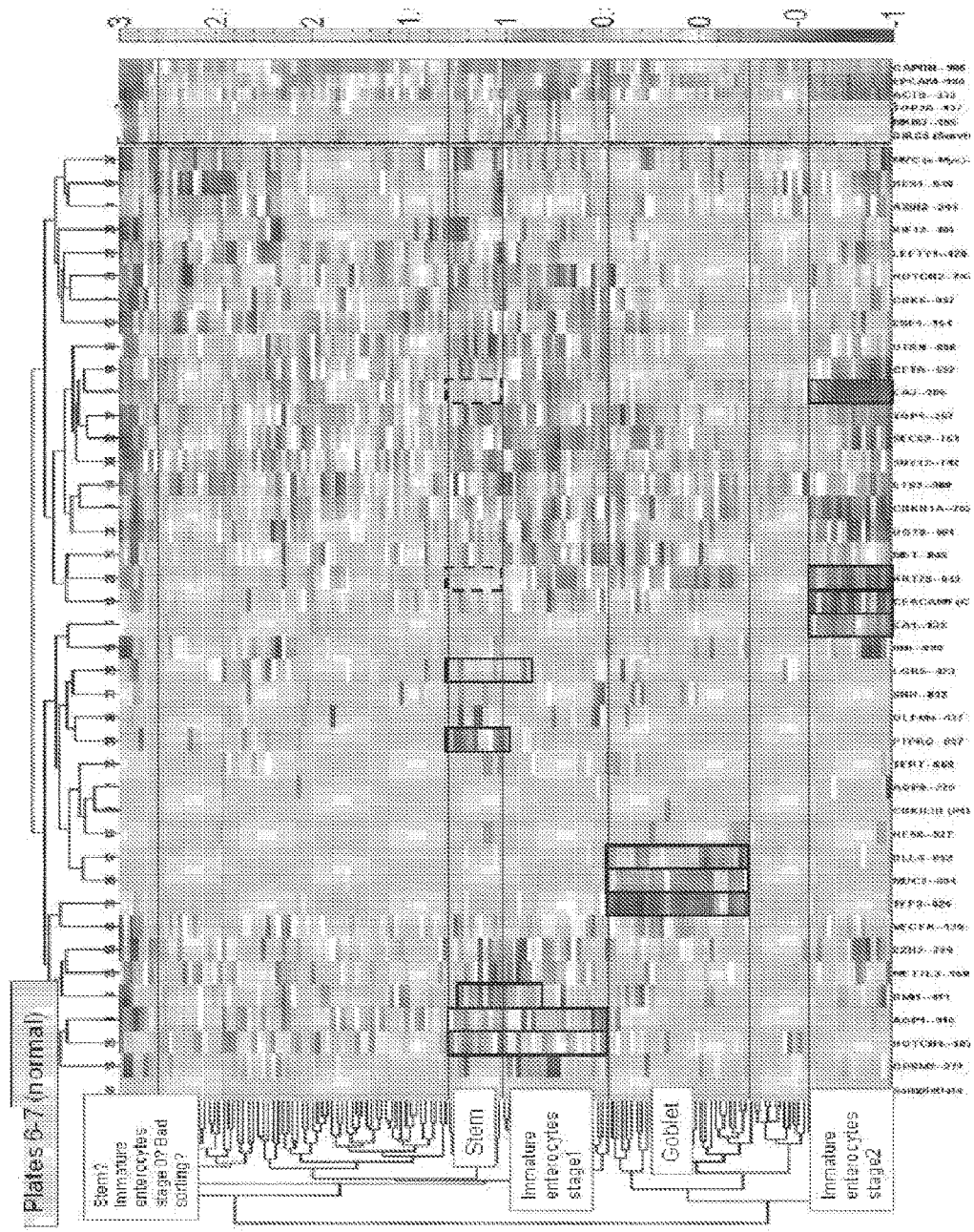

FIG. 392 a representative hierarchical clustering for normal cells.

Figure 393:
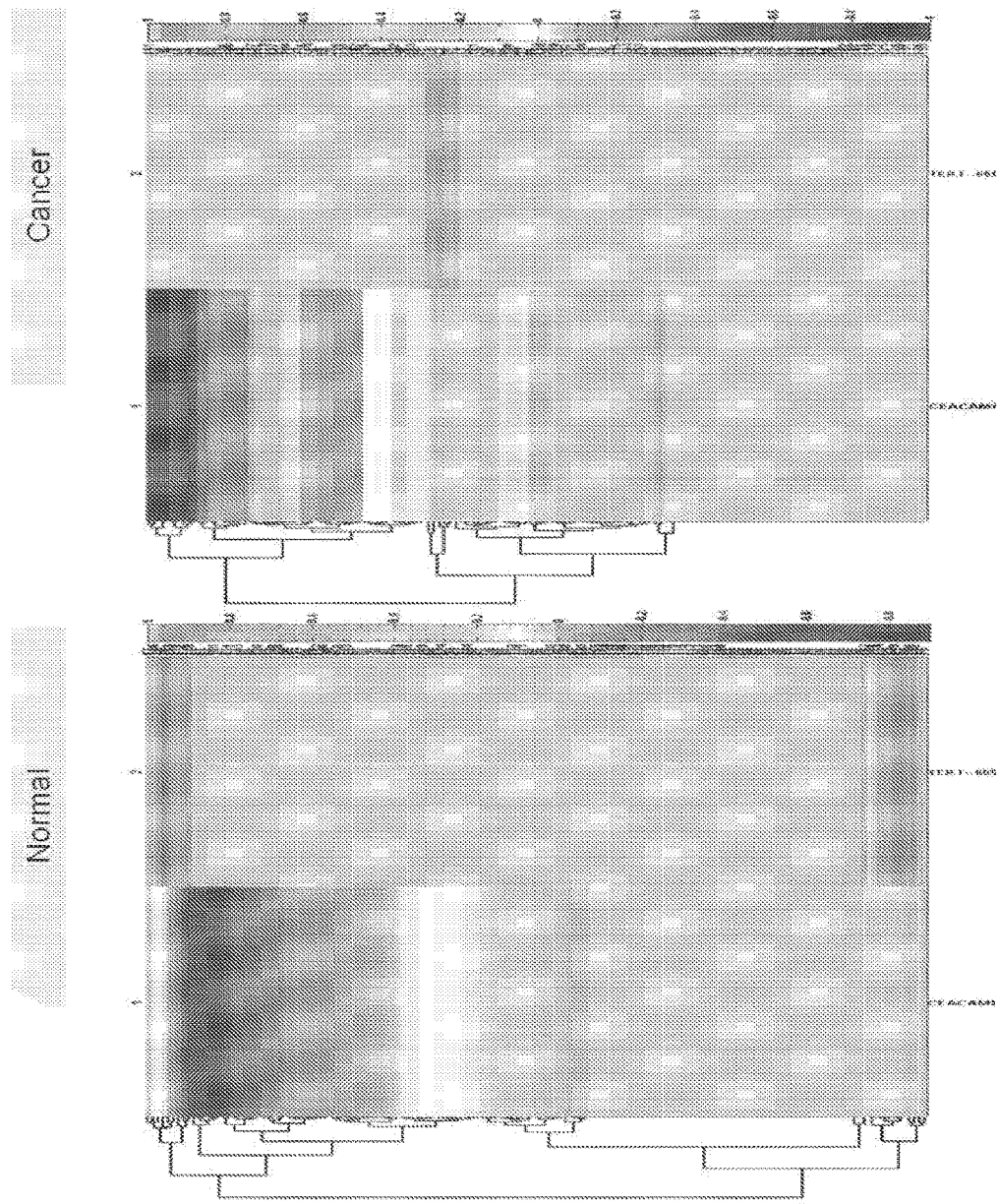

FIG. 393 a hierarchical clustering showing expression of CEACAM1 and TERT in normal or tumor sample.

FIG. 394 heat maps from 4 different chip-runs of samples. Cells were taken from two separate samples of mouse colons.

Figure 395:
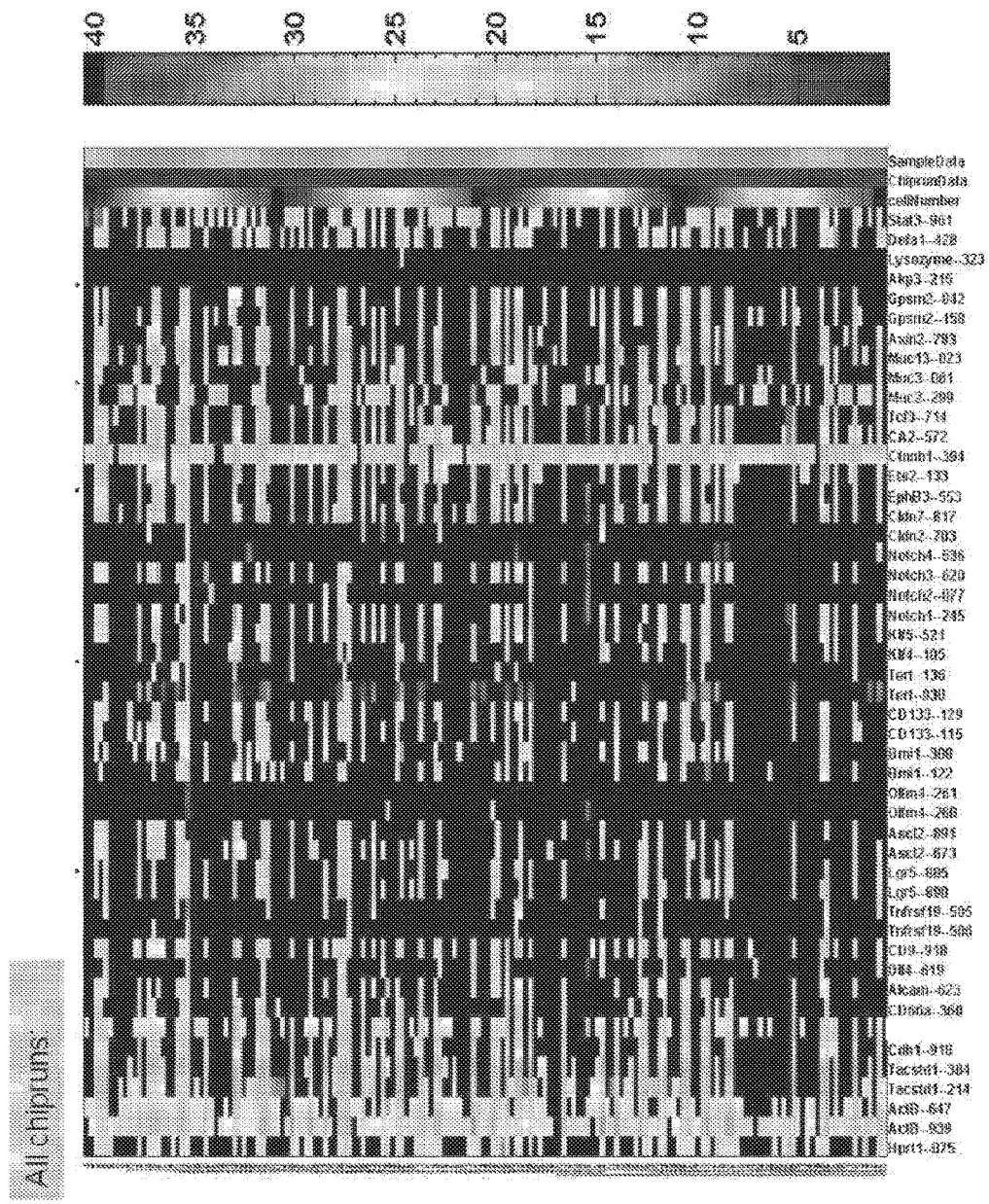

FIG. 395 a combined heat map comparing the 4 chip-runs.

Figure 396:
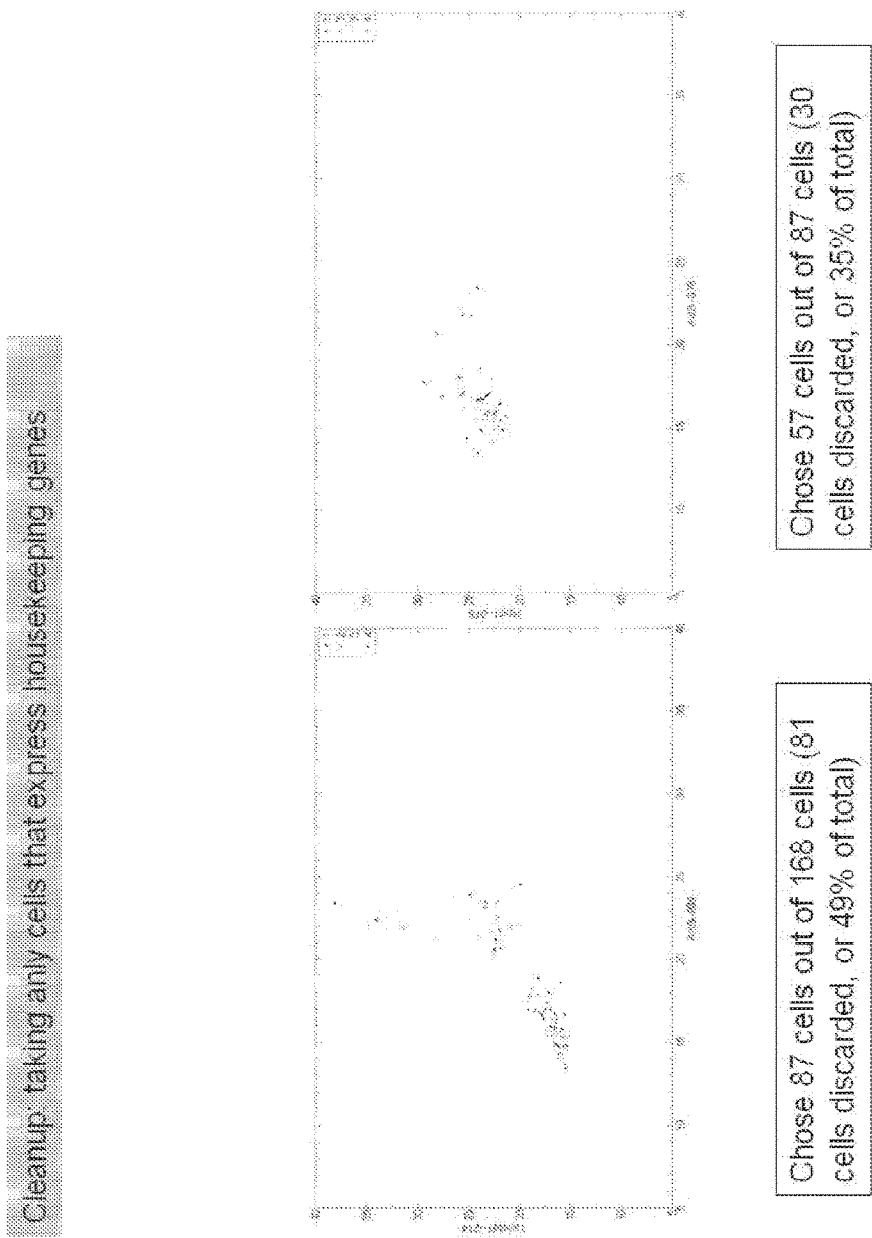

FIG. 396 selection of cells for single cell gene expression analysis. Out of 168 cells tested, 81 cells were discarded by examining TACSTD1 and ACTB gene expression levels, and 87 cells were selected. Of the 87 cells, 30 cells were further discarded by examining HPRT and ACTB gene expression levels, and 57 cells were selected for further analysis.

Figure 397:

FIG. 397 a combined heat map after the clean up of unwanted cells.

Figure 398:
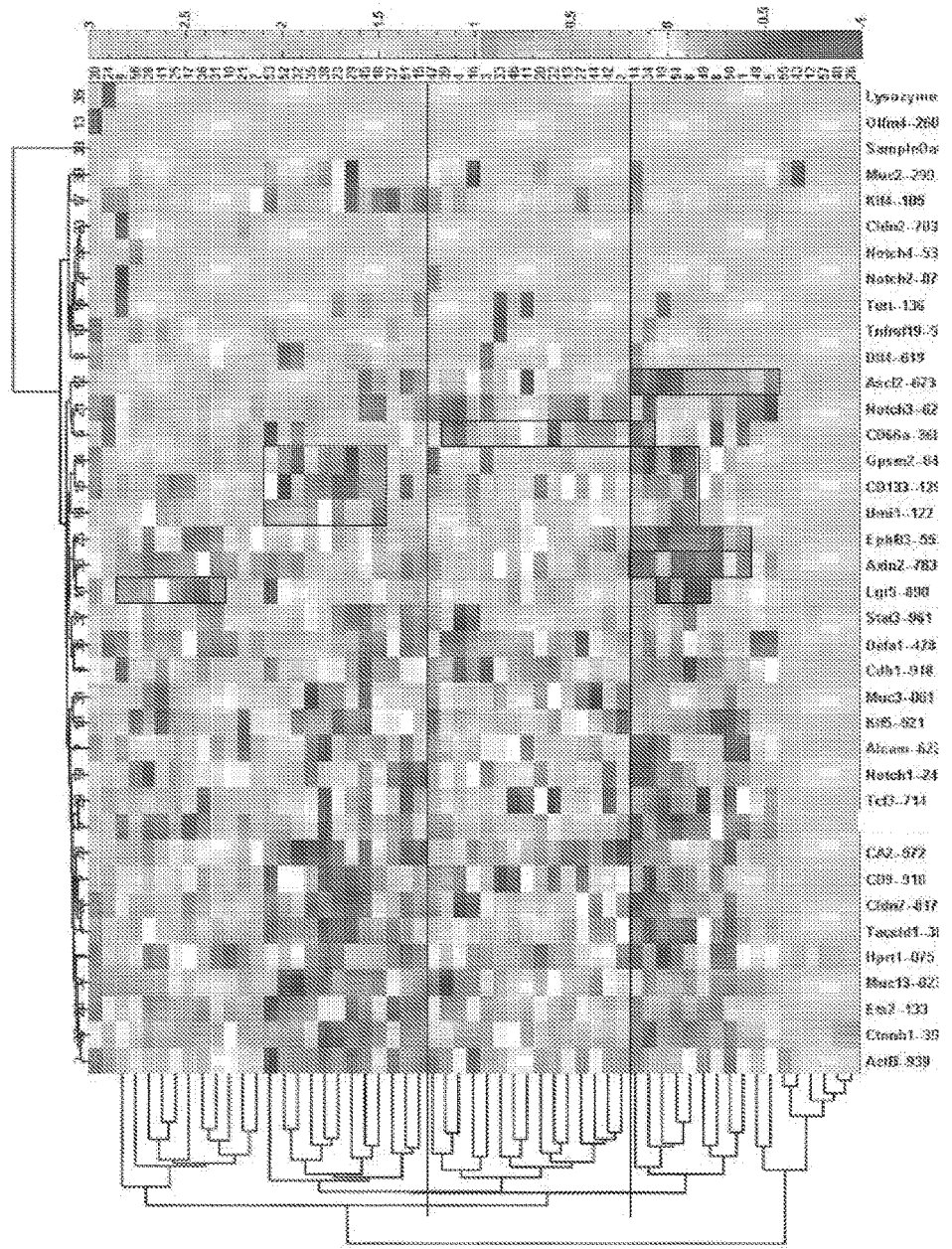

FIG. 398 a representative mean-centered standard normalized clustering.

Figure 399:
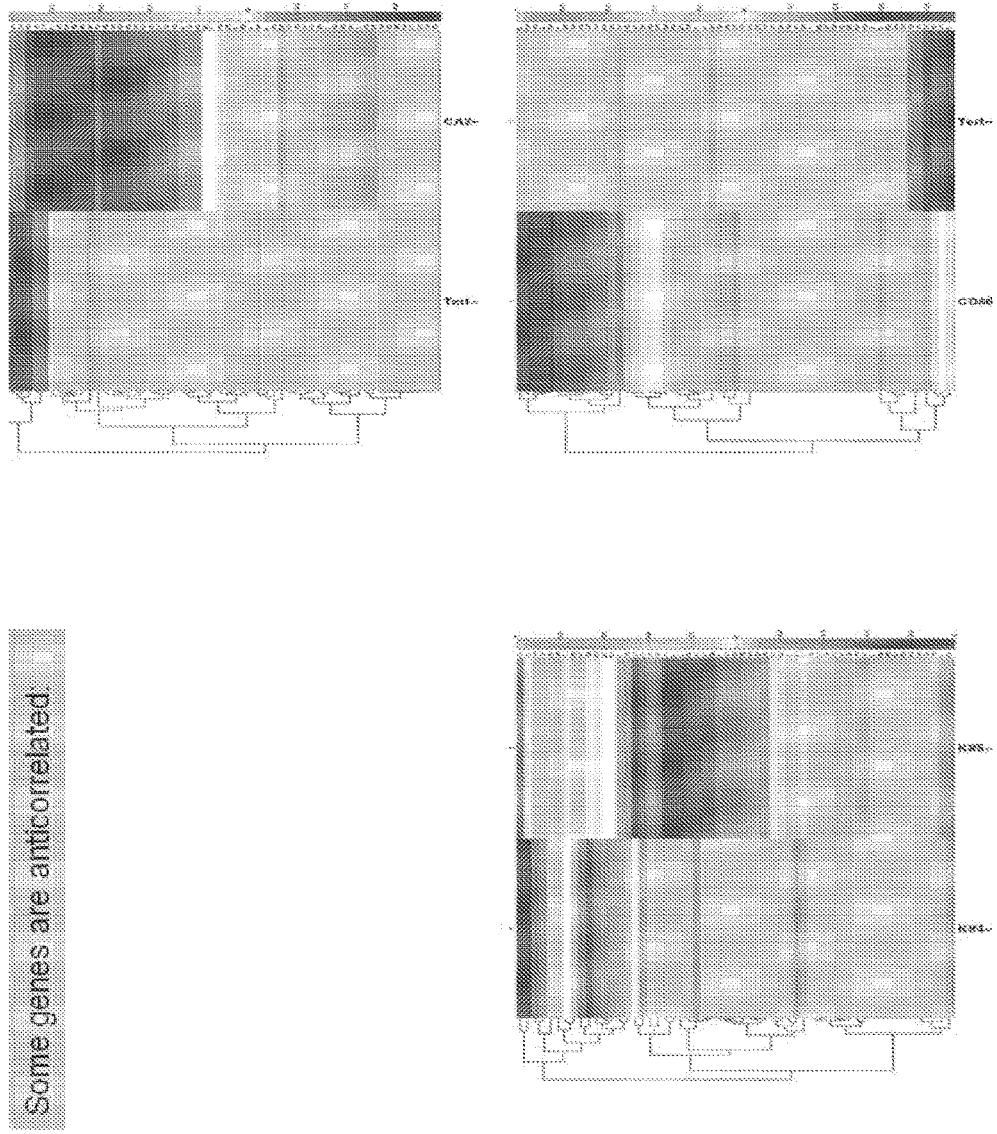

FIG. 399 some anti-correlated gene pairs were identified, including TERT and CA2, KLF4 and KLF5, CD66 and TERT.

Figure 400:
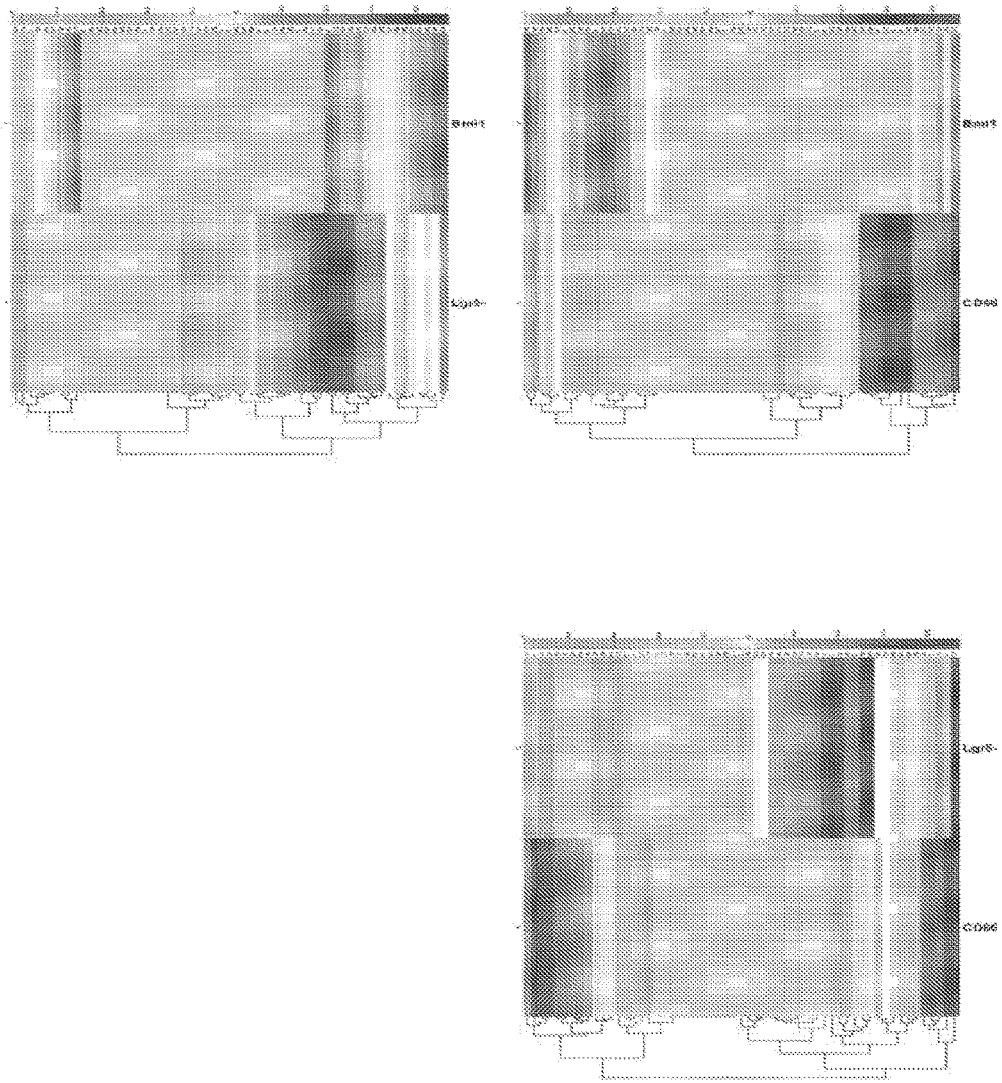

FIG. 400 some anti-correlated gene pairs were identified, including BMI1 and LGF5, LGR5 and CD66, and CD66 and BMI1.

Figure 401:
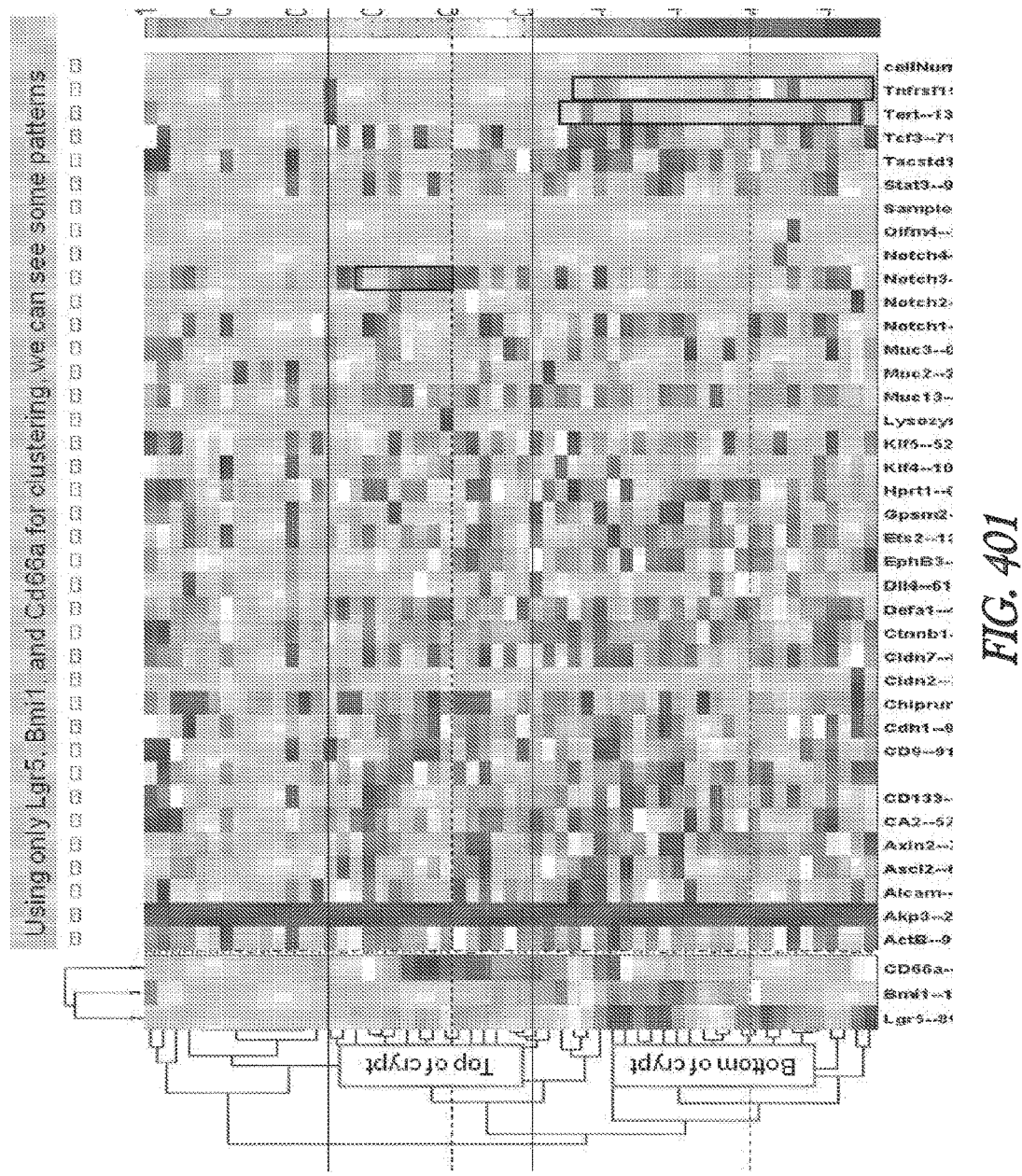

FIG. 401 a hierarchical clustering showing only LGR5, BMI1, and CD66a.

Figure 402:
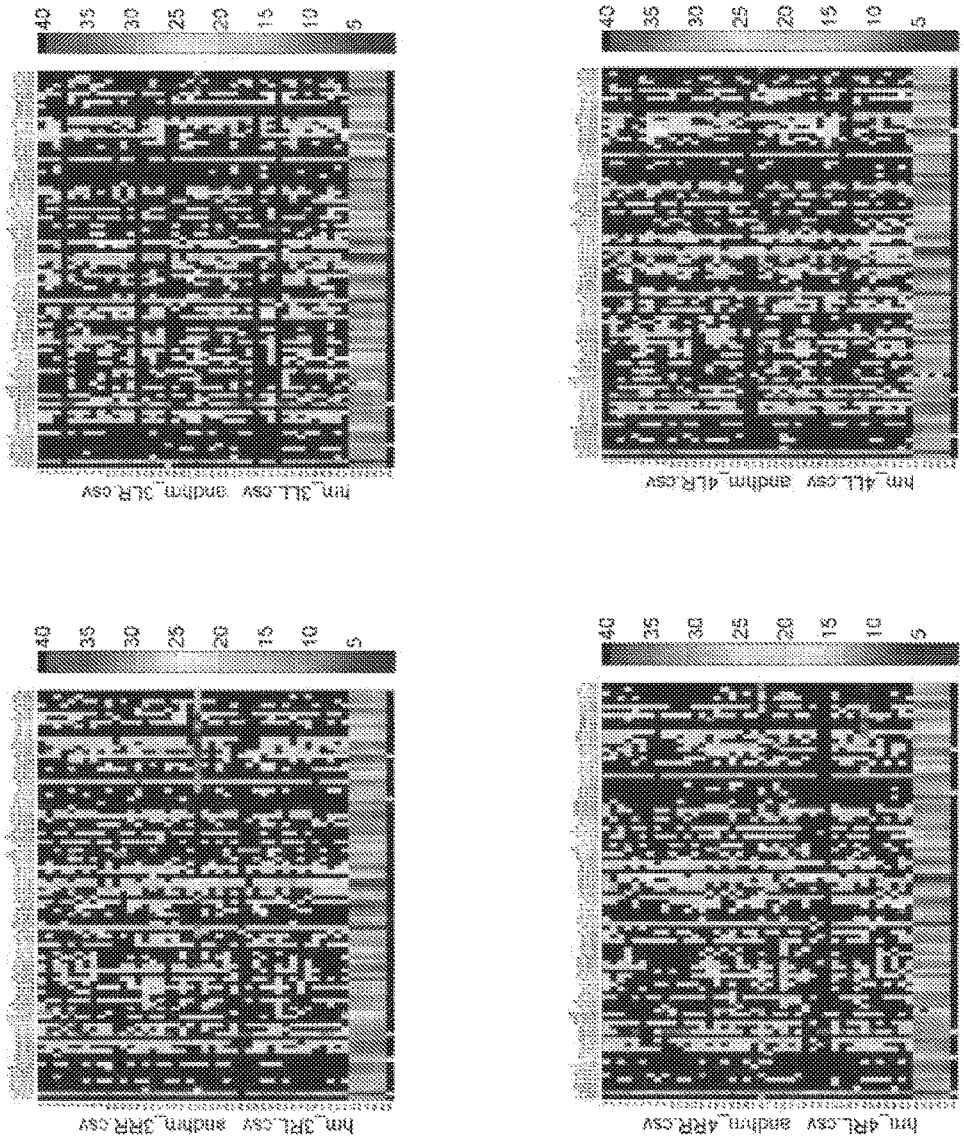

FIG. 402 heat maps from 4 different chip-runs of samples. Cells were taken from normal mammary epithelium. The cells were FACS sorted with EpCAM, Lin, and CD49f. Total epithelial cells were defined as EpCAM+/Lin–/CD49f+ cells Unknown stromal cells were defined as EpCAM–/Lin–/CD49f– cells.

Figure 403:

FIG. 403 a combined heat map comparing the 4 chip-runs.

Figure 404:
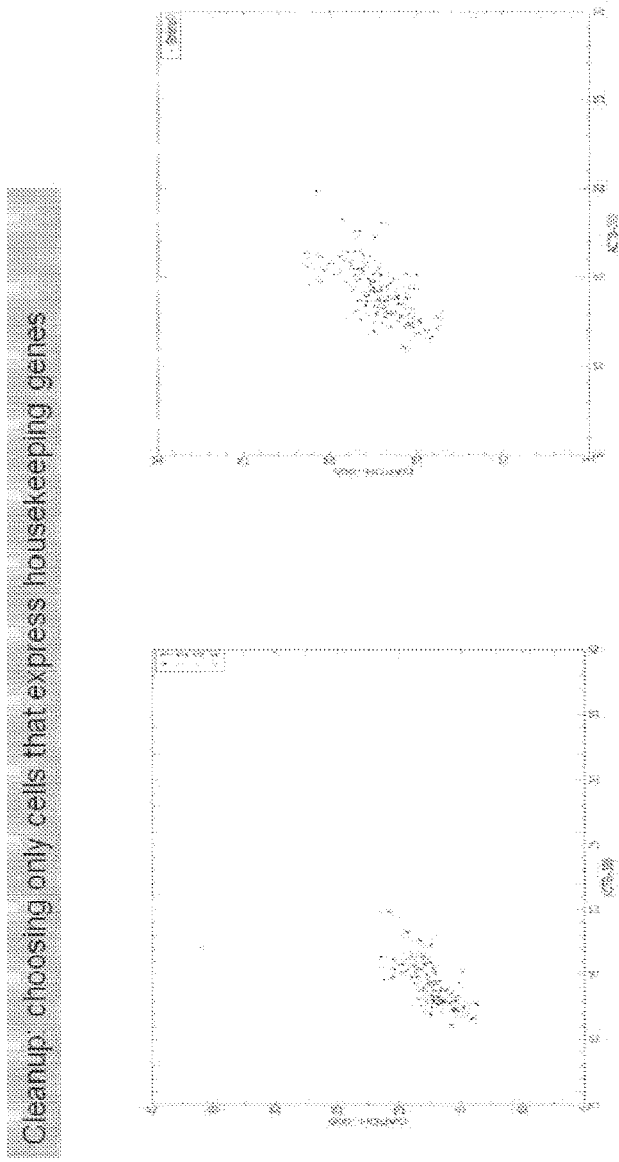

FIG. 404 selection of cells for single cell gene expression analysis. Out of 168 cells tested, 9 cells were discarded by examining GAPDH and ACTB gene expression levels, and 159 cells were selected for further analysis.

Figure 405:

FIG. 405 a combined heat map after the clean up of unwanted cells.

Figure 406:
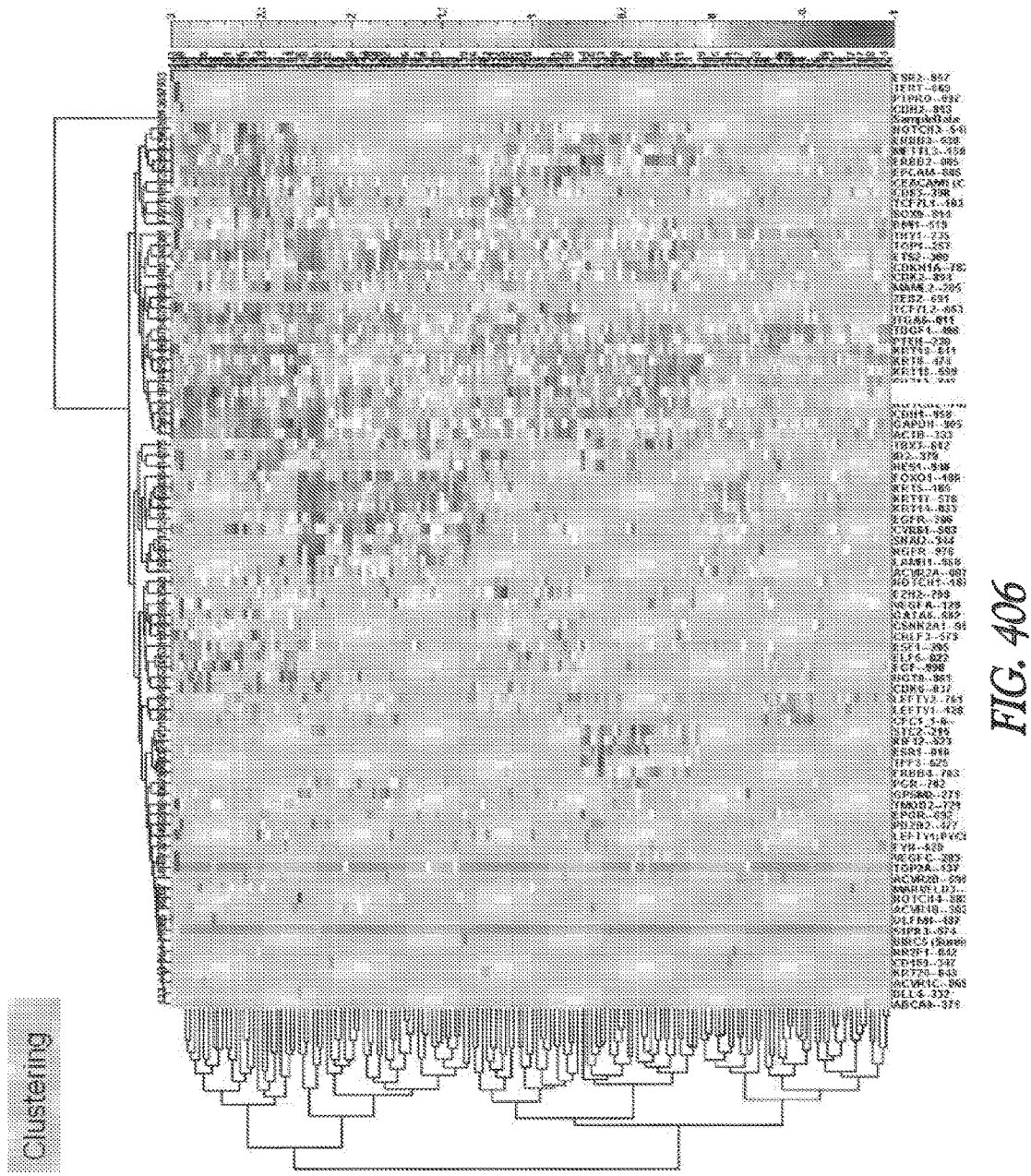

FIG. 406 a representative hierarchical clustering.

Figure 407:
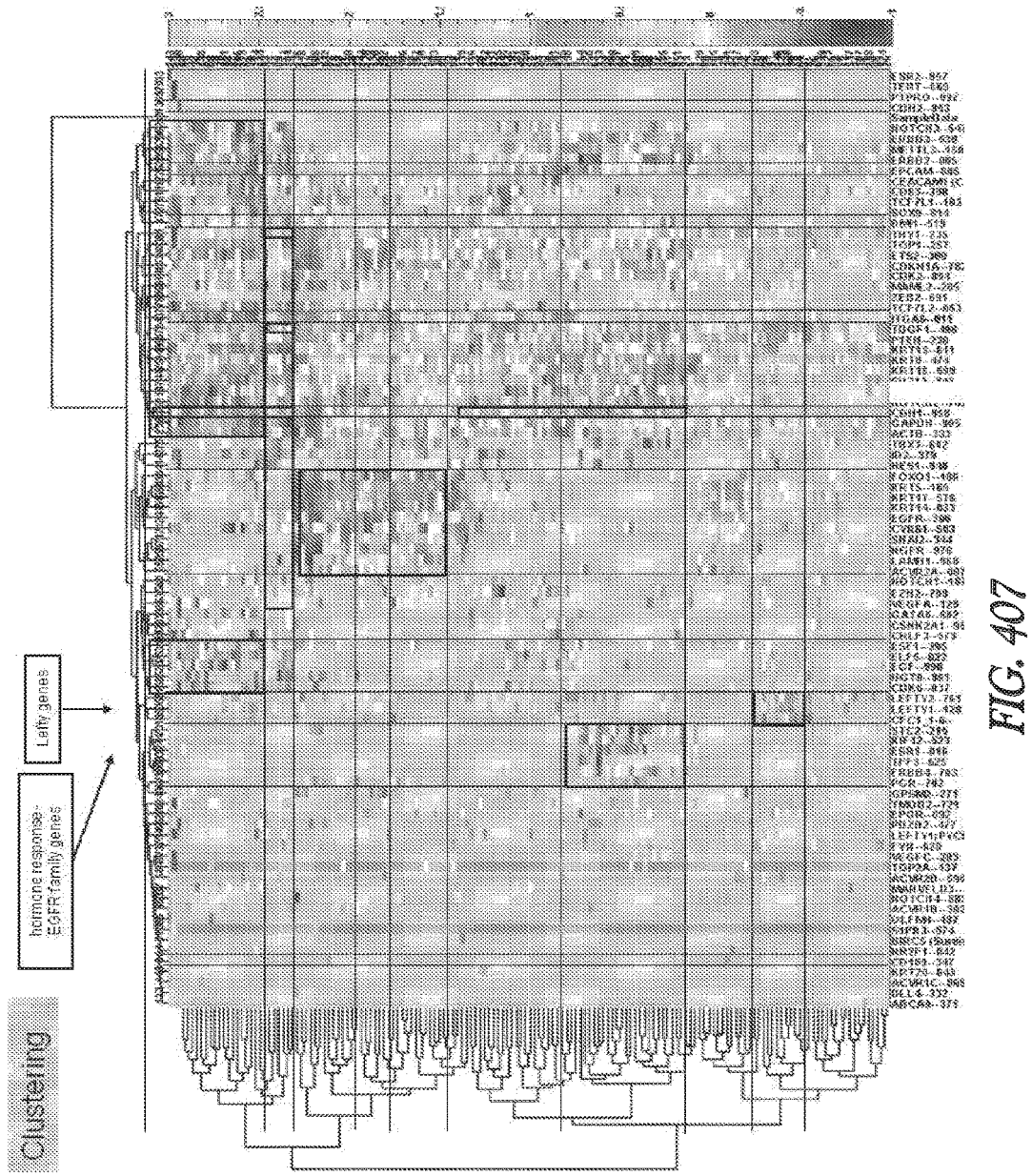

FIG. 407 a representative hierarchical clustering, showing hormone response EGFR family genes and LEFTY gene.

Figure 408:
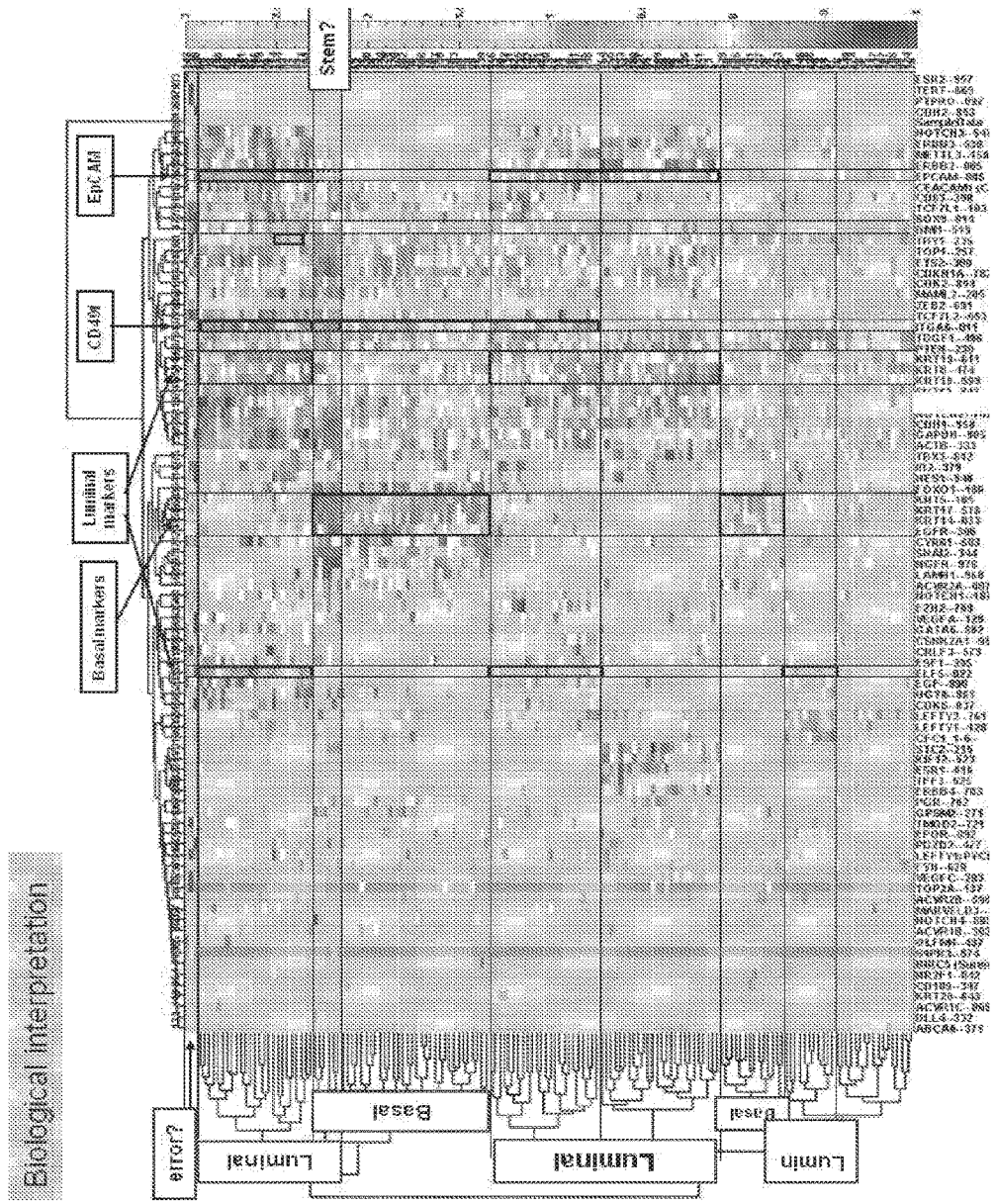

FIG. 408 a representative hierarchical clustering, showing basal markers, luminal markers, CD49f and EpCAM.

Figure 409:
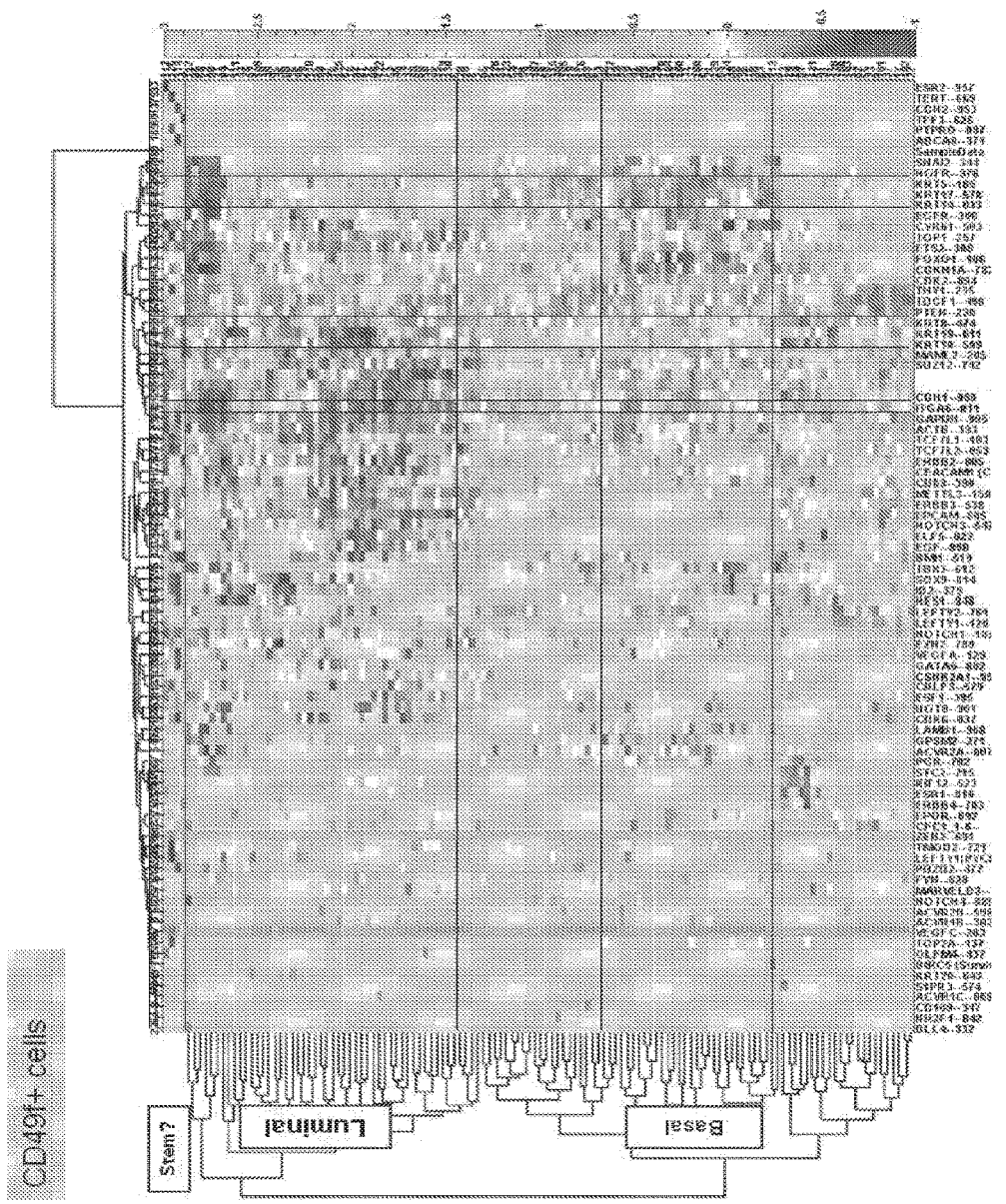

FIG. 409 a representative hierarchical clustering, showing CD49f+ only.

Figure 410:
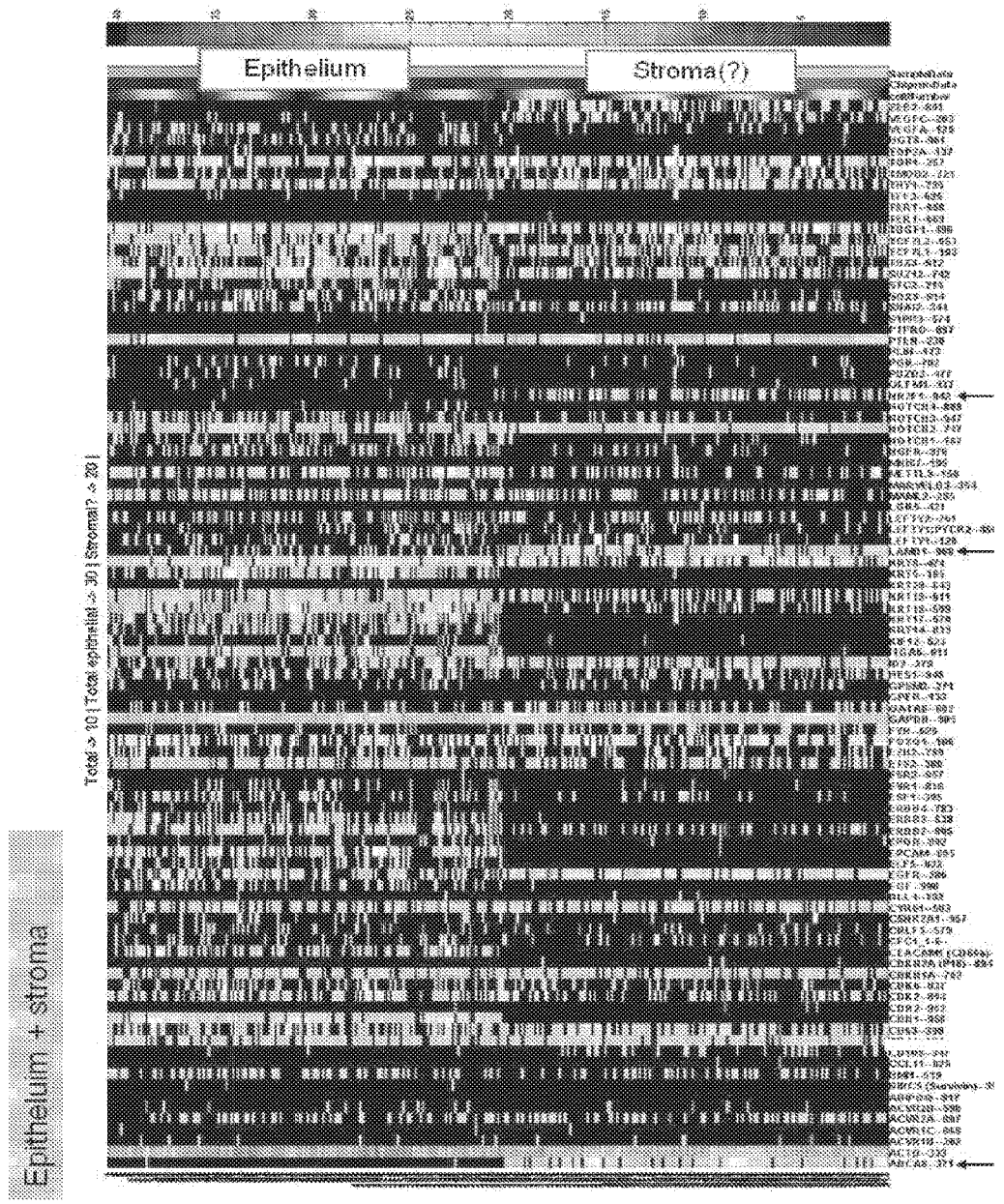

FIG. 410 a heat map of samples obtained from epithelium and stroma.

Figure 411:
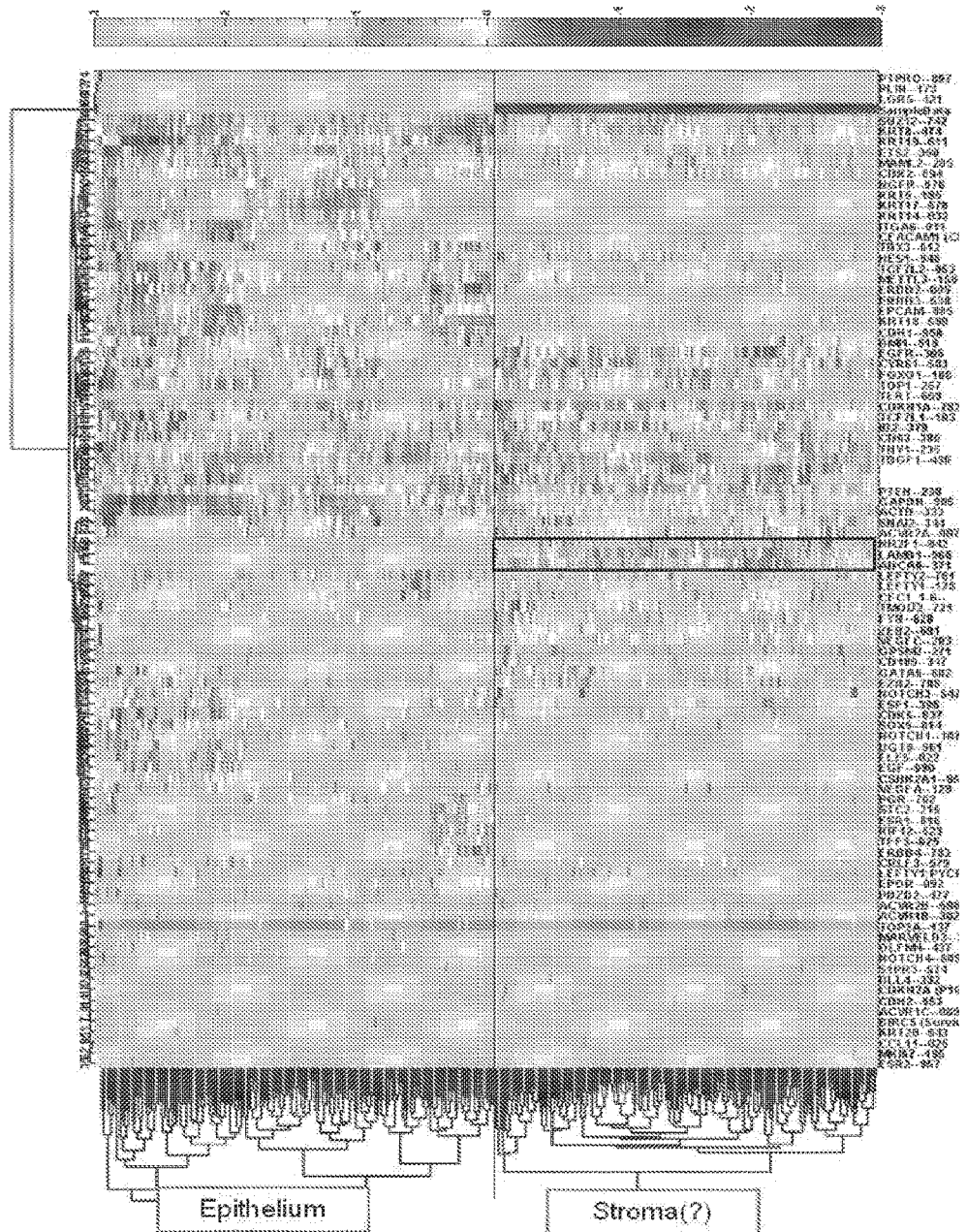

FIG. 411 a representative hierarchical clustering of FIG. 410.

Figure 412:
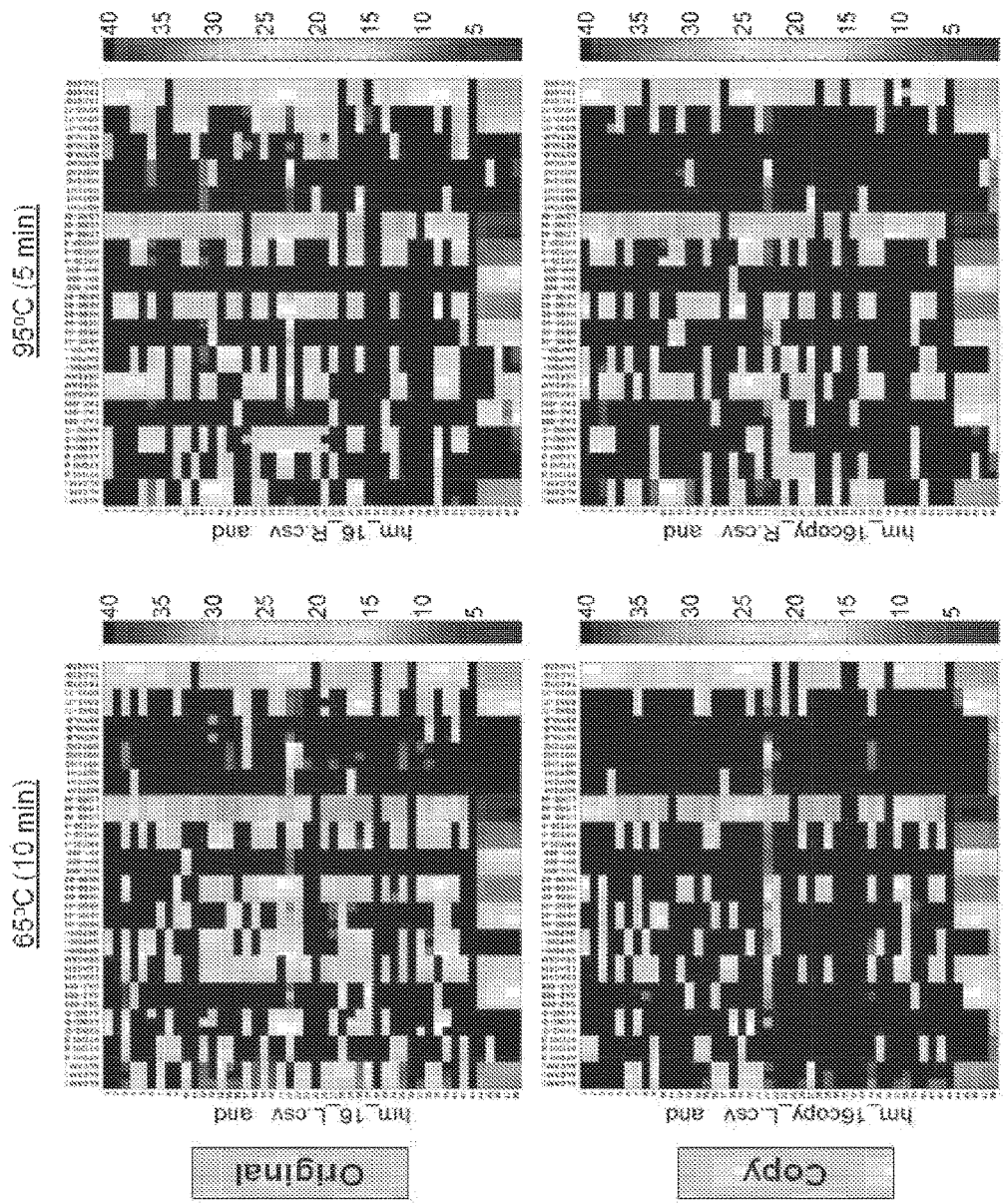

FIG. 412 heat maps from 4 different chip-runs of samples. Cells were obtained from a xenograft (m10). The cells were FACS sorted with EGFP and CD66a. Mature non-tumorigenic cells were defined as EGFP+/CD66a+ cells. CoCSC cells were defined as EGFP+ cells. The FACS sorted cells were subjected to a set of different experimental conditions: 5 ul of sort-mix with 0.025% Tween-20 (to examine if addition of Tween-20 is helpful); heated to 65° C. for 10 minutes or to 95° C. for 5 minutes. The sample was then split into an "original" and a "copy." Standards were added a day before the experiments and refroze. Heat maps from the first run of three sets in two different conditions (65° C., 10 min or 95° C., 5 min) are shown.

Figure 413:
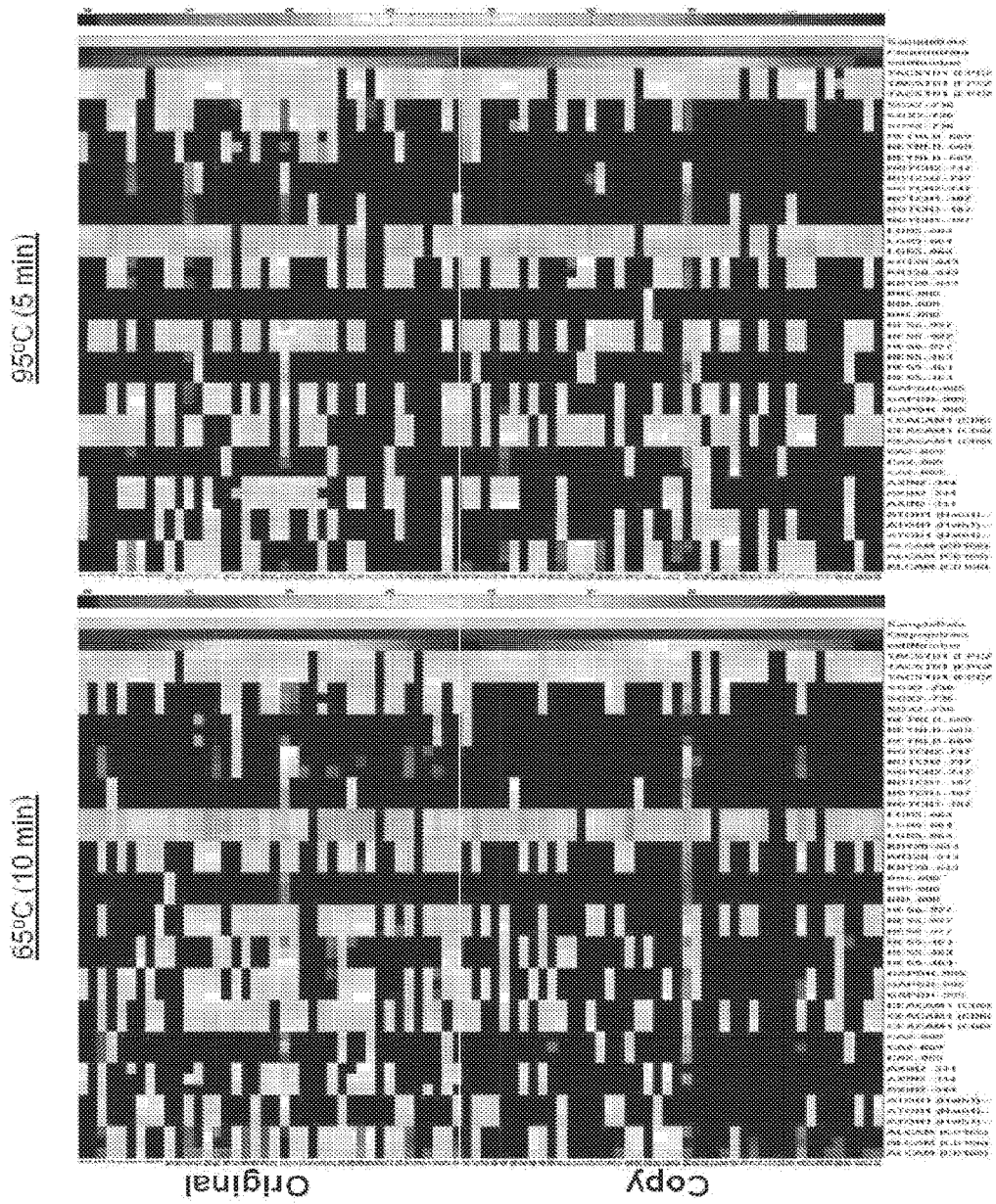

FIG. 413 a second set of heat maps from the experiments as described in FIG. 412.

Figure 414:
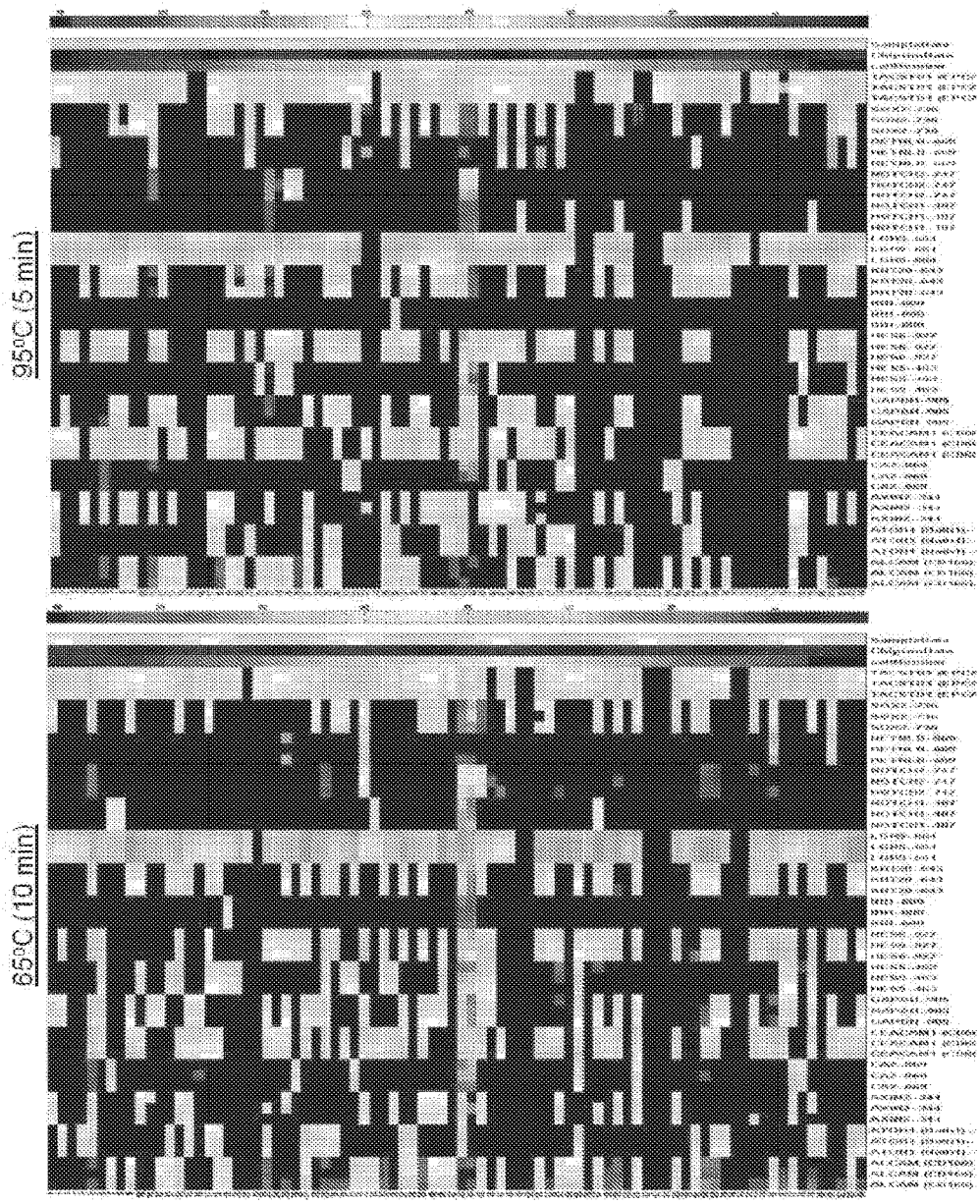

FIG. 414 a third set of heat maps from the experiments as described in FIG. 412.

Figure 415:
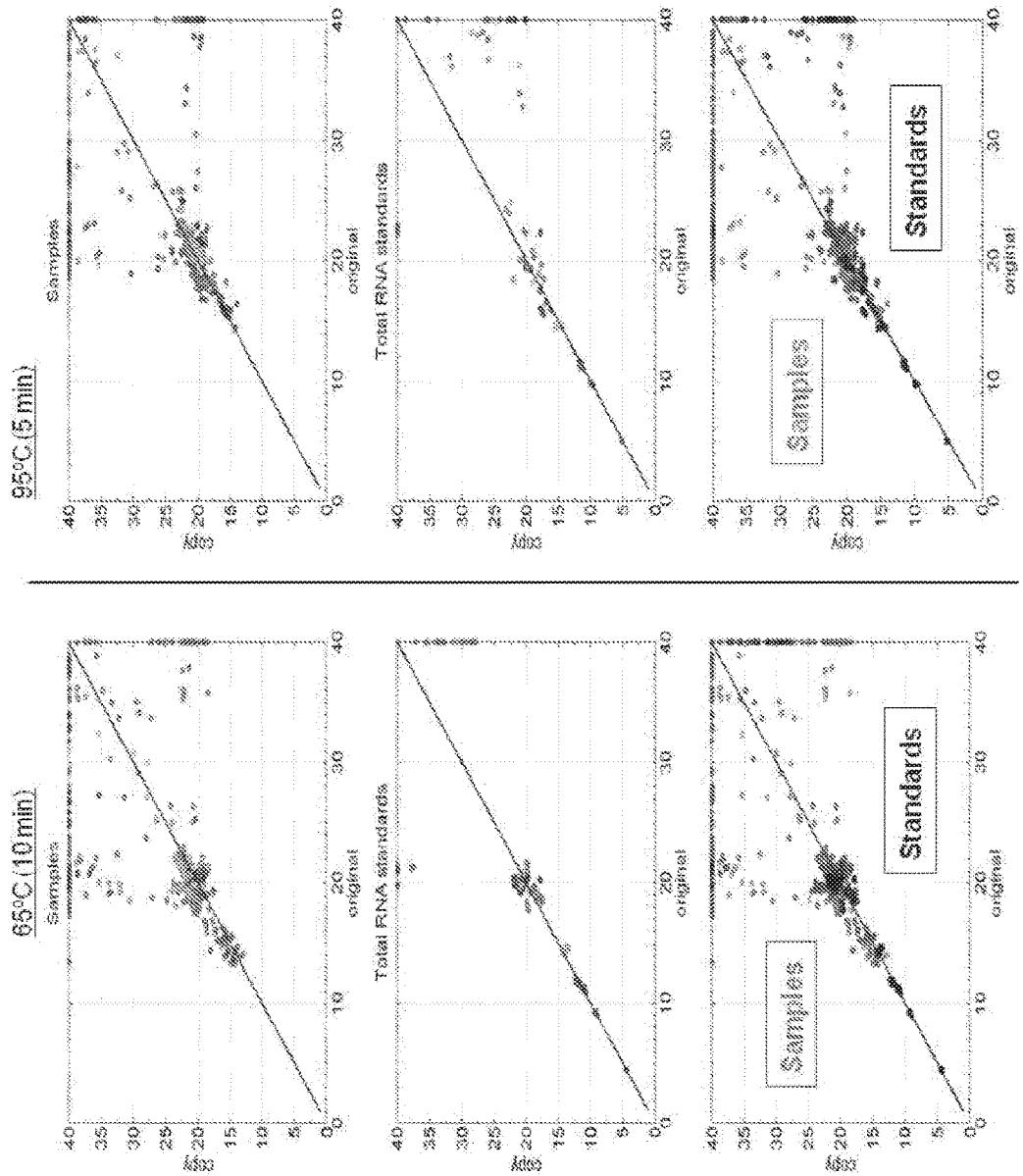

FIG. 415 standard curves showing linearity of qPCR.

Figure 416:
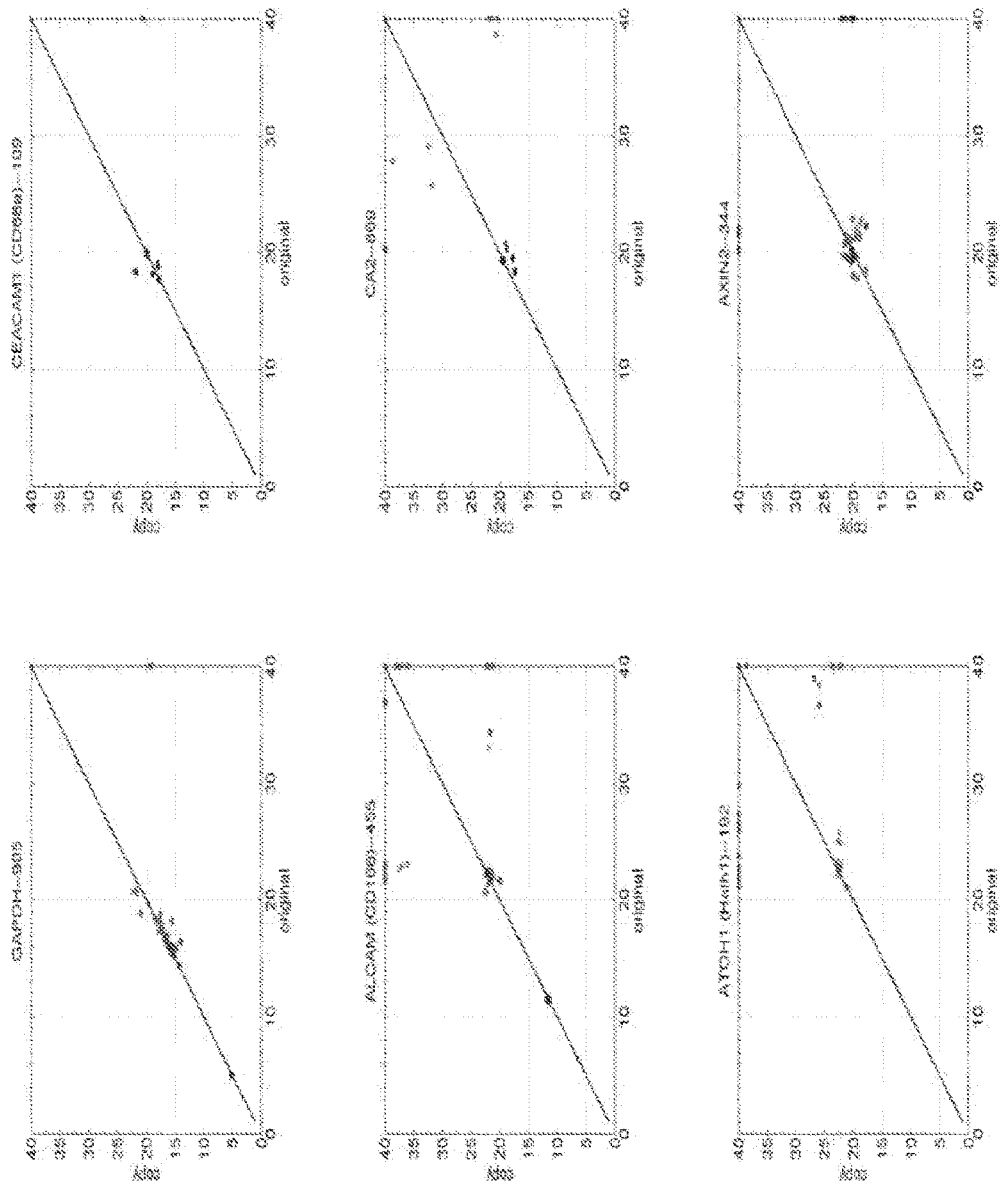

FIG. 416 levels of gene expressions between the original and copy are shown for certain genes including GAPDH, ALCAM, ATOH1, AXIN2, CA2, and CECAM1.

Figure 417:
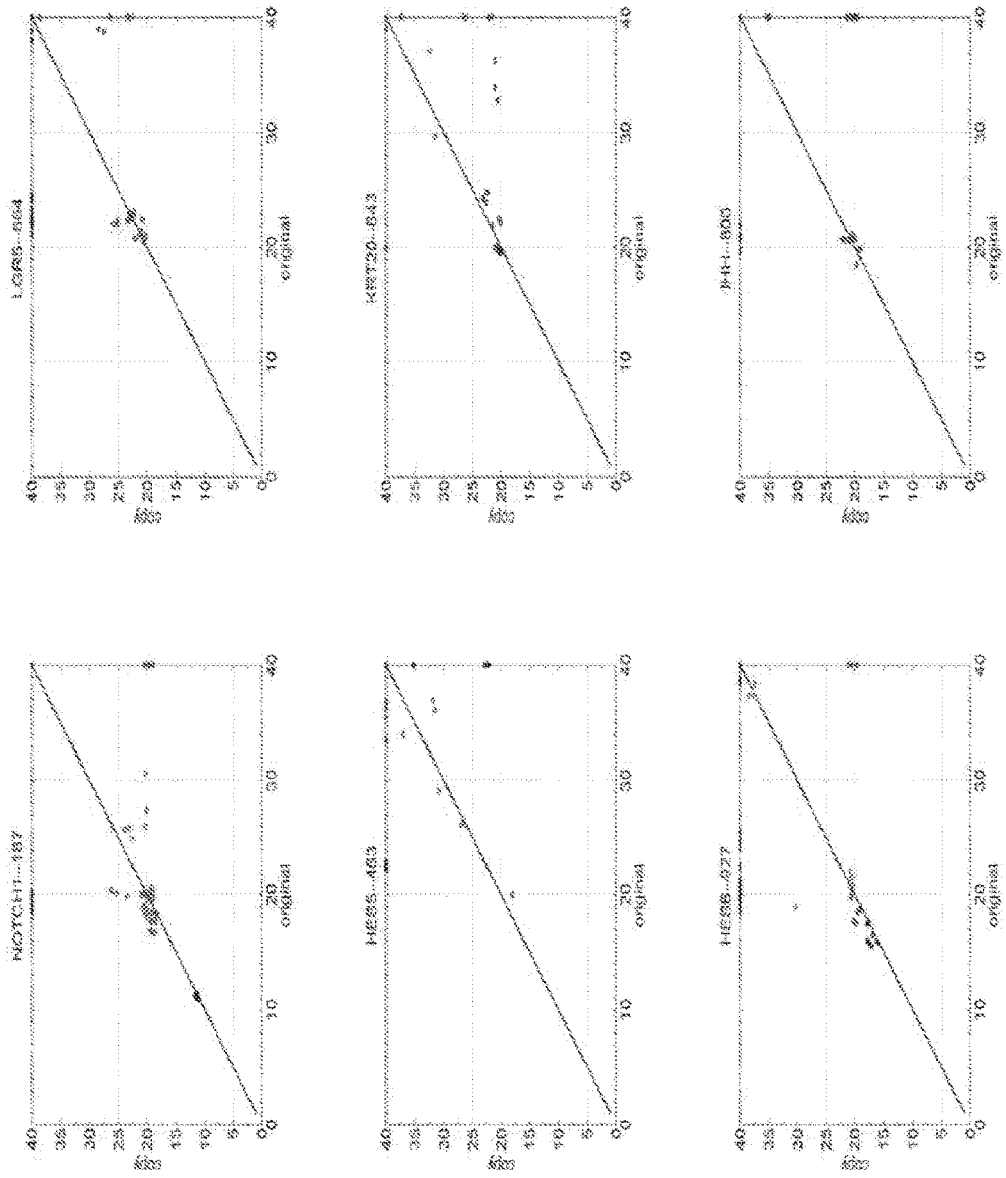

FIG. 417 levels of gene expressions between the original and copy are shown for certain genes including, NOTCH1, LGF5, HESS, KRT20, HES6, and IHH.

Figure 418:
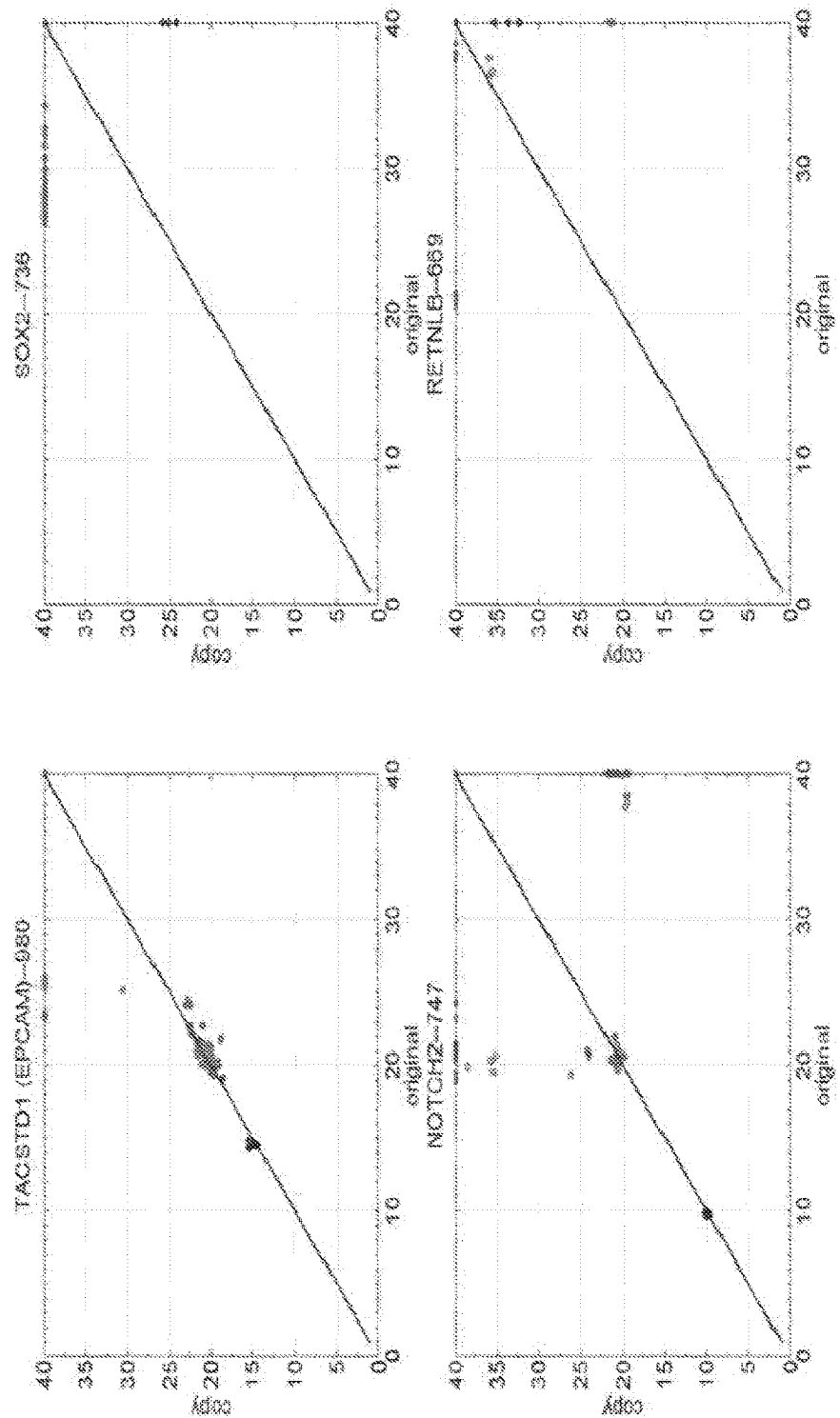

FIG. 418 levels of gene expressions between the original and copy are shown for certain genes including TACSTD1, SOX2, NOTCH2, and RETNLB.

Figure 419:
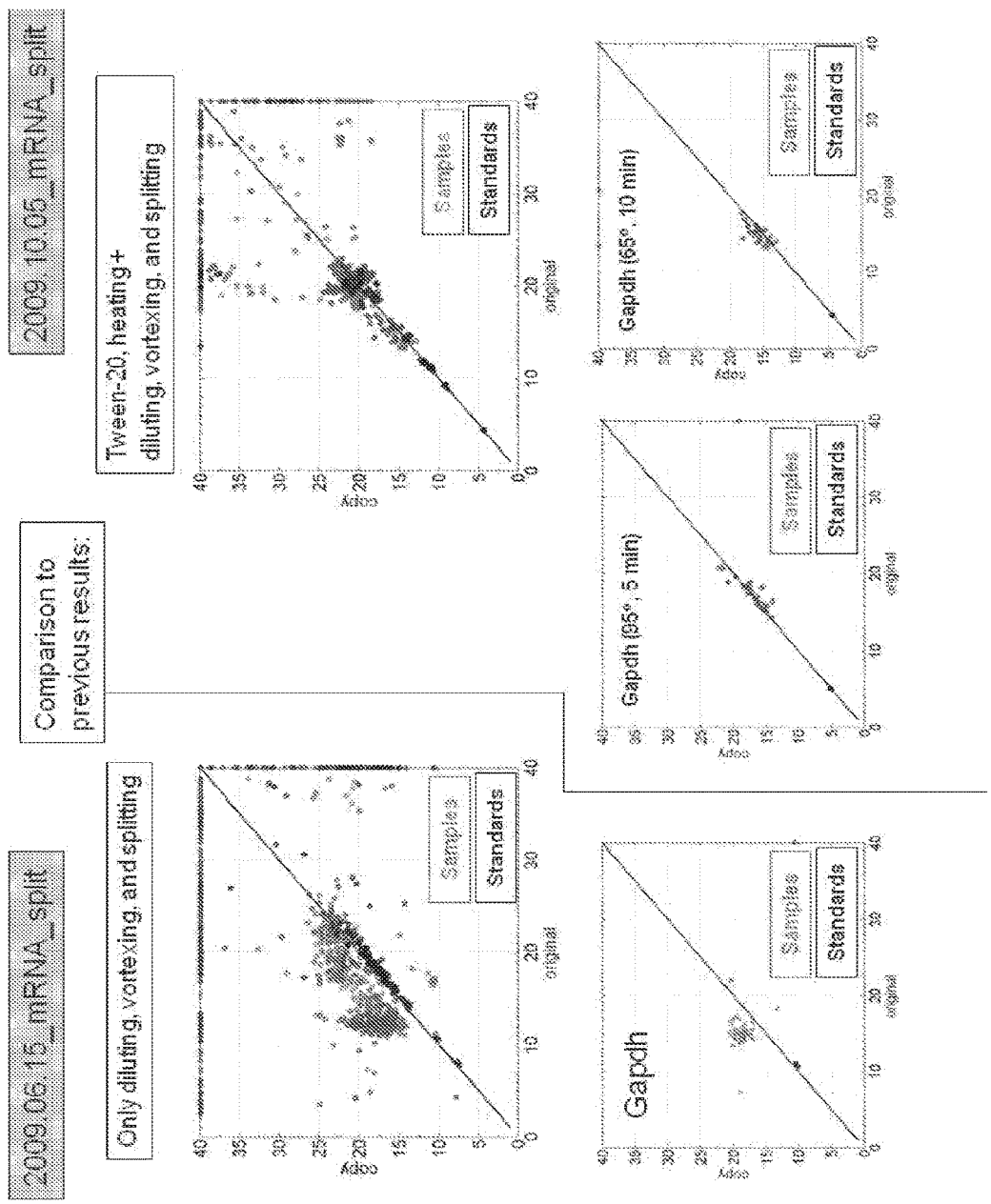

FIG. 419 comparison between results obtained in an independently performed set of experiments.

Figure 420:
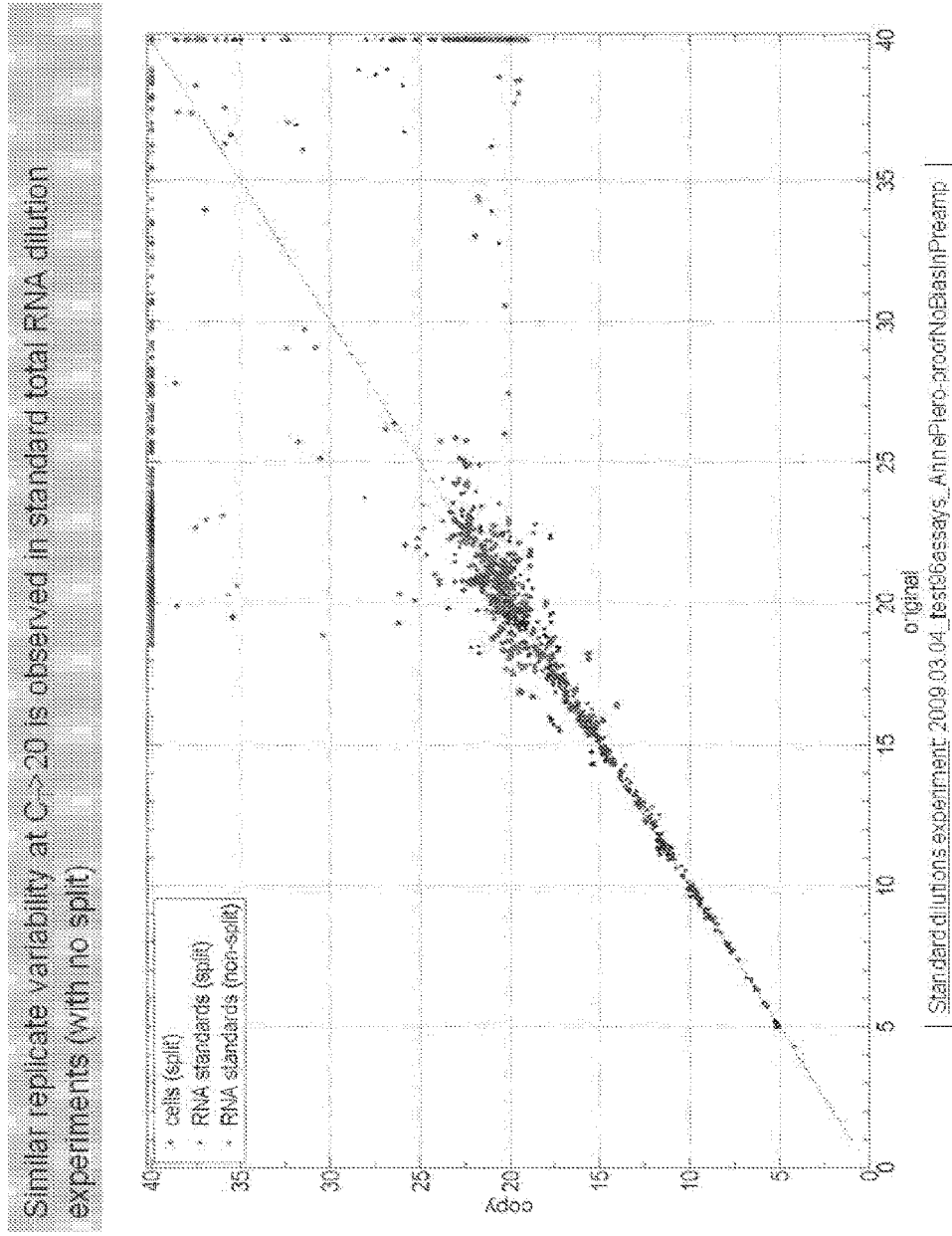

FIG. 420 that without mRNA split, similar replicate variability where $C_T$ is less then 20 is observed in standard total RNA dilution experiments.

Figure 421:
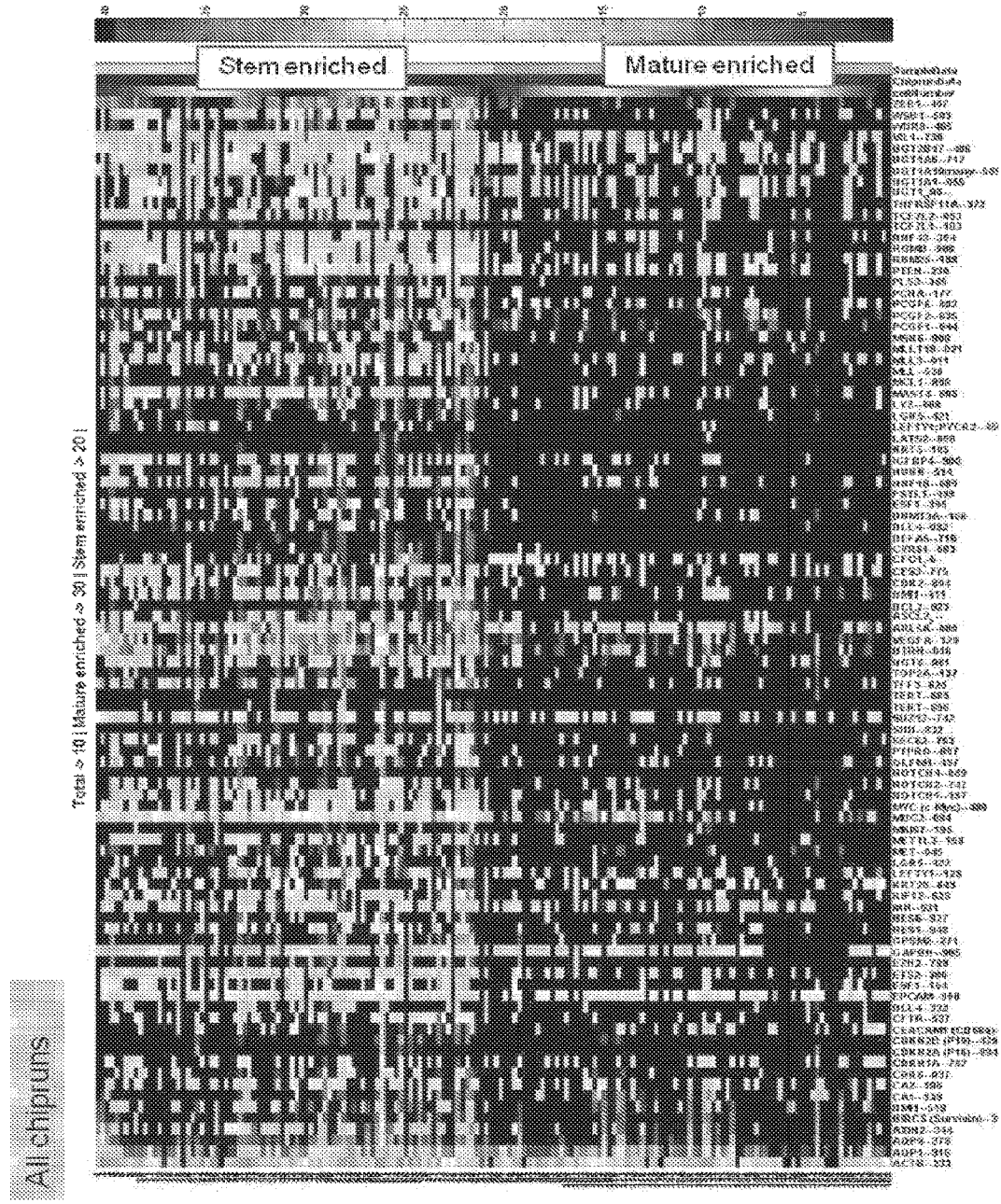

FIG. 421 a combined heat map. Cells were taken from normal colonic mucosa. The cells were FACS sorted with EpCAM and CD66a surface markers. Normal-NTCC cells were defined as EpCAM+/CD66a+ cells. Normal-CoCSC were defined as EpCAM+/CD66a+ cells.

Figure 422:
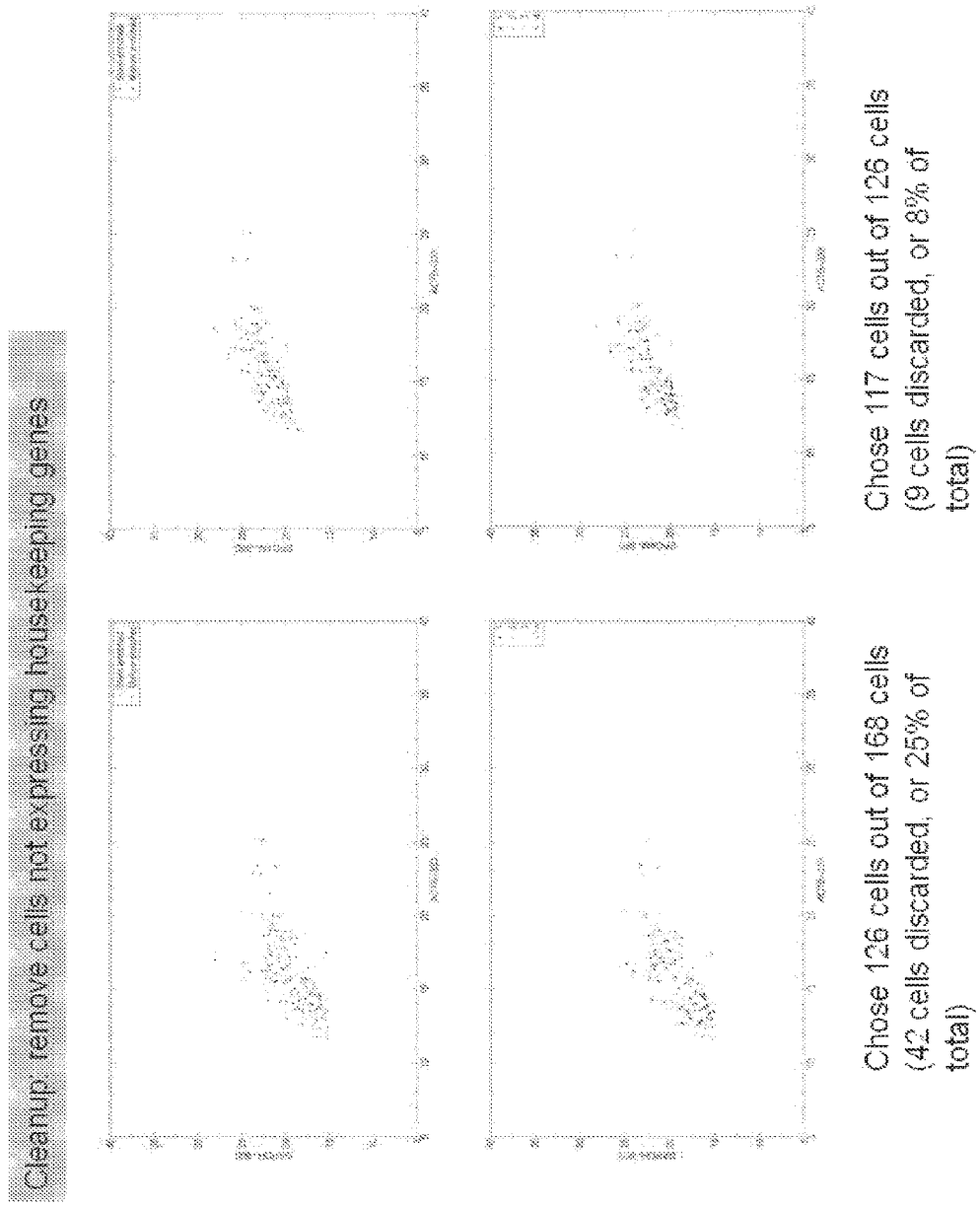

FIG. 422 selection of cells for single cell gene expression analysis. Out of 168 cells tested, 46 cells were discarded by examining GAPDH and ACTB expression levels, and 126 cells were selected. Of the 126 cells, 9 cells were further discarded by examining EPCAM and ACTB expression levels, and 117 cells were used for further analysis.

Figure 423:

FIG. 423 a combined heat map after the clean up of unwanted cells.

Figure 424:
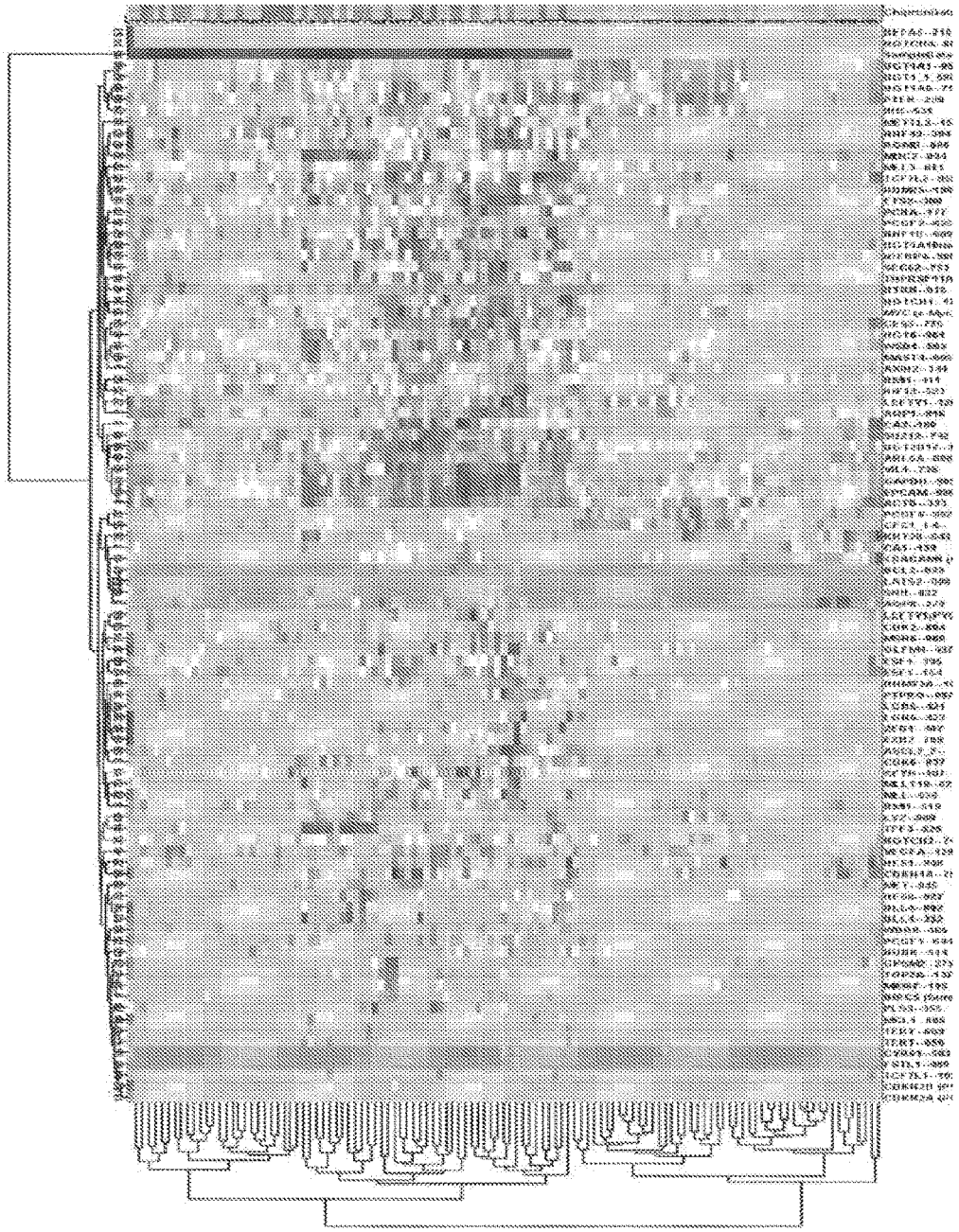

FIG. 424 a representative hierarchical clustering.

Figure 425:
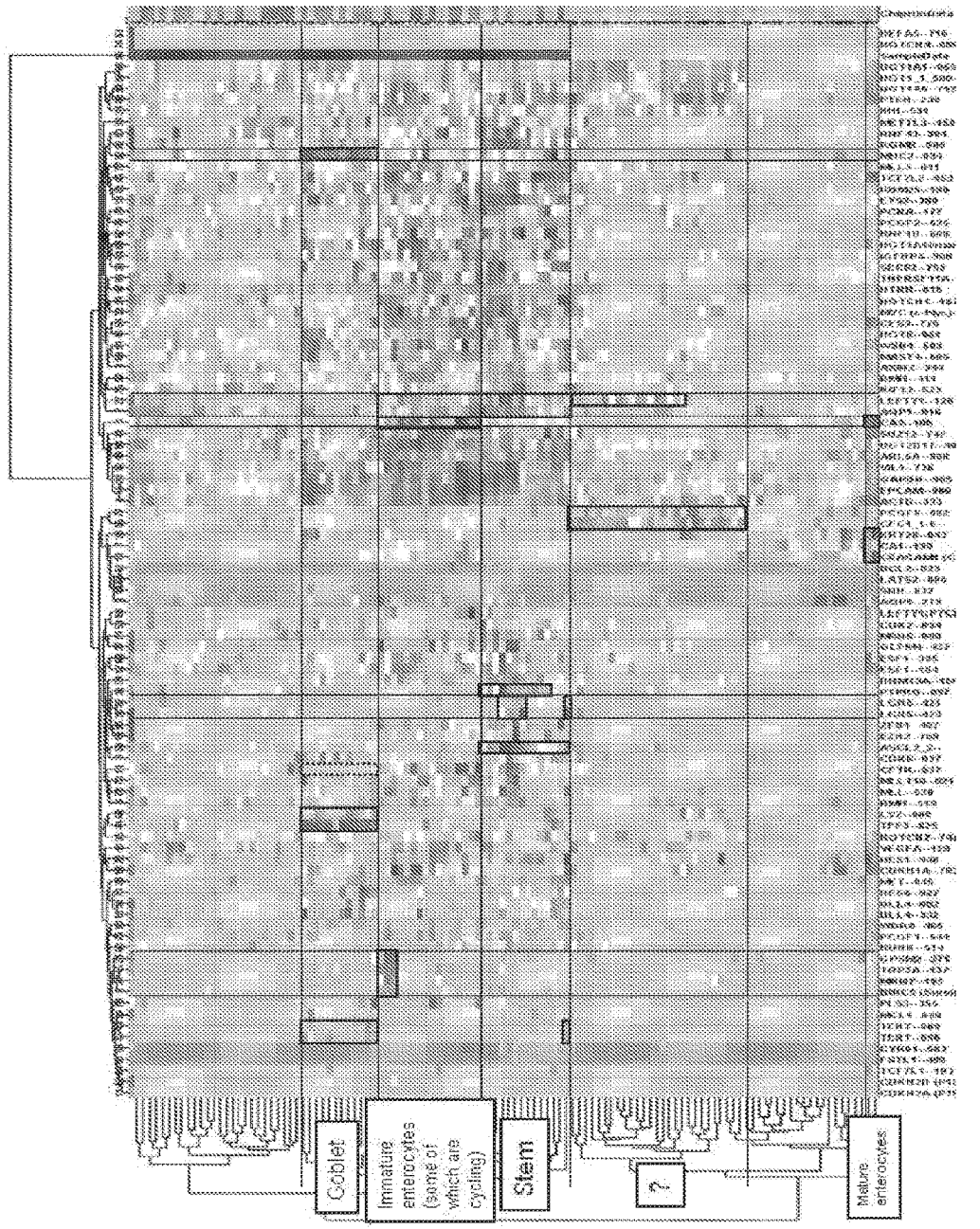

FIG. 425 a representative hierarchical clustering, showing goblet, stem, mature enterocytes, and immature enterocytes.

Figure 426:
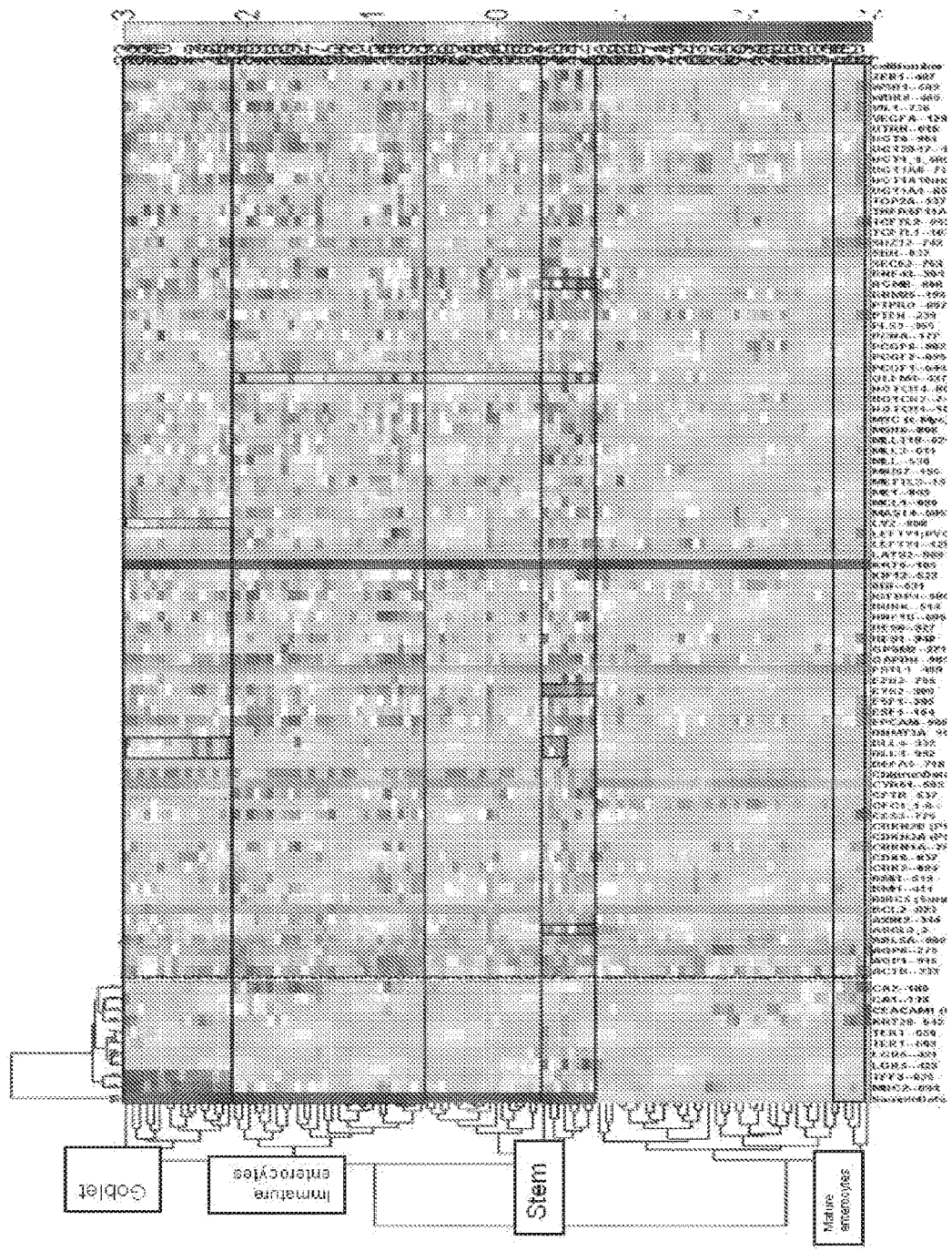

FIG. 426 a representative hierarchical clustering, showing genes differentially expressed in various cell types (square box).

Figure 427:
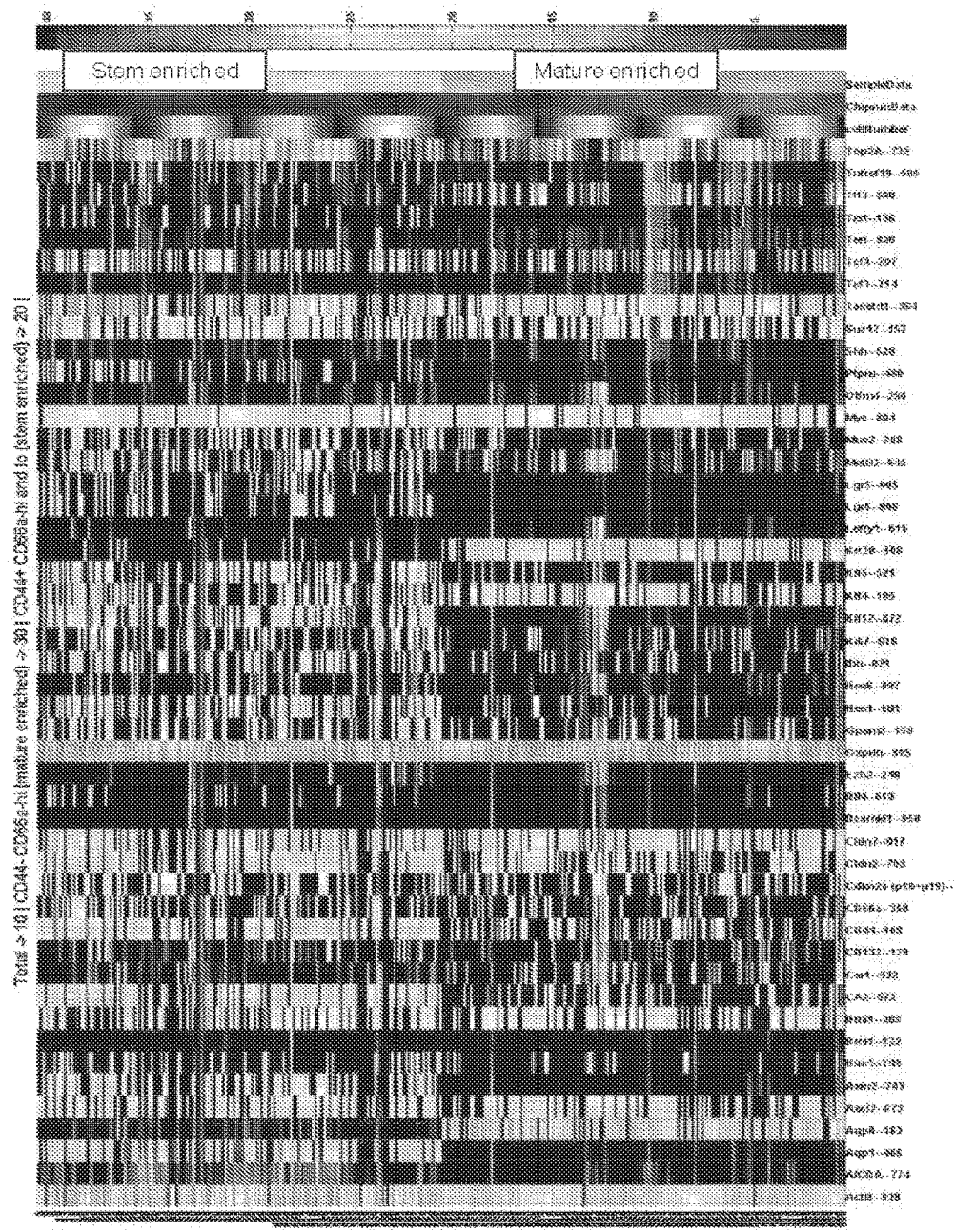

FIG. 427 a combined heat map. Cells were taken from the colon of FVB strain mouse. The cells were FACS sorted with Esa, CD45, and CD66a markers. Cells were grouped into two populations; Esa+/CD45−/CD66a$^{hi}$ or Esa+/CD45−/CD66a$^{hi/low}$.

Figure 428:
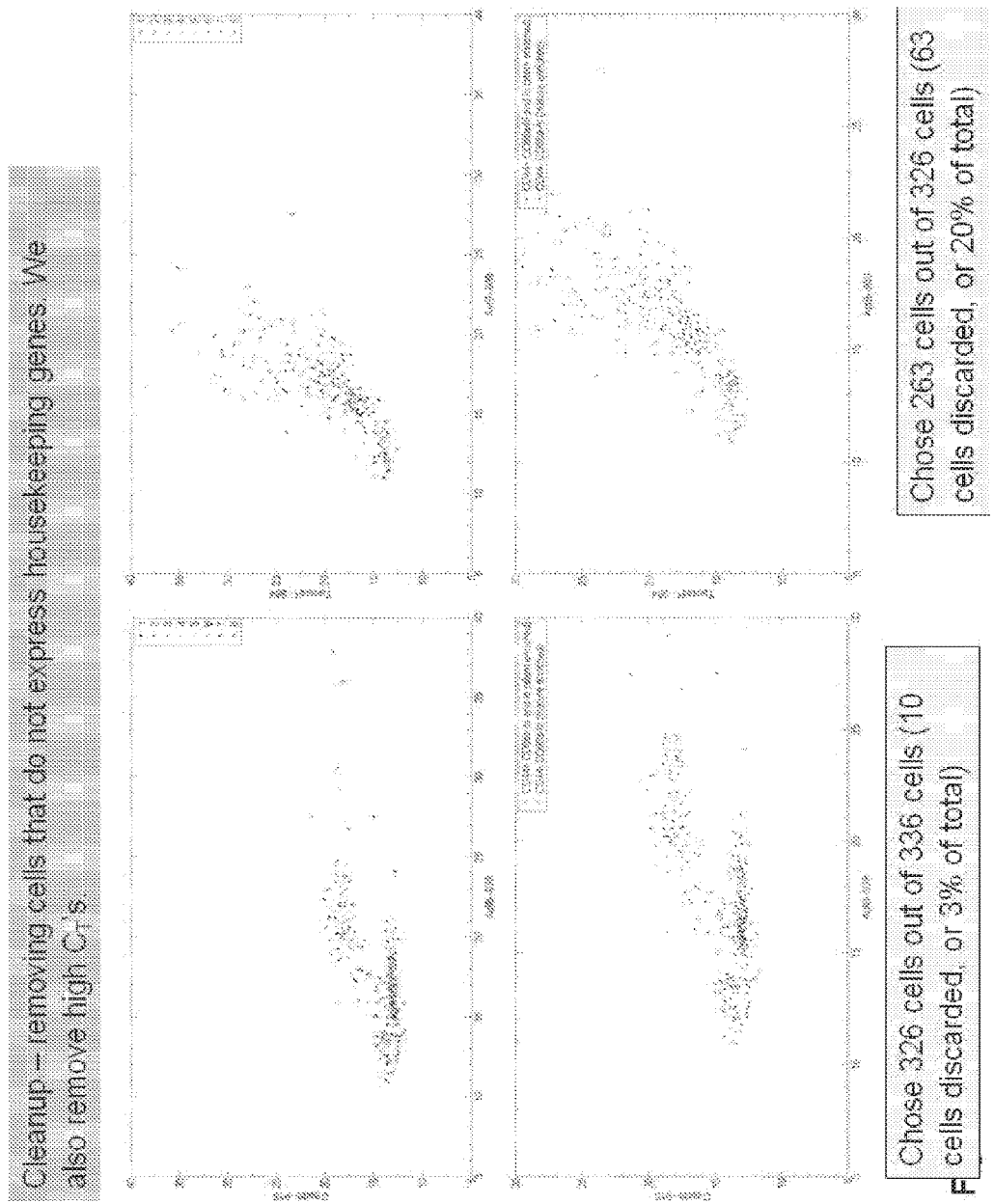

FIG. 428 selection of cells for single cell gene expression analysis. Out of 336 cells tested, 10 cells were discarded by examining GAPDH and ACTB expression levels, and 326 cells were selected. Of the 326 cells, 63 cells were further discarded by examining TACSTD1 and ACTB expression levels, and 263 cells were used for further analysis.

Figure 429:
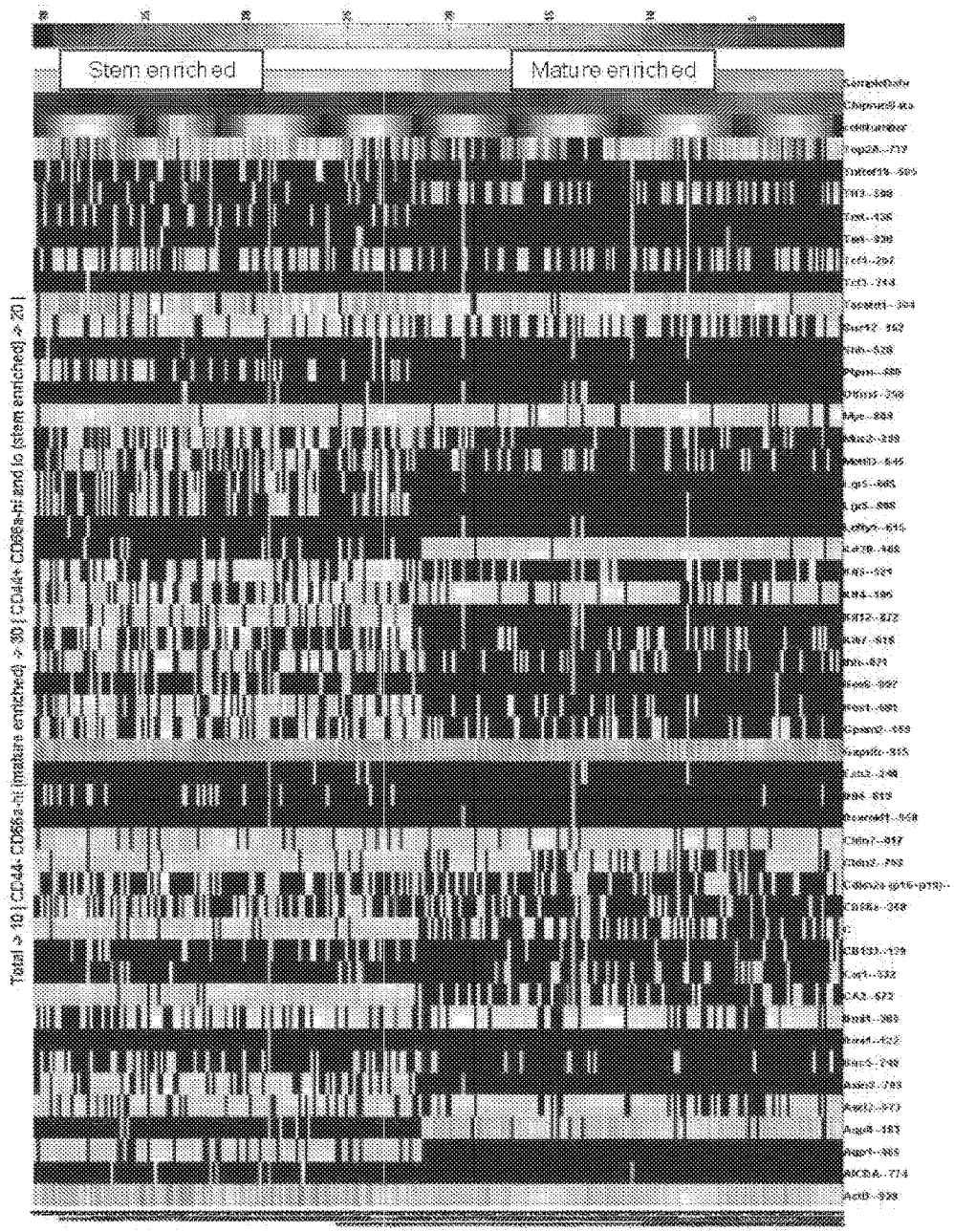

FIG. 429 a combined heat map after the clean up of unwanted cells.

Figure 430:
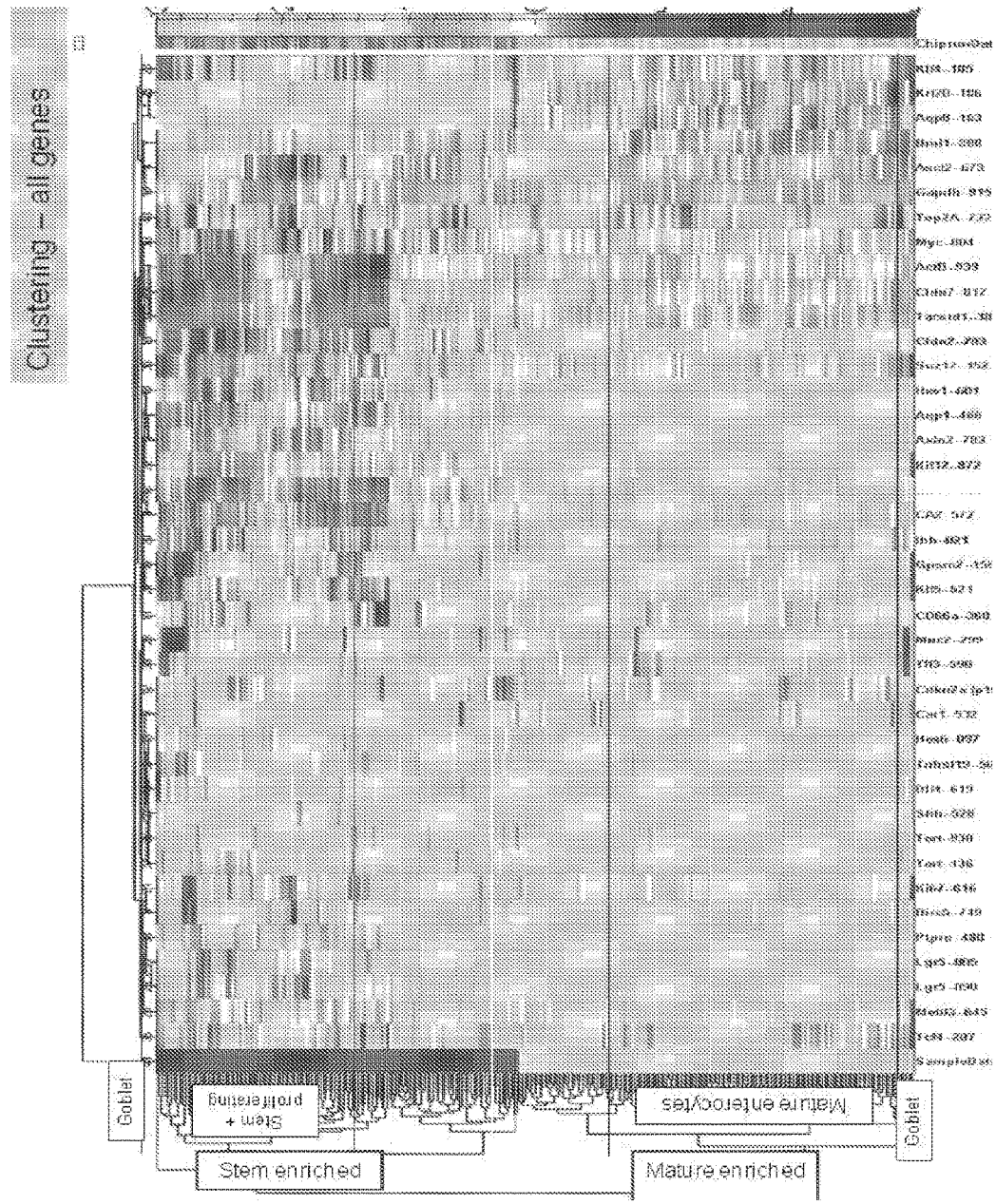

FIG. 430 a representative hierarchical clustering of all genes.

Figure 431:
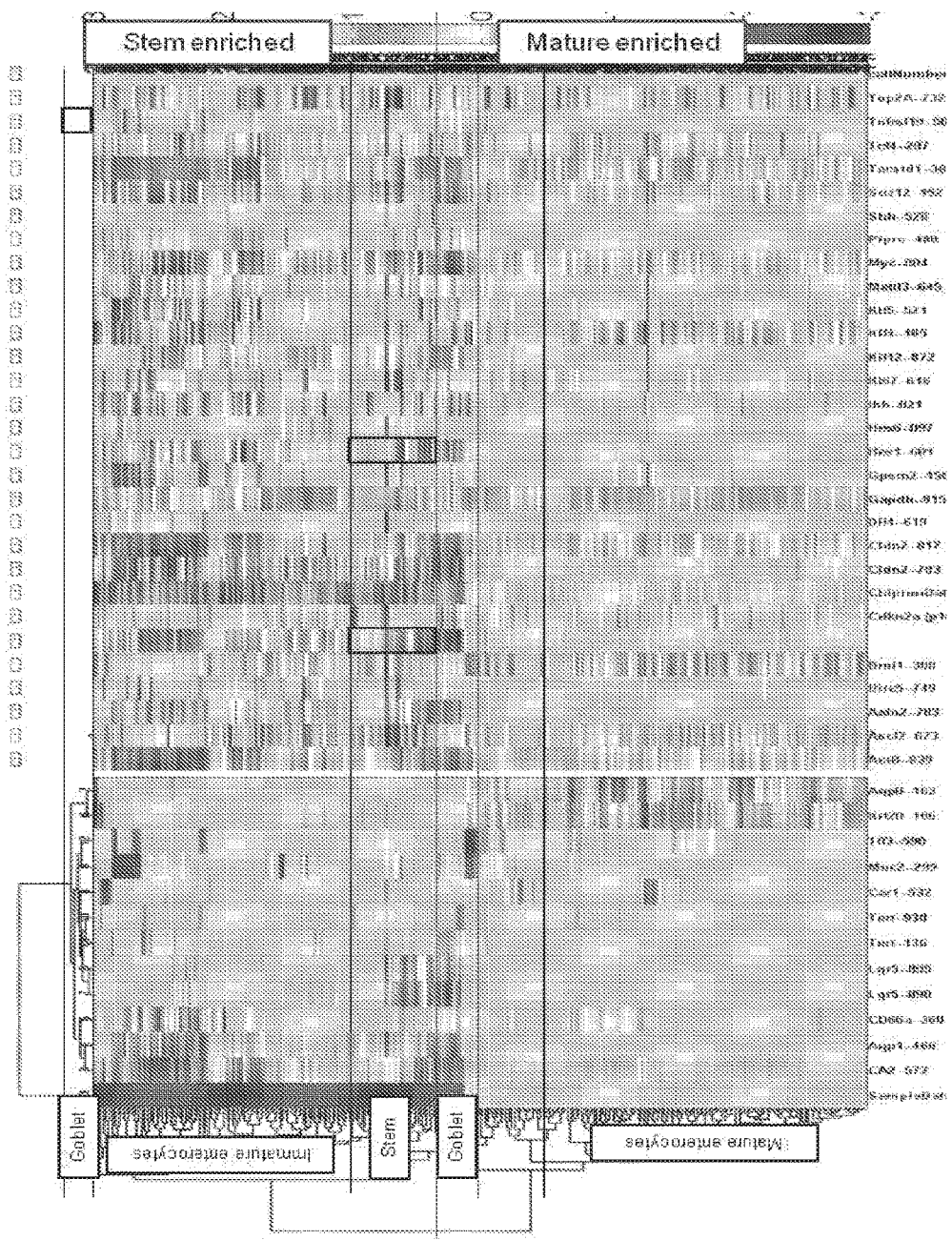

FIG. 431 a representative hierarchical clustering comparing stem enriched population to mature enriched population.

Figure 432:
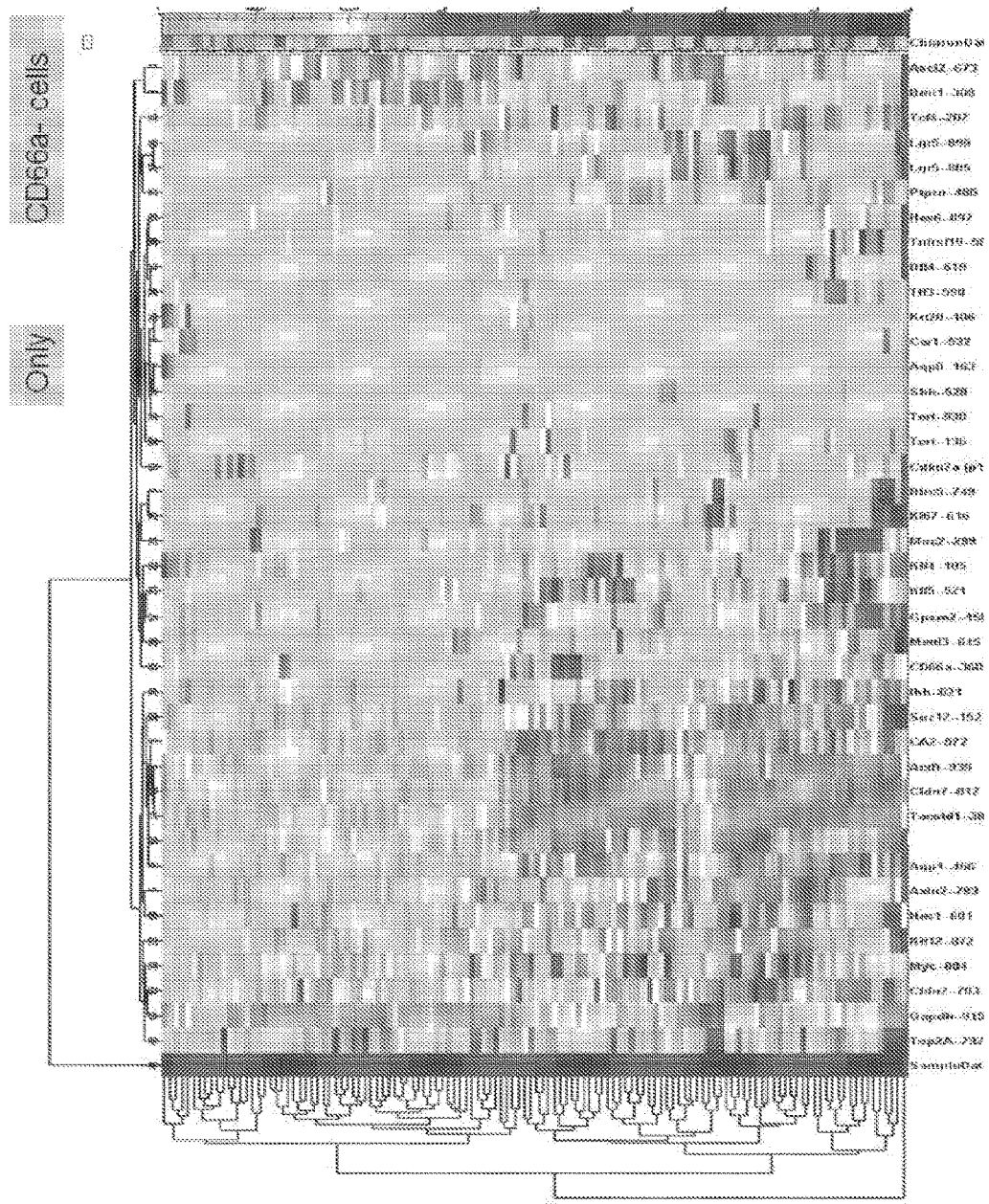

FIG. 432 hierarchical clustering of only CD66a− cells.

Figure 433:
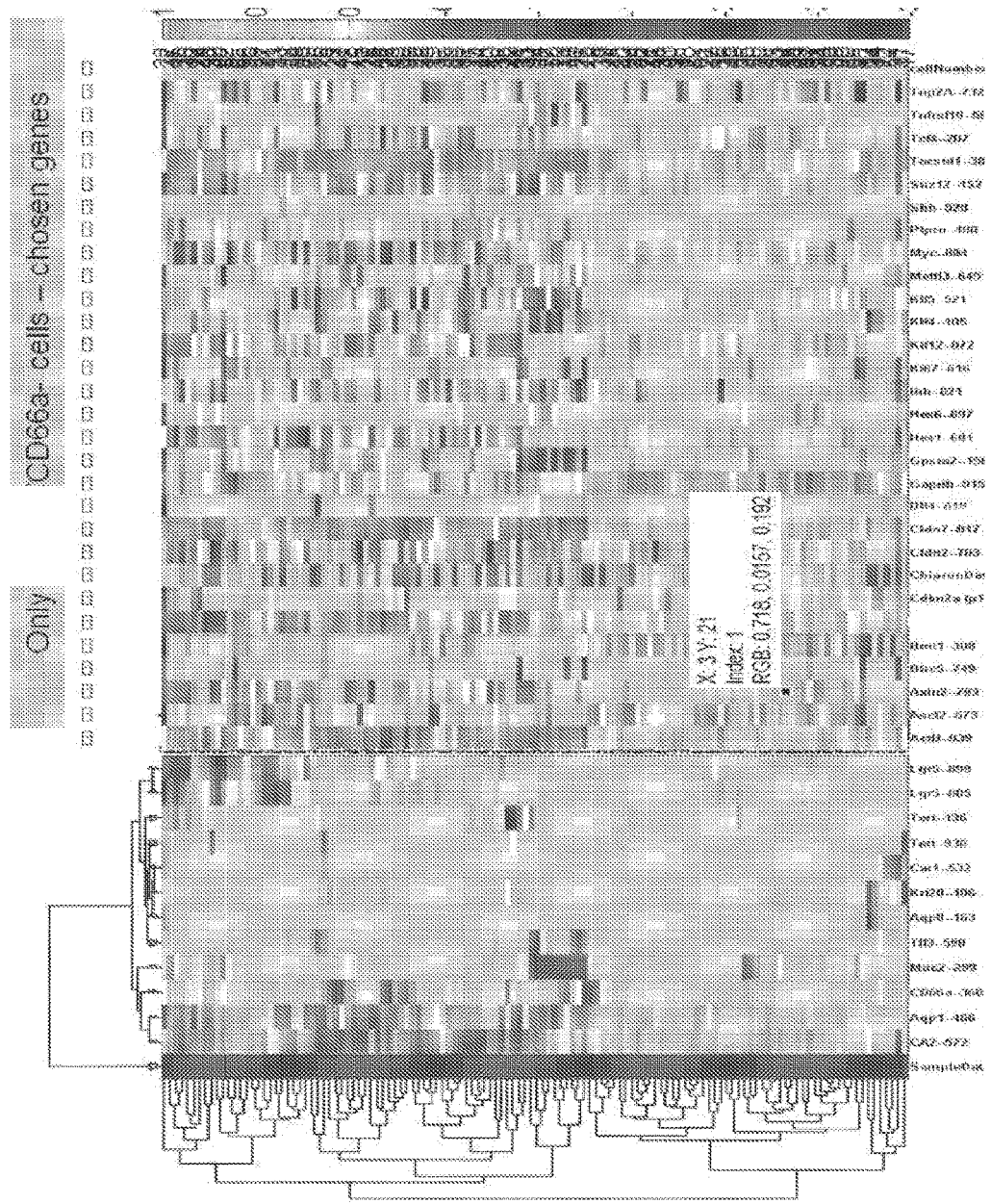

FIG. 433 hierarchical clustering of only CD66a− cells, excluding chosen cells.

Figure 434:
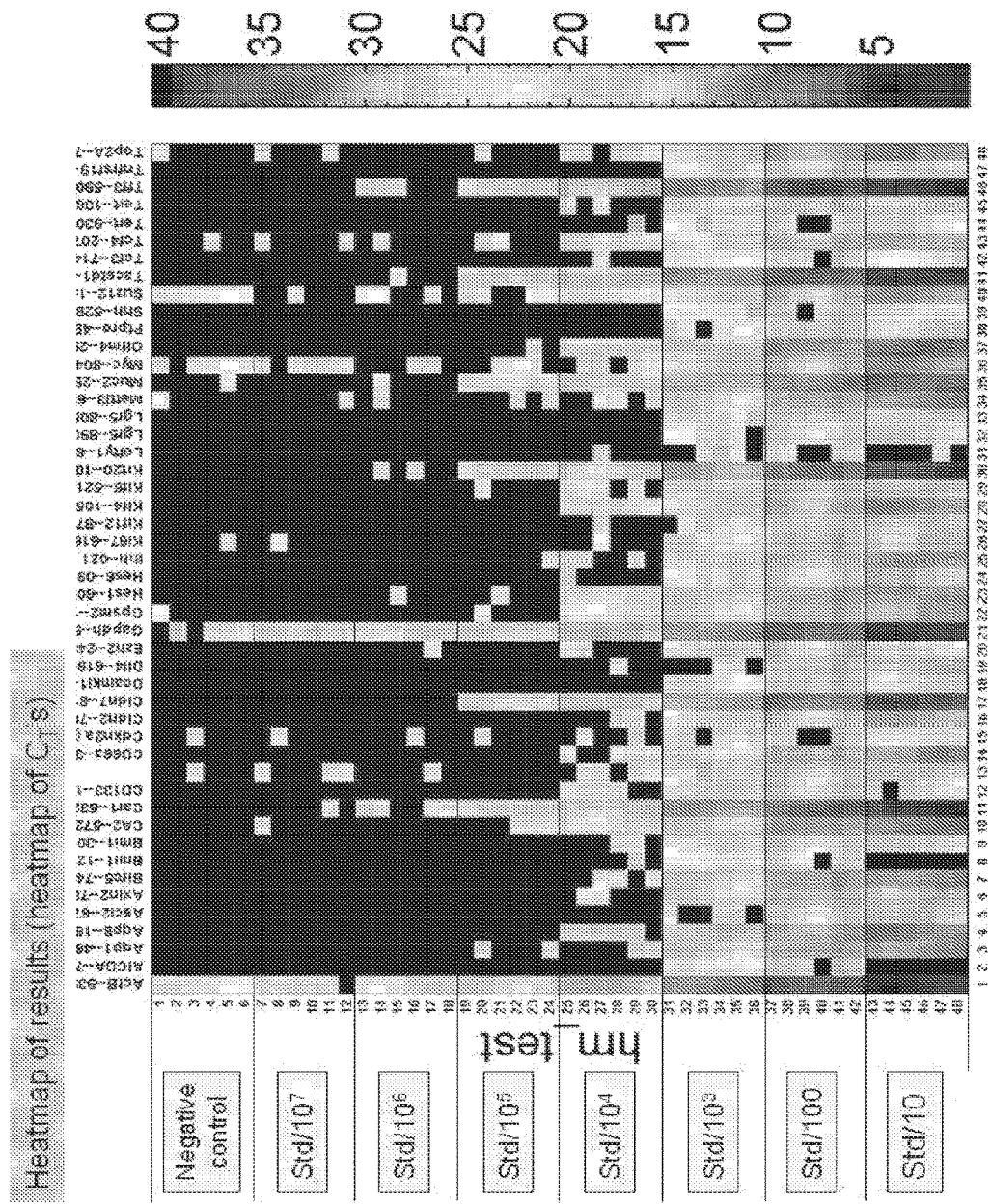

FIG. 434 heat maps from experiments prepared in 6 replicates per dilution.

Figure 435:
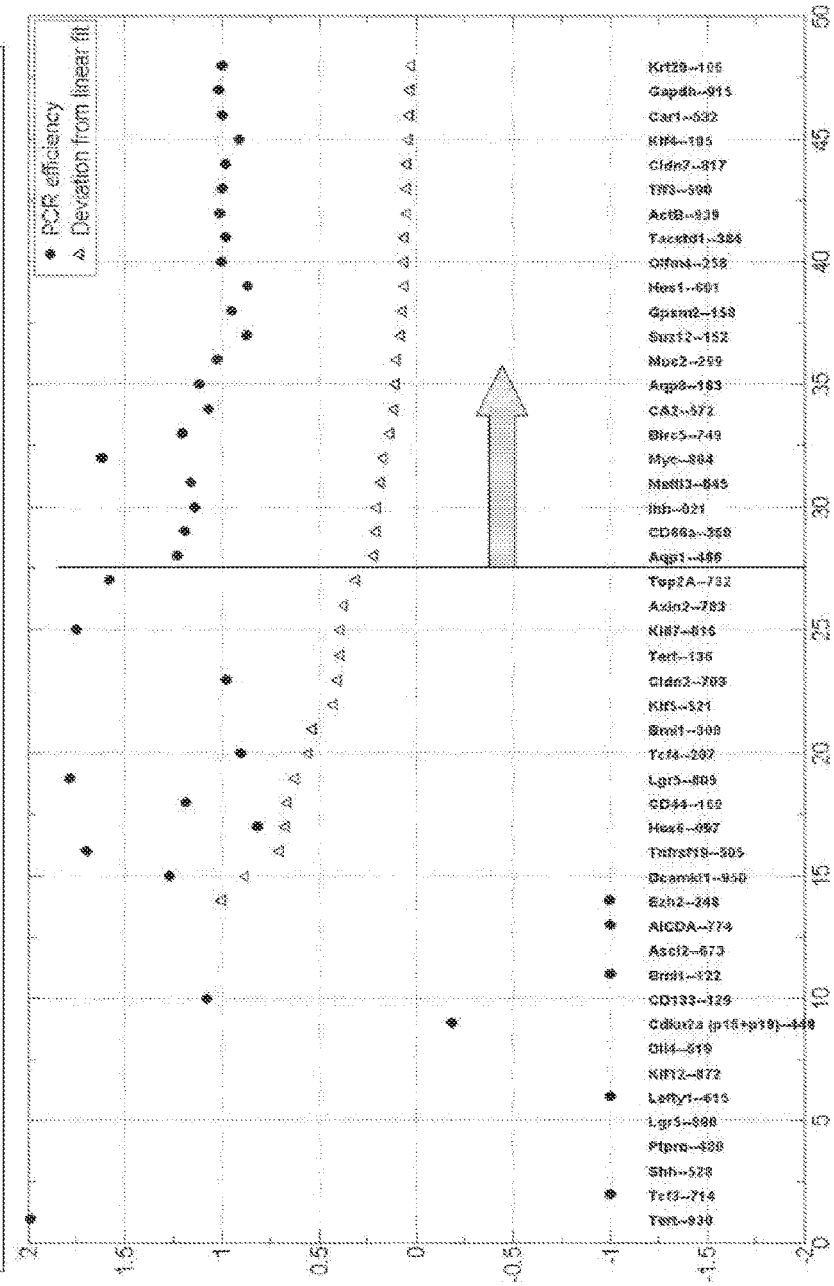

FIG. 435 qPCR efficiency in the standards.

Figure 436:
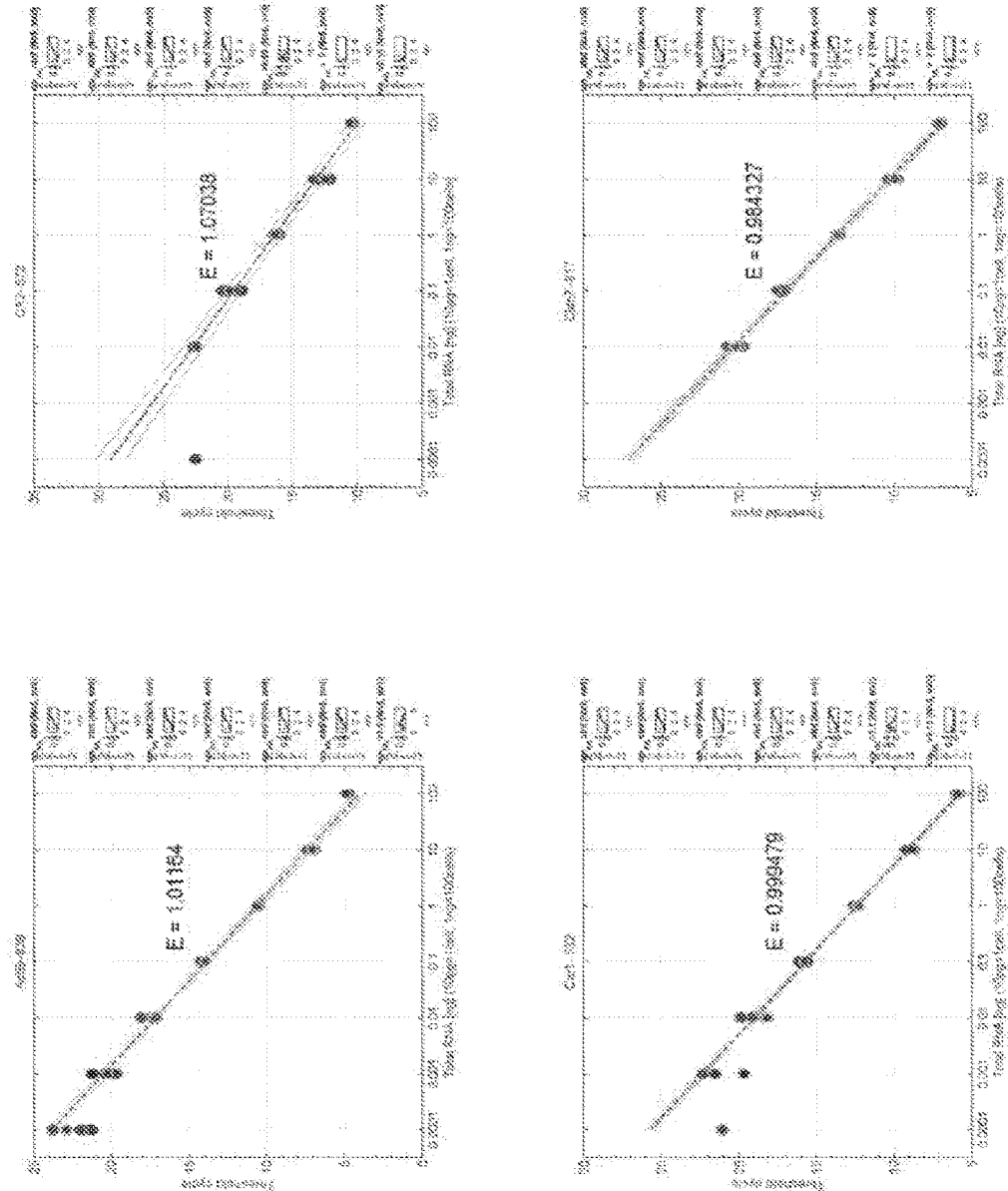

FIG. 436 amplification linearity that is demonstrated by linear amplification of selected genes such as ACTB, CA2, CAR1, and CLDN7.

Figure 437:
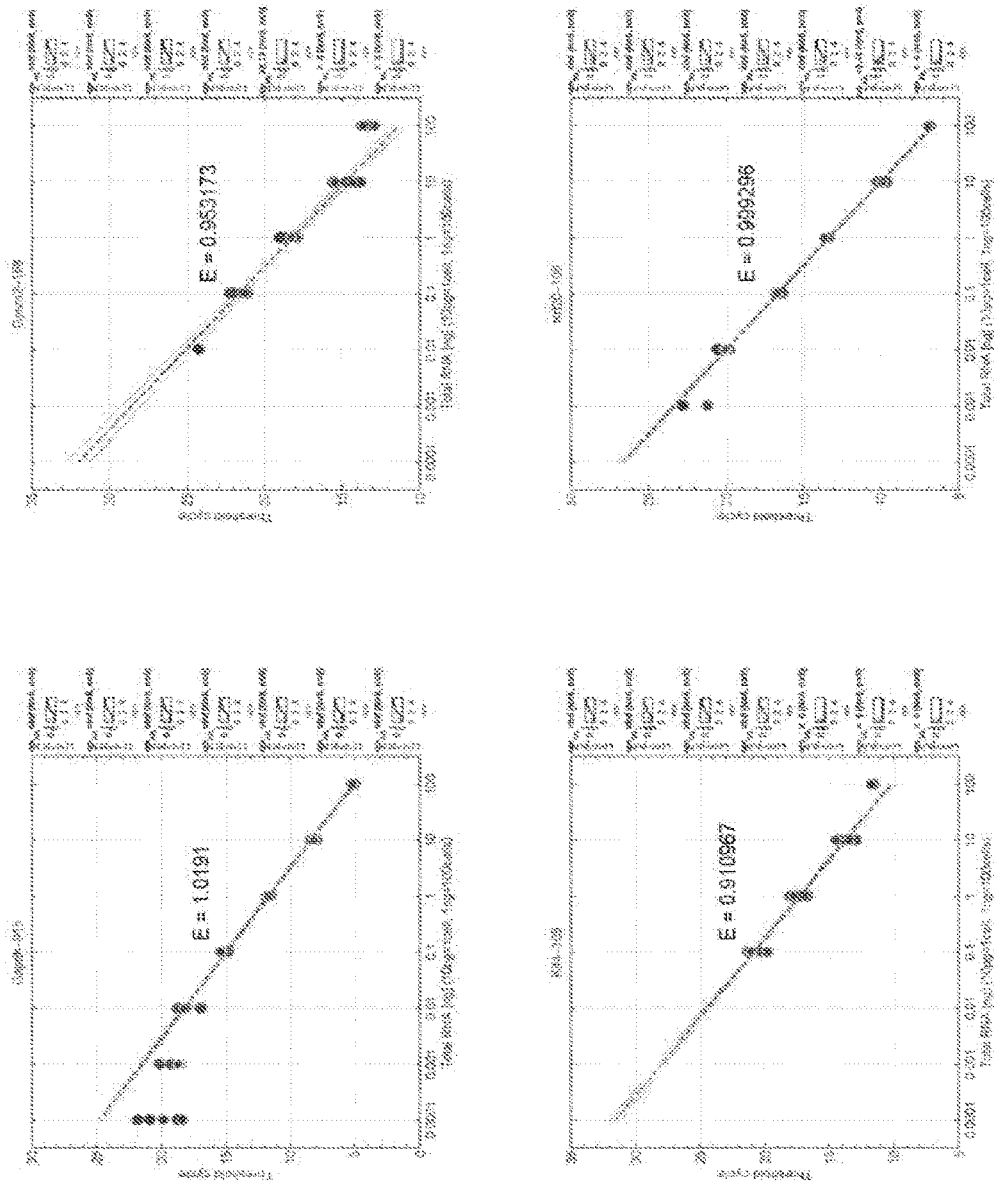

FIG. 437 amplification linearity that is demonstrated by linear amplification of selected genes such as GAPDH, GPSM2, KLF4, and KRT20.

Figure 438:
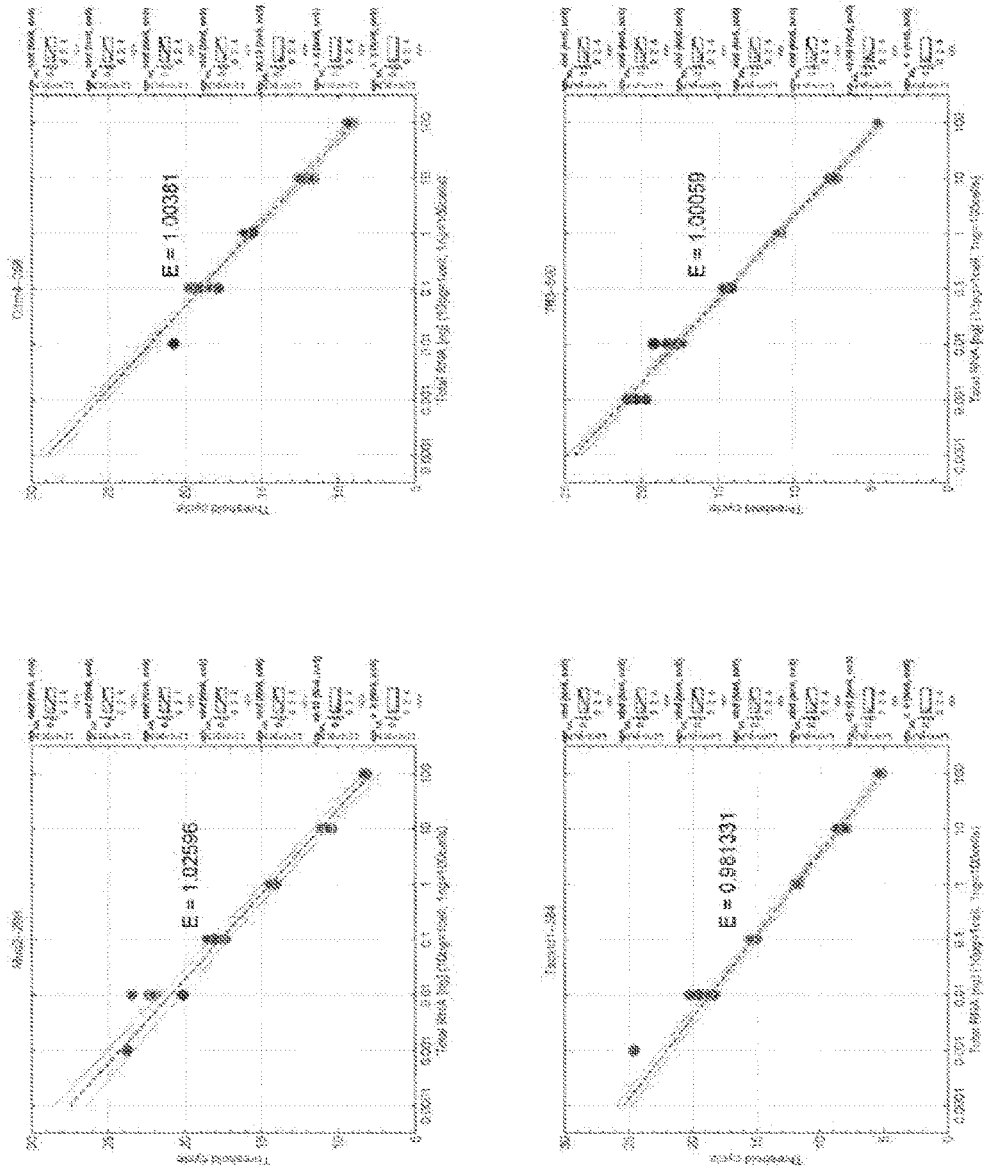

FIG. 438 amplification linearity that is demonstrated by linear amplification of selected genes such as MUC2, OLFM4, TACSTD1, and TFF3.

Figure 439:
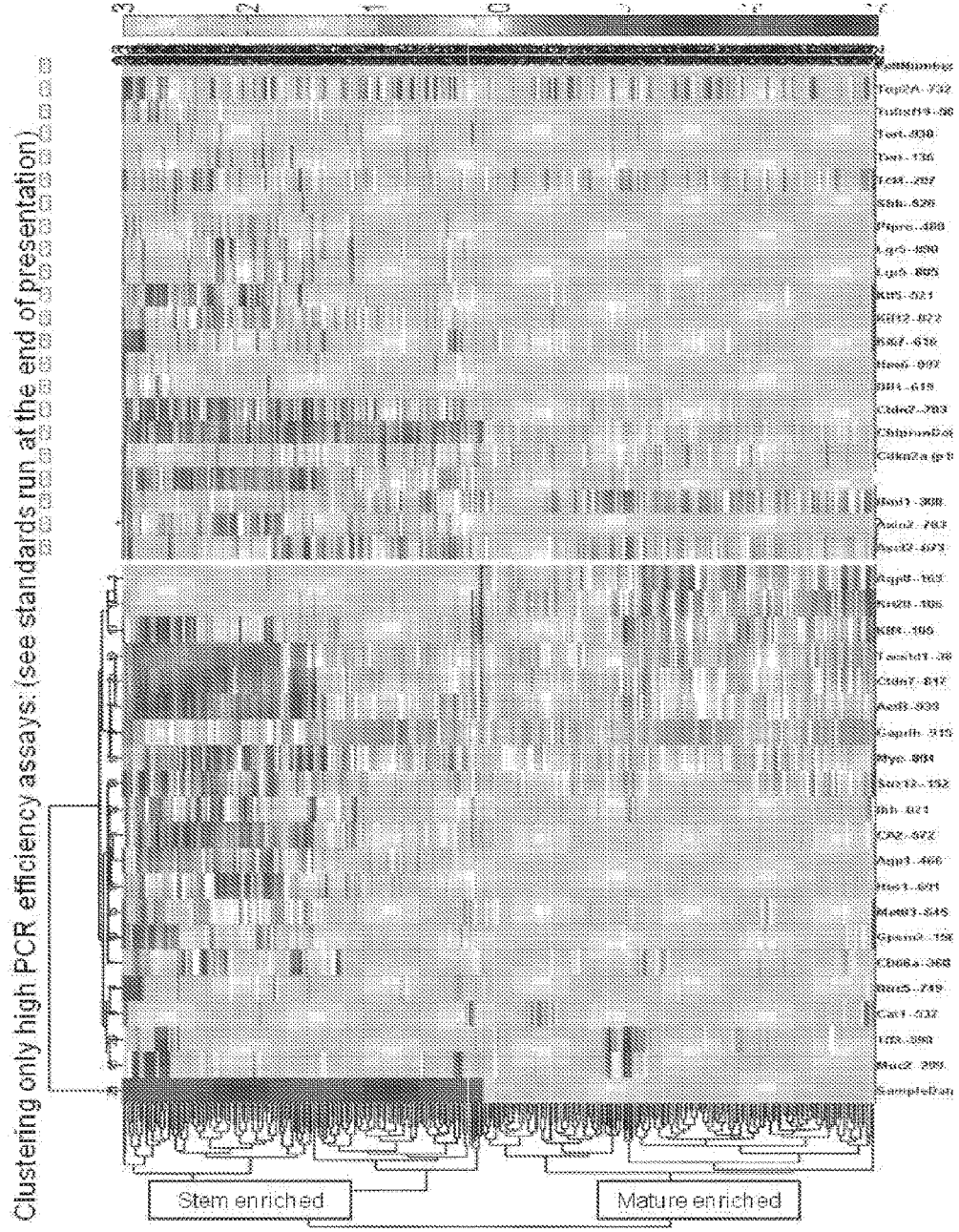

FIG. 439 a hierarchical clustering of genes with high PCR efficiency.

Figure 440:
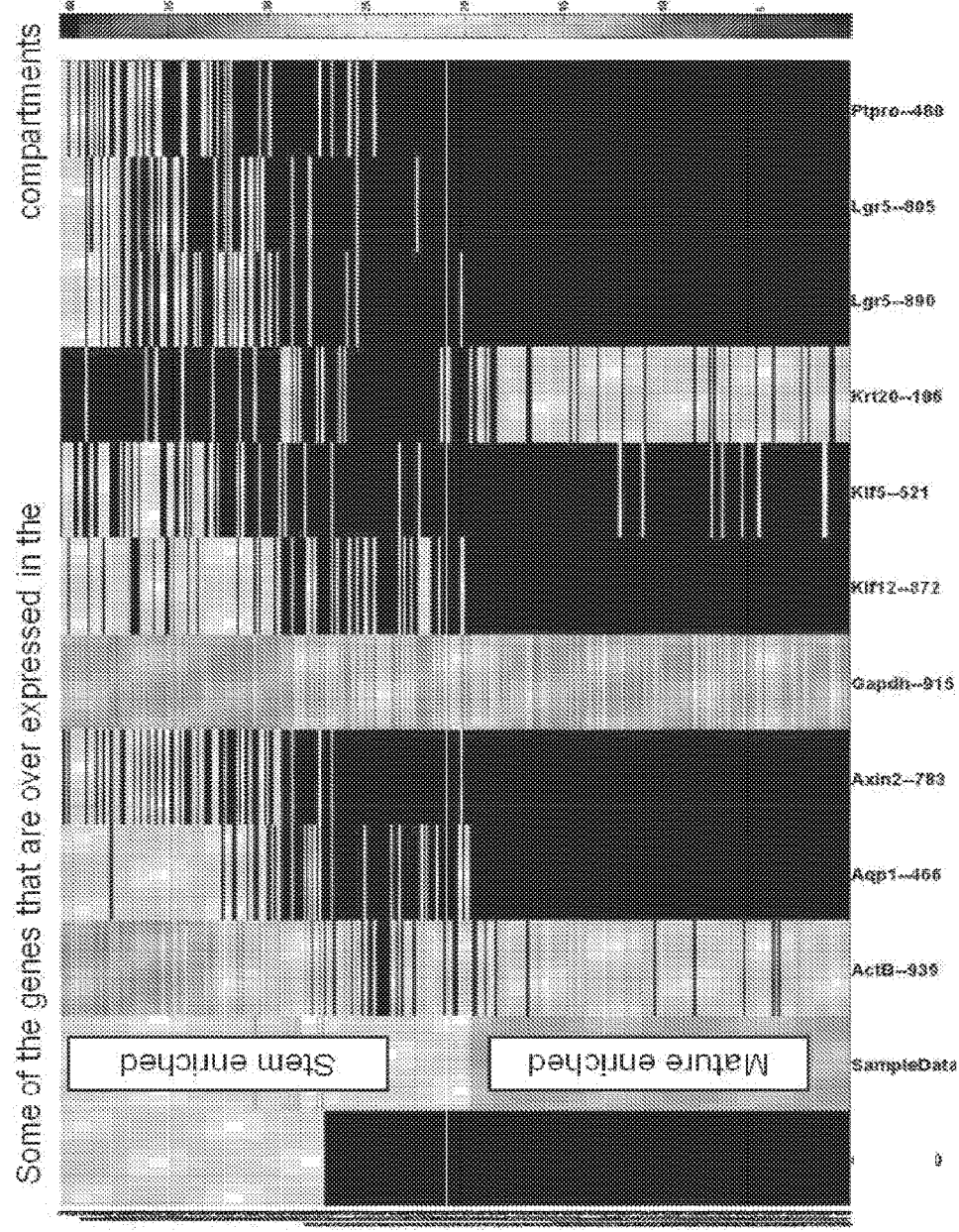

FIG. 440 that some genes over-expressed in sorted cells.

Figure 441:
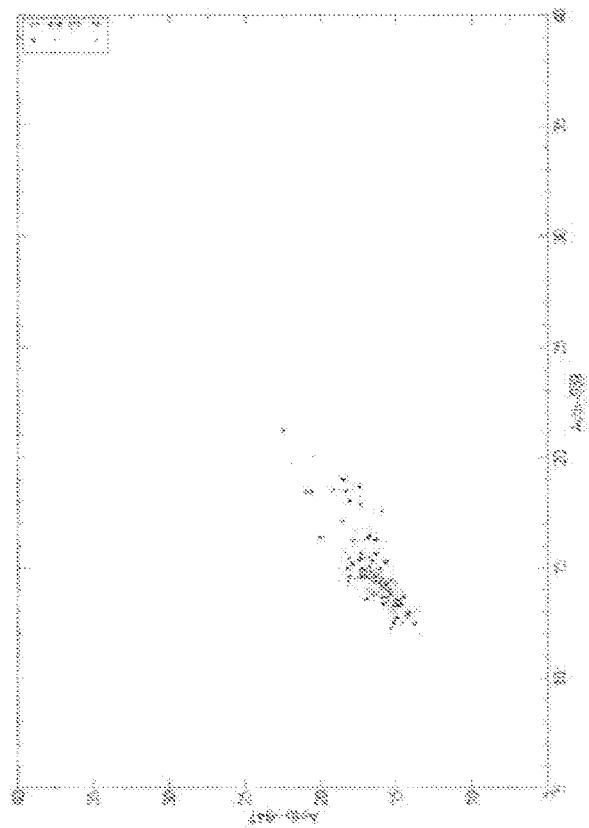

FIG. 441 selection of cells for single cell gene expression analysis. Cells were taken from normal mouse mammary epithelium. The cells were FACS sorted with CD24, CD49f, CD49 and Lin surface markers. Enriched stem cells were defined as CD24$^{med}$/CD49f$^{hi}$/Lin$^-$. Enriched progenitor cells were defined as CD24$^{hi}$/CD49$^{med}$/Lin$^-$. Out of 168 cells tested, 8 cells were discarded by examining ACTB expression levels, and 160 cells were selected.

Figure 442:
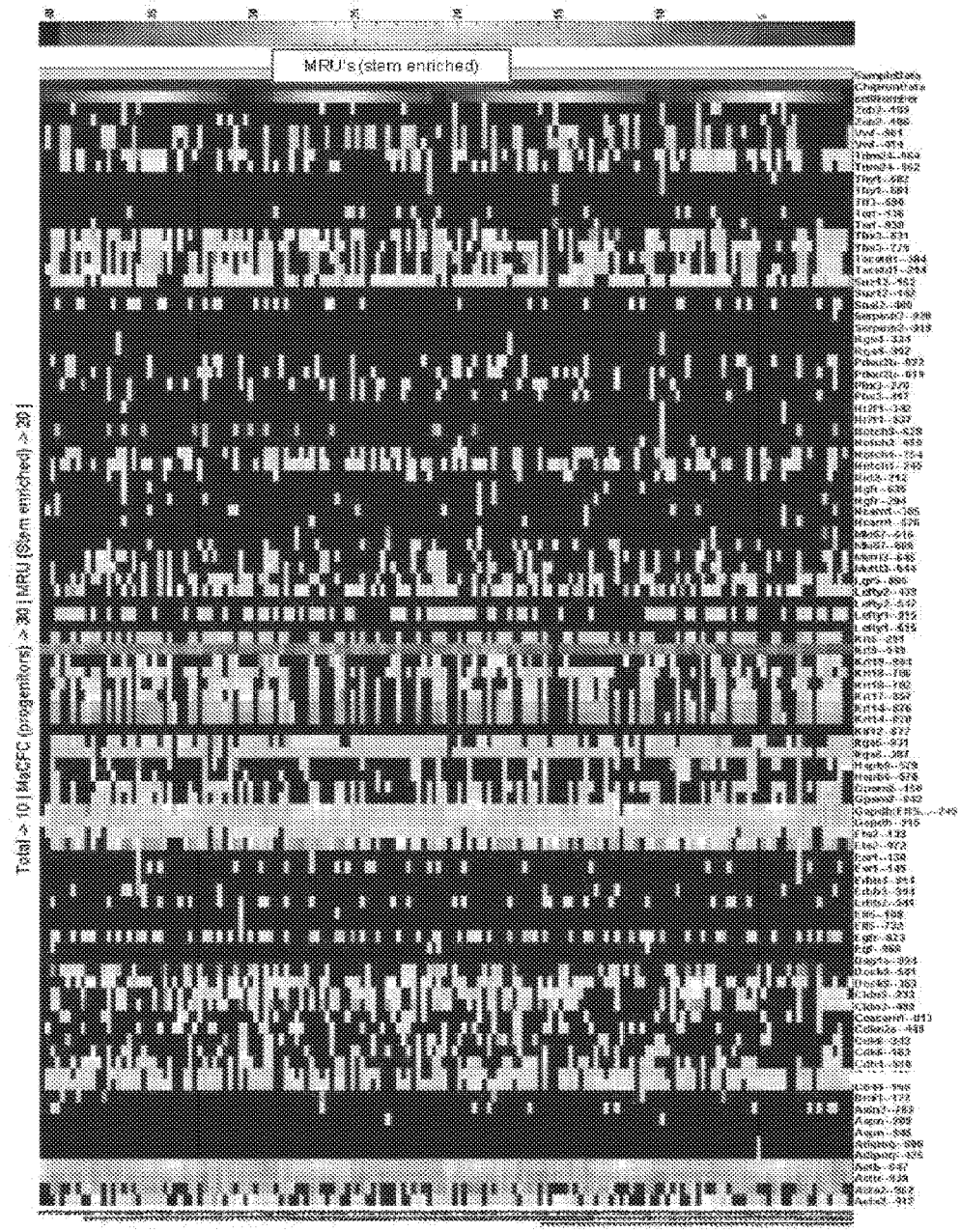

FIG. 442 a combined heat map of enriched stem cell.

Figure 443:
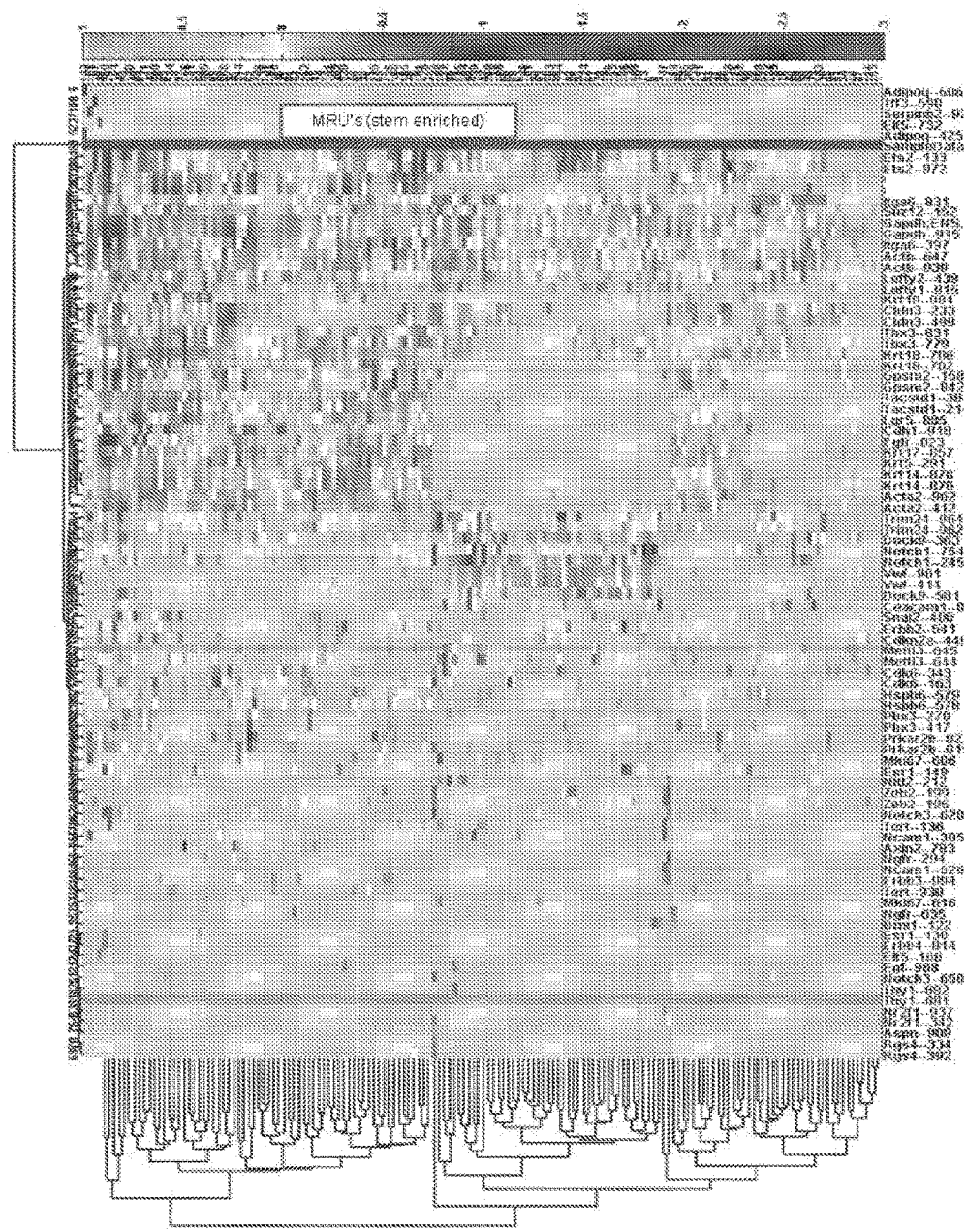

FIG. 443 a representative hierarchical clustering of enriched stem cell.

Figure 444:
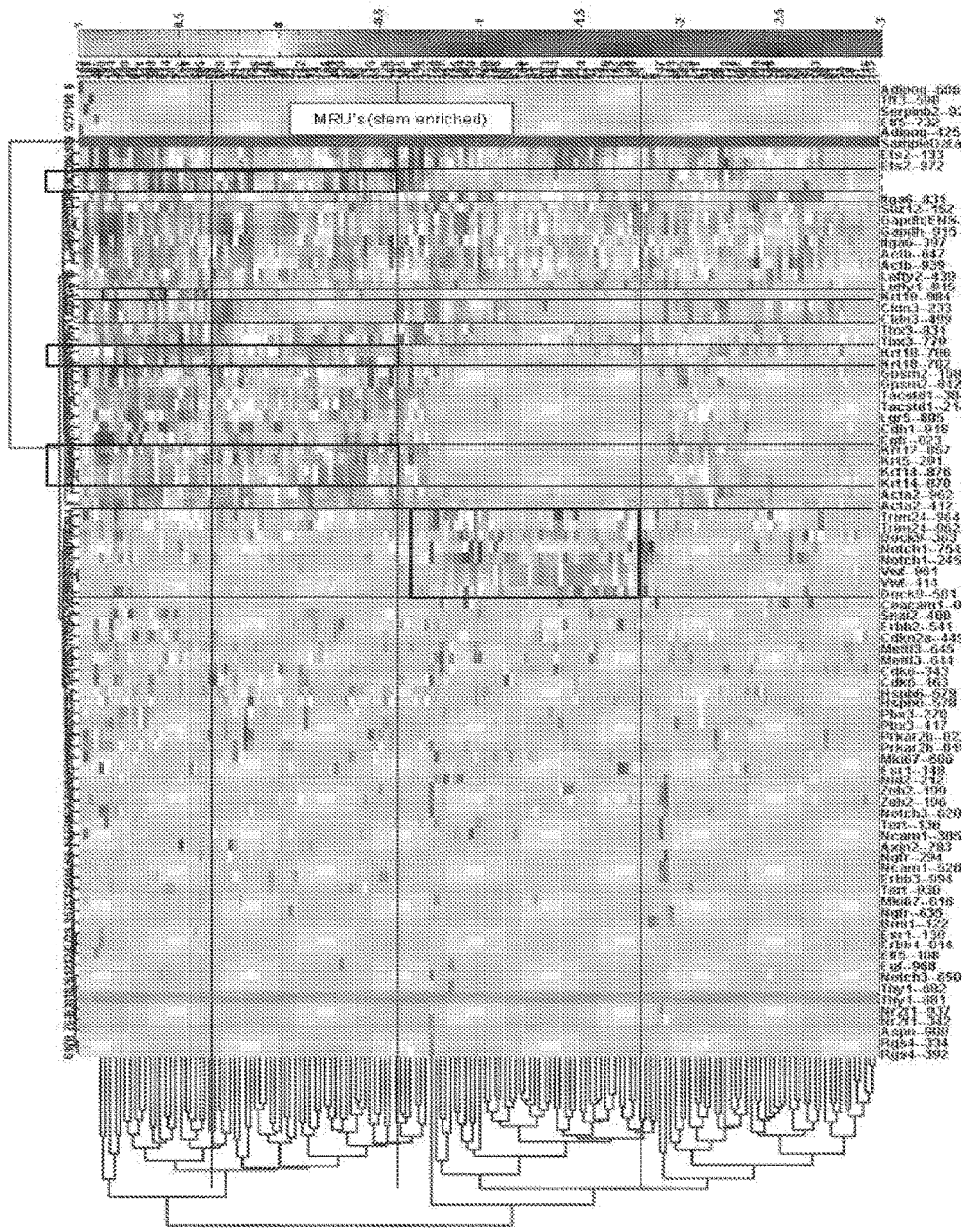

FIG. 444 a representative hierarchical clustering of enriched stem cell that genes differentially expressed are marked by a square.

Figure 455:
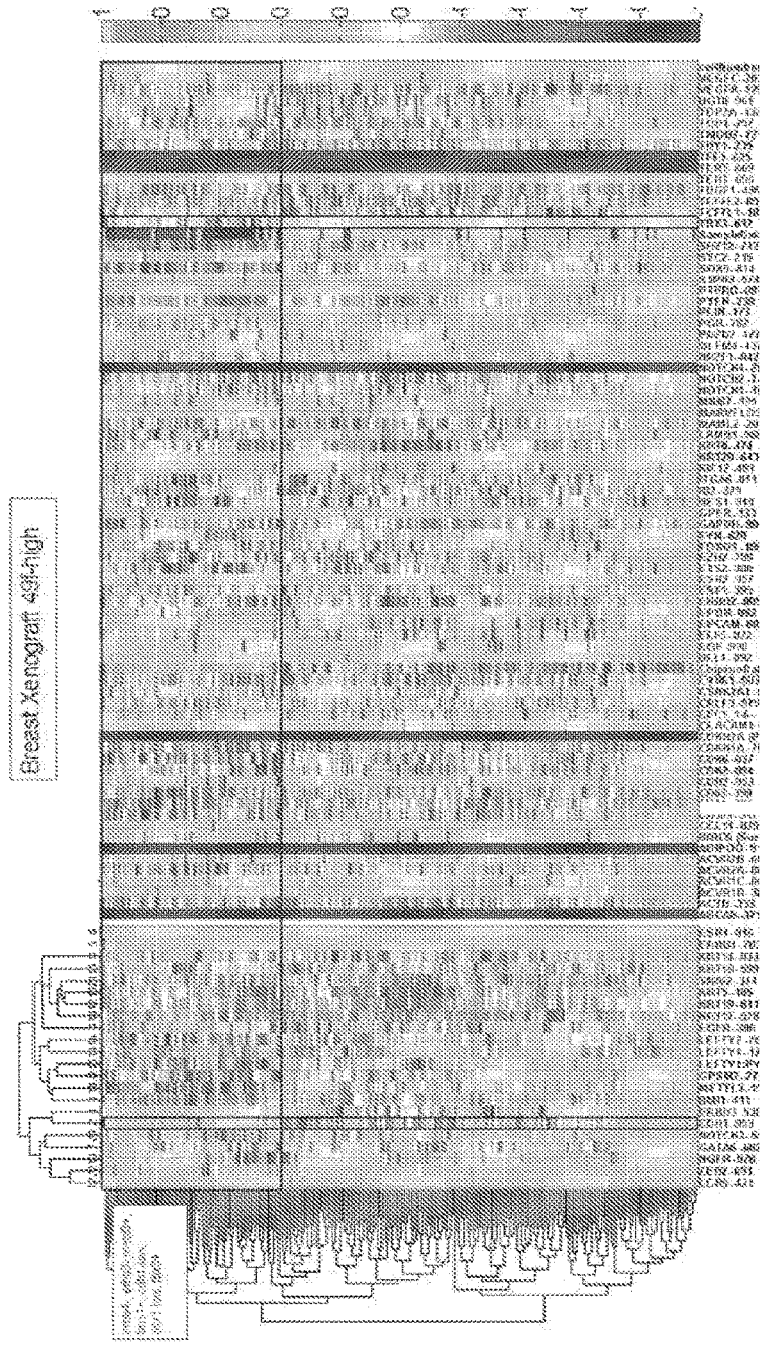

FIG. 455 a combined heat map of enriched progenitor cell.

Figure 456:
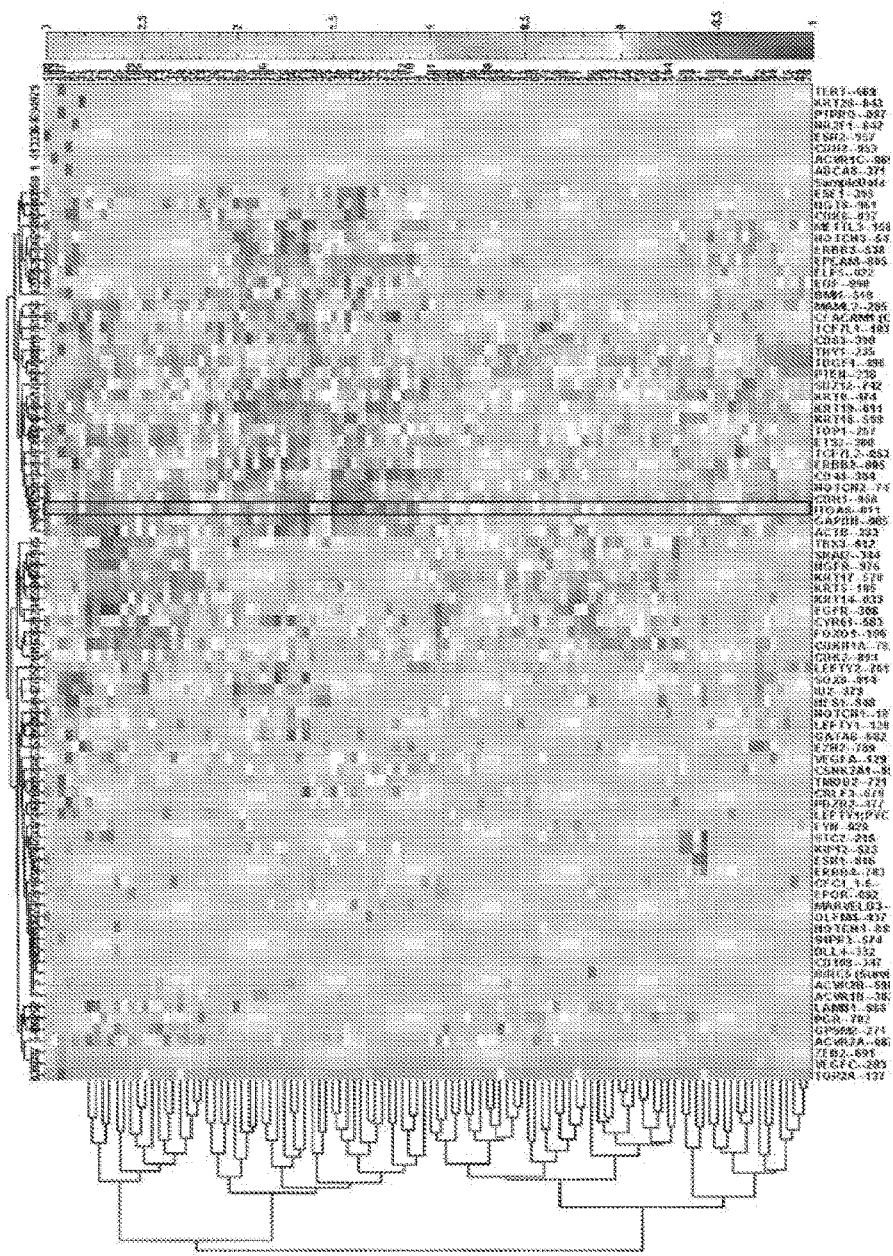

FIG. 456 selection of cells that progenitor cells were cleaned up by examining GAPDH and ACTB gene expressions.

Figure 457:
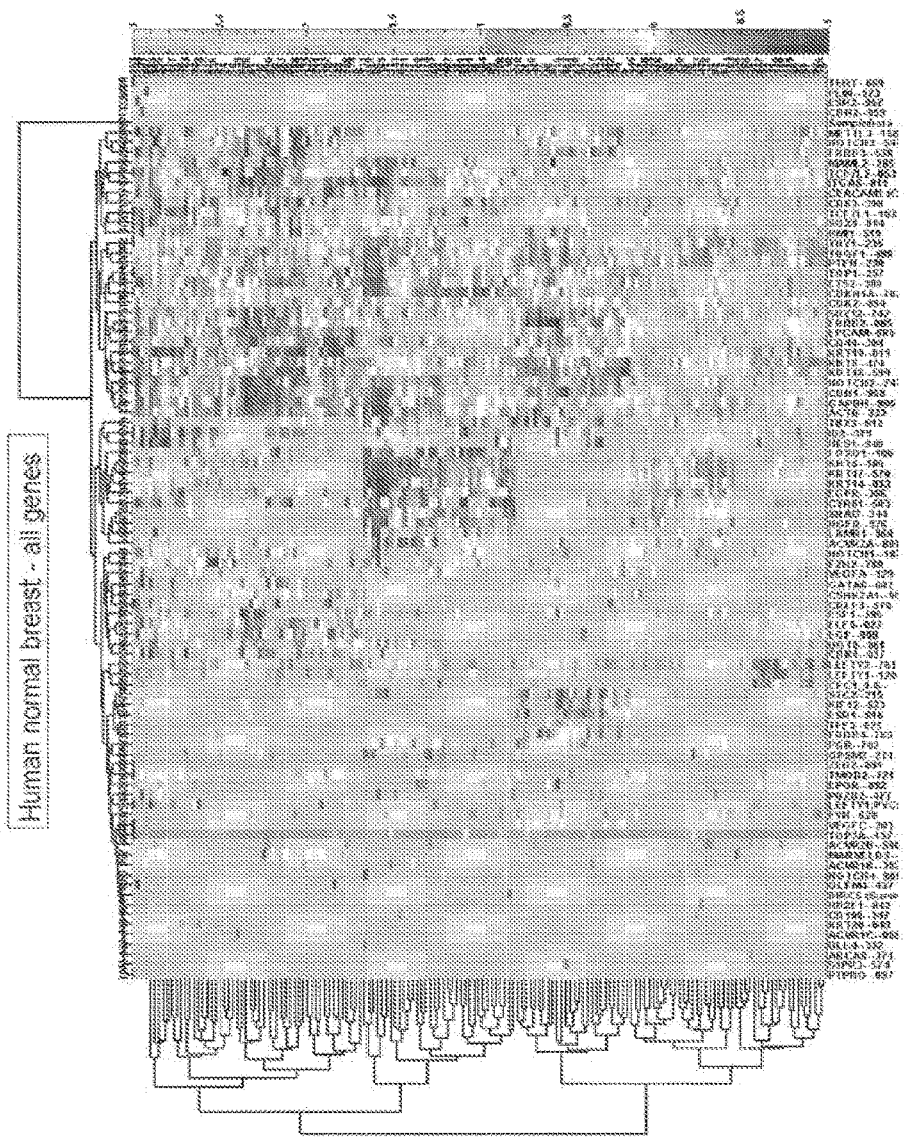

FIG. 457 a representative hierarchical clustering comparing MRUs to MaCFCs.

Figure 448:
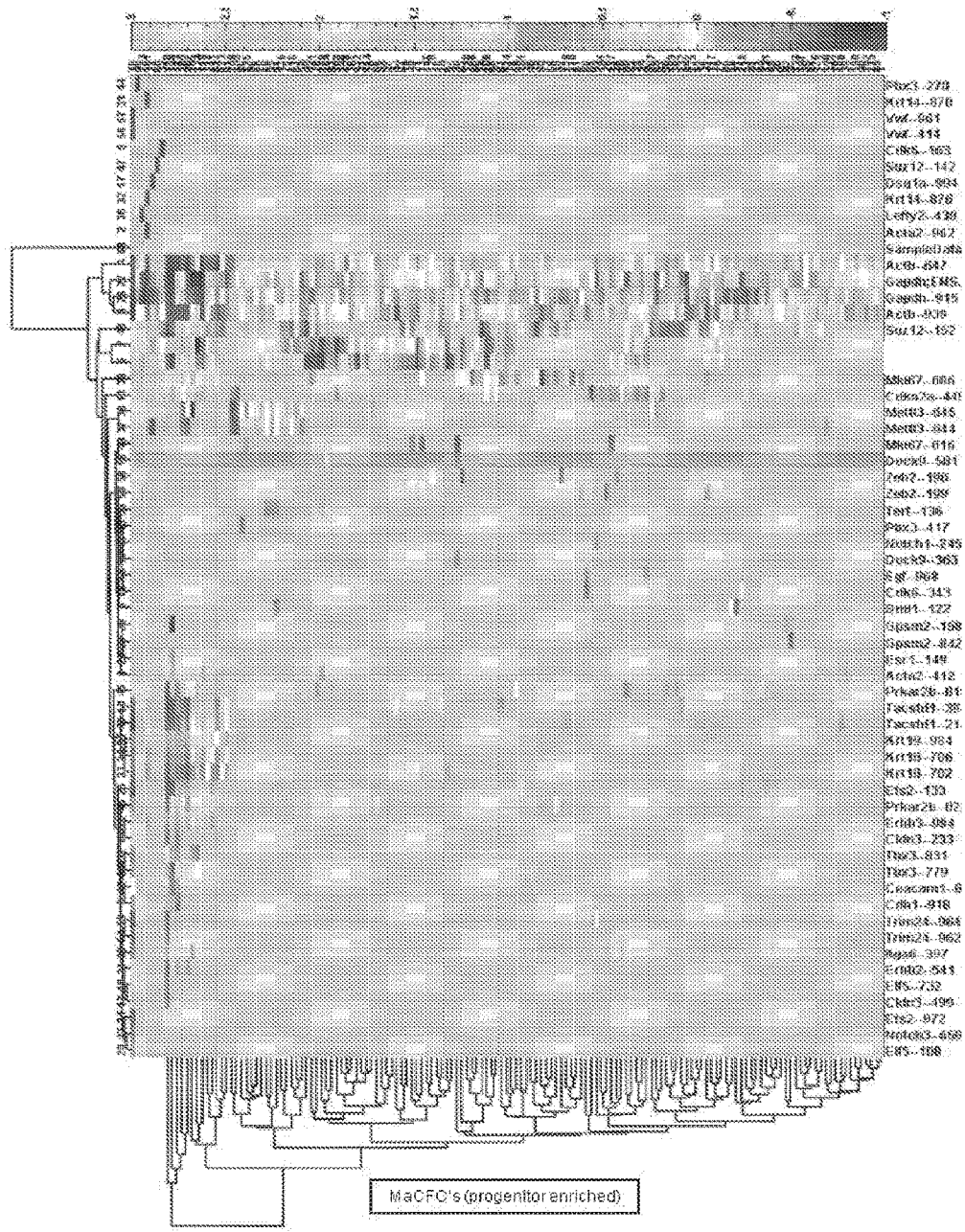

FIG. 448 a representative hierarchical clustering showing MaCFCs only.

Figure 449:

FIG. 449 a combined heat map of stem and goblet cells, and mature enterocytes.

Figure 450:
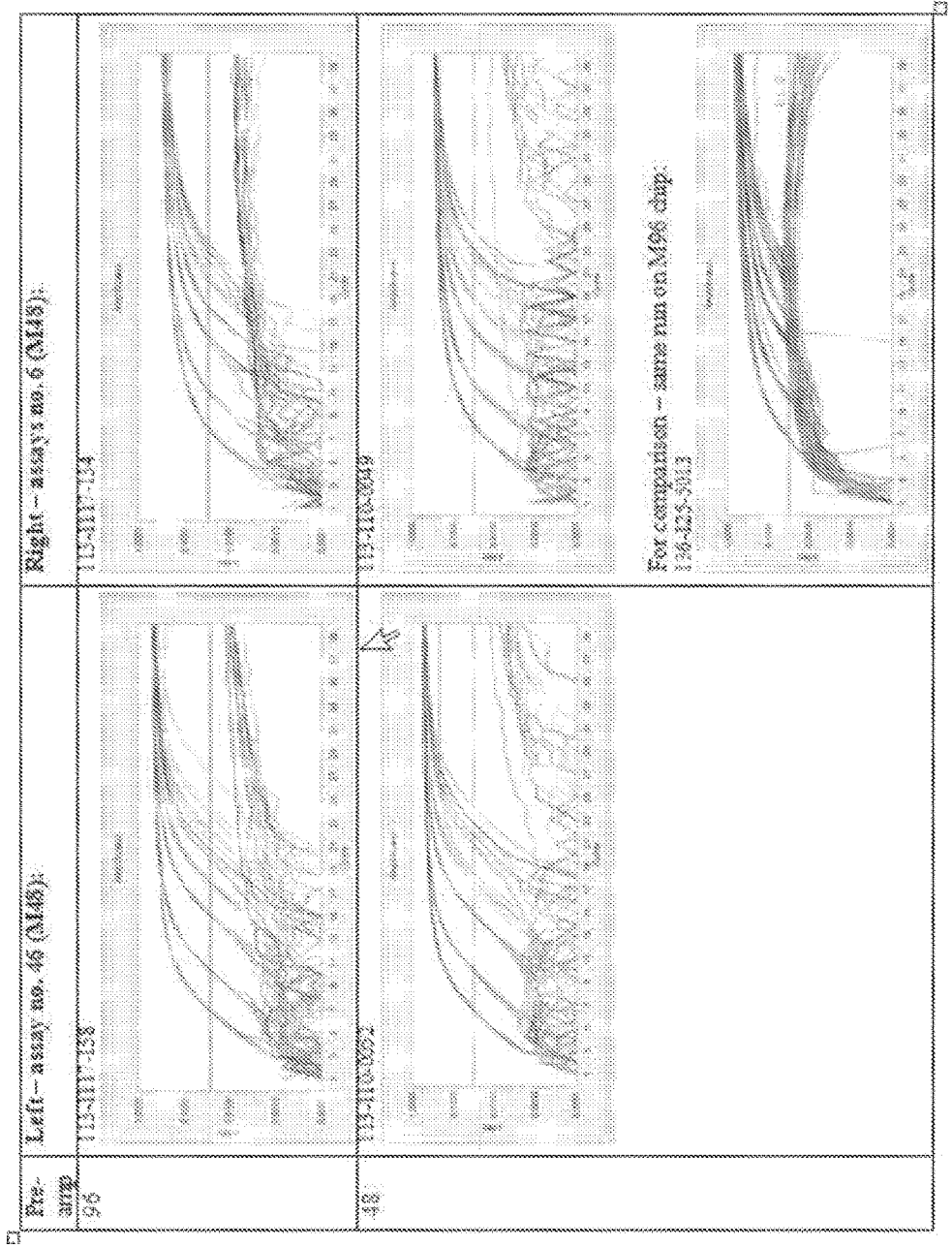

FIG. 450 that qPCR was performed on M48 chip or M96 chip and the results were compared to each other.

Figure 451:
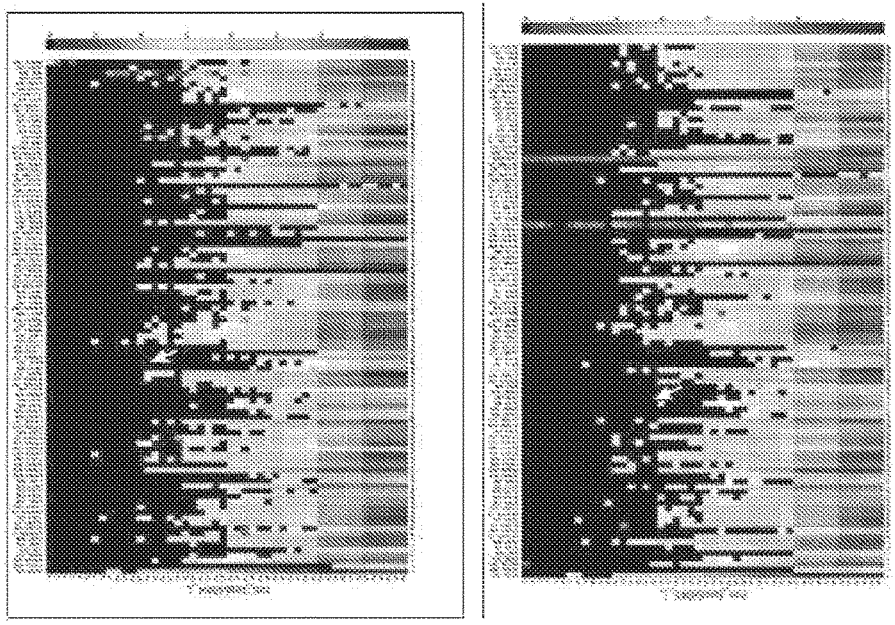

FIG. 451 heat maps of qPCR samples.

Figure 452:
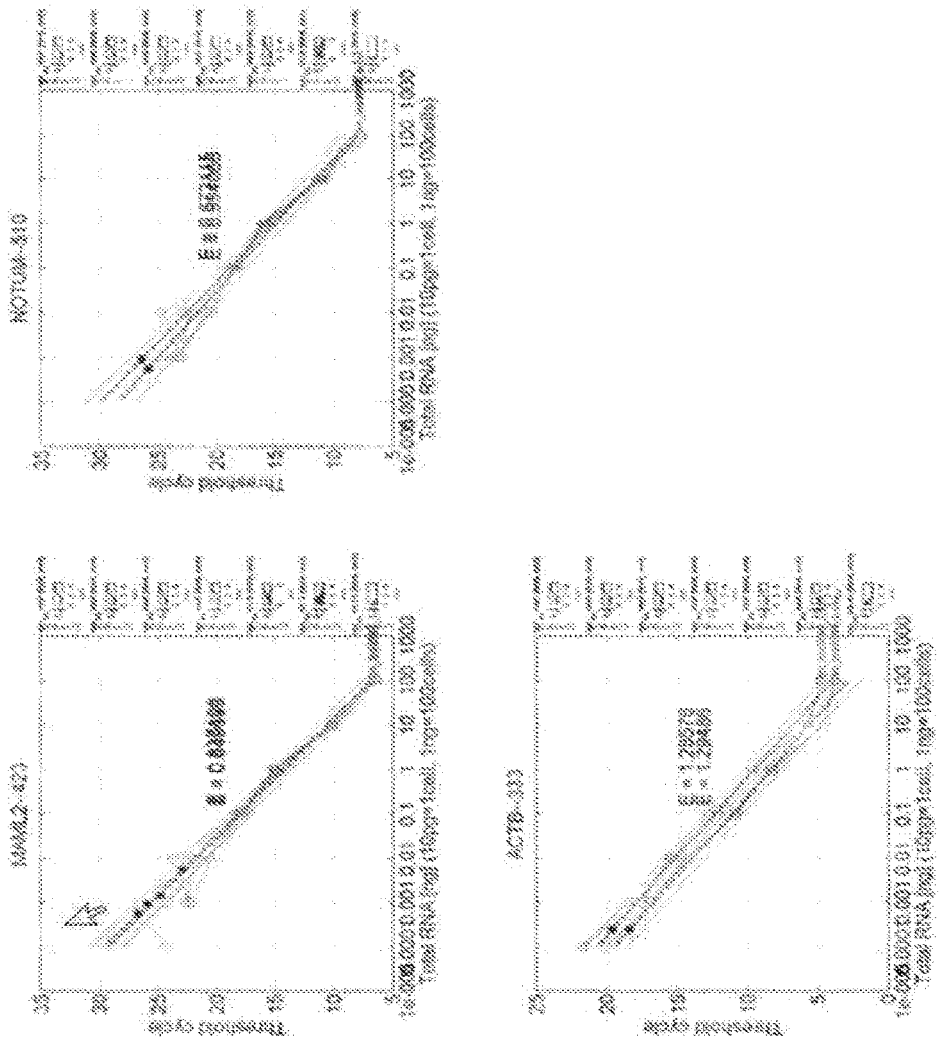

FIG. 452 standard curves generated from these runs, demonstrating that they are very close to each other.

Figure 453:
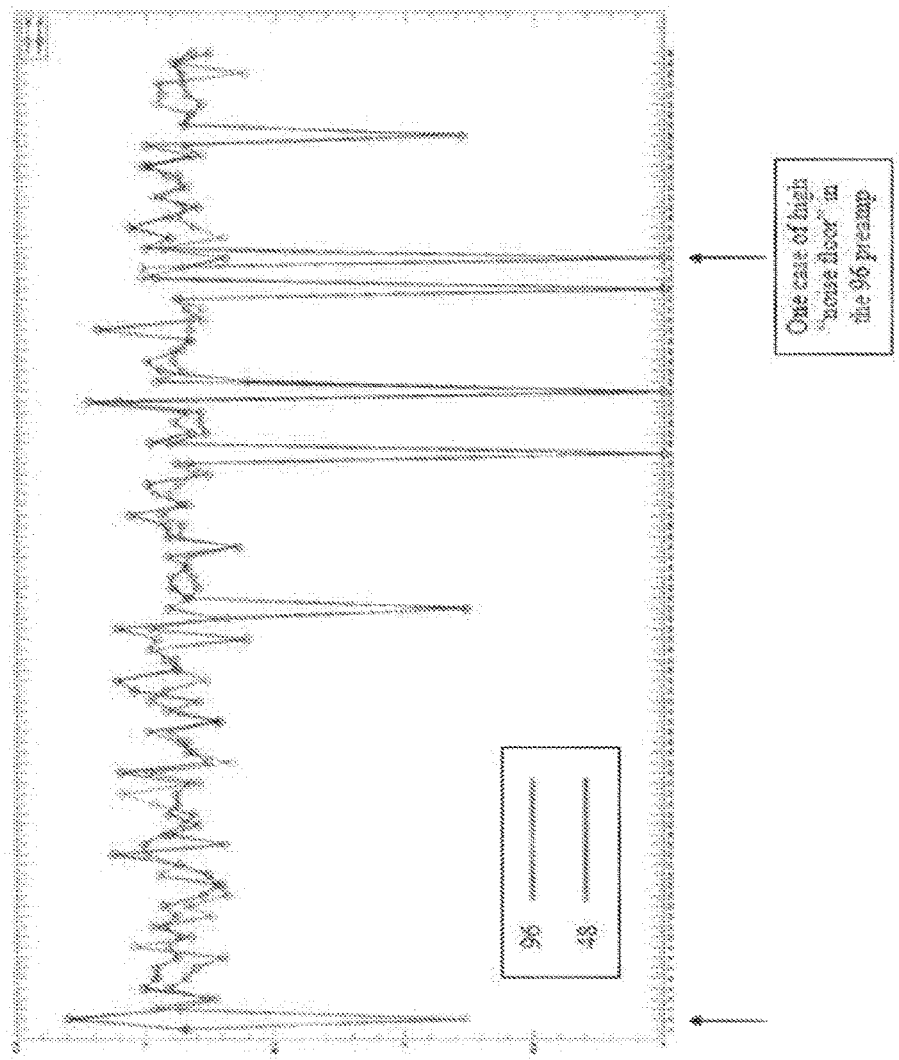

FIG. 453 efficiency between M48 and M96 chips is compared, with an exception of one high noise floor in the 96 preamp run.

Figure 454:
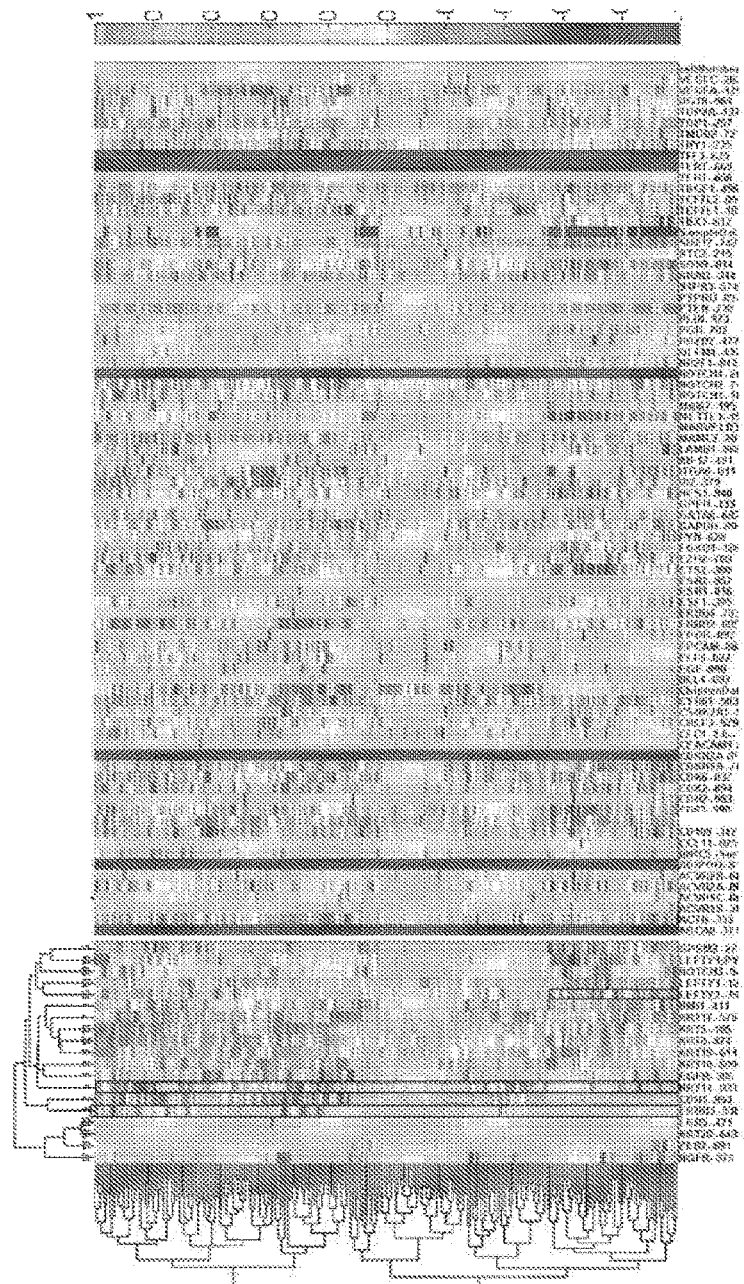

FIG. 454 illustrates hierarchical clustering of breast xenograph for selected genes.

FIG. 455 illustrates hierarchical clustering of CD49f$^{high}$ breast xenograph for selected genes.

FIG. 456 illustrates hierarchical clustering for ITGA6.

FIG. 457 illustrates hierarchical clustering for human normal breast sample.

Figure 458:

FIG. 458 illustrates hierarchical clustering of CD49f normal breast sample.

Figure 459:
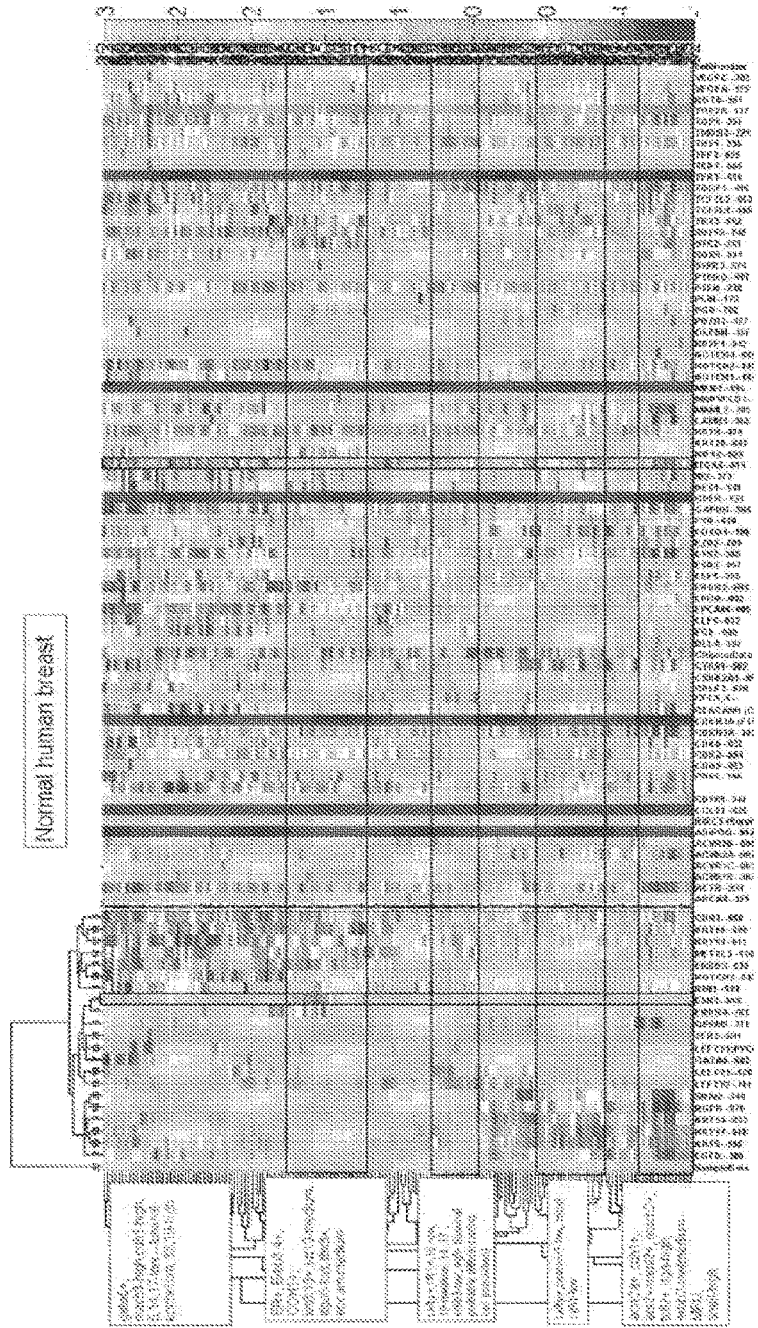

FIG. 459 illustrates another view of hierarchical clustering of CD49f normal breast sample.

Figure 460:
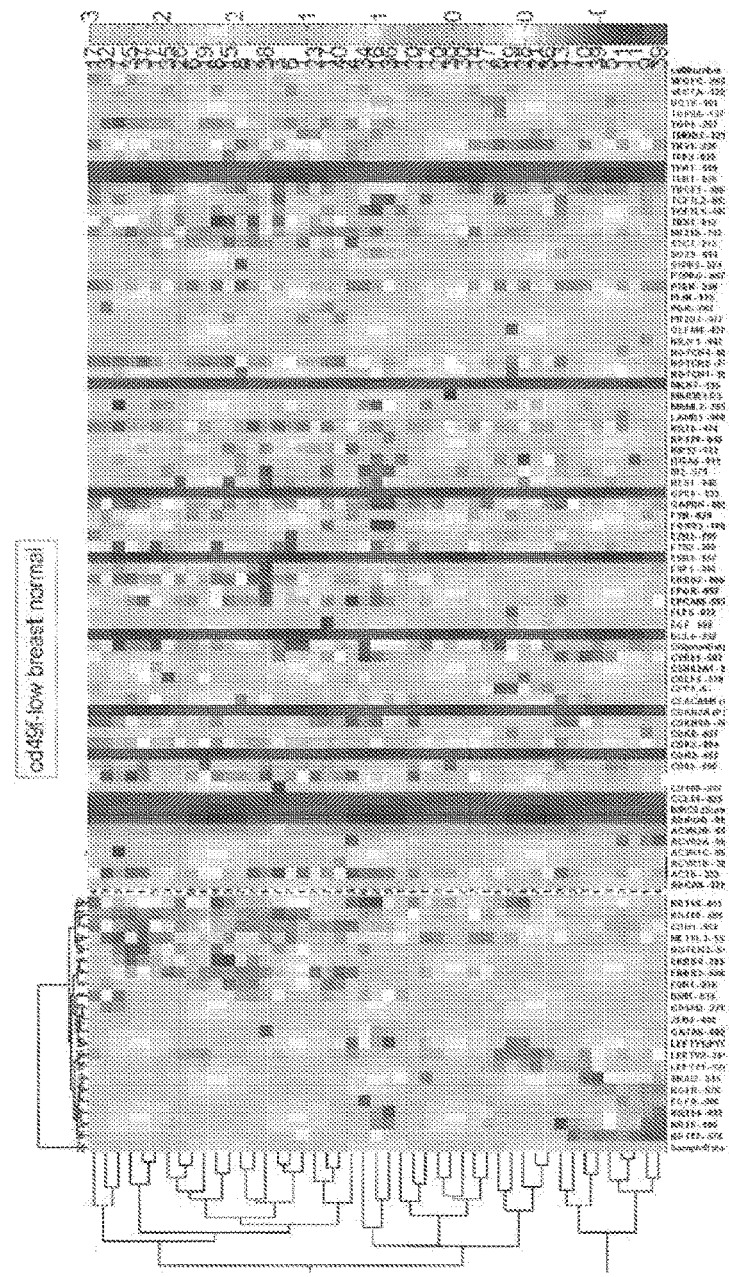

FIG. 460 illustrates hierarchical clustering of CD49f$^{low}$ normal breast sample.

Figure 461:
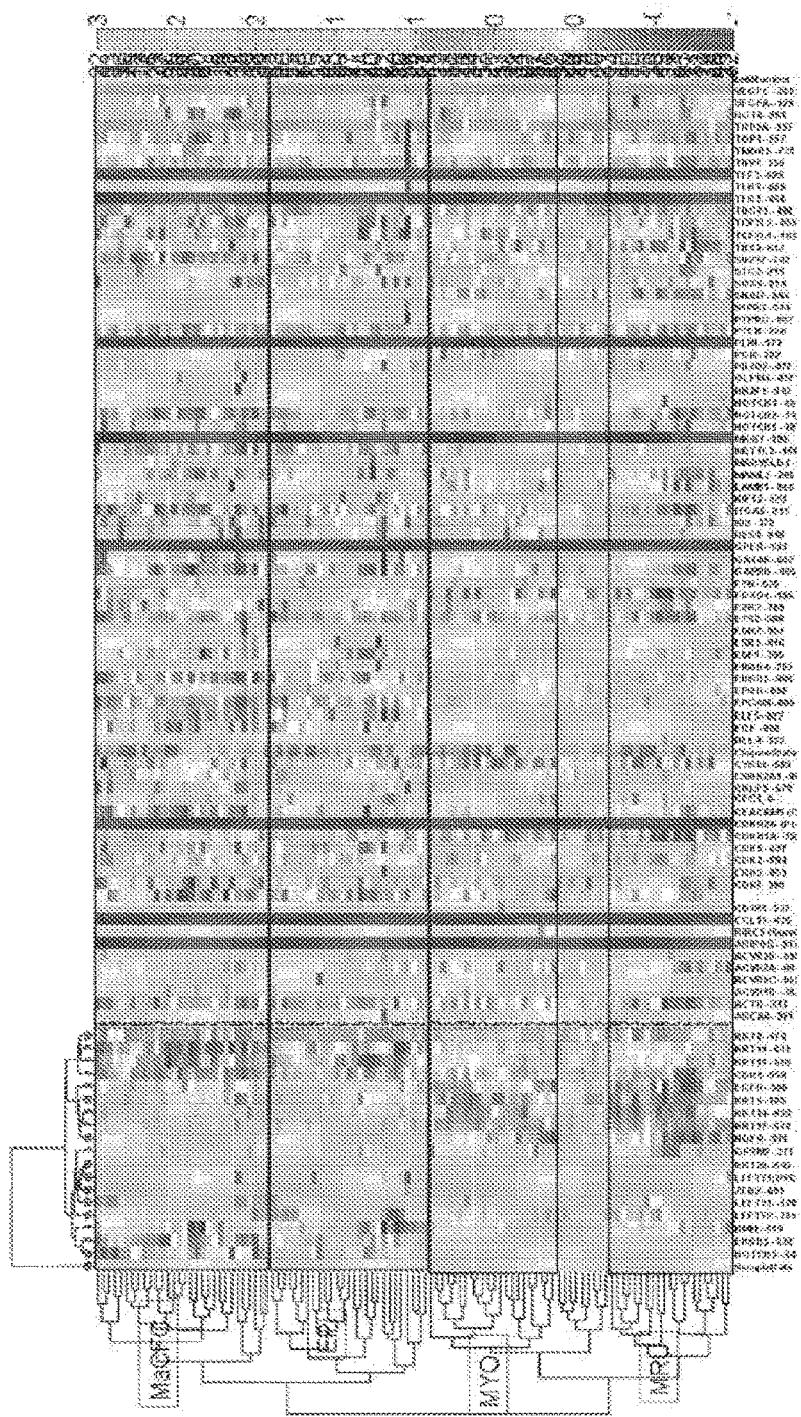

FIG. 461 illustrates hierarchical clustering of CD49f+ normal breast sample.

Figure 462:
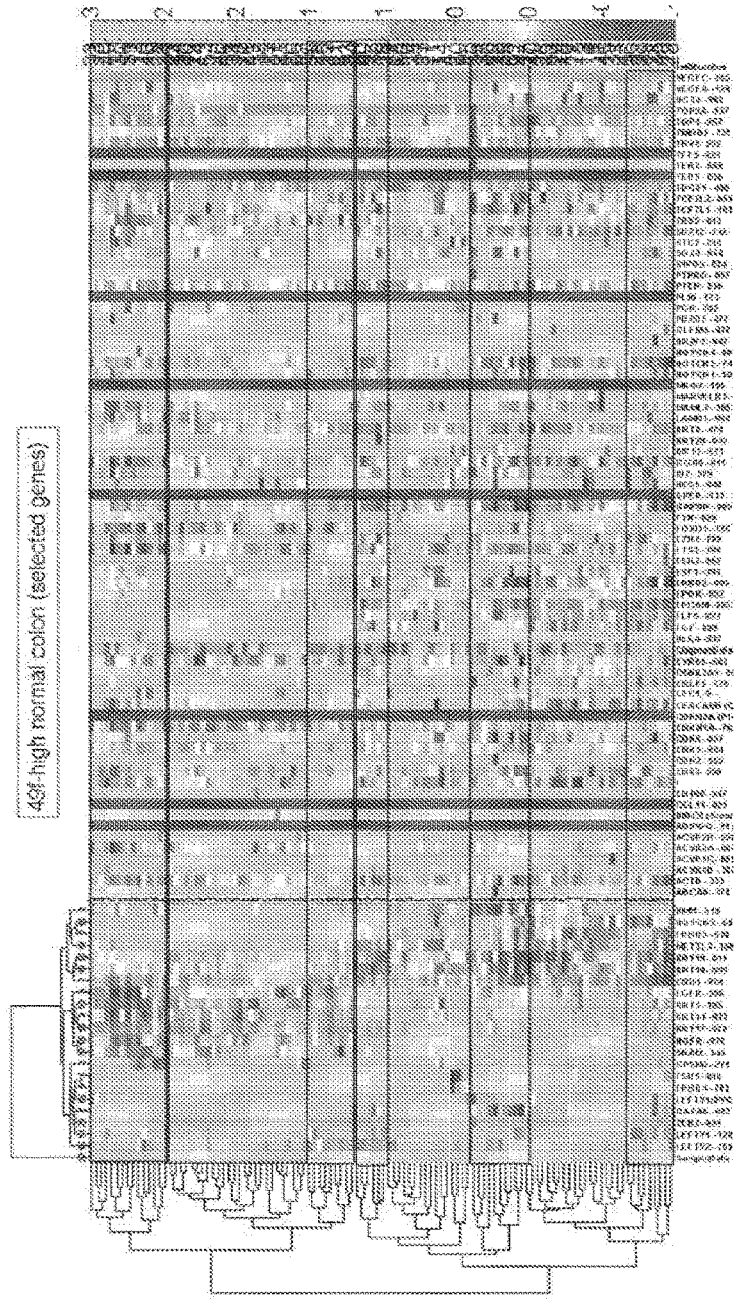

FIG. 462 illustrates hierarchical clustering of CD49f$^{high}$ normal breast sample.

Figure 463:
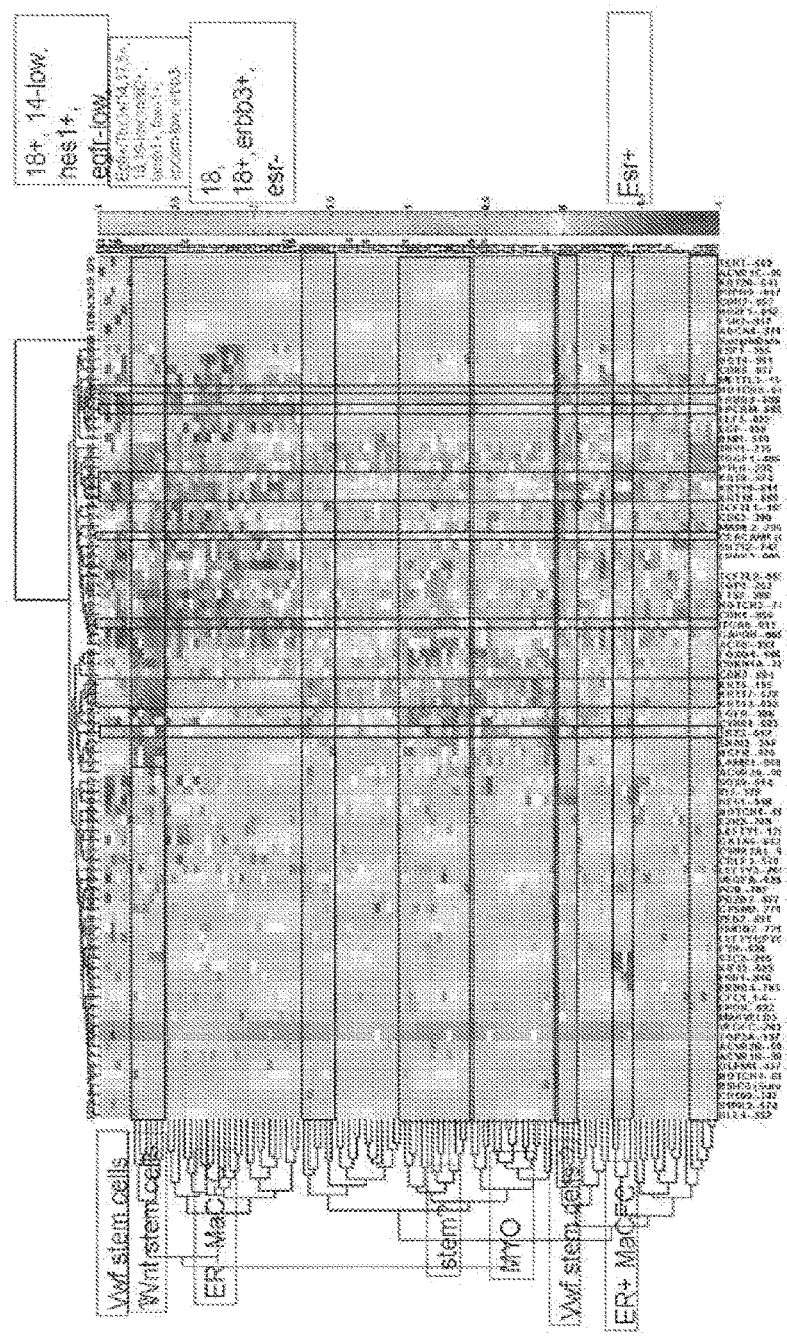

FIG. 463 illustrates hierarchical clustering of CD49f+ normal breast sample.

FIG. 464 illustrates hierarchical clustering for CDH1 and ESR1.

Figure 465:
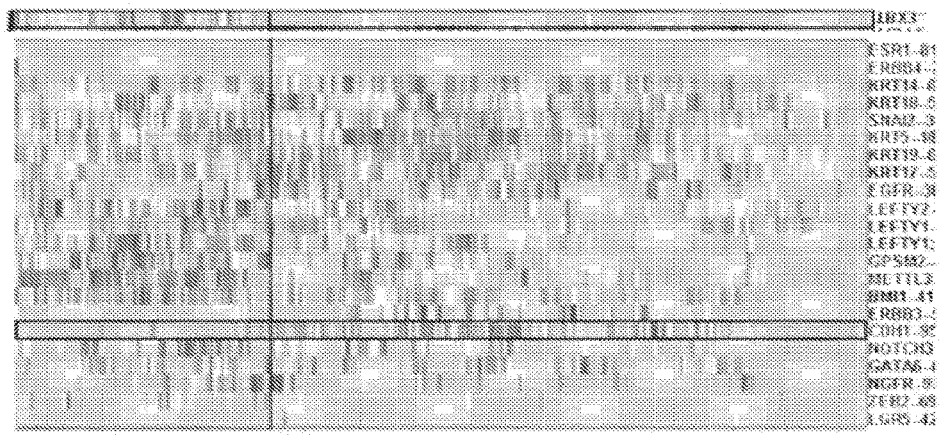

FIG. 465 illustrates hierarchical clustering for CDH1.

Figure 466:
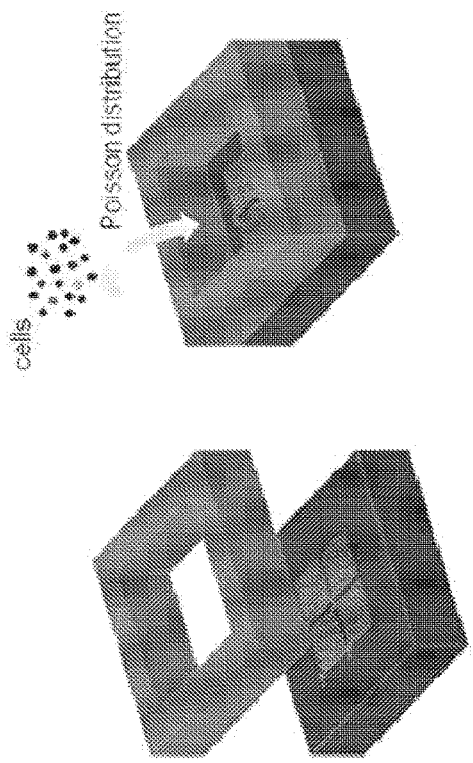

FIG. 466 Graphic depiction of a microwell array chip for on-chip washing and cell presenting.

Figure 467:
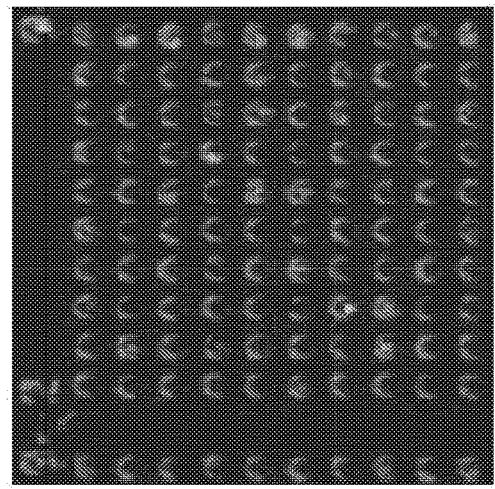

FIG. 467 illustrates on-chip washing of cells, with dual-stained cells.

Figure 468:
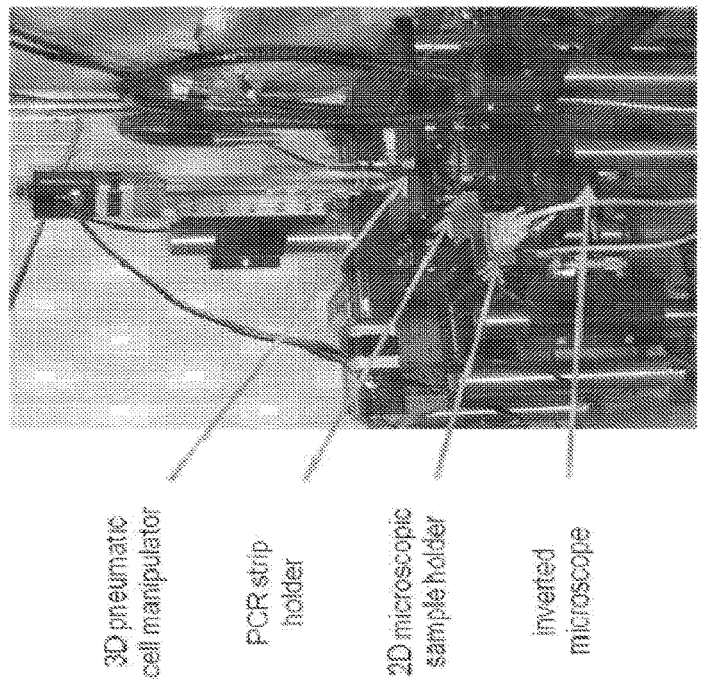

FIG. 468 a pictorial representation of one embodiment of a cell sorter/cell picker.

Figure 469:
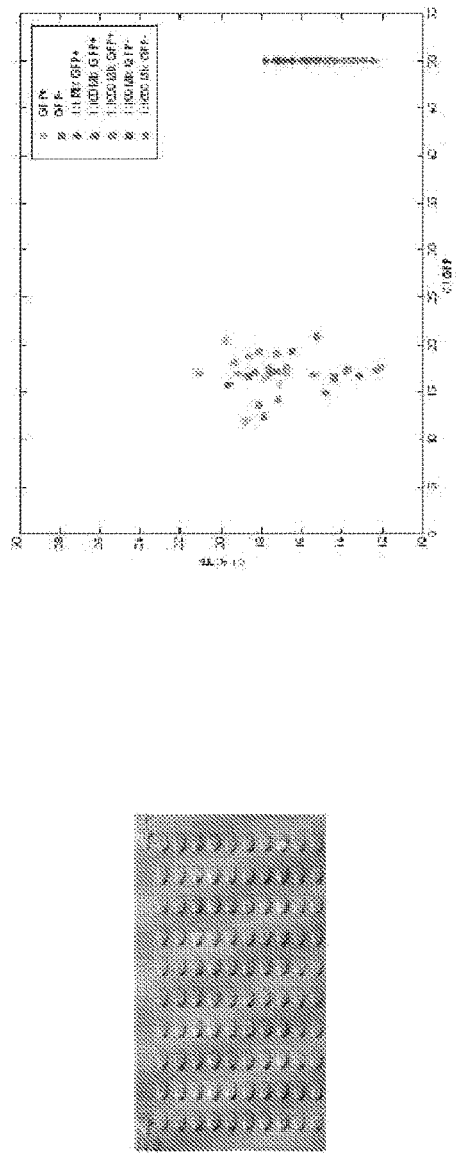

FIG. 469 is a graphic representation of a GFP cells demo sorting.

Figure 470:
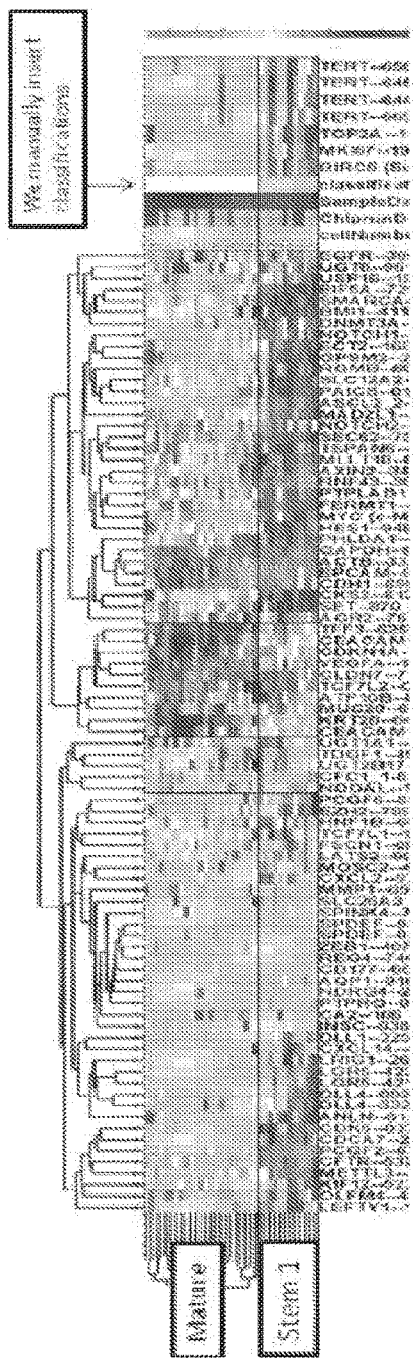

FIG. 470. illustrates single cell gene expression patterns from in vitro stem cell cultures.

Figure 471:
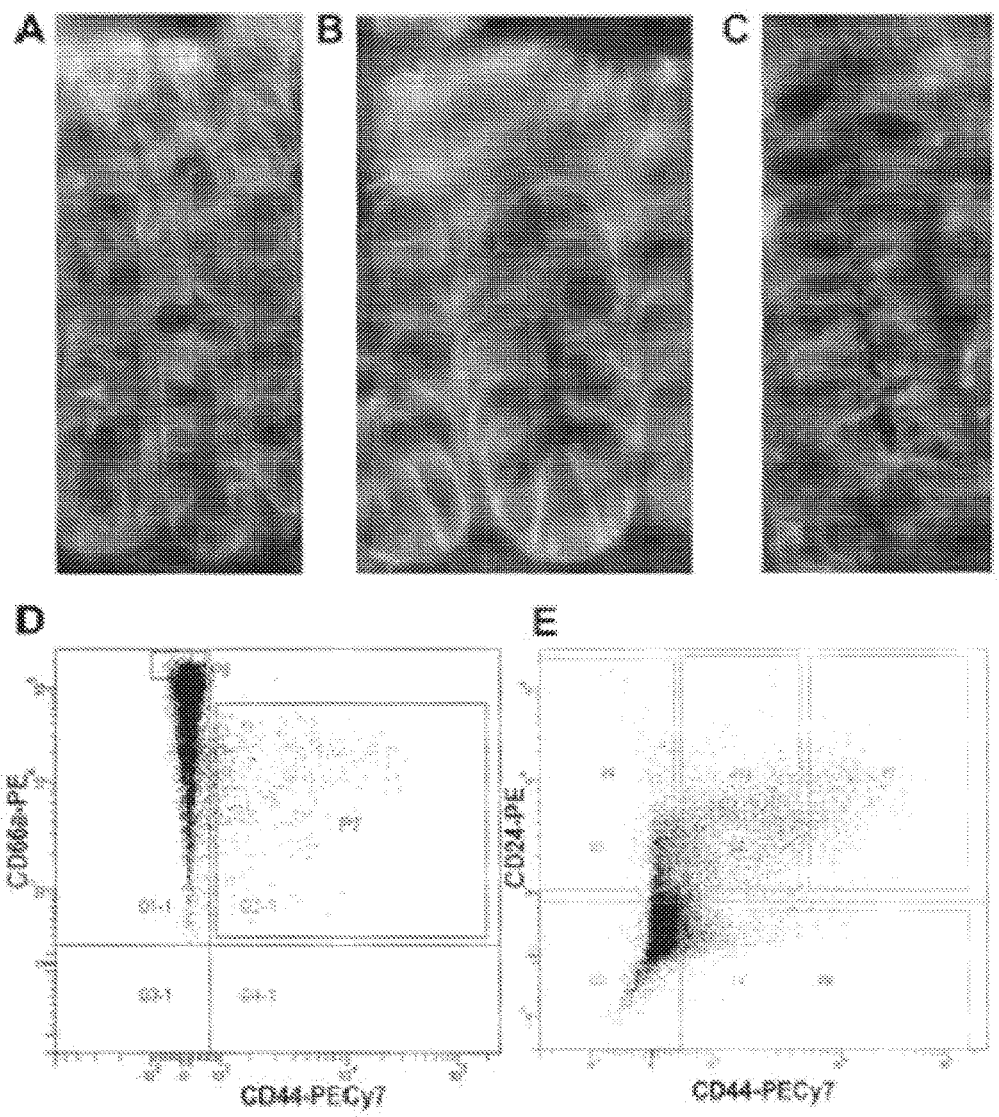

FIG. 471. Separation of colonic crypt subpopulations with CD44, CD66a, and CD24.

Figure 472:
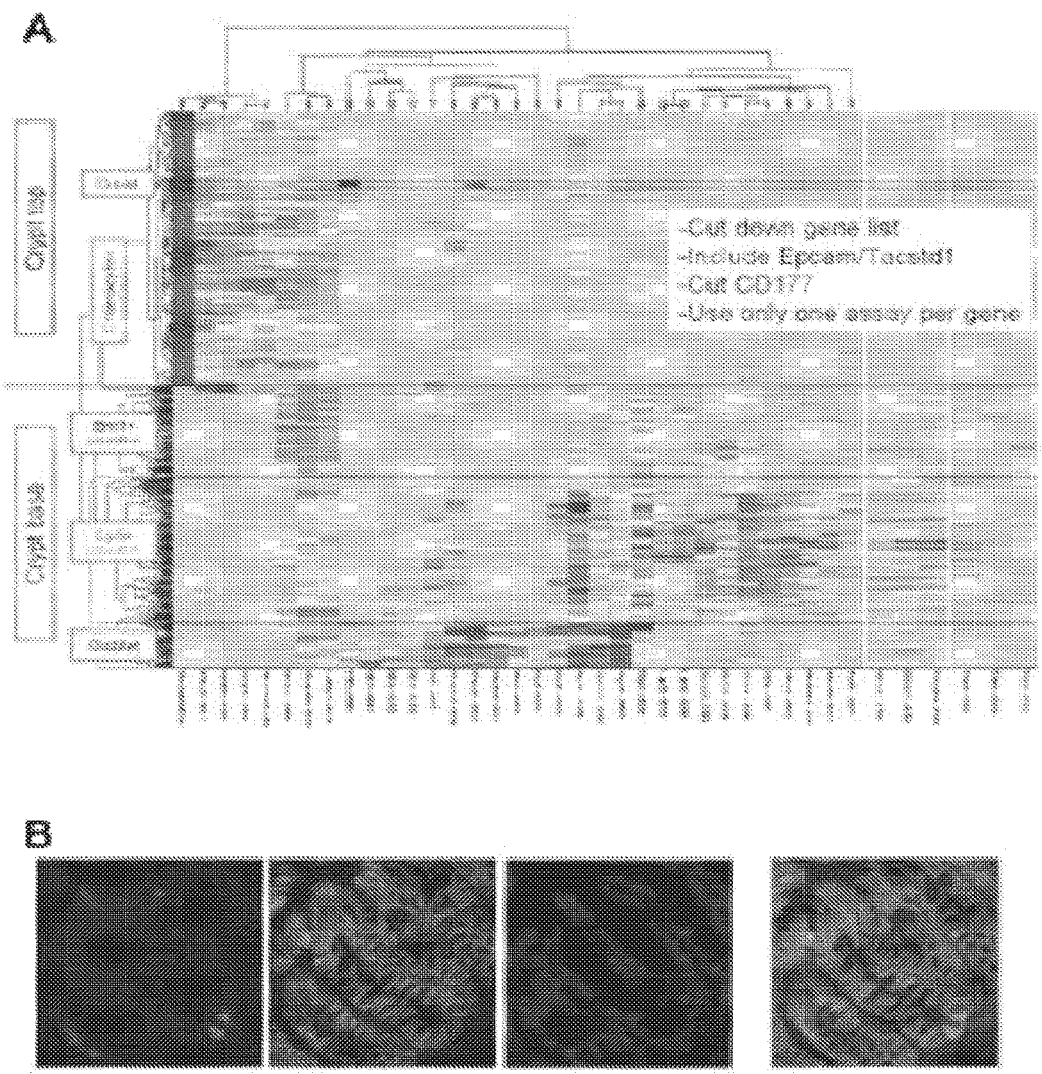

FIG. 472. Single cell gene expression analysis comparing the crypt base to the crypt top.

Figure 473:
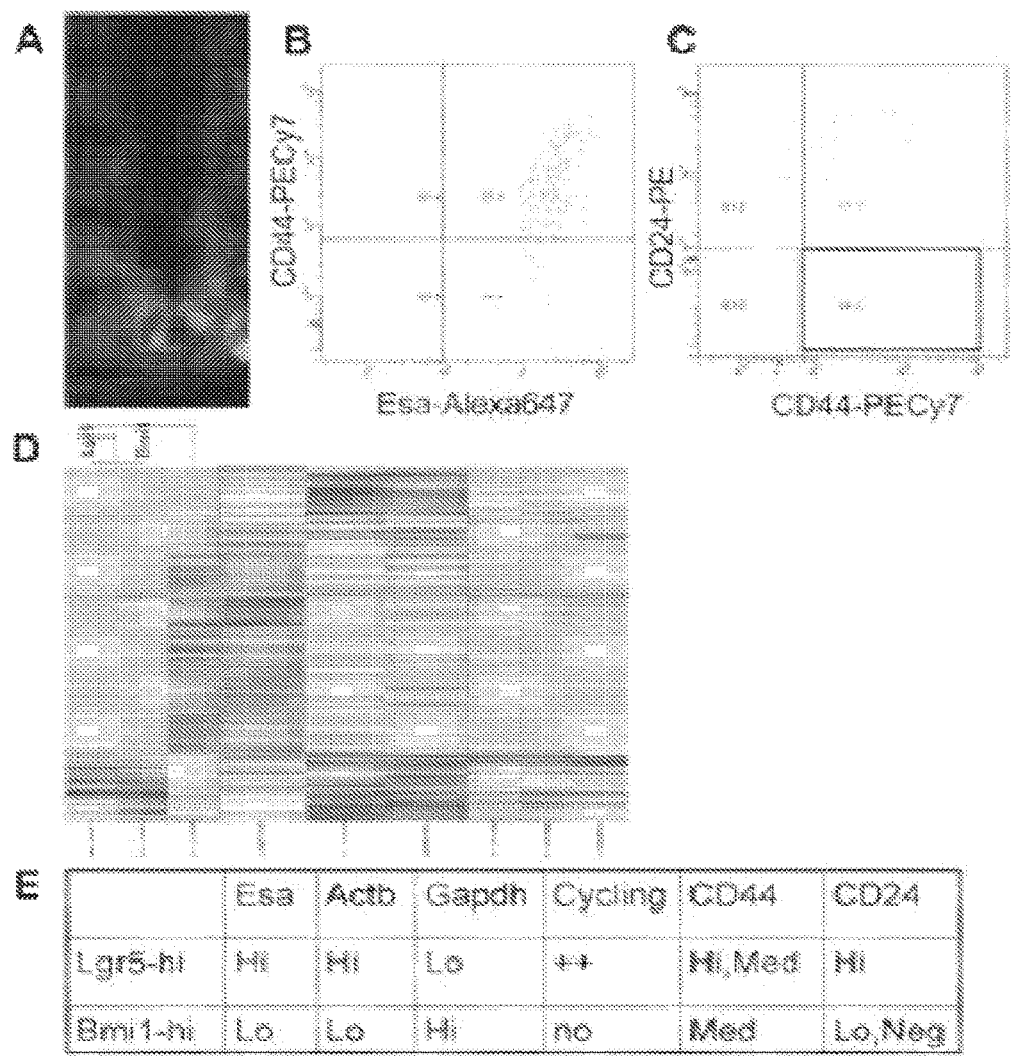

FIG. 473. Lgr5$^{high}$ and Bmi1$^{high}$ cells are phenotypically distinct

Figure 474:
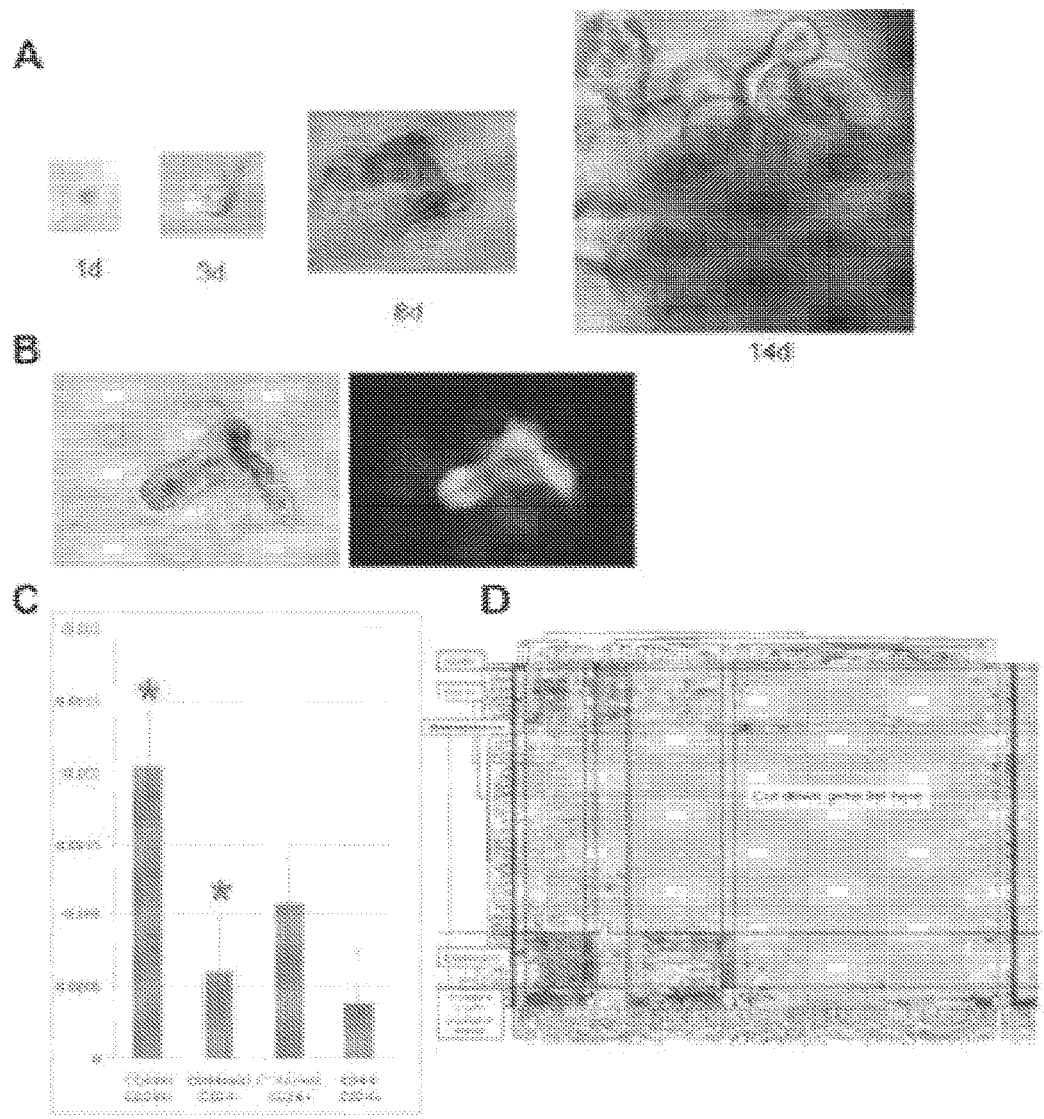
Figure 475:
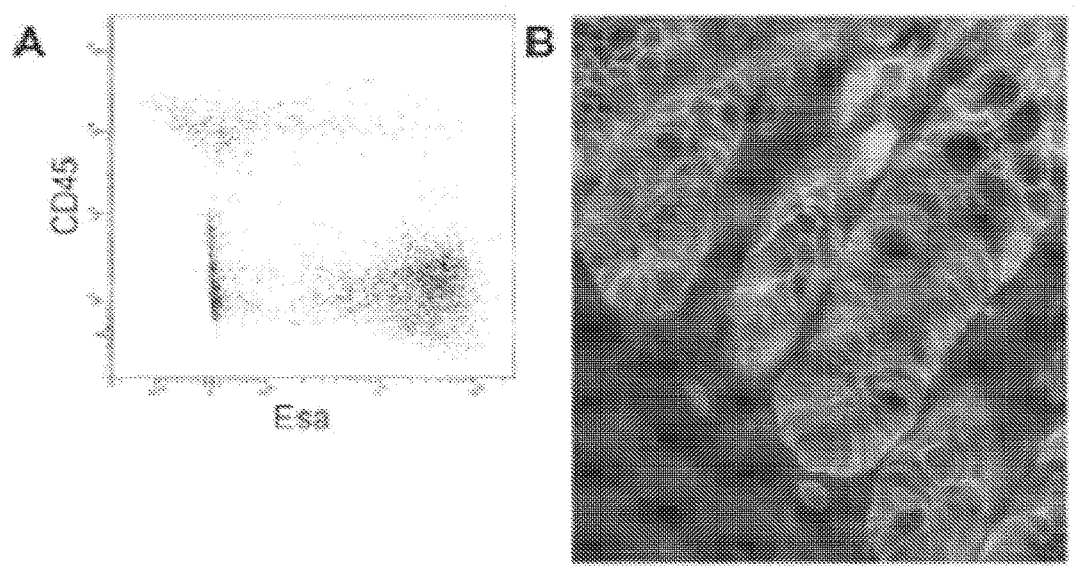

FIG. 474. CD44$^{med}$CD24$^{low/neg}$ and CD44$^{high}$CD24$^{high}$ cells can generate self-renewing colonic organoids FIG. 475. Isolation of epithelial, hematopoietic, and stromal cells from dissociated murine colon.

Figure 476:
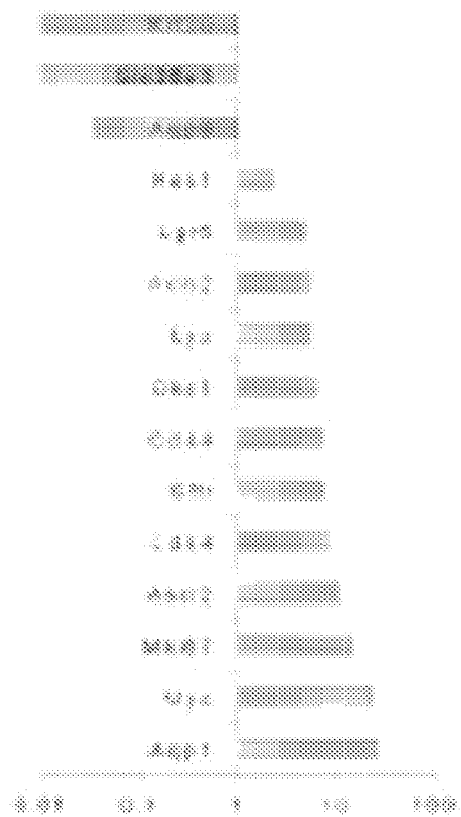

FIG. 476. Differential gene expression in sorted cells from the crypt base and the crypt top.

Figure 477:
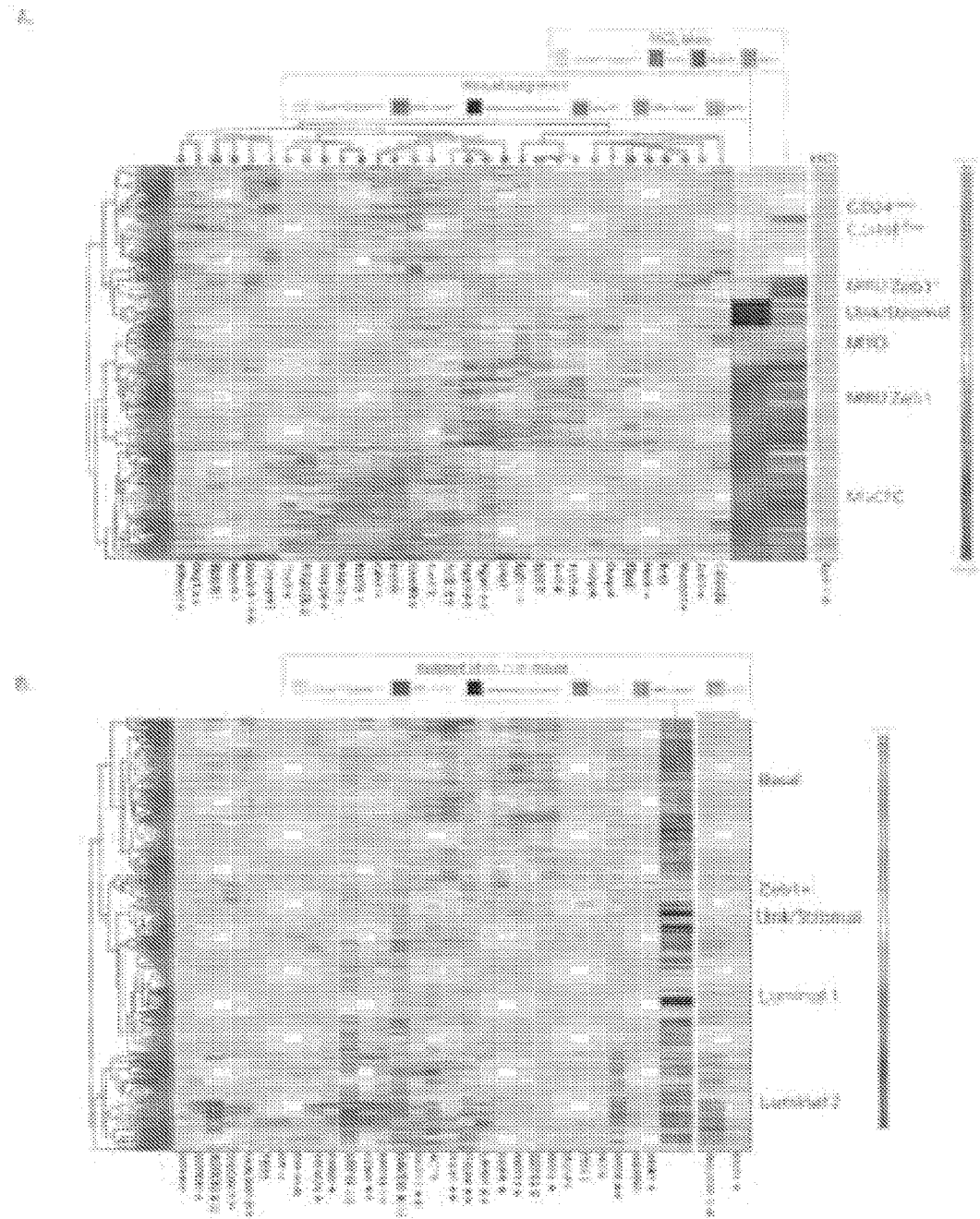

FIG. 477. Single cell analysis of mouse and human breast epithelial cells.

Figure 478:
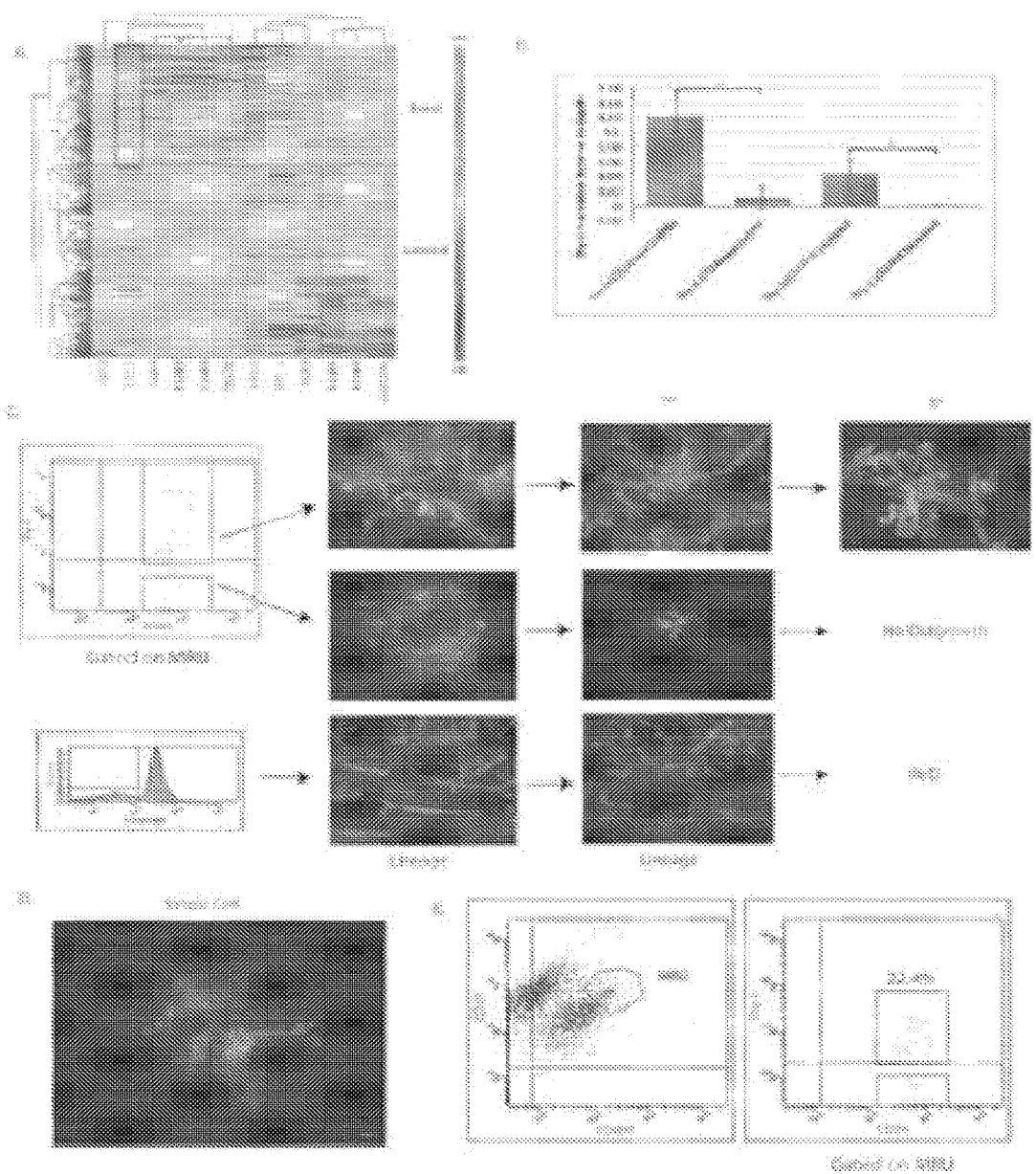

FIG. 478. Thy-1 enriches for mammary stem cells.

Figure 479:
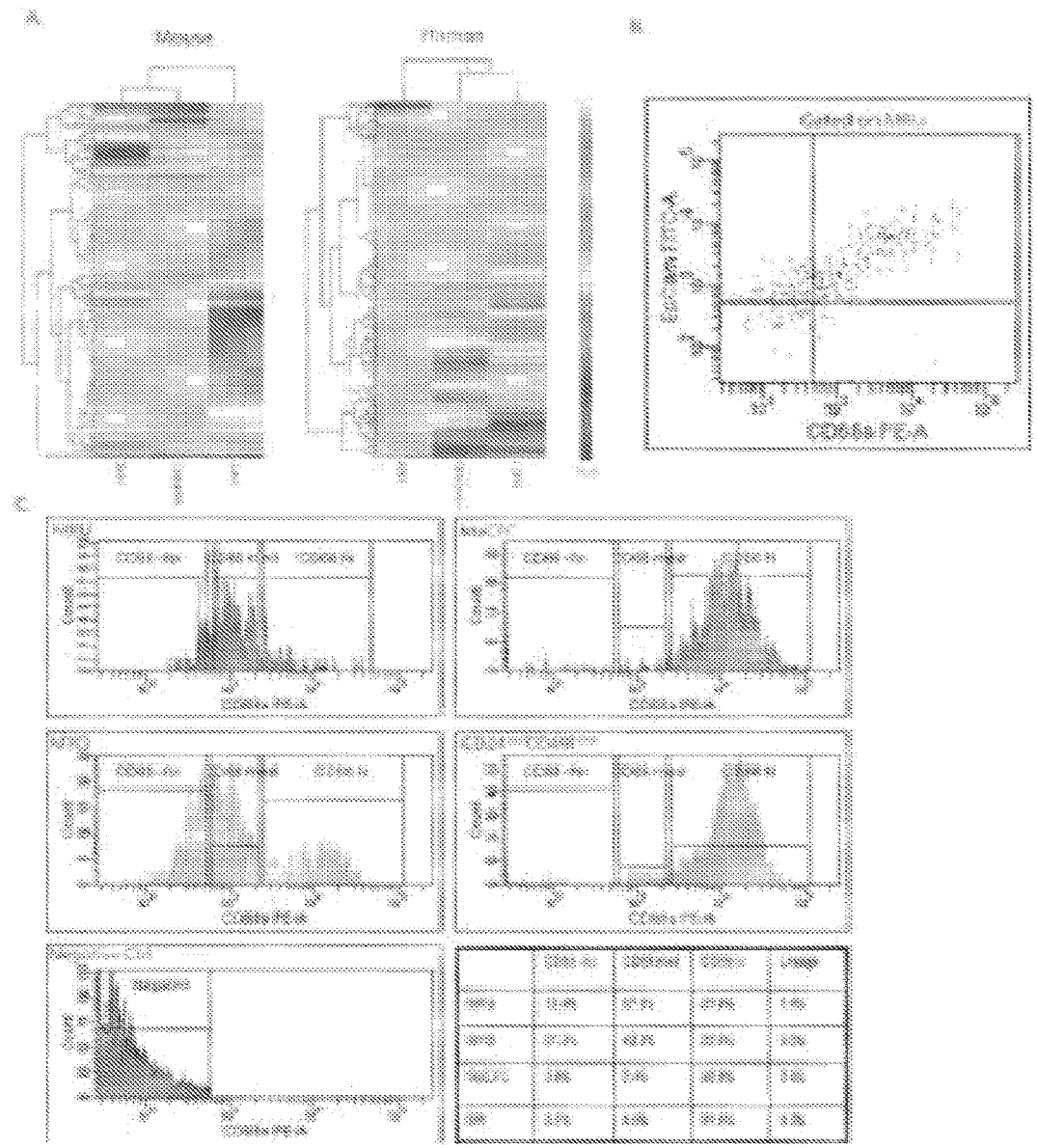

FIG. 479. CD66a discriminates between two stem enriched populations.

Figure 480:
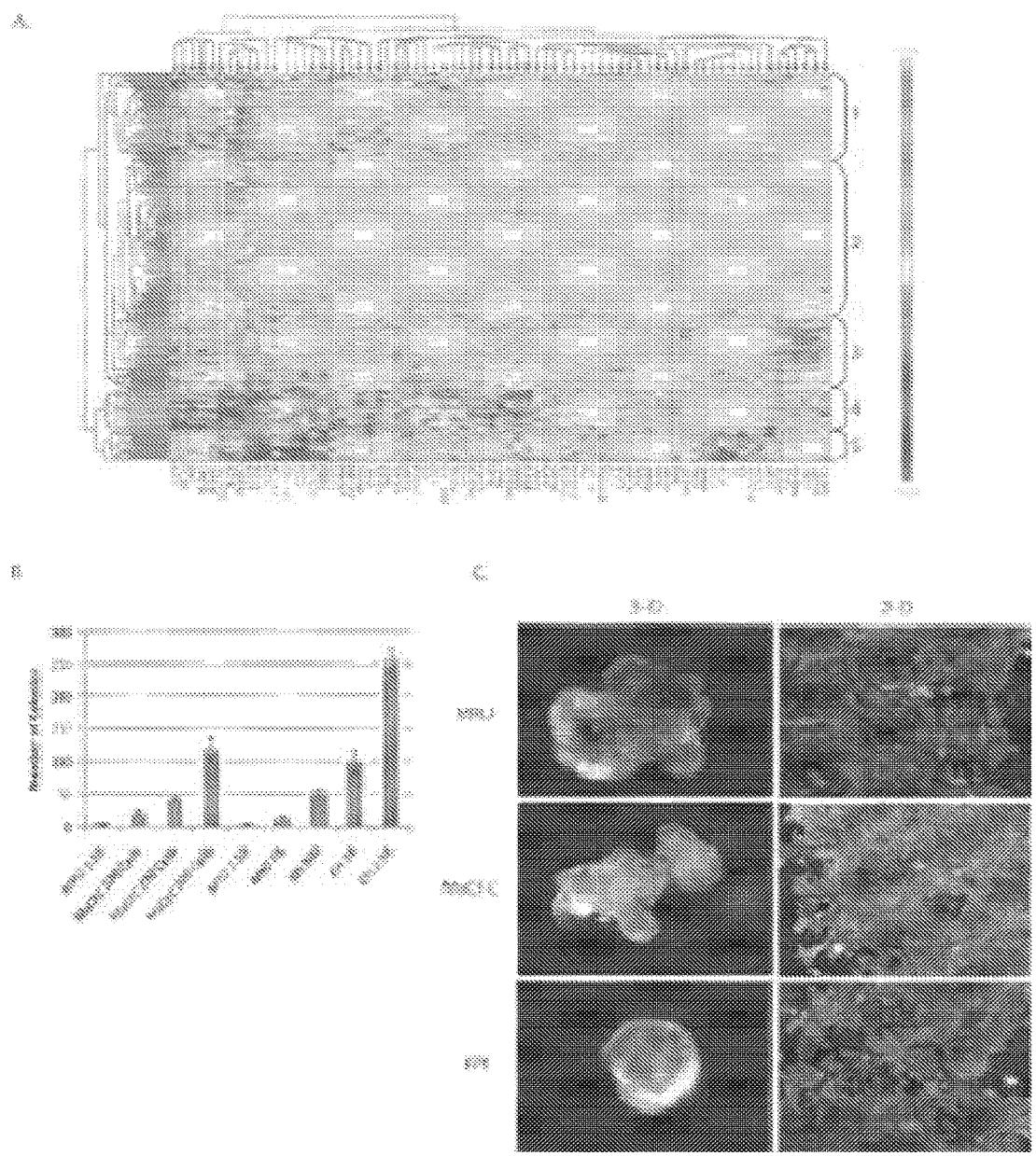

FIG. 480. ER$^-$ luminal cells contain cell populations with progenitor cell gene expression patterns.

Figure 481:
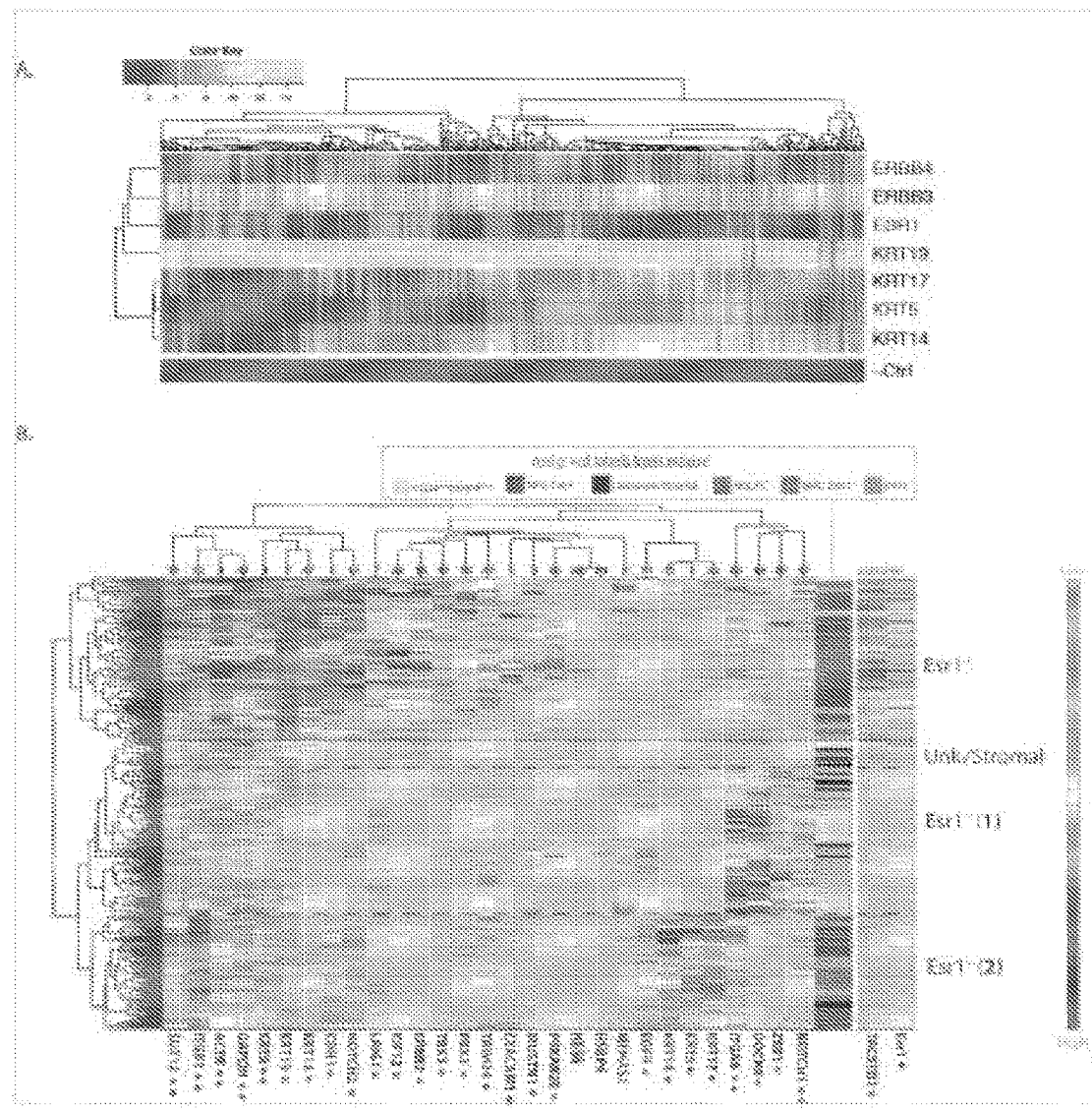

FIG. 481. Analysis of estrogen receptor positive breast tumors.

Figure 482:
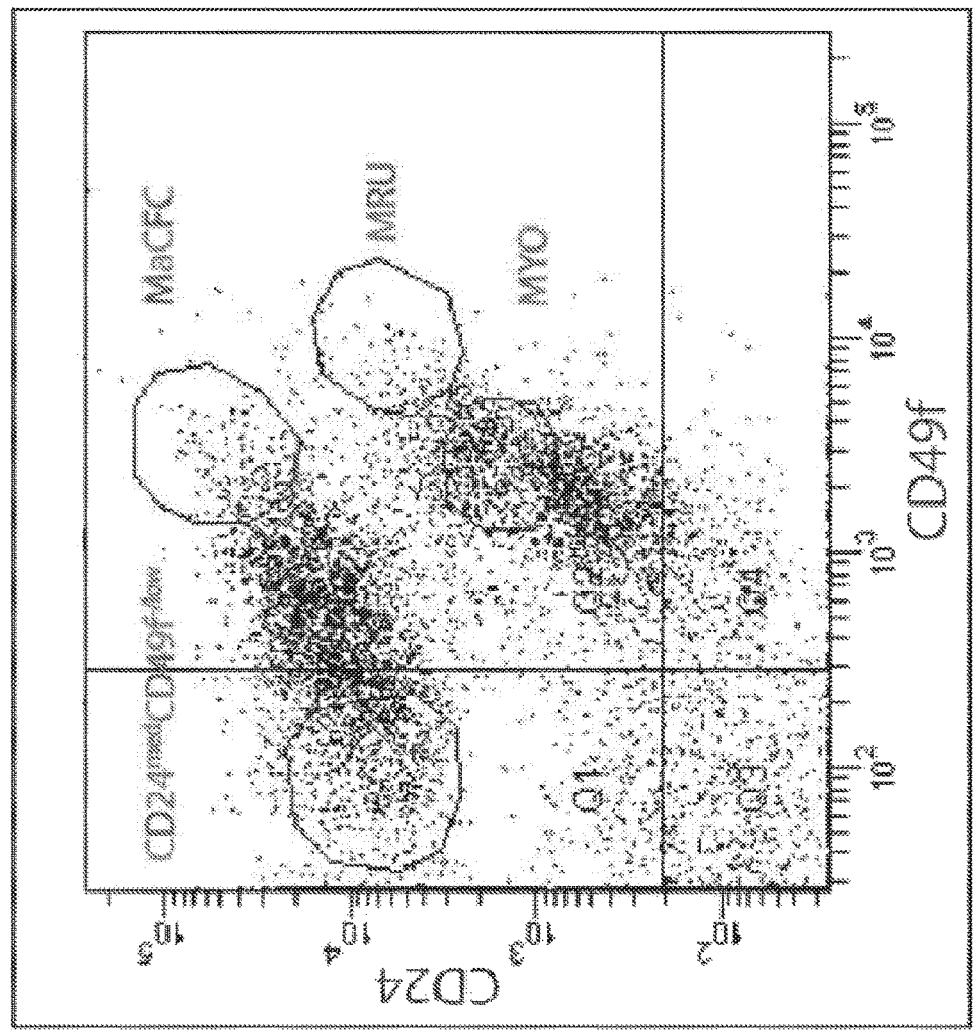

FIG. 482. Flow cytometry analysis of mouse breast cells based on CD24 and CD49f staining.

Figure 483:
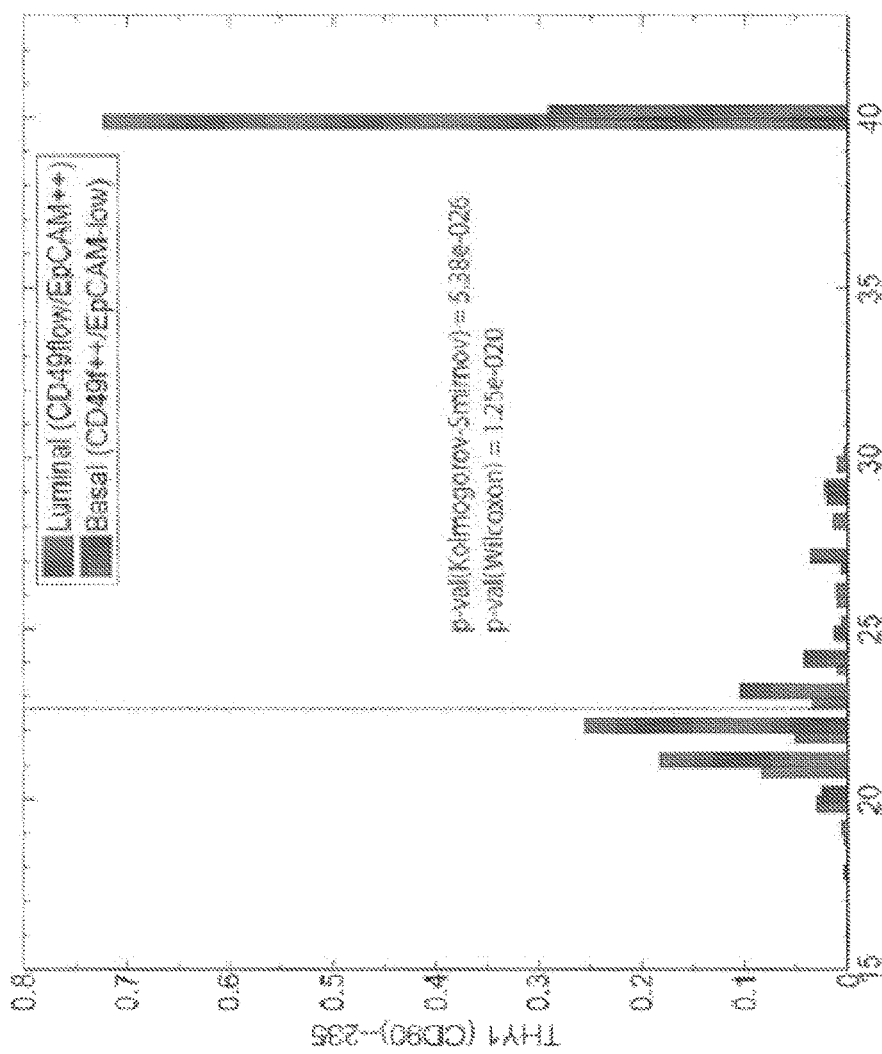

FIG. 483. Thy-1 is highly expressed in the basal population of human breast epithelial cells.

Figure 484:
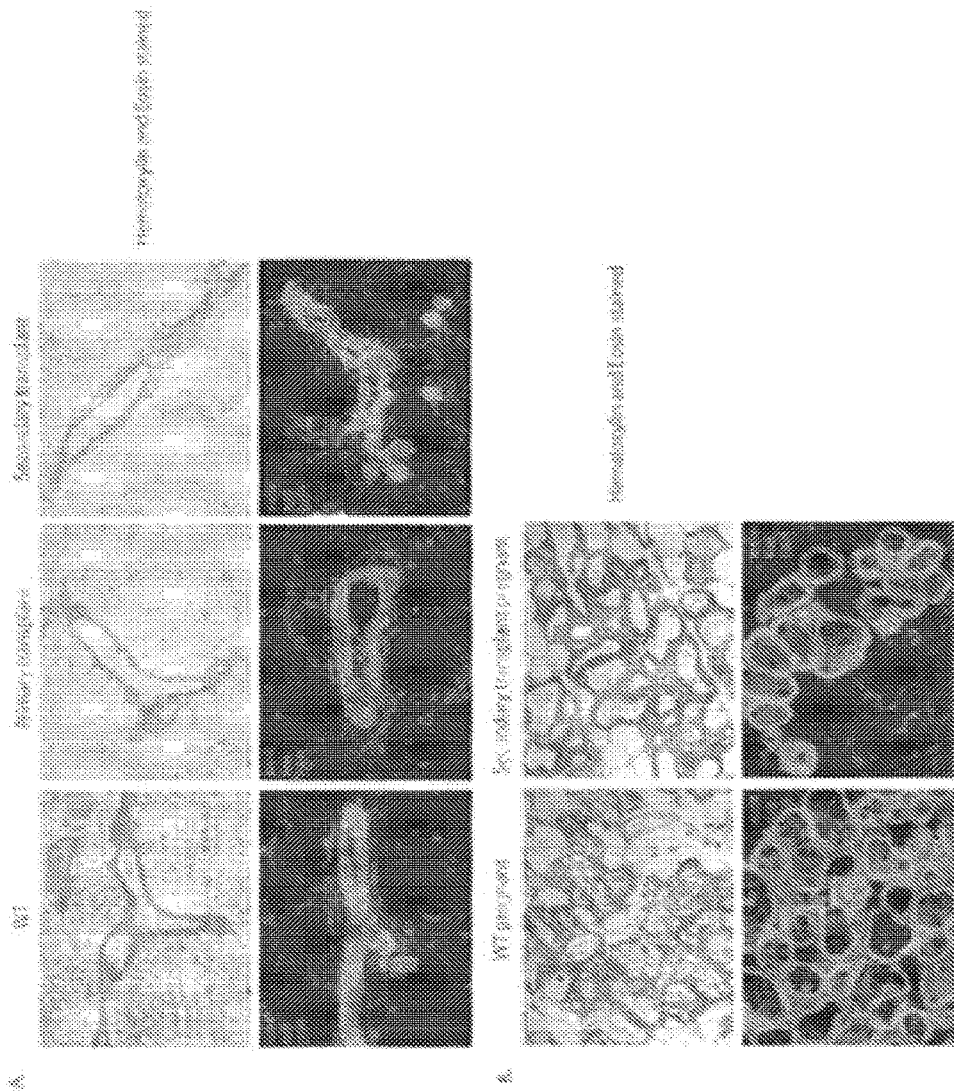

FIG. 484. Thy-1$^+$CD24$^{med}$CD49f$^{hi}$ cells give rise to functional mammary epithelium.

Figure 485:
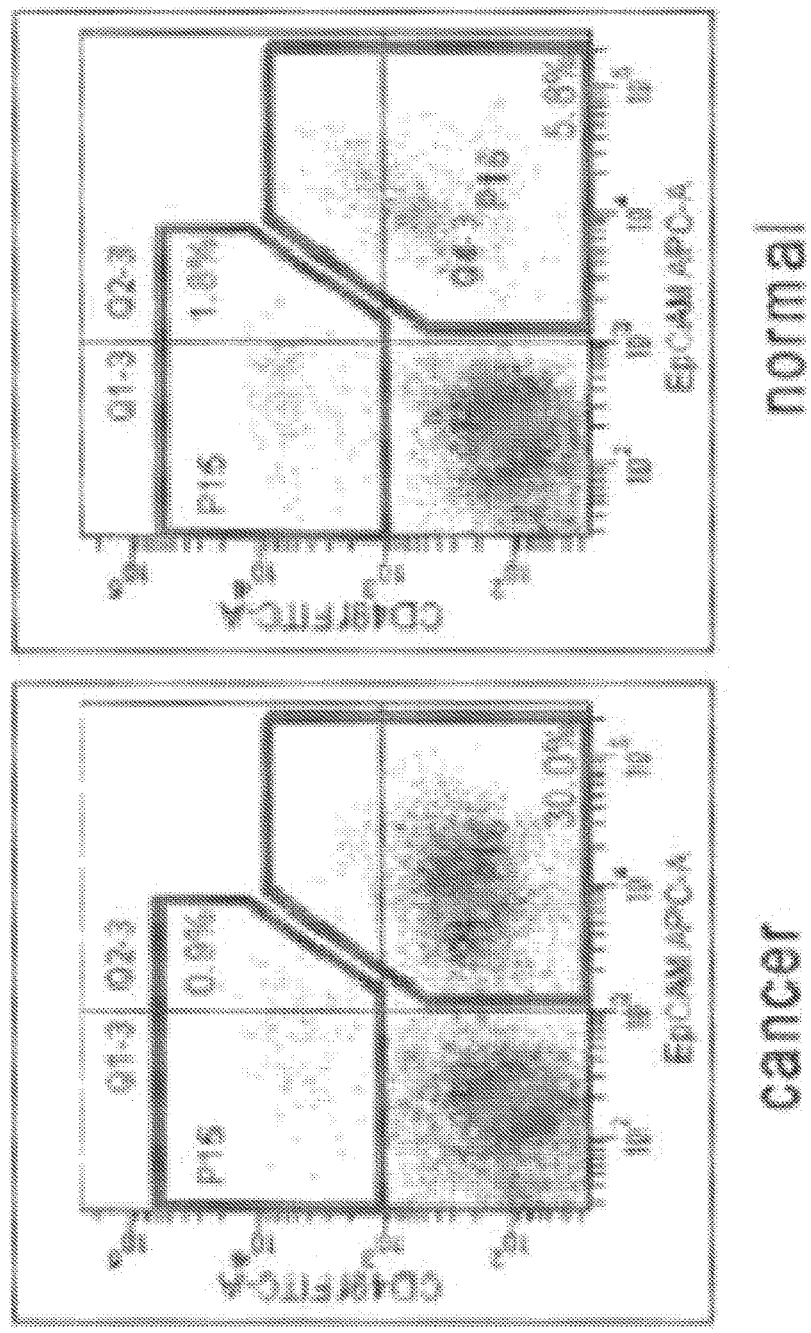

FIG. 485. Flow cytometric analysis of an ER$^+$ tumor and a paired normal breast sample.

Figure 486:
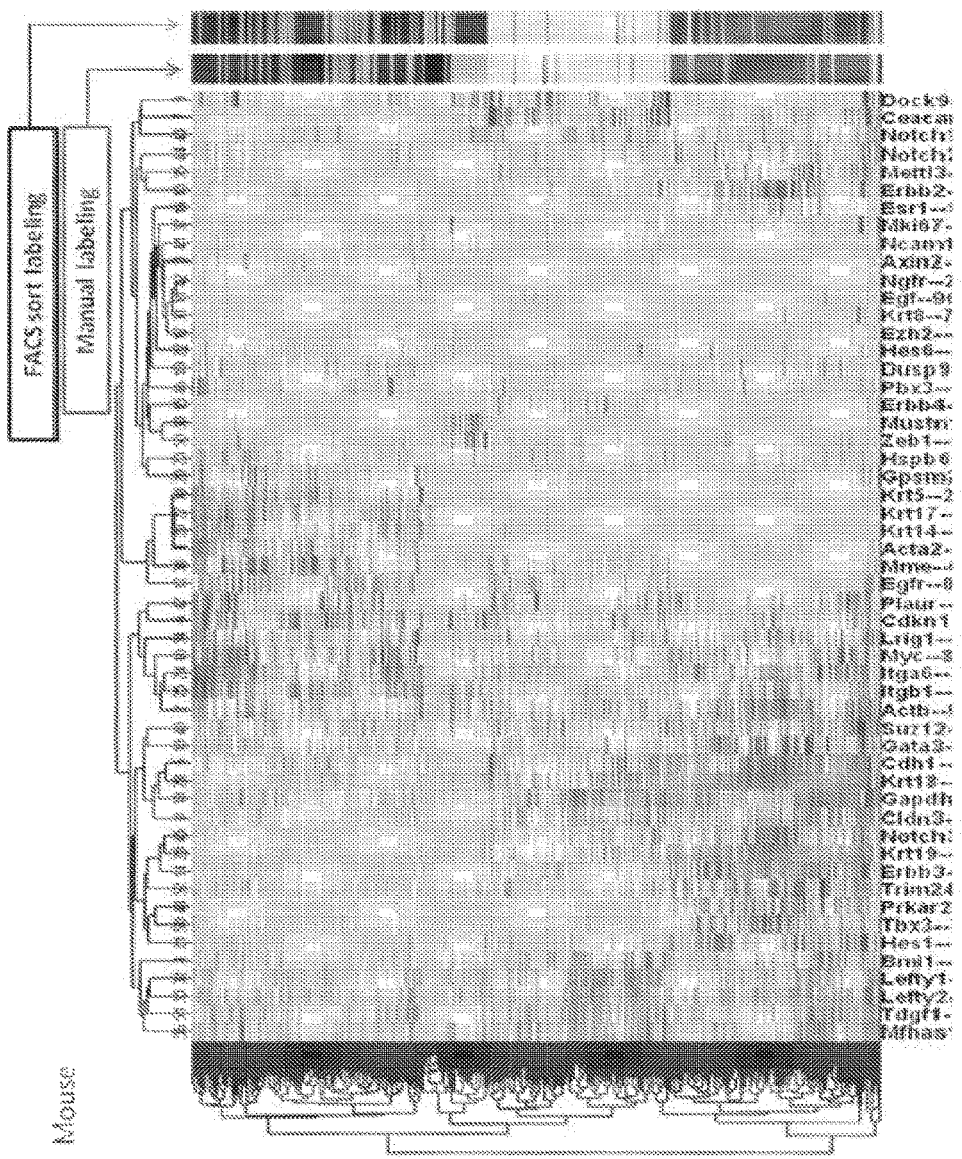

FIG. 486. Clustering of single cell gene expression data from the mouse mammary gland.

Figure 487:
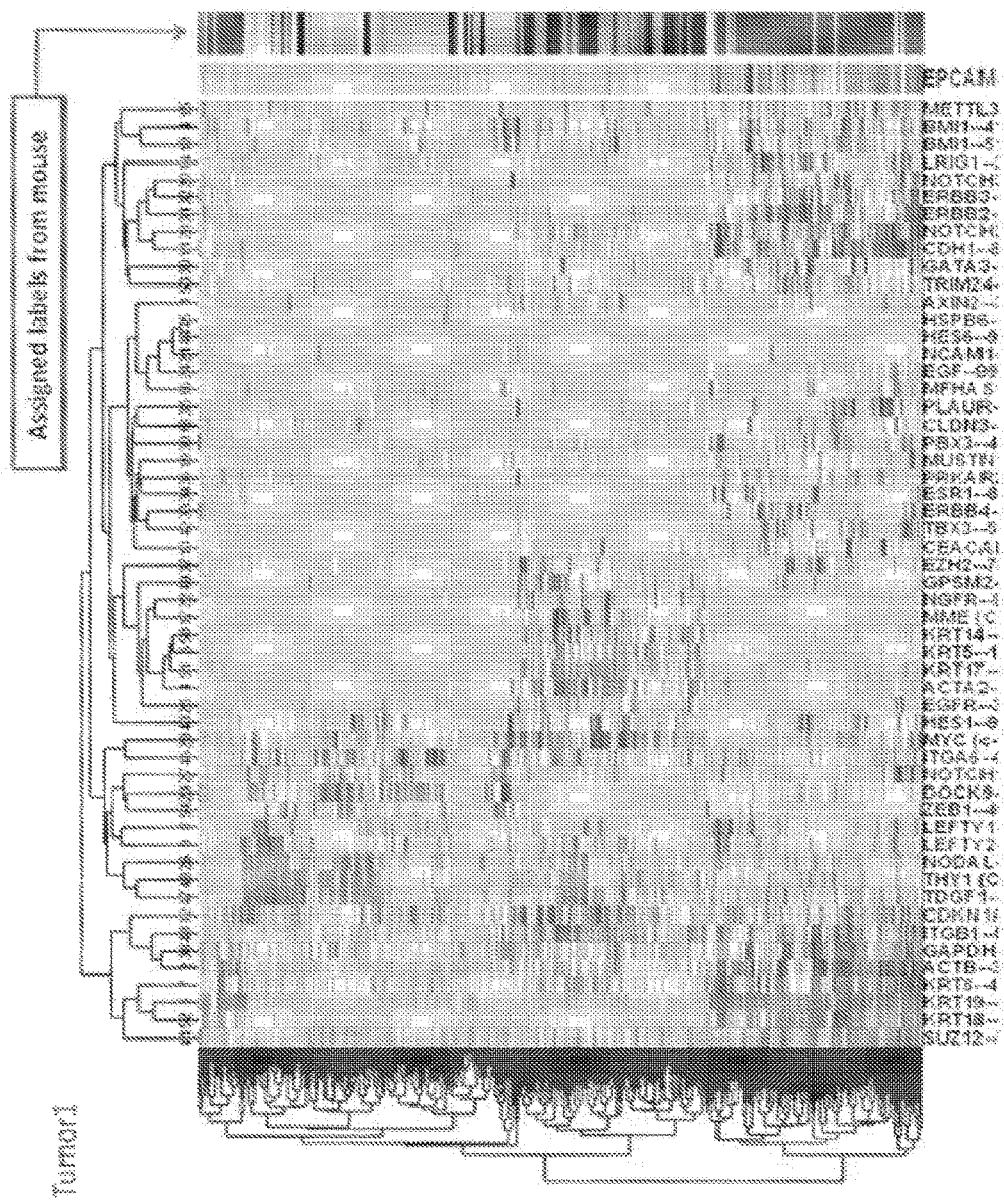

FIG. 487. Clustering of single cell gene expression data from the human breast cancer (Tumor 1).

Figure 488:
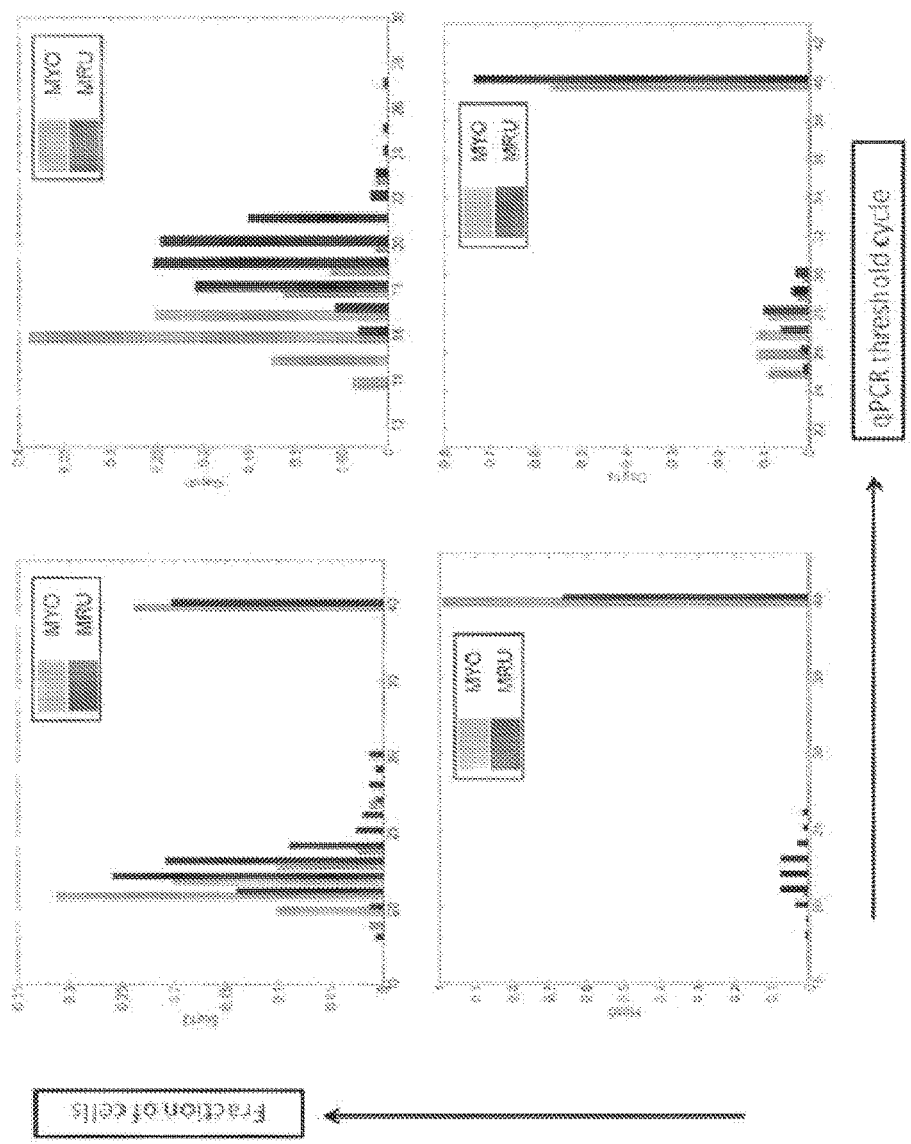

FIG. 488. Histograms for qPCR threshold cycles for some of the genes that were found to be differentially expressed between the MRU and MYO mammary FACS sorted compartments.

Figure 489:
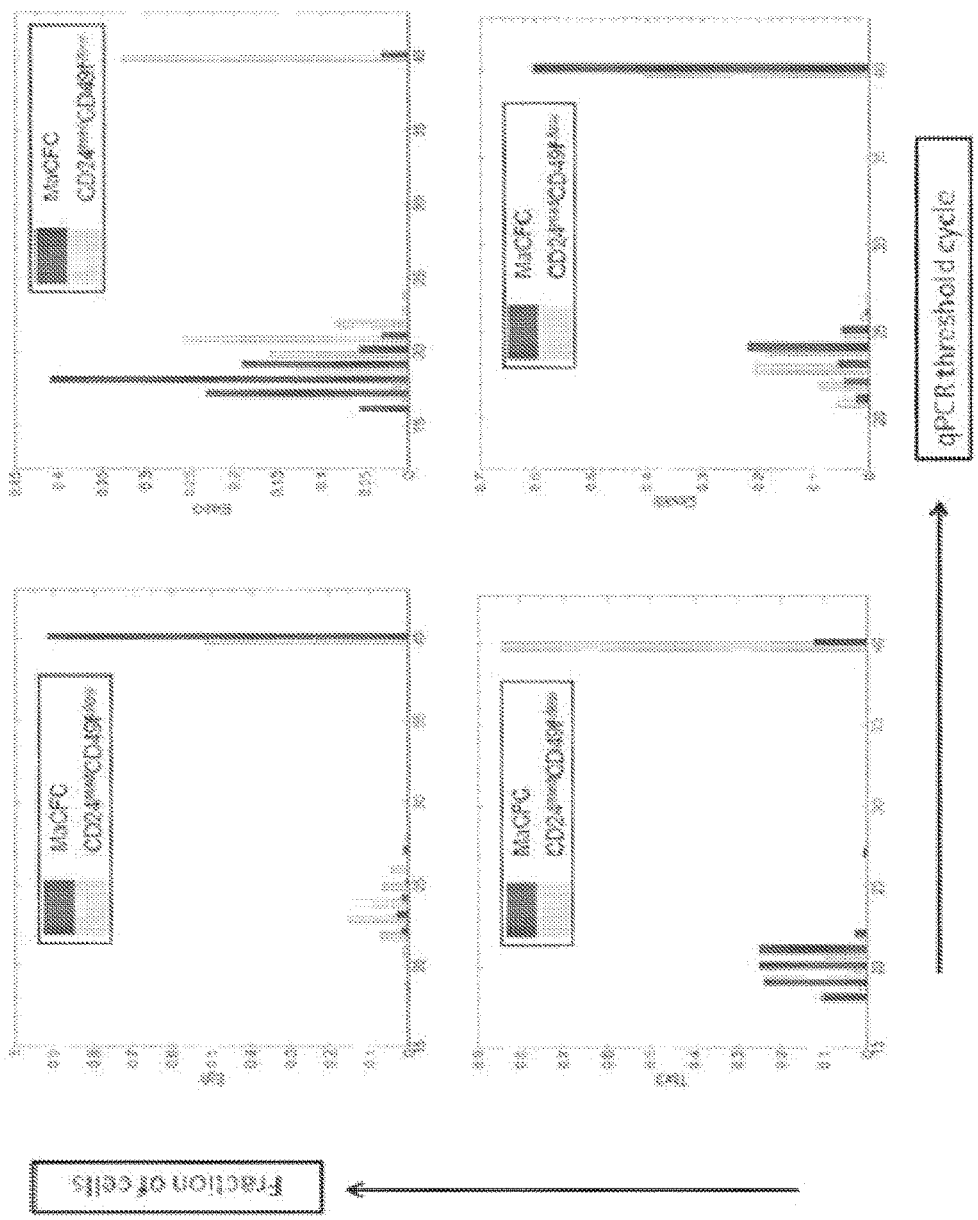

FIG. 489. Histograms for qPCR threshold cycles for some of the genes that were found to be differentially expressed between the MaCFC and CD24$^{med}$CD49f$^{low}$ mammary FACS sorted compartments.

DETAILED DESCRIPTION

The methods of the invention utilize single cell gene expression profiling of primary cells for characterization of populations of cells for disease diagnosis, sensitivity to a particular therapeutic intervention, prognostic applications, and identification of novel drug targets. A heterogeneous cell sample is divided into spatially separated single cells, which are optionally sorted for properties of interest (possibly including surface markers), then lysed and the contents amplified and individually analyzed for expression of genes of interest. The cells thus analyzed are classified according to the genetic signatures of individual cells. Such classification allows an accurate assessment of the cellular composition of the test sample.

Conventional methods of analyzing single cells for diagnostic purposes include the use of Coulter counters and flow cytometry to count the number of cells of a given type. However, these measurements are typically based on using antibodies to surface markers and do not assay gene expression at the mRNA level or protein expression. Previous examples of single cell PCR analysis exist, but these were performed on too small a number of cells and or genes to provide useful diagnostic information or to provide the ability to discriminate fine or related subpopulations of cells within a tissue. Tissue-staining methods used by pathologists suffer from similar drawbacks and depend strongly on qualitative judgments by the pathologist. Moreover, these measurements are limited to measuring a small number of parameters. The methods of the present invention, however, allow the measure of at least 10, at least 15, at least 20, at least 50, at least 100, at least 200, at least 300, at least 400, at least 500, or more different parameters, where parameters include mRNA expression, gene expression, protein expression and may further include cell surface markers in combination with mRNA, gene and/or protein expression.

In its several aspects, the invention usefully provides methods for screening for anti-cancer agents; for the testing of anti-cancer therapies; for the development of drugs targeting novel pathways; for the identification of new anti-cancer therapeutic targets; the identification and diagnosis of malignant cells in pathology specimens; for the testing and assaying of solid tumor stem cell drug sensitivity; for the measurement of specific factors that predict drug sensitivity; and for the screening of patients (e.g., as an adjunct for mammography). The invention can be used as a model to test patients' tumor sensitivity to known therapies; as a model for identification of new therapeutic targets for cancer treatment; as a system to establish a tumor bank for testing new therapeutic agents for treatment of cancer; and as a system to identify the tumorigenic cancer cells.

For example, various potential drug candidates, e.g., small molecules, siRNA, peptides, hormones, etc., can be screened (in vivo or in vitro) to determine if they can modulate any of the targets described herein or pathways of the targets described herein. Those drug candidates that are able to module the targets or target pathways can be further assayed to determine if they can be effective as therapeutic agents, anti-cancer agents, or if they can lead to other therapeutic agents or targets based on their binding agents, or whether a mechanism of action can be determined based on their activity.

Before the subject invention is described further, it is to be understood that the invention is not limited to the particular embodiments of the invention described below, as variations of the particular embodiments may be made and still fall within the scope of the appended claims. It is also to be understood that the terminology employed is for the purpose of describing particular embodiments, and is not intended to be limiting. In this specification and the appended claims, the singular forms "a," "an" and "the" include plural reference unless the context clearly dictates otherwise.

Where a range of values is provided, it is understood that each intervening value, to the tenth of the unit of the lower limit unless the context clearly dictates otherwise, between the upper and lower limit of that range, and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood to one of ordinary skill in the art to which this invention belongs. Although any methods, devices and materials similar or equivalent to those described herein can be used in the practice or testing of the invention, illustrative methods, devices and materials are now described.

All publications mentioned herein are incorporated herein by reference for the purpose of describing and disclosing the subject components of the invention that are described in the publications, which components might be used in connection with the presently described invention.

Identification and Classification of Cells into Populations and Subpopulations

The present disclosure is directed to methods of classification of identifying populations and subpopulations of cells and using populations and/or subpopulations to diagnose, prognose and/or identify therapeutic targets for conditions such as diseases. Diseases can include cancers of any sort (including but not limited to, solid tumors, breast cancer, colon cancer, lung cancer, leukemia), inflammatory bowel disease, ulcerative colitis, autoimmune diseases, inflammatory diseases and infectious diseases. The present disclosure also provides reagents and kits for use in practicing the subject methods, such as antibody and nucleic acid probes useful in detecting any of the biomarkers described herein, or reagents that modulate the biomarkers herein. The methods may also determine an appropriate level of treatment for a particular cancer.

Isolation of Single Cells

Single cell gene expression profiling is provided for disease diagnostic or prognostic applications, as well as a research tool to identify novel drug targets. Diseases of interest include, without limitation, immune-mediated dysfunction, cancer, and the like. In the methods of the invention, a heterogeneous cell mixture, e.g. a tumor needle biopsy, inflammatory lesion biopsy, synovial fluid, spinal tap, etc., is divided randomly or in a certain order into spatially separated single cells, e.g. into a multiwell plate, microarray, microfluidic device, or slide. Cells are then lysed, and the contents amplified and individually analyzed for expression of genes of interest. The cells thus analyzed are classified according to the genetic signatures of individual cells. Such classification allows an accurate assessment of the cellular composition of the test sample, which assessment may find use, for example, in determining the identity and number of cancer stem cells in a tumor; in determining the identity and number of immune-associated cells such as the number and specificity of T cells, dendritic cells, B cells and the like.

In some embodiments, the cell sample to be analyzed is a primary sample, which may be freshly isolated, frozen, etc. However, cells to be analyzed can be cultured cells. Usually the sample is a heterogeneous mixture of cells, comprising a plurality of distinct cell types, distinct populations, or distinct subpopulations, for example 2, 3, 4, 5, 6, 7, 8, 9, 10, 11, 12, 13, 14, 15, 16, 17, 18, 19, 20 or more cell types, populations, or subpopulations. In some embodiments the sample is a cancer sample from a solid tumor, leukemia, lymphoma, etc., which may be a biopsy, e.g. a needle biopsy, etc., a blood sample for disseminated tumors and leukemias, and the like. Samples may be obtained prior to diagnosis, may be obtained through a course of treatment, and the like.

For isolation of cells from tissue, an appropriate solution can be used for dispersion or suspension. Such solution will generally be a balanced salt solution, e.g. normal saline, PBS, Hank's balanced salt solution, etc., conveniently supplemented with fetal calf serum or other naturally occurring factors, in conjunction with an acceptable buffer at low concentration, generally from 5-25 mM. Convenient buffers include HEPES, phosphate buffers, lactate buffers, etc. The separated cells can be collected in any appropriate medium that maintains the viability of the cells, usually having a cushion of serum at the bottom of the collection tube. Various media are commercially available and may be used according to the nature of the cells, including dMEM, HBSS, dPBS, RPMI, Iscove's medium, etc., frequently supplemented with fetal calf serum.

In some embodiments, cells in a sample are separated on a microarray. For example, a highly integrated live-cell microarray system may utilize microwells each of which is just large enough to fit a single cell (see Tokimitsu et al. (2007) Cytometry Part A 71k 1003:1010; and Yamamura et al. (2005) Analytical Chemistry 77:8050; each herein specifically incorporated by reference). Prior enrichment of cells of interest—such as by FACS or other sorting—is optional and in some embodiments, cells from a sample are divided into discrete locations without any prior sorting or enrichment. For example, cells from a sample (e.g., blood sample, biopsy, solid tumor) can be individually isolated into distinct positions. Typically, for solid tissue samples, the samples are mechanically, chemically, and/or enzymatically separated (e.g., by treatment with trypsin or sonication). Cells from a sample can be placed into any cell sorting device (e.g., a microfluidic cell sorter) such that individual cells are isolated, such as at an addressable position on a planar surface. Planar surfaces can have indentations, barriers or other features ensuring isolation of individual cells. Isolated cells can then be analyzed according to the methods herein. Preferably, cells are separated into distinct positions wherein each position contains 1 or 0 cells.

Cells are optionally sorted, e.g. by flow cytometry, prior to the separation. For example, FACS sorting or size-differential sorting, can be used to increase the initial concentration of the cells of interest by at least 1,000, 10,000, 100,000, or more fold, according to one or more markers present on the cell surface. Such cells are optionally sorted according to the presence and/or absence of cell surface markers particularly markers of a population or subpopulation of interest. For example, antibodies to CD66a, EpCAM, CD24, ESDA and/or other antibodies can be used to enrich—by positive and/or negative selection—cancer stem cells in a sample (e.g., anti-CD66a where negative expression of CD66a is indicative of a CSC; EpCAM, where expression of EpCAM is indicative that a cell is a CSC; CD24, where negative expression of CD24 is indicative of a CSC; ESDA, where positive expression is indicative of a stem cells; and also including markers known in the art to be associated with. CSC, including CD47, CD96, CD99, EGFRv 1111, etc.)

Where the cells are isolated into distinct positions for analysis, the cells may be sorted with a microfluidic sorter, by flow cytometry, microscopy, etc. A microfabricated fluorescence-activated cell sorter is described by Fu et al. (1999) Nature Biotechnology 17: 1109 and Fu et al. (2002) Anal. Chem. 74:2451-2457, each herein specifically incorporated by reference. A sample can be sorted with an integrated microfabricated cell sorter using multilayer soft lithography. This integrated cell sorter may incorporate various microfluidic functionalities, including peristaltic pumps, dampers, switch valves, and input and output wells, to perform cell sorting in a coordinated and automated fashion. The active volume of an actuated valve on this integrated cell sorter can be as small as 1 pL, and the volume of optical interrogation as small as 100 fL. Compared with conventional FACS machines, the microfluidic FACS provides higher sensitivity, no cross-contamination, and lower cost.

Individual cells can be isolated into distinct positions (e.g., a 96-well plate or a microarray address) for further analysis and/or manipulation. For example, a cell population containing hematopoietic stem cells (HSCs) is sorted by FACS analysis utilizing antibodies capable of distinguishing HSCs from mature cells. The cells are sorted into 96-well plates, lysed by appropriate methods and the lysates are analyzed by qPCR, microarray analysis, and/or sequencing.

Devices for single cell isolation include a microfluidic cell sorter, which isolates live cells from cellular debris and sorts cells from a single cell suspension. Microfluidic devices can be used in combination with fluorescent signals (e.g., labeled antibodies to markers for a target population or subpopulation) from 1, 2, 3, 4, 5 or more different surface markers, and places them in individual bins for subsequent genetic studies. Other upstream steps such as digesting the tumor or cell culture to obtain a cell suspension and staining the cells with fluorescent surface markers may be incorporated in this system. The number of cells to be analyzed depends on the heterogeneity of the sample, and the expected frequency of cells of interest in the sample. Usually at least about $10^2$ cells are analyzed, at least about $10^3$, at least $5\times10^3$, at least about $10^4$, at least about $10^5$, at least about $10^6$, at least about $10^7$, at least about $10^8$, at least about $10^9$, at least about $10^{10}$, at least about $10^{11}$, at least about $10^{12}$, at least about $10^{13}$, at least about $10^{14}$, at least about $10^{15}$, or more cells are analyzed.

In some instances, a single cell analysis device (SCAD) is modular and can perform the following steps in an integrated, fully automated fashion 1) Digestion of the tissue. The tissue is placed in the input port of the device. Appropriate enzymes are introduced in the device and flowed to perform the digestion of the extracellular matrix in order to obtain a cell suspension. 2) Separation of live cells from the debris, for example by flowing a digested sample suspension through a microfluidic "metamaterial," which allows splitting the fluidic flow according to the size of the particles. 3) Staining. The filtered single cell suspension is optionally stained using appropriate surface markers in a compartment of the microfluidic device. Staining with up to five different markers may be useful in obtaining a high purity population of cancer cells. 4) Sorting. The stained single-cell suspension is flowed into the next compartment of the microfluidic device to sort out the cancer cells from the rest of the cells. Various embodiments of sorters are described in the Examples.

Expression Profiling

Sorted cells can be individually lysed to perform analysis of genetic (RNA, DNA) and/or protein composition of the cells. mRNA can be captured on a column of oligo-dT beads, reverse transcribed on beads, processed off chip, transferred to a macroscopic well, etc. Optionally, DNA or RNA is preamplified prior to analysis. Preamplification can be of an entire genome or transcriptome, or a portion thereof (e.g., genes/transcripts of interest). A polynucleotide sample can be transferred to a chip for analysis (e.g., by qRT-PCR) and determination of an expression profile.

The term "expression profile" is used broadly to include proteins expressed and/or nucleic acids expressed. A nucleic acid sample includes a plurality or population of distinct nucleic acids that can include the expression information of the phenotype determinative genes of interest of the individual cell. A nucleic acid sample can include RNA or DNA nucleic acids, e.g., mRNA, cRNA, cDNA, etc. Expression profiles can be generated by any convenient means for determining differential gene expression between two samples, e.g. quantitative hybridization of mRNA, labeled mRNA, amplified mRNA, cRNA, etc., quantitative PCR, and the like. A subject or patient sample, e.g., cells or collections thereof, e.g., tissues, is assayed. Samples are collected by any convenient method, as known in the art. Additionally, tumor samples can be collected and tested to determine the relative effectiveness of a therapy in causing differential death between normal and diseased cells. Genes/proteins of interest are genes/proteins that are found to be predictive, including the genes/proteins provided herein, where the expression profile may include expression data for 5, 10, 20, 25, 50, 100 or more (including all) of the listed genes/proteins.

The sample can be prepared in a number of different ways, as is known in the art, e.g., by mRNA isolation from a single cell, where the isolated mRNA is used as is, amplified, employed to prepare cDNA, cRNA, etc., as is known in the differential expression art (for example, see Marcus, et al., Anal. Chem. (2006); 78(9): 3084-89). The sample can be prepared from any tissue (e.g., a lesion, or tumor tissue) harvested from a subject. Analysis of the samples can be used for any purpose (e.g., diagnosis, prognosis, classification, tracking and/or developing therapy). Cells may be cultured prior to analysis.

The expression profile may be generated from the initial nucleic acid sample using any conventional protocol. While a variety of different manners of generating expression profiles are known, such as those employed in the field of differential gene expression analysis, one representative and convenient type of protocol for generating expression profiles is quantitative PCR (QPCR, or QT-PCR). Any available methodology for performing QPCR can be utilized, for example, as described in Valera, et al., J. Neurooncol. (2007) 85(1):1-10.

After obtaining an expression profile from the sample being assayed, the expression profile can be compared with a reference or control profile to make a diagnosis, prognosis, analysis of drug effectiveness, or other desired analysis. A reference or control profile is provided, or may be obtained by empirical methods. An obtained expression profile can be compared to a single reference/control profile to obtain information regarding the phenotype of the cell/tissue being assayed. Alternately, the obtained expression profile can be compared to two or more different reference/control profiles to obtain more in-depth information regarding the phenotype of the assayed cell/tissue. For example, the obtained expression profile may be compared to a positive and negative reference profile to obtain confirmed information regarding whether the cell/tissue has the phenotype of interest.

Determination or analysis of the difference values, i.e., the difference in expression between two profiles can be performed using any conventional methodology, where a variety of methodologies are known to those of skill in the array art, e.g., by comparing digital images of the expression profiles, by comparing databases of expression data, etc. Patents describing ways of comparing expression profiles include, but are not limited to, U.S. Pat. Nos. 6,308,170 and 6,228,575, the disclosures of which are herein incorporated by reference. Methods of comparing expression profiles are also described herein.

A statistical analysis step can then be performed to obtain the weighted contribution of the set of genes. For example, nearest shrunken centroids analysis may be applied as described in Tibshirani et al. (2002) P.N.A.S. 99:6567-6572 to compute the centroid for each class, then compute the average squared distance between a given expression profile and each centroid, normalized by the within-class standard deviation.

The classification can be probabilistically defined, where the cut-off may be empirically derived. In one embodiment of the invention, a probability of about 0.4 can be used to distinguish between quiescent and induced patients, more usually a probability of about 0.5, and can utilize a probability of about 0.6 or higher. A "high" probability can be at least about 0.75, at least about 0.7, at least about 0.6, or at least about 0.5. A "low" probability may be not more than about 0.25, not more than 0.3, or not more than 0.4. In many embodiments, the above-obtained information about the cell/tissue being assayed is employed to predict whether a host, subject or patient should be treated with a therapy of interest and to optimize the dose therein.

Characterization of Cell Populations and Subpopulations Using Cancer Cells as a Model In some embodiments of the invention, for example with epithelial cancers, including, without limitation, breast cancer and colon cancer, characterization of cancer stem cells according to expression of a cancer stem cell marker (e.g., CD66a) allows for the identification of CSC. There is a subpopulation of tumorigenic cancer cells with both self-renewal and differentiation capacity. These tumorigenic cells are responsible for tumor maintenance, and also give rise to large numbers of abnormally differentiating progeny that are not tumorigenic, thus meeting the criteria of cancer stem cells. Tumorigenic potential is contained within a subpopulation of cancer cells differentially expressing the markers of the present invention. As shown herein, within the population of cells that positively express markers for cancer stem cells, there is heterogeneity, e.g., where cells that are negative for CD66 (CD66$^-$) cells, are enriched for cancer stem cells (tumorigenic), while the CD66a$^+$ cells are not tumorigenic. Detection of such heterogeneity within populations allows for determination of subpopulations.

One of skill in the art will recognize that multiple sequences—representing genes, transcripts and/or proteins—can be analyzed. Such sequences can allow the determination and/or differentiation of the phenotypes of cells within a sample. For example, some genes may encode housekeeping proteins, proteins involved in glutathione (GSH) synthesis or metabolism, anti-reactive oxygen species (ROS) proteins, transcription factors, cancer cell markers, stem cell markers, or any other relevant protein. A non-limiting list of such genes (including homologues from humans and other animals) includes: Ca2, VEGFa, Ihh, CdkN1a, Krt20, Vdr, Tff3, Ceacam1, Top1, Nola3, Tcf712, Rfng, Llgl1, Cdk6, Ruvb12, Dkc1, ActB, Gapdh, Tacstd, Sox9, Hes1, Rnf43, Utg8, Wwox, Slco3a1, Lfng, Dll4, Mam12, Il1 1ra, Hes6, Tert, Muc2, Retn1b, Ca1, Ugt2b17, Tinf2, Pls3, Sox2, Lgr5, Pcna, Mk167, Birc5, Gss, Gclm, Gclc, Gpx1, Gpx4, Gpx7, Slpi, Prnp, Sod1, Sod2, Sod3, Cat, Nfkb1, Foxo1, Foxo3a, Foxo4, Krt19, Stat3, Chi3l1, Tert, Hif1a, Epas1 (Hif2a), Hprt, and Actb.

Markers, or marker panels, can be chosen on the basis of multiple aspects of a target population or subpopulation within a sample, for example, tissue source (e.g., neuronal vs. epithelial) or disease state (e.g., cancerous vs. non-cancerous). Other sequences useful for distinguishing cell populations (e.g., cancer stem cell from normal cell) can be determined using the methods described herein, such as by detecting changes (e.g., up- or down-regulation) in genes in target populations. For example, cells obtained from a breast tissue biopsy which are CD49f$^+$/CD24$^-$, CD49/EPCAM$^{low/-}$, or CD49f$^+$/EPCAM+ can be used to diagnose the patient with breast cancer.

Nucleic acids which are useful in distinguishing one population from another population can be up-regulated or down-regulated as compared between populations. For example, expression of some nucleic acids are up-regulated or down regulated in cancer versus normal cells, stem cells versus differentiated cells, and cancer stem cells versus differentiated cancer cells. In some instances up- or down-regulation of genes can be used to distinguish sub-populations within larger populations. For example, some nucleic acids are expressed in normal cells only, normal cells and cancer stem cells, or cancer stem cells only.

Additionally, expression of certain housekeeping nucleic acids can be used to determine cell viability. For example, TABLES 1 and 2, provide some exemplary nucleic acids which show differential expression between populations of normal cells and breast tissue-derived and colon tissue-derived cells.

TABLE 1

Gene that are differentially expressed in cell subpopulations in colon tissue cells

| Gene Name | Cell population | Regulation state |
|---|---|---|
| Met | Immature enterocytes | Upregulated |
| Notch1 | Stem cells, Immature enterocytes, cycling cells | Upregulated |
| Notch2 | Stem cells, Immature enterocytes, cycling cells | Upregulated |
| Ephrb2 | Stem cells, Immature enterocytes | Upregulated |
| Hes6 | Stem cells Cancer stem cells | Upregulated |
| Wnt6 | Stem cells | Upregulated |
| Tcf3 | Stem cells | Upregulated |
| lgr5 | Stem cells Cancer stem cells | Upregulated |
| tert | Stem cells, Goblet cells Cancer stem cells | Upregulated |
| ASCL2 | Stem cells Cancer stem cells | Upregulated |
| Tert + RBM25 | Cancer stem cells | Upregulated |
| Tert + SEC62 | Cancer stem cells | Upregulated |
| Tert + TFF3 | Cancer stem cells | Upregulated |
| Tert + Villin1 | Cancer stem cells | Upregulated |
| Tert + Ceacam1 | Cancer stem cells | Upregulated |
| Tert + DLL4 | Cancer stem cells | Upregulated |
| Tert + KRT20 | Cancer stem cells | Upregulated |
| Tert + CES3 | Cancer stem cells | Upregulated |
| Tert + PTPRO | Cancer stem cells | Upregulated |
| tert | Stem cells, Goblet cells | Upregulated |
| ceacam1 | Mature enterocytes, slowly cycling stem cells | Upregulated |
| ck20 | Mature enterocytes, Goblet cells, slowly cycling stem cells | Upregulated |
| Muc2 | Goblet cells | Upregulated |
| Ephb2 | Stem cells, cycling cells | Upregulated |
| Axin2 | Stem cells, cycling immature cells | Upregulated |
| cMyc | Stem cells, immature cycling cells Cancer stem cells | Upregulated |
| Sonic hedgehog | Immature enterocytes | Upregulated |
| Hes1 | Stem cells, cycling cells, immature enterocytes Cancer stem cells | Upregulated |
| Hes5 | Stem cells, cycling cells | Upregulated |
| Tcf4 | Immature enteroctyes | Upregulated |
| Tert | Stem cells, Cancer stem cells | Upregulated |
| Tff3 | Goblet cells, slowly cycling stem cells | Higher levels in goblet cells |
| Ca2 | Mature enterocytes | Upregulated |
| Cdk6 | Stem, immature enterocytes | Upregulated |
| Pcna | Stem cells, immature enterocytes | Upregulated |
| Tinf2 | Stem cells, immature enterocytes | Upregulated |

TABLE 1-continued

Gene that are differentially expressed in cell subpopulations in colon tissue cells

| Gene Name | Cell population | Regulation state |
|---|---|---|
| Pls3 | Stem cells, immature enterocytes | Upregulated |
| Maml2 | Stem cells, immature enterocytes) | Upregulated |
| Bmi1 | Stem cells, immature enterocytes Cancer stem cells | Upregulated |
| Vegfa | Immature enterocytes | Upregulated |
| Foxo1 | Stem cells, Immature enterocytes Cancer stem cells | Upregulated |
| Cdkn1a | Immature enterocytes, goblet cells | Upregulated |
| Krt20 | Mature enterocytes, goblet cells, slowly cycling stem cells | Lower levels in goblet cells |
| Indian hedgehog | immature enterocytes | Upregulated |
| Ruvb12 | Stem cells, immature enterocytes | Upregulated |
| Ugt8 | Stem cells, immature enterocytes Cancer stem cells | Upregulated |
| Ugt2b17 | Stem cells, immature | Upregulated |
| Top1 | Stem cells, immature enterocytes | Upregulated |
| Nola3 | Stem cells, immature | Upregulated |
| Tcf712 | Stem cells, immature enterocytes | Upregulated |
| Lgr5 | Stem cells, cycling cells Cancer stem cells | Upregulated |
| Wwox | Stem cells, cycling cells, immature enterocytes | Upregulated |
| Sloca3a1 | Stem cells, cycling cells, immature enterocytes | Upregulated |
| Dkc1 | Stem cells, cycling cells, immature enterocytes | Upregulated |
| Llgl1 | Stem cells, cycling cells, immature enterocytes | Upregulated |
| Rnf43 | Stem cells, cycling cells, immature enterocytes | Upregulated |
| Sox9 | Stem cells, cycling cells, immature enterocytes | Upregulated |
| Krt20 | Immature enterocytes, mature enterocytes | Upregulated |
| Birc5 | Stem cells, cycling cells, immature enterocytes | Upregulated |
| LAMB1 | Stem cells Cancer stem cells | Upregulated |
| Dll4 | Stem cells, immature enterocytes, goblet cells | Upregulated |
| IL11ra | Stem cells, cycling cells, immature enterocytes | Upregulated |
| Lfng | Stem cells, cycling cells, immature enterocytes | Upregulated |
| Mki67 | Stem cells, cycling cells, immature enterocytes ( ) | Upregulated |
| Pls3 | Stem cells, cycling cells, immature enterocytes | Upregulated |
| Rfng | Stem cells, cycling cells, immature enterocytes | Upregulated |
| Vdr | Stem cells, cycling cells, immature enterocytes | Upregulated |
| Aqp1 | Stem cells Cancer stem cells | Upregulated |
| Kif12 | Stem cells Cancer stem cells | Upregulated |
| Lgr5 | Stem cells Cancer stem cells | Upregulated |
| Ptpro | Stem cells Cancer stem cells | Upregulated |
| Gspm2 | Stem cells, immature enterocytes, goblet cells | Upregulated |
| Utrn | Stem cells, immature enterocytes, goblet cells | Upregulated |
| Esf1 | Stem cells, immature enterocytes | Upregulated |
| Hnf1b | Stem cells, immature enterocytes | Upregulated |
| Mett13 | Stem cells, immature enterocytes Cancer stem cells | Upregulated |
| Lefty1 | Stem cells, immature enterocytes Cancer stem cells | Upregulated |
| Cftr | Stem cells, immature enterocytes Cancer stem cells | Upregulated, downregulated in goblet cells |
| Ces3 | Stem cells, immature enterocytes Cancer stem cells | Upregulated |
| Myo5 | Stem cells, immature enterocytes, goblet cells | Upregulated |
| Rbm25 | Stem cells, immature enterocytes, goblet cells | Upregulated |
| Ets2 | Stem cells, immature enterocytes, goblet cells Cancer stem cells | Upregulated |
| Vil1 | Stem cells, immature enterocytes, goblet cells Cancer stem cells | Upregulated |
| Cdkn1b | Stem cells, immature enterocytes, goblet cells | Upregulated |
| Sec62 | Stem cells, immature enterocytes, goblet cells | Upregulated |
| Krt20 | Stem cells, immature enterocytes Cancer stem cells | Upregulated |
| Ca1 | Mature enterocytes | Upregulated |
| Aqp8 | Mature enterocytes | Upregulated |
| Acvr1c | Stem cells, immature enterocytes | Upregulated |
| Acvr2a | Stem cells, immature enterocytes | Upregulated |
| Olfm4 | Stem cells, immature enterocytes Cancer stem cells | Upregulated |
| Tnfrsf11a | Stem cells, immature enterocytes | Upregulated |
| Vegfb | Stem cells, immature enterocytes | Upregulated |
| Ezh2 | Stem cells, immature enterocytes Cancer stem cells | Upregulated |
| Gpsm2 | Stem cells, immature enterocytes Cancer stem cells | Upregulated |
| Cdk2 | Stem cells, cycling cells, immature enterocytes Cancer stem cells | Upregulated |
| Ccnd1 | Stem cells, cycling cells, immature enterocytes | Upregulated |
| Brd7 | Stem cells, cycling cells, immature enterocytes | Upregulated |
| Adam10 | Stem cells, cycling cells, immature enterocytes | Upregulated |
| Ets2 | Stem cells, cycling cells, immature enterocytes | Upregulated |
| Rmb25 | Stem cells, cycling cells, immature enterocytes Cancer stem cells | Upregulated |
| Esf1 | Stem cells, cycling cells, immature enterocytes Cancer stem cells | Upregulated |
| Suz12 | Stem cells, cycling cells, immature enterocytes Cancer stem cells | Upregulated |
| Gpr | Stem cells, cycling cells, immature enterocytes | Upregulated |
| Hunk | Stem cells, cycling cells | Upregulated |

TABLE 2

Genes differentially expressed in various cell populations in breast tissue cells

| Gene Name | Cell population | Regulation state |
|---|---|---|
| Cdh2 | Stem cells | Upregulated |
| CD109 | Stem cells | Upregulated |
| Cdk6 | Tumorigenic cells (cancer stem cell) | Upregulated |
| PTEN | Tumorigenic cells (cancer stem cell) | Upregulated |
| Top1 | Tumorigenic cells (cancer stem cell) | Upregulated |
| Suz12 | Cancer: Tumorigenic cells (cancer stem cell) Normal: Stem cells, Luminal epithelial cells | Upregulated |
| Bmi1 | Tumorigenic cells (cancer stem cell) | Upregulated |
| Sox9 | Tumorigenic cells (cancer stem cell) | Upregulated |

TABLE 2-continued

Genes differentially expressed in various cell populations in breast tissue cells

| Gene Name | Cell population | Regulation state |
|---|---|---|
| Mettl3 | Cancer: Tumorigenic cells (cancer stem cell), Normal Breast Luminal epithelial cells | Upregulated |
| Lefty2 | Cancer: Tumorigenic cells (cancer stem cell) Normal: Stem cell and Luminal epithelial cells | Upregulated |
| NR2F1 | Cancer stem cells | Upregulated |
| EpCAM | Normal breast: Luminal epithelial cells | Upregulated |
| Elf5 | Cancer: Non-tumorigenic cells Normal Breast: Luminal epithelial cells | Upregulated |
| Ugt8 | Non-tumorigenic cells, cycling cells Normal breast: GATA6+ Luminal epithelial cells | Upregulated |
| Erbb2 | Normal breast: Stem cells, luminal cells | Upregulated |
| Krt5 | Myoepithelial cells | Upregulated |
| Maml2 | Cancer stem cells Normal breast: stem cells, luminal epithelial cells | Upregulated |
| Krt19 | Normal breast: luminal epithelial cells | Upregulated |
| Krt8 | Normal breast: Stem cells, luminal epithelial cells | Upregulated |
| Ezh2 | Cancer: Cancer stem cells Normal: Stem cells, GATA6+ luminal epithelial cells | Upregulated |
| Notch1 | Normal: Stem cells, luminal epithelial cells | Upregulated |
| Krt14 | Normal breast: Stem cells, myoepithelial cells | Upregulated |
| Krt18 | Normal breast: Stem cells, luminal epithelial cells | Upregulated |
| Id2 | Normal breast: Stem cells, luminal epithelial cells | Upregulated |
| Krt17 | Normal breast: Stem cells, myoepithelial cells | Upregulated |
| Vegfa | Stem cells, luminal epithelial cells | Upregulated |
| Cdk6 | Luminal-CDK6+ Luminal epithelial cells | Upregulated |
| Egf1 | Luminal GATA6+ Luminal epithelial cells | Upregulated |
| Esf1 | Luminal GATA6+ Luminal epithelial cells | Upregulated |
| Notch2 | Stem cells, GATA6+ Luminal epithelial cells | Upregulated |
| Itga6 (CD49f) | stem cells, GATA6+ Luminal epithelial cells Cancer stem cells | Upregulated |
| Tcf7L2 | stem cells, GATA6+ Luminal epithelial cells | Upregulated |
| Erbb3 | Luminal epithelial cells Non-tumorigenic cancer clls | Upregulated |
| Hes1 | Luminal epithelial cells | Upregulated |
| Notch3 | GATA6+ Luminal epithelial cells Cancer stem cells | Upregulated |
| Acvr2a | stem cells, some GATA6+ Luminal epithelial cells Cancer Stem cells | Upregulated |
| Lamb1 | Normal stem cells Cancer stem cells | Upregulated |
| Ngfr | Normal stem cells Cancer stem cells | Upregulated |
| Snai2 | stem cells | Upregulated |
| Cyr61 | Myoepithelial cells (Basal-1), stem cells | Upregulated |
| Egfr | Myoepithelial cells (Basal-1), stem cells Cancer stem cells | Upregulated |
| Foxo1 | Normal stem cells Cancer stem cells | Upregulated |
| Tbx3 | Normal stem cells, GATA6+ Luminal epithelial cells Cancer stem cells | Upregulated |
| Cdkn1a | Stem cells | Upregulated |
| Ets2 | Normal: Stem cells, GATA6+luminal epithelial cells | Upregulated |
| Top1 | GATA6+luminal epithelial cells, stem cells | Upregulated |
| Pgr | ER+, ERBB3+ luminal epithelial cells, stem cells | Upregulated |
| Erbb4 | ER+ luminal epithelial cells (Luminal 2) | Upregulated |
| Tff3 | ER+ luminal epithelial cells (Luminal-2) | Upregulated |
| Esr1 | ER+ luminal epithelial cells (Luminal-2) | Upregulated |
| Kif12 | ER+ luminal epithelial cells (Luminal-2) | Upregulated |
| Stc2 | ER+ luminal epithelial cells (Luminal-2) | Upregulated |
| Lefty1 | Normal stem cells, GATA6+ luminal epithelial cells Cancer stem cells | Upregulated |
| Lefty2 | Normal stem cells, GATA6+ luminal epithelial cells, MRU Cancer stem cells | Upregulated |
| Cfc1 | Normal stem cells, GATA6+ luminal epithelial cells Cancer stem cells | Upregulated |
| ASCL2 | Normal breast stem cells Cancer stem cells | Upregulated |
| ZEB2 | Cancer stem cells | Upregulated |
| PTEN | Cancer stem cells | Upregulated |

Tables 1 and 2 provide an exemplary list of nucleic acids which are differentially expressed in different cells within a homogenous sample comprising multiple populations and subpopulations (e.g., a patient biopsy). Using the methods described herein, individual cells within heterogeneous sample can be analyzed to identify particular cell populations and/or subpopulations. For example, cells from breast tissue which show expression of CDK6, PTEN, Top1, Suz12, and/or Sox9 can be classified as tumorigenic cells, where expression may be high, intermediate or low. In another example, cells from colon tissue which show expression of Aqp1, Kif12, Tert, Ptpro, Mettl3, Lefty1, Cftr and/or Ezh2 can be classified as stem cells.

Nucleic acids can be up-regulated or down-regulated as compared to another population or subpopulation, a particular nucleic acid of known expression level, or a standard expression level. Alternately, when analyzing the expression of multiple genes, a heatmap can be created by subtracting the mean and dividing by the standard deviation for each gene independently and numerical values are assigned based on the degree of deviation from the mean. For example, values of +/−1 can represent 2.5-3 standard deviations from the mean. Such analyses can be further refined, such that genes in the "+/−3" range can be used to cluster different types of populations (e.g., cancer is given the value "+3" and normal tissue is given the value "−3" so that a clustering algorithm can discern between them). An upregulated gene may be a "+" value.

In some instances, combinations of differentially expressed nucleic acids can be used as profiles for a particular population or subpopulation. Profiles can comprise any number of differentially expressed nucleic acids and/or proteins, for instance, at least 1, 2, 3, 4, 5, 6, 7, 8, 9, 10, 11, 12, 13, 14, 15, 16, 17, 18, 19, 20, 25, 30, 35, 40, 45, 50 or more nucleic acids and/or proteins. In some instances, a nucleic acid utilized to identify a target population or subpopulation can be similarly expressed in a target and a non-target population or non-target subpopulation. Such similarly expressed nucleic acids will generally be utilized in combination with other differentially expressed nucleic acids to identify a target population or subpopulation.

Figure 11:
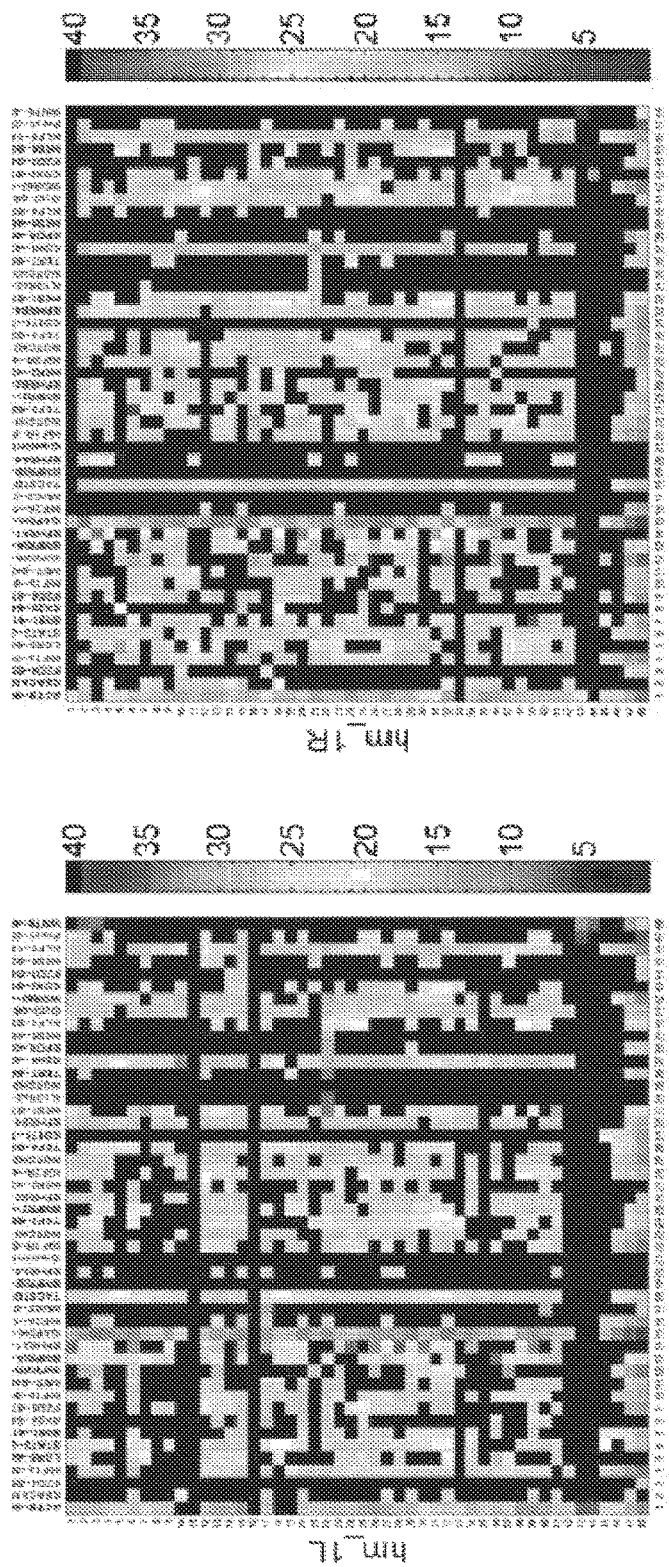
FIG. 11 A graphic representation of a heat map showing feasibility of single-cell analysis.

The data shown in FIGS. 11-465 show analyses of individual cells from different populations (e.g., differentiated non-cancerous cells, differentiated cancer cells, stem cells, pluripotent cells, cancer stem cells, etc.). Thus, the methods described herein can be used to analyze a heterogenous cell population from any source (e.g., biopsy, normal tissue, solid tumor, etc.). Such methods can be used to isolate and analyze any cell population, for example a target population within the larger heterogenous population or subpopulation, a heterogenous population or subpopulation for the presence of a target cell, cancer or other stem cells, or an entire heterogenous population.

Biomarker Discovery

The methods disclosed herein allow for determining new markers which are associated with a cell population or subpopulation (e.g., normal cells, cancer cells, disease-state cells). Markers can include any biomarker including, but not limited to DNA, RNA and proteins. In some instances, a marker for a cell population is a gene or mRNA not normally expressed in a given cell (e.g., expression of a stem cell gene by a progenitor cell or a cell expressing differentiation markers or expression of proliferation genes by cells also expressing differentiation markers). Typically, more than one marker is assessed, for example, 2, 3, 4, 5, 6, 7, 8, 9, 10, 11, 12, 13, 14, 15, 16, 17, 18, 19, 20, 30, 40, 50, 60, 70, 80, 90, 100, 200, 300, 400, 500, 600, 700, 800, 900, 1000 or more markers. Where markers are expressed RNAs, any portion of a transcriptome can be determined, up to and including the whole transcriptome.

Analysis of expression patterns of nucleic acids in certain target cell populations or subpopulations can lead to identification of new biomarkers which distinguish the target population or subpopulation from others. For example, where a unique surface-marker protein is expressed in a target population or subpopulation, an antibody which binds to that marker can be developed for use in isolating and/or identifying cells of that population or subpopulation in the same or other individuals (e.g., by FACS). Identification of population or subpopulation specific biomarkers includes the absence of certain markers on cell populations or subpopulations which would allow for negative selection. Table 3 lists some genes which can be used to distinguish between cancer stem cells and non-cancer stem cells and/or other types of cells.

TABLE 3

Differential gene expression profiles.

| Population | Genes | Regulation state |
|---|---|---|
| Colon cancer stem cells | AQP1, KIF1, TERT, PTPRO, METTL3, LEFTY1, CFTR, CA2, EZH2 | Up-regulated |
| Colon cancer stem cells | MUC2, AQP8, CEACAM1, TFF3 | Down-regulated |
| Breast cancer stem cells | LEFTY1, LEFTY2, CFC1, THY1, CDK1, PTEN, TOP1, SUZ12, SOX9 | Up-regulated |
| Breast cancer stem cells | PGR, ERBB4, TFF3, ESR1, KIF12, STC2, TBX3, ETS2, CDH2, EZH2, NOTCH1, NGFR, SNAI2, EGFR, FOXO1 | Down-regulated |

The presence of markers in a population or subpopulation can be determined using the methods described herein and can be used to define a cell population. mRNAs in analyzed cell populations or subpopulations have shown that certain genes are differentially expressed in normal and cancer cells. Differential expression can include increases or decreases in transcript level, lack of transcription, and/or altered regulation of expression (e.g., a different pattern of expression in response to a stimulus). mRNAs or other markers which serve as markers for a cell population or subpopulation can also comprise mutations which are present in that cell population or subpopulation (e.g., cancer cells and cancer stem cells, but not normal cells). One of skill in the art will recognize that such markers can represent a cell population from a single individual tested and/or may represent markers for many individuals. For example, a non-limiting list of expression phenotypes for breast cancer stem cells include, but is not limited to: CD49f+CD24−; CD49+epcam low/−; CD49f+epcam+; NGFR+; NGFR− (some patients tumors will have this phenotype); ACVR2A+; EGFR+; FOXO1+; Lefty1+; Lefty2+; NGFR+LEFTY1+LEFTY2+ (and other possible combinations); NGFR−/low LEFTY1−LEFTY2− (and other possible combinations); METTL3+; TBX3+; FOXO1+; LAMB1+; ZEB2+; GPSM2+; SOX9 high; SUZ12 high; ERBB3−/low; KIF12−/low; MARVELD3−; CEACAM1−/low; Lefty1+Lefty2+GPSM2+ (and/or CD49f high, and/or NGFR+, and/or EGFR+); or GPSM2+. As another example, a non-limiting list of expression phenotypes for colon cancer stem cells include, but is not limited to: TERT+; EZH2+; PTPRO+; LAMB1+; Lefty1+; GPSM2+; DLL4+; AQP1+; UGT8+; OLFM+; UTRN+; METTL3+; CFTR+; CA2−; TFF3−; CEACAM1$^{low}$; TFF3−/low; VEGFA −/low; or KRT20−/low. In some instances, the expressed mRNAs are translated into proteins which can be detected by any of a wide array of protein detection methods (e.g., immunoassay, Western blot, etc.).

Other markers which can be detected include microRNAs. In some instances, expression levels of microRNAs serve as a marker for a cell population where the expression of a particular microRNA is at increased or decreased by about 1.5, 1.6, 1.7, 1.8, 1.9, 2.0, 2.1, 2.2, 2.3, 2.4, 2.5, 2.6, 2.7, 2.8, 2.9, 3.0 or more fold as compared to a similar cell population. For example, in CD49f+/CD24− breast cancer stem cells and CD49f$^{high}$ colon cancer cells, a two-fold lower difference in the expression of one or more microRNAs (as compared to cells expressing the highest amount of the same miRNA) can be used as a marker. Non-limiting examples of such microRNAs include: miR-200c; miR-141; miR-200b; miR-200a; miR-429; miR-182; miR-183; and miR-96. As another example, in CD49f+/CD24− breast cancer stem cells and CD49f$^{high}$ colon cancer cells, a two-fold higher difference in the expression of one or more microRNAs (as compared to cells expressing the lowest amount of the same miRNA) can be used as a marker. Non-limiting examples of such microRNAs include: miR-214; miR-127; miR-142-3p; miR-199a; miR-409-3p; miR-125b; miR-146b; miR-199b; miR-222; miR-299-5p; miR-132; miR-221; miR-31; miR-432; miR-495; miR-150; miR-155; miR-338; miR-34b; miR-212; miR-146a; miR-126*; miR-223; miR-130b; and miR-196b.

Determination of Transcriptomes in Cell Populations and Subpopulations

To gain further information regarding the cells isolated by any of the methods of the present invention (e.g., FACS separation of cells from a population, followed by partial transcriptional analysis), it can be advantageous to further analyze cells. In some instances, individual cells isolated from a sample (e.g., by isolation of individual cells, with or without prior enrichment), are lysed and nucleic acids of interest (e.g., genomic DNA, mRNA, etc.) are collected. As described herein, transcriptional analysis of a gene or panel of genes can be utilized to categorize the isolated cells into groups which show similarities in their expression profiles (e.g., cancer stem cells vs. non-stem cells). Without being bound by theory, such information can suggest functional differences as the genes a cell is transcribing are tightly associated with its function. Once cells are organized into like-cell groups (e.g., those cells demonstrating similar or identical transcriptional profiles), lysates from individual cells and/or lysates comprising pooled nucleic acids from like-cells can be further analyzed at the transcriptome level. In some instances lysates (e.g., single-cell or like-cell pools) are subjected to methodologies (e.g., high-throughput sequencing) to define a portion of the transcriptome of each cell and/or like-cell pools. Transcriptome information from individual cells can be analyzed at the population level by comparing and/or combining the results from individual cells with the results from other like cells. Transcriptome information from like-cell pools can also be used to define the transcriptional characteristics of such pools.

Any cell population can be studied in such a manner, for example cell populations comprising stem cells. In some embodiments, cells include stem cells, including embryonic stem cells, adult stem cells—including, but not limited to cancer stem cells, hematopoietic stem cells (HSCs) and mesenchymal stem cells—and induced pluripotent stem cells. Generally, a cell population is a heterologous population (e.g., a clinical specimen). Sub-populations of interest within a larger cell population can be isolated by any method herein (e.g., FACS sorting) according to any relevant criteria (e.g., surface protein expression). In some embodiments, such sorted cells are compartmentalized such that each sorted population comprises 10 or fewer cells, 5 or fewer cells, 4 cells, 3 cells, 2 cells or 1 cell.

In some embodiments, cells are lysed and a split into two or more portions. One portion of the lysate is further analyzed (e.g., analysis of a panel of genes to detect expression) to detect and/or differentiate sub-populations within the larger heterologous population. Lysates from cells indicated to be in the sub-population of interest (e.g., hematopoietic stem cells) are further analyzed. Lysates from individual cells, or pooled lysates from like-cells can be analyzed. Determination of "like-cell" populations can be based on similarities in the expression of 1, 2, 3, 4, 5, 6, 7, 8, 9, 10, 15, 20, 25, 30, 35, 40, 45, 50, 55, 60, 65, 70, 75, 80, 85, 90, 100, 200, 300, 400, 500, 600, 700, 800, 900, 1000 or more genes.

Cells and cell populations or subpopulations of interest can be further analyzed. Cell populations or subpopulations can comprise cells which comprised a portion of the original sample, for example cells which comprised 1%, 2%, 3%, 4%, 5%, 6%, 7%, 8%, 9%, 10% or more of the original sample. Using the methods described herein, cell populations or subpopulations of interest can be isolated from heterogenous samples such that the isolated populations or subpopulations can be 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% free of cells which are not members of the target population or subpopulation. For example, using the methods described herein an isolated cell population can comprise cells of which 95% express CDK6, PTEN, TOP1, SUZ12, and/or SOX9. As lysates are prepared from cells which are isolated from the original population, study of like-cell populations can be accomplished by pooling lysates from like-cells.

Further analysis of cells, populations and/or subpopulations can include whole transcriptome analysis. In some instances, lysates will comprise mRNA which can be amplified (e.g., cDNA) for analysis, or directly analyzed (e.g., mRNA sequencing, microarray analysis). mRNA amplification can be performed by any method known in the art (e.g., in vitro transcription, ligation-PCR cDNA amplification). In some embodiments, mRNA amplification can be performed in, or with the use of, a microfluidic device. Whole transcriptome analysis can be performed by sequencing platforms, such as those commercially available from Illumina (RNA-Seq) and Helicos (Digital Gene Expression or "DGE"). In some embodiments, polynucleotides of interest are sequenced. Target nucleic acids may be sequenced by conventional gel electrophoresis-based methods using, for example, Sanger-type sequencing. Alternatively, sequencing may be accomplished by use of several "next generation" methods. Such "next generation" sequencing methods include, but are not limited to those commercialized by: 1) 454/Roche Lifesciences including but not limited to the methods and apparatus described in Margulies et al., Nature (2005) 437:376-380 (2005); and U.S. Pat. Nos. 7,244,559; 7,335,762; 7,211,390; 7,244,567; 7,264,929; 7,323,305; 2) Helicos BioSciences Corporation (Cambridge, Mass.) as described in U.S. application Ser. No. 11/167,046, and U.S. Pat. Nos. 7,501,245; 7,491,498; 7,276,720; and in U.S. Patent Application Publication Nos. US20090061439; US20080087826; US20060286566; US20060024711; US20060024678; US20080213770; and US20080103058; 3) Applied Biosystems (e.g. SOLiD sequencing); 4) Dover Systems (e.g., Polonator G.007 sequencing); 5) Illumina as described U.S. Pat. Nos. 5,750,341; 6,306,597; and 5,969,119; and 6) Pacific Biosciences as described in U.S. Pat. Nos. 7,462,452; 7,476,504; 7,405,281; 7,170,050; 7,462,468; 7,476,503; 7,315,019; 7,302,146; 7,313,308; and US Application Publication Nos. US20090029385; US20090068655; US20090024331; and US20080206764. All references are herein incorporated by reference. Such methods and apparatuses are provided here by way of example and are not intended to be limiting.

Whole transcriptome analysis can be performed for multiple reasons which allow further characterization of different cellular sub-populations, including but not limited to: 1) detecting activity of genes that can reveal unique biological properties of subpopulations and/or transcription factors controlling their development; 2) locating and/or characterizing surface markers which may be used to purify the sub-populations (e.g. by FACS sorting); and 3) detecting and/or characterizing cellular genes and/or gene products as potential drug targets for disease which distinguish the sub-population from the general population (e.g., cancer stem cells vs. normal tissue).

Analysis of populations and/or subpopulations (e.g., by transcriptome analysis) can allow for the refining of techniques for isolating cells which belong to the sub-population. For example, where the methods reveal a sub-population specific surface antigen, antibodies developed by any available antibody synthesis method can be used to isolate such cells from a heterologous population (e.g., patient sample). Additionally, transcriptome profiles can be used to develop gene expression panels which can be used to identify cells from other populations (e.g., samples from the same or different patients).

Diagnostics and Prognostics

The invention finds use in the prevention, treatment, detection or research into any condition, including cancer, inflammatory diseases, autoimmune diseases and infections. Examples of cancer include prostrate, pancreas, colon, brain, lung, breast, bone, and skin cancers. Examples of inflammatory conditions include irritable bowel syndrome and ulcerative colitis. Examples of autoimmune diseases include Chrohn's disease, lupus, and Graves' disease. For example, the invention finds use in the prevention, treatment, detection of or research into gastrointestinal cancers, such as cancer of the anus, colon, esophagus, gallbladder, stomach, liver, and rectum; genitourinary cancers such as cancer of the penis, prostate and testes; gynecological cancers, such as cancer of the ovaries, cervix, endometrium, uterus, fallopian tubes, vagina, and vulva; head and neck cancers, such as hypopharyngeal, laryngeal, oropharyngeal cancers, lip, mouth and oral cancers, cancer of the salivary gland, cancer of the digestive tract and sinus cancer; metastatic cancer; sarcomas; skin cancer; urinary tract cancers including bladder, kidney and urethral cancers; endocrine system cancers, such as cancers of the thyroid, pituitary, and adrenal glands and the pancreatic islets; and pediatric cancers.

Methods are also provided for optimizing therapy, by first classification of individual cells in a sample, and based on that classification information, selecting the appropriate therapy, dose, treatment modality, etc. which optimizes the differential between delivery of an anti-proliferative treatment to the undesirable target cells, while minimizing undesirable toxicity. The treatment is optimized by selection for a treatment that minimizes undesirable toxicity, while providing for effective anti-proliferative activity. Treatment can be selected to affect only a subset of the cells in a sample. In some instances a therapy is selected that affects less than about 5%, less than about 1%, less than about 0.5%, less than about 0.2%, less than about 0.1%, less than about 0.05%, less than about 0.02%, less than about 0.01%, or fewer of the cells in the sample.

A signature for a condition can refer to an expression pattern of one or more genes or proteins in a single cell that indicates the presence of a condition. A cancer stem cell signature can refer to an expression pattern of one or more genes and/or proteins whose expression is indicative of a cancer stem cell phenotype. An autoimmune or inflammatory cell signature refers to genes and/or proteins whose expression is indicative of an autoimmune or inflammatory cell signature. A signature can be obtained from all or a part of a dataset, usually a signature will comprise gene and/or protein expression information from at least about 5 genes and/or proteins, at least about 10 genes and/or proteins, at least about 15 genes and/or proteins, at least about 20 genes and/or proteins, at least about 25 genes and/or proteins, at least about 50 genes and/or proteins, at least about 75 genes and/or proteins, at least about 100 genes and/or proteins, at least about 150 genes and/or proteins, at least about 200 genes and/or proteins, at least about 300 genes and/or proteins, at least about 400 genes and/or proteins, at least about 500 genes and/or proteins, or more genes and/or proteins. Where a subset of the dataset is used, the subset may comprise up-regulated genes, down-regulated genes, or a combination thereof.

Analysis of Patient Samples for Clinical Applications

Although the description below focuses on cancer stem cells, the methods described herein can be used to isolate and/or analyze any cell population, including but not limited to normal cells of any tissue (e.g., normal stem cells, normal progenitor cells, and normal mature cells), virally infected cells, inflammatory cells, progenitor cells, cancer cells (e.g., tumorigenic cells, non-tumorigenic cells, cancer stem cells, and differentiated cancer cells), disease-state cells (e.g., cancer cells, inflammatory bowel disease cells, ulcerative colitis cells, etc.), microbial (bacterial, fungal, protist) cells, etc. Thus, the details provided using cancer stem cells (CSC) are illustrative of analysis that can be performed for any disease state or condition.

In some embodiments of the invention, the number of CSC in a patient sample can be determined relative to the total number of cancer cells. For example, cells from a biopsy sample are isolated and analyzed for expression of one or more mRNAs and/or proteins indicative of a cancer cell and cells that exhibit the CSC phenotype are quantitated. Alternately, data collected for particular populations or subpopulations of CSCs can be used to develop affinity (e.g., antibody) screens for the population or subpopulation and such affinity screens can be used to quantitate the number of cells. Typically, a greater percentage of CSC is indicative of the potential for continued self-renewal of cells with the cancer phenotype. The quantitation of CSC in a patient sample can be compared to a positive and/or negative reference sample, e.g. a patient sample such as a blood sample, a remission patient sample, etc. In some embodiments, the quantitation of CSC is performed during the course of treatment, where the number of cancer cells and the percentage of such cells that are CSC are quantitated before, during and as follow-up to a course of therapy. Desirably, therapy targeted to cancer stem cells results in a decrease in the total number, and/or percentage of CSC in a patient sample.

The CSC can be identified by their phenotype with respect to particular markers, and/or by their functional phenotype. In some embodiments, the CSC are identified and/or isolated by binding to the cell with reagents specific for the markers of interest. The cells to be analyzed may be viable cells, or may be fixed or embedded cells.

The presence of a CSC in a patient sample can also be indicative of the stage of the cancer (e.g., leukemia, breast cancer, prostate cancer). In addition, detection of CSC can be used to monitor response to therapy and to aid in prognosis. The presence of CSC can be determined by quantitating the cells having the phenotype of the stem cell. In addition to cell surface phenotyping, it may be useful to quantitate the cells in a sample that have a "stem cell" character, which may be determined by functional criteria, such as the ability to self-renew, to give rise to tumors in vivo, e.g. in a xenograft model, and the like.

Clinical samples for use in the methods of the invention may be obtained from a variety of sources, particularly blood, although in some instances samples such as bone marrow, lymph, cerebrospinal fluid, synovial fluid, and the like may be used. Samples can include biopsies, or other clinical specimens containing cells. Some samples comprise solid tumors or portions thereof. In instances where cell masses are to be assayed, such masses can be dissociated by any appropriate means known in the art (e.g., enzymatic digestion, physical separation). Such samples can be separated by centrifugation, elutriation, density gradient separation, apheresis, affinity selection, panning, FACS, centrifugation with Hypaque, etc. prior to analysis, and usually a mononuclear fraction (PBMC) is used. In this manner, individual cells from a sample (e.g., solid tumor) can be analyzed for differential gene expression and/or transcriptome analysis as described herein.

Once a sample is obtained, it can be used directly, frozen, or maintained in appropriate culture medium for short periods of time. Various media can be employed to maintain cells. The samples may be obtained by any convenient procedure, such as biopsy, the drawing of blood, venipuncture, or the like. In some embodiments, a sample will comprise at least about $10^2$ cells, more usually at least about $10^3$, $10^4$, $10^5$ or more cells. Typically, the samples are from human patients, although animal models may find use, e.g. equine, bovine, porcine, canine, feline, rodent, e.g. mice, rats, hamster, primate, etc.

An appropriate solution may be used for dispersion or suspension of a cell sample. Such solution will generally be a balanced salt solution, e.g. normal saline, PBS, Hank's balanced salt solution, etc., conveniently supplemented with fetal calf serum or other naturally occurring factors, in conjunction with an acceptable buffer at low concentration, generally from 5-25 mM. Convenient buffers include HEPES, phosphate buffers, lactate buffers, etc.

Analysis of cell staining can be performed using conventional methods. Techniques providing accurate enumeration include fluorescence activated cell sorters, which can have varying degrees of sophistication, such as multiple color channels, low angle and obtuse light scattering detecting channels, impedance channels, etc. The cells may be selected against dead cells by employing dyes associated with dead cells (e.g. propidium iodide).

The affinity reagents may be specific receptors or ligands for the cell surface molecules indicated above. In addition to antibody reagents, peptide-MHC antigen and T cell receptor pairs may be used; peptide ligands and receptors; effector and receptor molecules, and the like. Antibodies and T cell receptors may be monoclonal or polyclonal, and may be produced by transgenic animals, immunized animals, immortalized human or animal B-cells, cells transfected with DNA vectors encoding the antibody or T cell receptor, etc. The details of the preparation of antibodies and their suitability for use as specific binding members are well-known to those skilled in the art.

One approach is the use of antibodies as affinity reagents. Conveniently, these antibodies can be conjugated with a label for use in separation. Labels include any labels known in the art including, but not limited to, magnetic beads, which allow for direct separation, biotin, which can be removed with avidin or streptavidin bound to a support, fluorochromes, which can be used with a fluorescence activated cell sorter, or the like, to allow for ease of separation of the particular cell type. Fluorochromes that find use include phycobiliproteins, e.g. phycoerythrin and allophycocyanins, fluorescein and Texas red. Frequently each antibody is labeled with a different fluorochrome, to permit independent sorting for each marker.

Antibodies can be added to a suspension of cells, and incubated for a period of time sufficient to bind the available cell surface antigens. The incubation will usually be at least about 5 minutes and usually less than about 30 minutes. It is desirable to have a sufficient concentration of antibodies in the reaction mixture, such that the efficiency of the separation is not limited by lack of antibody. The appropriate concentration is determined by titration. The medium in which the cells are separated is any medium that maintains the viability of the cells. One medium which can be utilized is phosphate buffered saline containing from 0.1 to 0.5% BSA. Various media are commercially available and may be used according to the nature of the cells, including Dulbecco's Modified Eagle Medium (dMEM), Hank's Basic Salt Solution (HESS), Dulbecco's phosphate buffered saline (dPBS), RPMI, Iscove's medium, PBS with 5 mM EDTA, etc., frequently supplemented with fetal calf serum, BSA, HSA, etc. The labeled cells can then be quantitated as to the expression of cell surface markers as previously described.

The comparison of a differential progenitor analysis obtained from a patient sample, and a reference differential progenitor analysis can be accomplished by the use of suitable deduction protocols, AI systems, statistical comparisons, etc. A comparison with a reference differential progenitor analysis from normal cells, cells from similarly diseased tissue, and the like, can provide an indication of the disease staging. A database of reference differential progenitor analyses can be compiled. An analysis of particular interest tracks a patient, e.g. in the chronic and pre-leukemic stages of disease, such that acceleration of disease is observed at an early stage. The methods of the invention provide detection of acceleration prior to onset of clinical symptoms, and therefore allow early therapeutic intervention, e.g. initiation of chemotherapy, increase of chemotherapy dose, changing selection of chemotherapeutic drug, and the like.

Tumor Classification and Patient Stratification.

Methods are also provided for optimizing therapy, by first classification, and based on that information, selecting the appropriate therapy, dose, treatment modality, etc. which optimizes the differential between delivery of an anti-proliferative treatment to the undesirable target cells, while minimizing undesirable toxicity. The treatment is optimized by selection for a treatment that minimizes undesirable toxicity, while providing for effective anti-proliferative activity.

In one aspect, the disclosure provides for methods of classifying lesions, e.g. tumor lesions, immune disorder samples, and the like, and thus grouping or "stratifying" patients, according to the single cell (including CSC) gene expression signature. For example, tumors classified as having a high percentage of cancer stem cells carry a higher risk of metastasis and death, and therefore may be treated more aggressively than tumors of a more benign type. Thus, analysis of populations or subpopulations present in a patient sample can be utilized to characterize the status of a disease, monitor treatment regimens and/or develop therapeutic approaches.

The sample of each patient in a pool of potential patients for a clinical trial can be classified as described above. Patients having similarly classified lesions can then be selected for participation in an investigative or clinical trial of a therapeutic where a homogeneous patient population is desired. The classification of a patient can also be used in assessing the efficacy of a therapeutic in a heterogeneous patient population. Thus, comparison of an individual's expression profile to the population profile for disease classification permits the selection or design of drugs or other therapeutic regimens that are expected to be safe and efficacious for a particular patient or patient population (i.e., a group of patients having the same type of cancer). For example, some patients with breast cancer have cancerous cells (e.g., differentiated cancer cells, cancer stem cells) that expresses NGFR, while other patients exhibit no expression of NGFR. Thus, the patients can be classified, at least in part, according to NGFR expression. Classification can be based on the expression (or lack thereof) of 1, 2, 3, 4, 5, 6, 7, 8, 9, 10, 11, 12, 13, 14, 15, 16, 17, 18, 19, 20, 25, 30, 35, 40, 45, 50 or more nucleic acids and/or proteins.

Diagnosis, Prognosis, Assessment of Therapy (Therametrics), and Management of Disorders The classification methods described herein, as well as their gene products and corresponding genes and gene products, are of particular interest as genetic or biochemical markers (e.g., in blood or tissues) that will detect the earliest changes along a disease pathway (e.g., a carcinogenesis pathway, inflammatory pathway, etc.), and/or to monitor the efficacy of various therapies and preventive interventions.

Staging is a process used by physicians to describe how advanced the cancerous state is in a patient. Staging assists the physician in determining a prognosis, planning treatment and evaluating the results of such treatment. Staging systems vary with the types of cancer, but generally involve the following "TNM" system: the type of tumor, indicated by T; whether the cancer has metastasized to nearby lymph nodes, indicated by N; and whether the cancer has metastasized to more distant parts of the body, indicated by M. Generally, if a cancer is only detectable in the area of the primary lesion without having spread to any lymph nodes it is called Stage I. If it has spread only to the closest lymph nodes, it is called Stage II. In Stage III, the cancer has generally spread to the lymph nodes in near proximity to the site of the primary lesion. Cancers that have spread to a distant part of the body, such as the liver, bone, brain or other site, are Stage IV, the most advanced stage.

The methods described herein can facilitate fine-tuning of the staging process by identifying the aggressiveness of a cancer, e.g. the metastatic potential, as well as the presence in different areas of the body. Thus, a Stage II cancer with a classification signifying a high metastatic potential cancer can be used to change a borderline Stage II tumor to a Stage III tumor, justifying more aggressive therapy. Conversely, the presence of a polynucleotide signifying a lower metastatic potential allows more conservative staging of a tumor.

For example, a breast cancer biopsy from a Stage II patient is analyzed by the methods described herein. If the patient sample contains one or more cells which express a target gene above or below a threshold level, the breast cancer can be classified as having a high metastatic potential. Thus, a treating physician may use such information to more aggressively treat the patient than he or she would without the further classification. Determination of the expression of particular markers can also provide information on potential targets for drug therapy (e.g., tumorigenic cells from a patient expressing a drug target).

Development and Identification of Therapeutics.

The methods and compositions described herein can be utilized for the development or identification of new therapeutic agents and/or refining of existing therapies. For example, using single-cell analysis, expression profiles for target cell populations (e.g., cancer stem cells, cancer stem cells and differentiated cancer cells, or differentiated cancer cells) can be analyzed to detect potential targets for therapeutic agents. Potential targets include, without limitation, particular biomarkers and mis-regulated pathways. Targets of interest can include markers or pathways specific to the cell population(s) of interest.

In one instance, cells of a target population or subpopulation can be analyzed for expression of nucleic acids as described herein to detect novel biomarkers which can be targeted for treatment. For example, a particular cell surface molecule expressed exclusively in cancer stem cells and/or differentiated cancer cells can be investigated as a target for a potential therapeutic agent (e.g., an antibody or other binding moiety—potentially conjugated with a toxin or other such effector—with specificity for the surface molecule). In other instances, target cell populations can be analyzed for mis-regulation of pathways involved in disease processes (e.g., loss of control of cell-cycling machinery in cancer cells). Pathways can include, without limitation, activators and/or repressors of gene expression, expression of particular genes or sets of genes, and more complex, global pathways. Therapeutic agents that target such mis-regulation can potentially affect target cells to alter expression of nucleic acids associated with the target cells. Altered expression induced by therapeutic agents can result in up- or down-regulation of the nucleic acid. In some instances, treatment of cells and/or a subject with one or more therapeutic agents can result in expression of nucleic acids which imitates the expression in non-disease-state cells (e.g., treatment results in expression of cell-cycle related genes similar to that of non-cancerous cells).

Using the methods and compositions described herein, target cell populations can be analyzed for altered expression of one or more nucleic acids. The development of new and/or refined therapeutic agents can involve analyzing a target cell population (e.g., colon cancer stem cells, breast cancer cells, etc.) to determine nucleic acids which exhibit altered expression profiles as compared to "normal" cells. For example, some colon cancer stem cells show increased expression of, for example, TERT, PTPRO, AQP1, KIF12, METTL3, LEFTY1, CFTR, CA2, and/or EZH2. Such cells can be utilized to screen potential therapeutic agents for effect(s) on expression of these and/or other nucleic acids by exposing isolated cells of the target population to candidate agents and testing for altered expression of the genes following exposure.

The methods disclosed herein can also be utilized to analyze the effects of compounds which affect certain cellular phenotypes, including but not limited to, gene expression, pathway functioning (e.g., cell cycling, TERT pathway, oxidative stress pathways), and or cell type or morphology. Thus, compounds which affect such phenotypic characteristics can be analyzed in addition to or in lieu of analyzing a compound's potential as a therapeutic agent. For example, analysis of changes in gene expression in a target population (e.g., normal colon cells, normal breast cells, cancer cells, stem cells, cancer stem cells, etc.) exposed to one or more test compounds can performed to analyze the effect(s) of the test compounds on gene expression or other desired phenotypes (e.g., marker expression, cell viability). Such analyses can be useful for multiple purposes, for example cell cycle research or analysis of known or unknown pathways.

Agents to be analyzed for potential therapeutic value can be any compound, small molecule, protein, lipid, carbohydrate, nucleic acid or other agent appropriate for therapeutic use. Isolated cells of a target population can be exposed to libraries of potential therapeutic agents (e.g., antibody libraries, small molecule libraries) to determine effects on gene expression and/or cell viability. In some instances a candidate therapeutic agent will specifically target the cell population of interest. For example, upon single-cell analysis the existence of a mutation which is present in target cells (e.g., cancer stem cells and/or differentiated cancer cells) is revealed, a candidate therapeutic agent can target the mutation. In some instances, treated cells can be exposed to single-cell analysis to determine effects of the candidate therapeutic agent(s) on the expression of one or more genes of interest and/or effects on the transcriptome.

In other embodiments of the invention, agents are targeted to a disease-state cell population or subpopulation by specific binding to a marker or combination of markers present on the target population or subpopulation. In some embodiments, the agents include antibodies or antigen-binding derivatives thereof specific for a marker or combination of markers, which are optionally conjugated to a cytotoxic moiety. Such approaches can be used to deplete the target population or subpopulation in a patient (e.g., deplete cancer stem cell populations).

Therapeutic Agent Screening Assays

Cells (e.g., disease-state cells) expressing a marker or combination of markers are also useful for in vitro assays and screening to detect factors and chemotherapeutic agents that are active on differentiated cancer cells and/or cancer stem cells. Of particular interest are screening assays for agents that are active on human cells. A wide variety of assays may be used for this purpose, including immunoassays for protein binding; determination of cell growth, differentiation and functional activity; production of factors; and the like (see, e.g., Balis, (2002) *J. Nat'l Cancer Inst.* 94:2; 78). In other embodiments, isolated polypeptides corresponding to a marker or combination of markers of the present invention are useful in drug screening assays.

In screening assays for biologically active agents, antiproliferative drugs, etc. a marker or a target cell composition is contacted with the agent of interest, and the effect of the agent assessed by monitoring output parameters on cells, such as expression of markers, cell viability, and the like; or binding efficacy or effect on enzymatic or receptor activity for polypeptides. For example, a breast cancer cell composition known to have a "cancer stem cell" expression profile is exposed to a test agent and exposed cells are individually analyzed as described herein to determine whether the test agent altered the expression profile as compared to non-treated cells. Any isolated cell population described herein or produced by the methods described herein may be freshly isolated, cultured, genetically altered, and the like. The cells can be environmentally induced variants of clonal cultures: e.g., split into independent cultures and grown under distinct conditions, for example with or without drugs; in the presence or absence of cytokines or combinations thereof. The manner in which cells respond to an agent (e.g., a peptide, siRNA, small molecule, etc.), particularly a pharmacologic agent, including the timing of responses, is an important reflection of the physiologic state of the cell.

Parameters are quantifiable components of cells, particularly components that can be accurately measured, for instance in a high throughput system. A parameter can be any cell component or cell product including cell surface determinant, receptor, protein or conformational or post-translational modification thereof, lipid, carbohydrate, organic or inorganic molecule, nucleic acid, e.g. mRNA, DNA, etc. or a portion derived from such a cell component or combinations thereof. For example, in one embodiment, isolated cells as described herein are contacted with one or more agents and the level of expression of a nucleic acid of interest (e.g., TERT, PTPRO, AQP1, KIF12, METTL3, LEFTY1, CFTR, CA2, and/or EZH2) is determined Agents which alter the expression of the detected nucleic acid(s), e.g., where the cells exhibit an expression pattern more similar to a non-disease state cell, can be further analyzed for therapeutic potential. While most parameters (e.g., mRNA or protein expression) will provide a quantitative readout, in some instances a semi-quantitative or qualitative result is acceptable. Readouts may include a single determined value, or may include mean, median value or the variance, etc. Characteristically a range of parameter readout values is obtained for each parameter from a multiplicity of the same assays. Variability is expected and a range of values for each of the set of test parameters are obtained using standard statistical methods with a common statistical method used to provide single values.

Agents of interest for screening include known and unknown compounds that encompass numerous chemical classes, primarily organic molecules, which may include organometallic molecules, genetic sequences, etc. An important aspect of the invention is to evaluate candidate drugs, including toxicity testing; and the like.

In addition to complex biological agents candidate agents include organic molecules comprising functional groups necessary for structural interactions, particularly hydrogen bonding, and typically include at least an amine, carbonyl, hydroxyl or carboxyl group, frequently at least two of the functional chemical groups. The candidate agents can comprise cyclical carbon or heterocyclic structures and/or aromatic or polyaromatic structures substituted with one or more of the above functional groups. Candidate agents can also be found among biomolecules, including peptides, polynucleotides, saccharides, fatty acids, steroids, purines, pyrimidines, derivatives, structural analogs or combinations thereof. In some instances, test compounds may have known functions (e.g., relief of oxidative stress), but may act through an unknown mechanism or act on an unknown target.

Included are pharmacologically active drugs, genetically active molecules, etc. Compounds of interest include chemotherapeutic agents, hormones or hormone antagonists, etc. Exemplary of pharmaceutical agents suitable for this invention are those described in, "The Pharmacological Basis of Therapeutics," Goodman and Gilman, McGraw-Hill, New York, N.Y., (1996), Ninth edition, under the sections: Water, Salts and Ions; Drugs Affecting Renal Function and Electrolyte Metabolism; Drugs Affecting Gastrointestinal Function; Chemotherapy of Microbial Diseases; Chemotherapy of Neoplastic Diseases; Drugs Acting on Blood-Forming organs; Hormones and Hormone Antagonists; Vitamins, Dermatology; and Toxicology, all incorporated herein by reference. Also included are toxins, and biological and chemical warfare agents, for example see Somani, S. M. (Ed.), "Chemical Warfare Agents," Academic Press, New York, 1992).

Test compounds include all of the classes of molecules described above, and can further comprise samples of unknown content. Of interest are complex mixtures of naturally occurring compounds derived from natural sources such as plants, fungi, bacteria, protists or animals. While many samples will comprise compounds in solution, solid samples that can be dissolved in a suitable solvent may also be assayed. Samples of interest include environmental samples, e.g., ground water, sea water, mining waste, etc., biological samples, e.g. lysates prepared from crops, tissue samples, etc.; manufacturing samples, e.g. time course during preparation of pharmaceuticals; as well as libraries of compounds prepared for analysis; and the like (e.g., compounds being assessed for potential therapeutic value, i.e., drug candidates).

Samples or compounds can also include additional components, for example components that affect the ionic strength, pH, total protein concentration, etc. In addition, the samples may be treated to achieve at least partial fractionation or concentration. Biological samples may be stored if care is taken to reduce degradation of the compound, e.g. under nitrogen, frozen, or a combination thereof. The volume of sample used is sufficient to allow for measurable detection, for example from about 0.1 ml to 1 ml of a biological sample can be sufficient.

Compounds, including candidate agents, are obtained from a wide variety of sources including libraries of synthetic or natural compounds. For example, numerous means are available for random and directed synthesis of a wide variety of organic compounds, including biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs.

Agents are screened for biological activity by adding the agent to at least one and usually a plurality of cell samples, usually in conjunction with cells lacking the agent. The change in parameters in response to the agent is measured, and the result evaluated by comparison to reference cultures, e.g. in the presence and absence of the agent, obtained with other agents, etc.

The agents can be added in solution, or readily soluble form, to the medium of cells in culture. The agents may be added in a flow-through system, as a stream, intermittent or continuous, or alternatively, adding a bolus of the compound, singly or incrementally, to an otherwise static solution. In a flow-through system, two fluids are used, where one is a physiologically neutral solution, and the other is the same solution with the test compound added. The first fluid is passed over the cells, followed by the second. In a single solution method, a bolus of the test compound is added to the volume of medium surrounding the cells. The overall concentrations of the components of the culture medium should not change significantly with the addition of the bolus, or between the two solutions in a flow through method.

Some agent formulations do not include additional components, such as preservatives, that may have a significant effect on the overall formulation. Thus, such formulations consist essentially of a biologically active compound and a physiologically acceptable carrier, e.g. water, ethanol, DMSO, etc. However, if a compound is liquid without a solvent, the formulation may consist essentially of the compound itself.

A plurality of assays may be run in parallel with different agent concentrations to obtain a differential response to the various concentrations. As, known in the art, determining the effective concentration of an agent typically uses a range of concentrations resulting from 1:10, or other log scale, dilutions. The concentrations may be further refined with a second series of dilutions, if necessary. Typically, one of these concentrations serves as a negative control, i.e. at zero concentration or below the level of detection of the agent or at or below the concentration of agent that does not give a detectable change in the phenotype.

Various methods can be utilized for quantifying the presence of the selected markers. For measuring the amount of a molecule that is present, a convenient method is to label a molecule with a detectable moiety, which may be fluorescent, luminescent, radioactive, enzymatically active, etc., particularly a molecule specific for binding to the parameter with high affinity. Fluorescent moieties are readily available for labeling virtually any biomolecule, structure, or cell type.

Immunofluorescent moieties can be directed to bind not only to specific proteins but also specific conformations, cleavage products, or site modifications like phosphorylation. Individual peptides and proteins can be engineered to autofluoresce, e.g. by expressing them as green fluorescent protein chimeras inside cells (for a review see Jones et. al. (1999) Trends Biotechnol. 17(12):477-81). Thus, antibodies can be genetically modified to provide a fluorescent dye as part of their structure. Depending upon the label chosen, parameters may be measured using other than fluorescent labels, using such immunoassay techniques as radioimmunoassay (RIA) or enzyme linked immunosorbance assay (ELISA), homogeneous enzyme immunoassays, and related non-enzymatic techniques. The quantitation of nucleic acids, especially messenger RNAs, is also of interest as a parameter. These can be measured by hybridization techniques that depend on the sequence of nucleic acid nucleotides. Techniques include polymerase chain reaction methods as well as gene array techniques. See Current Protocols in Molecular Biology, Ausubel et al., eds, John Wiley & Sons, New York, N.Y., 2000; Freeman at al. (1999) Biotechniques 26(1):112-225; Kawamoto at al. (1999) Genome Res 9(12):1305-12; and Chen et al. (1998) Genomics 51(3): 313-24, for examples.

Databases of Expression Profiles and Data Analysis

Also provided are databases of gene expression profiles of cancer stem cells and other cell types and uses thereof. Such databases will typically comprise expression profiles derived from various cell subpopulations, such as cancer stem cells, cancer non-stem cells, normal counterparts to cancer cells, disease-state cells (e.g., inflammatory bowel cells, ulcerative colitis cells), virally infected cells, early progenitor cells, initially differentiated progenitor cells, late differentiated progenitor cells, and mature cells. The expression profiles and databases thereof may be provided in a variety of media to facilitate their use. "Media" refers to a manufacture that contains the expression profile information of the present invention. The databases of the present invention can be recorded on computer readable media, e.g. any medium that can be read and accessed directly by a computer. Such media include, but are not limited to: magnetic storage media, such as floppy discs, hard disc storage medium, and magnetic tape; optical storage media such as CD-ROM; electrical storage media such as RAM and ROM; and hybrids of these categories such as magnetic/optical storage media. One of skill in the art can readily appreciate how any of the presently known computer readable mediums can be used to create a manufacture comprising a recording of the present database information. "Recorded" refers to a process for storing information on computer readable medium, using any such methods as known in the art. Any convenient data storage structure may be chosen, based on the means used to access the stored information. A variety of data processor programs and formats can be used for storage, e.g. word processing text file, database format, etc.

As used herein, "a computer-based system" refers to the hardware means, software means, and data storage means used to analyze the information of the present invention. The minimum hardware of the computer-based systems of the present invention comprises a central processing unit (CPU), input means, output means, and data storage means. A skilled artisan can readily appreciate that any one of the currently available computer-based system are suitable for use in the present invention. The data storage means may comprise any manufacture comprising a recording of the present information as described above, or a memory access means that can access such a manufacture.

A variety of structural formats for the input and output means can be used to input and output the information in the computer-based systems of the present invention. Such presentation provides a skilled artisan with a ranking of similarities and identifies the degree of similarity contained in the test expression profile.

Various methods for analysis of a set of data may be utilized. In one embodiment, expression data is subjected to transformation and normalization. For example, ratios are generated by mean centering the expression data for each gene (by dividing the intensity measurement for each gene on a given array by the average intensity of the gene across all arrays), (2) then log-transformed (base 2) the resulting ratios, and (3) then median centered the expression data across arrays then across genes.

For cDNA microarray data, genes with fluorescent hybridization signals at least 1.5-fold greater than the local background fluorescent signal in the reference channel are considered adequately measured. The genes are centered by mean value within each dataset, and average linkage clustering carried out.

A scaled approach may also be taken to the data analysis. For example, Pearson correlation of the expression values of genes can provide a quantitative score reflecting the signature for each CSC. The higher the correlation value, the more the sample resembles a reference CSC phenotype. Similar correlation can be done for any cell type, including normal cells, progenitor cells, autoimmune phenotype cells, inflammatory phenotype cells, infected cells, differentiated cancer cells, normal stem cells, normal mature cells, etc. A negative correlation value indicates the opposite behavior. The threshold for the classification can be moved up or down from zero depending on the clinical goal. For example, sensitivity and specificity for predicting metastasis as the first recurrence event can be calculated for every threshold between −1 and +1 for the correlation score in 0.05 increments, and the threshold value giving a desired sensitivity, e.g. 80%, 90%, 95%, etc. for metastasis prediction can be selected.

To provide significance ordering, the false discovery rate (FDR) may be determined. First, a set of null distributions of dissimilarity values is generated. In one embodiment, the values of observed profiles are permuted to create a sequence of distributions of correlation coefficients obtained out of chance, thereby creating an appropriate set of null distributions of correlation coefficients (see Tusher et al. (2001) PNAS 98, 5118-21, herein incorporated by reference). The set of null distribution is obtained by: permuting the values of each profile for all available profiles; calculating the pairwise correlation coefficients for all profile; calculating the probability density function of the correlation coefficients for this permutation; and repeating the procedure for N times, where N is a large number, usually 300. Using the N distributions, one calculates an appropriate measure (mean, median, etc.) of the count of correlation coefficient values that their values exceed the value (of similarity) that is obtained from the distribution of experimentally observed similarity values at given significance level.

The FDR is the ratio of the number of the expected falsely significant correlations (estimated from the correlations greater than this selected Pearson correlation in the set of randomized data) to the number of correlations greater than this selected Pearson correlation in the empirical data (significant correlations). This cut-off correlation value may be applied to the correlations between experimental profiles.

Using the aforementioned distribution, a level of confidence is chosen for significance. This is used to determine the lowest value of the correlation coefficient that exceeds the result that would have obtained by chance. Using this method, one obtains thresholds for positive correlation, negative correlation or both. Using this threshold(s), the user can filter the observed values of the pairwise correlation coefficients and eliminate those that do not exceed the threshold(s). Furthermore, an estimate of the false positive rate can be obtained for a given threshold. For each of the individual "random correlation" distributions, one can find how many observations fall outside the threshold range. This procedure provides a sequence of counts. The mean and the standard deviation of the sequence provide the average number of potential false positives and its standard deviation.

The data can be subjected to non-supervised hierarchical clustering to reveal relationships among profiles. For example, hierarchical clustering may be performed, where the Pearson correlation is employed as the clustering metric. Clustering of the correlation matrix, e.g. using multidimensional scaling, enhances the visualization of functional homology similarities and dissimilarities. Multidimensional scaling (MDS) can be applied in one, two or three dimensions.

The analysis may be implemented in hardware or software, or a combination of both. In one embodiment of the invention, a machine-readable storage medium is provided, the medium comprising a data storage material encoded with machine readable data which, when using a machine programmed with instructions for using said data, is capable of displaying a any of the datasets and data comparisons of this invention. Such data may be used for a variety of purposes, such as drug discovery, analysis of interactions between cellular components, and the like. In some embodiments, the invention is implemented in computer programs executing on programmable computers, comprising a processor, a data storage system (including volatile and non-volatile memory and/or storage elements), at least one input device, and at least one output device. Program code is applied to input data to perform the functions described above and generate output information. The output information is applied to one or more output devices, in known fashion. The computer may be, for example, a personal computer, microcomputer, or workstation of conventional design.

Each program can be implemented in a high level procedural or object oriented programming language to communicate with a computer system. However, the programs can be implemented in assembly or machine language, if desired. In any case, the language may be a compiled or interpreted language. Each such computer program can be stored on a storage media or device (e.g., ROM or magnetic diskette) readable by a general or special purpose programmable computer, for configuring and operating the computer when the storage media or device is read by the computer to perform the procedures described herein. The system may also be considered to be implemented as a computer-readable storage medium, configured with a computer program, where the storage medium so configured causes a computer to operate in a specific and predefined manner to perform the functions described herein.

A variety of structural formats for the input and output means can be used to input and output the information in the computer-based systems of the present invention. One format for an output means tests datasets possessing varying degrees of similarity to a trusted profile. Such presentation provides a skilled artisan with a ranking of similarities and identifies the degree of similarity contained in the test pattern.

Storing and Transmission of Data

Further provided herein is a method of storing and/or transmitting, via computer, sequence, and other, data collected by the methods disclosed herein. Any computer or computer accessory including, but not limited to software and storage devices, can be utilized to practice the present invention. Sequence or other data (e.g., transcriptome data), can be input into a computer by a user either directly or indirectly. Additionally, any of the devices which can be used to sequence DNA or analyze DNA or analyze transcriptome data can be linked to a computer, such that the data is transferred to a computer and/or computer-compatible storage device. Data can be stored on a computer or suitable storage device (e.g., CD). Data can also be sent from a computer to another computer or data collection point via methods well known in the art (e.g., the internet, ground mail, air mail). Thus, data collected by the methods described herein can be collected at any point or geographical location and sent to any other geographical location.

Figure 10:
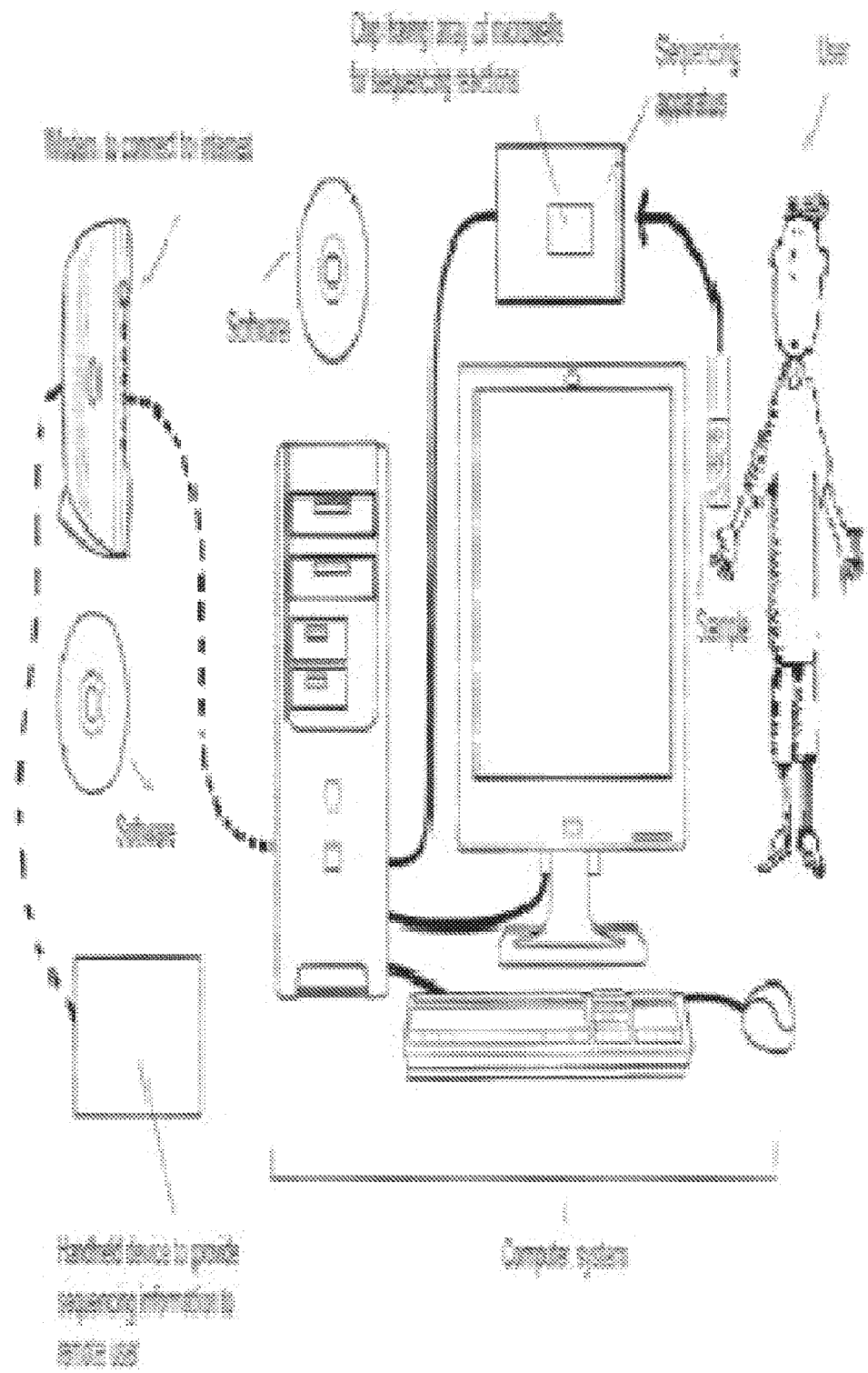
FIG. 10. A pictorial representation of data collection, storage and transport via computer.

An exemplary method is illustrated in FIG. 10. In this example, a user provides a sample into a sequencing apparatus. Data is collected and/or analyzed by the sequencing apparatus which is connected to a computer. Software on the computer allows for data collection and/or analysis. Data can be stored, displayed (via a monitor or other similar device), and/or sent to another location. As shown in FIG. 10, the computer is connected to the internet which is utilized to transmit data to a handheld device utilized by a remote user (e.g., a physician, scientist or analyst). It is understood that the data can be stored and/or analyzed prior to transmittal. In some embodiments, raw data can be collected and sent to a remote user who will analyze and/or store the data. Transmittal can occur, as shown in FIG. 10, via the internet, but can also occur via satellite or other connection. Alternately, data can be stored on a computer-readable medium (e.g., CD, memory storage device) and the medium can be shipped to an end user (e.g., via mail). The remote user can be in the same or a different geographical location including, but not limited to a building, city, state, country or continent.

Reagents and Kits

Also provided are reagents and kits thereof for practicing one or more of the above-described methods. The subject reagents and kits thereof may vary greatly. Reagents of interest include reagents specifically designed for use in production of the above described expression profiles of phenotype determinative genes. For example, reagents can include primer sets for genes known to be differentially expressed in a target population or subpopulation (e.g., reagents for detecting tumorigenic breast cancer cells can include primers and probes for expanding and detecting expression of CD49f, CD24, and/or EPCAM).

One type of reagent that is specifically tailored for generating expression profiles of target cell populations and subpopulations is a collection of gene specific primers that is designed to selectively amplify such genes, for use in quantitative PCR and other quantitation methods. Gene specific primers and methods for using the same are described in U.S. Pat. No. 5,994,076, the disclosure of which is herein incorporated by reference. Of particular interest are collections of gene specific primers that have primers for at least 5 of genes, often a plurality of these genes, e.g., at least 10, 15, 20, 30, 40, 50, 60, 70, 80, 90, 100, 200, 300, 400, 500, 600, 700, 800, 900, 1000 genes or more. The gene specific primer collections can include only primers for genes associated with a target population or subpopulation (e.g., mutations, known mis-regulated genes, etc.), or they may include primers for additional genes (e.g., housekeeping genes, controls).

The kits of the subject invention can include the above described gene specific primer collections. The kits can further include a software package for statistical analysis of one or more phenotypes, and may include a reference database for calculating the probability of susceptibility. The kit may include reagents employed in the various methods, such as primers for generating target nucleic acids, dNTPs and/or rNTPs, which may be either premixed or separate, one or more uniquely labeled dNTPs and/or rNTPs, such as biotinylated or Cy3 or Cy5 tagged dNTPs, gold or silver particles with different scattering spectra, or other post synthesis labeling reagent, such as chemically active derivatives of fluorescent dyes, enzymes, such as reverse transcriptases, DNA polymerases, RNA polymerases, and the like, various buffer mediums, e.g. hybridization and washing buffers, prefabricated probe arrays, labeled probe purification reagents and components, like spin columns, etc., signal generation and detection reagents, e.g. streptavidin-alkaline phosphatase conjugate, chemifluorescent or chemiluminescent substrate, and the like.

In addition to the above components, the subject kits will further include instructions for practicing the subject methods. These instructions may be present in the subject kits in a variety of forms, one or more of which may be present in the kit. One form in which these instructions may be present is as printed information on a suitable medium or substrate, e.g., a piece or pieces of paper on which the information is printed, in the packaging of the kit, in a package insert, etc. Yet another means would be a computer readable medium, e.g., diskette, CD, etc., on which the information has been recorded. Yet another means that may be present is a website address which may be used via the internet to access the information at a removed, site. Any convenient means may be present in the kits.

The above-described analytical methods may be embodied as a program of instructions executable by computer to perform the different aspects of the invention. Any of the techniques described above may be performed by means of software components loaded into a computer or other information appliance or digital device. When so enabled, the computer, appliance or device may then perform the above-described techniques to assist the analysis of sets of values associated with a plurality of genes in the manner described above, or for comparing such associated values. The software component may be loaded from a fixed media or accessed through a communication medium such as the internet or other type of computer network. The above features are embodied in one or more computer programs may be performed by one or more computers running such programs.

EXAMPLES

The following examples are offered by way of illustration and not by way of limitation.

Example 1: Analysis of Gene Expression in Single Cells

A significant fraction of murine breast CSCs contain relatively low levels of ROS, and so it was hypothesized that these cells may express enhanced levels of ROS defenses compared to their NTC counterparts.

Single Cell Gene Expression Analysis.

For the single cell gene expression experiments we used qPCR DynamicArray microfluidic chips (Fluidigm). Single MMTV-Wnt-1 Thy1$^+$CD24$^+$Lin– CSC-enriched cells (TG) and "Not Thy1$^+$CD24$^+$" Lin" non-tumorigenic (NTG) cells were sorted by FACS into 96 well plates containing PCR mix (CellsDirect, Invitrogen) and RNase Inhibitor (Superaseln, Invitrogen). After hypotonic lysis we added RT-qPCR enzymes (SuperScript III RT/Platinum Taq, Invitrogen), and a mixture containing a pool of low concentration assays (primers/probes) for the genes of interest (Gclm-Mm00514996_m1, Gss-Mm00515065 m 1, Foxo1-Mm00490672_m1, Foxo4-Mm00840140_g1, H ifla Mm00468875_m1, Epas1-Mm00438717 m1). Reverse transcription (15 minutes at 50° C., 2 minutes of 95° C.) was followed by pre-amplification for 22 PCR cycles (each cycle: 15 sec at 95° C., 4 minutes at 60° C.). Total RNA controls were run in parallel. The resulting amplified cDNA from each one of the cells was inserted into the chip sample inlets with Taqman qPCR mix (Applied Biosystems). Individual assays (primers/probes) were inserted into the chip assay inlets (2 replicates for each). The chip was loaded for one hour in a chip loader (Nanoflex, Fluidigm) and then transferred to a reader (Biomark, Fluidigm) for thermocycling and fluorescent quantification. To remove low quality gene assays, we discarded gene assays whose qPCR curves showed non-exponential increases. To remove low quality cells (e.g. dead cells) we discarded cells that did not express the housekeeping genes Actb (beta-actin) and Hprt1 (hypoxanthine guanine phosphoribosyl transferase 1). This resulted in a single cell gene expression dataset consisting of 248 cells (109 tumorigenic and 139 non-tumorigenic) from a total of 7 chip-runs. A two sample Kolmogorov-Smirnov (K-S) statistic was calculated to test if genes were differentially expressed in the two populations. We generated p values by permuting the sample labels (i.e. TG vs NTG) and comparing the actual K-S statistic to those in the permutation-derived null distribution. The p values were further corrected by Bonferroni correction to adjust for multiple hypothesis testing. EXAMPLE 2 Analysis and quantification of human "colorectal cancer stem cells" (Co-CSC) using SINCE-PCR, a novel method based on "single-cell gene expression analysis."

The SINCE-PCR method allows the identification, characterization and quantification of "cancer stem cells" in human colorectal cancer tissues, with a degree of purity and resolution that was previously not achievable. Cancer stem cells, which can be tumorigenic or tumor-initiating cells, are a subpopulation of cancer cells that can have the capacity to form tumors when transplanted in immunodeficient mice. Cancer stem cell populations have currently been identified in breast, brain, head & neck, pancreatic and colon cancer. Accurate functional definition and quantification of "cancer stem cells" has several important implications for diagnosis, prognosis, classification and therapeutic targeting of human, cancer.

We describe a novel method for the identification, analysis and quantification of "cancer stem cells" in human colorectal cancer tissues, based on single-cell gene expression analysis by real-time polymerase chain reaction (real-time PCR). We have identified a novel set of genes whose coordinated and differential expression can be used as a "signature" to identify distinct cancer cell subsets within the same tumor tissue. This novel set of genes includes housekeeping genes common to all epithelial cells (EpCAM, beta-Actin, GAPDH), genes related to stem-cell biology (hTERT, LGR5, Survivin) and genes involved in tissue-specific differentiation pathways related to the distinct cellular lineages (Carbonic Anhydrase II, MUC2, Trefoil Family Factor 3) and differentiation stages (Cytokeratin 20, CD66a/CEACAM1) of the normal colonic epithelium. Based on the expression pattern of this set of genes, epithelial cells purified from human colorectal cancer tissues and analyzed individually as single-cells can be "classified" and clustered in distinct groups, corresponding to more or less advanced stages of differentiation (e.g. terminally differentiated cells at the top of the human colonic crypt vs. more immature cells located at the bottom of the human colonic crypt) and to distinct differentiation lineages of the colonic epithelium (e.g. goblet cells, enterocytes, immature cells). Each group can be quantified as a percentage of the total population. We have named this approach and methodology for the analysis of the cellular composition of biological tissues "SINCE-PCR" (Single Cell Expression—Polymerase Chain Reaction).

Our discovery is based on several observations. Human "colorectal cancer stem cells" enriched by flow cytometry directly from freshly harvested solid tumor tissues can be reproducibly and robustly analyzed at the single-cell level (FIG. 1).

Figure 2:
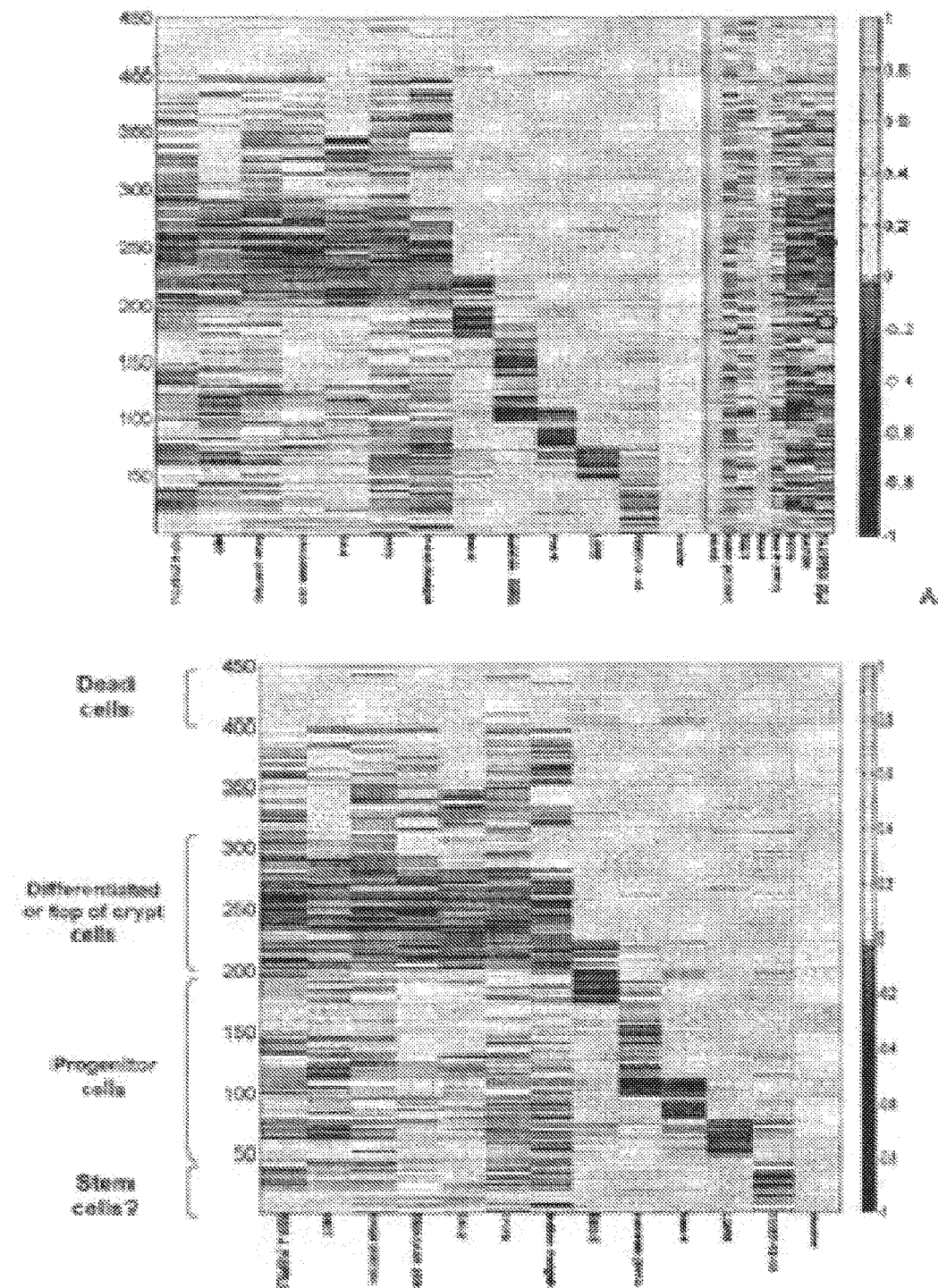
FIG. 2. Single-cell gene-expression analysis by real-time PCR of human "colorectal cancer stem cells" (EpCAM$^{high}$/CD166+ cells, from xenograft #8m3). In this figure each row identifies a single cell and each column identifies a distinct gene. The intensity of gene expression is depicted using a color code, where darker red indicates stronger intensity and darker green weaker intensity. The analysis clearly shows that, based on their transcriptional repertoire, EpCAM$^{high}$/CD166$^+$ tumor cells can be subdivided into distinct subsets. Most importantly, cell subsets that show coordinated and simultaneous expression of high levels of genes encoding for terminal differentiation markers of the colonic epithelium (e.g. Cytokeratin 20, CD66a/CEACAM1, Carbonic Anhydrase II, MUC2, Trefoil Family Factor 3) do not express or express lower levels of genes encoding for candidate intestinal stem cell markers or genes known to be necessary for stem cell function (e.g. hTERT, LGR5, Survivin) and vice-versa.

In human colon cancer xenografts, single-cell gene expression analysis by real-time PCR indicates that both EpCAM÷/CD44$^+$ and EpCAM-VCD166$^+$ cancer cells, which are known to be enriched for the "colorectal cancer stem cell" population, can be further subdivided in different cellular subsets characterized by the coordinated and differential expression of distinct groups of genes involved in stem cell biology and differentiation processes. Most interestingly, cell subsets that display higher levels of genes encoding for known colonic epithelial terminal differentiation markers (e.g. Cytokeratin 20, CD66a/CEACAM1 Carbonic Anhydrase II, MUC2, Trefoil Family Factor 3) do not express or express lower levels of genes encoding for candidate intestinal stem cell markers or genes known to be necessary for stem cell function (e.g. hTERT, LGR5, Survivin) and vice-versa. This suggests that EpCAM/CD44$^+$/CD166$^+$ cancer cells contain distinct cellular subsets characterized by different stages of differentiation (FIG. 2).

When purified by means of fluorescence-activated cell sorting (FACS) and re-injected in immunodeficient NOD/SCID mice, CD44$^+$/CD66a$^+$ and CD44$^+$/CD66anew1" cells display substantially different tumorigenic properties, with the CD44$^+$/CD66a$^{neglow}$ population behaving as the one endowed with the highest tumorigenic capacity (Table 4). This indicates that, within the EpCAM$^+$/CD44$^+$ cell population, the cell subset that is characterized by high levels of expression of genes that encode for differentiation markers such as CD66a/CEACAMl (i.e the more "mature" cell subset) is frequently relatively depleted of tumorigenic capacity. On the other hand, the cell subset that is characterized by the absence or low levels of expression of differentiation markers such as CD66a/CEACAMl (i.e the more "immature" cell subset) is enriched in "colorectal cancer stem cell" content.

TABLE 4

Tumorigenic properties of human colon cancer cells based on
CD66a/CEACAMI expression, in combination with EpCAM and/or CD44.

| Exp. | Tumor source[a] | | Lin[neg] sorted populations[b] | Cell dose | Tumor Take[c] | Experiment code |
|---|---|---|---|---|---|---|
| 1) | UM#4 | m4 | CD44[neg] | 10,000 | 2/10 | PD69- |
|  |  |  | CD44[+]/CD66a[+] | 450 | 1/3 |  |
|  |  |  | CD44[+]/CD66a[neg-low] | 250 | 2/3 |  |
| 2) | UM#4 | m6 | CD44[neg] | 10,000 | 1/5 | PD85 |
|  |  |  | CD44[+]/CD66a[+] | 500 | 0/2 |  |
|  |  |  | CD44[+]/CD66a[neg-low] | 1,000 | 3/3 |  |
| 3) | UM#4 | m4 | CD44[neg] | 10,000 | 0/5 | PD107 |
|  |  |  | CD44[+]/CD66a[+] | 1,000 | 0/1 |  |
|  |  |  | CD44[+]/CD66a[neg-low] | 1,000 | 3/4 |  |
| 4) | SU29 | m1 | CD44[neg] | 7,000 | 0/5 | PD88- |
|  |  |  | CD44[+]/CD66a[+] | 1,000 | 0/5 |  |
|  |  |  | CD44[+]/CD66a[neg-low] | 2,000 | 1/5 |  |
|  |  |  | " | 1,000 | 0/5 |  |
| 5) | SU43 | primary | EpCAM[+]/CD44[neg] | 12,000 | 0/5 | PD79 |
|  |  |  | EpCAM[+]/CD44[+]/CD66a[+] | 300 | 0/1 |  |
|  |  |  | EpCAM[+]/CD44[+]/CD66a[neg-low] | 1,000 | 1/3 |  |

[a]For each experiment, the in vivo serial passage of the tumor xenograft used as source for cancer cell purification is reported as follows: m1 indicates the first round of tumors obtained from primary tumor engraftment, m2 the second round of tumors obtained from engraftment of m1, m3 the third round of tumors obtained from engraftment of m2, and so on progressively; primary indicates a primary tumor, directly harvested from a surgical specimen.
[b]All sorted populations are to be considered as negative for lineage markers (Lin[neg]), which include mouse CD45 and mouse H2-Kd in the case of human tumor xenografts established in NOD/SCID mice, and human CD3 and CD45 in the case of primary human tumors (in this case EpCAM serves as a positive epithelial selection marker)
[c]Tumor take is reported as: number of tumors obtained/number of injections; tumor take is considered unsuccessful when no tumor mass is visible after 5 months follow-up.

Example 2: Generation and Imaging of Human Breast Cancer Xenograft Models with Pulmonary Metastases Patient-derived breast cancer specimens (chunks or TICs) were orthotopically transplanted into the mammary fat pads of NOD-SCID mice. Six xenograft tumor models were generated (1 ER[+], 1 Her2[+] and 4 triple negative ER-PR-Her2-). All four of the triple negative xenografts developed spontaneous lung micro-metastases, demonstrated by IHC stainings, i.e H&E, proliferation marker Ki67 and Vimentin (Vim) stainings. These data suggested that upon implantation into immunodeficent mice, breast tumor cells or TICs are able to adapt to the mouse microenvironment and recapitulate human tumor growth and progression with spontaneous lung metastasis.

To facilitate dynamic and semi-quantitative imaging of human breast cancer and metastasis in mice, the breast TICs were transduced with firefly luciferase-EGFP fusion gene via the pHRuKFG lentivirus (moi 50) 4 days after implantation, TICs at the primary site were detectable with weak bioluminescent signals. And one month later, both primary tumors (at the L4 and R2 mammary fat pads) and lung metastases were detected and imaged by Xenogen IVIS 200 system at the Small Animal Imaging Center of Stanford. We observed that tumor size or cell numbers correlated well with the signal intensity. The generation and bioluminescent imaging of xenograft tumors with metastasis provide us feasibility of validating functions of miRNAs in MTICs of human breast cancer in viva in this proposal.

Example 3: Microarray and Real-Time PCR Analysis of Human Breast MTICs

Human breast primary tumor initiating cells (TICs) or metastatic TICs (MTICs) (CD44[+]CD244I[-]ESA[+]lineage) were isolated from breast cancer primary site or pleural effusions. Once lung mets were detected in xenograft models, I dissociated lungs with blenzyme (Roche) and stained cells with mouse H2K and human CD44, CD24 and ESA for purifying MTIC populations (CD44[+]CD2441[-]ESA[+]H2K[-], FIG. 3a), which grow orthotopic tumors at a ratio of 5/8 with 200-1000 sorted cells, after transplanted into mouse mammary fat pads.

Figure 3:
FIG. 3A-B. a: Purification of MTICs 11'ESA$^+$H2K– from the lung cells of breast tumor-bearing NOD/SCID mice. Top panel gated H2K-Dapilviable lineage), lower left panel gated ESA$^+$ cells for furthering gating of CD2441' cells in the lower right panel. b: Real time PCR analysis of mRNA levels of HIF1a, Snail2, Zeb2, E-cadherin, Vimentin, VEGFC, CCR7, Lox, Cox2 in MTIC and non-TICs.

Shown by microarray analysis and real-time PCR, HIF1a and HIF1 regulated target genes were differentially expressed in MTICs compared to non-tumorigenic tumor cells, including Snail, Zeb2, Vimentin, E-cadherin, Lox, Cox2, VEGF, etc. (FIG. 3B). Co-localization of HIFI a, Vimentin and CD44 were confirmed by immunohistochemistry staining.

Example 4: MicroRNA Analysis

Figure 4:
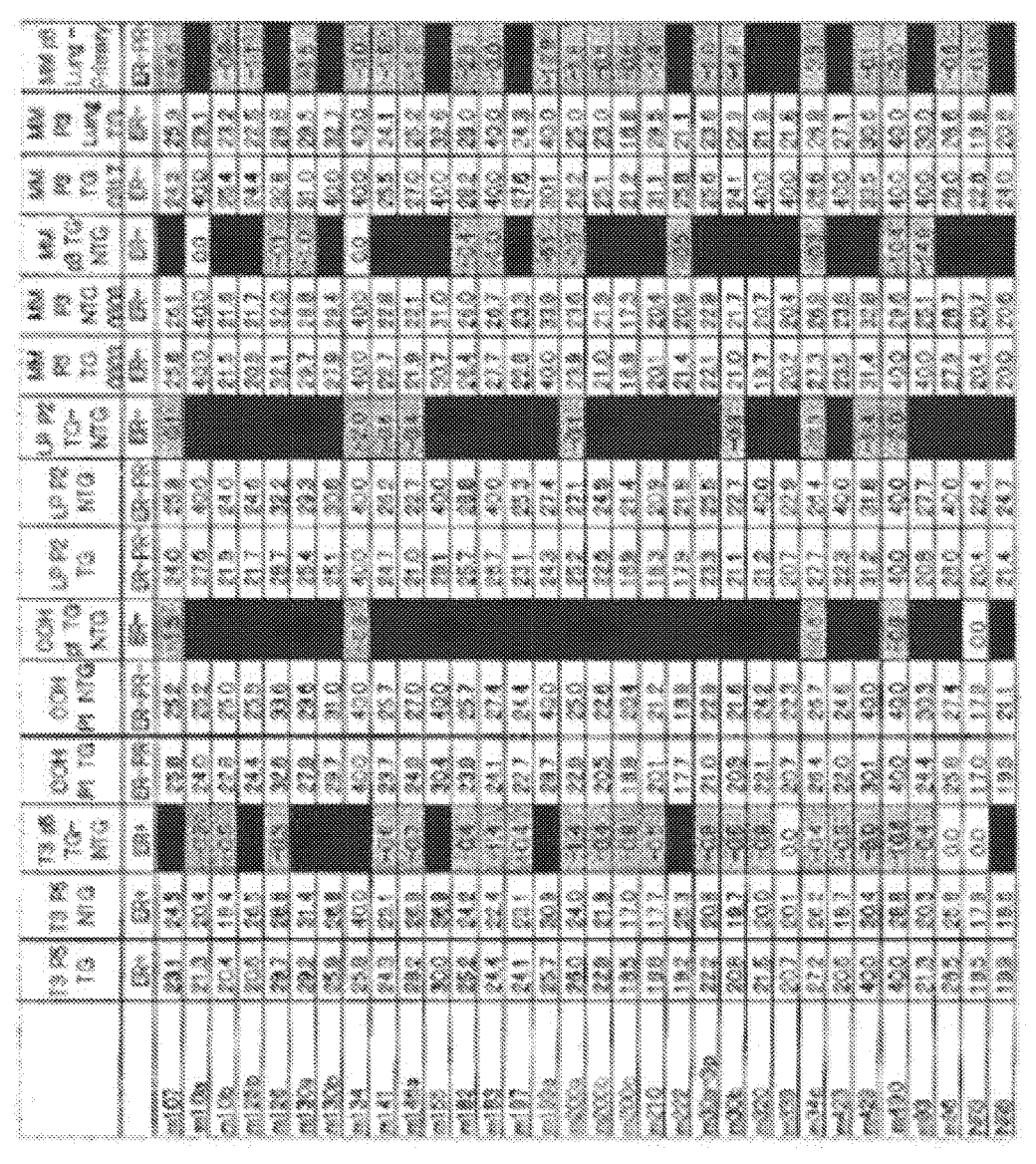

By microRNA screening, differential expression profiles of parental breast cancer stem cells and metastastic cancer cells isolated from the lungs were identified. For example, higher expression of miR-10a and lower levels of miR-490, miR-199a, etc in lung MTICs than that of primary breast TICs. As shown by triplicate real-time PCR in FIG. 4, comparison of mean CT values of lung MTICs versus primary TICs: miR-10a (-7.9), miR-490 ([+]3.0) and miR-199a ([+]12.9). NR3 was used as an internal control. The data indicated that miR-10a was upregulated by up to 27'9 fold, and miR-199a downregulated by 212-9 fold in MTICs than primary TICs of breast cancer.

Example 5: CD66a as a Non-Tumorigenic Cancer Cell Marker of Breast Cancer

Figure 5:
FIG. 5A-5D. CD66a as a non-tumorigenic cancer cell marker of breast cancer.

Breast cancer cells were sorted based on CD44 and CD66a while most of the cells were CD244bw. Cells were then implanted onto mammary fat pads of NOD/SCID mice and tumor growth monitored. CD44/CD66a- cells showed higher rate of transplantation as well as higher growth rate by bioluminescent imaging as shown in FIG. 5. CD66[+] cells showed a lower and delayed rate of tumor growth, the tumor size is much smaller and displayed very similar flow profiles compared to CD66- derived tumors.

In FIG. 5a, the flow profile was shown based on CD44 and CD66a markers. CD66–CD44+ and CD66+CD44+ cells were sorted for in vivo tumorigenic assays (100 cells or 1000 cells implanted to Zid or 41 h of mammary fat pads of NOD/SLID mice). As 10b indicated, 5 of 8 implantations from 100 CD66-cells grew tumors while 2 of 8 from 100 CD66+ cells grew. For 1000 cells, 8 of 8 from CD66– cell injections grew but only 3 of 8 from CD66+ cells grew tumors. Comparing the growth rate of palpable tumors, CD66+ cells had much lower and smaller sizes than those derived from CD66– cells (FIG. 5c). In FIG. 5d, 100K of CD66–CD44+ or CD66+CD44+ cells were infected with firefly luciferase-EGFP lentivirus prior to injection. The bioluminescent signals from CD66+ cells were higher than those of CD66- cells from the beginning (day 13). But after 1 month or 2 months, CD66– cells showed dominant bioluminescent signals and grew out palbable tumors in the end (day 68).

Example 6: Optimization of the Gene List Used to Identify and Measure Cancer Stem Cell Frequency Most markers used at this time to identify both normal stem cells and cancer stem cells are not linked to an essential stem cell function. Their expression is linked to the particular microenvironment in which the stem cell resides at the time of isolation. Thus, the utility of common markers that are used to identify stem cells can vary with the site from which they are collected.

Our approach has been to identify markers of critical stem cell functions. Since self renewal is the quintessential stem cell property, we have focused our efforts on renewal pathways. We have identified multiple genes that are highly expressed by normal HSCs, leukemia stem cells that originated from progenitor cells, and human epithelial cancer stem cells, but not by non-self renewing cells in each respective tissue. This genomics analysis described in the preliminary results identified a number of genes that had previously been linked to stem cell self renewal. Similarly, we identified candidate microRNAs that are differentially expressed by breast cancer stem cells and non-tumorigenic cancer cells. Evidence demonstrates that several of these genes and microRNAs have critical stem cell functions and that the function of these genes is also critical to hESC and iPSC self-renewal and maintenance.

To produce a device capable of measuring the frequency of cancer stem cells in a tumor cell population, it is desirable to optimize the gene list used to identify cancer stem cells. As shown in FIG. 1B, we have made great progress in doing so, identifying telomerase as a cancer stem cell marker as well as several genes linked to the process of self renewal. The telomerase component TERT is only expressed in colon cancer cells with an immature phenotype. Moreover, TERT is not efficiently-downregulated with differentiation of some hESC and iPSC lines.

Both normal and cancerous colon epithelial cells are analyzed for the expression of genes linked to crypt cell maturation and self renewal. The self renewal gene list is expanded beyond TERT to maximize confidence that a cell is a stem cell. The expression of genes identified in our analysis of normal and cancer stem cell are measured. Because cancer stem cells can potentially arise from either a stem cell that has escaped the constraints on expansion or progenitor cells that have escaped the counting mechanisms that limit the number of mitoses that they can undergo, the candidate genes are those that are expressed by normal murine HSCs, murine leukemia stem cells that were derived from a progenitor cell, and human breast cancer stem cells. The top candidate genes identified in this list, all of which have been linked to stem cell maintenance, include BMI1, —IDI, IGFBP3, the HOX family members HOXA3, HOXA5, MEIS1, ETS1, ETS2, RUNX2 and STAT3. We will validate which of these genes are linked to cancer stem cell self renewal. To do this, we will systematically test our candidate genes for a role in self renewal of cancer stem cells using in vitro and in vivo techniques.

The expression of genes that regulate self renewal are linked to the expression of genes specific to epithelial cells, including maturation markers, such as keratins and intestinal mucins. This will enable ascertaining that a cell in the analysis is not a normal cell contaminant in the biopsy. Mutations of tumor suppressor genes whose expression is downregulated by the self renewal gene BMI I enable early progenitor cells to self renew. These genes are frequently mutated in colon cancer, thus self renewing colon cancer stem cells will arise from both normal stem cells and early colon progenitor cells. Furthermore, oncogenic mutations will alter gene expression by colon cancer cells. Thus, there may be differences in expression of at least some genes linked to early crypt cell maturation between normal colon epithelial stem cells and their malignant counterpart that will make it possible to distinguish these 2 self renewing cell populations from each other.

We identified 37 miRNAS that were differentially expressed in cancer stem cells and non-tumorigenic cancer cells. Several miRNA clusters were down-regulated in normal tissue stem cells but not in cancer stem cells; moreover, the expression of some miRNAs, such as miR-200c and miR-183 suppressed growth of embryonal carcinoma cells in vitro, abolished their tumor-forming ability in vivo, and inhibited the clonogenicity of breast cancer cells in vitro. These miRNAs, and the other clusters we identified, provide a molecular link that connects breast cancer stem cells and normal stem cell biology. The expression of these microRNAs; which were consistently up-regulated or down-regulated in tumorigenic cells, are probed in single cells from undifferentiated and differentiated hESCs and iPSCs. Essentially, undifferentiated cells are sorted by cell surface markers distinct to pluripotent stem cells such as Tra and SSEA subtypes and assessed for miRNA expression, replating efficiency and population parameters in vivo (outcome of teratoma assays in terms of embryonal carcinoma, mixed embryonic carcinoma/differentiated cell index (% EC vs differentiated), and differentiated cells). Differentiated stem cell populations are obtained by production of embryoid bodies and sorted via positive and negative selection for SSENTRA markers, after 28 days differentiation. We will examine single cells within the sorted populations for: 1) microRNA profiles indicative of cancer stem cells 2) gene expression profile (below), and 3) outcome of transplantation/teratoma assays. We expect that cells "resistant to differentiation" in these populations will form malignant embryonal carcinoma derivatives and co-express markers of differentiated and undifferentiated cells within single cells.

Example 7: Gene Expression Profile at the Single Cell Level

Figure 6:
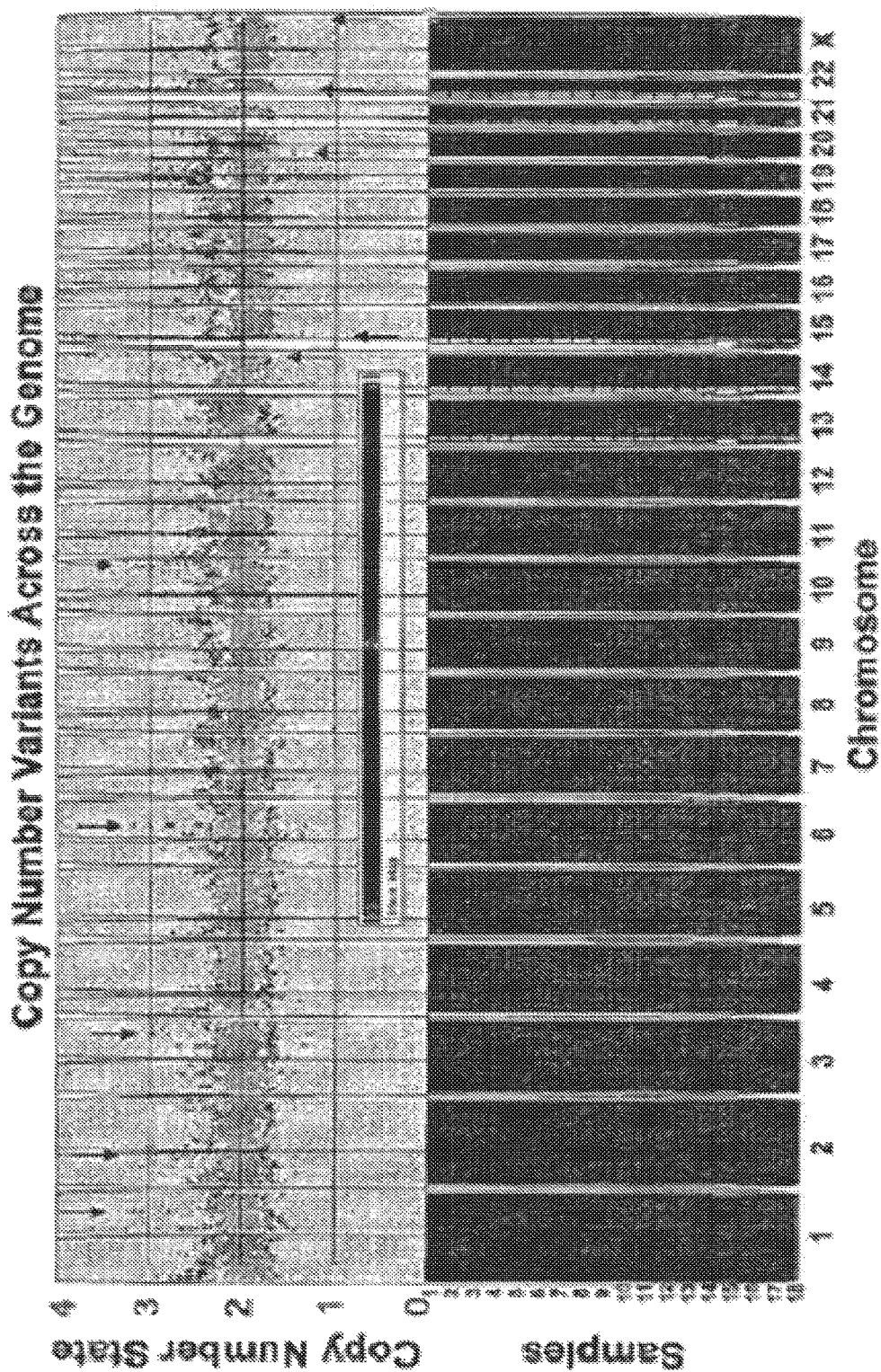
FIG. 6. Copy number variant analysis of 18 cell samples for several thousand CNVs. Several may be associated with genomic instability and give rise to altered pluripotent stem cell properties.

In populations of pluripotent cells, even after differentiation for 21 days, we observe lines that fail to downregulate key markers of tumorigenicity such as TERT (see FIG. 6). In addition, we have observed that approximately 50% of our iPSC lines fail to downregulate both exogenous and endogenous pluripotency markers, in the differentiated state.

Essentially, this suggests a "molecular war" between differentiation and self-renewal that we may predict an outcome of proclivity to tumorigenesis. We will optimize the gene list for identification of malignant cells in hESC and iPSC cell cultures by: 1) assaying genes overexpressed in EC (embryonal carcinoma) cells relative to undifferentiated hESCs and IPSCs, and human embryonic blastomeres, 2) cross-referencing the list of genes to include those from Aim 1 (for identification of cancer stem cells), and 3) adding genes of differentiated somatic and germ cell lineages (the later remain in pluripotent stem cells resistant to differentiation). We will then use immune deficient mouse assays to assess tumorigenic potential of subpopulations diagnosed according to malignant potential based on basal gene expression of single cells.

CNV analysis. Chromosomal variants are linked to instability in pluripotent human stem cell populations, with chromosome loss and gain frequently observed. However, few studies have addressed finer structure, high-throughput methods to assess copy number at multiple loci. We propose to adapt our technology for assessment of genome-wide CNV number in independently-derived pluripotent stem cell lines; changes in CNVs will reflect subchromosomal instability. Initially, we can design specific probe sets for addition to our gene/loci list that recognize duplications across the genome, including those previously observed in our laboratory (FIG. 6). The SCAD can accommodate analysis of up to 1000 markers, in its initial design. CNV assays are commercially available and can be correlated with genomic instability in hESCsIiPSCs.

Example 8: Engineering an Automated Device to Identify and Quantify Cancer Stem Cells An automated device is designed to identify cancer stem cells and calculate their frequency in tumors based on a combination of cell surface phenotype and gene expression. Using the optimized marker/genetic analysis described herein, a similar strategy is used to identify cells with malignant potentia, based on co-expression of markers of the differentiated and undifferentiated state in single cells. This device will make a single cell suspension of embryoid bodies or needle biopsies of a tumor, isolate the cell subpopulations (epithelial, differentiated, undifferentiated) and then do a qRT-PCR of hundreds or thousands of single cells and measure the stem cell content of a tumor or pluripotent cell culture. Such a fully automated device will eliminate the labor-intensive steps currently needed for flow-cytometry sorting of cancer stem cells, and allow a truly hands-off, bed-side diagnostic tool that will need less than 100,000 cells to isolate enough cancer cells for PCR assays to quantify cancer stem cells. Automated operation, effectiveness and low cost associated with microfluidic chip technology will make individualized, rapid genetic diagnosis possible.

At the heart of this system is a microfluidic cell sorter. This device isolates live cells (epithelial cells or cultured pluripotent cells or their products) from the debris (necrotic cells and other particles), sort out the cells from the single cell suspension using fluorescent signals from up to five different surface markers, and places them in individual bins for subsequent genetic studies. Other upstream steps such as digesting the tumor or cell culture to obtain a cell suspension and staining the cells with fluorescent surface markers may be incorporated in this system. How the system is used for tumor analysis is illustrated here: Once the biopsy is obtained, the physician will place the sample in the input port of this system. Utilizing a user friendly computer interface, the physician will set the necessary parameters in the sorting and genetic analysis such as the number and type of surface markers, the number of PCR cycles needed etc, and the machine will perform the rest of the steps without human intervention. Based on previously demonstrated technologies, the system will allow a sorting throughput of at least 30 cells/second.

Figure 7:
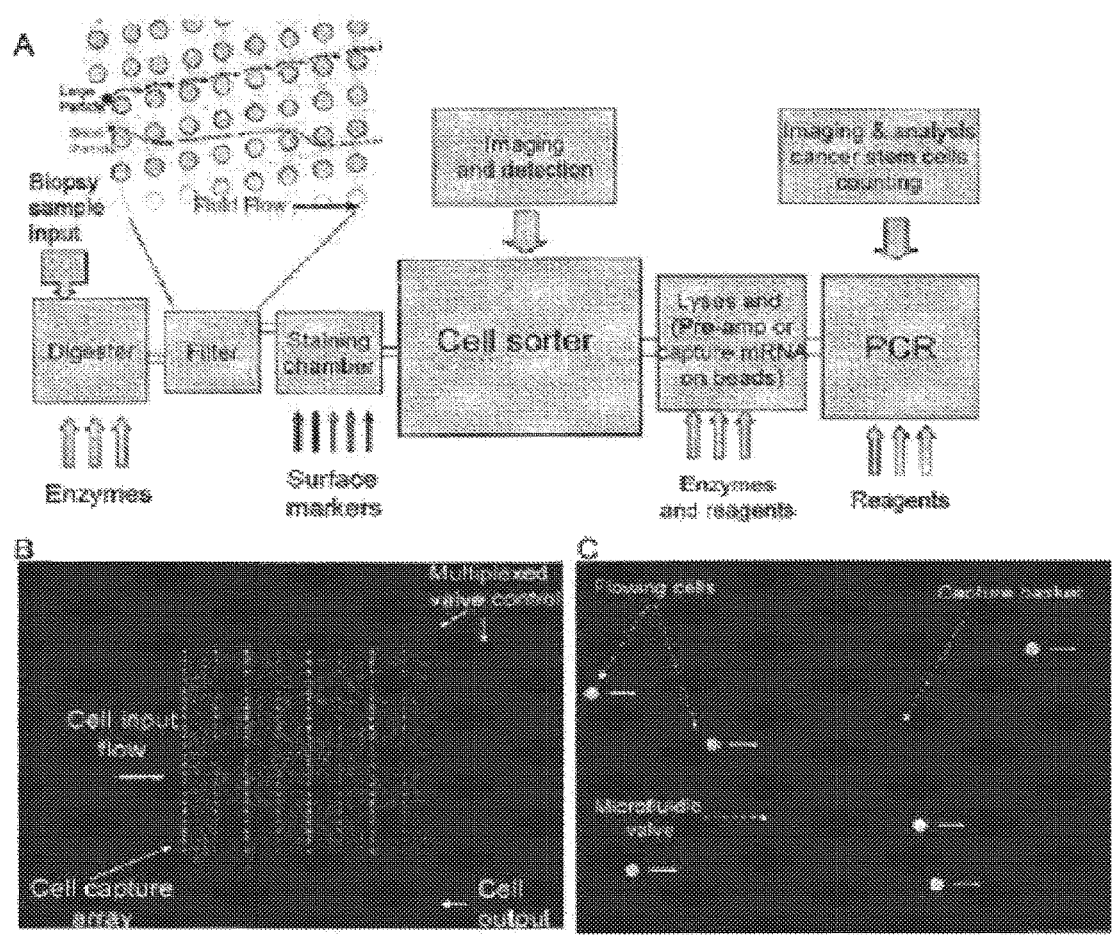
FIG. 7. Single Cell Analysis device, principle.

A single cell analysis device (SCAD) can be modular (FIG. 7) and will perform the following steps in an integrated, fully automated fashion: 1) Digestion of the tissue: The tissue is placed in the input port of the device. Appropriate enzymes are introduced in the device and flowed to perform the digestion of the extracellular matrix in order to obtain a cell suspension. 2) Separation of live cells from the debris: The suspension typically contains live cell with an average size of 10 to 15 micrometers, and debris material with an average size around 5 micrometers. The amount of dead material is sometimes relatively high compared to live cells, therefore it is critical to filter out the dead material for efficient isolation of cells. We accomplish this by flowing the digested tissue suspension through a microfluidic "metamaterial," which allows splitting the fluidic flow according to the size of the particles. 3) Staining: The filtered single cell suspension is stained using appropriate surface markers in a different compartment of the microfluidic device. Staining with up to five different markers may be useful in obtaining a high purity population of cancer cells. 4) Sorting: The stained single-cell suspension is flowed into the next compartment of the microfluidic device to sort out the cancer cells from the rest of the cells. Poisson statistics and the Monte Carlo simulations indicate that only 2,000-20,000 cancer cells need to be sorted in order to be able to detect two-fold changes in the cancer stem cells, within a confidence level of 99%. Such a small number of cells currently cannot be sorted efficiently using flow-cytometry, as the initial sample size needed for FACS is around one million cells. We will achieve this using microfluidic based sorting for cycling of the cell suspension indefinitely in an air-tight, isolated small volume environment that will not waste cells.

Flow based microfluidic cell sorter: A microfluidic cell sorter with a throughput of nearly 50 cells/second has been demonstrated, where cells were flowed at high speed through a laser beam (see Di Carlo et al. Lab Chip 2006; 6:1445-1449), and the scattered light was detected and analyzed. Faster electronics and more efficient imaging equipment allow an improvement of the throughput by an order of magnitude, which will bring down the sorting time to less than ten minutes.

Parallel sorting: a cell sorter is being developed based on capturing the cells on a dense, 2-D array of microfluidic chambers that can be individually addressed (FIGS. 7B and 7C above). The cells are flowed into the sorter array and are captured by microfabricated baskets. Such baskets were previously demonstrated to have more than 50% single cell capture efficiency in a freely flowing suspension (Di carlo et al., supra). After all the baskets are filled, the microfluidic valves are closed, and the array is imaged using custom designed, computer controlled optics in all 5 fluorescent colors needed to identify tumorigenic cells. This new chip also allows phase contrast imaging, which may prove useful to study cell morphology. The identified tumorigenic cells are flowed into the next module for lysis, while the rest of the cells are flowed out of the chip. This new cell sorter allows working with extremely small initial number of cells, as the cells can be cycled many times and therefore will not be wasted. Current microfluidic chip technology allows us to place nearly 10,000 of these elements on a 3×3 cm area, which can be rapidly interrogated (single shot) using state-of-the art imagers, such as the one used by Fluidigm Biomark system. This cell sorter will have a throughput of nearly 30 cells/second. One advantage of using the parallel sorting device as opposed to the flow based cell sorter is that imaging during sorting and PCR can be performed by the same imager, thus allowing us to relate fluorescence and morphology data to genetic data of individual cells.

Cell lysis and mRNA capture: Sorted cancer stem cells are flowed into the next module for lysis in individual chambers. mRNA may be captured on a column of oligo-dT beads, reverse transcribed on the beads as already demonstrated (Marcus et al. Anal Chem 2006; 78:3084-3089) and processed off chip via a new gene sequencing protocol developed for the Heliscope, or may be transferred to a macroscopic well (micro-liter range) and mixed with: reagents to preamplify a set of genes following current protocols. Preamplified samples are transferred to a module similar to the Fluidigm Dynamic array chip for qRT-PCR and determination of true cancer stem cell content.

Based on an analysis of normal breast and blood stern cells as well as colon, head and neck, and breast cancer stem cells, we have identified a novel single cell assay that for the first time makes it possible to accurately and unequivocally identify and count cancer stem cells in biopsy specimens and cultured pluripotent stem cell populations. As a proof of principle, we applied this assay to an analysis of single colon cancer cells. To do this, we used FACS to sort $CD66^+CD44$ lineage colon cancer cells from early passage xenografts established from 2 different patients. These markers allow an approximately 3-5 fold enrichment of colon cancer stem cells (CoCSCs) in a tumor. We had suspected that cancer cells isolated with these markers were only partially enriched for CoCSCs. The single cell gene expression analyses and subsequent tumorigenicity studies demonstrate that indeed $CD66^+CD44^+$Lineage– cells are a mixture of CoCSCs and non-tumorigenic cells and that this assay can be used to more accurately identify the frequency of CoCSCs in a biopsy specimen. The single cell analysis reveals a hierarchical developmental structure of colon cancer cells that is reminiscent of a normal colon crypt. Notably, we find that the most immature cells in the colon tumor express TERT, a component of the telomerase complex that is critical for long term maintenance of a tumor. Expression of LGR5, which marks normal colon stem cells, is also limited to immature cells. By contrast, genes expressed by maturing colon crypt cells including MUC2, 'CK20, CA-2, and especially CD66a were expressed by cells that do not co-express immature cell markers, most notably TERT. This suggests that these cells, like normal maturing epithelial crypt cells, have limitations on their ability to undergo extensive mitoses. Indeed, we have transplanted $CD66a^+$ (differentiated colon cancer cells) and CD66a''' colon cancer cells into immunodeficient mice. CD66a' cells formed tumors (5 of 6 injections) while $CD66^+$ cells did not (0 of 5 injections). Similarly, in 2 human breast cancer tumors that were tested the CD66ew cells were enriched for cancer stem cells when tested in the immunodeficient mouse model. These results demonstrate that single cell gene expression analysis enables identification and quantitation of cancer stem cells in biopsies and cultures.

Figure 8:
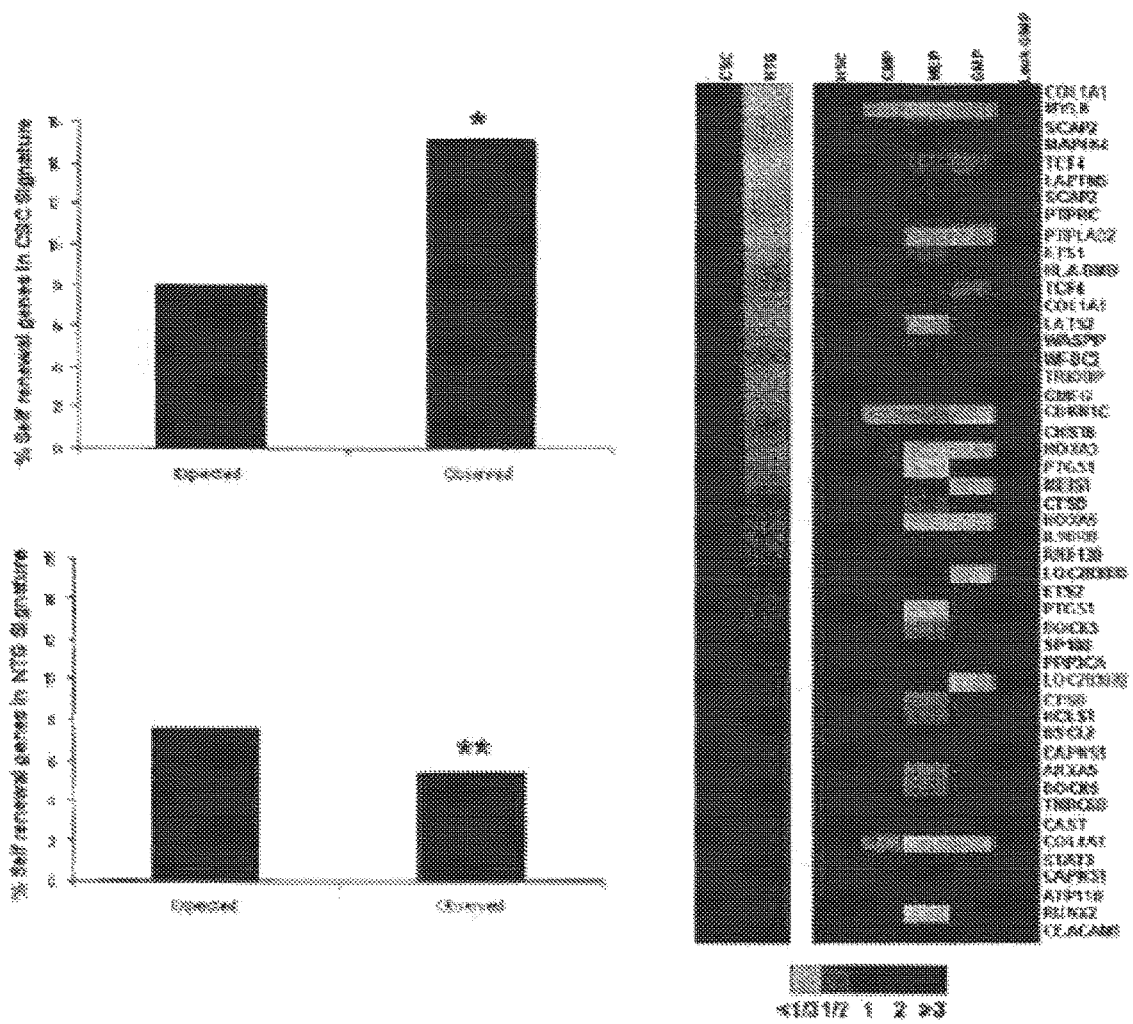
FIG. 8. Gene Set Enrichment analysis of the expression of stem-cell linked genes. Genes expressed by self renewing normal HSCs, leukemia stem cells derived from Granulocyte/Macrophage progenitors (GMPs) but not by non-self renewing normal GMPs were analyzed in breast cancer stem cells (CSC) and their non-tumorigenic progeny (NTG). As predicted, these genes were significantly overrepresented in the CSCs gene expression signature. A heat map of overexpressed genes is shown.

Example 9: A Gene Expression Signature Shared by Normal Stem Cells and Cancer Stem Cells, in Both Blood and Mammary Epithelial Tissues It has become apparent in recent years that cancer stem cells can arise from different cell compartments. Some likely arise from a mutant stem cell that has lost the constraints on: expansion of the stem cell pool. Others arise from a more differentiated early progenitor cell that has lost the counting mechanism that normally restricts the number of mitoses that they can undergo. Of course, many of the markers of cancer or leukemia stem cells that arise from a stem cell or a progenitor cell are different. Regardless of the cell of origin, however, the stem cells will retain the ability to self renew. We reasoned that it is likely that some of the pathways that regulate self renewal in cancer stem cells arising from either the stem cell compartment or a partially differentiated progeny are shared with each other and with normal HSCs. To test this hypothesis, we analyzed whether genes expressed by normal mouse HSCs and murine leukemia stem cells arising from progenitor cells (i.e. self renewing populations) but not normal progenitor cells (i.e. non-self renewing population) are also expressed by human breast cancer stem cells but not their non-tumorigenic counterparts. Remarkably, the human cancer stem cells, but not their non-tumorigenic counterparts, overexpress these genes (FIG. 8). We have also generated 2 other gene lists to identify other potential candidates: i) genes expressed by breast cancer stem cells and normal breast stem cells, but not by non-tumorigenic cancer cells or mature breast epithelial progenitor cells, ii) genes expressed by normal human HSCs and human breast cancer stem cells but not human blood progenitor cells or non-tumorigenic breast cells.

Many of these genes have been linked to self renewal and cancer. These include the insulin growth factor binding partner IGFBP3, the HOX family members HOXA3, HOXA5, ME1S1 as well as transcription factors like ETS1, ETS2, RUNX2 and STAT3. It was tested whether the transcription factor STAT3 is a bona fide cancer stem cell regulator. STAT3 plays a role in the maintenance of both ES cells and HSCs. The genomics analysis of both mouse and human breast cancer stem cells revealed that many STAT3 activated transcripts were overexpressed by the cancer stem cells. Next, when we examined immunochemistry analysis of breast tumors the STAT3 positive cells tended to be concentrated on the invasive edge of the cancer and the protein was not seen in the more differentiated-looking cells in the interior parts of tumors. Finally, there are small molecule inhibitors of STAT3. Such inhibitors can be tested in cancer stem cell models. The effect of the STAT3 inhibitor cucurbitacin on the clonogenic ability of murine breast cancer stem cells was tested. A short, 24 hour exposure to the inhibitor reduced the number of colonies by ~50% ($p<0.02$, t test). These results suggest that STAT3 plays a critical role in at least some breast cancer stem cells.

A second gene of interest is MEIS1. MEIS1 is preferentially expressed by normal blood and breast stem cells, leukemia stem cells, and breast cancer stem cells. Genetic studies have shown that expression of MEIS1 is absolutely required for the self renewal and maintenance of both normal blood stem cells and their leukemic counterparts. MEIS1 may regulate breast cancer stem cell renewal.

Particularly interesting candidate genes expressed by both normal and cancer stem cells include CAV1, GAS1, MAP4K4 (kinase) MYLK (kinase), PTK2 (kinase), DAPK1 (kinase), LATS (kinase), FOSL2, AKT3 (kinase), PTPRC (tyrosine phosphatase), MAFF (oncogene), RRAS2 (related to RAS), NFKB, ROBO1, IL6ST (activates STAT3), CR1M1, PLS3, SOX2, CXCL14, ETS1, ETS2, MEIS1 and STAT3, as well as CD47. Interesting candidate genes overexpressed by cancer stem cells but not normal stem cells include RGS4, CAV2, MAF (oncogene) WT1 (oncogene), SNAI2, FGFR2, MEIS2, 101, 103, ID4 and FOXC1.

Example 10: Whole Transcriptome Analysis of Hematopoietic Stem Cells

Figure 9:
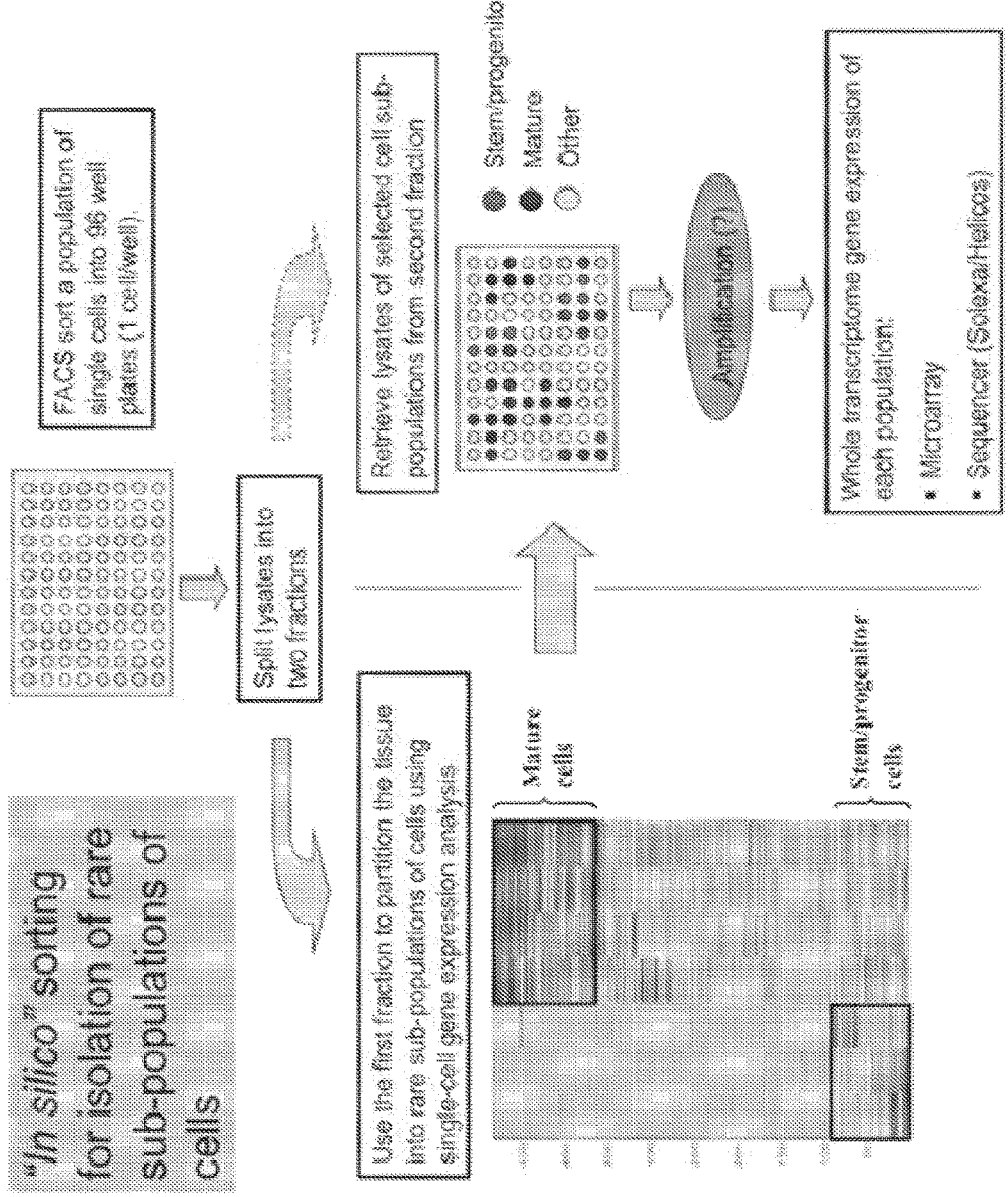
FIG. 9. A schematic of "in silico" sorting for isolation of rare sub-populations of cells. Cell populations, such as hematopoietic stem cells, are sorted by FACS into 96-well plates, containing a single cell. Cells are lysed and the lysate is divided into two fractions. One fraction of the lysate is analyzed for expression of a set of genes, allowing the cells to be characterized on the basis of transcription, rather than surface-protein expression. Utilizing this information, selected lysates and/or lysates pooled from like cells are subjected to whole-transcriptome analysis.

In this example we seek to use transcriptome analysis of hematopoietic stem cells. A general outline of this embodiment is shown in FIG. 9. In the present example a population of cells suspected of comprising hematopoietic stem cells is isolated from a test subject. Cells are then prepared for FACS analysis by exposing the cell population to fluorescent antibodies to known hematopoietic stem markers (e.g., CD34, Thy1, etc.). Cells are sorted into 96-well plates, such that each well contains no more than a single cell.

Isolated single cells are lysed and the lysates are divided into two portions. The first portion is subjected to single-cell gene expression analysis by real-time PCR, essentially as described in Example 1, using a selection of genes which allow for distinguishing between HSCs and non-HSCs, either by level or presence of expression (e.g., CD34+, CD19−, CD17−). After identifying HSCs within the population lysates from the single cells identified as being HSCs are pooled. A cDNA library is created by amplifying total mRNA using standard methods. The cDNA is then sequenced using a "next generation" method such as any of those described herein. The sequenced transcriptome is then analyzed to determine whether unique genes and/or surface markers are present.

Following identification of a surface marker unique to HSCs, antibodies which specifically bind to the surface markers are prepared by commercially available techniques. The specificity and effectiveness of the antibodies are confirmed (e.g., binding to isolated and/or recombinant protein). The antibodies are then labeled with a fluorescent moiety. FACS sorting and/or analysis can then be performed on other populations of cells (e.g., from the same or different subjects) using the antibodies to the newly discovered surface antigens.

Example 11: Analysis of Tumorigenic Cells

Figure 12:
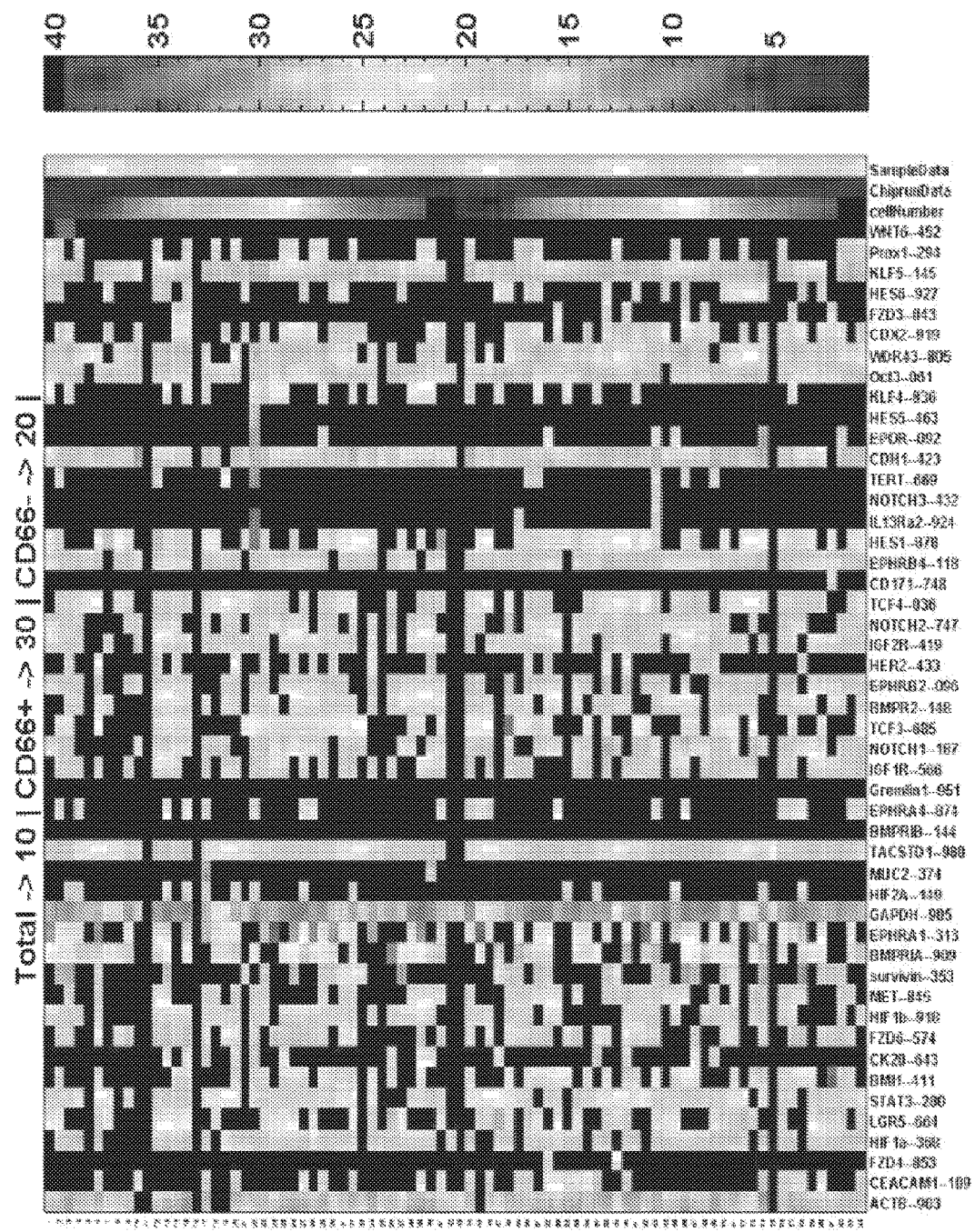
FIG. 12 A comparison of colon cancer cell populations (CD66+ and CD66–) using single cell analysis.
Figure 13:
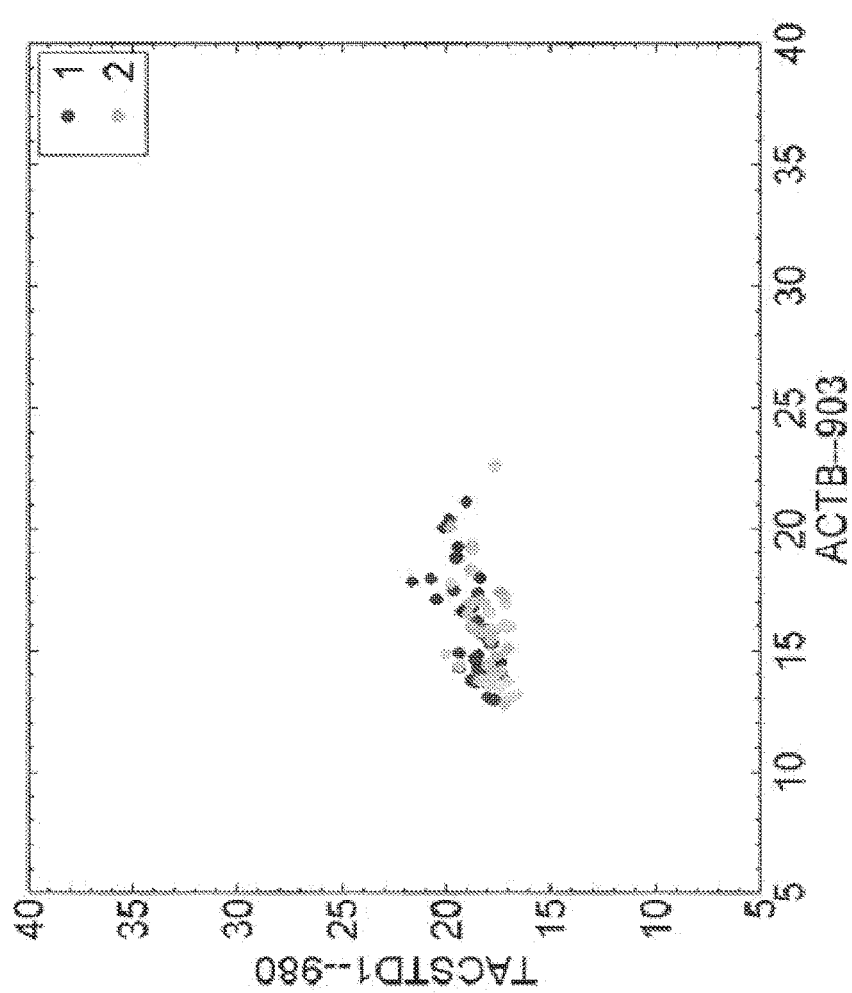
FIG. 13 A representation of using housekeeping genes to select cell samples.
Figure 14:
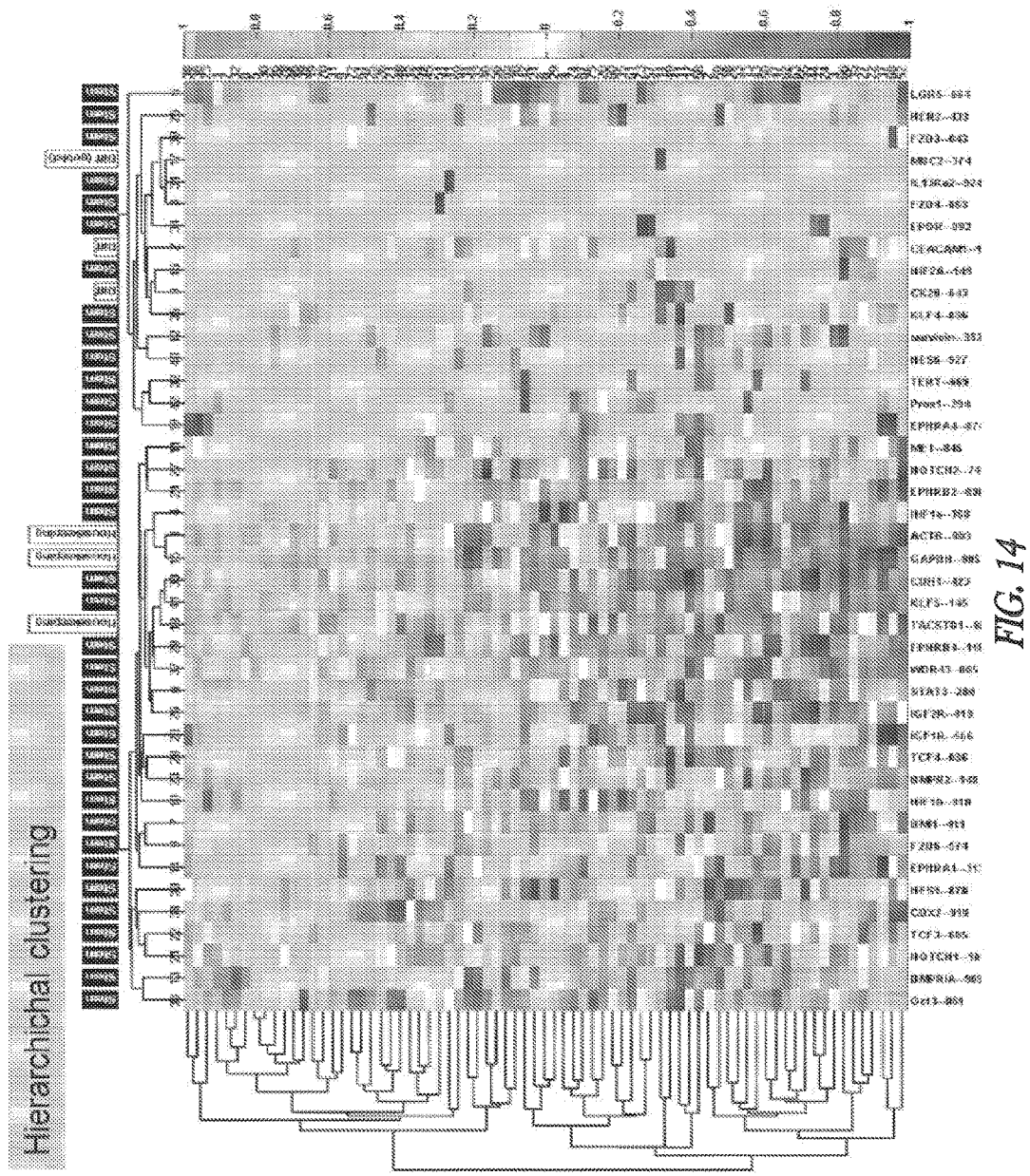
FIG. 14 A hierarchical clustering analysis showing TERT is expressed by early cell populations.
Figure 15:
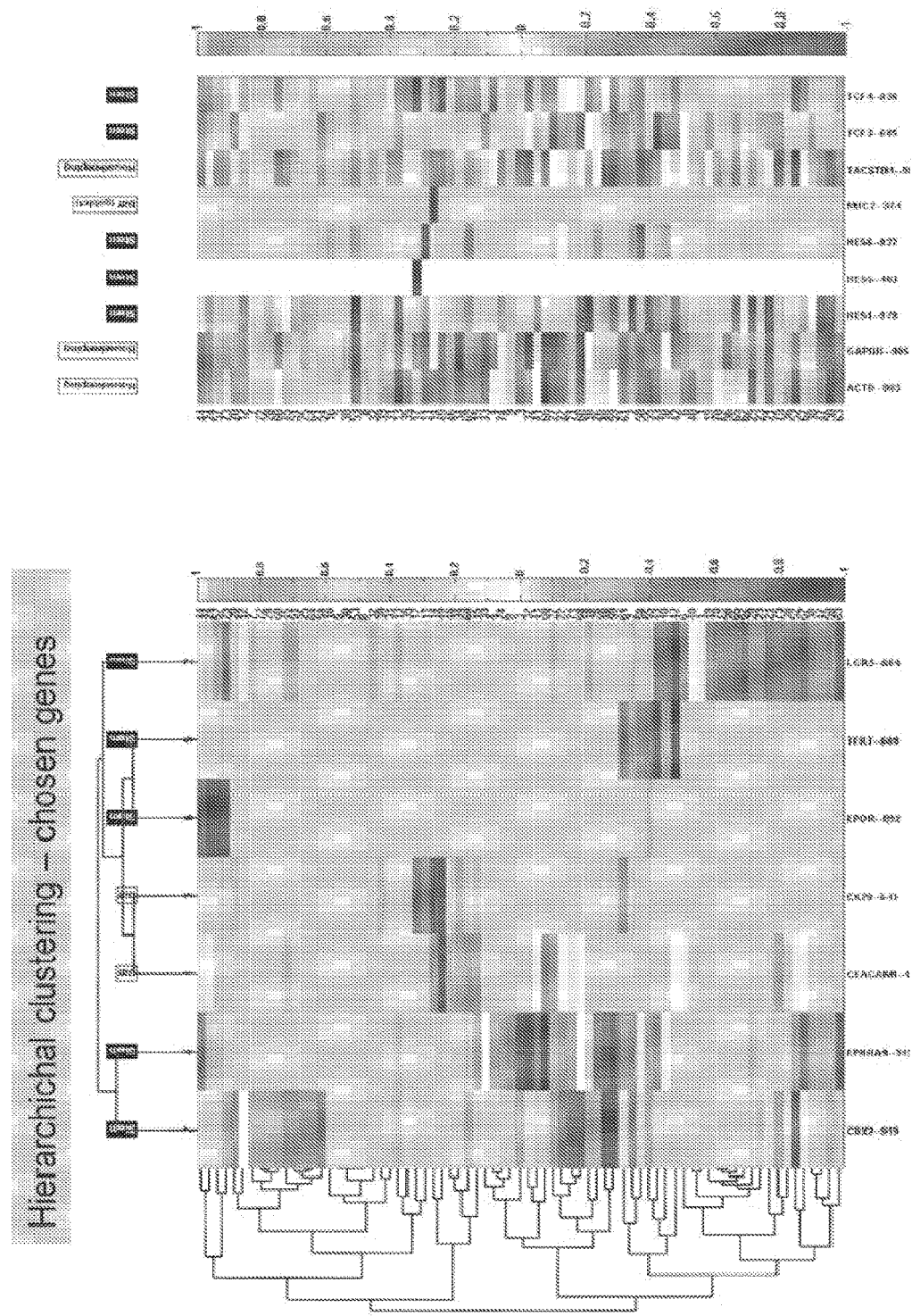
FIG. 15 A hierarchical clustering analysis on colon cells, showing the presence of LGR5+ and LGR– TERT+ stem cells.
Figure 16:
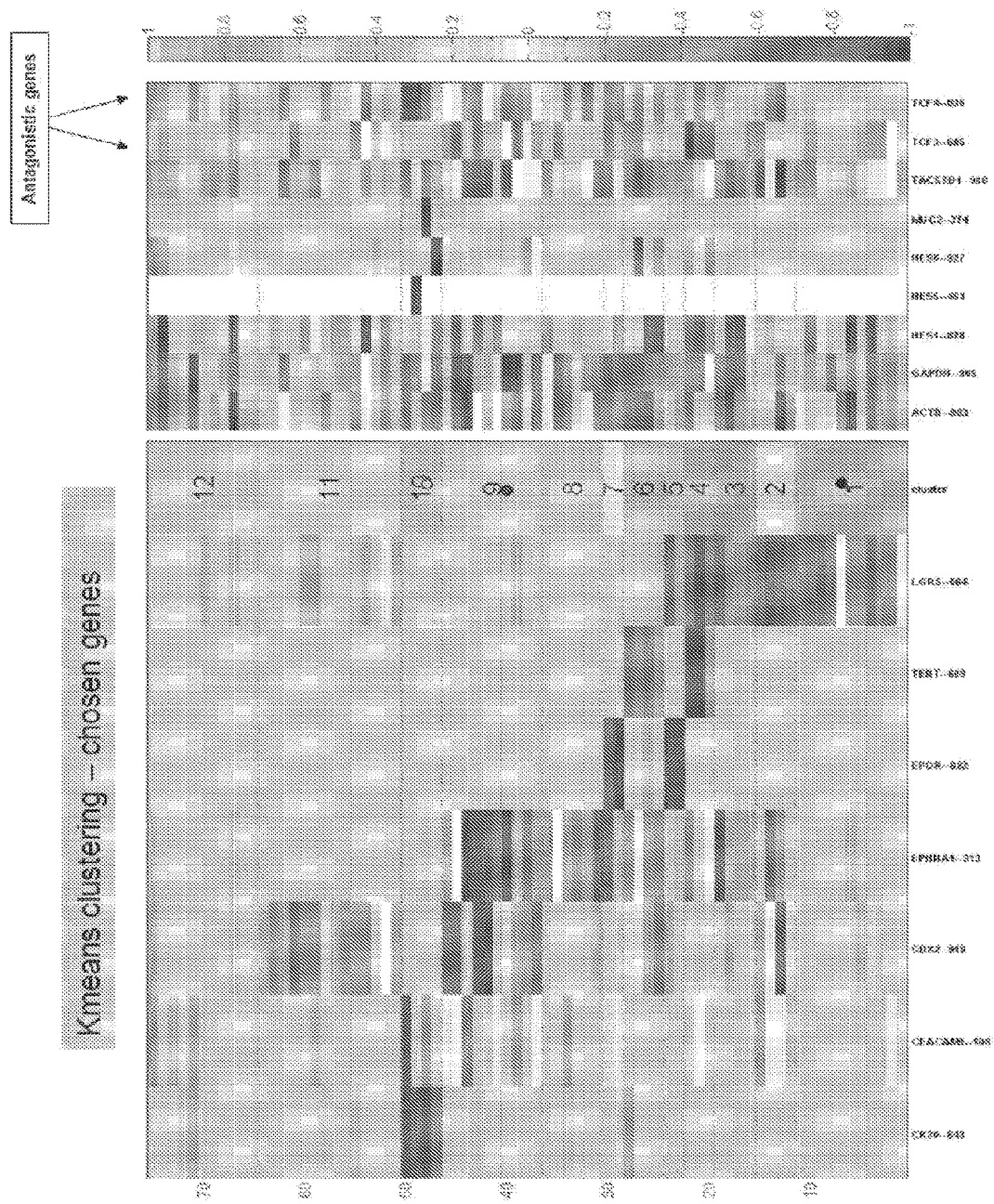
FIG. 16 A hierarchical clustering analysis showing heterogeneity based on developmental genes.
Figure 17:
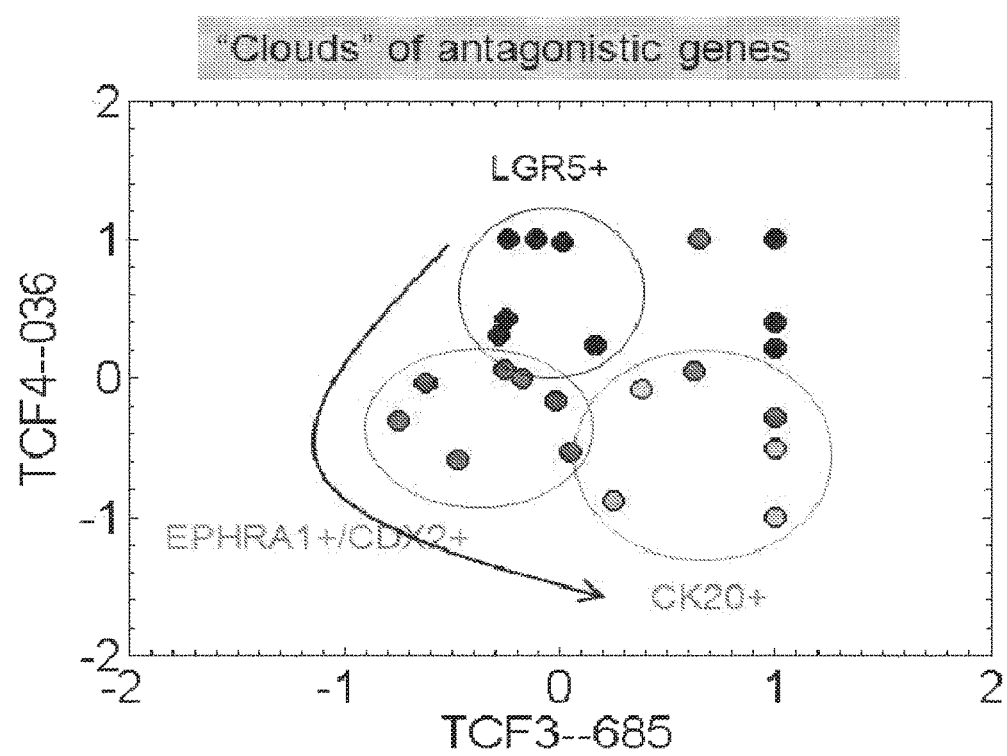
FIG. 17 Data showing various genes are expressed differently in various colon cancer cells.

Single cell gene expression analysis was performed as described above using antibodies which bind to ESA for initial sorting by FACS. Tumorigenic cells were obtained from a colon tumor Two chip-runs, hm_1L and hm_1R were performed (FIG. 11). These chip-runs were prepared either as pre-amplified replicates or as on-chip replicates. A combined heat map is illustrated in FIG. 12. Out of 84 cells tested, 9 cells that do not express housekeeping genes were discarded, and 75 cells were selected for further analysis (FIG. 13). Hierarchical clustering was performed and a representative illustration of the results is shown in FIG. 14. Hierarchical clustering for selected genes is illustrated in FIG. 15. Hierarchical clustering using k-means clustering were performed for selected genes and the results are illustrated in FIG. 16. In these clustering experiments, antagonistic expression of TCF4 and TCF3 were identified (FIG. 17). For example, where terminally differentiated colonic epithelial marker CK20 is expressed, TCF3 expression was higher than TCF4 expression. In contrast, where a candidate stem cell marker LGR5 is expressed, TCF4 expression was higher than TCF3 expression.

Figure 18:
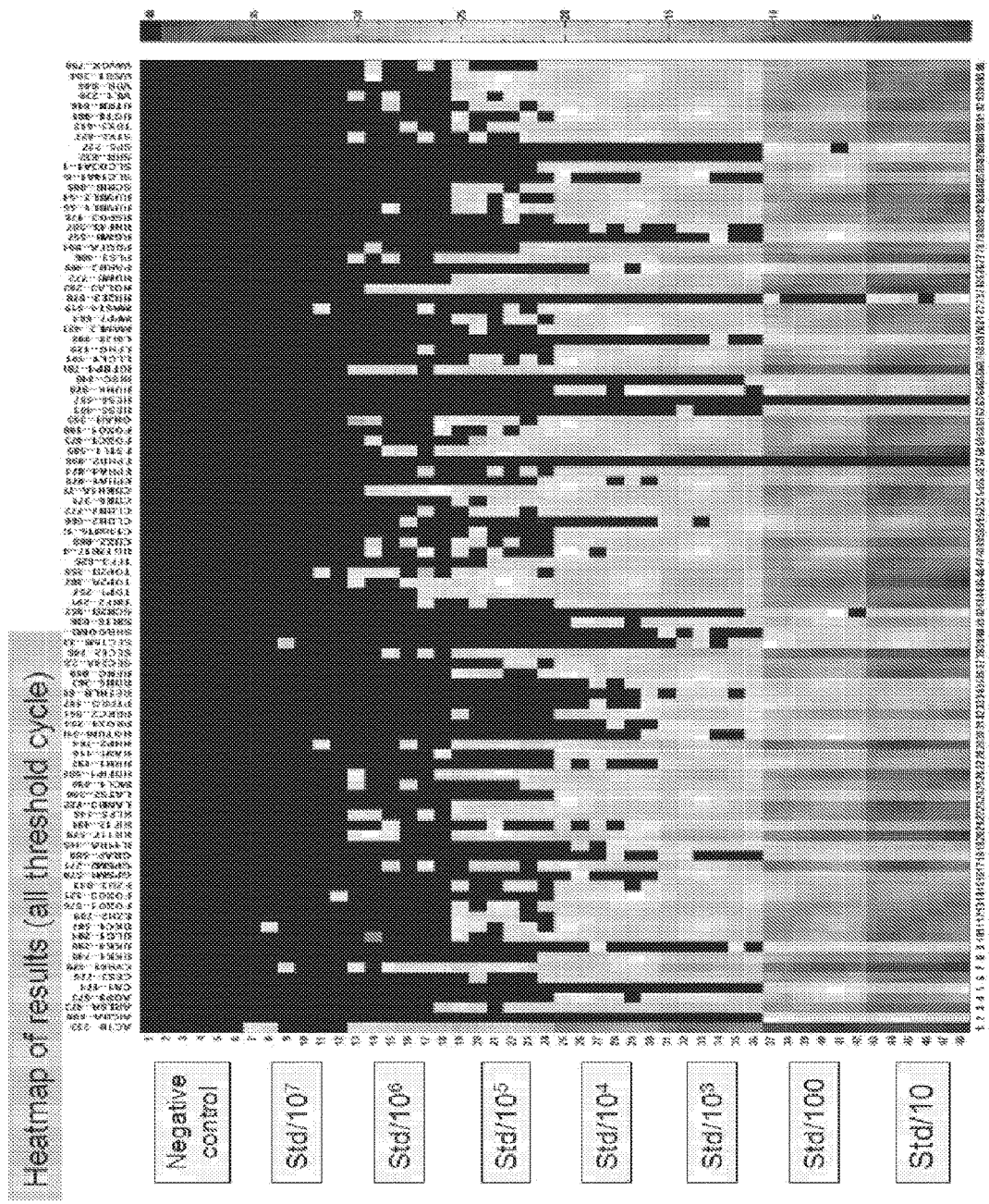
FIG. 18 Data showing methodology used to determine cutoff measurements for expression levels from single-cell qRT-PCR experiments. Expression relative to negative control is shown.
Figure 19:
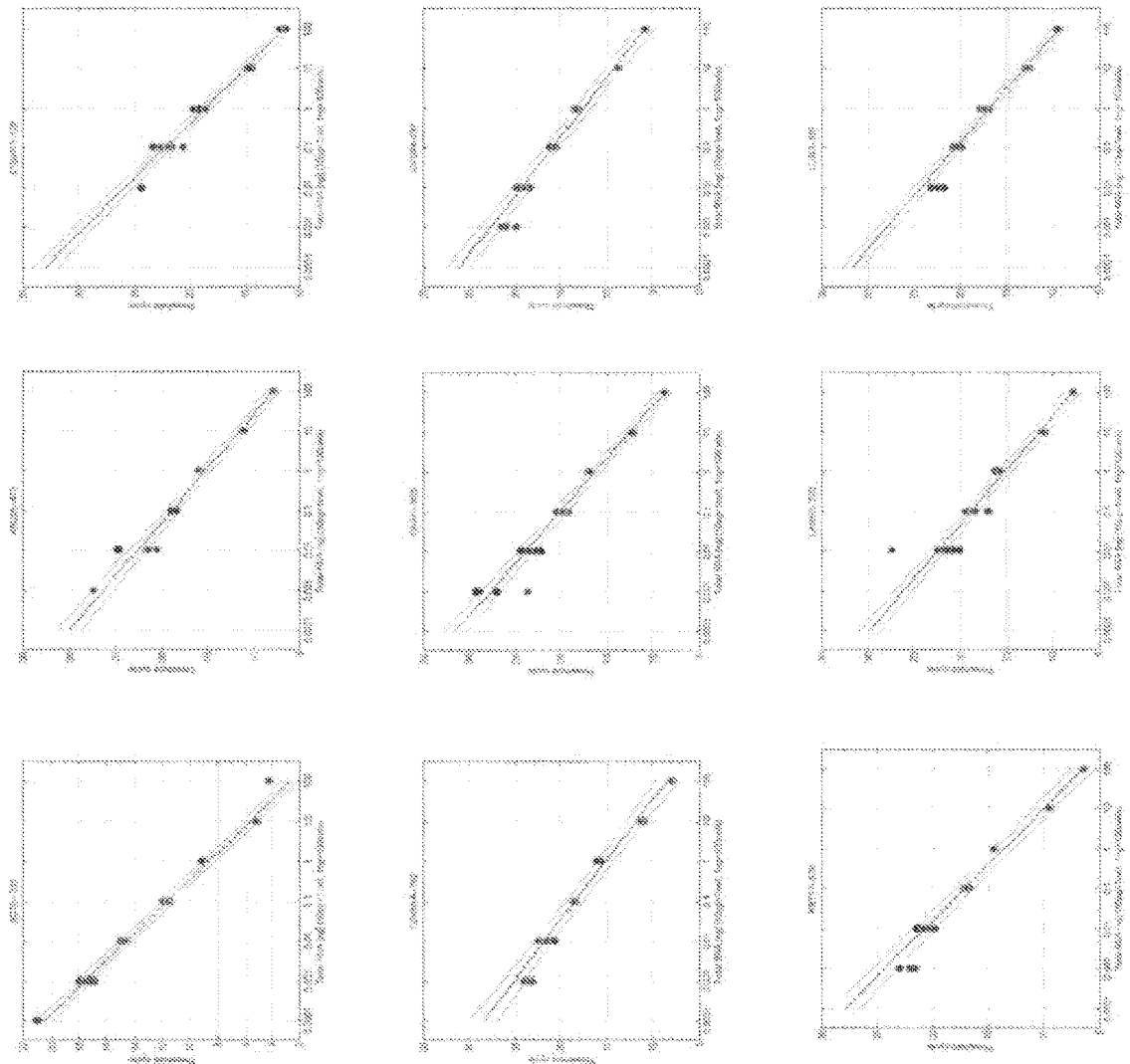
FIG. 19 Data showing methodology used to verify that quantification of RNA is possible on quantities of RNA collected from one cell. Testing of various RNA amounts and primer sets shown.
Figure 20:
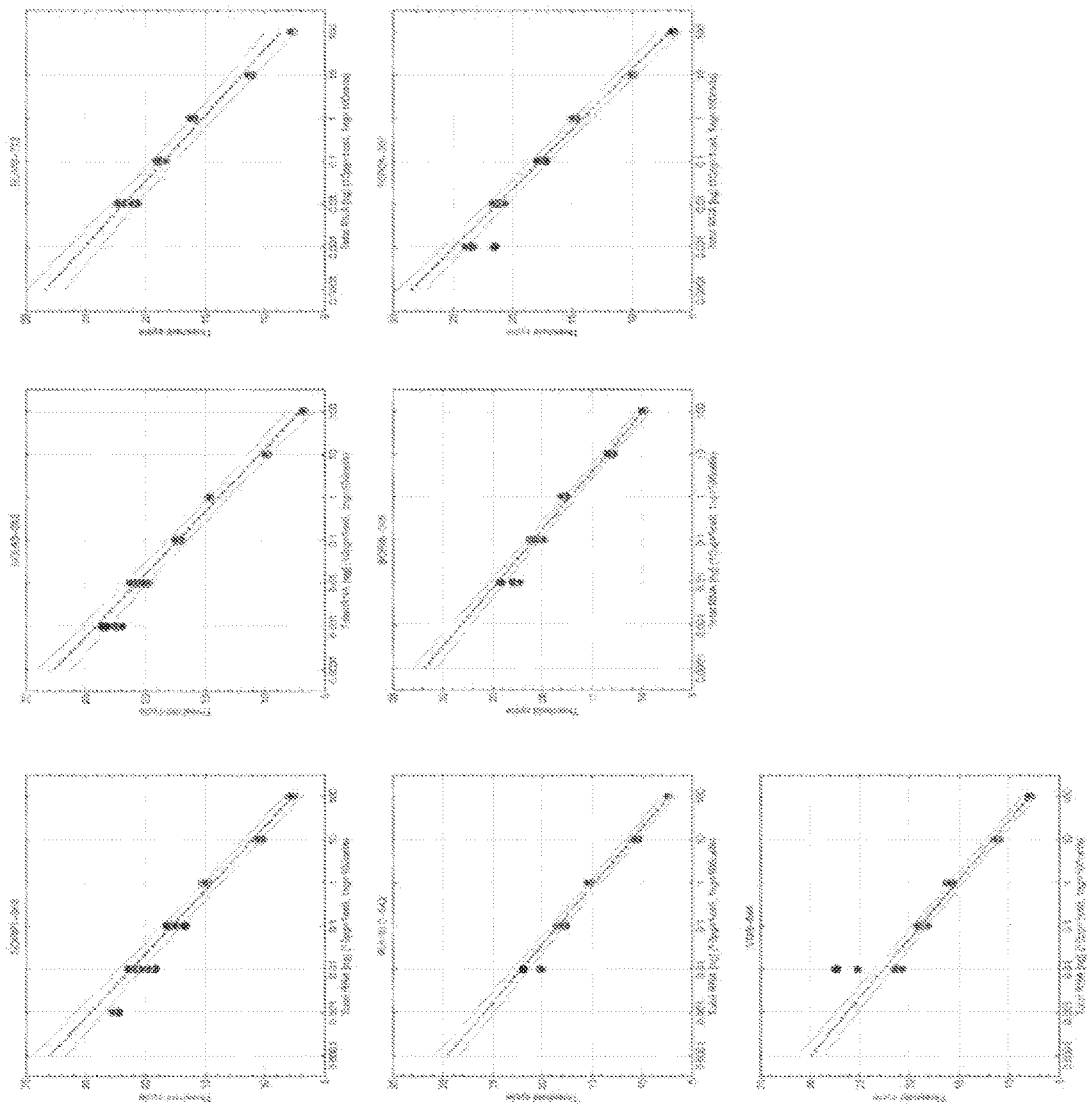
FIG. 20 Data showing methodology used to verify that quantification of RNA is possible on quantities of RNA collected from one cell. Testing of various RNA amounts and primer sets shown.
Figure 21:
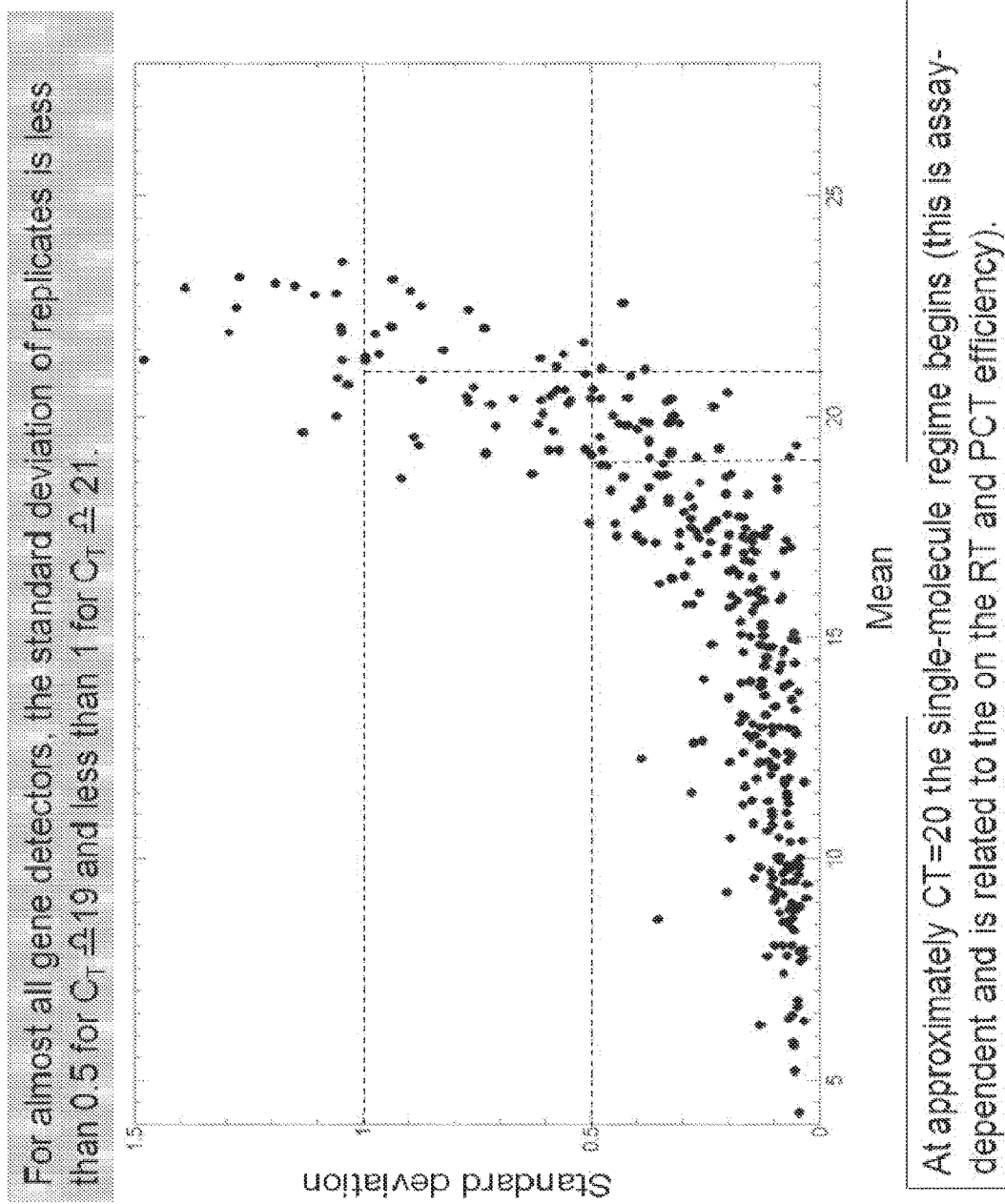
FIG. 21 data showing methodology used to verify that quantification of RNA is possible on quantities of RNA collected from one cell. Cycle threshold for amplification can be derived.
Figure 22:
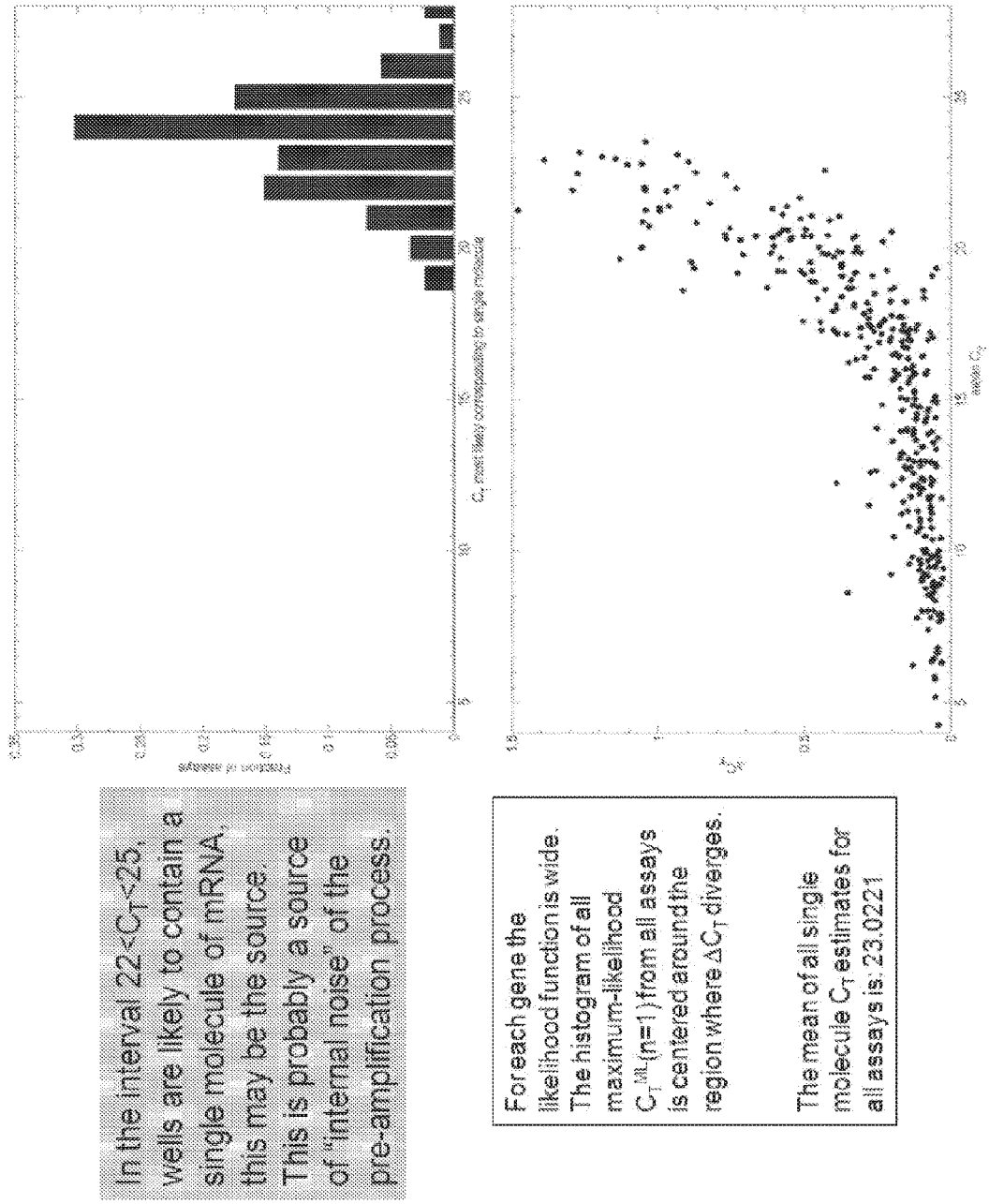
FIG. 22 Data showing methodology used to verify that quantification of RNA is possible on quantities of RNA collected from one cell. Cycle threshold for amplification can be derived.
Figure 23:
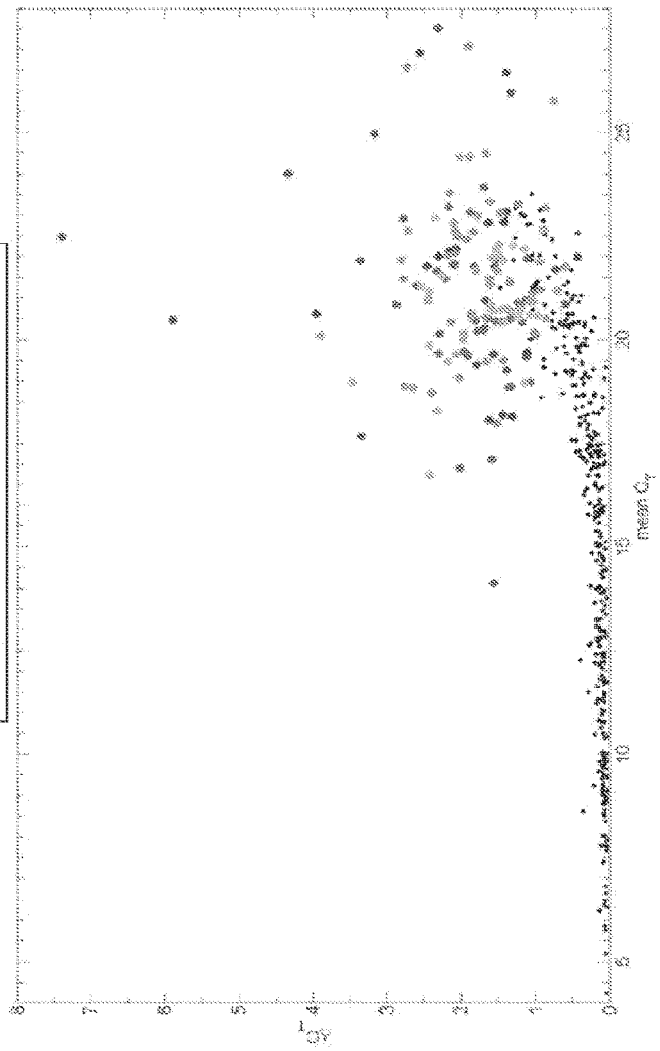
FIG. 23 The variability in gene expression between single cells from human tissue is higher than the variability of RNA standards.
Figure 24:
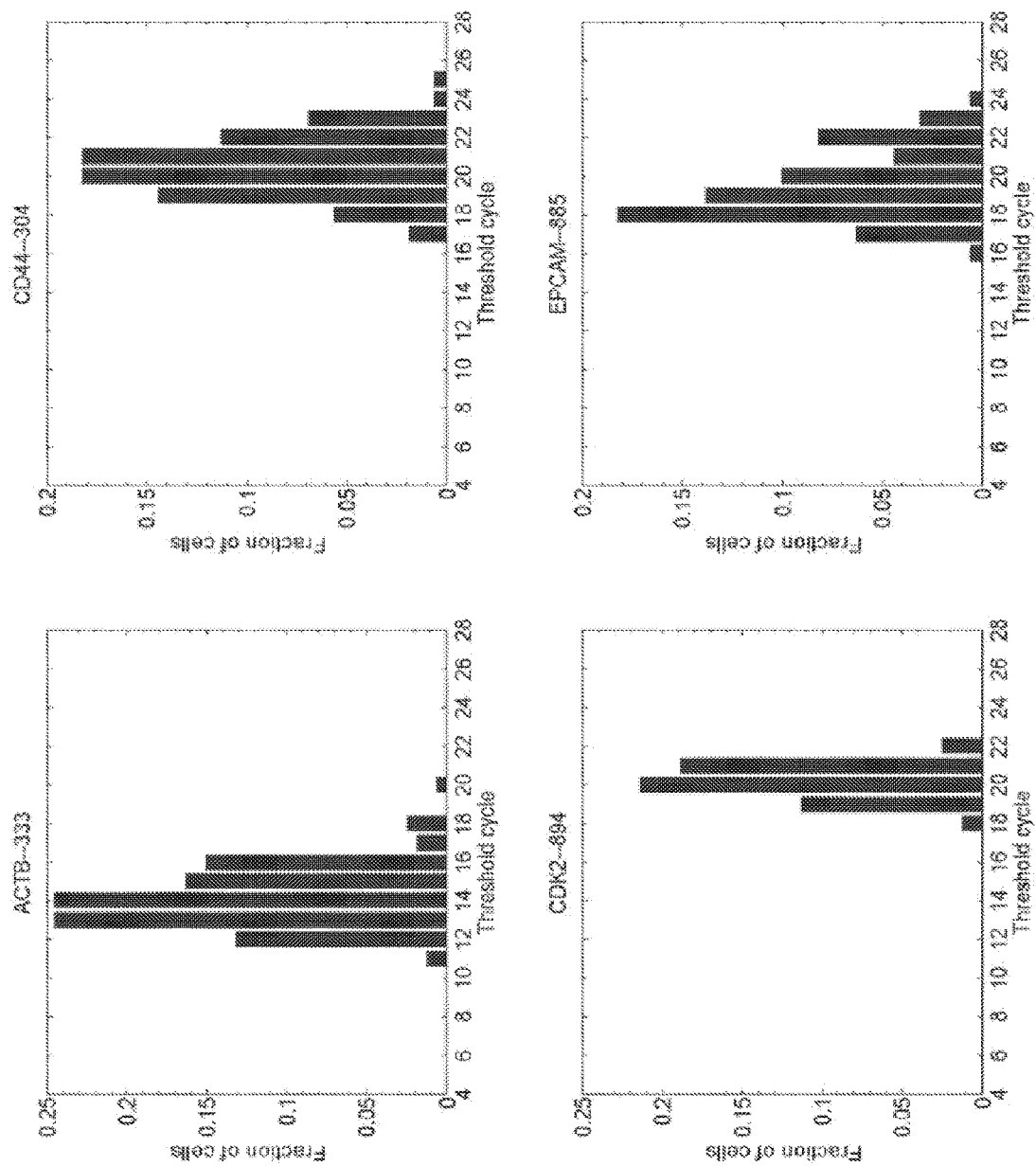
FIG. 24 Histograms of different assays demonstrating that the measured cell-cell variability (for most good quality assays) is higher than the internal noise of the measurement protocol.
Figure 25:
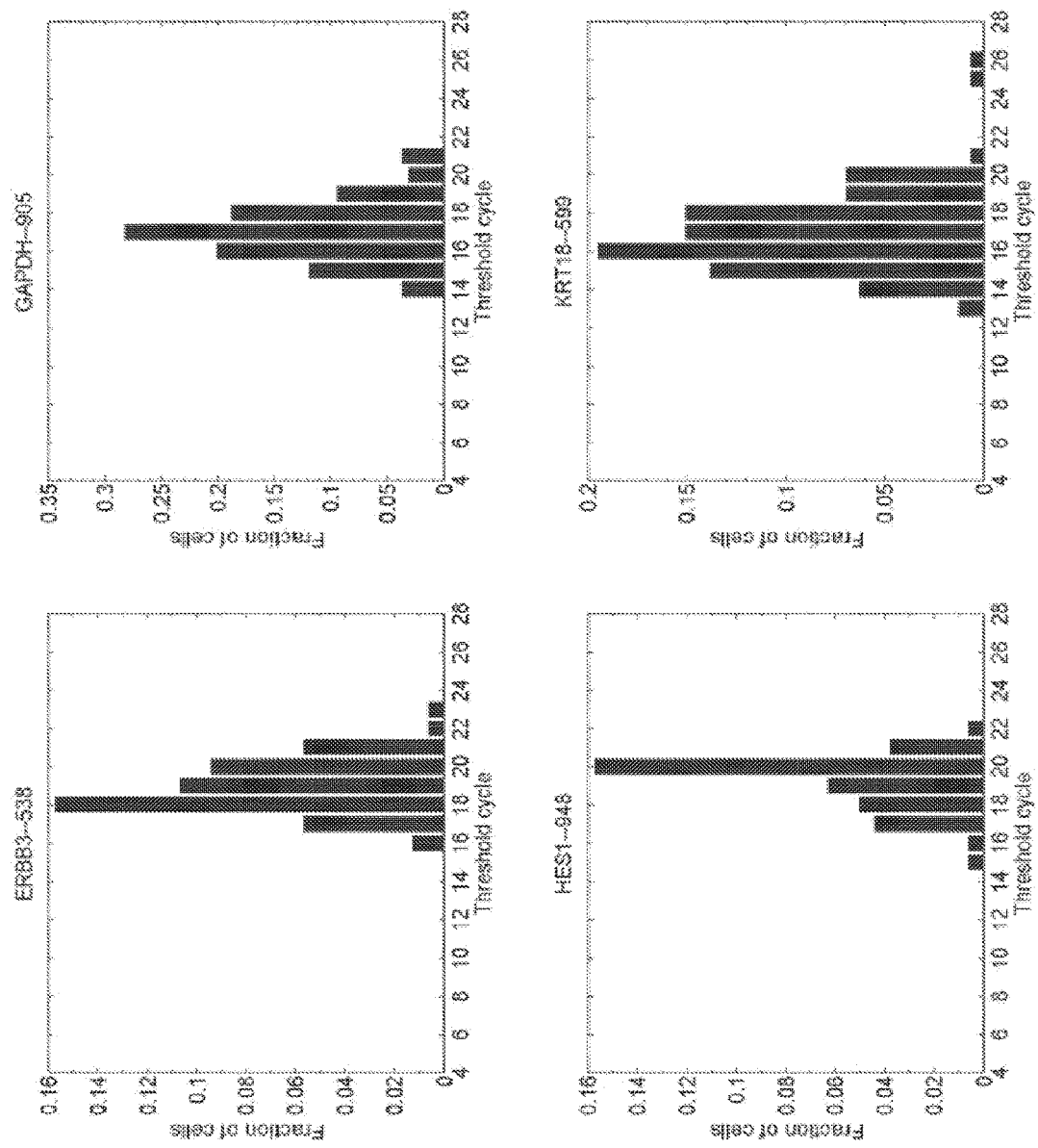
FIG. 25 Histograms of different assays demonstrating that the measured cell-cell variability is higher than the internal noise of the measurement protocol.
Figure 26:
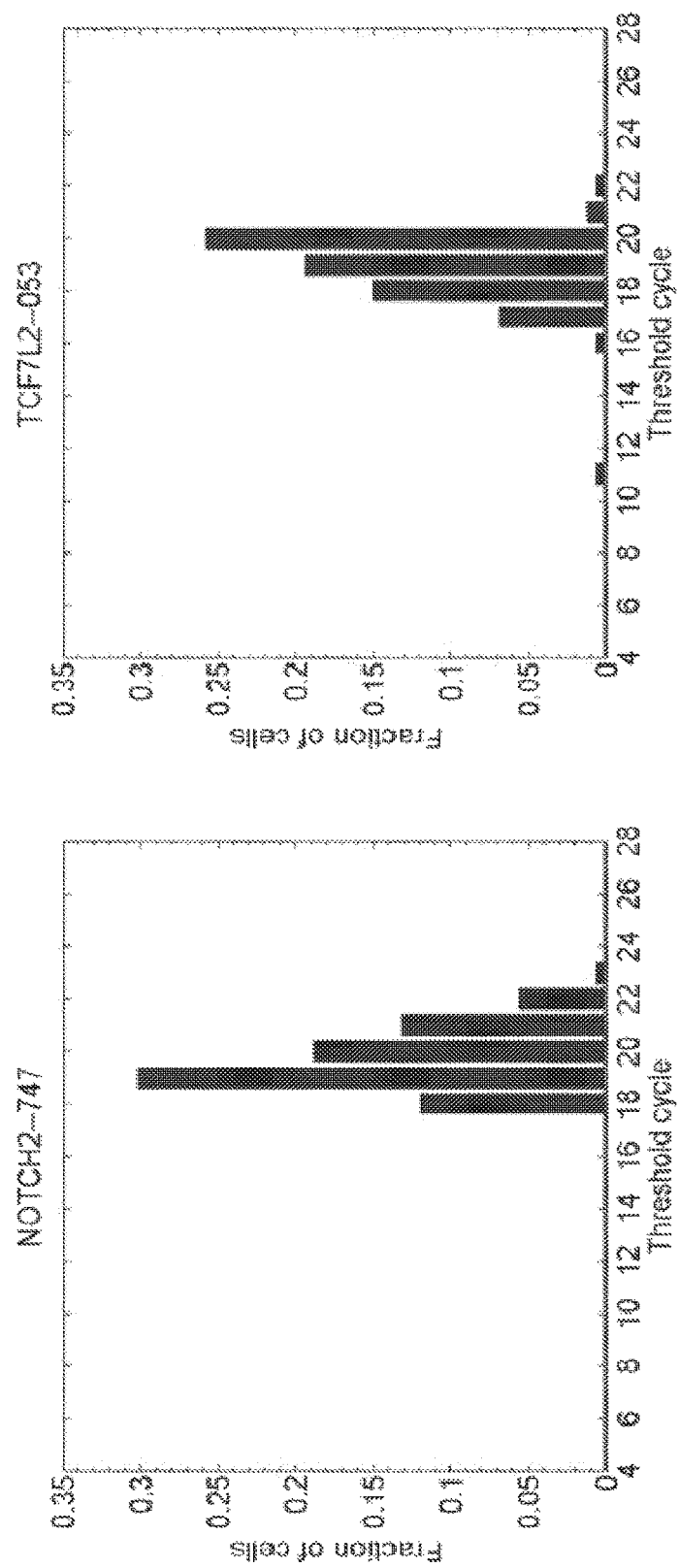
FIG. 26 Histograms of different assays demonstrating that the measured cell-cell variability (for most good quality assays) is higher than the internal noise of the measurement protocol.

Example 12: Standards Run with Reverse Transcription, Multiplex PCR Amplification, and qPCR on M48 Chips Total RNA was prepared in 7 different dilutions ranging from 10 fold dilution to $10^7$ fold dilution with one log interval. The diluted samples were then reverser transcribed and pre-amplified, mixed with 96 primer sets (Taqman gene expression assays, manufactured by ABI Biosystems). The experiments were prepared in 6 replicates per dilution. cDNAs from the pre-amplification were then quantified using two M48 chips. A representative heat map of various dilutions and the negative control is illustrated in FIG. 18. Amplification linearity is demonstrated by linear amplification of selected genes such as ACTB, ARL5A, C13ORF15, CDKN1A, GNAI1, IGFBP4, KRT17, LABM3, LLGL1, NDFIP1, NOLA3, NUMB, RUVBL, SCRIB, TOP2A, and VDR, as illustrated in FIG. 19 and FIG. 20. Standard deviation over mean is plotted and shown in FIG. 21. A $C_T$ that most likely corresponds to a single molecule for each gene is estimated to a range between 22 and 25 (FIG. 22). The variability in gene expression between single cells from human tissue is higher than the variability of RNA standards, as illustrated in FIG. 23. Histograms of different assays demonstrated the measured cell-cell variability is higher than the internal noise of the measurement protocol (FIGS. 24-26).

Example 13: Standards Run with Reverse Transcription, Multiplex PCR Amplification, and qPCR on M48 Chips Total RNA was prepared in 7 different dilutions ranging from 10 fold dilution to $10^7$ fold dilution with one log interval. The diluted samples were then reverser transcribed and pre-amplified, mixed with 96 primer sets (Taqman gene expression assays, manufactured by ABI Biosystems). The experiments were prepared in 6 replicates per dilution. cDNAs from the pre-amplification were then quantified using two M48 chips. A representative heat map of various dilutions and the negative control is illustrated in FIG. 18. Amplification linearity is demonstrated by linear amplification of selected genes such as ACTB, ARL5A, C13ORF15, CDKN1A, GNAI1, IGFBP4, KRT17, LABM3, LLGL1, NDFIP1, NOLA3, NUMB, RUVBL, SCRIB, TOP2A, and VDR, as illustrated in FIG. 19 and FIG. 20. Standard deviation over mean is plotted and shown in FIG. 21. A $C_T$ that most likely corresponds to a single molecule for each gene is estimated to a range between 22 and 25 (FIG. 22). The variability in gene expression between single cells from human tissue is higher than the variability of RNA standards, as illustrated in FIG. 23. Histograms of different assays demonstrated the measured cell-cell variability is higher than the internal noise of the measurement protocol (FIGS. 24-26).

Example 14: Analysis of Normal Colon Cancer Cells

Figure 27:
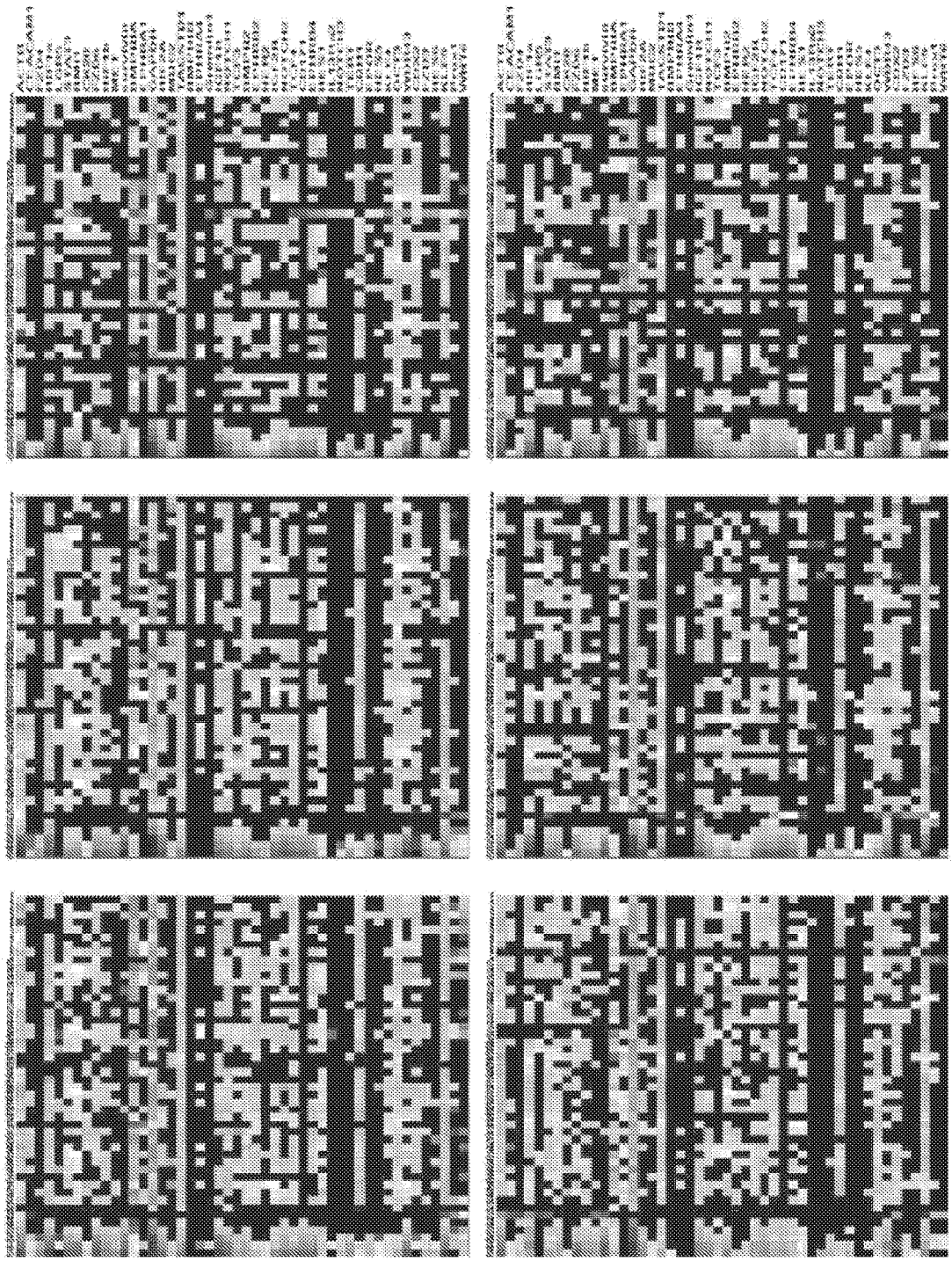
FIG. 27 Validation of various primer sets.
Figure 28:
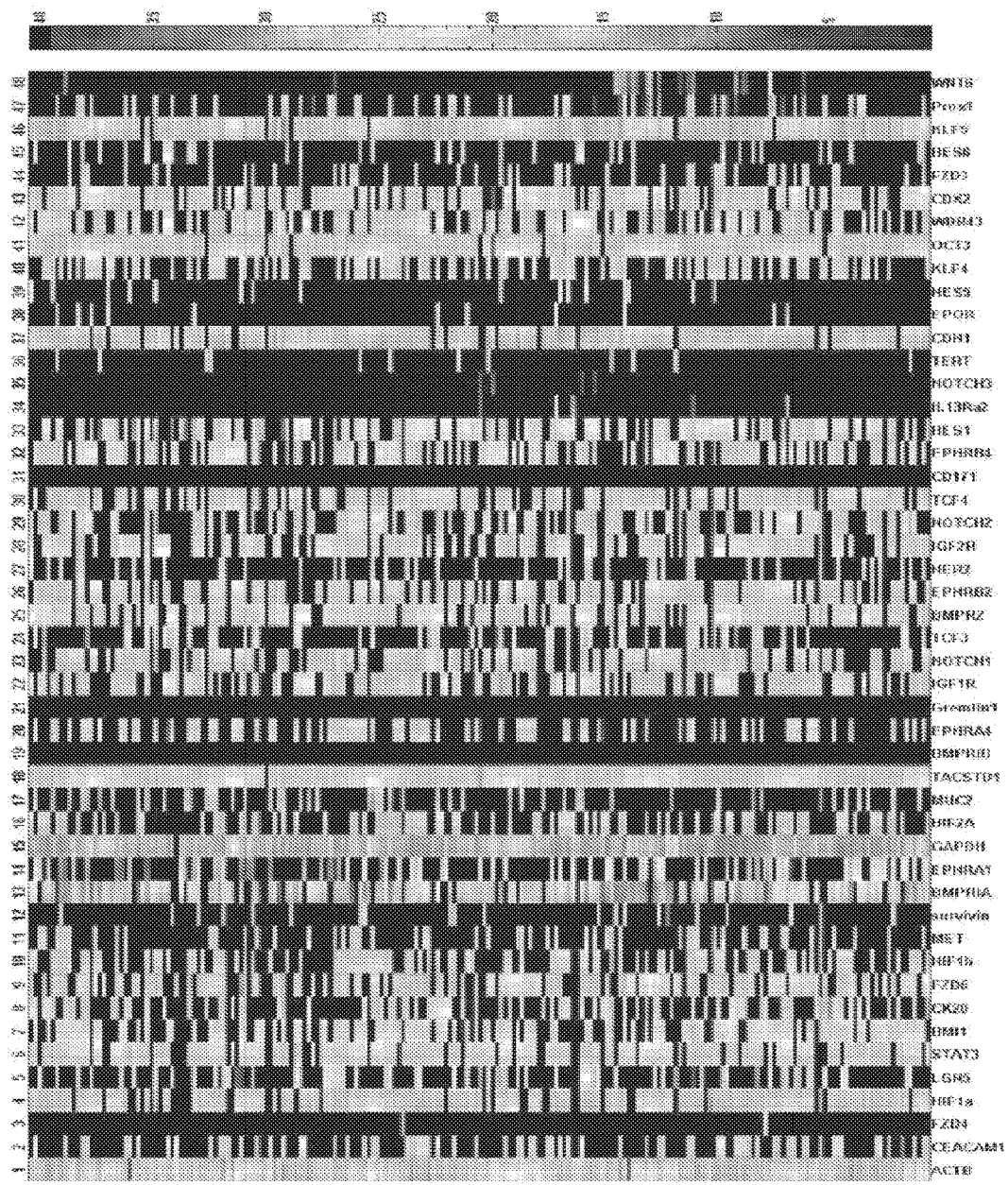
FIG. 28 Validation of various primer sets.
Figure 29:
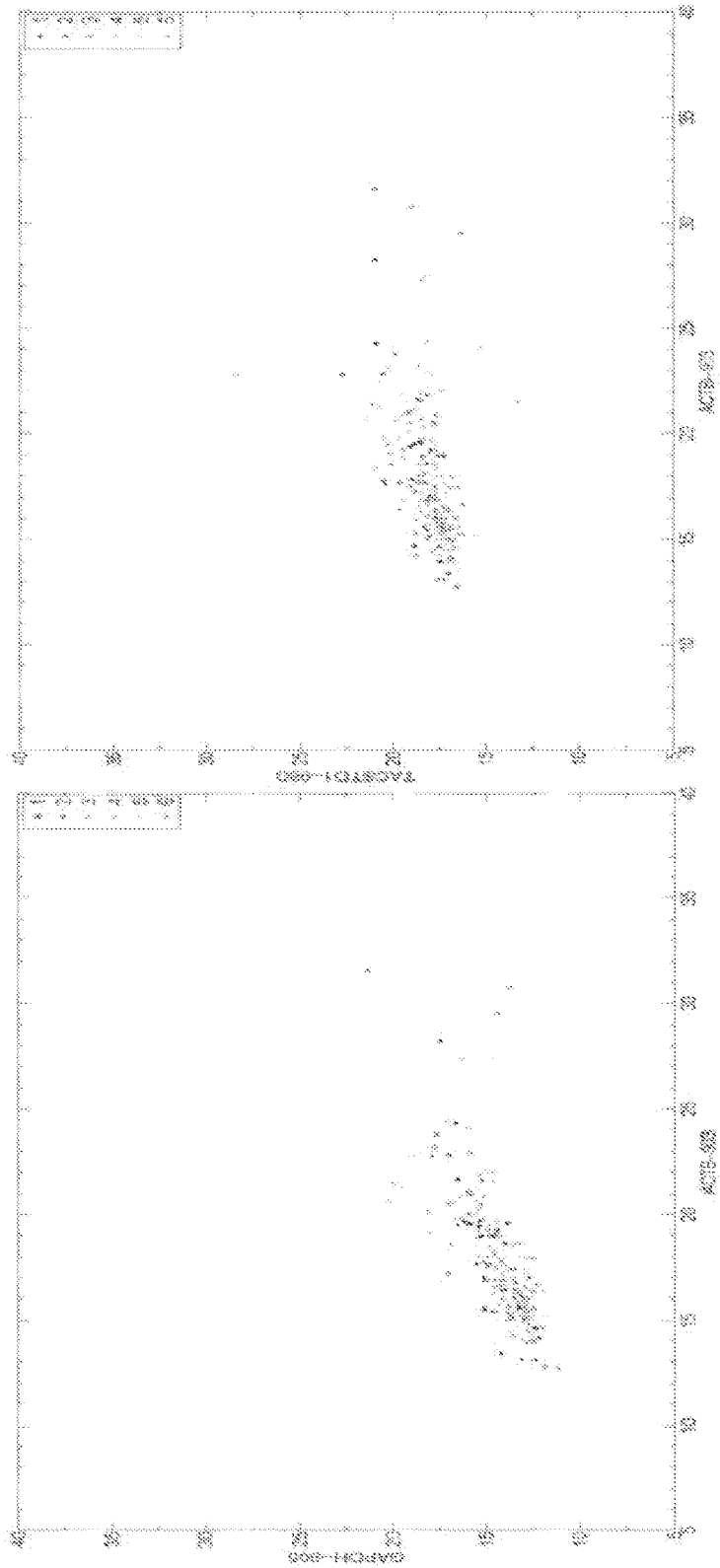
FIG. 29 Methodology to identify reliable cells.
Figure 30:
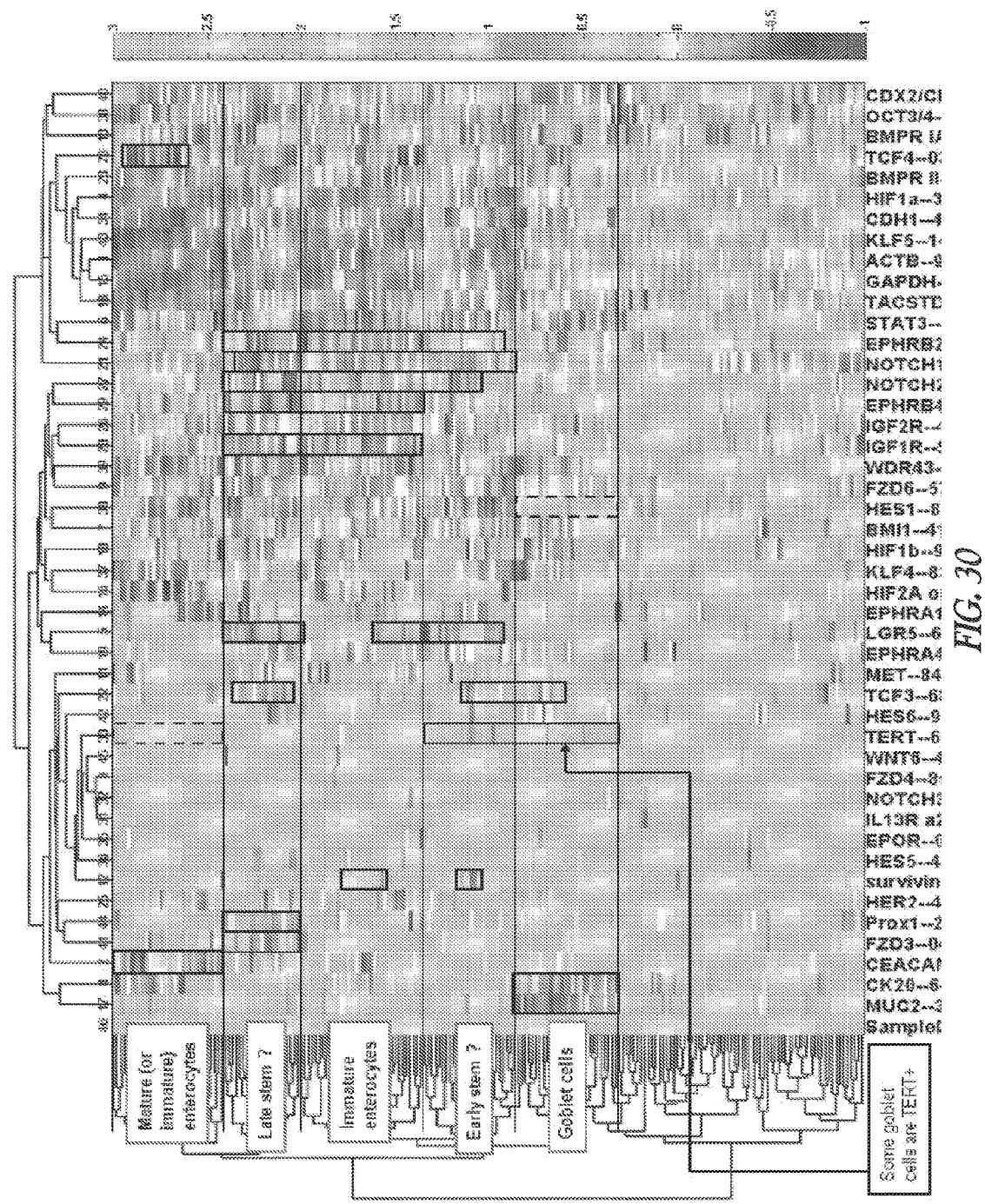
FIG. 30 Gene sets useful for the hierarchical clustering of colon cells are shown. Also shown are possible target genes such as Notch1, Notch2, Stat3, IGF1R, IGF2R, EphB4, and LGR5-6.
Figure 31:
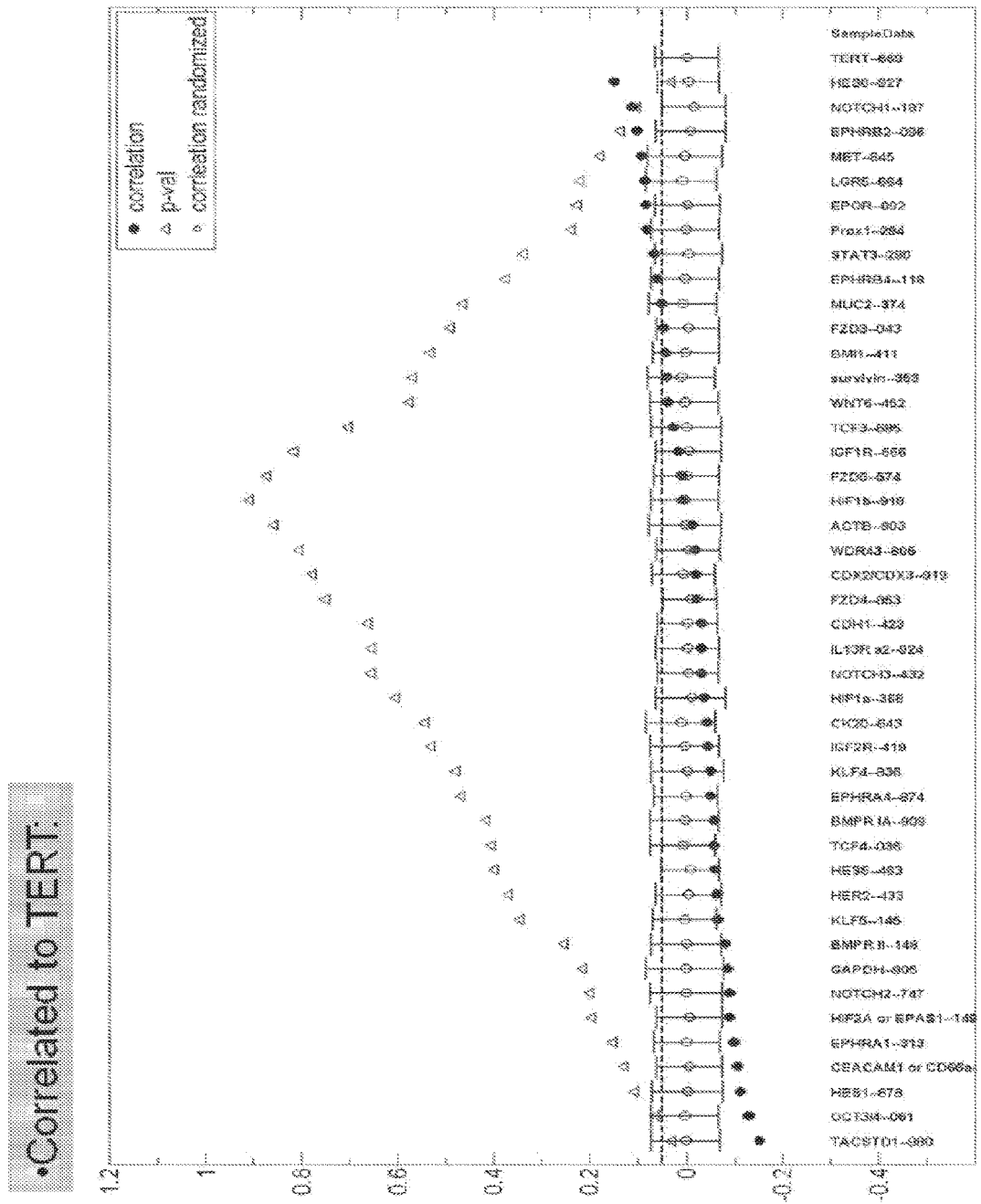
FIG. 31 Ability to correlate gene expression with TERT is shown. Possible application is to use this methodology to target cells expressing TERT. Listed on the x-axis are some genes that are possible targets.
Figure 32:
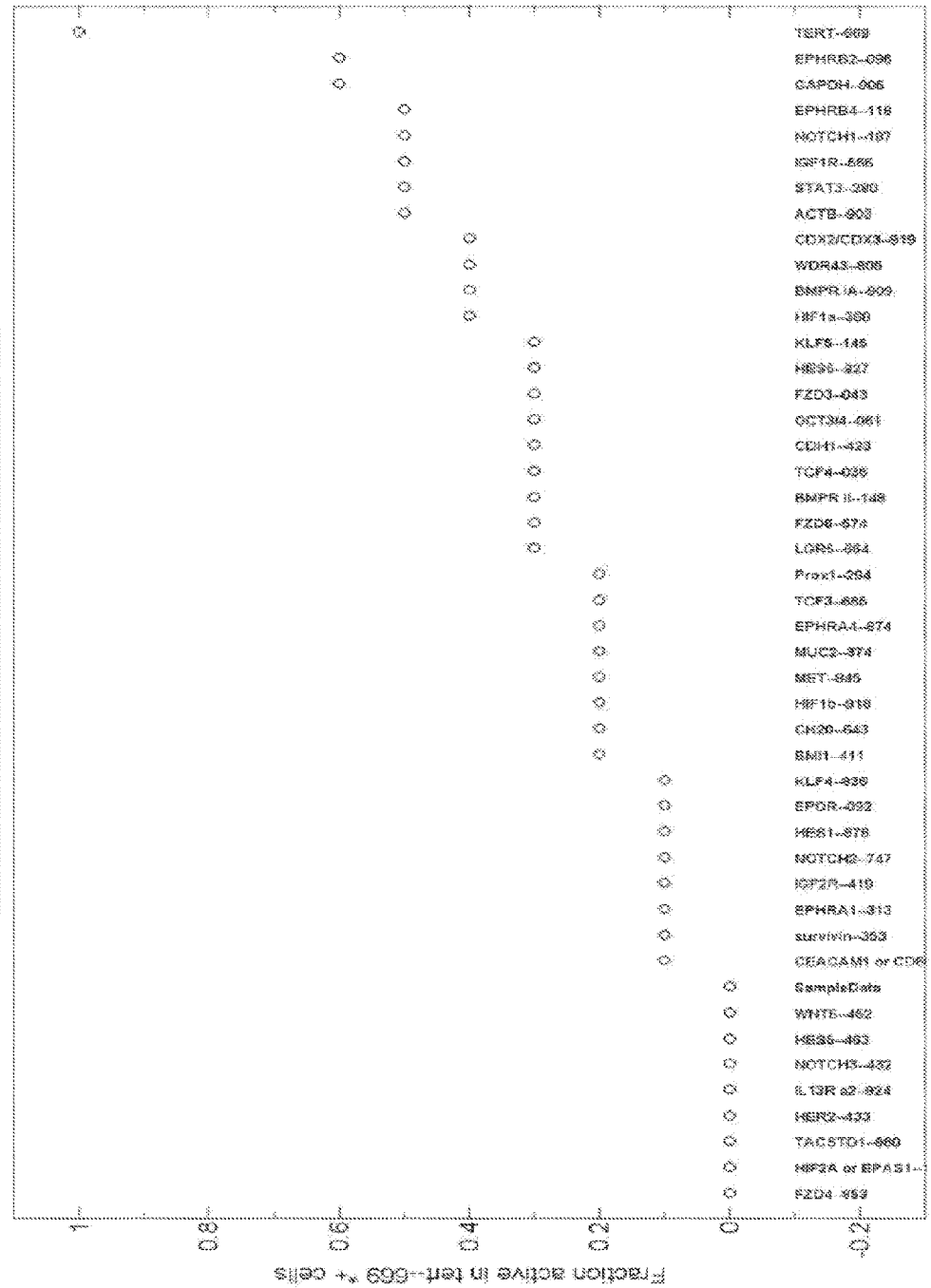
FIG. 32 Ability to correlate gene expression with TERT is shown. Possible application is to use this methodology to target cells expressing TERT. Listed on the x-axis are some genes that are possible targets.
Figure 33:
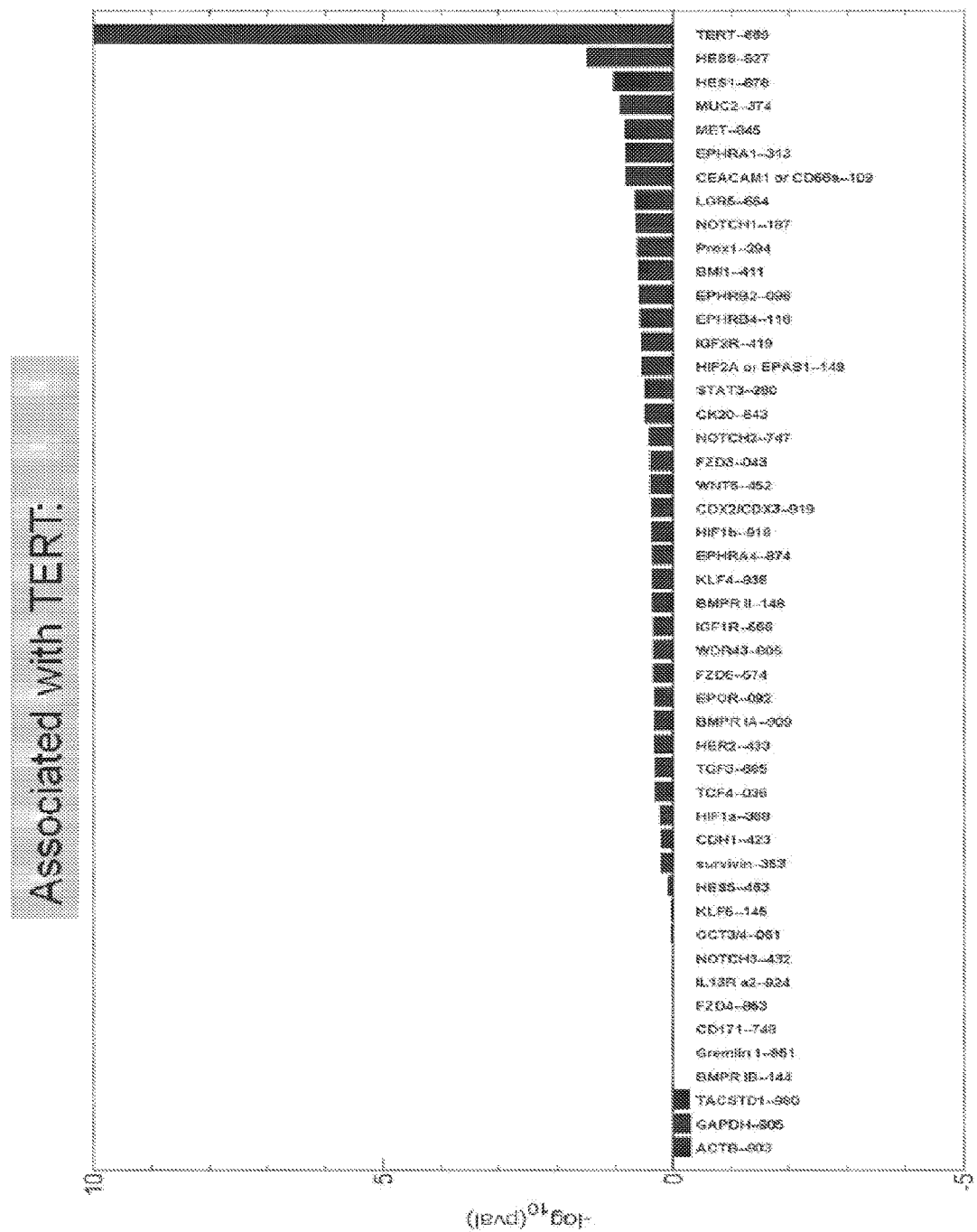
FIG. 33 Ability to correlate gene expression with TERT is shown. Possible application is to use this methodology to target cells expressing TERT. Listed on the x-axis are some genes that are possible targets.
Figure 34:
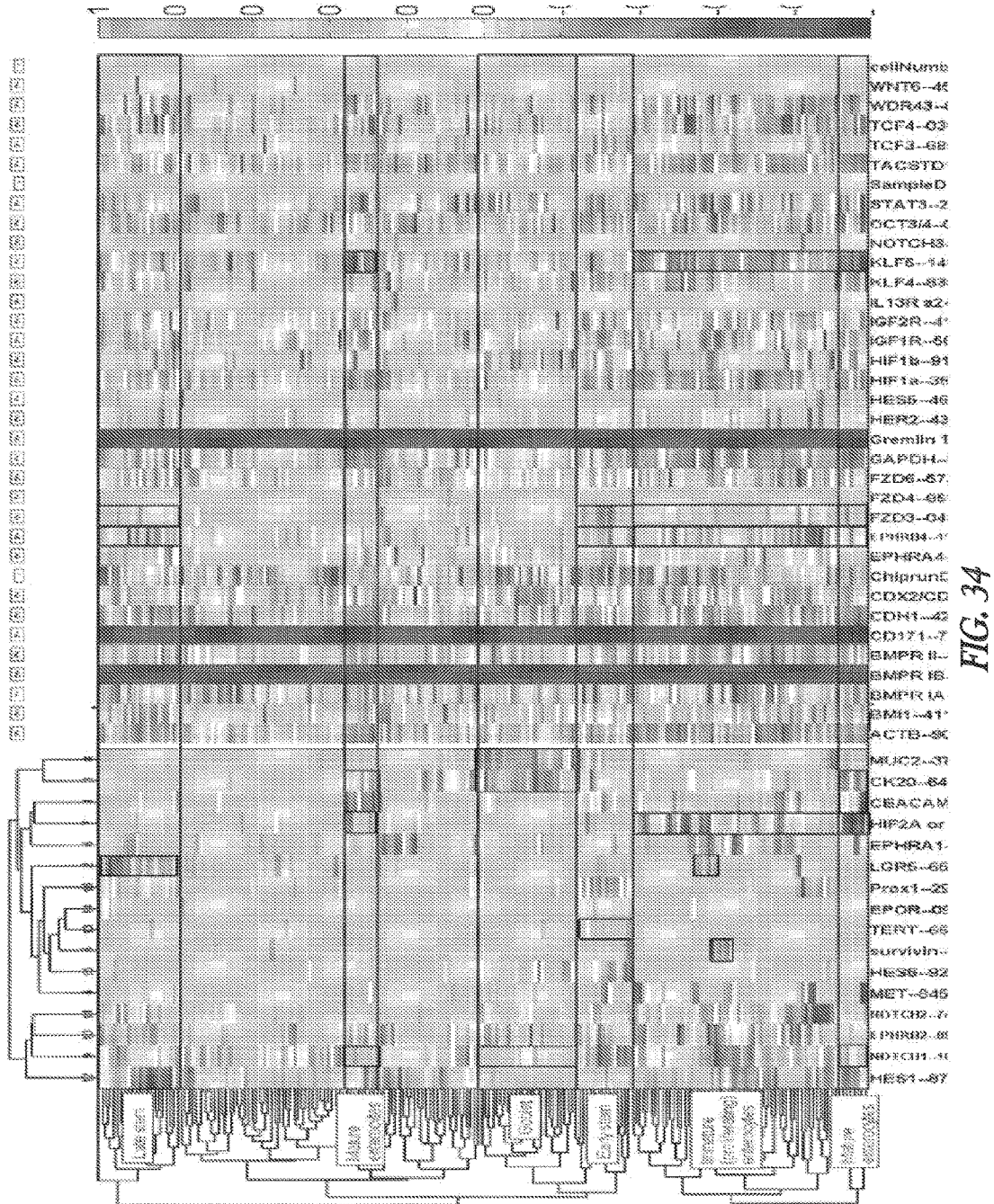
FIG. 34 Genes used for hierarchical clustering of colon cells are shown on the x-axis to the left. On the right side of the x-axis are possible gene targets. This methodology can be useful for the evaluation of colon cancers for treatment targets and normal colon for toxicity profiling.
Figure 35:
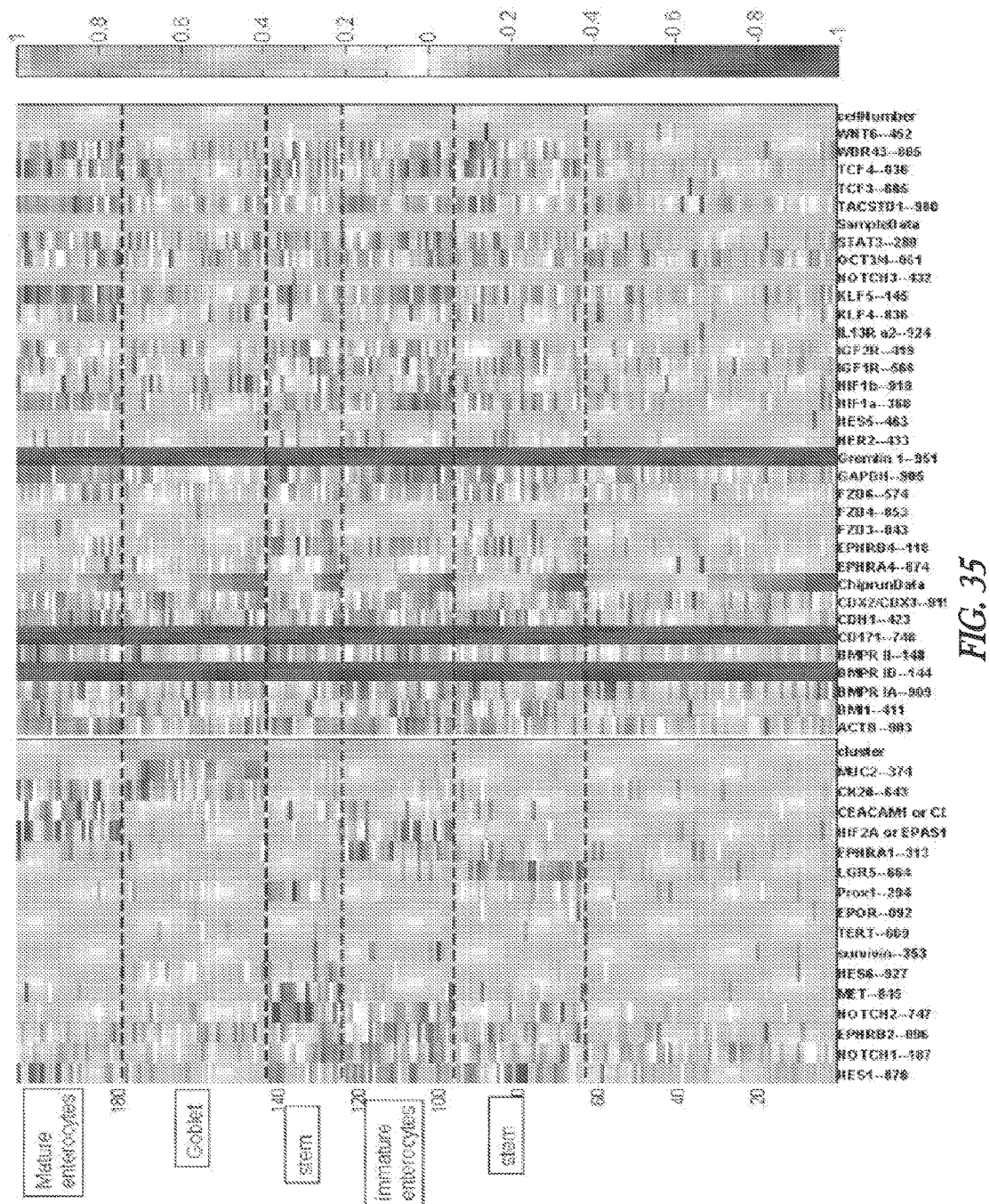
FIG. 35 hierarchical clustering by cell groups. Genes expressed in certain cell types are marked by a black square.
Figure 36:
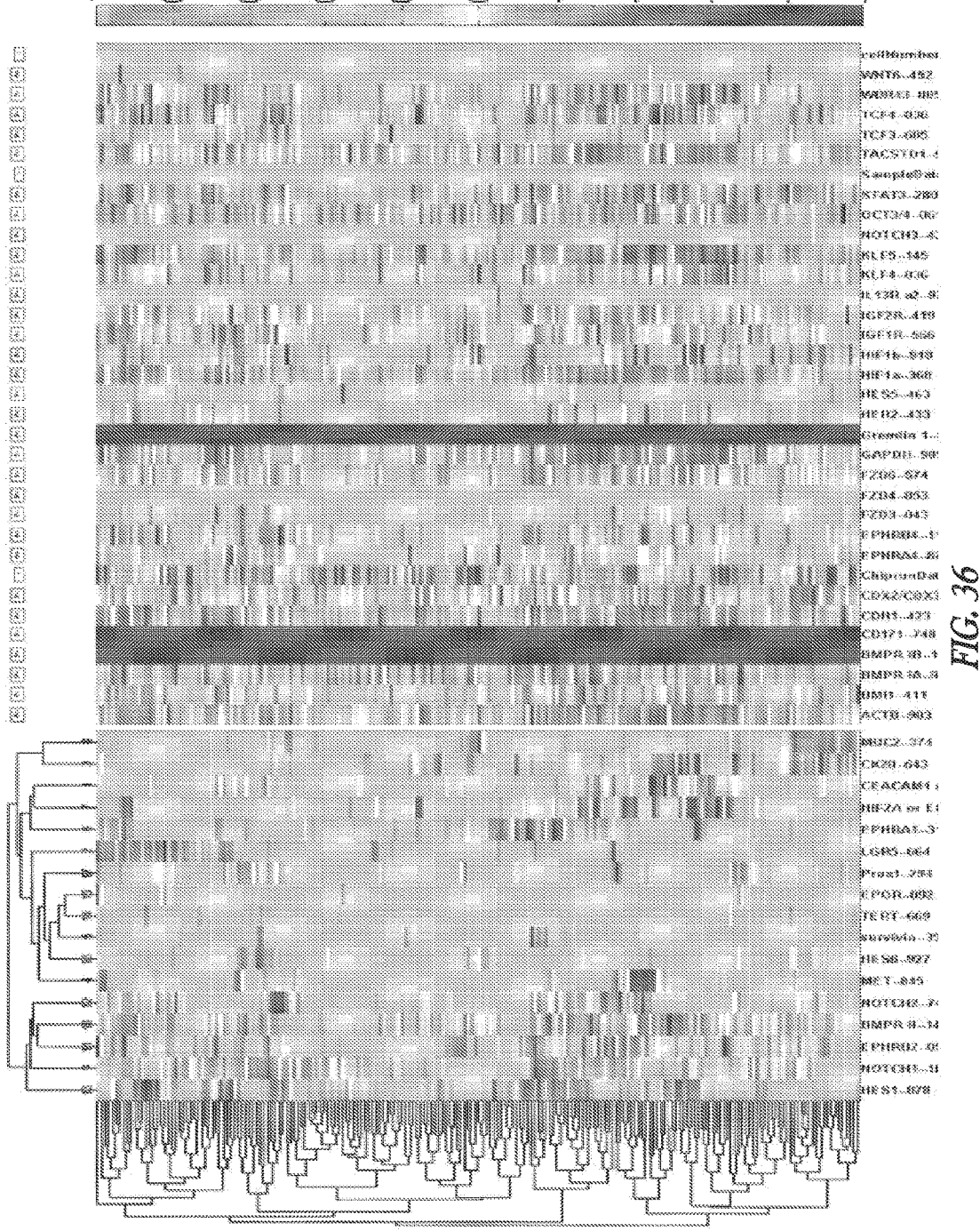
FIG. 36 Genes used for hierarchical clustering of colon cells are shown on the x-axis to the left. On the right side of the x-axis are possible gene targets. This methodology can be useful for the evaluation of colon cancers for treatment targets and normal colon for toxicity profiling.
Figure 37:
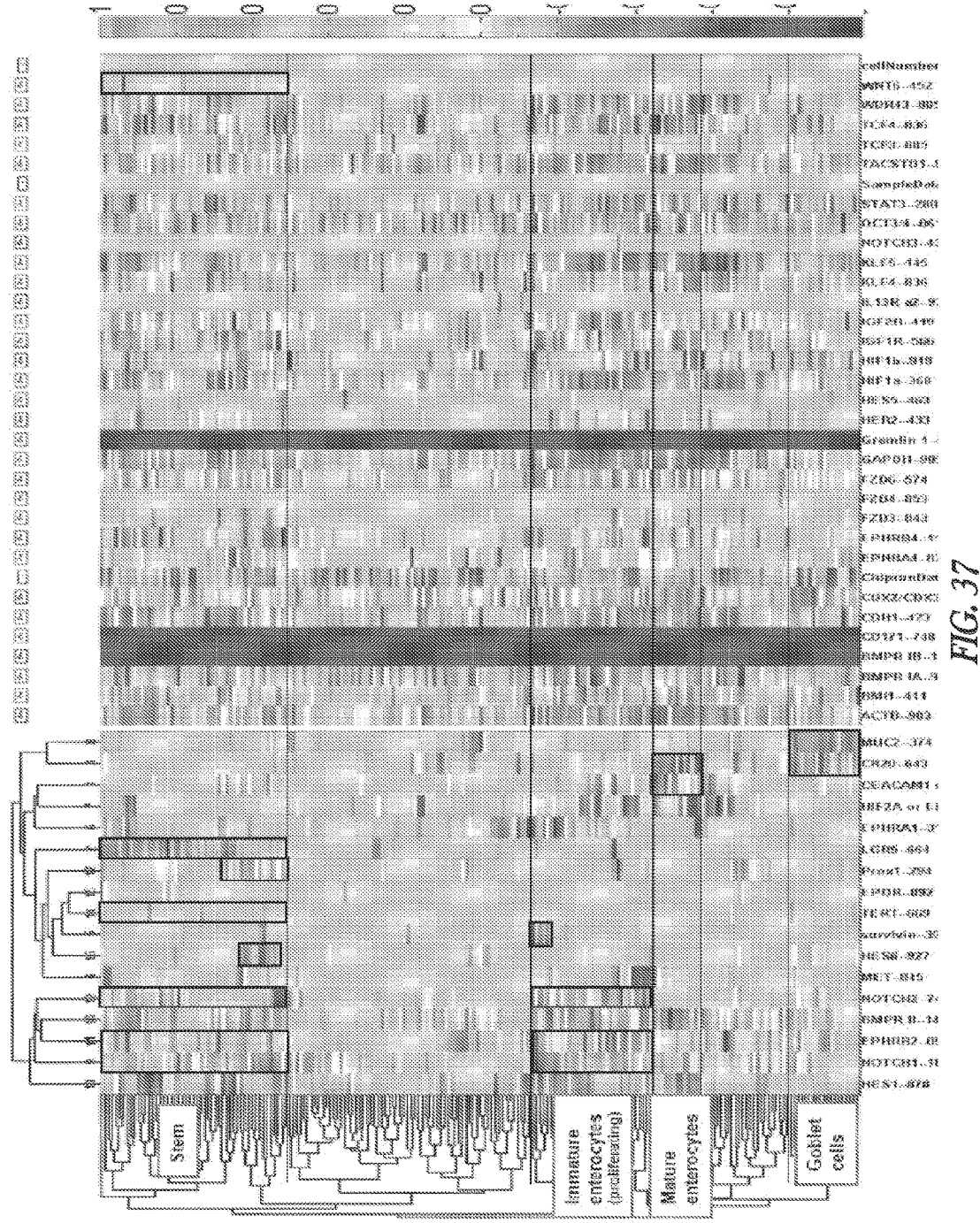
FIG. 37 Genes used for hierarchical clustering of colon cells are shown on the x-axis to the left. On the right side of the x-axis are possible gene targets. This methodology can be useful for the evaluation of colon cancers for treatment targets and normal colon for toxicity profiling.

Single cell gene expression analysis was performed as described above using antibodies for initial sorting by FACS. Normal colon cancer stem cells were analyzed in a multiple chip-runs (FIG. 27). A combined heat map is illustrated in FIG. 28. Out of 208 cells tested, 44 cells that do not express housekeeping genes were discarded, and 252 cells were selected. Of the 208 cells, 1 cell was further discarded and 207 cells were selected for further analysis (FIG. 29). Hierarchical clustering was performed and a representative illustration of the result is shown in FIG. 30. Gene expressions correlated to TERT expression were determined (FIG. 31). Genes co-activated with TERT were identified (FIG. 32). FIG. 33 shows the degree of TERT association in a bar graph. Hierarchical clustering was performed to group cells by their gene expression patterns and cell types (FIGS. 34-37). The clustering demonstrated that NOTCH1, NOTCH2, EPHRB2 expression were associated with stem or immature enterocytes. HES6, PROX1 AND WNT6 expression were associated with stem cells.

Example 15: Analysis of Colon Cancer Cells

Figure 38:
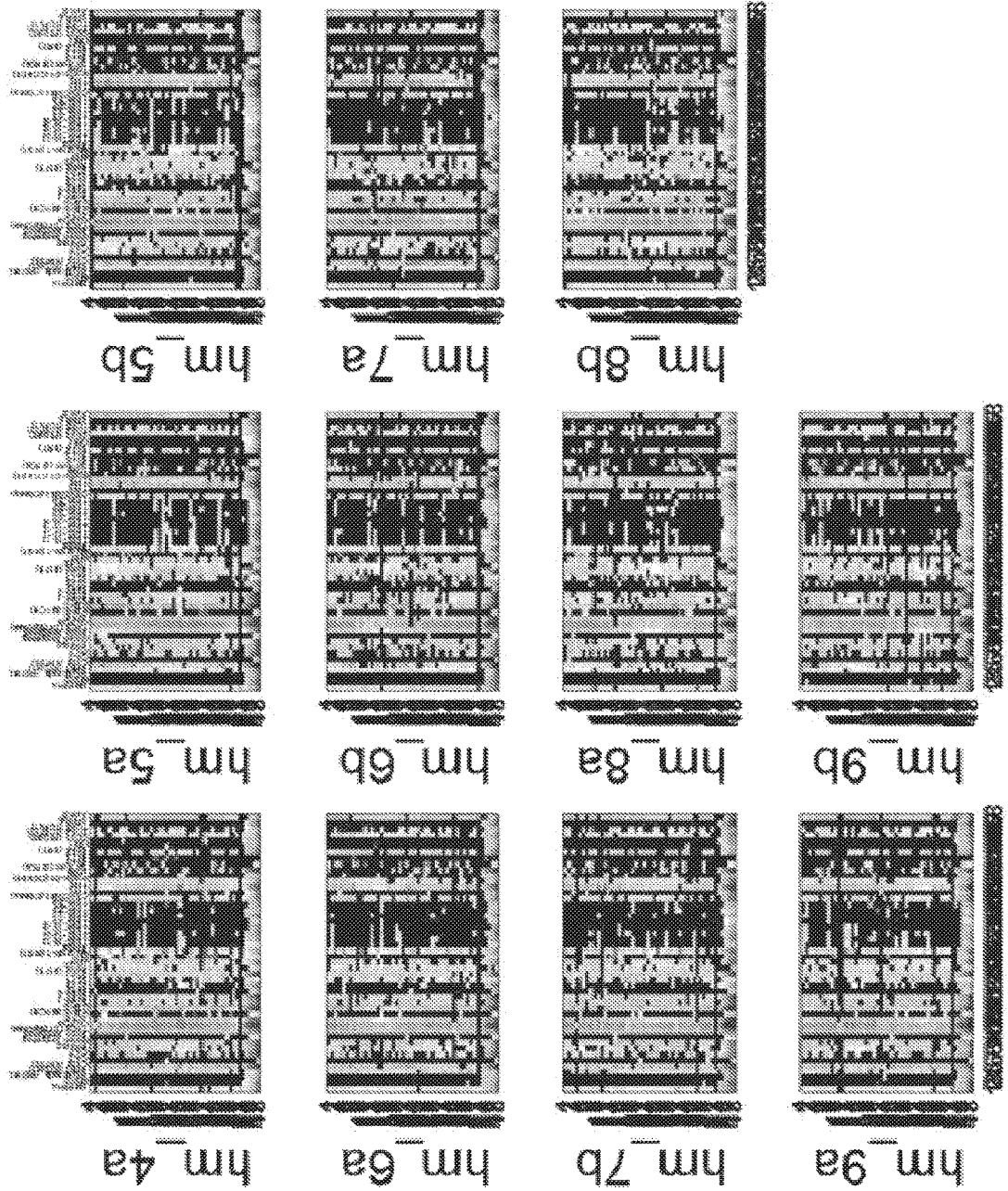
FIG. 38 colon cancer cells analyzed in a multiple chip-runs.
Figure 39:
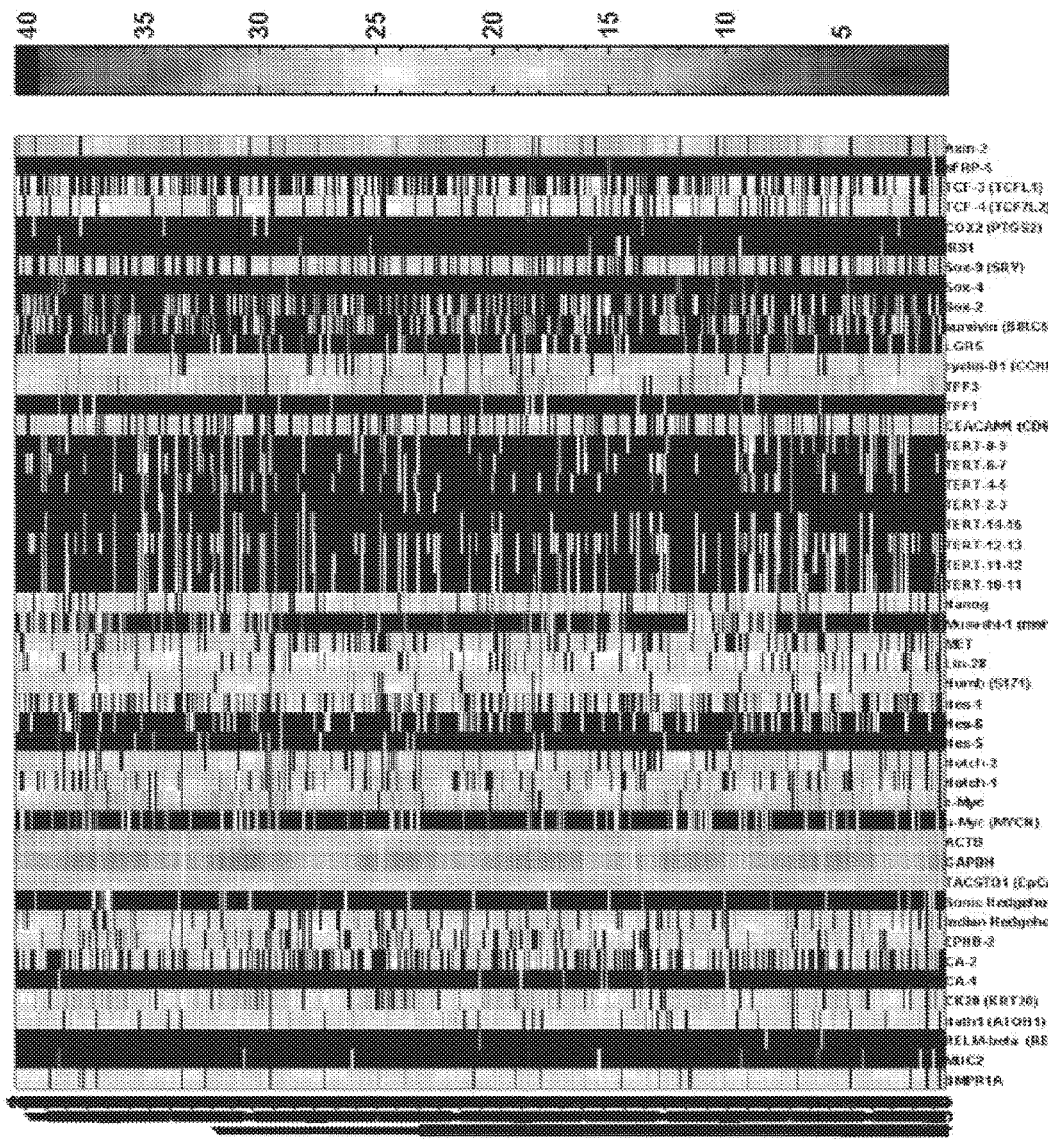
FIG. 39 Genes used for hierarchical clustering of colon cells are shown on the x-axis to the left. On the right side of the x-axis are possible gene targets. This methodology can be useful for the evaluation of colon cancers for treatment targets and normal colon for toxicity profiling.
Figure 40:
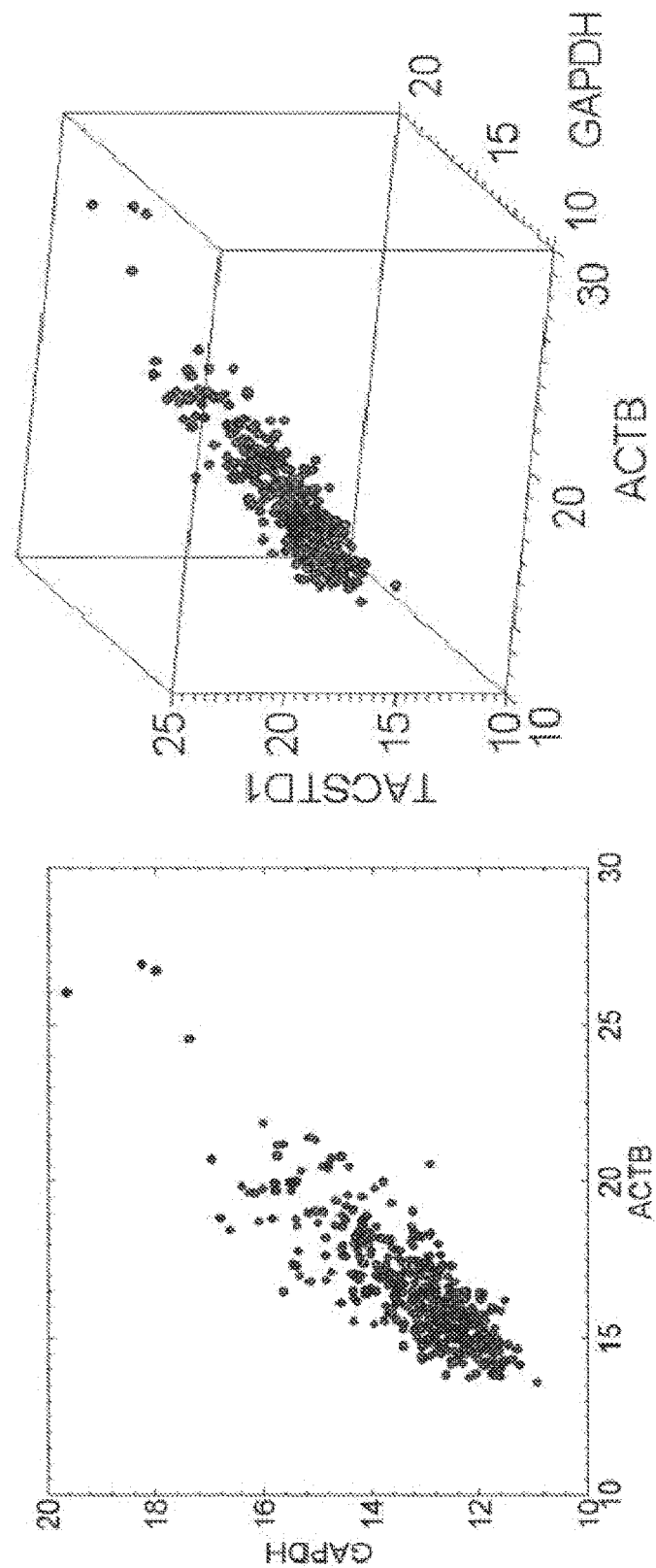
Figure 41:
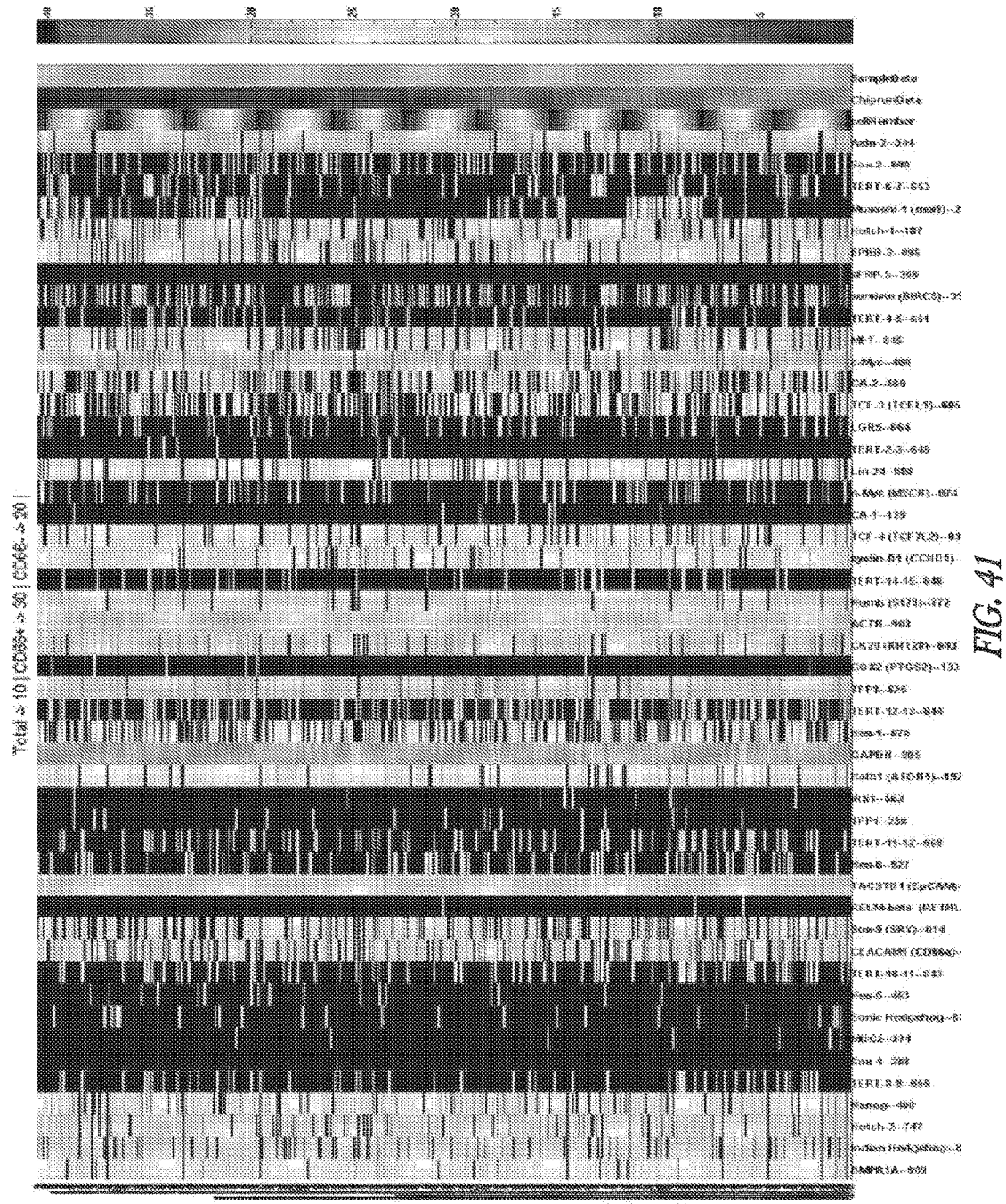
FIG. 41 a combined heat map after the clean up of unwanted cells.
Figure 42:
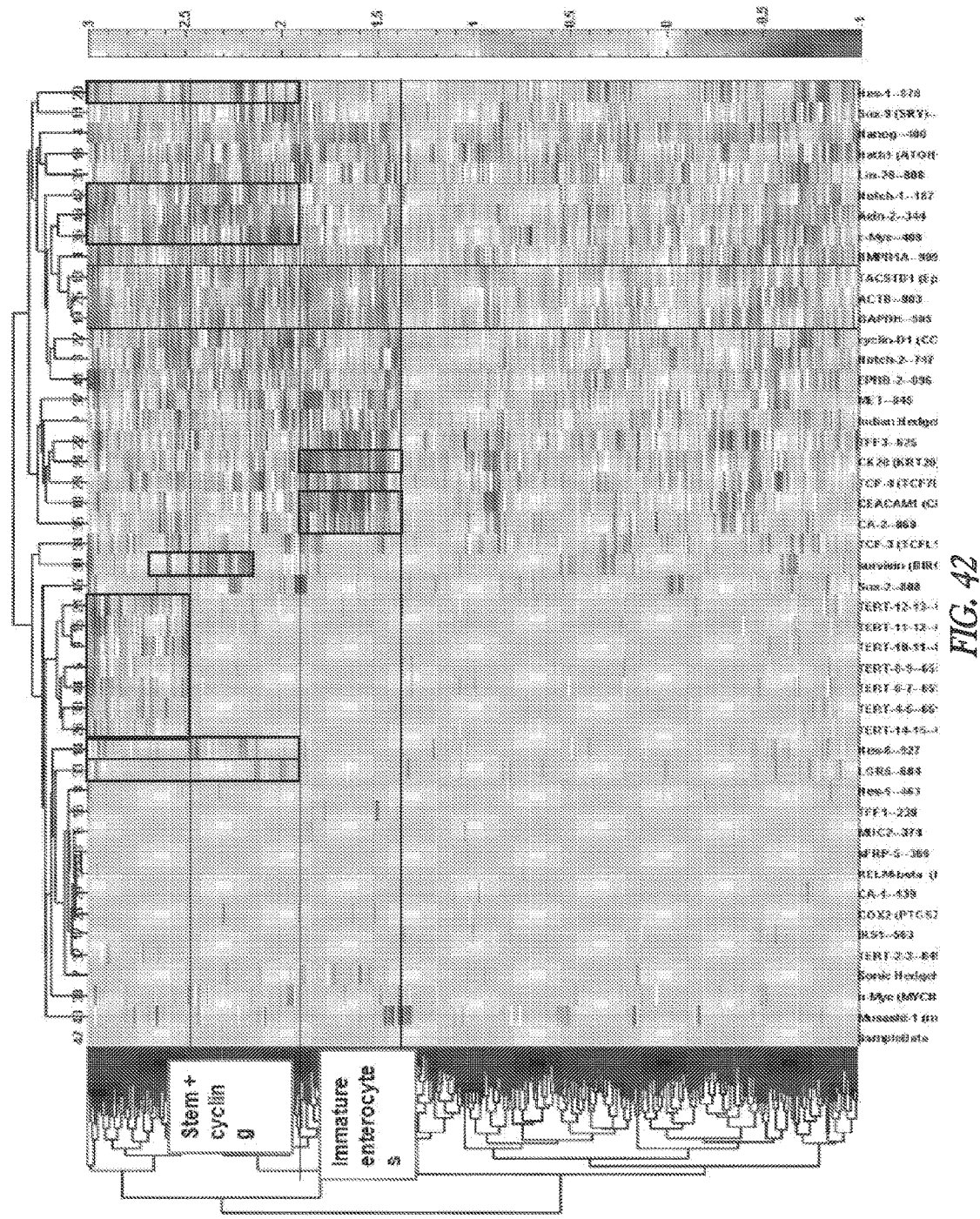
FIG. 42 hierarchical clustering by cell groups. Genes expressed in certain cell types are marked by a black square.
Figure 43:
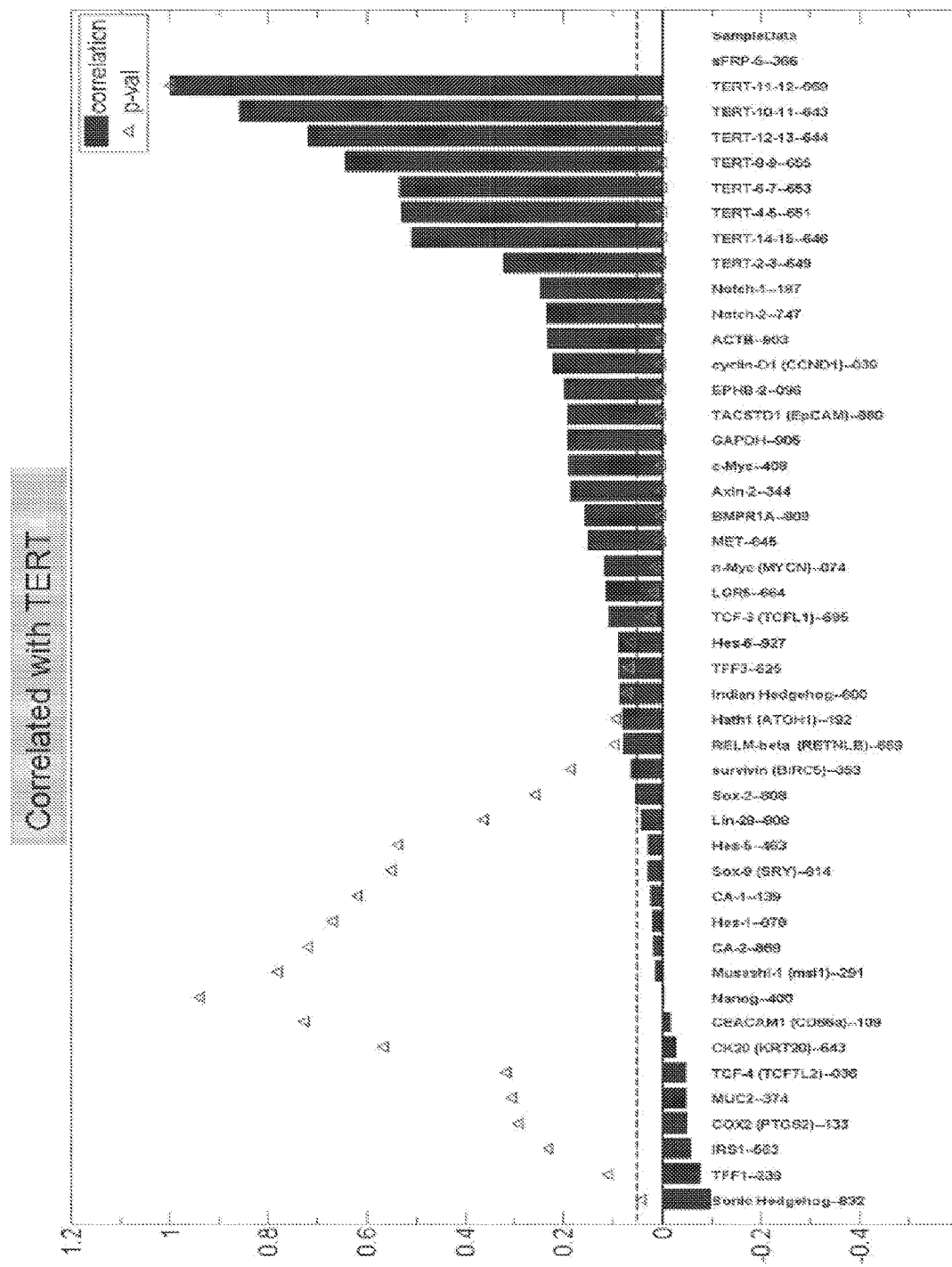
FIG. 43 shows the degree of TERT association in a bar graph.
Figure 44:
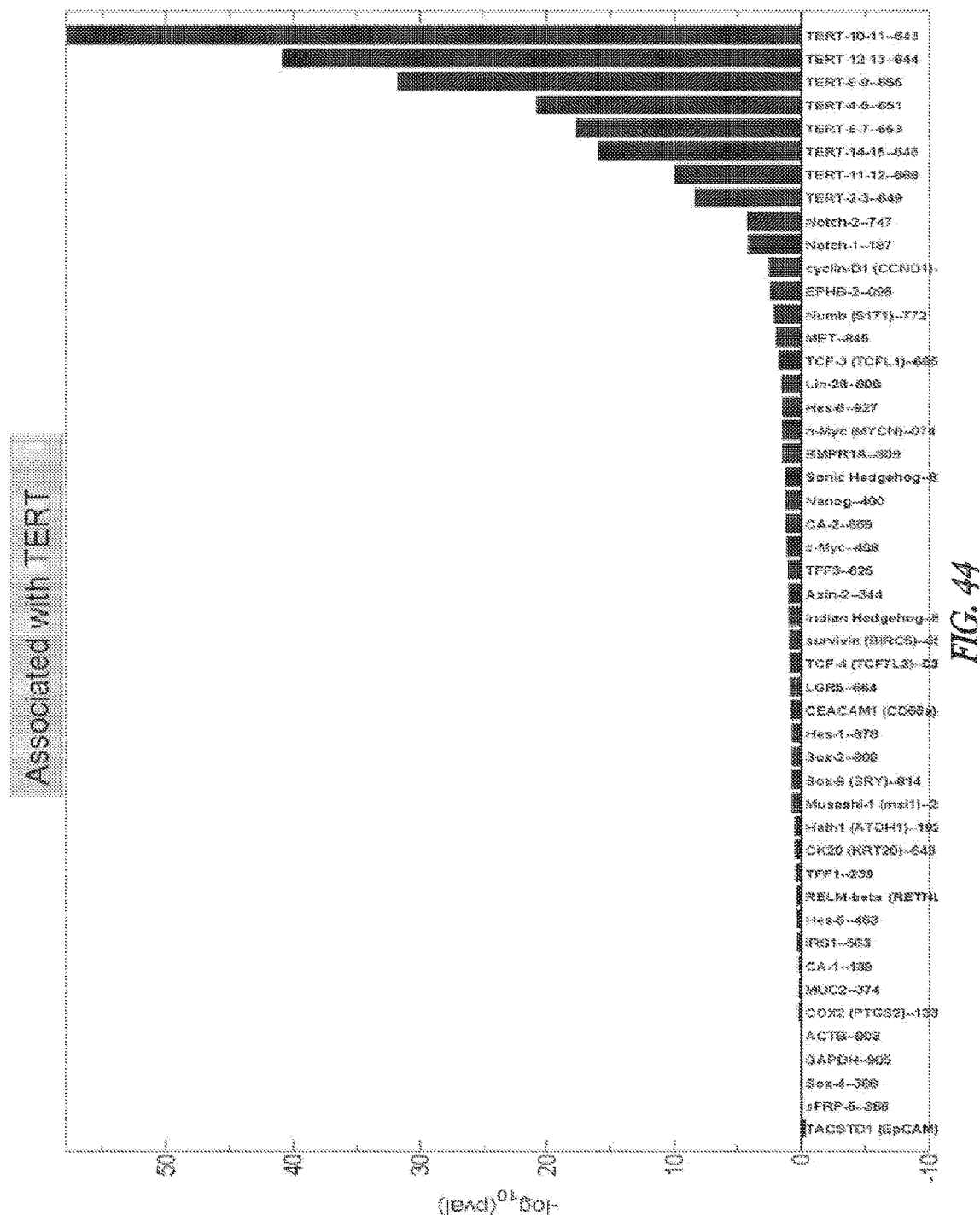
FIG. 44 gene expressions associated with TERT expression.
Figure 45:
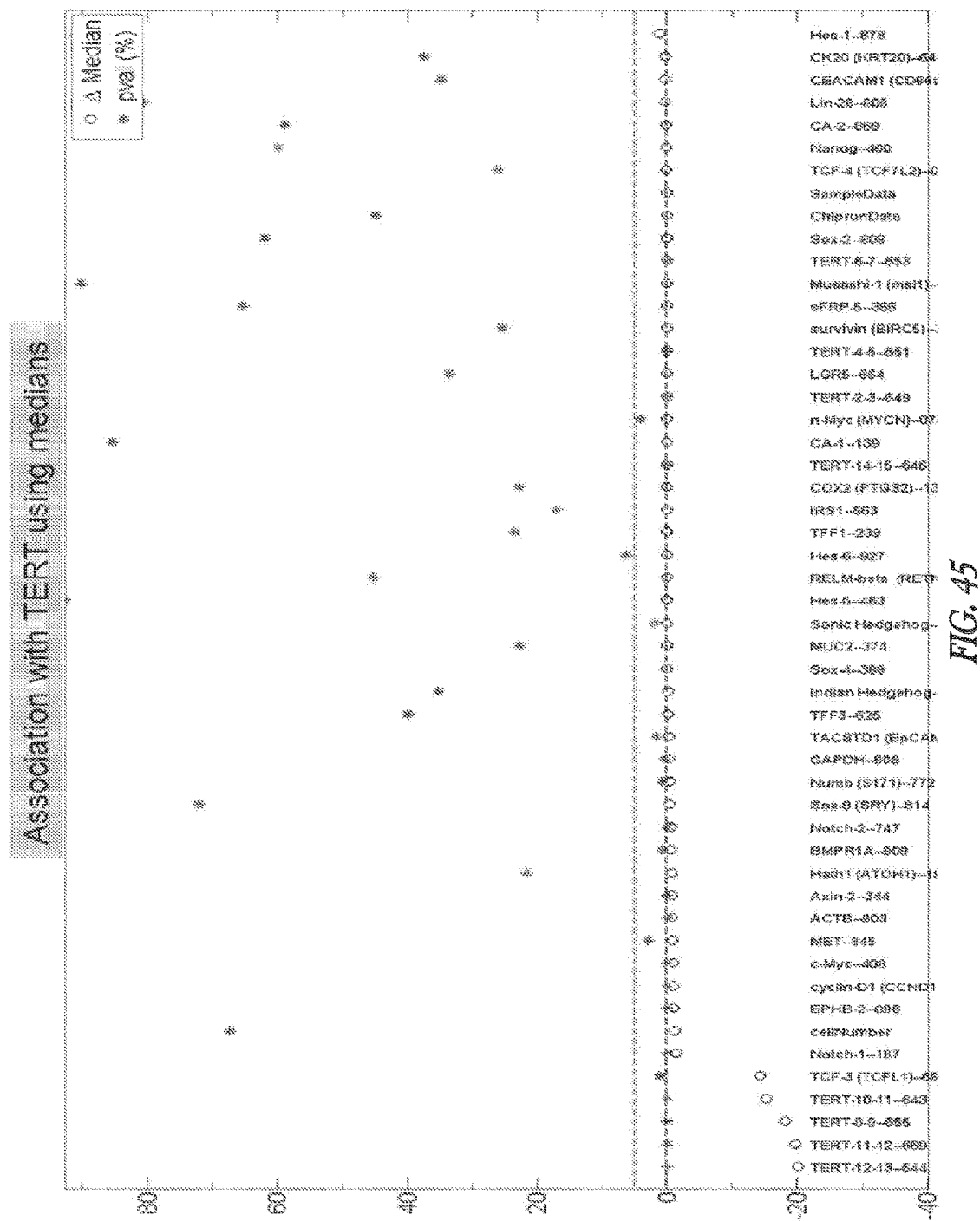
FIG. 45 gene expressions associated with TERT expression using median value.
Figure 46:
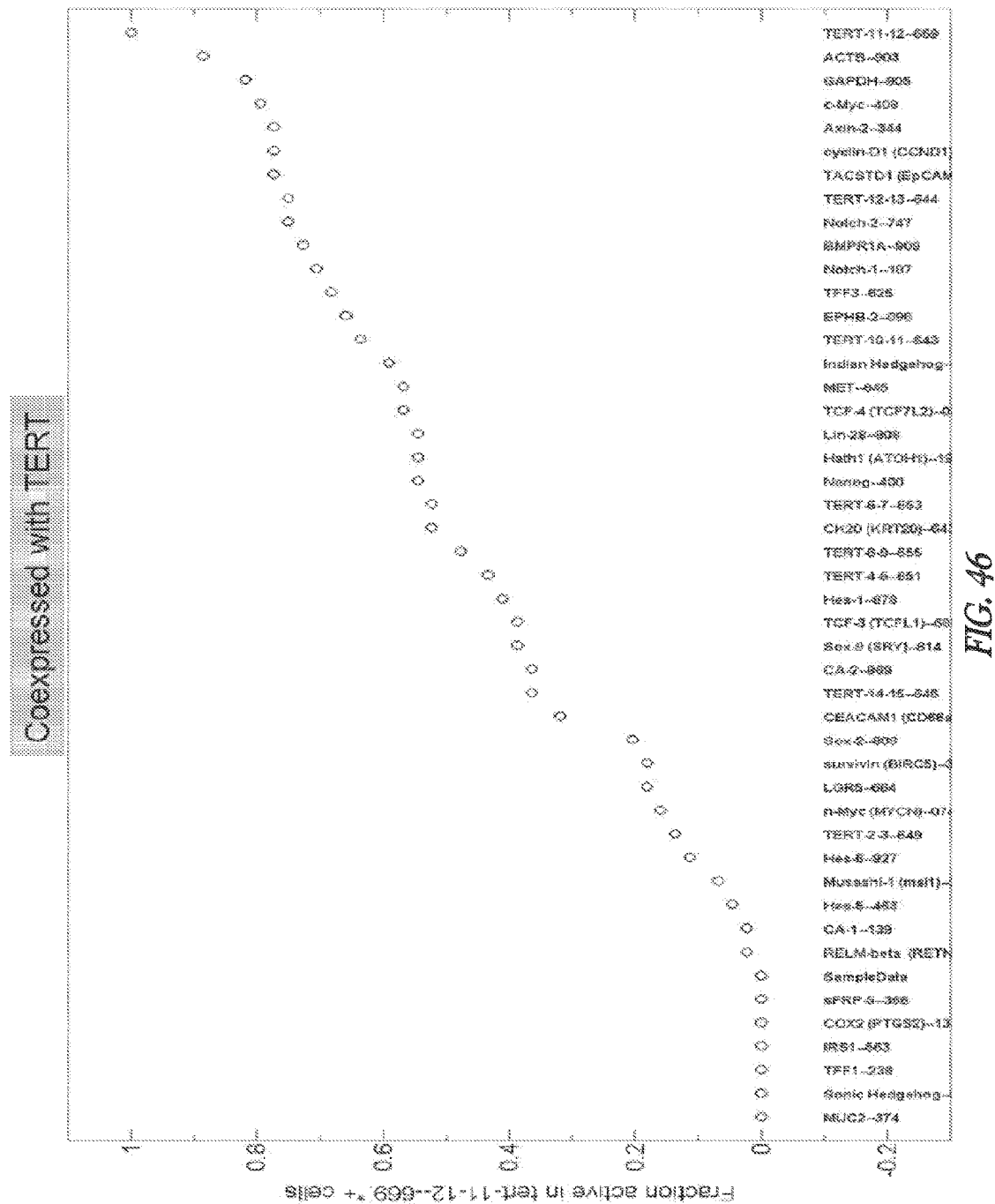
FIG. 46 genes co-expressed with TERT.
Figure 47:
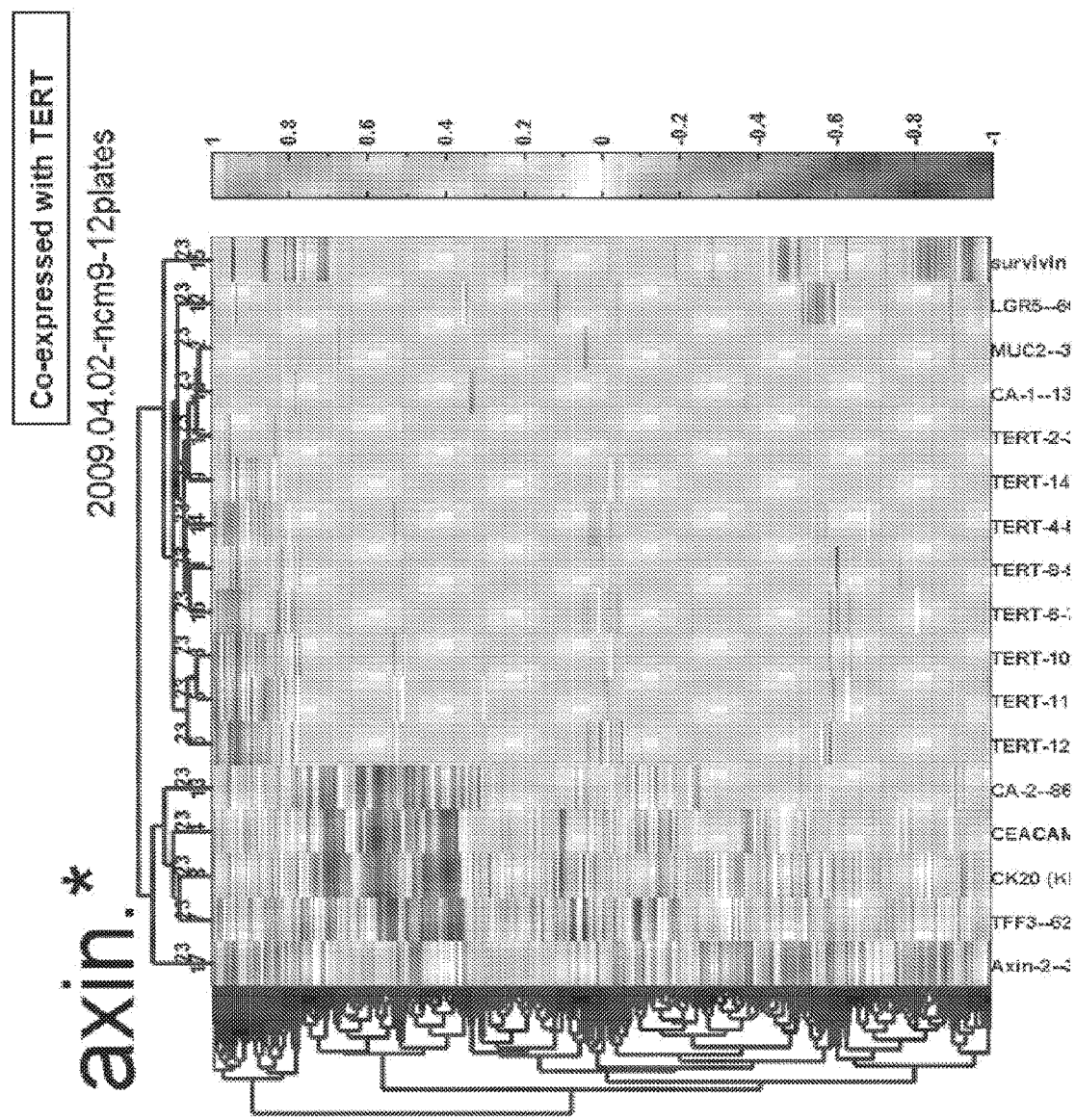
FIG. 47 AXIN is co-expressed with TERT.
Figure 63:
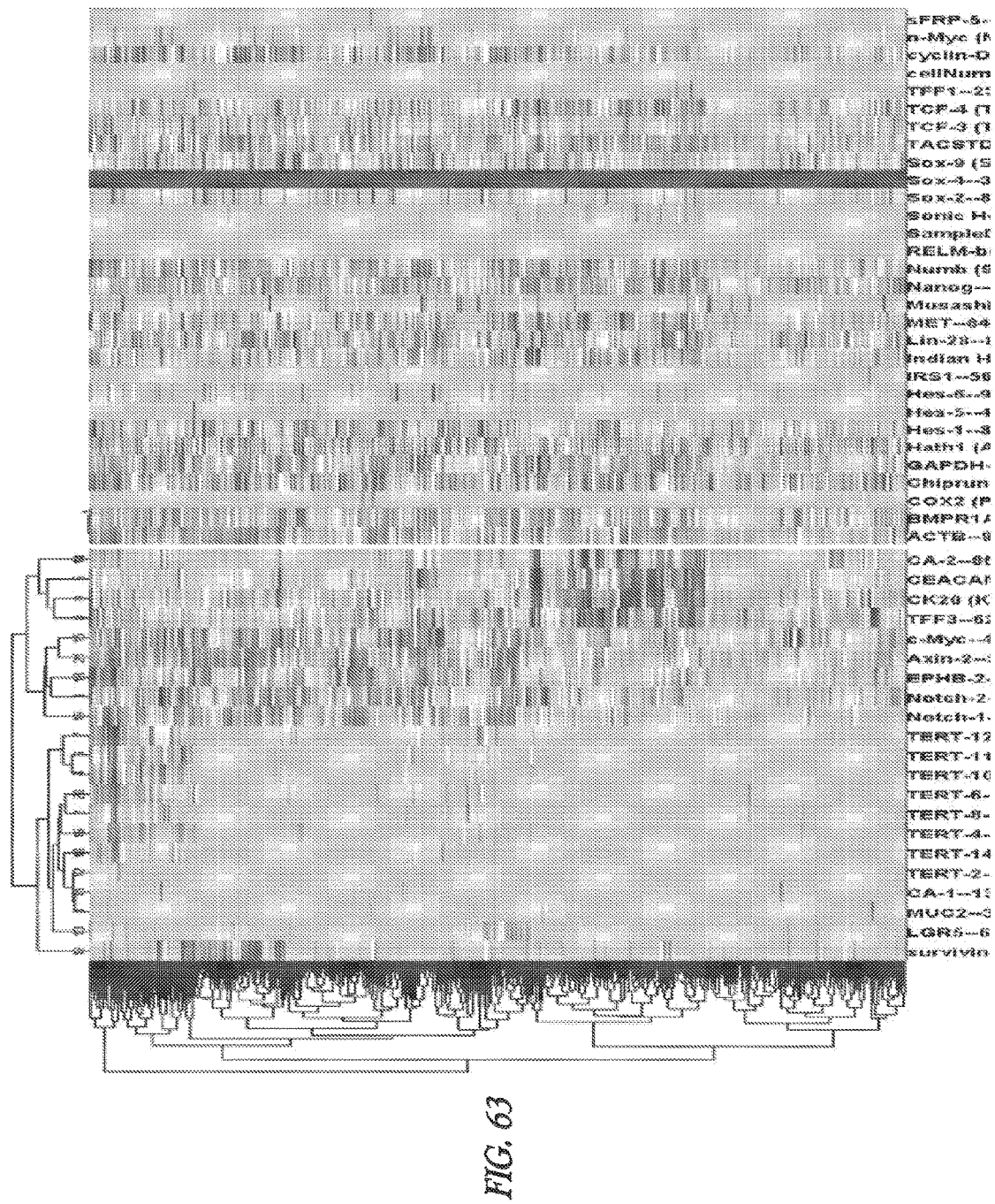
FIG. 63 hierarchical clustering of TERT expression. Gene expression patterns are identified by square box according to cell types.

Single cell gene expression analysis was performed as described above using antibodies for initial sorting by FACS. Single cell gene expression analysis was performed as described above. Colon cancer cells were analyzed in a multiple chip-runs (FIG. 38). A combined heat map is illustrated in FIG. 39. Out of 462 cells tested, 12 cells that do not express GAPDH, ACTB or EpCAM were discarded, and 450 cells were selected for further analysis (FIG. 40). A combined heat map after the clean up is illustrated in FIG. 41. Hierarchical clustering was performed and a representative illustration of the result is shown in FIG. 42. Gene expressions correlated to TERT expression were identified (FIG. 43). Gene expressions associated with TERT expression were identified (FIG. 44). Using median values, gene expressions associated with TERT expression were identified (FIG. 45). Genes co-expressed with TERT were then identified. (FIG. 46). The clustering demonstrated that AXIN, BMPR, C-MYC, CYCLIN-D1, EPHB, NOTCH, and to a certain degree TEC-3, TCF-4, and HATH were co-expressed with TERT. Genes such as IHH, LIN, MET, NANOG, N-MYC, SOX, Notch1, were not co-expressed with TERT (FIGS. 47-62). In colon8 sample, the stem cells (TERT+/LGR5+) were also SURVIVIN+. NOTCH1, NOTCH2, EPHB2, AXIN2, and C-MYC were associated with stem and cycling cell populations. SHH and TCF-4 were associated with immature enterocytes. HES-1, 5, 6 were associated with both stem and cycling, and immature enterocyte populations (FIG. 63).

Example 16: Analysis of Non-Tumorigenic and Tumorigenic Progeny

Figure 64:
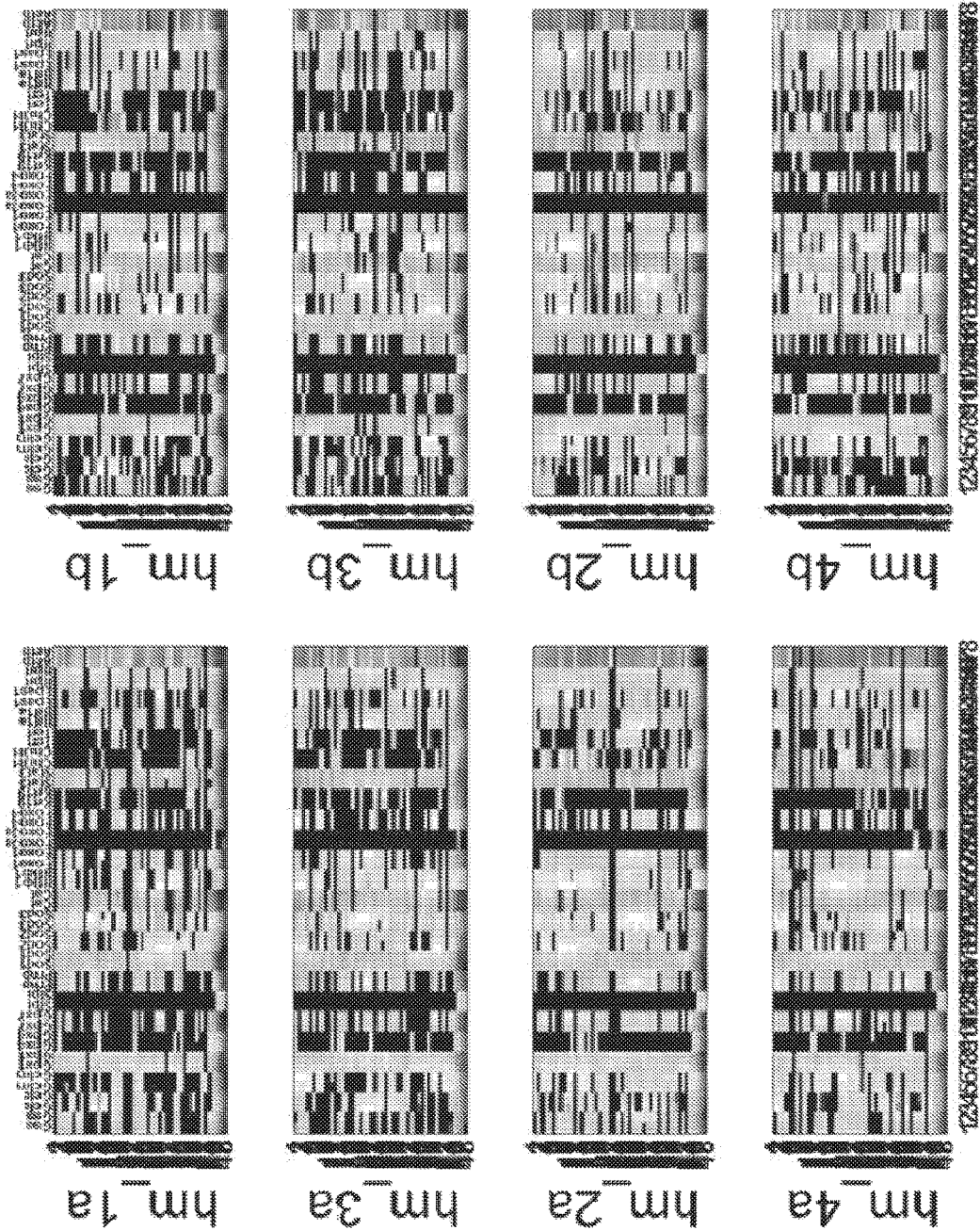
FIG. 64 chip-runs performed with cells from non-tumorigenic (NTG) progeny or tumorigenic (TG) progeny.
Figure 65:
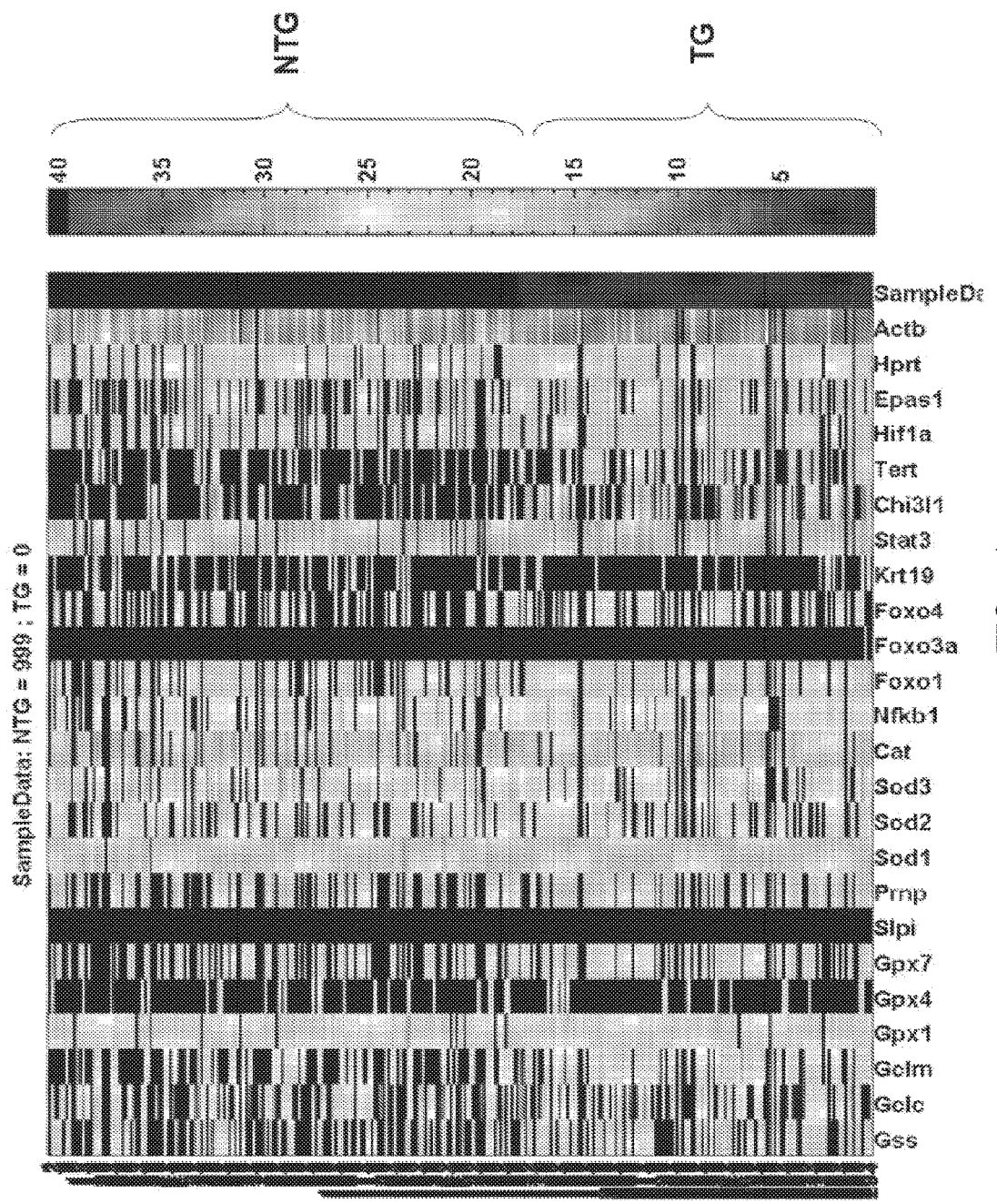
FIG. 65 a combined heat map comparing the eight chip-runs using cells from non-tumorigenic (NTG) progeny or tumorigenic (TG) progeny.
Figure 66:
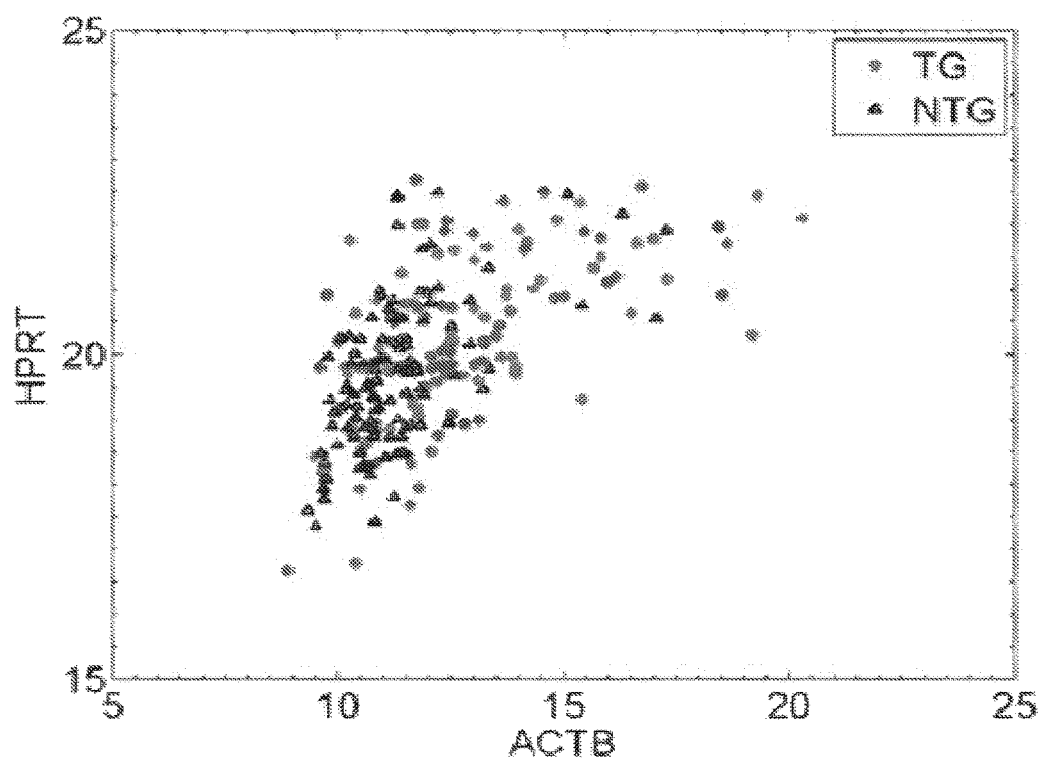
FIG. 66 selection of cells for single cell gene expression analysis. Both TG and NTG cells were plotted on a scatter-plot according to HPRT or ACTB expression levels.
Figure 67:
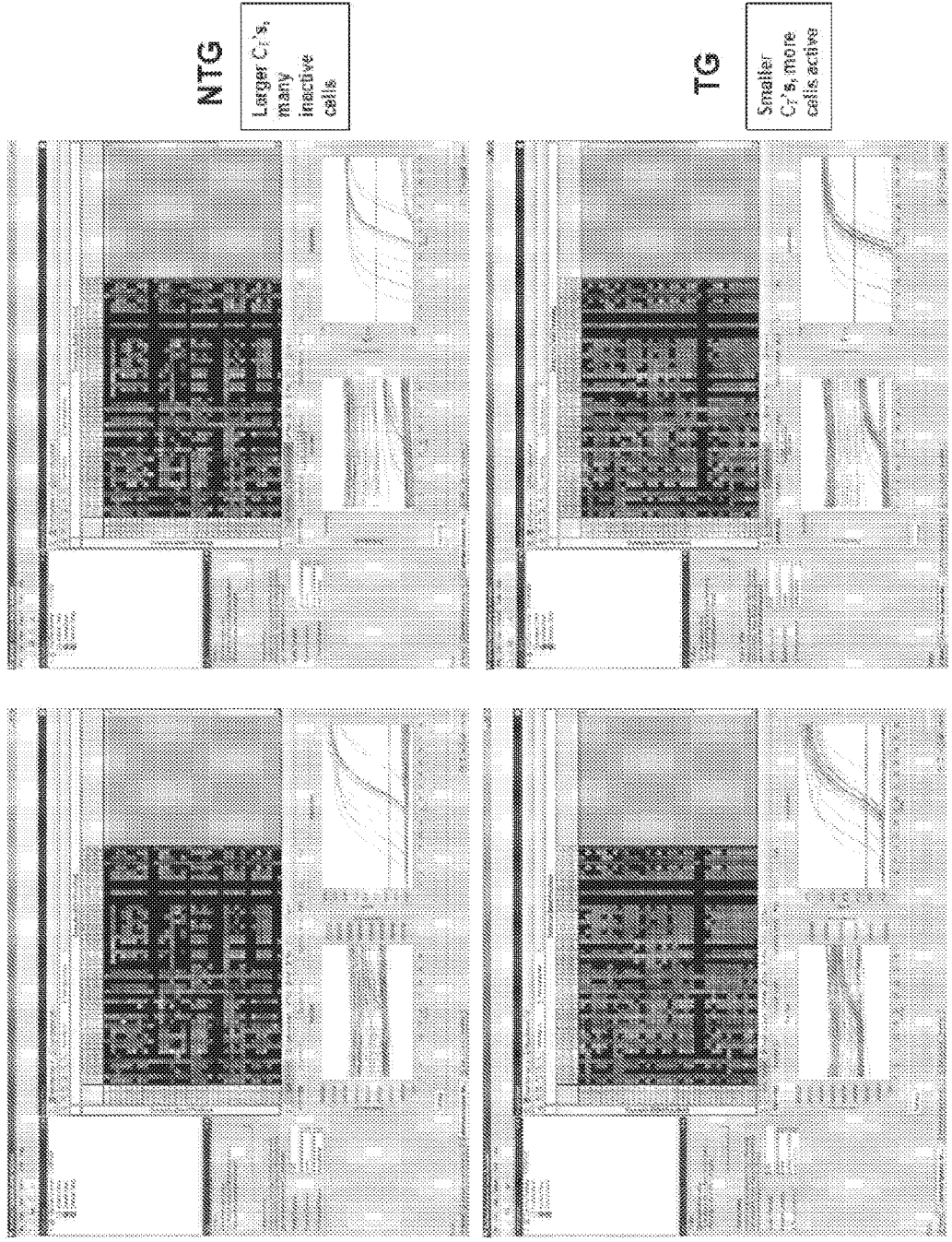
FIG. 67 Gclm qPCR curves generated from NTG and TG cells.
Figure 69:
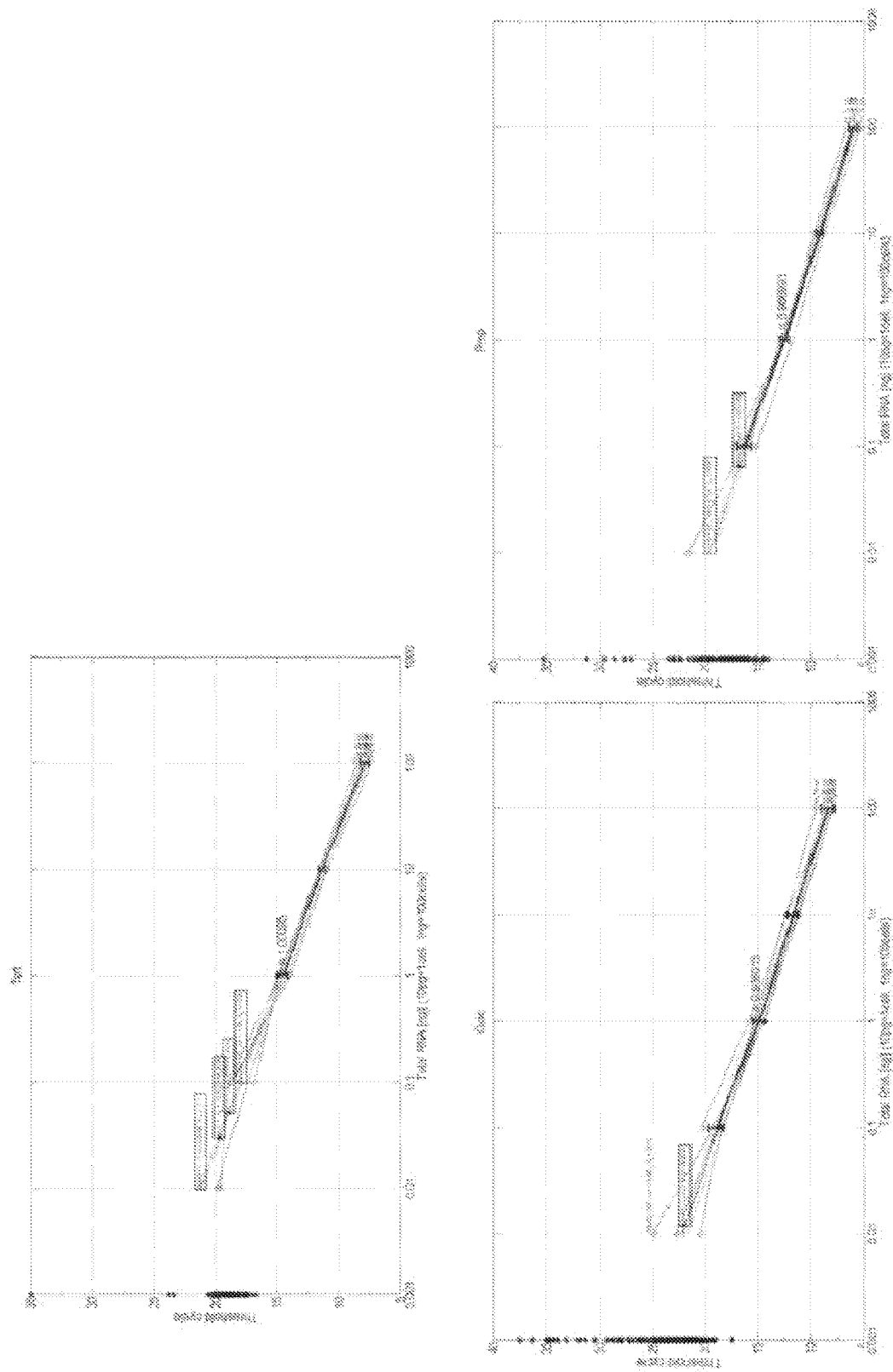
FIG. 69 standard curves of TERT, GCLC and PRNP generated from the qPCR reactions of NTG and TG cells.
Figure 70:
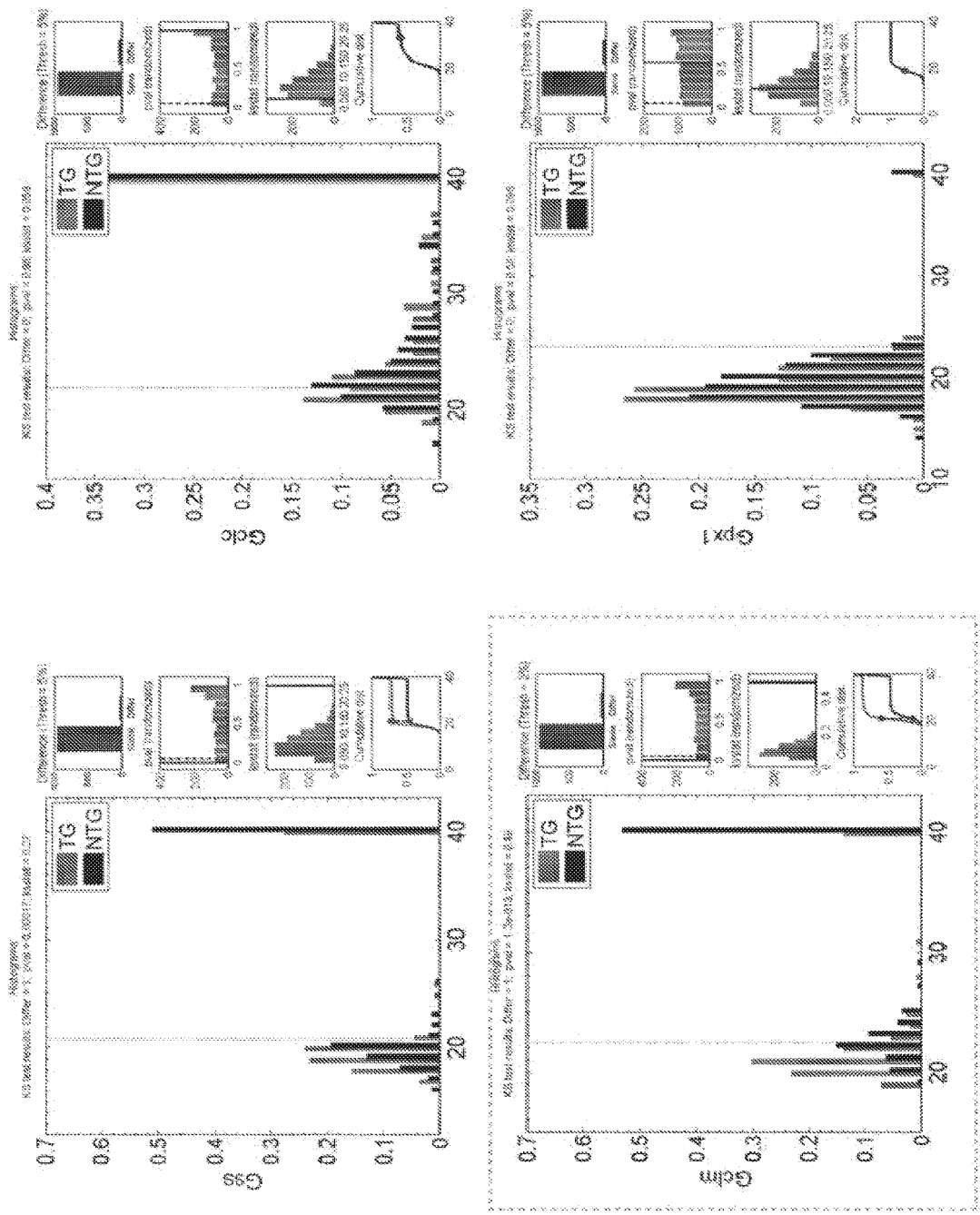
FIG. 70 histograms depicting gene expression levels in TG or NTG cells of GSS, GCLM, GCLC, and GPX.
Figure 71:
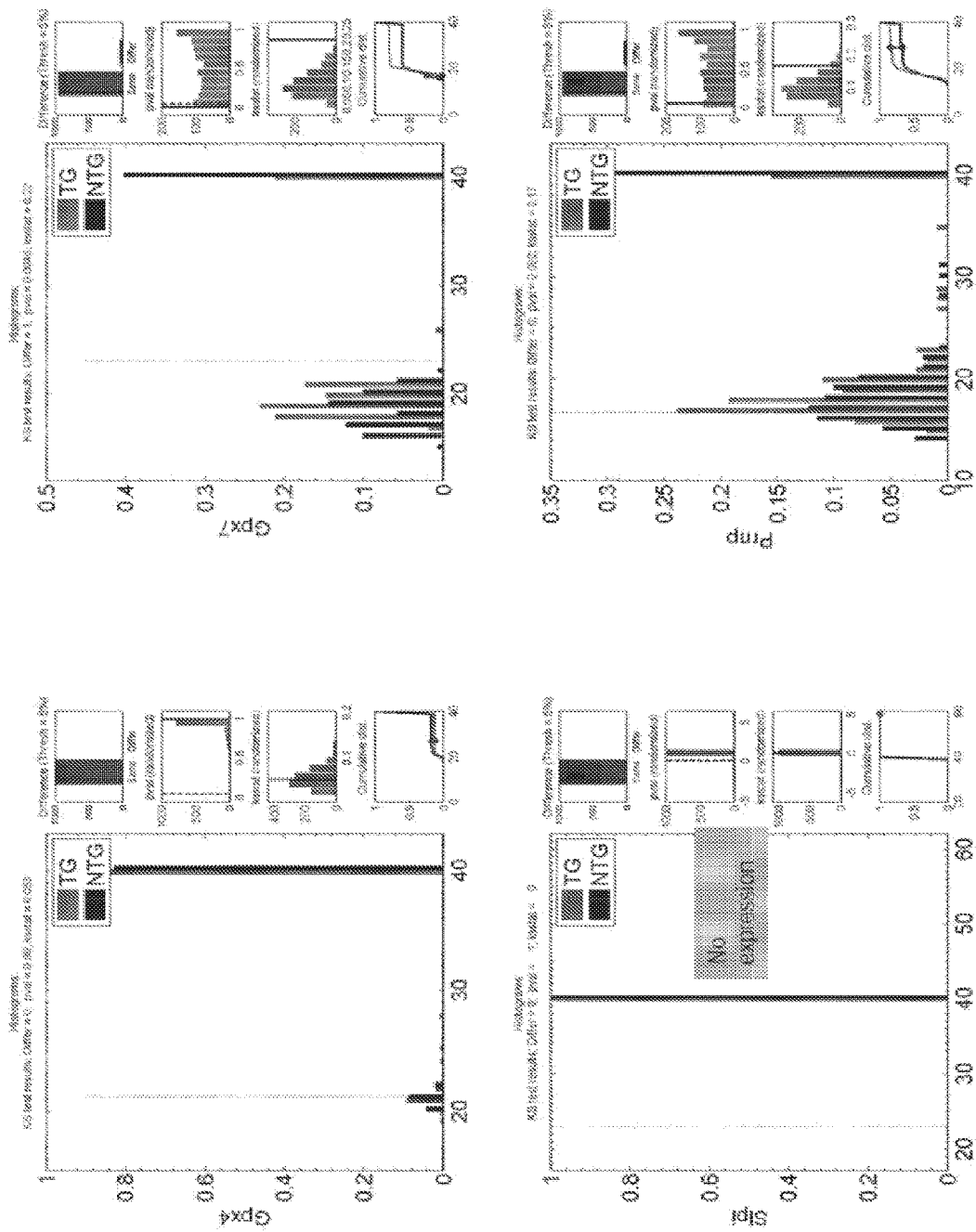
FIG. 71 histograms depicting gene expression levels in TG or NTG cells of gpx4, gpx7, slpi, AND prnp.
Figure 72:
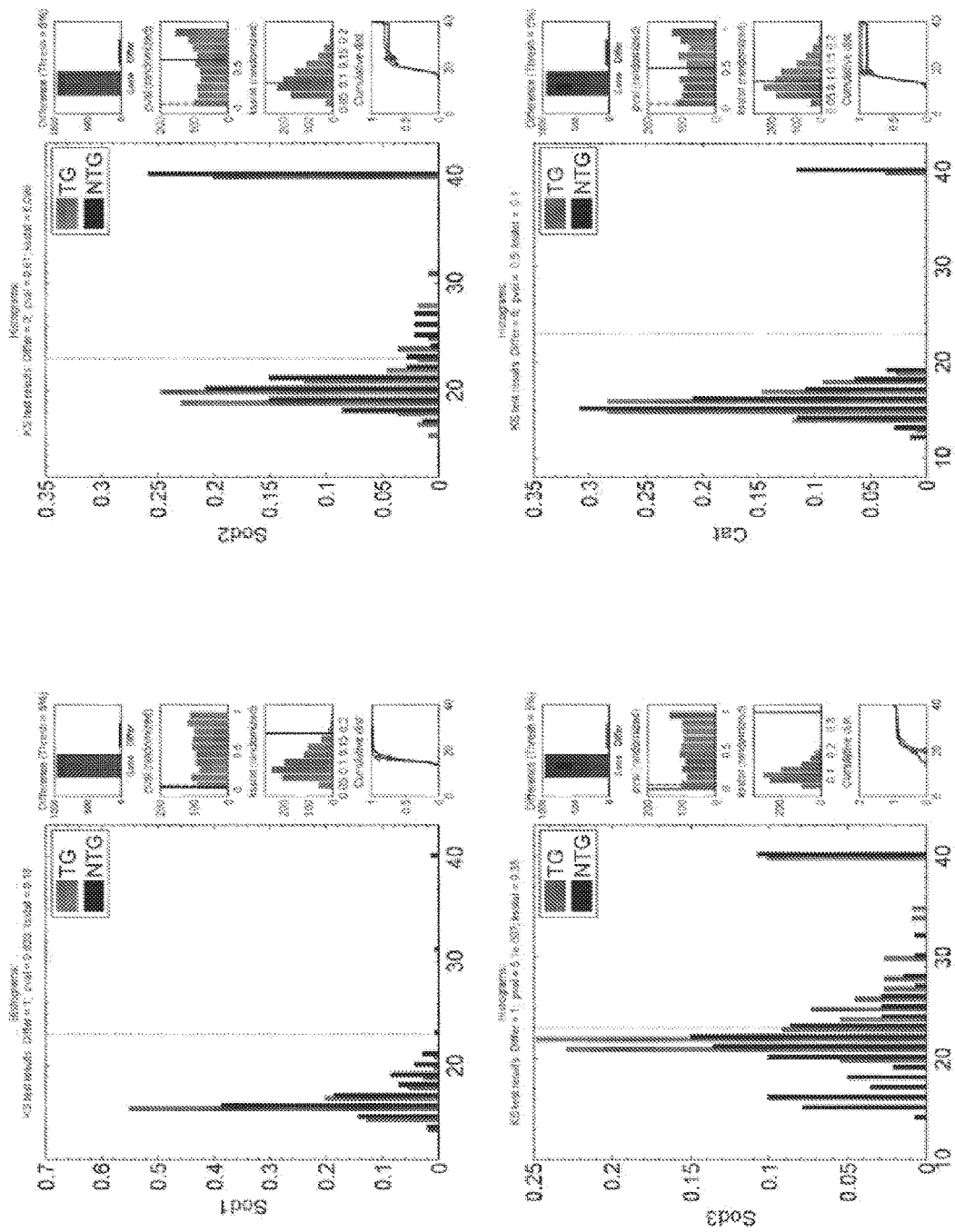
FIG. 72 histograms depicting gene expression levels in TG or NTG cells of SOD1, SOD2, SOD3, and CAT.
Figure 73:
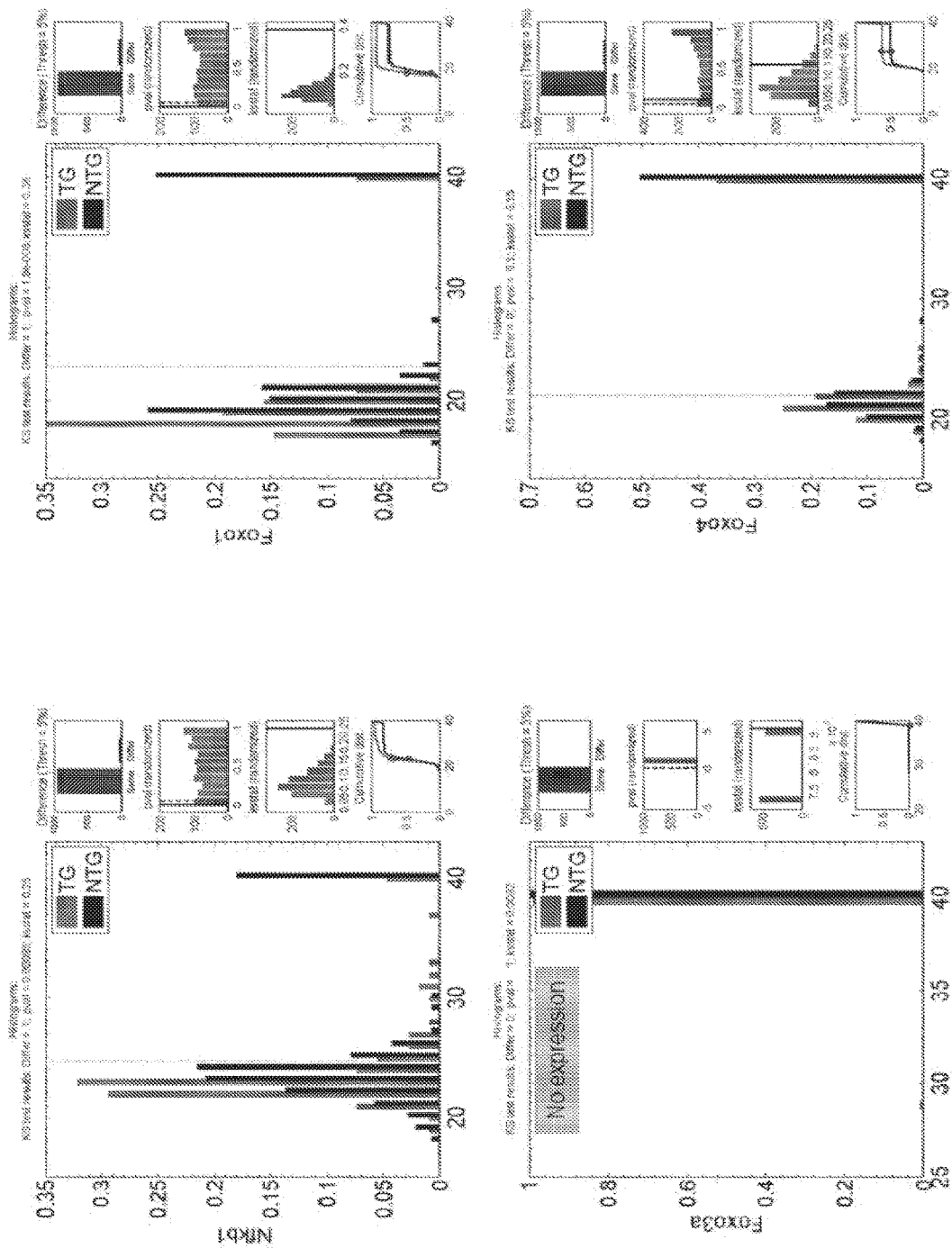
FIG. 73 histograms depicting gene expression levels in TG or NTG cells of NFKB1, FOXO1, FOX3A, and FOXO4.
Figure 74:
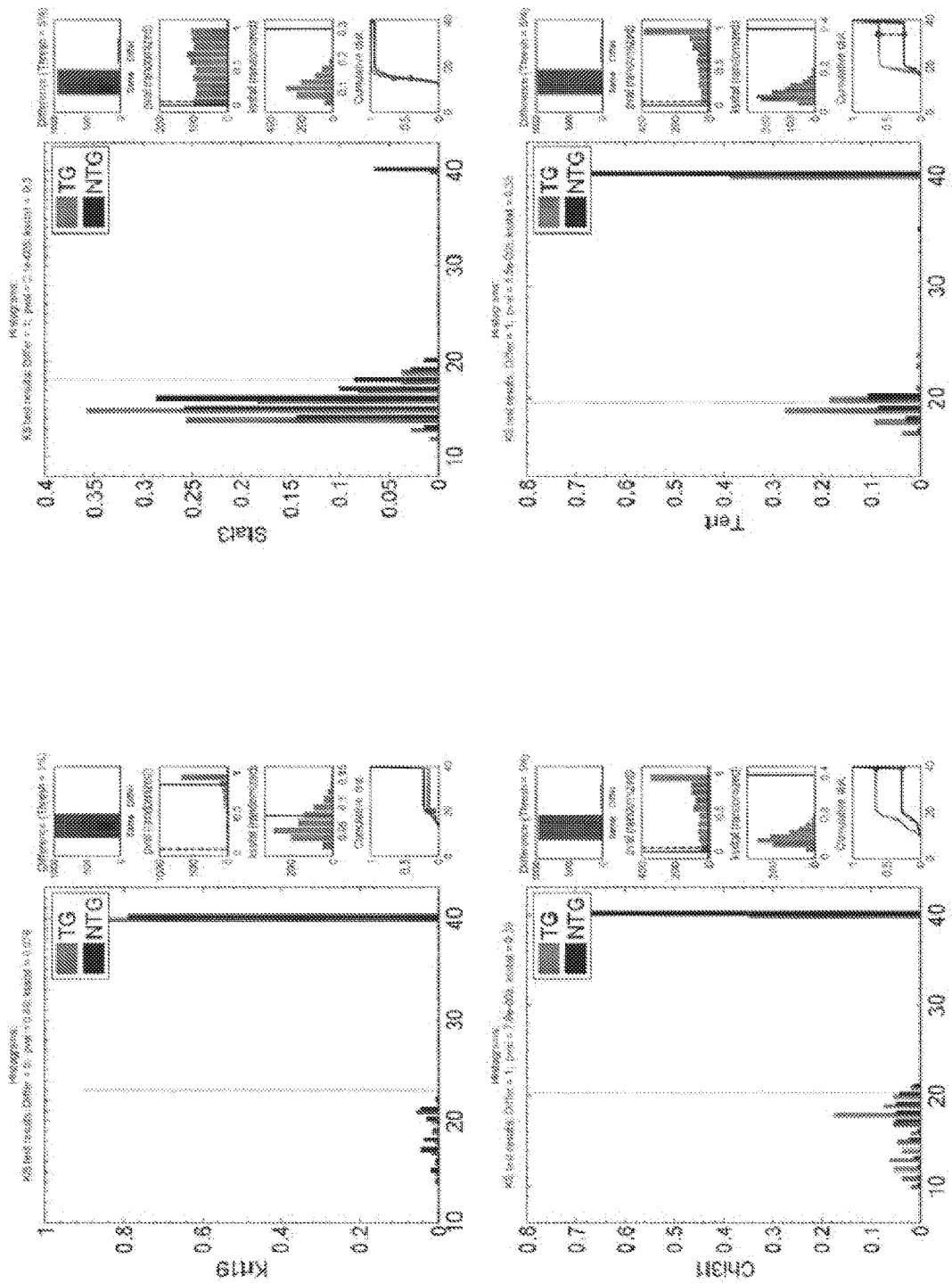
FIG. 74 histograms depicting gene expression levels in TG or NTG cells of KRT19, STAT3, CHI311, and TERT.
Figure 75:
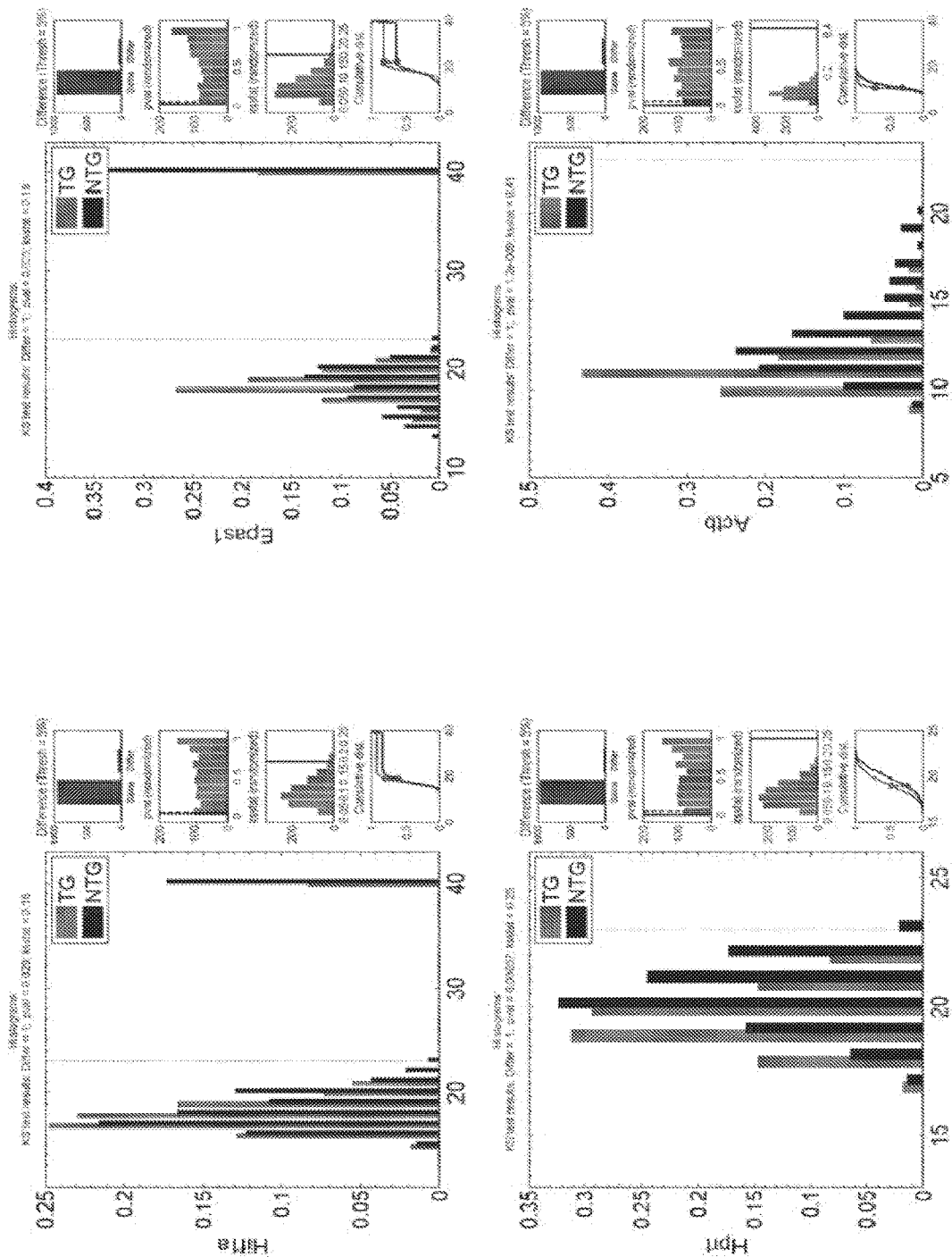
FIG. 75 histograms depicting gene expression levels in TG or NTG cells of HIF1, EPAS1, HPRT, and ACTB.
Figure 76:
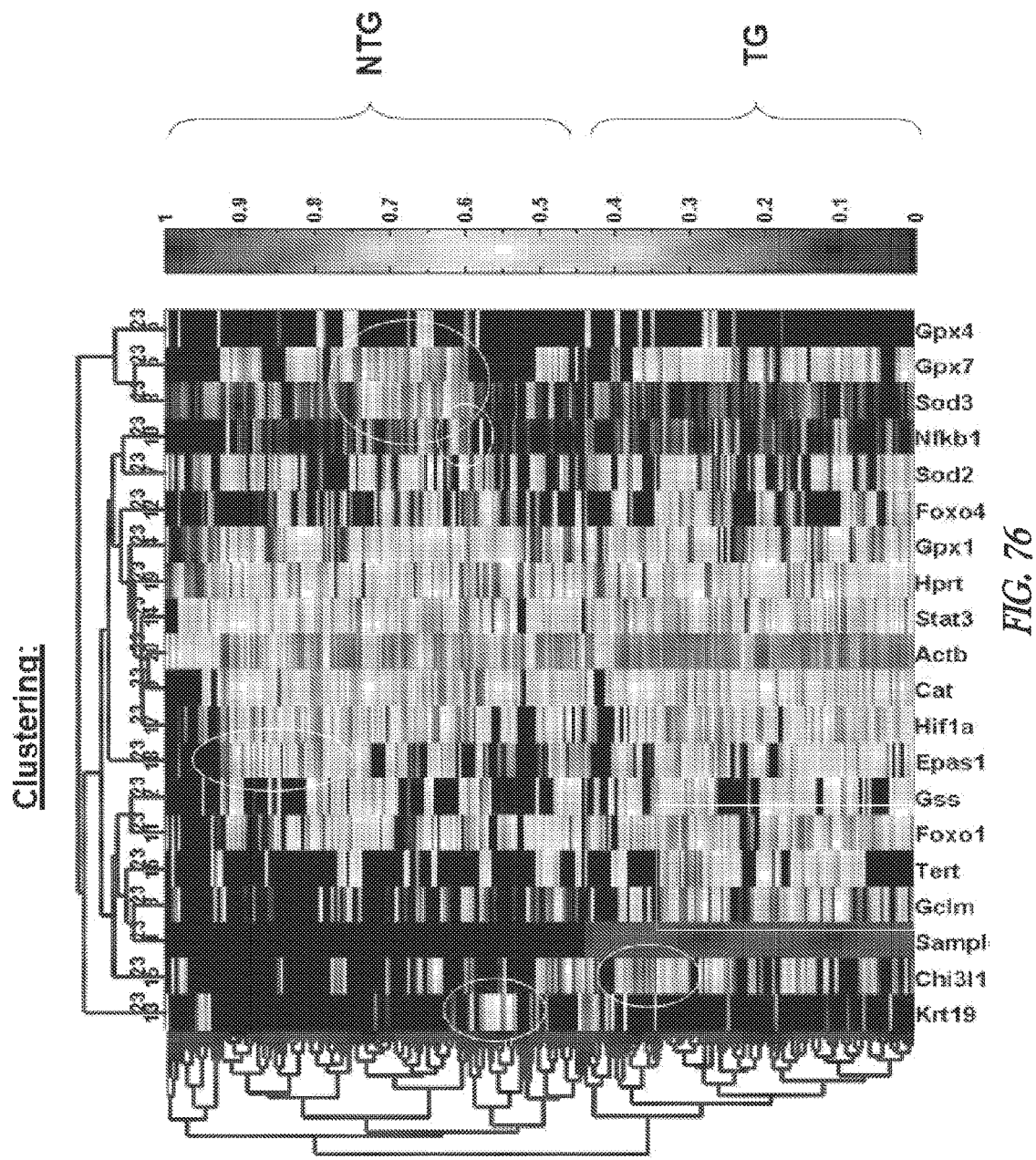
FIG. 76 hierarchical clustering of TG and NTG cells, identifying clusters of genes expressed in certain cells (circle and square).
Figure 77:
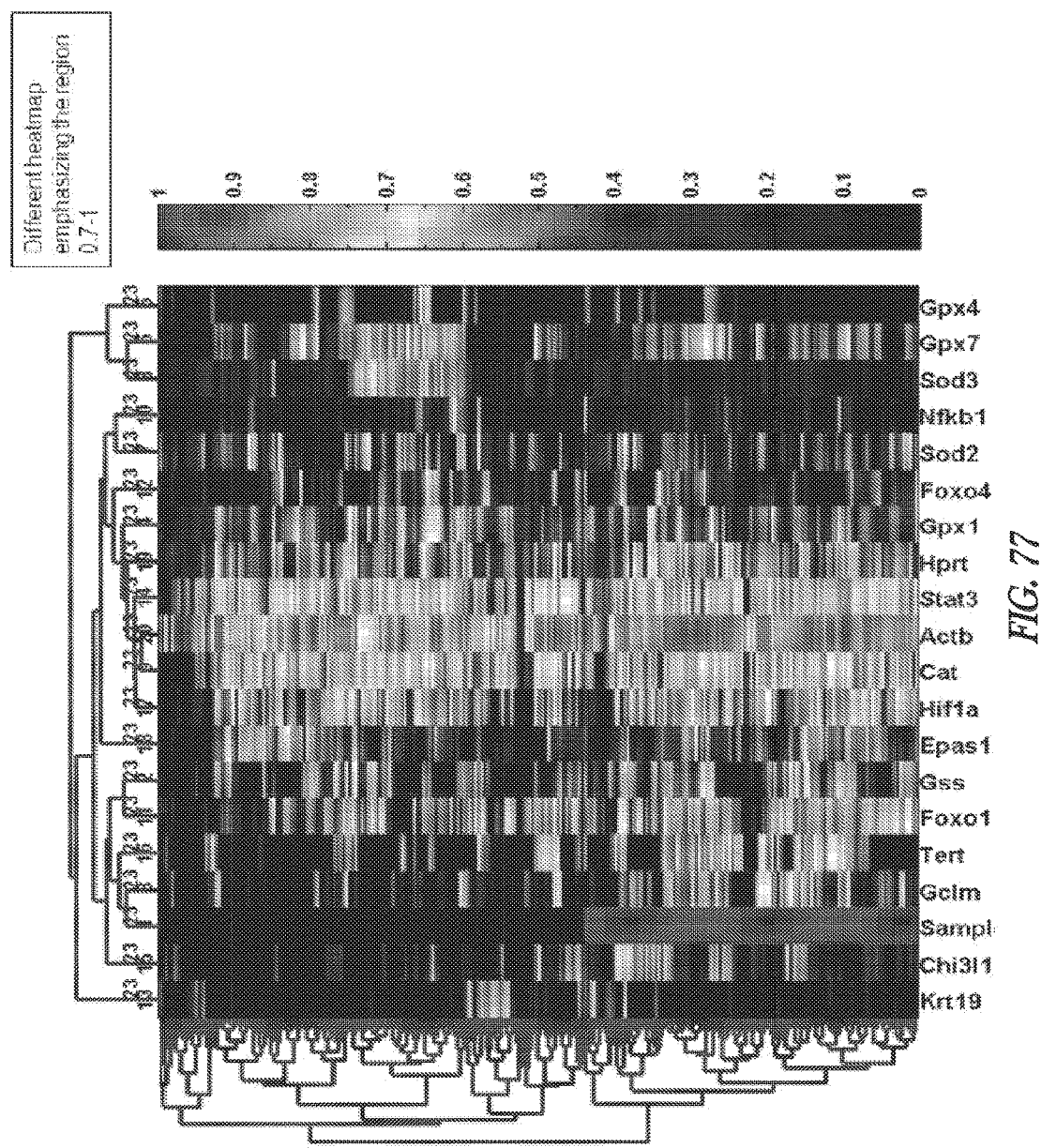
FIG. 77 differential heat map emphasizing the region 0.7 to 1.
Figure 78:
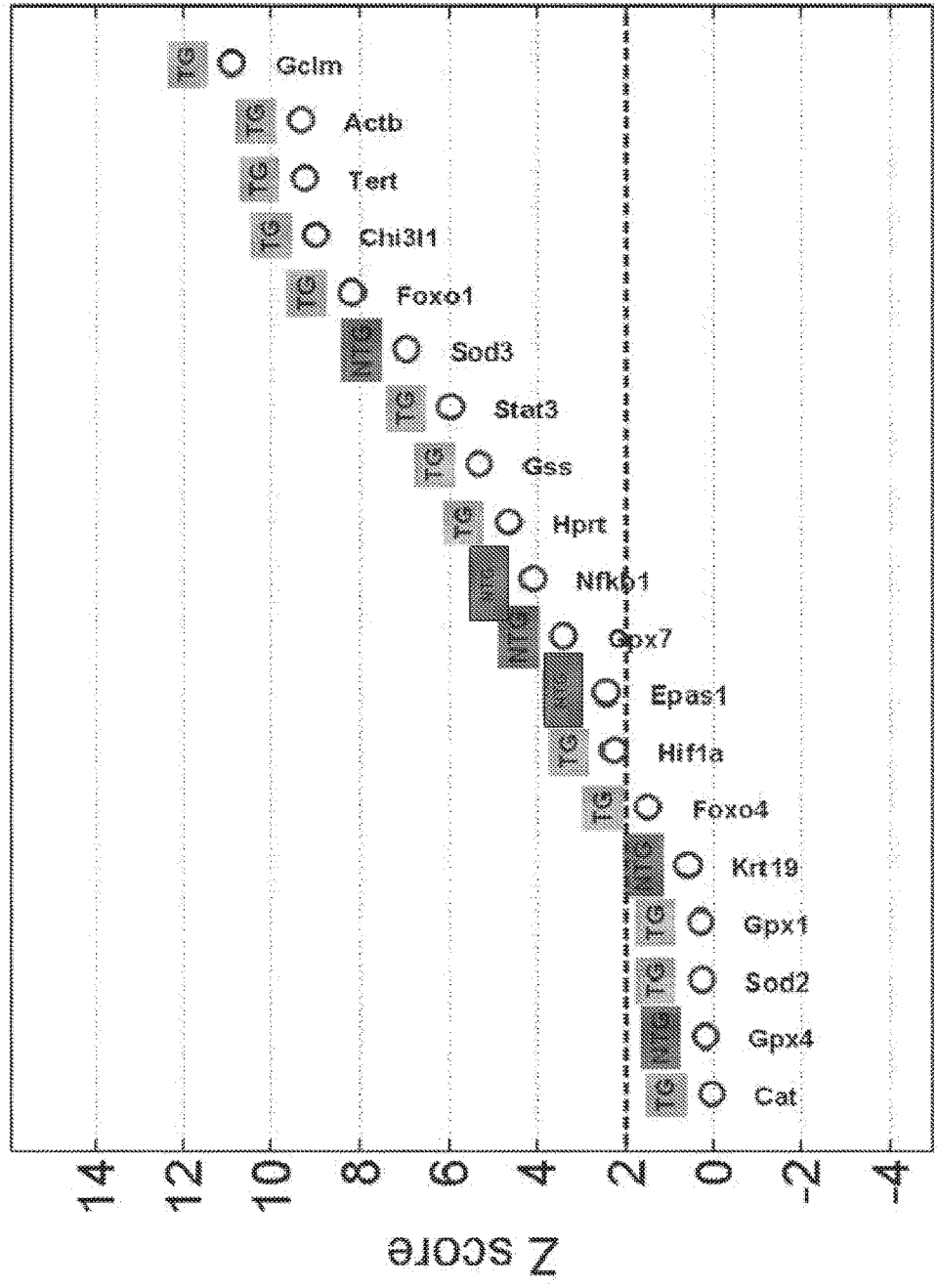
FIG. 78 Kolmogorov-Smirnov statistical significance test for genes expressed in TG or NTG cells, plotted against Z-score.
Figure 79:
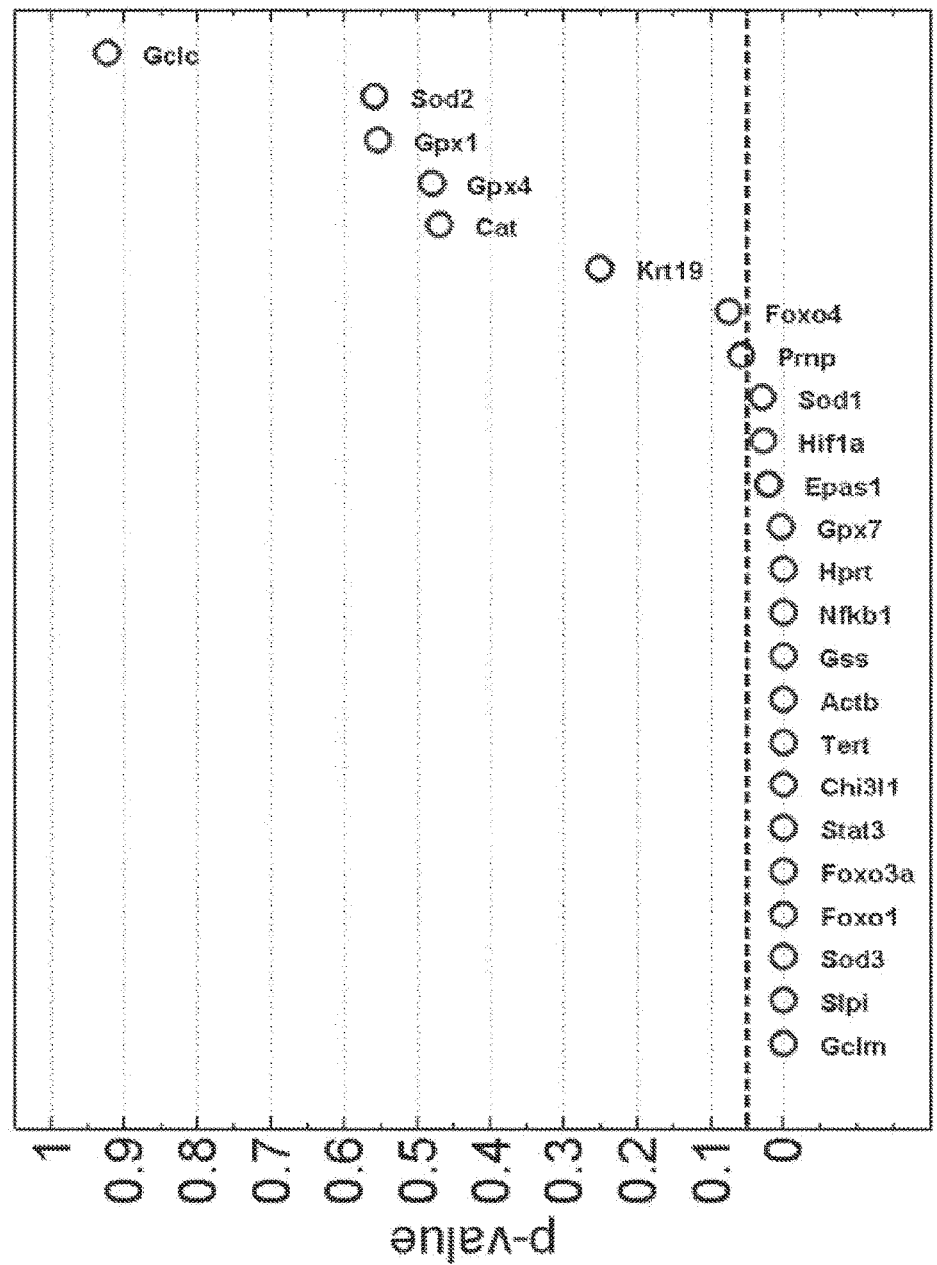
FIG. 79 Kolmogorov-Smirnov statistical significance test for genes expressed in TG or NTG cells, plotted against p-value.
Figure 80:
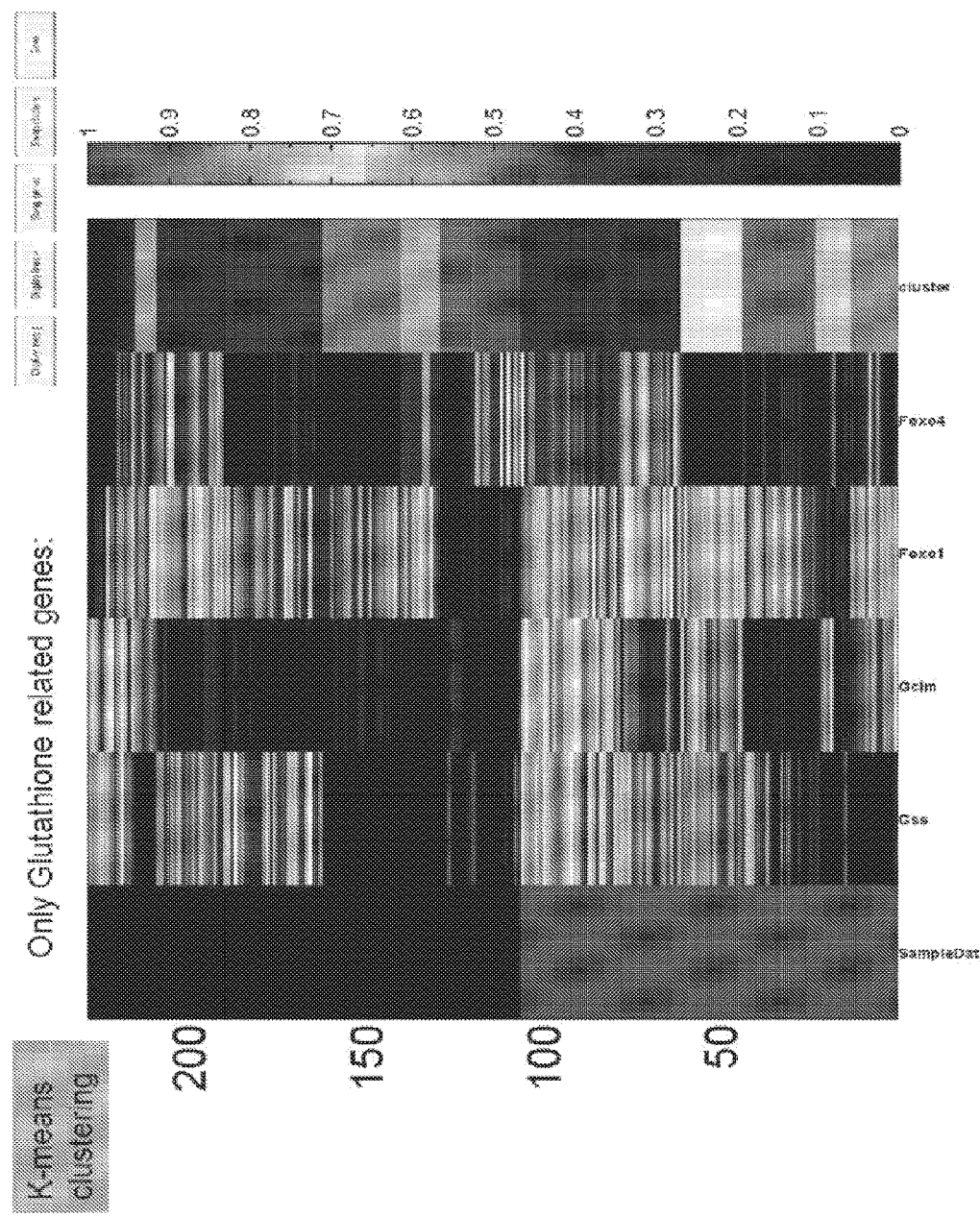
FIG. 80 hierarchical clustering of only glutathione-related genes as a heat map using k-means clustering method.
Figure 81:
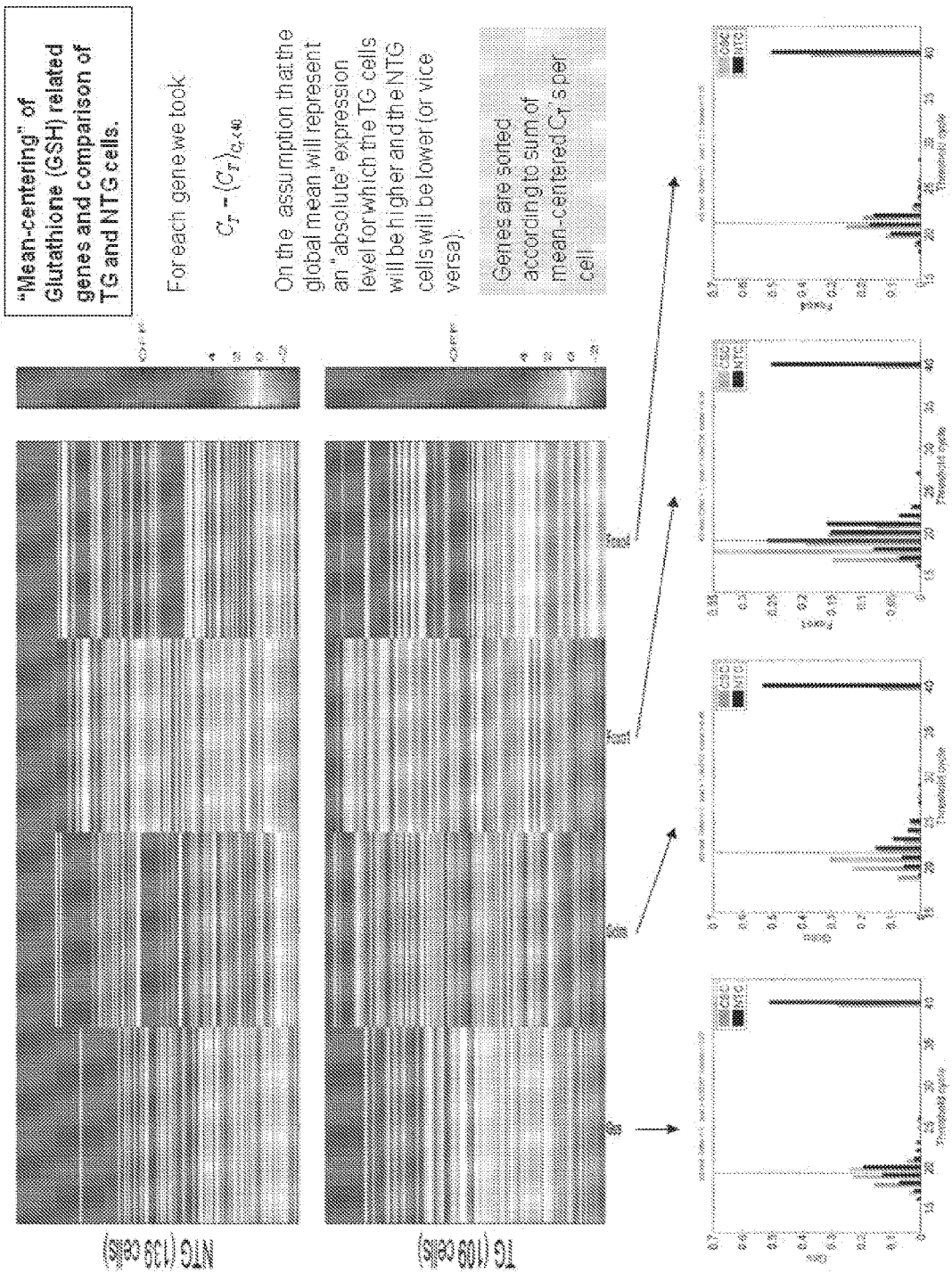
FIG. 81 TG and NTG cells compared in mean-clustering of glutathione-related genes such as GSS, GCLM, FOXO1, and FOXO4.
Figure 82:
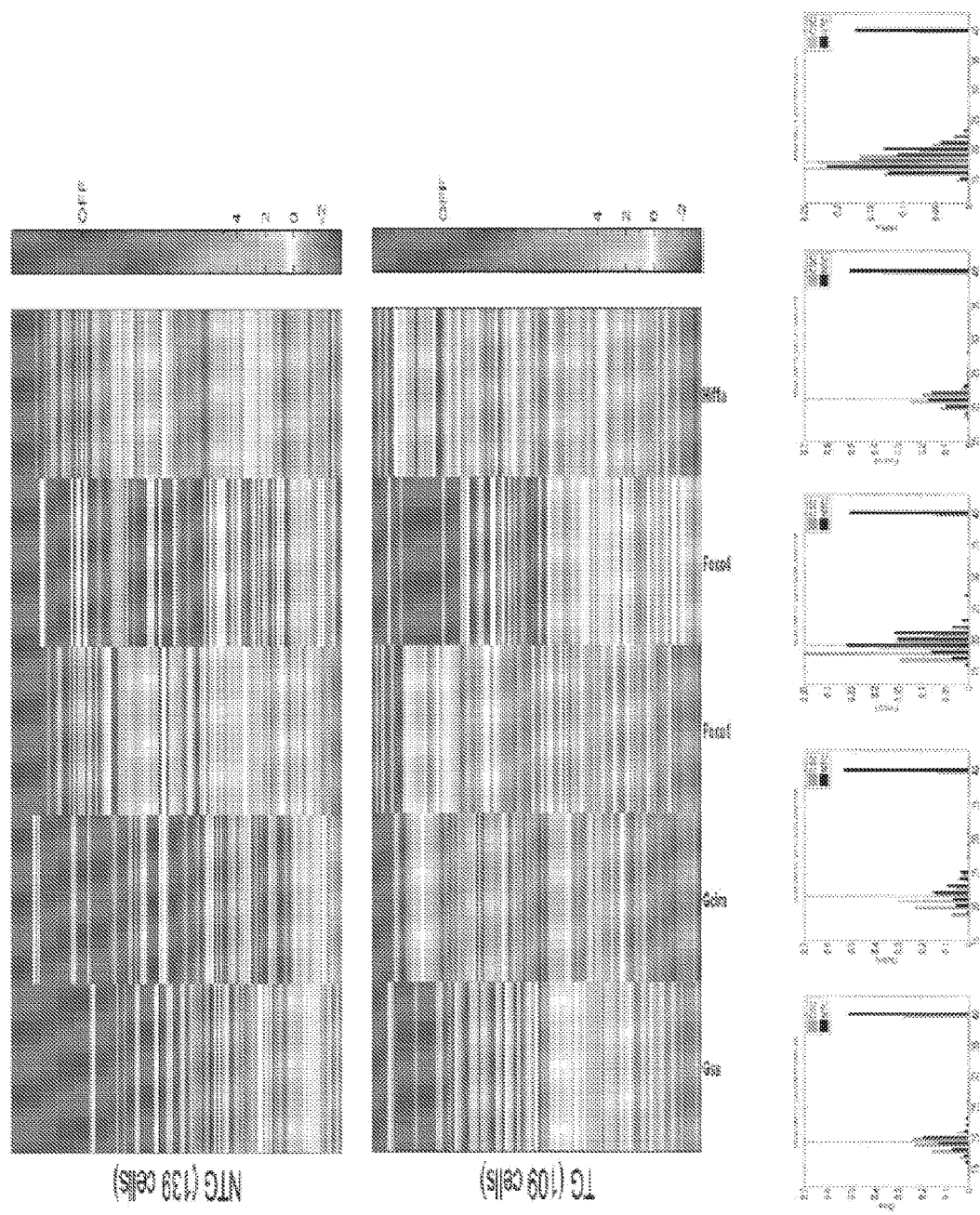
Figure 83:
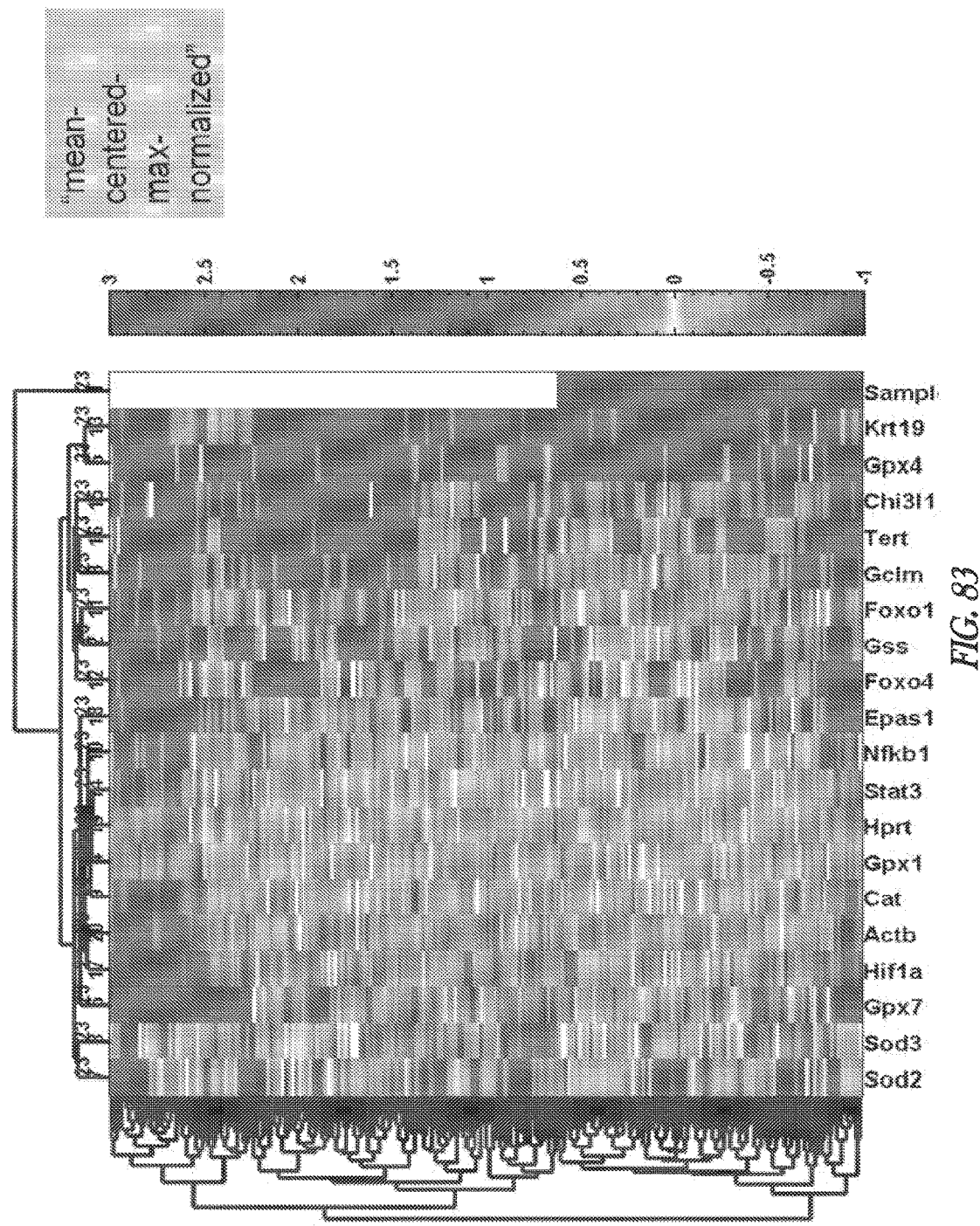
FIG. 83 mean-centered-max-normalized clustering comparing TG and NTG populations.
Figure 84:
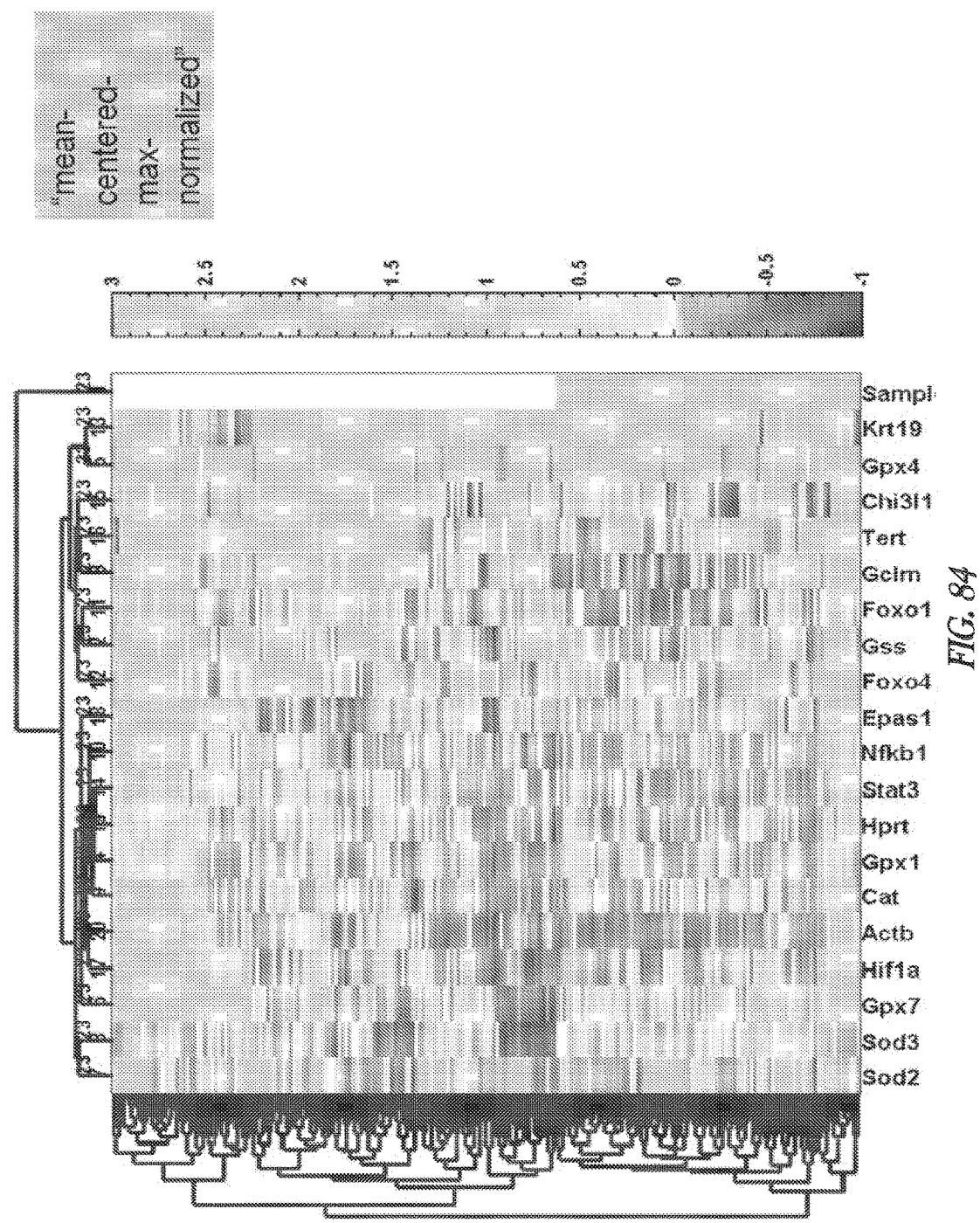
FIG. 84 different rendering of FIG. 88.
Figure 86:
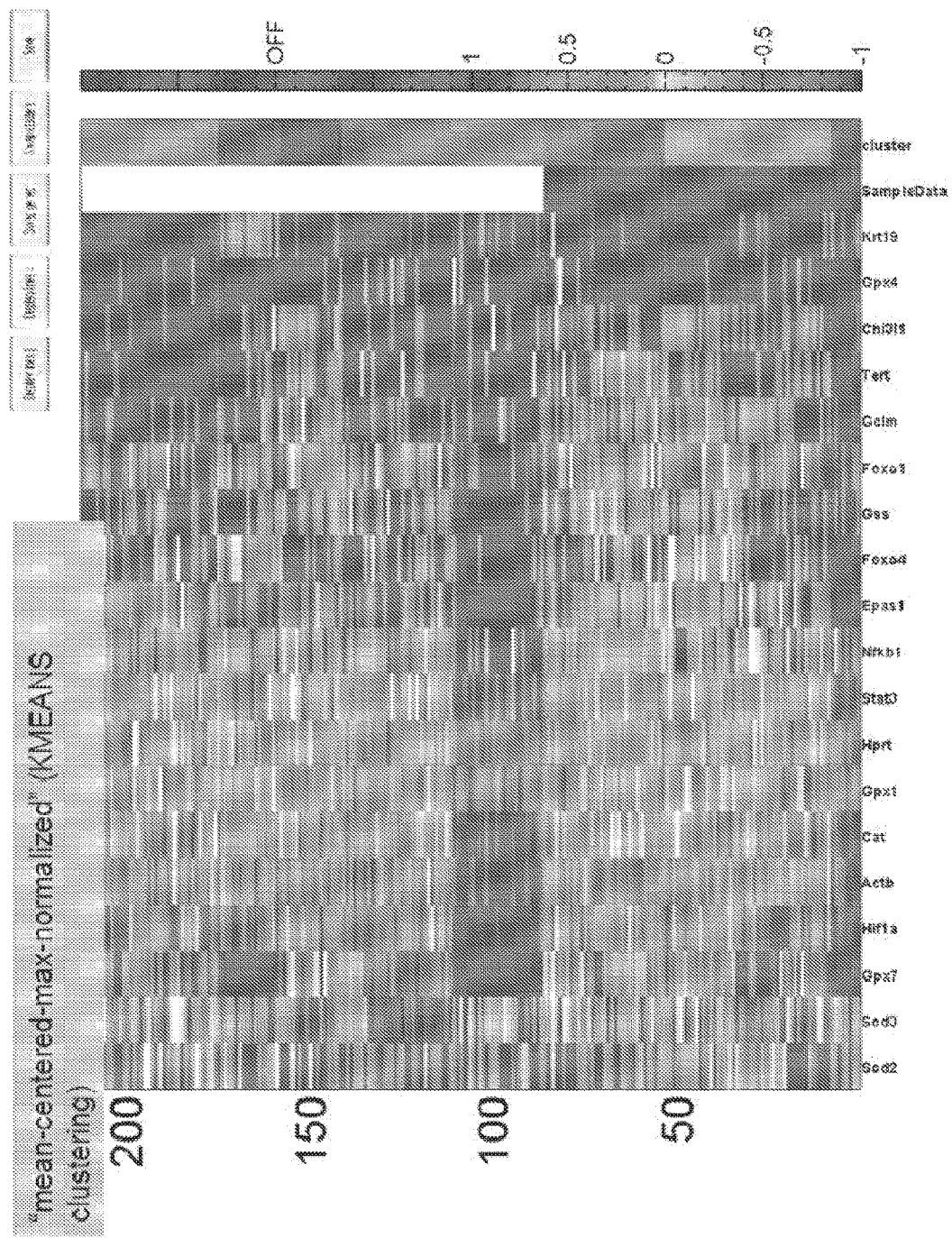
FIG. 86 results of "mean-centered-max-normalized", clustered by k-means clustering showed differential expressions of GPX7, SOD3, NFKB1, EPAS1, FOXO1, GCLM, TERT, CHI311, and KRT19 between TG and NTG cells.
Figure 87:
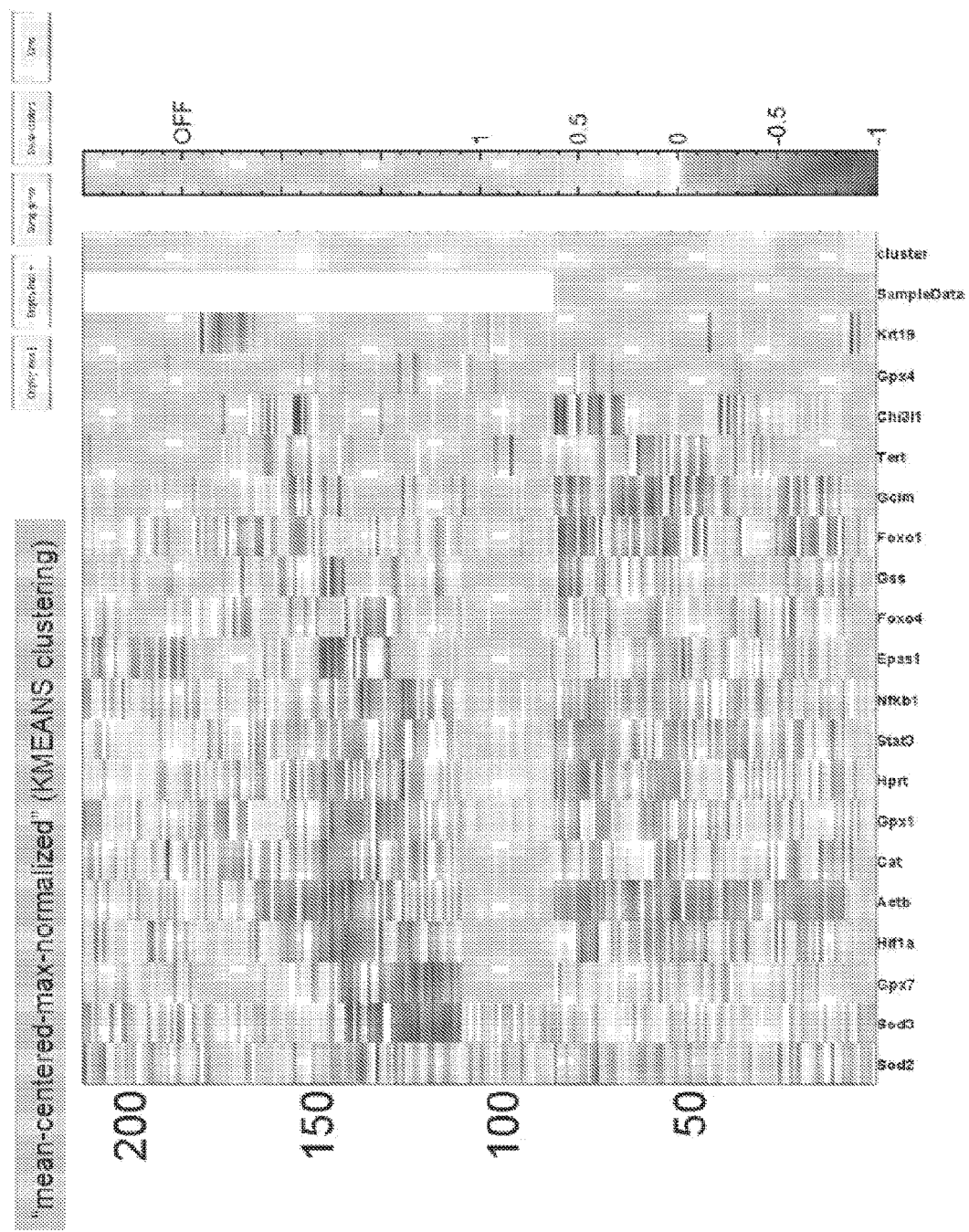
FIG. 87 different rendering of FIG. 86.
Figure 88:
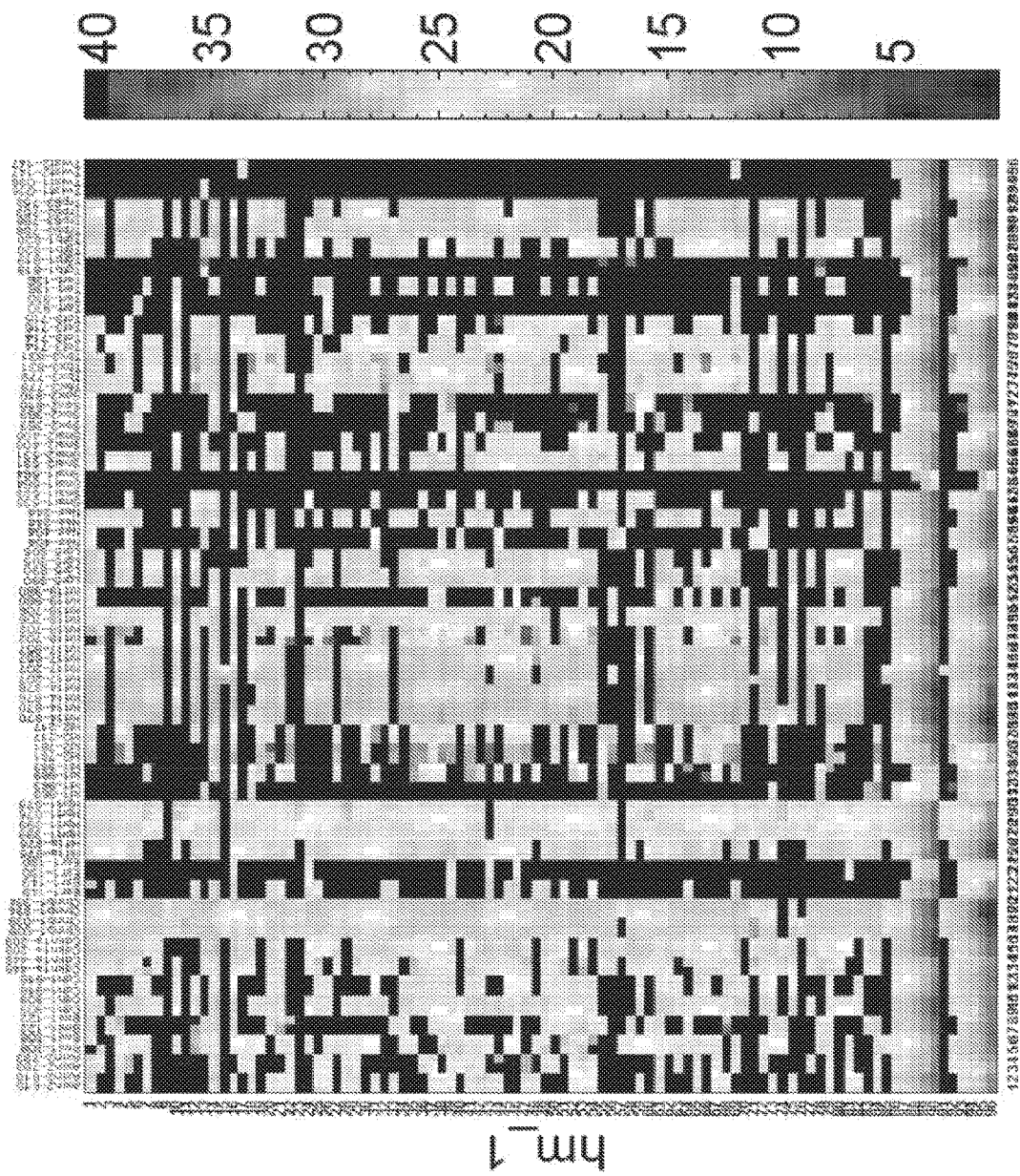
FIG. 88 a first heat map obtained from cells.
Figure 89:
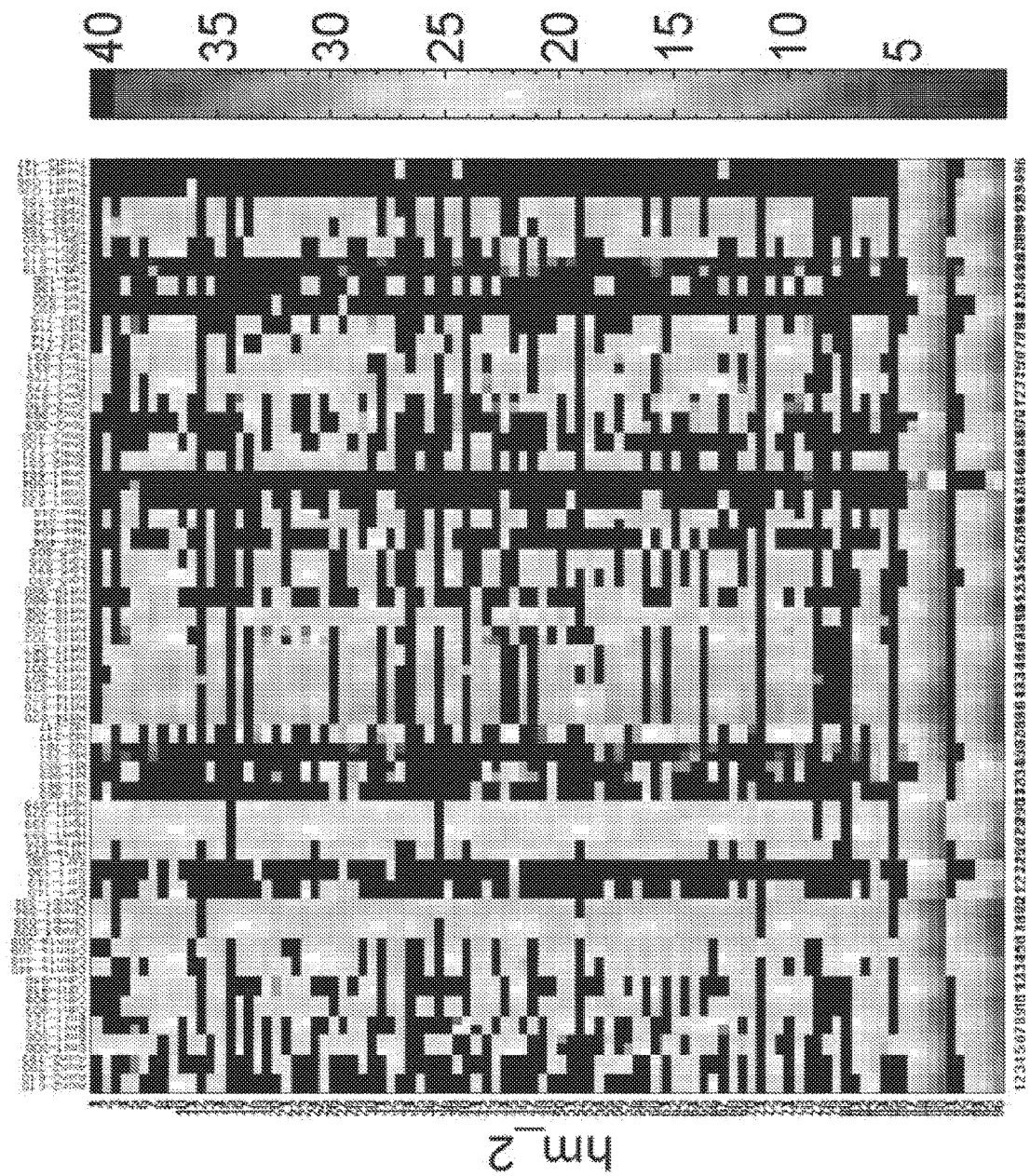
FIG. 89 a second heat map obtained from cells.
Figure 90:
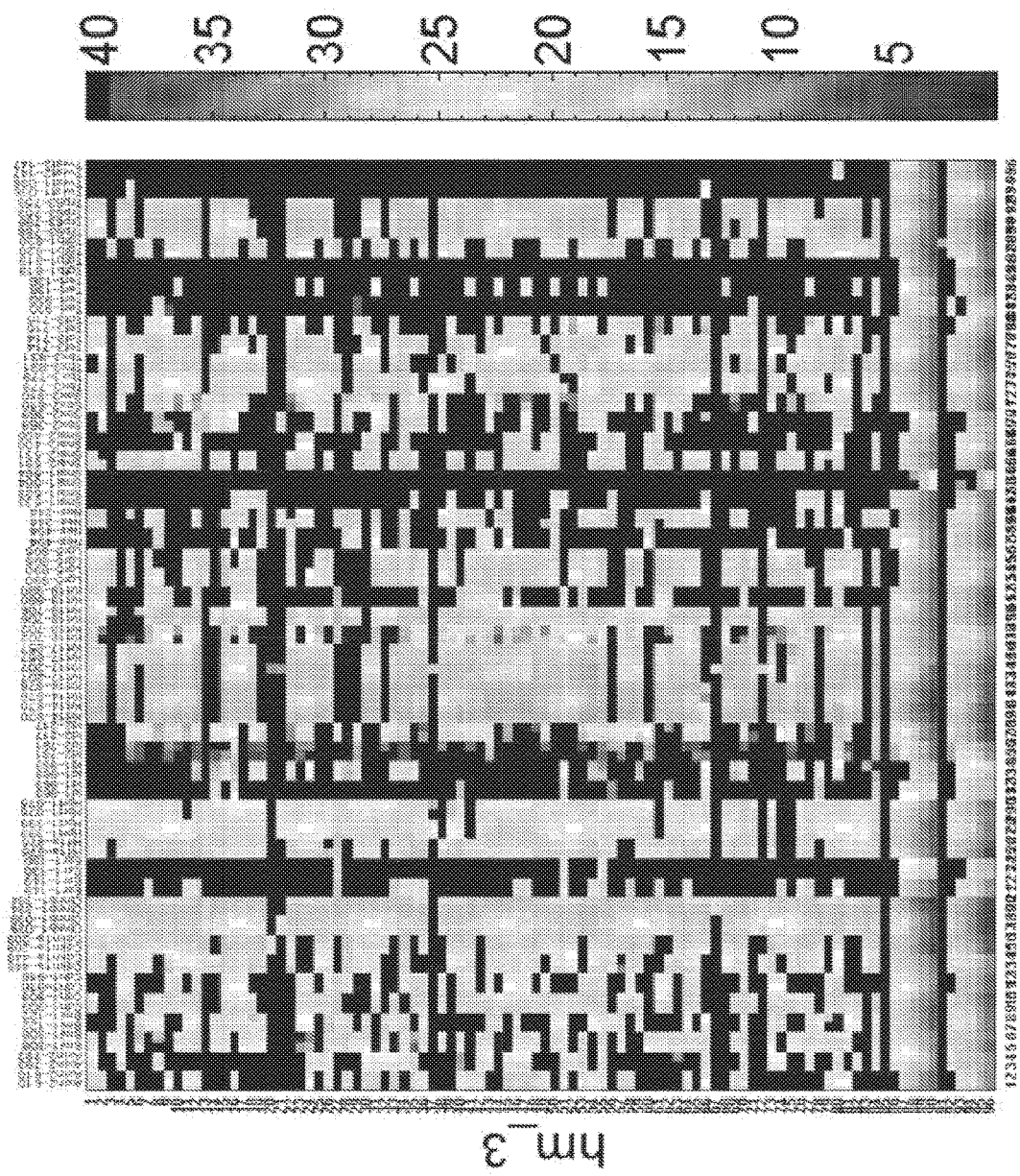
FIG. 90 a third heat map obtained from cells.
Figure 91:
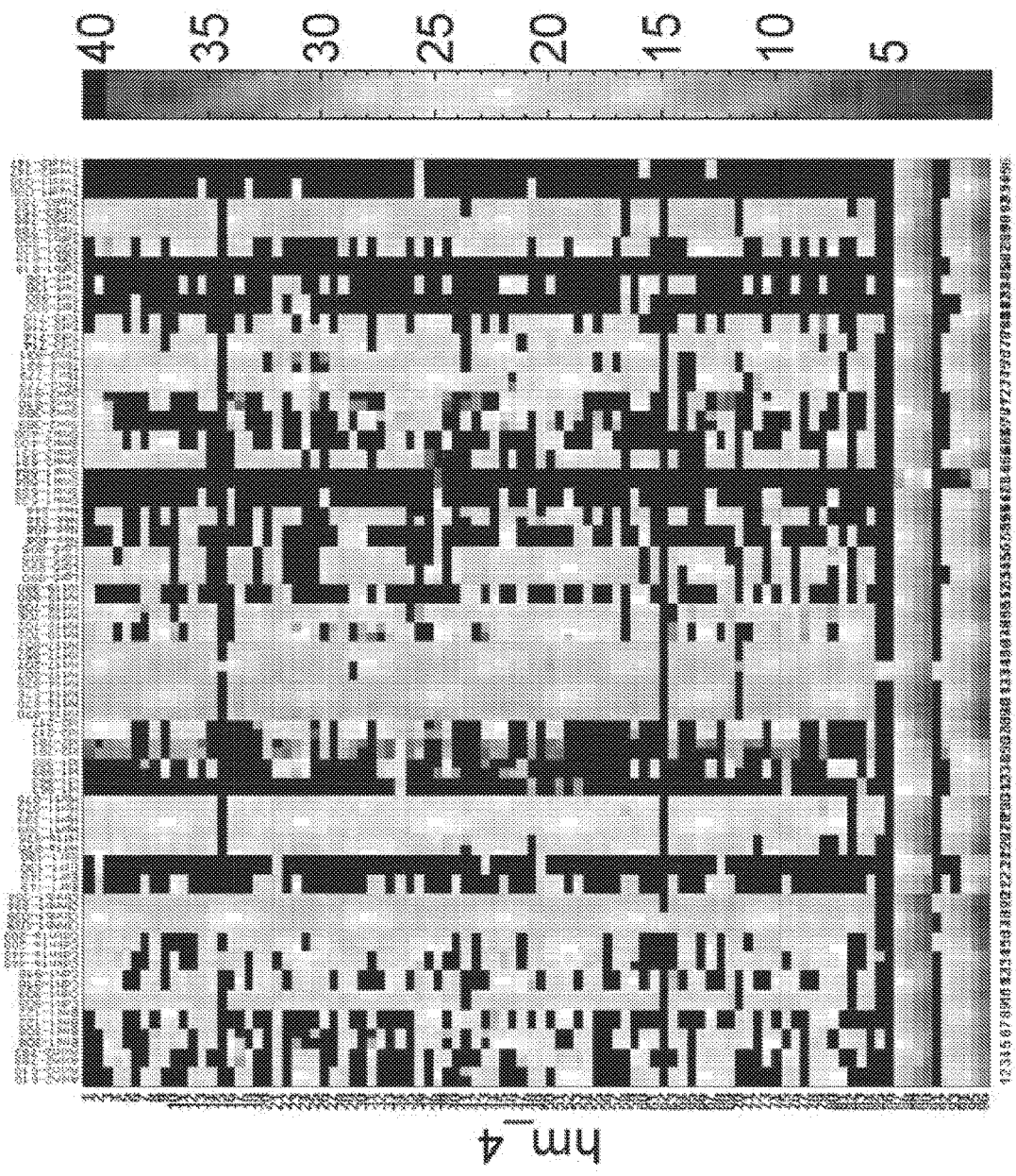
FIG. 91 a fourth heat map obtained from cells.
Figure 92:
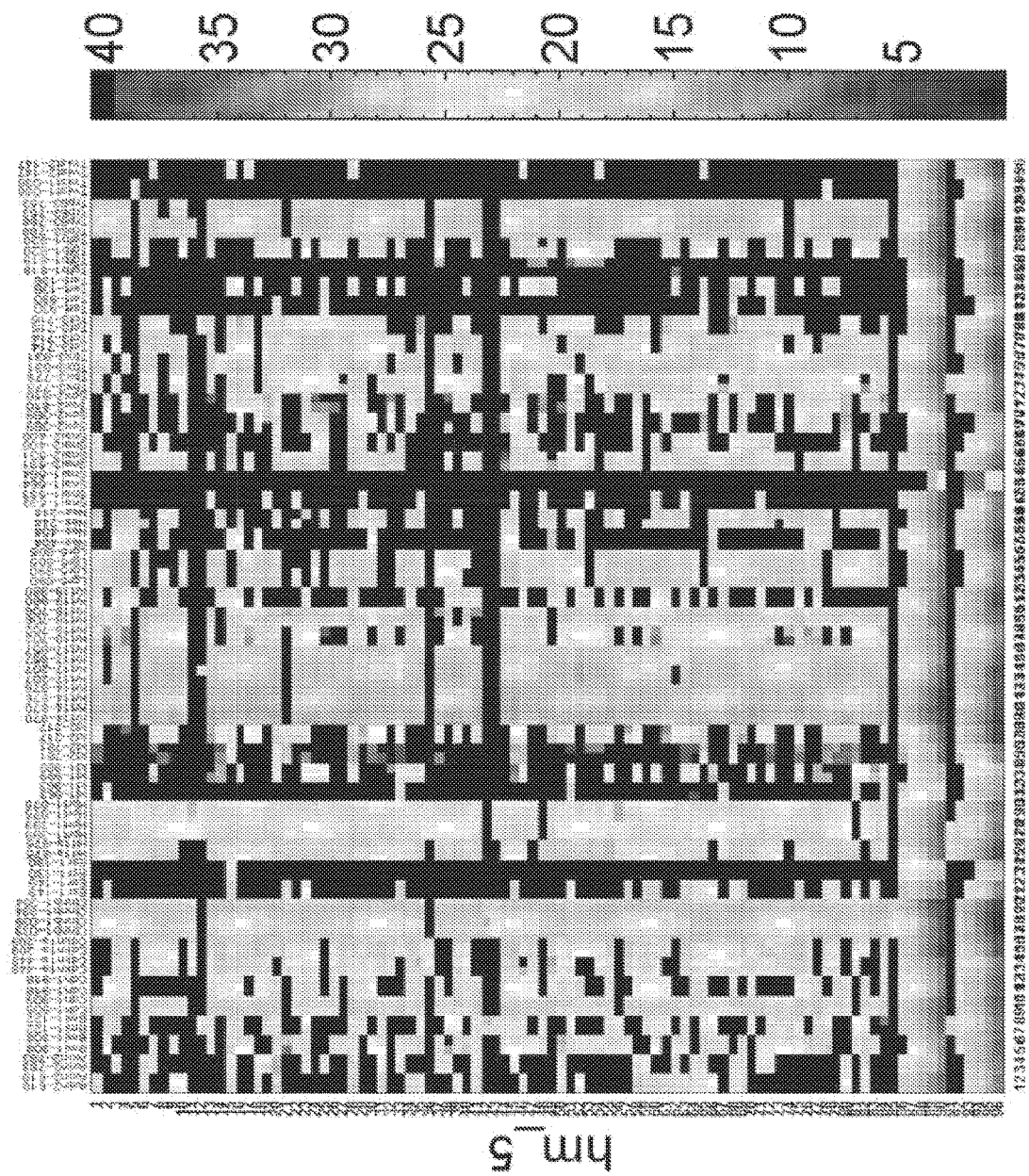
FIG. 92 a fifth heat map obtained from cells.
Figure 93:
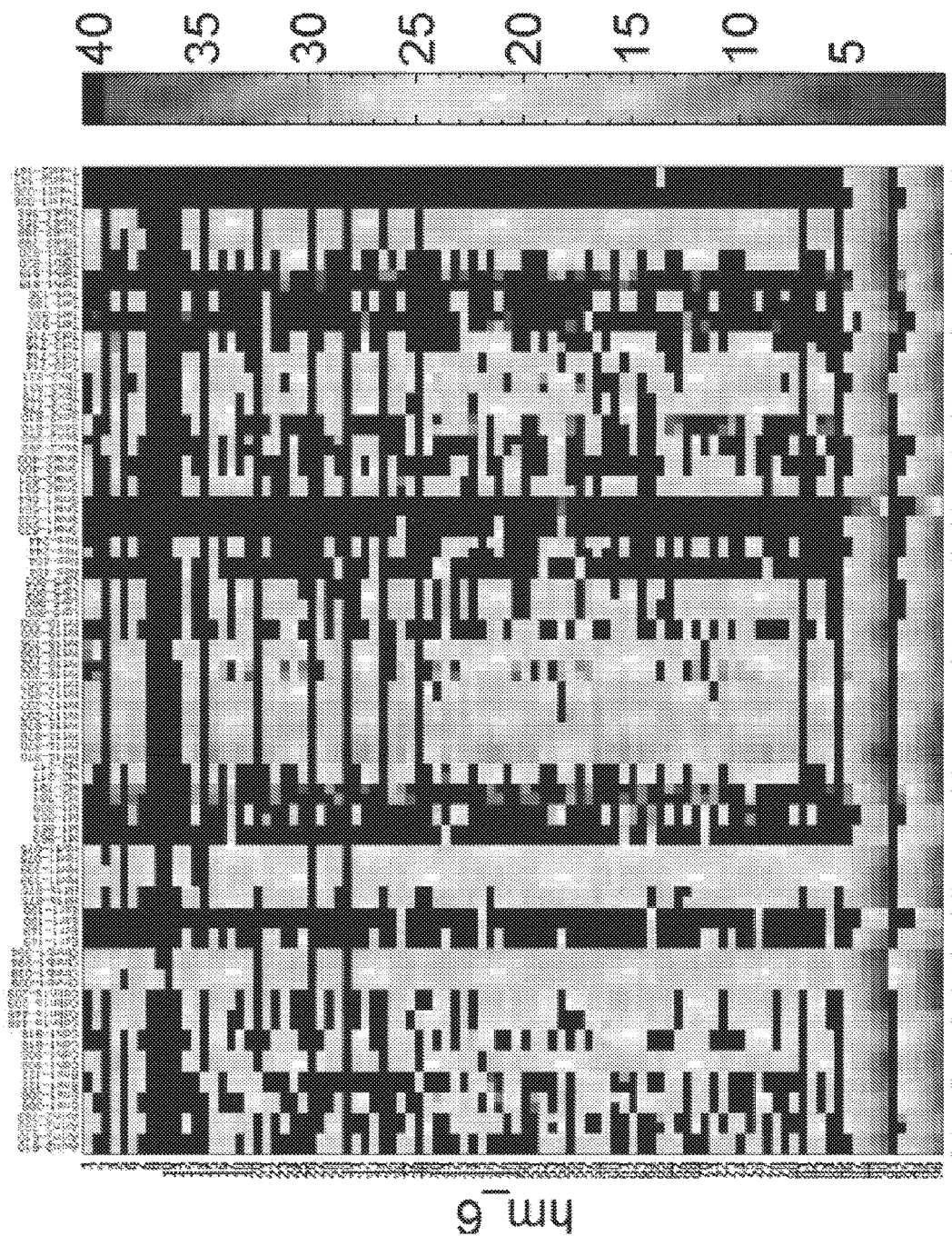
FIG. 93 a sixth heat map obtained from cells.

Chip-runs were performed with cells from non-tumorigenic (NTG) progeny or tumorigenic (TG) progeny (FIG. 64). A combined heat map is illustrated in FIG. 65. Both TG and NTG cells were plotted on a scatter-plot according to HPRT or ACTB expression levels (FIG. 66). qPCR curves for GCLM were obtained on different PCR cycle numbers, showing the correlation between identifying active cells and $C_T$ value (FIG. 67). From the qPCR reactions, standard curves were generated (FIGS. 68-69). Histograms depicting gene expression levels in TG or NTG cells are illustrated for the following genes: GSS, GCLC, GCLM, GPX1, GPX4, GPX7, SLPI, PRNP, SOD1, SOD2, SOD3, CAT, NFKB1, FOXO1, FOXO3A, FOXO4, KRT19, STAT3, CHI311, TERT, HIF1A, EPAS1, HPRT, and ACTB (FIGS. 70-75). Hierarchical clustering of TG and NTG cells are shown (FIGS. 76-77) Kolmogorov-Smirnov statistical significance test for genes expressed in TG or NTG cells are shown in FIGS. 78 and 79. Hierarchical clustering of only glutathione-related genes are shown as a heat map using k-means clustering method (FIG. 80). TG and NTG cells were compared in mean-clustering of glutathione-related genes (FIG. 81-82). Mean-centered-max-normalized clustering comparing TG and NTG are shown in two different renderings (FIGS. 83-84). Calculation of "mean-centered-max-normalized" is shown in FIG. 85. Results of "mean-centered-max-normalized", clustered by k-means clustering showed differential expressions of GPX7, SOD3, NFKB1, EPAS1, FOXO1, GCLM, TERT, CHI311, and KRT19 between TG and NTG cells. (FIGS. 86-87).

Example 17: Analysis of MMTV-Wnt-1 Cells

Figure 94:
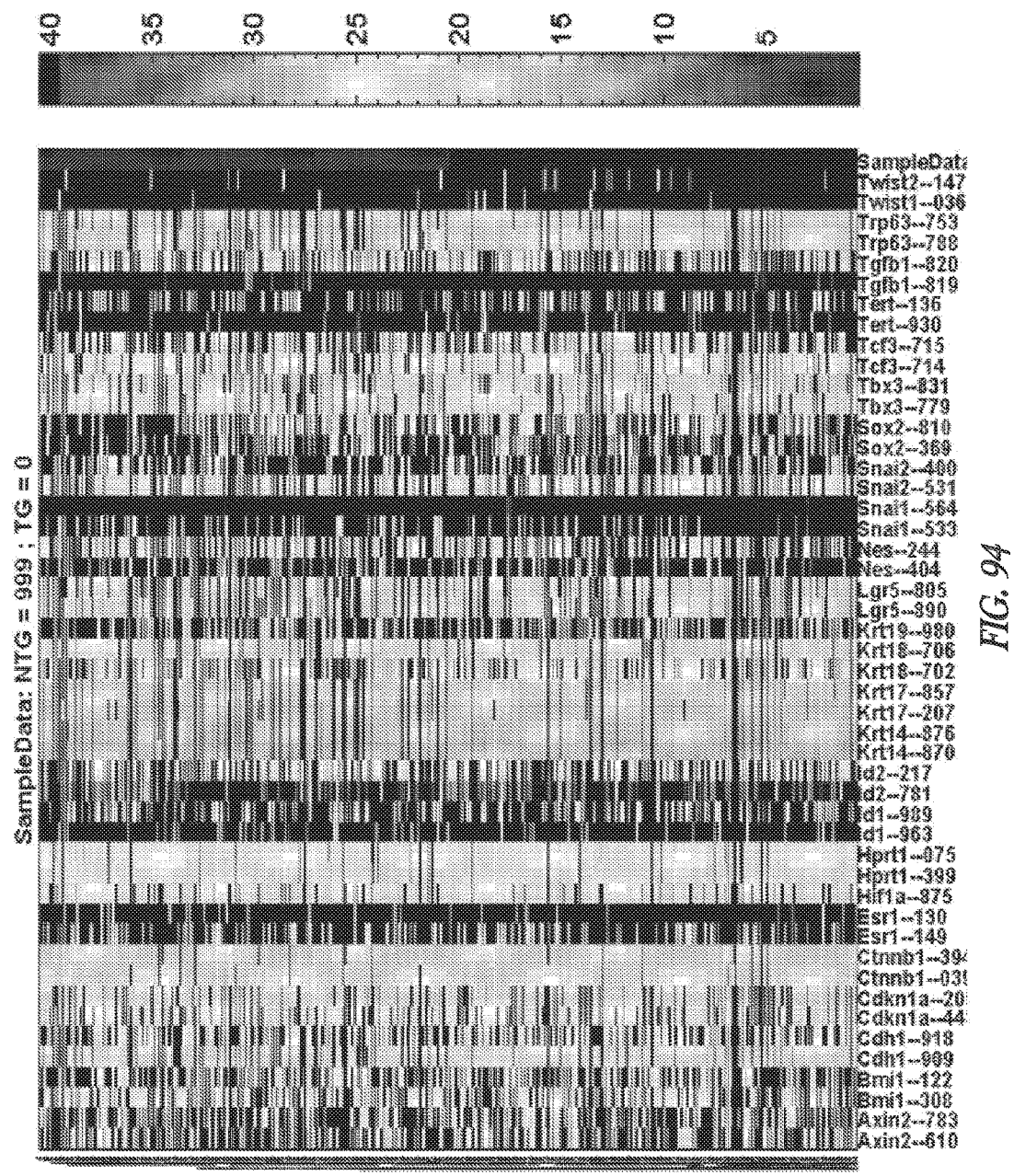
FIG. 94 a combined heat map comparing six chip-runs.
Figure 95:
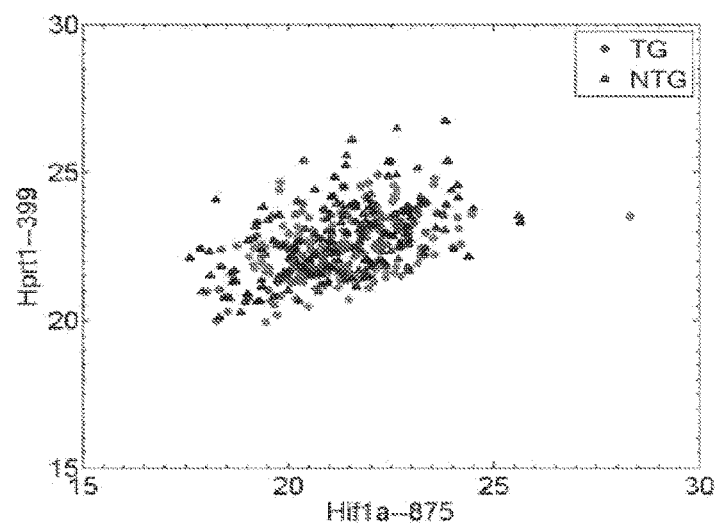
FIG. 95 selection of cells for single cell gene expression analysis. Out of 504 cells tested, 56 cells that do not express HPRT1 or any of the Keratins (KRT14-870, KRT17-207, KRT18-706, KRT19-980) were discarded, and 448 cells were selected for further analysis.
Figure 96:
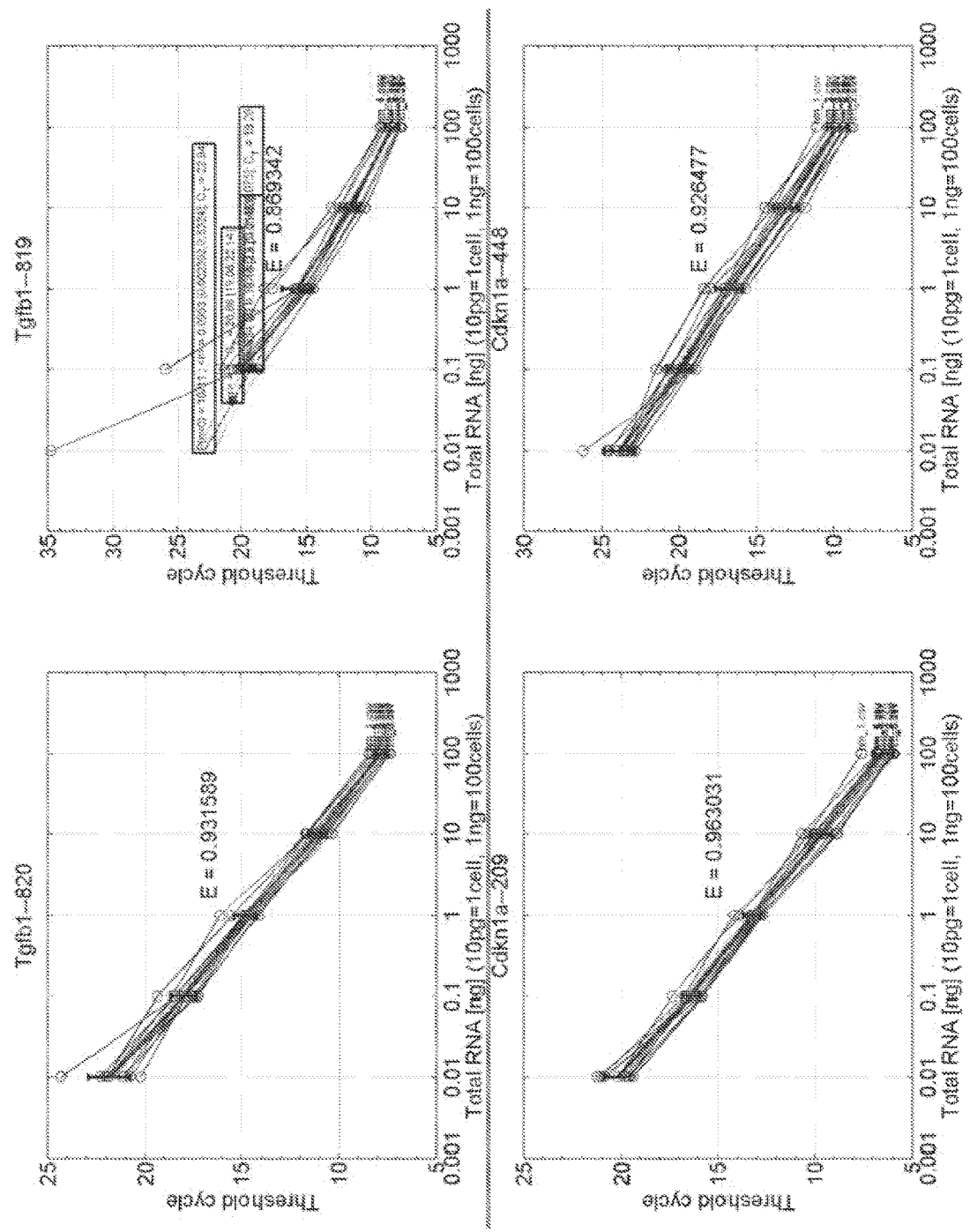
FIG. 96 standard curves showing linearity of pPCR reactions.
Figure 97:
FIG. 97 histograms depicting gene expression levels in TG or NTG cells of TGFB1, SNAI1, BMI1, and KRT19.
Figure 98:
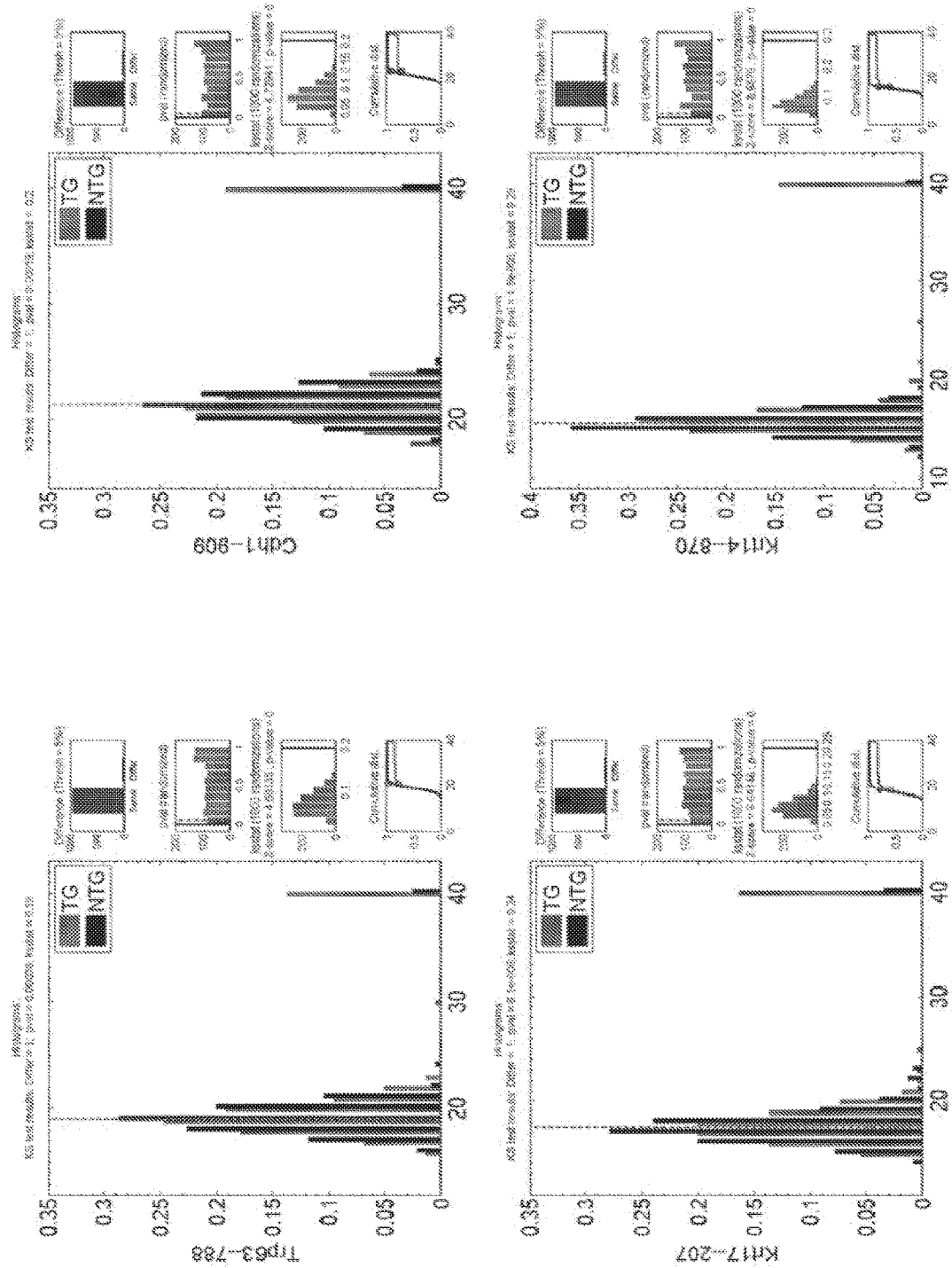
FIG. 98 histograms depicting gene expression levels in TG or NTG cells of TRP63, CDH1, KRT17, and KRT14.
Figure 99:
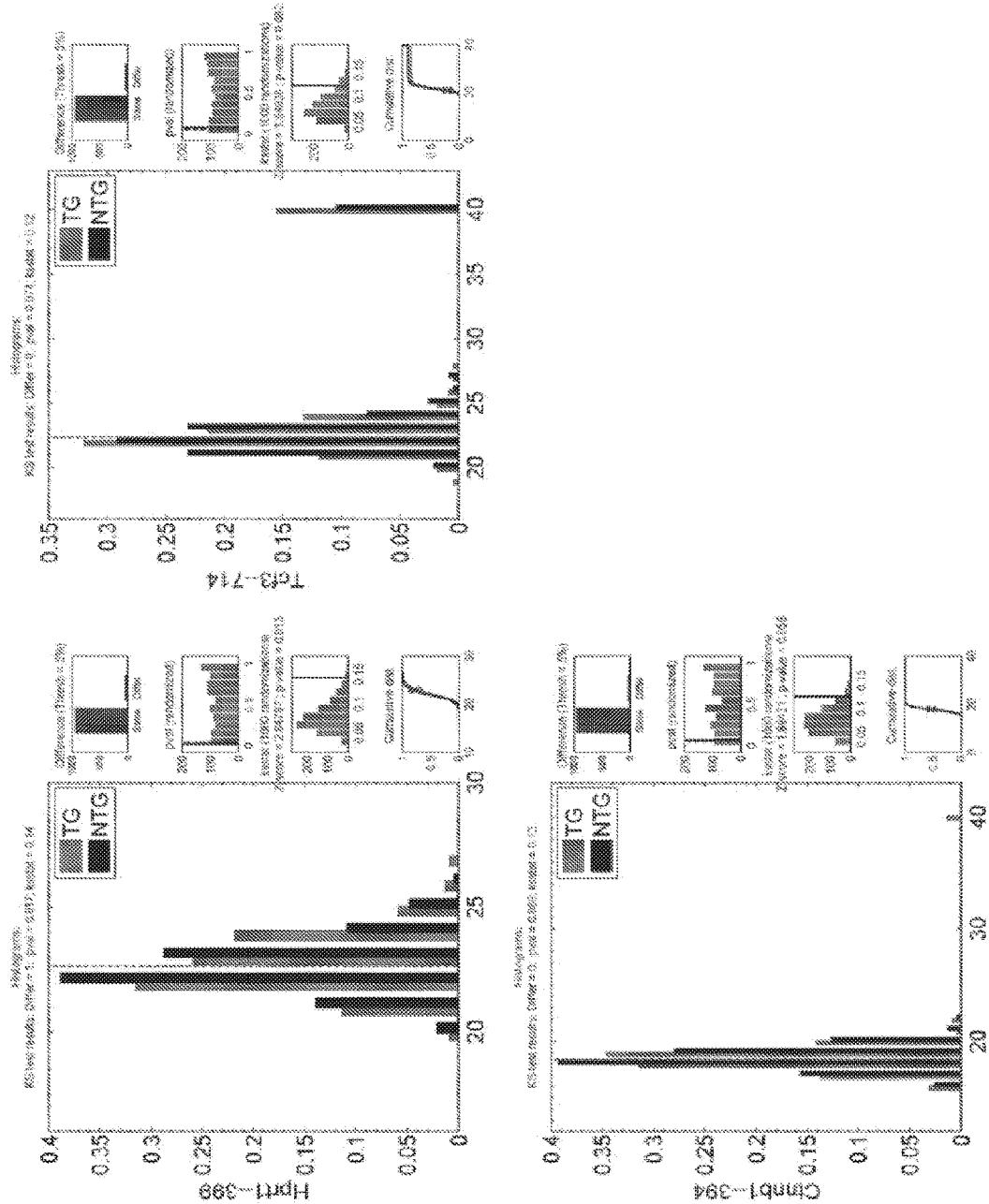
FIG. 99 histograms depicting gene expression levels in TG or NTG cells of HPRT1, TCF3, and CTNNB1.
Figure 100:
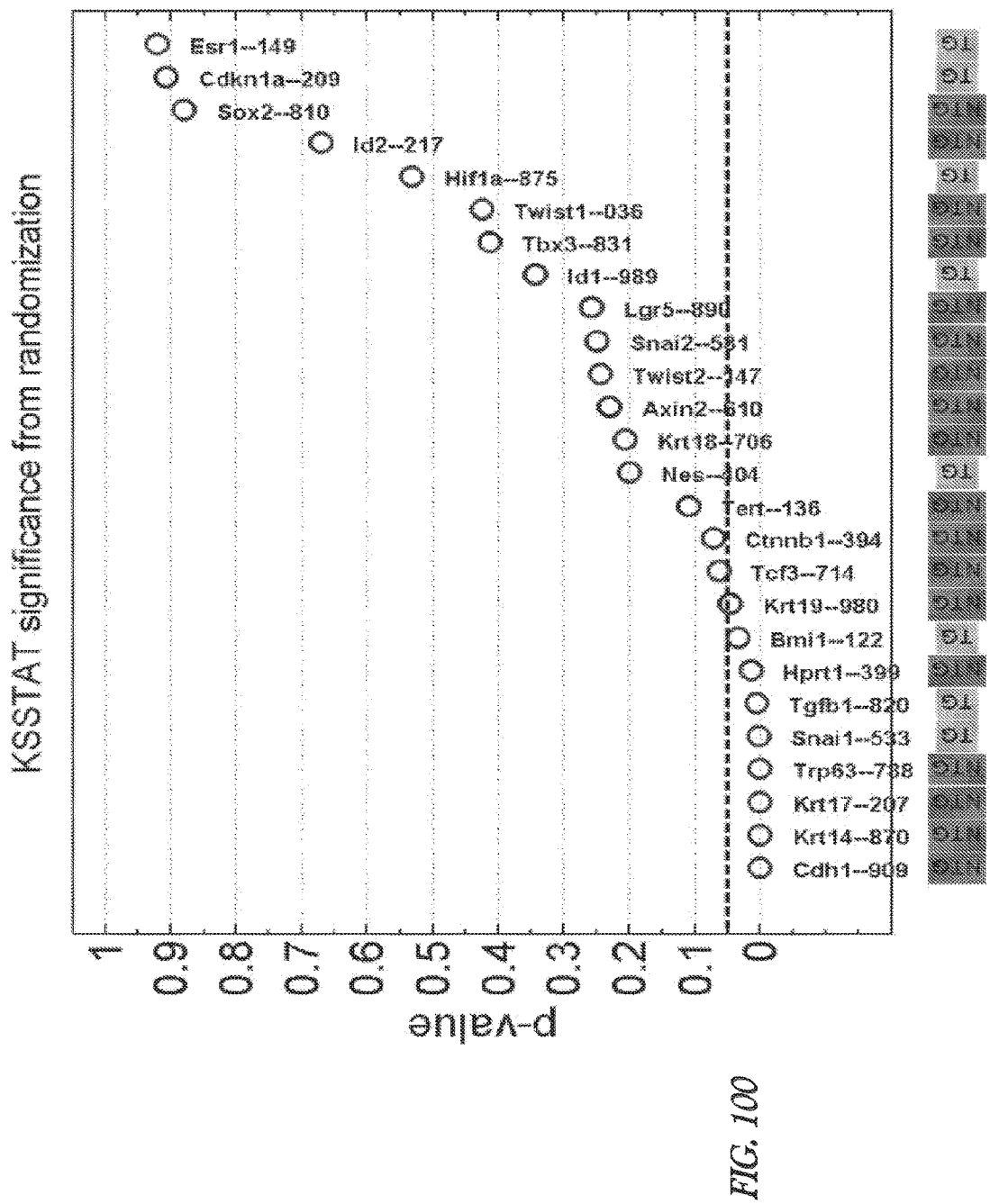
FIG. 100 Kolmogorov-Smirnov statistical significance test for genes expressed in TG or NTG cells, plotted against p-value FIG. 101 mean-centered-max-normalized clustering comparing TG and NTG.
Figure 101:
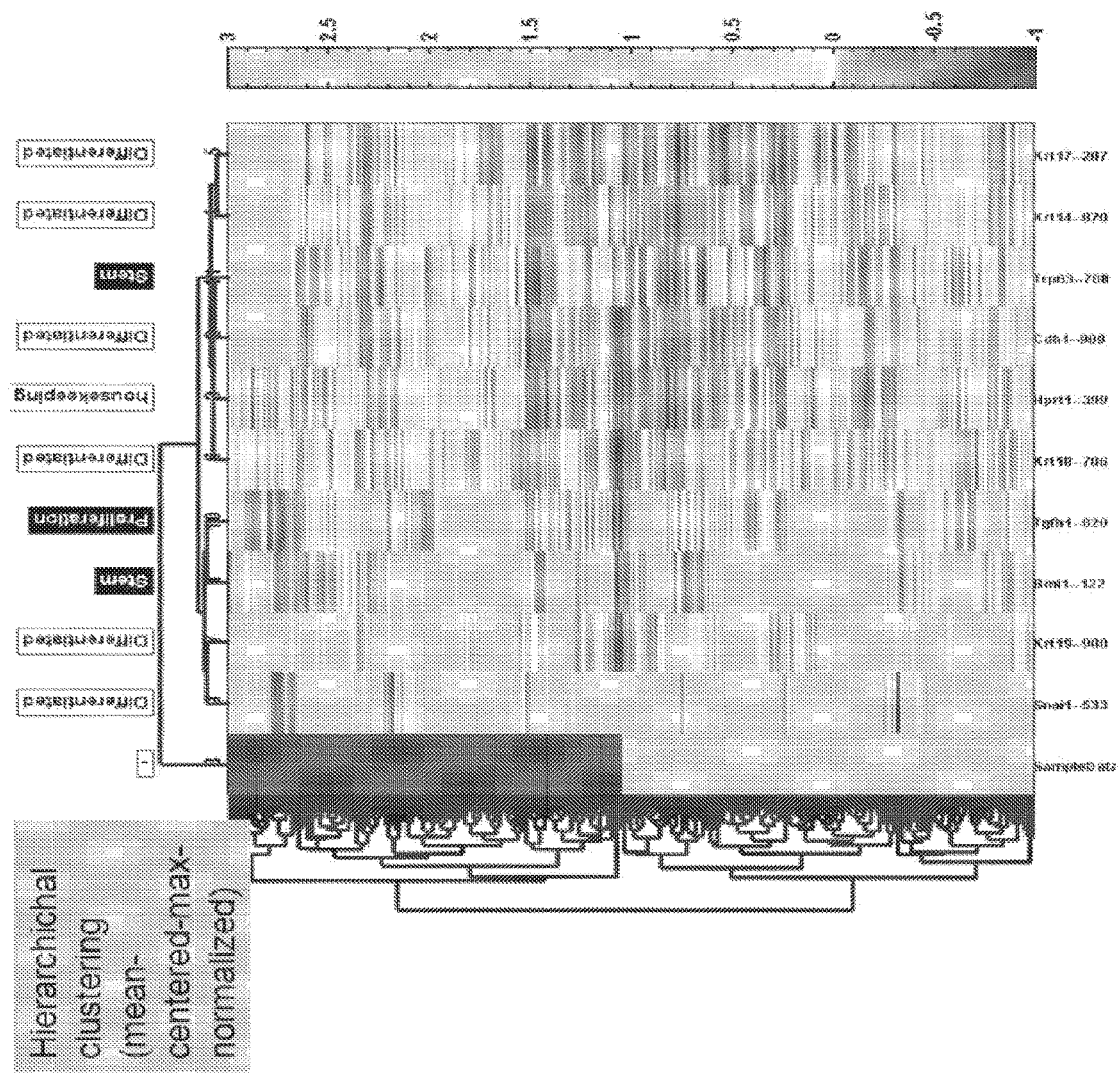
Figure 102:
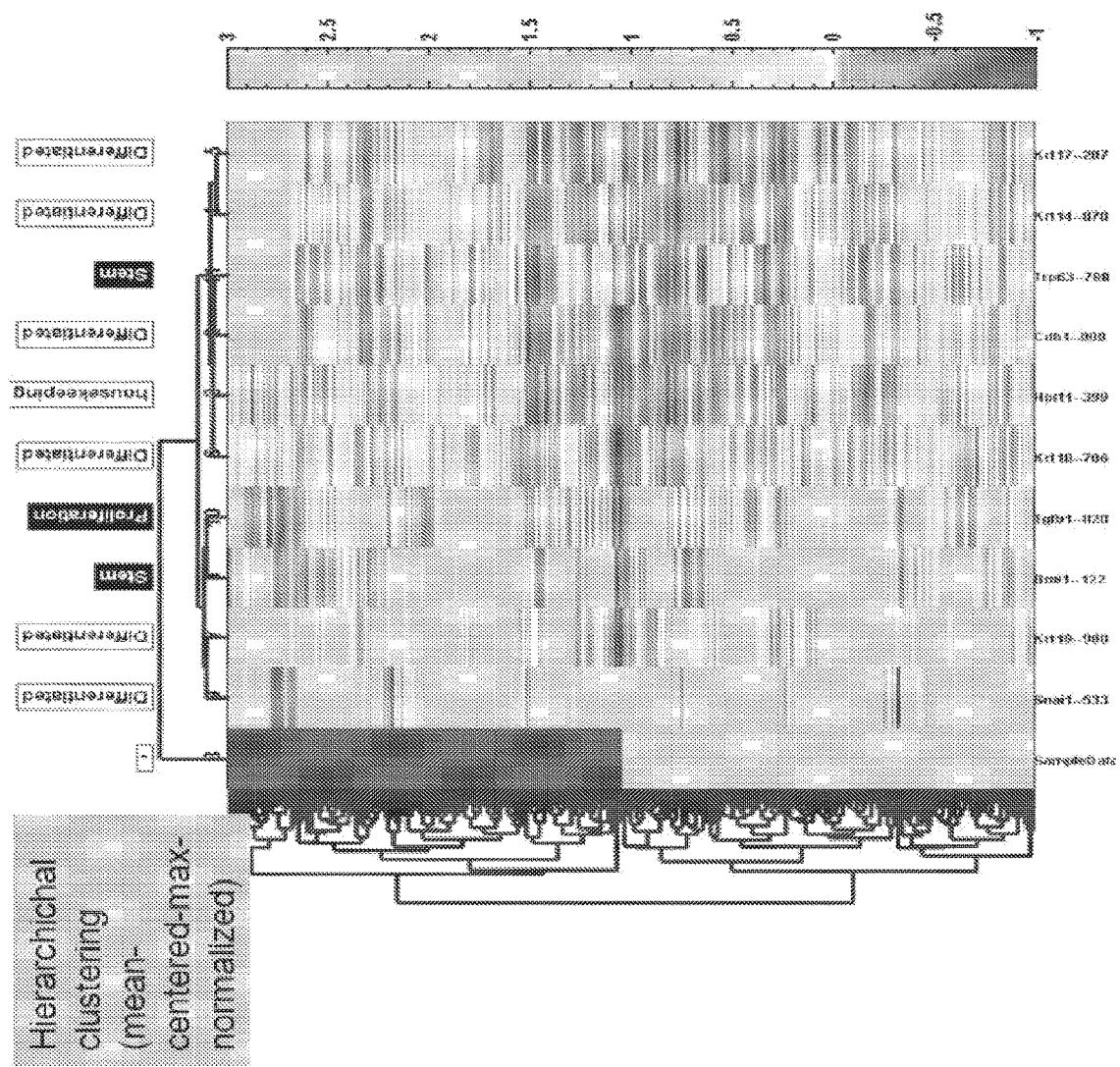
FIG. 102 a different rendering of FIG. 101.
Figure 103:
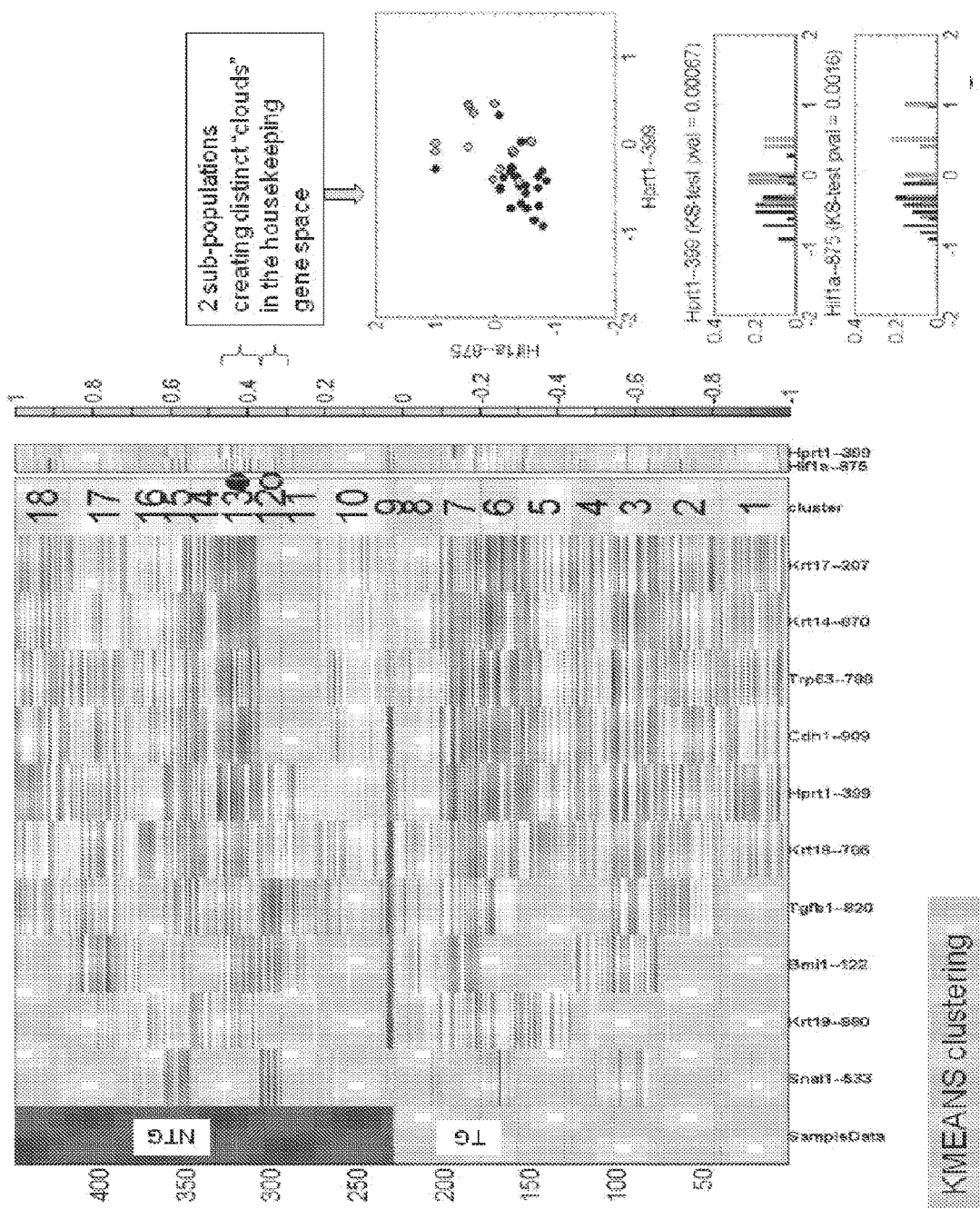
FIG. 103 k-means clustering showing HIF1a and HPRT are differentially expressed in TG and NTG cells.

Single cell gene expression analysis was performed essentially as described above. Heat maps from 6 different chip-runs are shown (FIGS. 88-93). A combined heat map is illustrated in FIG. 94. Out of 504 cells tested, 56 cells that do not express HPRT1 or any of the Keratins (KRT14-870, KRT17-207, KRT18-706, KRT19-980) were discarded, and 448 cells were selected for further analysis (FIG. 95). Standard curves showing linearity of pPCR is shown in FIG. 96. Histograms depicting gene expression levels in TG or NTG cells are illustrated for the following genes: TGFB, SNAI, BMI1, KRT19, TRP63, CDH1, KRT17, KRT14, HPRT1, TCF3 and CTNNB1 (FIGS. 97-99). Kolmogorov-Smirnov statistical significance for genes expressed in TG or NTG cells are shown in FIG. 100. Mean-centered-max-normalized clustering comparing TG and NTG are shown in two different rendering (FIGS. 101 and 102). K-means clustering showed HIF1a and HPRT are differentially expressed in TG and NTG cells (FIG. 103).

Example 18: Analysis of Colon Cancer Samples

Figure 105:
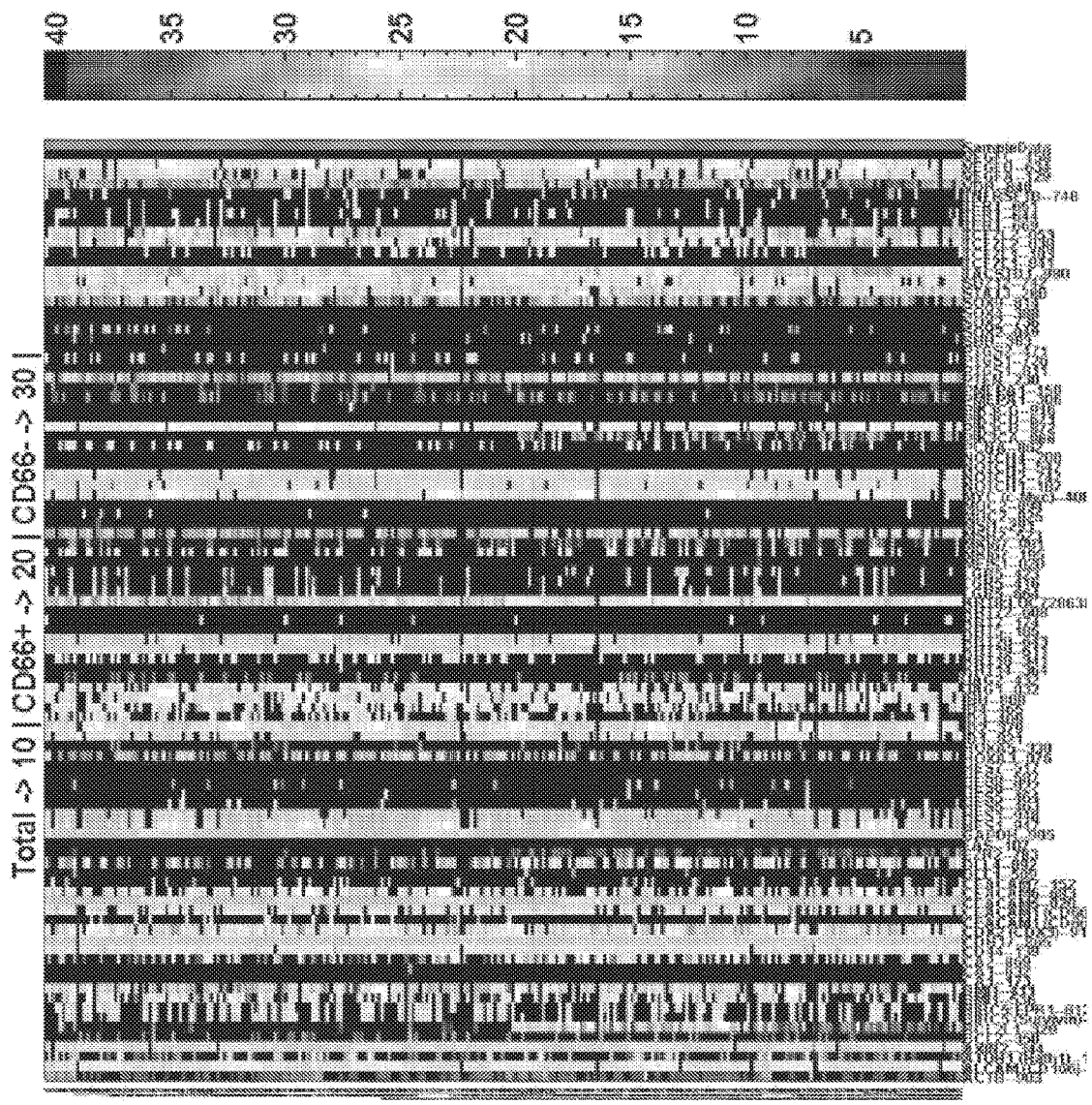
FIG. 105 a combined heat map comparing the four chip-runs.
Figure 106:
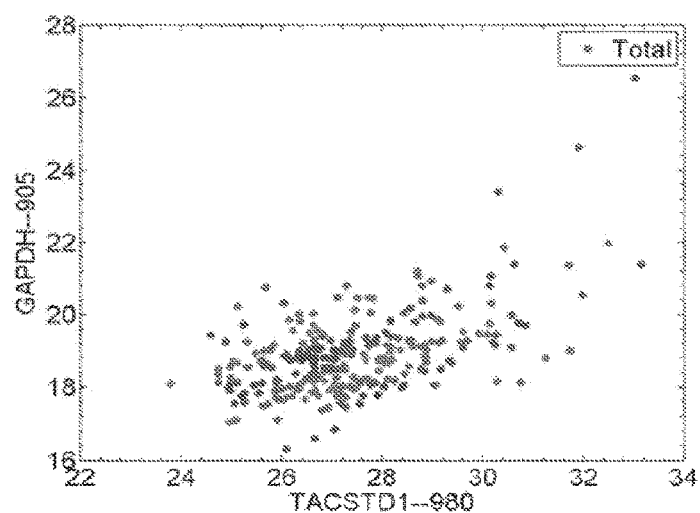
FIG. 106 selection of cells for single cell gene expression analysis. Out of 336 cells tested, 68 cells were discarded by examining GAPDH and TACSTD1 expression levels, and 268 cells were selected for further analysis.
Figure 107:
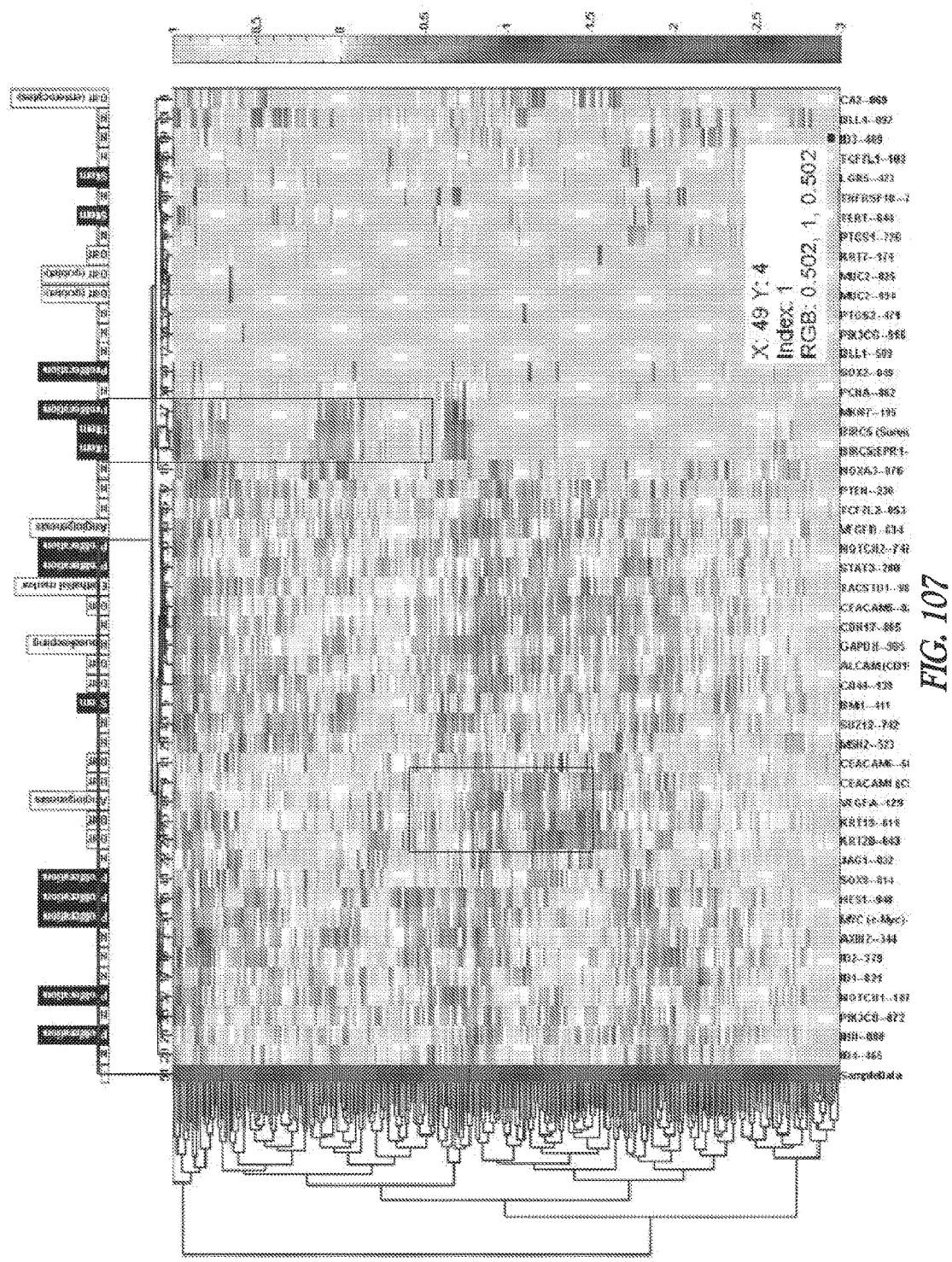
FIG. 107 hierarchical clustering showing uneven expressions of BIRC5, MKI67, VEFGA, KRT19, CD66, and KRT20 among cells.
Figure 108:
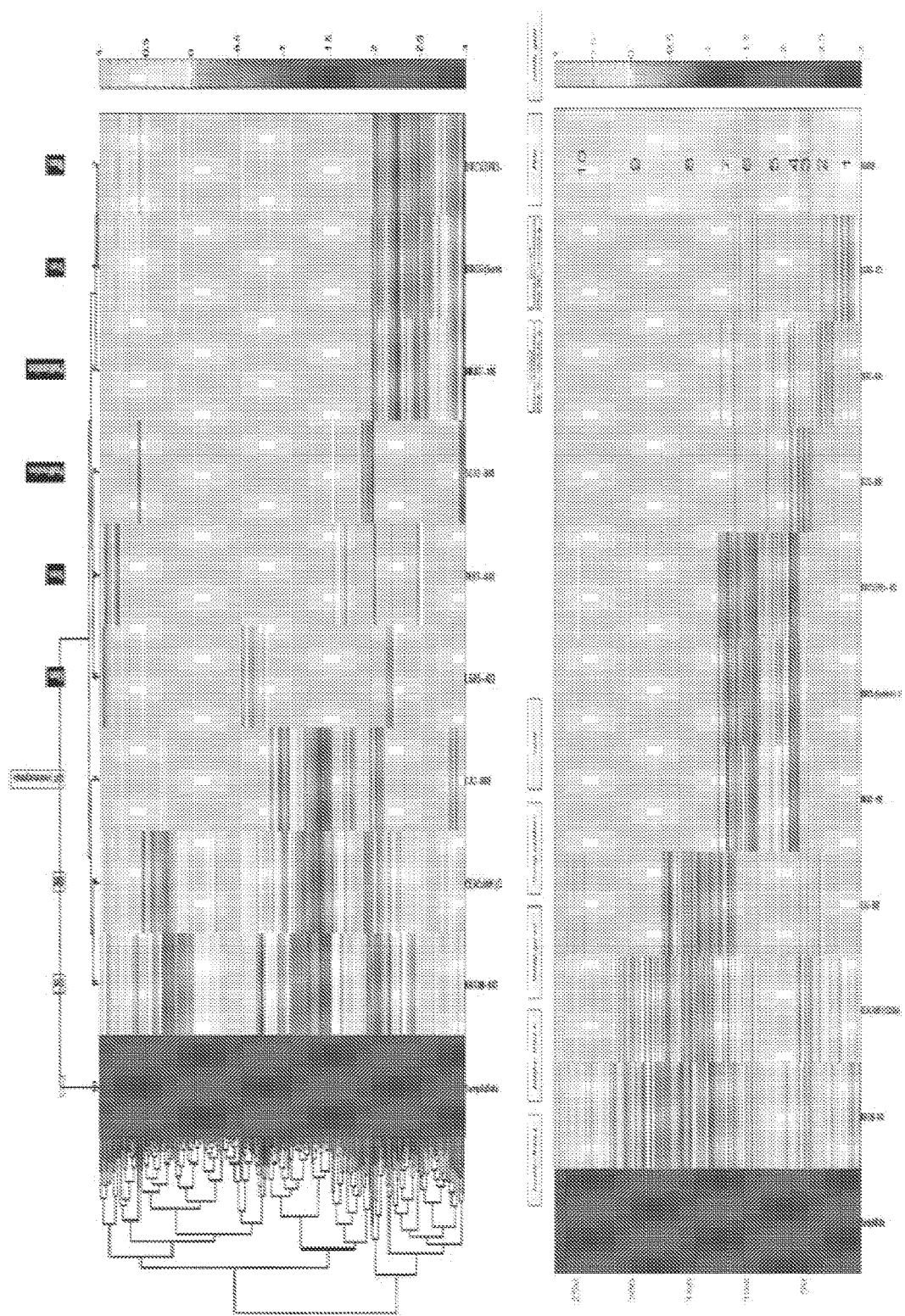
FIG. 108 Hierarchical clustering showing uneven expressions of BIRC5, MKI67, VEFGA, KRT19, CD66, and KRT20 (comparison of two chip-runs).
Figure 109:
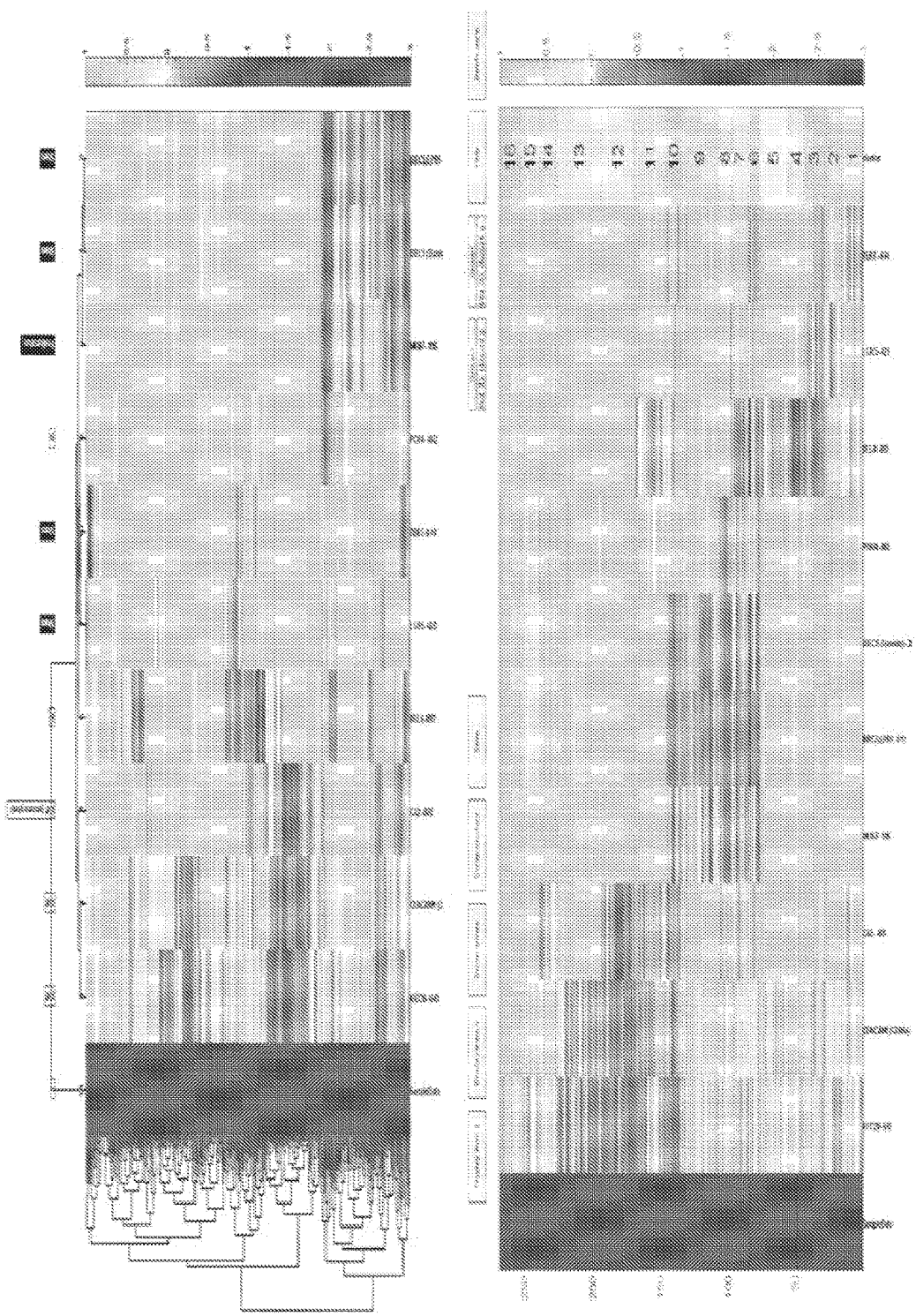
FIG. 109 Hierarchical clustering showed uneven expressions of BIRC5, MKI67, VEFGA, KRT19, CD66, and KRT20 among cells (comparison of two chip-runs).
Figure 110:
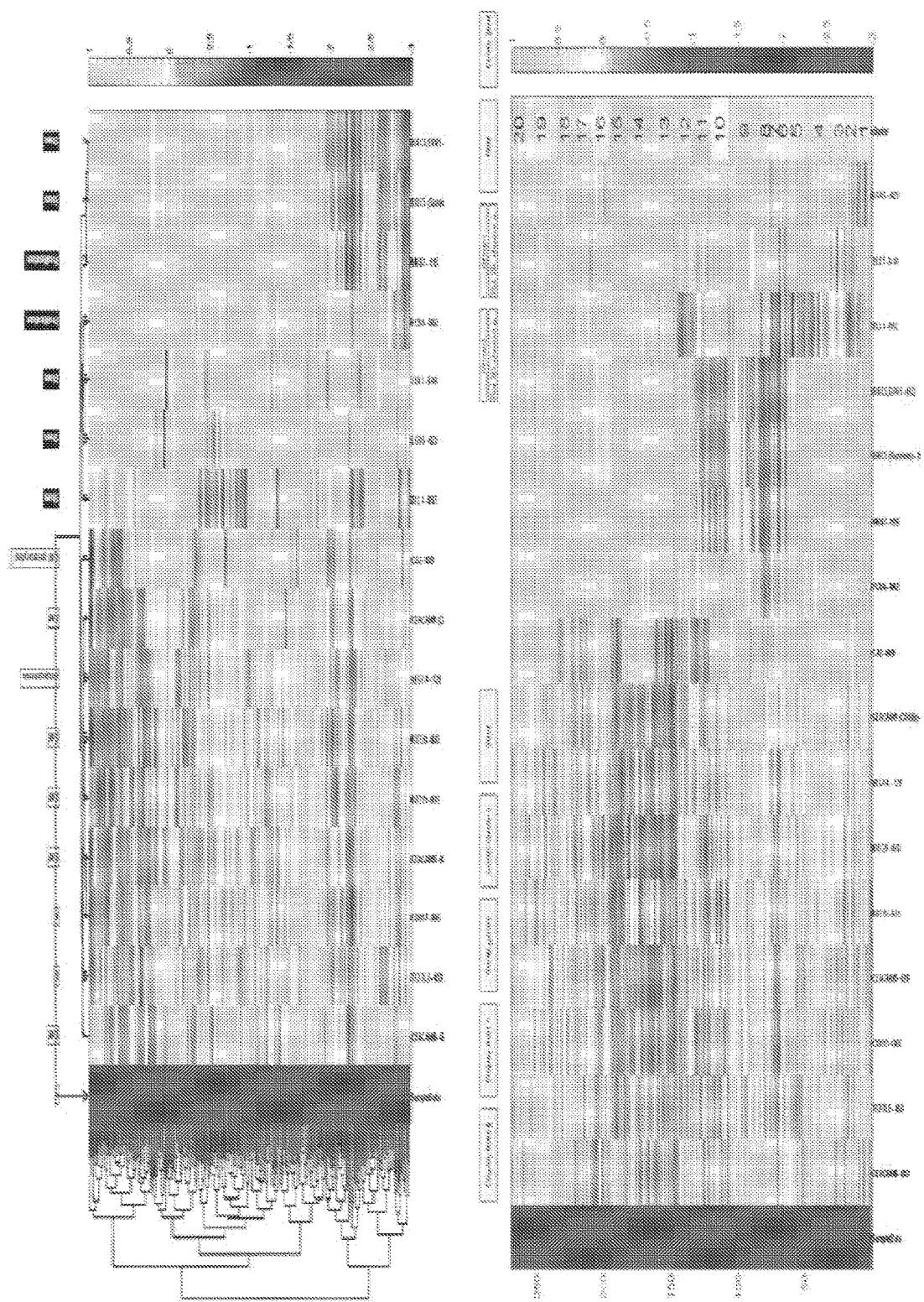
FIG. 110 Hierarchical clustering showed uneven expressions of BIRC5, MKI67, VEFGA, KRT19, CD66, and KRT20 among cells (comparison of two chip-runs).
Figure 111:
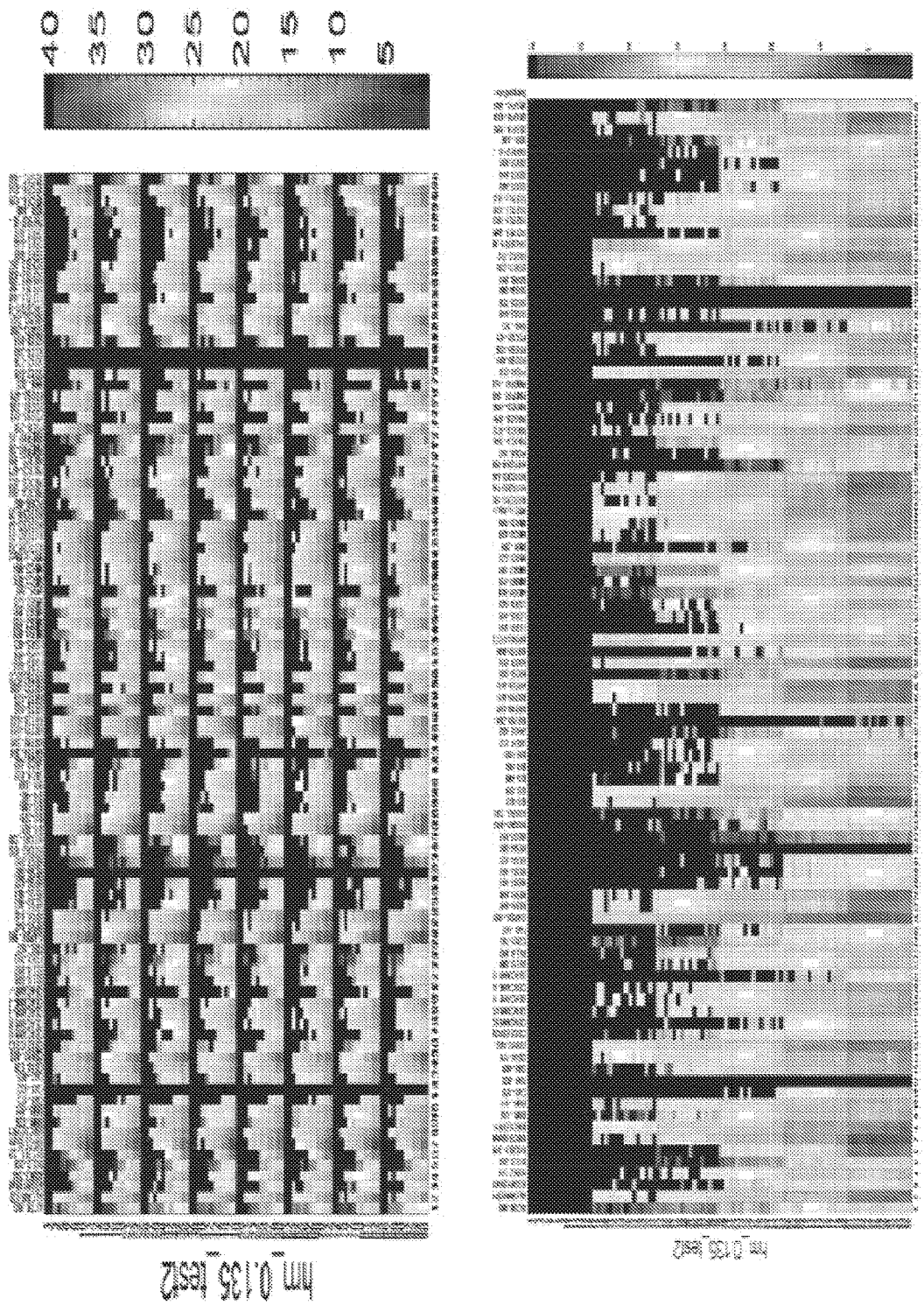
FIG. 111 heat maps from second round of experiment.
Figure 112:
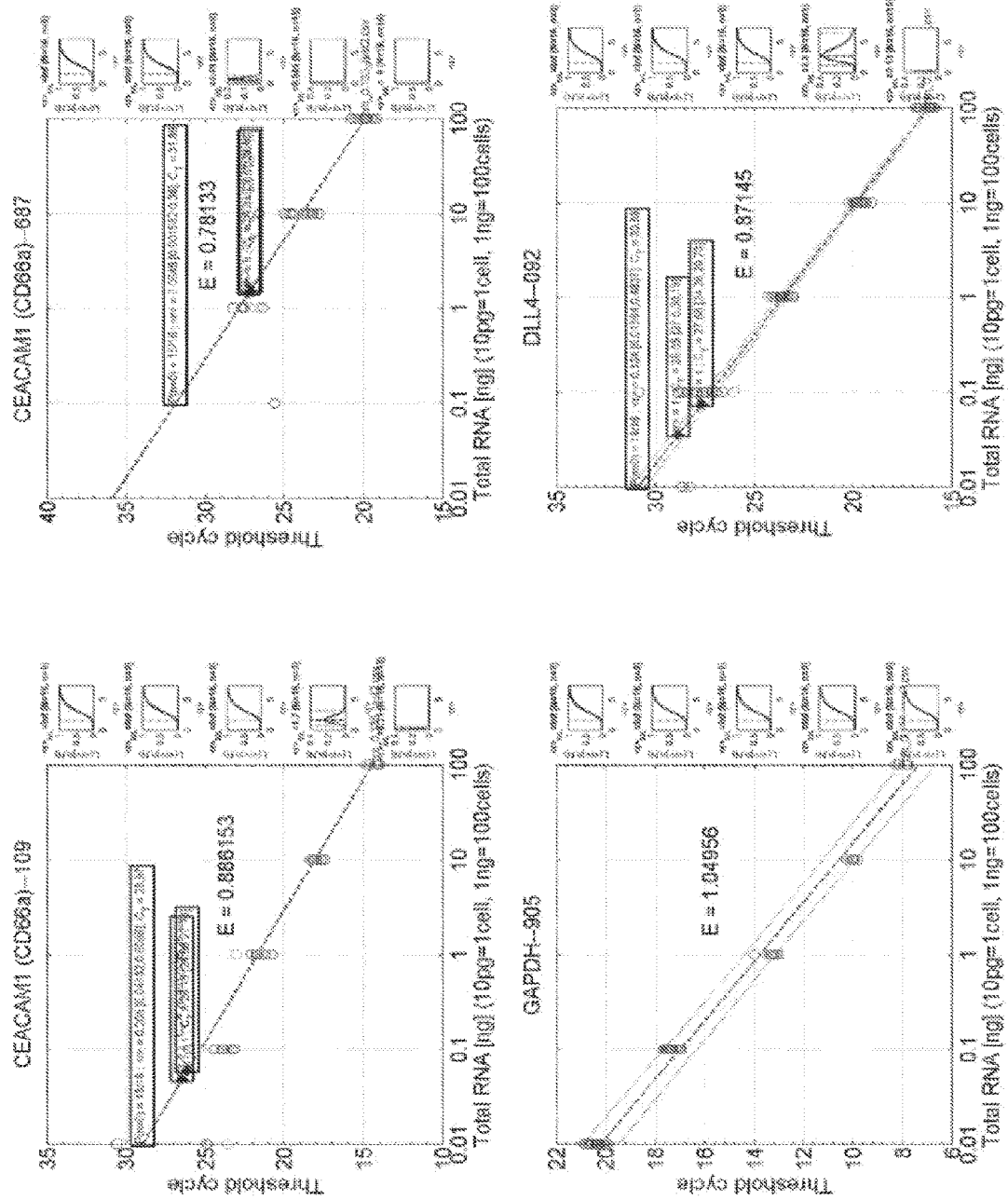
FIG. 112 standard curves showing linearity of qPCR of the second round.
Figure 113:
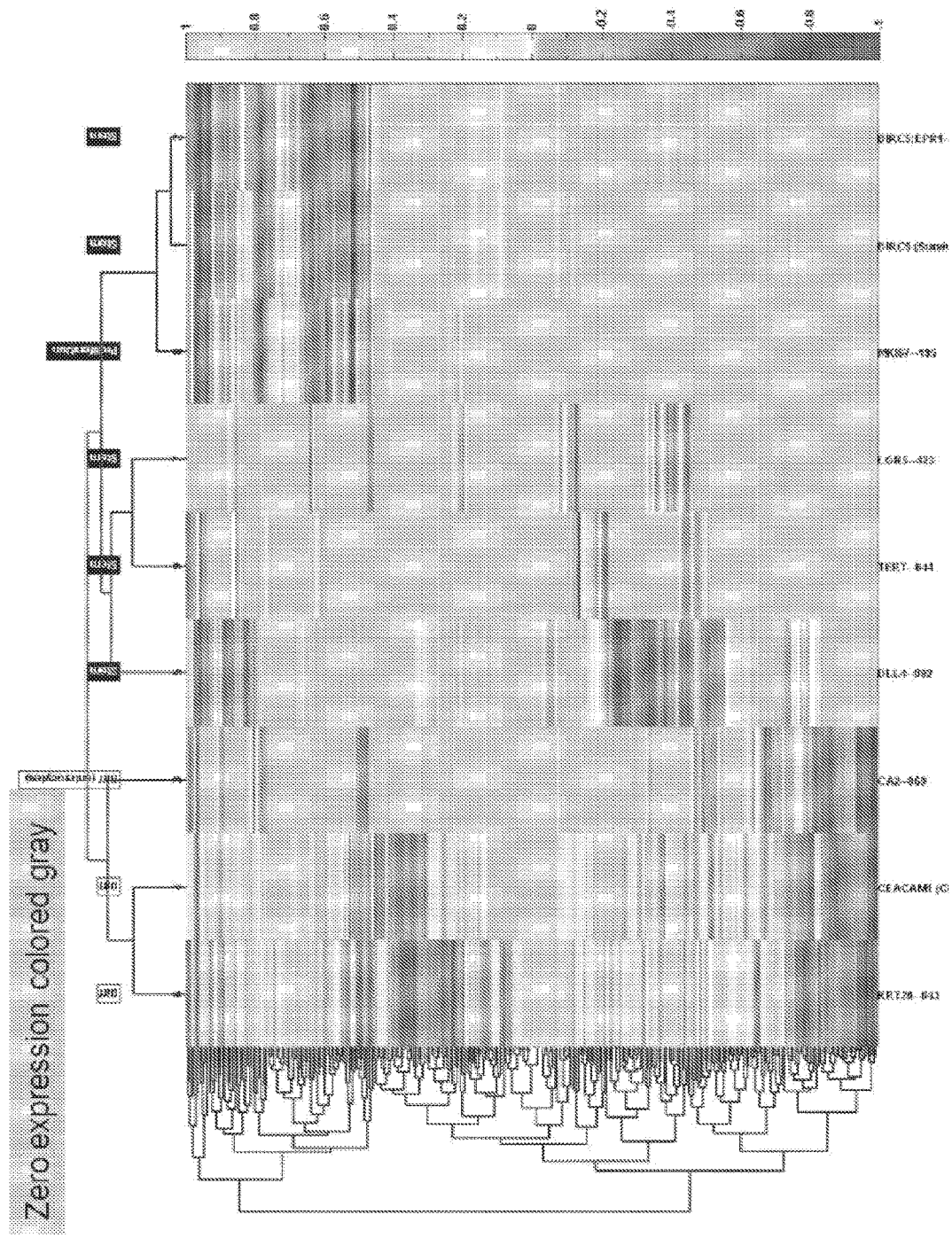
FIG. 113 results of clustering where no expression is marked with gray color.
Figure 114:
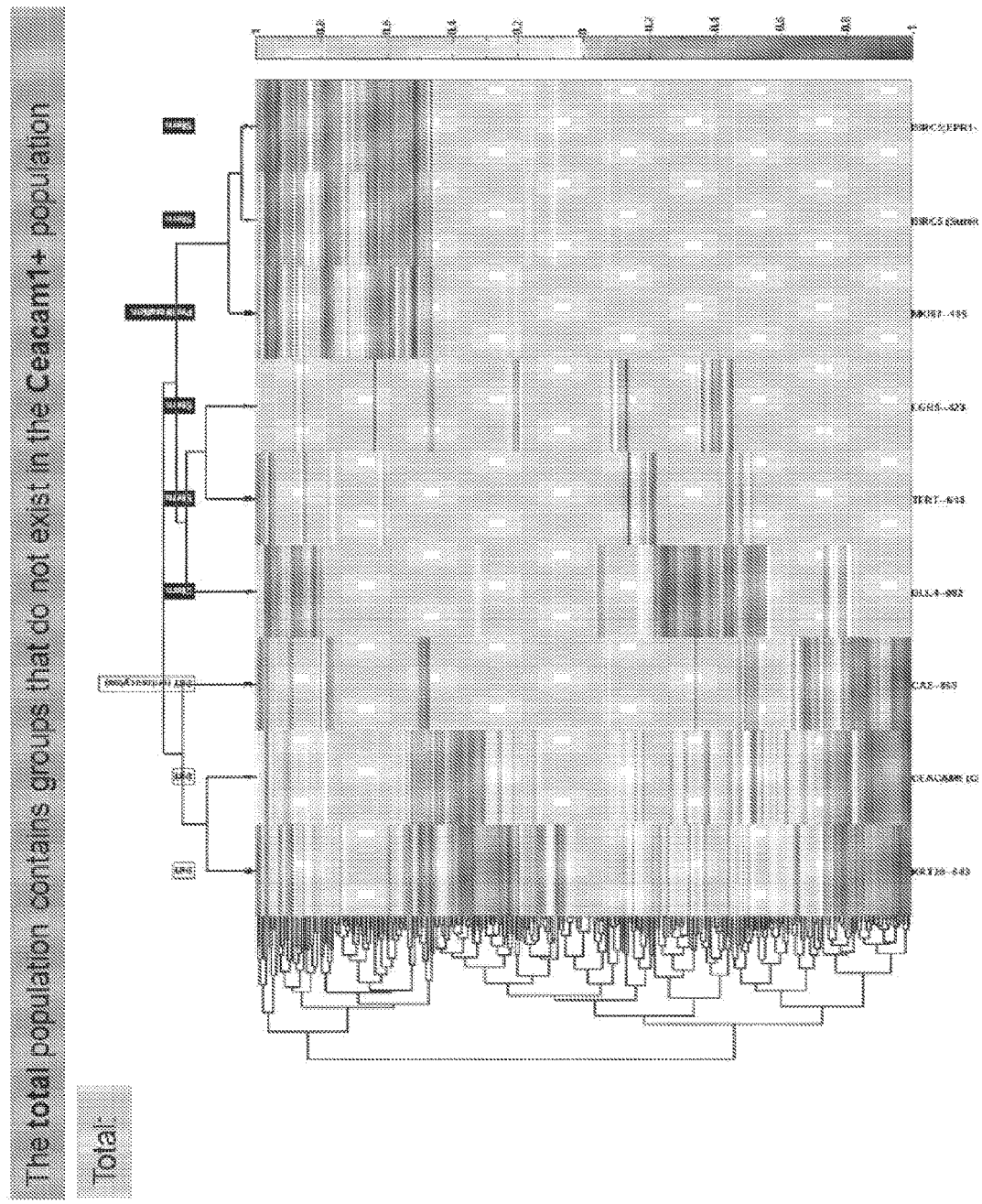
FIG. 114 results of clustering marking total populations containing cells that do not exist in the CD66+ population FIG. 115 results of clustering marking total populations containing CD66+ populations FIG. 116 heat maps from four different chip-runs of the samples. Cells were taken from normal colon mucosa. The cells were FACS sorted with EpCAM, and CD66a surface markers. Non-tumorigenic colon cells (NTCC non-stem) cells were defined as EpCAM+/CD66a+ cells. Colon cancer stem cells (CoCSC) were defined as EpCAM+/CD66a– cells.
Figure 115:
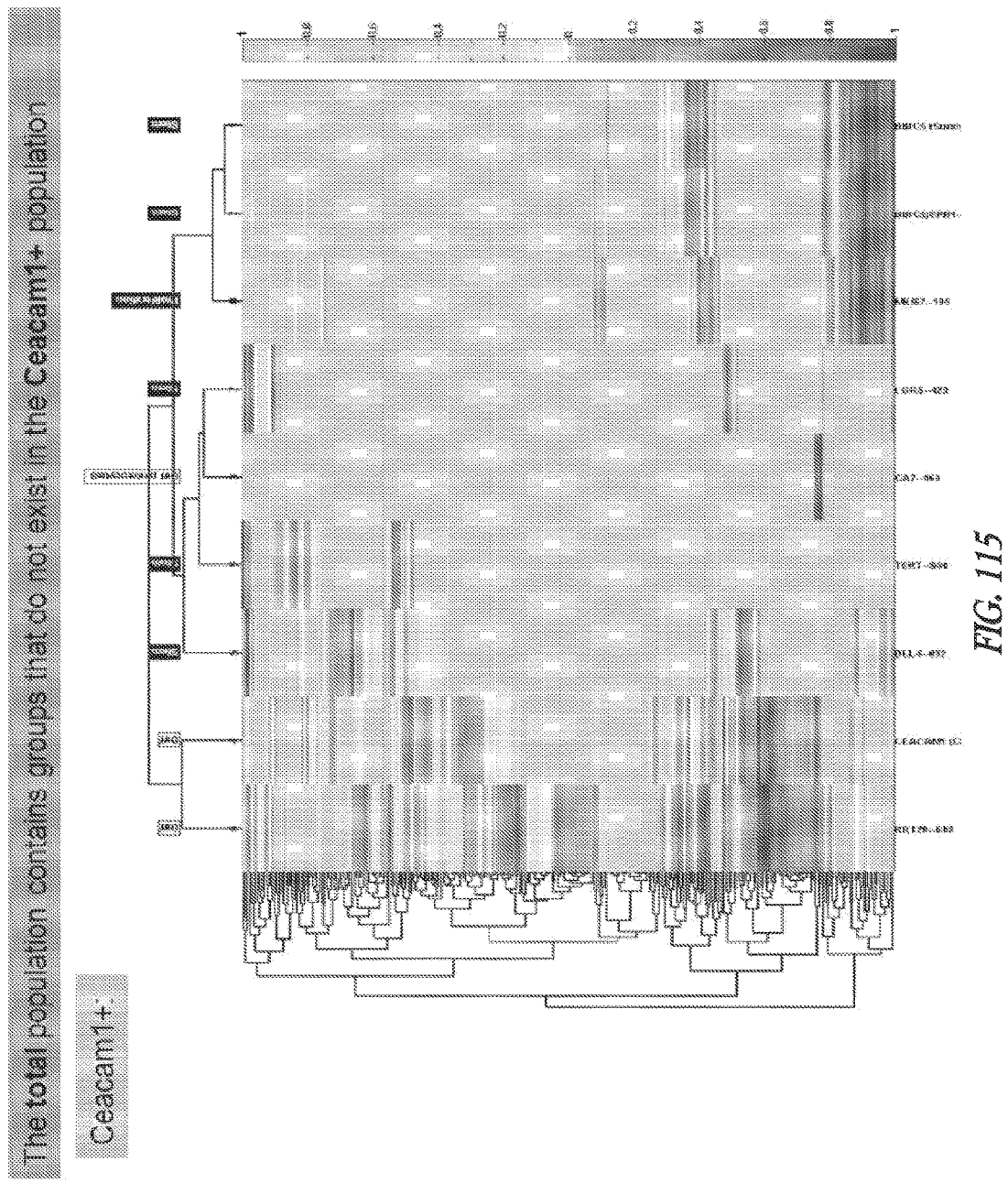

Heat maps from 4 different chip-runs are shown (FIG. 104). A combined heat map is illustrated in FIG. 105. Out of 336 cells tested, 68 cells were discarded by examining GAPDH and TACSTD1 expression levels, and 268 cells were selected for further analysis (FIG. 106). Hierarchical clustering showed uneven expressions of BIRC5, MKI67, VEFGA, KRT19, CD66, and KRT20 among cells. (FIGS. 107-110). Second round of chip-runs were performed (FIG. 111). Standard curves showing linearity of qPCR is shown in FIG. 112. Results of clustering are shown with different rendering: FIG. 113 (no expression is marked with gray color); FIG. 114 (total populations containing cells that do not exist in the CD66+ population; and FIG. 115 (CD66+ populations).

Example 19: Analysis of Normal Colon Mucosa

Figure 117:
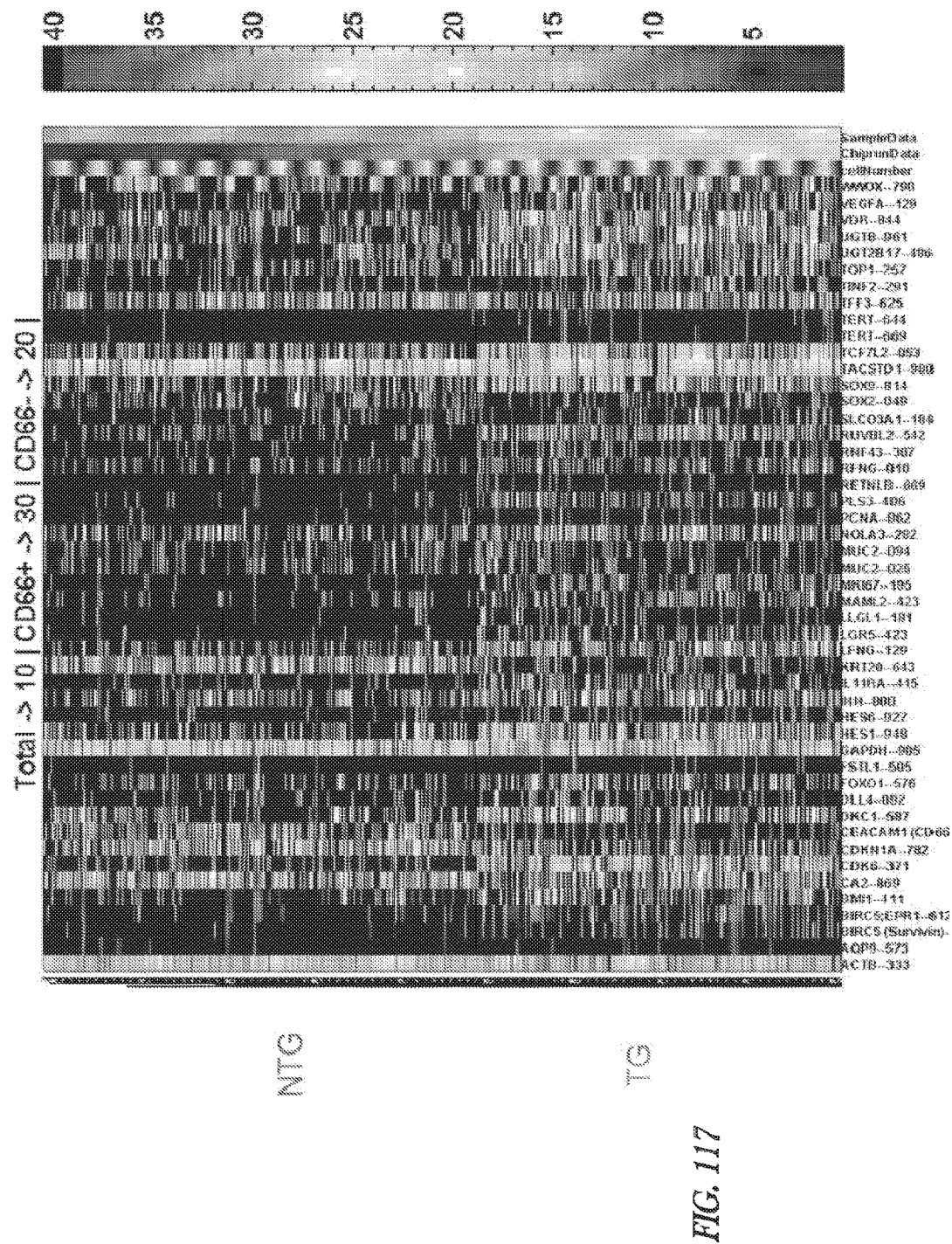
FIG. 117 a combined heat map comparing the four chip-runs.
Figure 118:
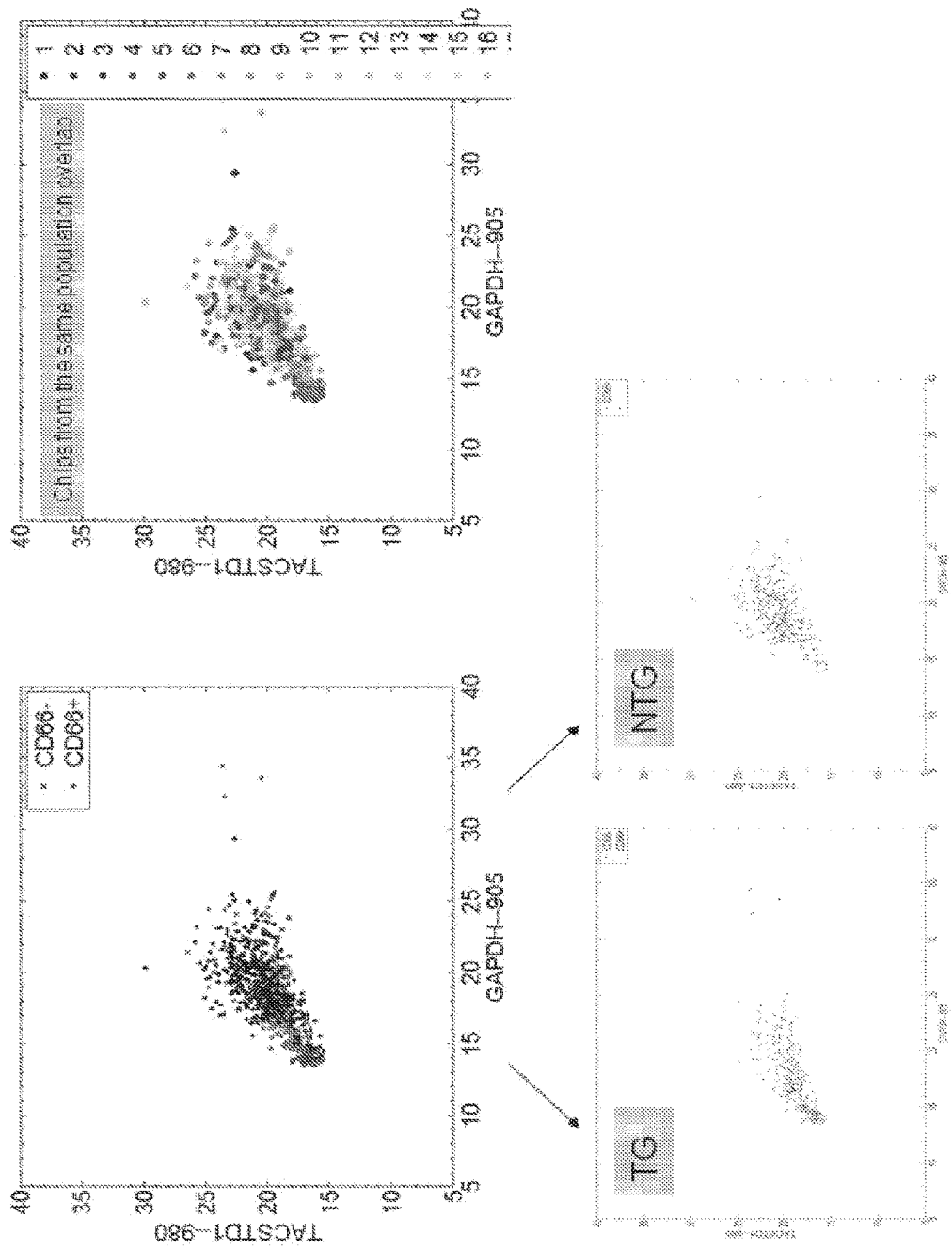
FIG. 118 selection of cells for single cell gene expression analysis. Out of 924 cells tested, 219 cells were discarded by examining GAPDH and TACSTD1 gene expression levels, and 705 cells were selected for further analysis FIG. 119 histograms depicting gene expression levels in CD66+ or CD66-cells of ACTB, AQP9, BIRC5 (SURVIVIN), BIRC5 (EPR1), BMI1, CA2, CDK6, CDKN1A, and CD66A.
Figure 119:
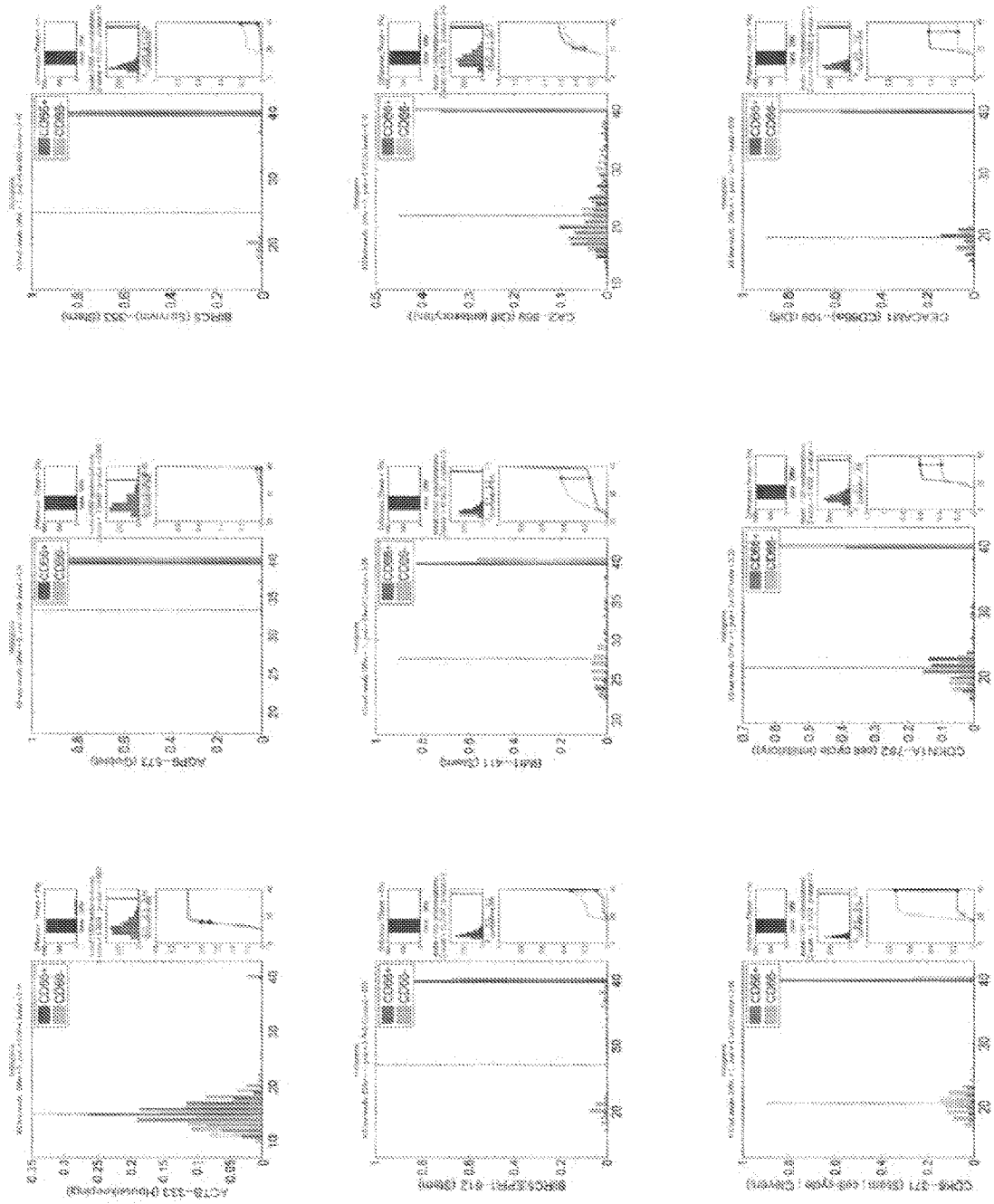
Figure 120:
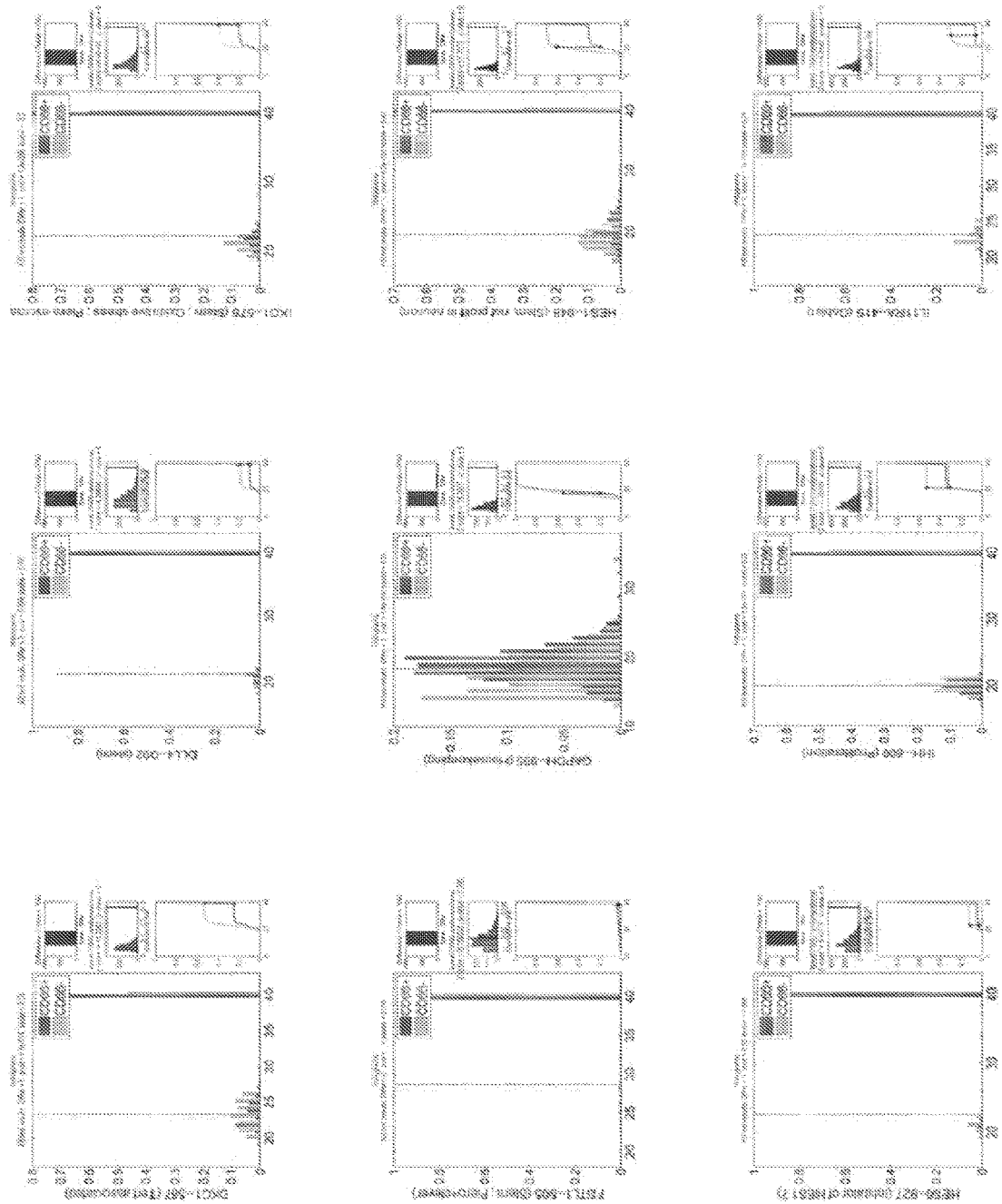
FIG. 120 histograms depicting gene expression levels in CD66+ or CD66-cells of DKC1, DLL4, FOXO1, FSTL1, GAPDH, HES1, HES6, IHH, and IL11RA.
Figure 121:
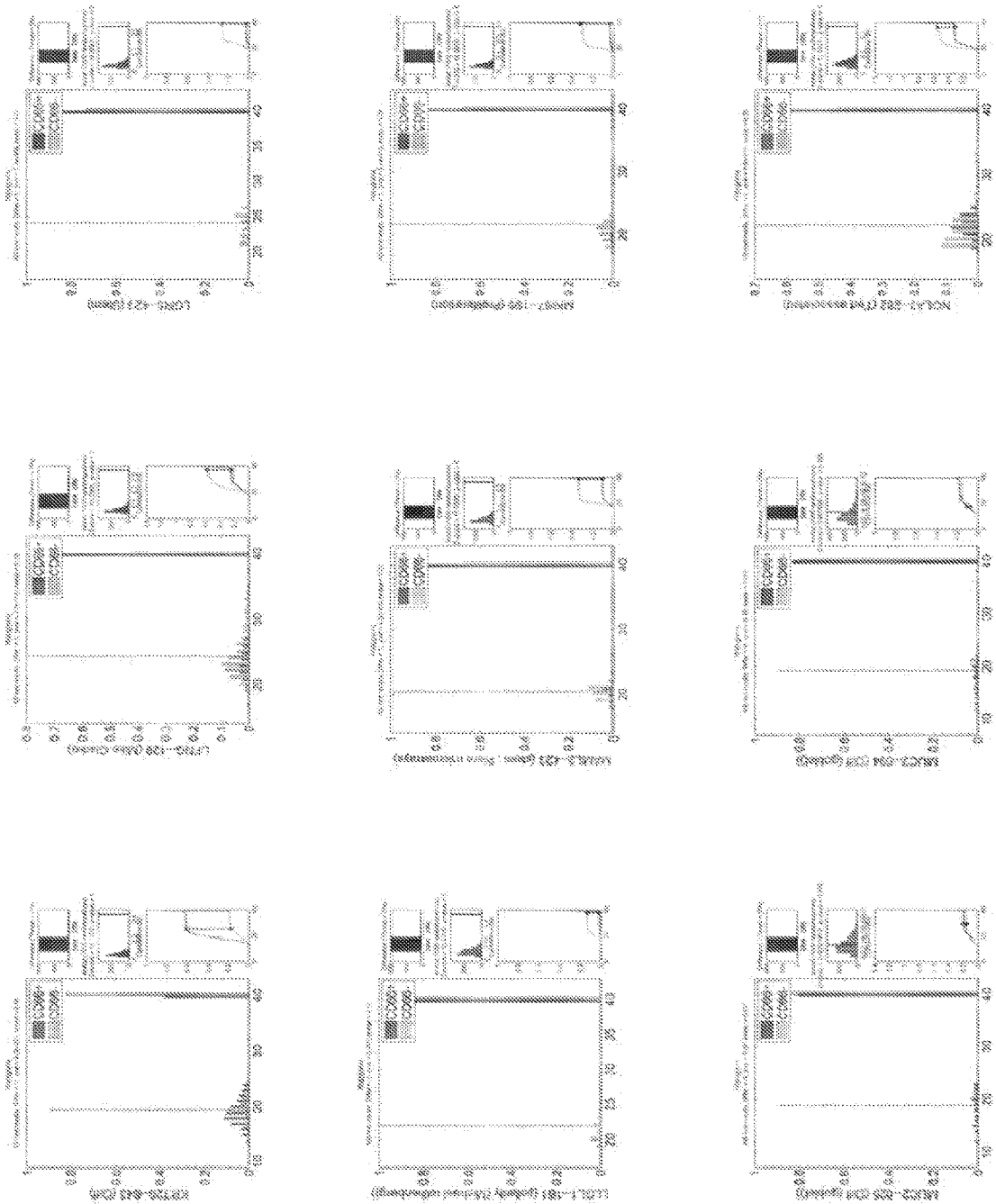
FIG. 121 histograms depicting gene expression levels in CD66+ or CD66-cells of KRT20, LFNG, LGR5, LLGL1, MAML2, MKI67, MUC2, MUC2-094, and NOLA3.
Figure 122:
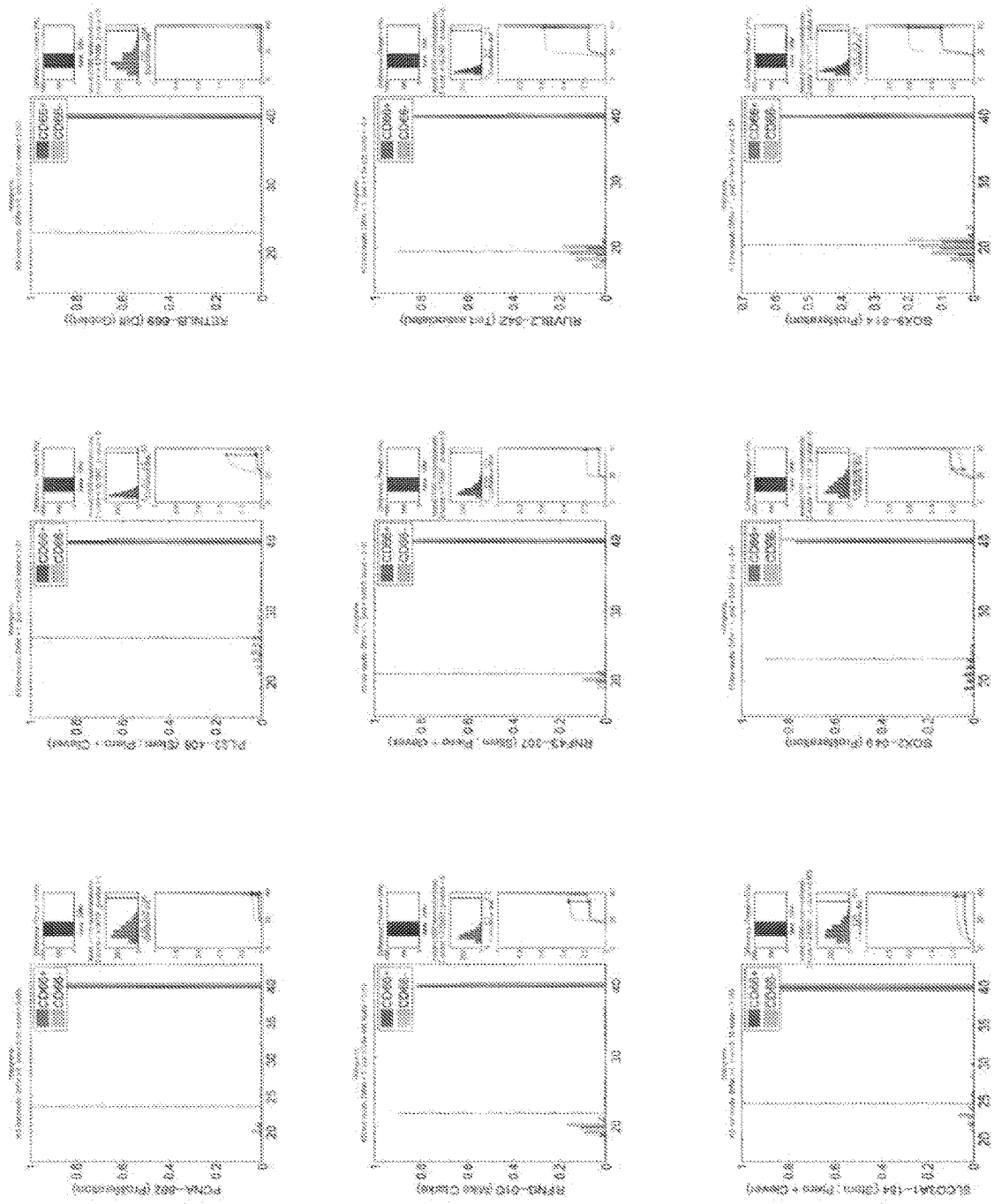
FIG. 122 histograms depicting gene expression levels in CD66+ or CD66-cells of PCNA, PLS3, RETNLB, RFNG, RNF43, RUVBL2, SLCO3A1, SOX2, and SOX9.

Cells were taken from normal colon mucosa. The cells were FACS sorted with EpCAM, CD44 and CD66a surface markers. Non-tumorigenic colon cells (NTCC non-stem) cells were defined as EpCAM+/CD44−/CD66a+ cells. Colon cancer stem cells (CoCSC) were defined as EpCAM+/CD44+/CD66a− cells. Heat maps from 4 different chip-runs are shown (FIG. 116). A combined heat map is illustrated in FIG. 117. Out of 924 cells tested, 219 cells were discarded by examining GAPDH and TACSTD1 gene expression levels, and 705 cells were selected for further analysis (FIG. 118). Histograms depicting gene expression levels are illustrated for the following genes: ACTB, AQP9, BIRC5 (SURVIVIN), BIRC5 (EPR1), BMI1, CA2, CDK6, CDKN1A, CD66A, DKC1, DLL4, FOXO1, FSTL1, GAPDH, HES1, HES6, 1HH, IL11RA, KRT20, LFNG, LGR5, LLLGL1, MAML2, MKI67, MUC2, MUC2-094, NOLA3, PCNA, PLS3, RETNLB, RFNG, RNF43, RUVBL2, SLCO3A1, SOX2, SOX9, TACSTD1, TCF7L2, TERT, TERT-669, TFF3, TINF2, TOP1, UGT8, UGT2B17, VDR, VEGFA, and WWOX (FIGS. 119-124). Kolmogorov-Smirnov statistical significance test for genes expressed in NTCC and CoCSC cells are shown in FIG. 125, demonstrating that the Goblet cells do not differ much between the NTCC and CoCSC populations. Genes were classified using median values and showed in a graph format (FIGS. 126 and 127). A heat map for 6 replicates is shown (FIG. 128). Hierarchical clustering showed MUC2, MK167, TERT, LGR5, TFF3 and CA2 were differentially expressed in stem enriched cells or in mature enriched cells (FIG. 129 and FIG. 130). Genes correlated with TERT are identified in a principal component analysis (FIG. 131). FIG. 132 shows the degree of TERT-correlation in a bar graph. FIG. 133 shows the degree of TERT-association in a bar graph. Using median values, gene expressions associated with TERT expression were identified. (FIG. 134) Genes co-activated with TERT were then identified (FIG. 135). The clustering demonstrated that CDK6, IFNG, UGT8, and WWOX were co-expressed with TERT. Genes such as DKC1, DLL4, HES6, PLS3, RFNG, TCF712, and TOP1 were not co-expressed with TERT. (FIGS. 136-146).

Example 20: Analysis of Colon Xenograft Cells

Cells were taken from xenograft of colon cells. The cells were FACS sorted with EpCAM, CD44 and CD66a surface markers. Colon cancer stem cells (CoCSC) were defined as EpCAM$^{high}$/CD44+/CD166+ cells. Heat maps from 4 different chip-runs are shown (FIG. 147). A combined heat map is illustrated in FIG. 148. Out of 504 cells tested, 21 cells were discarded by examining GAPDH and TACSTD1 gene expression levels, and 483 cells were selected for further analysis (FIG. 149). Furthermore, for every gene, where $C_T$ values are higher than some gene-dependent threshold, the cells were removed (FIG. 150). A combined heat map after the clean up is illustrated in FIG. 151. Hierarchical clustering and k-means clustering were performed to identify differentially expressed genes between mature population and stem/proliferating population (FIGS. 152-155). Patterns of anti-correlated gene expressions between the populations were identified, e.g., HES1 and TFF3, CDK6 and CDKN1A, and UGT8 and VEGFA (FIG. 156). Clustering of genes showed a difference between the two sub-populations (FIG. 157). Clustering after normalization with ACTB, GAPDH, and TACSTD1 showed a difference between the two sub-populations (FIG. 158). K-means clustering of genes showed a difference between the two sub-populations (FIG. 159). K-means clustering after normalization with ACTB, GAPDH, and TACSTD1 showed a difference between the two sub-populations (FIG. 160). A heat map from a standard run is shown in FIG. 161. Hierarchical clustering demonstrated certain genes are differentially expressed, e.g., PCNA, MK167, TERT, CD66a, TFF3, KRT20, WWOX, and BMI1 (FIGS. 162 and 163). Genes correlated with TERT are identified in a principal component analysis (FIG. 164). FIG. 165 shows the degree of TERT-correlation in a bar graph. FIG. 166 shows the degree of TERT-association in a bar graph. Genes having significant difference with TERT is shown in FIG. 167. The clustering demonstrated that CDK6, IFNG, ILGL, HES1, RNF43, RUVB, SLCO, SOX9, TOP1, NOLA3, DKC1, UGT8, WWOX, and HES6 were co-expressed with TERT. Genes such as DLL4, PCNA, UGT2B17, VEGFA, MAML2, and IL11RA were not co-expressed with TERT. (FIGS. 168-187). Hierarchical clustering showing only TERT-related gene is illustrated in FIGS. 188 and 189.

Example 21: Comparison of Normal Colon Cells to Cancer Cells

Single cell gene expression analysis was performed essentially as described above using antibodies which bind to EpCAM, CD44, and CD66a for initial sorting by FACS. Normal cells were defined as EpCAM+/CD44-/CD66a+ and EpCAM+/CD44+/CD66a-. Cancer cells were defined as EpCAM$^{high}$/CD44+/CD166+. Hierarchical clustering showing two normal populations (CD44-/CD66a- cells or CD44-/CD66a+) is illustrated in FIG. 190. Hierarchical clustering showing cancer cells is illustrated in FIG. 191. Hierarchical clustering depicted anti-correlated gene pairs such as CDKN1A and CDK6, and KRT20 and UGT8 (FIG. 192).

Example 22: Analysis of Colon Xenograft Cells

Single cell gene expression analysis was performed as described above using antibodies which bind to EGFP and CD66a for initial sorting by FACS. Cells were taken from xenograft (m10) of colon cells. The cells were FACS sorted with EGFP, CD44 and CD66a. Mature non-tumorigenic cells were defined as EGFP+/CD44-/CD66a+ cells. CoCSC cells were defined as EGFP+/CD44+ cells. Heat maps from 8 different chip-runs are shown (FIG. 193). A combined heat map is illustrated in FIG. 194. Out of 336 cells tested, 72 cells were discarded, by examining GAPDH and TACSTD1 gene expression levels, and 264 cells were selected. Of the 264 cells, 5 cells were further discarded by examining EGFP expression levels, and 259 cells were selected for further analysis (FIG. 195). Furthermore, for every gene, where $C_T$ values are higher than some gene-dependent threshold, the cells were removed (FIG. 196). All colon cells were confirmed to express EGFP (FIG. 197). Histograms depicting gene expression levels are illustrated for the following genes: EGFP, KRT20, CD66A, CA2, LGR5, TERT, OLFM4, MK167, LEFGY1, and LEFTY2 (FIGS. 198 and 199). Clustering was performed to identify differentially expressed genes (FIG. 200). FIG. 201 shows the degree of TERT-correlation in a bar graph. FIG. 202 shows the degree of TERT-association in a bar graph. Using median values, gene expressions associated with TERT expression were identified. (FIG. 203). The clustering demonstrated that ARL5, CES3, CLDN7, DLG1, DLL4, ETS2, EZH2, ID2, IGFBP4, METTL3, MPP7, NUMB, OLFM4, PRKCZ, PTEN, SCRIB, SEC24, SEC62, SUZ12, UGT1A6, UGT2B17, UGT8 and to a certain degree ERBB3, KIF12, NAV1, and UTRN were co-expressed with TERT. Genes such as GNAI, HUNK, LAMB, LEFTY, NRN1, PDGFA, PROX1, and STC2 were not co-expressed with TERT. (FIGS. 204-237). Hierarchical clustering illustrating immature enterocyte signature and genes differentially expressed in various cell types are shown in FIGS. 238 and 239.

Example 23: Analysis of Xenograft Colon Cells

Single cell gene expression analysis was performed essentially as described above using antibodies which bind to EGFP and CD66a for initial sorting by FACS. Cells were taken from xenograft (m10) of colon cells. Mature non-tumorigenic cells were defined as EGFP+/CD44-/CD66a+ cells. CoCSC cells were defined as EGFP+/CD44+ cells. Heat maps from 2 different chip-runs are shown (FIGS. 240 and 241). A difference between copy numbers was observed, as illustrated in FIG. 242.

Example 24: Analysis of Xenograft Colon Cells

Single cell gene expression analysis was performed as described above using antibodies which bind to EGFP and CD66a for initial sorting by FACS. Cells were taken from xenograft (m10) of colon cells. Mature non-tumorigenic cells were defined as EGFP+/CD44−/CD66a+ cells. CoCSC cells were defined as EGFP+/CD44+ cells. Heat maps from 2 different chip-runs are shown (FIG. 243). A combined heat map is illustrated in FIG. 244. FIG. 245 illustrates a heat map showing a simultaneous run of an original and a copy of samples. A difference between copy numbers was observed, as illustrated in FIG. 246. A comparison between samples and standards is illustrated in FIG. 247.

Example 25: Analysis of Normal Colon Cells

Single cell gene expression analysis was performed as described above using antibodies which bind to EpCAM and CD66a for initial sorting by FACS. Cells were taken from normal colonic mucosa. Normal NTCC was defined as EpCAM+/CD66a+ cells. Normal CoCSC cells were defined as EpCAM+/CD66a$^{low}$ cells. Heat maps from 4 different chip-runs for either stem-enriched samples or mature-enriched samples are shown (FIG. 248). A combined heat map is illustrated in FIG. 249. Out of 328 cells tested, 126 cells were discarded by examining GAPDH and ACTB gene expression levels, and 202 cells were selected. Of the 202 cells, 2 cells were further discarded by examining GAPDH and TACSTD1 gene expression levels, and 200 cells were selected for further analysis (FIG. 250). Furthermore, for every gene, where $C_T$ values are higher than some gene-dependent threshold, cells were removed (FIG. 251). A combined heat map after the clean up is illustrated in FIG. 252. A representative hierarchical clustering of all genes, subgroup 1, subgroup 2, k-means clustering of subgroup 2, are illustrated from FIGS. 253-259. Differential gene expressions among various cell types are illustrated from FIGS. 260-263. Markers for immature populations were identified as LGR5, ASCL2, LEFTY1, TERT, PTPRO, OLFM, METTL3, LIF12, EZH2, UTRN, UGT8, AQP1, ETS2, LAMB1, CDKN1B, SUZ12, ESF1, CFTR, RBM25, CES3, VIL1, VEGFB, SEC62, MAST4, and DLL4. Gene expressions for immature cycling populations were identified as BIRC, TOP2A, MKI67, and GPSM2. Gene expressions for mature goblet cells were identified as TFF3 and MUC2. Gene expressions for mature enterocytes were identified as KRT20, CEACAM1, CDKN1A, CA2 and VEGFA.

Example 26: Analysis of Normal Colon Cells

Single cell gene expression analysis was performed as described above using antibodies which bind to EpCAM and CD66a for initial sorting by FACS. Cells were taken from normal colonic mucosa. Normal NTCC was defined as EpCAM+/CD66a+ cells. Normal CoCSC cells were defined as EpCAM+/CD66a$^{low}$ cells. Heat maps from 2 different chip-runs for either stem-enriched samples or mature-enriched samples are shown (FIG. 264). A combined heat map is illustrated in FIG. 265. Out of 292 cells tested, 38 cells were discarded by examining GAPDH and ACTB gene expression levels, and 254 cells were selected. Of the 254 cells, 10 cells were further discarded by examining GAPDH and TACSTD1 gene expression levels, and 244 cells were selected for further analysis (FIG. 266). A combined heat map after the clean up is illustrated in FIG. 267. A representative clustering of TERT association is illustrated in FIG. 268. Hierarchical clustering was performed to identify differentially expressed genes between the groups (FIGS. 269-271). Genes correlated with TERT are illustrated in a bar graph (FIG. 272). Genes associated with TERT are illustrated in a bar graph (FIG. 273). Genes having significant difference in median between TERT+ and TERT− cells are illustrated in FIG. 274. The clustering demonstrated that AQP1, CDKN1B, CES3, CFTR, ESF1, ETS2, HNF1B, KIF12, LEFTY1, METTL3, MYO6, PTPRO, RBBP6, RBM25, SEC62, TOP1, UGT1A6, UGT2B17, UGT8, UTRN, VIL1, and CDK6 were co-expressed with TERT. Genes such as ACVR1B, ACVR1C, ACVR2A, ACVR2B, ADAM10, ID2, EZH2, and BRD7 were not co-expressed with TERT (FIGS. 275-306). Hierarchical clustering showing only TERT-related gene is illustrated from FIGS. 307-310. Genes correlated with TERT are identified in a principal component analysis (FIG. 311). TG and NTG populations are compared using median of $C_T$ value for every gene (FIGS. 312 and 313). Kolmogorov-Smirnov statistical significance test for genes expressed in TG or NTG cells are shown from FIGS. 314-316. A representation of hierarchical clustering by cell types is illustrated in FIG. 317.

Example 27: Analysis of Xenograft Colon Cancer Cells

Single cell gene expression analysis was performed as described above using antibodies which bind to EpCAM for initial sorting by FACS. Cells were taken from xenograft (m6). CoCSC cells were defined as EpCAM+ cells. Heat maps from 4 different chip-runs for either stem-enriched samples or mature-enriched samples are shown (FIG. 318). A combined heat map is illustrated in FIG. 319. Out of 335 cells tested, 5 cells were discarded by examining TACSTD1 and ACTB gene expression levels, and 330 cells were selected. Of the 330 cells, no cells were further discarded by examining GAPDH and ACTB gene expression levels, and 330 cells were selected for further analysis (FIG. 320). A combined heat map after the clean up is illustrated in FIG. 321. A representative clustering by mean-centered standard normalized, and a clustering of a subset are illustrated from FIGS. 322-325. In these experiments, gene expressions for immature population were identified as LGR5, ASCL2, LEFTY1, TERT, PTPRO, OLFM, METTL3, LIF12, EZH2, UTRN, UGT8, AQP1, ETS2, LAMB, SUZ12, ESF1, CFTR, RBM25, ARL5A, HNF1A, and SEC62. Gene expressions for immature cycling population were identified as BIRC, TOP2A, MKI67, and GPSM2. Markers for mature enterocytes were identified as KRT20, CEACAM1, CDKN1A, CA2 and VEGFA. FIG. 326 shows the degree of TERT-correlation in a bar graph. FIG. 327 shows the degree of TERT-association in a bar graph. The clustering demonstrated that LEFTY, EZH2, SUZ12, TOP1, and UTRN were correlated with TERT; and correlation of ACVR, ADAM10, AQP1, ARL5A, BRD7, CCND1, CDK2, CDK6, CES3, CFTR, DLL4, ESF1, ETS2, GPR, HNF1B, HUNK, KIF12, LAMB, METTL3, MYO6, OLFM4 PTPRO, RBBP6, RBM25, SEC62, UGT1A6, UGT2B17, UGT8, and VIL1 are illustrated from FIGS. 328-361. TERT+/cycling compartment population was positive for expression of ARL5A, CCND1, CDK2, ESF1, ETS2, EZH2, LEFTY, METTL3, OLMF4, RBBP6, SUZ12, TOP1, UGT9, UTRN, BRD7, HUNK, GPR89B, and to a certain extent ADAM10, CDK6, CES3, CFTR, DLL4, HNF1B, MYO6, RBM25, SEC62, UGT1A6, UGT2B17, and VIL1. A representation of hierarchical clustering by cell types is illustrated in FIGS. 362 and 363.

Example 28: Analysis of Breast Xenograft Cells

Single cell gene expression analysis was performed as described above using antibodies which bind to CD44 and CD24 for initial sorting by FACS. Cells were taken from xenograft (m4) breast cancer sample. Br-CSC cells were defined as CD44+/CD24− cells. Non-tumorigenic cells were defined as $CD44^{low/-}$ cells. A combined heat map is illustrated in FIG. 364. Out of 252 cells tested, 19 cells were discarded by examining GAPDH and ACTB gene expression levels, and 233 cells were selected for further analysis (FIG. 365). A combined heat map after the clean up is illustrated in FIG. 366. A representative clustering is illustrated in FIGS. 367 and 368. A correlation graph showing the genes that are most differentially expressed is illustrated in FIG. 369. A representation of clustering with only genes that are significantly differentially expressed between TG and NTG cells is illustrated in FIG. 370. Result of K-S stat test is shown in FIG. 371. A representation of clustering with only genes that are significantly differentially expressed between TG and NTG cells with pval (K-S) less then 0.05/96 well is illustrated in FIG. 372. Genes differentially expressed are identified as the following: CDH1, CDH2, SOX9, CD109, METTL3, CD44, CDK6, PTEN, TOP1, SUZ12, BMI1, LEFTY1, LEFTY2, E-CADHERIN, and N-CADHERIN. A representation of clustering with only TG population is shown in FIG. 373. A representation of clustering with only NTG population is shown in FIG. 374.

Example 29: Summary-all Single Cell Experiments for Colon Cells

A representation of hierarchical clustering for various cell types are illustrated from FIGS. 375-384.

Example 30: Analysis of Cells from Normal and Cancer Biopsy

Single cell gene expression analysis was performed as described above using antibodies which bind to EpCAM, CD44, and CD166 for initial sorting by FACS. Cells were taken from normal mucosal biopsy or primary tumor. Out of 335 cells tested, 37 cells were discarded by examining EPCAM and ACTB gene expression levels, and 298 cells were selected. Of the 298 cells, 4 cells were further discarded by examining GAPDH and ACTB gene expression levels, and 294 cells were selected for further analysis (FIG. 385). A combined heat map after the clean up is illustrated in FIG. 386. Histograms depicting gene expression levels in normal mucosa or in primary tumor cells are illustrated for the following genes: ACTB, CA1, GAPDH, SHH, BIRC5, CDKN1A, GPSM2, PRPRO, CFTR, LEFTY1, and OLFM4 (FIG. 387). Kolmogorov-Smirnov statistical significance test for genes expressed in normal or primary tumor cells identified samples expressing significantly higher levels of each gene (FIG. 388). Genes classified using medians are illustrated in FIG. 389. A representative hierarchical clustering for cancer samples and normal samples is illustrated in FIG. 390. Clustering of cell groups are illustrated in FIG. 391 for cancer sample, and in FIG. 392 for normal sample. As shown in these figures, most genes are expressed at higher levels in normal tissue. LEFTY1, OLFM, and CFTR were higher in the tumor. Both cell populations were CD44+. A hierarchical clustering showing expression of CEACAM1 and TERT in normal or tumor sample is illustrated in FIG. 393.

Example 31: Analysis of Mouse Colon Cells

Single cell gene expression analysis was performed as described above using antibodies which bind to CD44 for initial sorting by FACS. Cells were taken from two separate samples of mouse colons. Both samples were FACS sorted for $CD44^{high}$ cells. Heat maps from 4 different chip-runs for both samples are shown (FIG. 394). A combined heat map is illustrated in FIG. 395. Out of 168 cells tested, 81 cells were discarded by examining TACSTD1 and ACTB gene expression levels, and 87 cells were selected. Of the 87 cells, 30 cells were further discarded by examining HPRT and ACTB gene expression levels, and 57 cells were selected for further analysis (FIG. 396). A combined heat map after the clean up is illustrated in FIG. 397. A representative clustering of mean-centered standard normalized, and subset are illustrated in FIG. 398. Some anti-correlated gene pairs were identified, including TERT and CA2, KLF4 and KLF5, CD66 and TERT, BMI1 and LGF5, LGR5 and CD66, and CD66 and BMI1 (FIGS. 399 and 400). A hierarchical clustering showing only LGR5, BMI1, and CD66a is illustrated in FIG. 401.

Example 32: Analysis of Normal Primary Breast Tissue

Single cell gene expression analysis was performed as described above using antibodies which bind to EpCAM, Lin, and CD49f for initial sorting by FACS. Cells were taken from normal mammary epithelium. Total epithelial cells were defined as EpCAM+/Lin−/CD49f+ cells Unknown stromal cells were defined as EpCAM−/Lin−/CD49f− cells. Heat maps from 4 different chip-runs are shown (FIG. 402). A combined heat map is illustrated in FIG. 403. Out of 168 cells tested, 9 cells were discarded by examining GAPDH and ACTB gene expression levels, and 159 cells were selected for further analysis (FIG. 404). A combined heat map after the clean up is illustrated in FIG. 405. Representative hierarchical clustering is illustrated in FIGS. 406-408. In these experiments, no cells were identified as TOP2A+/BIRC5+/MKI67+, TERT+, or CDH1+/CD1-9+/CDH1−. Some CDH1+ cells were found in luminal population. One subpopulation was EpCAM−/CD49f+, and the other subpopulation was Thy1+. These data may suggest that basal cells express KRT5, KRT14, KRT17, and EGFR while luminal epithelium cells express krt18, krt8, krt19 AND ELF5. Important luminal-cell markers were discovered in these experiments: NOTCH3, HER3, and EGF Important basal-cell markers were discovered in these experiments: SNAI2, NGFR, and LAMB1. A hierarchical clustering showing only CD49f+ cells is illustrated in FIG. 409. A heat map of samples obtained from epithelium and stroma is illustrated in FIG. 410 and its hierarchical clustering is shown in FIG. 411. Between epithelium and stroma, an antagonistic expression pattern was observed between VEGFA and VEGFC.

Example 33: Analysis of Xenograft Colon Cells

Single cell gene expression analysis was performed as described above using antibodies which bind to EGFP, CD44 and CD66a for initial sorting by FACS. Cells were obtained from a xenograft (m10). Mature non-tumorigenic cells were defined as EGFP+/CD44−/CD66a+ cells. CoCSC cells were defined as EGFP+/CD44+ cells. The FACS sorted cells were subjected to a set of different experimental conditions: 5 ul of sort-mix with 0.025% Tween-20 (to examine if addition of Tween-20 is helpful); heated to 65° C. for 10 minutes or to 95° C. for 5 minutes. The sample was then split into an "original" and a "copy." Standards were added a day before the experiments and refrozen. Heat maps from 3 different chip-runs for each condition (65° C., 10 min or 95° C., 5 min) are shown (FIGS. 412-414). Standard curves showing linearity of qPCR is shown in FIG. 415. Levels of gene expressions between the original and copy are shown for certain genes including GAPDH, ALCAM, ATOH1, AXIN2, CA2, NOTCH1, LGF5, HESS, KRT20, HES6, 1HH, TACSTD1, SOX2, NOTCH2, RETNLB, and CEACAM1 (FIGS. 416-418). Results of the experiments were compared to a result obtained in an independently performed set of experiments (FIG. 419). It was noted that without mRNA split, similar replicate variability where $C_T$ is less then 20 is observed in standard total RNA dilution experiments (FIG. 420). Based on these experiments, the following conclusions were derived: unlike previous experiments, housekeeping genes show almost no bias; no significant difference between 65° C. condition and 95° C. condition; and other genes do show bias a bit towards the original plate, especially at high $C_T$.

Example 34: Analysis of Cells from Normal Colonic Mucosa

Single cell gene expression analysis was performed as described above using antibodies which bind to EpCAM, CD44 and CD66a for initial sorting by FACS. Cells were taken from normal colonic mucosa. Normal-NTCC cells were defined as EpCAM+/CD44−/CD66a+ cells. Normal-CoCSC were defined as EpCAM+/CD44+/CD66a$^{low}$ cells. A combined heat map is illustrated in FIG. 421. Out of 168 cells tested, 46 cells were discarded by examining GAPDH and ACTB expression levels, and 126 cells were selected. Of the 126 cells, 9 cells were further discarded by examining EPCAM and ACTB expression levels, and 117 cells were used for further analysis (FIG. 422). A combined heat map after the clean up is illustrated in FIG. 423. Representative clustering is illustrated in FIGS. 424-426. In these experiments, a possible connection between the expressions of ZEB1 and EZH2 were identified in the stem cell compartment. Stem cells expressed ETS2, ASCL1, TERT, and LGR5. Goblet cells expressed LYZ. RGMB, DLL4, and TERT were expressed in stem and goblet cells. AQP1 and LEFTY1 were expressed in stem and immature enterocytes. An unknown population of cells expression CFC1, PCGF6 and LEFTY1 were identified in the mature compartment.

Example 35: Analysis of Mouse Colon Mucosa Cells

Single cell gene expression analysis was performed as described above using antibodies which bind to Esa, CD45, CD44, and CD66a for initial sorting by FACS. Cells were taken from the colon of FVB strain mouse. Cells were grouped into two populations; Esa+/CD45−/CD44−/CD66a$^{hi}$ or Esa+/CD45−/CD44+/CD66a$^{hi/low}$. A combined heat map is illustrated in FIG. 427. Out of 336 cells tested, 10 cells were discarded by examining GAPDH and ACTB expression levels, and 326 cells were selected. Of the 326 cells, 63 cells were further discarded by examining TAC-STD1 and ACTB expression levels, and 263 cells were used for further analysis (FIG. 428). A combined heat map after the clean up is illustrated in FIG. 429. A representative hierarchical clustering of all samples is illustrated in FIGS. 430 and 431. Hierarchical clustering of only CD44+/CD66a− cells is illustrated in FIGS. 432 and 433. In these experiments, BMI1 expression seemed to be higher in mature cells. CA2 expression is high in the stem cells. Aqp1 was found in the goblet cells.

Example 36: Standards Run of Total RNA

Total RNA and one negative control were prepared in 7 different dilutions ranging from 10 fold dilution to $10^7$ fold dilution with one log interval. The diluted samples were pre-amplified, mixed with 48 primer sets (Taqman gene expression assays, manufactured by ABI Biosystems). The experiments were prepared in 6 replicates per dilution. A representative heat map of various dilutions and the negative control is illustrated in FIG. 434. PCR efficiency in the standards is shown in FIG. 435. Amplification linearity is demonstrated by linear amplification of selected genes such as CAR1, GAPDH, GPSM2, KLF4, KRT20, MUC2, OLFM4, TACSTD1, and TFF3, ACTB, CA2, CLDN7, as illustrated in FIGS. 436-438. A hierarchical clustering of genes with high PCR efficiency is shown in FIG. 439. Some genes over-expressed in CD44+ or CD44− cells are identified (FIG. 440).

Example 37: Analysis of Mouse Normal Mammary Epithelium Cells

Figure 445:
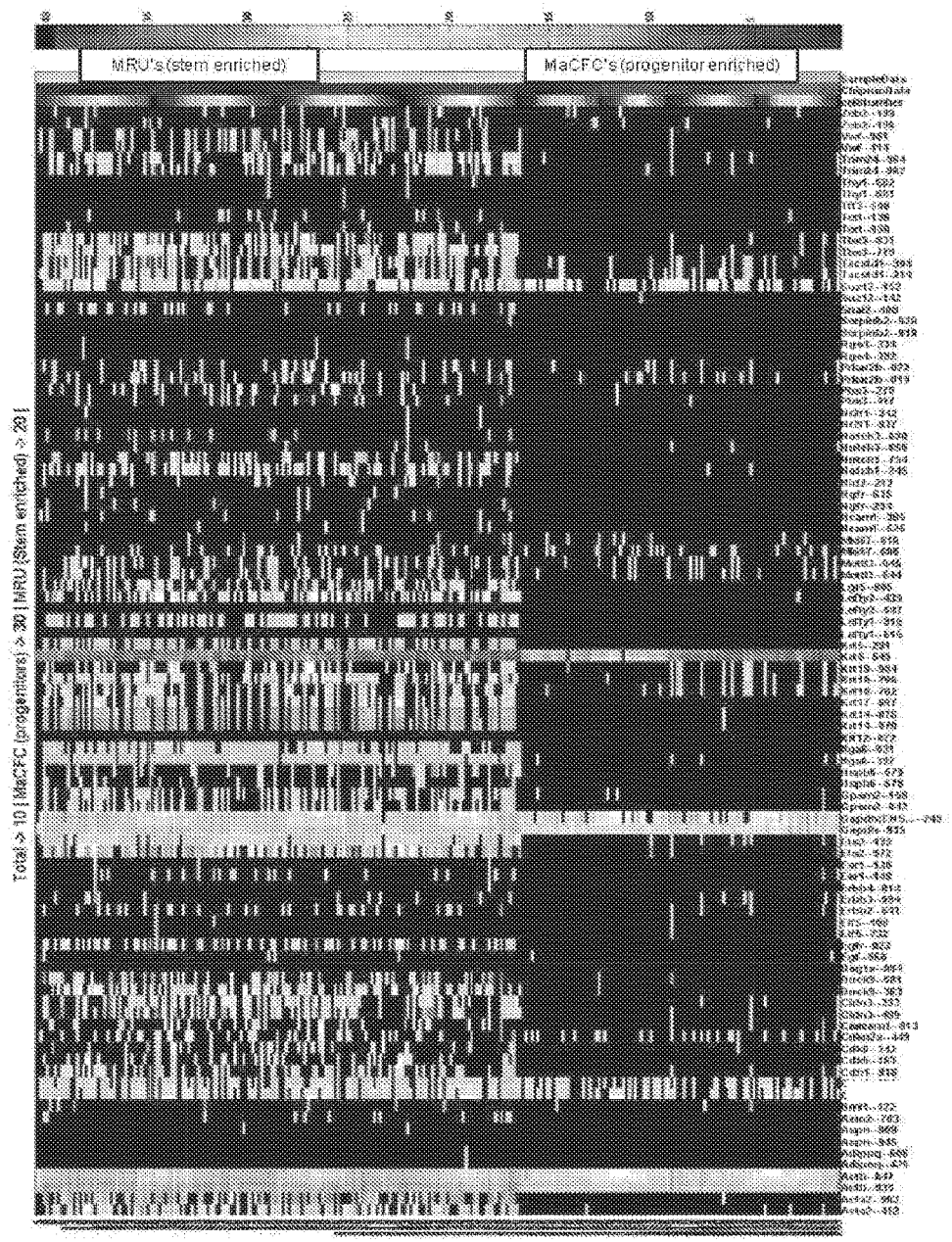
Figure 446:
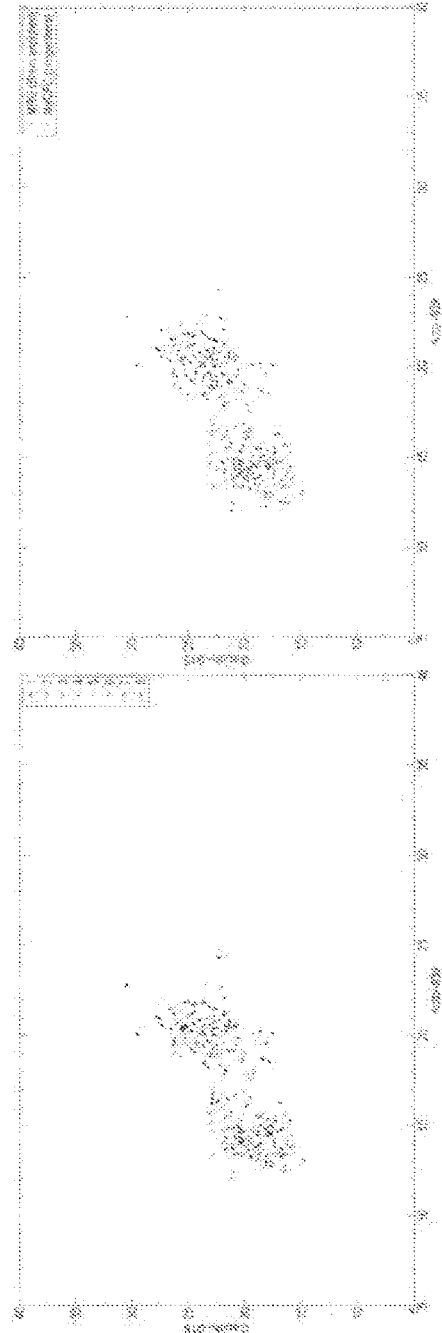
Figure 447:
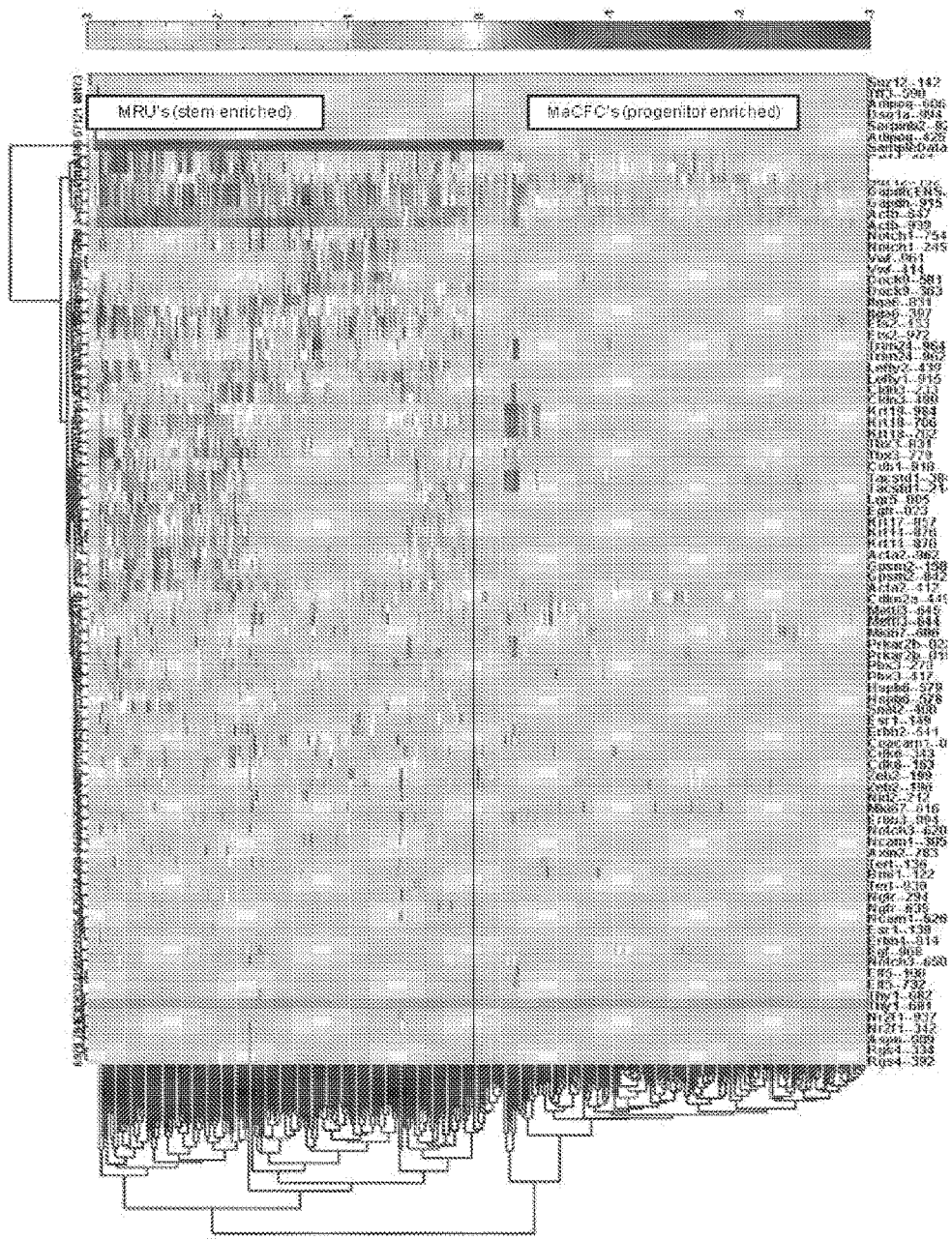

Single cell gene expression analysis was performed as described above using antibodies which bind to CD24, CD49f, CD49 and Lin for initial sorting by FACS. Cells were taken from normal mouse mammary epithelium. Enriched stem cells were defined as CD24$^{med}$/CD49f$^{hi}$/Lin$^-$. Enriched progenitor cells were defined as CD24$^{hi}$/CD49$^{med}$/Lin$^-$. Out of 168 cells tested, 8 cells were discarded by examining ACTB expression levels, and 160 cells were selected (FIG. 441). A combined heat map of enriched stem cell is illustrated in FIG. 442. A representative hierarchical clustering of enriched stem cell is illustrated in FIGS. 443 and 444. A combined heat map of enriched progenitor cell is illustrated in FIG. 445. Progenitor cells were cleaned up by examining GAPDH and ACTB gene expressions (FIG. 446). Representative hierarchical clustering or enriched progenitor cell is illustrated in FIGS. 447 and 448.

Example 38: Combined Analysis of Stem and Goblet Cells from Colonic Mucosa

A combined heat map of stem and goblet cells, and mature enterocytes are shown in FIG. 449.

Example 39: Comparison of Preamp 48 and Preamp 96 Run on M48 Chips qPCR was performed on M48 chip or M96 chip and the results were compared to each other (FIG. 450). Heat maps were obtained from each run for comparison purpose (FIG. 451). Standard curves generated from these runs showed that they are very close to each other (FIG. 452). The efficiency between M48 and M96 chips were comparable, with an exception of one high noise floor in the 96 preamp run (FIG. 453).

Example 40: The Cellular Hierarchy of the Normal Colon

We used normal human colon single cell gene expression to define the cellular hierarchy of normal human colon. To do this, we used several genes including those i) linked to the function of normal stem cells in multiple tissues, especially telomeras ii) cytokeratin genes, which can be used to identify myoepithelial luminal cells, and iii) developmental genes known to be involved in the differentiation of the colon and other tissues. We first did analyses to identify genes that were co-expressed with TERT (FIG. 466).

We then did a cluster analysis based on genes expressed by Tert, and identified the stem cell, enterocyte progenitor cells, and luminal cell compartments (FIG. 467). The following genes are co-expressed with the majority population of stem cells: AQP1, KIF12, PTPRO, METTL3 and LGR5. Note that the TERT+ stem cells can be divided into two main groups, those that express LGR5 and those that do not express LGR5. Thus, it appears that there are two distinct normal stem cell populations in the normal colon: an LGR5+ population and an LGR5− population (FIG. 467). Using this clustering strategy, we can define the cellular hierarchy of the normal colon, including the intestinal stem cells (FIG. 467).

These findings show that single cell technology can be used to identify the cellular hierarchy of the normal colon, including the identification of the colon stem cells.

We next used the single cell technology to identify the cancer stem cell population in human colon tumors. Again, we used TERT to identify the stem cells in a tumor (QC8). In this tumor, there is a distinct minority cell population of cancer stem cells that express TERT (FIG. 468). In addition, there is a second population of mature cancer cells that are non-tumorigenic, do not express TERT, and express mature colon cell markers including TFF3, CK20, and CA2. These cells do not form tumors when transplanted into immunodeficient mice. Note that like the normal colon, there is a population of LGR5+ cells that express TERT and a population of cells that do not (FIG. 468).

We next looked at genes whose expression is correlated with TERT. The following genes are correlated: LGR5, MET, BMPR1A, AXIN2, c-MYC, EPHB2, CYCLIND1, NOTCH1 and NOTCH2 (FIG. 469). In addition, the following genes are correlated to the non-tumorigenic cells TFF1, IRS1, COX2, MUC2, CK20, and to a lesser extent, CEACAM1 (FIG. 469).

Clustering analysis can be used to define the hierarchy of the cancer cells. In this example, two distinct populations of TERT+ stem cells can be seen in QC8. The first TERT+ population expresses proliferation genes, BIRC5 and MKI67, while the second dos not (FIG. 470). Some markers that can be used to identify the cycling stem cells include the following markers: GPSM2, SUZ12, OLFM, ETS2, CDK2, EZH2, AQP1, Lefty1 and PTPRO. Some markers that can be used to identify the slow cycling stem cells include the following markers: LAMB1, LEFTY, AQP1, EZH2 and PTPRO. EZH2 expression by the cancer stem cells is important, because both TERT and EZH2 are important for normal stem cell maintenance. Notably, these cells seem to express markers associated with differentiated goblet cells, albeit at lower levels. These markers include KRT20, TFF3, GNA1, CEACAM1 and CES3. This data is shown in FIG. 470.

As another example, colon tumor QC4 was analyzed. This tumor has been propagated in immunodeficient mice and has a very high frequency of cells that grow a tumor when injected into immunodeficient mice. These tumors grow quite rapidly, with an extremely rapid rate of tumor doubling time. A single cell analysis of this tumor was done. This analysis revealed several important points relevant to this xenografted tumor. First, there is a much higher frequency of cells that express immature cell makers including LGR5, GPSM2 and LAMB1 but these cells also express high levels of maturation markers including TFF3 and KRT20 (FIG. 471). Next, all cell populations, even mature cells, express detectable levels of telomerase, and unlike the previous example even the most mature appearing cells are proliferating as measured by expression of MKI67 expression. This shows how one can identify tumors that are more aggressive, and it enables one to see different populations of cancer cells, and specifically cancer stem cells, in a tumor.

These data show that linking telomerase to expression of maturation markers can identify the frequency of cancer stem cells in a particular tumor (from low to high), the specific cell populations that can self renew in a particular tumor, i.e. the identity of the cancer stem cells, and molecular targets for eliminating the different populations of cancer cells, including the cancer stem cells.

Example 41: Examination of Normal Breast and Breast Cancer Cells

Experimental procedures are substantially as described above. Single cell analysis of normal and breast cancer cells was performed. Results for analysis on normal human breast cells is shown in FIGS. 456-469 and clustering analysis is shown in FIG. 461. Analysis of breast cancer cells is shown in FIG. 460 and clustering analysis is shown in FIG. 470.

Example 42: Cell Sorting Apparatus

Modern cancer biology researches have shown cumulated evidence that cancer progression is driven by a minority "cancer stem cells" population which combines both cancerous features and stem cell properties. As a consequence, finding and monitoring these cancer stem cells rather than the differentiated ones will be the effective way to detect and evaluate cancer. Furthermore, the ultimate way to cure cancer would be the elimination of the cancer stem cells. With the ability to identify cancer stem cells from clinical samples, we may improve both the basic science research and clinical outcomes.

Current cancer diagnosis and prognosis procedures consist of biopsy sampling and followed by histology examination. Such method can only offer the general idea about cell morphology. A complete evaluation requires the isolation of the cancer stem cells followed by genetic and epigenetic examination. The prevalent cell sorting apparatus, flow cytometer, offers high throughput and full automation. However it has two main drawbacks which are not compatible with the stem cell identification from primary samples. First, it requires too much sample for each running. The minimum sample consumption is about millions of cells, which is hard to meet when we are doing primary samples. Second, despite of the sophisticated optical system, a flow cytometer can only guess the cell morphology by light scattering. Therefore the single cell resolution is never guaranteed.

To improve the performance of primary sample sorting, we developed a cell sorting system to process immunostained live cells, measure fluorescent intensities and automatically sort the cells for downstream single cell analysis with minimum sample consumption. The central part of the cell sorting system is a small PDMS chip for cell washing and presenting (FIG. 466). It consists 10,000 microwells in array format. We put immunostained single-cell suspension onto the chip without washing and let the cells settle randomly into the wells. The high aspect-ration microwells can trap the cells inside when we flow buffer above them for washing. A multi-color microarray scanner then interrogates the fluorescent intensities from the cell microarray. As a prove-of-principle, we stained a cell mixture of fibroblasts and epithelial cells with epithelial-specific antibodies (anti-ESA) and washed them on-chip. Fluorescent and light scattering images show great contrast and definite phenotype distinguishing (FIG. 467).

We further built an automatic device based on an inverted microscope (FIG. 468) to sort the cells from the microarray. The part in action is a micro cell manipulator controlled by 3D motorized stages and solenoid pneumatic valves. Another automatic 2D microscopic stage keeps the target cells at the center of the view for real time imaging. After the picking, the manipulator can inject the cells directly into the PCR tubes filled with either medium or lysis buffer for later examination.

As a demo sorting, we mixed GFP$^+$ cells with GFP$^-$ ones with different ratio and sorted the cells based on GFP intensities. Single cell Taqman gene expression assays verified the genotypes of the sorted cells and exhibited very low false positive and false negative rates (FIG. 469).

To prove the ability to sort rare samples, we dissociated a primary human colon sample from the operation room and stained the cells with epithelial cell specific (ESA) and stem cell specific (CD44) antibodies. We then sorted the cells based on their immunostaining results and performed single cell gene expression measurement on each single cell with ~100 Taqman assays. The putative stem cell enriched group showed elevated gene expression levels in stem specific genes such us telomerase, suggesting a successful cell sorting. We further used the system on an in vitro cancer stem cell culture, which has even fewer cells than primary samples and obtained remarkable difference between stem cells and mature cells (FIG. 470).

As a conclusion, we built an automatic cells sorter enabling to sort single cells from rare sample such as clinical biopsy and stem cell culture for downstream single cell analysis. The device has a microwell array chip for on-chip washing and cell presenting, and an automatic picker featured with real time imaging and true single cell resolution. The above applications prove that our cell sorter can process both clinical and laboratory rare samples and measure single cell gene expression pattern for stem cell identification.

Example 43: Single Cell Characterization of the Adult Murine Colonic Epithelium Distinguishes Novel Populations In mammals, the epithelial lining of the colon is continuously replaced every few days throughout the lifetime of the organism. This process is driven by self-renewing stem cells that are thought to reside at or near the crypt base. The progeny of these multipotent stem cells migrate toward the lumen as they divide and differentiate into the three main mature cell types in the colonic epithelium: absorptive enterocytes, mucous-secreting goblet cells, and hormone-secreting enteroendocrine cells. Mature cells are eventually extruded from the epithelium into the lumen.

Understanding the mechanisms underlying this process is important since stem cells likely play a role in the recovery from various causes of epithelial injury (chemical, infectious, autoimmune, or ischemic) as well as in the origins of colon adenocarcinoma, a major cause of cancer-related deaths. Colon stem cells are the only colonic epithelial cells that persist long-term in the tissue, and their importance in tumorigenesis has been suggested by experiments in which intestinal tumors can be induced by driving oncogenic changes in stem cells.

Recently, several different genetic markers have been identified which are expressed in long-term intestinal stem cells as demonstrated by in-vivo lineage tracing experiments using knock-in technology. Such markers include Lgr5 (a Wnt-target and orphan G-protein coupled receptor), Bmi1 (a polycomb ring finger), and CD133/Prominin1 (a cell-surface marker implicated in stem-cell biology). In addition, in accordance with the prediction that colon stem cells undergo numerous mitoses throughout the lifetime of the organism, the stem cell compartment at the crypt base harbors cells with relatively long telomeres and thus likely has a mechanism to maintain telomere length, such as the expression of telomerase and the other components of the telomerase holoenzyme.

In this study, we utilize multiplexed high-resolution (single-cell) gene expression analysis, a novel approach to understanding tissue heterogeneity, together with a classic approach combining flow cytometry using widely-available cell surface markers with in-vitro culture of sorted cells into colonic organoids, to obtain an unprecedented high-resolution portrait of the murine colon. We show that CD44 and CD24 can be used to sort two distinct clonogenic populations at the crypt base (CD44$^{high}$CD24$^{high}$ and CD44$^{med}$CD24$^{low/neg}$) that both express telomerase, but only one of which contains Lgr5-expressing cells. We characterize the gene expression of cells from these populations at the single cell level, identifying several known and several novel markers of immature colonocytes. We then use this analysis to demonstrate that secretory cells at the crypt base express several trophic factors (e.g., Wnt-activators, EGF, Indian Hedgehog (Ihh), and Notch-pathway activators), including a growth factor (Nov/CCN3) which has not previously been implicated in intestinal biology.

Methods

Mice

Mice were fed water and chow ad-libitum and were maintained at the Stanford University Research Animal Facility in accordance with Stanford University guidelines. Mouse strains used included C57B16, FVB, pCx-GFP, and Lgr5-CreER-GFP.

Tissue Preparation

Colons (consisting of ascending colon, transverse colon, descending colon, and rectum, but not including the cecum) from adult (4-16 weeks) male mice were dissected, flushed with PBS to remove debris and fecal matter, sliced into 1-2 mm$^3$ pieces with a razor blade, and washed in PBS. The tissue was then digested at 37 degrees Celsius for approximately 2 hours with regular (every 15-20 minutes) pipetting in serum-free Advanced DMEM (Invitrogen) or RPMI-1640 supplemented with 2 mM L-glutamine, 120 µg/ml penicillin, 100 µg/ml streptomycin, 50 µg/ml ceftazidime, 0.25 µg/ml amphotericin-B, 20 mM Hepes, 1 mM sodium pyruvate, with 200 units/ml Collagenase type III (Worthington, Lakewood, N.J.) and 100 units/ml DNase I (Worthington). After the digestion reached completion, cells were diluted with an equal volume of PBS with 10 mM EDTA (final concentration of EDTA 5 mM), pipetted to disrupt residual clumps, and filtered with 40-µm nylon mesh (BD Biosciences, San Jose, Calif.). Contaminating red blood cells were removed by osmotic lysis (i.e., incubation in ammonium chloride potassium phosphate hypotonic buffer for 5 min on ice), and then cells were washed with cold PBS and resuspended at a density of 0.5–1×10$^6$ cells per mL in cold staining buffer consisting of HBSS supplemented with 2% heat-inactivated calf serum, 20 mM Hepes, 1 mM sodium pyruvate, and antibiotics.

Antibody Staining and Flow Cytometry

To reduce nonspecific binding, cells suspended in staining buffer were blocked on ice for 10 minutes with rat IgG (Sigma, St. Louis, Mo.) 10 mg/mL at 1:1000. Cells were then stained (in the dark, on ice for 30 minutes) with antibodies after optimal antibody concentrations had been determined for each antibody by titration experiments. Antibodies used include: Esa-Alexa488 (clone G8.8, Biolegend™), Esa-Alexa647 (clone G8.8, Biolegend™), CD45-PECy5 (clone 30E-11, eBioscience™), CD44-PECy7 (clone IM7, eBioscience™) CD44-APC (clone IM7, eBioscience™), CD66a-PE (clone MAb-CC1, eBioscience™), CD24-PE (clone M1/69, Biolegend™), CD166-PE (eBioscience™, clone eBioALC48). Several of the antibodies (including CD44, CD66a, and CD45) were occasionally used in biotinylated form with a subsequent staining step with Streptavidin APC-Cy7 or Streptavidin Pacific Blue (Invitrogen™). In such cases, the flow cytometry plots were no different from when primary conjugates were used. Viable cells were identified by exclusion of DAPI (Molecular Probes) or 7AAD (BD Biosciences™). Flow Cytometry was performed with a BD FacsAria II with FacsDiva software. For all experiments, side scatter and forward scatter profiles were used to eliminate debris and cell doublets. Dead cells were eliminated by excluding DAPI+ cells.

Immunohistochemistry

Colons were dissected, washed with PBS, flushed gently with fixative (10% buffered formalin, Sigma, St. Louis, Mo.) and then placed in fixative overnight at 4 degrees Celsius. The next day, the tissue was washed in PBS, and placed in 30% sucrose for cryoprotection. Then, the tissue was embedded in OCT, frozen, and sectioned. Thin (8 uM or less) sections were then permeabilized with PBS+0.1% Triton X-100 (PBS-T), incubated in block (5% normal goat serum in PBS-T) for 30 minutes at room temperature, and then stained with antibodies diluted in PBS-T for 1 hour at room temperature. In general the same antibodies used for flow cytometry were used for immunohistochemistry. For Nov experiments, we used biotinylated anti-Nov (clone CATZ01, R&D™). After extensive washing in PBS-T, slides were washed in PBS-T with DAPI (1:1000), mounted in anti-fade (Molecular Probes™), sealed with nail polish, and imaged with a Leica DMI 6000B microscope. Images were captured with a CCD camera, and processed with ImagePro 5.1™ and post-processed with Adobe Photoshop™

Gene Expression Analysis

RNA was harvested from selected cells using the Trizol™ method as previously described. cDNA was generated using the Superscript III™ kit (Invitrogen™) according to the manufacturer's instructions, and then real time PCR was carried out on an ABI 7900HT Thermocycler using Taqman assays (Applied Biosystems™) for select genes.

Cell Culture

Colon organoids were grown from primary dissociated or sorted cells using a modified version of a previously published method (Sato, et. al. Nature 2009). Briefly, the day prior to plating, 3T3 cells were trypsinized and lethally irradiated, plated into culture wells with Advanced DMEM/F12 (Invitrogen™), and allowed to adhere. The next day, primary dissociated mouse colon or sorted colon cells were plated in growth factor reduced matrigel (BD Biosciences™) supplemented with 1 uM Jag-1 peptide (AnaSpec™) and grown in Advanced DMEM/F12 (Invitrogen™) with 10% heat-inactivated fetal bovine serum, 1×ITES (Gibco™), supplemented with 500 ng/mL hRspo1 or hRspo3 (Peprotech™), 50 ng/mL recombinant hEGF (Peprotech™), 100 ng/mL hNoggin (Peprotech™), and 10 uM Y-27632 (Sigma™). Cells were grown at 37 degrees Celsius in 5% CO2. The media was spiked with growth factors every 2-3 days and was changed weekly. Recombinant Nov/CCN3 (Peprotech™) was added to cultures at the described concentrations.

Single Cell Gene Expression

For single cell gene expression studies, all cells were double-sorted. Final purity was >95% for all populations analyzed. Individual cells were sorted into individual wells of 96 well plates containing 5 microliters of lysis buffer (CellsDirect qRT-PCR mix, Invitrogen™) and RNAse inhibitor (Superasln, Invitrogen™). After reverse transcription, genes were pre-amplified (20 cycles) using the same Taqman primers used for quantification. The resulting pre-amplified cDNA from each cell was then diluted and loaded into a Fluidigm™ M48 or M96 chip sample inlet. Individual Taqman assays (primers and probes) were loaded into the Fluidigm M48 or M96 chip assay inlets. This loading was performed by a Hamilton STARlet™ pipetting robot. Loaded Fluidigm chips then underwent thermocycling and fluorescent quantification with a Fluidigm Biomark thermocycler/reader. For analysis, we removed low quality gene assays, i.e., those in which the qPCR amplification curves show non-exponential increases. We then removed low quality and non-epithelial cells, i.e., cells that did not express housekeeping genes (Actb or GAPDH) or EpCAM. We then generated a histogram of Ct values for each assay in each cell. We normalized the data to bring all genes into the same dynamic range and then clustered cells together based on their gene expression pattern, using both unsupervised and supervised clustering algorithms. P values were calculated for different cells and genes to determine whether observed clustering occurred by chance.

Results

We hypothesized that flow cytometry with widely-available cell surface markers could be used to prospectively isolate and characterize distinct cell populations from dissociated mouse colon. By staining individual dissociated live colon cells for ESA (also known as EpCAM/Tacstd1/CD326), an epithelial-specific cell adhesion molecule, and CD45, a hematopoietic-specific surface marker, we were able to show by FACS analysis that dissociated total colon consists of three main populations: ESA$^+$CD45$^-$ epithelial cells (60-80%), ESA$^-$CD45$^+$ hematopoietic-derived cells (5-10%), and ESA$^-$CD45$^-$ non-epithelial non-hematopoietic cells (10-35%) (FIG. 475A). In agreement with this, immunohistochemistry with Esa and CD45 showed that Esa labels the entire colonic epithelium while CD45 labels a distinct stromal population (FIG. 475B).

FIG. 475A shows a flow cytometry plot of individual live mouse colon cells stained for Esa (x-axis) and CD45 (y-axis) reveals three distinct clouds: 1) ESA$^+$CD45$^-$ (epithelial), 2) ESA$^-$CD45$^+$ (hematopoietic), and 3) ESA$^-$CD45$^-$ (stromal). FIG. 5B shows immunohistochemistry on fixed mouse colon stained for ESA (green), CD45 (red), and DAPI (blue) shows that CD45 and ESA stain non-overlapping cells.

We next sought to separate the crypt base (enriched for immature cells) from the crypt top (enriched for mature cells), since prior studies have demonstrated that colon stem cells reside in the base of the crypt. Staining murine colon for the Wnt-target gene CD44, a well-established marker for the colon crypt base and for CEACAM1/CD66a, a marker of mature cells at the top of the crypt, confirmed that we were able to stain opposite ends of the crypts with these markers (FIG. 471A,B). CD44 labeled basolateral membranes, while CD66a labeled apical membranes.

We next isolated mRNA from sorted CD44+CD66a-low epithelial cells (Esa$^+$CD45$^-$) and the CD44$^-$CD66a$^{high}$ epithelial cells (FIG. 1D), and compared gene expression patterns using microarray analysis as well as real-time PCR for various known markers of the crypt base and crypt top. FIG. 471A shows fixed mouse colon stained for CD66a (red), ESA (green), and DAPI (blue) shows a gradient of CD66a expression, with the strongest staining near the lumen. CD66a stains apical membranes. FIG. 471B shows fixed mouse colon stained for CD44 (red), ESA (green), and DAPI (blue) shows a gradient of CD44 expression, with the strongest staining at the crypt base. CD44 stains basolateral membranes. FIG. 471C shows fixed mouse colon stained for CD24 (red), ESA (green), and DAPI (blue) shows a gradient of CD24 expression, with the strongest staining at the crypt base. CD24 stains apical membranes. FIG. 471D shows a flow cytometry plot of individual live colonic epithelial cells (ESA$^+$CD45$^-$) stained for CD44 (x-axis) and CD66a (y-axis) shows the same populations predicted by immunohistochemistry. A large box (P7) highlights crypt base cells (CD44$^+$CD66a$^{low}$) while a small box (P8) highlights cells near the lumen (CD44$^-$CD66a$^{high}$). FIG. 471E shows a flow cytometry plot of individual live colonic epithelial cells (ESA$^+$CD45$^-$) stained for CD44 (x-axis) and CD24 (y-axis) shows crypt base subpopulations that are not readily apparent from immunostaining: CD44$^{high}$CD24$^{high}$, CD44$^{med}$CD24$^{high}$, CD44$^{med}$CD24$^{low/neg}$, and CD44$^{neg}$CD24$^{pos}$.

FIG. 472A shows Individual sorted CD44$^+$CD66a$^{low}$ cells (marked "crypt base") and CD44$^-$CD66a$^{high}$ cells (marked "crypt top") were profiled by single cell qPCR. Each row indicates a single cell, and each column indicates a gene. Red indicates strong expression, green indicates weak expression, and gray indicates no expression. Unsupervised k-means clustering (dendrograms are indicated on the x- and y-axes) shows distinct clusters as indicated: Lgr5$^{high}$ cells, Bmi1$^{high}$ cells, goblet cells, and enterocytes. FIG. 472B shows Nov/CCN3 is expressed in cells at the crypt base. As predicted by the single cell gene expression analysis, immunohistochemistry on adult mouse colon stained with anti-Nov (A), ESA (B), and DAPI (C) shows scattered Nov$^+$ cells at the crypt base (overlay, D). This analysis revealed that the CD44$^+$CD66a$^{low}$ population was highly enriched for genes known to be differentially upregulated at the crypt base, including CD44, Lysozyme, Lgr5, Ascl2, Axin2, Myc, Notch1, Hes1, Klf5, Mki67, Cdk4, Aqp1, and others (some are shown in FIGS. 2, and 6). FIG. 6 shows a logarithmic plot of fold-expression of selected differentially-expressed genes (CD44$^+$CD66a$^{low}$ relative to CD44$^-$CD66a$^{high}$) shows that genes enriched in the CD44$^+$CD66a$^{low}$ cells (crypt base) include: Aqp1, Myc, Mki67, Ascl2, Cdk4, Cftr, CD44, Dkc1, Lyz, Axin2, Lgr5, and Hes1. Genes enriched in CD44$^-$CD66a$^{high}$ cells (crypt top) include Aqp8, Slc26a3, and Krt20.

Of note, telomerase (TERT) and Dkc1, the essential telomerase holoenzyme protein that binds the telomerase RNA component (Terc), were also differentially expressed in this population. On the other hand, the CD44$^-$CD66a$^{high}$ population was enriched for genes known to be upregulated at the top of the crypt, including CD66a/Ceacam1, Klf4, Slc26a3, Krt20, and Aqp8 (some are shown in FIGS. 472, and 476).

Because only a few cell surface markers could be tested at any time, flow cytometry was only able to crudely separate cells from the top and bottom of the crypt but could not easily distinguish different types of cells within the top or bottom of the crypts. To rapidly define the different cell populations at high (single cell) resolution in the normal (steady state) colonic epithelium, we next conducted single cell multiplexed gene expression of up to 96 genes per cell. Single cell transcriptional profiling of CD44$^+$CD66a$^{low/-}$ and CD44$^-$CD66a$^{high}$ cells (FIG. 472) provided independent validation of our microarray data showing genes differentially expressed at the crypt base or the crypt top. It also confirmed that cycling cells (strongly mKi67-positive) were present in the CD44$^+$ but not the CD66a$^{high}$ cells (FIG. 472), in agreement with published data.

Importantly, the single cell gene expression analysis identified several distinct clusters of cells with similar transcriptional profiles. For example, a goblet cell cluster could be identified by coexpression of Muc2, Tff3, and Spdef, all of which have been previously shown to be goblet cell genes. Remarkably, at the crypt base (in the CD44$^+$ cells), but not the crypt top, these cells showed high expression of various growth factors that have been implicated in crypt homeostasis, including EGF, the Notch ligands Dll1 and Dll4, and Ihh. They were also strongly ESA$^+$ (FIG. 472). One of the genes specifically expressed in this cluster of cells was Nov/CCN3, a gene that was checked because it was one of the most highly differentially-expressed genes in the CD44$^+$CD66a$^{low}$ vs. the CD44$^-$CD66a$^{high}$ cells and has been implicated in the regulation of self-renewal. Interestingly, Nov is a secreted growth factor which has been shown to bind Notch1, a receptor which is expressed by many immature cells in the crypt base, including Lgr5$^+$ crypt base columnar cells.

To check for Nov protein expression, we then stained fixed mouse colon with anti-Nov antibody and found that it labeled a small number of ESA$^+$ cells at the crypt base (FIG. 473), as predicted by the single cell gene expression analysis. FIG. 473A shows a section of colon from an adult Lgr5-GFP knockin mouse stained for DAPI shows several GFP+ crypt-base columnar cells at the crypt base. FIG. 473B shows a flow cytometry plot of GFP$^{high}$ cells from Lgr5-GFP colon stained for ESA (x-axis) and CD44 (y-axis) shows that GFP$^{high}$ cells, i.e., Lgr5$^{high}$ cells, are ESA$^{high}$ and mostly (>80%) CD44$^+$. FIG. 473C shows a flow cytometry plot of GFP$^{high}$ cells from Lgr5-GFP colon stained for CD44 (x-axis) and CD24 (y-axis) shows that GFP$^{high}$ cells, i.e., Lgr5$^{high}$ cells, are excluded from the CD44$^{med}$CD24$^{low/-}$ quadrant (red box). Refer to FIG. 471E for reference. FIG. 473D shows single cell gene expression for cells expressing Lgr5 or Bmi1 show distinct expression patterns, summarized in FIG. 476C. FIG. 473E shows a summary of differences between Lgr5$^{high}$ and Bmi1$^{high}$ cells.

Another population of cells that the single cell gene expression analysis revealed was an enterocyte cluster (which was especially abundant in the CD66a$^{high}$ population). The mature enterocytes could be identified by expression of Krt20, Slc26a3, and Aqp8. Our microarray and single cell analysis identified CD24a as a gene upregulated in the CD44$^+$CD66a$^{low}$ cells at the base of the crypt (FIG. 472), so we next asked whether CD24a and CD44 could be used to subfractionate the crypt base. Of note, CD24 (also know as Heat Stable Antigen), has been found to mark cancer stem cells as well as a clonogenic population of cells from mouse intestine. Immunohistochemistry with CD24 confirmed that this protein is enriched at the colon crypt base, where it labels apical membranes (FIG. 471C). Based on the staining and the single cell gene expression analysis, CD24 was chosen as a potential marker to separate different colonic cell populations. Flow cytometry with CD24 and CD44 on colonic epithelial cells (Esa$^+$CD45$^-$) revealed four distinct populations that were not readily apparent from immunohistochemistry alone (FIG. 471E): $CD44^{high}CD24^{high}$, $CD24^+CD44^-$, $CD44^{med}CD24^{low/-}$, and $CD44^{med}CD24^{high}$. These populations were all $CD66a^{low}$, as predicted from the immunohistochemistry which shows $CD66a^{high}$ cells are at the top of the crypt.

To identify which crypt base population(s) contain Lgr5+ cells, we then used our surface markers to stain dissociated colon from the Lgr5-GFP knockin mouse. All the strongly-positive GFP-expressing cells (FIG. 474A) were strongly positive for ESA, i.e., $Lgr5^{high}$ cells are $ESA^{high}$ (FIG. 474A,B). This agreed with our single cell gene expression data (FIG. 2). Also, the large majority of $GFP^{high}$ cells (>80%) were positive for CD44 (FIG. 474B,C), also in agreement with our single cell data as well as previously-published microarray data showing that one of the most highly upregulated genes in the $Lgr5^{high}$ cells is CD44. We observed $GFP^{high}$ cells to be both $CD44^{med}$ and $CD44^{high}$ (FIG. 474B,C). Interestingly, all the $LGR5$-$GFP^{high}$ cells were also $CD24^{high}$; while the $CD44^{med}CD24^{low/-}$ population was devoid of $GFP^{high}$ cells (FIG. 474C, red box). Thus, $Lgr5^{high}$ cells are confined to the $CD44^{med}CD24^{high}$ and $CD44^{high}CD24^{high}$ cells and are excluded from the $CD44^{med}CD24^{low/-}$ population (FIG. 474B,C). This was confirmed by single cell gene expression analysis (data not shown).

Single cell qRT-PCR allowed for precise analysis of Lgr5 and Bmi1 gene expression (FIG. 474D), two intestinal stem cell markers whose exact relationship has previously been uncertain. Interestingly, the highest-expressing Lgr5+ and Bmi1+ cells were generally different (FIG. 474D). FIG. 474A shows representative bright field images of colonic organoids (shown at different indicated time points) grown from individual sorted cells. All images were taken at the same magnification. By 3 days, multicellular spheroids have formed. By one week, organoids with well-defined lumens and crypt-like outgrowths can be identified. At 2 weeks, the organoids are substantially larger with more complex crypt-like outgrowths. FIG. 4B shows a 1-week old organoid grown from a sorted CD44' cell was fixed and stained. Brightfield imaging (left) demonstrates a crypt-like outgrowth while immunostaining (right) for CD44 (red), Esa (green), and DAPI (blue) shows that CD44' cells are at the base of the crypt-like outgrowth but not higher up toward the lumen. FIG. 474C shows colony formation of the indicated CD24/CD44 populations was quantified at one week after plating individual FACS-sorted cells. Although all four populations gave rise to some colonies, only the $CD44^{high}CD24^{high}$ and $CD44^{med}CD24^{low/-}$ were able to generate organoids with the features shown in FIGS. 475A and B. FIG. 474D shows single cell gene expression of organoids grown from $CD44^{med}CD24^{low/-}$ cells (lacking $Lgr5^{high}$ cells) reveals all major colon epithelial cell types, including enterocytes, goblet cells, enteroendocrine (ChromograninA+) cells, Lgr5+ cells, and Bmi1+ cells.

Comparing cells expressing either Lgr5 or Bmi1 (FIG. 474) showed the two genes to be inversely-correlated (Pearson correlation coefficient −0.43, p<0.0012). Single cell gene expression analysis on sorted colonic epithelial cells from the Lgr5-GFP mouse yielded the same result. These two populations exhibited largely distinct transcriptional profiles. Lgr5-high cells were Esa-high, CD24-high, Actb-high, and Gapdh-low, with a high proportion of cycling (mKi67-positive) cells (FIG. 476A, C). Bmi1-high cells, however, were Esa-low, CD24-low/neg, Actb-low, Gapdh-high, with a low proportion of cycling cells. Of note, the Lgr5-high cells were found to express high levels of several genes previously found by microarray analysis to be highly expressed in those cells, including CD44, Tcf4, Axin2, Myc, Ptpro, Kif12, Notch1, and CFTR (FIG. 472). Unlike Lgr5-high cells, Bmi1-high cells strongly expressed Lefty1, Lefty2, and TDGF1/Cripto (FIG. 472), members of a signaling pathway that has previously been implicated in colon cancer. Thus, in the colon, $Lgr5^{high}$ and $Bmi1^{high}$ appear to mark generally distinct cell types with different transcriptional profiles.

To define the functional characteristics of the different sorted populations we next employed a colonic "organoid" formation assay on sorted colonic epithelial cells, using a protocol modified from what has been published for small intestinal organoids. By one week in culture, plated cells formed identifiable colon organoids with a well-defined lumen and crypt-like structures. These features became more pronounced by two weeks as the organoids grew and underwent crypt fission. Immunostaining of these organoids revealed that they preserved normal colon crypt architecture with CD44+ cells at the crypt base and CD44− cells closer to the lumen. Sorting primary colon epithelial cells for CD44 showed that CD44+ cells (crypt base cells) possessed organoidogenic activity, while CD44− cells did not. We next compared the organoidogenic activity of the different crypt base subpopulations, using CD44 and CD24 (i.e., comparing four populations: $CD44^{high}CD24^{high}$ vs. $CD44^{med}CD24^{high}$ vs. $CD44^{med}CD24^{low/-}$ vs. $CD44^-CD24^{high}$). Although all four populations were able to generate colonies to some extent (FIG. 475C), the $CD44^{high}CD24^{high}$ cells were the most efficient at colony formation. Furthermore, only two of the four populations were capable of generating true organoids with crypt-like architecture and a lumen: $CD44^{high}CD24^{high}$ (which harbor Lgr5-high cells) and $CD44^{med}CD24^{low/-}$ (which lack Lgr5-high cells).

To determine whether the $CD44^{med}CD24^{low/-}$ cells could generate organoids with all the differentiated cell types of normal colon—as well as Lgr5+ cells—we isolated three one-month old organoids grown from $CD44^{med}CD24^{low/-}$ cells, dissociated them into a single cell suspension, placed individual cells into individual wells of several 96-well plates using a specially-designed novel microscopic cell manipulator, and then conducted single cell gene expression profiling using the Fluidigm™ system. The analysis demonstrated that the organoids contained both CD44+ and CD44− cells and had the various cell types present in normal colon, including goblet cells (Muc2+Tff3+Spdef+), enterocytes (Aqp8+Slc26a3+Krt20+), enteroendocrine cells (ChromograninA+), Lgr5+ cells, and Bmi1+ cells. Because total (unsorted) cells were profiled, rather than sorted CD44+ $CD66a^{low}$ or $CD44^-CD66a^{high}$ cells, the proportions of the different colonic epithelial cell types were somewhat different from what was seen with CD44+CD66a-low vs CD44-CD66a-high cells (FIG. 472). The fact that cells without Lgr5 expression ($CD44^{med}CD24^{low/-}$ cells) are able to give rise to Lgr5+ cells argues that self-renewal is a property not unique to the Lgr5+ cells in the colonic epithelium.

Example 44: Cellular Hierarchies of Normal and Malignant Breast Epithelium are Revealed by Single Cell Gene Expression Analysis The blood, brain, mammary gland, small intestine and colon are examples of tissues maintained by stem cells that undergo a series of maturation divisions to produce progenitor cells that eventually differentiate into the short lived mature cells of their respective tissue. Each cellular compartment of normal tissue expresses a unique repertoire of receptors and signaling pathway components that govern how they respond to cytokines and other components of the microenvironment. Identification of each cell compartment of an organ or tissue allows one to dissect the factors that govern essential processes such as self renewal, the mechanism by which stem cells regenerate themselves, survival, differentiation, and proliferation. Cancers often contain cells that resemble those in the normal organ where they arise. Therefore, understanding the molecular regulation of these processes has major ramifications for both regenerative medicine and developing new cancer therapies.

Based on the blood system model, the characterization of the cellular hierarchy within a tissue involves an extensive process in which cells are isolated by FACS based on the expression of combinations of cell surface markers, and then subjected to functional assays for regeneration, proliferation or differentiation potential. Most markers that are differentially expressed by a partially enriched stem or progenitor compartment do not enable further enrichment of the cell of interest. In addition, RNA and proteomic analyses of partially enriched cells isolated by flow cytometry or magnetic beads are clouded by the progenitor and mature cells that can sometimes share marker expression with stem cells. These population averaged assays can mask important information about stem cells since they often constitute small or rare subpopulations of cells. Despite these difficulties, the effort to identify cells in the differentiation hierarchy in some tissues has been remarkably productive. For example, classical stem cell biology approaches revealed many compartments such as common myeloid and lymphoid progenitor cells in the blood system. In addition, the ability to identify a highly enriched blood (hematopoietic) stem cell (HSC) has permitted the identification of critical regulators of HSC functions such as self renewal.

In epithelial tissues such as breast, the cellular hierarchy and relevant regulatory networks have been partially characterized. Two groups found that the cell surface markers CD49f, CD29 and CD24 (α6-Integrin, β1-integrin and small cell lung carcinoma cluster 4 antigen, respectively) could be used to partially enrich for murine mammary stem cells (MRU) as well as a luminal cell population with clonogenic potential (MaCFCs). Weinberg and colleagues found higher levels of genes associated with an epithelial-mesenchymal cell transition (EMT) in cell populations isolated using the phenotypes associated with normal mammary stem cells and a subset of cancer cells enriched for cells that were tumorigenic in xenotransplantation assays than in more differentiated populations of normal or malignant mammary epithelial cells. Furthermore, they found that enforced expression of the EMT genes Snail and Twist in Her2/neu transformed immortalized human mammary epithelial cells produced cells with the cancer stem cell phenotype. However, it is not known whether all endogenous mammary stem cells have undergone an EMT. Similarly, the phenotype of the mammary stem cell is unclear. Some groups have suggested that the phenotype of the early human breast progenitor cells is $CD49f^+EPCAM^{-/low}$ while other evidence suggests that it might be $CD49f^+EPCAM^+$.

The cellular heterogeneity of breast cancers is not well understood. Microarray analysis of whole tumors reveals at least 6 potentially different subtypes of breast cancer based on gene expression patterns. There are 3 types of tumors that express estrogen receptor and luminal cell type specific genes (luminal A, B and C). It has been speculated that these $ER^+$ tumors arise from a luminal cell. The observation that enforced activation of the Notch pathway led to luminal cell specification and proliferation in mouse mammary stem cells reinforced the notion that these tumors are composed of transformed $ER^+$ luminal cells. However, because the stem and progenitor cell compartments of the breast are not well defined, it is unknown whether $ER^+$ breast cancer cells are exclusively luminal cells. These tumors may be comprised of an enriched population of mammary stem cells or luminal epithelial cells. Similarly, the origin of tumors with a "basal cell" phenotype, commonly seen in patients with BRCA mutations, is actively debated. Finally, the "claudin-low" subtype has been proposed to be a tumor composed of mammary stem cells, but again this has not been fully validated. These hypotheses about the cell of origin are based on gene expression studies of whole tumors that assume the tumor is comprised of a homogeneous population of cells derived from a mammary epithelial cell arrested at a particular differentiation stage. It is possible that tumors contain minority populations of cells at other stages of differentiation and the gene expression profile mainly reflects only a majority cell population. To gain further insight into mammary stem cell and tumor biology, we undertook a study to analyze partially enriched cell populations at a single cell level. We show this system may be successfully used to discover stem cell markers and yield insights into normal and malignant tissue architecture.

EXPERIMENTAL PROCEDURES

Tissues, Breast Dissociation and Flow Cytometry

All animals used in the study were C57BL/6 or pCx-GFP mice that were maintained at the Stanford Animal Facility in accordance with the guidelines of both Institutional Animal Care Use Committees. Human normal and cancer tissue was obtained from consented patients as approved by the Research Ethics Boards at Stanford University. Six to ten week old mice were euthanized and all fat pads surgically resected. Tissue was digested in L-15 or DMEM/F12 for 1.5 hrs, and then processed as previously described. Human breast specimens were mechanically dissociated and incubated with 200 units/ml Collagenase Type III (Worthington) and 100 units/ml DNase I. For mouse antibodies, CD24-PE, CD24-Cyc Thy-1.1-APC, Thy-1.1-PE-Cy7, Thy-1.2-APC, Thy-1.2-PE-Cy7, CD66a-PE were obtained from eBioscience™, CD49f-Cyc, CD45-Bio, Ter119-Bio, CD31-Bio and CD140a were obtained from BD Pharmingen™, and Streptavidin-Pacific Blue™ was obtained from Invitrogen™. For human samples, flow cytometry was performed as described previously. CD49f-FITC and EpCam-APC were obtained from BD. Flow cytometry for all experiments was performed using a BD FACSAria™ or FACSAria II™ equipped with a UV laser.

In Vitro Colony Forming Assays

NIH3T3 in vitro colony forming assays was performed as previously described. Briefly, irradiated NIH3T3 cells were plated into 24 well tissue culture plates (Costar™) in Epicult™ media plus 5% FBS (Stem Cell Technologies™). Sorted cells were then plated and media was changed to serum free media 24 hrs later. After 7 days, colonies were stained with Wright Giemsa and counted. For 3D/2D assays, 8-well chambered culture slides (BD™) were prepared with a feeder layer of irradiated NIH3T3 cells covered by 100 μl of growth factor reduced Matrigel (BD™). Sorted cells were then plated into liquid media as previously described, except 250 ng/ml Rspo I (R&D Systems™) and 10% FBS were used. After 10 days, colonies were fixed with 4% PFA and stained as previously described. All images were produced on a Leica DMI6000B™ inverted fluorescence microscope with Image Pro Software.

In Vivo Transplants

Sorted cell populations were collected in staining media and resuspended in 10 μl of sterile PBS per transplant before being injected into the cleared fat pads of 21-28 day old recipient C57Bl/6 mice as previously described. For all injections of 600 cells and below, cell counts were verified using either a nuclear staining count (1% Trypan Blue/0.1% Triton-X 100 in PBS) or GFP$^+$ cell count. For single cell injections, GFP$^+$ cells were sorted into 4 μl of 25% growth factor reduced Matrigel (BD™) in Terasaki plates and each cell scored and visually confirmed prior to transplant. After transplantation, empty wells were again checked under a microscope to verify delivery of the cell. Cells were injected in either 10 or 5 μl volumes using a 25 μl Hamilton syringe. All transplants were allowed to grow for at least 5 weeks but not more than 10 weeks before analysis. In the case of secondary transplants, whole glands were dissected under fluorescence to obtain 1-2 mm pieces of tissue that contained GFP$^+$ ductal structures that were transplanted into recipient mice.

RNA Isolation and qRT-PCR

Sorted cell populations were collected in staining media directly and then centrifuged at 5000 rpm for 5 min at 4 C. Supernatant was then carefully removed from the cell pellet which was immediately frozen in liquid $N_2$ and stored at −80° C. until RNA extraction. RNA was extracted from frozen cell pellets by Trizol. For RT-PCR, RNA was then converted to cDNA using the Superscript III Reverse Transcriptase system (Invitrogen™). qRT-PCR was then performed on fresh cDNA with 2× Taqman Master Mix (Applied Biosystems™) according to manufacturer's instructions with Taqman primers against Thy-1 (Mm01174153_ml, Applied Biosystems™) on a 7900HT realtime PCR machine (Applied Biosystems™).

Single Cell Gene Expression

Single cell gene expression experiments were done as previously described. Briefly, we used the M48 and M96 qPCR DynamicArray microfluidic chips (Fluidigm™) with 48 (96) gene and 48 (96) sample inlets. Single cells were sorted by FACS into 96 well plates containing PCR mix (CellsDirect, Invitrogen™) and RNase Inhibitor (Superaseln, Invitrogen™). The cells were lysed in the hypotonic environment and the plates were immediately frozen. Later we thawed the cell lysates, added RT-qPCR enzymes (SuperScript III RT/Platinum Taq, Invitrogen™), and also a mixture containing a diluted pool of assays (primers/probes) from a list of 96 predetermined genes. The mRNA from the cell lysates was reverse transcribed (15 minutes at 50° C., 2 minutes of 95° C.) and pre-amplified for 20 PCR cycles (each cycle: 15 sec at 95° C., 4 minutes at 60° C.). Total RNA controls (Mouse Embryonic Total RNA or Hela RNA; Applied Biosystems™) were run in parallel to validate the results. The resulting amplified cDNA from each one of the cells was inserted into the chip sample inlets with Taqman qPCR mix (Applied Biosystems™). Individual assays (primers/probes) were inserted into the chip assay inlets. The chip was loaded for one hour in a chip loader (Nanoflex, Fluidigm™) and then transferred to a reader (Biomark, Fluidigm™) for thermocycling and fluorescent quantification. Single cell gene expression data was further analyzed using MATLAB (MathWorks™).

Analysis of Single Cell Data

Single cell qPCR data from hundreds of cells was analyzed. We removed cells that were not expressing the housekeeping genes ACTB (Beta-actin) and GAPDH (Glyceraldehyde 3-phosphate dehydrogenase) on the assumption that these cells were dead or damaged; these were a minority and accounted for 5% of the mouse cells, 15% of human normal cells, and 5% of cancer cells. Genes were standardized by mean centering and dividing by the standard deviation of expressing cells, and clustered using standard tools from the MATLAB bioinformatics toolbox. Hierarchical clustering was performed on both genes and cells with Euclidean distance and complete linkage. The clustering revealed distinct groups of cells, each characterized by its own gene expression profile. These groups correspond to different cell phenotypes in the tissue. For the mouse mammary data, we used R package pamr (Predicted Analysis for microarrays for R) to cross validate the single cell gene expression profiles with the flow cytometry phenotypes. We refined the mouse cell phenotype labeling according to both flow cytometry and gene expression data. We used R package clusterRepro™ to assign labels to the human single cell data according to mouse cell types and to calculate p-values for cell type reproducibility.

Analysis of Previously Published Gene Expression Data on Bulk Breast Tumors

Affymetrix microarray data of bulk breast tumor specimens GSE1456, GSE3494, and GSE19615 was analyzed. We downloaded the raw CEL files from the NCBI Gene Expression Omnibus and pre-processed the three datasets separately with an identical pipeline. We normalized the data with the GC-RMA algorithm, and combined HG-U133A and HG-U133B arrays by calculating the mean of identical probesets. We mapped probes to genes using Bioconductor software (http://www.bioconductor.org) and for each gene chose the single probeset with the highest standard deviation. Negative control values were calculated as the mean of 24 probesets (3 each for LysX, PheX, ThrX TrpnX, Bs-dap, Bs-lys, Bs-phe, and Bs-thr). We selected ER positive tumors from each dataset based on the available clinical annotations and applied hierarchical clustering with average linkage based on the expression of known luminal and basal markers.

RESULTS

Single Cell Analysis of Mouse and Human Breast Epithelial Cells

Figure 48:
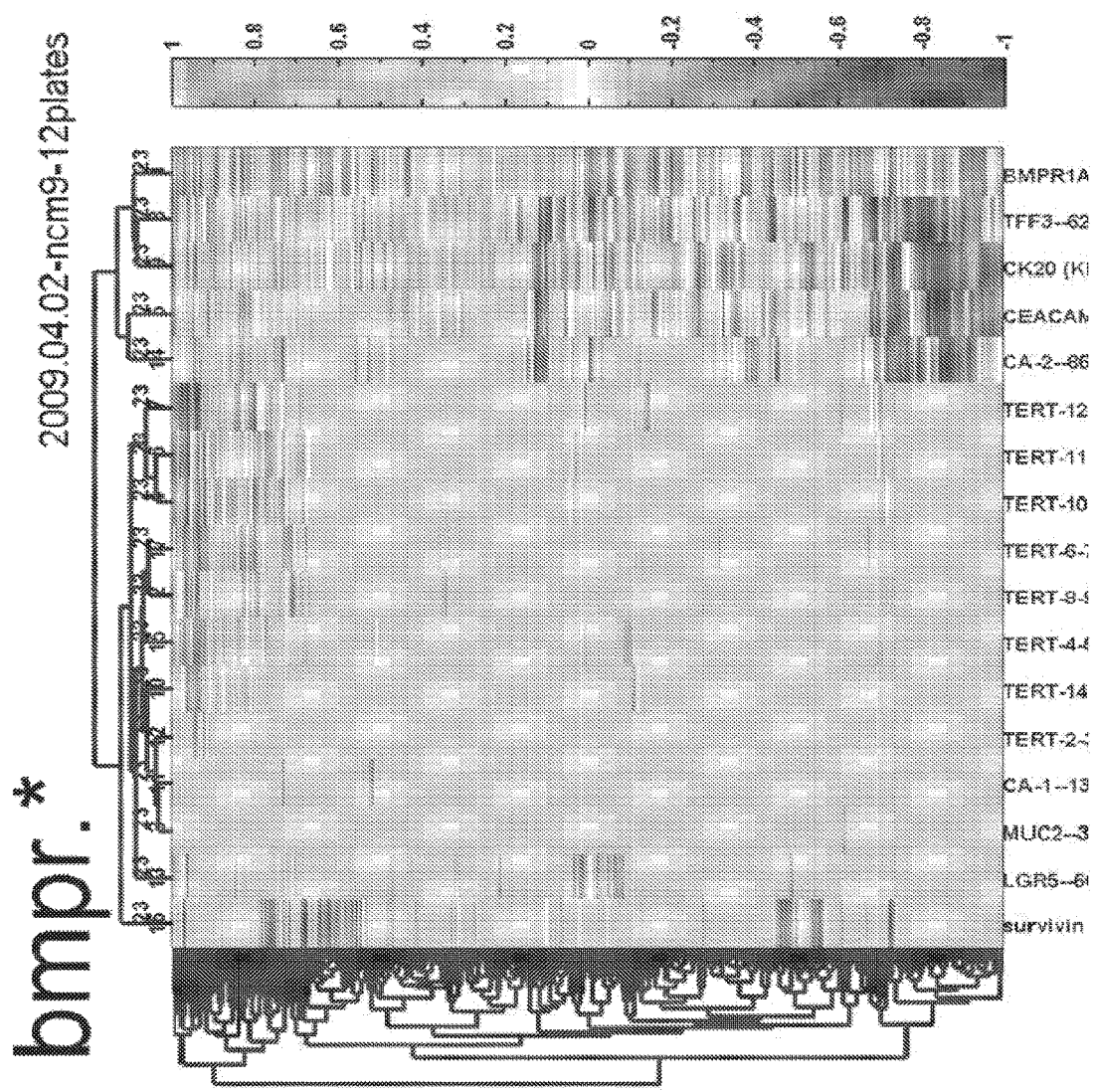
FIG. 48 BMPR expression in relation to TERT expression.
Figure 49:
FIG. 49 C-MYC is co-expressed with TERT
Figure 50:
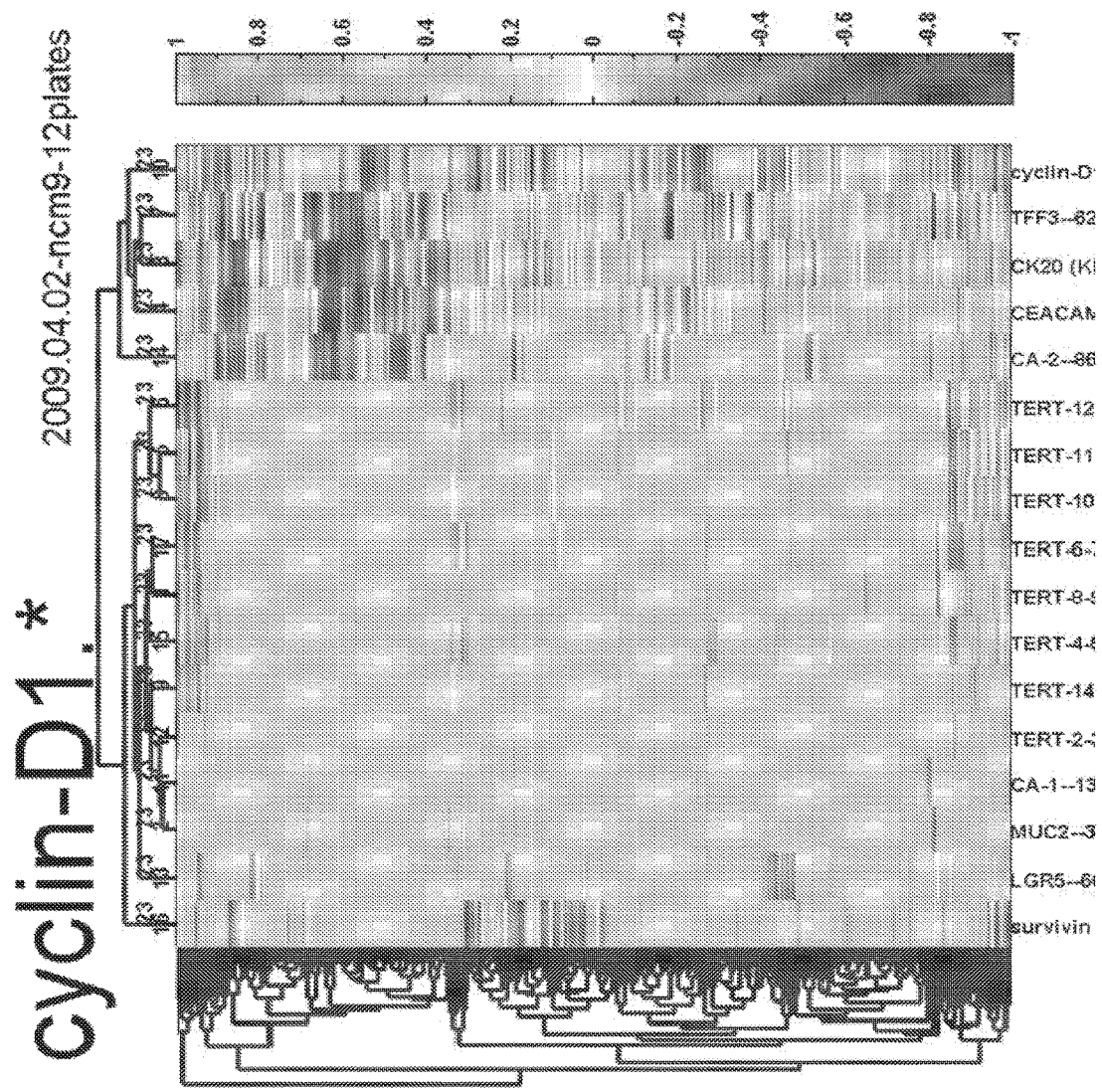
FIG. 50 CYCLIN-D 1 expression in relation to TERT expression.
Figure 51:
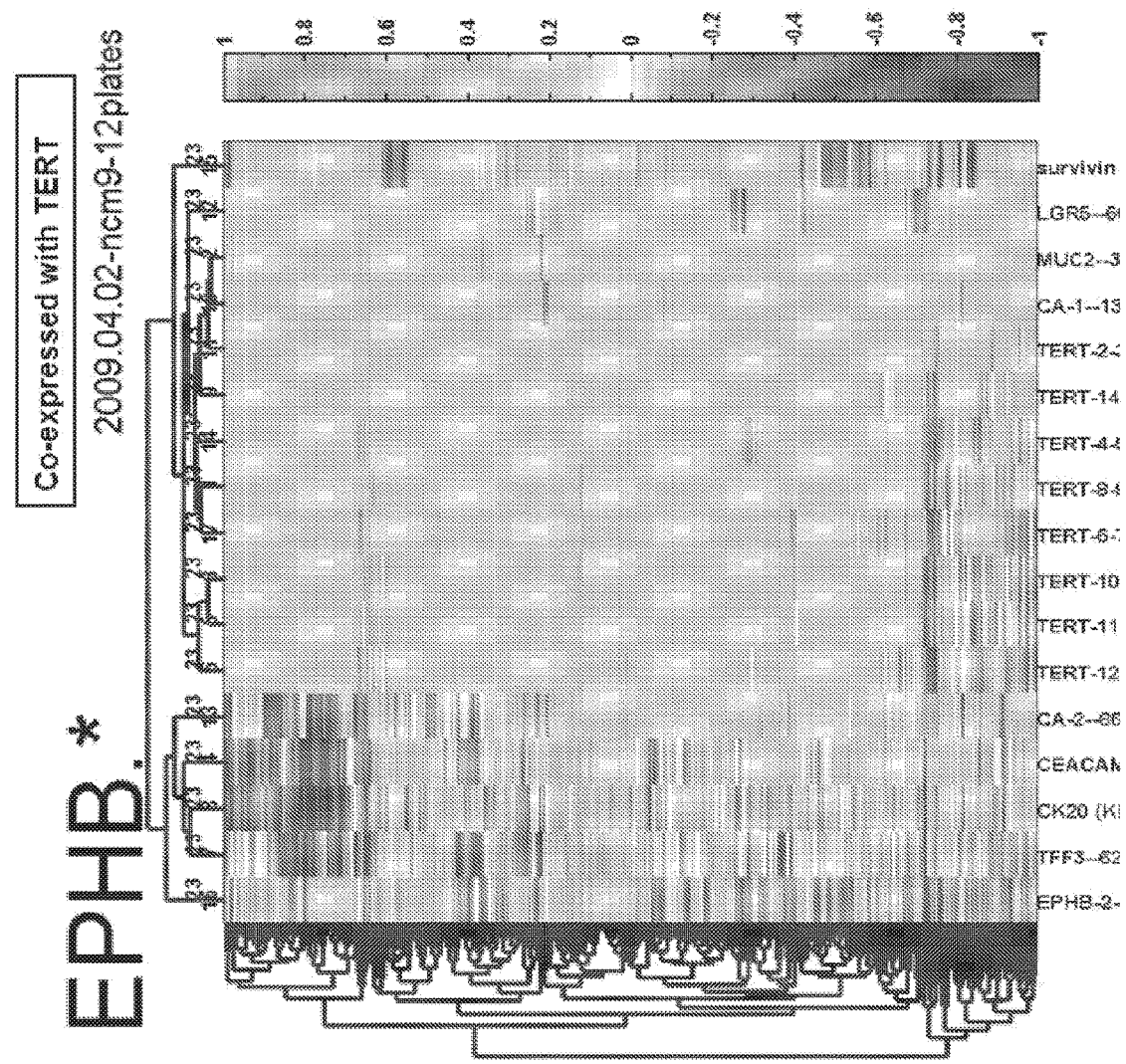
FIG. 51 EPHB is co-expressed with TERT
Figure 52:
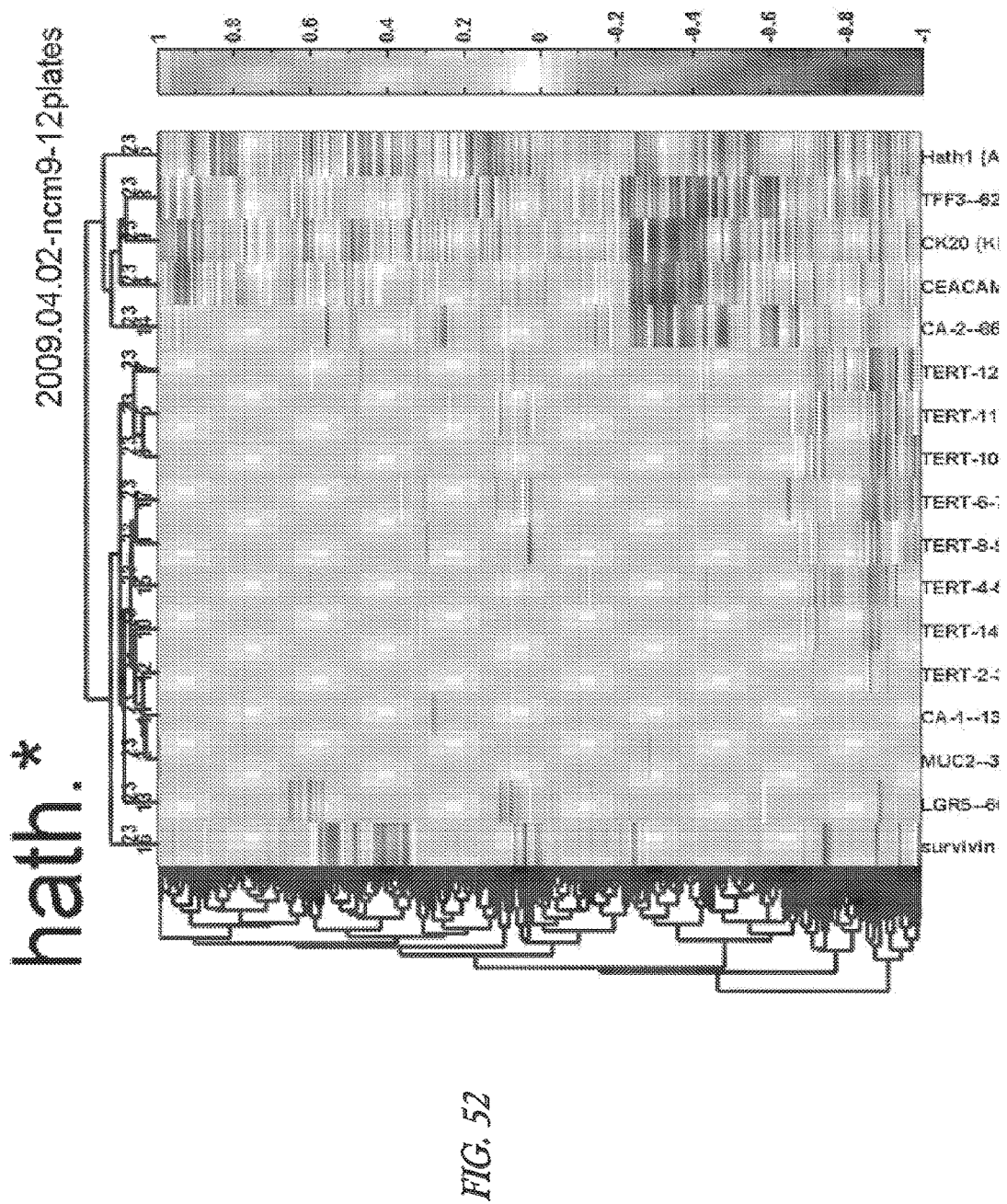
FIG. 52 HATH expression in relation to TERT expression.
Figure 53:
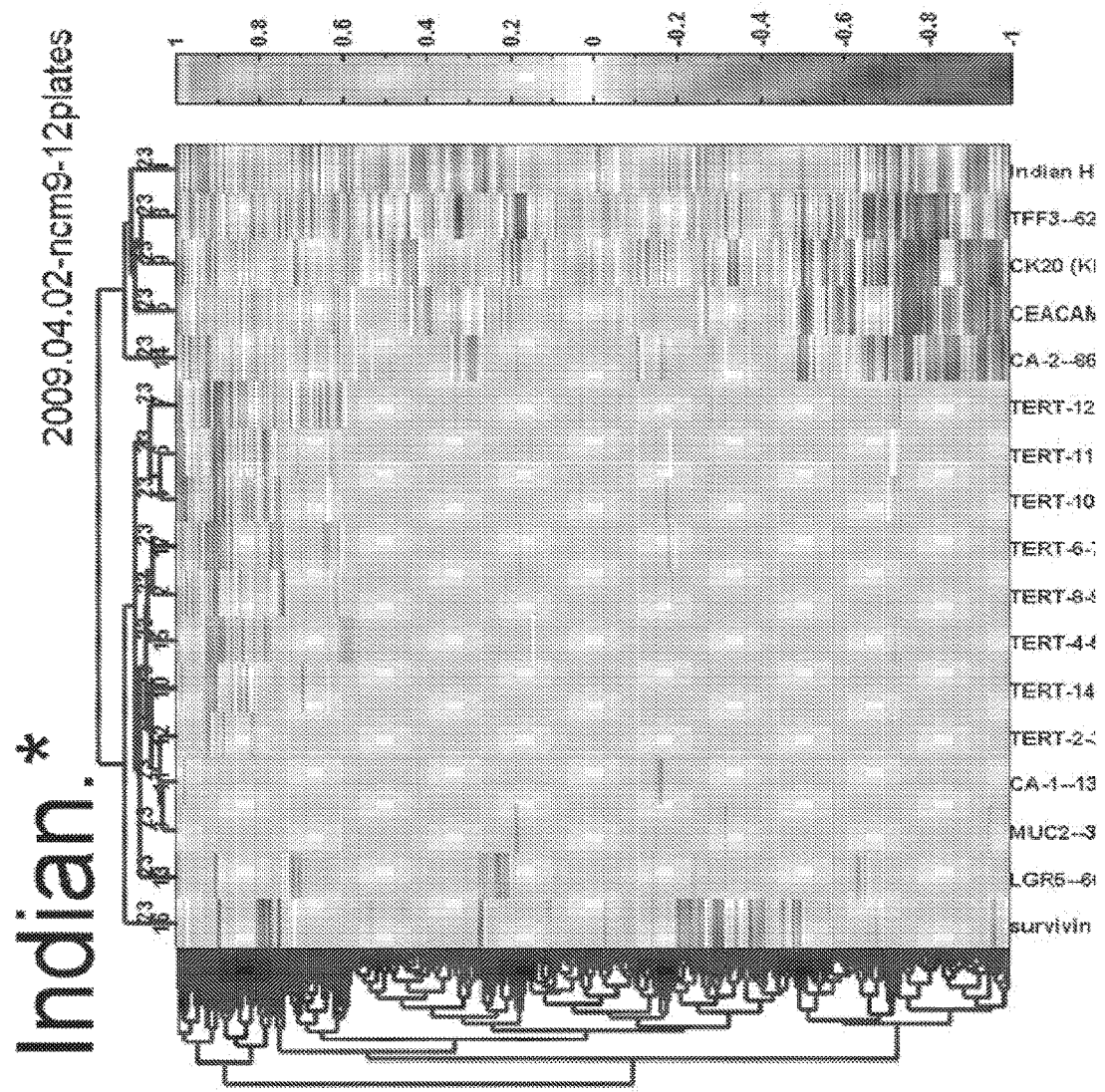
FIG. 53 INDIAN expression in relation to TERT expression.
Figure 54:
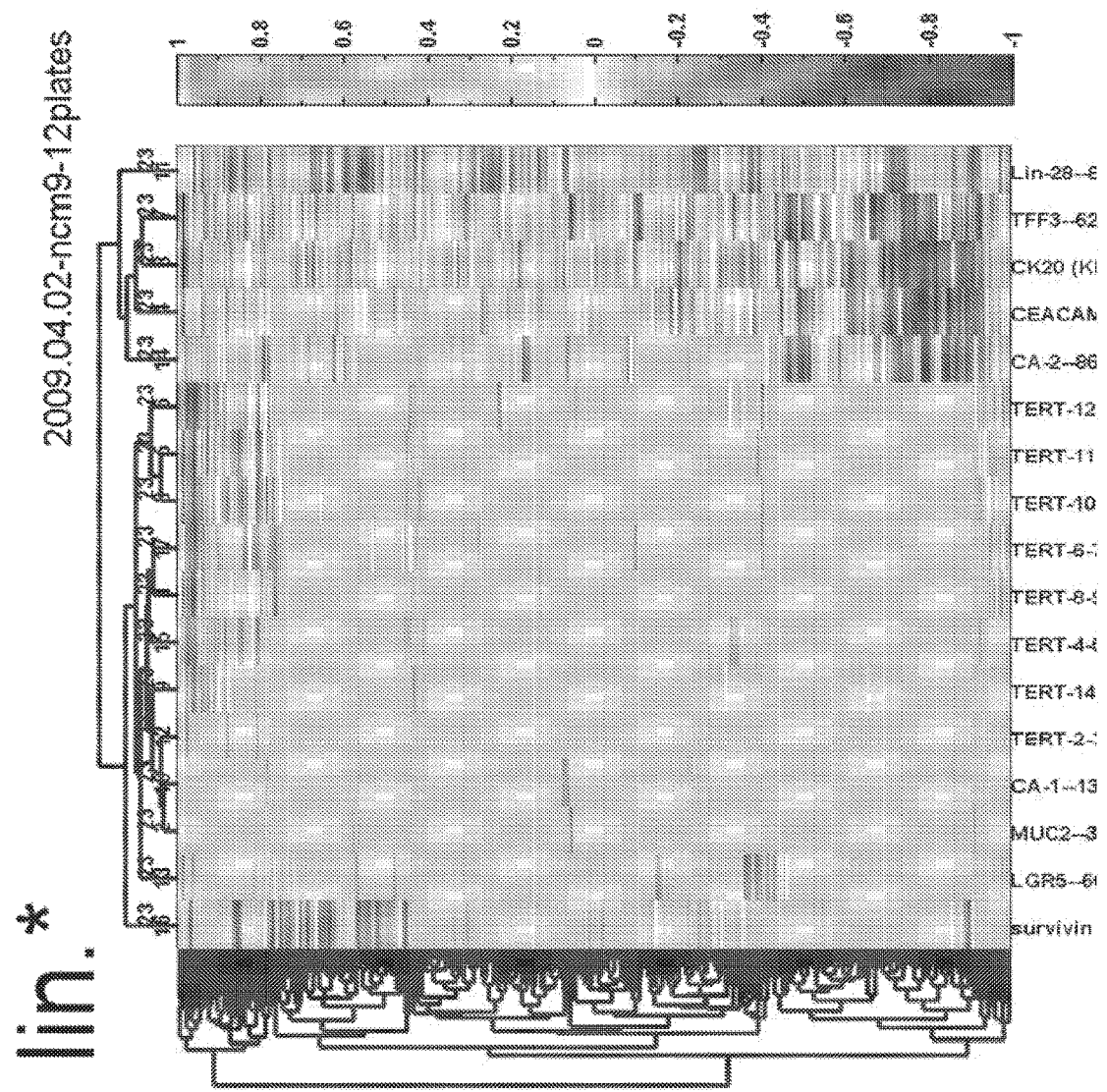
FIG. 54 LIN expression in relation to TERT expression.
Figure 55:
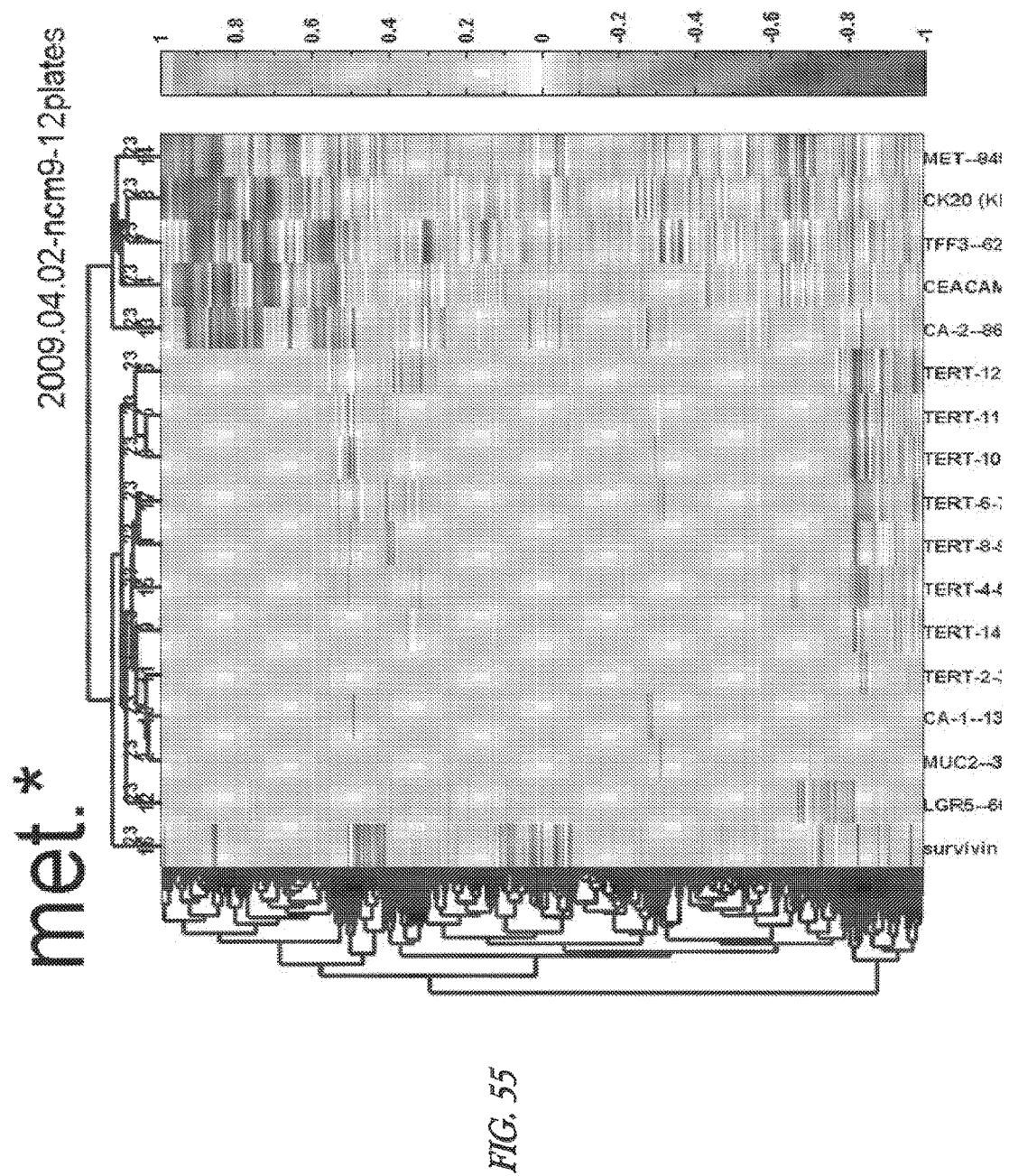
FIG. 55 MET expression in relation to TERT expression.
Figure 56:
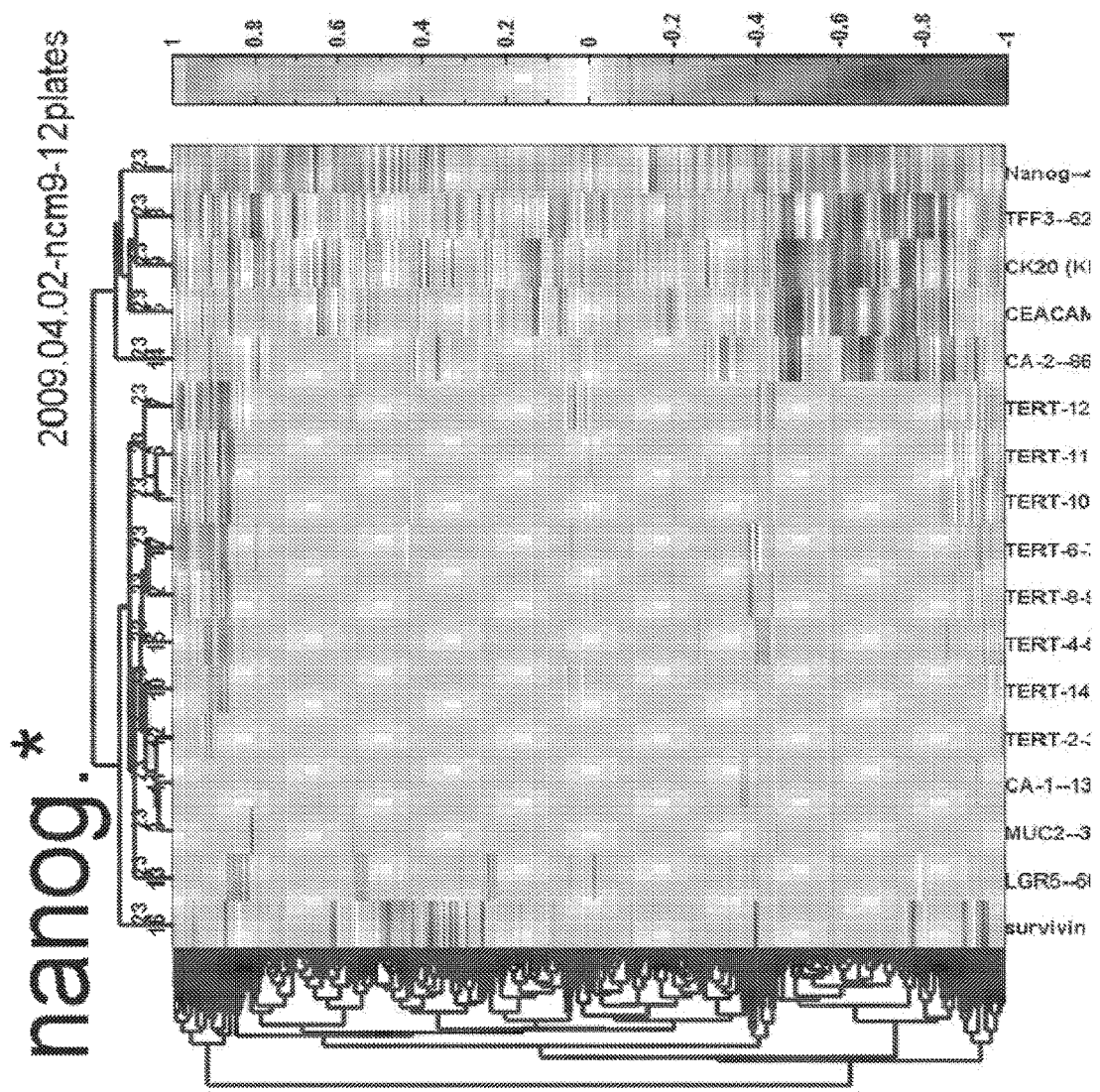
FIG. 56 NANOG expression in relation to TERT expression.
Figure 57:
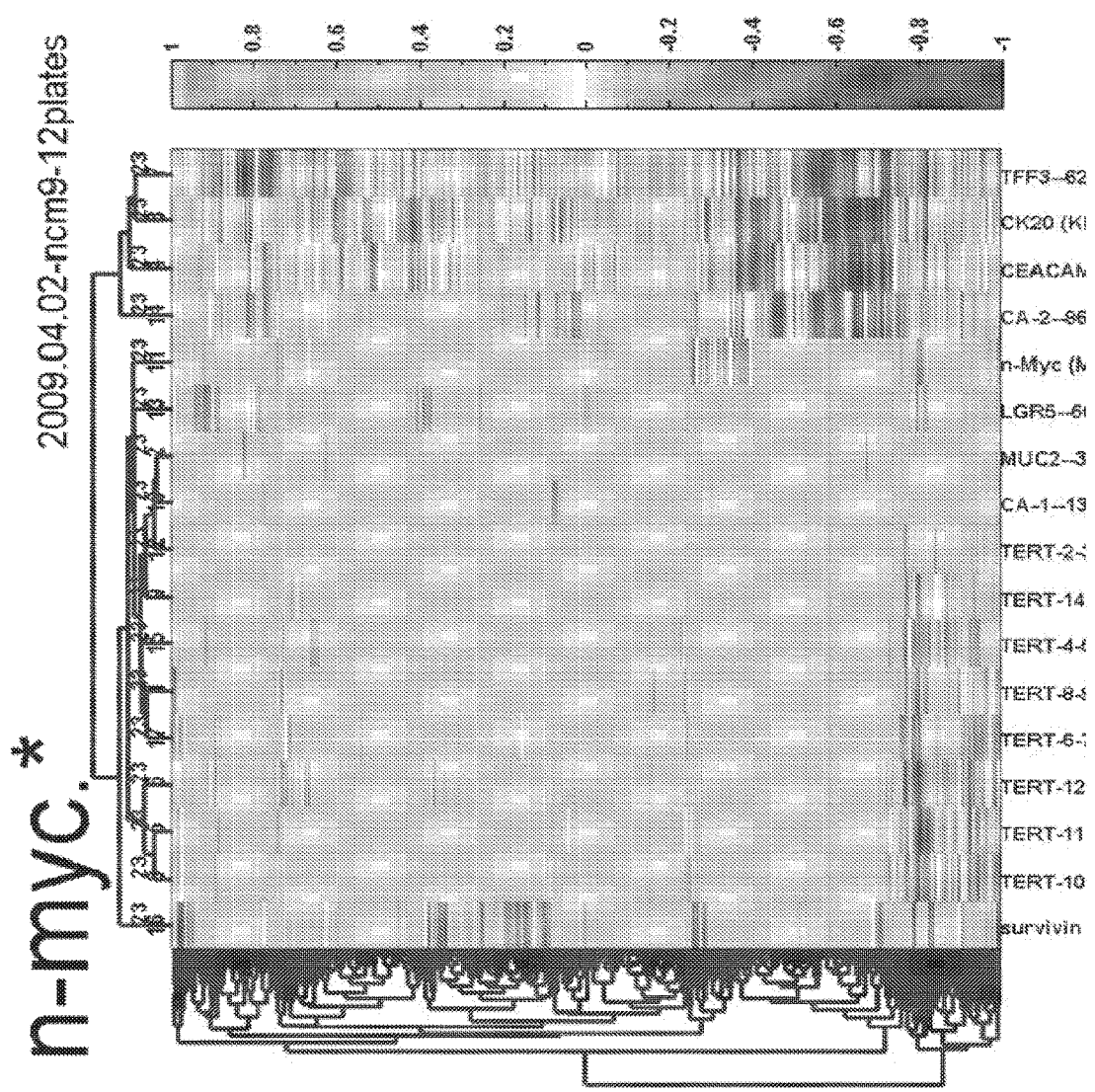
FIG. 57 N-MYC expression in relation to TERT expression
Figure 58:
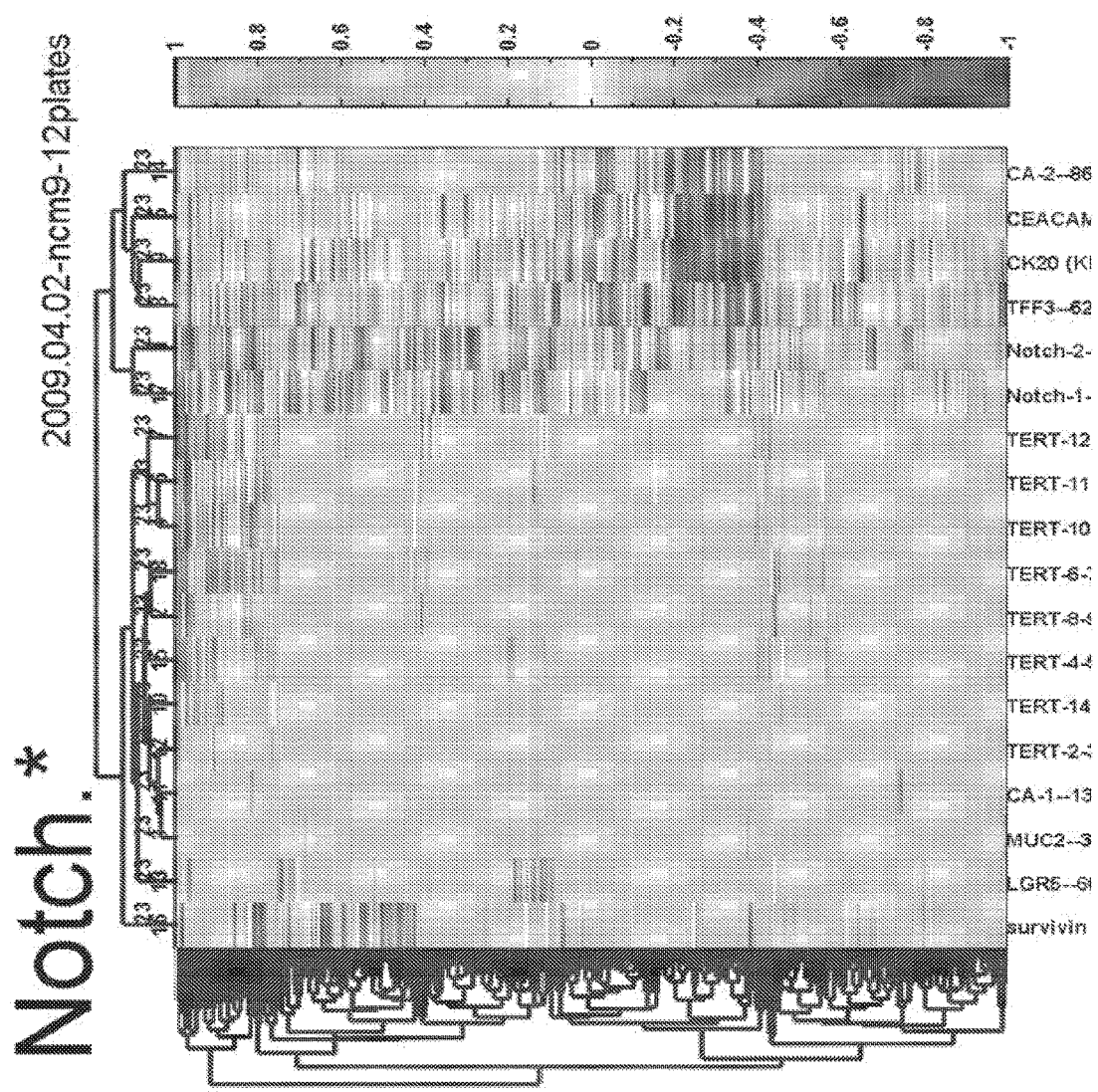
FIG. 58 NOTCH is co-expressed with TERT.
Figure 59:
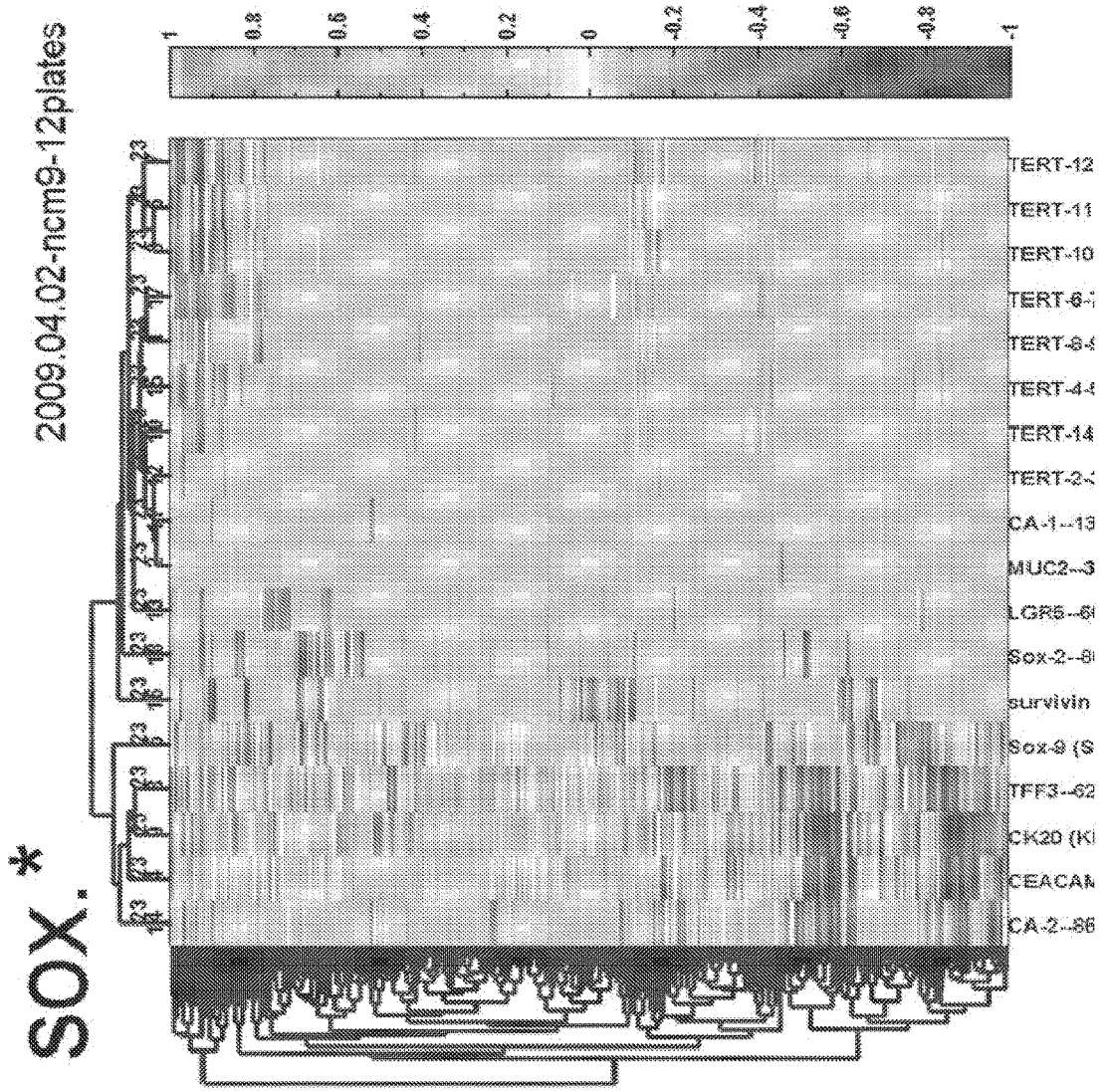
FIG. 59 SOX expression in relation to TERT expression.
Figure 60:
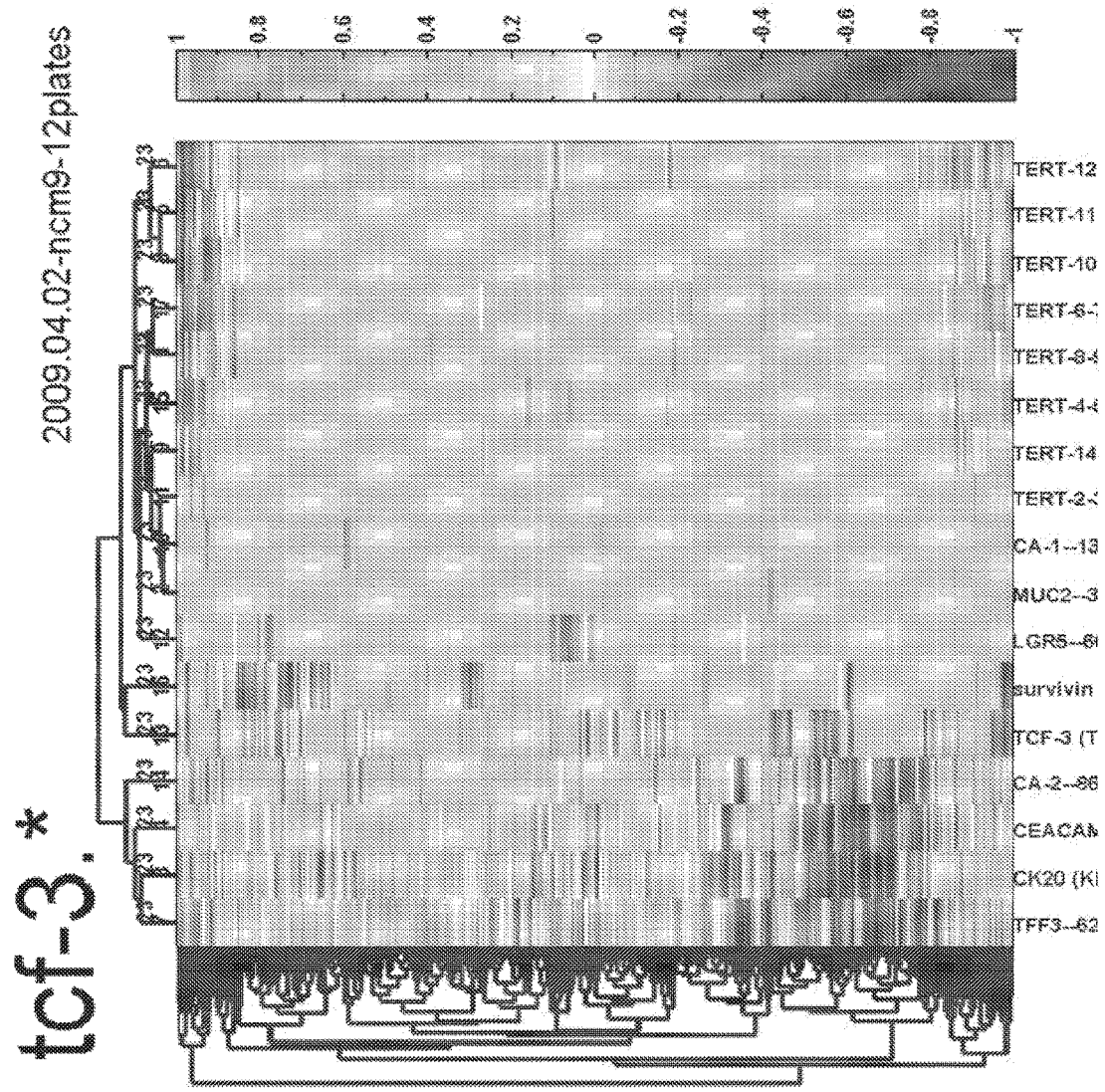
FIG. 60 TCF-3 expression in relation to TERT expression
Figure 61:
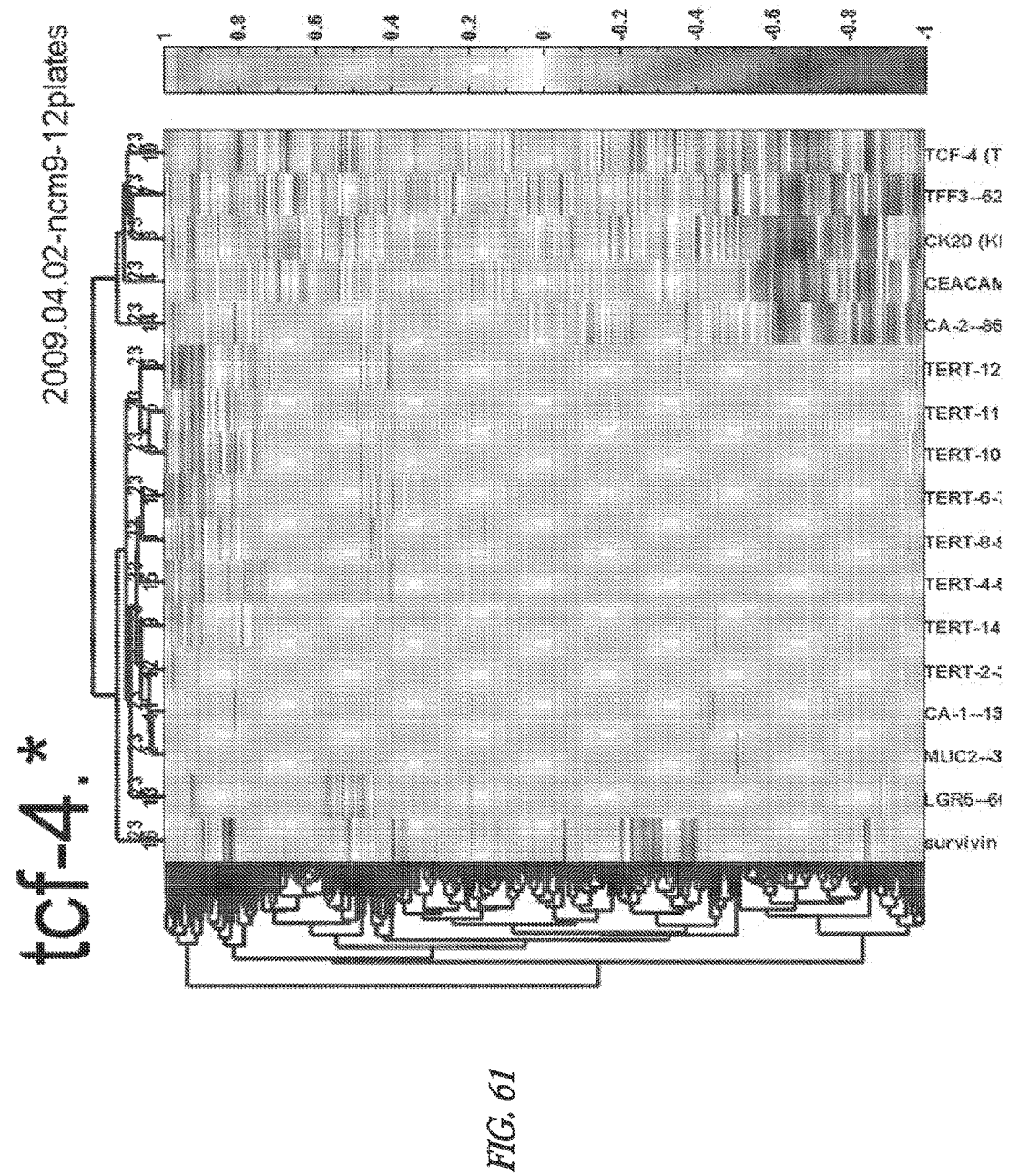
FIG. 61 TCF-4 expression in relation to TERT expression
Figure 62:
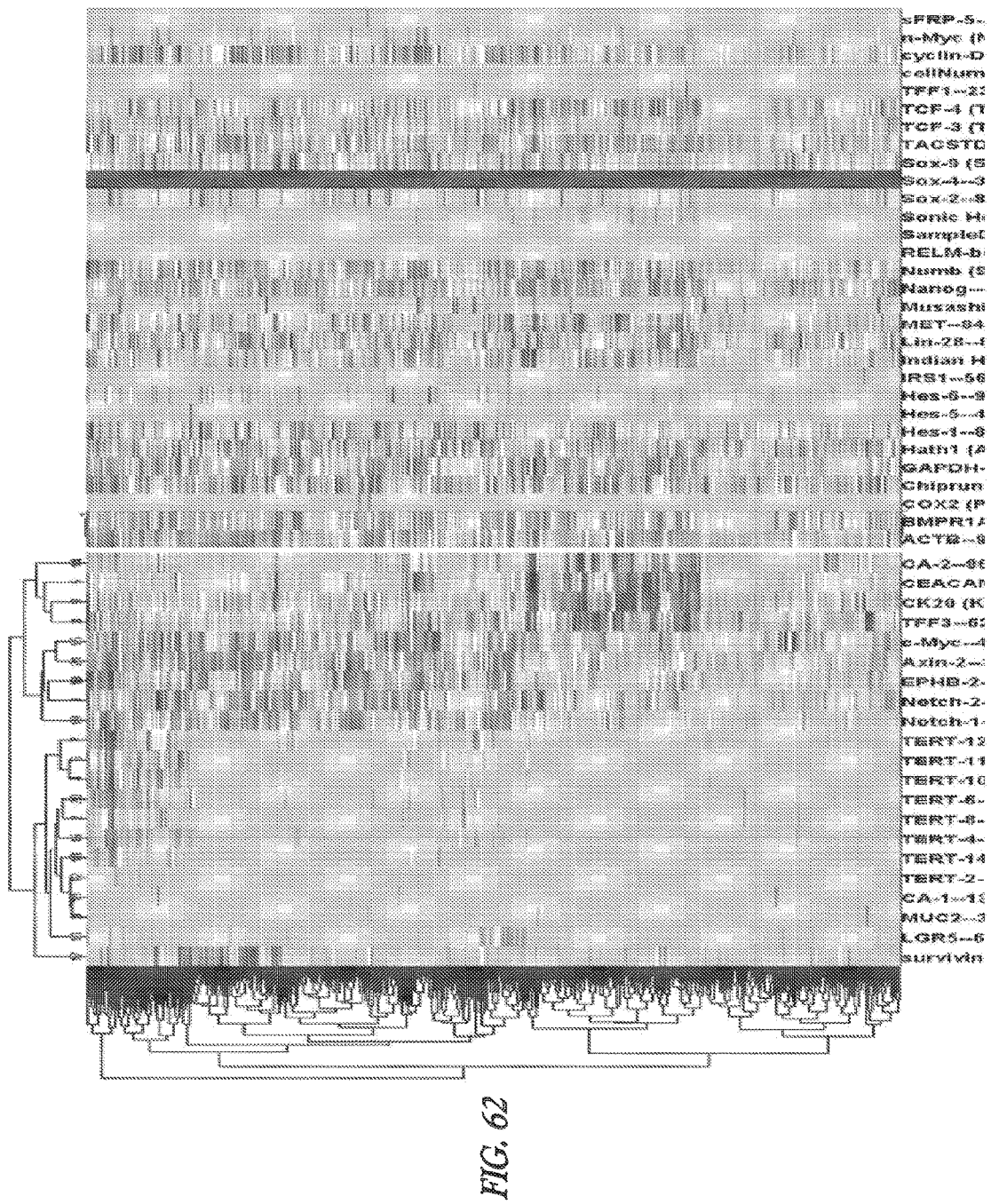
FIG. 62 hierarchical clustering of TERT expression.

The cellular hierarchy of breast epithelium has only been partially defined. We asked whether we could develop a single cell profile to analyze and better define different cell compartments. Flow cytometry was used to separate mouse mammary epithelial cells into the following compartments: $CD24^{med}CD49f^{hi}$ (MRU), $CD24^{hi}CD49f^{med}$ (MaCFC), $CD24^{low}CD49f^{med}$ (MYO) and $CD24^{med}CD49f^{low}$ (FIG. 48). FIG. 482 shows dissociated mouse mammary epithelial cells were stained for lineage antibodies (CD45, CD31 and Ter119). Lineage cells were analyzed for the expression of CD24 and CD49f. Gates are drawn to indicate the phenotype for MRU, MYO, MaCFC and $CD24^{med}CD49f^{low}$ cells.

We sorted single cells from each of these compartments and analyzed them with microfluidically multiplexed real time PCR. Hierarchical clustering of the single cell data on the basis of a curated list of 31 gene expression assays showed that the resulting dendrogram is roughly consistent with the 4 mouse mammary compartments based on flow cytometry (Table 5). In table 5, the cross validation confusion matrix shows that the FACS sorting labels are consistent with gene expression clustering using an extended panel of 53 genes for most classes (error rate<0.09), apart from the MRU's and MYO's that are not very well separated. The Overall error rate is 0.107. K-fold cross validation (K=10) was done using the "pamr" R package.

TABLE 5

Single cell gene expression profiles roughly separate the 4 FACS sorting phenotypes in mouse mammary tissue.

| | Pred: $CD24^{med}CD49f^{-/low}$ | Pred: MaCFC | Pred: MRU | Pred: MYO | Error rate for this cells type |
|---|---|---|---|---|---|
| Actual: $CD24^{med}CD49f^{-/low}$ | 148 | 11 | 0 | 0 | 0.06918239 |
| Actual: MaCFC | 7 | 153 | 1 | 3 | 0.06707317 |
| Actual: MRU | 4 | 3 | 144 | 7 | 0.08860759 |
| Actual: MYO | 0 | 2 | 22 | 56 | 0.30000000 |

Consistent with previous reports, keratins were differentially expressed between cells in the basal (MRU and MYO) and luminal compartments (MaCFC and $CD24^{med}CD49f^{low}$). A previous report demonstrated the difficulty in distinguishing between the two populations that make up the basal compartment by microarray analysis. In our data, MRUs have high expression of Krt5, Itgb1 (CD29), Actb, Hes6, Dock9 and Itga6 (CD49f) whereas MYOs expressed higher levels of Gapdh, Egfr, Dsg1a and Mfhas1 (FIG. 486). FIG. 486 shows The colored "FACS sort labeling" column corresponds to mouse mammary cell types defined by flow cytometry. Colored "manual labeling" column corresponds to cell types that were manually labeled according to single cell gene expression clustering and the flow cytometry phenotypes (FIG. 471). (Manual labeling: $CD24^{med}CD49f^{low}$—Yellow, MRU Zeb1$^-$—Cyan, Unknown/Stromal—Black, MYO—Green, MRU Zeb1$^-$—Blue, MaCFC—Red; FACS sort labeling: $CD24^{med}CD49f^{low}$—Yellow, MYO—Green, MRU—Blue, MaCFC—Red). These genes were significantly differentially expressed between the MRU and MYO mammary FACS sorted compartments with p-val <0.0009 (see Table 6 and 18). In table 6, if either both medians were the same or if one statistical test gave significance (i.e. low p-value) and the other did not, we checked the histograms visually. Most p-values are well below 0.0009 which is the significance threshold with Bonferroni correction for 55 genes. In FIG. 488, Gapdh for example is highly expressed in the MYO's because there is a higher fraction of MYO cells expressing lower qPCR threshold cycles than MRU's. Hes6 is highly expressed in the MRU's because there is a higher fraction of MRU's expressing lower qPCR threshold cycles than MYO's.

TABLE 6

Genes that were found to be differentially expressed between the MRU and MYO mammary FACS sorted compartments.

| Gene name | Median (MYO) | Median (MRU) | Compartment with higher gene expression | p-value (Wilcoxon) | p-value (Kolmogorov-Smirnov) | Notes |
|---|---|---|---|---|---|---|
| Suz12 | 21.9582 | 22.8171 | MYO | 0.001171461 | 0.000366734 | Approaching significance |
| Mfhas1 | 23.6298 | 27.6984 | MYO | 0.000880318 | 0.000109467 | Significant |
| Krt5 | 19.1204 | 17.4047 | MRU | 1.3855E−08 | 5.73459E−14 | Significant |
| Itgb1 | 17.7798 | 17.0602 | MRU | 1.2911E−08 | 2.2413E−08 | Significant |
| Itga6 | 18.9102 | 18.19 | MRU | 0.000167178 | 0.000147685 | Significant |
| Hes6 | 40 | 40 | MRU | 3.91471E−08 | 2.04173E−05 | Also according to histograms |
| Gapdh | 16.3425 | 19.3483 | MYO | 3.09622E−25 | 5.91433E−26 | Significant |
| Egfr | 22.7161 | 26.8397 | MYO | 4.91702E−08 | 8.46838E−10 | Significant |
| Dsg1a | 40 | 40 | MYO | 0.00053549 | 0.000756916 | Also according to histograms |
| Dock9 | 40 | 24.5234 | MRU | 5.40548E−06 | 3.72054E−05 | Significant |
| Cdkn2a | 40 | 40 | MYO | 0.4439157 | 9.8621E−05 | Also according to histograms |
| Actb | 14.9435 | 14.0226 | MRU | 8.68264E−08 | 4.71069E−07 | Significant |

Two recent papers reported that $CD24^{med}CD49f^{low}$ phenotype cells may have different functional capacity compared to MaCFCs. Based on the single cell analysis, it appears that MaCFCs and $CD24^{med}CD49f^{low}$ have different gene expression signatures. MaCFCs expressed higher levels of Tbx3, Prkar2b, Trim24, Erbb3, Krt19, Cdh1, Actb, Itgb1 and Itga6 (FIG. 486). Relative to MaCFC cells, $CD24^{med}CD49f^{low}$ cells have elevated expression of Dock9 and Egfr, suggesting this phenotype enriched for a distinct luminal cell type. These genes were significantly differentially expressed between the MaCFC and $CD24^{med}CD49f^{low}$ mammary FACS sorted compartments with p-val<0.0009 (see Table 7 and FIG. 489). In table 7, If either both medians were the same we checked the histograms visually. Most p-values are well below 0.0009 which is the significance threshold with Bonferroni correction for 55 genes.

TABLE 7

Genes that were found to be differentially expressed between the
MaCFC and CD24$^{med}$CD49f$^{-/low}$ mammary FACS sorted compartments.

| Gene name | Median (CD24$^{med}$CD49f$^{-/low}$) | Median (MaCFC) | Compartment with higher gene expression | p-value (Wilcoxon) | p-value (Kolmogorov-Smirnov) | Notes |
|---|---|---|---|---|---|---|
| Trim24 | 40 | 20.6554 | MaCFC | 1.81818E−22 | 2.17019E−18 | Significant |
| Tbx3 | 40 | 19.9284 | MaCFC | 8.41071E−38 | 5.84983E−38 | Significant |
| Prkar2b | 40 | 19.1424 | MaCFC | 3.85283E−40 | 1.94057E−40 | Significant |
| Krt19 | 18.486 | 15.7842 | MaCFC | 1.22132E−36 | 1.99648E−37 | Significant |
| Itgb1 | 18.8572 | 17.7852 | MaCFC | 4.60042E−24 | 4.08945E−18 | Significant |
| Itga6 | 20.7919 | 18.3212 | MaCFC | 2.57968E−39 | 1.3924E−36 | Significant |
| Erbb3 | 21.2842 | 18.0199 | MaCFC | 5.59807E−41 | 3.91214E−40 | Significant |
| Egfr | 40 | 40 | CD24$^{med}$CD49f$^{-/low}$ | 8.83815E−15 | 2.94421E−12 | Also according to histograms |
| Dsg1a | 27.3583 | 34.9702 | CD24$^{med}$CD49f$^{-/low}$ | 0.002027662 | 0.001301938 | Approaching significance |
| Dock9 | 24.1156 | 40 | CD24$^{med}$CD49f$^{-/low}$ | 7.31942E−06 | 3.65688E−06 | Significant |
| Ceacam1 | 19.8382 | 20.4104 | CD24$^{med}$CD49f$^{-/low}$ | 0.02848461 | 0.00259607 | Marginally significant |
| Cdh1 | 17.3463 | 16.0728 | MaCFC | 1.74142E−21 | 6.05545E−21 | Significant |
| Actb | 15.1494 | 13.3641 | MaCFC | 2.15836E−26 | 4.95824E−24 | Significant |

Recent reports have demonstrated that human breast epithelium is also hierarchically organized. The populations that have been described using flow cytometry are MRU, MaCFC and differentiated luminal cells. These populations had CD49F$^{hi}$EPCAM$^{-/low}$, CD49F$^+$EPCAM$^+$ and CD49F$^{-/low}$EPCAM$^+$ phenotypes, respectively. To investigate if a gene expression list could distinguish similar populations as we observed in mouse mammary epithelium, we analyzed a specimen of human breast cells at a single cell level. Cells were sorted using a "reverse L-gate" strategy based on CD49f and EpCam expression to eliminate stromal cells. The analysis showed that clusters of cells with signatures that resembled mouse cell phenotypes are also present in the human data with high statistical significance (Table 5). We added EpCam (Tacstd1) expression independent of genes used for clustering to validate the phenotypes of distinct clusters of cells. CD49F$^{mRNAhi}$EPCAM$^{mRNA-/low}$ basal cells expressed NOTCH2, CEACAM1, CDH1, GAPDH, SUZ12, ACTB, ITGB1, EGFR, KRT17, KRT14, KRT5 and KRT8 genes at a high to intermediate level. Within the luminal compartment, two distinct clusters of luminal cells were observed: CD49F$^{mRNA+}$EPCAM$^{mRNhi+}$ and CD49F$^{mRNA-/low}$EPCAM$^{mRNAmed/low}$ cells. CD49F$^{mRNA-}$EPCAM$^{mRNmed/low}$ cells expressed high levels of KRT19, KRT18 and GAPDH. CD49F$^{mRNA+}$EPCAM$^{mRNhi+}$ cells expressed NOTCH1, NOTCH2, DOCK9, CEACAM1, TRIM24, ERBB3, KRT19, CDH1, KRT18, GAPDH, SUZ12, ITGB1, LRIG1, and KRT8 at a high level. These results show that a single cell multiplex quantitative gene expression analysis can be used to identify cells in the mouse and human mammary epithelium differentiation hierarchy. In addition, our data shows the striking resemblance of mouse and human breast epithelium.

Single Cell Analysis of Flow Cytometry Sorted Mammary Stem Cell Enriched Phenotype Identifies Multiple Distinct Stem and Progenitor Cell Compartments A number of groups have shown ~1/64 single mouse mammary epithelial cells isolated using flow cytometry using markers defining their MRU phenotype can produce a ductal outgrowth. The reason why all MRUs cannot produce ductal outgrowths could be due to the technical limitations of the transplant procedure and/or the heterogeneity of cell types that express the "MRU" markers. Our single cell analysis suggested that MRUs are a heterogeneous population in both mouse and human breast. Double sorted cells were analyzed for expression of multiple genes for each cell. The left hand dendrogram shows hierarchical clustering of cells based on similarity of gene expression profile. The top dendrogram shows clustering of gene assay expression across cells. Esr1 gene expression is displayed independently in the right column since it was not used for clustering the cells. The flow cytometry phenotype of each cell is color coded and shown in the "FACS labels" column and the attached legend. The assignment of each cell to one of six cell types is shown in the "Manual Assignment" column and the attached legend. Solid black lines show the divisions between cell clusters. The enrichment for a manually assigned cell type in a cell cluster is described by the right hand text labels. Bottom labels show the official gene symbol. The colored circle(s) below a gene symbol indicates which manually assigned cell type expresses that gene at a high level as described by the comparisons in the main text. Scale bar shows the expression gradient represented in the heat map. Double sorted cells were analyzed for expression of a similar set of genes used in the mouse analysis. The left hand dendrogram shows hierarchical clustering of cells based on similarity of gene expression profile. The two assays labeled "Independent" (Esr1, Tacstd1) were not used for clustering. On the basis of correlation to one of the 6 centroids computed on the mouse data, each cell was assigned a cell type to which it is most similar by gene expression profile ("Assigned labels from mouse" column and attached legend). Each of these 6 mouse cell types was found to be significantly present in human normal tissue. Based on the hierarchical clustering of the cells and the cell assignments, the cells were divided into groups shown by the dashed lines. Enrichment for a cell type is described by the text labels to the right of the heatmap. Bottom labels show the official gene symbol. The colored circle(s) below a gene symbol indicates which cell cluster expresses that gene at a high level as described by the comparisons in the main text. Scale bar shows expression gradient represented in heat map.

To investigate if a multiplexed quantitative RT-PCR gene expression analysis could be used to discover markers that enrich for mammary stem cells, we screened for the expression of cell surface markers. We found that Thy-1, a marker we had previously found marked cancer stem cells in MMTV-Wnt-1 transgenic mouse breast tumors, marked a subset of basal cells in human breast (FIG. 483). Shown in FIG. 483 are histograms of qPCR threshold cycles for THY-1 from basal (CD49f$^{++}$/EpCam$^{-low}$) and luminal (CD49f$^{low}$EpCam$^{++}$) single cell population. A larger fraction of basal cells express significantly higher mRNA levels (lower threshold cycles) of THY-1. Both the Kolmogorov-Smirnov (for testing the difference the two distributions) and the Wilcoxon ranksum test (for testing the difference between the two medians) give p-values<0.001.

FIG. 478 shows single cell gene expression of normal human breast epithelial cells including Thy-1. The arrow indicates the expression assay for Thy-1. Cells were hierarchically clustered by similarity of their gene expression profile (left hand dendrogram). Assays (bottom labels) were also hierarchically clustered (top dendrogram). Right hand labels and purple line demarcate clusters of cells that express basal and luminal keratins. Scale bar shows expression gradient represented in heat map. FIG. 478B shows real-time PCR expression of Thy-1 in double sorted mouse epithelial populations isolated by flow cytometry according to the indicated phenotypes. Data represents three independent experiments. Error bars are ±standard deviation. FIG. 478 C shows left hand flow cytometry plot shows Thy-1 expression in the MRU compartment. Lineage histogram shows gating to remove non-epithelial cells (CD45$^+$CD31$^+$Ter119+). Representative pictures are shown of GFP$^+$ ductal outgrowths through primary, secondary and tertiary (where applicable) transplantation. All images taken at 100× magnification. FIG. 478 D shows image of a primary single cell transplant produced from the GFP$^+$Thy-1$^+$CD24$^{med}$CD49f$^{hi}$ phenotype. E. Representative flow cytometry plots of a secondary GFP$^+$Thy-1$^+$CD24$^{med}$CD49f$^{hi}$ ductal outgrowth based on CD24, CD49f and Thy-1 expression. Plots are gated on Lineage$^-$GFP$^+$ cells.

We asked whether Thy-1 could further enrich for mammary stem cells using transplantation. Immature mouse breast cells had differential expression of Thy-1 at the mRNA and protein levels (FIG. 478B, 478C). Using flow cytometry, mouse mammary epithelial cells were subdivided into Thy-1$^+$CD24$^{med}$CD49f$^{hi}$ and Thy-1$^-$CD24$^{med}$CD49f$^{hi}$ cells and transplanted in limiting dilution (Table 8). In table 8, cells from the indicated population (top labels) were double sorted and transplanted in limiting dilution into the cleared fat pads of wild-type recipient mice. Transplants are represented as positive outgrowths/total transplants.

TABLE 8

Engraftment of flow cytometry isolated phenotypic mouse mammary populations.

|  | Bulk | Lin- | CD24$^{med}$CD49f$^{hi}$ (MRU) | Thy-1$^+$ CD24$^{med}$CD49f$^{hi}$ | Thy-1$^-$ CD24$^{med}$CD49f$^{hi}$ |
|---|---|---|---|---|---|
| 250K | 1/1 | — | — | — | — |
| 133K | 2/2 | — | — | — | — |
| 100K | 3/4 | — | — | — | — |
| 50K | — | 3/3 | — | — | — |
| 25K | 4/8 | 11/18 | — | — | — |
| 20K | — | 5/7 | — | — | — |
| 10K | — | 13/22 | 2/2 | — | — |
| 5K | — | 1/4 | — | — | — |
| 3K | — | — | 2/3 | 2/2 | 1/2 |
| 1K | — | — | 4/4 | 3/7 | 1/3 |
| 600 Cells | — | — | — | 1/2 | 0/2 |
| 400 Cells | — | — | — | 2/4 | 0/4 |
| 300 Cells | — | — | 2/3 | 3/6 | 1/3 |
| 250 Cells | — | — | — | 2/2 | 0/3 |
| 200 Cells | — | — | 5/11 | 5/11 | 0/5 |
| 100 Cells | — | — | 4/13 | 25/44 | 2/30 |
| 50 Cells | — | — | — | 13/31 | 1/24 |
| 30 Cells | — | — | — | 12/15 | 0/9 |
| 5 Cells | — | — | 2/14 | 7/29 | 2/30 |
| 1 Cell | — | — | — | 4/35 | — |

Thy-1$^+$CD24$^{med}$CD49f$^{hi}$ cells gave rise to ductal outgrowths that could be serially transplanted (FIG. 478C, 478E). These cells were also capable of alveolar differentiation, demonstrating they can produce functional ductal epithelium (FIG. 484). In FIG. 484, sections from transplanted primary, secondary and pregnant epithelium derived from Thy-1$^+$CD24$^{med}$CD49f$^{hi}$ cells. FIG. 484A top panels show Hematoxylin and Eosin staining to demonstrate transplanted epithelium had similar morphology compared to wild type. Bottom immunofluorescence pictures show sections stained for Krt8 (green, to mark luminal cells) and Krt14 (red, to mark myoepithelial cells). Staining shows transplanted epithelium contains both types of cell compartments. All pictures taken at 200× magnification. FIG. 484 B shows transplanted epithelium is capable of alveolar differentiation. Top panels show Hematoxylin and Eosin staining of wild type and secondary transplanted epithelium in pregnant mice. Bottom immunofluorescence panels staining for Krt14 (red), Krt8 (green) and nuclear DAPI (blue) shows transplanted epithelium resembled wild type morphology. Note the red auto-fluorescent milk inside the lumen of the ducts. All pictures taken at 200× magnification. Single cell transplantation showed 1 in 8 Thy-1$^+$CD24$^{med}$CD49f$^{hi}$ cells could produce a ductal outgrowth (FIG. 478D). In contrast, Thy-1$^-$CD24$^{med}$CD49f$^{hi}$ cells had reduced proliferative and self-renewal capacities (FIG. 478C, Table 9). Therefore, the single cell PCR system successfully identified a new mammary stem cell marker.

TABLE 9

Self-renewal transplantation of donor primary epithelium.

| Original Transplanted Population | Engrafted/ Transplanted | Efficiency |
|---|---|---|
| Lineage− 25K (n = 3) | 10/11 | 91% |
| Thy-1$^{lo}$CD24$^{med}$CD49f$^{hi}$ 600 cells (n = 1) | 5/6 | 83% |
| Thy-1$^{lo}$CD24$^{med}$CD49f$^{hi}$ 100 cells (n = 5) | 6/10 | 60% |
| Thy-1$^{lo}$CD24$^{med}$CD49f$^{hi}$ 30 cells (n = 3) | 6/9 | 67% |
| Thy-1$^{hi}$CD24$^{med}$CD49f$^{hi}$ 100 cells (n = 4) | 6/8 | 75% |
| Thy-1$^{-}$CD24$^{med}$CD49f$^{hi}$ cells (n = 3) | 1/9 | 11% |

A number of groups have shown that EMT may be linked to mammary stem cells. However, it is unknown if all stem cells or only a subset of them has undergone EMT. We used single cell analysis to distinguish between these two possibilities.

The immature compartment of human normal breast had two sub-populations: ZEB1$^{mRNAhi}$CDH1$^{mRNA-/low}$ CEACAM1$^{mRNA-}$EPCAM$^{mRNA-}$ cells and ZEB1$^{mRNA-}$CDH1$^{mRNA+}$CEACAM1$^{mRNA+}$EPCAM$^{mRNA+}$ cells. Two similar sub-populations exist in the mouse MRU compartment (FIG. 479A). Previous studies have shown Zeb1 promotes EMT in part by repressing Cdh1 (E-cadherin) expression, suggesting there are immature breast cells that have undergone an EMT and cells that haven't. Because we have not found an antibody against mouse E-cadherin that can be used for flow cytometry, we used Ceacam1 (CD66a) as a tool to separate the Zeb1$^{mRNA-}$Cdh1$^{mRNA-/low}$ (EMT gene expression-like) and the Zeb1$^{mRNA-}$Cdh1$^{mRNA+}$ populations, allowing analysis of the stem cell activity of the two subpopulations. Dissociated mouse mammary cells were stained with antibodies against CD24, CD49f, Ceacam1 (CD66a) and EpCam to assess CD66a protein expression in MRU, MaCFC, MYO and CD24$^{med}$CD49f$^{low}$ cells (FIG. 479C). The results show CD66a is expressed at a high level in luminal MaCFC and CD24$^{med}$CD49f$^{low}$ cells (FIGS. 479C and 477A). MYO cells were mostly CD66a−$^{/low}$ and CD66a$^{med}$, with a discrete CD66a$^{hi}$ population. Although the majority of MRU cells were CD66a$^{med}$, about 13% of the cells were CD66a−$^{/low}$ and 22% were CD66a$^{hi}$ (FIG. 479B, 479C). This corresponds to the three expression levels of CD66a mRNA seen in the single cell gene expression analyses (FIG. 479A). FIG. 479A shows human immature and mouse MRU single cell gene expression for Zeb1, Ceacam1 (CD66a) and Cdh1 (E-cadherin). Cells were hierarchically clustered by similarity of gene expression profile (left hand dendrogram). Assays (bottom labels) were also hierarchically clustered (top dendrogram). The scale bar shows expression gradient represented in heat map. FIG. 479B shows flow cytometry plot of mouse Lineage$^{-}$CD24$^{med}$CD49f$^{hi}$ (MRU) cells gated for expression of CD66a and EpCam shows that CD66a and EpCam are correlated. C. Expression of CD66a in MRU, MYO, MaCFC and CD24$^{med}$CD49f$^{low}$ cells shown by histogram analysis from flow cytometry. Gates drawn in each plot indicate the CD66$^{low}$, CD66$^{med}$ and CD66$^{hi}$ cells in each population. Percentages of cells that express CD66a in each population (including Lineage$^{-}$) are shown in the accompanying table. When we transplanted CD66$^{hi}$, CD66$^{med}$ and CD66−$^{/low}$Lineage$^{-}$ cells we did not observe an engraftment advantage in any of the populations (Table 2). In table 2, number of positive outgrowths/total transplants for each indicated cell population is shown. For each cell population, "Frequency" was derived by pooling the data from several limiting dilution experiments analyzed by applying Poisson statistics to the single-hit model.

TABLE 10

CD66a transplants of mouse mammary epithelial cells.

| Population | 20,000 Cells Transplanted | 200 Cells Transplanted | 100 Cells Transplanted | Frequency |
|---|---|---|---|---|
| CD66−$^{/low}$Lineage$^{-}$ | 2/3 | — | — | 1 in 18,205 |
| CD66$^{med}$Lineage$^{-}$ | 3/3 | — | — | 1 in 14,427 |
| CD66$^{hi}$Lineage$^{-}$ | 2/3 | — | — | 1 in 18,205 |
| CD66−$^{/low}$CD24$^{med}$CD49f$^{hi}$ | — | 2/4 | 1/5 | 1 in 343 |
| CD66$^{med}$CD24$^{med}$CD49f$^{hi}$ | — | 1/3 | 2/4 | 1 in 260 |
| CD66$^{hi}$CD24$^{med}$CD49f$^{hi}$ | — | 2/4 | 1/4 | 1 in 309 |

Next, we isolated CD66$^{hi}$, CD66$^{med}$ and CD66−$^{/low}$ MRU phenotype cells from GFP$^{+}$ mouse mammary epithelium and performed a limiting dilution transplantation study to determine if any of these phenotypes enriched for duct forming cells (Table 10). Again, all three of the phenotypes had similar engraftment potential, and produced outgrowths of similar size and morphology (data not shown). However, we did note that in both series of transplantation experiments the CD66$^{med}$ cells performed marginally worse than the CD66−$^{/low}$ and CD66$^{hi}$ cells, but these differences were not statistically significant as determined by two-tailed t-tests (data not shown). Therefore, single cell analysis allowed us to identify stem cells that had undergone EMT and those that had not. Our transplant data suggests that both subtypes of cells are stem cells that have similar engraftment capacity.

Single Cell Analysis Identifies Different Populations of Esr1$^{mRNA+}$ and Esr1$^{mRNA-}$ Luminal Cells Although estrogen receptor (ER) is expressed in the luminal compartment, not all luminal epithelial cells express the protein. The difference between ER positive and negative cells is poorly understood other than their response to estrogen stimulation. To further characterize the luminal compartment of breast epithelium for estrogen receptor expression, we used our PCR system to assay for Esr1 (estrogen receptor a) in human and mouse cells (FIG. 477). In mouse, MaCFC luminal cells expressed high levels of Esr1 but CD24$^{med}$CD49f$^{low}$ luminal cells had negligible expression. Using single cell gene expression, the luminal compartment was examined in more detail. Cluster analyses found five distinct populations of human luminal cells (FIG. 480C). There was a CD49f$^{mRNAmed}$EpCam$^{mRNAmed}$ population that contained cells that expressed MYC$^{mRNA+}$GAPDH$^{mRNAhi}$, KRT18$^{mRNAhi}$KRT19$^{mRNAhi}$SUZ12$^{mRNA+}$ and contain cells that expressed ESR1 at a low level (FIG. 480A). There was a CD49f$^{mRNA-/low}$EpCam$^{mRNA-/low}$ population that expressed luminal keratins at low levels (FIG. 480A). Within the CD49f$^{mRNA-/low}$EpCam$^{mRNA-/low}$ cells there was a subpopulation of KRT8$^{mRNA+}$LEFTY2$^{mRNA+}$CFC1$^{mRNA+}$NODAL$^{mRNA+}$THY-1$^{mRNA+}$TDGF1$^{mRNA+}$ELF5$^{mRNA+}$ expressing cells (FIG. 480A). Both of these populations expressed little or no detectable ESR1. We also found the following two populations were enriched for ESR1 expressing cells. The CD49f$^{mRNAhi}$EpCam$^{mRNAhi}$ cells expressed TCF7L2$^{mRNA+}$GATA3$^{mRNA+}$MAML2$^{mRNA+}$TCF7L1$^{mRNA+}$CEACAM1$^{mRNA+}$FOX O1$^{mRNA+}$CYR61$^{mRNA+}$ELF5$^{mRNA+}$ (FIG. 480A). The CD49f$^{mRNA-}$EpCam$^{mRNA+}$ cells expressed pGR$^{mRNA+}$BX3$^{mRNA+}$STC2$^{mRNA+}$ERBB4$^{mRNA+}$TFF3$^{mRNA+}$ KIF12$^{mRNA+}$MUC1$^{mRNA+}$MUSTN1$^{mRNA+}$METTL3$^{mRNA+}$ (FIG. 480A). This latter ERBB4$^{mRNA+}$ luminal population is likely comprised of cells that have received an estrogen signal, since they expressed PGR. FIG. 474A shows single cell analysis of luminal enriched cells from human normal breast cells. The left hand dendrogram shows hierarchical clustering of cells based on similarity of gene expression profile. The top dendrogram shows clustering of gene assay expression across cells. Numbered labels highlight the cell clusters that are described in the main text. Dashed lines show division between numbered cell clusters. Bottom labels correspond to genes that were tested. Genes used to describe flow cytometry markers' mRNA phenotype determination are boxed. The scale bar shows expression gradient represented as a heat map. B. NIH3T3 in vitro colony forming assay results of plated MRU, MaCFC and CD24$^{med}$CD49f$^{low}$ (EPI) cells. Results are the average of three independent experiments. Error bars indicate±standard deviation.

The expression of Esr1 only in MaCFC cells supported our earlier data that the CD24$^{med}$CD49f$^{low}$ cells enriched for a distinct luminal cell type. We then plated MRU, MaCFC and CD24$^{med}$CD49f$^{low}$ cells into colony forming assays to test each population for proliferation and differentiation potential. Our data indicates that mouse CD49f$^{low}$CD24$^{med}$ luminal cells have proliferative potential (FIG. 480B), but are approximately half as efficient at colony formation compared to MaCFC cells (approximately 1 in 10 vs 1 in 5, respectively). FIG. 479B shows that left labels indicate the population that colonies were grown from. The left hand images show a 3-d colony from each population. The right hand panels show a 2-D colony from each population. Colonies were stained for Krt14 (red) to indicate basal/myoepithelial cells and Krt8 (green) to indicate luminal cells. 3-D images taken at 200×, and 2-D images taken at 100×.

These cells can also make 3D and 2D colonies that have basal and luminal keratin expression, similar to MRU and MaCFC cells (FIG. 480C). Using flow cytometry, we plated CD49F$^-$EPCAM$^-$, CD49F$^{-/low}$EPCAM$^+$, CD49F$^+$EPCAM$^+$ and CD49F$^-$EPCAM$^+$ cells to investigate the colony forming ability of each population. Similar to mouse, we found CD49F$^{-/low}$EPCAM$^+$ cells had a reduced colony forming frequency compared to CD49F$^+$EPCAM$^+$ cells (data not shown). Taken together, our single cell analyses were able to distinguish an estrogen receptor negative progenitor population that had a distinct gene expression profile and colony formation ability in vitro compared to previously characterized estrogen receptor positive luminal cells.

Single Cell Analysis of an ER$^+$ Breast Tumor Identifies Distinct ER$^+$ and ER$^-$ Cancer Cell Populations Cancer is a disease defined by the progressive loss of proliferative restraints of a cell in the tissue from which the tumor forms. In the breast, the cells in the most common type of breast cancer express estrogen receptor (ER).

It is well known that expression of ER is heterogeneous in tumor specimens. Since there are ER$^-$ immature mammary ductal cells and ER$^-$ luminal cells, the ER$^-$ cells in a tumor could represent either or both of these populations. To begin to understand the origins of the ER$^-$ cells, we performed a database search of ER$^+$ breast cancers and found that the majority of tumors expressed both luminal cell markers (based on KRT19, ERBB3, ERBB4, ESR1) and basal cytokeratins (based on KRT5, KRT14 KRT17) (FIG. 481A). There are two possible explanations for this data. First, it is possible that the cancer cells have lost their developmental identity and co-express high levels of both basal and luminal cytokeratins. Second, it is possible that the tumor has retained some of its developmental potential and that this accounts for at least some of the heterogeneity in marker expression. FIG. 481A shows absolute expression of basal and luminal lineage markers in estrogen receptor positive breast tumors. Publicly available Affymetrix microarray data was normalized using the GC-RMA algorithm, then hierarchically clustered. Negative control values represent the mean of 24 Affymetrix control probesets. ER$^+$ breast tumors express both basal cytokeratins (KRT5, KRT14, KRT17) and luminal cell markers (ERBB4, ERBB3, ESR1, KRT19). FIG. 481B shows single cell multiplex PCR analysis of estrogen receptor positive human breast tumor. The left hand dendrogram shows hierarchical clustering of cells based on similarity of gene expression profile. The top dendrogram shows clustering of gene assay expression across cells. The two assays labeled "Independent" were not used for clustering. Right hand labels correspond to enrichment of Esr1 expression for that group of cells (divided by black line). Colored "Assigned labels from mouse" column and attached legend shows the assignment of each cell to the 6 mouse cell types, where each cell was assigned based on maximal correlation to the cell type centroid. Dashed lines show cell clusters that are enriched for an assigned cell type. Most of the mouse cell types are significantly present in this tissue (Table 11), apart from CD24$^{med}$/CD49f$^{-/low}$ cells which were not significantly present in this tumor (p-value=0.312). In table 11, based on the In Group Proportion (IGP), all phenotypes are significantly present in human normal tissue. In the tumor sample there is no evidence for the presence of the "CD24$^{med}$CD49f$^{low}$" phenotype (p-val=0.31). The p-value for the "MYO" phenotype is approaching significance. p-values were computed by performing 50,000 permutations using the clusterRepro R™ package. Note also that the MYO's (p-val=0.085) are less easy to identify as a group distinct from the MRU Zeb1$^{mRNA-}$ cells. ITGA6, which marks stem cells, is highly expressed in a population of cells phenotypically resembling a mixture of MRU Zeb1$^+$, MRU Zeb1$^-$MYO cells The gene expression pattern of these 2 groups of cells resembles immature mouse mammary epithelial cells. Scale bar shows expression gradient represented as a heat map.

TABLE 11 p-values for the extent to which each cell type in the mouse data is present in the human normal and tumor data.

| | MRU Zeb$^-$ | Unknown/ Stromal | MRU Zeb1$^+$ | MYO | MaCFC | CD24$^{med}$ CD49f$^{-/low}$ |
|---|---|---|---|---|---|---|
| Human normal | 0.00673968 | 0.00000000 | 0.00000000 | 0.01850781 | 0.04371585 | 0.02339803 |
| Tumor 1 | 0.02092479 | 0.06105834 | 0.01042069 | 0.08598774 | 0.00000000 | 0.31236937 |

Single cell gene expression studies were therefore done to understand the cellular heterogeneity within an ER+ breast tumor. We first examined dissociated cancer cells from an ER+PR+Her2− breast cancer and a paired non-tumorous breast sample by flow cytometry, staining for CD49F and EPCAM (FIG. 485). In FIG. 485, a primary ER+ breast cancer and paired non-tumorous breast specimen were dissociated into single cells and analyzed by flow cytometry for the expression of EPCAM and CD49F. Shown are epithelial cells based on Lineage gating. Note the similarity between the normal and cancer phenotypes. The cancer has an enlarged CD49f$^{low}$EPCAM+ population. The flow data shows the cancer cells had a similar phenotypic distribution compared to the non-tumorous sample (Table 11), but there was a large expansion of the CD49F$^{-/low}$EPCAM+ population (5.8% of the normal mammary epithelial cells, 30% of the tumor cells in this patient, FIG. 485). Similar to the normal breast, the EPCAM$^{mRNA+}$ cancer cells expressed luminal cell markers including KIF12, TBX3, PRKAR2B and ERBB3. These luminal epithelial-like cancer cells were the cells that expressed ESR1 (FIG. 481B). There were 3 distinct populations of ESR1$^{mRNA-}$cells. One population [Esr-1− (1)] resembled the human and mouse normal CD49F$^{mRNAhi}$ZEB1$^{mRNA+}$ (stem cells whose gene expression pattern resembled an EMT cell) and the other [Esr-1− (2)] resembled the CD49F$^{mRNAhi}$ZEB1$^{mRNA-}$ population whose gene expression resembled that of the normal mouse basal stem and myoepithelial cells. The third ER− population resembled the human normal KRT8$^{mRNA+}$LEFTY2$^{mRNA+}$ CFC1$^{mRNA+}$NODAL$^{mRNA+}$THY1$^{mRNA+}$TDGF1$^{mRNA+}$ ELF5$^{mRNA+}$ population (FIG. 487). In FIG. 487, the "Assigned labels from mouse" column was obtained by assigning each cell to the cell type for which the correlation with its centroid is maximal. Centroids were computed based on the mouse data. The "CD24$^{med}$CD49f$^{low}$" phenotype, which corresponds to differentiated luminal cells in mouse is not significantly present in this tumor (CD24$^{med}$CD49f$^{low}$—Yellow, MRU Zeb1+—Cyan, Unknown/Stromal—Black, MYO—Green, MRU Zeb1−—Blue, MaCFC—Red). Taken together, these results suggest there are basal and luminal cells in the analyzed ER+ breast tumor similar to normal immature and mature cell populations.

What is claimed is:

1. A method of treating heterogeneous tumors in a human subject, comprising:
   i. dissociating a tumor biopsy into individual cells, flowing the dissociated tumor biopsy through a microfluidic metamaterial to split the flow according to particle size and randomly partition the cells into a prefabricated microwell array;
   ii. picking individual cells by expression of at least one cell surface marker from the microwell array and transferring each individual cell into a discrete location using an automated microfluidic system;
   iii. performing transcriptome analysis on at least 50 genes of the individually selected cells; and
   iv. identifying one or more therapeutic targets from transcriptome data obtained from the transcriptome analysis for treatment of said heterogeneous tumor.

2. The method of claim 1, wherein the one or more therapeutic targets is a DNA or RNA methyltransferase, methyltransferase-like enzyme or a derivative thereof.

3. The method of claim 1, wherein the one or more therapeutic targets is a histone lysine methyltransferase, histone arginine methyltransferase or a derivative thereof.

4. The method of claim 1, wherein the one or more therapeutic targets is a histone demethylase or a derivative thereof.

5. The method of claim 1, wherein the one or more therapeutic targets is a protein kinase or a derivative thereof.

6. A method of analyzing a heterogeneous tumor biopsy from a human subject or treatment of the tumor from the human subject, comprising:
   i. dissociating the tumor biopsy into individual cells, flowing the dissociated tumor biopsy through a microfluidic metamaterial to split the flow according to particle size and randomly partition the cells into a prefabricated microwell array;
   ii. picking individual cells by expression of at least one cell surface marker from the microwell array and transferring each individual cell into a discrete location using an automated microfluidic system;
   iii. performing transcriptome analysis on at least 50 genes of the individually selected cells; and
   iv. identifying one or more diagnostic markers present in the tumor biopsy from transcriptome data obtained from the transcriptome analysis for the detection of cancer and determining of the cancer stage or the effectiveness of treatment of the tumor from the human subject.

7. The method of claim 6, wherein the one or more diagnostic markers is a DNA or RNA methyltransferase, methyltransferase-like enzyme or a derivative thereof.

8. The method of claim 6, wherein the one or more diagnostic markers is a histone lysine methyltransferase, histone arginine methyltransferase or a derivative thereof.

9. The method of claim 6, wherein the one or more diagnostic markers is a histone demethylase or a derivative thereof.

10. The method of claim 6, wherein the one or more diagnostic markers is a protein kinase or a derivative thereof.

11. The method of claim 1, wherein the at least 50 genes comprise one or more of STAT3, MEIS1, CAV1, GAS1, MAP4K4 (kinase) MYLK (kinase), PTK2 (kinase), DAPK1 (kinase), LATS (kinase), FOSL2, AKT3 (kinase), PTPRC (tyrosine phosphatase), MAFF (oncogene), RRAS2, NFKB, ROBO1, IL6ST, CR1M1, PLS3, CXCL14, ETS1, ETS2, CD47, RGS4, CAV2, MAF, WT1, SNAI2, MEIS2, ID4, FOXC1, GSS, GCLC, GCLM, GPX1, GPX4, GPX7, SLPI, PRNP, SOD1, SOD2, SOD3, CAT, NFKB1, FOXO1, FOXO3A, FOXO4, KRT19, CHI311, TERT, HIF1A, EPAS1, HPRT, and ACTB.

* * * * *

UNITED STATES PATENT AND TRADEMARK OFFICE
CERTIFICATE OF CORRECTION

PATENT NO. : 9,850,483 B2  
APPLICATION NO. : 13/811065  
DATED : December 26, 2017  
INVENTOR(S) : Clarke et al.

Page 1 of 1

It is certified that error appears in the above-identified patent and that said Letters Patent is hereby corrected as shown below:

On the Title Page

On page 2, in Column 1, under item (56) "Other Publications", Line 13, delete "Hight-Throughput" and insert --High-Throughput-- therefor In the Specification In Column 1, Lines 18-19, delete "federal grants U54 CA 126524 awarded by the National Cancer Institute" and insert --contracts CA104987, CA126524, and OD000251 awarded by the National Institutes of Health-- therefor In the Claims In Column 100, Line 32, in Claim 6, after "determining", delete "of"

Signed and Sealed this  
Twenty-sixth Day of March, 2019

Andrei Iancu  
*Director of the United States Patent and Trademark Office*